US012435078B2

(12) United States Patent
Yu et al.

(10) Patent No.: US 12,435,078 B2
(45) Date of Patent: Oct. 7, 2025

(54) PYRIDAZINONES AND METHODS OF USE THEREOF

(71) Applicant: Goldfinch Bio, Inc., Cambridge, MA (US)

(72) Inventors: Maolin Yu, West Roxbury, MA (US); Matthew H. Daniels, Somerville, MA (US); Jean-Christophe P. Harmange, Andover, MA (US); Thomas T. Tibbitts, Westford, MA (US); Mark W. Ledeboer, Acton, MA (US); Goran Malojcic, Boston, MA (US); Liron Walsh, Newton, MA (US); Peter H. Mundel, Brookline, MA (US)

(73) Assignee: GFB (ABC), LLC, Foxboro, MA (US)

(*) Notice: Subject to any disclaimer, the term of this patent is extended or adjusted under 35 U.S.C. 154(b) by 342 days.

(21) Appl. No.: 16/648,606

(22) PCT Filed: Sep. 18, 2018

(86) PCT No.: PCT/US2018/051465
§ 371 (c)(1),
(2) Date: Mar. 18, 2020

(87) PCT Pub. No.: WO2019/055966
PCT Pub. Date: Mar. 21, 2019

(65) Prior Publication Data

US 2023/0203028 A1 Jun. 29, 2023

Related U.S. Application Data

(60) Provisional application No. 62/655,985, filed on Apr. 11, 2018, provisional application No. 62/559,840, filed on Sep. 18, 2017.

(51) Int. Cl.

| | |
|---|---|
| ***C07D 471/04*** | (2006.01) |
| ***A61P 13/12*** | (2006.01) |
| ***C07D 237/22*** | (2006.01) |
| ***C07D 401/12*** | (2006.01) |
| ***C07D 401/14*** | (2006.01) |
| ***C07D 403/04*** | (2006.01) |
| ***C07D 487/08*** | (2006.01) |
| ***C07D 487/10*** | (2006.01) |

(52) U.S. Cl.
CPC ............ *C07D 471/04* (2013.01); *A61P 13/12* (2018.01); *C07D 237/22* (2013.01); *C07D 401/12* (2013.01); *C07D 401/14* (2013.01); *C07D 403/04* (2013.01); *C07D 487/08* (2013.01); *C07D 487/10* (2013.01)

(58) Field of Classification Search
None
See application file for complete search history.

(56) References Cited

U.S. PATENT DOCUMENTS

| | | | |
|---|---|---|---|
| 9,139,573 | B2 | 9/2015 | Chong et al. |
| 10,654,850 | B2 | 5/2020 | Ledeboer et al. |
| 11,046,690 | B2 | 6/2021 | Ledeboer et al. |
| 2005/0176722 | A1 | 8/2005 | Bono et al. |
| 2007/0287696 | A1 | 12/2007 | Burgey et al. |
| 2008/0027041 | A1 | 1/2008 | Hudkins et al. |
| 2008/0207902 | A1 | 8/2008 | Kohno et al. |
| 2009/0163545 | A1 | 6/2009 | Goldfarb |
| 2014/0275528 | A1 | 9/2014 | Chenard et al. |
| 2016/0046624 | A1 | 2/2016 | Chenard et al. |
| 2019/0127370 | A1 | 5/2019 | Kc et al. |

FOREIGN PATENT DOCUMENTS

| | | | |
|---|---|---|---|
| CN | 103201277 | A | 7/2013 |
| CN | 104718201 | A | 6/2015 |
| TW | 2009/32237 | A | 8/2009 |
| WO | 9932448 | A1 | 7/1999 |
| WO | 0142241 | A1 | 6/2001 |
| WO | 03104225 | A1 | 12/2003 |
| WO | WO-2003/104225 | A1 | 12/2003 |
| WO | 2005080391 | A1 | 9/2005 |
| WO | WO-2006/044504 | A1 | 4/2006 |
| WO | 2006113704 | A2 | 10/2006 |
| WO | 2007008143 | A1 | 1/2007 |
| WO | WO-2007/106349 | A2 | 9/2007 |
| WO | 2008009406 | A1 | 1/2008 |

(Continued)

OTHER PUBLICATIONS

Gokçe et al. (Il Farmaco, 56:233-237, 2001).*

(Continued)

*Primary Examiner* — Bong-Sook Baek

(74) *Attorney, Agent, or Firm* — Honigman LLP; Andrew Chipouras; Jonathan P. O'Brien

(57) ABSTRACT

Disclosed are compounds according to Formula (A), and related tautomers and pharmaceutical compositions. Also disclosed are therapeutic methods, e.g., of treating kidney diseases, using the compounds of Formula (A).

(I)

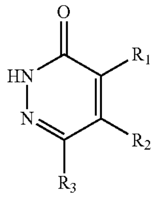

10 Claims, 86 Drawing Sheets

Specification includes a Sequence Listing.

(56) References Cited

FOREIGN PATENT DOCUMENTS

| | | | |
|---|---|---|---|
| WO | 2008012440 | A2 | 1/2008 |
| WO | 2008041075 | A1 | 4/2008 |
| WO | 2008115381 | A1 | 9/2008 |
| WO | WO-2008/115385 | A2 | 9/2008 |
| WO | 2008146064 | A1 | 12/2008 |
| WO | 2009054794 | A1 | 4/2009 |
| WO | 2009090039 | A1 | 7/2009 |
| WO | 2009097309 | A1 | 8/2009 |
| WO | WO-2014/058747 | A1 | 4/2014 |
| WO | 2014140592 | A1 | 10/2014 |
| WO | 2015032840 | A1 | 12/2015 |
| WO | WO-2017/197051 | A1 | 11/2017 |
| WO | WO-2019/055966 | A2 | 3/2019 |
| WO | WO-2020/061162 | A1 | 3/2020 |
| WO | WO-2020/191056 | A1 | 9/2020 |
| WO | WO-2020/210639 | A1 | 10/2020 |
| WO | WO-2022/001767 | A1 | 1/2022 |

OTHER PUBLICATIONS

STN Registry Record (RN 1436193-11-1; entered date: Jun. 9, 2013).*

STN Registry Record (RN 2108904-72-7; entered date: Aug. 6, 2017).*

Barbaro et al., "Synthesis, Biological Evaluation, and Pharmacophore Generation of New Pyridazinone Derivatives with Affinity toward $\alpha_1$- and $\alpha_2$-Adrenoceptors," J. Med. Chem., 44(13): 2118-2132 (2001).

Betti et al., "$\alpha_1$-Adrenoceptor Antagonists. 6. Structural Optimization of Pyridazinone-Arylpiperazines. Study of the Influence on Affinity and Selectivity of Cyclic Substituents at the Pyridazinone Ring and Alkoxy Groups at the Arylpiperazine Moiety," J. Med. Chem., 46: 3555-3558 (2003).

Corsano et al., "New pyridazinones: synthesis and correlation between structure and $\alpha$-blocking activity," Eur J Med Chem, 28: 647-651 (1993).

Corsano et al., "Synthesis And Bronchospasmolytic Properties of Some Pyridazinone Derivatives," Bioorganic & Medicinal Chemistry Letters, 3(12): 2713-2716 (1993).

Corsano et al., "Synthesis and pharmacological activity of some new pyridazinones," Eur J Med Chem, 27: 545-549 (1992).

Extended European Search Report for EP Application No. 18857094 dated May 3, 2021.

Extended European Search Report for EP Application No. 19863481.8 dated May 17, 2022.

International Preliminary Report on Patentability for International Application No. PCT/US2018/051465 mailed Apr. 2, 2020.

Pablo et al., "Charting a TRP to Novel Therapeutic Destinations for Kidney Diseases," Trends in Pharmacological Sciences, 40(12):911-918 (2019).

Yu et al., "Discovery of a Potent and Selective TRPC5 Inhibitor, Efficacious in a Focal Segmental Glomerulosclerosis Model," ACS Med Chem Lett, 10:1579-1585 (2019).

Castle et al., "Pyridazines. III. The synthesis of substituted pyridazines," Journal of Heterocyclic Chemistry, 2:463-472 (1965).

International Search Report and Written Opinion for International Application No. PCT/US18/51465 mailed Feb. 27, 2019.

International Search Report and Written Opinion for International Application No. PCT/US19/51680 dated Jan. 9, 2020.

Miller et al., "Identification of ML204, a Novel Potent Antagonist That Selectively Modulates Native TRPC4/C5 Ion Channels," Journal of Biological Chemistry, 286(38):33436-33446 (2011).

Minard et al, "Remarkable Progress with Small-Molecule Modulation of TRPC1/4/5 Channels: Implications for Understanding the Channels in Health and Disease," Cells, 7(52):1-20 (2018).

Pubmed Compound Summary for CID 45834084, "4-Chloro-4[4-(4-methoxyphenoxy)piperidin-1-yl]-2,3-dihydropyridazin-3-one," https://pubchem.ncbi.nlm.nih.gov/compound/45834084, (2015).

Pubmed Compound Summary for CID 75420213, "4-Chloro-2-phenyl-5-{5H,6H,7H,8H-pyrido[3,4-d]pyrimidin-7-yl}-2,3-dihydropropyridazin-3-one," https://pubchem.ncbi.nlm.nih.gov/compound/75420213 (2014).

Pubmed Compound Summary for CID 86805598, "LNRUODMAEBORIK-UHFFFAOYSA-N," https://pubchem.ncbi.nlm.nih.gov/compound/86805598, (2015).

Pubmed Compound Summary for CID 86942850, "YDHFXQRLHBDRHD-UHFFFAOYSA-N," https://pubchem.ncbi.nlm.nih.gov/compound/86942850 (2015).

Strappaghetti et al., "Adenosine receptors: synthesis, structure-activity relationships and biological activity of new 6-amino purine derivatives," European Journal of Medicinal Chemistry, 33(6):501-508 (1998).

Alawi et al., "Transient receptor potential canonical 5 channels plays an essential role in hepatic dyslipidemia associated with cholestasis," Scientific Reports, 7: 2338 (9 pages)(2017).

Gaunt et al., "Transient receptor potential canonical 4 and 5 proteins as targets in cancer therapeutics," Eur Biophys J, 45: 611-620 (2016).

Just et al., "Treatment with HC-070, a potent inhibitor of TRPC4 and TRPC5, leads to anxiolytic and antidepressant effects in mice," Plos One, 13(1): e0191225 (32 pages)(2018).

Ma et al., "Transient receptor potential channel TRPC5 is essential for P-glycoprotein induction in drug-resistant cancer cells," PNAS, 109(40): 16282-16287 (2012).

Sachdeva et al., "TRPC proteins contribute to development of diabetic retinopathy and regulate glyoxalase 1 activity and methylglyoxal accumulation," Molecular Metabolism, 9, 156-167 (2018).

Schaldecker et al., "Inhibition of the TRPC5 ion channel protects the kidney filter," J Clin Invest., 123(12):5298-5309 (2013).

Wei et al., "Regulation of neuropathic pain behavior by amygdaloid TRPC4/C5 channels," Neuroscience Letters, 608: 12-17 (2015).

Wei et al., "Therapeutic Effects of FK506 on IgA Nephropathy Rat," Kidney & Blood Pressure Research, 42: 983-998 (2017).

Westlund et al., "A Rat Knockout Model Implicates TRPC4 In Visceral Pain Sensation," Neuroscience, 262: 165-175 (2014).

Zhou et al., "A small-molecule inhibitor of TRPC5 ion channels suppresses progressive kidney disease in animal models," Science, 358:1332-1336 (2017).

Zhou et al., "Human relevance of blocking the Rac1-TRPC5 pathway as a podocyte-protective strategy for progressive kidney diseases," bioRxiv: 41 pages (2020).

CAS Registry No. 1354526-97-8; STN Entry date Jan. 26, 2012.

CAS Registry No. 1427907-65-0; STN Entry date Apr. 11, 2013.

CAS Registry No. 1593374-28-7; STN Entry date Apr. 30, 2014.

CAS Registry No. 1602976-93-1; STN Entry date May 12, 2014.

CAS Registry No. 2092061-72-6; STN Entry date Apr. 19, 2017.

CAS Registry No. 932140-24-4; STN Entry date Apr. 24, 2007.

CAS Registry No. 940271-83-0; STN Entry date Jun. 29, 2007.

CAS Registry No. 1866845-79-5; STN Entry date Feb. 15, 2016.

CAS Registry No. 1030737-98-4; STN Entry date Jun. 26, 2008.

CAS Registry No. 1147349-21-0; STN Entry date May 19, 2009.

CAS Registry No. 940805-31-2; STN Entry date Jul. 2, 2007.

Humphries, P.S. et al, "Facile synthesis of 4,5-disubstituted-3(2H)-pyridazinones", Tetrahedron Letters, 2009, 50, pp. 2682-2684.

Pattison, G. et al., "Polysubstituted Pyridazinones from Sequential Nucleophilic Substitution Reactions of Tetrafluoropyridazine", J. Org. Chem., 2009, 74, pp. 5533-5540.

Toure, B. B. et al., "The Role of the Acidity of N-Heteroaryl Sulfonamides as Inhibitors of Bcl-2 Family Protein-Protein Interactions", ACS Med. Chem. Lett., 2013, vol. 4, No. 2, pp. 186-190.

Wroblowski, B. et al, "The Discovery of a Selective, Small Molecule Agonist for the Mas-Related Gene X1 Receptor", J. Med. Chem., 2009, 52, pp. 818-825.

* cited by examiner

| Structure | NMR | MS |
|---|---|---|
| 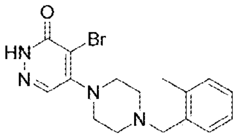 | 1H NMR (300 MHz, Methanol-d4) chemical shifts 7.79 (s, 1 H), 7.29 - 7.26 (m, 1 H), 7.20 - 7.13 (m, 3H), 3.58 (s, 2 H), 3.52 - 3.48 (m, 4H), 2.66 - 2.63 (m, 4H), 2.42 (s, 3H). | 363 |
| 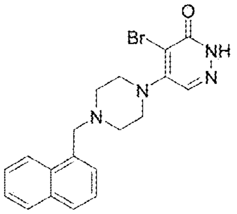 | | |
| 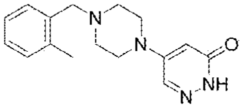 | 1H NMR (300 MHz, Methanol-d4) chemical shifts 7.97 (d, J = 2.7 Hz, 1H), 7.30-7.08 (m, 4H), 5.87 (d, J = 2.7 Hz, 1H), 3.54 (s, 2H), 3.42 (t, J = 5.2 Hz, 4H), 2.62-2.52 (m, 4H), 2.40 (s, 3H) | 285 |
| 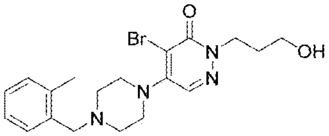 | 1H NMR (300 MHz, Methanol-d4) chemical shifts 7.79 (s, 1 H), 7.26-7.08 (m, 4H), 4.25 (t, J = 7.1 Hz, 2H), 3.64-3.53 (m, 4H), 3.46 (t, J = 4.9 Hz, 4H), 2.62 (t, J = 4.8 Hz, 4H), 2.40 (s, 3H), 1.98 (p, J = 6.7 Hz, 2H) | 421 |
| 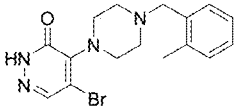 | 1H NMR (400 MHz, DMSO-d6) chemical shifts 12.88 (s, 1H), 7.90-7.81 (m, 1H), 7.34-7.15 (m, 4 H), 3.51-3.21 (m, 6H), 2.50-2.12 (m, 7H) | 365 |
| 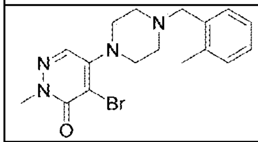 | 1H NMR (300 MHz, DMSO-d6) chemical shifts 7.77 (s, 1H), 7.27-7.07 (m, 4H), 3.61 (s, 3H), 3.47 (s, 2H), 3.35-3.30 (m, 4 H), 2.50-2.48 (m, 4 H), 2.32 (s, 3H) | 377 |
| 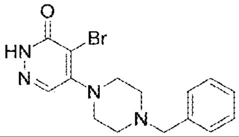 | 1H NMR (400 MHz, DMSO-d6) chemical shifts 12.88 (s, 1H), 7.74 (s, 1H), 7.37 -7.20 (m, 5H), 3.51 (s, 2H), 3.36 - 3.31 (m, 4H), 2.05 - 2.49 (m, 4H) | 349 |
| 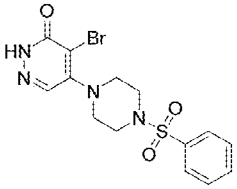 | 1H NMR (400 MHz, DMSO-d6) chemical shifts 12.94 (s, 1H), 7.80 -7.62 (m, 6H), 3.40 (t, J = 4.9 Hz, 4H), 3.00 (t, J = 4.8 Hz, 4H). | 399 |

Figure 1

| | | |
|---|---|---|
| 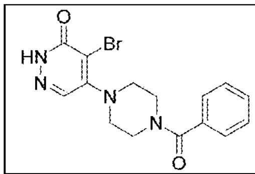 | 1H NMR (400 MHz, DMSO-d6) chemical shifts 12.94 (s, 1H), 7.76 (s, 1H), 7.49 -7.38 (m, 5H), 3.73- 3.40 (m, 8H). | 365 |
| 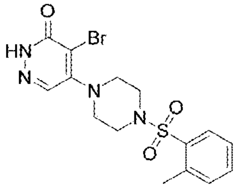 | 1H NMR (400 MHz, DMSO-d6) chemical shifts 12.95 (s, 1H), 7.85 -7.78 (m, 1H), 7.74 (s, 1H), 7.64 -7.55 (m, 1H), 7.50 -7.39 (m, 2H), 3.39 (t, J = 4.8 Hz, 4H), 3.16 (t, J = 4.7 Hz, 4H), 2.58 (s, 3H). | 415 |
| 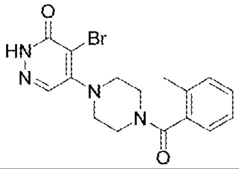 | 1H NMR (400 MHz, DMSO-d6) chemical shifts 12.94 (s, 1H), 7.76 (s, 1H), 7.35 -7.16 (m, 4H), 3.77 (t, J = 5.0 Hz, 2H), 3.43 (t, J = 5.1 Hz, 2H), 3.25 (m, 4H), 2.22 (s, 3H). | 377 |
| 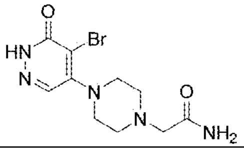 | 1H NMR (400 MHz, DMSO-d6) chemical shifts 12.86 (s, 1H), 7.75 (s, 1H), 7.22 (s, 1H), 7.11 (s, 1H), 3.41 - 3.39 (m, 4H), 2.91 (s, 2H), 2.55 (t, J = 4.8 Hz, 4H). | 316 |
| 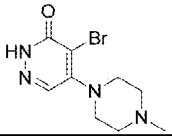 | 1H NMR (400 MHz, DMSO-d6) chemical shifts 12.84 (s, 1H), 7.74 (s, 1H), 3.34 (t, J = 4.9 Hz, 4H), 2.41 (t, J = 4.8 Hz, 4H), 2.20 (s, 3H). | 275 |
| 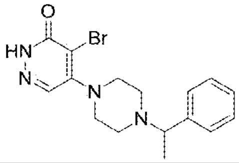 | 1H NMR (400 MHz, DMSO-d6) chemical shifts 12.85 (s, 1H), 7.72 (s, 1H), 7.37 - 7.18 (m, 5H), 3.45 (q, J = 6.7 Hz, 1H), 3.32 (p, J = 2.9 Hz, 4H), 2.56 - 2.48 (m, 2H), 2.41 (dt, J = 10.8, 4.8 Hz, 2H), 1.30 (d, J = 6.7 Hz, 3H). | 365 |
| 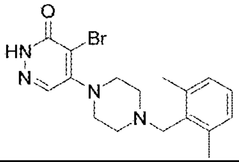 | 1H NMR (400 MHz, DMSO-d6) chemical shifts 12.86 (s, 1H), 7.73 (s, 1H), 7.08 - 6.94 (m, 3H), 3.49 (s, 2H), 3.28 (br, 4H), 2.49 (br, 4H), 2.34 (s, 6H). | 377 |
| 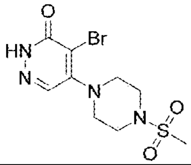 | 1H NMR (400 MHz, DMSO-d6) chemical shifts 13.00 (s, 1H), 7.80 (s, 1H), 3.45 (dd, J = 6.1, 3.6 Hz, 4H), 3.25 (dd, J = 6.1, 3.6 Hz, 4H), 2.95 (s, 3H). | 339 |
| 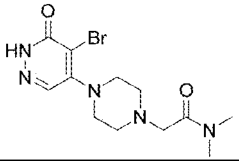 | 1H NMR (300 MHz, DMSO-d6) chemical shifts 12.89 (s, 1H), 7.78 (s, 1H), 3.37 (t, J = 4.8 Hz, 4H), 3.21 (s, 2H), 3.03 (s, 3H), 2.82 (s, 3H), 2.59 (t, J = 4.8 Hz, 4H). | 344 |

Figure 2

| | | |
|---|---|---|
| 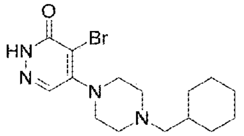 | 1H NMR (300 MHz, DMSO-d6) chemical shifts 12.88 (s, 1H), 7.77 (s, 1H), 3.41 - 3.31 (m, 4H), 2.45 (t, J = 4.9 Hz, 4H), 2.13 (d, J = 7.2 Hz, 2H), 1.70 (dd, J = 27.1, 7.8 Hz, 5H), 1.51 (ddd, J = 11.1, 7.6, 3.8 Hz, 1H), 1.32 - 1.08 (m, 3H), 0.85 (q, J = 11.5 Hz, 2H). | 357 |
| 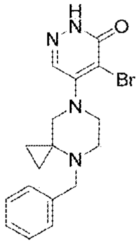 | 1H NMR (400 MHz, DMSO-d6)chemical shifts 12.85 (s, 1H), 7.77 (s, 1H), 7.34 - 7.17 (m, 5H), 3.85 (s, 2H), 3.41 (t, J = 4.8 Hz, 2H), 3.31 (t, J = 4.8 Hz, 2H), 2.79 (t, J = 4.8 Hz, 2H), 0.64 (d, J = 6.9 Hz, 4H). | 375 |
| 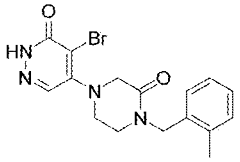 | 1H NMR (400 MHz, DMSO-d6)chemical shifts 12.95 (s, 1H), 7.77 (s, 1H), 7.22 - 7.08 (m, 4H), 4.58 (s, 2H), 4.15 (s, 2H), 3.68 (t, J = 5.3 Hz, 2H), 3.29 (d, J = 3.2 Hz, 2H), 2.23 (s, 3H). | 377 |
| 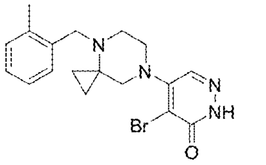 | 1H NMR (400 MHz, DMSO-d6)chemical shifts 12.85 (s, 1H), 7.78 (s, 1H), 7.27 - 7.19 (m, 1H), 7.16 - 7.08 (m, 3H), 3.84 (s, 2H), 3.43 (t, J = 4.8 Hz, 2H), 3.31 (t, J = 4.8 Hz, 2H), 2.78 (t, J = 4.9 Hz, 2H), 2.26 (s, 3H), 0.64 (d, J = 7.4 Hz, 4H). | 389 |
| 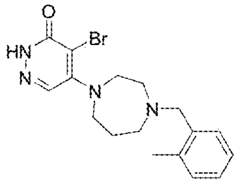 | 1H NMR (400 MHz, DMSO-d6) chemical shifts 12.61 (s, 1H), 7.69 (s, 1H), 7.23 - 7.16 (m, 1H), 7.18 - 7.05 (m, 3H), 3.73 - 3.63 (m, 4H), 3.54 (s, 2H), 2.70 (t, J = 4.9 Hz, 2H), 2.59 (t, J = 5.4 Hz, 2H), 2.26 (s, 3H), 1.82 (p, J = 5.5 Hz, 2H). | 379 |
| 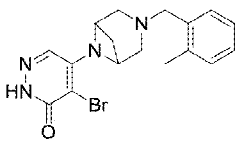 | 1H NMR (400 MHz, DMSO-d6) chemical shifts 12.53 (s, 1H), 7.45 (s, 1H), 7.08 (p, J = 7.9, 7.5 Hz, 4H), 3.57 (s, 2H), 3.28 (s, 2H), 2.98 (d, J = 10.8 Hz, 2H), 2.74 - 2.66 (m, 2H), 2.62 (d, J = 6.7 Hz, 1H), 2.08 (s, 3H), 1.68 (d, J = 8.0 Hz, 1H). | 377 |
| 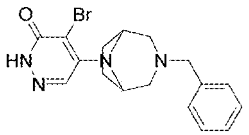 | 1H NMR (300 MHz, DMSO-d6) chemical shifts 12.67 (s, 1H), 7.78 (s, 1H), 7.41 - 7.19 (m, 5H), 4.77 (d, J = 3.7 Hz, 2H), 3.49 (s, 2H), 2.72 - 2.61 (m, 2H), 2.32 (d, J = 10.8 Hz, 2H), 2.01 - 1.77 (m, 4H). | 377 |
| 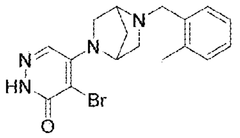 | 1H NMR (300 MHz, DMSO-d6) chemical shifts 12.53 (s, 1H), 7.64 (s, 1H), 7.33 - 7.24 (m, 1H), 7.13 (d, J = 3.1 Hz, 3H), 4.95 - 4.88 (m, 1H), 3.99 - 3.88 (m, 1H), 3.75 - 3.50 (m, 4H), 2.93 - 2.83 (m, 1H), 2.67 (d, J = 9.9 Hz, | 375 |

Figure 3

| | | |
|---|---|---|
| | 1H), 2.29 (s, 3H), 1.99 (d, J = 9.5 Hz, 1H), 1.78 (d, J = 8.8 Hz, 1H). | |
| 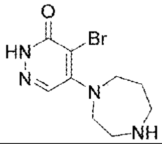 | 1H NMR (400 MHz, Methanol-d4) chemical shifts 7.79 (s, 1H), 3.86 - 3.76 (m, 4H), 3.11 - 3.03 (m, 2H), 2.97 - 2.89 (m, 2H), 2.04 - 1.93 (m, 2H). | 273 |
| 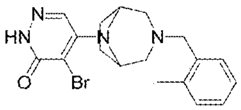 | 1H NMR (300 MHz, DMSO-d6) chemical shifts 12.67 (s, 1H), 7.79 (s, 1H), 7.25 - 7.06 (m, 4H), 4.77 (s, 2H), 3.43 (s, 2H), 2.66 - 2.55 (m, 2H), 2.36 (s, 5H), 1.89 - 1.73 (m, 4H). | 389 |
| 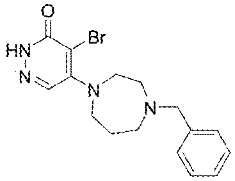 | 1H NMR (400 MHz, DMSO-d6) chemical shifts 12.62 (s, 1H), 7.71 (s, 1H), 7.34 - 7.18 (m, 5H), 3.73 - 3.64 (m, 4H), 3.59 (s, 2H), 2.73 - 2.66 (m, 2H), 2.59 (t, J = 5.4 Hz, 2H), 1.84 (p, J = 5.7 Hz, 2H). | 363 |
| 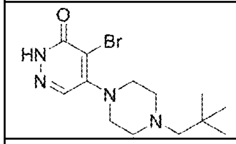 | 1H NMR (400 MHz, DMSO-d6) chemical shifts 12.87 (s, 1H), 7.74 (s, 1H), 3.33 (t, J = 4.7 Hz, 4H), 2.57 (t, J = 4.8 Hz, 4H), 2.08 (s, 2H), 0.85 (s, 9H). | 331 |
| 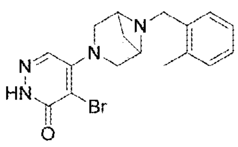 | 1H NMR (400 MHz, DMSO-d6) chemical shifts 12.64 (s, 1H), 7.91 (s, 1H), 7.36 - 7.29 (m, 1H), 7.11 (dd, J = 4.3, 3.0 Hz, 3H), 4.06 (d, J = 12.2 Hz, 2H), 3.86 (d, J = 12.1 Hz, 2H), 3.56 (d, J = 4.8 Hz, 3H), 3.28 (s, 1H), 2.27 (s, 3H), 1.59 (d, J = 8.4 Hz, 1H). | 375 |
| 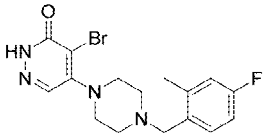 | 1H NMR (300 MHz, Methanol-d4) chemical shifts 7.78 (s, 1H), 7.26 (dd, J = 8.4, 6.0 Hz, 1H), 6.98 - 6.79 (m, 2H), 3.57 - 3.43 (m, 6H), 2.66 - 2.56 (m, 4H), 2.41 (s, 3H). | 381 |
| 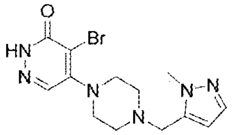 | 1H NMR (300 MHz, DMSO-d6) chemical shifts 12.90 (s, 1H), 7.77 (s, 1H), 7.32 (d, J = 1.8 Hz, 1H), 6.17 (d, J = 1.8 Hz, 1H), 3.80 (s, 3H), 3.59 (s, 2H), 3.34 (m, 4H), 2.51 - 2.48 (m, 4H). | 355 |
| 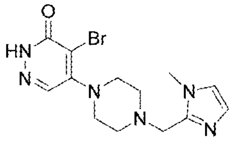 | 1H NMR (300 MHz, DMSO-d6) chemical shifts 12.89 (s, 1H), 7.76 (s, 1H), 7.10 (d, J = 1.2 Hz, 1H), 6.77 (d, J = 1.2 Hz, 1H), 3.67 (s, 3H), 3.59 (s, 2H), 3.40 - 3.26 (m, 4H), 2.51 - 2.48 (m, 4H). | 355 |
| 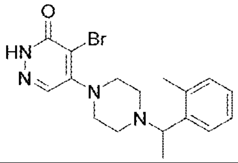 | 1H NMR (400 MHz, DMSO-d6) chemical shifts 12.87 (s, 1H), 7.73 (s, 1H), 7.36 (d, J = 7.4 Hz, 1H), 7.20 - 7.05 (m, 3H), 3.62 (q, J = 6.6 Hz, 1H), 3.40 - 3.23 (m, 4H), 2.56 (ddd, J = 10.2, 6.5, 3.0 Hz, 2H), 2.41 (ddd, J = | 377 |

| | | |
|---|---|---|
| | 10.6, 6.4, 2.9 Hz, 2H), 2.32 (s, 3H), 1.23 (d, J = 6.6 Hz, 3H). | |
| 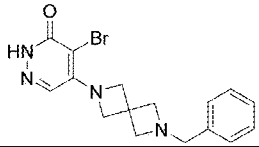 | 1H NMR (300 MHz, DMSO-d6) chemical shifts 12.45 (s, 1H), 7.36 - 7.17 (m, 6H), 4.43 (br, 4H), 3.52 (s, 2H), 3.32 (br, 4H). | 361 |
| 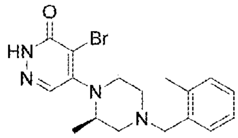 | 1H NMR (300 MHz, DMSO-d6) chemical shifts 12.92 (s, 1H), 7.78 (s, 1H), 7.29 - 7.08 (m, 4H), 4.06 (dd, J = 7.4, 4.1 Hz, 1H), 3.53 - 3.27 (m, 3H), 3.20 (dt, J = 12.7, 3.6 Hz, 1H), 2.66 (dt, J = 11.0, 3.4 Hz, 1H), 2.36 (s, 4H), 2.25 (td, J = 10.5, 3.0 Hz, 1H), 1.14 (d, J = 6.4 Hz, 3H). | 379 |
| 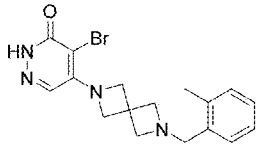 | 1H NMR (300 MHz, DMSO-d6) chemical shifts 12.45 (s, 1H), 7.30 (s, 1H), 7.26 - 7.06 (m, 4H), 4.44 (br, 4H), 3.49 (s, 2H), 3.32 (br, 4H), 2.25 (s, 3H). | 375 |
| 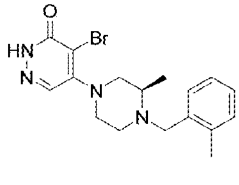 | 1H NMR (300 MHz, DMSO-d6) chemical shifts 12.87 (s, 1H), 7.74 (s, 1H), 7.26 (dd, J = 6.9, 2.5 Hz, 1H), 7.19 - 7.06 (m, 3H), 4.02 (d, J = 13.1 Hz, 1H), 3.57 (d, J = 11.5 Hz, 1H), 3.47 (d, J = 12.3 Hz, 1H), 3.10 (d, J = 13.1 Hz, 2H), 2.97 (dd, J = 12.2, 8.3 Hz, 1H), 2.61 (t, J = 10.9 Hz, 2H), 2.34 (s, 3H), 2.26 - 2.13 (m, 1H), 1.16 (d, J = 6.2 Hz, 3H). | 377 |
| 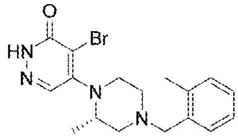 | 1H NMR (300 MHz, DMSO-d6) chemical shifts 12.91 (s, 1H), 7.77 (s, 1H), 7.29 - 7.08 (m, 4H), 4.05 (d, J = 3.2 Hz, 0H), 4.04 (s, 1H), 3.42 (dd, J = 13.0, 2.7 Hz, 3H), 3.30 (s, 1H), 3.20 (d, J = 12.6 Hz, 1H), 2.66 (d, J = 11.3 Hz, 1H), 2.42 (dd, J = 11.1, 3.4 Hz, 1H), 2.36 (s, 3H), 2.29 - 2.19 (m, 1H), 1.14 (d, J = 6.5 Hz, 3H). | 377 |
| 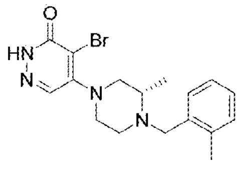 | 1H NMR (300 MHz, DMSO-d6) chemical shifts 12.52 (s, 1H), 7.74 (s, 1H), 7.31 - 7.21 (m, 1H), 7.19 - 7.06 (m, 3H), 4.02 (d, J = 13.1 Hz, 1H), 3.57 (d, J = 12.0 Hz, 1H), 3.47 (d, J = 12.5 Hz, 1H), 3.15 - 3.04 (m, 2H), 3.09 - 2.90 (m, 1H), 2.68 - 2.52 (m, 2H), 2.34 (s, 3H), 2.26 - 2.10 (m, 1H), 1.16 (d, J = 6.2 Hz, 3H). | 377 |
| 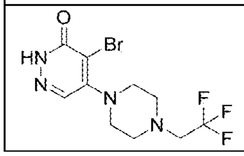 | 1H NMR (300 MHz, DMSO-d6) chemical shifts 12.92 (s, 1H), 7.76 (s, 1H), 3.35 (t, J = 4.9 Hz, 4H), 3.25 (q, J = 10.2 Hz, 2H), 2.74 (t, J = 4.8 Hz, 4H). | 341 |

Figure 5

| | | |
|---|---|---|
| 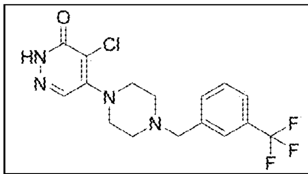 | 1H NMR (300 MHz, DMSO-d6) chemical shifts 12.92 (s, 1H), 7.84 (s, 1H), 7.66-7.55 (m, 4H), 3.62 (s, 2H), 3.38 (t, 4H) | 373.28 |
| 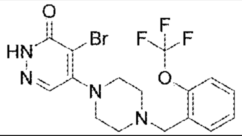 | 1H NMR (300 MHz, DMSO-d6) chemical shifts 12.89 (s, 1H), 7.75(s, 1H), 7.59-7.57(m, 1H), 7.44-7.33(m, 3H), 3.59 (s, 2H), | 435.2 |
| 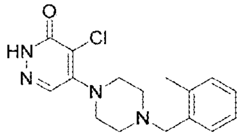 | 1H NMR (300 MHz, DMSO-d6) chemical shifts 12.91 (s, 1H), 7.84 (s, 1H), 7.24-7.10 (m, 4H), 3.47 (s, 2H), 3.35 (t, 4H), | 319.25 |
| 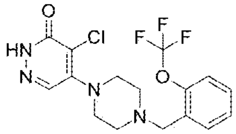 | 1H NMR (300 MHz, DMSO-d6) chemical shifts 12.92 (s, 1H), 7.84 (s, 1H), 7.59-7.57 (m, 1H), 7.42-7.33 (m, 3H), | 389.28 |
| 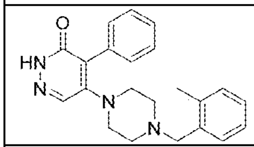 | 1H NMR (300 MHz, DMSO-d6) chemical shifts 12.52(s, 1H), 7.88 (s, 1H), 7.40-7.06 (m, 9 H), 3.35 (s, 2H), 2.92 (t, 4H) | 361.36 |
| 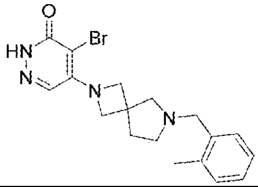 | | 391.2 |
| 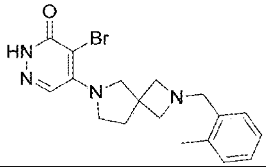 | 1H NMR (300 MHz, DMSO-d6) chemical shifts 12.91 (s, 1H), 7.84 (s, 1H), 7.24-7.10 (m, 4H), 3.91 (s, 2H), | 391.2 |
| 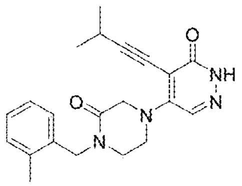 | 1H NMR (300 MHz, DMSO-d6) chemical shifts 8.65 (s, 1H), 7.16 (dd, J = 7.5, 3.5 Hz, 4H), 6.93 (s, 1H), 4.61 (s, 2H), 4.33 (s, 2H), 3.85 (t, J = 5.3 Hz, 2H), 3.41 - 3.32 (m, 2H), 3.08 (p, J = 6.9 Hz, 1H), 2.23 (s, 3H), 1.29 (d, J = 6.8 Hz, 6H). | 365 |
| 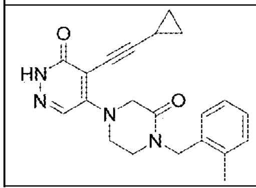 | 1H NMR (300 MHz, DMSO-d6) chemical shifts 8.61 (s, 1H), 7.16 (d, J = 8.0 Hz, 4H), 6.95 (s, 1H), 4.60 (s, 2H), 4.30 (s, 2H), 3.82 (s, 2H), 3.35(s,2H), 2.22 (s, 3H), 2.12 (s, 1H), 1.08 - 0.93 (m, 4H). | 363 |

Figure 6

| | | |
|---|---|---|
| 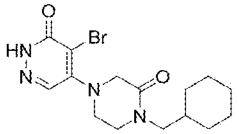 | 1H NMR (400 MHz, DMSO-d6) chemical shifts 12.91 (s, 1H), 7.74 (s, 1H), 4.04 (s, 2H), 3.66 (t, J = 5.3 Hz, 2H), 3.41 (t, J = 5.3 Hz, 2H), 3.18 (d, J = 7.3 Hz, 2H), 1.67 - 1.54 (m, 6H), 1.15 (p, J = 13.8 Hz, 3H), 0.90 (t, J = 11.7 Hz, 2H). | 371 |
| 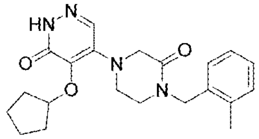 | 1H NMR (300 MHz, DMSO-d6) chemical shifts 12.44 (s, 1H), 8.00 (s, 1H), 7.18 (d, J = 15.7 Hz, 4H), 5.83 (s, 1H), 5.54 (s, 1H), 4.69 (d, J = 15.3 Hz, 1H), 4.50 (d, J = 15.4 Hz, 1H), 4.26 (s, 1H), 3.58 (s, 1H), 3.51 (d, J = 15.1 Hz, 1H), 3.42 (s, 4H), 2.25 (s, 3H), 1.87 - 1.37 (m, 8H). | 383 |
| 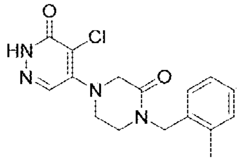 | 1H NMR (300 MHz, DMSO-d6) chemical shifts 7.85 (s, 1H), 7.14 (dq, J = 13.8, 3.9, 3.3 Hz, 4H), 4.57 (s, 2H), 4.16 (s, 2H), 3.68 (t, J = 5.2 Hz, 2H), 3.27 (d, J = 10.2 Hz, 2H), 2.22 (s, 3H). | 333 |
| 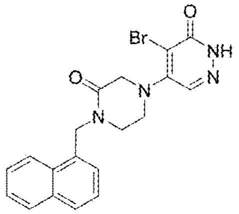 | 1H NMR (300 MHz, DMSO-d6) chemical shifts 12.94 (s, 1H), 8.17 - 8.08 (m, 1H), 8.02 - 7.85 (m, 2H), 7.75 (s, 1H), 7.63 - 7.40 (m, 4H), 5.07 (s, 2H), 4.20 (s, 2H), 3.65 (t, J = 5.3 Hz, 2H), 3.34 (s, 1H), 3.30 (d, J = 2.1 Hz, 1H). | 413 |
| 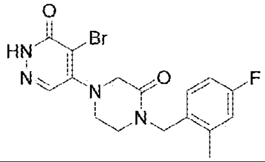 | 1H NMR (300 MHz, DMSO-d6) chemical shifts 12.95 (s, 1H), 7.77 (s, 1H), 7.18 (dd, J = 8.5, 6.0 Hz, 1H), 7.12 - 6.94 (m, 2H), 4.57 (s, 2H), 4.16 (s, 2H), 3.68 (s, 2H), 3.29 (s, 2H), 2.26 (s, 3H). | 395 |
| 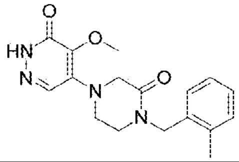 | 1H NMR (300 MHz, DMSO-d6) chemical shifts 7.81 (s, 1H), 7.24 - 7.09 (m, 4H), 4.59 (s, 2H), 4.11 (s, 2H), 3.84 (s, 3H), 3.64 (t, J = 5.4 Hz, 2H), 3.25 (t, J = 5.4 Hz, 2H), 3.09 (s, 0H), 2.25 (s, 3H). | 329 |
| 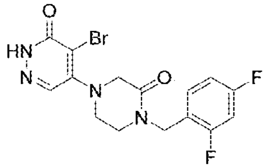 | 1H NMR (300 MHz, DMSO-d6) chemical shifts 12.94 (s, 1H), 7.76 (s, 1H), 7.38 (td, J = 8.6, 6.7 Hz, 1H), 7.26 (td, J = 10.1, 2.6 Hz, 1H), 7.09 (td, J = 8.5, 2.6 Hz, 1H), 4.59 (s, 2H), 4.13 (s, 2H), 3.69 (t, J = 5.2 Hz, 2H), 3.42 (t, J = 5.3 Hz, 2H). | 399 |
| 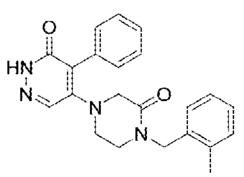 | 1H NMR (400 MHz, Methanol-d4) chemical shifts 8.01 (s, 1H), 7.45 - 7.31 (m, 5H), 7.24 - 7.15 (m, 3H), 7.11 (d, J = 6.6 Hz, 1H), 4.63 (s, 2H), 3.79 (s, 2H), 3.40 (t, J = 5.4 Hz, 2H), 3.08 (t, J = 5.5 Hz, 2H), 2.27 (s, 3H). | 375 |

Figure 7

| | | |
|---|---|---|
| 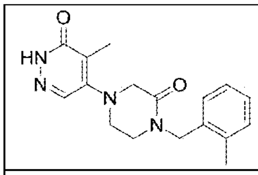 | 1H NMR (300 MHz, DMSO-d6) chemical shifts 12.67 (s, 1H), 7.78 (s, 1H), 7.25 - 7.10 (m, 4H), 4.61 (s, 2H), 3.93 (s, 2H), 3.43 (t, J = 5.3 Hz, 2H), 3.26 (t, J = 5.4 Hz, 2H), 2.26 (s, 3H), 1.96 (s, 3H). | 313 |
| 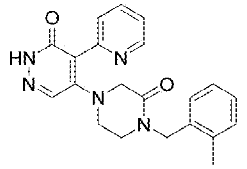 | 1H NMR (300 MHz, DMSO-d6) chemical shifts 12.56 (s, 1H), 8.59 (d, J = 4.4 Hz, 1H), 8.00 (s, 1H), 7.81 (td, J = 7.7, 1.9 Hz, 1H), 7.53 (d, J = 7.9 Hz, 1H), 7.36 - 7.25 (m, 1H), 7.21 - 7.10 (m, 3H), 7.07 (d, J = 4.5 Hz, 1H), 4.49 (s, 2H), 3.54 (s, 2H), 3.42 (t, J = 5.3 Hz, 2H), 3.11 (t, J = 5.3 Hz, 2H), 2.20 (s, 3H). | 376 |
| 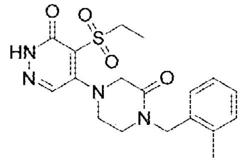 | 1H NMR (300 MHz, DMSO-d6) chemical shifts 12.70 (s, 1H), 8.12 (s, 1H), 7.19 (q, J = 3.7 Hz, 4H), 4.57 (s, 2H), 4.34 (s, 2H), 3.95 (d, J = 5.6 Hz, 2H), 3.58 (q, J = 7.4 Hz, 2H), 3.33 (d, 2H), 2.25 (s, 3H), 1.07 (t, J = 7.3 Hz, 3H). | 391 |
| 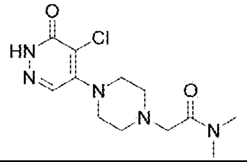 | 1H NMR (300 MHz, DMSO-d6) chemical shifts 12.93 (s, 1H), 7.87 (s, 1H), 3.38 (t, J = 4.8 Hz, 4H), 3.21 (s, 2H), 3.02 (s, 3H), 2.82 (s, 3H), 2.57 (t, J = 4.8 Hz, 4H). | 300 |
| 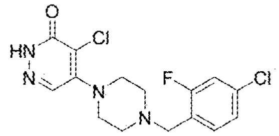 | 1H NMR (400 MHz, Methanol-d4) chemical shifts 7.89 (s, 1H), 7.48 (t, J = 8.2 Hz, 1H), 7.23 (dt, J = 9.9, 2.3 Hz, 2H), 3.67 (s, 2H), 3.53 (t, J = 4.9 Hz, 4H), 2.66 (t, J = 4.9 Hz, 4H). | 357 |
| 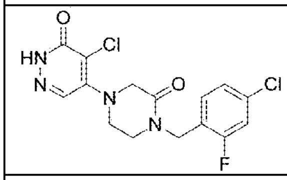 | 1H NMR (300 MHz, DMSO-d6) chemical shifts 12.92 (s, 1H), 7.87 (s, 1H), 7.46 (dd, J = 10.0, 2.0 Hz, 1H), 7.43 - 7.25 (m, 2H), 4.61 (s, 2H), 4.16 (s, 2H), 3.71 (t, J = 5.2 Hz, 2H), 3.42 (t, J = 5.3 Hz, 2H). | 371 |
| 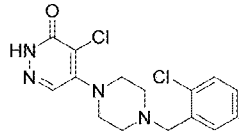 | 1H NMR (400 MHz, DMSO-d6) chemical shifts 12.95 (s, 1H), 7.86 (s, 1H), 7.51 (dd, J = 7.4, 2.0 Hz, 1H), 7.45 (dd, J = 7.6, 1.7 Hz, 1H), 7.39 - 7.26 (m, 2H), 3.63 (s, 2H), 3.39 (t, J = 4.8 Hz, 4H), 2.55 (t, J = 4.8 Hz, 4H). | 339 |
| 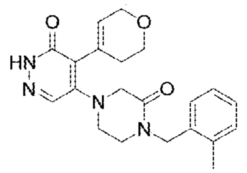 | 1H NMR (400 MHz, Methanol-d4) chemical shifts 7.91 (s, 1H), 7.21 (dd, J = 10.1, 3.7 Hz, 4H), 5.80 (s, 1H), 4.73 (s, 2H), 4.24 (q, J = 2.7 Hz, 2H), 4.13 (s, 2H), 3.90 (t, J = 5.4 Hz, 2H), 3.67 (t, J = 5.4 Hz, 2H), 3.34 (d, J = 3.3 Hz, 2H), 2.42 (d, J = 2.1 Hz, 2H), 2.32 (s, 3H). | 381 |

Figure 8

| | | |
|---|---|---|
| 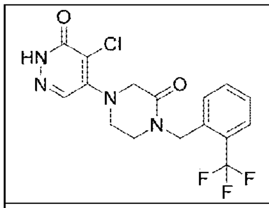 | 1H NMR (400 MHz, DMSO-d6) chemical shifts 12.98 (s, 1H), 7.91 (s, 1H), 7.78 (d, J = 7.8 Hz, 1H), 7.69 (t, J = 7.6 Hz, 1H), 7.52 (t, J = 7.6 Hz, 1H), 7.41 (d, J = 7.8 Hz, 1H), 4.77 (s, 2H), 4.25 (s, 2H), 3.77 (d, J = 5.6 Hz, 2H), 3.43 (d, J = 5.5 Hz, 2H). | 387 |
| 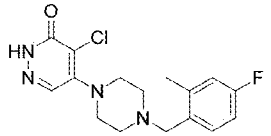 | 1H NMR (400 MHz, Chloroform-d) chemical shifts 11.73 (s, 1H), 7.67 (s, 1H), 7.21 (dd, J = 8.3, 6.1 Hz, 1H), 6.95 - 6.81 (m, 2H), 3.53 - 3.42 (m, 6H), 2.60 (t, J = 4.7 Hz, 4H), 2.40 (s, 3H). | 337 |
| 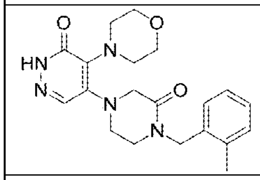 | 1H NMR (300 MHz, DMSO-d6) chemical shifts 12.49 (s, 1H), 7.72 (s, 1H), 7.24 - 7.07 (m, 4H), 4.60 (s, 2H), 4.06 (s, 2H), 3.60 (t, J = 4.8 Hz, 6H), 3.31 - 3.13 (m, 5H), 2.25 (s, 3H), 1.24 (s, 1H). | 384 |
| 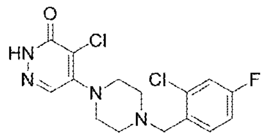 | 1H NMR (300 MHz, DMSO-d6) chemical shifts 12.94 (s, 1H), 7.86 (s, 1H), 7.55 (dd, J = 8.6, 6.4 Hz, 1H), 7.44 (dd, J = 8.9, 2.7 Hz, 1H), 7.23 (td, J = 8.5, 2.7 Hz, 1H), 3.60 (s, 2H), 3.39 (t, J = 4.8 Hz, 4H), 2.55 (t, J = 4.8 Hz, 4H). | 357 |
| 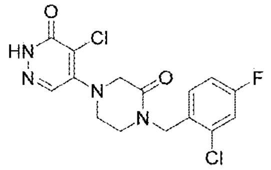 | 1H NMR (400 MHz, DMSO-d6) chemical shifts 12.99 (s, 1H), 7.89 (s, 1H), 7.50 (dd, J = 8.8, 2.6 Hz, 1H), 7.37 (dd, J = 8.6, 6.3 Hz, 1H), 7.24 (td, J = 8.5, 2.6 Hz, 1H), 4.64 (s, 2H), 4.20 (s, 2H), 3.74 (t, J = 5.3 Hz, 2H), 3.41 (t, J = 5.3 Hz, 2H). | 371 |
| 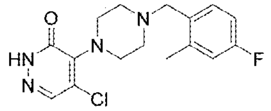 | 1H NMR (400 MHz, Chloroform-d) chemical shifts 10.62 (s, 1H), 7.61 (s, 1H), 7.23 (t, J = 7.2 Hz, 1H), 6.94 - 6.80 (m, 2H), 3.55 (t, J = 4.7 Hz, 4H), 3.48 (s, 2H), 2.56 (t, J = 4.8 Hz, 4H), 2.39 (s, 3H). | 337 |
| 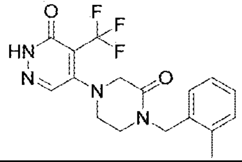 | 1H NMR (300 MHz, DMSO-d6) chemical shifts 12.70 (s, 1H), 8.02 (s, 1H), 7.23 - 7.11 (m, 4H), 4.58 (s, 2H), 4.11 (s, 2H), 3.78 (d, J = 5.7 Hz, 2H), 3.27 (s, 2H), 2.24 (s, 3H). | 367 |
| 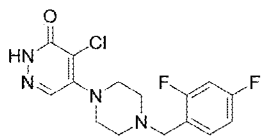 | 1H NMR (400 MHz, DMSO-d6) chemical shifts 12.94 (s, 1H), 7.85 (d, J = 1.3 Hz, 1H), 7.47 (q, J = 8.2 Hz, 1H), 7.23 (td, J = 10.2, 9.2, 2.4 Hz, 1H), 7.13 - 7.04 (m, 1H), 3.57 (s, 2H), 3.37 (t, J = 4.7 Hz, 4H), 2.49 (s, 4H). | 341 |

Figure 9

| | | |
|---|---|---|
| 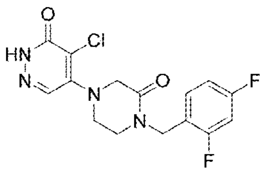 | 1H NMR (300 MHz, DMSO-d6) chemical shifts 12.99 (s, 1H), 7.87 (s, 1H), 7.40 (td, J = 8.6, 6.6 Hz, 1H), 7.28 (ddd, J = 10.5, 9.3, 2.6 Hz, 1H), 7.16 - 7.03 (m, 1H), 4.60 (s, 2H), 4.16 (s, 2H), 3.71 (t, J = 5.3 Hz, 2H), 3.42 (t, J = 5.3 Hz, 2H). | 355 |
| 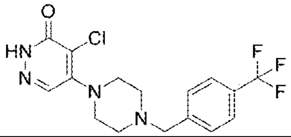 | 1H NMR (400 MHz, Methanol-d4) chemical shifts 7.90 (s, 1H), 7.70 - 7.56 (m, 4H), 3.69 (s, 2H), 3.58 - 3.51 (m, 4H), 2.65 (t, J = 4.9 Hz, 4H). | 373 |
| 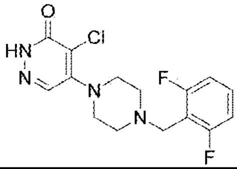 | 1H NMR (400 MHz, Methanol-d4) chemical shifts 7.87 (s, 1H), 7.40 (tt, J = 8.3, 6.5 Hz, 1H), 7.02 (t, J = 7.9 Hz, 2H), 3.78 (t, J = 1.6 Hz, 2H), 3.51 (t, J = 4.9 Hz, 4H), 2.69 (t, J = 4.8 Hz, 4H), 2.06 (s, 1H). | 341 |
| 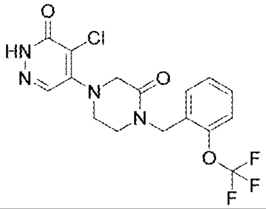 | 1H NMR (300 MHz, Methanol-d4) chemical shifts 7.91 (s, 1H), 7.51 - 7.32 (m, 4H), 4.80 (s, 2H), 4.30 (s, 2H), 3.83 (t, J = 5.3 Hz, 2H), 3.50 (t, J = 5.3 Hz, 2H). | 403 |
| 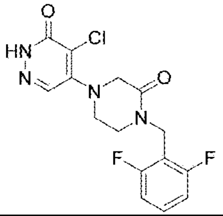 | 1H NMR (300 MHz, DMSO-d6) chemical shifts 12.98 (s, 1H), 7.85 (s, 1H), 7.53 - 7.37 (m, 1H), 7.14 (t, J = 8.0 Hz, 2H), 4.70 (s, 2H), 4.12 (s, 2H), 3.68 (t, J = 5.3 Hz, 2H), 3.38 (t, J = 5.3 Hz, 2H). | 355 |
| 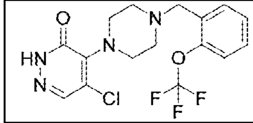 | 1H NMR (300 MHz, DMSO-d6) chemical shifts 12.86 (s, 1H), 7.72 (s, 1H), 7.59-7.56 (m, 1H), 7.42-7.33 (m, 3H), | 389.2 |
| 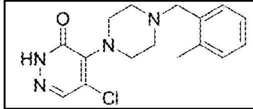 | 1H NMR (300 MHz, DMSO-d6) chemical shifts 12.85 (s, 1H), 7.72 (s, 1H), 7.23-7.24 (m, 1H), 7.11-7.15 (m, 3H), | 319.2 |
| 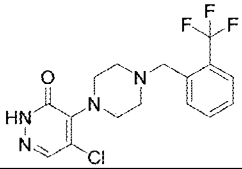 | 1H NMR (300 MHz, DMSO-d6) chemical shifts 12.87 (s, 1H), 7.84 (s, 1H), 7.80-7.82 (m, 1H), 7.64-7.72 (m, 3H) | 373.2 |
| 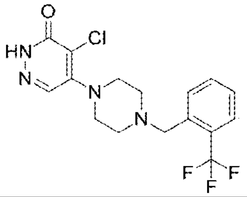 | 1H NMR (300 MHz, DMSO-d6) chemical shifts 12.92 (s, 1H), 7.85 (s, 1H), 7.78-7.80 (m, 1H), 7.65-7.69 (m, 2 H), | 373.2 |

Figure 10

| | | |
|---|---|---|
| 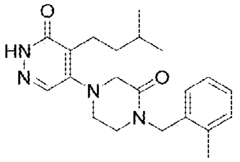 | 1H NMR (400 MHz, DMSO-d6) chemical shifts 12.70 (s, 1H), 7.81 (s, 1H), 7.24 ï¿½C 7.12 (m, 3H), 7.13 (d, J = 6.4 Hz, 1H), 4.61 (s, 2H), 3.85 (s, 2H), 3.38 (t, J = 5.3 Hz, 2H), 3.26 (dd, J = 6.2, 4.5 Hz, 2H), 2.46 ï¿½C 2.37 (m, 2H), 2.25 (s, 3H), 1.58 ï¿½C 1.45 (m, 1H), 1.39 (q, J = 7.1 Hz, 2H), 0.87 (d, J = 6.5 Hz, 6H). | 369 |
| 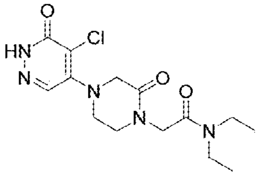 | 1H NMR (400 MHz, DMSO-d6) chemical shifts 12.97 (s, 1H), 7.88 (s, 1H), 4.23 (s, 2H), 4.11 (s, 2H), 3.72 (t, J = 5.4 Hz, 2H), 3.46 (t, J = 5.4 Hz, 2H), 3.28 (dd, J = 11.4, 7.0 Hz, 4H), 1.14 (t, J = 7.0 Hz, 3H), 1.02 (t, J = 7.1 Hz, 3H). | 342 |
| 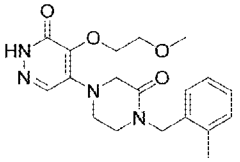 | 1H NMR (400 MHz, DMSO-d6) chemical shifts 12.71 (s, 1H), 7.89 (d, J = 58.6 Hz, 1H), 7.50 ï¿½C 6.91 (m, 4H), 4.58 (d, J = 11.7 Hz, 2H), 4.39 ï¿½C 4.21 (m, 2H), 4.15 (s, 1H), 4.03 (s, 1H), 3.74 ï¿½C 3.45 (m, 4H), 3.27 ï¿½C 3.10 (m, 5H), 2.26 (s, 3H). | 373 |
| 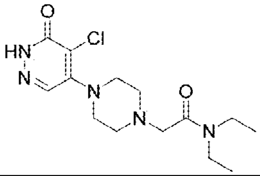 | 1H NMR (300 MHz, DMSO-d6) chemical shifts 12.93 (s, 1H), 7.87 (s, 1H), 3.39 (d, J = 9.9 Hz, 6H), 3.29 ï¿½C 3.16 (m, 4H), 2.57 (t, J = 4.8 Hz, 4H), 1.14 (t, J = 7.0 Hz, 3H), 1.02 (t, J = 7.0 Hz, 3H). | 328 |
| 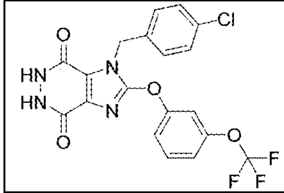 | 1H NMR (300 MHz, DMSO-d6) chemical shifts 11.87 (s, 1H), 11.22 (s, 1H), 7.62 (t, J = 8.3 Hz, 1H), 7.47 (d, J = 16.1 Hz, 6H), 7.35 (d, J = 8.5 Hz, 1H), 5.59 (s, 2H) | 454 |
| 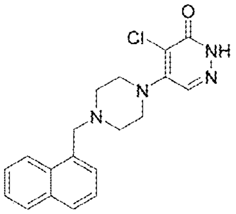 | 1H NMR (400 MHz, DMSO-d6) chemical shifts 12.93 (s, 1H), 8.34 ï¿½C 8.27 (m, 1H), 7.97 ï¿½C 7.89 (m, 1H), 7.93 ï¿½C 7.82 (m, 2H), 7.60 ï¿½C 7.48 (m, 2H), 7.53 ï¿½C 7.42 (m, 2H), 3.94 (s, 2H), 3.35 (t, J = 4.6 Hz, 3H), 2.57 (t, J = 4.8 Hz, 5H). | 355 |
| 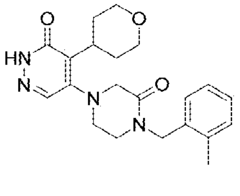 | 1H NMR (400 MHz, DMSO-d6) chemical shifts 12.73 (s, 1H), 7.85 (s, 1H), 7.26 ï¿½C 7.12 (m, 4H), 4.62 (s, 2H), 3.91 (dd, J = 11.1, 4.2 Hz, 2H), 3.82 (s, 2H), 3.35 ï¿½C 3.25 (m, 6H), 2.96 (t, J = 11.9 Hz, 1H), 2.56 (d, J = 4.6 Hz, 2H), 2.28 (s, 3H),1.30 (d, J = 11.8 Hz, 2H). | 383 |

Figure 11

| | | |
|---|---|---|
| 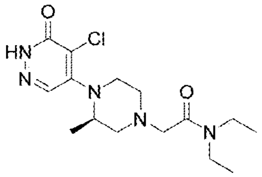 | 1H NMR (300 MHz, DMSO-d6) chemical shifts 12.93 (s, 1H), 7.87 (s, 1H), 4.06 (s, 1H), 3.57 - 3.33 (m, 3H), 3.31 - 3.11 (m, 2H), 3.10-3.07 (m, 3H), 2.76 (d, J = 11.3 Hz, 1H), 2.60 (d, J = 10.1 Hz, 1H), 2.48 - 2.38 (m, 1H), 2.28 (t, J = 9.7 Hz, 1H), 1.24 - 1.10 (m, 6H), 1.02 (t, J = 7.0 Hz, 3H). | 342 |
| 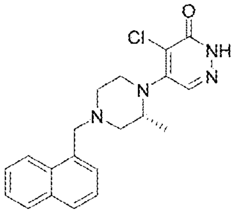 | 1H NMR (300 MHz, DMSO-d6) chemical shifts 12.93 (s, 1H), 8.40 - 8.30 (m, 1H), 7.98 - 7.80 (m, 3H), 7.54 (tt, J = 6.9, 5.1 Hz, 2H), 7.47 (q, J = 2.6, 2.1 Hz, 2H), 4.10 - 4.02 (m,1H), 3.99 - 3.81 (m, 2H), 3.38 (dd, J = 11.5, 8.6 Hz, 1H), 3.27 (d, J = 12.8 Hz, 1H), 2.75 (d, J = 11.3 Hz, 1H), 2.69 - 2.58 (m, 1H), 2.52 - 2.40 (m, 1H), 2.30 (dt, J = 11.1, 5.5 Hz, 1H), 1.14 (d, J = 6.5 Hz, 3H). | 369 |
| 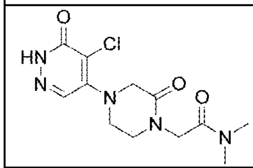 | 1H NMR (300 MHz, DMSO-d6) chemical shifts 7.86 (s, 1H), 4.21 (s, 2H), 4.09 (s, 2H), 3.70 (s, 2H), 3.41 (s, 2H), 2.94 (s, 3H), 2.81 (s, 3H). | 314 |
| 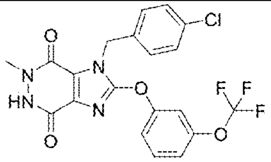 | 1H NMR (400 MHz, DMSO-d6) chemical shifts 11.46 (s, 1H), 7.63 (t, J = 8.3 Hz, 1H), 7.54 - 7.40 (m, 6H), 7.36 (ddt, J = 8.3, 2.3, 1.1 Hz, 1H), 5.63 (s, 2H), 3.59 (s, 3H). | 467 |
| 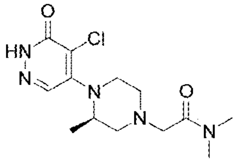 | 1H NMR (300 MHz, DMSO-d6) chemical shifts 12.37 (s, 1H), 7.86 (s, 1H), 4.04 (dd, J = 7.2, 4.0 Hz, 1H), 3.43 (ddd, J = 13.0, 10.3, 3.0 Hz, 1H), 3.28 (d, J = 12.9 Hz, 1H), 3.24 - 3.07 (m, 2H), 3.05 (s, 3H), 2.82 (s, 4H), 2.57 (dd, J = 10.8, 3.0 Hz, 1H), 2.45 (dd, J = 11.1, 3.5 Hz, 1H), 2.30 (td, J = 10.7, 3.3 Hz, 1H), 1.19 (d, J = 6.5 Hz, 3H). | 314 |
| 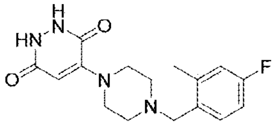 | 1H NMR (400 MHz, DMSO-d6) chemical shifts 11.65 (s, 1H), 10.31 (s, 1H), 7.26 (dd, J = 8.4, 6.2 Hz, 1H), 7.02 (dd, J = 10.1, 2.8 Hz, 1H), 6.95 (td, J = 8.6, 2.8 Hz, 1H), 5.98 (s, 1H), 3.57 (s, 2H),3.43 (t, J = 5.0 Hz, 4H) 2.45 (t, J = 5.0 Hz, 4H), 2.34 (s, 3H). | 319 |
| 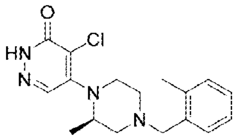 | 1H NMR (300 MHz, DMSO-d6) chemical shifts 12.93 (s, 1H), 7.86 (s, 1H), 7.29 - 7.08 (m, 4H), 4.07 (s, 1H), 3.52 - 3.35 (m, 2H), 3.27 (s, 1H),3.26-3.24(m,1H) 2.69 (d, J = 11.4 Hz, 1H), 2.57 (s, 1H), 2.39 (d, J = 3.5 Hz, 1H), 2.36 (s, 3H), 2.21 (td, J = 10.7, 3.2 Hz, 1H), 1.18 (d, J = 6.5 Hz, 3H). | 333 |

Figure 12

| | | |
|---|---|---|
| 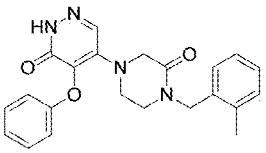 | 1H NMR (300 MHz, DMSO-d6) chemical shifts 12.72 (s, 1H), 7.97 (s, 1H), 7.36 - 7.24 (m, 2H), 7.22 - 7.07 (m, 3H), 7.09 - 6.97 (m, 2H), 6.94 - 6.84 (m, 2H), 4.50 (s, 2H), 4.13 (s, 2H), 3.68 (t, J = 5.3 Hz, 2H), 3.12 (t, J = 5.3 Hz, 2H), 2.18 (s, 3H). | 391 |
| 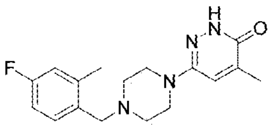 | 1H NMR (400 MHz, Chloroform-d) chemical shifts 10.43 (s, 1H), 7.23 (t, J = 7.2 Hz, 1H), 7.04 (q, J = 1.3 Hz, 1H), 6.94 - 6.80 (m, 2H), 3.48 (s, 2H), 3.25 (t, J = 4.9 Hz, 4H), 2.53 (t, J = 5.0 Hz, 4H), 2.38 (s, 3H), 2.22 (d, J = 1.3 Hz, 3H), 1.27 (s, 0H), 0.86 (d, J = 8.4 Hz, 0H). | 317 |
| 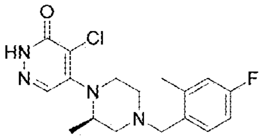 | 1H NMR (300 MHz, DMSO-d6) chemical shifts 12.93 (s, 1H), 7.85 (s, 1H), 7.26 (dd, J = 8.4, 6.2 Hz, 1H), 7.10 - 6.89 (m, 2H), 4.06 (d, J = 6.9 Hz, 1H), 3.45 - 3.31 (m, 4H), 2.67 (d, J = 11.3 Hz, 1H), 2.54 (s, 1H), 2.37 (s, 3H), 2.37 (d, J = 14.3 Hz, 1H), 2.20 (td, J = 10.8, 3.3 Hz, 1H), 1.17 (d, J = 6.5 Hz, 3H). | 351 |
| 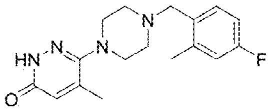 | 1H NMR (400 MHz, DMSO-d6) chemical shifts 11.99 (s, 1H), 7.39 (d, J = 1.5 Hz, 1H), 7.26 (dd, J = 8.4, 6.2 Hz, 1H), 7.02 (dd, J = 10.1, 2.7 Hz, 1H), 6.95 (td, J = 8.6, 2.8 Hz, 1H),3.43(s, 2H ),3.19 - 3.12 (m, 4H), 2.44 (t, J = 4.9 Hz, 4H), 2.34 (s, 3H), 2.01 (d, J = 1.2 Hz, 3H). | 317 |
| 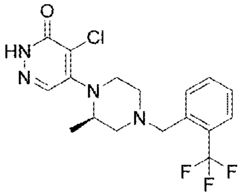 | 1H NMR (300 MHz, DMSO-d6) chemical shifts 12.94 (s, 1H), 7.90 - 7.63 (m, 4H), 7.49 (t, J = 7.6 Hz, 1H), 4.08 (d, J = 6.9 Hz, 1H), 3.64 (s, 2H), 3.48 (t, J = 10.2 Hz, 1H), 3.30 (s, 1H), 2.73 (d, J = 10.9 Hz, 1H), 2.57 (s, 1H), 2.41 (dd, J = 11.0, 3.4 Hz, 1H), 2.34 - 2.21 (m, 1H), 1.23 (d, J = 6.5 Hz, 3H). | 386 |
| 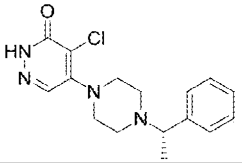 | 1H NMR (300 MHz, DMSO-d6) chemical shifts 12.90 (s, 1H), 7.81 (s, 1H), 7.35 - 7.20 (m, 5H), 3.45 (d, J = 6.8 Hz, 1H), 3.35 (s, 6H), 2.44 - 2.33 (m, 2H), 1.30 (d, J = 6.7 Hz, 3H). | 319 |
| 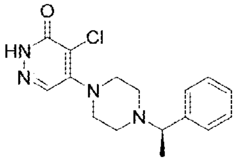 | 1H NMR (300 MHz, DMSO-d6) chemical shifts 12.89 (s, 1H), 7.81 (s, 1H), 7.38 - 7.17 (m, 5H), 3.45 (d, J = 6.7 Hz, 1H), 3.35 (s, 6H), 2.44 - 2.33 (m, 2H), 1.30 (d, J = 6.7 Hz, 3H). | 319 |

Figure 13

| | | |
|---|---|---|
| 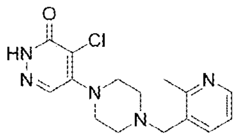 | 1H NMR (400 MHz, DMSO-d6) chemical shifts 12.93 (s, 1H), 8.35 (dd, J = 4.8, 1.8 Hz, 1H), 7.86 (s, 1H), 7.62 (dd, J = 7.6, 1.7 Hz, 1H), 7.19 (dd, J = 7.6, 4.8 Hz, 1H), 3.52 (s, 2H), 3.38 (t, J = 4.9 Hz, 4H), 2.52 (s, 4H), 2.50 (d, J = 2.0 Hz, 3H). | 320 |
| 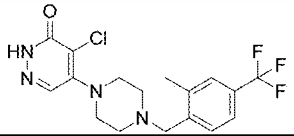 | 1H NMR (400 MHz, DMSO-d6) chemical shifts 12.94 (s, 1H), 7.86 (s, 1H), 7.53 (d, J = 13.0 Hz, 3H), 3.58 (s, 2H), 3.38 (t, J = 4.7 Hz, 4H), 2.53 (s, 4H), 2.42 (s, 3H). | 387 |
| 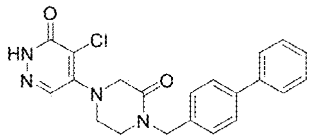 | 1H NMR (400 MHz, DMSO-d6) chemical shifts 12.99 (s, 1H), 7.89 (s, 1H), 7.70 ï¿½C 7.62 (m, 4H), 7.47 (t, J = 7.5 Hz, 2H), 7.41 ï¿½C 7.32 (m, 3H), 4.63 (s, 2H), 4.20 (s, 2H), 3.71 (t, J = 5.2 Hz, 2H), 3.42 (d, J = 5.4 Hz, 2H). | 395 |
| 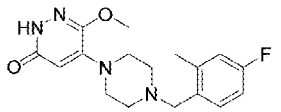 | 1H NMR (400 MHz, Methanol-d4) chemical shifts 7.54 (s, 1H), 7.14 ï¿½C 7.01 (m, 2H), 6.12 (s, 1H), 4.29 (s, 2H), 3.91 (s, 3H), 3.51-3.33 (m, 4H),3.32-3.27 (m, 4H), 2.50 (s, 3H). | 333 |
| 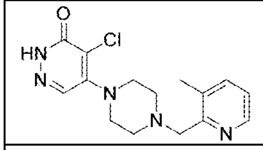 | 1H NMR (400 MHz, DMSO-d6) chemical shifts 12.94 (s, 1H), 7.86 (s, 1H), 7.53 (d, J = 13.0 Hz, 3H), 3.58 (s, 2H), 3.38 (t, J = 4.7 Hz, 4H), 2.53 (s, 4H), 2.42 (s, 3H). | 320 |
| 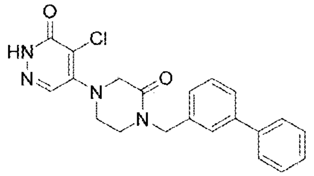 | 1H NMR (400 MHz, DMSO-d6) chemical shifts 12.98 (s, 1H), 7.88 (s, 1H), 7.69 ï¿½C 7.61 (m, 2H), 7.62 ï¿½C 7.53 (m, 2H), 7.47 (td, J = 7.5, 5.5 Hz, 3H), 7.38 (t, J = 7.2 Hz, 1H), 7.29 (d, J = 7.6 Hz, 1H), 4.66 (s, 2H), 4.20 (s, 2H), 3.71 (t, J = 5.3 Hz, 2H), 3.43 (t, J = 5.4 Hz, 2H). | 395 |
| 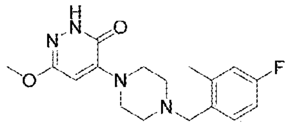 | 1H NMR (400 MHz, Methanol-d4) chemical shifts 7.27 (dd, J = 8.4, 6.0 Hz, 1H), 6.98 ï¿½C 6.82 (m, 2H), 6.20 (s, 1H), 3.78 (s, 3H), 3.52 (s, 2H), 3.43 (s, 4H), 2.67 ï¿½C 2.56 (m, 4H), 2.41 (s, 3H). | 333 |
| 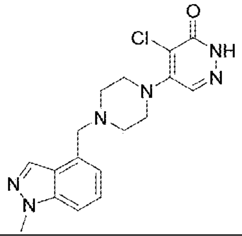 | 1H NMR (300 MHz, DMSO-d6) chemical shifts 12.93 (s, 1H), 8.25 (s, 1H), 7.86 (s, 1H), 7.55 (d, J = 8.5 Hz, 1H), 7.35 (t, J = 7.7 Hz, 1H), 7.08 (d, J = 7.0 Hz, 1H), 4.05 (s, 3H), 3.85 (s, 2H), 3.39 (t, J = 4.9 Hz, 4H), 2.59 ï¿½C 2.48 (m, 4H). | 359 |

Figure 14

| | | |
|---|---|---|
| 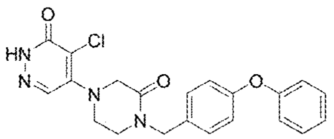 | 1H NMR (400 MHz, DMSO-d6) chemical shifts 12.98 (s, 1H), 7.87 (s, 1H), 7.45 ï¿½C 7.35 (m, 2H), 7.35 ï¿½C 7.27 (m, 2H), 7.15 (tt, J = 7.3, 1.2 Hz, 1H), 7.05 ï¿½C 6.95 (m, 4H), 4.56 (s, 2H), 4.17 (s, 2H), 3.69 (t, J = 5.2 Hz, 2H), 3.39 (t, J = 5.3 Hz, 2H). | 411 |
| 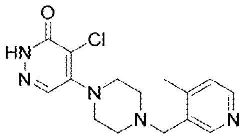 | 1H NMR (400 MHz, DMSO-d6) chemical shifts 12.93 (s, 1H), 8.39 ï¿½C 8.32 (m, 2H), 7.86 (s, 1H), 7.21 (d, J = 5.0 Hz, 1H), 3.54 (s, 2H), 3.36 (t, J = 4.8 Hz, 4H), 2.49 (d, J = 5.1 Hz, 4H), 2.38 (s, 3H). | 320 |
| 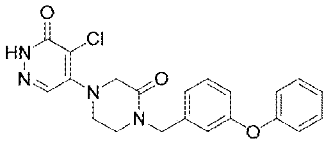 | 1H NMR (400 MHz, DMSO-d6) chemical shifts 12.99 (s, 1H), 7.86 (s, 1H), 7.38 (q, J = 7.5 Hz, 3H), 7.14 (t, J = 7.4 Hz, 1H), 7.03 (dd, J = 14.8, 7.8 Hz, 3H), 6.92 (s, 2H), 4.57 (s, 2H), 4.15 (s, 2H), 3.68 (t, J = 5.2 Hz, 2H), 3.38 (t, J = 5.3 Hz, 2H). | 411 |
| 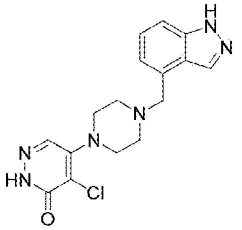 | 1H NMR (300 MHz, DMSO-d6) chemical shifts 13.07 (s, 1H), 8.88 (s, 1H), 8.28 (s, 1H), 7.87 (s, 1H), 7.46 (d, J = 8.3 Hz, 1H), 7.30 (t, J = 7.6 Hz, 1H), 7.05 (d, J = 6.9 Hz, 1H), 3.86 (s, 2H), 3.40 (d, J = 9.3 Hz, 4H), 2.56 (d, J = 4.7 Hz, 4H). | 345 |
| 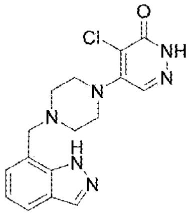 | 1H NMR (300 MHz, DMSO-d6) chemical shifts 12.96 (s, 1H), 12.89 (s, 1H), 8.06 (s, 1H), 7.84 (s, 1H), 7.66 (d, J = 8.1 Hz, 1H), 7.23 (d, J = 6.9 Hz, 1H), 7.11 ï¿½C 6.99 (m, 1H), 3.80 (s, 2H), 3.39 (s, 4H), 2.53 (s, 4H). | 345 |
| 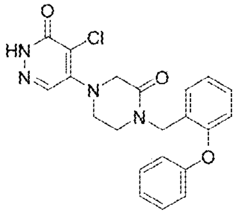 | 1H NMR (400 MHz, DMSO-d6) chemical shifts 12.99 (s, 1H), 7.86 (s, 1H), 7.38 (q, J = 7.5 Hz, 3H), 7.14 (t, J = 7.4 Hz, 1H), 7.03 (dd, J = 15.4, 7.8 Hz, 3H), 6.91 (d, J = 8.5 Hz, 2H), 4.57 (s, 2H), 4.15 (s, 2H), 3.68 (t, J = 5.3 Hz, 2H), 3.39 (d, J = 5.5 Hz, 2H). | 411 |
| 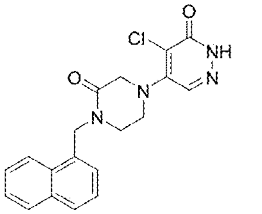 | 1H NMR (400 MHz, DMSO-d6) chemical shifts 12.98 (s, 1H), 8.17 ï¿½C 8.10 (m, 1H), 8.02 ï¿½C 7.94 (m, 1H), 7.95 ï¿½C 7.83 (m, 2H), 7.62 ï¿½C 7.43 (m, 4H), 5.08 (s, 2H), 4.22 (s, 2H), 3.67 (t, J = 5.2 Hz, 2H), 3.33 (s, 2H). | 369 |

Figure 15

| | | |
|---|---|---|
| 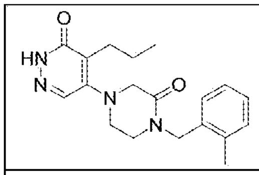 | 1H NMR (300 MHz, DMSO-d6) chemical shifts 12.68 (s, 1H), 7.82 (s, 1H), 7.20 (s, 4H), 4.61 (s, 2H), 3.87 (s, 2H), 3.27 (s, 3H), 2.40 (s, 4H), 2.26 (s, 3H), 1.53 (s, 2H), 0.90 (t, J = 7.6 Hz, 3H). | 341 |
| 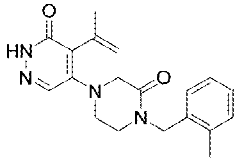 | 1H NMR (300 MHz, DMSO-d6) chemical shifts 12.45 (s, 1H), 7.84 (s, 1H), 7.24 ï¿½C 7.08 (m, 4H), 5.25 (s, 1H), 4.90 (s, 1H), 4.58 (s, 2H), 3.96 (s, 2H), 3.55 (t, J = 5.4 Hz, 2H), 3.23 (t, J = 5.3 Hz, 2H), 2.24 (s, 3H), 1.99 (s, 3H). | 339 |
| 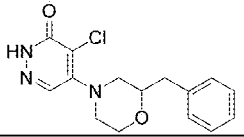 | | 306.1 |
| 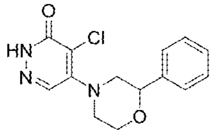 | | 292.1 |
| 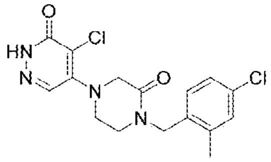 | 1H NMR (400 MHz, DMSO- d6) chemical shifts 12.98 (s, 1H), 7.88 (s, 1H), 7.33 - 7.21 (m, 2H), 7.16 (d, J = 8.2 Hz, 1H), 4.58 (s, 2H), 4.19 (s, 2H), 3.71 (t, J = 5.3 Hz, 2H), 3.31 (t, J = 5.3 Hz, 2H), 2.26 (s, 3H). | 367 |
| 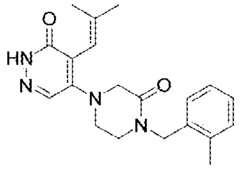 | 1H NMR (300 MHz, DMSO-d6) chemical shifts 12.47 (s, 1H), 7.82 (s, 1H), 7.25 - 7.08 (m, 4H), 5.86 (d, J = 1.7 Hz, 1H), 4.58 (s, 2H), 3.91 (s, 2H), 3.55 (t, J = 5.4 Hz, 2H), 3.34 - 3.16 (m, 2H), 2.24 (s, 3H), 1.83 (d, J = 1.4 Hz, 3H), 1.44 (d, J = 1.2 Hz, 3H). | 353 |
| 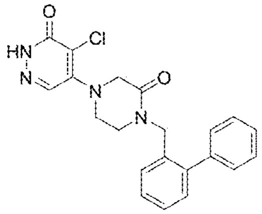 | 1H NMR (400 MHz, DMSO-d6) chemical shifts 12.97 (s, 1H), 7.83 (s, 1H), 7.46 - 7.21 (m, 9H), 4.57 (s, 2H), 4.05 (s, 2H), 3.62 (t, J = 5.3 Hz, 2H), 3.14 (t, J = 5.3 Hz, 2H). | 395 |
| 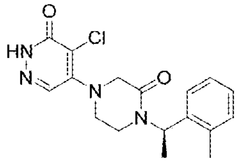 | 1H NMR (300 MHz, DMSO-d6) chemical shifts 12.95 (s, 1H), 7.82 (s, 1H), 7.47 - 7.37 (m, 1H), 7.30 - 7.19 (m, 3H), 5.84 (q, J = 7.0 Hz, 1H), 4.25 - 4.05 (m, 2H), 3.57 (q, J = 6.8, 6.2 Hz, 2H), 3.21 (s, 1H), 2.69 - 2.55 (m, 1H), 2.17 (s, 3H), 1.47 (d, J = 7.0 Hz, 3H). | 347 |

Figure 16

| | | |
|---|---|---|
| 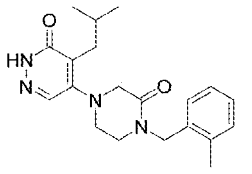 | 1H NMR (300 MHz, Methanol-d4) chemical shifts 7.92 (s, 1H), 7.22 (q, J = 3.4 Hz, 4H), 4.75 (s, 2H), 3.93 (s, 2H), 3.46 (t, J = 5.3 Hz, 2H), 3.37 (s, 2H), 2.53 (d, J = 7.2 Hz, 2H), 2.33 (s, 3H), 2.11 (dt, J = 13.5, 6.8 Hz, 1H), 0.90 (d, J = 6.6 Hz, 6H). | 353 |
| 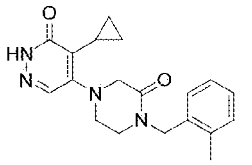 | 1H NMR (300 MHz, Methanol-d4) chemical shifts 7.85 (s, 1H), 7.22 (q, J = 3.6 Hz, 4H), 4.75 (s, 2H), 4.21 (s, 2H), 3.70 (t, J = 5.4 Hz, 2H), 3.39 (t, J = 5.5 Hz, 2H), 2.33 (s, 3H), 1.76 - 1.60 (m, 1H), 1.08 - 0.90 (m, 2H), 0.94 - 0.79 (m, 2H). | 339 |
| 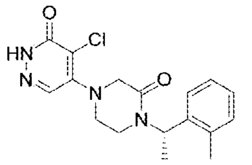 | 1H NMR (300 MHz, DMSO-d6) chemical shifts 12.96 (s, 1H), 7.82 (s, 1H), 7.47 - 7.37 (m, 1H), 7.30 - 7.17 (m, 3H), 5.84 (q, J = 7.1 Hz, 1H), 4.25 - 4.05 (m, 2H), 3.35 (s, 2H), 3.29 (s, 1H), 2.69 - 2.55 (m, 1H), 2.17 (s, 3H), 1.47 (d, J = 7.0 Hz, 3H). | 347 |
| 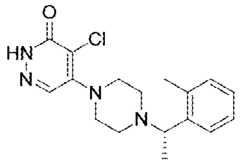 | 1H NMR (400 MHz, DMSO-d6) chemical shifts 12.93 (s, 1H), 7.85 (s, 1H), 7.43 - 7.36 (m, 1H), 7.23 - 7.09 (m, 3H), 3.65 (q, J = 6.6 Hz, 1H), 3.36 (s, 2H), 3.33 (s, 2H), 2.63 - 2.53 (m, 2H), 2.44 (dd, J = 9.5, 5.7 Hz, 2H), 2.35 (s, 3H), 1.26 (d, J = 6.6 Hz, 3H). | 333 |
| 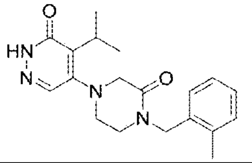 | 1H NMR (300 MHz, DMSO-d6) chemical shifts 12.66 (s, 1H), 7.82 (s, 1H), 7.25 - 7.11 (m, 4H), 4.61 (s, 2H), 3.78 (s, 2H), 3.35 - 3.22 (m, 4H), 3.09 (p, J = 6.9 Hz, 1H), 2.27 (s, 3H), 1.28 (d, J = 6.8 Hz, 6H). | 341 |
| 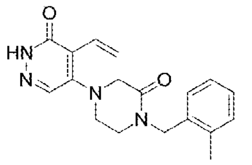 | 1H NMR (300 MHz, DMSO-d6) chemical shifts 12.73 (s, 1H), 7.88 (s, 1H), 7.25 - 7.10 (m, 4H), 6.56 - 6.35 (m, 2H), 5.57 (dd, J = 9.8, 4.9 Hz, 1H), 4.60 (s, 2H), 3.98 (s, 2H), 3.51 (t, J = 5.5 Hz, 2H), 3.35 - 3.24 (m, 2H), 2.26 (s, 3H). | 325 |
| 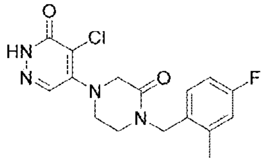 | 1H NMR (300 MHz, DMSO-d6) chemical shifts 12.99 (s, 1H), 7.88 (s, 1H), 7.19 (dd, J = 8.5, 6.0 Hz, 1H), 7.13 - 6.94 (m, 2H), 4.58 (s, 2H), 4.19 (s, 2H), 3.71 (t, J = 5.3 Hz, 2H), 3.29 (t, J = 5.3 Hz, 2H), 2.27 (s, 3H). | 351 |
| 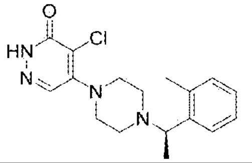 | 1H NMR (300 MHz, DMSO-d6) chemical shifts 12.92 (s, 1H), 7.84 (s, 1H), 7.39 (d, J = 7.4 Hz, 1H), 7.24 - 7.06 (m, 3H), 3.64 (d, J = 6.6 Hz, 1H), 3.35 (s, 4H), 2.58 (t, J = 7.3 Hz, 2H), 2.35 (s, 5H), 1.26 (d, J = 6.6 Hz, 3H). | 333 |

Figure 17

| | | |
|---|---|---|
| 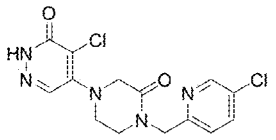 | 1H NMR (400 MHz, DMSO- d6) chemical shifts 12.99 (s, 1H), 8.58 (d, J = 2.5 Hz, 1H), 7.97 - 7.86 (m, 2H), 7.37 (d, J = 8.4 Hz, 1H), 4.66 (s, 2H), 4.18 (s, 2H), 3.74 (t, J = 5.3 Hz, 2H), 3.52 (t, J = 5.3 Hz, 2H). | 354 |
| 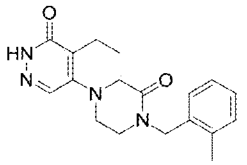 | 1H NMR (400 MHz, Methanol-d4) chemical shifts 7.88 (d, J = 3.4 Hz, 1H), 7.26 - 7.18 (m, 4H), 4.75 (d, J = 3.0 Hz, 2H), 4.00 (d, J = 3.0 Hz, 2H), 3.50 (s, 2H), 3.38 (d, J = 6.7 Hz, 2H), 2.64 - 2.56 (m, 2H), 2.33 (d, J = 3.2 Hz, 3H), 1.22 (t, J = 7.6 Hz, 3H). | 327 |
| 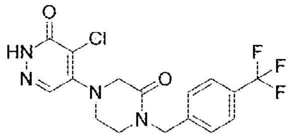 | 1H NMR (400 MHz, DMSO-d6) chemical shifts 12.98 (s, 1H), 7.89 (s, 1H), 7.73 (d, J = 8.0 Hz, 2H), 7.51 (d, J = 8.0 Hz, 2H), 4.68 (s, 2H), 4.20 (s, 2H), 3.72 (t, J = 5.3 Hz, 2H), 3.41 (t, J = 5.3 Hz, 2H). | 387 |
| 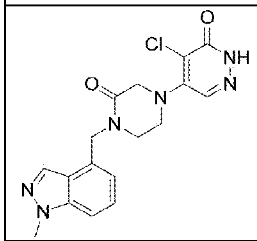 | 1H NMR (300 MHz, DMSO-d6)chemical shifts 12.97 (s, 1H), 8.08 (d, J = 1.0 Hz, 1H), 7.85 (s, 1H), 7.60 (d, J = 8.5 Hz, 1H), 7.44 - 7.32 (m, 1H), 7.06 (d, J = 7.0 Hz, 1H), 4.91 (s, 2H), 4.21 (s, 2H), 4.06 (s, 3H), 3.64 (t, J = 5.3 Hz, 2H), 3.40 (s, 2H). | 373 |
| 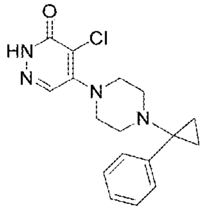 | 1H NMR (400 MHz, DMSO-d6) chemical shifts 12.90 (s, 1H), 7.79 (s, 1H), 7.40 - 7.31 (m, 2H), 7.34 - 7.24 (m, 3H), 3.29 (d, J = 9.7 Hz, 4H), 2.55 (d, J = 4.8 Hz, 4H), 0.92 (q, J = 4.0 Hz, 2H), 0.78 (q, J = 4.1 Hz, 2H). | 331 |
| 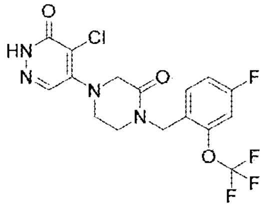 | 1H NMR (300 MHz, Methanol-d4) chemical shifts 7.87 (s, 1H), 7.52 (td, J = 8.4, 6.3 Hz, 1H), 7.31 - 7.16 (m, 2H), 4.91 (s, 2H), 4.23 (s, 2H), 3.78 (t, J = 5.4 Hz, 2H), 3.45 (t, J = 5.3 Hz, 2H). | 421 |
| 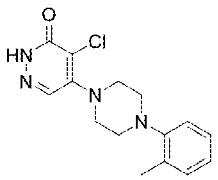 | 1H NMR (300 MHz, DMSO-d6) chemical shifts 12.97 (s, 1H), 8.08 (d, J = 1.0 Hz, 1H), 7.85 (s, 1H), 7.60 (d, J = 8.5 Hz, 1H), 7.44 - 7.32 (m, 1H), 7.06 (d, J = 7.0 Hz, 1H), 4.91 (s, 2H), 4.21 (s, 2H), 4.06 (s, 3H), 3.64 (t, J = 5.3 Hz, 2H), 3.40 (s, 2H). | 305 |
| 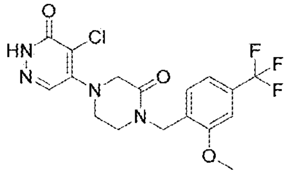 | 1H NMR (400 MHz, DMSO-d6) chemical shifts 12.99 (s, 1H), 7.89 (s, 1H), 7.31 (d, J = 6.1 Hz, 3H), 4.57 (s, 2H), 4.19 (s, 2H), 3.91 (s, 3H), 3.75 (t, J = 5.3 Hz, 2H), 3.45 (t, J = 5.3 Hz, 2H). | 417 |

Figure 18

| | | |
|---|---|---|
| 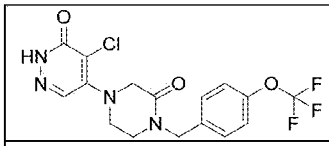 | 1H NMR (400 MHz, DMSO-d6) chemical shifts 12.91 (s, 1H), 7.87 (s, 1H), 7.45 - 7.32 (m, 4H), 4.61 (s, 2H), 4.17 (s, 2H), 3.69 (t, J = 5.3 Hz, 2H), 3.41 (s, 2H). | 403 |
| 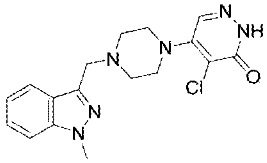 | 1H NMR (300 MHz, DMSO-d6) chemical shifts 12.92 (s, 1H), 7.93 - 7.82 (m, 2H), 7.60 (d, J = 8.5 Hz, 1H), 7.40 (t, J = 7.7 Hz, 1H), 7.14 (t, J = 7.5 Hz, 1H), 4.01 (s, 3H), 3.88 (s, 2H), 3.37 (d, J = 5.4 Hz, 4H), 2.56 (d, J = 5.7 Hz, 4H). | 359 |
| 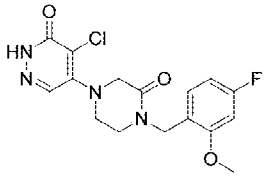 | 1H NMR (300 MHz, DMSO-d6) chemical shifts 12.95 (s, 1H), 7.87 (s, 1H), 7.16 (dd, J = 8.4, 6.9 Hz, 1H), 6.94 (dd, J = 11.4, 2.5 Hz, 1H), 6.75 (td, J = 8.5, 2.5 Hz, 1H), 4.49 (s, 2H), 4.15 (s, 2H), 3.82 (s, 3H), 3.71 (t, J = 5.3 Hz, 2H), 3.39 (t, J = 5.3 Hz, 2H). | 367 |
| 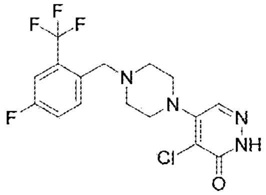 | 1H NMR (400 MHz, DMSO-d6) chemical shifts 12.96 (s, 1H), 7.90 - 7.79 (m, 2H), 7.65 - 7.52 (m, 2H), 3.66 (s, 2H), 3.40 (d, J = 9.5 Hz, 4H), 2.53 (s, 4H). | 391 |
| 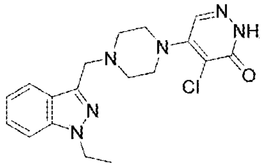 | 1H NMR (300 MHz, DMSO-d6) chemical shifts 12.92 (s, 1H), 7.93 - 7.81 (m, 2H), 7.63 (d, J = 8.5 Hz, 1H), 7.38 (dd, J = 8.2, 6.9 Hz, 1H), 7.13 (t, J = 7.5 Hz, 1H), 4.41 (q, J = 7.2 Hz, 2H), 3.89 (s, 2H), 3.38 (t, J = 4.8 Hz, 4H), 2.56 (d, J = 5.5 Hz, 4H), 1.38 (t, J = 7.2 Hz, 3H). | 373 |
| 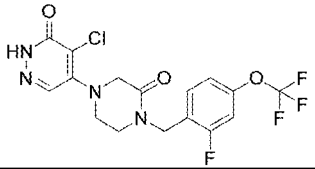 | 1H NMR (300 MHz, DMSO-d6) chemical shifts 12.92 (s, 1H), 7.88 (s, 1H), 7.53 - 7.38 (m, 2H), 7.26 (d, J = 8.2 Hz, 1H), 4.64 (s, 2H), 4.17 (s, 2H), 3.73 (t, J = 5.2 Hz, 2H), 3.45 (t, J = 5.3 Hz, 2H). | 421 |
| 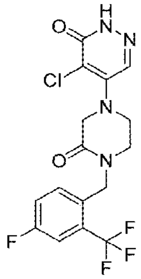 | 1H NMR (300 MHz, DMSO-d6) chemical shifts 13.00 (s, 1H), 7.91 (s, 1H), 7.73 - 7.42 (m, 3H), 4.73 (s, 2H), 4.24 (s, 2H), 3.77 (t, J = 5.3 Hz, 2H), 3.42 (t, J = 5.3 Hz, 2H). | 405 |
| 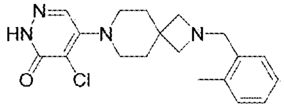 | | 359.3 |

Figure 19

| | | |
|---|---|---|
| 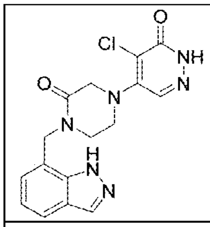 | 1H NMR (400 MHz, DMSO-d6) chemical shifts 12.94 (s, 1H), 8.14 (s, 1H), 7.89 (s, 1H), 7.72 (dd, J = 8.1, 1.0 Hz, 1H), 7.24 - 7.18 (m, 1H), 7.12 (dd, J = 8.0, 7.0 Hz, 1H), 4.89 (s, 2H), 4.23 (s, 2H), 3.72 (t, J = 5.3 Hz, 2H), 3.47 (t, J = 5.3 Hz, 2H). | 359 |
| 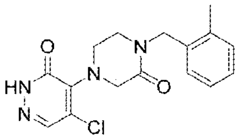 | 1H NMR (300 MHz, DMSO-d6) chemical shifts 13.01 (s, 1H), 7.80 (s, 1H), 7.23 - 7.13 (m, 4H), 4.59 (s, 2H), 4.14 (s, 2H), 3.67 (t, J = 5.3 Hz, 2H), 3.24 (t, J = 5.3 Hz, 2H), 2.26 (s, 3H). | 333 |
| 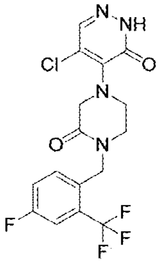 | 1H NMR (400 MHz, DMSO-d6) chemical shifts 13.05 (s, 1H), 7.83 (s, 1H), 7.67 (dt, J = 9.0, 1.6 Hz, 1H), 7.53 (dd, J = 7.0, 1.6 Hz, 2H), 4.71 (s, 2H), 4.17 (s, 2H), 3.70 (t, J = 5.2 Hz, 2H), 3.34 (t, J = 5.4 Hz, 2H). | 405 |
| 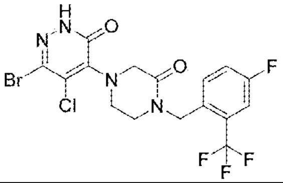 | 1H NMR (300 MHz, Methanol-d4)chemical shifts 7.65 - 7.46 (m, 2H), 7.47 - 7.35 (m, 1H),4.86 (s, 2H), 4.28 (s, 2H), 3.80 (t, J = 5.3 Hz, 2H), 3.42 (t, J = 5.3 Hz, 2H). | 483 |
| 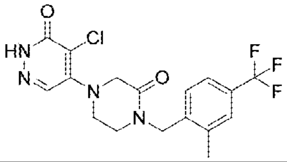 | 1H NMR (300 MHz, DMSO-d6) chemical shifts 12.98 (s, 1H), 7.90 (s, 1H), 7.62 - 7.50 (m, 2H), 7.35 (d, J = 8.0 Hz, 1H), 4.67 (s, 2H), 4.22 (s, 2H), 3.75 (t, J = 5.4 Hz, 2H), 3.37 (t, J = 5.3 Hz, 2H), 2.36 (s, 3H). | 401 |
| 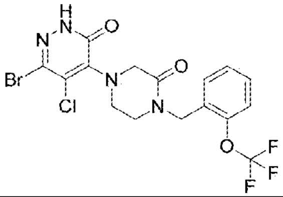 | 1H NMR (400 MHz, DMSO-d6)chemical shifts 13.21 (s, 1H), 7.49 - 7.34 (m, 4H), 4.65 (s, 2H), 4.15 (s, 2H), 3.71 (t, J = 5.2 Hz, 2H), 3.35 (d, J = 5.1 Hz, 2H). | 481 |
| 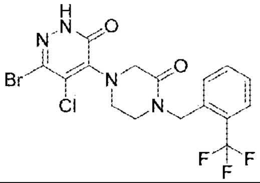 | 1H NMR (300 MHz, Methanol-d4)chemical shifts 7.79 - 7.59 (m, 2H), 7.50 (dd, J = 18.6, 8.0 Hz, 2H), 4.89 (s, 2H), 4.30 (s, 2H), 3.80 (t, J = 5.3 Hz, 2H), 3.43 (t, J = 5.3 Hz, 2H). | 465 |
| 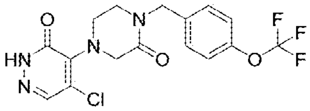 | 1H NMR (400 MHz, DMSO-d6) chemical shifts 13.02 (s, 1H), 7.81 (s, 1H), 7.46 - 7.39 (m, 2H), 7.34 (d, J = 8.3 Hz, 2H), 4.60 (s, 2H), 4.13 (s, 2H), 3.66 (t, J = 5.2 Hz, 2H), 3.33 (s, 2H). | 403 |

Figure 20

| | | |
|---|---|---|
| 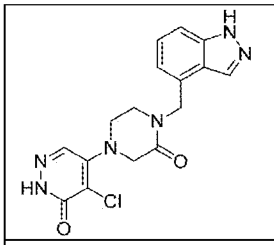 | 1H NMR (400 MHz, DMSO-d6) chemical shifts 13.18 (s, 1H), 12.13 (s, 1H), 8.12 (d, J = 1.0 Hz, 1H), 7.86 (s, 1H), 7.50 (d, J = 8.4 Hz, 1H), 7.33 (dd, J = 8.4, 6.9 Hz, 1H), 7.03 (d, J = 6.9 Hz, 1H), 4.92 (s, 2H), 4.22 (s, 2H), 3.65 (t, J = 5.3 Hz, 2H), 3.36 (s, 2H). | 359 |
| 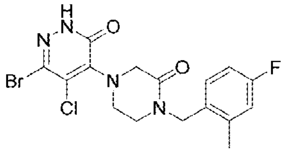 | 1H NMR (400 MHz, DMSO-d6)chemical shifts 13.19 (s, 1H), 7.21 (dd, J = 8.5, 6.1 Hz, 1H), 7.06 (dd, J = 10.1, 2.8 Hz, 1H), 6.98 (td, J = 8.6, 2.8 Hz, 1H), 4.56 (s, 2H), 4.15 (s, 2H), 3.69 (t, J = 5.3 Hz, 2H), 3.24 (t, J = 5.2 Hz, 2H), 2.27 (s, 3H). | 429 |
| 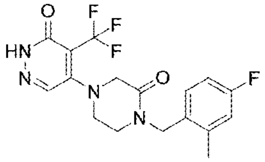 | 1H NMR (400 MHz, DMSO-d6) chemical shifts 12.64 (s, 1H), 8.00 (s, 1H), 7.20 (dd, J = 8.5, 6.1 Hz, 1H), 7.07 (dd, J = 10.0, 2.8 Hz, 1H), 7.00 (td, J = 8.6, 2.8 Hz, 1H), 4.55 (s, 2H), 4.08 (s, 2H), 3.75 (t, J = 5.2 Hz, 2H), 3.26 (t, J = 5.3 Hz, 2H), 2.25 (s, 3H). | 385 |
| 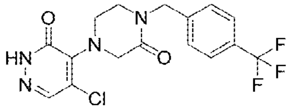 | 1H NMR (400 MHz, DMSO-d6) chemical shifts 13.03 (s, 1H), 7.81 (s, 1H), 7.71 (d, J = 8.0 Hz, 2H), 7.52 (d, J = 8.0 Hz, 2H), 4.67 (s, 2H), 4.14 (s, 2H), 3.66 (t, J = 5.3 Hz, 2H), 3.34 (d, J = 10.4 Hz, 2H). | 387 |
| 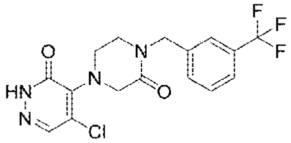 | 1H NMR (300 MHz, DMSO-d6) chemical shifts 13.02 (s, 1H), 7.80 (s, 1H), 7.62 (t, J = 9.7 Hz, 4H), 4.67 (s, 2H), 4.13 (s, 2H), 3.66 (t, J = 5.2 Hz, 2H), 3.31 (s, 2H). | 387 |
| 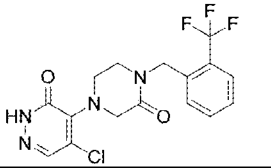 | 1H NMR (400 MHz, DMSO-d6) chemical shifts 13.06 (s, 1H), 7.83 (s, 1H), 7.76 (d, J = 7.7 Hz, 1H), 7.67 (t, J = 7.6 Hz, 1H), 7.55 - 7.45 (m, 2H), 4.75 (s, 2H), 4.18 (s, 2H), 3.72 (t, J = 5.3 Hz, 2H), 3.36 (d, J = 5.3 Hz, 2H). | 387 |
| 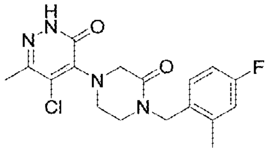 | 1H NMR (400 MHz, DMSO-d6)chemical shifts 12.81 (s, 1H), 7.22 (dd, J = 8.5, 6.0 Hz, 1H), 7.10 - 6.93 (m, 2H), 4.56 (s, 2H), 4.07 (s, 2H), 3.61 (t, J = 5.3 Hz, 2H), 3.21 (t, J = 5.3 Hz, 2H), 2.27 (d, J = 2.0 Hz, 6H). | 365 |
| 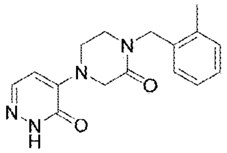 | 1H NMR (400 MHz, DMSO-d6) chemical shifts 12.74 (s, 1H), 7.68 (d, J = 4.9 Hz, 1H), 7.24 - 7.13 (m, 3H), 7.15 - 7.08 (m, 1H), 6.48 (d, J = 5.0 Hz, 1H), 4.59 (s, 2H), 4.12 (s, 2H), 3.89 (t, J = 5.5 Hz, 2H), 3.28 (dd, J = 6.3, 4.6 Hz, 2H), 2.25 (s, 3H). | 299 |

Figure 21

| | | |
|---|---|---|
| 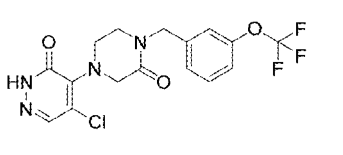 | 1H NMR (400 MHz, DMSO-d6) chemical shifts 13.02 (s, 1H), 7.81 (s, 1H), 7.54 - 7.45 (m, 1H), 7.37 - 7.25 (m, 3H), 4.63 (s, 2H), 4.13 (s, 2H), 3.66 (t, J = 5.3 Hz, 2H), 3.33 (d, J = 5.5 Hz, 2H) | 403 |
| 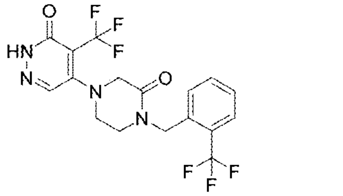 | 1H NMR (400 MHz, DMSO-d6) chemical shifts 12.72 (s, 1H), 8.04 (s, 1H), 7.77 (d, J = 7.9 Hz, 1H), 7.68 (t, J = 7.6 Hz, 1H), 7.52 (t, J = 7.6 Hz, 1H), 7.45 (d, J = 7.8 Hz, 1H), 4.74 (s, 2H), 4.15 (s, 2H), 3.86 (t, J = 5.3 Hz, 2H), 3.40 (d, J = 10.7 Hz, 2H). | 421 |
| 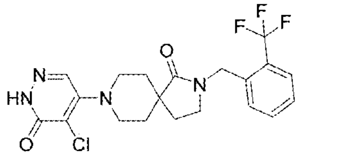 | 7.90 (1 H, s), 7.72-7.74 (1 H, m), 7.65-7.62 (1 H, m), 7.49-7.51 (1 H, m), 7.37-7.39 (1 H, m), 4.69 (2 H, s), 3.87-3.91 (2 H, m), 3.25-3.33 (4 H, m), 2.03-2.16 (4 H, m), 1.65-1.69 (2 H, m) | 441.2 |
| 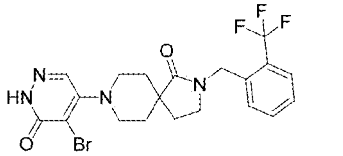 | 7.81 (1 H, s), 7.72-7.74 (1 H, m), 7.62-7.66 (1 H, m), 7.47-7.49 (1 H, m), 7.37-7.39 (1 H, m), 4.69 (2 H, s), 3.84-3.89 (2 H, m), 3.22-3.34 (4 H, m), 2.06-2.16 (4 H, m), 1.66-1.69 (2 H, m) | 487.1 |
| 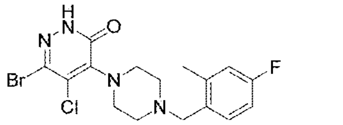 | 1H NMR (400 MHz, Methanol-d4) chemical shifts 7.28 (dd, J = 8.4, 6.0 Hz, 1H), 6.98 - 6.82 (m, 2H), 3.57 - 3.49 (m, 6H), 2.60 (t, J = 4.8 Hz, 4H), 2.42 (s, 3H). | 415 |
| 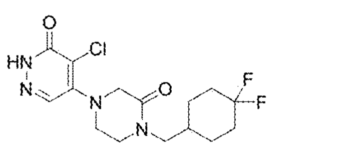 | 1H NMR (400 MHz, DMSO-d6) chemical shifts 12.97 (s, 1H), 7.87 (s, 1H), 4.10 (s, 2H), 3.71 (t, J = 5.3 Hz, 2H), 3.35 (s, 2H), 3.27 (s, 2H), 2.00 (s, 2H), 1.87 - 1.74 (m, 5H), 1.27 - 1.15 (m, 2H). | 361 |
| 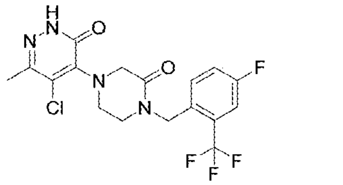 | 1H NMR (400 MHz, Methanol-d4) chemical shifts 7.62 (dd, J = 8.8, 5.3 Hz, 1H), 7.51 (dd, J = 9.1, 2.8 Hz, 1H), 7.41 (td, J = 8.3, 2.8 Hz, 1H), 4.86 (s, 2H),4.23 (s, 2H), 3.74 (t, J = 5.3 Hz, 2H), 3.39 (t, J = 5.3 Hz, 2H), 2.39 (s, 3H). | 419 |
| 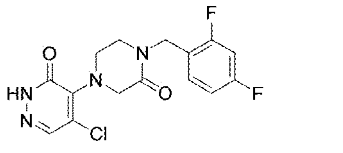 | 1H NMR (300 MHz, DMSO-d6) chemical shifts 13.01 (s, 1H), 7.80 (s, 1H), 7.49 - 7.34 (m, 1H), 7.33 - 7.19 (m, 1H), 7.14 - 7.01 (m, 1H), 4.58 (s, 2H), 4.11 (s, 2H), 3.66 (t, J = 5.3 Hz, 2H), 3.40 - 3.26 (m, 2H). | 355 |
| 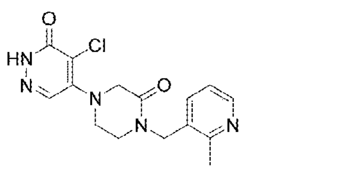 | 1H NMR (400 MHz, DMSO-d6) chemical shifts 12.99 (s, 1H), 8.37 (dd, J = 4.8, 1.7 Hz, 1H), 7.89 (s, 1H), 7.51 (dd, J = 7.7, 1.7 Hz, 1H), 7.22 (dd, J = 7.7, 4.8 Hz, 1H), 4.62 (s, 2H), 4.21 (s, 2H), 3.74 (t, J = 5.3 Hz, 2H), 3.40 - 3.32 (m, 2H), 2.46 (s, 3H). | 334 |

Figure 22

| | | |
|---|---|---|
| 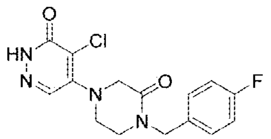 | 1H NMR (300 MHz, DMSO-d6) chemical shifts 12.51 (s, 1H), 7.87 (s, 1H), 7.34 (dd, J = 8.7, 5.6 Hz, 2H), 7.19 (t, J = 8.9 Hz, 2H), 4.57 (s, 2H), 4.17 (s, 2H), 3.69 (t, J = 5.3 Hz, 2H), 3.37 (t, J = 5.3 Hz, 2H). | 337 |
| 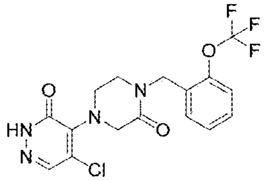 | 1H NMR (400 MHz, DMSO-d6) chemical shifts 13.04 (s, 1H), 7.82 (s, 1H), 7.50 - 7.35 (m, 4H), 4.66 (s, 2H), 4.14 (s, 2H), 3.68 (t, J = 5.3 Hz, 2H), 3.34 (s, 2H). | 403 |
| 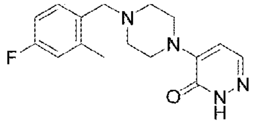 | 1H NMR (400 MHz, DMSO-d6) chemical shifts 12.63 (s, 1H), 7.64 (d, J = 4.8 Hz, 1H), 7.27 (dd, J = 8.4, 6.2 Hz, 1H), 7.04 (dd, J = 10.1, 2.8 Hz, 1H), 6.96 (td, J = 8.6, 2.9 Hz, 1H), 6.42 (d, J = 4.9 Hz, 1H), 3.42 (d, J = 24.0 Hz, 2H), 3.32 (s, 4H), 2.47 (t, J = 5.0 Hz, 4H), 2.35 (s, 3H). | 303 |
| 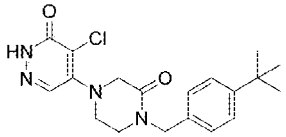 | 1H NMR (300 MHz, DMSO-d6) chemical shifts 12.98 (s, 1H), 7.88 (s, 1H), 7.43 - 7.32 (m, 2H), 7.21 (d, J = 8.2 Hz, 2H), 4.55 (s, 2H), 4.17 (s, 2H), 3.69 (t, J = 5.4 Hz, 2H), 3.37 (t, J = 5.3 Hz, 2H), 1.28 (s, 9H). | 375 |
| 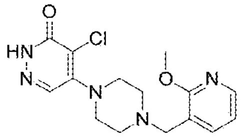 | 1H NMR (300 MHz, DMSO-d6) chemical shifts 12.93 (s, 1H), 8.09 (dd, J = 5.0, 1.9 Hz, 1H), 7.86 (s, 1H), 7.71 (dd, J = 7.2, 2.0 Hz, 1H), 7.00 (dd, J = 7.2, 5.0 Hz, 1H), 3.88 (s, 3H), 3.51 (s, 2H), 3.39-3.33 (m, 4H), 2.53 -2.51(m, 4H). | 336 |
| 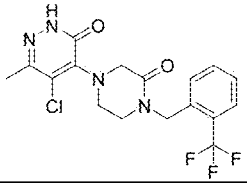 | 1H NMR (300 MHz, Methanol-d4) chemical shifts 7.74 (d, J = 7.8 Hz, 1H), 7.65 (t, J = 7.5 Hz, 1H), 7.58 - 7.44 (m, 2H), 4.90 (s, 2H), 4.25 (s, 2H), 3.74 (t, J = 5.3 Hz, 2H), 3.40 (t, J = 5.3 Hz, 2H), 2.39 (s, 3H). | 399 |
| 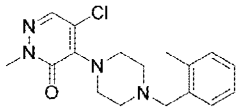 | 1H NMR (300 MHz, DMSO-d6) chemical shifts 7.78 (s, 1H), 7.25 (d, J = 6.5 Hz, 1H), 7.17 (s, 3H), 3.59 (s, 3H), 3.47 (s, 2H), 3.38 (s, 5H), 2.47 (s, 3H), 2.35 (s, 3H). | 333 |
| 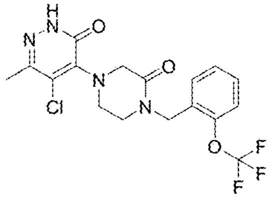 | 1H NMR (400 MHz, Methanol-d4) chemical shifts 7.54 - 7.46 (m, 1H), 7.46 - 7.33 (m, 3H), 4.79 (s, 2H), 4.21 (s, 2H), 3.71 (t, J = 5.3 Hz, 2H), 3.40 (t, J = 5.3 Hz, 2H), 2.38 (s, 3H). | 417 |

Figure 23

| | | |
|---|---|---|
| 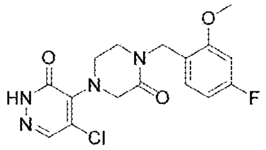 | 1H NMR (300 MHz, DMSO-d6) chemical shifts 7.80 (s, 1H), 7.25 - 7.13 (m, 1H), 6.93 (dd, J = 11.4, 2.5 Hz, 1H), 6.73 (td, J = 8.4, 2.4 Hz, 1H), 4.47 (s, 2H), 4.11 (s, 2H), 3.82 (s, 3H), 3.66 (t, J = 5.3 Hz, 2H), 3.33 (s, 2H). | 367 |
| 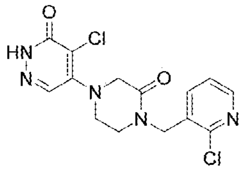 | 1H NMR (300 MHz, DMSO-d6) chemical shifts 12.92 (s, 1H), 8.36 (dd, J = 4.7, 1.9 Hz, 1H), 7.90 (s, 1H), 7.73 (dd, J = 7.6, 1.9 Hz, 1H), 7.45 (dd, J = 7.6, 4.8 Hz, 1H), 4.64 (s, 2H), 4.22 (s, 2H), 3.79 (t, J = 5.3 Hz, 2H), 3.49 (t, J = 5.3 Hz, 2H). | 354 |
| 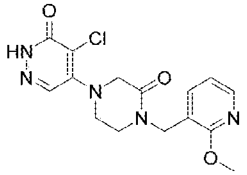 | 1H NMR (300 MHz, DMSO-d6) chemical shifts 12.95 (s, 1H), 8.10 (dd, J = 5.0, 1.9 Hz, 1H), 7.88 (s, 1H), 7.51 (dd, J = 7.3, 1.8 Hz, 1H), 6.99 (dd, J = 7.3, 5.0 Hz, 1H), 4.49 (s, 2H), 4.18 (s, 2H), 3.90 (s, 3H), 3.75 (t, J = 5.3 Hz, 2H), 3.46 (t, J = 5.4 Hz, 2H). | 350 |
| 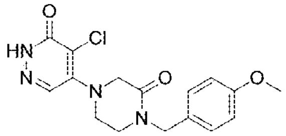 | 1H NMR (300 MHz, DMSO-d6) chemical shifts 12.97 (s, 1H), 7.86 (s, 1H), 7.22 (d, J = 8.6 Hz, 2H), 6.92 (d, J = 8.6 Hz, 2H), 4.51 (s, 2H), 4.16 (s, 2H), 3.75 (s, 3H), 3.67 (t, J = 5.4 Hz, 2H), 3.36 (s, 2H). | 349 |
| 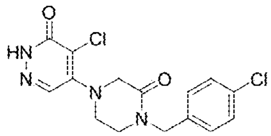 | 1H NMR (300 MHz, DMSO-d6) chemical shifts 12.98 (s, 1H), 7.87 (s, 1H), 7.43 (d, J = 8.4 Hz, 2H), 7.32 (d, J = 8.4 Hz, 2H), 4.58 (s, 2H), 4.18 (s, 2H), 3.69 (t, J = 5.3 Hz, 2H), 3.34 (s, 2H). | 353 |
| 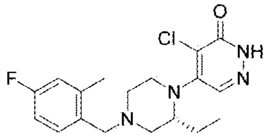 | 1H NMR (400 MHz, DMSO-d6) chemical shifts 12.83 (s, 1H), 7.85 (s, 1H), 7.25 (dd, J = 8.4, 6.2 Hz, 1H), 7.04 (dd, J = 10.1, 2.7 Hz, 1H), 6.96 (td, J = 8.6, 2.9 Hz, 1H), 3.88 (s, 1H), 3.37 (s, 4H), 2.71 (t, J = 11.1 Hz, 2H), 2.36 (s, 3H), 2.27 (dd, J = 11.3, 3.4 Hz, 1H), 2.16 - 2.06 (m, 1H), 1.73 (tt, J = 14.2, 7.1 Hz, 2H), 0.68 (t, J = 7.4 Hz, 3H). | 365 |
| 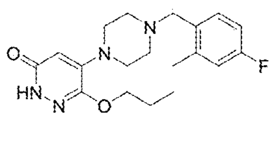 | 1H NMR (300 MHz, Methanol-d4) chemical shifts 7.55 (dd, J = 8.5, 5.7 Hz, 1H), 7.21 - 7.04 (m, 2H), 6.15 (s, 1H), 4.48 (s, 2H), 4.21 (t, J = 6.5 Hz, 2H), 3.53 (s, 4H),3.33(s,4H), 2.51 (s, 3H), 1.85 (m, 2H), 1.06 (t, J = 7.4 Hz, 3H). | 361 |
| 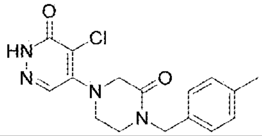 | 1H NMR (300 MHz, DMSO-d6) chemical shifts 12.98 (s, 1H), 7.87 (s, 1H), 7.17 (s, 4H), 4.54 (s, 2H), 4.17 (s, 2H), 3.67 (t, J = 5.3 Hz, 2H), 3.34 (m, 2H), 2.29 (s, 3H). | 333 |

Figure 24

| | | |
|---|---|---|
| 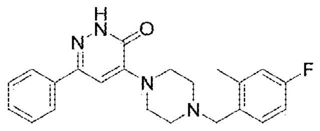 | 1H NMR (400 MHz, DMSO-d6) chemical shifts 12.80 (s, 1H), 7.89 - 7.81 (m, 2H), 7.51 - 7.37 (m, 3H), 7.29 (dd, J = 8.4, 6.2 Hz, 1H), 7.09 - 6.89 (m, 3H), 3.54 (s, 4H), 3.47 (s, 2H), 2.54 (s, 4H), 2.37 (s, 3H). | 379 |
| 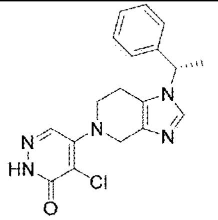 | 1H NMR (300 MHz, DMSO-d6) chemical 12.86 (s, 1H), 7.88 (d, J = 8.0 Hz, 2H), 7.43 - 7.17 (m, 5H), 5.47 - 5.35 (m, 1H), 4.37 (s, 2H), 3.72 - 3.60 (m, 1H), 3.56 (d, J = 7.1 Hz, 1H), 2.69 (s, 1H), 2.44 (s, 1H), 1.81 (d, J = 7.1 Hz, 3H). | 356 |
| 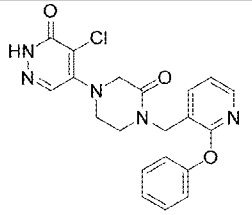 | 1H NMR (300 MHz, DMSO-d6) chemical shifts 12.99 (s, 1H), 8.05 (d, J = 3.2 Hz, 1H), 7.89 (s, 1H), 7.74 (d, J = 7.9 Hz, 1H), 7.41 (t, J = 7.8 Hz, 2H), 7.26 - 7.08 (m, 4H), 4.68 (s, 2H), 4.18 (s, 2H), 3.77 (s, 2H), 3.54 (s, 2H). | 412 |
| 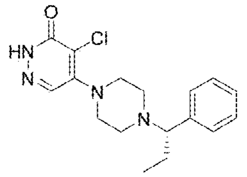 | 1H NMR (400 MHz, DMSO-d6) chemical shifts 12.90 (s, 1H), 7.82 (s, 1H), 7.39 - 7.21 (m, 6H), 3.35 (s, 4H), 3.30 (s, 1H), 2.44 (d, J = 4.7 Hz, 4H), 1.92 (dt, J = 13.5, 6.8 Hz, 1H), 1.71 (dt, J = 14.2, 7.6 Hz, 1H), 0.73 (t, J = 7.3 Hz, 3H). | 333 |
| 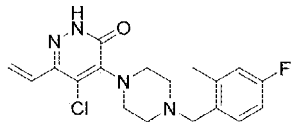 | 1H NMR (400 MHz, DMSO-d6) chemical shifts 12.99 (s, 1H), 7.28 (dd, J = 8.4, 6.2 Hz, 1H), 7.04 (dd, J = 10.1, 2.8 Hz, 1H), 6.96 (td, J = 8.6, 2.8 Hz, 1H), 6.85 (dd, J = 17.1, 10.9 Hz, 1H), 5.94 (dd, J = 17.1, 1.9 Hz, 1H), 5.45 (dd, J = 10.9, 1.9 Hz, 1H), 3.45 (s, 2H),3.34((t, J = 4.5 Hz, 4H), 2.46 (t, J = 4.5 Hz, 4H), 2.36 (s, 3H). | 363 |
| 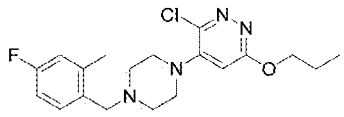 | 1H NMR (400 MHz, DMSO-d6) chemical shifts 7.29 (q, J = 8.7, 8.0 Hz, 1H), 7.11 - 6.95 (m, 2H), 6.70 (dd, J = 10.2, 4.7 Hz, 1H), 4.33 (dq, J = 10.3, 6.4 Hz, 2H), 3.54 - 3.45 (m, 2H), 3.18 (d, J = 10.2 Hz, 4H),2.53 (d, J = 10.2 Hz, 4H), 2.42 - 2.33 (m, 3H), 1.77 (h, J = 7.3 Hz, 2H), 1.06 - 0.93 (m, 3H). | 379 |
| 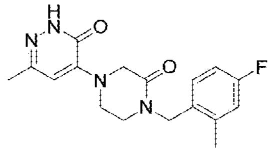 | 1H NMR (400 MHz, DMSO-d6) chemical shifts 12.45 (s, 1H), 7.17 (dd, J = 8.5, 6.0 Hz, 1H), 7.12 - 6.96 (m, 2H), 6.44 (s, 1H), 4.57 (s, 2H), 4.09 (s, 2H), 3.88 (t, J = 5.4 Hz, 2H), 3.26 (t, J = 5.4 Hz, 2H), 2.27 (s, 3H), 2.17 (s, 3H). | 331 |

Figure 25

| | | |
|---|---|---|
| 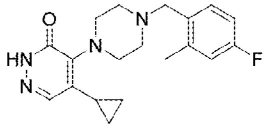 | 1H NMR (400 MHz, DMSO-d6) chemical shifts 12.57 (s, 1H), 7.34 - 7.23 (m, 2H), 7.08 - 6.91 (m, 2H), 3.44 (s, 2H), 3.28 (t, J = 4.8 Hz, 4H), 2.44 (d, J = 5.2 Hz, 4H), 2.37 (s, 3H), 2.06 (tt, J = 8.5, 5.2 Hz, 1H), 1.06 - 0.94 (m, 2H), 0.86 - 0.75 (m, 2H). | 343 |
| 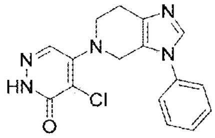 | 1H NMR (400 MHz, DMSO-d6) chemical shifts 12.91 (s, 1H), 7.92 (d, J = 4.3 Hz, 2H), 7.61 - 7.42 (m, 5H), 4.58 (s, 2H), 3.73 (t, J = 5.5 Hz, 2H), 2.82 (s, 2H). | 328 |
| 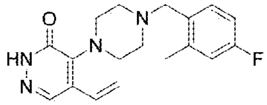 | 1H NMR (400 MHz, DMSO-d6) chemical shifts 12.63 (s, 1H), 7.96 - 7.88 (m, 1H), 7.30 ( t, J = 7.4 Hz, 1H), 7.07 (d, J = 10.3 Hz, 1H), 6.98 (d, J = 11.4 Hz, 1H), 6.73 (d, J = 16.8 Hz, 1H), 5.88 (d, J = 17.5 Hz, 1H), 5.49 (d, J = 11.7 Hz, 1H), 3.47 (d, J = 10.0 Hz, 2H), 3.31 (s, 4H), 2.53 (d, J = 9.5 Hz, 4H), 2.42 - 2.34 (m, 3H). | 329 |
| 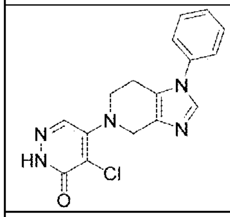 | 1H NMR (300 MHz, DMSO-d6) chemical shifts 12.90 (s, 1H), 7.95 (d, J = 12.6 Hz, 2H), 7.60 - 7.42 (m, 5H), 4.49 (s, 2H), 3.71 (s, 2H), 2.88 (s, 2H). | 328 |
| 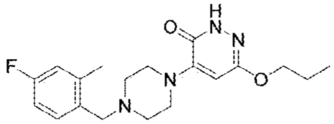 | 1H NMR (300 MHz, Methanol-d4) chemical shifts 7.55 (dd, J = 8.5, 5.8 Hz, 1H), 7.21 - 7.04 (m, 2H), 6.37 (s, 1H), 4.47 (s, 2H), 4.09 (t, J = 6.5 Hz, 2H), 3.51 (s, 4H), 3.34(s, 4H), 2.51 (s, 3H), 1.76 (h, J = 7.1 Hz, 2H), 1.01 (t, J = 7.4 Hz, 3H). | 361 |
| 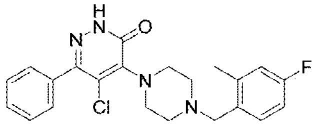 | 1H NMR (400 MHz, DMSO-d6) chemical shifts 13.04 (s, 1H), 7.53 - 7.42 (m, 5H), 7.29 (dd, J = 8.4, 6.2 Hz, 1H), 7.04 (dd, J = 10.1, 2.7 Hz, 1H), 6.96 (td, J = 8.6, 2.8 Hz, 1H), 3.42 (d, J = 9.3 Hz, 2H),3.35 (d, J = 4.9 Hz, 4H) 2.48 (d, J = 4.9 Hz, 4H), 2.37 (s, 3H). | 413 |
| 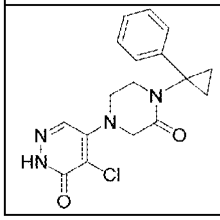 | 1H NMR (400 MHz, DMSO-d6) chemical shifts 12.97 (s, 1H), 7.88 (s, 1H), 7.31 (t, J = 7.6 Hz, 2H), 7.25 - 7.17 (m, 1H), 7.21 - 7.11 (m, 2H), 4.15 (s, 2H), 3.77 (t, J = 5.3 Hz, 2H), 3.50 (t, J = 5.3 Hz, 2H), 1.43 - 1.34 (m, 2H), 1.27 (dt, J = 13.2, 6.1 Hz, 2H). | 345 |

Figure 26

| | | |
|---|---|---|
| 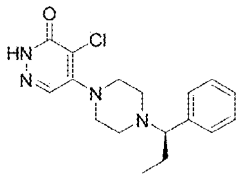 | 1H NMR (400 MHz, DMSO-d6) chemical shifts 12.90 (s, 1H), 7.82 (s, 1H), 7.39 - 7.21 (m, 6H), 3.35 (s, 4H), 3.30 (s, 1H), 2.44 (d, J = 4.7 Hz, 4H), 1.92 (dt, J = 13.5, 6.8 Hz, 1H), 1.71 (dt, J = 14.2, 7.6 Hz, 1H), 0.73 (t, J = 7.3 Hz, 3H). | 333 |
| 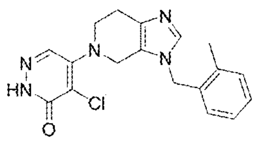 | 1H NMR (300 MHz, DMSO-d6) chemical shifts 12.88 (s, 1H), 7.80 (s, 1H), 7.57 (s, 1H), 7.27 - 7.14 (m, 3H), 6.82 (d, J = 7.1 Hz, 1H), 5.18 (s, 2H), 4.30 (s, 2H), 3.65 (t, J = 5.4 Hz, 2H), 2.72 (s, 2H), 2.29 (s, 3H). | 356 |
| 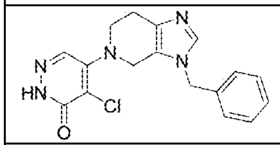 | 1H NMR (300 MHz, DMSO-d6) chemical shifts 12.89 (s, 1H), 7.83 (s, 1H), 7.74 (s, 1H), 7.44 - 7.22 (m, 5H), 5.16 (s, 2H), 4.36 (s, 2H), 3.63 (t, J = 5.6 Hz, 2H), 2.69 (s, 2H). | 342 |
| 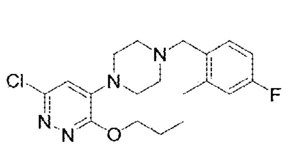 | 1H NMR (400 MHz, Methanol-d4) chemical shifts 7.26 (dd, J = 8.4, 6.0 Hz, 1H), 6.97 - 6.82 (m, 3H), 4.41 (t, J = 6.4 Hz, 2H), 3.52 (s, 2H), 3.43 (s, 4H), 2.63 - 2.56 (m, 4H), 2.41 (s, 3H), 1.87 (h, J = 7.1 Hz, 2H), 1.08 (t, J = 7.4 Hz, 3H). | 379 |
| 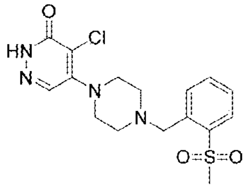 | 1H NMR (400 MHz, DMSO-d6) chemical shifts 12.95 (s, 1H), 8.00 (dd, J = 7.9, 1.4 Hz, 1H), 7.86 (s, 1H), 7.71 (td, J = 7.4, 1.5 Hz, 1H), 7.60 (ddd, J = 10.4, 7.0, 1.7 Hz, 2H), 3.94 (s, 2H), 3.45 (s, 3H), 3.38 (t, J = 4.8 Hz, 4H), 2.56 (t, J = 4.8 Hz, 4H). | 383 |
| 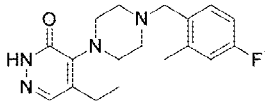 | 1H NMR (300 MHz, DMSO-d6) chemical shifts 12.67 (s, 1H), 7.69 (s, 1H), 7.27 (dd, J = 8.4, 6.2 Hz, 1H), 7.08 - 6.88 (m, 2H), 3.44 (s, 2H), 3.11 (t, J = 4.7 Hz, 4H), 2.59 - 2.45 (m, 2H), 2.49 - 2.33 (m, 7H), 1.12 (t, J = 7.5 Hz, 3H). | 331 |
| 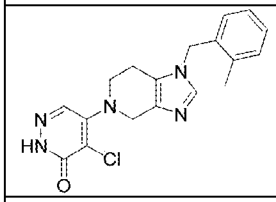 | 1H NMR (400 MHz, DMSO-d6) chemical shifts 12.88 (s, 1H), 7.92 (s, 1H), 7.60 (s, 1H), 7.26 - 7.13 (m, 3H), 6.74 (d, J = 7.5 Hz, 1H), 5.19 (s, 2H), 4.41 (s, 2H), 3.65 (t, J = 5.5 Hz, 2H), 2.60 (s, 2H), 2.30 (s, 3H). | 356 |
| 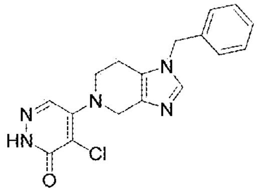 | 1H NMR (400 MHz, DMSO-d6) chemical shifts 12.87 (s, 1H), 7.91 (s, 1H), 7.72 (s, 1H), 7.38 (dd, J = 8.1, 6.6 Hz, 2H), 7.31 (t, J = 7.2 Hz, 1H), 7.25 - 7.18 (m, 2H), 5.17 (s, 2H), 4.38 (s, 2H), 3.64 (t, J = 5.6 Hz, 2H), 2.64 (s, 2H). | 342 |

Figure 27

| | | |
|---|---|---|
| 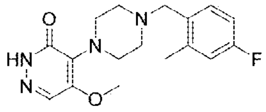 | 1H NMR (300 MHz, DMSO-d6) chemical shifts 12.61 (s, 1H), 7.90 (s, 1H), 7.26 (dd, J = 8.3, 6.3 Hz, 1H), 7.10 - 6.76 (m, 2H), 3.84 (s, 3H), 3.42 (s, 2H), 3.25 (t, J = 4.8 Hz, 4H), 2.40 (t, J = 4.8 Hz, 4H), 2.35 (s, 3H). | 333 |
| 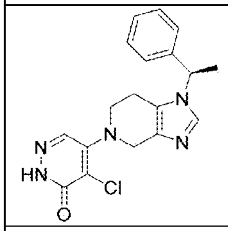 | 1H NMR (300 MHz, DMSO-d6) chemical 12.87 (s, 1H), 7.88 (d, J = 5.6 Hz, 2H), 7.43 - 7.17 (m, 5H), 5.43 (d, J = 6.9 Hz, 1H), 4.37 (s, 2H), 3.72 - 3.60 (m, 1H), 3.57 (s, 1H), 2.69 (s, 1H), 2.44 (s, 1H),1.81 (d, J = 7.1 Hz, 3H). | 356 |
| 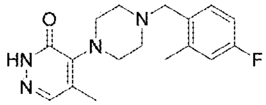 | 1H NMR (300 MHz, DMSO-d6) chemical shifts 12.58 (s, 1H), 7.59 (s, 1H), 7.27 (dd, J = 8.4, 6.2 Hz, 1H), 7.08 - 6.89 (m, 2H), 3.44 (s, 2H), 3.19 (t, J = 4.7 Hz, 4H), 2.47 - 2.33 (m, 7H), 2.10 (s, 3H). | 317 |
| 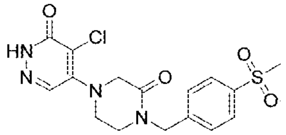 | 1H NMR (400 MHz, DMSO-d6) chemical shifts 13.00 (s, 1H), 7.96 - 7.87 (m, 3H), 7.56 (d, J = 8.1 Hz, 2H), 4.70 (s, 2H), 4.21 (s, 2H), 3.73 (t, J = 5.3 Hz, 2H), 3.43 (t, J = 5.4 Hz, 2H), 3.23 (s, 3H). | 397 |
| 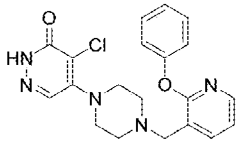 | 1H NMR (400 MHz, DMSO-d6) chemical shifts 12.94 (s, 1H), 8.04 (dd, J = 4.9, 1.9 Hz, 1H), 7.93 - 7.85 (m, 2H), 7.45 - 7.36 (m, 2H), 7.24 - 7.12 (m, 2H), 7.14 - 7.06 (m, 2H), 3.69 (s, 2H), 3.44 (s, 4H), 2.60 (t, J = 4.8 Hz, 4H). | 398 |
| 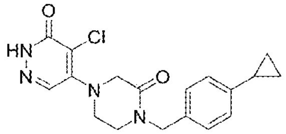 | 1H NMR (300 MHz, DMSO-d6) chemical shifts 12.99 (s, 1H), 7.87 (s, 1H), 7.16 (d, J = 8.1 Hz, 2H), 7.11 - 7.01 (m, 2H), 4.53 (s, 2H), 4.17 (s, 2H), 3.67 (t, J = 5.3 Hz, 2H), 3.35 (d, J = 10.6 Hz, 2H), 1.90 (ddd, J = 13.4, 8.4, 5.1 Hz, 1H), 1.01 - 0.86 (m, 2H), 0.72 - 0.60 (m, 2H). | 359 |
| **Structure** | **NMR** | **MS** |
| 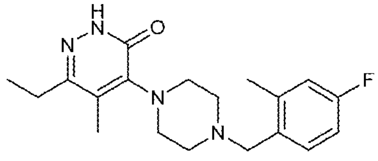 | 1H NMR (400 MHz, Methanol-d4) chemical shifts 7.26 (dd, J = 8.4, 6.0 Hz, 1H), 6.95 - 6.79 (m, 2H), 3.53 (s, 2H), 3.24 (t, J = 4.8 Hz, 4H), 2.68 - 2.54 (m, 6H), 2.40 (s, 3H), 2.21 (s, 3H), 1.19 (t, J = 7.4 Hz, 3H). | 345 |
| 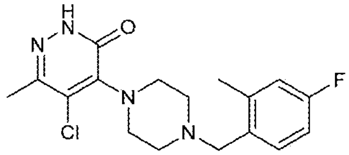 | 1H NMR (400 MHz, DMSO-d6) chemical shifts 12.66 (s, 1H), 7.26 (dd, J = 8.4, 6.2 Hz, 1H), 7.02 (dd, J = 10.1, 2.8 Hz, 1H), 6.95 (td, J = 8.7, 2.8 Hz, 1H), 3.44(s, 2H),3.33 (dd, J = | 351 |

Figure 28

| | | |
|---|---|---|
| | 7.7, 3.2 Hz, 4H), 2.44 (t, J = 4.7 Hz, 4H), 2.35 (s, 3H), 2.24 (s, 3H). | |
| 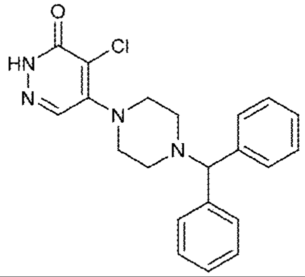 | 1H NMR (400 MHz, DMSO-d6) chemical shifts 12.92 (s, 1H), 7.85 (d, J = 4.0 Hz, 1H), 7.45 (dd, J = 7.4, 4.5 Hz, 4H), 7.31 (td, J = 7.4, 4.4 Hz, 4H), 7.22 (d, J = 7.4 Hz, 2H), 4.37 (d, J = 5.0 Hz, 1H), 3.42 (s, 4H), 2.42 (s, 4H) | 381 |
| 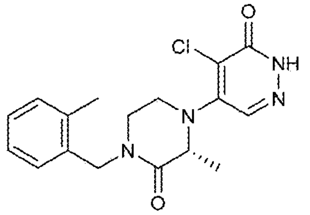 | 1H NMR (400 MHz, DMSO-d6) chemical shifts 12.98 (s, 1H), 7.92 (s, 1H), 7.23 - 7.15 (m, 3H), 7.11 (d, J = 4.8 Hz, 1H), 4.72 - 4.59 (m, 2H), 4.49 (d, J = 15.3 Hz, 1H), 3.78 (d, J = 13.7 Hz, 1H), 3.73 - 3.61 (m, 1H), 3.34 (m, 1H), 3.14 (d, J = 12.3 Hz, 1H), 2.24 (s, 3H), 1.44 (d, J = 6.9 Hz, 3H) | 347 |
| 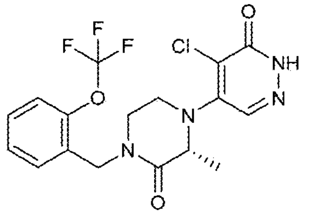 | 1H NMR (400 MHz, DMSO-d6) chemical shifts 12.98 (s, 1H), 7.92 (s, 1H), 7.50 - 7.36 (m, 3H), 7.36 (dd, J = 7.5, 1.9 Hz, 1H), 4.70 (d, J = 15.6 Hz, 1H), 4.69 - 4.56 (m, 2H), 3.81 (d, J = 13.9 Hz, 1H), 3.74 - 3.62 (m, 1H), 3.48 (td, J = 11.4, 4.4 Hz, 1H), 3.21 (d, J = 11.9 Hz, 1H), 1.44 (d, J = 6.9 Hz, 3H) | 417 |
| 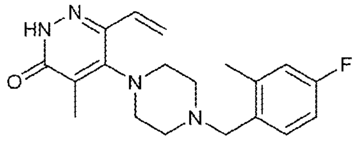 | 1H NMR (400 MHz, DMSO-d6) chemical shifts 12.67 (s, 1H), 7.26 (dd, J = 8.5, 6.2 Hz, 1H), 7.02 (dd, J = 10.1, 2.7 Hz, 1H), 6.95 (td, J = 8.6, 2.9 Hz, 1H), 6.70 (dd, J = 17.1, 10.9 Hz, 1H), 5.83 (dd, J = 17.1, 2.1 Hz, 1H), 5.36 (dd, J = 10.9, 2.0 Hz, 1H), 3.32 (s, 2H), 3.14 (t, J = 4.8 Hz, 4H), 2.42 (d, J = 6.0 Hz, 4H), 2.35 (s, 3H), 2.14 (s, 3H) | 343 |
| 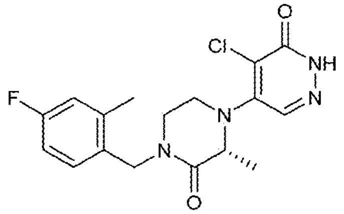 | 1H NMR (400 MHz, DMSO-d6) chemical shifts 12.98 (s, 1H), 7.91 (s, 1H), 7.16 (dd, J = 8.5, 6.0 Hz, 1H), 7.08 (dd, J = 9.9, 2.7 Hz, 1H), 7.01 (td, J = 8.6, 2.7 Hz, 1H), 4.69 - 4.58 (m, 2H), 4.47 (d, J = 15.1 Hz, 1H), 3.78 (d, J = 14.0 Hz, 1H), 3.71 - 3.59 (m, 1H), 3.44 - 3.33 (m, 1H), | 365 |

Figure 29

| | | |
|---|---|---|
| | 3.13 (d, J = 12.1 Hz, 1H), 2.25 (s, 3H), 1.43 (d, J = 6.9 Hz, 3H). | |
| 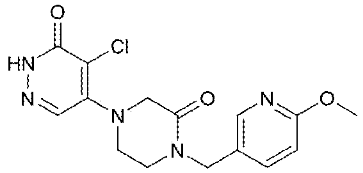 | 1H NMR (400 MHz, DMSO-d6) chemical shifts 12.92 (s, 1H), 8.11 (d, J = 2.1 Hz, 1H), 7.86 (s, 1H), 7.67 - 7.60 (m, 1H), 6.82 (d, J = 8.5 Hz, 1H), 4.52 (s, 2H), 4.15 (s, 2H), 3.84 (s, 3H), 3.67 (d, J = 5.7 Hz, 2H), 3.39 (d, J = 5.4 Hz, 2H) | 350 |
| 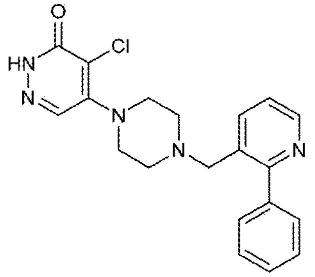 | 1H NMR (400 MHz, DMSO-d6) chemical shifts 12.92 (s, 1H), 8.58 (d, J = 4.7 Hz, 1H), 7.95 (d, J = 7.8 Hz, 1H), 7.84 (s, 1H), 7.63 (d, J = 7.2 Hz, 2H), 7.52 - 7.37 (m, 4H), 3.53 (s, 2H), 3.37 (s, 4H), 2.47 - 2.37 (s, 4H) | 382 |
| 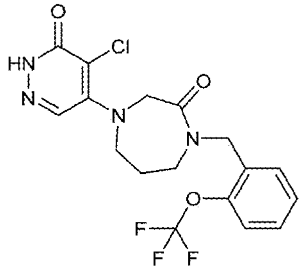 | 1H NMR (400 MHz, DMSO-d6) chemical shifts 12.89 (s, 1H), 7.83 (s, 1H), 7.48 - 7.39 (m, 1H), 7.43 - 7.31 (m, 3H), 4.61 (s, 2H), 4.36 (s, 2H), 3.72 - 3.64 (m, 2H), 3.51 - 3.44 (m, 2H), 1.91 (s, 2H) | 417 |
| 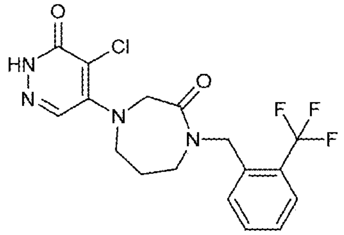 | 1H NMR (400 MHz, DMSO-d6) chemical shifts 12.89 (s, 1H), 7.86 (s, 1H), 7.75 (d, J = 7.7 Hz, 1H), 7.62 (t, J = 7.6 Hz, 1H), 7.50 (t, J = 7.6 Hz, 1H), 7.36 (d, J = 7.8 Hz, 1H), 4.72 (s, 2H), 4.40 (s, 2H), 3.71 (t, J = 5.7 Hz, 2H), 3.55 - 3.47 (m, 2H), 2.02 (s, 2H). | 401 |
| 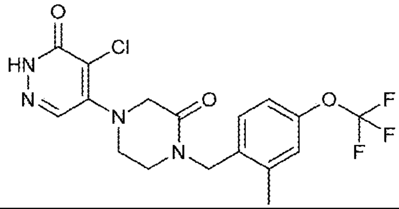 | 1H NMR (400 MHz, DMSO-d6) chemical shifts 13.01 (s, 1H), 7.90 (s, 1H), 7.26 (d, J = 8.6 Hz, 2H), 7.19 (d, J = 8.8 Hz, 1H), 4.61 (s, 2H), 4.21 (s, 2H), 3.74 (t, J = 5.4 Hz, 2H), 3.34 (s, 2H), 2.31 (s, 3H). | 417 |
| 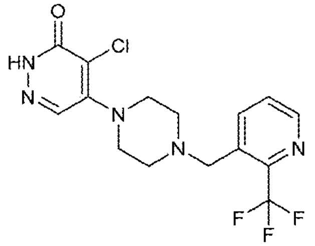 | 1H NMR (400 MHz, DMSO-d6) chemical shifts 12.97 (s, 1H), 8.65 (dd, J = 4.8, 1.5 Hz, 1H), 8.25 - 8.18 (m, 1H), 7.88 (s, 1H), 7.75 (dd, J = 7.9, 4.6 Hz, 1H), 3.73 (d, J = 1.9 Hz, 2H), 3.41 (t, J = 4.8 Hz, 4H), 2.54 (t, J = 4.7 Hz, 4H). | 374 |

Figure 30

| | | |
|---|---|---|
| 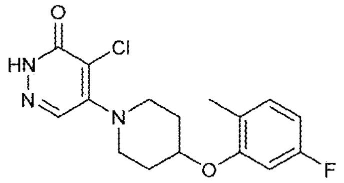 | 1H NMR (400 MHz, DMSO-d6) chemical shifts 12.93 (s, 1H), 7.92 (s, 1H), 7.17 (t, J = 7.7 Hz, 1H), 6.98 (dd, J = 11.5, 2.5 Hz, 1H), 6.67 (td, J = 8.4, 2.5 Hz, 1H), 4.75 - 4.66 (m, 1H), 3.60 (ddd, J = 12.0, 7.6, 3.5 Hz, 2H), 3.43 - 3.35 (m, 2H), 2.14 (s, 3H), 2.12 - 2.00 (m, 2H), 1.78 (q, J = 10.0, 9.5 Hz, 2H). | 338 |
| 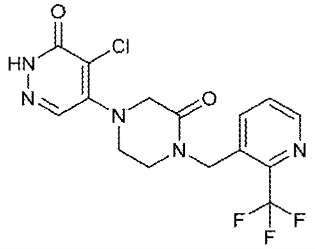 | 1H NMR (400 MHz, DMSO-d6) chemical shifts 13.01 (s, 1H), 8.67 (d, J = 4.6 Hz, 1H), 7.95 - 7.85 (m, 2H), 7.75 (dd, J = 8.0, 4.6 Hz, 1H), 4.79 (s, 2H), 4.25 (s, 2H), 3.80 (t, J = 5.3 Hz, 2H), 3.48 (t, J = 5.3 Hz, 2H). | 388 |
| 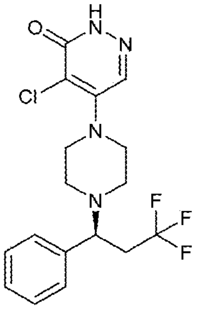 | 1H NMR (400 MHz, Methanol-d4) chemical shifts 7.82 (s, 1H), 7.45 - 7.30 (m, 5H), 4.02 - 3.94 (m, 1H), 3.56 - 3.42 (m, 4H), 3.06 - 2.93 (m, 1H), 2.78 (ddd, J = 15.1, 10.9, 8.2 Hz, 1H), 2.58 (dt, J = 19.0, 5.4 Hz, 4H) | 387 |
| 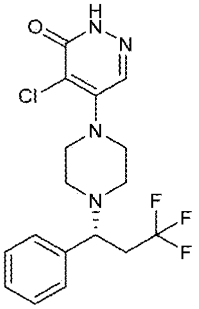 | 1H NMR (400 MHz, Methanol-d4) chemical shifts 7.82 (s, 1H), 7.45 - 7.30 (m, 5H), 4.02 - 3.94 (m, 1H), 3.56 - 3.42 (m, 4H), 3.06 - 2.93 (m, 1H), 2.78 (ddd, J = 15.1, 10.9, 8.2 Hz, 1H), 2.58 (dt, J = 19.0, 5.4 Hz, 4H) | 387 |
| 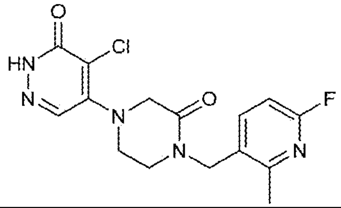 | 1H NMR (400 MHz, DMSO-d6) chemical shifts 7.86 (t, J = 8.3 Hz, 1H), 6.95 (dd, J = 8.2, 3.1 Hz, 1H), 5.30 (t, J = 5.2 Hz, 1H), 4.50 (d, J = 4.5 Hz, 2H), 2.37 (s, 3H) | 352 |
Figure 31

| | | |
|---|---|---|
| 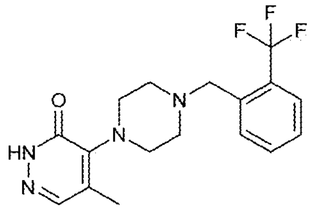 | 1H NMR (400 MHz, DMSO-d6) chemical shifts 12.60 (s, 1H), 7.83 (d, J = 7.8 Hz, 1H), 7.69 (q, J = 7.8 Hz, 2H), 7.60 (s, 1H), 7.48 (t, J = 7.6 Hz, 1H), 3.66 (s, 2H), 3.23 (t, J = 4.7 Hz, 4H), 2.47 (t, J = 4.7 Hz, 4H), 2.10 (s, 3H) | 353 |
| 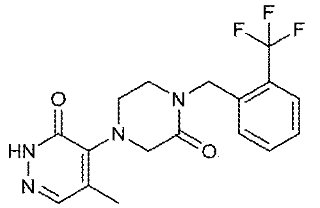 | 1H NMR (400 MHz, DMSO-d6) chemical shifts 12.82 (s, 1H), 7.76 (d, J = 7.9 Hz, 1H), 7.71 - 7.63 (m, 2H), 7.51 (d, J = 7.0 Hz, 2H), 4.75 (s, 2H), 3.98 (s, 2H), 3.48 (t, J = 5.3 Hz, 2H), 3.27 (t, J = 5.3 Hz, 2H), 2.14 (s, 3H) | 367 |
| 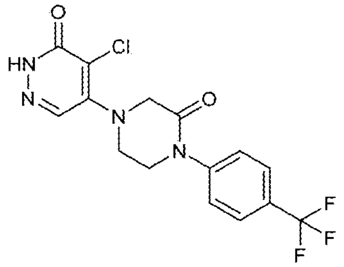 | 1H NMR (400 MHz, DMSO-d6) chemical shifts 13.01 (s, 1H), 7.94 (s, 1H), 7.80 (d, J = 8.5 Hz, 2H), 7.67 (d, J = 8.4 Hz, 2H), 4.32 (s, 2H), 3.90 (q, J = 4.5 Hz, 4H) | 373 |
| 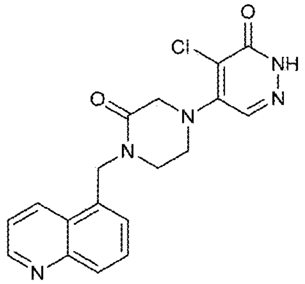 | 1H NMR (400 MHz, Methanol-d4) chemical shifts 8.90 (s, 1H), 8.72 (d, J = 8.8 Hz, 1H), 8.06 (d, J = 8.6 Hz, 1H), 7.87 (s, 1H), 7.80 (t, J = 7.8 Hz, 1H), 7.68 - 7.58 (m, 2H), 5.22 (s, 2H), 4.32 (s, 2H), 3.75 (s, 2H), 3.44 (d, J = 5.6 Hz, 2H) | 370 |
| 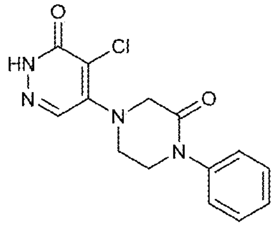 | 1H NMR (400 MHz, DMSO-d6) chemical shifts 13.00 (s, 1H), 7.94 (s, 1H), 7.48 - 7.35 (m, 4H), 7.29 (t, J = 7.0 Hz, 1H), 4.27 (s, 2H), 3.90 - 3.80 (m, 4H) | 305 |
| 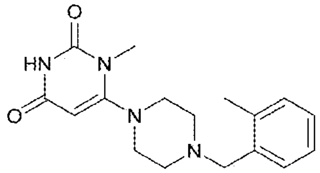 | 1H NMR (400 MHz, DMSO-d6) chemical shifts 10.97 (s, 1H), 7.26 - 7.19 (m, 1H), 7.20 - 7.09 (m, 3H), 4.99 (s, 1H), 3.49 (s, 2H), 3.21 (s, 3H), 2.89 (s, 4H), 2.44 (s, 4H), 2.33 (s, 3H) | 315 |

Figure 32

| | | |
|---|---|---|
| 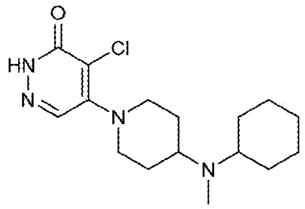 | 1H NMR (400 MHz, DMSO-d6) chemical shifts 12.89 (s, 1H), 7.85 (s, 1H), 3.79 (d, J = 12.7 Hz, 2H), 2.99 (t, J = 12.2 Hz, 2H), 2.76 (s, 1H), 2.51 (s, 1H), 2.22 (s, 3H), 1.71 (s, 6H), 1.56 (t, J = 11.3 Hz, 3H), 1.25 (q, J = 10.9 Hz, 4H), 1.07 (d, J = 11.7 Hz, 1H) | 325 |
| 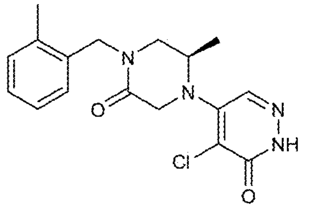 | 1H NMR (400 MHz, DMSO-d6) chemical shifts 12.99 (s, 1H), 7.88 (s, 1H), 7.18 (d, J = 12.2 Hz, 4H), 4.60 (s, 2H), 4.34 (s, 1H), 4.25 (d, J = 17.1 Hz, 1H), 4.05 (d, J = 17.2 Hz, 1H), 3.53 (d, J = 12.1 Hz, 1H), 3.03 (d, J = 12.5 Hz, 1H), 2.25 (s, 3H), 1.16 (d, J = 6.7 Hz, 3H) | 347 |
| 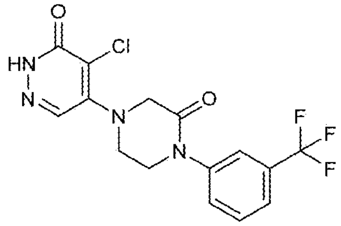 | 1H NMR (400 MHz, DMSO-d6) chemical shifts 13.00 (s, 1H), 7.95 (s, 1H), 7.85 (s, 1H), 7.76 - 7.64 (m, 3H), 4.31 (s, 2H), 3.90 (s, 4H) | 373 |
| 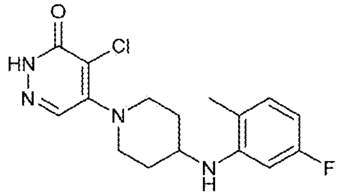 | 1H NMR (400 MHz, DMSO-d6) chemical shifts 12.90 - 12.85 (m, 1H), 7.89 (s, 1H), 6.94 (t, J = 7.6 Hz, 1H), 6.50 - 6.42 (m, 1H), 6.30 - 6.20 (m, 1H), 4.80 (d, J = 8.3 Hz, 1H), 3.82 (d, J = 12.9 Hz, 2H), 3.55 (s, 1H), 3.16 (t, J = 12.0 Hz, 2H), 2.01 (d, J = 24.0 Hz, 5H), 1.61 (q, J = 10.0 Hz, 2H) | 337 |
| 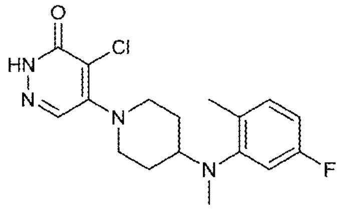 | 1H NMR (400 MHz, DMSO-d6) chemical shifts 12.88 (s, 1H), 7.85 (s, 1H), 7.20 (t, J = 7.8 Hz, 1H), 6.94 (dd, J = 11.3, 2.7 Hz, 1H), 6.78 (td, J = 8.3, 2.6 Hz, 1H), 3.78 (d, J = 12.7 Hz, 2H), 3.09 - 2.95 (m, 3H), 2.60 (s, 3H), 2.23 (s, 3H), 1.74 (d, J = 8.8 Hz, 4H). | 351 |

Figure 33

| | | |
|---|---|---|
| 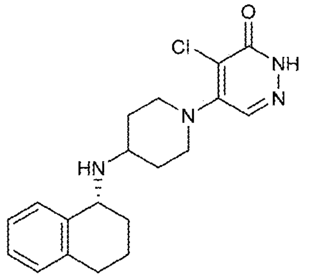 | 1H NMR (400 MHz, DMSO-d6) chemical shifts 12.86 (s, 1H), 7.87 (s, 1H), 7.52 - 7.35 (m, 1H), 7.12 (dd, J = 9.7, 5.6 Hz, 2H), 7.04 (d, J = 5.8 Hz, 1H), 3.82 (d, J = 5.0 Hz, 1H), 3.74 (t, J = 14.6 Hz, 2H), 3.09 (dt, J = 18.2, 9.2 Hz, 2H), 2.93 - 2.83 (m, 1H), 2.74 (dt, J = 16.6, 5.7 Hz, 1H), 2.65 (dt, J = 16.3, 6.7 Hz, 1H), 2.11 - 1.99 (m, 1H), 1.83 (dd, J = 26.6, 12.1 Hz, 3H), 1.69 (d, J = 36.0 Hz, 3H), 1.43 (d, J = 11.7 Hz, 2H) | 359 |
| 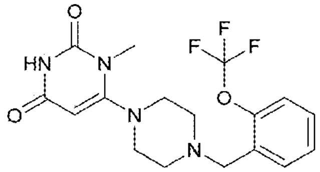 | 1H NMR (400 MHz, DMSO-d6) chemical shifts 10.98 (s, 1H), 7.58 (dd, J = 6.8, 2.5 Hz, 1H), 7.48 - 7.35 (m, 2H), 7.36 (dt, J = 7.4, 1.7 Hz, 1H), 5.00 (s, 1H), 3.61 (s, 2H), 3.20 (s, 3H), 2.91 (s, 4H), 2.55 (s, 4H) | 385 |
| 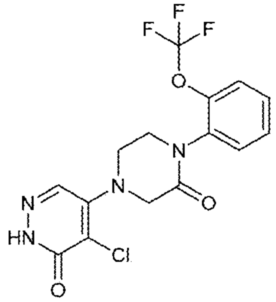 | 1H NMR (400 MHz, DMSO-d6) chemical shifts 13.05 (s, 1H), 7.94 (s, 1H), 7.58 (s, 1H), 7.50 (s, 3H), 4.28 (s, 2H), 3.86 (s, 2H), 3.74 (s, 2H) | 389 |
| 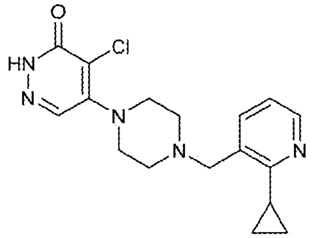 | 1H NMR (400 MHz, DMSO-d6) chemical shifts 12.94 (s, 1H), 8.31 (d, J = 4.8 Hz, 1H), 7.87 (s, 1H), 7.59 (d, J = 7.6 Hz, 1H), 7.10 (t, J = 6.1 Hz, 1H), 3.66 (s, 2H), 3.38 (s, 4H), 3.23 (s, 1H), 2.54 (d, J = 4.9 Hz, 4H), 2.42 (s, 1H), 0.98 - 0.89 (m, 4H) | 346 |
| 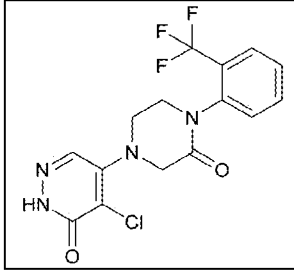 | 1H NMR (400 MHz, DMSO-d6) chemical shifts 12.90 (s, 1H), 7.94 (s, 1H), 7.88 - 7.77 (m, 2H), 7.63 (q, J = 7.3 Hz, 2H), 4.27 (s, 2H), 3.99 - 3.90 (m, 1H), 3.80 (d, J = 8.2 Hz, 2H), 3.65 - 3.56 (m, 1H) | 373 |

Figure 34

| | | |
|---|---|---|
| 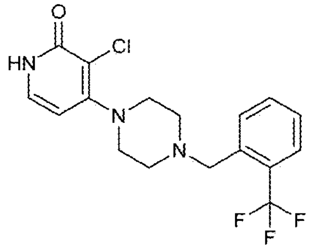 | 1H NMR (400 MHz, DMSO-d6) chemical shifts 11.62 (s, 1H), 7.80 (d, J = 7.8 Hz, 1H), 7.75 - 7.63 (m, 2H), 7.48 (t, J = 7.8 Hz, 1H), 7.28 (d, J = 7.2 Hz, 1H), 6.10 (d, J = 7.3 Hz, 1H), 3.68 (s, 2H), 3.22 (t, J = 4.6 Hz, 4H), 2.54 (s, 4H). | 372 |
| 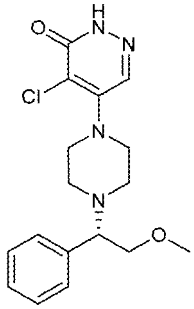 | 1H NMR (400 MHz, DMSO-d6) chemical shifts 12.91 (s, 1H), 7.82 (d, J = 2.1 Hz, 1H), 7.31 (dq, J = 14.2, 6.8 Hz, 5H), 3.74 (s, 1H), 3.63 (d, J = 6.3 Hz, 2H), 3.22 (d, J = 2.0 Hz, 3H), 2.56 (s, 4H), 2.46 (s, 4H). | 349 |
| 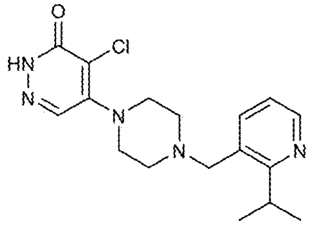 | 1H NMR (400 MHz, DMSO-d6) chemical shifts 12.94 (s, 1H), 8.45 (d, J = 4.8 Hz, 1H), 7.86 (s, 1H), 7.61 (d, J = 7.7 Hz, 1H), 7.16 (t, J = 6.0 Hz, 1H), 3.56 (s, 2H), 3.44 (p, J = 6.2 Hz, 1H), 3.36 (s, 4H), 2.48 (s, 4H), 1.21 (d, J = 6.7 Hz, 6H) | 348 |
| 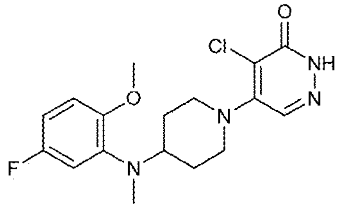 | 1H NMR (400 MHz, DMSO-d6) chemical shifts 12.89 (s, 1H), 7.85 (s, 1H), 6.91 (t, J = 7.3 Hz, 1H), 6.79 - 6.65 (m, 2H), 3.85 - 3.75 (m, 5H), 3.47 (s, 1H), 2.97 (t, J = 11.8 Hz, 2H), 2.62 (s, 3H), 1.74 (d, J = 19.8 Hz, 4H). | 367 |
| 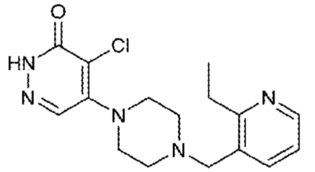 | 1H NMR (400 MHz, DMSO-d6) chemical shifts 12.93 (s, 1H), 8.41 (d, J = 4.7 Hz, 1H), 7.86 (s, 1H), 7.64 (d, J = 7.6 Hz, 1H), 7.23 - 7.14 (m, 1H), 3.54 (s, 2H), 3.39-3.36 (m, 4H), 2.85 (q, J = 7.5 Hz, 2H) ,2.50 - 2.51 (m, 4H), 1.23 (t, J = 7.5 Hz, 3H). | 334 |
| 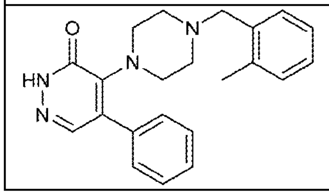 | 9,93 (s, 1H), 7.10-7.58 (m, 10 H), 3.42 (s, 2H), 3.05 (bs, 4H), 2.42-2.45 (m, 4H), 2.32 (s, 3H) | 361.3 |

Figure 35

| | | |
|---|---|---|
| 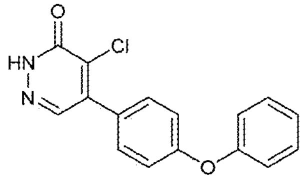 | 1H NMR (400 MHz, DMSO-d6) chemical shifts 13.54 (s, 1H), 7.97 (s, 1H), 7.67 - 7.59 (m, 2H), 7.46 (t, J = 7.9 Hz, 2H), 7.23 (t, J = 7.4 Hz, 1H), 7.13 (dd, J = 8.5, 3.2 Hz, 4H). | 298 |
| 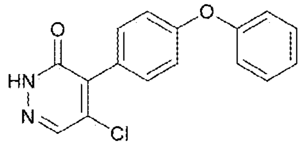 | 1H NMR (400 MHz, DMSO-d6) chemical shifts 13.10 (s, 1H), 8.10 (s, 1H), 7.52 - 7.41 (m, 4H), 7.21 (t, J = 7.3 Hz, 1H), 7.14 - 7.03 (m, 4H). | 298 |
| 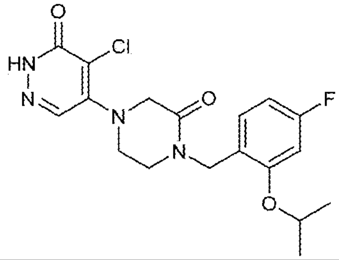 | 1H NMR (400 MHz, DMSO-d6) chemical shifts 12.46 (s, 1H), 7.87 (s, 1H), 7.20 (t, J = 7.7 Hz, 1H), 6.94 (d, J = 11.7 Hz, 1H), 6.71 (t, J = 8.5 Hz, 1H), 4.71 - 4.63 (m, 1H), 4.47 (s, 2H), 4.14 (s, 2H), 3.69 (s, 2H), 3.36 (s, 2H), 1.30 - 1.23 (m, 6H). | 395 |
| 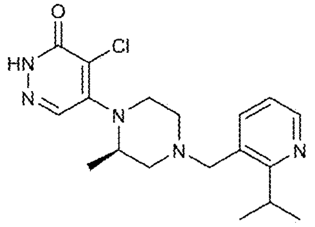 | 1H NMR (400 MHz, DMSO-d6) chemical shifts 12.92 (s, 1H), 8.45 (d, J = 4.7 Hz, 1H), 7.85 (s, 1H), 7.60 (d, J = 7.8 Hz, 1H), 7.16 (dd, J = 7.5, 5.0 Hz, 1H), 4.08 (s, 1H), 3.50 (d, J = 15.9 Hz, 4H), 3.32 (s, 1H), 2.67 (d, J = 10.6 Hz, 1H), 2.57 (d, J = 10.7 Hz, 1H), 2.40 (d, J = 10.6 Hz, 1H), 2.21 (t, J = 10.9 Hz, 1H), 1.20 (dd, J = 14.5, 6.6 Hz, 9H). | 362 |
| 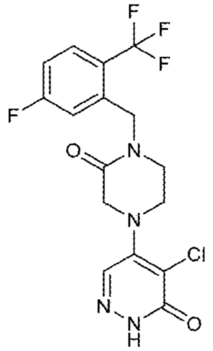 | 1H NMR (400 MHz, DMSO-d6) chemical shifts 12.99 (s, 1H), 7.89 (d, J = 18.5 Hz, 2H), 7.37 (t, J = 8.4 Hz, 1H), 7.24 (d, J = 9.9 Hz, 1H), 4.76 (s, 2H), 4.27 (s, 2H), 3.81 (t, J = 5.3 Hz, 2H), 3.47 (t, J = 5.3 Hz, 2H). | 405 |
| 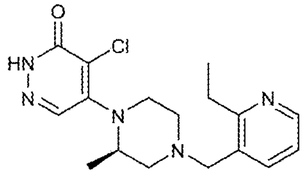 | 1H NMR (400 MHz, DMSO-d6) chemical shifts 12.93 (s, 1H), 8.41 (d, J = 4.8 Hz, 1H), 7.85 (s, 1H), 7.63 (d, J = 7.7 Hz, 1H), 7.19 (t, J = 6.4 Hz, 1H), 4.05 (s, 1H), 3.56 - 3.38 (m, 3H), 3.25 (s, 1H), 2.87 (d, J = 9.0 Hz, 2H), 2.67 (d, J = 10.9 Hz, 1H), 2.56 (s, 1H), 2.41 (d, J = 10.6 Hz, 1H), | 348 |

Figure 36

| | | |
|---|---|---|
| | 2.24 (t, J = 10.6 Hz, 1H), 1.28 - 1.14 (m, 6H). | |
| 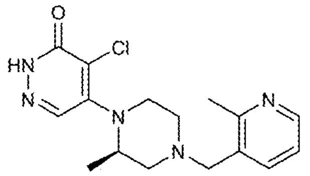 | 1H NMR (400 MHz, DMSO-d6) chemical shifts 12.93 (s, 1H), 8.35 (d, J = 4.8 Hz, 1H), 7.86 (s, 1H), 7.63 (d, J = 7.6 Hz, 1H), 7.20 (t, J = 6.4 Hz, 1H), 4.07 (s, 1H), 3.46 (d, J = 16.9 Hz, 3H), 3.29 (s, 1H), 2.69 (d, J = 10.8 Hz, 1H), 2.54 (s, 4H), 2.41 (d, J = 11.4 Hz, 1H), 2.25 (t, J = 10.6 Hz, 1H), 1.19 (d, J = 6.5 Hz, 3H). | 334 |
| 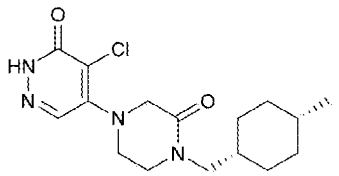 | 1H NMR (400 MHz, DMSO-d6) chemical shifts 12.96 (s, 1H), 7.86 (s, 1H), 4.08 (d, J = 2.6 Hz, 2H), 3.69 (t, J = 5.3 Hz, 2H), 3.43 (d, J = 5.3 Hz, 2H), 3.34 (s, 1H), 3.19 (d, J = 7.1 Hz, 1H), 1.85 (s, 1H), 1.66 (d, J = 14.7 Hz, 1H), 1.59 (d, J = 11.6 Hz, 1H), 1.46 - 1.23 (m, 3H), 1.24 (s, 3H), 0.88 (dd, J = 16.2, 6.7 Hz, 5H). | 339 |
| 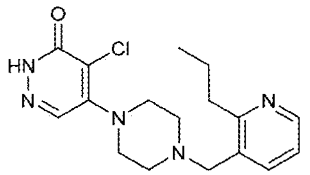 | 1H NMR (400 MHz, DMSO-d6) chemical shifts 12.93 (s, 1H), 8.40 (d, J = 4.7 Hz, 1H), 7.86 (s, 1H), 7.65 (d, J = 7.6 Hz, 1H), 7.22 - 7.14 (m, 1H), 3.54 (s, 2H), 3.37 (d, J = 5.2 Hz, 4H), 2.79 (t, J = 7.7 Hz, 2H), 2.51 (d, J = 2.0 Hz, 4H), 1.70 (p, J = 7.5 Hz, 2H), 0.95 (t, J = 7.3 Hz, 3H). | 348 |
| 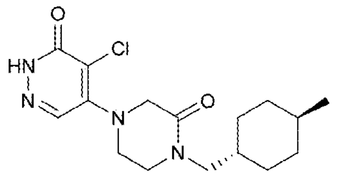 | 1H NMR (400 MHz, DMSO-d6) chemical shifts 12.96 (s, 1H), 7.86 (s, 1H), 4.08 (s, 2H), 3.69 (d, J = 5.4 Hz, 2H), 3.43 (d, J = 5.3 Hz, 2H), 3.19 (d, J = 6.9 Hz, 2H), 1.70 - 1.57 (m, 4H), 1.24 (s, 2H), 1.00 - 0.82 (m, 7H). | 339 |
| 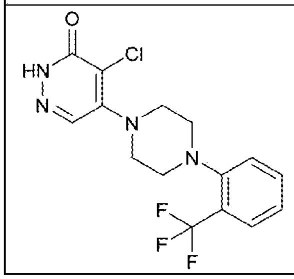 | 1H NMR (400 MHz, DMSO-d6) chemical shifts 12.97 (s, 1H), 7.94 (s, 1H), 7.73 - 7.60 (m, 3H), 7.38 (t, J = 7.5 Hz, 1H), 3.51 (t, J = 4.5 Hz, 4H), 2.99 (t, J = 4.7 Hz, 4H). | 359 |

Figure 37

| | | |
|---|---|---|
| 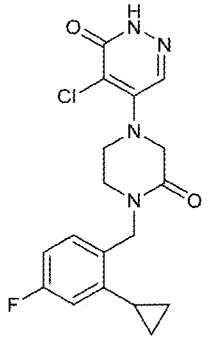 | 1H NMR (400 MHz, DMSO-d6) chemical shifts 12.94 (s, 1H), 7.88 (s, 1H), 7.22 (dd, J = 8.5, 6.1 Hz, 1H), 6.99 (td, J = 8.5, 2.7 Hz, 1H), 6.81 (dd, J = 10.6, 2.8 Hz, 1H), 4.77 (s, 2H), 4.19 (s, 2H), 3.70 (t, J = 5.3 Hz, 2H), 3.28 (t, J = 5.4 Hz, 2H), 2.04 - 1.92 (m, 1H), 0.96 - 0.87 (m, 2H), 0.73 - 0.64 (m, 2H). | 377 |
| 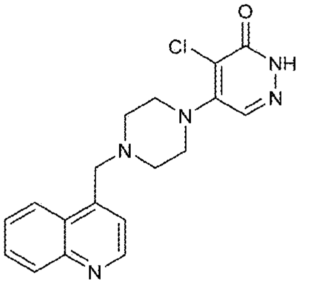 | 1H NMR (400 MHz, DMSO-d6) chemical shifts 12.94 (s, 1H), 8.86 (d, J = 4.3 Hz, 1H), 8.33 (d, J = 8.4 Hz, 1H), 8.04 (d, J = 8.4 Hz, 1H), 7.86 (s, 1H), 7.77 (dd, J = 8.1, 6.6 Hz, 1H), 7.64 (t, J = 7.6 Hz, 1H), 7.53 (d, J = 4.3 Hz, 1H), 4.02 (s, 2H), 3.40 (t, J = 4.7 Hz, 4H), 2.61 (t, J = 4.8 Hz, 4H). | 356 |
| 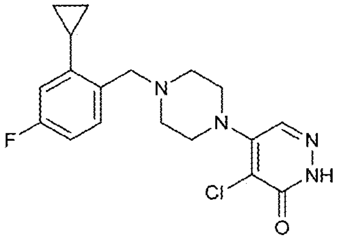 | 1H NMR (400 MHz, DMSO-d6) chemical shifts 12.93 (s, 1H), 7.86 (s, 1H), 7.29 (dd, J = 8.4, 6.3 Hz, 1H), 6.94 (td, J = 8.5, 2.7 Hz, 1H), 6.76 (dd, J = 10.9, 2.7 Hz, 1H), 3.64 (s, 2H), 3.38 (t, J = 4.6 Hz, 4H), 2.54 (s, 4H), 2.23 (q, J = 8.4, 7.2 Hz, 1H), 0.95 (dt, J = 8.9, 3.1 Hz, 2H), 0.72 - 0.63 (m, 2H). | 363 |
| 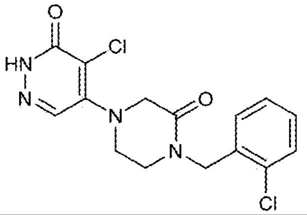 | 1H NMR (400 MHz, DMSO-d6) chemical shifts 12.98 (s, 1H), 7.90 (s, 1H), 7.53 - 7.46 (m, 1H), 7.41 - 7.26 (m, 3H), 4.67 (s, 2H), 4.22 (s, 2H), 3.76 (t, J = 5.4 Hz, 2H), 3.43 (d, J = 10.7 Hz, 2H). | 353 |
| 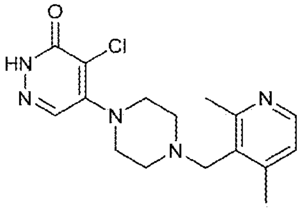 | 1H NMR (400 MHz, DMSO-d6) chemical shifts 12.93 (s, 1H), 8.19 (d, J = 4.9 Hz, 1H), 7.85 (s, 1H), 7.04 (d, J = 4.9 Hz, 1H), 3.55(s,2H),3.33 (dd, J = 8.7, 3.7 Hz, 4H), 2.55(s,3H),2.51 (d, J = 7.9 Hz, 4H), 2.37 (s, 3H). | 334 |
| 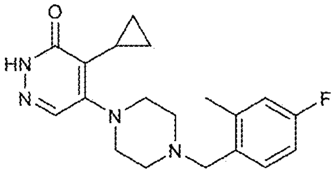 | 1H NMR (400 MHz, DMSO-d6) chemical shifts 12.41 (s, 1H), 7.73 (s, 1H), 7.27 (dd, J = 8.3, 6.2 Hz, 1H), 7.12 - 6.85 (m, 2H), 3.47 (s, 2H), 3.20 (t, J = 4.6 Hz, 4H), 2.53- | 343 |

Figure 38

| | | |
|---|---|---|
| | 2.49 (m, 4H), 2.36 (s, 3H), 1.63 (ddd, J = 11.0, 8.6, 5.5 Hz, 1H), 1.08 (dq, J = 5.9, 3.6 Hz, 2H), 0.83 (dt, J = 8.6, 3.1 Hz, 2H). | |
| 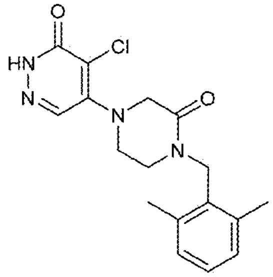 | 1H NMR (400 MHz, DMSO-d6) chemical shifts 12.96 (s, 1H), 7.85 (s, 1H), 7.13 (dd, J = 8.5, 6.3 Hz, 1H), 7.07 (d, J = 7.4 Hz, 2H), 4.71 (s, 2H), 4.15 (s, 2H), 3.59 (t, J = 5.3 Hz, 2H), 3.03 (t, J = 5.3 Hz, 2H), 2.27 (s, 6H). | 347 |
| 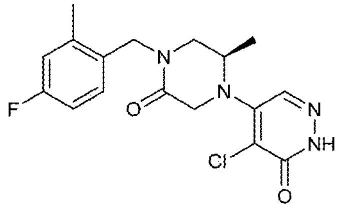 | 1H NMR (400 MHz, DMSO-d6) chemical shifts 12.97 (s, 1H), 7.88 (s, 1H), 7.22 (dd, J = 8.5, 6.0 Hz, 1H), 7.12 - 6.96 (m, 2H), 4.65 - 4.52 (m, 2H), 4.34 (s, 1H), 4.25 (d, J = 17.1 Hz, 1H), 4.05 (d, J = 17.2 Hz, 1H), 3.53 (dd, J = 12.5, 4.5 Hz, 1H), 3.03 (dd, J = 12.4, 3.0 Hz, 1H), 2.28 (s, 3H), 1.15 (d, J = 6.6 Hz, 3H). | 365 |
| 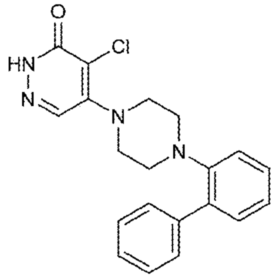 | 1H NMR (400 MHz, DMSO-d6) chemical shifts 12.90 (s, 1H), 7.82 (s, 1H), 7.65 (d, J = 7.6 Hz, 2H), 7.45 (t, J = 7.5 Hz, 2H), 7.33 (q, J = 7.1 Hz, 2H), 7.23 (d, J = 7.6 Hz, 1H), 7.12 (dt, J = 7.1, 3.1 Hz, 2H), 3.31 (d, J = 7.3 Hz, 4H), 2.87 (t, J = 4.4 Hz, 4H). | 367 |
| 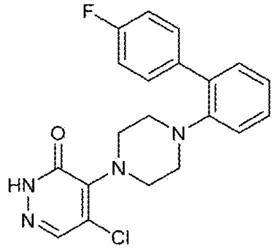 | 1H NMR (400 MHz, DMSO-d6) chemical shifts 12.88 (s, 1H), 7.76 - 7.65 (m, 3H), 7.30 (dt, J = 17.7, 8.1 Hz, 3H), 7.22 (d, J = 7.5 Hz, 1H), 7.12 (d, J = 7.6 Hz, 2H), 3.32 (d, J = 1.2 Hz, 4H), 2.84 (d, J = 5.1 Hz, 4H). | 385 |
| 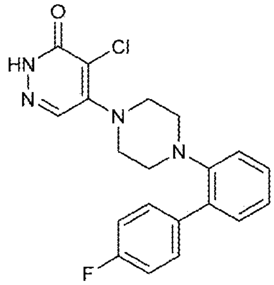 | 1H NMR (400 MHz, DMSO-d6) chemical shifts 12.92 (s, 1H), 7.84 (s, 1H), 7.70 (dd, J = 8.3, 5.7 Hz, 2H), 7.28 (td, J = 17.1, 16.2, 7.8 Hz, 5H), 7.13 (d, J = 7.6 Hz, 2H), 3.33 (s, 4H), 2.87 (t, J = 4.6 Hz, 4H). | 385 |

Figure 39

| | | |
|---|---|---|
| 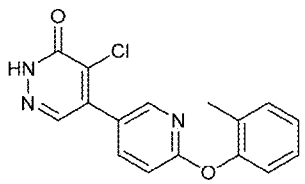 | 1H NMR (400 MHz, DMSO-d6) chemical shifts 13.53 (s, 1H), 8.35 (d, J = 2.4 Hz, 1H), 8.12 (dd, J = 9.1, 2.3 Hz, 1H), 8.03 (s, 1H), 7.34 (d, J = 7.5 Hz, 1H), 7.28 (t, J = 7.7 Hz, 1H), 7.24 - 7.15 (m, 2H), 7.12 (d, J = 7.9 Hz, 1H), 2.12 (s, 3H). | 314 |
| 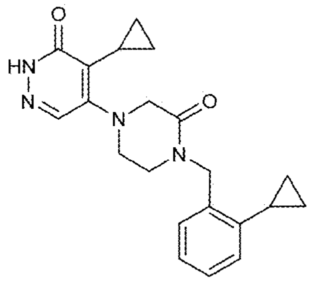 | 1H NMR (400 MHz, DMSO-d6) chemical shifts 12.48 (s, 1H), 7.76 (s, 1H), 7.36 - 7.15 (m, 3H), 7.01 (d, J = 7.4 Hz, 1H), 4.80 (s, 2H), 4.03 (s, 2H), 3.56 (d, J = 5.9 Hz, 2H), 3.28 (s, 2H), 1.95 (s, 1H), 1.64 (s, 1H), 1.01 (d, J = 5.0 Hz, 2H), 0.90 (d, J = 8.1 Hz, 2H), 0.83 (d, J = 8.3 Hz, 2H), 0.63 (d, J = 5.4 Hz, 2H). | 365 |
| 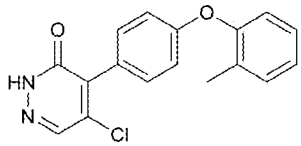 | 1H NMR (400 MHz, DMSO-d6) chemical shifts 13.40 (s, 1H),8.09 (s, 1H), 7.45 (d, J = 8.1 Hz, 2H), 7.37 (d, J = 7.5 Hz, 1H), 7.29 (t, J = 7.7 Hz, 1H), 7.18 (t, J = 7.5 Hz, 1H), 7.04 - 6.94 (m, 3H), 2.19 (s, 3H). | 313 |
| 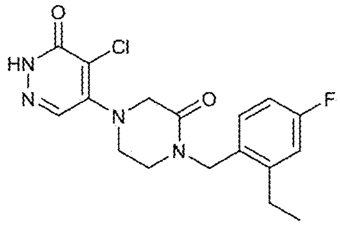 | 1H NMR (400 MHz, DMSO-d6) chemical shifts 12.99 (s, 1H), 7.88 (d, J = 1.8 Hz, 1H), 7.22 (t, J = 7.3 Hz, 1H), 7.13 - 7.05 (m, 1H), 7.02 (td, J = 8.3, 2.1 Hz, 1H), 4.62 (s, 2H), 4.19 (s, 2H), 3.69 (d, J = 11.0 Hz, 1H), 3.69 (s, 1H), 3.37 - 3.25 (m, 2H), 2.63 (q, J = 7.6 Hz, 2H), 1.14 (td, J = 7.5, 1.8 Hz, 3H). | 365 |
| 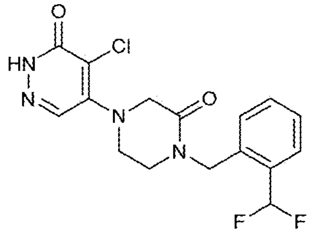 | 1H NMR (400 MHz, DMSO-d6) chemical shifts 12.96 (s, 1H), 7.88 (s, 1H), 7.64 (d, J = 7.7 Hz, 1H), 7.56 (t, J = 7.5 Hz, 1H), 7.47 (t, J = 7.6 Hz, 1H), 7.38 (s, 1H), 7.24 (dd, J = 48.0 Hz, 1H), 4.77 (s, 2H), 4.21 (s, 2H), 3.71 (d, J = 5.4 Hz, 2H), 3.37 (d, J = 5.3 Hz, 2H). | 369 |
| 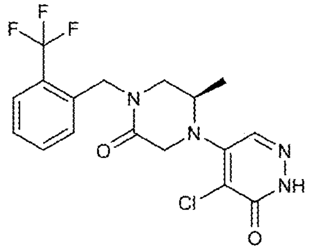 | 1H NMR (400 MHz, Methanol-d4) chemical shifts 7.93 (s, 1H), 7.76 (d, J = 7.8 Hz, 1H), 7.67 (t, J = 7.7 Hz, 1H), 7.51 (t, J = 8.4 Hz, 2H), 5.01 (d, J = 16.1 Hz, 1H), 4.81 (d, J = 16.0 Hz, 1H), 4.51 (s, 1H), 4.43 (d, J = 17.4 Hz, 1H), 4.24 (d, J = 17.5 Hz, 1H), 3.78 (dd, J = 12.4, 4.6 Hz, 1H), 3.15 | 401 |

Figure 40

| | | |
|---|---|---|
| | (d, J = 12.2 Hz, 1H), 1.33 (d, J = 6.8 Hz, 3H). | |
| 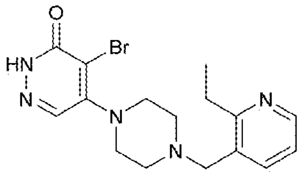 | 1H NMR (400 MHz, DMSO-d6) chemical shifts 12.19 (s, 1H), 8.41 (d, J = 4.8 Hz, 1H), 7.77 (s, 1H), 7.64 (d, J = 7.6 Hz, 1H), 7.18 (t, J = 6.5 Hz, 1H), 3.55 (s, 2H), 3.34 (s, 4H), 2.85 (q, J = 7.5 Hz, 2H), 2.53 (s, 4H), 1.27 - 1.19 (m, 3H). | 378 |
| 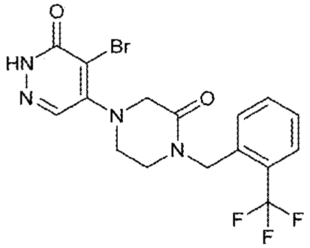 | 1H NMR (400 MHz, DMSO-d6) chemical shifts 12.96 (s, 1H), 7.84 - 7.74 (m, 2H), 7.69 (t, J = 7.7 Hz, 1H), 7.52 (t, J = 7.9 Hz, 1H), 7.41 (d, J = 7.8 Hz, 1H), 4.77 (s, 2H), 4.23 (s, 2H), 3.77 (t, J = 5.3 Hz, 2H), 3.44 (t, J = 5.3 Hz, 2H). | 431 |
| 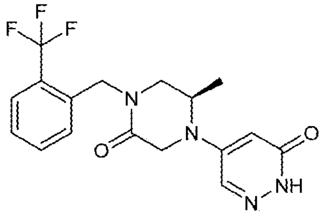 | 1H NMR (400 MHz, DMSO-d6) chemical shifts 12.29 (s, 1H), 7.92 (s, 1H), 7.77 (d, J = 7.9 Hz, 1H), 7.69 (t, J = 7.6 Hz, 1H), 7.53 (t, J = 7.7 Hz, 1H), 7.46 (d, J = 7.8 Hz, 1H), 5.68 (s, 1H), 4.87 - 4.72 (m, 2H), 4.43 (s, 1H), 4.23 (d, J = 17.7 Hz, 1H), 3.83 (d, J = 17.7 Hz, 1H), 3.75 (d, J = 9.6 Hz, 1H), 3.12 (d, J = 12.7 Hz, 1H), 1.12 (d, J = 6.5 Hz, 3H). | 367 |
| 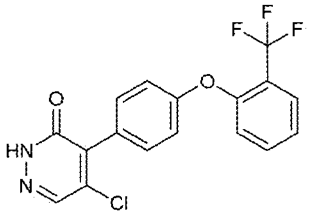 | 1H NMR (400 MHz, DMSO-d6) chemical shifts 13.43 (s, 1H), 8.11 (s, 1H), 7.84 (dd, J = 7.6, 1.5 Hz, 1H), 7.77 - 7.68 (m, 1H), 7.57 - 7.48 (m, 2H), 7.40 (t, J = 7.6 Hz, 1H), 7.20 (d, J = 8.3 Hz, 1H), 7.17 - 7.08 (m, 2H). | 367 |
| 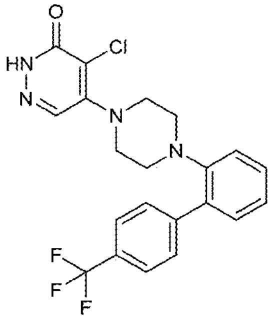 | 1H NMR (400 MHz, DMSO-d6) chemical shifts 12.91 (s, 1H), 7.90 (d, J = 8.1 Hz, 2H), 7.86 - 7.76 (m, 3H), 7.39 (ddd, J = 8.7, 7.2, 1.7 Hz, 1H), 7.30 (dd, J = 7.6, 1.7 Hz, 1H), 7.22 - 7.12 (m, 2H), 3.34 (s, 4H), 2.88 (t, J = 4.8 Hz, 4H). | 435 |

Figure 41

| | | |
|---|---|---|
| 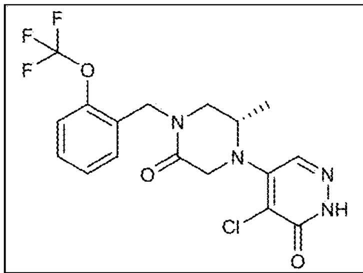 | 1H NMR (400 MHz, DMSO-d6) chemical shifts 7.89 (s, 1H), 7.48 - 7.38 (m, 4H), 4.68 (s, 1H), 4.65 (d, J = 15.0 Hz, 1H), 4.36 (s, 1H), 4.26 (d, J = 17.2 Hz, 1H), 4.05 (d, J = 17.2 Hz, 1H), 3.64 (d, J = 11.0 Hz, 1H), 3.09 (d, J = 12.5 Hz, 1H), 1.18 (d, J = 6.7 Hz, 3H), 1.10 (t, J = 7.4 Hz, 1H). | 417 |
| 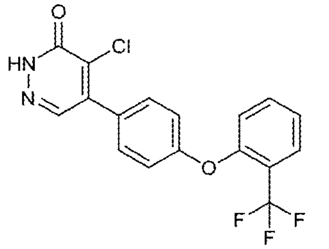 | 1H NMR (400 MHz, DMSO-d6) chemical shifts 13.55 (s, 1H), 7.99 (s, 1H), 7.85 (dd, J = 7.8, 1.5 Hz, 1H), 7.79 - 7.69 (m, 1H), 7.71 - 7.63 (m, 2H), 7.43 (t, J = 7.7 Hz, 1H), 7.21 (dd, J = 19.1, 8.5 Hz, 3H) | 367 |
| 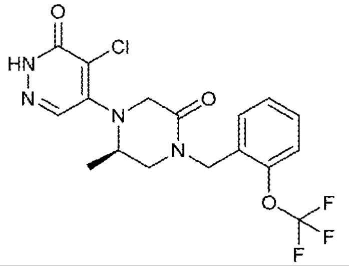 | 1H NMR (400 MHz, DMSO-d6) chemical shifts 12.99 (s, 1H), 7.89 (s, 1H), 7.51 - 7.37 (m, 4H), 4.68 (d, J = 3.5 Hz, 2H), 4.37 (s, 1H), 4.26 (d, J = 17.2 Hz, 1H), 4.06 (d, J = 17.2 Hz, 1H), 3.65 (dd, J = 12.3, 4.5 Hz, 1H), 3.10 (dd, J = 12.4, 2.8 Hz, 1H), 1.19 (d, J = 6.6 Hz, 3H). | 417 |
| 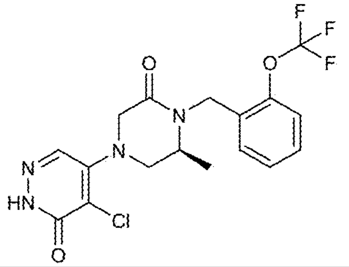 | 1H NMR (400 MHz, DMSO-d6) chemical shifts 7.90 (s, 1H), 7.46 - 7.35 (m, 4H), 4.95 (d, J = 16.2 Hz, 1H), 4.35 (dd, J = 25.9, 16.5 Hz, 2H), 4.15 (d, J = 17.1 Hz, 1H), 3.76 (d, J = 13.6 Hz, 1H), 3.68 (d, J = 12.6 Hz, 1H), 3.59 (s, 1H), 1.23 (d, J = 6.4 Hz, 3H), 1.09 (t, J = 7.3 Hz, 1H). | 417 |
| 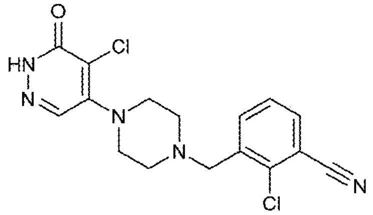 | 1H NMR (400 MHz, DMSO-d6) chemical shifts 12.94 (s, 1H), 7.96 - 7.83 (m, 3H), 7.57 (t, J = 7.7 Hz, 1H), 3.70 (s, 2H), 3.41 (d, J = 9.7 Hz, 4H), 2.58 (t, J = 4.8 Hz, 4H). | 364 |
| 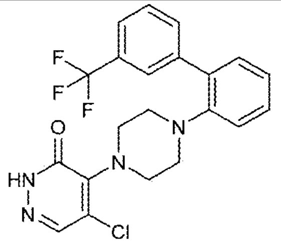 | 1H NMR (400 MHz, DMSO-d6) chemical shifts 12.87 (s, 1H), 8.10 (s, 1H), 7.92 (s, 1H), 7.75 - 7.67 (m, 3H), 7.43 - 7.33 (m, 1H), 7.32 (dd, J = 7.5, 1.6 Hz, 1H), 7.17 (t, J = 8.2 Hz, 2H), 3.32 (s, 4H), 2.85 (d, J = 5.0 Hz, 4H). | 435 |

Figure 42

| | | |
|---|---|---|
| 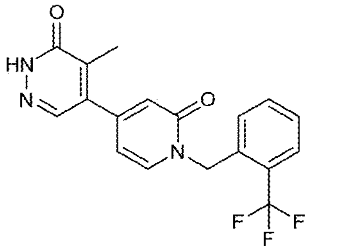 | 1H NMR (400 MHz, DMSO-d6) chemical shifts 13.13 (s, 1H), 7.87 (d, J = 6.9 Hz, 1H), 7.82 - 7.81 (m, 2H), 7.66 (t, J = 7.7 Hz, 1H), 7.53 (t, J = 7.7 Hz, 1H), 6.96 (d, J = 7.8 Hz, 1H), 6.57 (d, J = 1.9 Hz, 1H), 6.42 (dd, J = 6.9, 1.9 Hz, 1H), 5.36 (s, 2H), 2.08 (s, 3H). | 362 |
| 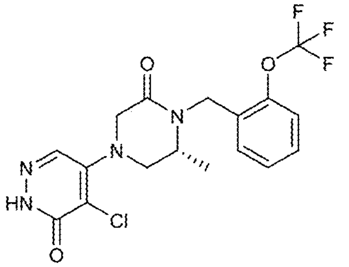 | 1H NMR (400 MHz, DMSO-d6) chemical shifts 12.98 (s, 1H), 7.91 (s, 1H), 7.49 - 7.36 (m, 4H), 4.96 (d, J = 16.2 Hz, 1H), 4.36 (dd, J = 26.0, 16.5 Hz, 2H), 4.15 (d, J = 17.0 Hz, 1H), 3.77 (dd, J = 13.5, 4.4 Hz, 1H), 3.68 (dd, J = 13.2, 3.7 Hz, 1H), 3.59 (s, 1H), 1.23 (d, J = 6.3 Hz, 3H). | 417 |
| 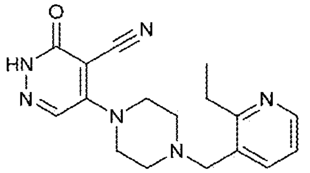 | 1H NMR (400 MHz, DMSO-d6) chemical shifts 12.67 (s, 1H), 8.42 (dd, J = 4.8, 1.8 Hz, 1H), 8.01 (s, 1H), 7.65 (dd, J = 7.6, 1.8 Hz, 1H), 7.19 (dd, J = 7.6, 4.8 Hz, 1H), 3.77 (t, J = 4.9 Hz, 4H), 3.55 (s, 1H), 2.85 (q, J = 7.5 Hz, 2H), 2.54 (d, J = 4.9 Hz, 4H), 1.23 (t, J = 7.5 Hz, 3H). | 325 |
| 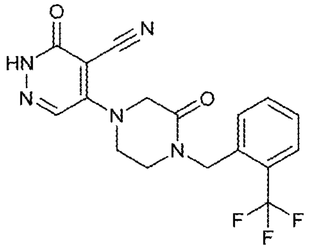 | 1H NMR (400 MHz, DMSO-d6) chemical shifts 12.18 (s, 1H), 8.26 (s, 1H), 7.81 - 7.74 (m, 1H), 7.68 (t, J = 7.4 Hz, 1H), 7.61 - 7.46 (m, 2H), 5.54 (s, 2H), 4.86 (s, 2H), 4.39 - 4.31 (m, 2H), 3.76 - 3.68 (m, 2H). | 378 |
| 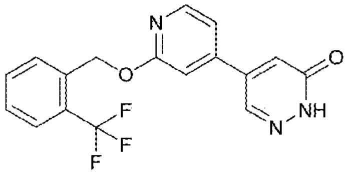 | 1H NMR (400 MHz, DMSO-d6) chemical shifts 13.24 (s, 1H), 8.34 (dd, J = 8.1, 3.7 Hz, 2H), 7.77 (dt, J = 25.3, 8.2 Hz, 3H), 7.59 (t, J = 7.6 Hz, 1H), 7.51 - 7.45 (m, 1H), 7.42 (s, 1H), 7.33 (d, J = 2.0 Hz, 1H), 5.59 (s, 2H). | 348 |
| 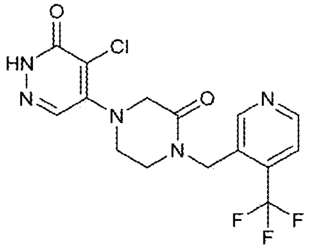 | 1H NMR (400 MHz, DMSO-d6) chemical shifts 12.98 (s, 1H), 8.81 (d, J = 5.1 Hz, 1H), 8.70 (s, 1H), 7.91 (s, 1H), 7.78 (d, J = 5.1 Hz, 1H), 4.81 (s, 2H), 4.26 (s, 2H), 3.80 (t, J = 5.3 Hz, 2H), 3.50 (t, J = 5.0 Hz, 2H). | 388 |

Figure 43

| | | |
|---|---|---|
| 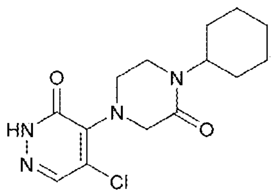 | 1H NMR (400 MHz, DMSO-d6) chemical shifts 7.78 (s, 1H), 4.26 (s, 1H), 4.03 (s, 2H), 3.62 (d, J = 5.5 Hz, 2H), 3.38 (t, J = 5.3 Hz, 2H),1.77 (d, J = 12.9 Hz, 2H), 1.60 (d, J = 16.4 Hz, 2H), 1.53 - 1.41 (m, 3H), 1.35 - 1.22 (m, 2H), 1.08 (d, J = 12.7 Hz, 1H). | 311 |
| 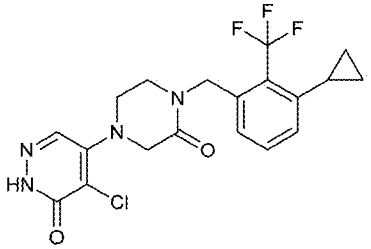 | 1H NMR (400 MHz, DMSO-d6) chemical shifts 12.99 (s, 1H), 7.90 (s, 1H), 7.52 (t, J = 7.9 Hz, 1H), 7.18 (dd, J = 14.9, 7.9 Hz, 2H), 4.77 (s, 2H), 4.23 (s, 2H), 3.77 (t, J = 5.3 Hz, 2H), 3.40 (t, J = 5.4 Hz, 2H),2.09 (s, 1H), 1.04 - 0.96 (m, 2H), 0.78 - 0.71 (m, 2H). | 427 |
| 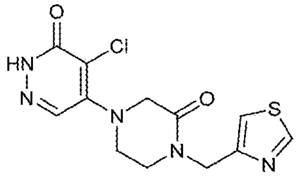 | 1H NMR (400 MHz, DMSO-d6) chemical shifts 9.10 (s, 1H), 7.88 (s, 1H), 7.58 (s, 1H), 4.71 (s, 2H), 4.15 (s, 2H), 3.72 (d, J = 5.9 Hz, 2H), 3.52 (t, J = 5.2 Hz, 2H) | 326 |
| 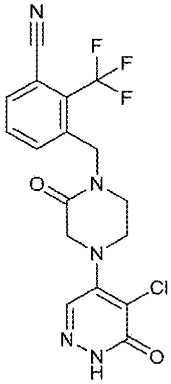 | 1H NMR (400 MHz, DMSO-d6) chemical shifts 12.99 (s, 1H), 8.09 (d, J = 7.7 Hz, 1H), 7.94 - 7.84 (m, 2H), 7.75 (d, J = 8.1 Hz, 1H), 4.81 (s, 2H), 4.26 (s, 2H), 3.80 (t, J = 5.3 Hz, 2H), 3.47 (t, J = 5.3 Hz, 2H). | 412 |
| 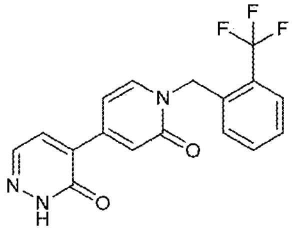 | 1H NMR (400 MHz, Methanol-d4) chemical shifts 8.04 (d, J = 4.2 Hz, 1H), 7.80 (d, J = 7.7 Hz, 1H), 7.72 (d, J = 4.2 Hz, 1H), 7.66 (d, J = 7.1 Hz, 1H), 7.59 (t, J = 7.6 Hz, 1H), 7.51 (t, J = 7.7 Hz, 1H), 7.22 (d, J = 1.9 Hz, 1H), 7.08 (d, J = 7.8 Hz, 1H), 6.85 (dd, J = 7.2, 1.9 Hz, 1H), 5.48 (s, 2H). | 348 |
| 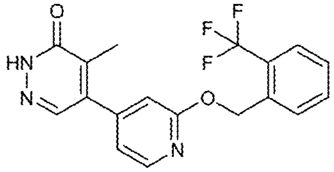 | 1H NMR (400 MHz, DMSO-d6) chemical shifts 13.13 (s, 1H), 8.32 (d, J = 5.3 Hz, 1H), 7.84 - 7.75 (m, 3H), 7.73 (t, J = 7.6 Hz, 1H), 7.59 (t, J = 7.5 Hz, 1H), 7.12 (d, J = 5.2 Hz, | 362 |

Figure 44

| | | |
|---|---|---|
| | 1H), 7.03 (s, 1H), 5.58 (s, 2H), 2.02 (s, 3H).. | |
| 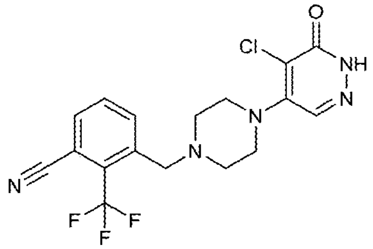 | 1H NMR (400 MHz, DMSO-d6) chemical shifts 12.94 (s, 1H), 8.10 (dd, J = 19.9, 7.8 Hz, 2H), 7.93 - 7.84 (m, 2H), 3.76 (s, 2H), 3.39 (t, J = 4.7 Hz, 4H), 2.52 (t, J = 6.2 Hz, 4H). | 398 |
| 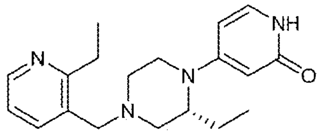 | 1H NMR (400 MHz, DMSO-d6) chemical shifts 10.52 (s, 1H), 8.41 (dd, J = 4.9, 1.6 Hz, 1H), 7.62 (d, J = 7.6 Hz, 1H), 7.18 (dd, J = 7.6, 4.8 Hz, 1H), 7.07 (d, J = 7.6 Hz, 1H), 5.98 (dd, J = 7.7, 2.5 Hz, 1H), 5.30 (d, J = 2.5 Hz, 1H), 3.75 (s, 1H), 3.55 - 3.41 (m, 3H), 2.99 - 2.73 (m, 5H), 2.16 - 2.01 (m, 2H), 1.77 (dt, J = 15.5, 7.8 Hz, 1H), 1.43 (dt, J = 13.5, 6.9 Hz, 1H), 1.23 (t, J = 7.5 Hz, 3H), 0.70 (t, J = 7.4 Hz, 3H). | 327 |
| 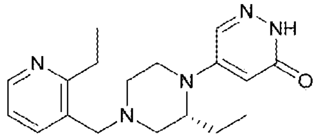 | 1H NMR (400 MHz, DMSO-d6) chemical shifts 12.13 (s, 1H), 8.42 (dd, J = 4.8, 1.6 Hz, 1H), 7.91 (d, J = 2.8 Hz, 1H), 7.67 - 7.60 (m, 1H), 7.19 (dd, J = 7.5, 4.8 Hz, 1H), 5.64 (s, 1H), 3.93 (s, 1H), 3.56 (d, J = 17.2 Hz, 1H), 3.53 - 3.42 (m, 2H), 2.99 (t, J = 11.5 Hz, 1H), 2.94 - 2.73 (m, 4H), 2.20 - 2.04 (m, 2H), 1.76 (dq, J = 15.4, 7.6 Hz, 1H), 1.49 (dt, J = 13.7, 6.8 Hz, 1H), 1.23 (t, J = 7.5 Hz, 3H), 0.71 (t, J = 7.4 Hz, 3H). | 327 |
| 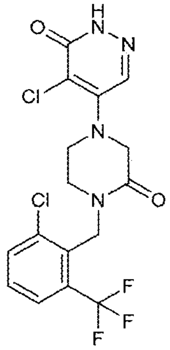 | 1H NMR (400 MHz, DMSO-d6) chemical shifts 12.98 (s, 1H), 7.93 - 7.81 (m, 3H), 7.65 (t, J = 8.1 Hz, 1H), 4.90 (s, 2H), 4.17 (s, 2H), 3.61 (t, J = 5.2 Hz, 2H), 3.03 (t, J = 5.4 Hz, 2H). | 421 |

Figure 45

| | | |
|---|---|---|
| 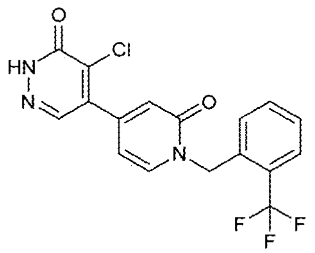 | 1H NMR (400 MHz, Methanol-d4) chemical shifts 7.97 (s, 1H), 7.81 (d, J = 7.8 Hz, 1H), 7.76 (d, J = 7.0 Hz, 1H), 7.62 (t, J = 7.6 Hz, 1H), 7.53 (t, J = 7.6 Hz, 1H), 7.11 (d, J = 7.9 Hz, 1H), 6.81 (d, J = 2.0 Hz, 1H), 6.60 (dd, J = 7.0, 2.0 Hz, 1H), 5.50 (s, 2H). | 382 |
| 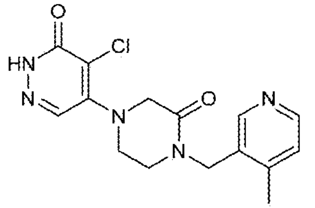 | 1H NMR (400 MHz, DMSO-d6) chemical shifts 12.99 (s, 1H), 8.38 (d, J = 4.9 Hz, 2H), 7.90 (s, 1H), 7.10 (d, J = 5.0 Hz, 1H), 4.60 (s, 2H), 4.23 (s, 2H), 3.81 - 3.74 (m, 2H), 3.41 (t, J = 5.3 Hz, 2H), 2.26 (s, 3H). | 334 |
| 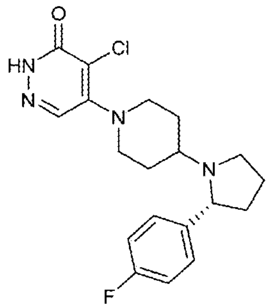 | 1H NMR (400 MHz, DMSO-d6) chemical shifts 12.85 (s, 1H), 7.78 (s, 1H), 7.44 - 7.35 (m, 2H), 7.17 - 7.07 (m, 2H), 3.82 (dd, J = 8.3, 6.2 Hz, 1H), 3.74 (d, J = 12.8 Hz, 1H), 3.65 (d, J = 12.8 Hz, 1H), 3.16 - 3.06 (m, 1H), 2.84 (t, J = 12.3 Hz, 2H), 2.60 (q, J = 8.4 Hz, 1H), 2,51 (s, 1H), 2.13 (dq, J = 12.3, 8.1 Hz, 1H), 1.82-1.67 (m, 3H), 1.64 (d, J = 12.7 Hz, 1H), 1.57 - 1.37 (m, 3H). | 377 |
| 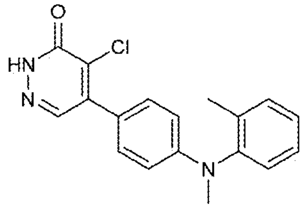 | 1H NMR (400 MHz, DMSO-d6) chemical shifts 13.36 (s, 1H), 7.94 (s, 1H), 7.47 (d, J = 8.3 Hz, 2H), 7.43 - 7.24 (m, 3H), 7.20 (d, J = 7.5 Hz, 1H), 6.56 (d, J = 8.3 Hz, 2H), 3.25 (s, 3H), 2.11 (s, 3H). | 326 |
| 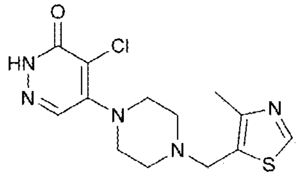 | 1H NMR (400 MHz, DMSO-d6) chemical shifts 12.93 (s, 1H), 8.92 (s, 1H), 7.86 (s, 1H), 3.72 (s, 2H), 3.39 (s, 4H), 2.54 (d, J = 4.7 Hz, 4H), 2.35 (s, 3H). | 326 |
| 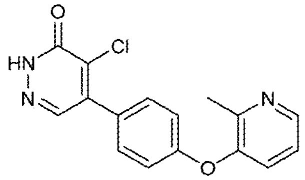 | 1H NMR (400 MHz, DMSO-d6) chemical shifts 13.37 (s, 1H), 8.36 (dd, J = 4.8, 1.4 Hz, 1H), 7.97 (s, 1H), 7.67 - 7.60 (m, 2H), 7.48 (dd, J = 8.2, 1.4 Hz, 1H), 7.33 (dd, J = 8.2, 4.7 Hz, 1H), 7.11 - 7.04 (m, 2H), 2.40 (s, 3H). | 314 |

Figure 46

| | | |
|---|---|---|
| 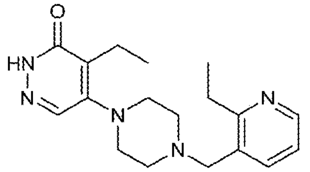 | 1H NMR (400 MHz, DMSO-d6) chemical shifts 12.58 (s, 1H), 8.40 (dd, J = 5.0, 1.6 Hz, 1H), 7.77 (s, 1H), 7.67 - 7.60 (m, 1H), 7.18 (dd, J = 7.6, 4.8 Hz, 1H), 3.54 (s, 2H), 3.06 (t, J = 4.7 Hz, 4H), 2.85 (q, J = 7.5 Hz, 2H), 2.50 (q, J = 3.1, 2.6 Hz, 4H), 2.42 (q, J = 7.3 Hz, 2H), 1.23 (t, J = 7.5 Hz, 3H), 1.09 (t, J = 7.3 Hz, 3H). | 328 |
| 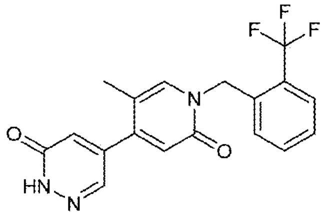 | 1H NMR (400 MHz, DMSO-d6) chemical shifts 13.24 (s, 1H), 7.98 (d, J = 2.0 Hz, 1H), 7.81 (d, J = 7.8 Hz, 1H), 7.72 (s, 1H), 7.65 (t, J = 7.7 Hz, 1H), 7.52 (t, J = 7.7 Hz, 1H), 6.96 - 6.89 (m, 2H), 6.52 (s, 1H), 5.31 (s, 2H), 1.98 (s, 3H). | 362 |
| 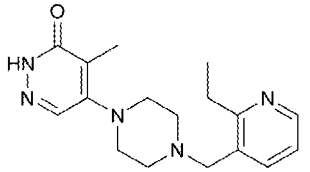 | 1H NMR (400 MHz, Methanol-d4) chemical shifts 8.38 (d, J = 5.0 Hz, 1H), 7.86 (s, 1H), 7.79 (d, J = 7.7 Hz, 1H), 7.25 (dd, J = 7.7, 5.0 Hz, 1H), 3.64 (s, 2H), 3.24 (t, J = 4.7 Hz, 4H), 2.95 (q, J = 7.5 Hz, 2H), 2.64 (t, J = 4.8 Hz, 4H), 2.08 (s, 3H), 1.30 (t, J = 7.5 Hz, 3H). | 314 |
| 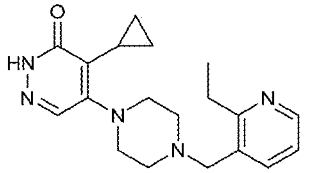 | 1H NMR (400 MHz, Methanol-d4) chemical shifts 8.38 (d, J = 4.9 Hz, 1H), 7.85 - 7.76 (m, 2H), 7.25 (dd, J = 7.7, 4.9 Hz, 1H), 3.64 (s, 2H), 3.42 (t, J = 4.8 Hz, 4H), 2.95 (q, J = 7.6 Hz, 2H), 2.64 (t, J = 4.8 Hz, 4H), 1.64 (td, J = 8.4, 4.1 Hz, 1H), 1.30 (t, J = 7.5 Hz, 3H), 1.05 - 0.95 (m, 2H), 0.86 (dt, J = 5.6, 3.0 Hz, 2H). | 340 |
| 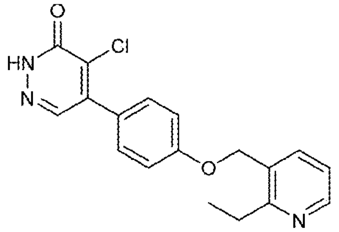 | 1H NMR (400 MHz, DMSO-d6) chemical shifts 13.50 (s, 1H), 8.50 (dd, J = 4.8, 1.6 Hz, 1H), 7.96 (s, 1H), 7.87 - 7.80 (m, 1H), 7.59 (d, J = 8.6 Hz, 2H), 7.31 - 7.18 (m, 3H), 5.23 (s, 2H), 2.84 (q, J = 7.5 Hz, 2H), 1.25 (t, J = 7.5 Hz, 3H). | 342 |
| 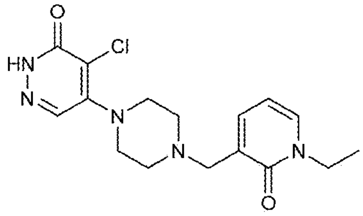 | 1H NMR (400 MHz, DMSO-d6) chemical shifts 12.86 (s, 1H), 7.86 (s, 1H), 7.63 (dd, J = 6.7, 2.1 Hz, 1H), 7.42 (dd, J = 6.8, 2.1 Hz, 1H), 6.24 (t, J = 6.7 Hz, 1H), 3.92 (q, J = 7.1 Hz, 2H), 3.40 (dd, J = 9.4, 4.4 Hz, | 350 |

Figure 47

| | | |
|---|---|---|
| | 6H), 2.53 (d, J = 4.6 Hz, 4H), 1.21 (t, J = 7.1 Hz, 3H). | |
| 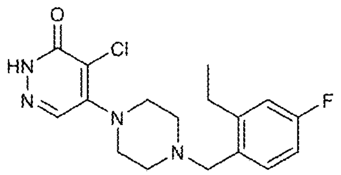 | 1H NMR (400 MHz, Methanol-d4) chemical shifts 7.88 (s, 1H), 7.14 (q, J = 7.3 Hz, 2H), 6.99 (t, J = 8.6 Hz, 1H), 3.60 (s, 2H), 3.51 (t, J = 4.8 Hz, 4H), 2.82 (q, J = 7.6 Hz, 2H), 2.62 (t, J = 4.9 Hz, 4H), 1.22 (t, J = 7.4 Hz, 3H). | 351 |
| 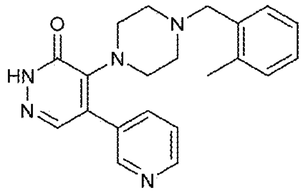 | 1H NMR (400 MHz, DMSO-d6) chemical shifts 12.77 (s, 1H), 8.60 - 8.53 (m, 2H), 7.78 (dt, J = 7.9, 2.0 Hz, 1H), 7.66 (s, 1H), 7.50 (dd, J = 7.9, 4.8 Hz, 1H), 7.18 (d, J = 6.9 Hz, 1H), 7.16 - 7.05 (m, 3H), 3.38 (s, 2H), 2.94 (d, J = 5.2 Hz, 4H), 2.30 (d, J = 15.0 Hz, 7H). | 362 |
| 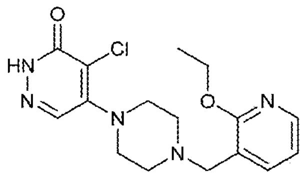 | 1H NMR (400 MHz, DMSO-d6) chemical shifts 12.06 (s, 1H), 8.06 (dd, J = 4.9, 1.9 Hz, 1H), 7.86 (s, 1H), 7.70 (dd, J = 7.3, 1.9 Hz, 1H), 6.97 (dd, J = 7.2, 5.0 Hz, 1H), 4.33 (q, J = 7.0 Hz, 2H),3.51 (s, 2H) 3.40 (t, J = 4.8 Hz, 4H), 2.54 (t, J = 4.7 Hz, 4H), 1.32 (t, J = 7.0 Hz, 3H). | 350 |
| 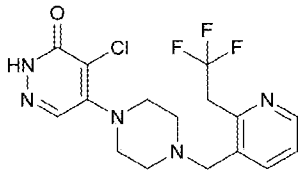 | 1H NMR (400 MHz, DMSO-d6) chemical shifts 12.94 (s, 1H), 8.52 (dd, J = 4.8, 1.7 Hz, 1H), 7.86 (s, 1H), 7.79 (dd, J = 7.7, 1.8 Hz, 1H), 7.38 (dd, J = 7.7, 4.8 Hz, 1H), 3.99 (q, J = 11.3 Hz, 2H), 3.61 (s, 2H), 3.41 - 3.34 (m, 4H), 2.49 (d, J = 5.1 Hz, 4H). | 388 |
| 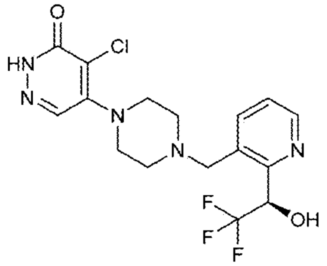 | 1H NMR (400 MHz, DMSO-d6) chemical shifts 12.95 (s, 1H), 8.57 (dd, J = 4.7, 1.7 Hz, 1H), 7.90 - 7.83 (m, 2H), 7.45 (dd, J = 7.7, 4.7 Hz, 1H), 6.93 (d, J = 7.7 Hz, 1H), 5.66 (p, J = 7.6 Hz, 1H), 3.75 (d, J = 13.7 Hz, 1H), 3.64 (d, J = 13.6 Hz, 1H), 3.35 (m, 4H), 2.53 (m, 4H). | 404 |

Figure 48

| | | |
|---|---|---|
| 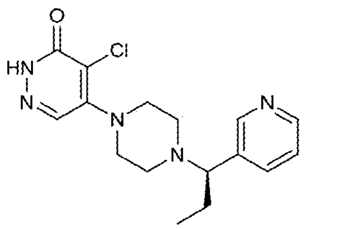 | 1H NMR (400 MHz, DMSO-d6) chemical shifts 12.90 (s, 1H), 8.52 - 8.45 (m, 2H), 7.82 (s, 1H), 7.68 (dt, J = 7.9, 2.0 Hz, 1H), 7.39 (dd, J = 7.8, 4.8 Hz, 1H), 3.44 (dd, J = 8.6, 6.0 Hz, 1H), 3.39 - 3.32 (m, 4H), 2.44 (t, J = 5.0 Hz, 4H), 1.95 (dq, J = 13.8, 6.9 Hz, 1H), 1.75 (dp, J = 15.3, 7.6 Hz, 1H), 0.75 (t, J = 7.3 Hz, 3H). | 334 |
| 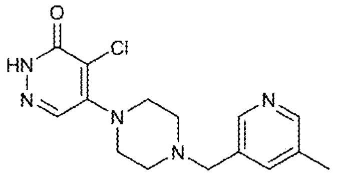 | 1H NMR (400 MHz, DMSO-d6) chemical shifts 12.93 (s, 1H), 8.32 (t, J = 2.8 Hz, 2H), 7.86 (s, 1H), 7.55 (d, J = 2.3 Hz, 1H), 3.53 (s, 2H), 3.39 (d, J = 9.8 Hz, 4H), 2.49 (d, J = 4.7 Hz, 4H), 2.31 (s, 3H). | 320 |
| 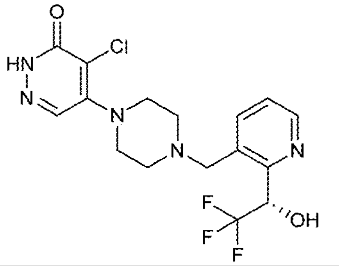 | 1H NMR (400 MHz, DMSO-d6) chemical shifts 12.95 (s, 1H), 8.57 (dd, J = 4.7, 1.7 Hz, 1H), 7.90 - 7.83 (m, 2H), 7.45 (dd, J = 7.7, 4.7 Hz, 1H), 6.93 (d, J = 7.7 Hz, 1H), 5.65 (q, J = 7.3 Hz, 1H), 3.75 (d, J = 13.6 Hz, 1H), 3.64 (d, J = 13.7 Hz, 1H), 3.34 (m,4H), 2.51(m, 4H). | 404 |
| 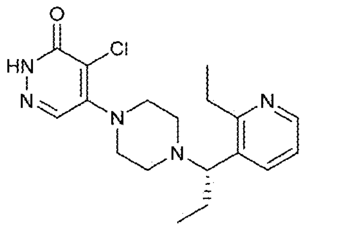 | 1H NMR (400 MHz, DMSO-d6) ¦Ä 12.92 (s, 1H), 8.40 (dd, J = 4.7, 1.7 Hz, 1H), 7.83 (s, 1H), 7.77 - 7.64 (m, 1H), 7.22 (dd, J = 7.7, 4.7 Hz, 1H), 3.62 (d, J = 8.1 Hz, 1H), 3.32 (s, 3H), 2.87 (q, J = 7.5 Hz, 2H), 2.59 (m, 2H), 2.48 - 2.36 (m, 3H), 1.90 (s, 1H), 1.83 - 1.63 (m, 1H), 1.22 (t, J = 7.5 Hz, 3H), 0.67 (t, J = 7.3 Hz, 3H). | 362 |
| 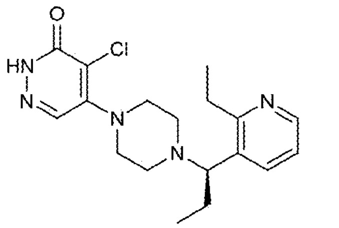 | 1H NMR (400 MHz, DMSO-d6) ¦Ä 12.80 (s, 1H) 8.41 (dd, J = 4.7, 1.7 Hz, 1H), 7.84 (s, 1H), 7.69 (dd, J = 7.9, 1.7 Hz, 1H), 7.23 (dd, J = 7.8, 4.7 Hz, 1H), 3.63 (dd, J = 9.1, 4.2 Hz, 1H), 3.35 (s, 1H), 2.87 (q, J = 7.5 Hz, 2H), 2.62 - 2.55 (m, 3H), 2.45 (s, 2H), 1.90 (dd, J = 11.9, 6.3 Hz, 1H), 1.73 (dt, J = 14.2, 7.6 Hz, 1H), 1.23 (t, J = 7.5 Hz, 3H), 1.09 (t, J = 7.3 Hz, 0H), 0.68 (t, J = 7.3 Hz, 3H). | 362 |

Figure 49

| | | |
|---|---|---|
| 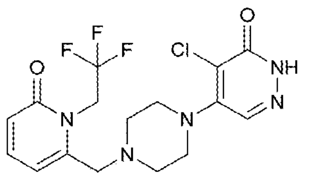 | 1H NMR (400 MHz, DMSO-d6) chemical shifts 12.95 (s, 1H), 7.86 (s, 1H), 7.45 (dd, J = 9.3, 6.7 Hz, 1H), 6.48 (d, J = 9.2 Hz, 1H), 6.34 (d, J = 6.7 Hz, 1H), 5.18 (q, J = 9.1 Hz, 2H),3.53 (s, 2H), 3.39 (t, J = 4.8 Hz, 4H), 2.53 (d, J = 4.2 Hz, 4H). | 404 |
| 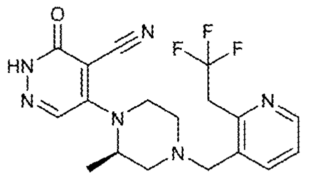 | 1H NMR (400 MHz, DMSO-d6) chemical shifts 12.68 (s, 1H), 8.53 (d, J = 4.8 Hz, 1H), 8.01 (s, 1H), 7.79 (d, J = 7.8 Hz, 1H), 7.38 (t, J = 6.4 Hz, 1H), 4.58 (s, 1H), 4.25 - 3.84 (m, 3H), 3.62 (d, J = 13.5 Hz, 1H), 3.47 (dd, J = 25.8, 13.1 Hz, 2H), 2.73 (dd, J = 16.3, 12.1 Hz, 2H), 2.36 (d, J = 12.0 Hz, 1H), 2.16 (t, J = 11.5 Hz, 1H), 1.36 (d, J = 6.6 Hz, 3H). | 393 |
| 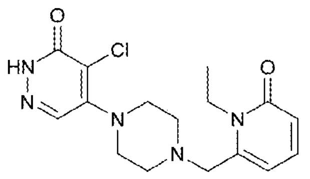 | 1H NMR (400 MHz, DMSO-d6) chemical shifts 12.95 (s, 1H), 7.87 (s, 1H), 7.34 (dd, J = 9.1, 6.8 Hz, 1H), 6.35 (d, J = 9.1 Hz, 1H), 6.22 (d, J = 6.8 Hz, 1H), 4.10 (q, J = 6.9 Hz, 2H), 3.52 (s, 2H), 3.38 (d, J = 5.1 Hz, 4H), 2.56 (t, J = 4.7 Hz, 4H), 1.24 (t, J = 6.9 Hz, 3H). | 350 |
| 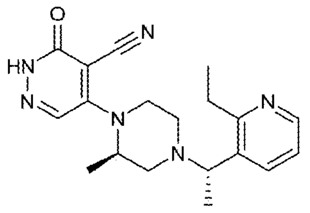 | 1H NMR (400 MHz, DMSO-d6) chemical shifts 12.66 (s, 1H), 8.40 (dd, J = 4.7, 1.6 Hz, 1H), 7.98 (s, 1H), 7.77 (d, J = 7.4 Hz, 1H), 7.23 (dd, J = 7.8, 4.7 Hz, 1H), 4.49 (s, 1H), 4.17 (d, J = 13.8 Hz, 1H), 3.68 (q, J = 6.3 Hz, 1H), 3.47 (dd, J = 14.0, 11.0 Hz, 1H), 3.07 (d, J = 11.2 Hz, 1H), 2.85 (dh, J = 22.1, 7.3 Hz, 2H), 2.48 (s, 0H), 2.29 (dd, J = 11.5, 3.5 Hz, 1H), 2.26 - 2.15 (m, 1H), 1.29 (dd, J = 10.5, 6.6 Hz, 6H), 1.22 (t, J = 7.5 Hz, 3H). | 353 |
| 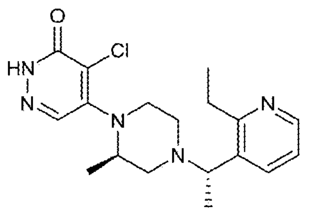 | 1H NMR (400 MHz, Methanol-d4) chemical shifts 8.36 (d, J = 4.8 Hz, 1H), 7.99 (d, J = 7.8 Hz, 1H), 7.86 (s, 1H), 7.30 (dd, J = 7.9, 4.9 Hz, 1H), 4.26 (s, 1H), 3.73 (q, J = 6.5 Hz, 1H), 3.54 (t, J = 12.0 Hz, 1H), 3.38 (s, 1H), 3.08 - 2.84 (m, 3H), 2.68 (d, J = 11.4 Hz, 1H), 2.61 - 2.46 (m, 1H), 2.38 (t, J = 10.8 Hz, 1H), 1.43 - 1.27 (m, 9H). | 362 |

Figure 50

| | | |
|---|---|---|
| 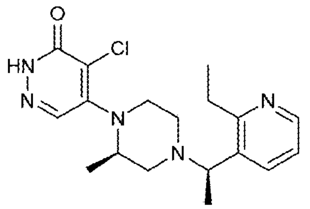 | 1H NMR (400 MHz, Methanol-d4) chemical shifts 8.36 (s, 1H), 7.99 (d, J = 8.0 Hz, 1H), 7.88 (s, 1H), 7.35 - 7.21 (m, 1H), 4.15 (s, 1H), 3.79 - 3.69 (m, 1H), 3.67 - 3.48 (m, 2H), 3.12 (d, J = 11.6 Hz, 1H), 2.95 (q, J = 7.8 Hz, 2H), 2.50 (s, 2H), 2.39 (d, J = 10.9 Hz, 1H), 1.38 (d, J = 6.6 Hz, 3H), 1.30 (t, J = 6.0 Hz, 6H). | 362 |
| 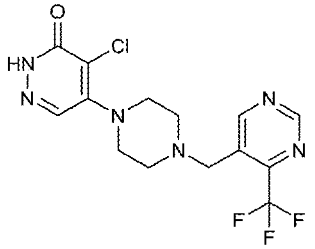 | 1H NMR (400 MHz, DMSO-d6) chemical shifts 12.95 (s, 1H), 9.36 (s, 1H), 9.22 (s, 1H), 7.87 (s, 1H), 3.77 (s, 2H),3.40 (s, 4H), 2.56 (s, 4H). | 375 |
| 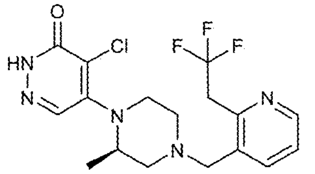 | 1H NMR (400 MHz, DMSO-d6) chemical shifts 12.93 (s, 1H), 8.52 (d, J = 4.7 Hz, 1H), 7.85 (s, 1H), 7.78 (d, J = 7.6 Hz, 1H), 7.38 (dd, J = 7.7, 4.8 Hz, 1H), 4.17 - 3.95 (m, 3H), 3.56 (q, J = 13.6 Hz, 2H), 3.43 (t, J = 11.3 Hz, 1H), 3.29 (s,1H), 2.65 (d, J = 12.5 Hz, 2H), 2.42 (d, J = 9.5 Hz, 1H), 2.37 - 2.17 (m, 1H), 1.19 (d, J = 6.5 Hz, 3H). | 402 |
| 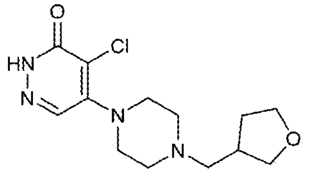 | 1H NMR (400 MHz, CHLOROFORM-d) δ = 10.12 - 9.99 (m, 1H), 7.69 - 7.60 (m, 1H), 3.92 - 3.87 (m, 1H), 3.83 - 3.71 (m, 1H), 3.57 (dd, J = 5.6, 8.6 Hz, 1H), 3.49 (t, J = 4.9 Hz, 2H), 3.22 - 2.98 (m, 4H), 2.72 - 2.53 (m, 4H), 2.11 - 1.99 (m, 2H), 1.70 - 1.61 (m, 2H) | 299.2 |
| 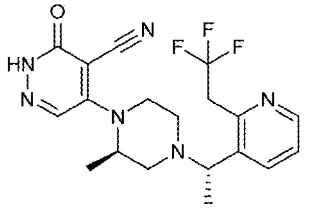 | 1H NMR (300 MHz, DMSO-d6) chemical shifts 12.67 (s, 1H), 8.51 (dd, J = 4.7, 1.7 Hz, 1H), 7.99 (s, 1H), 7.91 (d, J = 7.6 Hz, 1H), 7.42 (dd, J = 7.9, 4.7 Hz, 1H), 4.51 (s, 1H), 4.15 (d, J = 14.0 Hz, 1H), 4.12 - 3.85 (m, 2H), 3.79 (d, J = 6.6 Hz, 1H), 3.46 (t, J = 12.1 Hz, 1H), 3.00 (d, J = 11.3 Hz, 1H), 2.53 (s, 1H), 2.37 (d, J = 8.8 Hz, 1H), 2.23 (t, J = 11.7 Hz, 1H), 1.30 (t, J = 6.7 Hz, 6H). | 407 |

Figure 51

| | | |
|---|---|---|
| 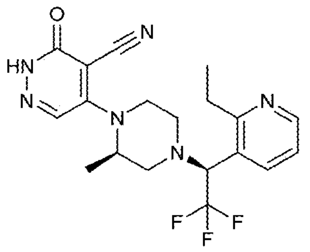 | 1H NMR (400 MHz, Methanol-d4) chemical shifts 8.53 (dd, J = 4.9, 1.7 Hz, 1H), 8.01 (d, J = 7.9 Hz, 1H), 7.95 (s, 1H), 7.37 (dd, J = 8.0, 4.8 Hz, 1H), 4.69 (q, J = 8.4 Hz, 1H), 4.60 (s, 1H), 4.20 (d, J = 13.9 Hz, 1H), 3.58 (ddd, J = 13.8, 11.9, 3.3 Hz, 1H), 3.24 (d, J = 11.8 Hz, 1H), 3.08 - 2.86 (m, 3H), 2.76 (t, J = 11.2 Hz, 2H), 1.47 (d, J = 6.7 Hz, 3H), 1.32 (t, J = 7.6 Hz, 3H). | 407 |
| 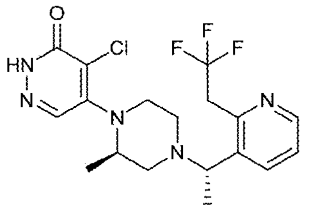 | 1H NMR (300 MHz, DMSO-d6) chemical shifts 12.92 (s, 1H), 8.50 (dd, J = 4.7, 1.7 Hz, 1H), 7.89 (dd, J = 7.8, 1.8 Hz, 1H), 7.85 (s, 1H), 7.41 (dd, J = 7.9, 4.7 Hz, 1H), 4.39 - 3.84 (m, 3H), 3.77 (d, J = 6.6 Hz, 1H), 3.51 - 3.34 (m, 2H), 2.84 (d, J = 11.2 Hz, 1H), 2.50 - 2.34 (m, 2H), 2.33 - 2.11 (m, 1H), 1.29 (d, J = 6.5 Hz, 3H), 1.16 (d, J = 6.5 Hz, 3H). | 416 |
| 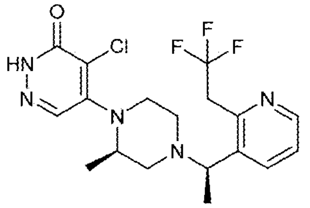 | 1H NMR (300 MHz, DMSO-d6) chemical shifts 12.94 (s, 1H), 8.50 (dd, J = 4.7, 1.7 Hz, 1H), 7.89 (dd, J = 7.9, 1.7 Hz, 1H), 7.84 (s, 1H), 7.41 (dd, J = 7.9, 4.7 Hz, 1H), 4.23 - 4.05 (m, 2H), 4.05 - 3.86 (m, 1H), 3.78 (t, J = 6.6 Hz, 1H), 3.39 (t, J = 10.1 Hz, 1H), 3.23 (d, J = 12.9 Hz, 1H), 2.66 (d, J = 10.9 Hz, 1H), 2.50 (s, 1H), 2.46 - 2.29 (m, 2H), 1.27 (d, J = 6.7 Hz, 3H), 1.15 (d, J = 6.5 Hz, 3H). | 416 |
| 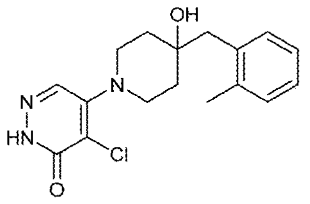 | 1H NMR (400 MHz, CHLOROFORM-d) δ = 10.78 - 10.55 (m, 1H), 7.68 (s, 1H), 7.28 - 7.12 (m, 4H), 3.72 - 3.59 (m, 2H), 3.38 (d, J = 2.5 Hz, 2H), 2.90 (s, 2H), 2.42 (s, 3H), 1.98 - 1.84 (m, 2H), 1.77 - 1.67 (m, 2H), 1.58 (s, 1H), 1.33 - 1.29 (m, 1H) | 334.2 |
| 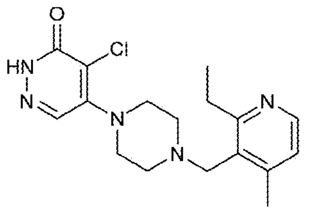 | 1H NMR (400 MHz, DMSO-d6) chemical shifts 12.93 (s, 1H), 8.26 (d, J = 4.9 Hz, 1H), 7.85 (s, 1H), 7.03 (d, J = 4.9 Hz, 1H), 3.56 (s, 2H), 2.87 (q, J = 7.5 Hz, 2H), 2.52 (d, J = 1.9 Hz, 8H), 2.37 (s, 3H), 1.21 (t, J = 7.5 Hz, 3H). | 348 |

Figure 52

| | | |
|---|---|---|
| 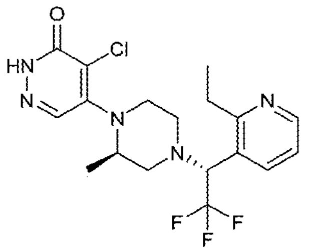 | 1H NMR (400 MHz, Methanol-d4) chemical shifts 8.52 (dd, J = 4.8, 1.7 Hz, 1H), 8.00 (d, J = 7.9 Hz, 1H), 7.85 (s, 1H), 7.36 (dd, J = 8.0, 4.8 Hz, 1H), 4.65 (q, J = 8.5 Hz, 1H), 4.24 - 4.09 (m, 1H), 3.63 - 3.50 (m, 1H), 3.44 (d, J = 12.9 Hz, 1H), 3.13 (d, J = 11.6 Hz, 1H), 3.05 - 2.91 (m, 2H), 2.86 - 2.69 (m, 3H), 1.49 - 1.16 (m, 6H). | 416 |
| 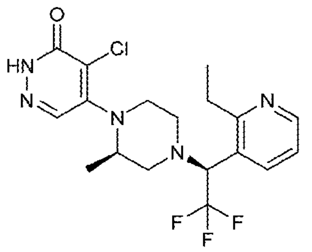 | 1H NMR (400 MHz, Methanol-d4) chemical shifts 8.51 (dd, J = 4.9, 1.7 Hz, 1H), 7.97 (d, J = 7.9 Hz, 1H), 7.85 (s, 1H), 7.36 (dd, J = 8.0, 4.8 Hz, 1H), 4.69 (q, J = 8.5 Hz, 1H), 4.16 (d, J = 6.3 Hz, 1H), 3.65 - 3.52 (m, 1H), 3.39 (d, J = 12.6 Hz, 1H), 3.16 - 2.83 (m, 5H), 2.75 (t, J = 11.0 Hz, 1H), 1.34 (t, J = 7.6 Hz, 3H), 1.18 (d, J = 6.5 Hz, 3H). | 416 |
| 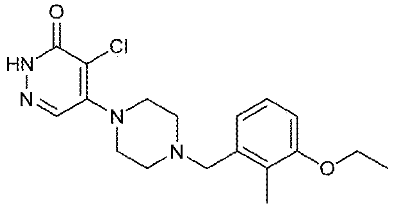 | 1H NMR (400 MHz, DMSO-d6) chemical shifts 12.92 (s, 1H), 7.85 (s, 1H), 7.09 (t, J = 7.9 Hz, 1H), 6.86 (t, J = 6.9 Hz, 2H), 4.01 (q, J = 6.9 Hz, 2H), 3.47 (s, 2H), 3.36 (t, J = 4.8 Hz, 4H), 2.48 (s, 4H), 2.19 (s, 3H), 1.35 (t, J = 6.9 Hz, 3H). | 363 |
| 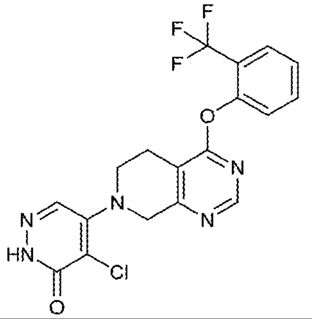 | 1H NMR (400 MHz, DMSO-d6) chemical shifts 13.00 (s, 1H), 8.56 (s, 1H), 8.03 (s, 1H), 7.85 (d, J = 7.8 Hz, 1H), 7.80 (t, J = 7.9 Hz, 1H), 7.58 - 7.48 (m, 2H), 4.68 (s, 2H), 3.80 (t, J = 5.7 Hz, 2H), 2.99 (t, J = 5.8 Hz, 2H). | 424 |
| 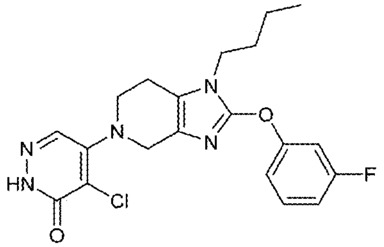 | 1H NMR (400 MHz, DMSO-d6) chemical shifts 12.89 (s, 1H), 7.92 (s, 1H), 7.45 (q, J = 7.9 Hz, 1H), 7.19 (d, J = 10.5 Hz, 1H), 7.11 - 7.00 (m, 2H), 4.32 (s, 2H), 3.81 (t, J = 7.1 Hz, 2H), 3.77 - 3.70 (m, 2H), 2.80 (s, 2H), 1.61 (p, J = 7.4 Hz, 2H), 1.26 (p, J = 7.5 Hz, 2H), 0.88 (t, J = 7.3 Hz, 3H). | 418 |

Figure 53

| | | |
|---|---|---|
| 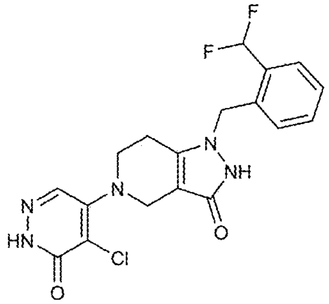 | 1H NMR (400 MHz, DMSO-d6) chemical shifts 12.89 (s, 1H), 9.86 (s, 1H), 7.88 (s, 1H), 7.61 (d, J = 7.6 Hz, 1H), 7.54 - 7.39 (m, 2H), 7.45 - 7.19 (s,1H), 6.92 (d, J = 7.6 Hz, 1H), 5.22 (s, 2H), 4.27 (s, 2H), 3.64 (s, 2H), 2.74 (s, 2H). | 408 |
| 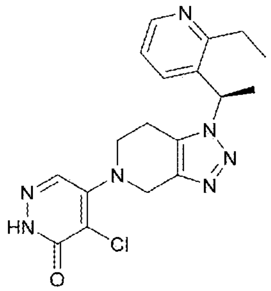 | 1H NMR (400 MHz, DMSO-d6) chemical shifts 12.93 (s, 1H), 8.47 (dd, J = 4.8, 1.7 Hz, 1H), 7.92 (s, 1H), 7.52 - 7.46 (m, 1H), 7.25 (dd, J = 7.9, 4.7 Hz, 1H), 6.10 (d, J = 6.9 Hz, 1H), 4.58 (s, 2H), 3.65 - 3.55 (m, 2H), 2.85 (ddq, J = 31.1, 14.8, 7.5 Hz, 3H), 2.45 (d, J = 15.3 Hz, 1H), 1.89 (d, J = 6.9 Hz, 3H), 1.17 (t, J = 7.4 Hz, 3H). | 386 |
| 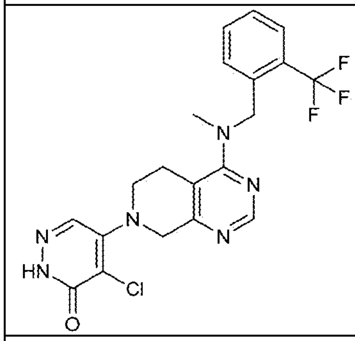 | 1H NMR (400 MHz, Methanol-d4) chemical shifts 8.39 (s, 1H), 8.00 (s, 1H), 7.77 (d, J = 8.0 Hz, 1H), 7.63 (t, J = 7.7 Hz, 1H), 7.51 - 7.46 (m, 2H), 5.04 (s, 2H), 4.65 (s, 2H), 3.73 (t, J = 5.3 Hz, 2H), 3.21 (t, J = 5.3 Hz , 3H), 3.07 (s, 3H). | 451 |
| 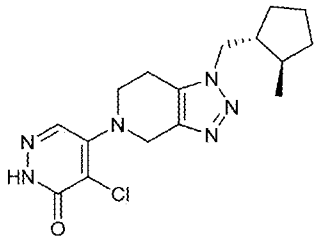 | 1H NMR (400 MHz, DMSO-d6) chemical shifts 12.95 (s, 1H), 7.96 (s, 1H), 4.59 (s, 2H), 4.32 (dd, J = 13.9, 6.1 Hz, 1H), 4.18 (dd, J = 14.0, 8.3 Hz, 1H), 3.69 (d, J = 10.9 Hz, 2H), 2.95 (t, J = 5.5 Hz, 2H), 1.95 - 1.77 (m, 2H), 1.71 - 1.49 (m, 4H), 1.38 - 1.25 (m, 1H), 1.25 - 1.10 (m, 1H), 0.88 (d, J = 6.6 Hz, 3H). | 349 |
| 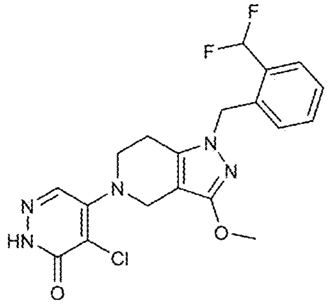 | 1H NMR (400 MHz, DMSO-d6) chemical shifts 12.89 (s, 1H), 7.91 (s, 1H), 7.63 (d, J = 7.5 Hz, 1H), 7.51 (d, J = 7.3 Hz, 1H), 7.51 - 7.36 (m, 2H), 6.87 (d, J = 7.6 Hz, 1H), 5.31 (s, 2H), 4.29 (s, 2H), 3.79 (s, 3H), 3.63 (t, J = 5.6 Hz, 2H), 2.75 (s, 2H). | 422 |

Figure 54

| | | |
|---|---|---|
| 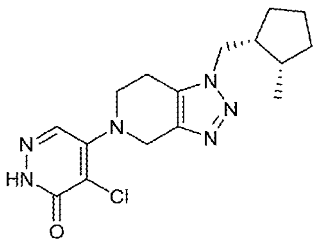 | 1H NMR (400 MHz, DMSO-d6) chemical shifts 12.95 (s, 1H), 7.96 (s, 1H), 4.59 (s, 2H), 4.33 (dd, J = 13.9, 6.5 Hz, 1H), 4.12 (dd, J = 13.9, 9.3 Hz, 1H), 3.69 (t, J = 5.5 Hz, 2H), 2.96 (t, J = 5.6 Hz, 2H), 2.37 (q, J = 7.9 Hz, 1H), 2.06 (dt, J = 13.5, 6.9 Hz, 1H), 1.74 (ddq, J = 32.5, 16.7, 7.7 Hz, 2H), 1.52 (t, J = 7.7 Hz, 2H), 1.35 (tt, J = 12.3, 6.9 Hz, 2H), 0.93 (d, J = 7.1 Hz, 3H). | 349 |
| 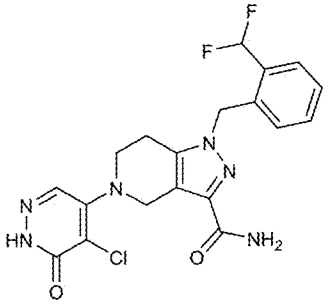 | 1H NMR (400 MHz, DMSO-d6) chemical shifts 12.86 (s, 1H), 7.86 (s, 1H), 7.65 (d, J = 7.1 Hz, 1H), 7.57 - 7.39 (m, 4H), 7.27 (s, 1H), 6.86 (d, J = 7.4 Hz, 1H), 5.53 (s, 2H), 4.61 (s, 2H), 3.66 (t, J = 5.7 Hz, 2H), 2.82 (d, J = 5.1 Hz, 2H). | 435 |
| 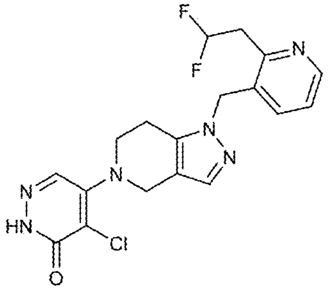 | 1H NMR (400 MHz, Methanol-d4) chemical shifts 8.48 (d, J = 3.9 Hz, 1H), 7.95 (s, 1H), 7.49 (s, 1H), 7.31 (dd, J = 7.9, 4.9 Hz, 1H), 7.13 (d, J = 7.9 Hz, 1H), 6.28 (t, J = 4.6 Hz, 1H), 5.48 (s, 2H), 4.57 (s, 2H), 3.82 (t, J = 5.6 Hz, 2H), 3.50 (td, J = 16.7, 4.5 Hz, 2H), 2.85 (t, J = 5.7 Hz, 2H). | 407 |
| 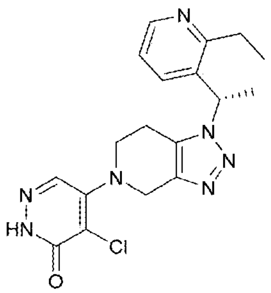 | 1H NMR (400 MHz, DMSO-d6) chemical shifts 12.93 (s, 1H), 8.47 (dd, J = 4.7, 1.7 Hz, 1H), 7.92 (s, 1H), 7.49 (dd, J = 7.9, 1.7 Hz, 1H), 7.25 (dd, J = 7.9, 4.7 Hz, 1H), 6.10 (q, J = 6.9 Hz, 1H), 4.58 (s, 2H), 3.60 (q, J = 6.5, 6.1 Hz, 2H), 2.83 (ddd, J = 31.2, 14.9, 7.4 Hz, 3H), 2.45 (d, J = 15.3 Hz, 1H), 1.89 (d, J = 6.9 Hz, 3H), 1.17 (t, J = 7.5 Hz, 3H). | 386 |

Figure 55

| | | |
|---|---|---|
| 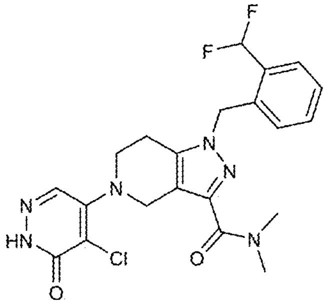 | 1H NMR (400 MHz, DMSO-d6) chemical shifts 12.89 (s, 1H), 7.86 (s, 1H), 7.69 - 7.62 (m, 1H), 7.56 - 7.43 (m, 2H), 7.38 (s, 0H), 6.93 (d, J = 7.4 Hz, 1H), 5.53 (s, 2H), 4.55 (s, 2H), 3.68 (t, J = 5.6 Hz, 2H), 3.31 (d, J = 9.8 Hz, 4H), 2.96 (s, 3H) ,2.86 - 2.79 (m, 2H). | 463 |
| 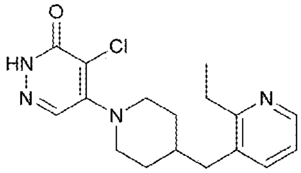 | 1H NMR (400 MHz, DMSO-d6) chemical shifts 12.87 (s, 1H), 8.35 (dd, J = 4.8, 1.9 Hz, 1H), 7.83 (s, 1H), 7.51 (dd, J = 7.7, 1.8 Hz, 1H), 7.14 (dd, J = 7.6, 4.7 Hz, 1H), 3.75 (d, J = 12.6 Hz, 2H), 2.92 (t, J = 12.3 Hz, 2H), 2.79 (q, J = 7.5 Hz, 2H), 2.60 (d, J = 7.1 Hz, 2H), 1.74 (s, 1H), 1.64 (d, J = 12.8 Hz, 2H), 1.42 - 1.30 (m, 2H), 1.22 (t, J = 7.5 Hz, 3H). | 0 |
| 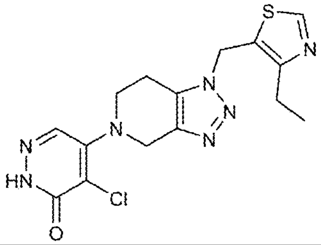 | 1H NMR (400 MHz, DMSO-d6) chemical shifts 12.89 (dr, 1H), 9.00 (s, 1H), 7.95 (s, 1H), 5.83 (s, 2H), 4.58 (s, 2H), 3.68 (d, J = 5.7 Hz, 2H), 2.97 - 2.75 (m, 4H), 1.19 (t, J = 7.5 Hz, 3H). | 0 |
| 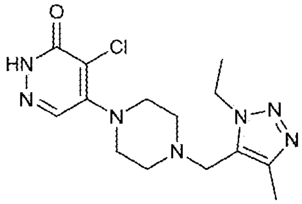 | 1H NMR (CHLOROFORM-d) δ: 10.40-10.63 (m, 1H), 7.61 (s, 1H), 4.39 (q, J=7.3 Hz, 2H), 3.56 (s, 2H), 3.38-3.46 (m, 4H), 2.53-2.63 (m, 4H), 2.31 (s, 3H), 1.51-1.56 (m, 3H) | 338.4 |
| 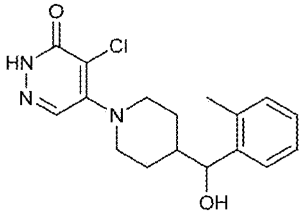 | 1H NMR (DMSO-d6 ) δ: 12.83 (s, 1H), 7.80 (s, 1H), 7.37 (d, J=7.6 Hz, 1H), 7.01-7.20 (m, 3H), 5.07 (br d, J=4.4 Hz, 1H), 4.47-4.64 (m, 1H), 3.67-3.86 (m, 2H), 2.80-2.93 (m, 2H), 2.28 (s, 3H), 1.58-1.89 (m, 2H), 1.25-1.52 (m, 3H) | 334.3 |
Figure 56

| | | |
|---|---|---|
| 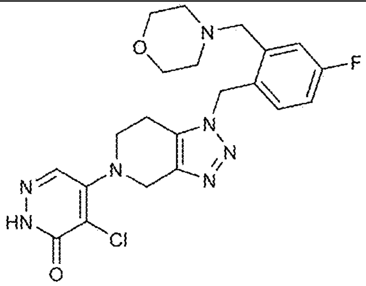 | 1H NMR (400 MHz, DMSO-d6) chemical shifts 12.94 (s, 1H), 7.95 (s, 1H), 7.21 (dd, J = 9.8, 2.8 Hz, 1H), 7.12 (td, J = 8.5, 2.8 Hz, 1H), 7.02 (dd, J = 8.5, 5.7 Hz, 1H), 5.73 (s, 2H), 4.60 (s, 2H), 3.64 (t, J = 5.6 Hz, 2H), 3.52 (s, 6H), 2.75 (t, J = 5.6 Hz, 2H), 2.34 (s, 4H). | 460 |
| 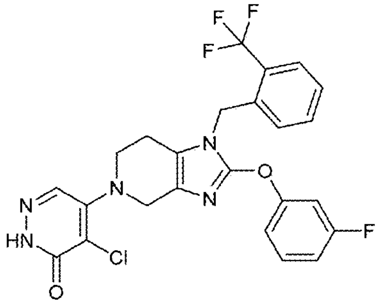 | 1H NMR (400 MHz, DMSO-d6) chemical shifts 12.89 (s, 1H), 7.92 (s, 1H), 7.79 (d, J = 7.9 Hz, 1H), 7.67 (t, J = 7.7 Hz, 1H), 7.53 (t, J = 7.7 Hz, 1H), 7.39 (q, J = 7.8 Hz, 1H), 7.13 (d, J = 10.6 Hz, 1H), 7.06 - 6.94 (m, 3H), 5.27 (s, 2H), 4.38 (s, 2H), 3.71 (s, 2H), 2.62 (s, 2H). | 520 |
| 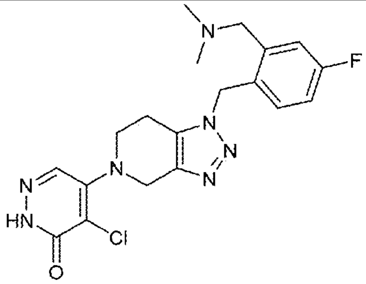 | 1H NMR (400 MHz, DMSO-d6) chemical shifts 12.94 (s, 1H), 7.94 (s, 1H), 7.19 (dd, J = 10.0, 2.7 Hz, 1H), 7.15 - 7.07 (m, 1H), 7.01 (dd, J = 8.5, 5.8 Hz, 1H), 5.71 (s, 2H), 4.60 (s, 2H), 3.65 (t, J = 5.5 Hz, 2H), 3.45 (s, 2H), 2.77 (t, J = 5.4 Hz, 2H), 2.16 (s, 6H). | 418 |
| 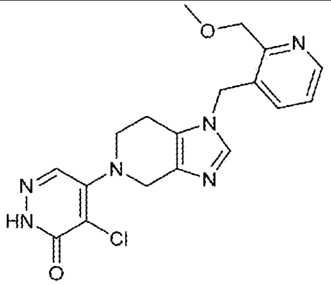 | 1H NMR (400 MHz, DMSO-d6) chemical shifts 12.86 (s, 1H), 8.46 (d, J = 4.6 Hz, 1H), 7.91 (s, 1H), 7.68 (s, 1H), 7.36 (dd, J = 7.8, 5.0 Hz, 1H), 7.10 (d, J = 7.7 Hz, 1H), 5.33 (s, 2H), 4.63 (s, 2H), 4.41 (s, 2H), 3.65 (d, J = 5.7 Hz, 2H), 3.33 (dd, J = 5.3, 1.6 Hz, 3H), 2.56 (s, 2H). | 387 |
| 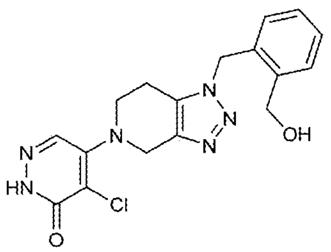 | 1H NMR (400 MHz, DMSO-d6) chemical shifts 12.93 (s, 1H), 7.95 (s, 1H), 7.46 (d, J = 7.6 Hz, 1H), 7.33 (t, J = 7.5 Hz, 1H), 7.25 (t, J = 7.5 Hz, 1H), 6.90 (d, J = 7.6 Hz, 1H), 5.64 (s, 2H), 5.25 (t, J = 5.4 Hz, 1H), 4.65 - 4.58 (m, 4H), 3.65 (t, J = 5.5 Hz, 2H), 2.78 (t, J = 5.6 Hz, 2H). | 373 |

Figure 57

| | | |
|---|---|---|
| 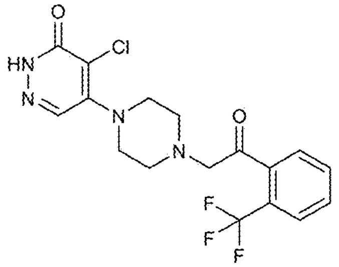 | 1H NMR (CHLOROFORM-d) δ: 10.25 (br s, 1H), 7.71-7.76 (m, 1H), 7.56-7.67 (m, 3H), 7.40-7.45 (m, 1H), 3.75 (s, 2H), 3.47-3.56 (m, 4H), 2.75-2.85 (m, 4H) | 401.4 |
| 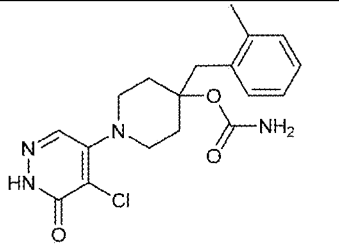 | 1H NMR (CHLOROFORM-d) δ: 10.15 (br s, 1H), 7.60 (s, 1H), 7.09-7.21 (m, 4H), 4.65 (br s, 2H), 3.64 (br d, J=12.7 Hz, 2H), 3.36 (s, 2H), 3.17-3.28 (m, 2H), 2.45 (br d, J=12.3 Hz, 2H), 2.37 (s, 3H), 1.77 (td, J=13.2, 4.4 Hz, 2H) | 377.4 |
| 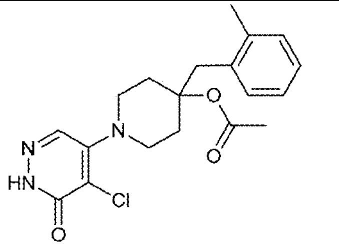 | 1H NMR (CHLOROFORM-d) δ: 10.36 (br s, 1H), 7.61 (s, 1H), 7.04-7.25 (m, 4H), 3.65 (br d, J=12.8 Hz, 2H), 3.35 (s, 2H), 3.13-3.26 (m, 2H), 3.09-3.11 (m, 1H), 2.46 (br d, J=12.5 Hz, 2H), 2.36 (s, 3H), 2.13 (s, 3H), 1.77 (td, J=13.1, 4.4 Hz, 2H) | 376.4 |
| 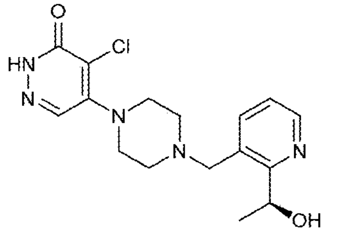 | 1H NMR (400 MHz, DMSO-d6) chemical shifts 12.95 (s, 1H), 8.51 - 8.45 (m, 1H), 7.86 (s, 1H), 7.76 - 7.70 (m, 1H), 7.29 (dd, J = 7.6, 4.9 Hz, 1H), 5.43 (d, J = 5.5 Hz, 1H), 5.10 (t, J = 5.9 Hz, 1H), 3.72 (d, J = 13.2 Hz, 1H), 3.63 (d, J = 13.3 Hz, 1H), 3.33 (m, 4H), 2.54 (m, 4H), 1.43 (d, J = 6.4 Hz, 3H). | 350 |
| 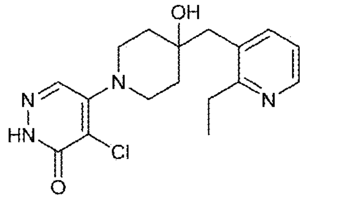 | 1H NMR (400 MHz, DMSO-d6) chemical shifts 12.85 (s, 1H), 8.13 (d, J = 6.2 Hz, 1H), 7.84 (s, 1H), 7.18 (dt, J = 15.7, 7.6 Hz, 2H), 3.77 (d, J = 12.6 Hz, 2H), 3.08 - 2.77 (m, 4H), 2.62 (d, J = 7.1 Hz, 2H), 1.74 (s, 1H), 1.67 (d, J = 13.7 Hz, 2H), 1.37 (dd, J = 13.7, 10.0 Hz, 2H), 1.14 (t, J = 7.3 Hz, 3H). | 349 |
Figure 58

| | | |
|---|---|---|
| 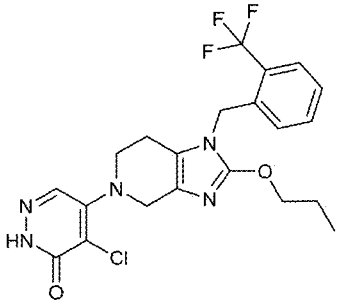 | 1H NMR (400 MHz, DMSO-d6) chemical shifts 12.87 (s, 1H), 7.90 (s, 1H), 7.79 (d, J = 7.8 Hz, 1H), 7.66 (t, J = 7.7 Hz, 1H), 7.52 (t, J = 7.7 Hz, 1H), 6.83 (d, J = 7.8 Hz, 1H), 5.10 (s, 2H), 4.34 (s, 2H), 4.18 (t, J = 6.4 Hz, 2H), 3.67 (t, J = 5.4 Hz, 2H), 2.55 (s, 2H), 1.60 (h, J = 7.1 Hz, 2H), 0.77 (t, J = 7.4 Hz, 3H). | 468 |
| 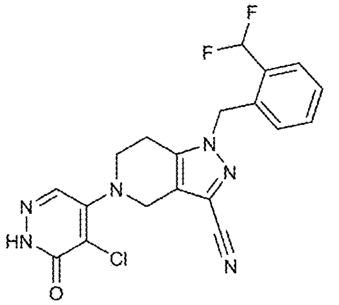 | 1H NMR (400 MHz, DMSO-d6) chemical shifts 12.92 (s, 1H), 7.97 (s, 1H), 7.67 (d, J = 7.2 Hz, 1H), 7.58 - 7.44 (m, 2H), 7.33 (s, 1H), 6.99 (d, J = 7.2 Hz, 1H), 5.61 (s, 2H), 4.58 (s, 2H), 3.67 (d, J = 11.1 Hz, 2H), 2.88 (d, J = 5.7 Hz, 2H). 12.92 (s, 1H), 7.97 (s, 1H), 7.67 (d, J = 7.2 Hz, 1H), 7.58 - 7.44 (m, 2H), 7.33 (s, 1H), 6.99 (d, J = 7.2 Hz, 1H), 5.61 (s, 2H), 4.58 (s, 2H), 3.67 (d, J = 11.1 Hz, 2H), 2.88 (d, J = 5.7 Hz, 2H). | 417 |
| 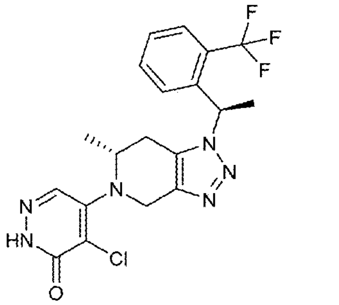 | 1H NMR (400 MHz, DMSO-d6) chemical shifts 12.96 (s, 1H), 7.89 (s, 1H), 7.80 (d, J = 7.9 Hz, 1H), 7.68 (t, J = 7.7 Hz, 1H), 7.55 (t, J = 7.7 Hz, 1H), 7.32 (d, J = 7.9 Hz, 1H), 6.05 (q, J = 6.8 Hz, 1H), 4.64 (d, J = 14.9 Hz, 1H), 4.46 - 4.35 (m, 2H), 2.71 (d, J = 16.1 Hz, 1H), 2.55 (s, 1H), 1.97 (d, J = 6.8 Hz, 3H), 1.08 (d, J = 6.7 Hz, 3H). | 439 |
| 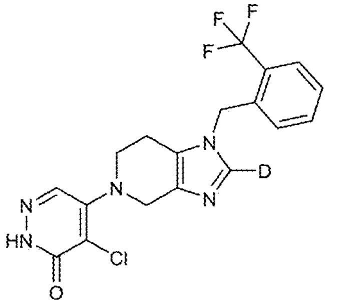 | 1H NMR (400 MHz, DMSO-d6) chemical shifts 12.87 (s, 1H), 7.91 (s, 1H), 7.81 (d, J = 7.8 Hz, 1H), 7.67 (dd, J = 16.0, 8.3 Hz, 1H), 7.54 (t, J = 7.6 Hz, 1H), 6.79 (d, J = 7.8 Hz, 1H), 5.40 (s, 2H), 4.43 (s, 2H), 3.64 (t, J = 5.5 Hz, 2H), 2.54 (d, J = 5.4 Hz, 2H). | 411 |
| 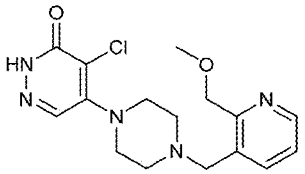 | 1H NMR (400 MHz, Methanol-d4) chemical shifts 8.44 (d, J = 4.9 Hz, 1H), 7.92 (d, J = 8.0 Hz, 1H), 7.89 (s, 1H), 7.40 (dd, J = 7.7, 4.9 Hz, 1H), 4.74 (s, 2H), 3.72 (s, 2H), 3.53 (t, J = 4.8 Hz, 4H), 3.43 (s, 3H), 2.64 (t, J = 4.8 Hz, 4H). | 350 |

Figure 59

| | | |
|---|---|---|
| 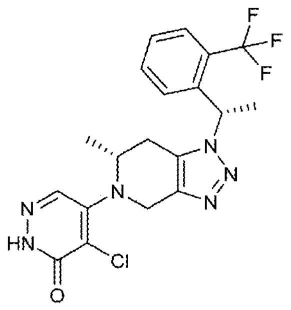 | 1H NMR (400 MHz, DMSO-d6) chemical shifts 12.99 (s, 1H), 7.91 (s, 1H), 7.81 (d, J = 7.9 Hz, 1H), 7.70 (t, J = 7.6 Hz, 1H), 7.57 (t, J = 7.6 Hz, 1H), 7.28 (d, J = 8.0 Hz, 1H), 6.00 (q, J = 6.9 Hz, 1H), 4.59 (d, J = 15.0 Hz, 1H), 4.46 (d, J = 15.0 Hz, 1H), 4.41 - 4.34 (m, 1H), 3.21 (dd, J = 16.2, 5.9 Hz, 1H), 2.02 (d, J = 16.2 Hz, 1H), 1.96 (d, J = 6.8 Hz, 3H), 0.82 (d, J = 6.7 Hz, 3H). | 439 |
| 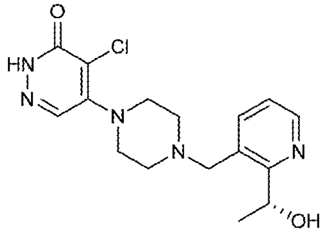 | 1H NMR (400 MHz, DMSO-d6) chemical shifts 12.94 (s, 1H), 8.51 - 8.45 (m, 1H), 7.86 (s, 1H), 7.73 (d, J = 7.6 Hz, 1H), 7.29 (dd, J = 7.6, 4.8 Hz, 1H), 5.43 (d, J = 5.4 Hz, 1H), 5.10 (t, J = 6.1 Hz, 1H), 3.72 (d, J = 13.3 Hz, 1H), 3.63 (d, J = 13.3 Hz, 1H), 3.33 (m, 4H), 2.54 (m, 4H), 1.43 (d, J = 6.4 Hz, 3H). | 350 |
| 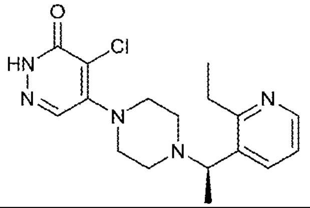 | 1H NMR (400 MHz, DMSO-d6) chemical shifts 12.93 (s, 1H), 8.41 (s, 1H), 7.85 (s, 1H), 7.81 (s, 1H), 7.26 (s, 1H), 3.74 (s, 1H), 2.89 (t, J = 7.5 Hz, 2H), 2.59 (s, 4H), 2.44 (s, 4H), 1.32 - 1.19 (m, 6H). | 348 |
| 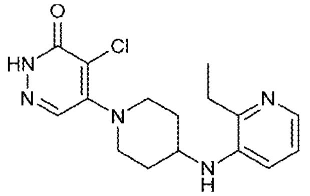 | 1H NMR (400 MHz, DMSO-d6) chemical shifts 12.83 (s, 1H), 7.88 (s, 1H), 7.74 (dd, J = 4.0, 2.0 Hz, 1H), 6.99 (d, J = 3.9 Hz, 2H), 4.83 (d, J = 8.2 Hz, 1H), 3.82 (d, J = 12.9 Hz, 2H) ,3.55 - 3.54 (m, 1H), 3.15 (t, J = 12.2 Hz, 2H), 2.65 (q, J = 7.4 Hz, 2H), 2.03 - 1.94 (m, 2H), 1.65- 1.61 (m, 2H), 1.18 (t, J = 7.4 Hz, 3H). | 334 |
| 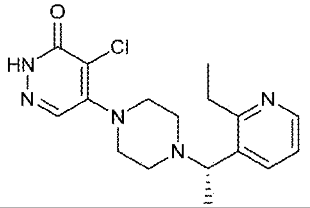 | 1H NMR (400 MHz, DMSO-d6) chemical shifts 12.93 (s, 1H), 8.41 (s, 1H), 7.85 (s, 1H), 7.81 (s, 1H), 7.27 (s, 1H), 3.74 (s, 1H), 2.89 (t, J = 7.5 Hz, 2H), 2.59 (s, 4H), 2.43 (s, 4H), 1.32 - 1.19 (m, 6H). | 348 |

Figure 60

| | | |
|---|---|---|
| 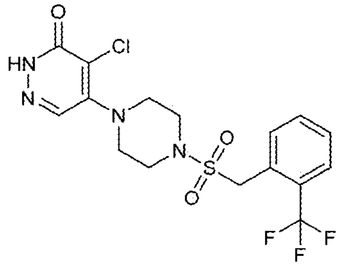 | 1H NMR (DMSO-d6 ) δ: 13.00 (s, 1H), 7.88 (s, 1H), 7.79 (d, J=7.9 Hz, 1H), 7.67-7.75 (m, 2H), 7.57-7.63 (m, 1H), 4.57 (s, 2H), 3.43-3.49 (m, 4H), 3.33-3.39 (m, 4H) | 437.2 |
| 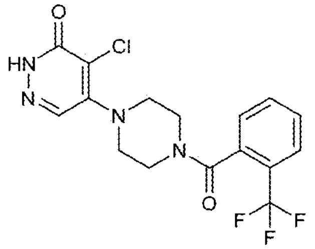 | 1H NMR (DMSO-d6 ) δ: 12.97 (s, 1H), 7.86 (s, 1H), 7.83 (d, J=7.9 Hz, 1H), 7.73-7.78 (m, 1H), 7.63-7.70 (m, 1H), 7.53 (d, J=7.5 Hz, 1H), 3.69-3.84 (m, 2H), 3.46-3.55 (m, 1H), 3.34-3.44 (m, 2H), 3.19-3.28 (m, 2H), 3.08-3.19 (m, 1H) | 387.3 |
| 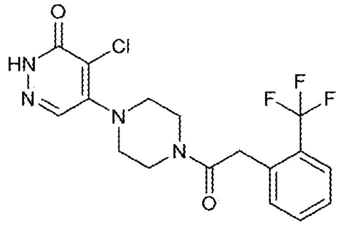 | 1H NMR (DMSO-d6 ) δ: 12.97 (s, 1H), 7.88 (s, 1H), 7.68 (d, J=7.8 Hz, 1H), 7.56-7.64 (m, 1H), 7.41-7.52 (m, 1H), 7.38 (d, J=7.6 Hz, 1H), 3.91 (s, 2H), 3.52-3.74 (m, 4H), 3.34-3.50 (m, 4H) | 401.3 |
| 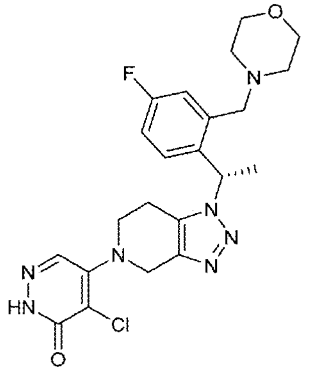 | 1H NMR (400 MHz, DMSO-d6) chemical shifts 12.94 (s, 1H), 7.92 (s, 1H), 7.29 - 7.00 (m, 3H), 6.16 (q, J = 6.7 Hz, 1H), 4.58 (m, 2H), 3.74 - 3.42 (m, 8H), 2.97 - 2.88 (m, 1H), 2.47 - 2.31 (m, 5H), 1.91 (d, J = 6.9 Hz, 3H). | 474 |
| 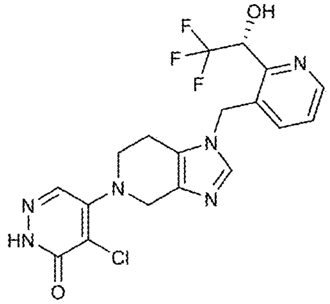 | 1H NMR (400 MHz, Methanol-d4) chemical shifts 8.57 (d, J = 4.8 Hz, 1H), 7.93 (s, 1H), 7.74 (s, 1H), 7.44 (dd, J = 8.0, 4.8 Hz, 1H), 7.22 (d, J = 8.2 Hz, 1H), 5.61 (d, J = 16.8 Hz, 1H), 5.53 - 5.42 (m, 2H), 4.54 (s, 2H), 3.80 (t, J = 5.5 Hz, 2H), 2.65 (q, J = 15.5 Hz, 2H). | 441 |
Figure 61

| | | |
|---|---|---|
| 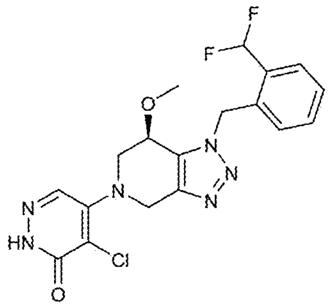 | 1H NMR (400 MHz, DMSO-d6) chemical shifts 12.97 (s, 1H), 7.84 (s, 1H), 7.68 (d, J = 7.3 Hz, 1H), 7.58 - 7.19 (m, 3H), 7.03 (d, J = 7.2 Hz, 1H), 5.86 (d, J = 16.0 Hz, 1H), 5.77 (d, J = 15.8 Hz, 1H), 4.74 (d, J = 15.1 Hz, 1H), 4.66 (s, 1H), 4.56 (d, J = 15.1 Hz, 1H), 3.95 - 3.86 (m, 1H), 3.75 (d, J = 13.2 Hz, 1H), 2.08 (s, 1H). | 423 |
| 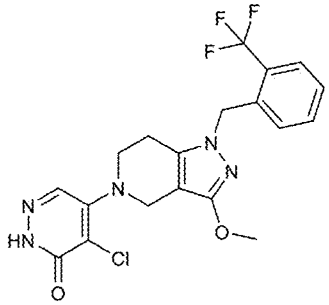 | 1H NMR (400 MHz, DMSO-d6) chemical shifts 12.90 (s, 1H), 7.92 (s, 1H), 7.78 (d, J = 7.8 Hz, 1H), 7.63 (t, J = 7.6 Hz, 1H), 7.51 (t, J = 7.6 Hz, 1H), 6.76 (d, J = 7.8 Hz, 1H), 5.31 (s, 2H), 4.32 (s, 2H), 3.80 (s, 3H), 3.64 (t, J = 5.6 Hz, 2H), 2.73 (t, J = 5.7 Hz, 2H). | 440 |
| 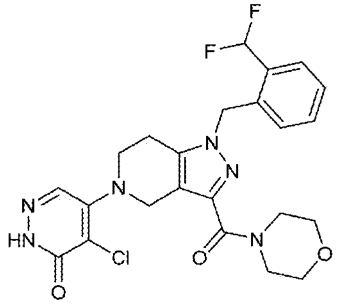 | 1H NMR (400 MHz, DMSO-d6) chemical shifts 12.90 (s, 1H), 7.87 (s, 1H), 7.66 (d, J = 7.3 Hz, 1H), 7.50 (p, J = 7.8 Hz, 2H), 7.40-7.38 (m, 1H), 6.94 (d, J = 7.4 Hz, 1H), 5.54 (s, 2H), 4.57 (s, 2H), 4.03 (s, 2H), 3.69 (d, J = 11.1 Hz, 2H), 3.67-3.64 (m, 6H), 2.84 (t, J = 5.6 Hz, 2H). | 505 |
| 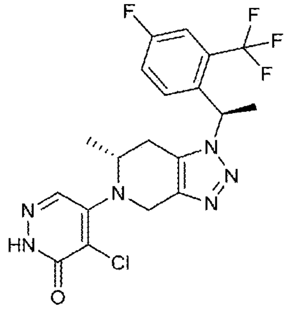 | 1H NMR (400 MHz, DMSO-d6) chemical shifts 12.96 (s, 1H), 7.92 (s, 1H), 7.76 (d, J = 10.4 Hz, 1H), 7.64 (d, J = 8.1 Hz, 1H), 7.45 (t, J = 7.7 Hz, 1H), 6.15 (d, J = 6.9 Hz, 1H), 4.64 (d, J = 15.3 Hz, 1H), 4.44 (d, J = 14.8 Hz, 2H), 2.82 (s, 2H), 1.97 (d, J = 7.0 Hz, 3H), 1.10 (d, J = 6.7 Hz, 3H). | 457 |
| 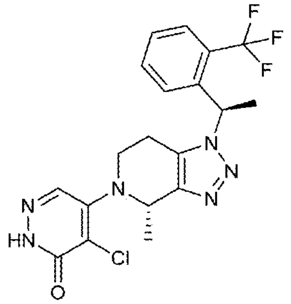 | 1H NMR (400 MHz, DMSO-d6) chemical shifts 12.88 (s, 1H), 7.85 (s, 1H), 7.80 (d, J = 7.9 Hz, 1H), 7.68 (t, J = 7.8 Hz, 1H), 7.55 (t, J = 7.6 Hz, 1H), 7.34 (d, J = 8.0 Hz, 1H), 6.00 (q, J = 6.8 Hz, 1H), 5.14 (q, J = 6.6 Hz, 1H), 3.87 - 3.79 (m, 1H), 3.51 - 3.41 (m, 1H), 2.86 (d, J = 16.1 Hz, 1H), | 438 |

Figure 62

| | | |
|---|---|---|
| | 2.30 (d, J = 10.3 Hz, 1H), 1.97 (d, J = 6.8 Hz, 3H), 1.50 (d, J = 6.5 Hz, 3H). | |
| 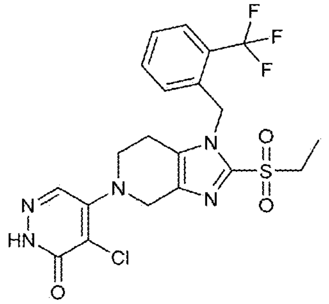 | 1H NMR (400 MHz, Methanol-d4) chemical shifts 7.97 (s, 1H), 7.82 (d, J = 7.4 Hz, 1H), 7.59 (t, J = 7.6 Hz, 1H), 7.52 (t, J = 7.6 Hz, 1H), 6.62 (d, J = 7.7 Hz, 1H), 5.86 (s, 2H), 4.62 (d, J = 1.5 Hz, 2H), 3.83 (t, J = 5.5 Hz, 2H), 3.38 (t, J = 7.4 Hz, 2H), 2.72 (t, J = 5.7 Hz, 2H), 1.31 (t, J = 7.4 Hz, 3H). | 502 |
| 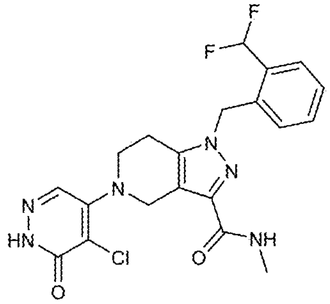 | 1H NMR (400 MHz, DMSO-d6) chemical shifts 12.90 (s, 1H), 8.05 (d, J = 5.0 Hz, 1H), 7.87 (s, 1H), 7.66 (d, J = 7.3 Hz, 1H), 7.55 - 7.43 (m, 2H), 7.40-7.38 (m, 1H), 6.83 (d, J = 7.4 Hz, 1H), 5.54 (s, 2H), 4.64 (s, 2H), 3.72 - 3.64 (m, 2H), 2.81 (t, J = 5.6 Hz, 2H), 2.73 (d, J = 4.6 Hz, 3H). | 449 |
| 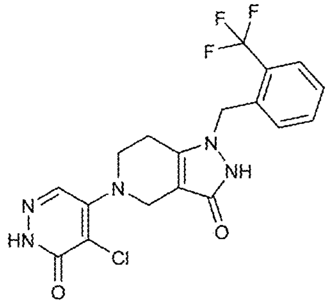 | 1H NMR (400 MHz, DMSO-d6) chemical shifts 12.89 (s, 1H), 9.91 (s, 1H), 7.89 (s, 1H), 7.76 (d, J = 7.8 Hz, 1H), 7.63 (t, J = 7.7 Hz, 1H), 7.50 (t, J = 7.7 Hz, 1H), 6.84 (d, J = 7.9 Hz, 1H), 5.22 (s, 2H), 4.29 (s, 2H), 3.64 (d, J = 5.9 Hz, 2H), 2.74 (s, 2H). | 426 |
| 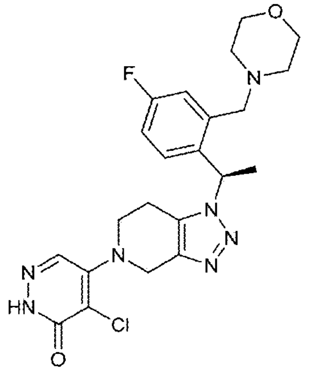 | 1H NMR (400 MHz, DMSO-d6) chemical shifts 12.94 (s, 1H), 7.92 (s, 1H), 7.31 - 7.02 (m, 3H), 6.16 (q, J = 6.8 Hz, 1H), 4.64 - 4.52 (m, 2H), 3.68 - 3.44 (m, 8H), 2.97 - 2.88 (m, 1H), 2.48 - 2.34 (m, 5H), 1.91 (d, J = 6.8 Hz, 3H). | 474 |
Figure 63

| | | |
|---|---|---|
| 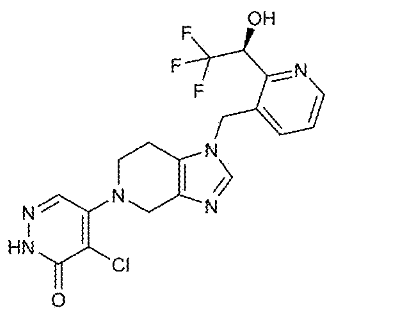 | 1H NMR (400 MHz, DMSO-d6) chemical shifts 12.87 (s, 1H), 8.56 (d, J = 4.7 Hz, 1H), 7.91 (s, 1H), 7.71 (s, 1H), 7.44 (dd, J = 8.0, 4.7 Hz, 1H), 7.09 (d, J = 7.1 Hz, 1H), 6.99 (d, J = 7.6 Hz, 1H), 5.56 (q, J = 7.8 Hz, 1H), 5.48 (d, J = 16.7 Hz, 1H), 5.39 (d, J = 16.8 Hz, 1H), 4.42 (s, 2H), 3.64 (t, J = 5.4 Hz, 2H), 2.59 (d, J = 15.6 Hz, 2H). | 441 |
| 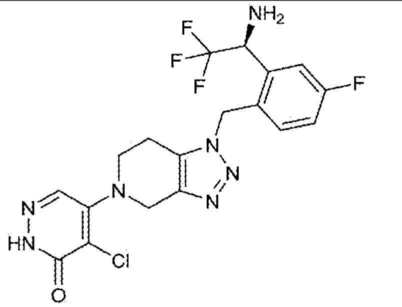 | 1H NMR (400 MHz, DMSO-d6) chemical shifts 12.95 (s, 1H), 7.94 (s, 1H), 7.55 (d, J = 10.0 Hz, 1H), 7.23 (td, J = 8.4, 2.8 Hz, 1H), 7.11 (dd, J = 8.7, 5.8 Hz, 1H), 5.75 (d, J = 15.8 Hz, 1H), 5.66 (d, J = 15.9 Hz, 1H), 5.04 (s, 1H), 4.59 (s, 2H), 3.63 (d, J = 7.5 Hz, 2H), 2.85 (d, J = 16.0 Hz, 1H), 2.73 (s, 1H), 2.66 (m, 2H). | 458 |
| 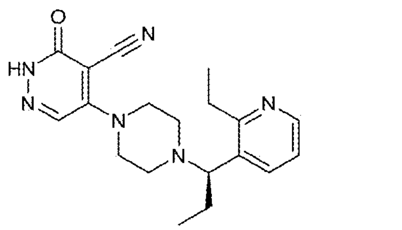 | 1H NMR (400 MHz, Methanol-d4) chemical shifts 8.39 (d, J = 4.8 Hz, 1H), 7.94 (s, 1H), 7.89 (d, J = 8.1 Hz, 1H), 7.34 - 7.27 (m, 1H), 3.85 (d, J = 4.0 Hz, 4H), 3.71 (d, J = 5.3 Hz, 1H), 2.94 (t, J = 7.6 Hz, 2H), 2.76 (s, 2H), 2.60 (s, 2H), 2.02 (s, 1H), 1.84 (dt, J = 15.1, 8.2 Hz, 1H), 1.30 (t, J = 7.6 Hz, 3H), 0.77 (t, J = 7.3 Hz, 3H). | 353 |
| 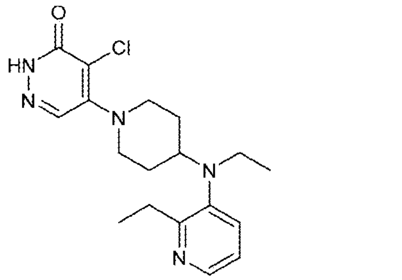 | 1H NMR (400 MHz, DMSO-d6) chemical shifts 12.86 (s, 1H), 8.27 (d, J = 4.3 Hz, 1H), 7.83 (s, 1H), 7.59 (d, J = 8.0 Hz, 1H), 7.20 (dd, J = 8.0, 4.6 Hz, 1H), 3.76 (d, J = 12.6 Hz, 2H), 3.12 - 2.92 (m, 5H), 2.86 (q, J = 7.5 Hz, 2H), 1.81 (d, J = 12.5 Hz, 2H), 1.65 - 1.51 (m, 2H), 1.22 (t, J = 7.5 Hz, 3H), 0.81 (t, J = 7.0 Hz, 3H). | 362 |
| 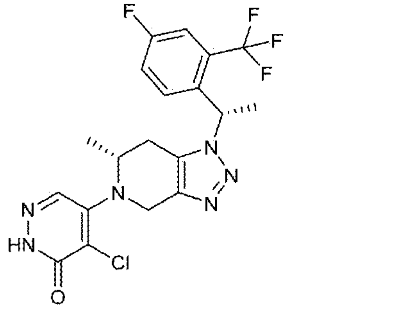 | 1H NMR (400 MHz, DMSO-d6) chemical shifts 12.96 (s, 1H), 7.89 (s, 1H), 7.71 (d, J = 6.8 Hz, 1H), 7.58 (s, 1H), 7.46 - 7.38 (m, 1H), 6.04 (d, J = 6.5 Hz, 1H), 4.64 (d, J = 14.7 Hz, 1H), 4.42 (d, J = 14.7 Hz, 2H), 2.73 (d, J = 16.0 Hz, 1H), 2.61 (d, J = 6.1 Hz, 1H), 1.96 (d, J = 6.8 Hz, 3H), 1.09 (d, J = 6.7 Hz, 3H). | 457 |

Figure 64

| | | |
|---|---|---|
| 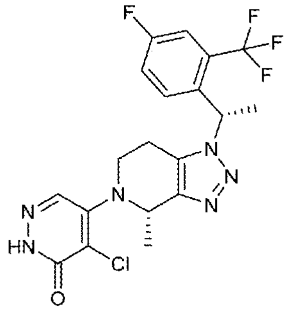 | 1H NMR (400 MHz, DMSO-d6) chemical shifts 12.94 (s, 1H), 7.92 (s, 1H), 7.74 - 7.67 (m, 1H), 7.62 (t, J = 8.9 Hz, 1H), 7.55 (t, J = 7.2 Hz, 1H), 5.97 (q, J = 6.9 Hz, 1H), 5.17 - 5.09 (m, 1H), 3.80 (d, J = 14.7 Hz, 1H), 3.41 (t, J = 9.5 Hz, 1H), 3.07 (d, J = 14.0 Hz, 1H), 2.32 (d, J = 14.6 Hz, 1H), 1.92 (d, J = 6.8 Hz, 3H), 1.47 (d, J = 6.5 Hz, 3H). | 457 |
| 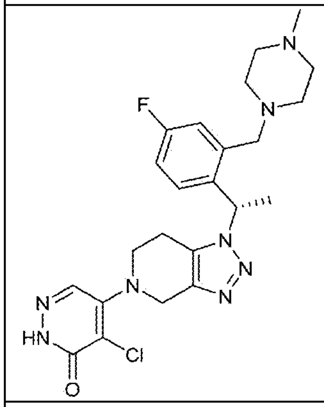 | 1H NMR (400 MHz, DMSO-d6) chemical shifts 12.94 (s, 1H), 7.93 (s, 1H), 7.35 - 7.02 (m, 3H), 6.12 (q, J = 6.8 Hz, 1H), 4.58 (d, J = 3.3 Hz, 2H), 3.71 - 3.40 (m, 4H), 2.97 - 2.88 (m, 1H), 2.44 - 2.22 (m, 8H), 2.14 (s, 3H), 1.89 (d, J = 6.9 Hz, 3H). | 487 |
| 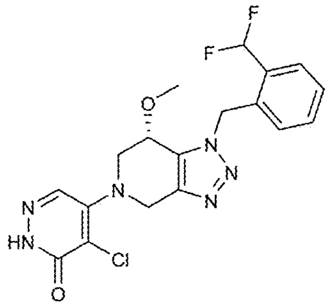 | 1H NMR (400 MHz, DMSO-d6) chemical shifts 12.97 (s, 1H), 7.85 (s, 1H), 7.68 (d, J = 7.3 Hz, 1H), 7.57 - 7.48 (m, 2H), 7.03 (d, J = 7.3 Hz, 1H), 5.86 (d, J = 15.9 Hz, 1H), 5.77 (d, J = 16.0 Hz, 1H), 4.74 (d, J = 15.0 Hz, 1H), 4.66 (s, 1H), 4.56 (d, J = 15.2 Hz, 1H), 3.91 (d, J = 14.6 Hz, 1H), 3.75 (d, J = 14.4 Hz, 1H), 2.09 (d, J = 1.7 Hz, 1H). | 423 |
| 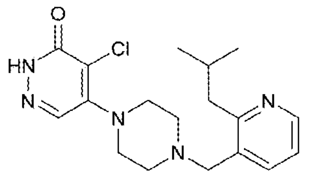 | 1H NMR (400 MHz, DMSO-d6) chemical shifts 12.92 (s, 1H), 8.41 (dd, J = 4.8, 1.8 Hz, 1H), 7.86 (s, 1H), 7.66 (dd, J = 7.7, 1.8 Hz, 1H), 7.18 (dd, J = 7.6, 4.7 Hz, 1H), 3.53 (s, 2H), 3.42 - 3.35 (m, 4H), 2.71 (d, J = 7.2 Hz, 2H), 2.51 - 2.45 (m, 4H), 2.18 (hept, J = 6.7 Hz, 1H), 0.91 (d, J = 6.6 Hz, 6H). | 362 |

Figure 65

| | | |
|---|---|---|
| 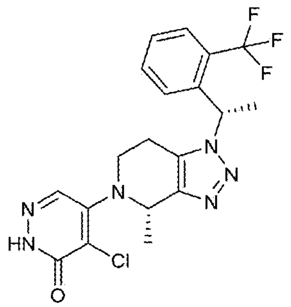 | 1H NMR (400 MHz, DMSO-d6) chemical shifts 12.92 (s, 1H), 7.92 (s, 1H), 7.81 (d, J = 7.9 Hz, 1H), 7.73 (t, J = 7.8 Hz, 1H), 7.57 (t, J = 7.7 Hz, 1H), 7.48 (d, J = 8.1 Hz, 1H), 5.99 (d, J = 7.0 Hz, 1H), 5.13 (q, J = 6.6 Hz, 1H), 3.80 (d, J = 13.6 Hz, 1H), 3.44-3.38 (m, 1H), 3.07 (dt, J = 10.8, 6.6 Hz, 1H), 2.29 (d, J = 15.9 Hz, 1H), 1.94 (d, J = 6.8 Hz, 3H), 1.47 (d, J = 6.5 Hz, 3H). | 439 |
| 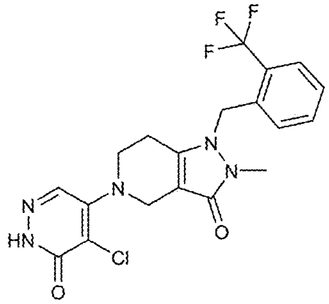 | 1H NMR (400 MHz, DMSO-d6) chemical shifts 12.92 (s, 1H), 7.94 (s, 1H), 7.81 (d, J = 7.8 Hz, 1H), 7.66 (t, J = 7.7 Hz, 1H), 7.54 (t, J = 7.7 Hz, 1H), 6.85 (d, J = 7.8 Hz, 1H), 5.17 (s, 2H), 4.18 (s, 2H), 3.66 (t, J = 5.5 Hz, 2H), 3.08 (s, 3H), 2.72 (d, J = 5.5 Hz, 2H). | 440 |
| 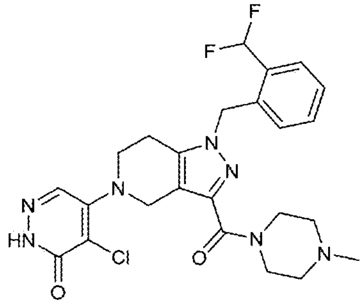 | 1H NMR (400 MHz, DMSO-d6) chemical shifts 12.90 (s, 1H), 7.87 (s, 1H), 7.67 (d, J = 7.4 Hz, 1H), 7.55 - 7.45 (m, 2H), 7.40-7.38 (m, 1H), 6.95 (d, J = 7.3 Hz, 1H), 5.53 (s, 2H), 4.55 (s, 2H), 3.98 (s, 2H), 3.69 (t, J = 5.5 Hz, 2H), 3.60 (s, 2H), 2.85 (d, J = 5.5 Hz, 2H), 2.33 (s, 4H), 2.20 (s, 3H). | 518 |
| 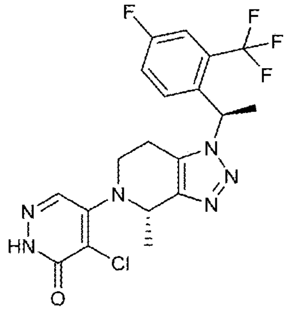 | 1H NMR (400 MHz, DMSO-d6) chemical shifts 12.89 (s, 1H), 7.86 (s, 1H), 7.74 - 7.67 (m, 1H), 7.57 (t, J = 8.2 Hz, 1H), 7.44 (dd, J = 9.0, 5.4 Hz, 1H), 6.00 (t, J = 6.8 Hz, 1H), 5.14 (q, J = 6.4 Hz, 1H), 3.84 (d, J = 12.5 Hz, 1H), 3.52 - 3.41 (m, 1H), 2.86 (d, J = 15.9 Hz, 1H), 2.39 (d, J = 8.4 Hz, 1H), 1.95 (d, J = 6.8 Hz, 3H), 1.50 (d, J = 6.5 Hz, 3H). | 457 |

Figure 66

| | | |
|---|---|---|
| 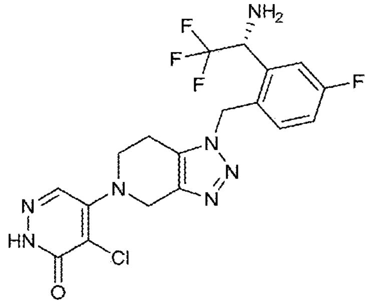 | 1H NMR (400 MHz, DMSO-d6) chemical shifts 12.95 (s, 1H), 7.94 (s, 1H), 7.55 (d, J = 10.6 Hz, 1H), 7.28 - 7.19 (m, 1H), 7.15 - 7.07 (m, 1H), 5.75 (d, J = 15.8 Hz, 1H), 5.66 (d, J = 15.8 Hz, 1H), 5.04 (d, J = 6.8 Hz, 1H), 4.59 (s, 2H), 3.64 (s, 2H), 2.85 (d, J = 16.2 Hz, 1H), 2.73 (s, 1H), 2.66 (m, 2H). | 458 |
| 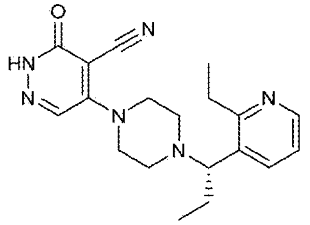 | 1H NMR (400 MHz, Methanol-d4) chemical shifts 8.39 (d, J = 4.8 Hz, 1H), 7.94 (s, 1H), 7.89 (d, J = 7.8 Hz, 1H), 7.34 - 7.27 (m, 1H), 3.86 (s, 4H), 3.75 - 3.68 (m, 1H), 2.95 (q, J = 7.5 Hz, 2H), 2.77 (d, J = 5.3 Hz, 2H), 2.60 (s, 2H), 2.02 (s, 1H), 1.84 (dt, J = 15.1, 8.2 Hz, 1H), 1.30 (t, J = 7.5 Hz, 3H), 0.77 (t, J = 7.4 Hz, 3H). | 353 |
| 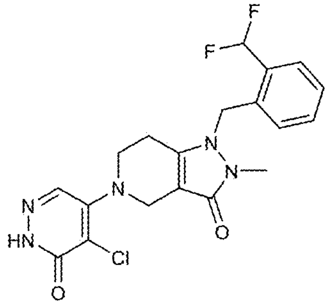 | 1H NMR (400 MHz, DMSO-d6) chemical shifts 12.88 (s, 1H), 7.94 (s, 1H), 7.65 (d, J = 7.5 Hz, 1H), 7.49 (dt, J = 22.6, 7.7 Hz, 2H), 7.45-7.19 (t, 1H), 6.78 (d, J = 7.6 Hz, 1H), 5.16 (s, 2H), 4.17 (s, 2H), 3.66 (t, J = 5.5 Hz, 2H), 3.09 (s, 3H), 2.70 (t, J = 5.3 Hz, 2H). | 422 |
| 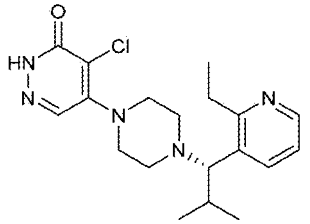 | 1H NMR (400 MHz, DMSO-d6) chemical shifts 12.90 (s, 1H), 8.42 (s, 1H), 7.82 (s, 1H), 7.62 (d, J = 7.8 Hz, 1H), 7.23 (s, 1H), 3.61 (d, J = 9.1 Hz, 1H), 3.33 (m, 2H), 2.89 (dt, J = 27.2, 7.2 Hz, 3H), 2.44 (s, 5H), 2.35 (s, 1H), 1.20 (dd, J = 8.3, 6.5 Hz, 3H), 1.04 (d, J = 6.3 Hz, 3H), 0.65 (d, J = 6.6 Hz, 3H). | 376 |
| 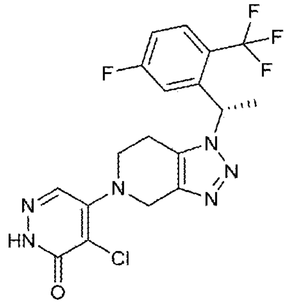 | 1H NMR (400 MHz, DMSO-d6) chemical shifts 12.94 (s, 1H), 7.96 - 7.87 (m, 2H), 7.43 (td, J = 8.3, 2.7 Hz, 1H), 7.21 (dd, J = 9.8, 2.7 Hz, 1H), 6.04 (q, J = 6.8 Hz, 1H), 4.60 (s, 2H), 3.62 (dtd, J = 19.8, 13.7, 5.3 Hz, 2H), 3.06 - 2.97 (m, 1H), 2.48 - 2.38 (m, 1H), 1.96 (d, J = 6.8 Hz, 3H). | 443 |

Figure 67

| | | |
|---|---|---|
| 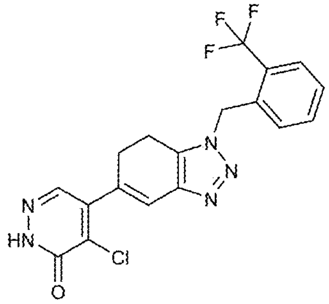 | 1H NMR (400 MHz, Methanol-d4) chemical shifts 7.93 (s, 1H), 7.84 (d, J = 7.8 Hz, 1H), 7.65 (t, J = 7.6 Hz, 1H), 7.58 (t, J = 7.6 Hz, 1H), 7.06 (d, J = 7.9 Hz, 1H), 7.01 (s, 1H), 5.85 (s, 2H), 2.96 - 2.89 (m, 4H). | 408 |
| 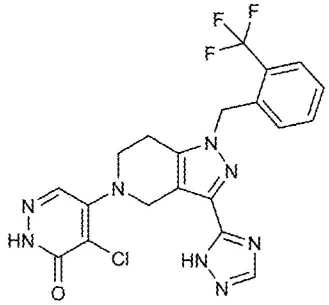 | 1H NMR (400 MHz, Methanol-d4) chemical shifts 8.38 (s, 1H), 8.05 (s, 1H), 7.79 (d, J = 7.8 Hz, 1H), 7.56 (t, J = 7.5 Hz, 1H), 7.50 (t, J = 7.6 Hz, 1H), 6.83 (d, J = 7.8 Hz, 1H), 5.66 (s, 2H), 4.82 (s, 2H), 3.85 (t, J = 5.6 Hz, 2H), 2.87 (t, J = 5.6 Hz, 2H). | 477 |
| 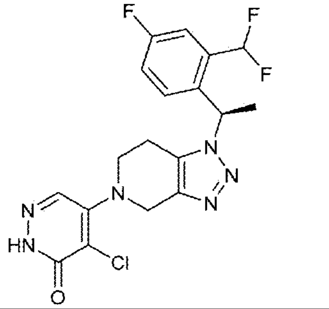 | 1H NMR (400 MHz, DMSO-d6) chemical shifts 12.94 (s, 1H), 7.93 (s, 1H), 7.54 - 7.33 (m, 4H), 6.12 (q, J = 6.8 Hz, 1H), 4.58 (d, J = 2.9 Hz, 2H), 3.68 - 3.51 (m, 2H), 2.99 - 2.91 (m, 1H), 2.47 - 2.38 (m, 1H), 1.92 (d, J = 6.8 Hz, 3H). | 425 |
| 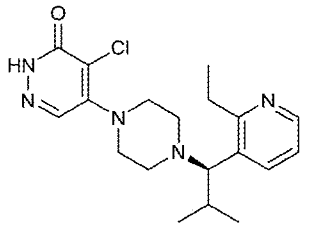 | 1H NMR (400 MHz, DMSO-d6) chemical shifts 12.90 (s, 1H), 8.41 (d, J = 4.5 Hz, 1H), 7.81 (s, 1H), 7.62 (d, J = 7.8 Hz, 1H), 7.23 (dd, J = 7.7, 4.7 Hz, 1H), 3.61 (d, J = 9.2 Hz, 1H), 3.33 (m, 2H), 2.98 - 2.80 (m, 2H), 2.44 (s, 6H), 2.35 (s, 1H), 1.20 (t, J = 7.4 Hz, 3H), 1.03 (d, J = 6.3 Hz, 3H), 0.65 (d, J = 6.5 Hz, 3H). | 376 |
| 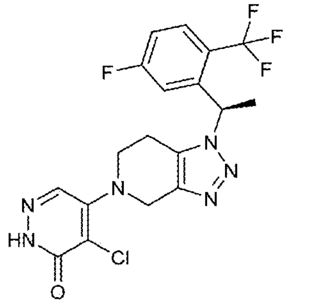 | 1H NMR (400 MHz, DMSO-d6) chemical shifts 12.94 (s, 1H), 7.96 - 7.87 (m, 2H), 7.48 - 7.38 (m, 1H), 7.22 (dd, J = 9.9, 2.6 Hz, 1H), 6.04 (q, J = 6.8 Hz, 1H), 4.60 (s, 2H), 3.71 - 3.53 (m, 2H), 3.06 - 2.97 (m, 1H), 2.47 - 2.38 (m, 1H), 1.96 (d, J = 6.8 Hz, 3H). | 443 |

Figure 68

| | | |
|---|---|---|
| 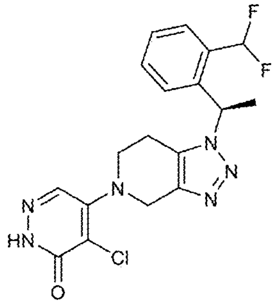 | 1H NMR (400 MHz, DMSO-d6) chemical shifts 12.94 (s, 1H), 7.92 (s, 1H), 7.65 (d, J = 7.6 Hz, 1H), 7.60 - 7.44 (m, 2H), 7.38 (s, 1H), 7.30 - 7.23 (m, 1H), 6.15 (q, J = 6.8 Hz, 1H), 4.58 (d, J = 2.5 Hz, 2H), 3.67 - 3.51 (m, 2H), 2.94 (d, J = 16.1 Hz, 1H), 2.38 (s, 1H), 1.93 (d, J = 6.8 Hz, 3H). | 407 |
| 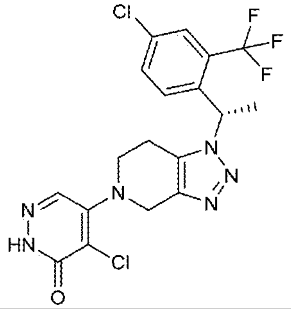 | 1H NMR (400 MHz, DMSO-d6) chemical shifts 12.95 (s, 1H), 7.93 (s, 1H), 7.88 (d, J = 2.2 Hz, 1H), 7.80 (dd, J = 8.5, 2.3 Hz, 1H), 7.42 (d, J = 8.6 Hz, 1H), 6.02 (q, J = 6.6 Hz, 1H), 4.65 - 4.52 (m, 2H), 3.60 (dtd, J = 19.9, 13.8, 5.3 Hz, 2H), 3.00 (dd, J = 15.9, 5.2 Hz, 1H), 2.43 - 2.35 (m, 1H), 1.94 (d, J = 6.8 Hz, 3H). | 459 |
| 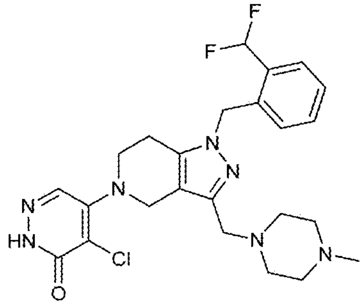 | 1H NMR (400 MHz, DMSO-d6) chemical shifts 12.91 (s, 1H), 7.88 (s, 1H), 7.63 (d, J = 7.2 Hz, 1H), 7.46 (t, J = 7.8 Hz, 2H), 7.43 - 7.19 (m, 1H), 6.81 (d, J = 7.3 Hz, 1H), 5.42 (s, 2H), 4.45 (s, 2H), 3.68 (t, J = 5.7 Hz, 2H), 3.44 (s, 2H), 2.74 (t, J = 5.5 Hz, 2H), 2.38 (s, 8H), 2.19 (s, 3H). | 504 |
| 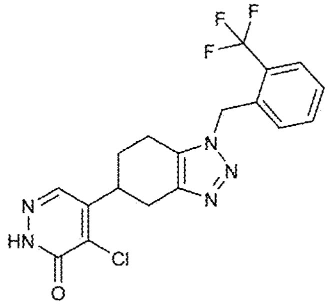 | 1H NMR (400 MHz, Methanol-d4) chemical shifts 8.00 (s, 1H), 7.83 (d, J = 7.8 Hz, 1H), 7.59 (dt, J = 27.6, 7.7 Hz, 2H), 6.95 (d, J = 7.9 Hz, 1H), 5.80 (s, 2H), 3.49 (d, J = 9.3 Hz, 1H), 3.12 (dd, J = 15.8, 5.2 Hz, 1H), 3.03 - 2.87 (m, 1H), 2.84 - 2.58 (m, 2H), 2.16 (d, J = 15.2 Hz, 2H). | 410 |
| 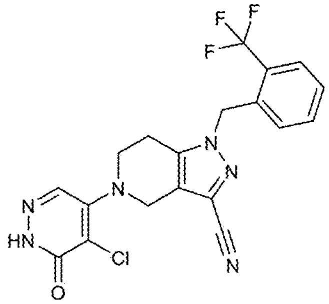 | 1H NMR (400 MHz, DMSO-d6) chemical shifts 12.97 (s, 1H), 7.98 (s, 1H), 7.83 (d, J = 7.8 Hz, 1H), 7.67 (t, J = 7.6 Hz, 1H), 7.58 (t, J = 7.7 Hz, 1H), 6.96 (d, J = 7.8 Hz, 1H), 5.60 (s, 2H), 4.60 (s, 2H), 3.67 (t, J = 5.5 Hz, 2H), 2.87 (d, J = 5.5 Hz, 2H). | 435 |

Figure 69

| | | |
|---|---|---|
| 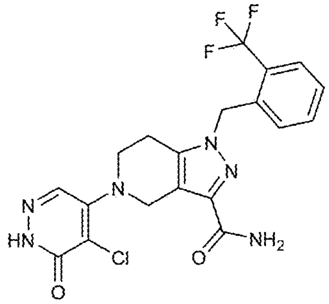 | 1H NMR (400 MHz, DMSO-d6) chemical shifts 12.91 (s, 1H), 7.88 (s, 1H), 7.81 (d, J = 7.8 Hz, 1H), 7.64 (t, J = 7.6 Hz, 1H), 7.54 (t, J = 7.7 Hz, 1H), 7.45 (s, 1H), 7.29 (s, 1H), 6.72 (d, J = 7.8 Hz, 1H), 5.54 (s, 2H), 4.64 (s, 2H), 3.67 (t, J = 5.6 Hz, 2H), 2.79 (t, J = 5.6 Hz, 2H). | 453 |
| 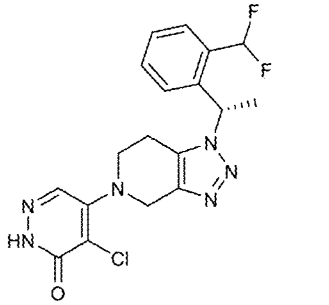 | 1H NMR (400 MHz, DMSO-d6) chemical shifts 12.93 (s, 1H), 7.92 (s, 1H), 7.65 (d, J = 7.5 Hz, 1H), 7.60 - 7.44 (m, 2H), 7.38 (s, 1H), 7.30 - 7.23 (m, 1H), 6.15 (q, J = 6.9 Hz, 1H), 4.58 (d, J = 2.5 Hz, 2H), 3.67 - 3.49 (m, 2H), 2.94 (d, J = 16.1 Hz, 1H), 2.37 (d, J = 7.4 Hz, 1H), 1.93 (d, J = 6.8 Hz, 3H). | 407 |
| 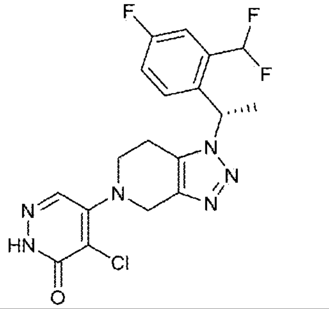 | 1H NMR (400 MHz, DMSO-d6) chemical shifts 12.93 (s, 1H), 7.93 (s, 1H), 7.54 - 7.42 (m, 2H), 7.45 - 7.33 (m, 2H), 6.12 (q, J = 6.6 Hz, 1H), 4.58 (d, J = 2.8 Hz, 2H), 3.60 (dtd, J = 19.8, 13.6, 5.3 Hz, 2H), 2.95 (d, J = 16.3 Hz, 1H), 2.43 (d, J = 16.0 Hz, 1H), 1.92 (d, J = 6.9 Hz, 3H). | 425 |
| 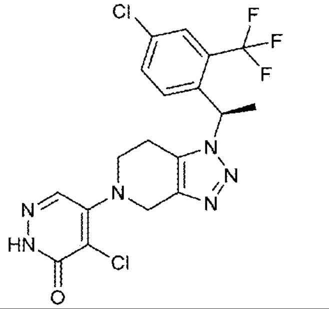 | 1H NMR (400 MHz, DMSO-d6) chemical shifts 12.95 (s, 1H), 7.93 (s, 1H), 7.88 (d, J = 2.3 Hz, 1H), 7.80 (dd, J = 8.5, 2.3 Hz, 1H), 7.42 (d, J = 8.6 Hz, 1H), 6.02 (q, J = 6.8 Hz, 1H), 4.65 - 4.52 (m, 2H), 3.60 (dtd, J = 20.2, 13.8, 5.1 Hz, 2H), 3.03 - 2.95 (m, 1H), 2.43 - 2.33 (m, 1H), 1.94 (d, J = 6.8 Hz, 3H). | 459 |
| 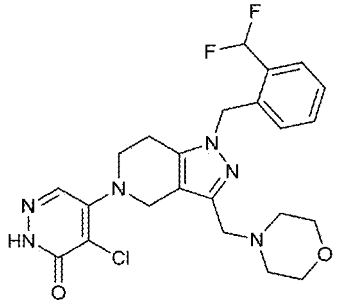 | 1H NMR (400 MHz, DMSO-d6) chemical shifts 12.91 (s, 1H), 7.90 (s, 1H), 7.63 (d, J = 7.2 Hz, 1H), 7.47 (d, J = 8.8 Hz, 2H), 7.43 - 7.16 (m, 1H), 6.80 (d, J = 7.3 Hz, 1H), 5.42 (s, 2H), 4.46 (s, 2H), 3.72 - 3.65 (m, 2H), 3.58 (t, J = 4.4 Hz, 4H), 3.45 (s, 2H), 2.74 (s, 2H), 2.37 (s, 4H). | 491 |

Figure 70

| | | |
|---|---|---|
| 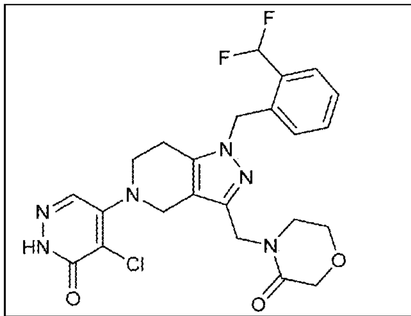 | 1H NMR (400 MHz, Methanol-d4) chemical shifts 7.93 (s, 1H), 7.63 (d, J = 6.9 Hz, 1H), 7.44 (q, J = 7.6, 6.8 Hz, 2H), 7.07 (s, 1H), 6.81 (d, J = 7.0 Hz, 1H), 5.52 (s, 2H), 4.63 (s, 2H), 4.50 (s, 2H), 4.19 (s, 2H), 3.88 (t, J = 5.3 Hz, 2H), 3.78 (t, J = 5.8 Hz, 2H), 3.44 (t, J = 4.9 Hz, 2H), 2.85 - 2.77 (m, 2H). | 505 |
| 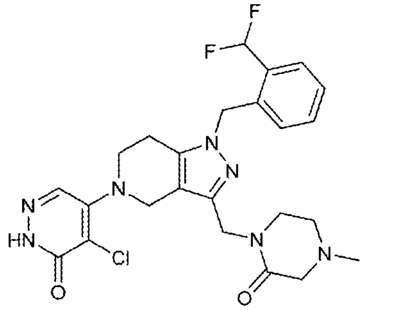 | 1H NMR (400 MHz, DMSO-d6) chemical shifts 7.92 (s, 1H), 7.62 (d, J = 7.0 Hz, 1H), 7.46 (q, J = 6.6, 5.7 Hz, 2H), 7.07 (s, 1H), 6.80 (d, J = 7.0 Hz, 1H), 5.52 (s, 2H), 4.62 (s, 2H), 4.49 (s, 2H), 3.77 (t, J = 5.7 Hz, 2H), 3.41 (t, J = 5.7 Hz, 2H), 3.17 (s, 2H), 2.81 (s, 2H), 2.71 (t, J = 5.7 Hz, 2H), 2.35 (s, 3H). | 518 |
| 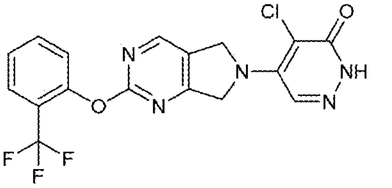 | 1H NMR (400 MHz, DMSO-d6) chemical shifts 12.77 (s, 1H), 8.65 (s, 1H), 7.84 (d, J = 7.2 Hz, 2H), 7.79 (t, J = 7.6 Hz, 1H), 7.55 - 7.44 (m, 2H), 5.23 (s, 2H), 5.10 (s, 2H). | 410 |
| 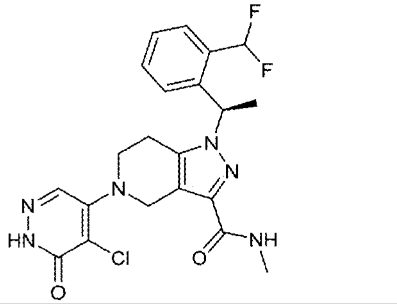 | 1H NMR (400 MHz, DMSO-d6) chemical shifts 12.89 (s, 1H), 8.11 (d, J = 4.9 Hz, 1H), 7.82 (s, 1H), 7.63 (d, J = 7.6 Hz, 1H), 7.52 (d, J = 7.0 Hz, 1H), 7.49 - 7.34 (m, 3H), 5.97 (d, J = 6.8 Hz, 1H), 4.58 (s, 2H), 3.59 (s, 2H), 3.00 (d, J = 15.8 Hz, 1H), 2.79 (d, J = 4.7 Hz, 3H), 2.50-2.38 (m, 1H), 1.85 (d, J = 6.8 Hz, 3H). | 463 |
| 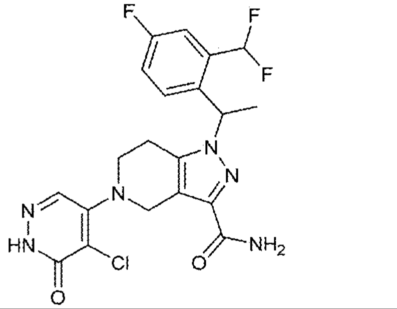 | 1H NMR (400 MHz, DMSO-d6) chemical shifts 12.90 (s, 1H), 7.83 (s, 1H), 7.57 - 7.48 (m, 2H), 7.47 (dd, J = 8.3, 5.6 Hz, 1H), 7.47 - 7.36 (m, 1H), 7.34 (s, 1H), 5.93 (q, J = 6.7 Hz, 1H), 4.62 - 4.49 (m, 2H), 3.59 (q, J = 5.6 Hz, 2H), 3.04 - 2.96 (m, 1H), 2.47 - 2.37 (m, 1H), 1.82 (d, J = 6.7 Hz, 3H). | 467 |

Figure 71

| | | |
|---|---|---|
| 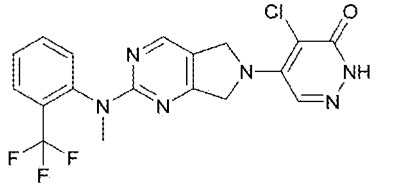 | 1H NMR (400 MHz, DMSO-d6) chemical shifts 12.71 (s, 1H), 8.40 - 8.33 (m, 1H), 7.87 - 7.76 (m, 3H), 7.59 (t, J = 7.7 Hz, 1H), 7.50 (d, J = 7.9 Hz, 1H), 5.10 - 4.81 (m, 4H), 3.38 (s, 3H). | 423 |
| 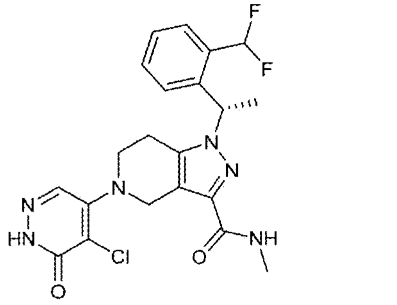 | 1H NMR (400 MHz, DMSO-d6) chemical shifts 12.87 (s, 1H), 8.11 (d, J = 4.9 Hz, 1H), 7.82 (s, 1H), 7.63 (d, J = 7.7 Hz, 1H), 7.53 (t, J = 7.6 Hz, 1H), 7.49 - 7.26 (m, 3H), 5.97 (q, J = 6.7 Hz, 1H), 4.65 - 4.51 (m, 2H), 3.59 (s, 2H), 3.04 - 2.95 (m, 1H), 2.79 (d, J = 4.8 Hz, 3H), 2.36 (d, J = 16.4 Hz, 1H), 1.85 (d, J = 6.8 Hz, 3H). | 463 |
| 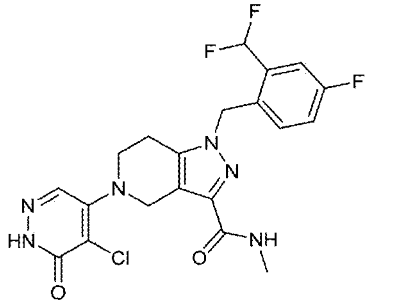 | 1H NMR (400 MHz, DMSO-d6) chemical shifts 12.92 (s, 1H), 8.05 (d, J = 4.9 Hz, 1H), 7.87 (s, 1H), 7.57-7.34 (m, 3H), 6.95 (dd, J = 8.7, 5.5 Hz, 1H), 5.50 (s, 2H), 4.63 (s, 2H), 3.68 (t, J = 5.4 Hz, 2H), 2.84 (d, J = 5.7 Hz, 2H), 2.73 (d, J = 4.7 Hz, 3H). | 467 |
| 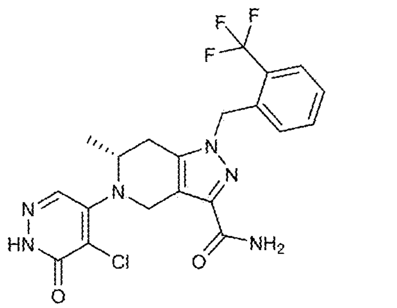 | 1H NMR (400 MHz, DMSO-d6) chemical shifts 12.95 (s, 1H), 7.88 (s, 1H), 7.82 (d, J = 7.8 Hz, 1H), 7.65 (t, J = 7.7 Hz, 1H), 7.54 (t, J = 7.7 Hz, 1H), 7.46 (s, 1H), 7.30 (s, 1H), 6.63 (d, J = 7.9 Hz, 1H), 5.62 - 5.47 (m, 2H), 4.61 (d, J = 16.1 Hz, 1H), 4.54 (d, J = 15.9 Hz, 1H), 4.41 (t, J = 6.4 Hz, 1H), 3.01 (dd, J = 16.3, 5.9 Hz, 1H), 2.57 (s, 1H), 1.13 (d, J = 6.6 Hz, 3H). | 467 |
| 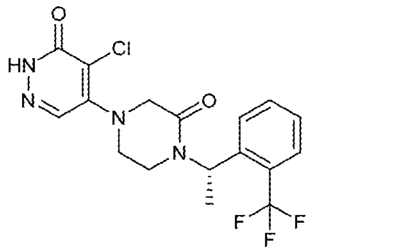 | 1H NMR (400 MHz, DMSO-d6) chemical shifts 12.96 (s, 1H), 7.81 (d, J = 8.4 Hz, 2H), 7.75 (q, J = 8.0 Hz, 2H), 7.57 (t, J = 7.6 Hz, 1H), 5.97 (q, J = 6.9 Hz, 1H), 4.11 (s, 2H), 3.71 - 3.62 (m, 2H), 3.43 (s, 1H), 2.91 - 2.84 (m, 1H), 1.53 (d, J = 6.9 Hz, 3H). | 401 |

Figure 72

| | | |
|---|---|---|
| 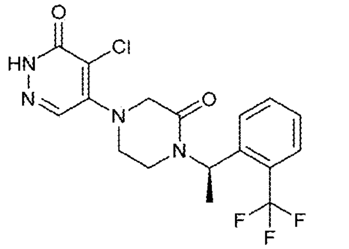 | 1H NMR (400 MHz, DMSO-d6) chemical shifts 12.97 (s, 1H), 7.84 - 7.76 (m, 4H), 7.57 (t, J = 7.5 Hz, 1H), 5.97 (q, J = 6.8 Hz, 1H), 4.11 (s, 2H), 3.71 - 3.62 (m, 2H), 3.43 (s, 1H), 2.91 - 2.84 (m, 1H), 1.53 (d, J = 7.0 Hz, 3H). | 401 |
| 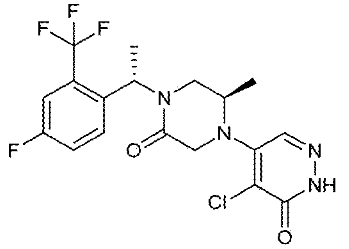 | 1H NMR (400 MHz, DMSO-d6) chemical shifts 12.93 (s, 1H), 7.99 - 7.87 (m, 1H), 7.80 (s, 1H), 7.72 - 7.58 (m, 2H), 6.01 (d, J = 6.9 Hz, 1H), 4.30 (s, 1H), 4.16 (d, J = 17.3 Hz, 1H), 4.02 (d, J = 17.4 Hz, 1H), 3.12 (dd, J = 12.2, 2.9 Hz, 1H), 2.96 (dd, J = 12.4, 4.5 Hz, 1H), 1.50 (d, J = 6.9 Hz, 3H), 1.18 (d, J = 6.6 Hz, 3H). | 433 |
| 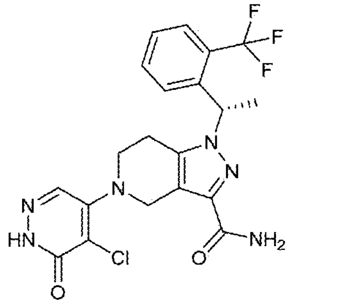 | 1H NMR (400 MHz, DMSO-d6) chemical shifts 12.88 (s, 1H), 7.83 (s, 1H), 7.77 (d, J = 8.0 Hz, 1H), 7.67 (t, J = 7.7 Hz, 1H), 7.60 - 7.48 (m, 3H), 7.36 (s, 1H), 5.86 (d, J = 7.2 Hz, 1H), 4.64 - 4.50 (m, 2H), 3.58 (d, J = 5.4 Hz, 2H), 3.01 (d, J = 15.9 Hz, 1H), 2.32 (d, J = 15.5 Hz, 1H), 1.86 (d, J = 6.7 Hz, 3H). | 467 |
| 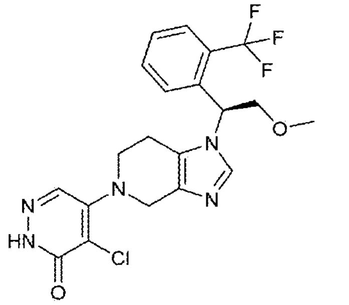 | 1H NMR (400 MHz, Chloroform-d) chemical shifts 10.38 (s, 1H), 7.99 (s, 1H), 7.79 (d, J = 7.6 Hz, 1H), 7.66 (s, 1H), 7.57 (t, J = 7.5 Hz, 1H), 7.51 (t, J = 7.5 Hz, 1H), 7.13 (d, J = 7.6 Hz, 1H), 5.74 (dd, J = 8.0, 3.3 Hz, 1H), 4.58 - 4.45 (m, 2H), 4.06 - 401 (m, 1H), 3.98 - 3.94 (m, 1H), 3.76 - 3.70 (m, 1H), 3.69 - 3.59 (m, 1H), 3.44 (s, 3H), 2.76 - 2.68 (m, 1H), 2.24 - 2.15 (m, 1H). | 454 |
| 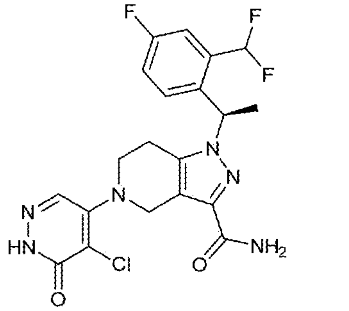 | 1H NMR (400 MHz, DMSO-d6) chemical shifts 12.89 (s, 1H), 7.83 (s, 1H), 7.53 (s, 2H), 7.48 (dd, J = 13.6, 7.4 Hz, 1H), 7.40 (s, 2H), 7.33 (s, 1H), 5.93 (d, J = 7.0 Hz, 1H), 4.56 (d, J = 3.5 Hz, 2H), 3.59 (s, 2H), 3.00 (d, J = 16.2 Hz, 1H), 2.42 (d, J = 15.6 Hz, 1H), 1.82 (d, J = 6.6 Hz, 3H). | 467 |

Figure 73

| | | |
|---|---|---|
| 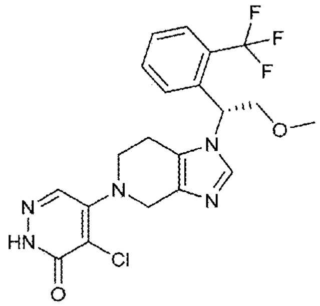 | 1H NMR (400 MHz, Chloroform-d) chemical shifts 10.37 (s, 1H), 7.98 (s, 1H), 7.79 (d, J = 7.8 Hz, 1H), 7.65 (s, 1H), 7.57 (t, J = 7.5 Hz, 1H), 7.50 (t, J = 7.5 Hz, 1H), 7.13 (d, J = 7.8 Hz, 1H), 5.73 (dd, J = 8.0, 3.3 Hz, 1H), 4.58 - 4.45 (m, 2H), 4.06 - 401 (m, 1H), 3.98 - 3.94 (m, 1H), 3.76 - 3.70 (m, 1H), 3.69 - 3.59 (m, 1H), 3.44 (s, 3H), 2.76 - 2.68 (m, 1H), 2.24 - 2.15 (m, 1H). | 454 |
| 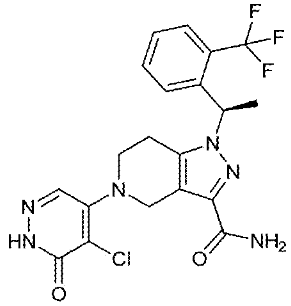 | 1H NMR (400 MHz, DMSO-d6) chemical shifts 12.89 (s, 1H), 7.83 (s, 1H), 7.77 (d, J = 7.9 Hz, 1H), 7.67 (t, J = 7.7 Hz, 1H), 7.60 - 7.48 (m, 3H), 7.36 (s, 1H), 5.86 (d, J = 7.0 Hz, 1H), 4.58 (t, J = 11.3 Hz, 2H), 3.59 (d, J = 6.5 Hz, 2H), 3.01 (d, J = 16.3 Hz, 1H), 2.33 (d, J = 15.4 Hz, 1H), 1.86 (d, J = 6.7 Hz, 3H). | 467 |
| 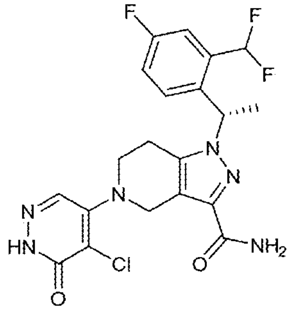 | 1H NMR (400 MHz, DMSO-d6) chemical shifts 12.89 (s, 1H), 7.83 (s, 1H), 7.53 (s, 2H), 7.48 (dd, J = 13.6, 7.4 Hz, 1H), 7.40 (s, 2H), 7.33 (s, 1H), 5.93 (d, J = 7.0 Hz, 1H), 4.56 (d, J = 3.5 Hz, 2H), 3.59 (s, 2H), 3.00 (d, J = 16.2 Hz, 1H), 2.42 (d, J = 15.6 Hz, 1H), 1.82 (d, J = 6.6 Hz, 3H). | 467 |
| 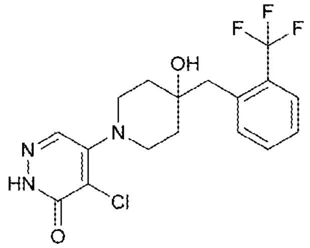 | 1H NMR (400 MHz, DMSO-d6) chemical shifts 12.80 (s, 1H), 7.85 (s, 1H), 7.79 (d, J = 7.8 Hz, 1H), 7.68 (dd, J = 8.1, 1.3 Hz, 1H), 7.61 (t, J = 7.5 Hz, 1H), 7.44 (t, J = 7.6 Hz, 1H), 4.75 (s, 1H), 3.53 (d, J = 12.6 Hz, 2H), 3.31 - 3.20 (m, 2H), 2.94 (s, 2H), 1.60 (dt, J = 12.6, 6.6 Hz, 2H), 1.49 (d, J = 13.0 Hz, 2H). | 388 |

Figure 74

| | | |
|---|---|---|
| 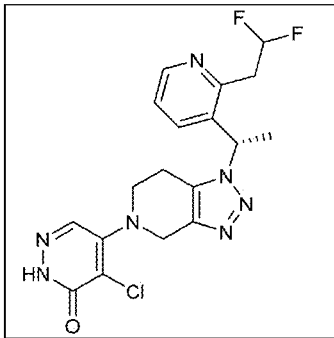 | 1H NMR (400 MHz, DMSO-d6) chemical shifts 12.94 (s, 1H), 8.54 (dd, J = 4.7, 1.6 Hz, 1H), 7.93 (s, 1H), 7.74 - 7.51 (m, 1H), 7.37 (dd, J = 8.0, 4.7 Hz, 1H), 6.83 - 6.34 (m, 1H), 6.16 (q, J = 6.9 Hz, 1H), 4.59 (s, 2H), 3.76 - 3.40 (m, 4H), 2.92 (d, J = 16.0 Hz, 1H), 2.48 (d, J = 17.6 Hz, 1H), 1.90 (d, J = 6.8 Hz, 3H). | 422 |
| 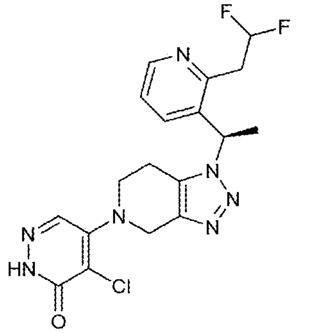 | 1H NMR (400 MHz, DMSO-d6) chemical shifts 12.88 (s, 1H), 7.83 (s, 1H), 7.77 (d, J = 8.0 Hz, 1H), 7.67 (t, J = 7.7 Hz, 1H), 7.60 - 7.48 (m, 3H), 7.36 (s, 1H), 5.86 (d, J = 7.2 Hz, 1H), 4.64 - 4.50 (m, 2H), 3.58 (d, J = 5.4 Hz, 2H), 3.01 (d, J = 15.9 Hz, 1H), 2.32 (d, J = 15.5 Hz, 1H), 1.86 (d, J = 6.7 Hz, 3H). | 422 |
| 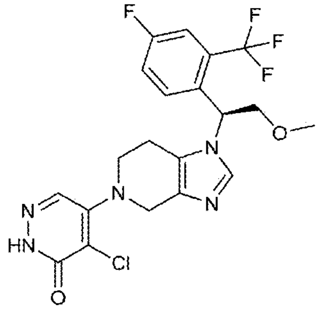 | 1H NMR (400 MHz, Chloroform-d) chemical shifts 10.21 (s, 1H), 8.05 (s, 1H), 7.66 (s, 1H), 7.50 (dd, J = 8.7, 2.6 Hz, 1H), 7.30 - 7.24 (m, 1H), 7.17 (dd, J =8.6 Hz, 5.5H), 5.69 (s, 1H), 4.53 (s, 2H), 3.99 (d, J = 6.7 Hz, 2H), 3.75 - 3.62 (m, 2H), 3.43 (s, 3H), 2.72 (d, J = 15.1 Hz, 1H), 2.25 (d, J = 15.1 Hz, 1H). | 472 |
| 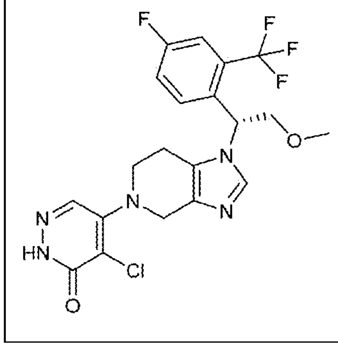 | 1H NMR (400 MHz, Chloroform-d) chemical shifts 10.38 (s, 1H), 7.99 (s, 1H), 7.79 (d, J = 7.6 Hz, 1H), 7.66 (s, 1H), 7.57 (t, J = 7.5 Hz, 1H), 7.51 (t, J = 7.5 Hz, 1H), 7.13 (d, J = 7.6 Hz, 1H), 5.74 (dd, J = 8.0, 3.3 Hz, 1H), 4.58 - 4.45 (m, 2H), 4.06 - 401 (m, 1H), 3.98 - 3.94 (m, 1H), 3.76 - 3.70 (m, 1H), 3.69 - 3.59 (m, 1H), 3.44 (s, 3H), 2.76 - 2.68 (m, 1H), 2.24 - 2.15 (m, 1H). | 472 |

Figure 75

| | | |
|---|---|---|
| 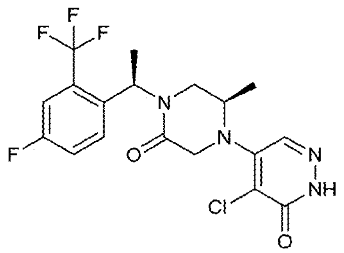 | 1H NMR (400 MHz, DMSO-d6) chemical shifts 12.98 (s, 1H), 7.85 (d, J = 9.7 Hz, 2H), 7.70 - 7.58 (m, 2H), 5.93 (d, J = 6.9 Hz, 1H), 4.35 (s, 1H), 4.15 (d, J = 17.0 Hz, 1H), 3.94 (d, J = 17.0 Hz, 1H), 3.66 (dd, J = 12.5, 4.3 Hz, 1H), 2.88 (dd, J = 12.5, 3.6 Hz, 1H), 1.51 (d, J = 7.0 Hz, 3H), 1.01 (d, J = 6.5 Hz, 3H). | 433 |
| 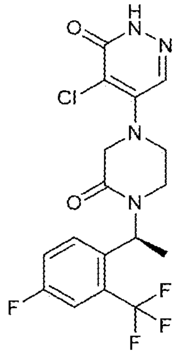 | 1H NMR (400 MHz, DMSO-d6) chemical shifts 12.93 (s, 1H), 7.86 (dd, J = 8.7, 5.4 Hz, 1H), 7.82 (s, 1H), 7.64 (ddd, J = 19.1, 8.9, 4.2 Hz, 2H), 5.93 (q, J = 6.9 Hz, 1H), 4.10 (s, 2H), 3.70 - 3.54 (m, 2H), 3.40 (dt, J = 10.8, 4.6 Hz, 1H), 2.89 (ddd, J = 11.9, 7.4, 4.1 Hz, 1H), 1.52 (d, J = 6.9 Hz, 3H). | 419 |
| 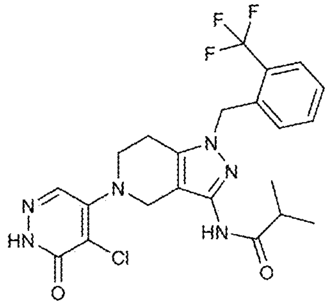 | 1H NMR (400 MHz, Methanol-d4) chemical shifts 7.97 (s, 1H), 7.76 (d, J = 7.8 Hz, 1H), 7.55 (t, J = 7.6 Hz, 1H), 7.48 (t, J = 7.6 Hz, 1H) , 6.75 (d, J = 7.8 Hz, 1H), 5.47 (s, 2H), 4.49 (s, 2H), 3.84 (t, J = 5.7 Hz, 2H), 2.78 (t, J = 5.7 Hz, 2H), 2.69 (p, J = 6.8 Hz, 1H), 1.24 (d, J = 6.8 Hz, 6H). | 495 |
| 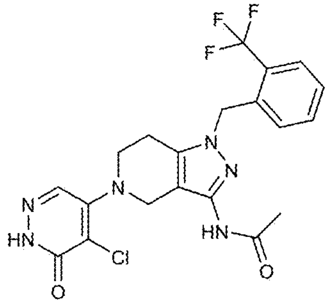 | 1H NMR (400 MHz, Methanol-d4) chemical shifts 7.96 (s, 1H), 7.76 (d, J = 8.0 Hz, 1H), 7.55 (t, J = 8.0 Hz, 1H), 7.49 (d, J = 7.6 Hz, 1H), 6.74 (d, J = 7.6 Hz, 1H), 5.47 (s, 2H), 4.51 (s, 2H), 3.84 (t, J = 578 Hz, 2H), 2.79 (d, J = 5.7 Hz, 2H), 2.16 (s, 3H). | 467 |
| 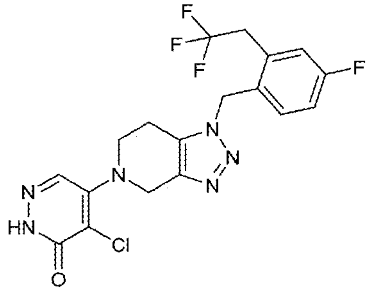 | 1H NMR (400 MHz, DMSO-d6) chemical shifts 12.97 (s, 1H), 7.95 (s, 1H), 7.35 – 7.20 (m, 2H), 7.11 (dd, J = 8.7, 5.9 Hz, 1H), 5.67 (s, 2H), 4.59 (s, 2H), 3.98 (d, J = 11.1 Hz, 1H), 3.93 (d, J = 11.3 Hz, 1H), 3.64 (t, J = 5.4 Hz, 2H), 2.78 (s, 2H). | 443 |

Figure 76

| | | |
|---|---|---|
| 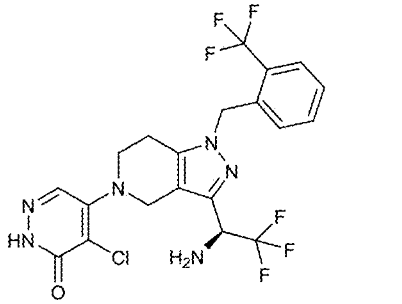 | 1H NMR (400 MHz, DMSO-d6) chemical shifts 12.94 (s, 1H), 7.92 (s, 1H), 7.79 (d, J = 7.7 Hz, 1H), 7.62 (d, J = 7.6 Hz, 1H), 7.52 (t, J = 7.6 Hz, 1H), 6.68 (d, J = 7.8 Hz, 1H), 5.46 (s, 2H), 4.71 – 4.34 (m, 3H), 3.66 (q, J = 6.2 Hz, 2H), 2.87 – 2.68 (m, 2H), 2.45 (s, 2H). | 507 |
| 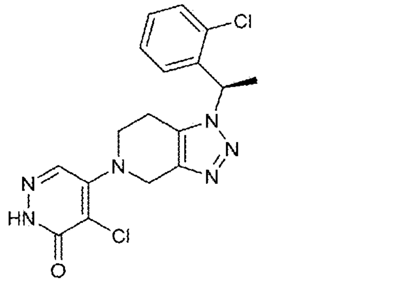 | 1H NMR (400 MHz, DMSO-d6) chemical shifts 12.95 (s, 1H), 7.94 (s, 1H), 7.58 – 7.44 (m, 1H), 7.44 – 7.31 (m, 2H), 7.26 (dd, J = 5.9, 3.6 Hz, 1H), 6.10 (q, J = 6.9 Hz, 1H), 4.59 (s, 2H), 3.63 (tq, J = 14.3, 8.3, 6.8 Hz, 2H), 2.99 – 2.86 (m, 1H), 2.70 – 2.57 (m, 1H), 1.91 (d, J = 6.9 Hz, 3H). | 391 |
| 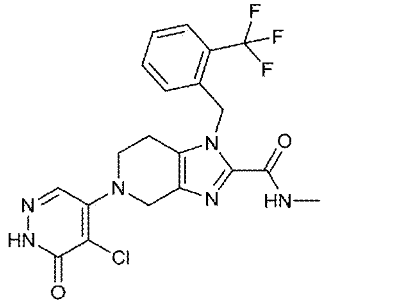 | 1H NMR (400 MHz, DMSO-d6) chemical shifts 12.93 (s, 1H), 8.54 (d, J = 5.2 Hz, 1H), 7.95 (s, 1H), 7.81 (d, J = 7.7 Hz, 1H), 7.59 (t, J = 7.6 Hz, 1H), 7.50 (t, J = 7.6 Hz, 1H), 6.44 (d, J = 7.8 Hz, 1H), 5.91 (s, 2H), 4.50 (s, 2H), 3.68 (s, 2H), 2.68 (d, J = 4.8 Hz, 3H), 2.62 (s, 2H). | 467 |
| 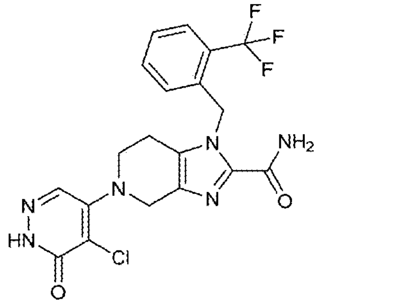 | 1H NMR (400 MHz, DMSO-d6) chemical shifts 12.93 (s, 1H), 7.95 (s, 1H), 7.86 (s, 1H), 7.81 (d, J = 7.8 Hz, 1H), 7.60 (t, J = 7.6 Hz, 1H), 7.50 (t, J = 7.6 Hz, 1H), 7.44 (s, 1H), 6.47 (d, J = 7.8 Hz, 1H), 5.90 (s, 2H), 4.50 (s, 2H), 3.67 (t, J = 5.3 Hz, 2H), 2.61 (s, 2H). | 453 |
| 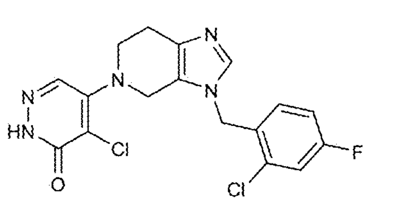 | 1H NMR (400 MHz, DMSO-d6) chemical shifts 12.91 (s, 1H), 7.86 (s, 1H), 7.65 (s, 1H), 7.54 (dd, J = 8.8, 2.6 Hz, 1H), 7.27 (td, J = 8.5, 2.6 Hz, 1H), 7.13 (dd, J = 8.7, 6.1 Hz, 1H), 5.24 (s, 2H), 4.38 (s, 2H), 3.65 (t, J = 5.5 Hz, 2H), 2.71 (s, 2H). | 394 |

Figure 77

| | | |
|---|---|---|
| 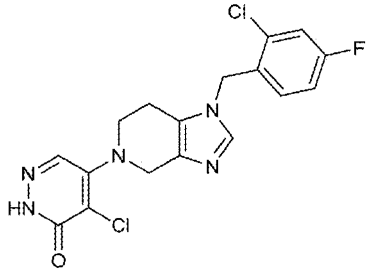 | 1H NMR (400 MHz, DMSO-d6) chemical shifts 12.89 (s, 1H), 7.92 (s, 1H), 7.67 (s, 1H), 7.54 (dd, J = 8.8, 2.6 Hz, 1H), 7.26 (td, J = 8.5, 2.7 Hz, 1H), 7.07 (dd, J = 8.7, 6.1 Hz, 1H), 5.25 (s, 2H), 4.39 (s, 2H), 3.65 (t, J = 5.5 Hz, 2H), 2.66 (d, J = 5.6 Hz, 2H). | 394 |
| 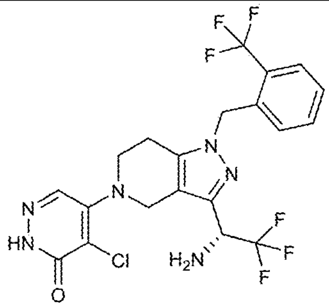 | 1H NMR (400 MHz, DMSO-d6) chemical shifts 12.93 (s, 1H), 7.92 (s, 1H), 7.79 (d, J = 7.7 Hz, 1H), 7.62 (d, J = 7.6 Hz, 1H), 7.52 (t, J = 7.6 Hz, 1H), 6.68 (d, J = 7.8 Hz, 1H), 5.45 (s, 2H), 4.71 – 4.33 (m, 3H), 3.66 (q, J = 6.2 Hz, 2H), 2.87 – 2.68 (m, 2H), 2.46 (s, 2H). | 507 |
| 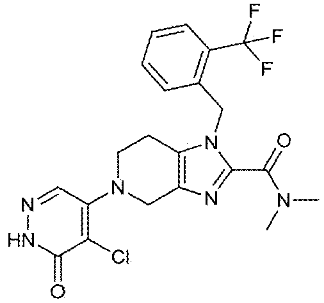 | 1H NMR (400 MHz, DMSO-d6) chemical shifts 12.91 (s, 1H), 7.94 (s, 1H), 7.79 (d, J = 7.8 Hz, 1H), 7.62 (t, J = 7.6 Hz, 1H), 7.51 (t, J = 7.6 Hz, 1H), 6.63 (d, J = 7.9 Hz, 1H), 5.61 (s, 2H), 4.49 (s, 2H), 3.67 (t, J = 5.2 Hz, 2H), 3.39 (s, 3H), 2.91 (s, 3H), 2.59 (s, 2H). | 481 |
| 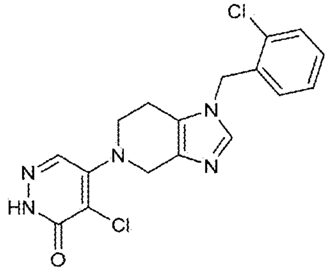 | 1H NMR (400 MHz, DMSO-d6) chemical shifts 12.89 (s, 1H), 7.92 (s, 1H), 7.68 (s, 1H), 7.56 – 7.49 (m, 1H), 7.42 – 7.31 (m, 2H), 6.99 – 6.92 (m, 1H), 5.28 (s, 2H), 4.40 (s, 2H), 3.65 (t, J = 5.6 Hz, 2H), 2.64 (s, 2H). | 376 |
| 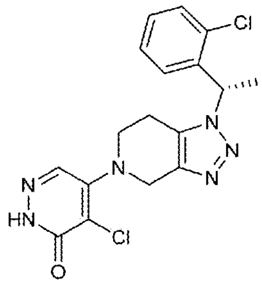 | 1H NMR (400 MHz, DMSO-d6) chemical shifts 12.95 (s, 1H), 7.94 (s, 1H), 7.61 – 7.46 (m, 1H), 7.44 – 7.32 (m, 2H), 7.26 (d, J = 4.5 Hz, 1H), 6.09 (t, J = 7.0 Hz, 1H), 4.59 (s, 2H), 3.63 (td, J = 12.7, 11.1, 7.4 Hz, 2H), 3.16 – 2.84 (m, 1H), 2.62 (d, J = 48.0 Hz, 1H), 1.91 (d, J = 6.9 Hz, 3H). | 391 |

Figure 78

| | | |
|---|---|---|
| 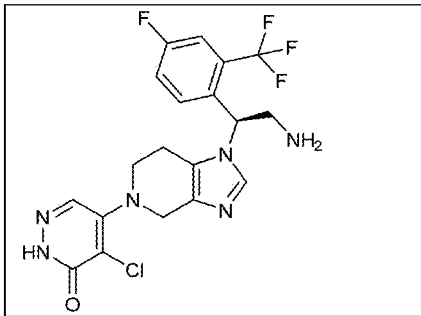 | 1H NMR (400 MHz, Methanol-d4) chemical shifts 8.12 (s, 1H), 7.91 (s, 1H), 7.62 (dd, J = 9.0, 2.4 Hz, 1H), 7.50 - 7.38 (m, 2H), 5.66 (dd, J = 9.9, 4.4 Hz, 1H), 4.56 - 4.43 (m, 2H), 3.77 (t, J = 5.5 Hz, 2H), 3.68 - 3.56 (m, 1H), 3.37 - 3.32 (m, 1H), 2.94 - 2.86 (m, 1H), 2.49 - 2.41 (m, 1H). | 457 |
| 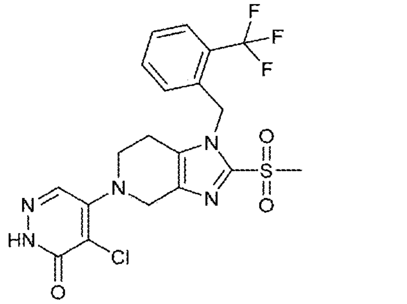 | 1H NMR (400 MHz, DMSO-d6) chemical shifts 12.95 (s, 1H), 7.95 (s, 1H), 7.83 (d, J = 7.8 Hz, 1H), 7.65 (t, J = 7.7 Hz, 1H), 7.55 (t, J = 7.6 Hz, 1H), 6.57 (d, J = 7.8 Hz, 1H), 5.74 (s, 2H), 4.53 (s, 2H), 3.69 (t, J = 5.5 Hz, 2H), 3.36 (s, 3H), 2.64 (s, 2H). | 488 |
| 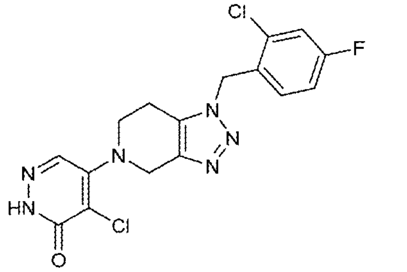 | 1H NMR (400 MHz, DMSO-d6) chemical shifts 12.93 (s, 1H), 7.96 (s, 1H), 7.55 (dd, J = 8.8, 2.5 Hz, 1H), 7.34 - 7.17 (m, 2H), 5.63 (s, 2H), 4.60 (s, 2H), 3.67 (t, J = 5.5 Hz, 2H), 2.87 (d, J = 5.6 Hz, 2H). | 395 |
| 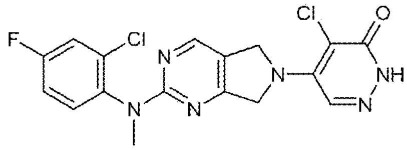 | 1H NMR (400 MHz, DMSO-d6) chemical shifts 12.72 (s, 1H), 8.41 (s, 1H), 7.82 (s, 1H), 7.59 (dd, J = 8.6, 2.9 Hz, 1H), 7.53 (dd, J = 8.8, 5.8 Hz, 1H), 7.32 (td, J = 8.5, 2.9 Hz, 1H), 5.10 (s, 2H), 5.00 (bs, 2H), 3.36 (d, J = 17.9 Hz, 3H). | 407 |
| 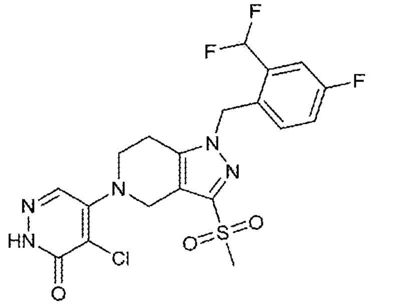 | 1H NMR (400 MHz, DMSO-d6) chemical shifts 12.96 (s, 1H), 7.89 (s, 1H), 7.61 - 7.17 (m, 3H), 7.13 - 7.07 (m, 1H), 5.59 (s, 2H), 4.60 (s, 2H), 3.67 (t, J = 5.6 Hz, 2H), 3.24 (s, 3H), 2.88 (s, 2H). | 488 |

Figure 79

| | | |
|---|---|---|
| 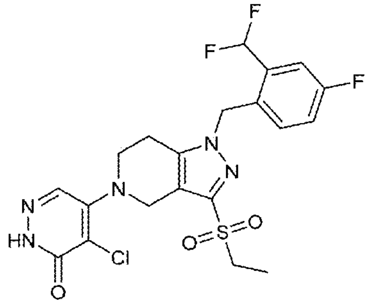 | 1H NMR (400 MHz, Chloroform-d) chemical shifts 7.78 (s, 1H), 7.31 (s, 1H), 7.19 (s, 1H), 7.01 (d, J = 21.3 Hz, 1H), 6.78 (d, J = 54.7 Hz, 1H), 5.54 (s, 2H), 4.65 (s, 2H), 3.76 (s, 2H), 3.34 (d, J = 7.7 Hz, 2H), 2.86 (s, 2H), 1.40 (t, J = 7.3 Hz, 3H). | 502 |
| 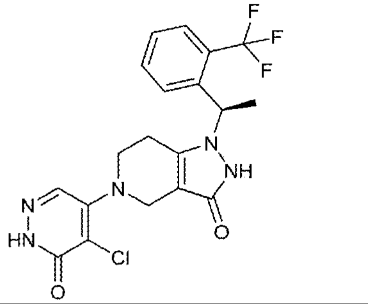 | 1H NMR (400 MHz, DMSO-d6) chemical shifts 12.89 (s, 1H), 9.97 (s, 1H), 7.85 (s, 1H), 7.73 (d, J = 7.8 Hz, 1H), 7.70 - 7.58 (m, 2H), 7.48 (t, J = 7.6 Hz, 1H), 5.60 (d, J = 7.1 Hz, 1H), 4.22 (d, J = 3.9 Hz, 2H), 3.54 (s, 2H), 2.89 (d, J = 15.6 Hz, 1H), 2.37 - 2.17 (m, 1H), 1.73 (d, J = 6.7 Hz, 3H). | 440 |
| 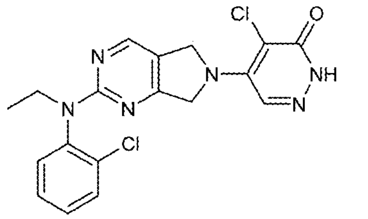 | 1H NMR (400 MHz, DMSO-d6) chemical shifts 12.72 (s, 1H),8.41 (bs, 1 H), 7.82 (s, 1H), 7.60 (d, J = 7.8 Hz, 1H), 7.43 (s, 3H), 7.38 (t, J = 7.8 Hz, 1H), 5.10 (s, 2H), 4.92 (s, 2H), 4.06 (s, 1H), 3.80 (s, 1H), 1.16 (t, J = 7.0 Hz, 3H). | 403 |
| 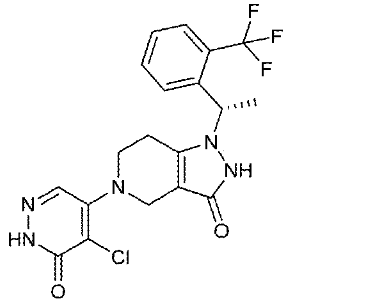 | 1H NMR (400 MHz, DMSO-d6) chemical shifts 12.88 (s, 1H), 9.97 (s, 1H), 7.84 (s, 1H), 7.73 (d, J = 7.9 Hz, 1H), 7.70 - 7.59 (m, 2H), 7.48 (t, J = 7.5 Hz, 1H), 5.60 (d, J = 7.0 Hz, 1H), 4.34 - 4.10 (m, 2H), 3.56 (t, J = 11.2 Hz, 2H), 2.89 (d, J = 15.6 Hz, 1H), 2.29 (d, J = 16.1 Hz, 1H), 1.73 (d, J = 6.8 Hz, 3H). | 440 |
| 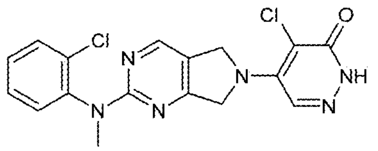 | 1H NMR (400 MHz, DMSO-d6) chemical shifts 12.72 (s, 1H), 8.38 (s, 1H), 7.82 (s, 1H), 7.59 (d, J = 7.9 Hz, 1H), 7.48 - 7.33 (m, 3H), 5.11 (s, 2H), 4.97 (s, 2H), 3.40 (s, 3H). | 389 |

Figure 80

| | | |
|---|---|---|
| 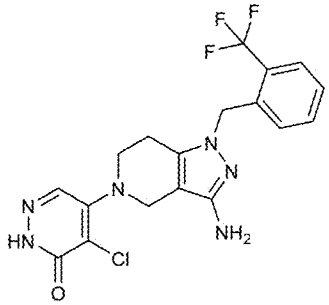 | 1H NMR (400 MHz, DMSO-d6) chemical shifts 12.90 (s, 1H), 7.82 (s, 1H), 7.75 (d, J = 7.7 Hz, 1H), 7.60 (t, J = 7.7 Hz, 1H), 7.48 (t, J = 7.7 Hz, 1H), 6.78 (d, J = 7.7 Hz, 1H), 5.18 (s, 2H), 4.72 (s, 2H), 4.28 (s, 2H), 3.65 (t, J = 5.6 Hz, 2H), 2.68 (t, J = 5.6 Hz, 2H). | 425 |
| 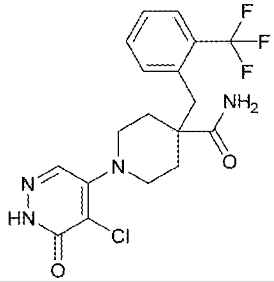 | | 415.4 |
| 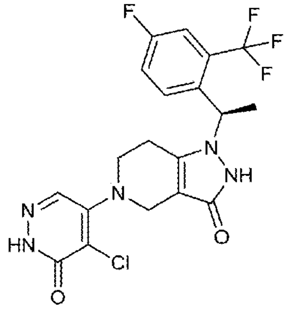 | 1H NMR (400 MHz, DMSO-d6) chemical shifts 12.87 (s, 1H), 10.00 (s, 1H), 7.85 (s, 1H), 7.69 (dd, J = 8.8, 5.7 Hz, 1H), 7.65 - 7.52 (m, 2H), 5.59 (q, J = 6.7 Hz, 1H), 4.32 - 4.14 (m, 2H), 3.56 (tq, J = 14.7, 8.2, 6.7 Hz, 2H), 2.89 (dd, J = 13.6, 8.3 Hz, 1H), 2.33 (dd, J = 14.6, 7.6 Hz, 1H), 1.71 (d, J = 6.7 Hz, 3H). | 458 |
| 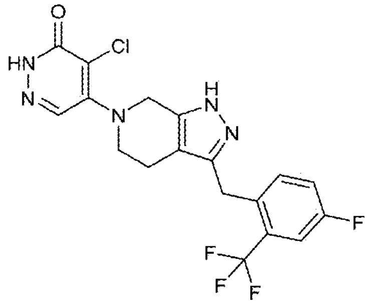 | 1H NMR (400 MHz, DMSO-d6) chemical shifts 12.92 (s, 1H), 12.55 (brs, 1H), 7.90 (s, 1H), 7.62 (d, J = 9.3 Hz, 1H), 7.53 - 7.47 (m, 1H), 7.36 - 7.31 (m, 1H), 4.52 (s, 2H), 4.08 (s, 2H), 3.55 (t, J = 5.6 Hz, 2H), 2.41 (d, J = 5.6 Hz, 2H). | 428 |
| 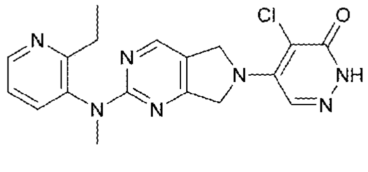 | 1H NMR (400 MHz, DMSO-d6) chemical shifts 12.72 (s, 1H), 8.48 (d, J = 4.7 Hz, 1H), 8.40 (bs, 1H), 7.82 (s, 1H), 7.65 (d, J = 7.9 Hz, 1H), 7.33 (dd, J = 7.9, 4.7 Hz, 1H), 5.10 (s, 2H), 4.95 (s, 2H), 3.40 (s, 3H), 2.60 - 2.52 (m, 2H), 1.15 (t, J = 7.5 Hz, 3H). | 384 |
Figure 81

| | | |
|---|---|---|
| 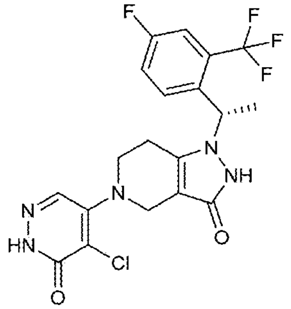 | 1H NMR (400 MHz, DMSO-d6) chemical shifts 12.87 (s, 1H), 9.99 (s, 1H), 7.85 (s, 1H), 7.69 (dd, J = 8.8, 5.8 Hz, 1H), 7.60 (ddd, J = 18.8, 9.0, 4.3 Hz, 2H), 5.59 (q, J = 6.9 Hz, 1H), 4.31 - 4.13 (m, 2H), 3.55 (tq, J = 13.1, 6.8, 5.2 Hz, 2H), 2.89 (dd, J = 13.3, 8.0 Hz, 1H), 2.32 (d, J = 15.9 Hz, 1H), 1.71 (d, J = 6.7 Hz, 3H). | 458 |
| 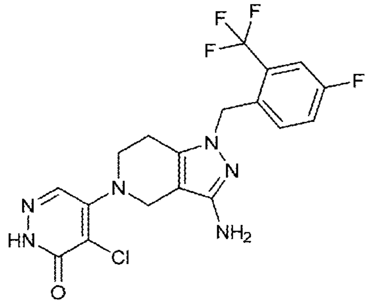 | 1H NMR (400 MHz, DMSO-d6) chemical shifts 12.92 (s, 1H), 7.82 (s, 1H), 7.66 (dd, J = 9.3, 2.7 Hz, 1H), 7.58 - 7.46 (m, 1H), 6.84 (dd, J = 8.7, 5.5 Hz, 1H), 5.14 (s, 2H), 4.75 (s, 2H), 4.27 (s, 2H), 3.65 (t, J = 5.5 Hz, 2H), 2.70 (s, 2H). | 443 |
| 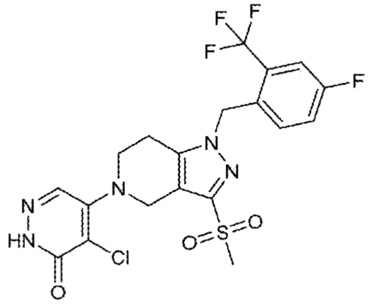 | 1H NMR (400 MHz, DMSO-d6) chemical shifts 12.97 (s, 1H), 7.91 (s, 1H), 7.76 (dd, J = 9.0, 2.7 Hz, 1H), 7.56 (t, J = 8.4 Hz, 1H), 7.07 - 7.00 (m, 1H), 5.58 (s, 2H), 4.63 (s, 2H), 3.68 (d, J = 5.9 Hz, 2H), 3.25 (s, 3H), 2.87 (s, 2H). | 506 |
| 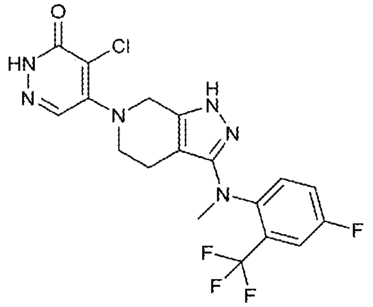 | 1H NMR (400 MHz, DMSO-d6) chemical shifts 12.88 (s, 1H), 11.75 (s, 1H), 7.80 (s, 1H), 7.69 (dd, J = 8.9, 3.0 Hz, 1H), 7.56 (s, 1H), 7.38 (s, 1H), 4.47 (s, 2H), 3.07 (s, 3H), 1.71 (s, 2H). | 443 |
| 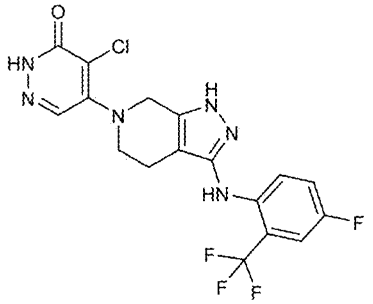 | 1H NMR (400 MHz, DMSO-d6) chemical shifts 12.90 (s, 1H), 12.20 (s, 1H), 7.90 (s, 1H), 7.37 (dd, J = 30.7, 8.8 Hz, 2H), 7.26 (s, 1H), 7.08 (s, 1H), 4.59-4.53 (m, 2H), 3.60 (s, 2H), 2.45 (s, 2H). | 429 |
Figure 82

| | | |
|---|---|---|
|  | 1H NMR (400 MHz, DMSO-d6) chemical shifts 12.89 (s, 1H), 12.78 - 12.44 (m, 1H), 7.87 (s, 1H), 7.50 (d, J = 6.3 Hz, 3H), 4.51 (s, 3H), 3.58 - 3.45 (m, 2H), 2.45 (s, 1H), 2.13 (s, 1H), 1.58 (s, 3H). | 442 |

Figure 86A
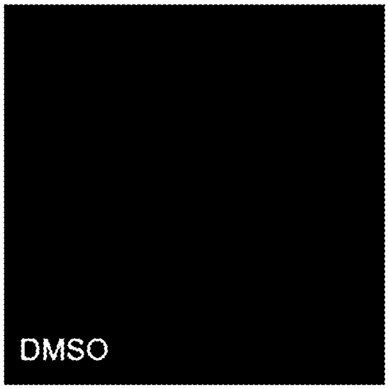
Figure 86B
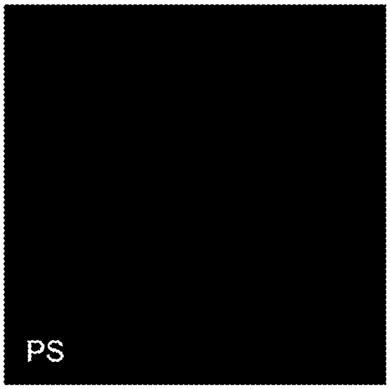
Figure 86C
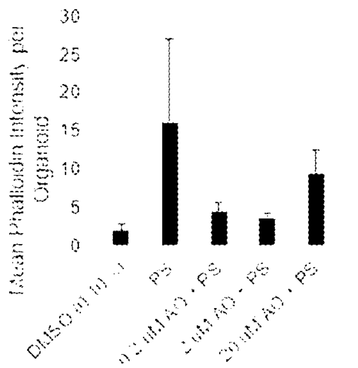
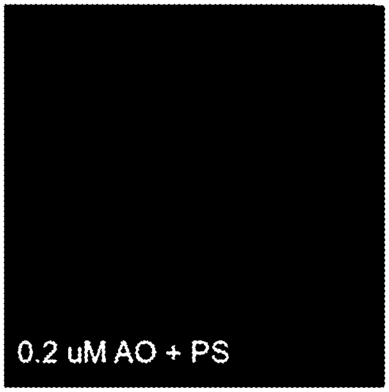
Figure 86D
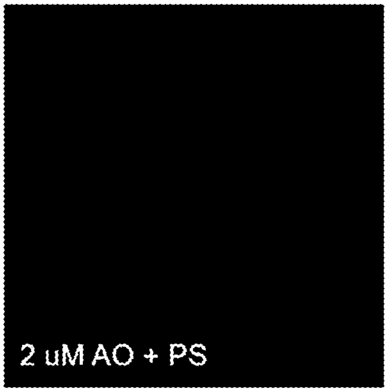
Figure 86E
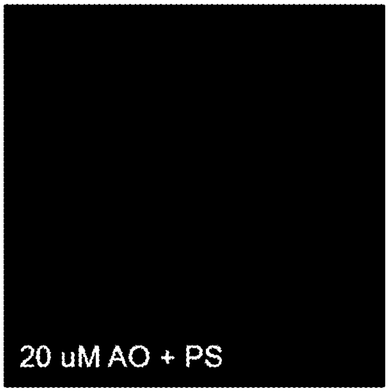
Figure 86F

PYRIDAZINONES AND METHODS OF USE THEREOF

RELATED APPLICATIONS

This application is a U.S. national stage of International Patent Application No. PCT/US2018/051465, filed Sep. 18, 2018, which claims the benefit of priority to U.S. Provisional Patent Application No. 62/559,840, filed Sep. 18, 2017; and U.S. Provisional Patent Application No. 62/655,985, filed Apr. 11, 2018.

INCORPORATION-BY-REFERENCE OF SEQUENCE LISTING

The contents of the sequence listing text file named "GFX-00601_SL.txt, which was created on Jun. 25, 2020 and is 22,975 bytes in size, is hereby incorporated by reference in its entirety.

BACKGROUND

Proteinuria is a condition in which an excessive amount of protein in the blood leaks into the urine. Proteinuria can progress from a loss of 30 mg of protein in the urine over a 24-hour period (called microalbuminuria) to >300 mg/day (called macroalbuminuria), before reaching levels of 3.5 grams of protein or more over a 24-hour period, or 25 times the normal amount. Proteinuria occurs when there is a malfunction in the kidney's glomeruli, causing fluid to accumulate in the body (edema). Prolonged protein leakage has been shown to result in kidney failure. Nephrotic Syndrome (NS) disease accounts for approximately 12% of prevalent end stage renal disease cases at an annual cost in the United States of more than $3 billion. Approximately 5 out of every 100,000 children are diagnosed with NS every year and 15 out of every 100,000 children are living with it today. For patients who respond positively to treatment, the relapse frequency is extremely high. Ninety % of children with Nephrotic Syndrome will respond to treatment, however, an estimated 75% will relapse. There is a need for more effective methods of treating, or reducing risk of developing, kidney disease, e.g., proteinuria.

Mammalian TRP channel proteins form six-transmembrane cation-permeable channels that may be grouped into six subfamilies on the basis of amino acid sequence homology (TRPC, TRPV, TRPM, TRPA, TRPP, and TRPML). Recent studies of TRP channels indicate that they are involved in numerous fundamental cell functions and are considered to play an important role in the pathophysiology of many diseases. Many TRPs are expressed in kidney along different parts of the nephron and growing evidence suggest that these channels are involved in hereditary, as well as acquired kidney disorders. TRPC6, TRPM6, and TRPP2 have been implicated in hereditary focal segmental glomerulosclerosis (FSGS), hypomagnesemia with secondary hypocalcemia (HSH), and polycystic kidney disease (PKD), respectively.

TRPC5 has also been reported to contribute to the mechanisms underlying regulation of innate fear responses. (J Neurosci. 2014 Mar. 5; 34(10): 3653-3667).

Hence, there is a need for additional inhibitors of TRPC5.

SUMMARY

This invention is based, at least in part, on the discovery that Transient Receptor Potential Cation Channel, subfamily C, member 5 (TRPC5), activity abolishes actin stress fibers and diminishes focal adhesion formation, rendering a motile, migratory podocyte phenotype.

One aspect of the invention is compounds that are antagonists of TRPC5. In some embodiments, the compound of the invention is a compound of Formula (A), or a tautomer or a pharmaceutically acceptable salt thereof;

(A)

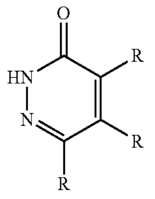

wherein each R is independently selected from the group consisting of H, alkyl, alkenyl, alkynyl, aryl, heterocyclyl, heteroaryl, halogen, —OH, CN, cycloalkyl, —O-alkyl, —O-cycloalkyl, —O-aryl, -aryl-O-aryl, —$CF_3$, —C(H)$F_2$, alkylene-$CF_3$, alkylene-C(H)$F_2$, —$SO_2$-alkyl, —O-alkylene-O-alkyl, -heterocyclyl-L-$R^4$, and heteroaryl-L-$R^4$;

$R^4$ is absent or selected from the group consisting of alkyl, cycloalkyl, polycyclyl, aryl, heterocyclyl, heteroaryl, —C(O)N($R^5$)$_2$, and $CF_3$;

$R^5$ is independently H or alkyl;

$R^6$ is selected from the group consisting of alkyl, cycloalkyl, aryl, heterocyclyl, heteroaryl, alkylene-aryl, —C(O)N($R^5$)$_2$, and $CF_3$;

L is absent or selected from the group consisting of methylene, —C(O)—, —$SO_2$—, —$CH_2$N(Me)-, —N(R5)(R6)-, —C(R5)(R6)-, and —O—$R^6$; and one and only one R is -heterocyclyl-L-$R^4$ or -heteroaryl-L-$R^4$.

In some embodiments, the compound of the invention is a compound of Formula (I), (II), or (III), or a tautomer or a pharmaceutically acceptable salt thereof;

(I)

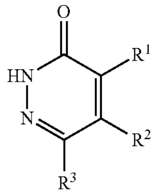

(II)

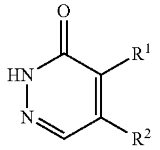

(III)

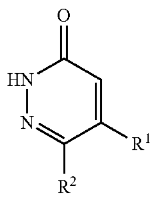

wherein $R^1$ and $R^3$ are independently selected from the group consisting of H, alkyl, alkenyl, alkynyl, aryl, heterocyclyl, heteroaryl, halogen, —OH, —CN, -cycloalkyl, —O-alkyl, —O-cycloalkyl, —O-aryl, -aryl-O-aryl —$CF_3$, —C(H)$F_2$, alkylene-$CF_3$, alkylene-C(H)$F_2$, —$SO_2$-alkyl, and —O-alkylene-O-alkyl, -heterocyclyl-L-$R^4$, and -heteroaryl-L-$R^4$;

$R^2$ is -heterocyclyl-L-$R^4$;

$R^4$ is absent or selected from the group consisting of alkyl, cycloalkyl, aryl, alkylene-aryl, alkylene-heteroaryl, heteroaryl, heterocyclyl, —C(O)N($R^5$)$_2$, and $CF_3$;

$R^5$ is independently H or alkyl;

$R^6$ is selected from the group consisting of alkyl, cycloalkyl, aryl, heterocyclyl, heteroaryl, alkylene-aryl, —C(O)N($R^5$)$_2$, and $CF_3$;

L is absent or selected from the group consisting of methylene, —C(O)—, —$SO_2$—, —$CH_2$N(Me)-, —N($R^5$)($R^6$)—, —C($R^5$)($R^6$)—, and —O—$R^6$; and one and only one of $R^1$, $R^2$, and $R^3$ is -heterocyclyl-L-$R^4$ or -heteroaryl-L-$R^4$.

In one aspect, the invention features a composition, comprising a compound of any one of Formula (I), (II), or (III) or a pharmaceutically acceptable salt thereof; and a pharmaceutically acceptable excipient.

In one aspect, the invention relates to methods of treating, or reducing risk of developing, kidney disease (e.g., proteinuria, microalbuminuria, macroalbuminuria), anxiety, depression, or cancer, in a subject by administering a therapeutically effective amount of a TRPC5 inhibitor to the subject. In some embodiments, the methods include administering a small molecule that inhibits TRPC5.

The methods are effective for a variety of subjects including mammals, e.g., humans and other animals, such as laboratory animals, e.g., mice, rats, rabbits, or monkeys, or domesticated and farm animals, e.g., cats, dogs, goats, sheep, pigs, cows, or horses.

In one aspect, the invention features methods of treating, or the reducing risk of developing, a kidney disease, pulmonary arterial hypertension, anxiety, or depression, cancer, diabetic retinopathy, or pain, comprising administering to a subject in need thereof a therapeutically effective amount of a compound of Formula (I), (II) or (III). In certain embodiments, a kidney disease is treated or the risk of developing a kidney disease is reduced. In certain embodiments, a kidney disease is treated. In certain embodiments, the kidney disease is selected from the group consisting of Focal Segmental Glomerulosclerosis (FSGS), Diabetic nephropathy, Alport syndrome, hypertensive kidney disease, nephrotic syndrome, steroid-resistant nephrotic syndrome, minimal change disease, membranous nephropathy, idiopathic membranous nephropathy, membranoproliferative glomerulonephritis (MPGN), immune complex-mediated MPGN, complement-mediated MPGN, Lupus nephritis, postinfectious glomerulonephritis, thin basement membrane disease, mesangial proliferative glomerulonephritis, amyloidosis (primary), c1q nephropathy, rapidly progressive GN, anti-GBM disease, C3 glomerulonephritis, hypertensive nephrosclerosis, and IgA nephropathy. In certain embodiments, the kidney disease is proteinuria. In certain embodiments, the kidney disease is proteinuric kidney disease. In certain embodiments, the kidney disease is microalbuminuria or macroalbuminuria. In certain embodiments, the kidney disease is microalbuminuria or macroalbuminuria kidney disease. In some embodiments, the disease or condition to be treated is pulmonary arterial hypertension. In some embodiments, the disease or condition to be treated is pain selected from neuropathic pain and visceral pain.

In some embodiments, the disease or condition is cancer selected from chemoresistant breast carcinoma, adriamycin-resistant breast cancer, chemoresistant colorectal cancer, medulloblastoma, and tumor angiogenesis.

In some embodiments, disease or condition to be treated is transplant-related FSGS, transplant-related nephrotic syndrome, transplant-related proteinuria, cholestatic liver disease, polycystic kidney disease, autosomal dominant polycystic kidney disease (ADPKD), obesity, insulin resistance, Type II diabetes, prediabetes, metabolic syndrome, non-alcoholic fatty liver disease (NAFLD), or non-alcoholic steatohepatitis (NASH).

In certain embodiments, the subject is a mammal. In certain embodiments, the mammal is a human.

In some embodiments, the invention comprises administering the compound of Formula (I) to a mammal and evaluating an effect of the compound on calcium transport, wherein a compound that reduces or inhibits calcium transport is a therapeutic agent for treating or reducing risk of developing a kidney disease, anxiety, depression, or cancer.

The invention provides several advantages. The prophylactic and therapeutic methods described herein are effective in treating kidney disease, e.g., proteinuria, and have minimal, if any, side effects. Further, methods described herein are effective to identify compounds that treat or reduce risk of developing a kidney disease, anxiety, depression, or cancer.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features, objects, and advantages of the invention will be apparent from the detailed description, and from the claims.

BRIEF DESCRIPTION OF THE DRAWINGS

FIGS. 1-83 tabulate characterization data for representative compounds of the invention.

FIGS. 86A-F show confocal microscopy images (FIGS. 86A, 86B, 86D, 86E, 86F) of human iPSC derived kidney organoids pretreated with compound AO or DMSO, and then insulted with protamine sulfate (PS), and quantitation of mean phalloidin intensity per organoid (FIG. 86C).

DETAILED DESCRIPTION

Definitions

Figure 83:
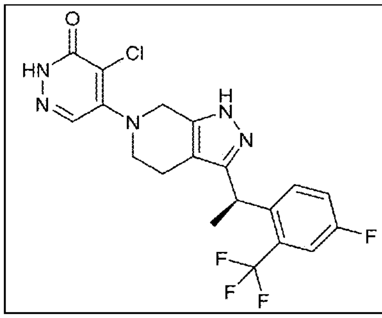
Figure 84:
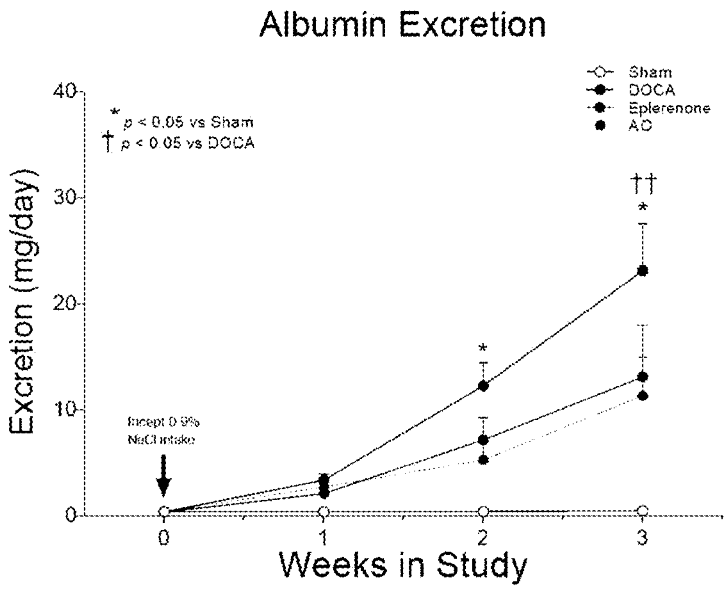
FIG. 84 shows a plot of the effect of compound AO on alumbin excretion in DOCA-salt hypertensive rats.
Figures 85A, 85B, 85C, 85D, 85E, 85F:
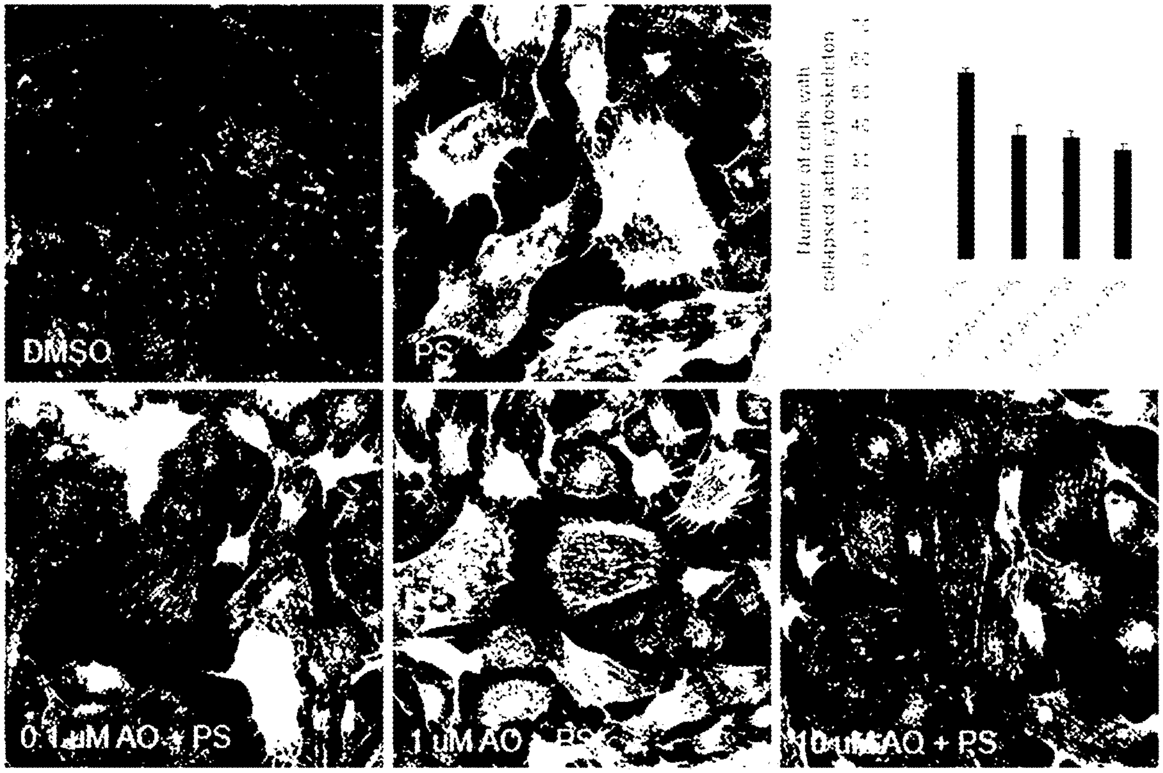
FIGS. 85A-F show confocal microscopy images (FIGS. 85A, 85B, 85D, 85E, 85F) of murine podocytes pretreated with compound AO or DMSO, and then insulted with protamine sulfate (PS), and quantitation of treated podocytes with collapsed actin cytoplasm (FIG. 85C).

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, trifluoromethoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen (e.g., fluoro), a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. In preferred embodiments, the substituents on substituted alkyls are selected from $C_{1-6}$ alkyl, $C_{3-6}$ cycloalkyl, halogen, carbonyl, cyano, or hydroxyl. In more preferred embodiments, the substituents on substituted alkyls are selected from fluoro, carbonyl, cyano, or hydroxyl. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), $—CF_3$, —CN and the like. Exemplary substituted alkyls are described below. Cycloalkyls can be further substituted with alkyls, alkenyls, alkoxys, alkylthios, aminoalkyls, carbonyl-substituted alkyls, $—CF_3$, —CN, and the like.

Unless otherwise specified, "alkylene" by itself or as part of another substituent refers to a saturated straight-chain or branched divalent group having the stated number of carbon atoms and derived from the removal of two hydrogen atoms from the corresponding alkane. Examples of straight chained and branched alkylene groups include $—CH_2—$ (methylene), $—CH_2—CH_2$-(ethylene), $—CH_2—CH_2—CH_2—$ (propylene), $—C(CH_3)_2—$, $—CH_2—CH(CH_3)—$, $—CH_2—CH_2—CH_2—CH_2—$, $—CH_2—CH_2—CH_2—CH_2—CH_2—$ (pentylene), $—CH_2—CH(CH_3)—CH_2—$, and $—CH_2—C(CH_3)_2—CH_2—$.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$ alkyl" refers to substituted or unsubstituted saturated hydrocarbon groups, including straight-chain alkyl and branched-chain alkyl groups that contain from x to y carbons in the chain, including haloalkyl groups. Preferred haloalkyl groups include trifluoromethyl, difluoromethyl, 2,2,2-trifluoroethyl, and pentafluoroethyl. $C_0$ alkyl indicates a hydrogen where the group is in a terminal position, a bond if internal. The terms "$C_{2-y}$ alkenyl" and "$C_{2-y}$ alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive.

For example, substitution of alkynyl groups by one or more alkyl, carbocyclyl, aryl, heterocyclyl, or heteroaryl groups is contemplated.

The term "amide", as used herein, refers to a group

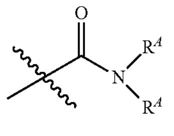

wherein each $R^A$ independently represent a hydrogen or hydrocarbyl group, or two $R^A$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

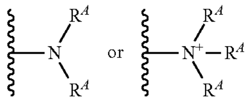

wherein each $R^A$ independently represents a hydrogen or a hydrocarbyl group, or two $R^A$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 6- or 10-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, aryls, heteroaryls, and/or heterocyclyls. Aryl groups include benzene, naphthalene, phenanthrene, phenol, aniline, and the like.

The term "carbamate" is art-recognized and refers to a group

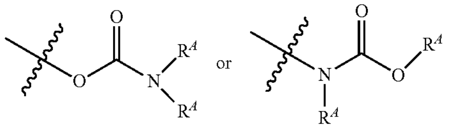

wherein each $R^A$ independently represent hydrogen or a hydrocarbyl group, such as an alkyl group, or both $R^A$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group —$OCO_2$—$R^A$, wherein $R^A$ represents a hydrocarbyl group.

The term "carboxy", as used herein, refers to a group represented by the formula —$CO_2H$.

The term "ester", as used herein, refers to a group —C(O)$OR^A$ wherein $R^A$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, aryls, heteroaryls, and/or heterocyclyls. Heterocyclyl groups include, for example, piperidine, piperazine, pyrrolidine, tetrahydropyran, tetrahydrofuran, morpholine, lactones, lactams, and the like.

The term "heterocyclylalkyl" or "heterocycloalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. In preferred embodiments, the substituents on substituted alkyls are selected from $C_{1-6}$ alkyl, $C_{3-6}$ cycloalkyl, halogen, carbonyl, cyano, or hydroxyl. In more preferred embodiments, the substituents on substituted alkyls are selected from fluoro, carbonyl, cyano, or hydroxyl. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —$OSO_3H$, or a pharmaceutically acceptable salt thereof.

The term "sulfonamide" is art-recognized and refers to the group represented by the general formulae

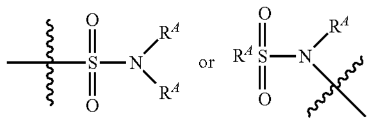

wherein each $R^A$ independently represents hydrogen or hydrocarbyl, such as alkyl, or both $R^A$ taken together with the intervening atom(s) complete a heterocycle having from 4 to 8 atoms in the ring structure.

The term "sulfoxide" is art-recognized and refers to the group —S(O)—$R^A$, wherein $R^A$ represents a hydrocarbyl.

The term "sulfonate" is art-recognized and refers to the group $SO_3H$, or a pharmaceutically acceptable salt thereof.

The term "sulfone" is art-recognized and refers to the group —$S(O)_2$—$R^A$, wherein $R^A$ represents a hydrocarbyl.

The term "thioalkyl", as used herein, refers to an alkyl group substituted with a thiol group.

The term "thioester", as used herein, refers to a group —C(O)S$R^A$ or —SC(O)$R^A$ wherein $R^A$ represents a hydrocarbyl.

The term "thioether", as used herein, is equivalent to an ether, wherein the oxygen is replaced with a sulfur.

The term "urea" is art-recognized and may be represented by the general formula

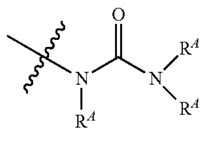

wherein each $R^A$ independently represents hydrogen or a hydrocarbyl, such as alkyl, or any occurrence of $R^A$ taken together with another and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry,* $3^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The phrases "conjoint administration" and "administered conjointly" refer to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, an individual who receives such treatment can benefit from a combined effect of different therapeutic compounds.

The term "prodrug" is intended to encompass compounds which, under physiologic conditions, are converted into the therapeutically active agents of the present invention. A common method for making a prodrug is to include one or more selected moieties which are hydrolyzed under physiologic conditions to reveal the desired molecule. In other embodiments, the prodrug is converted by an enzymatic activity of the host animal. For example, esters or carbonates (e.g., esters or carbonates of alcohols or carboxylic acids) are preferred prodrugs of the present invention. In certain embodiments, some or all of the compounds of the invention in a formulation represented above can be replaced with the corresponding suitable prodrug, e.g., wherein a hydroxyl in the parent compound is presented as an ester or a carbonate or carboxylic acid present in the parent compound is presented as an ester.

As used herein, "small molecules" refers to small organic or inorganic molecules of molecular weight below about 3,000 Daltons. In general, small molecules useful for the invention have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

In some embodiments, a "small molecule" refers to an organic, inorganic, or organometallic compound typically having a molecular weight of less than about 1000. In some embodiments, a small molecule is an organic compound, with a size on the order of 1 nm. In some embodiments, small molecule drugs of the invention encompass oligopeptides and other biomolecules having a molecular weight of less than about 1000.

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a composition depends on the composition selected. The compositions can be administered from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions described herein can include a single treatment or a series of treatments.

Compounds of the Invention

One aspect of the invention provides small molecule inhibitors of TRPC5.

In some embodiments, the compound of the invention is a compound of (A), or a tautomer or a pharmaceutically acceptable salt thereof, (A)

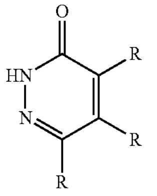

wherein each R is independently selected from the group consisting of H, alkyl, alkenyl, alkynyl, aryl, heterocyclyl, heteroaryl, halogen, —OH, CN, cycloalkyl, —O-alkyl, —O-cycloalkyl, —O-aryl, -aryl-O-aryl, —$CF_3$, —C(H)$F_2$, alkylene-$CF_3$, alkylene-C(H)$F_2$, —$SO_2$-alkyl, —O-alkylene-O-alkyl, -heterocyclyl-L-$R^4$, and heteroaryl-L-$R^4$;

$R^4$ is absent or selected from the group consisting of alkyl, cycloalkyl, polycyclyl, aryl, heterocyclyl, heteroaryl, —C(O)N($R^5$)$_2$, and $CF_3$;

$R^5$ is independently H or alkyl;

$R^6$ is selected from the group consisting of alkyl, cycloalkyl, aryl, heterocyclyl, heteroaryl, alkylene-aryl, —C(O)N($R^5$)$_2$, and $CF_3$;

L is absent or selected from the group consisting of methylene, —C(O)—, —$SO_2$—, —$CH_2$N(Me)-, —N(R5)(R6)-, —C(R5)(R6)-, and —O—$R^6$; and one and only one R is -heterocyclyl-L-$R^4$ or -heteroaryl-L-$R^4$.

In some embodiments, the compound of the invention is a compound of Formula ((I), (II), or (III), or a tautomer or a pharmaceutically acceptable salt thereof;

(I)

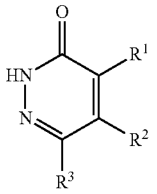

(II)

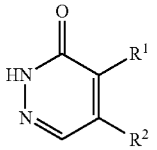

(III)

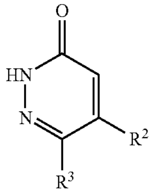

wherein $R^1$ and $R^3$ are independently selected from the group consisting of H, alkyl, alkenyl, alkynyl, aryl, heterocyclyl, heteroaryl, halogen, —OH, —CN, -cycloalkyl, —O-alkyl, —O-cycloalkyl, —O-aryl, -aryl-O-aryl —$CF_3$, —C(H)$F_2$, alkylene-$CF_3$, alkylene-C(H)$F_2$, —$SO_2$-alkyl, and —O-alkylene-O-alkyl, -heterocyclyl-L-$R^4$, and -heteroaryl-L-$R^4$;

$R^2$ is -heterocyclyl-L-$R^4$;

$R^4$ is absent or selected from the group consisting of alkyl, cycloalkyl, aryl, alkylene-aryl, alkylene-heteroaryl, heteroaryl, heterocyclyl, —C(O)N($R^5$)$_2$, and $CF_3$;

$R^5$ is independently H or alkyl;

$R^6$ is selected from the group consisting of alkyl, cycloalkyl, aryl, heterocyclyl, heteroaryl, alkylene-aryl, —C(O)N($R^5$)$_2$, and $CF_3$;

L is absent or selected from the group consisting of methylene, —C(O)—, —$SO_2$—, —$CH_2$N(Me)-, —N(R5)(R6)-, —C(R5)(R6)-, and —O—$R^6$; and one and only one of $R^1$, $R^2$, and $R^3$ is -heterocyclyl-L-$R^4$ or -heteroaryl-L-$R^4$.

In some embodiments, the compound of the invention is a tautomer or geometric isomer of a compound of Formula (I), (II) or (III).

In some embodiments, the compound of the invention is represented by Formula (I), or a tautomer or a pharmaceutically acceptable salt thereof;

(I)

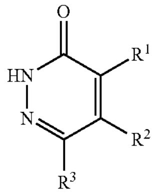

wherein $R^1$ is selected from the group consisting of H, alkyl, alkenyl, alkynyl, aryl, heterocyclyl, heteroaryl, halogen, —OH, —CN, -cycloalkyl, —O-alkyl, —O-cycloalkyl, —O-aryl, -aryl-O-aryl —$CF_3$, —C(H)$F_2$, alkylene-$CF_3$, alkylene-C(H)$F_2$, —$SO_2$-alkyl, and —O-alkylene-O-alkyl, -heterocyclyl-L-$R^4$, and -heteroaryl-L-$R^4$;

$R^2$ is -heterocyclyl-L-$R^4$;

$R^3$ is selected from the group consisting of alkyl, alkenyl, alkynyl, aryl, heterocyclyl, heteroaryl, halogen, —OH, —CN, -cycloalkyl, —O-alkyl, —O-cycloalkyl, —O-aryl, -aryl-O-aryl —$CF_3$, —C(H)$F_2$, alkylene-$CF_3$, alkylene-C(H)$F_2$, —$SO_2$-alkyl, and —O-alkylene-O-alkyl, -heterocyclyl-L-$R^4$, and -heteroaryl-L-$R^4$;

$R^4$ is absent or selected from the group consisting of alkyl, cycloalkyl, aryl, alkylene-aryl, alkylene-heteroaryl, heteroaryl, heterocyclyl, —C(O)N($R^5$)$_2$, and $CF_3$;

$R^5$ is independently H or alkyl;

$R^6$ is selected from the group consisting of alkyl, cycloalkyl, aryl, heterocyclyl, heteroaryl, alkylene-aryl, —C(O)N($R^5$)$_2$, and $CF_3$;

L is absent or selected from the group consisting of methylene, —C(O)—, —$SO_2$—, —$CH_2$N(Me)-, —N($R^5$)($R^6$)—, —C($R^5$)($R^6$)—, and —O—$R^6$; and one and only one of $R^1$, $R^2$, and $R^3$ is -heterocyclyl-L-$R^4$ or -heteroaryl-L-$R^4$.

In some embodiments, the compound of the invention is represented by Formula (II) or a tautomer or a pharmaceutically acceptable salt thereof;

(II)

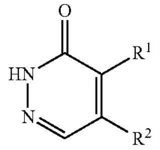

wherein $R^1$ is selected from the group consisting of H, alkyl, alkenyl, alkynyl, aryl, heterocyclyl, heteroaryl, halogen, —OH, —CN, -cycloalkyl, —O-alkyl, —O-cycloalkyl, —O-aryl, -aryl-O-aryl —$CF_3$, —C(H)$F_2$, alkylene-$CF_3$, alkylene-C(H)$F_2$, —$SO_2$-alkyl, and —O-alkylene-O-alkyl, -heterocyclyl-L-$R^4$, and -heteroaryl-L-$R^4$;

$R^2$ is -heterocyclyl-L-$R^4$;

$R^4$ is absent or selected from the group consisting of alkyl, cycloalkyl, aryl, alkylene-aryl, alkylene-heteroaryl, heteroaryl, heterocyclyl, —C(O)N($R^5$)$_2$, and $CF_3$;

$R^5$ is independently H or alkyl;

$R^6$ is selected from the group consisting of alkyl, cycloalkyl, aryl, heterocyclyl, heteroaryl, alkylene-aryl, —C(O)N($R^5$)$_2$, and $CF_3$;

L is absent or selected from the group consisting of methylene, —C(O)—, —$SO_2$—, —$CH_2$N(Me)-, —N($R^5$)($R^6$)—, —C($R^5$)($R^6$)—, and —O—$R^6$; and one and only one of $R^1$ and $R^2$ is -heterocyclyl-L-$R^4$ or -heteroaryl-L-$R^4$.

In some embodiments, the compound of the invention is represented by Formula (III), or a tautomer or a pharmaceutically acceptable salt thereof;

(III)

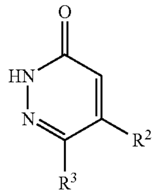

wherein $R^1$ is selected from the group consisting of H, alkyl, alkenyl, alkynyl, aryl, heterocyclyl, heteroaryl, halogen, —OH, —CN, -cycloalkyl, —O-alkyl, —O-cycloalkyl, —O-aryl, -aryl-O-aryl —$CF_3$, —C(H)$F_2$, alkylene-$CF_3$, alkylene-C(H)$F_2$, —$SO_2$-alkyl, and —O-alkylene-O-alkyl, -heterocyclyl-L-$R^4$, and -heteroaryl-L-$R^4$;

$R^2$ is -heterocyclyl-L-$R^4$;

$R^4$ is absent or selected from the group consisting of alkyl, cycloalkyl, aryl, alkylene-aryl alkylene-heteroaryl, heteroaryl, heterocyclyl, —C(O)N($R^5$)$_2$, and $CF_3$;

$R^5$ is independently H or alkyl;

$R^6$ is selected from the group consisting of alkyl, cycloalkyl, aryl, heterocyclyl, heteroaryl, alkylene-aryl, —C(O)N($R^5$)$_2$, and $CF_3$;

L is absent or selected from the group consisting of methylene, —C(O)—, —$SO_2$—, —$CH_2$N(Me)-, —N($R^5$)($R^6$)—, —C($R^5$)($R^6$)—, and —O—$R^6$; and one and only one of $R^1$ and $R^2$ is -heterocyclyl-L-$R^4$ or -heteroaryl-L-$R^4$.

In some embodiments, $R^1$ is H. In some embodiments, $R^1$ is alkyl. In some embodiments, $R^1$ is selected from the group consisting of methyl, ethyl, n-propyl, i-propyl, n-butyl, i-butyl, and t-butyl. In some embodiments, alkyl is substituted alkyl.

In some embodiments, $R^1$ is alkenyl. In some embodiments, alkenyl is ethenyl, propenyl, butenyl. In some embodiments, alkenyl is substituted alkenyl. In some embodiments, substituted alkenyl is methyl-substituted ethenyl.

In some embodiments, $R^1$ is alkynyl. In some embodiments, alkynyl is substituted alkynyl. In some embodiments, substituted alkynyl is alkynyl substituted with alkyl or cycloalkyl.

In some embodiments, $R^1$ is aryl. In some embodiments, aryl is phenyl. In some embodiments, aryl is biaryl. In some embodiments, aryl is a 5 to 12 membered ring.

In some embodiments, substituted phenyl is substituted with at least one moiety independently selected from the group consisting of alkyl, halogen, CN, OMe, OH, $NO_2$, $NH_2$, N(Me)$_2$, $CF_3$, $OCF_3$, $CHF_2$, and $OCHF_2$. In some embodiments, substituted phenyl is substituted with at least one moiety independently selected from the group consisting of halogen, methyl, ethyl, n-propyl, i-propyl, n-butyl, i-butyl, or t-butyl.

In some embodiments, $R^1$ is heterocyclyl. In some embodiments, heterocyclyl is heterocycloalkyl. In some embodiments, heterocycloalkyl is substituted heterocycloalkyl.

In some embodiments, heterocyclyl is heteroaryl. In some embodiments, heteroaryl is substituted heteroaryl.

In some embodiments, $R^1$ is halogen. In some embodiments. In some embodiments, $R^1$ is Cl. In some embodiments, $R^1$ is F. In some embodiments, $R^1$ is Br.

In some embodiments, $R^1$ is $R^1$ is —O-alkyl. In some embodiments, $R^1$ is —OMe. In some embodiments, $R^1$ is -OEt.

In some embodiments, $R^1$—O-cycloalkyl. In some embodiments, —O-cycloalkyl is —O— cyclopropyl.

In some embodiments, $R^1$ is —O-aryl. In some embodiments, —O-aryl is —OPh.

In some embodiments, $R^1$ is —$CF_3$.

In some embodiments, $R^1$ is —$SO_2$-alkyl. In some embodiments, $R^1$ is —$SO_2$-alkyl is —$SO_2$Me.

In some embodiments, $R^1$ is —O-alkylene-O-alkyl. In some embodiments, —O-alkylene-O-alkyl is —O-alkylene-OMe. In some embodiments, —O-alkylene-OMe is —O-ethylene-OMe.

In some embodiments, the heterocyclyl of $R^2$ is selected from

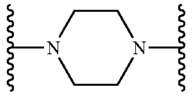,
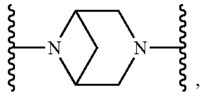,
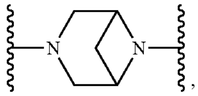,
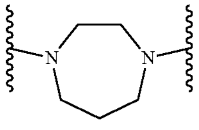

-continued

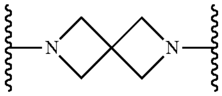,
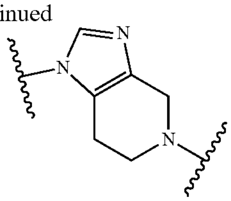,
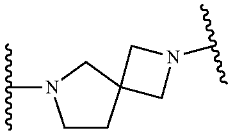,
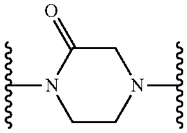,
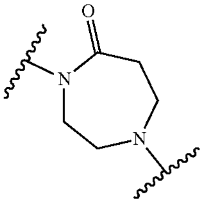,
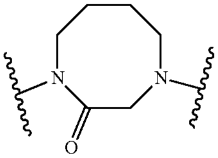,
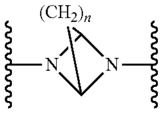, and
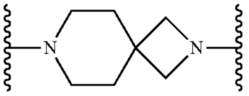, each of which is optionally substituted with one or two substituents (e.g., one or two alkyl groups).

In some embodiments, heterocyclyl in $R^2$ is

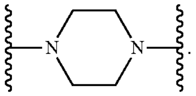 [SMILES: *N1CCN(*)CC1].

In some embodiments, heterocyclyl in $R^2$ is

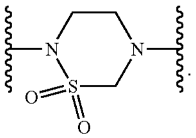 [SMILES: *N1CCN(*)S(=O)(=O)C1].

In some embodiments, heterocyclyl in $R^2$ is selected from

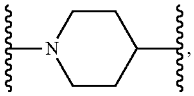,
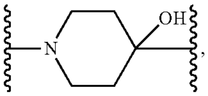,
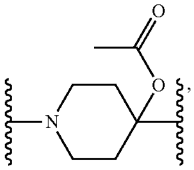,
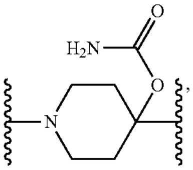, and
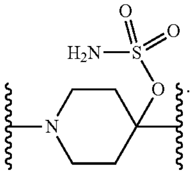.

In some embodiments, $R^2$ is -substituted heterocyclyl-L-$R^4$.

In some embodiments, substituted heterocyclyl in $R^2$ is substituted

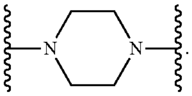.

In some embodiments, substituted heterocyclyl in $R^2$ is substituted

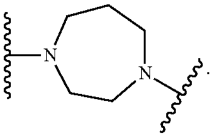 [SMILES: *N1CCCN(*)CC1].

In some embodiments, substituted heterocyclyl in $R^2$ is substituted

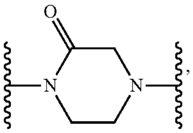,
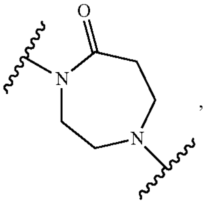,
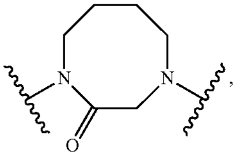, or
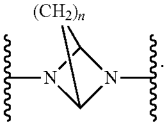.

In some embodiments, $R^2$ is selected from

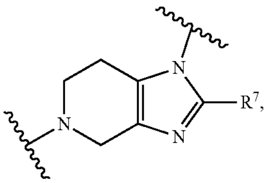, and
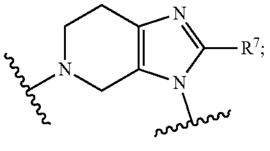;

wherein $R^7$ is H, alkyl, —O-aryl, —O-alkyl, or cycloalkyl.

In some embodiments, $R^2$ is selected from

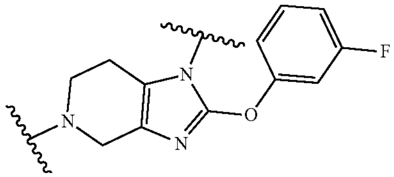

and

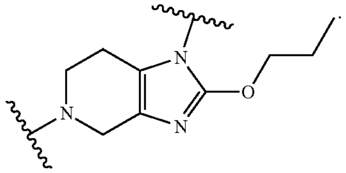

In some embodiments, $R^2$ is selected from

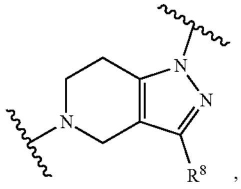

,

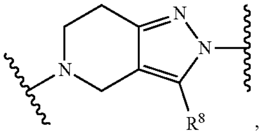

,

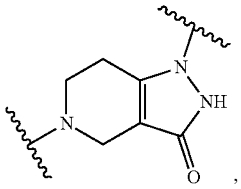

, and

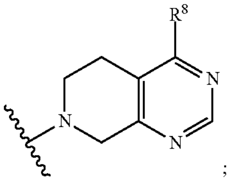

;

wherein $R^8$ is H, —C(O)N($R^5$)$_2$, —N($R^5$In some embodiments, $R^2$ is selected from $R^6$), —O-aryl, or —O— heteroaryl.

In some embodiments, $R^2$ is selected from

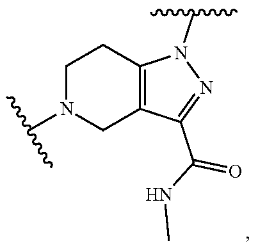

,

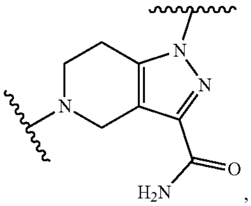

,

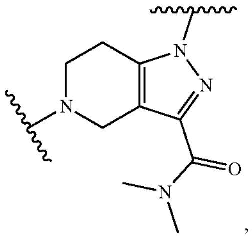

,

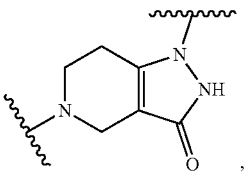

,

-continued

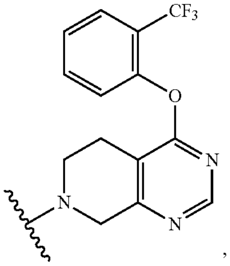

,

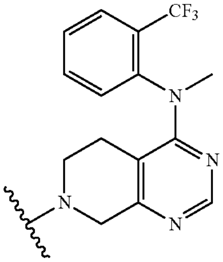

, or

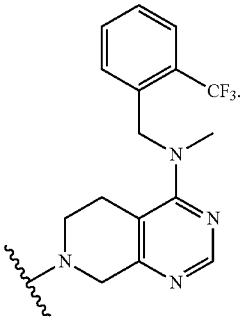

In some embodiments, $R^2$ is

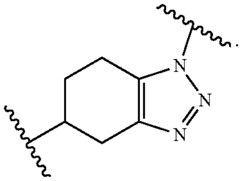 [SMILES: *C1CCc2c(nnn2*)C1]

In some embodiments, $R^4$ is absent.

In some embodiments, $R^4$ is alkyl. In some embodiments, $R^4$ is methyl, ethyl, propyl, or butyl. In some embodiments, alkyl is t-Bu.

In some embodiments, $R^4$ is cycloalkyl.

In some embodiments, $R^4$ is aryl. In some embodiments, aryl is phenyl. In some embodiments, phenyl is substituted phenyl. In some embodiments, substituted phenyl is substituted with at least one moiety independently selected from the group consisting of alkyl, cycloalkyl, aryl, halogen, —CN, $CF_3$, C(H)$F_2$, —O$CF_3$, —O-aryl, —O-alkyl, —$SO_2$Me, OH, alkylene-O$R^5$, alkylene-$CF_3$, and alkylene-C(H)$F_2$.

In some embodiments, $R^4$ is alkylene-aryl. In some embodiments, the aryl of alkylene-aryl is substituted phenyl.

In some embodiments, $R^4$ is alkylene-heteroaryl. In some embodiments, the heteroaryl of alkylene-heteroaryl is substituted pyridinyl.

In some embodiments, $R^4$ is heterocyclyl. In some embodiments, heterocyclyl is heteroaryl. In some embodiments, heteroaryl is substituted heteroaryl. In some embodiments, heteroaryl is pyridinyl. In some embodiments, heteroaryl is substituted with at least one moiety independently elected from the group consisting of alkyl, cycloalkyl, aryl, halogen, —CN, $CF_3$, C(H)$F_2$, —O$CF_3$, —O-aryl, —O-alkyl, —$SO_2$Me, OH, alkylene-O$R^5$, alkylene-$CF_3$, and alkylene-C(H)$F_2$.

In some embodiments, $R^4$ is —C(O)N($R^5$)$_2$.

In some embodiments, $R^4$ is $CF_3$.

In some embodiments, $R^5$ is H. In some embodiments, $R^5$ is alkyl. In some embodiments, $R^5$ is methyl or ethyl. In some embodiments, alkyl is substituted alkyl.

In some embodiments, $R^6$ is alkyl. In some embodiments, alkyl is substituted alkyl.

In some embodiments, $R^6$ is cycloalkyl. In some embodiments, cycloalkyl is substituted cycloalkyl. In some embodiments, $R^6$ is aryl. In some embodiments, aryl is substituted aryl. In some embodiments, $R^6$ is heterocyclyl. In some embodiments, heterocyclyl is substituted heterocyclyl. In some embodiments, $R^6$ is —C(O)N($R^5$)$_2$. In some embodiments, $R^6$ is $CF_3$.

In some embodiments, L is absent. In some embodiments, L is methylene. In some embodiments, methylene is substituted methylene. In some embodiments, substituted methylene is substituted with at least one moiety independently selected from the group consisting of alkyl, cycloalkyl, aryl, halogen, $CF_3$, C(H)$F_2$, —O$CF_3$, OH, alkylene-O$R^5$, alkylene-$CF_3$, alkylene-C(H)$F_2$, and —C(O)N($R^5$).

In some embodiments, L is —C(O)—. In some embodiments, L is —$SO_2$—. In some embodiments, L is —$CH_2$N(Me)-. In some embodiments, L is —N($R^5$)($R^6$). In some embodiments, L is O—$R^6$.

In some embodiments, at least one of $R^1$ and $R^3$ is H.

In some embodiments, the compound is selected from the group consisting of:

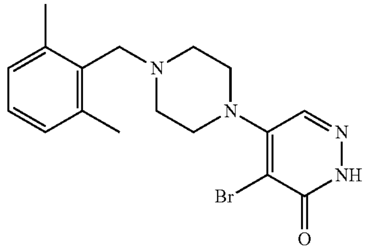

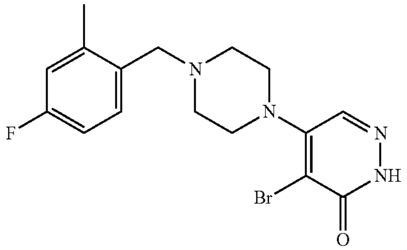

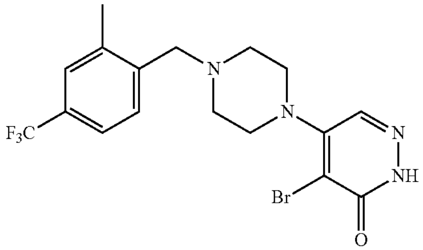

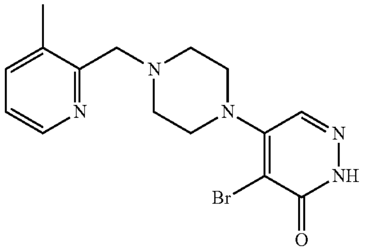

-continued

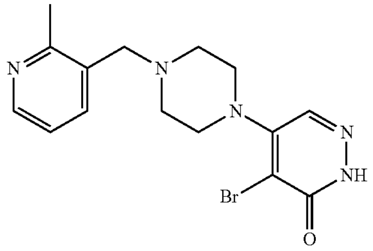

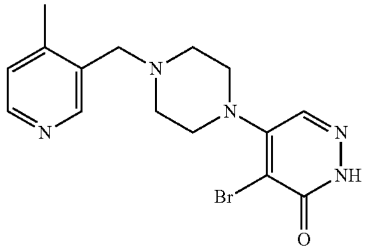

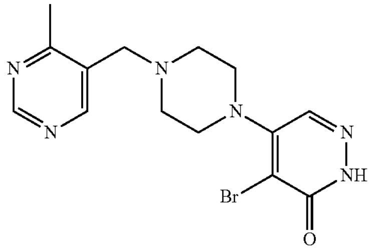

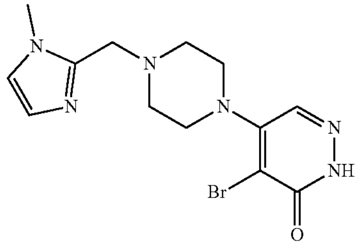

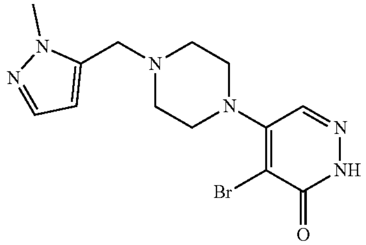

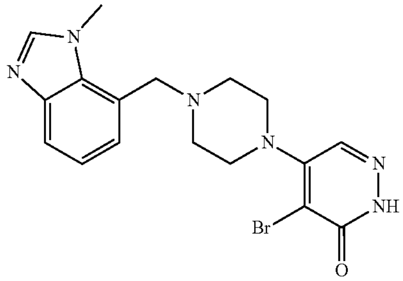

-continued
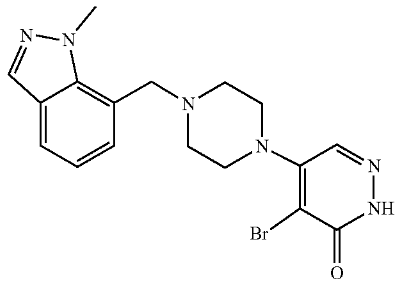
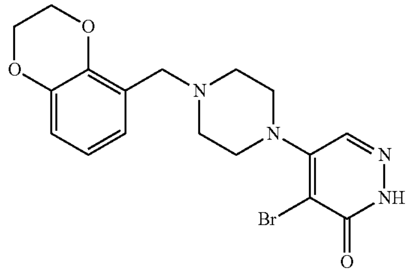
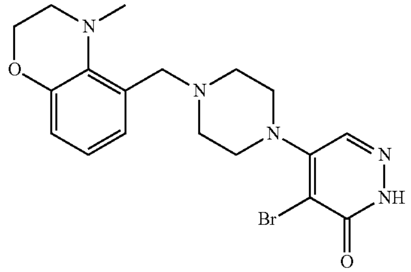
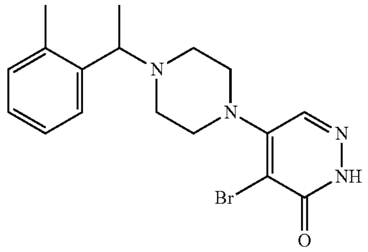
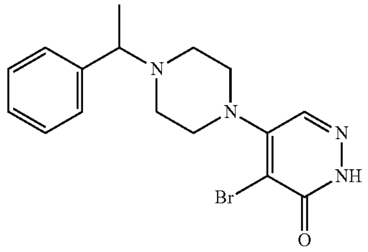
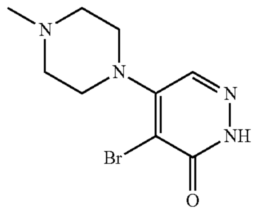
-continued
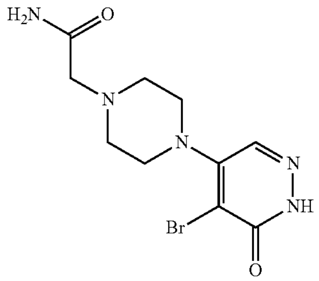
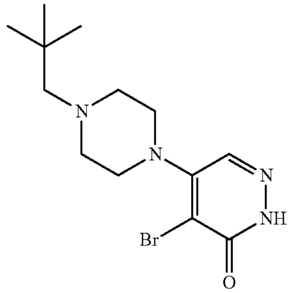
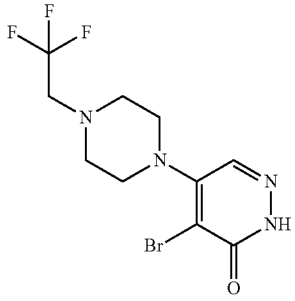
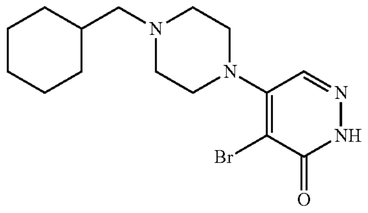
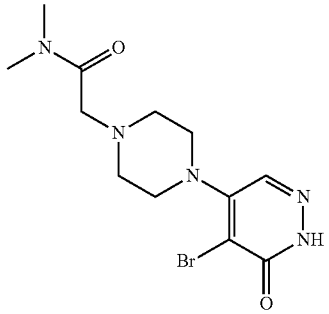
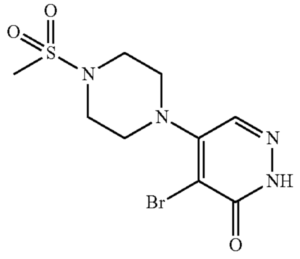
and -continued
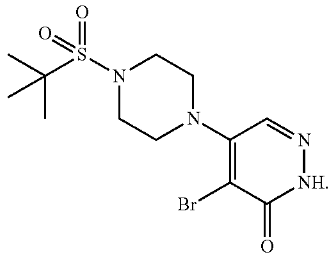
In some embodiments, the compound is selected from the group consisting of:
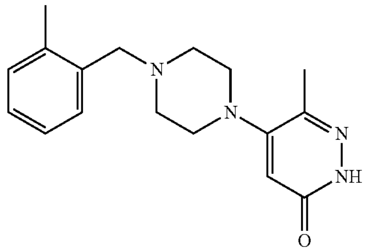
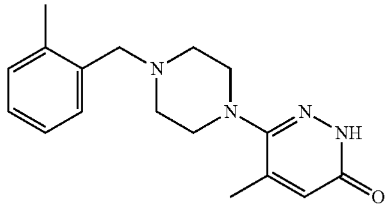
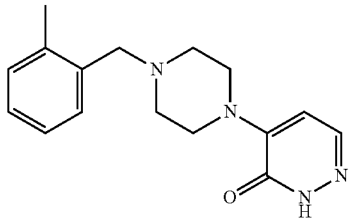
and
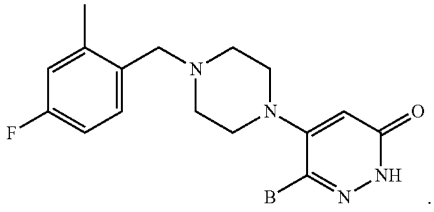
.
In some embodiments, the compound is selected from the group consisting of:
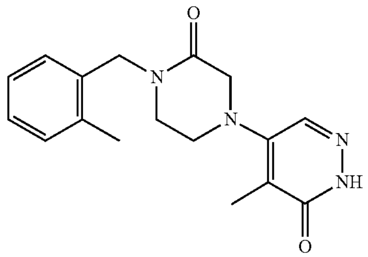
-continued
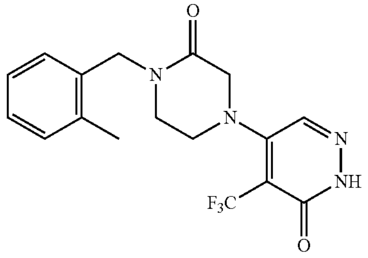
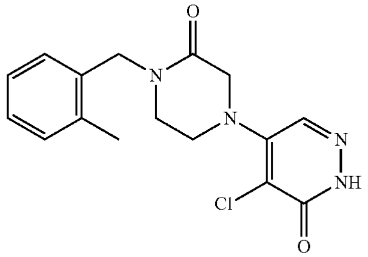
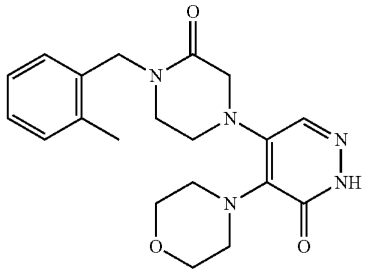
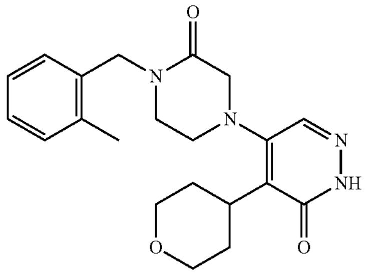
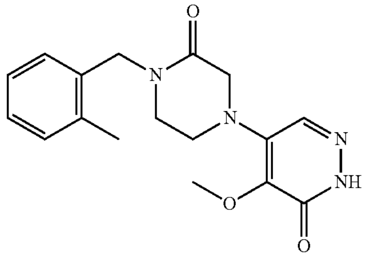
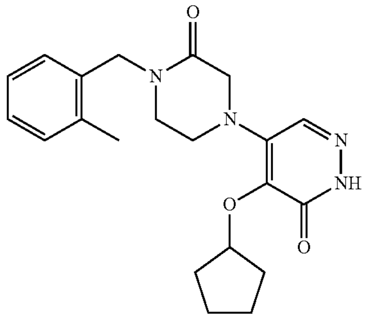

-continued
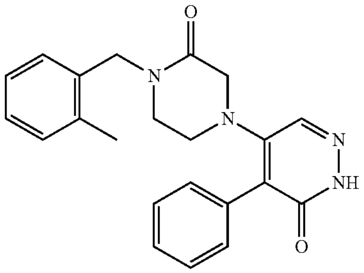
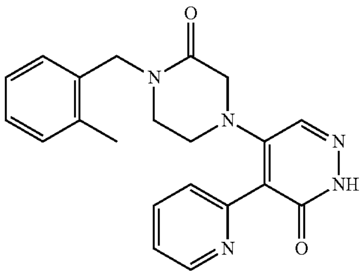
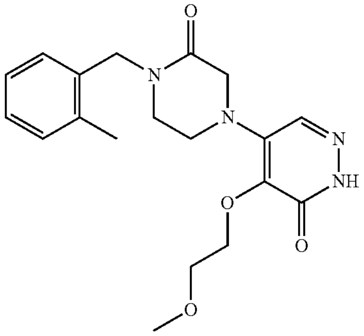
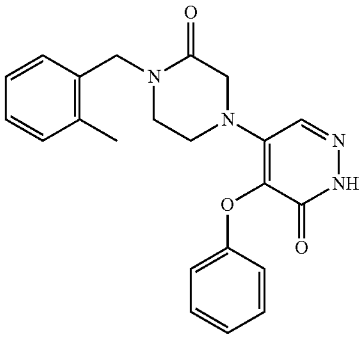
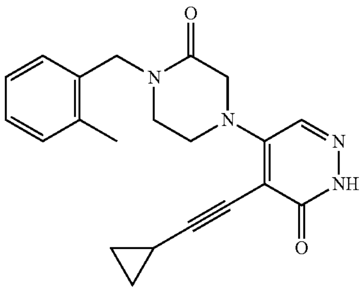
-continued
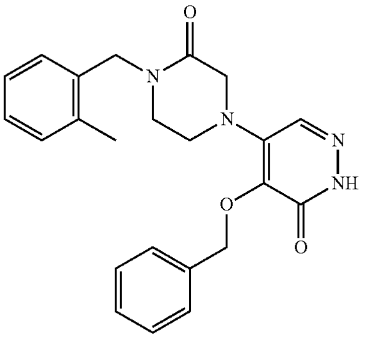
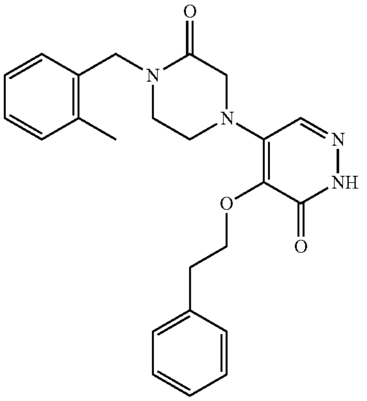
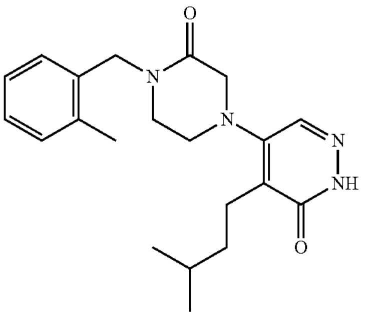
and
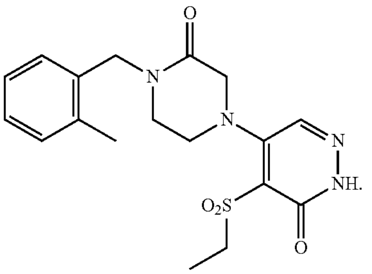
In some embodiments, the compound is selected from the group consisting of:
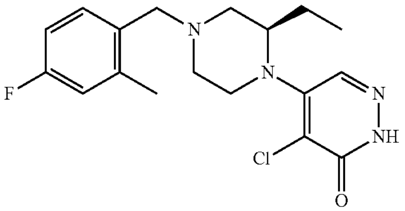

-continued
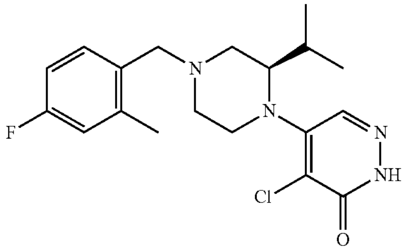
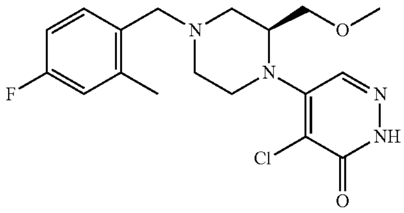
and
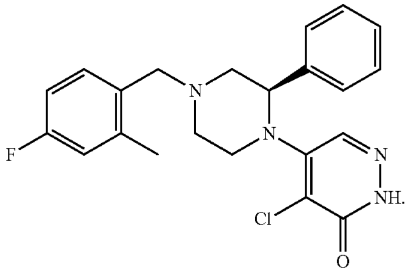
In some embodiments, the compound is selected from the group consisting of:
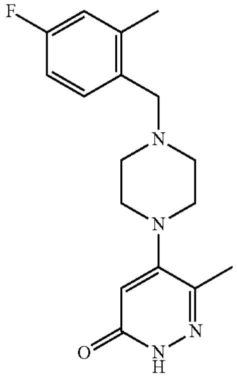
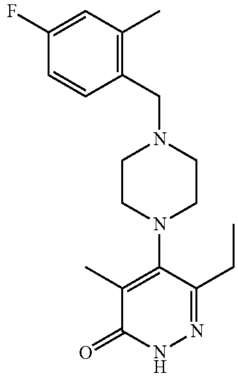
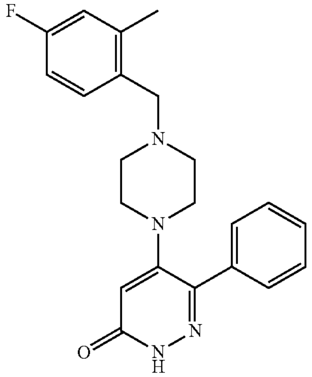
-continued
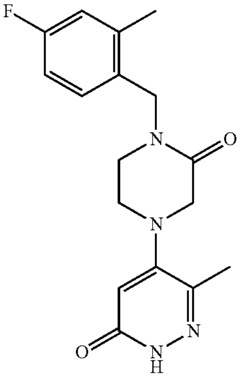
and
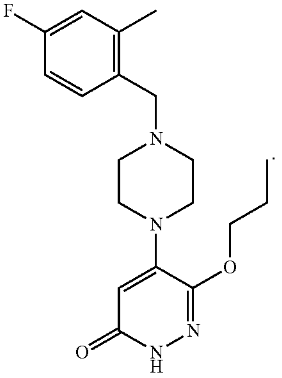
In some embodiments, the compound is selected from the group consisting of:
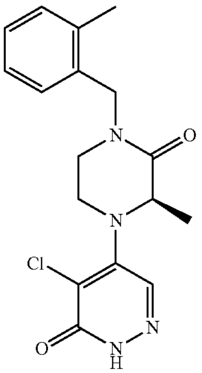
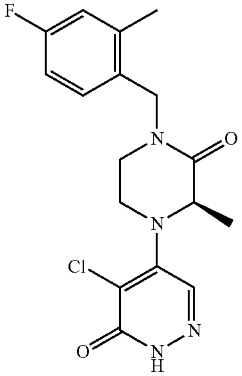
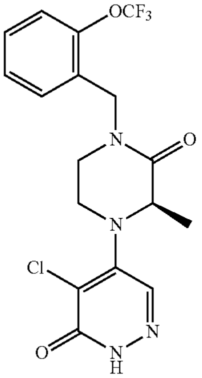
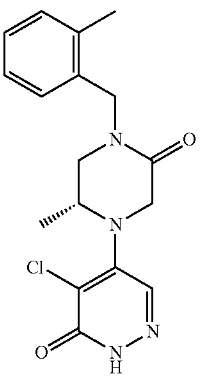

-continued
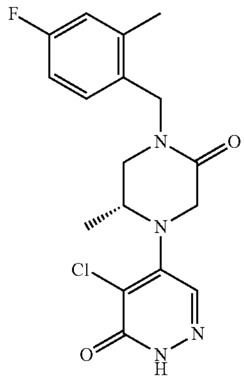
and
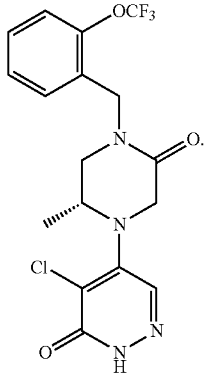
In some embodiments, the compound is selected from the group consisting of:
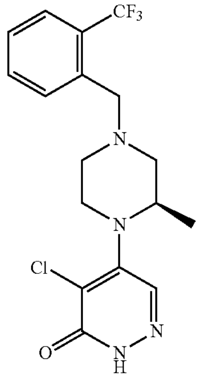
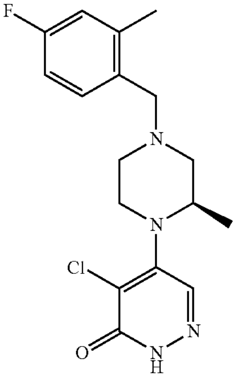
and
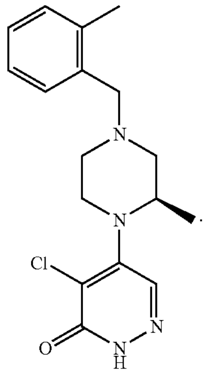
In some embodiments, the compound is selected from the group consisting of:
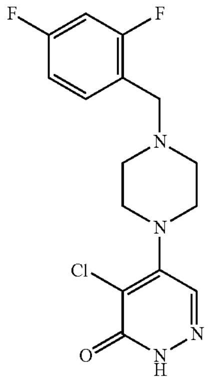
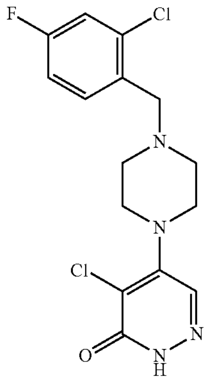
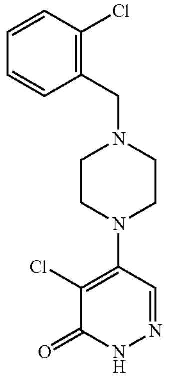
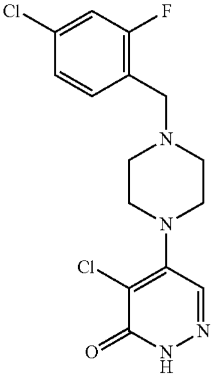
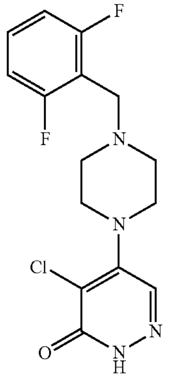
and
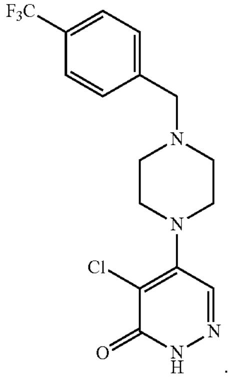
In some embodiments, the compound is selected from the group consisting of:
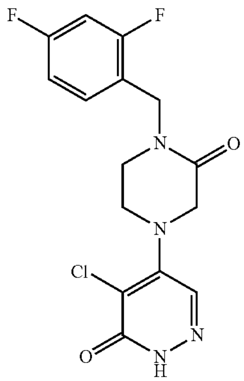
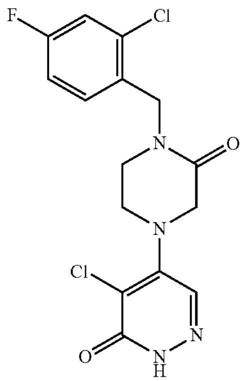

-continued
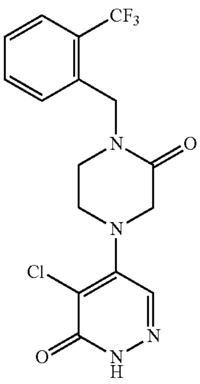
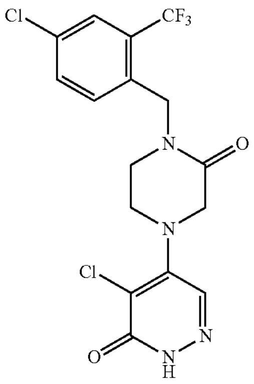
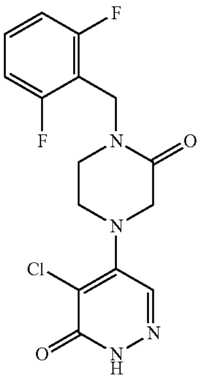
and
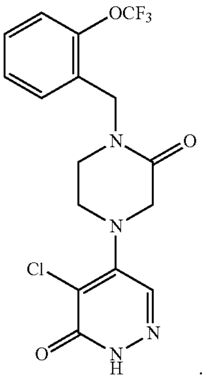
.
In some embodiments, the compound is selected from the group consisting of:
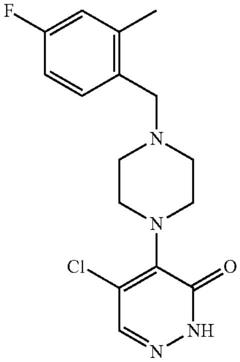
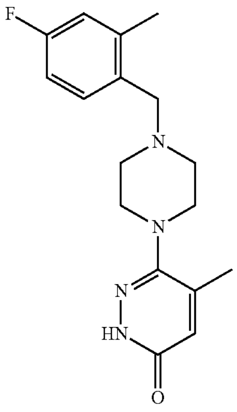
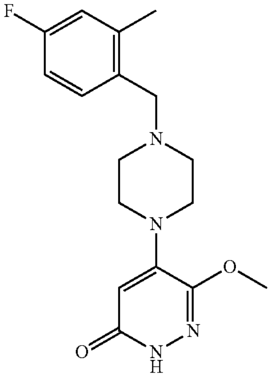
and
-continued
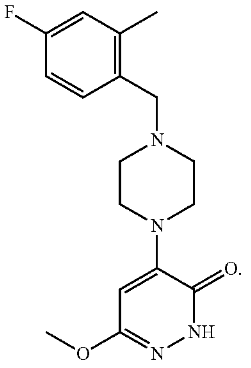
In some embodiments, the compound is selected from the group consisting of:
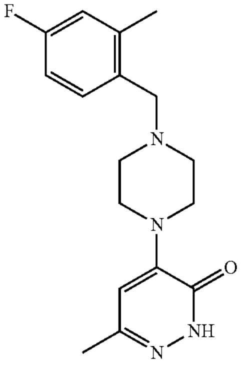
and
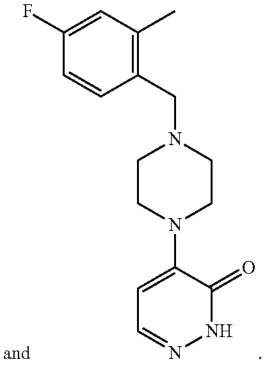
.
In some embodiments, the compound is selected from the group consisting of:
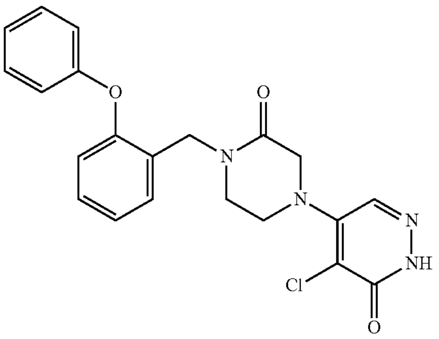
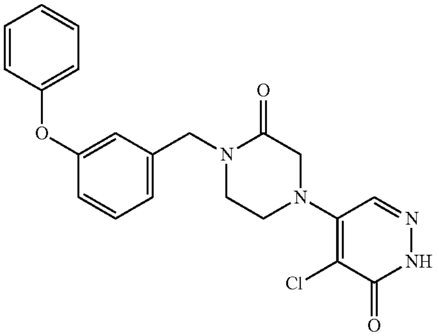

-continued
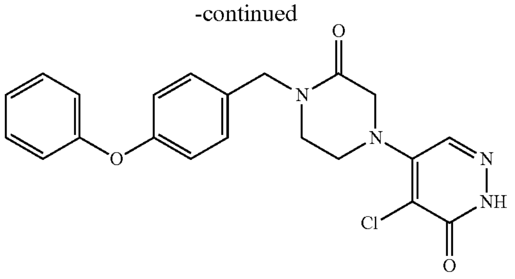
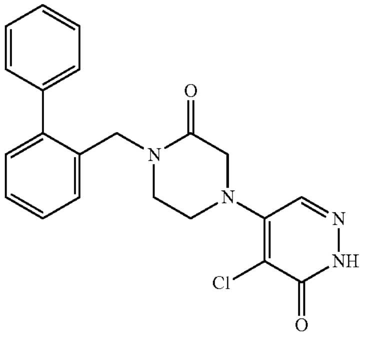
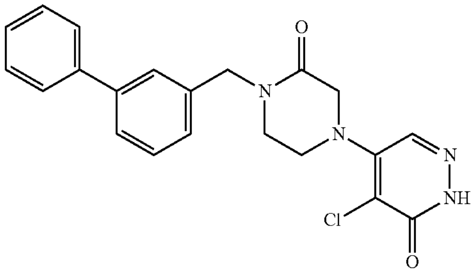
and
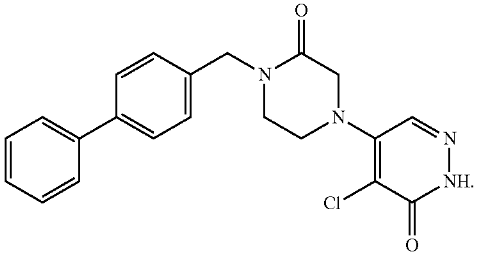
In some embodiments, the compound is selected from the group consisting of:
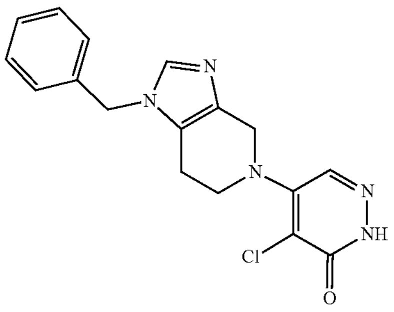
-continued
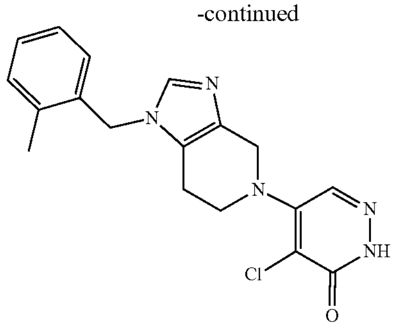
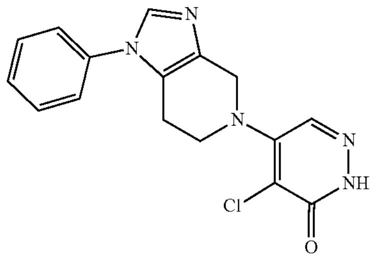
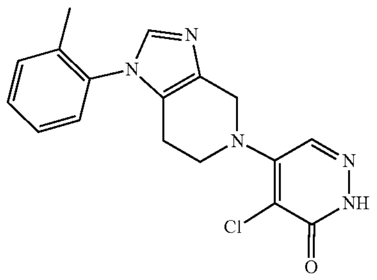
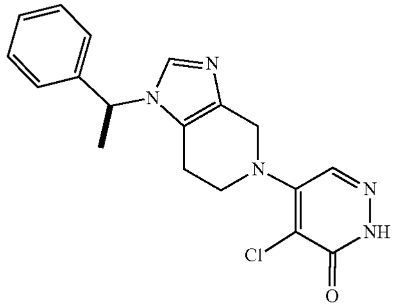
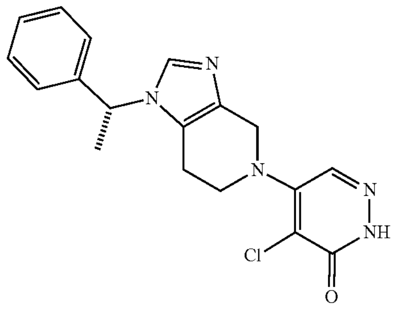

-continued
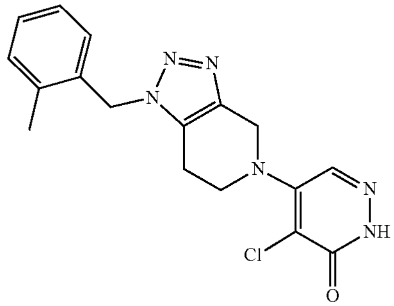
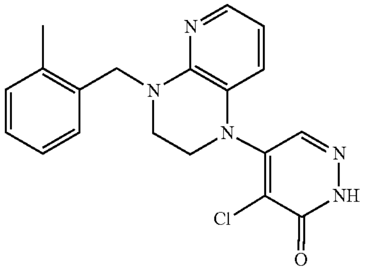
and
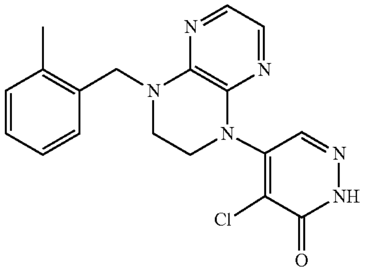
In some embodiments, the compound is selected from the group consisting of:
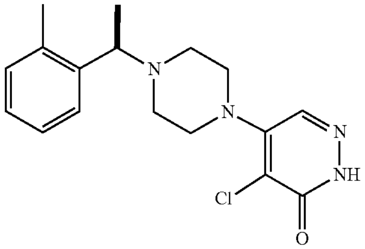
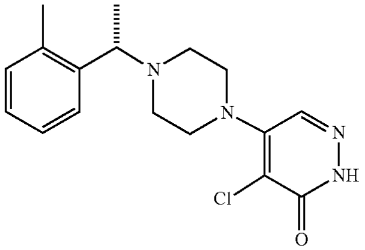
-continued
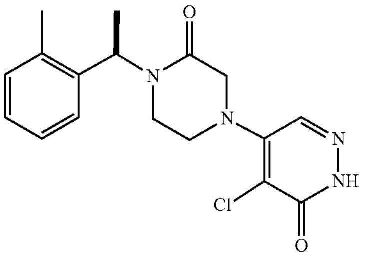
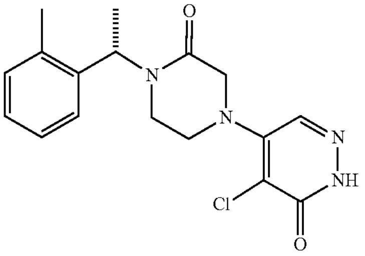
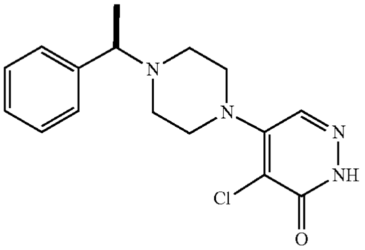
and
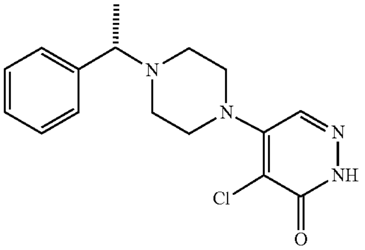
In some embodiments, the compound is selected from the group consisting of:
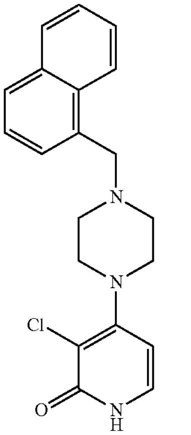
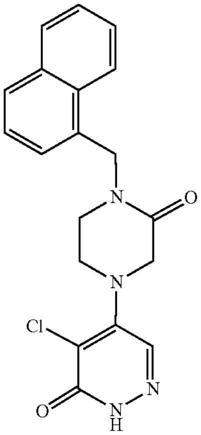

-continued
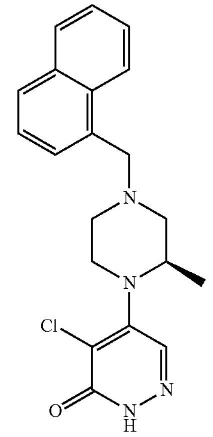
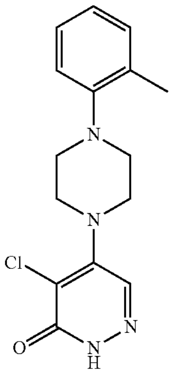
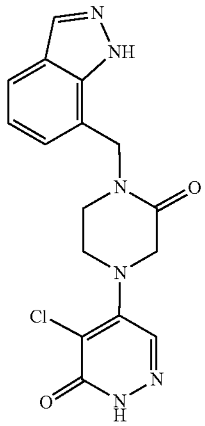
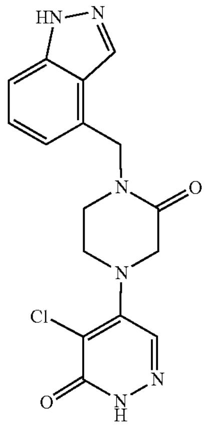
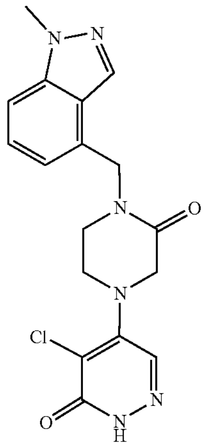
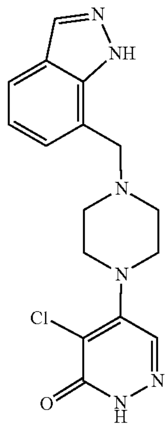
-continued
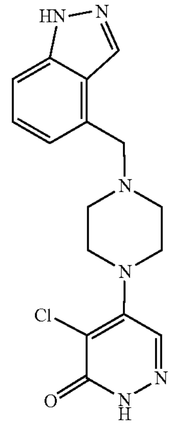
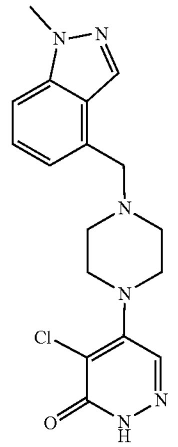
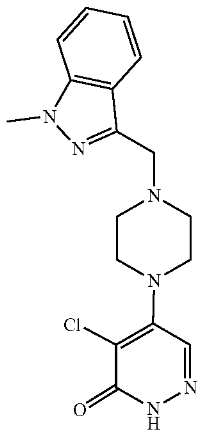
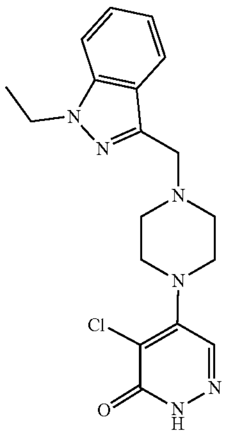
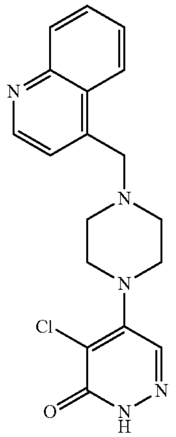
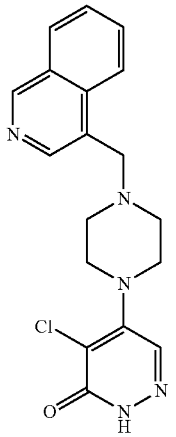
and
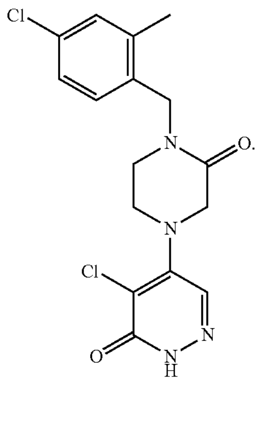

In some embodiments, the compound is selected from the group consisting of:
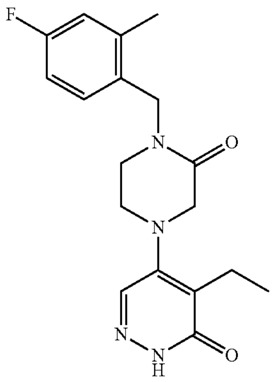
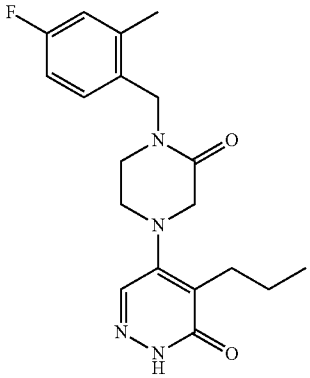
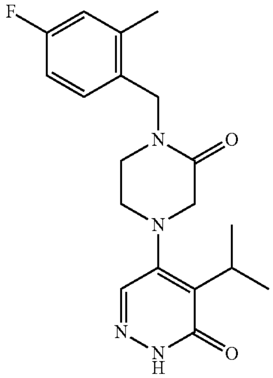
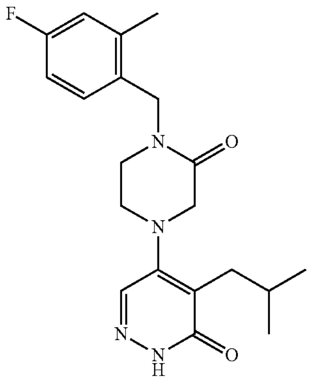
-continued
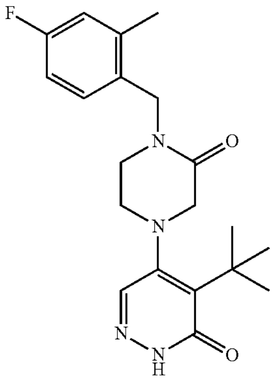
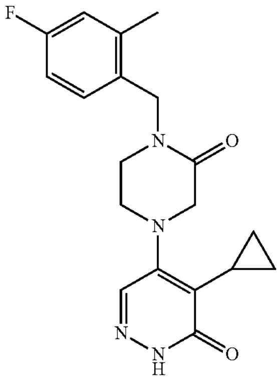
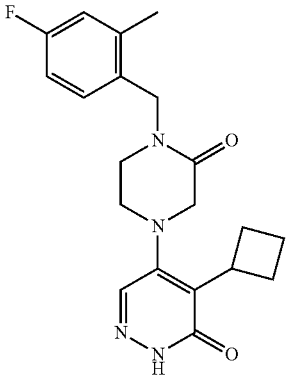
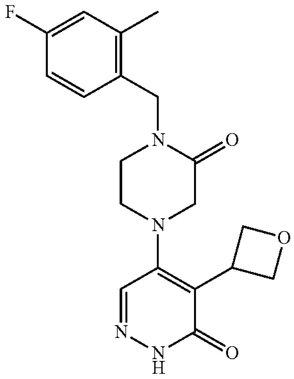

-continued
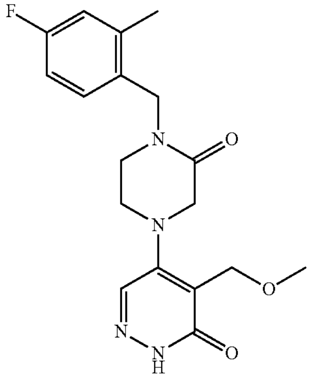
and
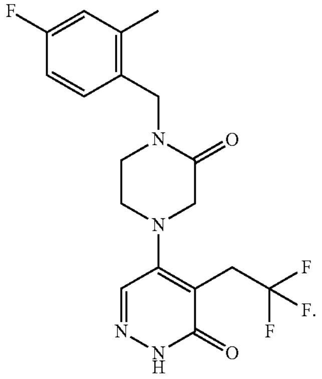
In some embodiments, the compound is selected from the group consisting of:
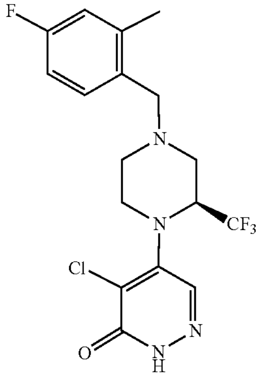
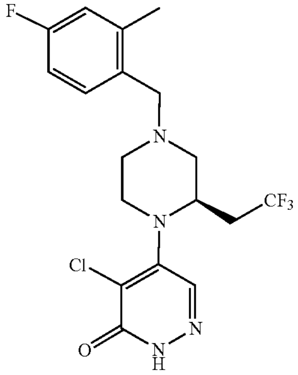
and
-continued
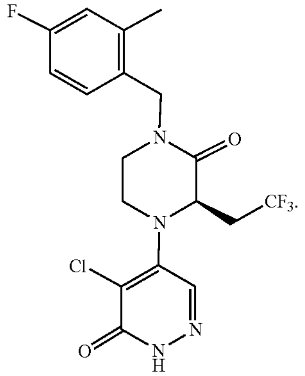
In some embodiments, the compound is selected from the group consisting of:
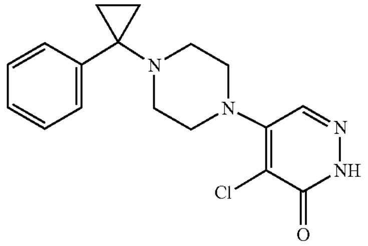
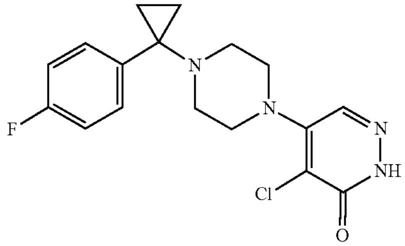
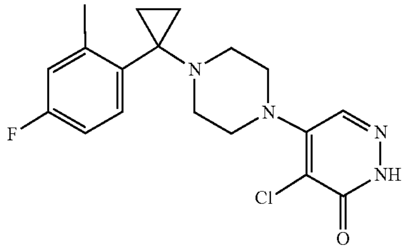
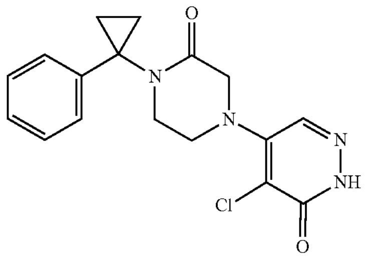

-continued
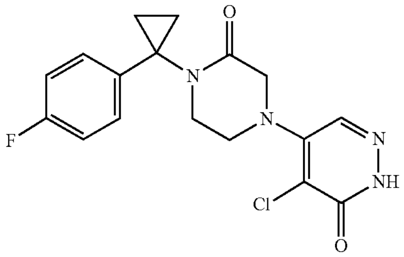
and
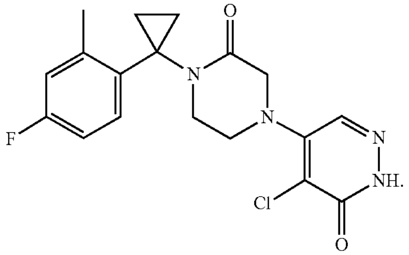
In some embodiments, the compound is selected from the group consisting of:
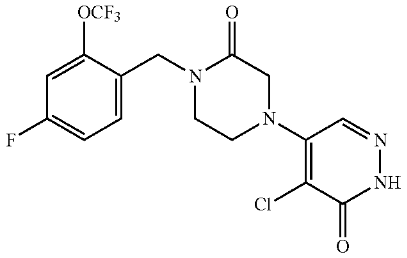
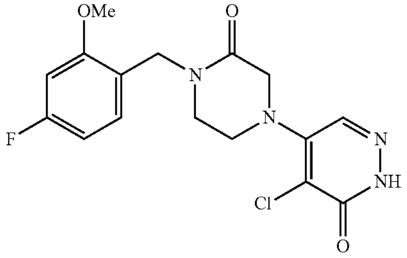
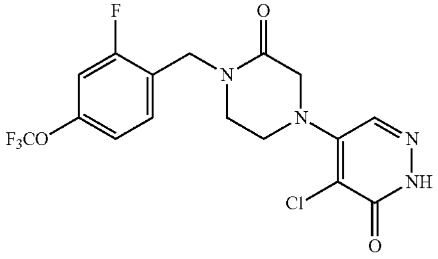
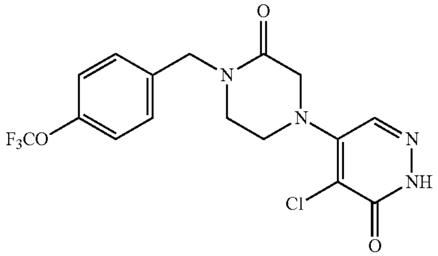
-continued
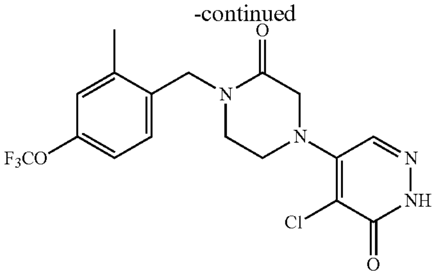
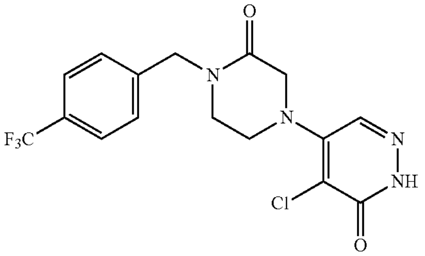
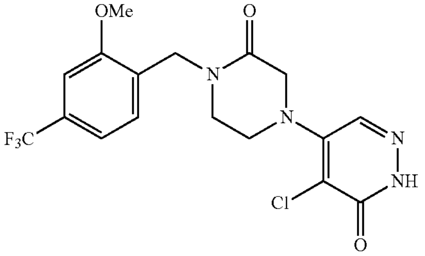
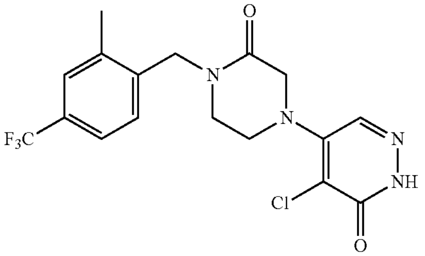
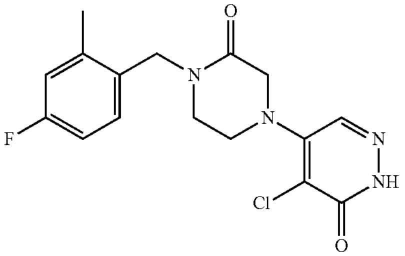
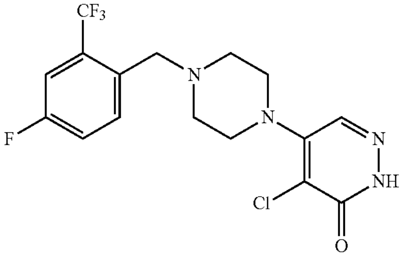

-continued
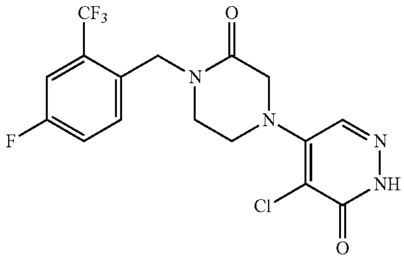
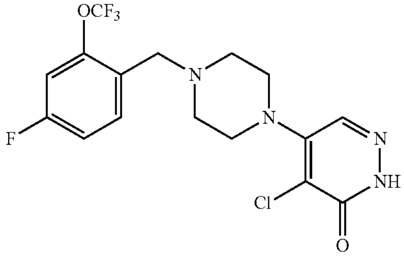
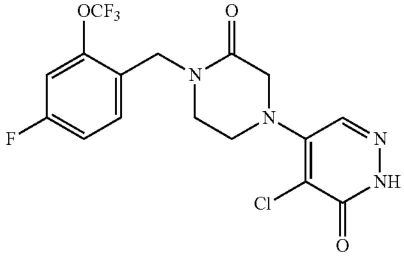
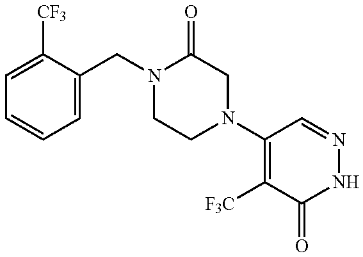
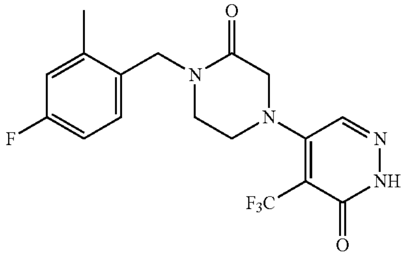
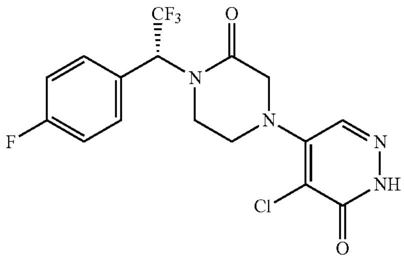
-continued
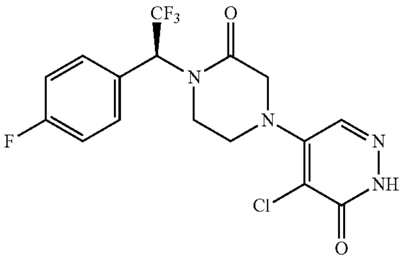
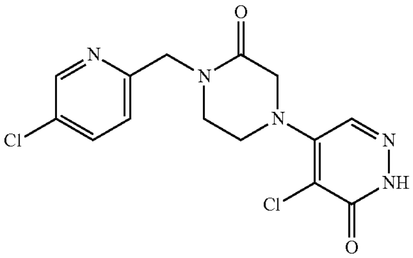
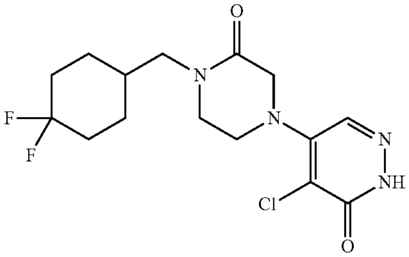
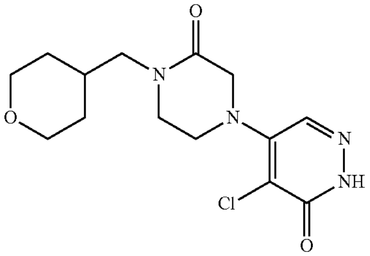
and
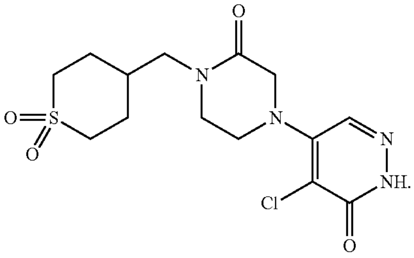
In some embodiments, the compound is selected from the group consisting of:
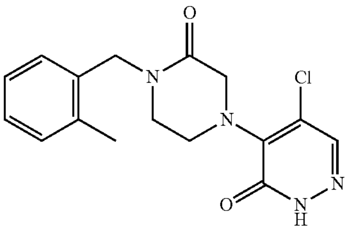

-continued
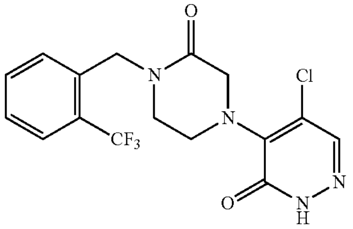
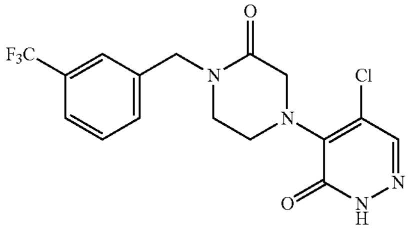
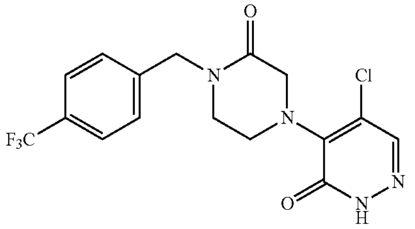
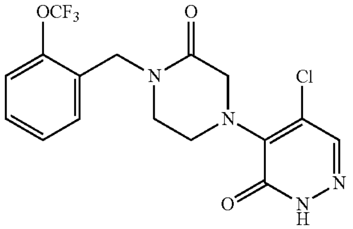
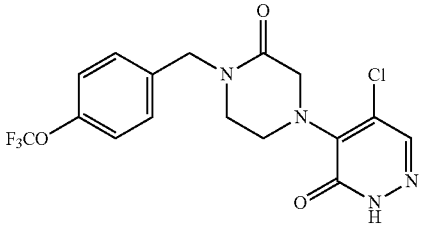
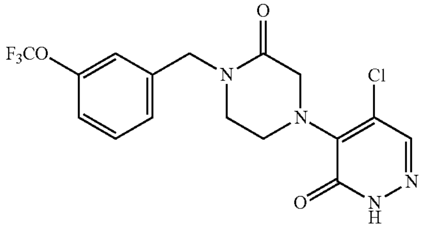
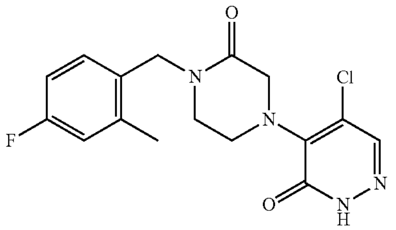
-continued
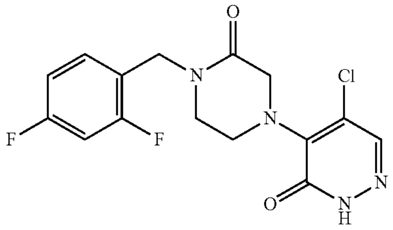
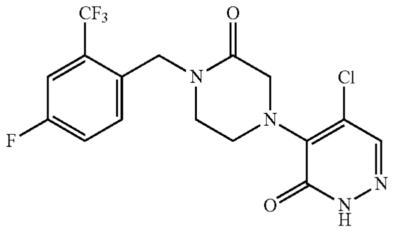
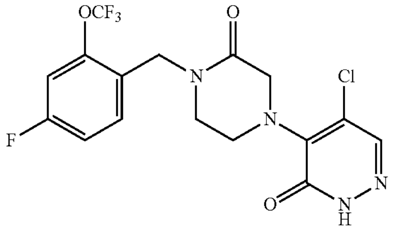
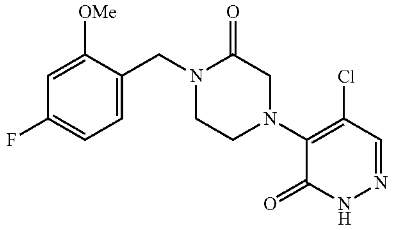
and
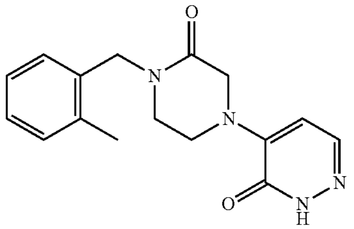
In some embodiments, the compound is selected from the group consisting of:
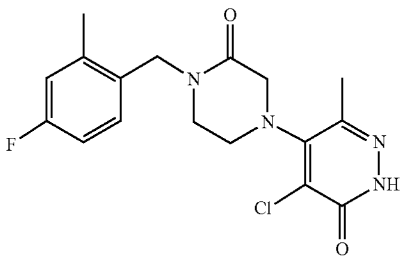

-continued
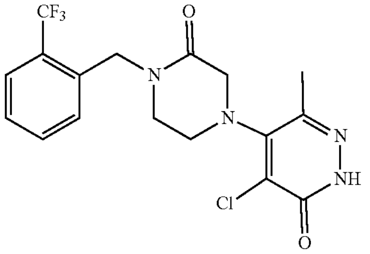
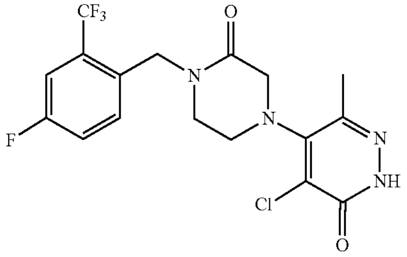
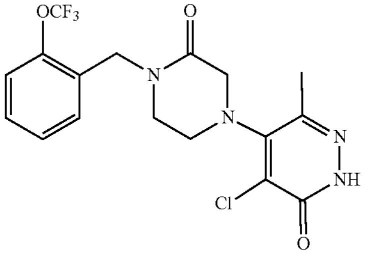
and
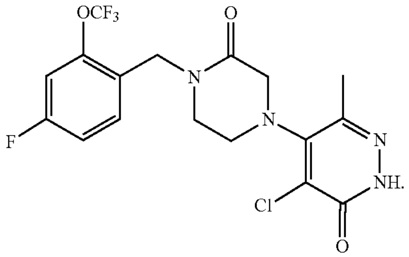
In some embodiments, the compound is:
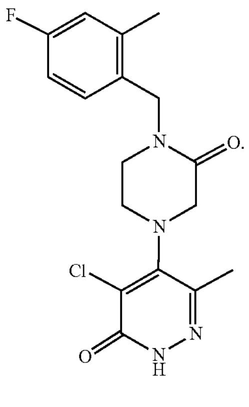 [SMILES: Cc1cc(F)ccc1CN1CCN(c2c(C)n[nH]c(=O)c2Cl)CC1=O]
In some embodiments, the compound is selected from the group consisting of:
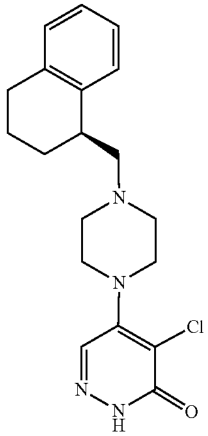
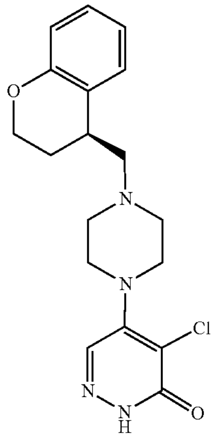
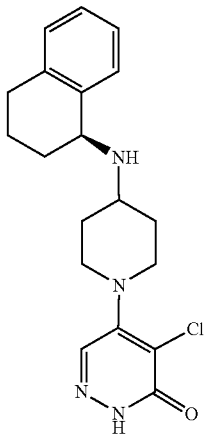

-continued
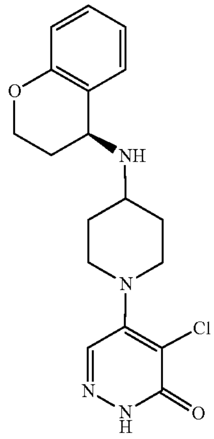
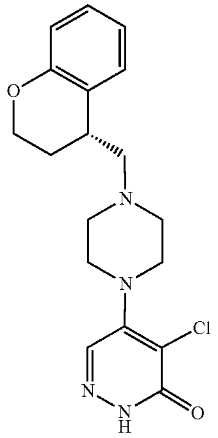
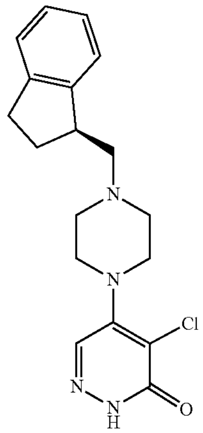
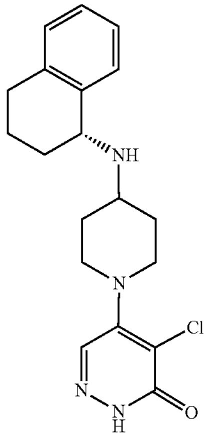
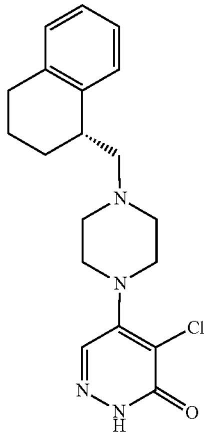
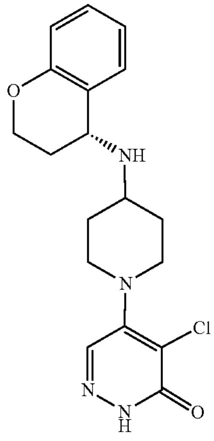
and -continued
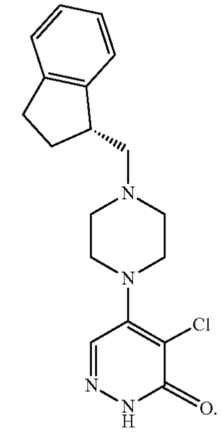
In some embodiments, the compound is selected from the group consisting of:
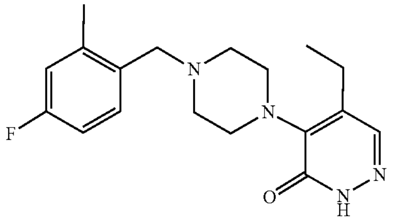
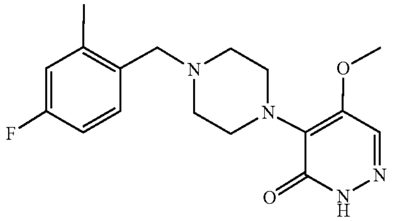
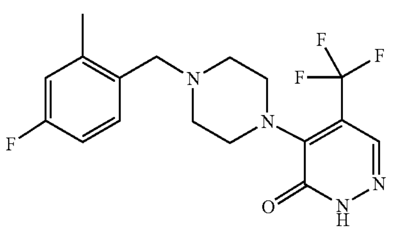
and
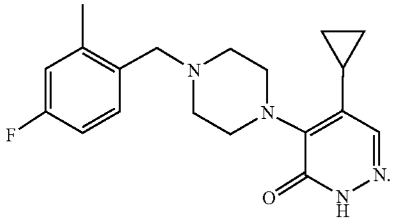
In some embodiments, the compound is selected from the group consisting of:
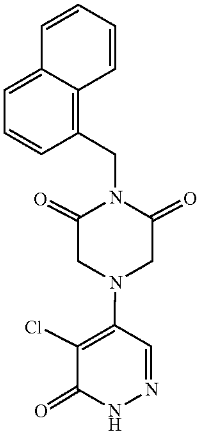
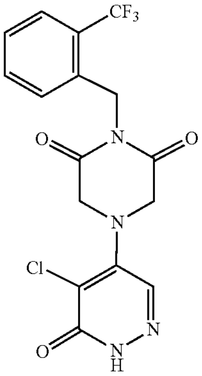
and
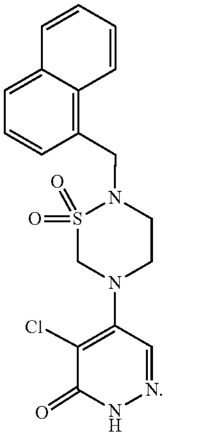
In some embodiments, the compound is selected from the group consisting of:
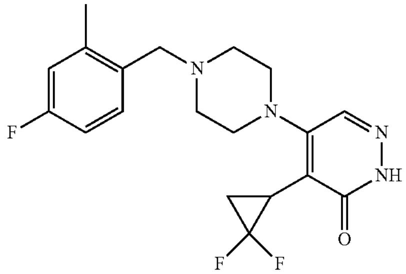

-continued
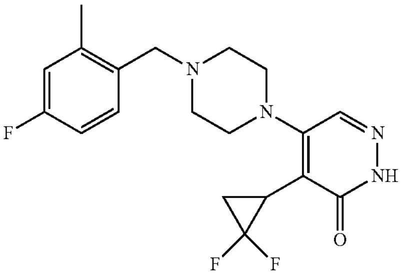
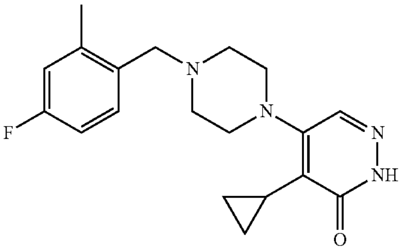
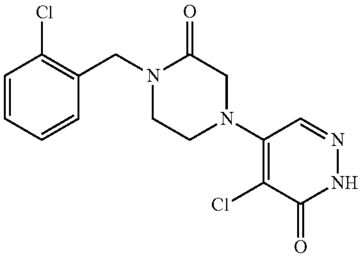
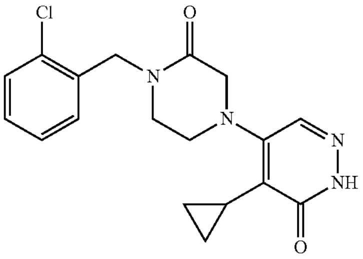
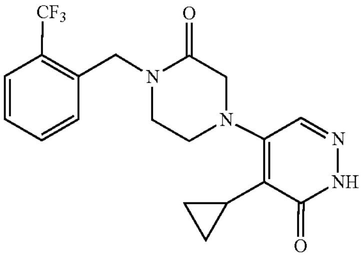
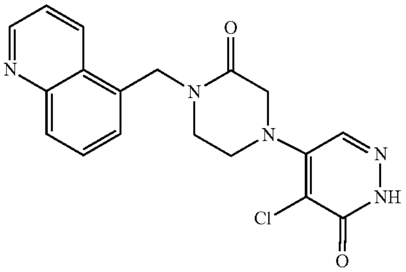
-continued
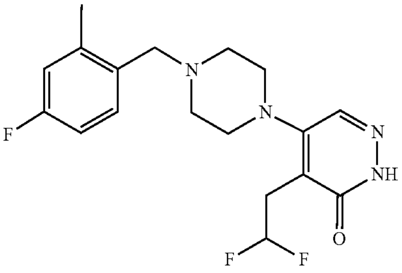
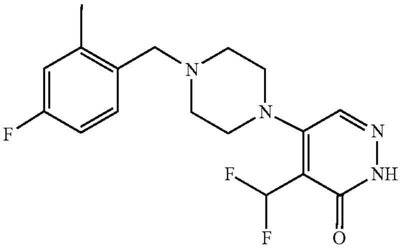
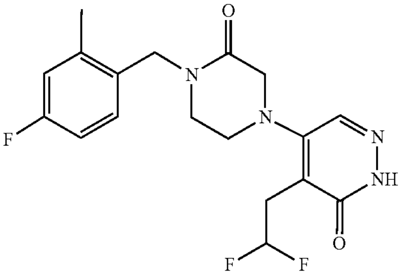
and
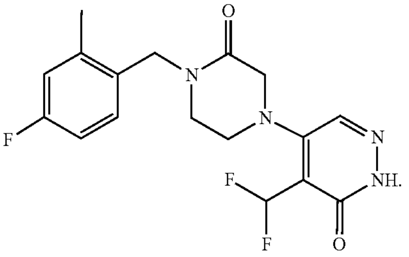
In some embodiments, the compound is selected from the group consisting of:
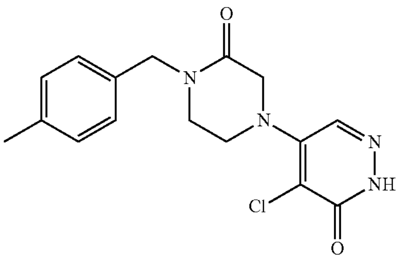
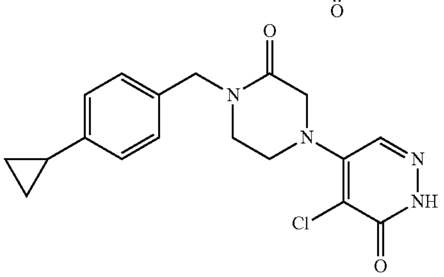

-continued
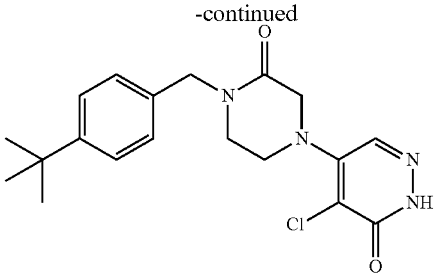
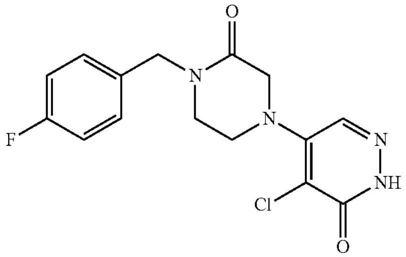
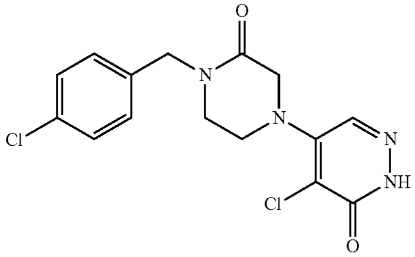
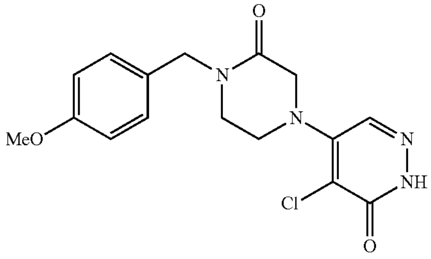
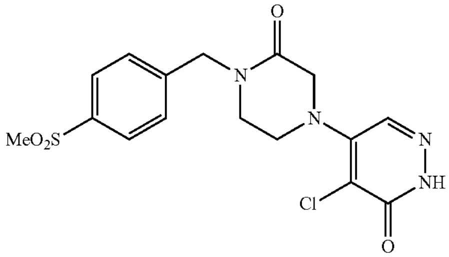
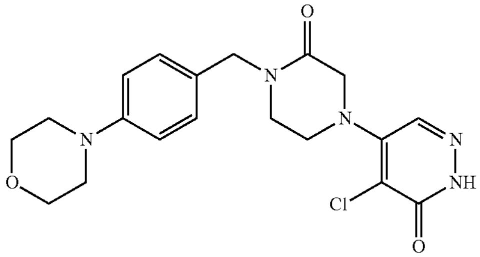
-continued
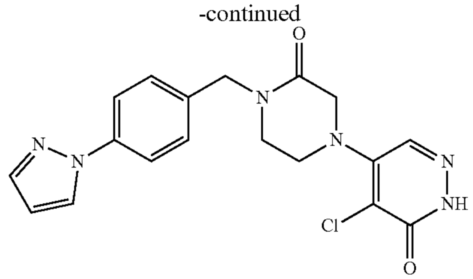
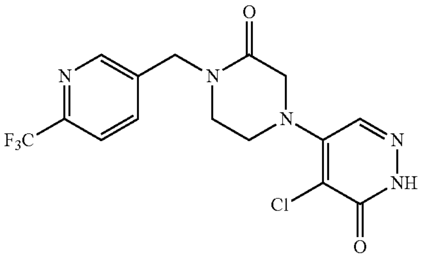
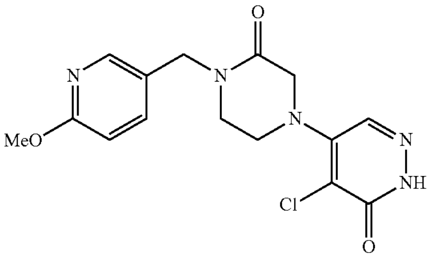
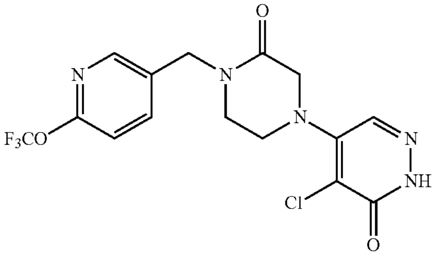
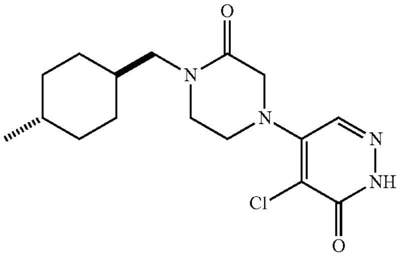
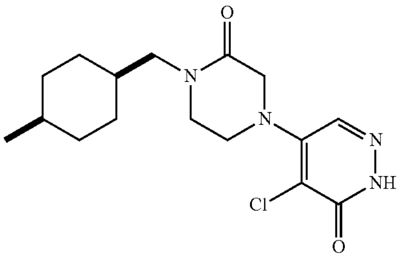
and -continued
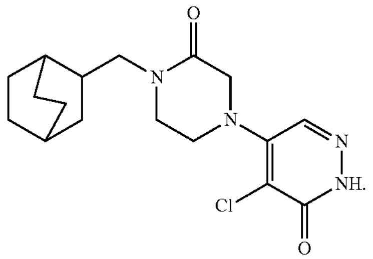
In some embodiments, the compound is selected from the group consisting of:
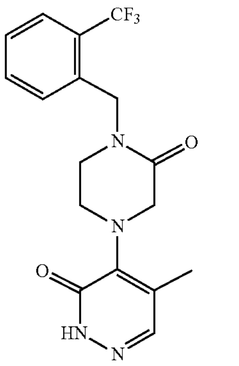
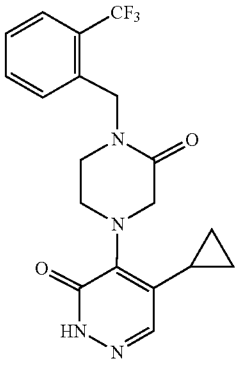
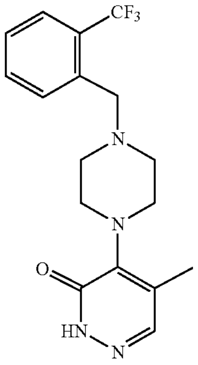
and
-continued
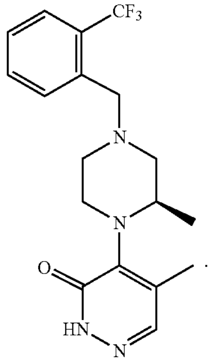
In some embodiments, the compound is selected from the group consisting of:
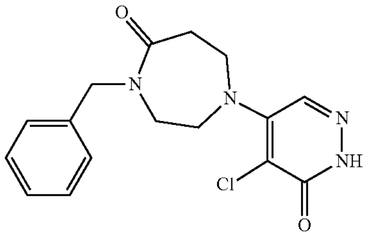
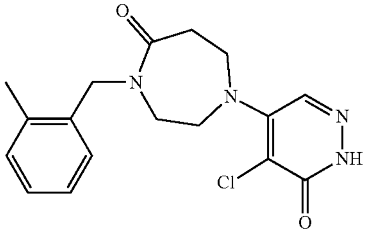
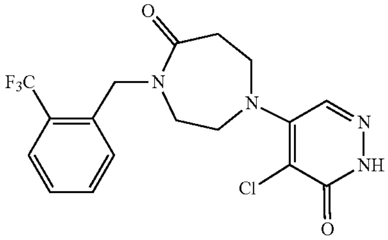
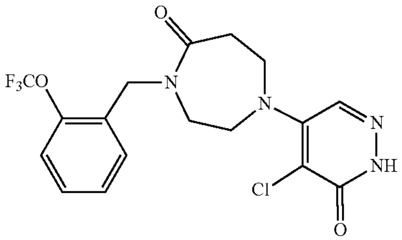
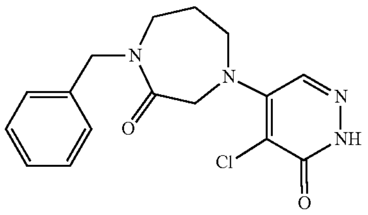

-continued
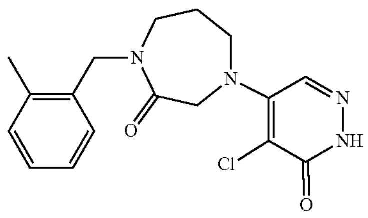
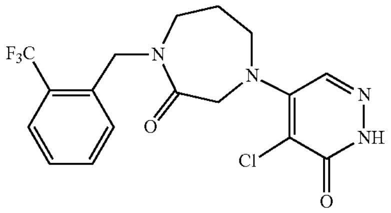
and
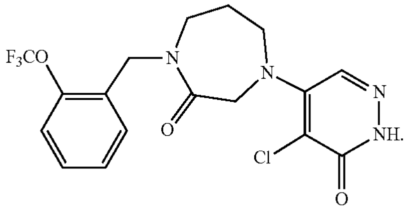
In some embodiments, the compound is selected from the group consisting of:
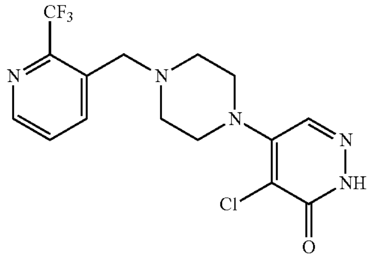
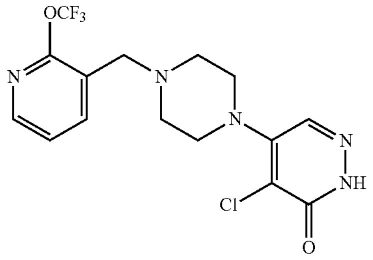
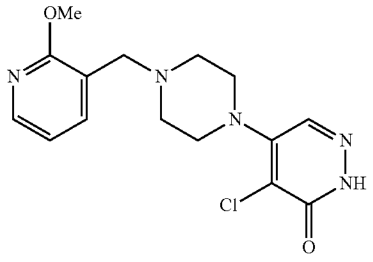
-continued
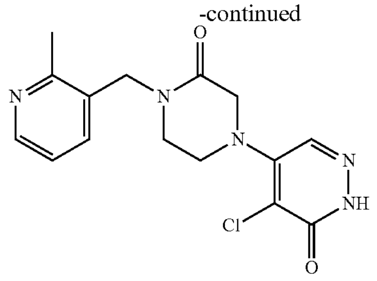
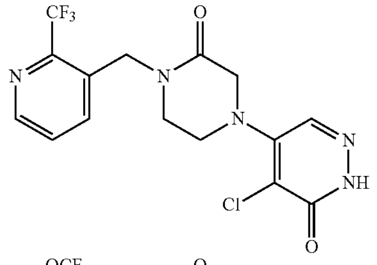
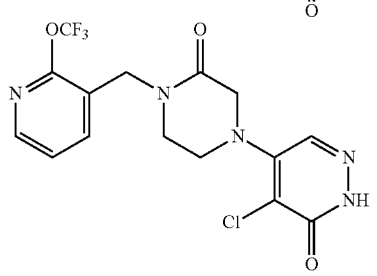
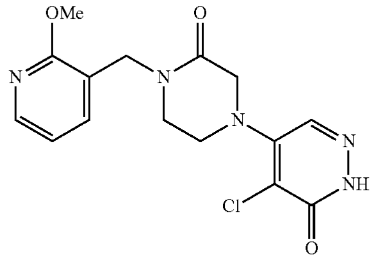
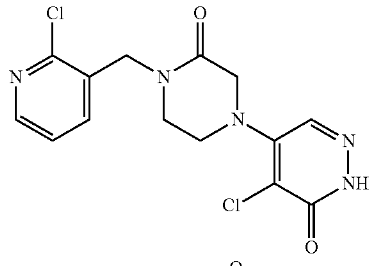
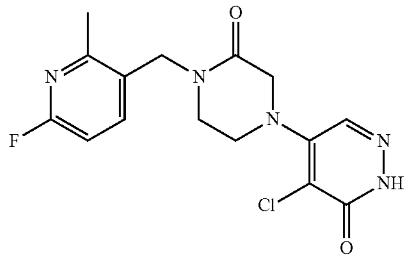

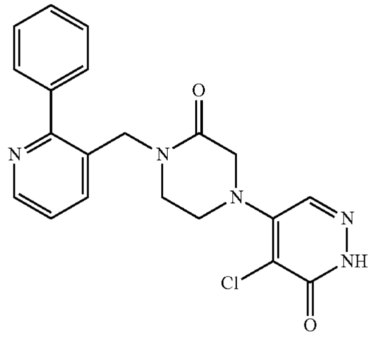
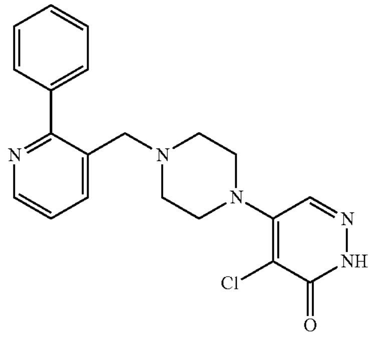
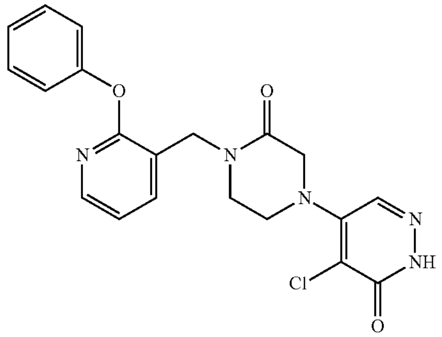
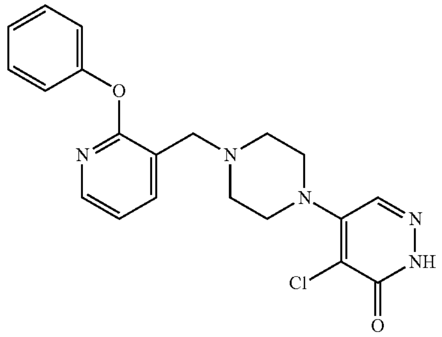
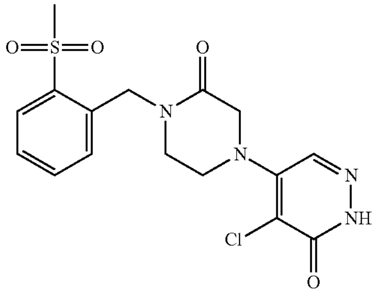
and
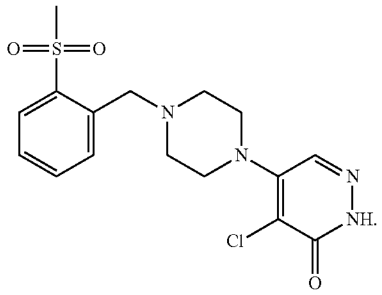
In some embodiments, the compound is selected from the group consisting of:
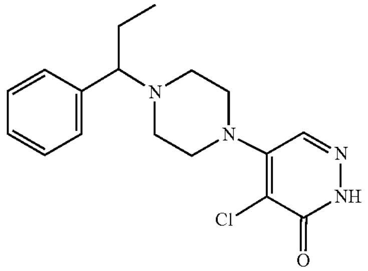
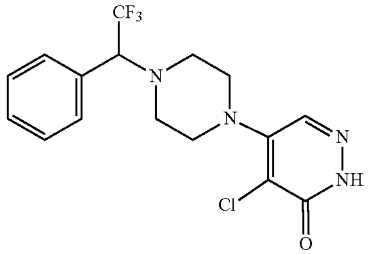
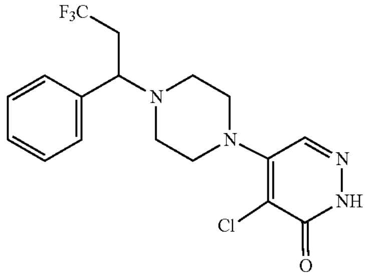
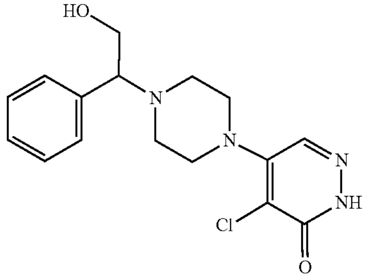

-continued
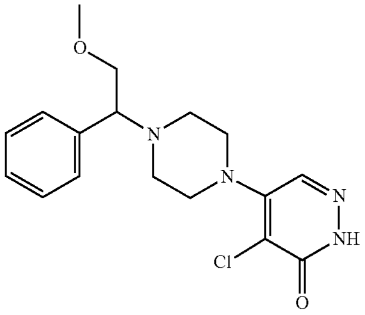
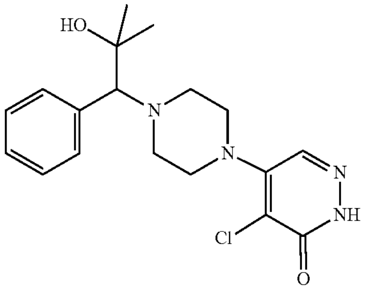
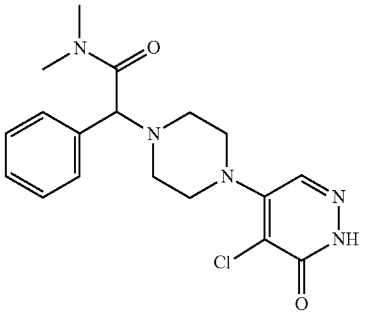
and
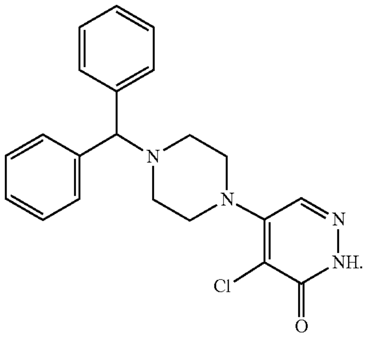
In some embodiments, the compound is selected from the group consisting of:
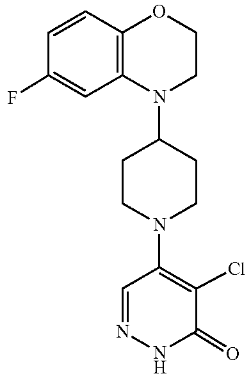
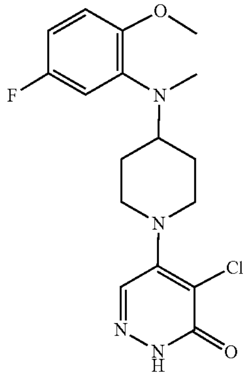
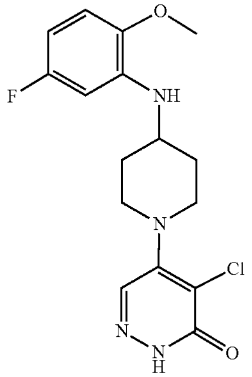
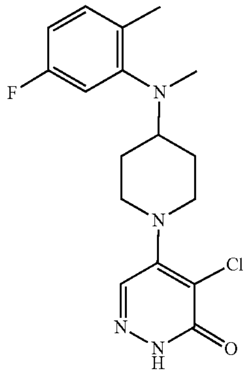

-continued
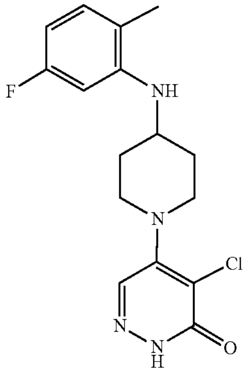
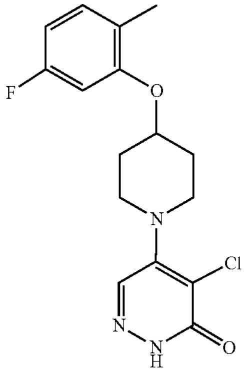
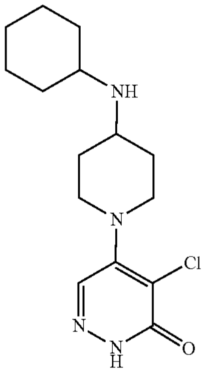
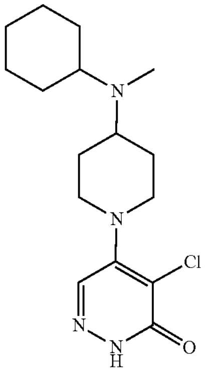
and
-continued
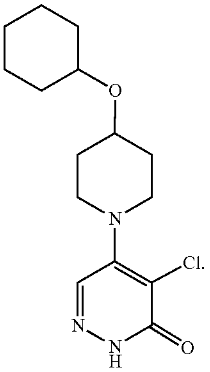 [SMILES: O=c1[nH]ncc(N2CCC(OC3CCCCC3)CC2)c1Cl]
In some embodiments, the compound is selected from the group consisting of:
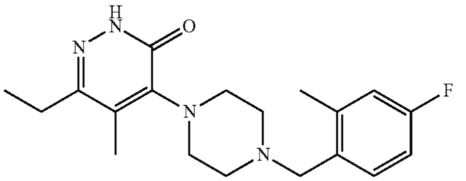
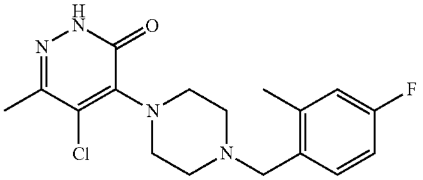
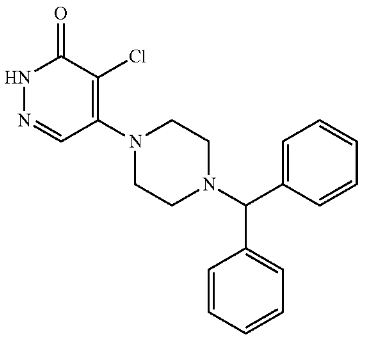
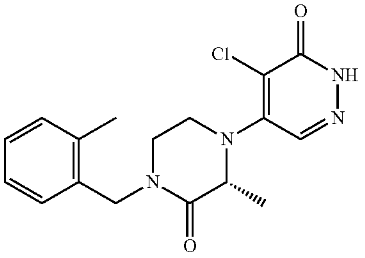
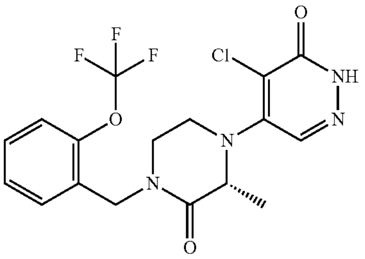

-continued
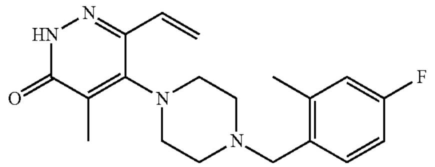
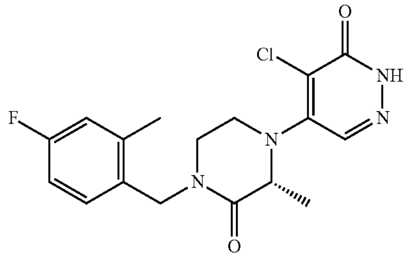
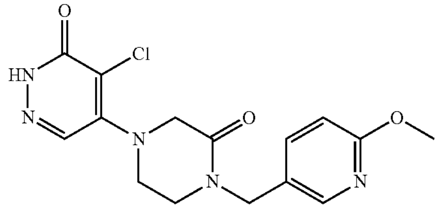
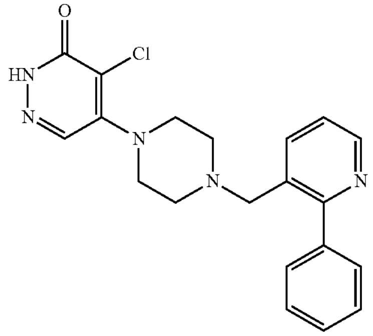
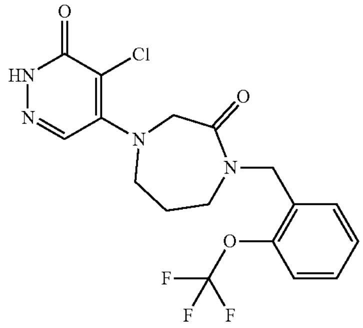
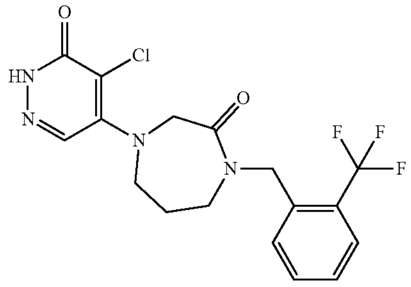
-continued
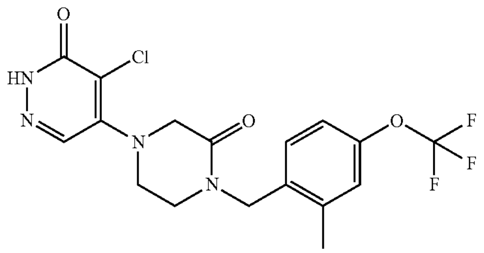
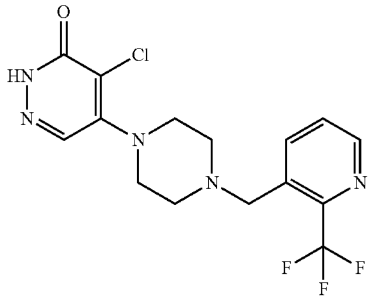
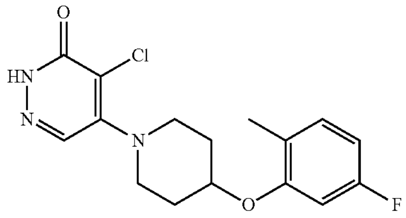
and
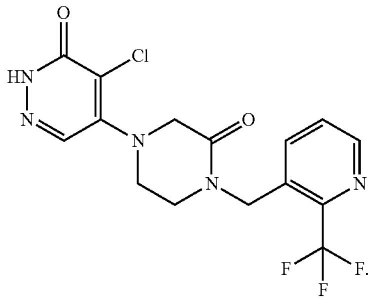
In some embodiments, the compound is selected from the group consisting of:
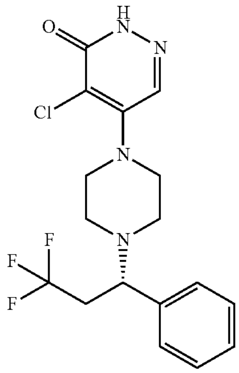
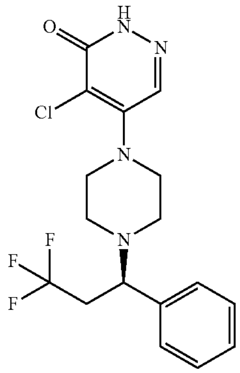

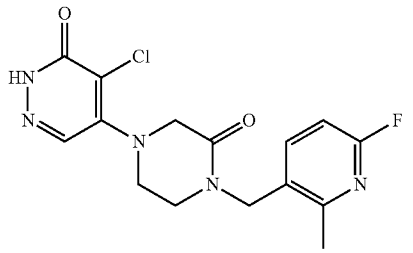
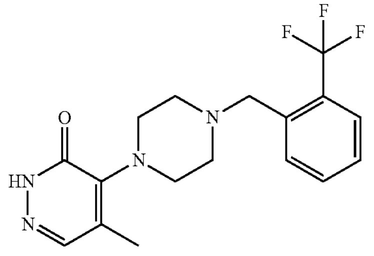
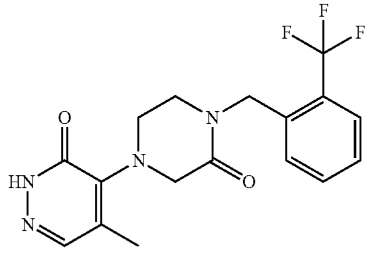
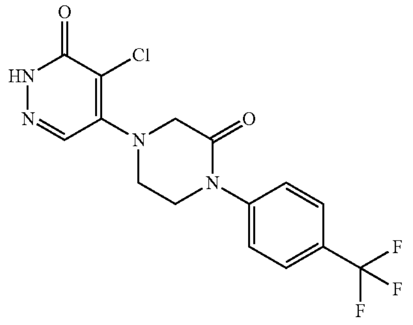
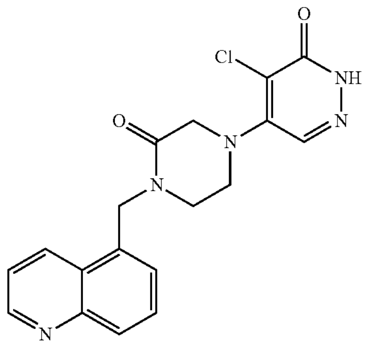
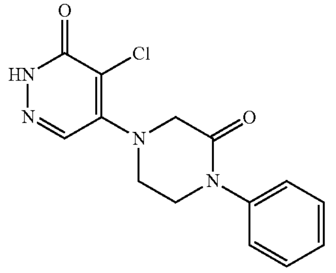
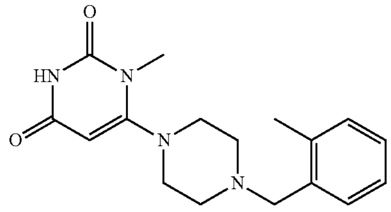
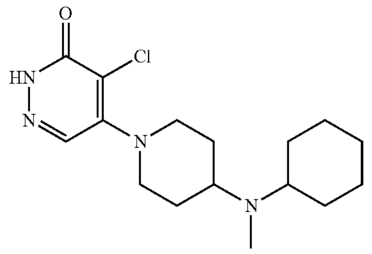
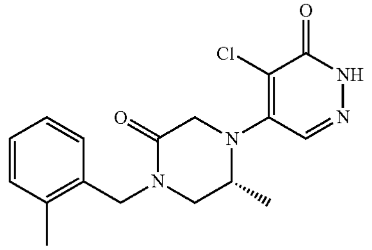
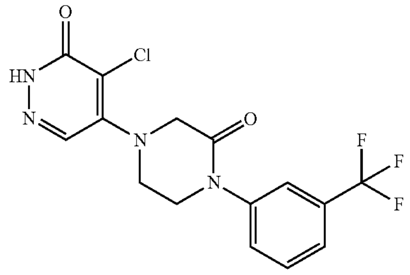
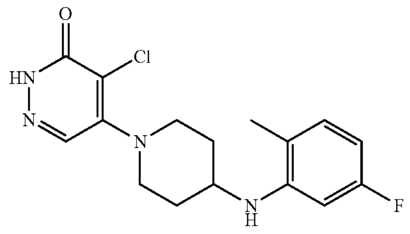
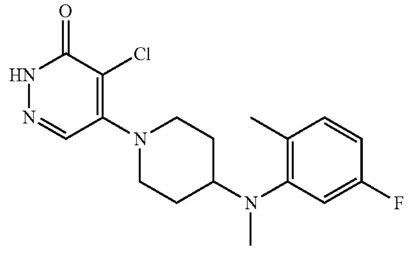
and -continued
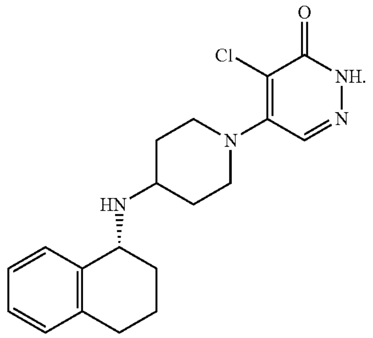
In some embodiments, the compound is selected from the group consisting of:
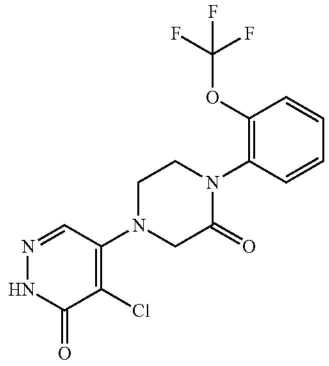
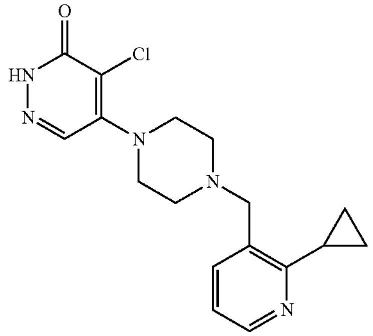
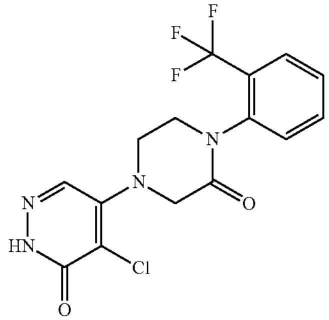
-continued
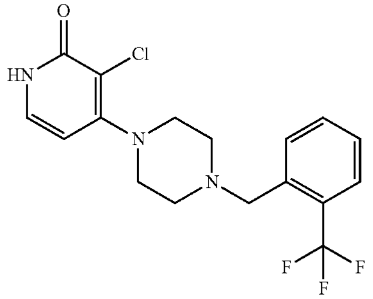
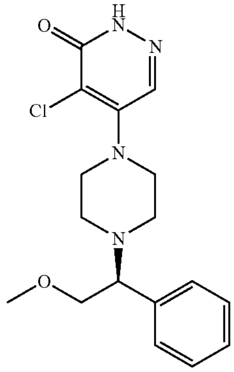
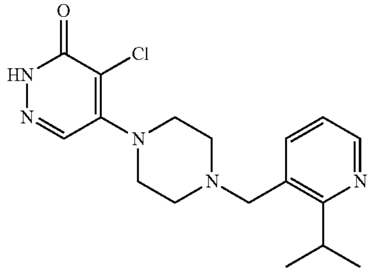
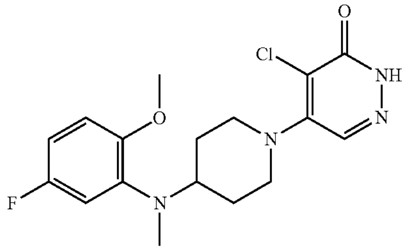
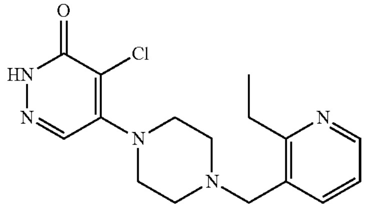
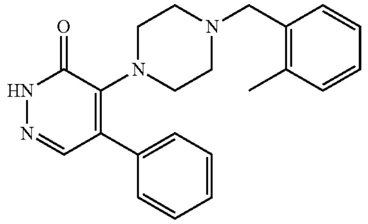

-continued
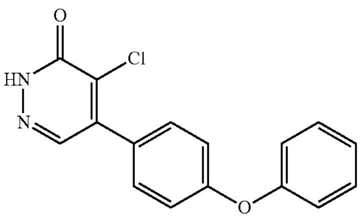
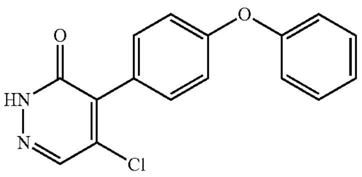
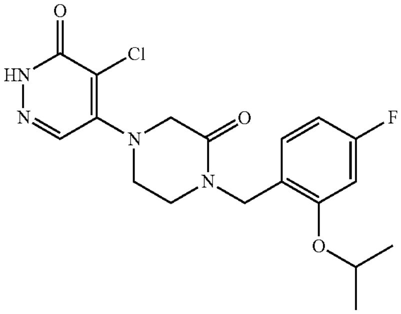
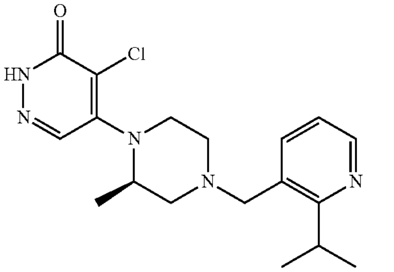
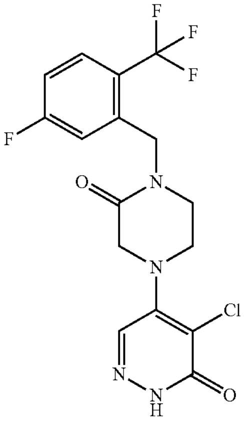
and
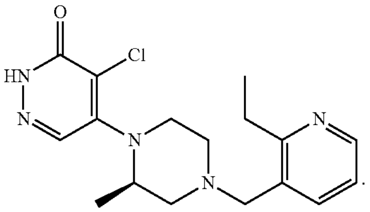
In some embodiments, the compound is selected from the group consisting of:
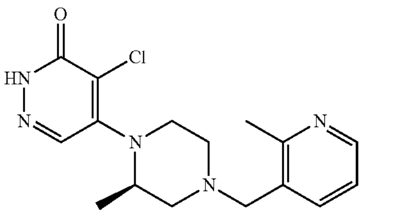
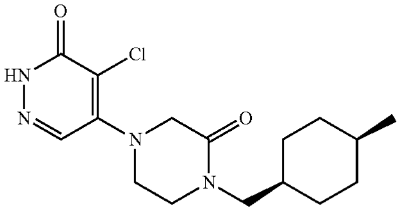
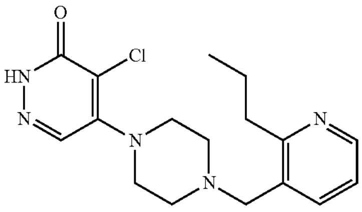
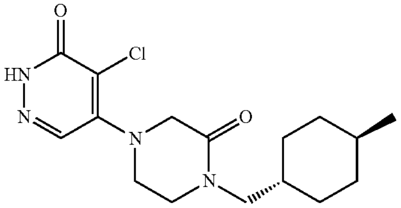
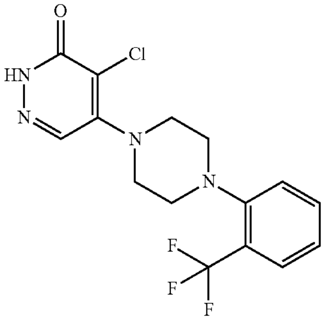
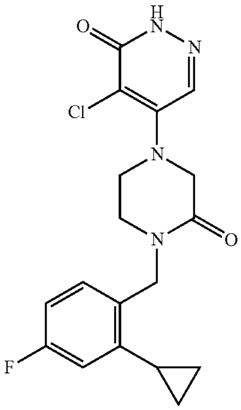

-continued
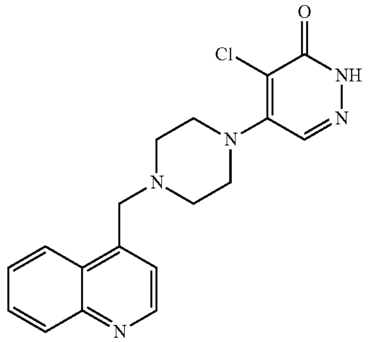
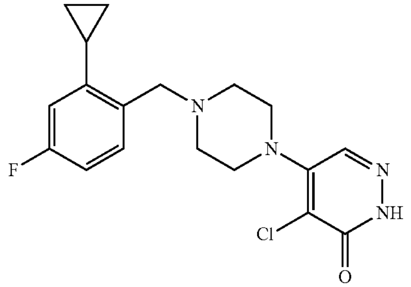
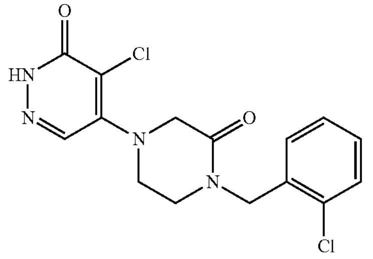
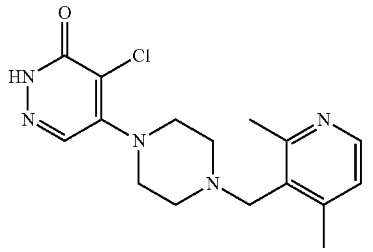
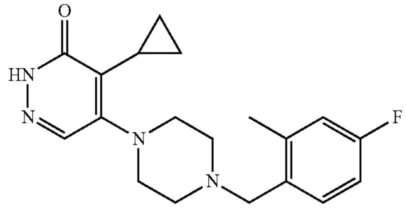
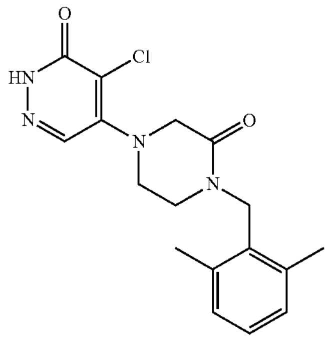
-continued
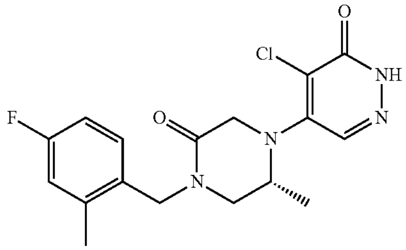
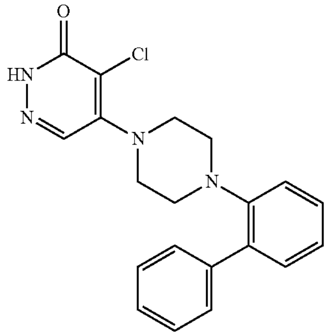
and
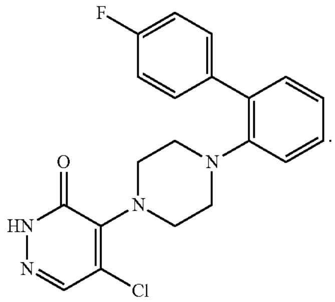
.
In some embodiments, the compound is selected from the group consisting of:
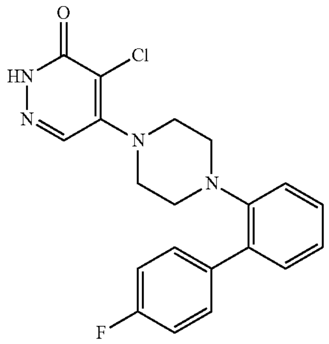
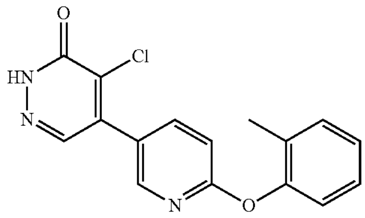

-continued
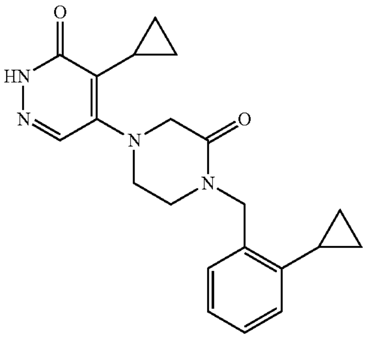
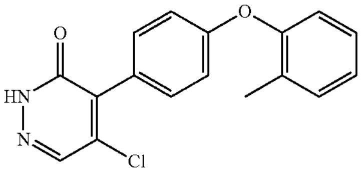
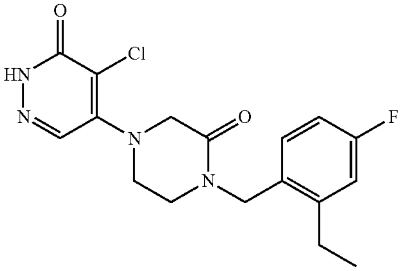
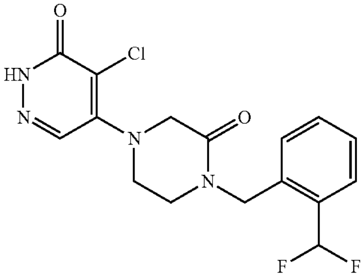
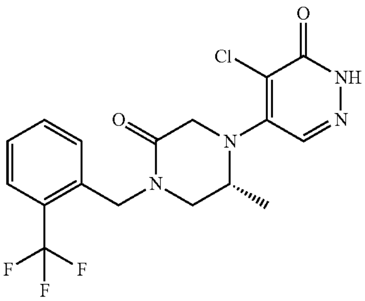
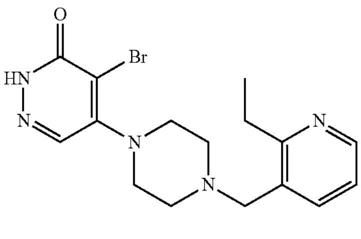
-continued
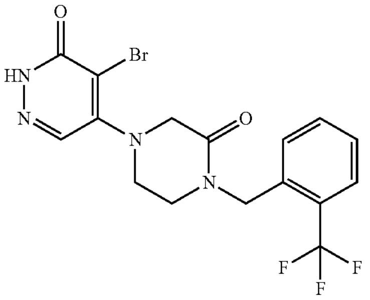
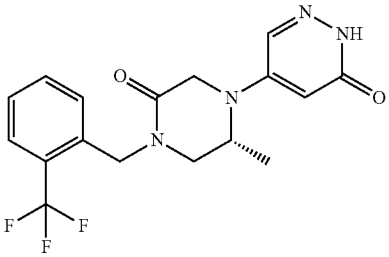
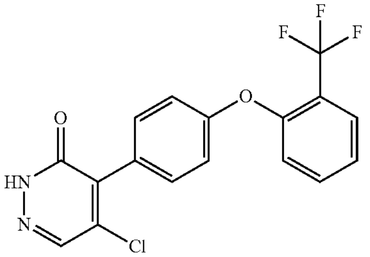
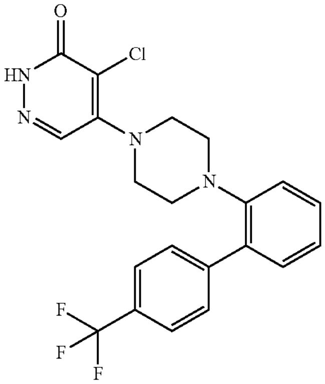
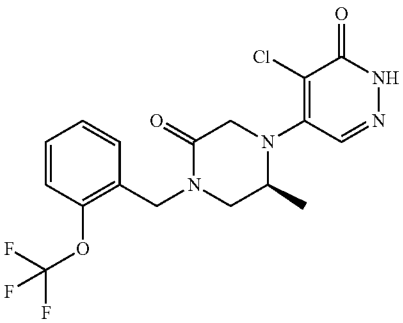

-continued
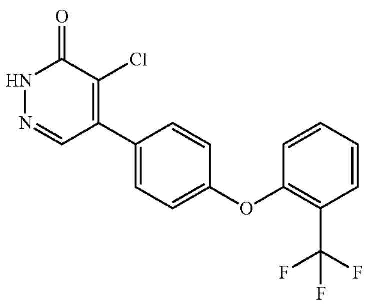
and
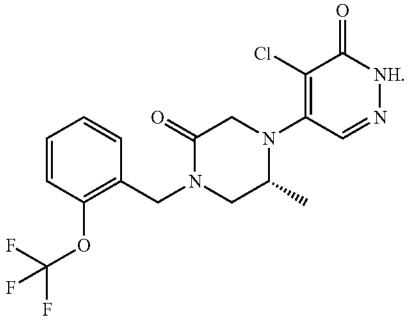
In some embodiments, the compound is selected from the group consisting of:
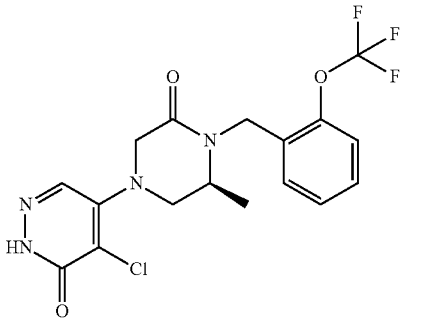
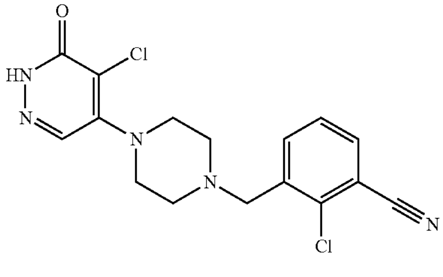
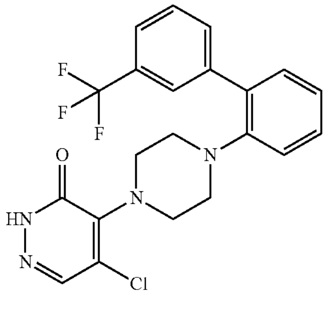
-continued
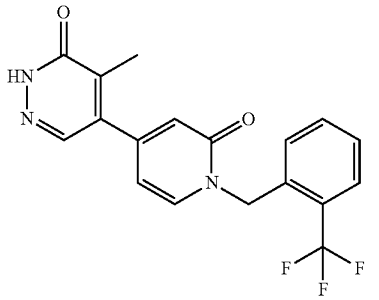
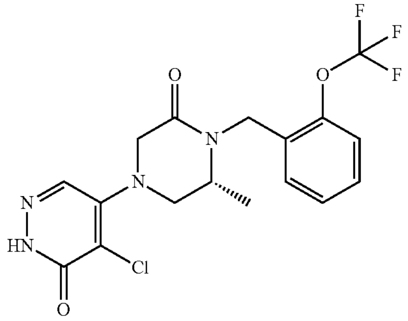
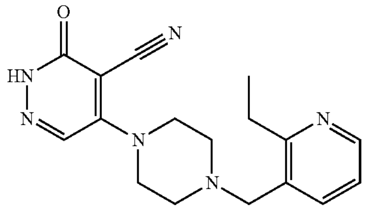
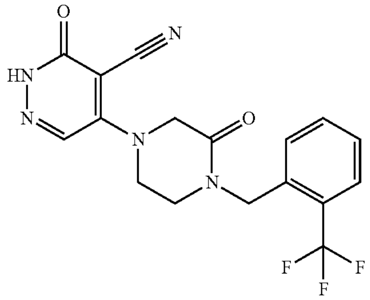
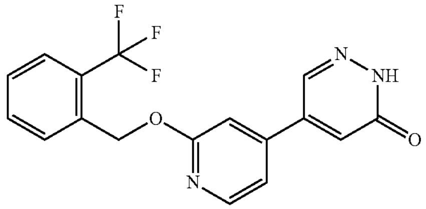
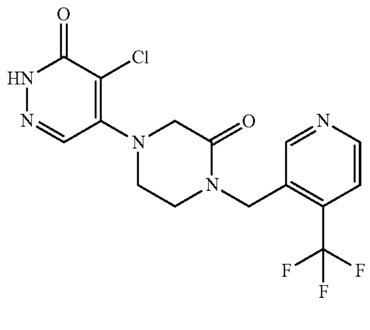

-continued
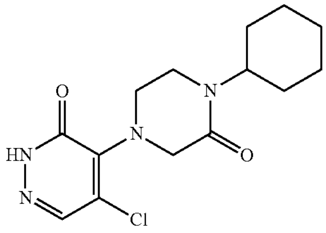
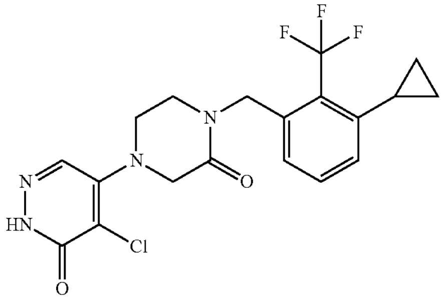
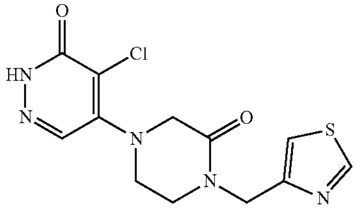
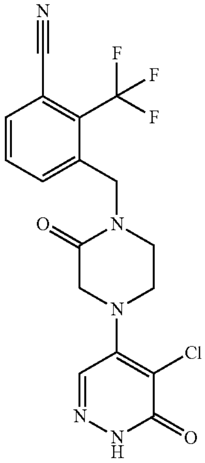
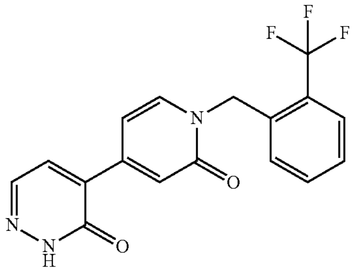
and
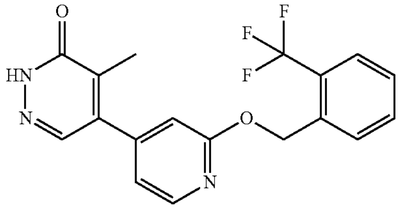
.
In some embodiments, the compound is selected from the group consisting of:
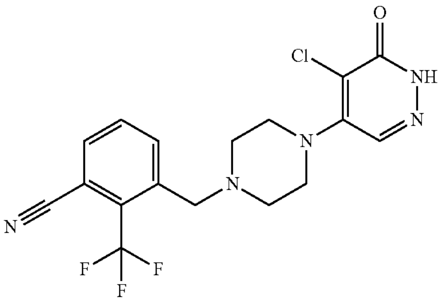
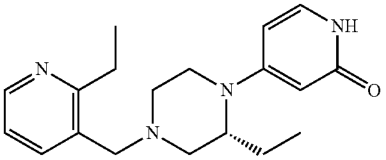
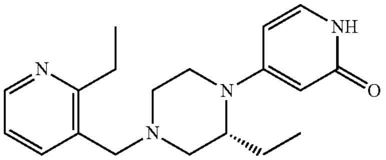
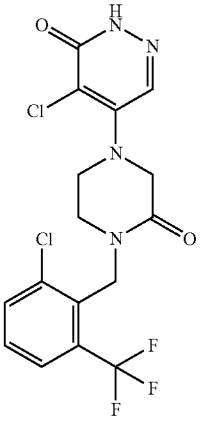
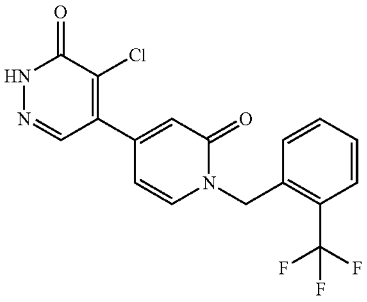
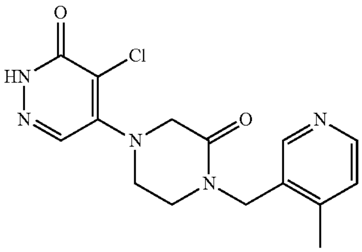

-continued
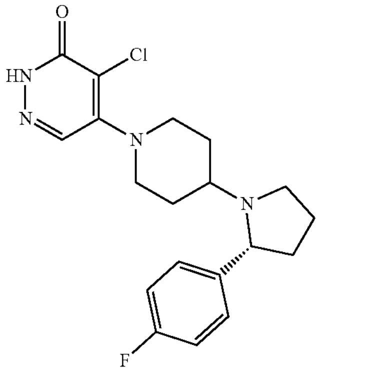
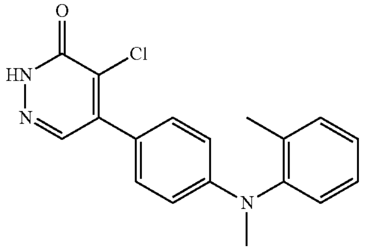
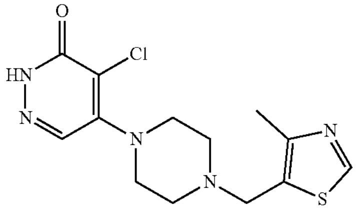
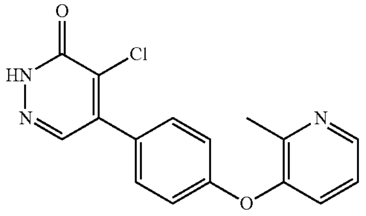
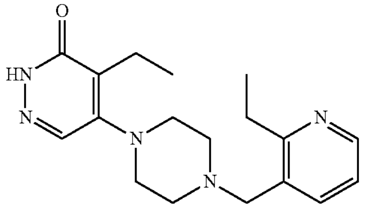
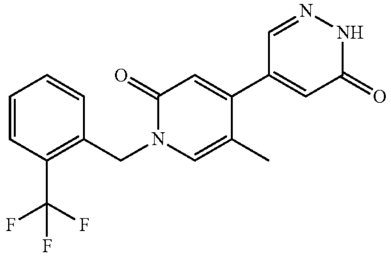
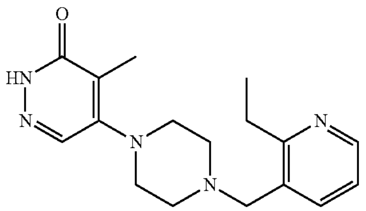
-continued
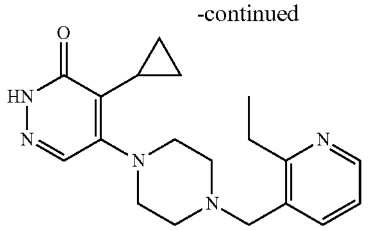
and
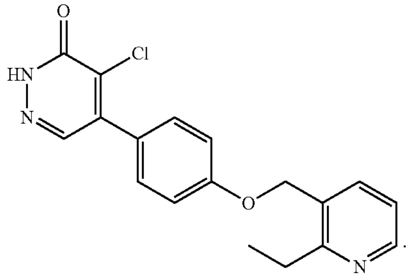
In some embodiments, the compound is selected from the group consisting of:
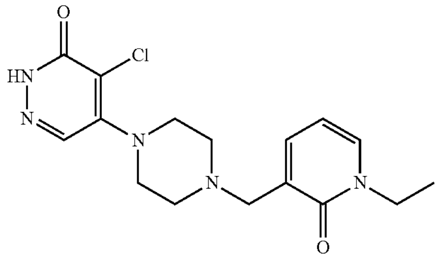
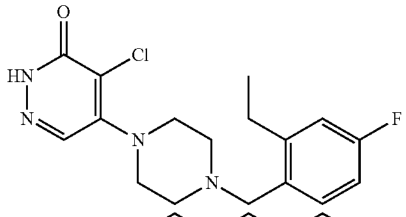
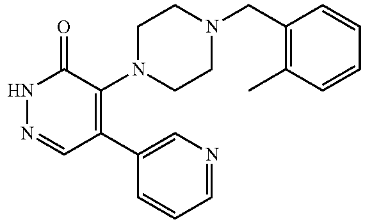
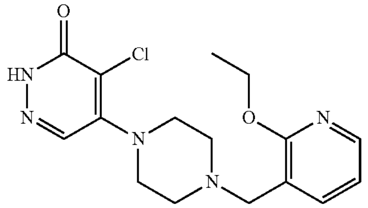
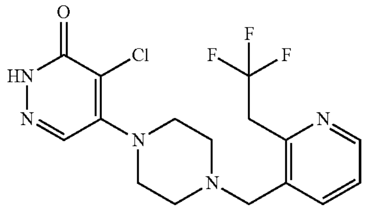

-continued
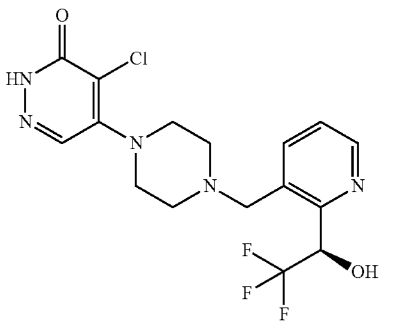
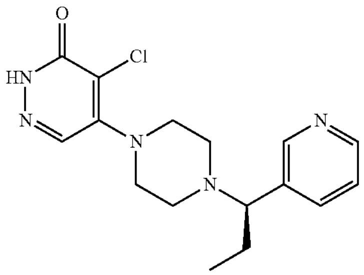
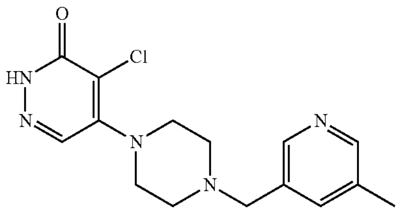
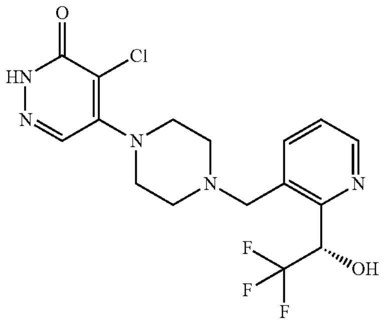
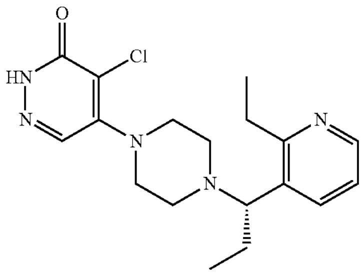
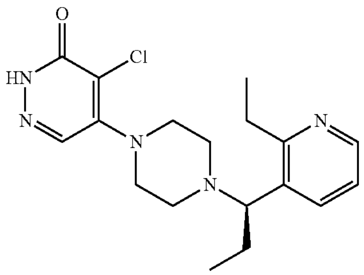
-continued
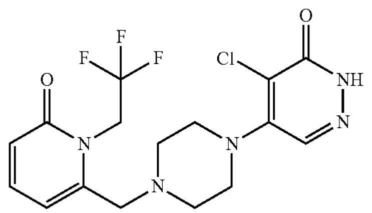
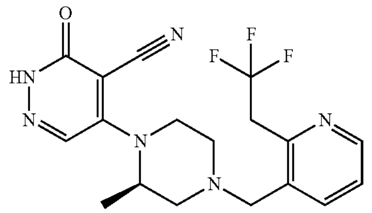
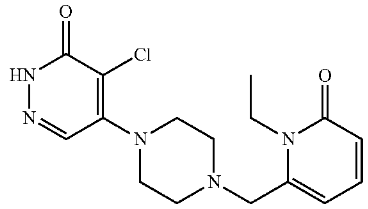
and
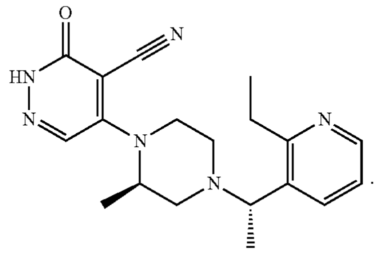
In some embodiments, the compound is selected from the group consisting of:
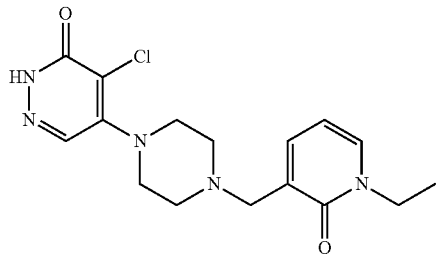
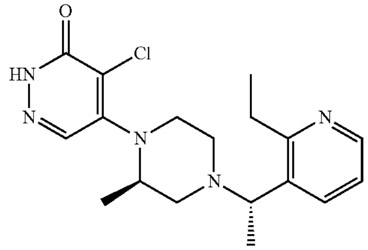

-continued
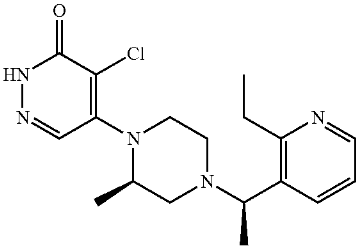
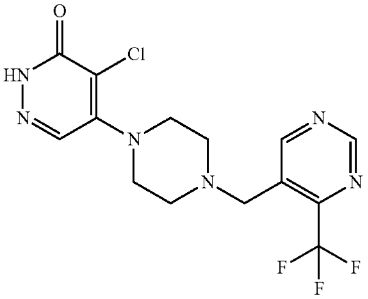
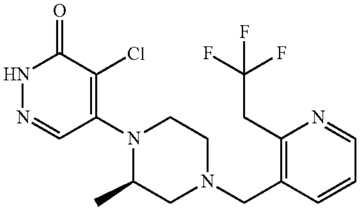
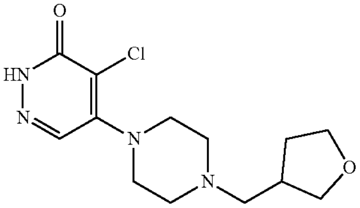
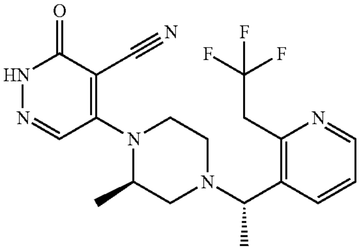
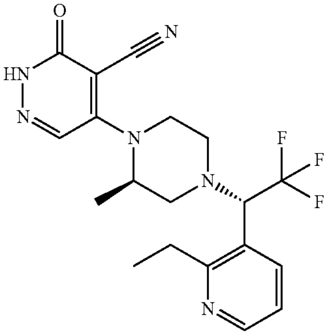
-continued
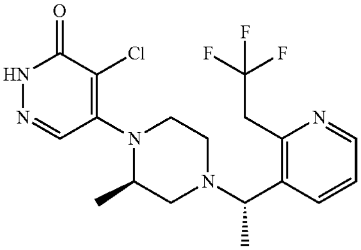
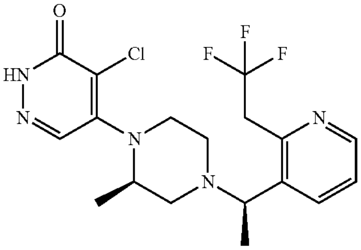
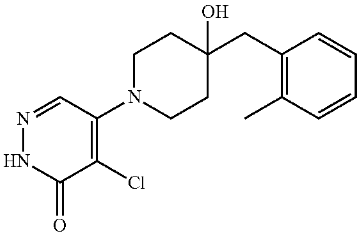
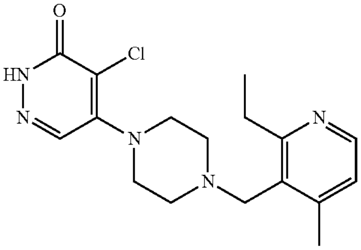
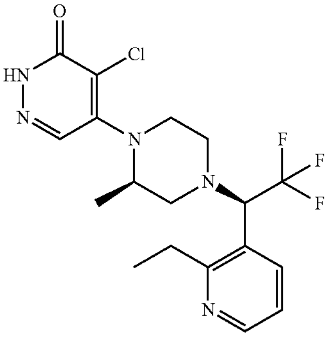
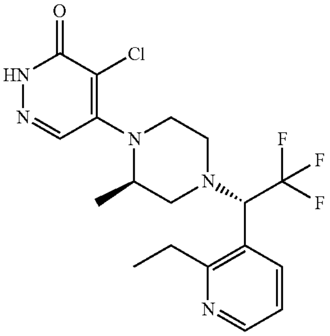
and -continued
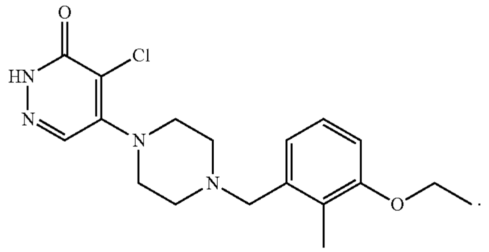
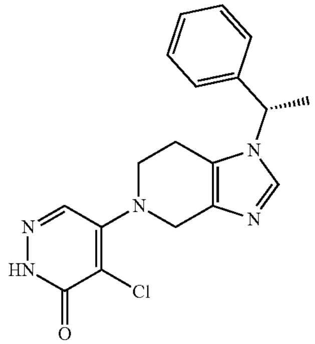
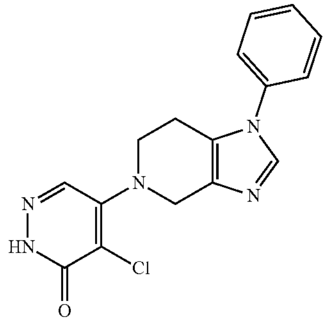
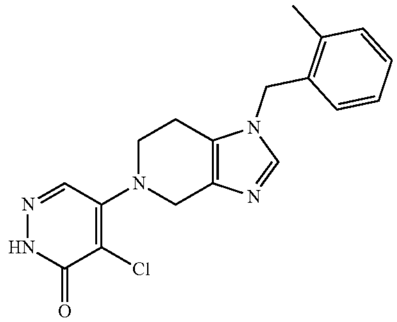
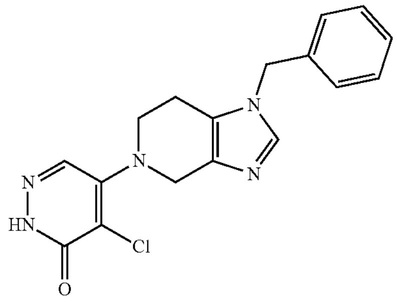
-continued
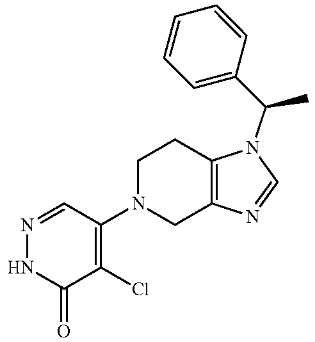
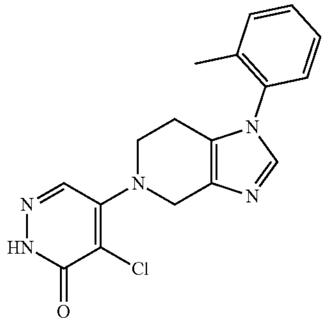
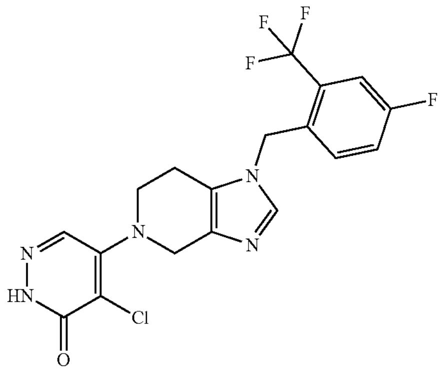
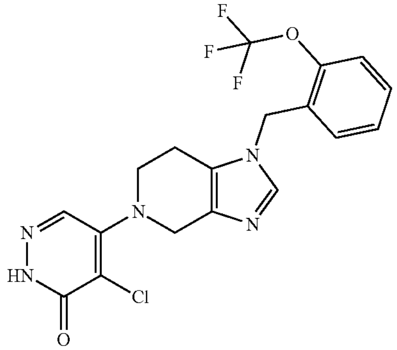
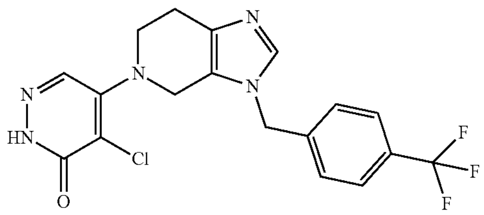

-continued
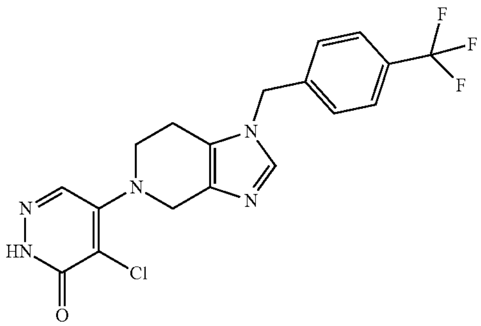
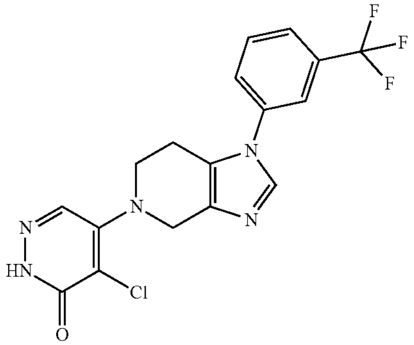
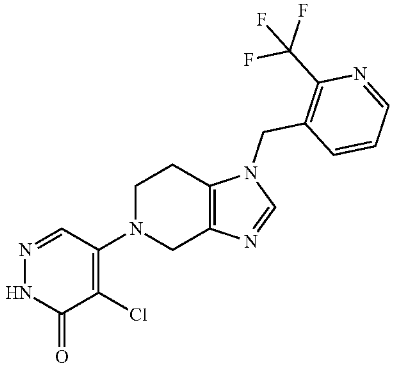
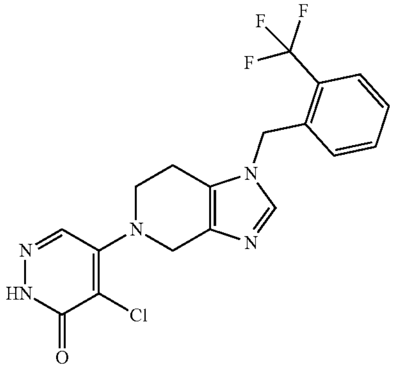
and
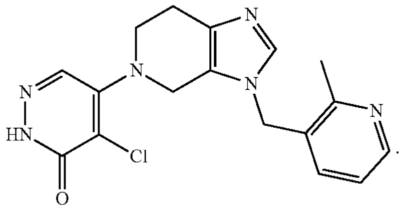
In some embodiments, the compound is selected from the group consisting of:
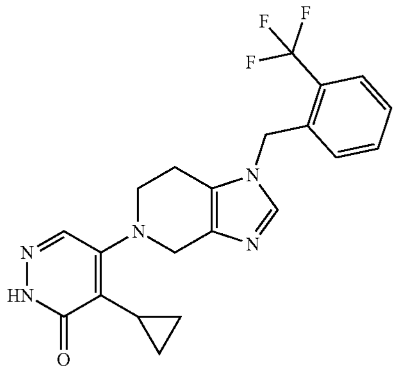
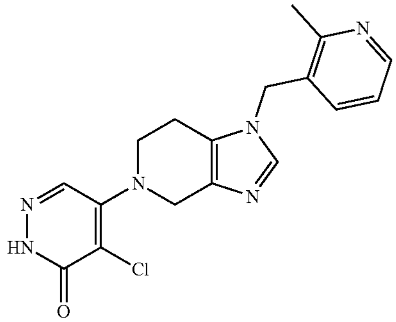
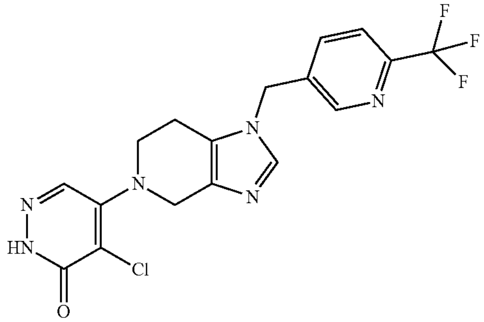
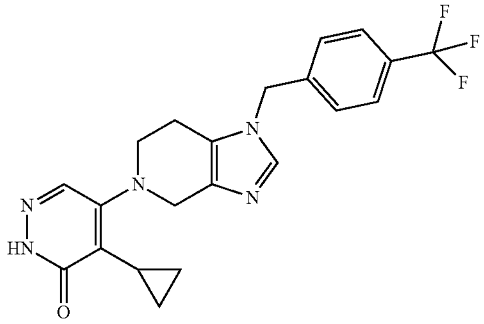
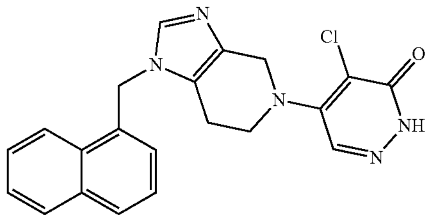

-continued
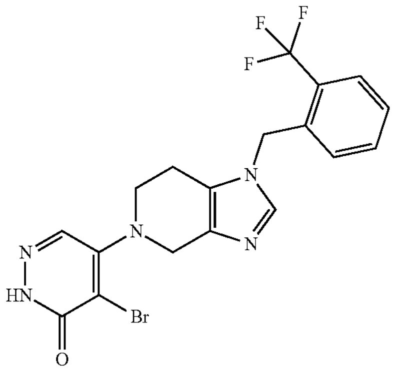
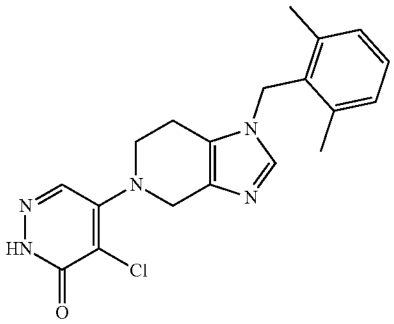
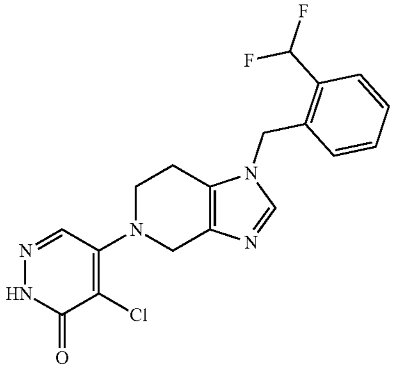
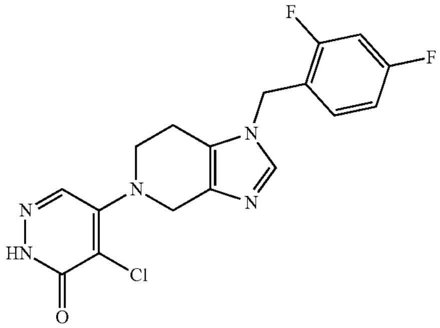
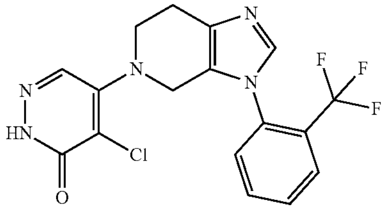
-continued
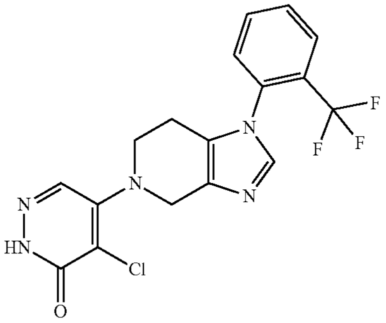
and
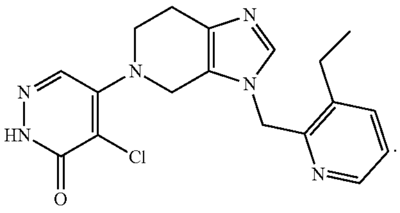
.
In some embodiments, the compound is selected from the group consisting of:
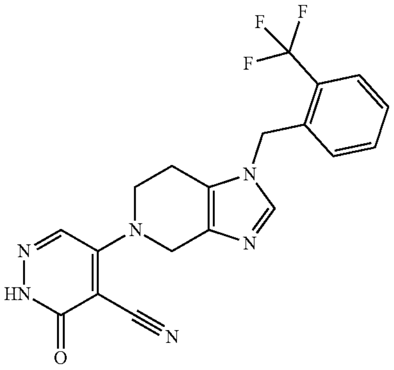
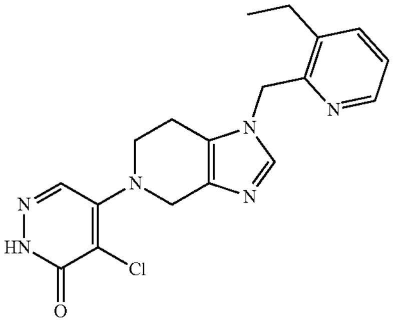
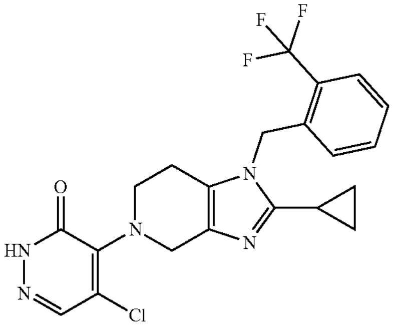

-continued
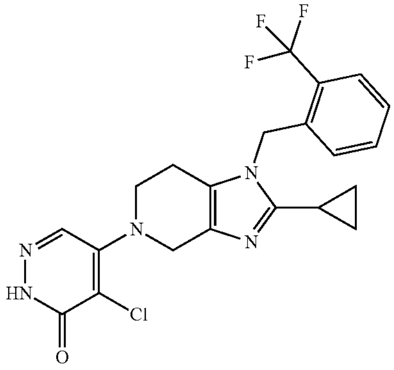
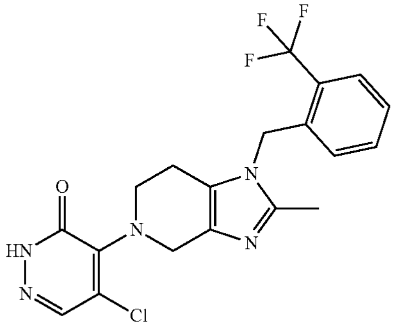
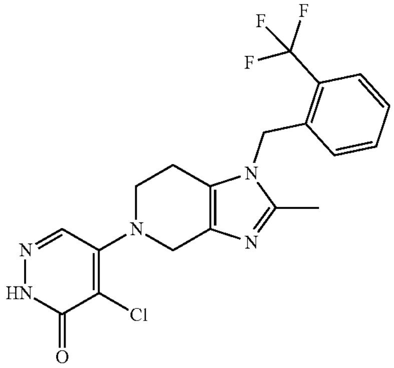
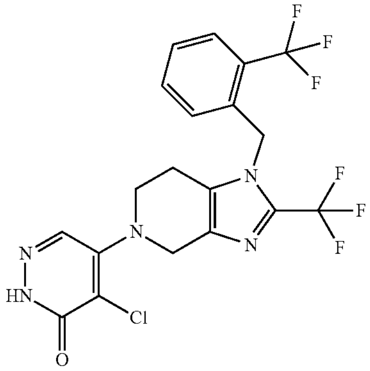
-continued
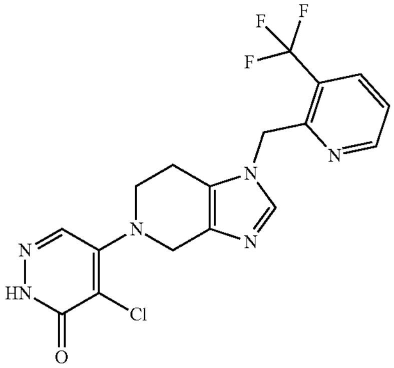
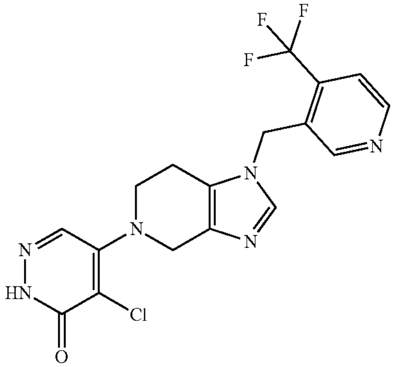
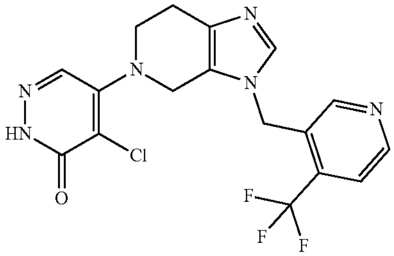
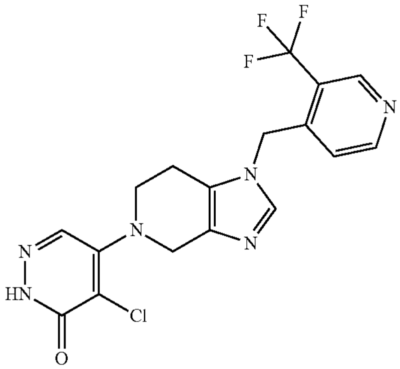
and
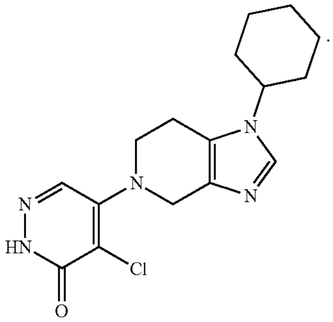

In some embodiments, the compound is selected from the group consisting of:
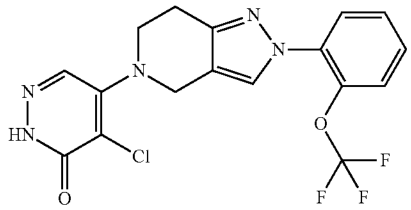
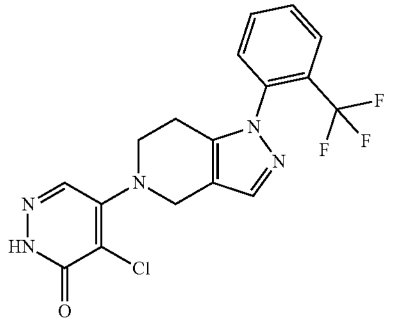
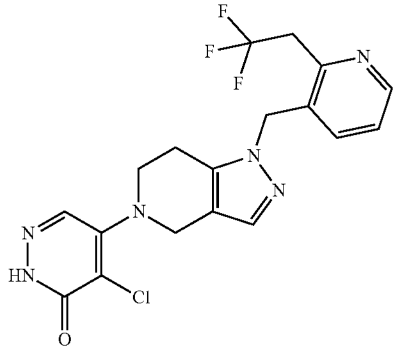
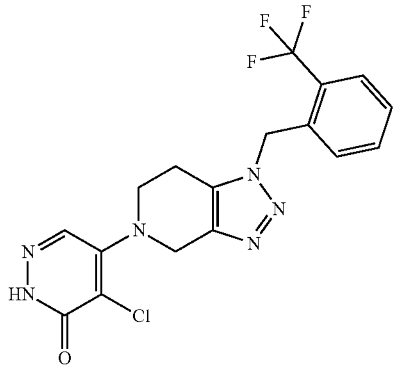
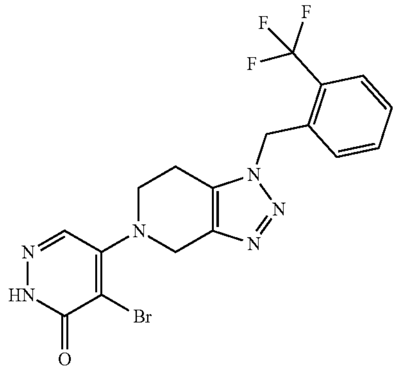
-continued
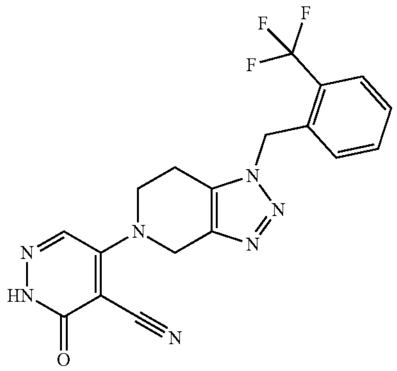
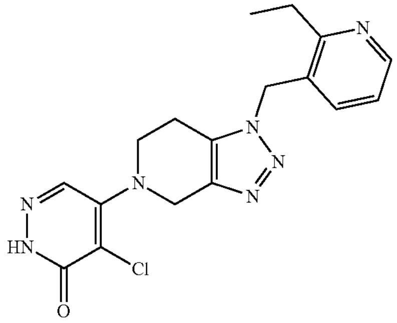
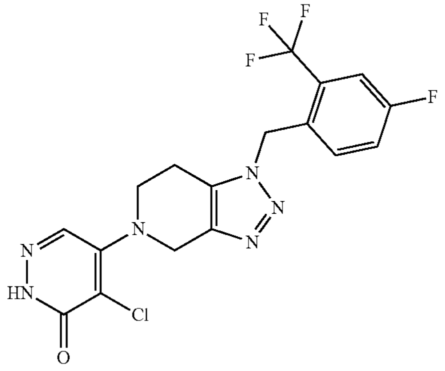
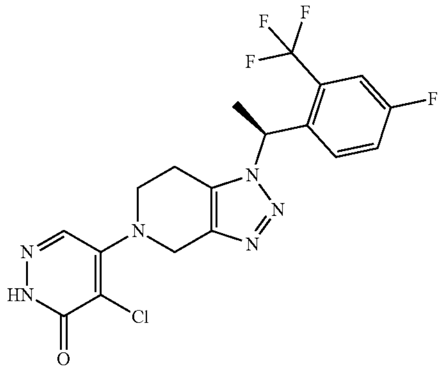

-continued
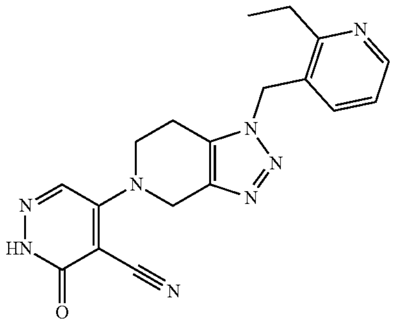
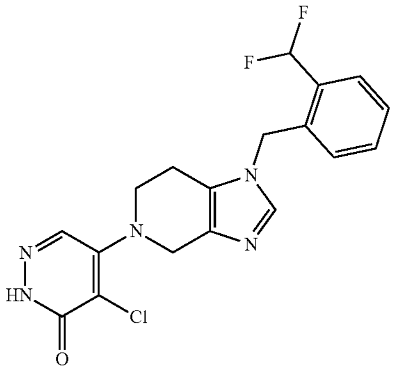
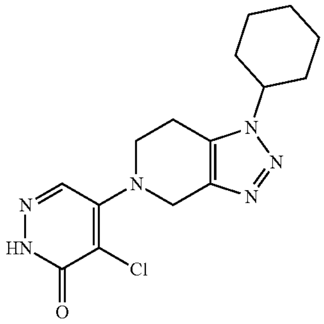
and
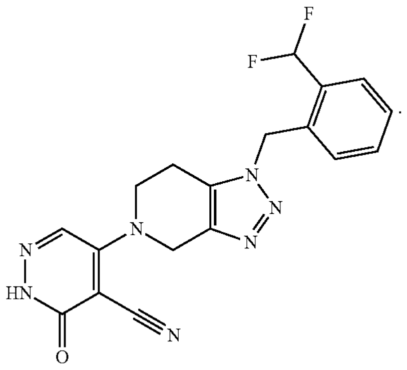
In some embodiments, the compound is selected from the group consisting of:
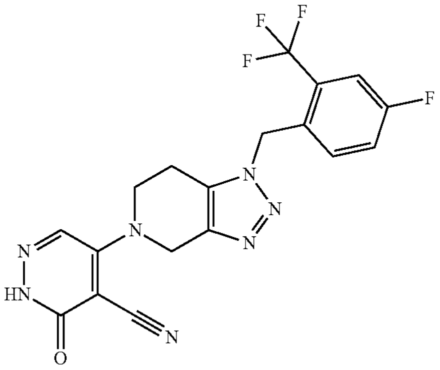
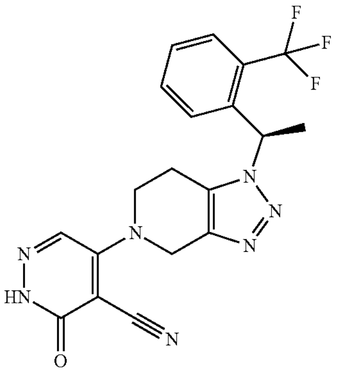
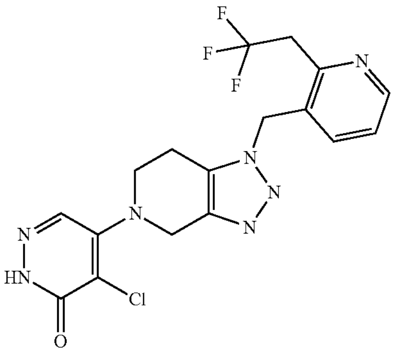
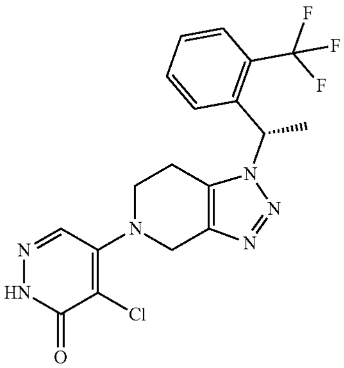

-continued
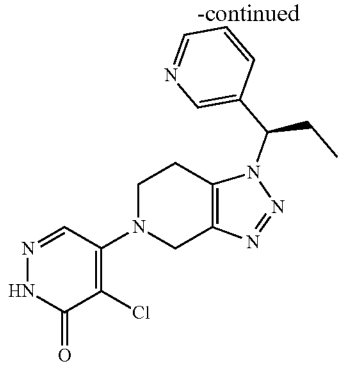
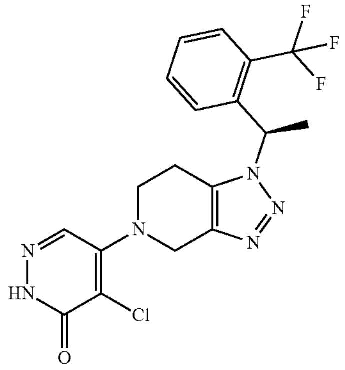
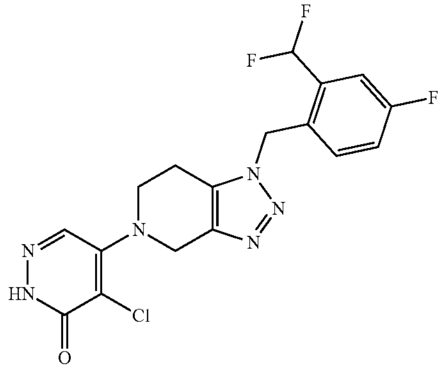
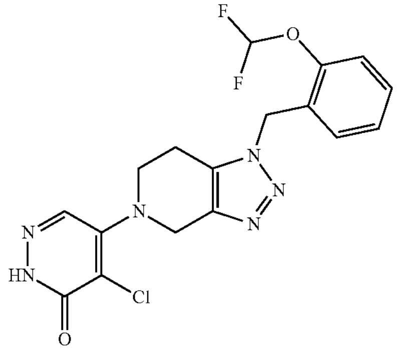
-continued
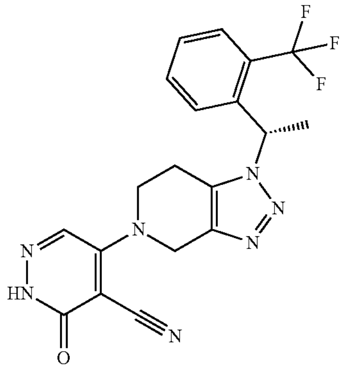
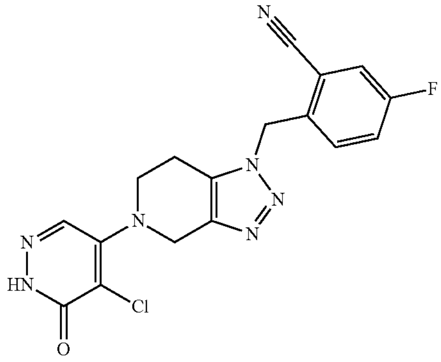
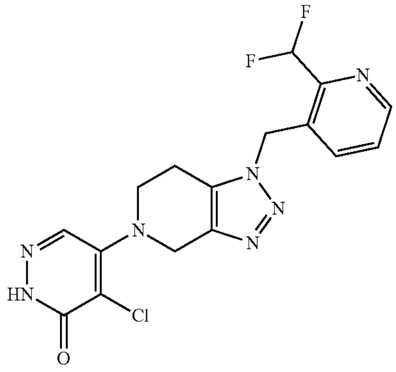
and
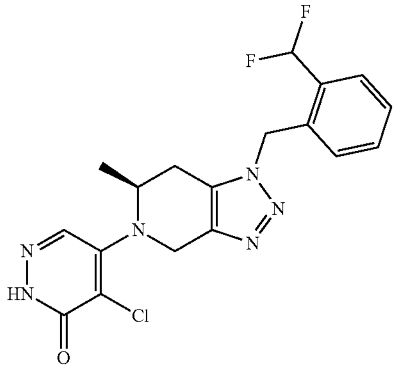
.

In some embodiments, the compound is selected from the group consisting of:
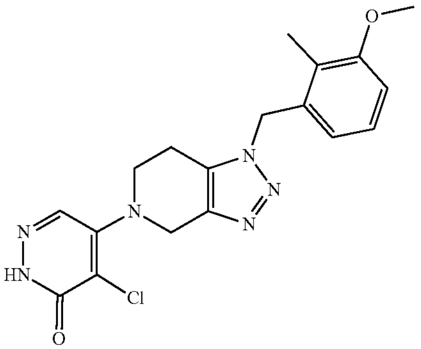
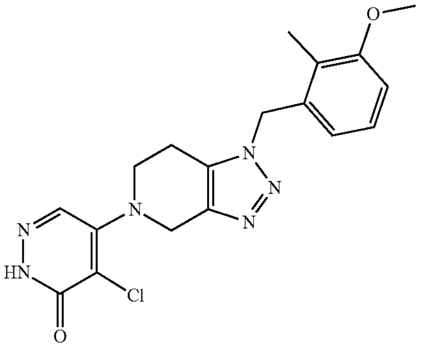
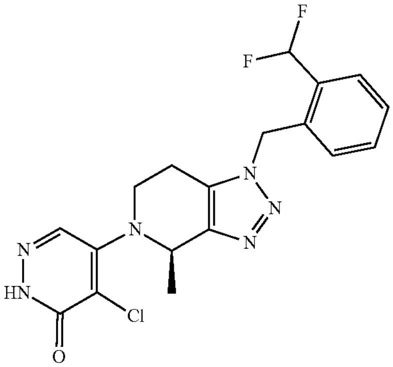
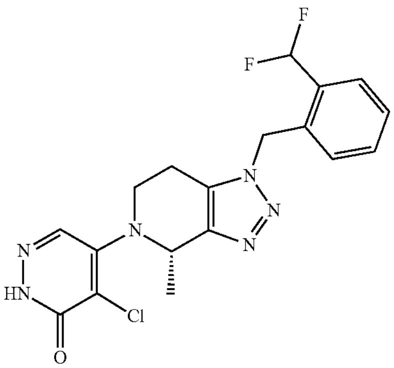
-continued
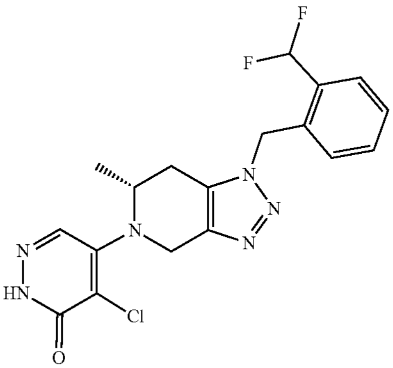
and
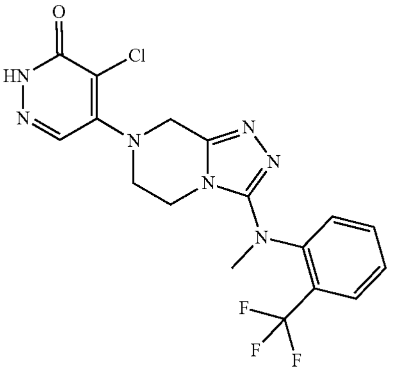
.
In some embodiments, the compound is selected from the group consisting of:
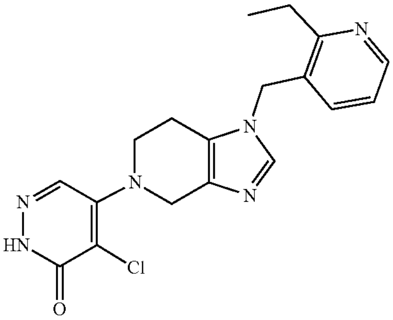
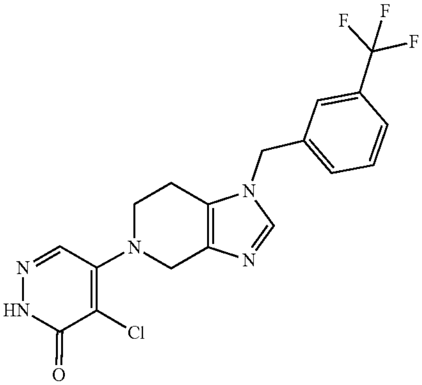

-continued
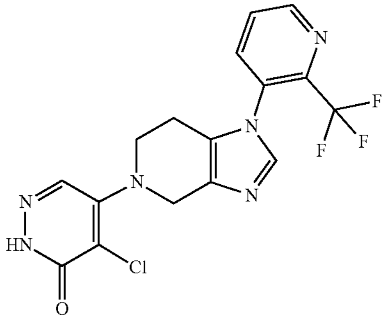
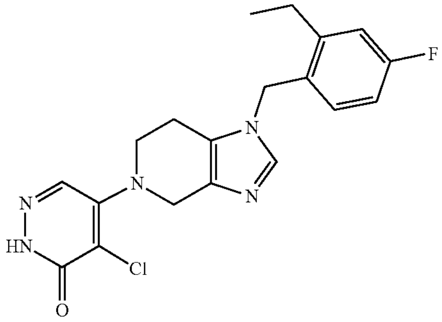
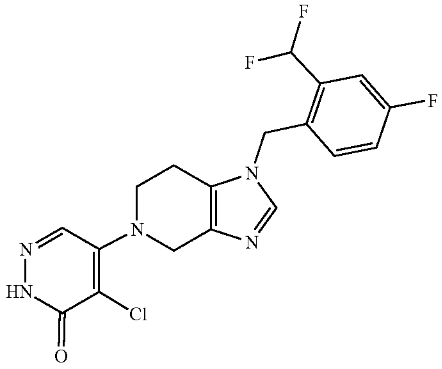
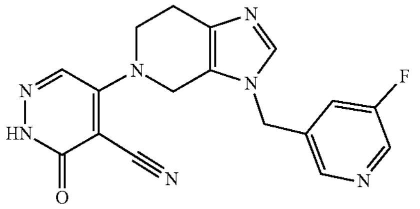
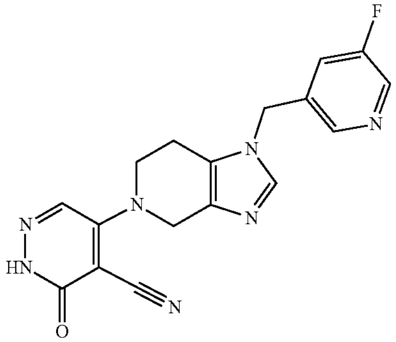
-continued
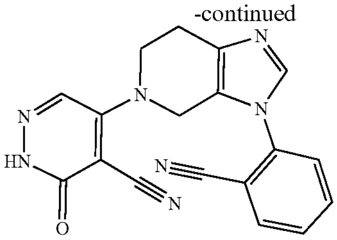
and
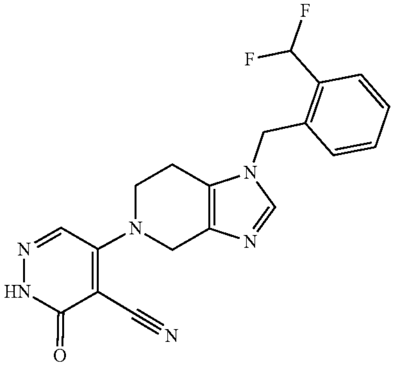
In some embodiments, the compound is selected from the group consisting of:
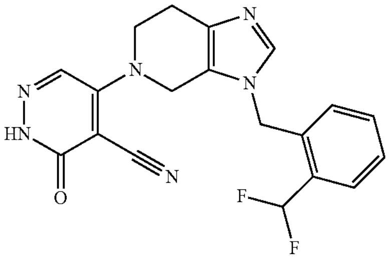
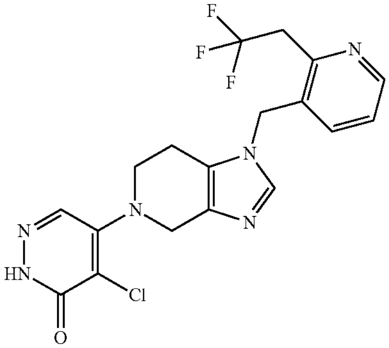
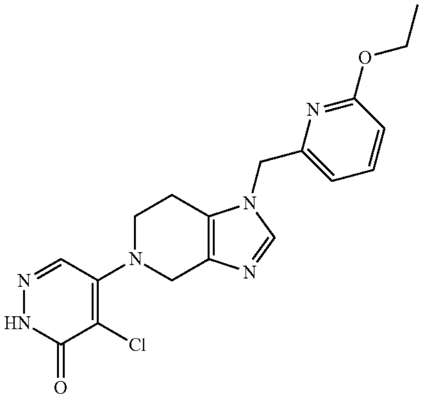

-continued
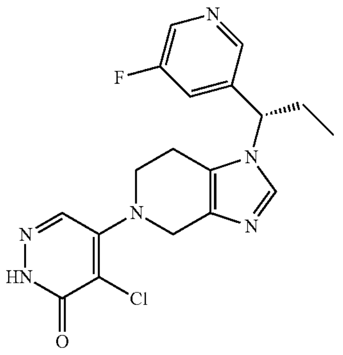
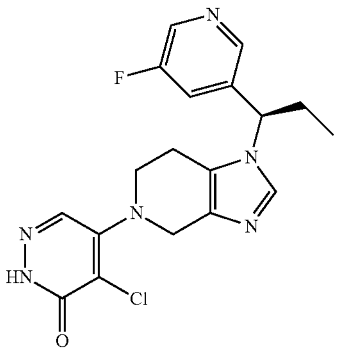
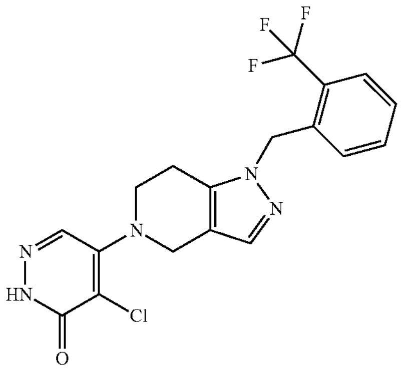
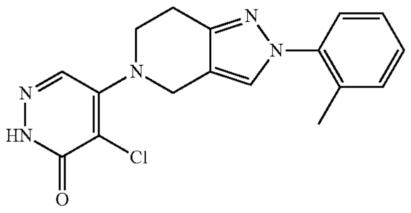
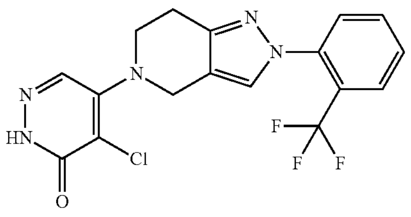
-continued
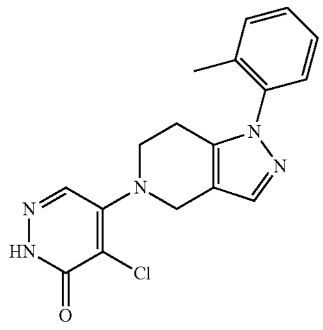
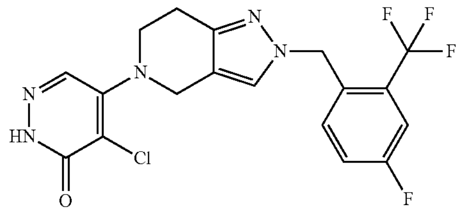
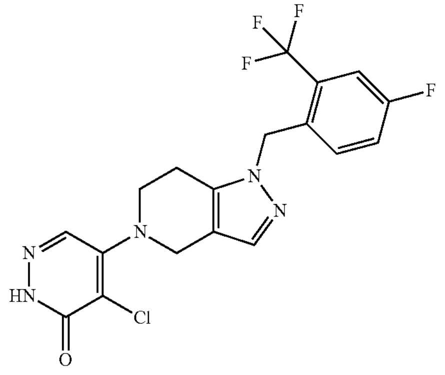
and
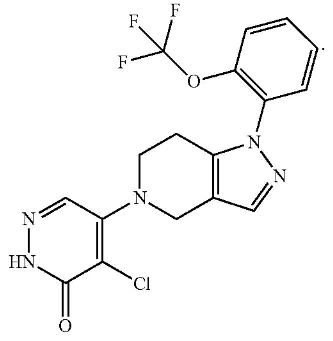
In some embodiments, the compound is selected from the group consisting of:
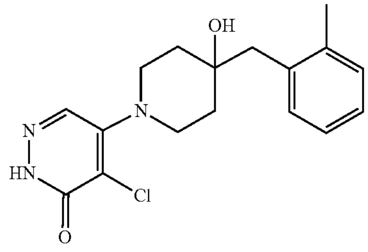
, -continued
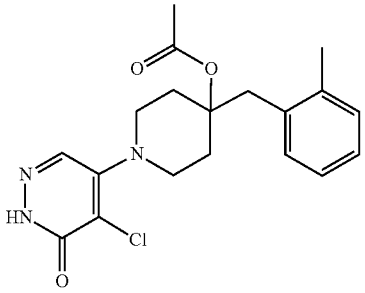
,
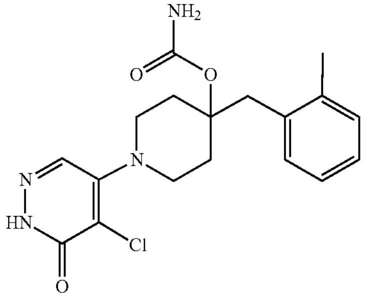
, and
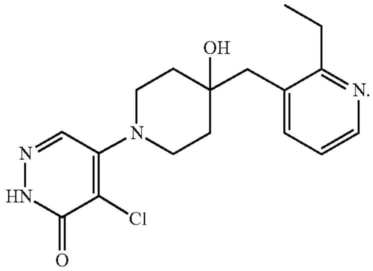
In some embodiments, the compound is selected from the group consisting of:
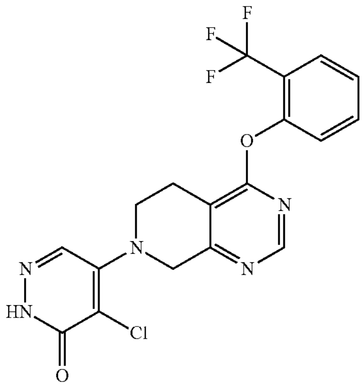
,
-continued
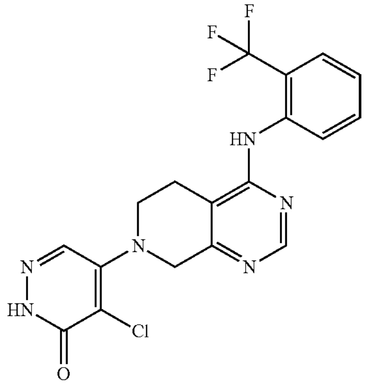
,
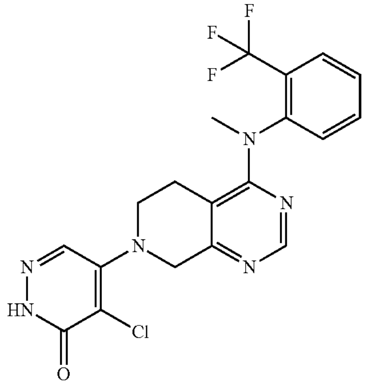
, and
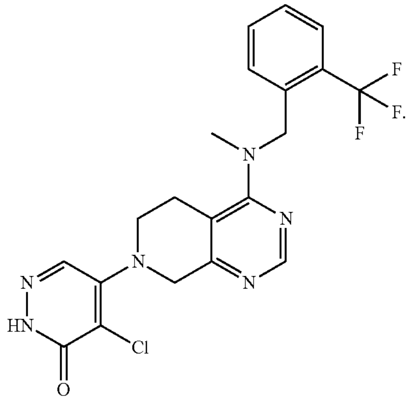
In some embodiments, the compound is selected from the group consisting of:
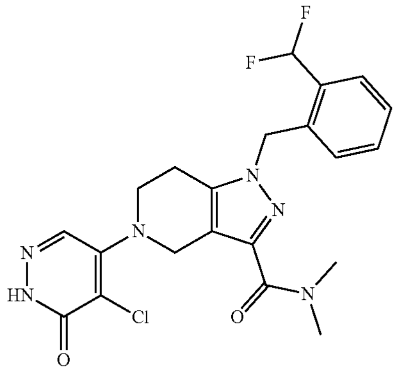
, -continued
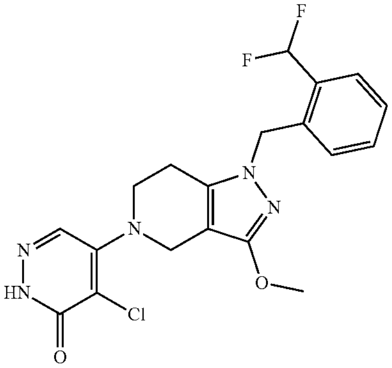
,
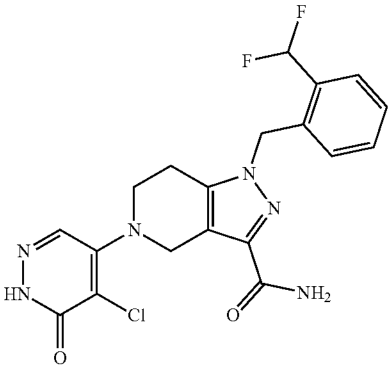
, and
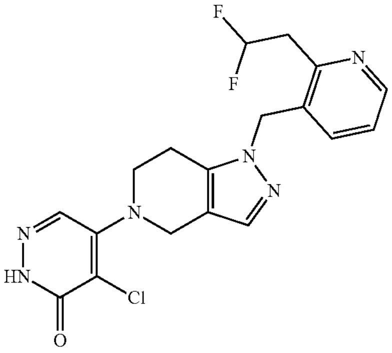
.
In some embodiments, the compound is selected from the group consisting of:
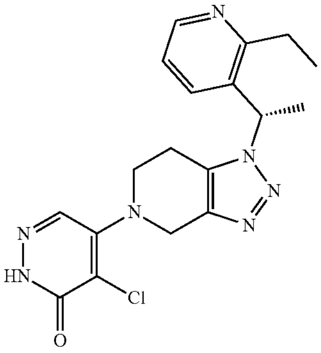
and
-continued
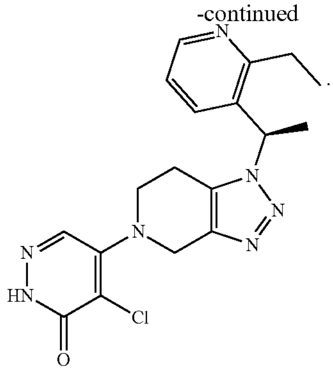
.
In some embodiments, the compound is:
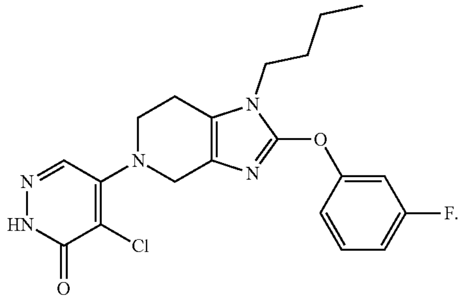 [SMILES: CCCCn1c(Oc2cccc(F)c2)nc2c1CCN(c1cn[nH]c(=O)c1Cl)C2]
In some embodiments, the compound is selected from the group consisting of:
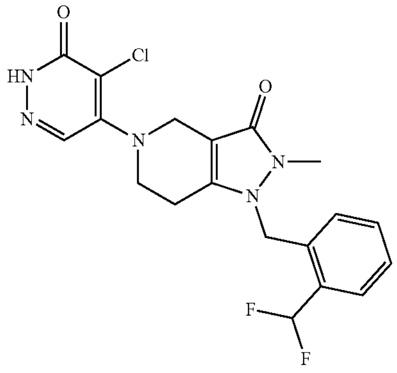
and
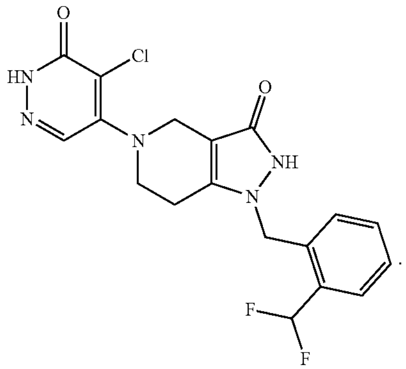
.

In some embodiments, the compound is selected from the group consisting of:
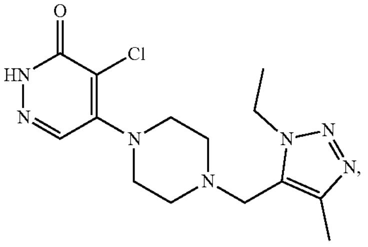
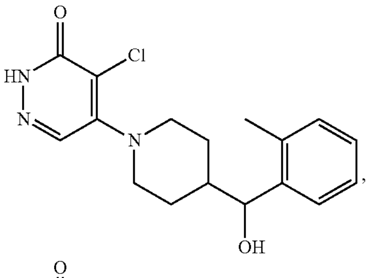
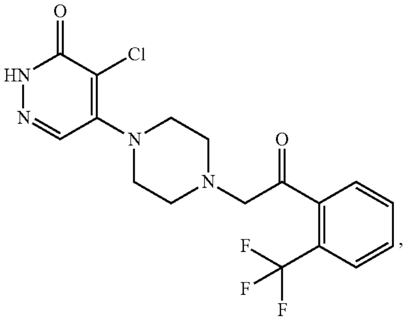
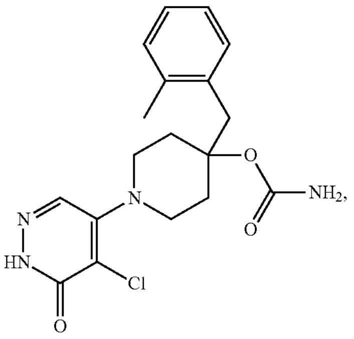
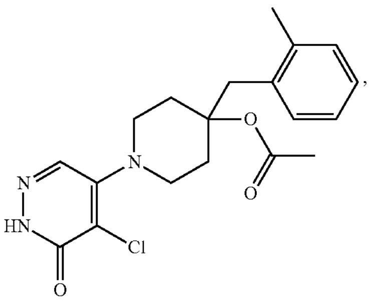
-continued
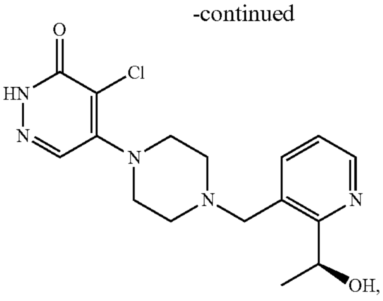
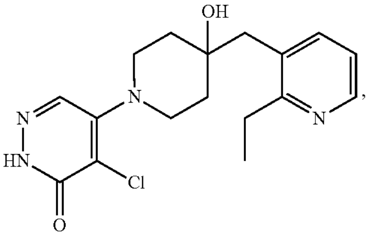
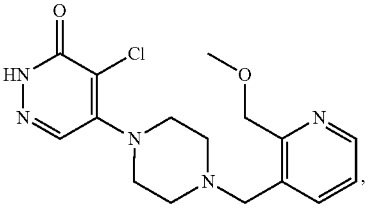
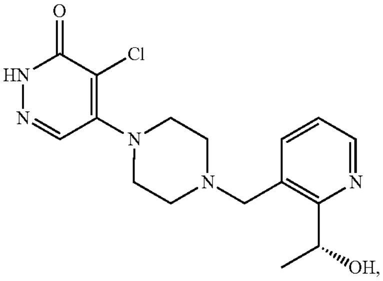
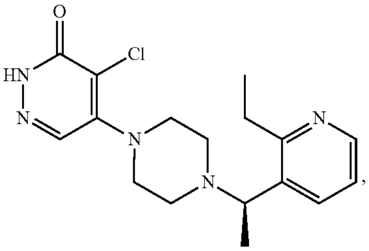
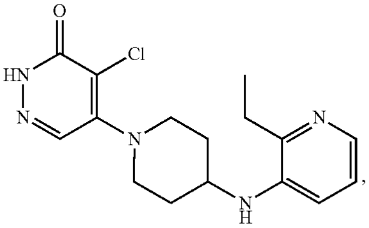
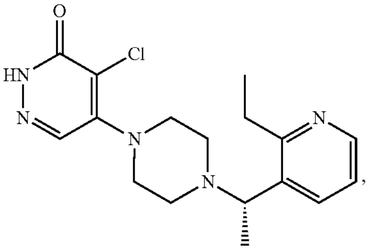

-continued
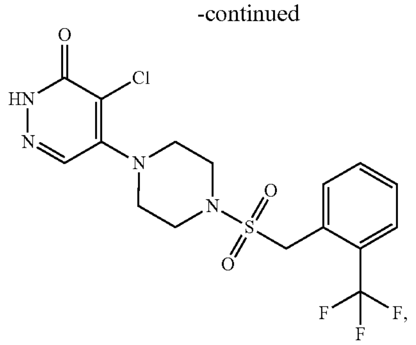
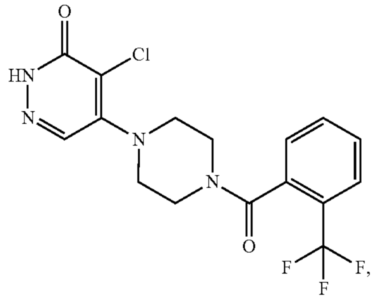
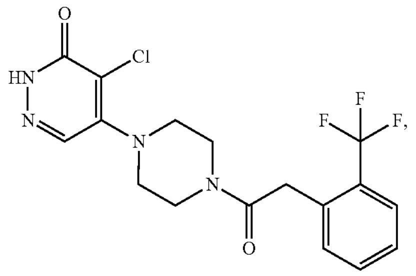
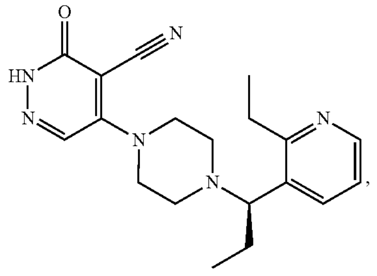
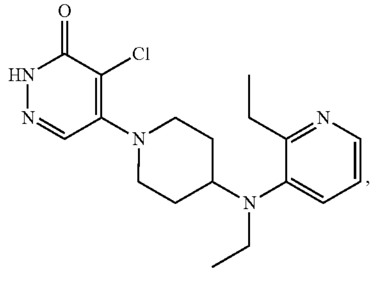
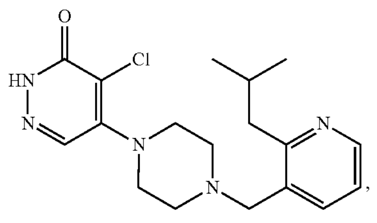
-continued
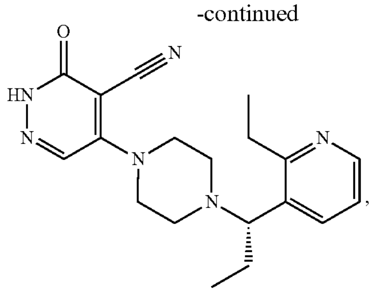
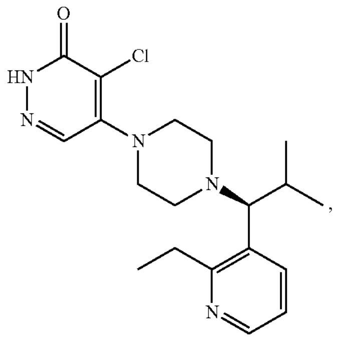
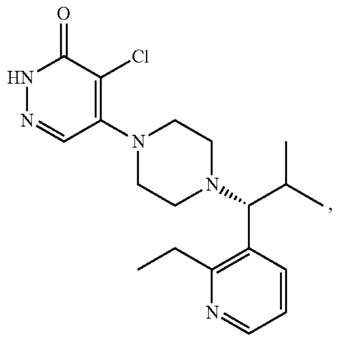
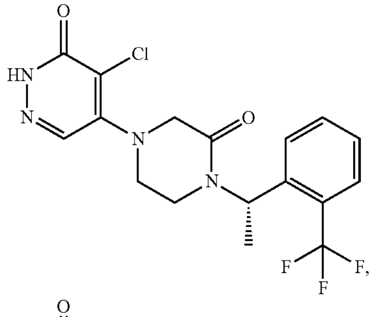
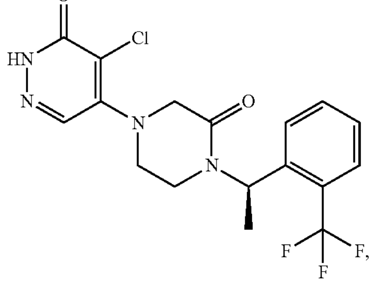

-continued
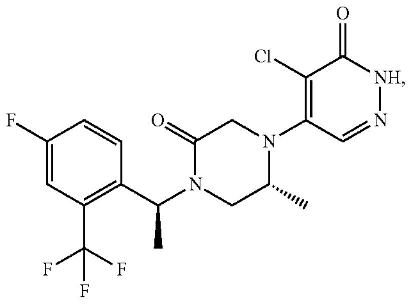
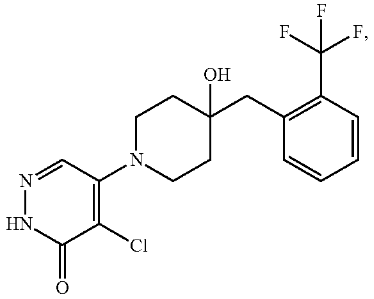
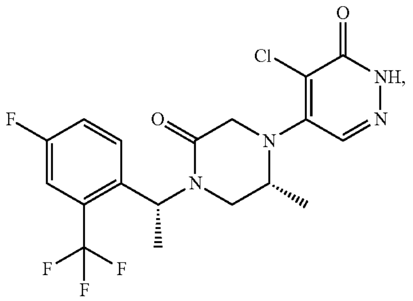
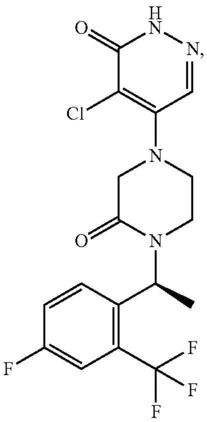
and
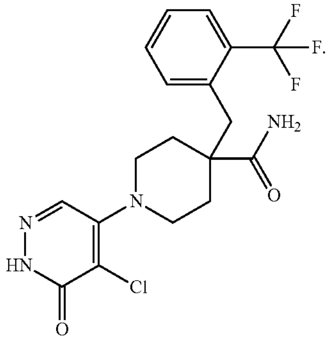
In some embodiments, the compound is selected from the group consisting of:
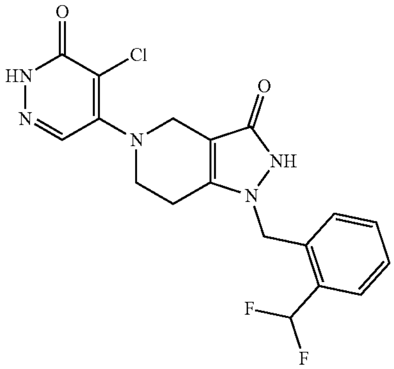
,
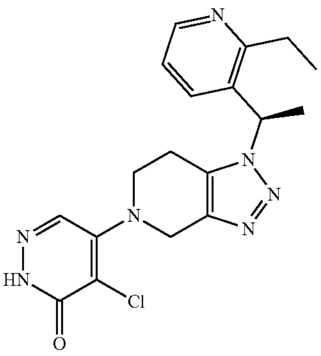
,
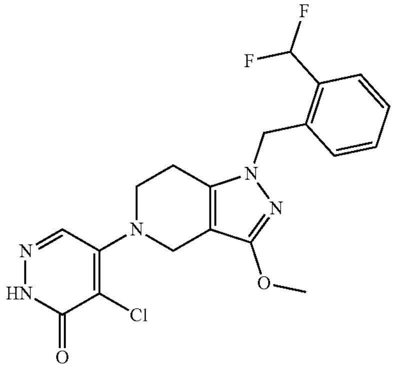
,
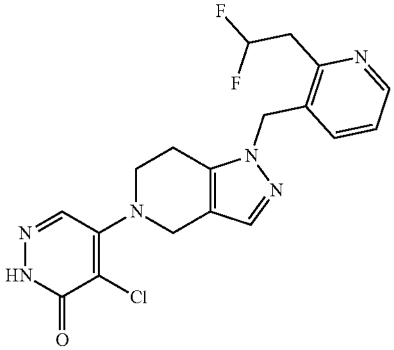
, -continued
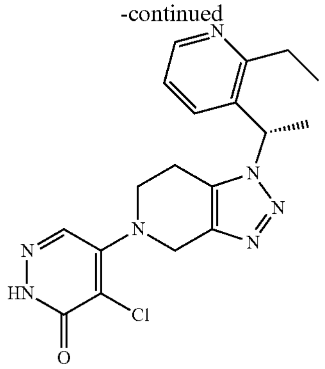
,
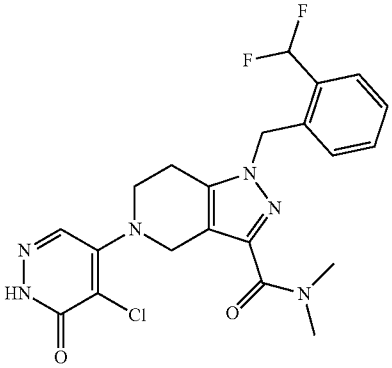
,
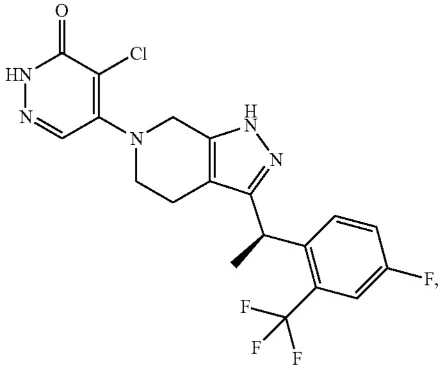
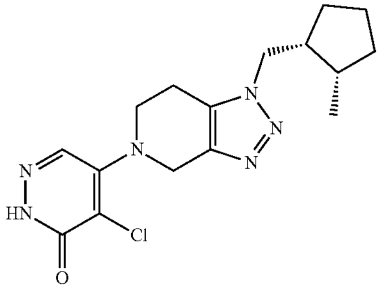
,
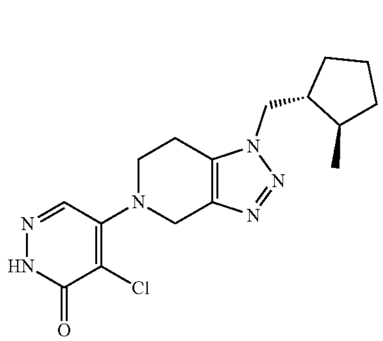
,
-continued
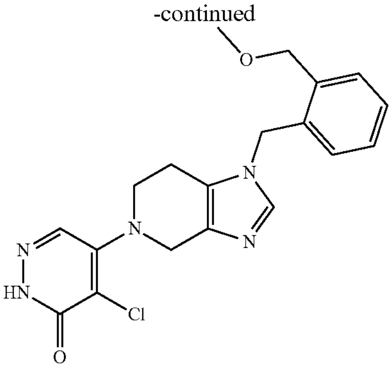
,
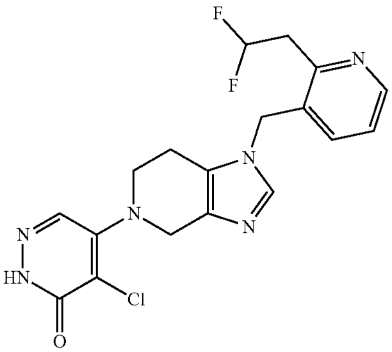
,
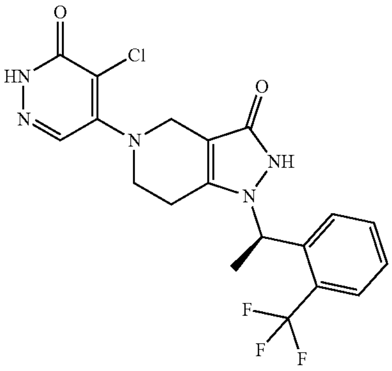
,
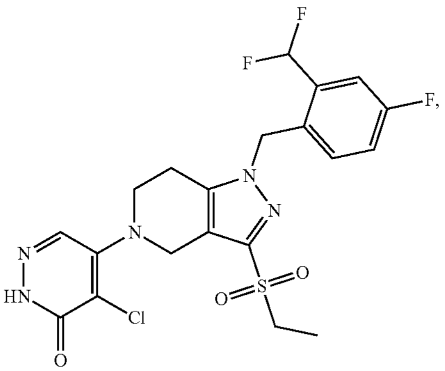

-continued
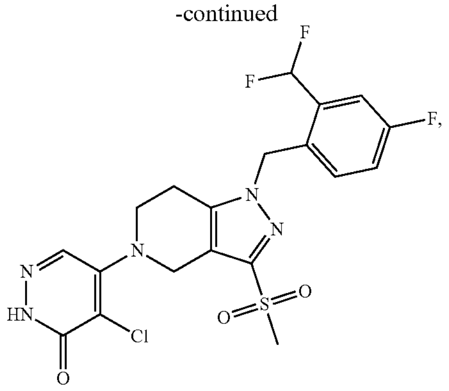
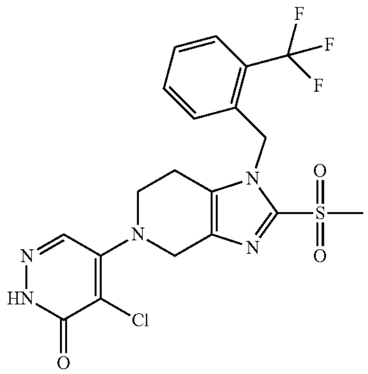
,
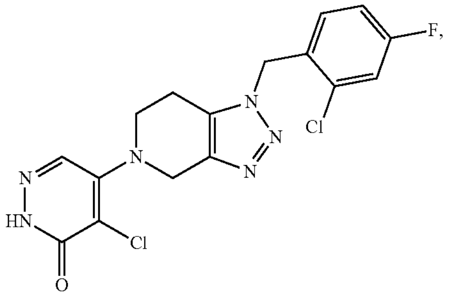
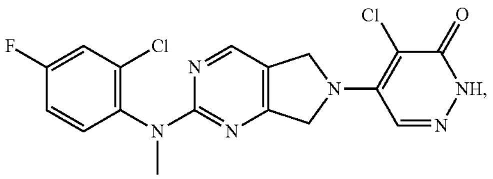
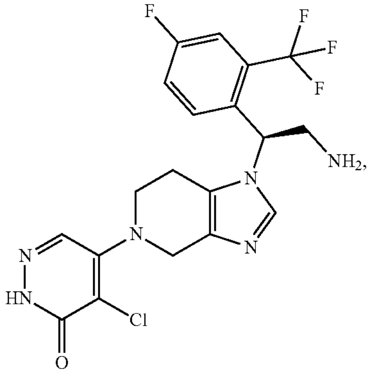
-continued
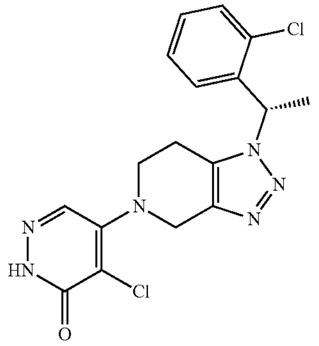
,
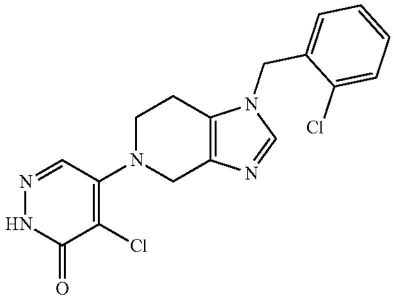
,
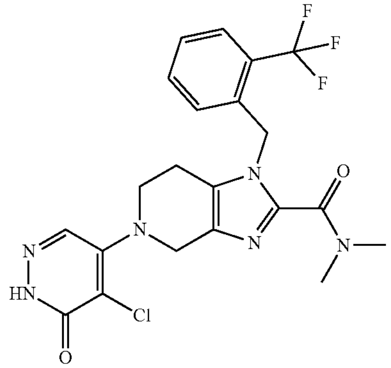
,
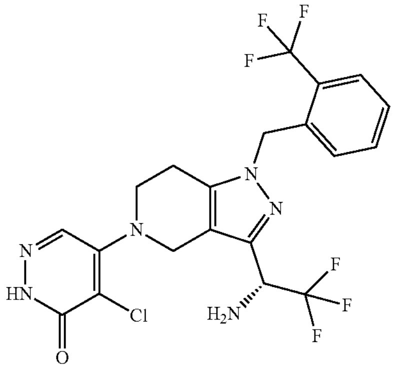
,
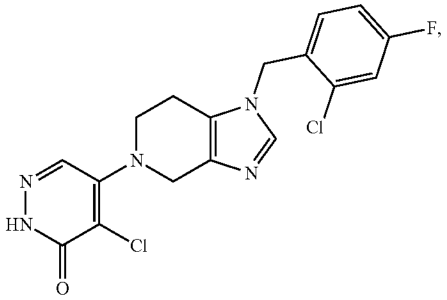

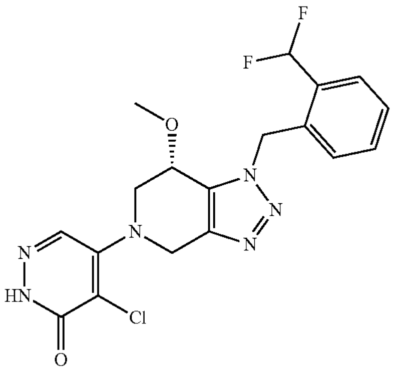
,
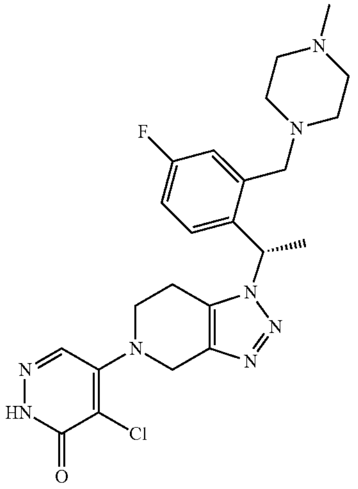
,
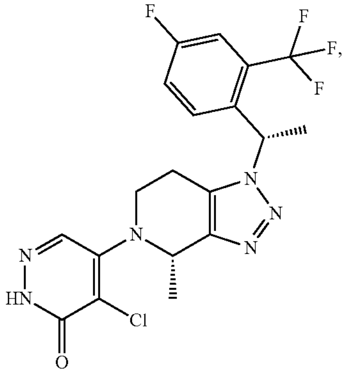
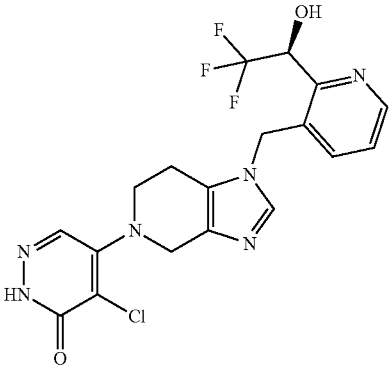
,
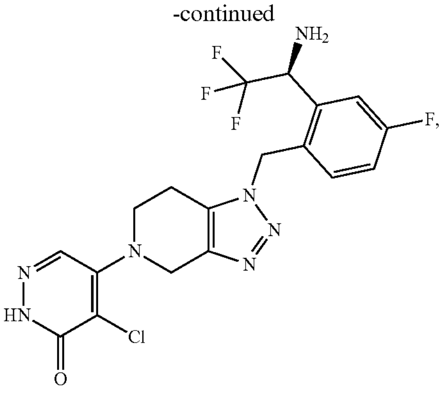
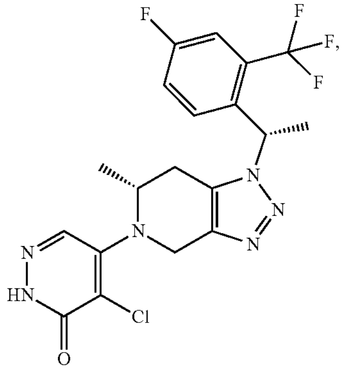
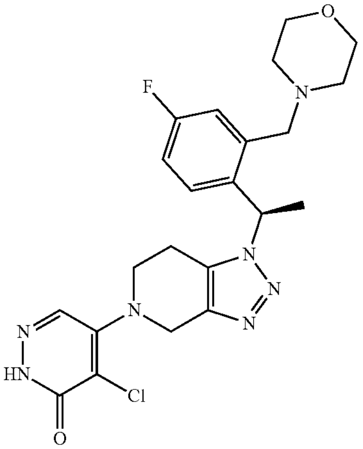
,
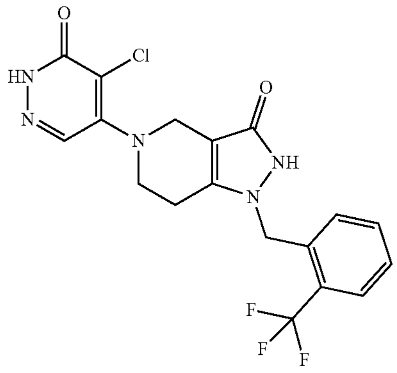
, -continued
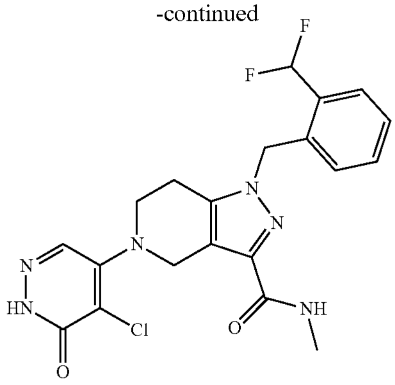
,
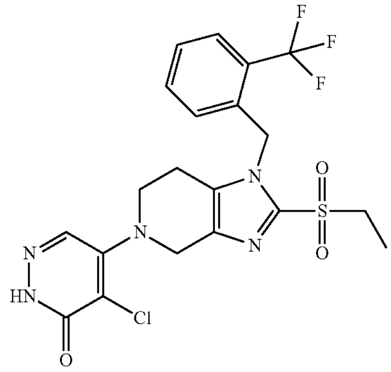
,
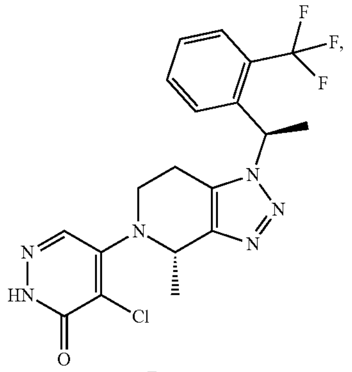
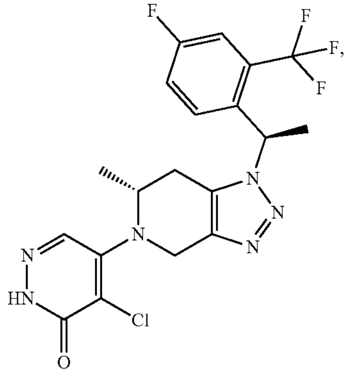
-continued
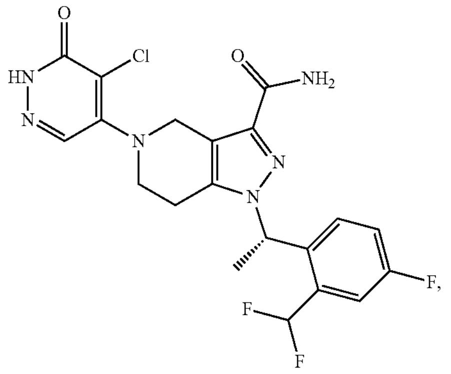
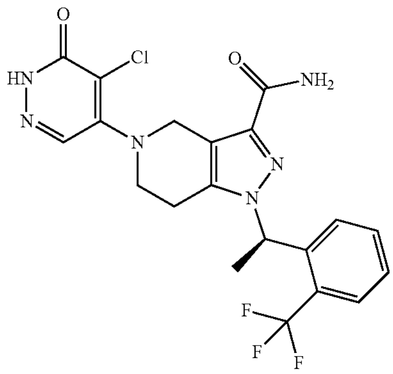
,
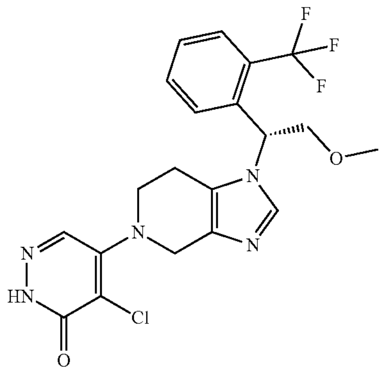
,
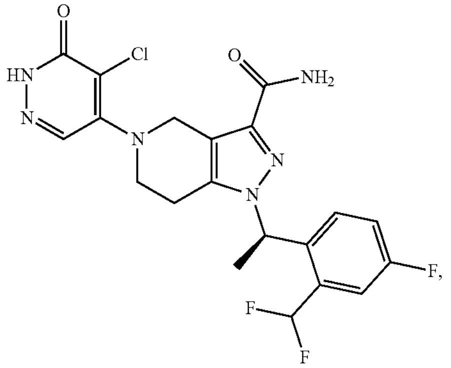

-continued
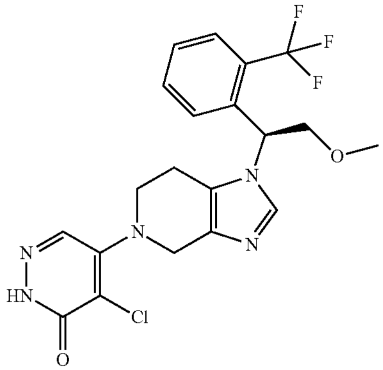
,
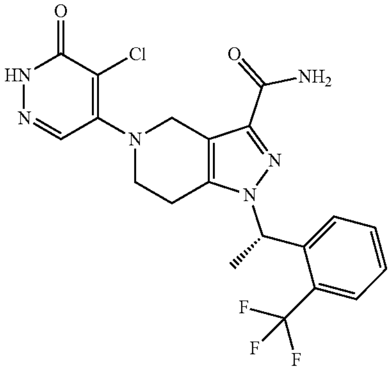
,
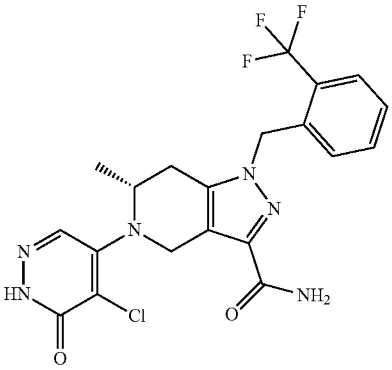
,
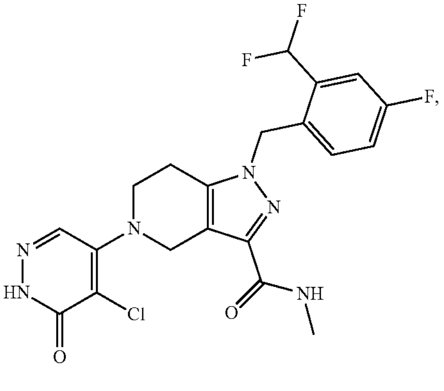
-continued
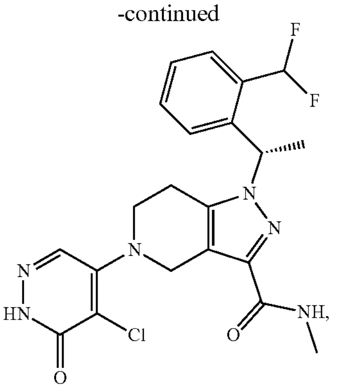
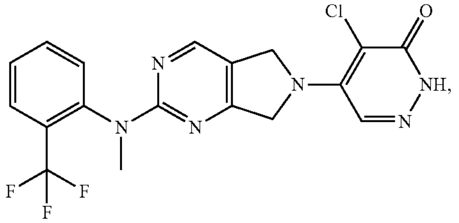
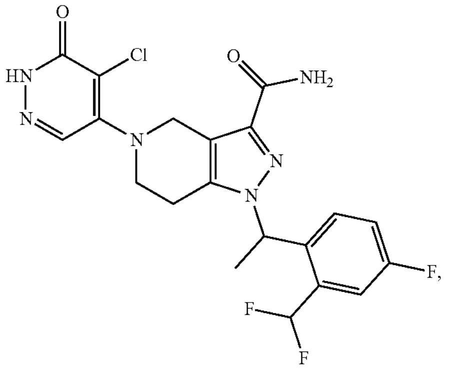
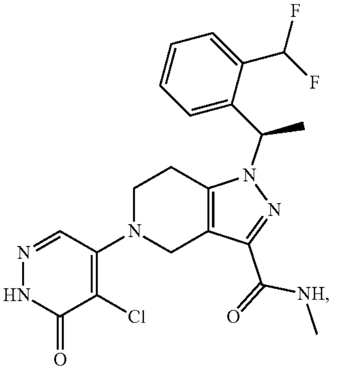
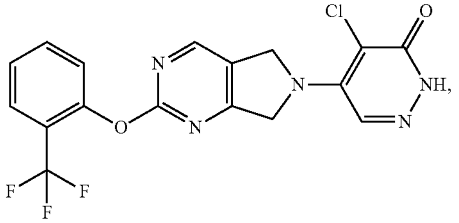

-continued
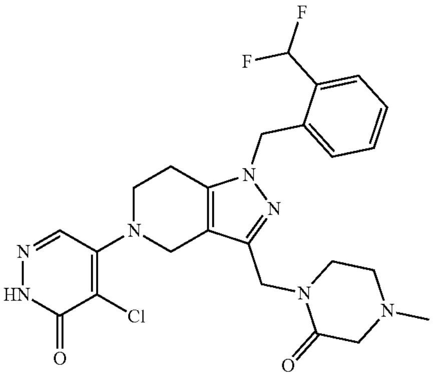
,
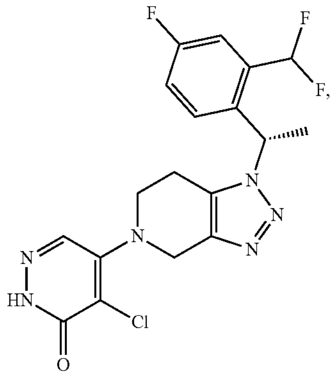
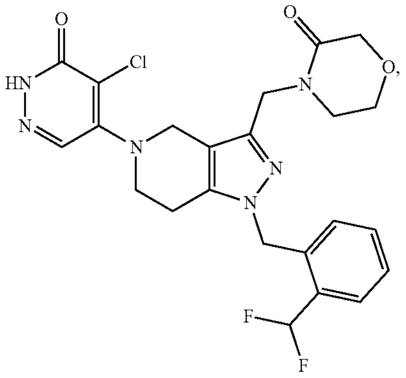
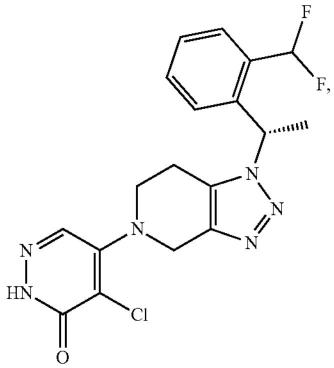
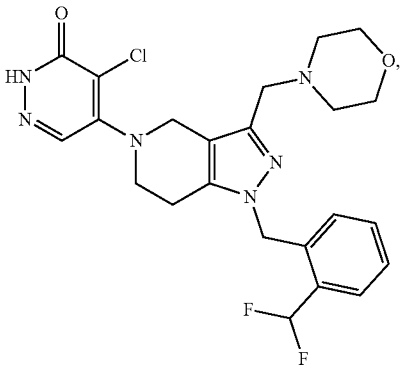
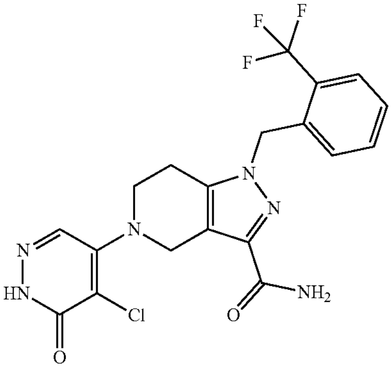
,
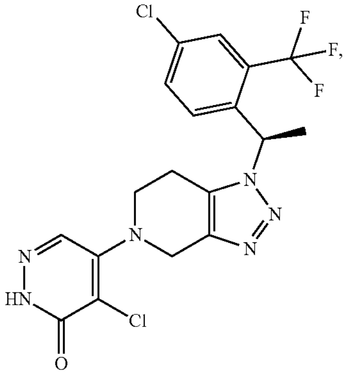
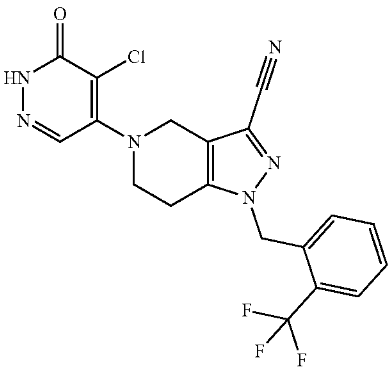
, -continued
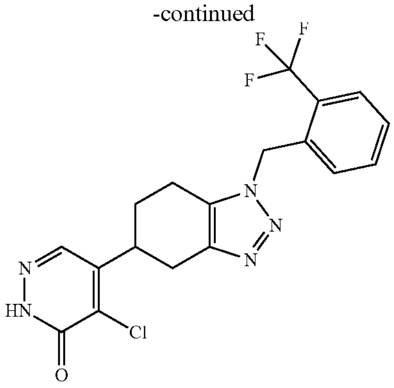
,
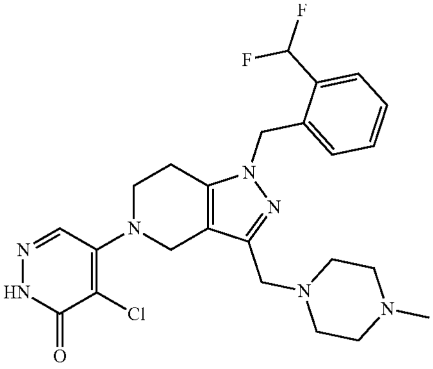
,
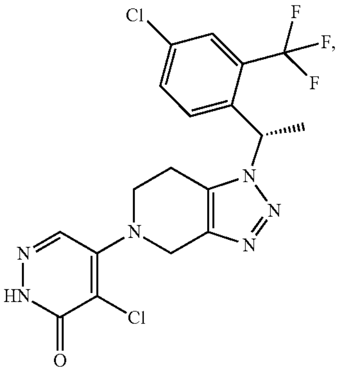
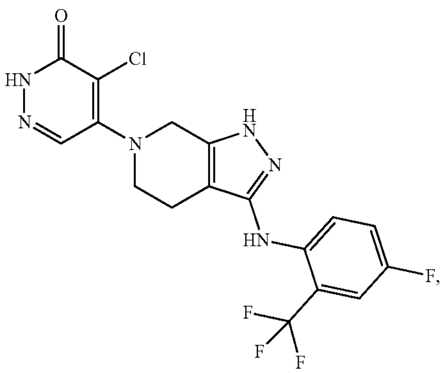
-continued
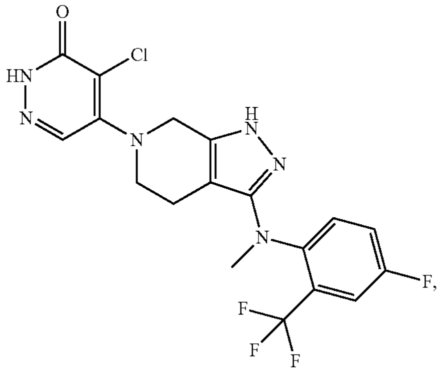
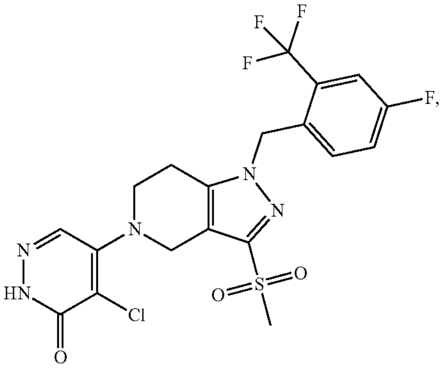
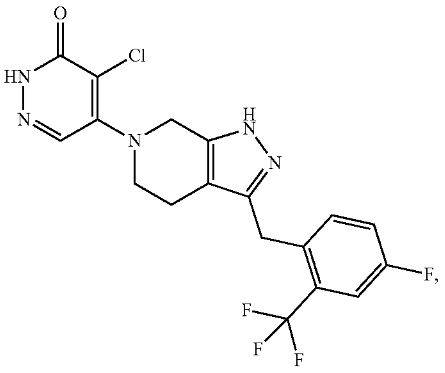
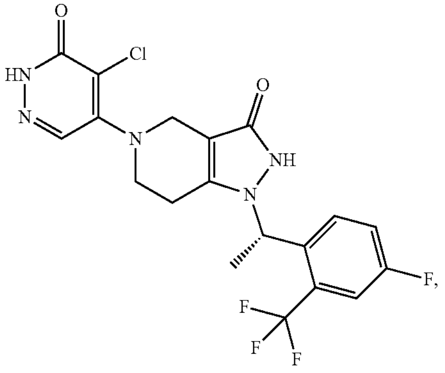

-continued
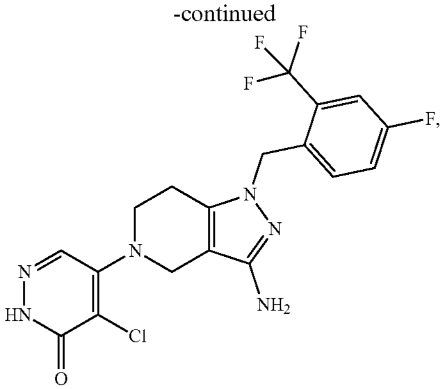
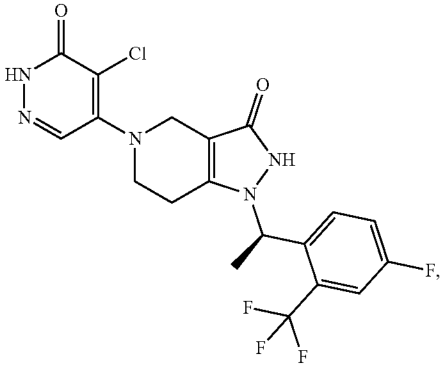
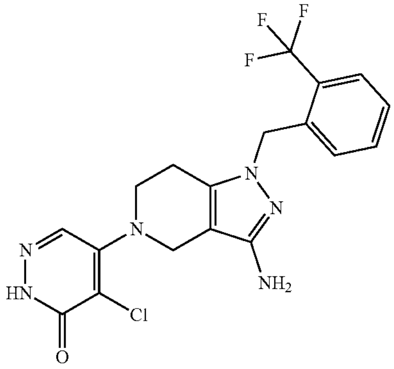
,
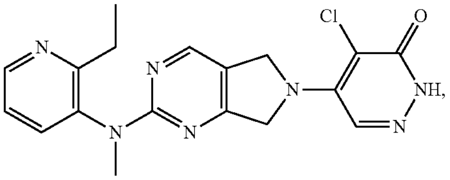
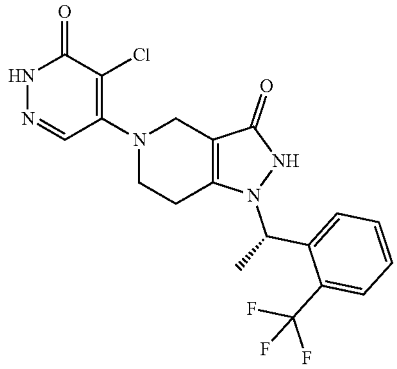
,
-continued
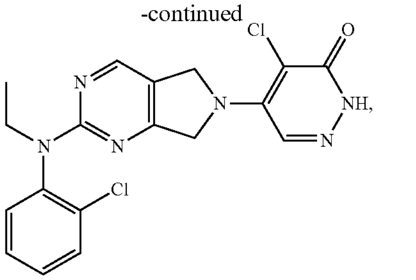
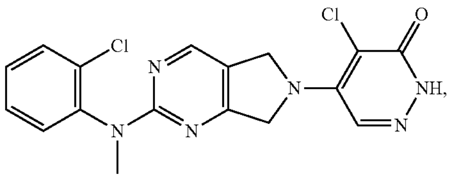
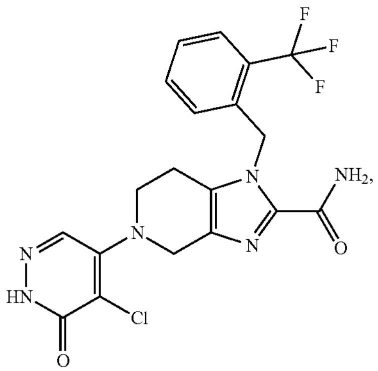
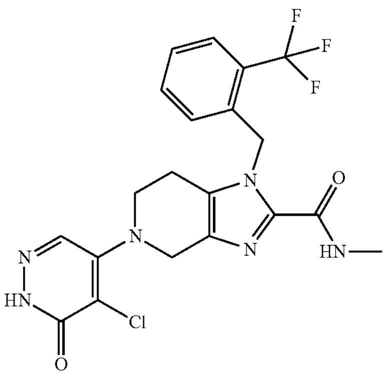
,
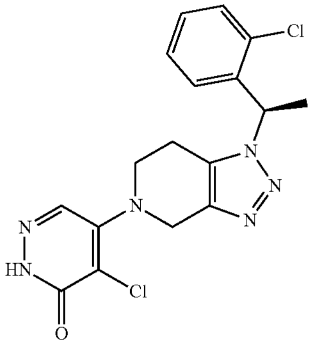
, -continued
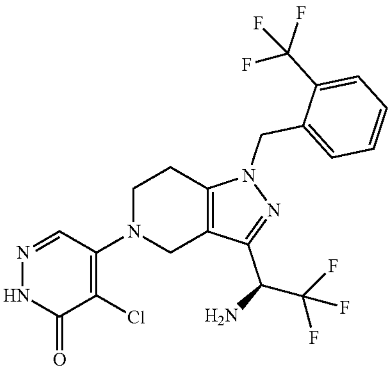
,
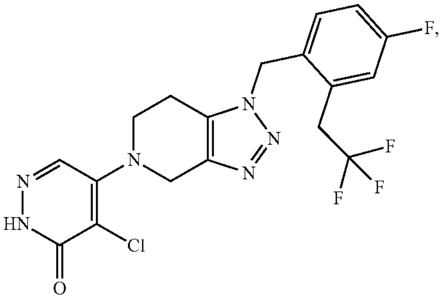
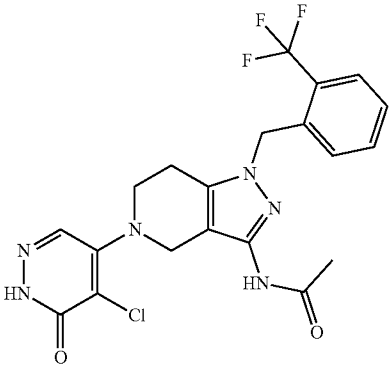
,
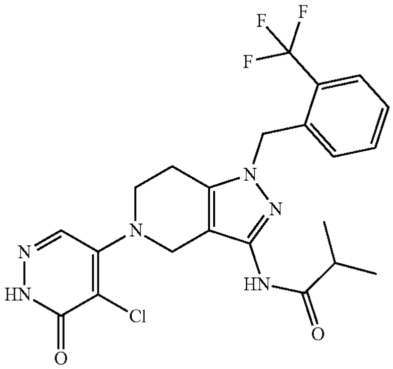
,
-continued
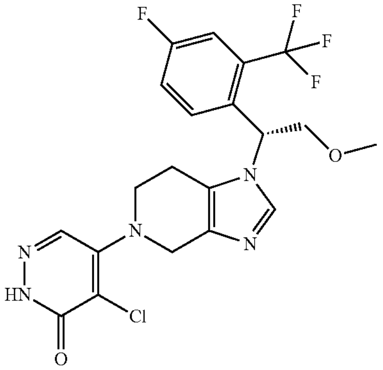
,
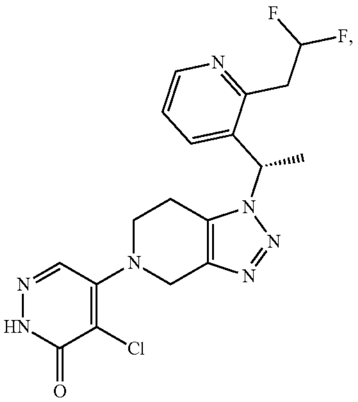
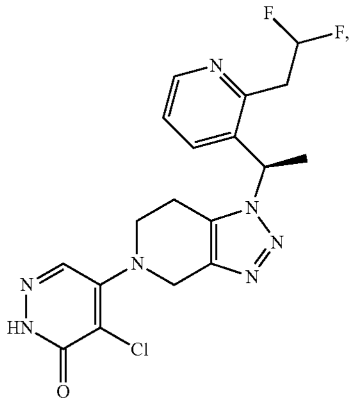
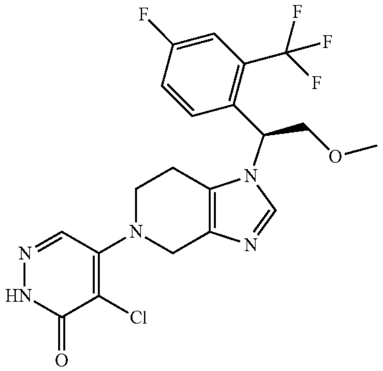
, -continued
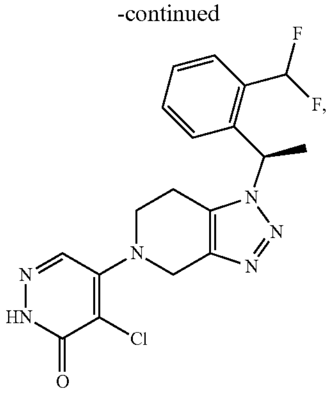
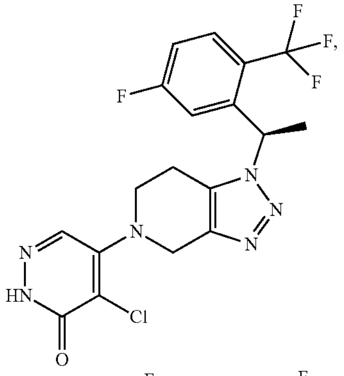
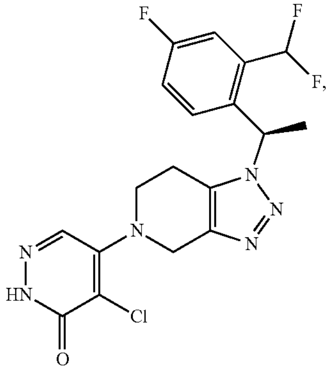
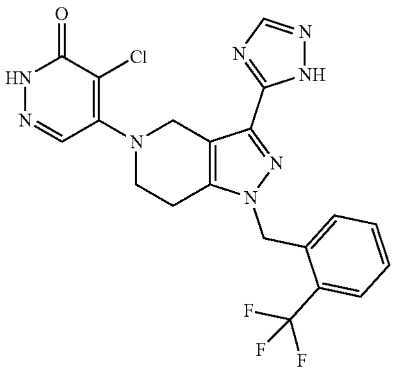
,
-continued
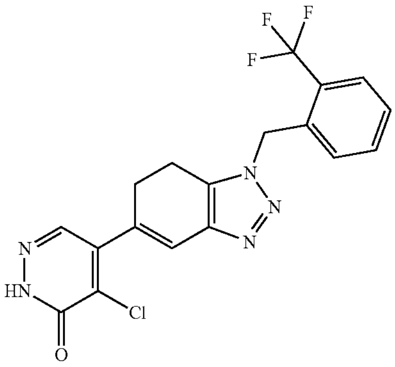
,
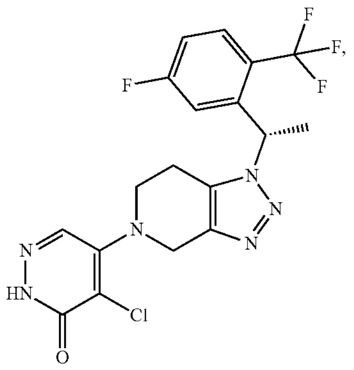
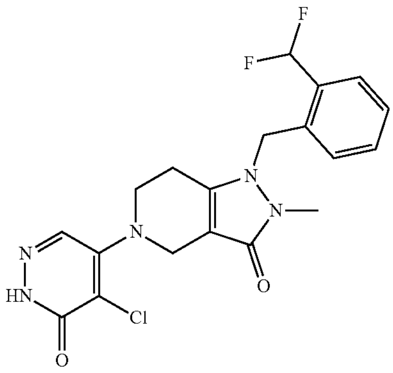
,
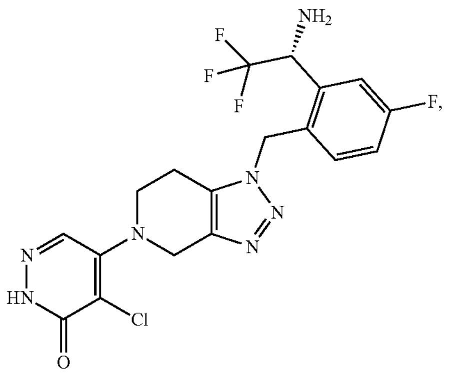

-continued
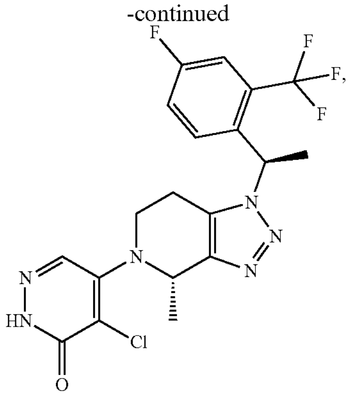
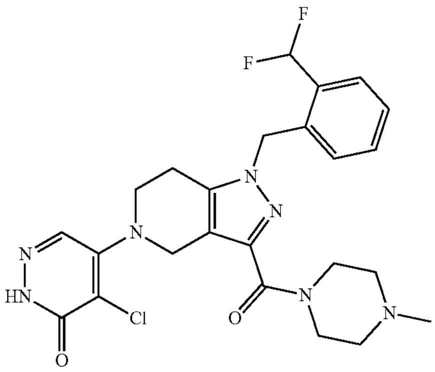
,
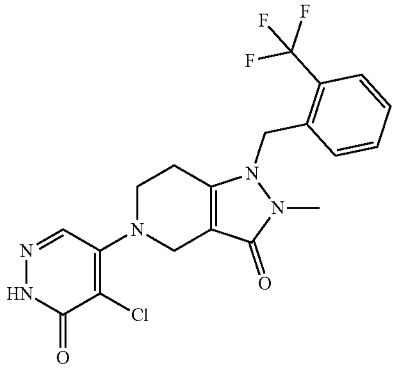
,
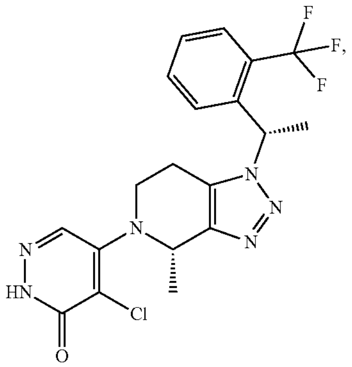
-continued
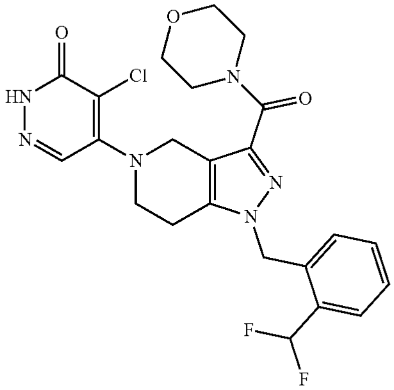
,
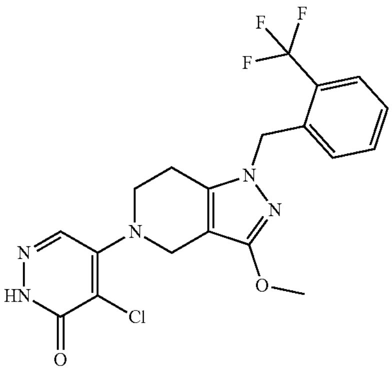
,
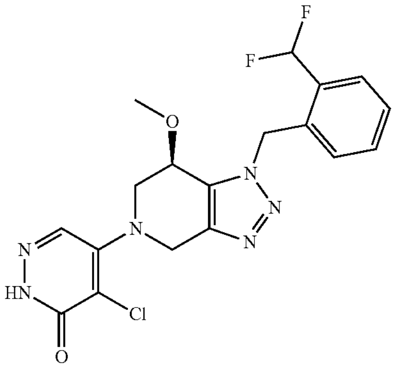
,
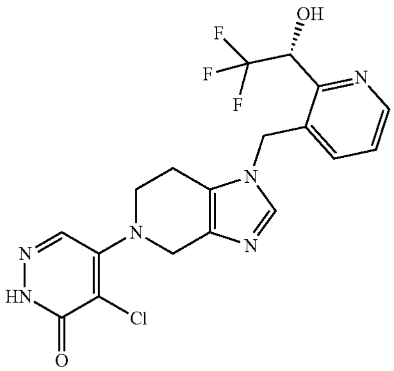
, -continued
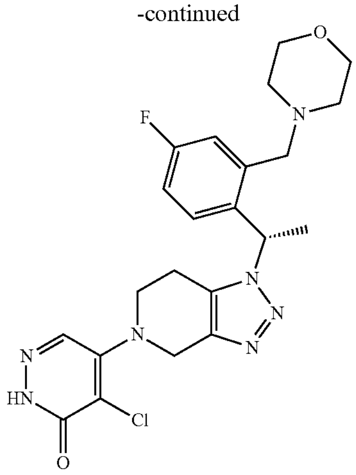
,
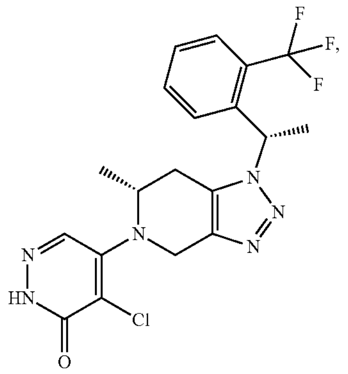
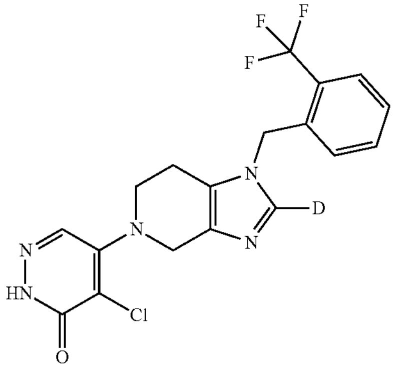
,
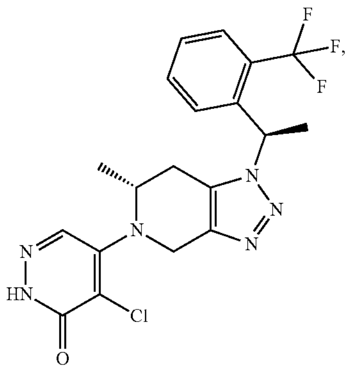
-continued
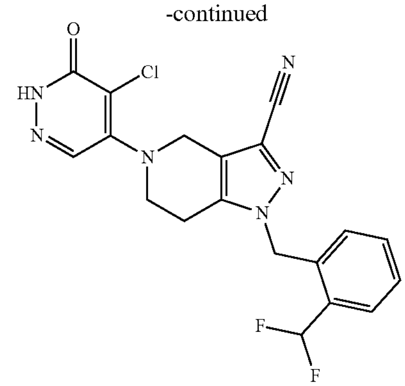
,
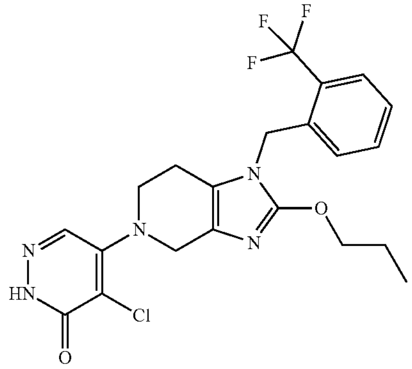
,
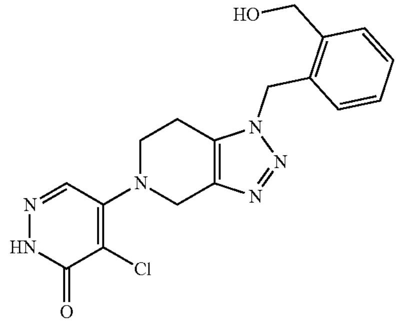
,
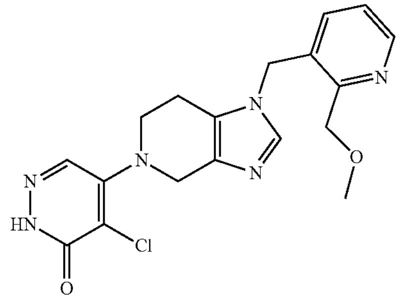
,
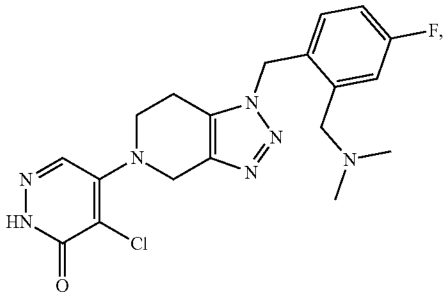

-continued

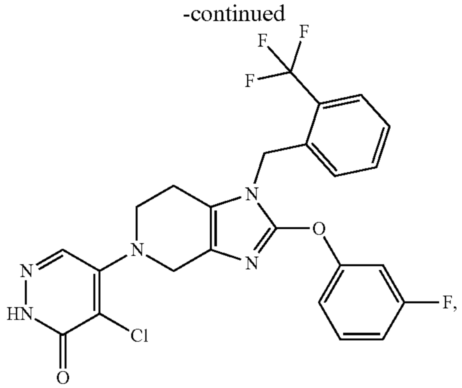

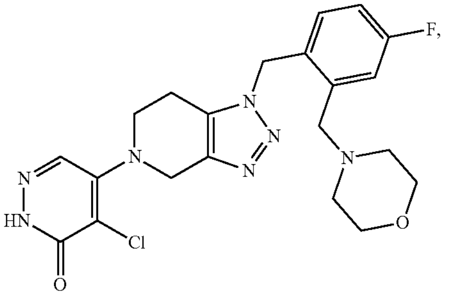

and

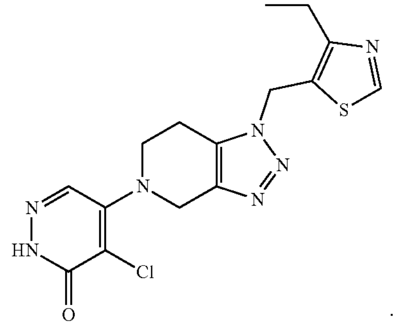

In certain embodiments, the compounds of the invention may be racemic. In certain embodiments, the compounds of the invention may be enriched in one enantiomer. For example, a compound of the invention may have greater than 30% ee, 40% ee, 50% ee, 60% ee, 70% ee, 80% ee, 90% ee, or even 95% or greater ee.

The compounds of the invention have more than one stereocenter. Accordingly, the compounds of the invention may be enriched in one or more diastereomers. For example, a compound of the invention may have greater than 30% de, 40% de, 50% de, 60% de, 70% de, 80% de, 90% de, or even 95% or greater de. In certain embodiments, the compounds of the invention have substantially one isomeric configuration at one or more stereogenic centers, and have multiple isomeric configurations at the remaining stereogenic centers.

In certain embodiments, the enantiomeric excess of the stereocenter is at least 40% ee, 50% ee, 60% ee, 70% ee, 80% ee, 90% ee, 92% ee, 94% ee, 95% ee, 96% ee, 98% ee or greater ee.

As used herein, single bonds drawn without stereochemistry do not indicate the stereochemistry of the compound.

As used herein, hashed or bolded non-wedge bonds indicate relative, but not absolute, stereochemical configuration (e.g., do not distinguish between enantiomers of a given diastereomer).

As used herein, hashed or bolded wedge bonds indicate absolute stereochemical configuration.

In certain embodiments, a therapeutic preparation of the compound of the invention may be enriched to provide predominantly one enantiomer of a compound. An enantiomerically enriched mixture may comprise, for example, at least 60 mol percent of one enantiomer, or more preferably at least 75, 90, 95, or even 99 mol percent. In certain embodiments, the compound enriched in one enantiomer is substantially free of the other enantiomer, wherein substantially free means that the substance in question makes up less than 10%, or less than 5%, or less than 4%, or less than 3%, or less than 2%, or less than 1% as compared to the amount of the other enantiomer, e.g., in the composition or compound mixture. For example, if a composition or compound mixture contains 98 grams of a first enantiomer and 2 grams of a second enantiomer, it would be said to contain 98 mol percent of the first enantiomer and only 2% of the second enantiomer.

In certain embodiments, a therapeutic preparation may be enriched to provide predominantly one diastereomer of the compound of the invention. A diastereomerically enriched mixture may comprise, for example, at least 60 mol percent of one diastereomer, or more preferably at least 75, 90, 95, or even 99 mol percent.

Methods of Treatment

The non-selective $Ca^{2+}$-permeable Transient Receptor Potential (TRP) channels act as sensors that transduce extracellular cues to the intracellular environment in diverse cellular processes, including actin remodeling and cell migration (Greka et al., Nat Neurosci 6, 837-845, 2003; Ramsey et al., Annu Rev Physiol 68, 619-647, 2006; Montell, Pflugers Arch 451, 19-28, 2005; Clapham, Nature 426, 517-524, 2003). Dynamic rearrangement of the actin cytoskeleton relies on spatiotemporally regulated $Ca^{2+}$ influx (Zheng and Poo, Annu Rev Cell Dev Biol 23, 375-404, 2007); Brandman and Meyer, Science 322, 390-395, 2008); Collins and Meyer, Dev Cell 16, 160-161, 2009) and the small GTPases RhoA and Rac1 serve as key modulators of these changes (Etienne-Manneville and Hall, Nature 420, 629-635, 2002); Raftopoulou and Hall, Dev Biol 265, 23-32, 2004). RhoA induces stress fiber and focal adhesion formation, while Rac1 mediates lamellipodia formation (Etienne-Manneville and Hall, Nature 420, 629-635, 2002). The Transient Receptor Potential Cation Channel, subfamily C, member 5 (TRPC5) acts in concert with TRPC6 to regulate Ca2+ influx, actin remodeling, and cell motility in kidney podocytes and fibroblasts. TRPC5-mediated $Ca^{2+}$ influx increases Rac1 activity, whereas TRPC6-mediated Ca2+ influx promotes RhoA activity. Gene silencing of TRPC6 channels abolishes stress fibers and diminishes focal contacts, rendering a motile, migratory cell phenotype. In contrast, gene silencing of TRPC5 channels rescues stress fiber formation, rendering a contractile cell phenotype. The results described herein unveil a conserved signaling mechanism whereby TRPC5 and TRPC6 channels control a tightly regulated balance of cytoskeletal dynamics through differential coupling to Rac1 and RhoA.

$Ca^{2+}$-dependent remodeling of the actin cytoskeleton is a dynamic process that drives cell migration (Wei et al., Nature 457, 901-905, 2009). RhoA and Rac1 act as switches responsible for cytoskeletal rearrangements in migrating cells (Etienne-Manneville and Hall, Nature 420, 629-635, 2002); Raftopoulou and Hall, Dev Biol 265, 23-32, 2004). Activation of Rac1 mediates a motile cell phenotype, whereas RhoA activity promotes a contractile phenotype (Etienne-Manneville and Hall, Nature 420, 629-635, 2002). $Ca^{2+}$ plays a central role in small GTPase regulation (Aspenstrom et al., Biochem J 377, 327-337, 2004). Spatially and temporally restricted flickers of $Ca^{2+}$ are enriched near the leading edge of migrating cells (Wei et al., Nature 457, 901-905, 2009). Ca2+ microdomains have thus joined local bursts in Rac1 activity (Gardiner et al., Curr Biol 12, 2029-2034, 2002; Machacek et al., Nature 461, 99-103, 2009) as critical events at the leading edge. To date, the sources of Ca2+ influx responsible for GTPase regulation remain largely elusive. TRP (Transient Receptor Potential) channels generate time and space-limited $Ca^{2+}$ signals linked to cell migration in fibroblasts and neuronal growth cones0. Specifically, TRPC5 channels are known regulators of neuronal growth cone guidance1 and their activity in neurons is dependent on PI3K and Rac1 activity (Bezzerides et al., Nat Cell Biol 6, 709-720, 2004).

Podocytes are neuronal-like cells that originate from the metanephric mesenchyme of the kidney glomerulus and are essential to the formation of the kidney filtration apparatus (Somlo and Mundel, Nat Genet. 24, 333-335, 2000; Fukasawa et al., J Am Soc Nephrol 20, 1491-1503, 2009). Podocytes possess an exquisitely refined repertoire of cytoskeletal adaptations to environmental cues (Somlo and Mundel, Nat Genet 24, 333-335, 2000; Garg et al., Mol Cell Biol 27, 8698-8712, 2007; Verma et al., J Clin Invest 116, 1346-1359, 2006; Verma et al., J Biol Chem 278, 20716-20723, 2003; Barletta et al., J Biol Chem 278, 19266-19271, 2003; Holzman et al., Kidney Int 56, 1481-1491, 1999; Ahola et al., Am J Pathol 155, 907-913, 1999; Tryggvason and Wartiovaara, N Engl J Med 354, 1387-1401, 2006; Schnabel and Farquhar, J Cell Biol 111, 1255-1263, 1990; Kurihara et al., Proc Natl Acad Sci USA 89, 7075-7079, 1992). Early events of podocyte injury are characterized by dysregulation of the actin cytoskeleton (Faul et al., Trends Cell Biol 17, 428-437, 2007; Takeda et al., J Clin Invest 108, 289-301, 2001; Asanuma et al., Nat Cell Biol 8, 485-491, 2006) and Ca2+ homeostasis (Hunt et al., J Am Soc Nephrol 16, 1593-1602, 2005; Faul et al., Nat Med 14, 931-938, 2008). These changes are associated with the onset of proteinuria, the loss of albumin into the urinary space, and ultimately kidney failure (Tryggvason and Wartiovaara, N Engl J Med 354, 1387-1401, 2006). The vasoactive hormone Angiotensin II induces $Ca^{2+}$ influx in podocytes, and prolonged treatment results in loss of stress fibers (Hsu et al., J Mol Med 86, 1379-1394, 2008). While there is a recognized link between Ca2+ influx and cytoskeletal reorganization, the mechanisms by which the podocyte senses and transduces extracellular cues that modulate cell shape and motility remain elusive. TRP Canonical 6 (TRPC6) channel mutations have been linked to podocyte injury (Winn et al., Science 308, 1801-1804, 2005; Reiser et al., Nat Genet 37, 739-744, 2005; Moller et al., J Am Soc Nephrol 18, 29-36, 2007; Hsu et al., Biochim Biophys Acta 1772, 928-936, 2007), but little is known about the specific pathways that regulate this process. Moreover, TRPC6 shares close homology with six other members of the TRPC channel family (Ramsey et al., Annu Rev Physiol 68, 619-647, 2006; Clapham, Nature 426, 517-524, 2003). TRPC5 channels antagonize TRPC6 channel activity to control a tightly regulated balance of cytoskeletal dynamics through differential coupling to distinct small GTPases.

Proteinuria

Proteinuria is a pathological condition wherein protein is present in the urine. Albuminuria is a type of proteinuria. Microalbuminuria occurs when the kidney leaks small amounts of albumin into the urine. In a properly functioning body, albumin is not normally present in urine because it is retained in the bloodstream by the kidneys. Microalbuminuria is diagnosed either from a 24-hour urine collection (20 to 200 μg/min) or, more commonly, from elevated concentrations (30 to 300 mg/L) on at least two occasions. Microalbuminuria can be a forerunner of diabetic nephropathy. An albumin level above these values is called macroalbuminuria. Subjects with certain conditions, e.g., diabetic nephropathy, can progress from microalbuminuria to macroalbuminuria and reach a nephrotic range (>3.5 g/24 hours) as kidney disease reaches advanced stages.

Causes of Proteinuria

Proteinuria can be associated with a number of conditions, including focal segmental glomerulosclerosis, IgA nephropathy, diabetic nephropathy, lupus nephritis, membranoproliferative glomerulonephritis, progressive (crescentic) glomerulonephritis, and membranous glomerulonephritis.

A. Focal Segmental Glomerulosclerosis (FSGS)

Focal Segmental Glomerulosclerosis (FSGS) is a disease that attacks the kidney's filtering system (glomeruli) causing serious scarring. FSGS is one of the many causes of a disease known as Nephrotic Syndrome, which occurs when protein in the blood leaks into the urine (proteinuria).

Very few treatments are available for patients with FSGS. Many patients are treated with steroid regimens, most of which have very harsh side effects. Some patients have shown to respond positively to immunosuppressive drugs as well as blood pressure drugs which have shown to lower the level of protein in the urine. To date, there is no commonly accepted effective treatment or cure and there are no FDA approved drugs to treat FSGS. Therefore, more effective methods to reduce or inhibit proteinuria are desirable.

B. IgA Nephropathy

IgA nephropathy (also known as IgA nephritis, IgAN, Berger's disease, and synpharyngitic glomerulonephritis) is a form of glomerulonephritis (inflammation of the glomeruli of the kidney). IgA nephropathy is the most common glomerulonephritis throughout the world. Primary IgA nephropathy is characterized by deposition of the IgA antibody in the glomerulus. There are other diseases associated with glomerular IgA deposits, the most common being Henoch-Schonlein purpura (HSP), which is considered by many to be a systemic form of IgA nephropathy. Henoch-Schönlein purpura presents with a characteristic purpuric skin rash, arthritis, and abdominal pain and occurs more commonly in young adults (16-35 yrs old). HSP is associated with a more benign prognosis than IgA nephropathy. In IgA nephropathy there is a slow progression to chronic renal failure in 25-30% of cases during a period of 20 years.

C. Diabetic Nephropathy

Diabetic nephropathy, also known as Kimmelstiel-Wilson syndrome and intercapillary glomerulonephritis, is a progressive kidney disease caused by angiopathy of capillaries in the kidney glomeruli. It is characterized by nephrotic syndrome and diffuse glomerulosclerosis. It is due to longstanding diabetes mellitus and is a prime cause for dialysis. The earliest detectable change in the course of diabetic nephropathy is a thickening in the glomerulus. At this stage, the kidney may start allowing more serum albumin than normal in the urine. As diabetic nephropathy progresses, increasing numbers of glomeruli are destroyed by nodular glomerulosclerosis and the amount of albumin excreted in the urine increases.

D. Lupus Nephritis

Lupus nephritis is a kidney disorder that is a complication of systemic lupus erythematosus. Lupus nephritis occurs when antibodies and complement build up in the kidneys, causing inflammation. It often causes proteinuria and may progress rapidly to renal failure. Nitrogen waste products build up in the bloodstream. Systemic lupus erythematosus causes various disorders of the internal structures of the kidney, including interstitial nephritis. Lupus nephritis affects approximately 3 out of 10,000 people.

E. Membranoproliferative Glomerulonephritis I/II/III

Membranoproliferative glomerulonephritis is a type of glomerulonephritis caused by deposits in the kidney glomerular mesangium and basement membrane thickening, activating complement and damaging the glomeruli. There are three types of membranoproliferative glomerulonephritis. Type I is caused by immune complexes depositing in the kidney and is believed to be associated with the classical complement pathway. Type II is similar to Type 1, however, it is believed to be associated with the alternative complement pathway. Type III is very rare and it is characterized by a mixture of subepithelial deposits and the typical pathological findings of Type I disease.

F. Progressive (Crescentic) Glomerulonephritis

Progressive (crescentic) glomerulonephritis (PG) is a syndrome of the kidney that, if left untreated, rapidly progresses into acute renal failure and death within months. In 50% of cases, PG is associated with an underlying disease such as Goodpasture's syndrome, systemic lupus erythematosus, or Wegener granulomatosis; the remaining cases are idiopathic. Regardless of the underlying cause, PG involves severe injury to the kidney's glomeruli, with many of the glomeruli containing characteristic crescent-shaped scars. Patients with PG have hematuria, proteinuria, and occasionally, hypertension and edema. The clinical picture is consistent with nephritic syndrome, although the degree of proteinuria may occasionally exceed 3 g/24 hours, a range associated with nephrotic syndrome. Untreated disease may progress to decreased urinary volume (oliguria), which is associated with poor kidney function.

G. Membranous Glomerulonephritis

Membranous glomerulonephritis (MGN) is a slowly progressive disease of the kidney affecting mostly patients between ages of 30 and 50 years, usually Caucasian. It can develop into nephrotic syndrome. MGN is caused by circulating immune complex. Current research indicates that the majority of the immune complexes are formed via binding of antibodies to antigens in situ to the glomerular basement membrane. The said antigens may be endogenous to the basement membrane, or deposited from systemic circulation.

Measurement of Urine Protein Levels

Protein levels in urine can be measured using methods known in the art. Until recently, an accurate protein measurement required a 24-hour urine collection. In a 24-hour collection, the patient urinates into a container, which is kept refrigerated between trips to the bathroom. The patient is instructed to begin collecting urine after the first trip to the bathroom in the morning. Every drop of urine for the rest of the day is to be collected in the container. The next morning, the patient adds the first urination after waking and the collection is complete.

More recently, researchers have found that a single urine sample can provide the needed information. In the newer technique, the amount of albumin in the urine sample is compared with the amount of creatinine, a waste product of normal muscle breakdown. The measurement is called a urine albumin-to-creatinine ratio (UACR). A urine sample containing more than 30 milligrams of albumin for each gram of creatinine (30 mg/g) is a warning that there may be a problem. If the laboratory test exceeds 30 mg/g, another UACR test should be performed 1 to 2 weeks later. If the second test also shows high levels of protein, the person has persistent proteinuria, a sign of declining kidney function, and should have additional tests to evaluate kidney function.

Tests that measure the amount of creatinine in the blood will also show whether a subject's kidneys are removing wastes efficiently. Too much creatinine in the blood is a sign that a person has kidney damage. A physician can use the creatinine measurement to estimate how efficiently the kidneys are filtering the blood. This calculation is called the estimated glomerular filtration rate, or eGFR. Chronic kidney disease is present when the eGFR is less than 60 milliliters per minute (mL/min).

TRPC5

TRPC is a family of transient receptor potential cation channels in animals. TRPC5 is subtype of the TRPC family of mammalian transient receptor potential ion channels. Three examples of TRPC5 are highlighted below in Table 1.

Accordingly, in certain embodiments, the invention provides methods for treating, or the reducing risk of developing, a disease or condition selected from kidney disease, pulmonary arterial hypertension, anxiety, depression, cancer, diabetic retinopathy, or pain, comprising administering to a subject in need thereof a therapeutically effective amount of a compound of the invention (e.g., a compound of Formula I), or a pharmaceutical composition comprising said compound.

In some embodiments, the disease is kidney disease, anxiety, depression, cancer, or diabetic retinopathy.

In some embodiments, the disease or condition is kidney disease is selected from the group consisting of Focal Segmental Glomerulosclerosis (FSGS), Diabetic nephropathy, Alport syndrome, hypertensive kidney disease, nephrotic syndrome, steroid-resistant nephrotic syndrome, minimal change disease, membranous nephropathy, idiopathic membranous nephropathy, membranoproliferative glomerulonephritis (MPGN), immune complex-mediated MPGN, complement-mediated MPGN, Lupus nephritis, postinfectious glomerulonephritis, thin basement membrane disease, mesangial proliferative glomerulonephritis, amyloidosis (primary), c1q nephropathy, rapidly progressive GN, anti-GBM disease, C3 glomerulonephritis, hypertensive nephrosclerosis, and IgA nephropathy. In some embodiments, the kidney disease is proteinuric kidney disease. In some embodiments, the kidney disease is proteinuria. In some embodiments, the kidney disease is microalbuminuria or macroalbuminuria. In some embodiments, the kidney disease is microalbuminuria or macroalbuminuria kidney disease.

In some embodiments, the disease or condition to be treated is pulmonary arterial hypertension.

In some embodiments, the disease or condition to be treated is pain selected from neuropathic pain and visceral pain.

In some embodiments, the disease or condition is cancer selected from chemoresistant breast carcinoma, adriamycin-resistant breast cancer, chemoresistant colorectal cancer, medulloblastoma, and tumor angiogenesis.

The invention also provides methods of treating, or the reducing risk of developing, anxiety, or depression, or cancer, comprising administering to a subject in need thereof a therapeutically effective amount of a compound of the invention (e.g., a compound of Formula I), or a pharmaceutical composition comprising said compound.

In some embodiments, the invention provides methods for treating, or reducing the risk of developing, pain, neuropathic pain, visceral pain, transplant-related FSGS, transplant-related nephrotic syndrome, transplant-related proteinuria, cholestatic liver disease, polycystic kidney disease, autosomal dominant polycystic kidney disease (ADPKD), obesity, insulin resistance, Type II diabetes, prediabetes, metabolic syndrome, non-alcoholic fatty liver disease (NAFLD), or non-alcoholic steatohepatitis (NASH).

Subjects to be Treated

In one aspect of the invention, a subject is selected on the basis that they have, or are at risk of developing, a kidney disease, anxiety, depression, or cancer. In another aspect of the invention, a subject is selected on the basis that they have, or are at risk of developing, pain, neuropathic pain, visceral pain, transplant-related FSGS, transplant-related nephrotic syndrome, transplant-related proteinuria, cholestatic liver disease, polycystic kidney disease, autosomal dominant polycystic kidney disease (ADPKD), obesity, insulin resistance, Type II diabetes, prediabetes, metabolic syndrome, non-alcoholic fatty liver disease (NAFLD), or non-alcoholic steatohepatitis (NASH).

Subjects that have, or are at risk of developing, proteinuria include those with diabetes, hypertension, or certain family backgrounds. In the United States, diabetes is the leading cause of end-stage renal disease (ESRD). In both type 1 and type 2 diabetes, albumin in the urine is one of the first signs of deteriorating kidney function. As kidney function declines, the amount of albumin in the urine increases. Another risk factor for developing proteinuria is hypertension. Proteinuria in a person with high blood pressure is an indicator of declining kidney function. If the hypertension is not controlled, the person can progress to full kidney failure. African Americans are more likely than Caucasians to have high blood pressure and to develop kidney problems from it, even when their blood pressure is only mildly elevated. Other groups at risk for proteinuria are American Indians, Hispanics/Latinos, Pacific Islander Americans, older adults, and overweight subjects.

In one aspect of the invention, a subject is selected on the basis that they have, or are at risk of developing proteinuria. A subject that has, or is at risk of developing, proteinuria is one having one or more symptoms of the condition. Symptoms of proteinuria are known to those of skill in the art and include, without limitation, large amounts of protein in the urine, which may cause it to look foamy in the toilet. Loss of large amounts of protein may result in edema, where swelling in the hands, feet, abdomen, or face may occur. These are signs of large protein loss and indicate that kidney disease has progressed. Laboratory testing is the only way to find out whether protein is in a subject's urine before extensive kidney damage occurs.

The methods are effective for a variety of subjects including mammals, e.g., humans and other animals, such as laboratory animals, e.g., mice, rats, rabbits, or monkeys, or domesticated and farm animals, e.g., cats, dogs, goats, sheep, pigs, cows, or horses. In some embodiments, the subject is a mammal. In some embodiments, the subject is a human.

EXAMPLES

The invention is further described in the following examples, which do not limit the scope of the invention described in the claims.

Example 1: Synthesis of Examplary Compounds of the Invention

The following illustrate synthetic routes to exemplary compounds of the invention.

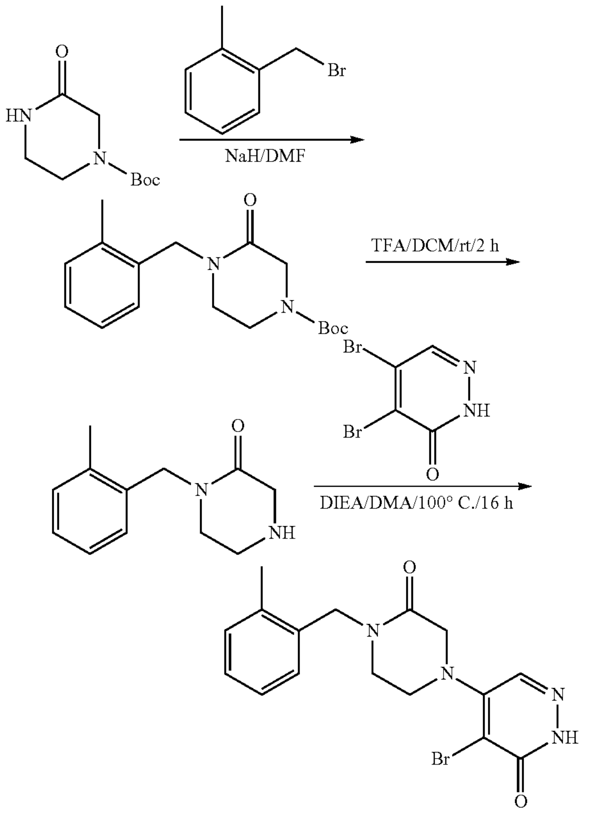

A

Preparation of Compound A

Tert-Butyl 4-[(2-methylphenyl)methyl]-3-oxopiperazine-1-carboxylate

To a solution of tert-butyl 3-oxopiperazine-1-carboxylate (1000 mg, 4.99 mmol, 1 equiv.) in DMF (20 mL, 258.44 mmol, 51.748 equiv.) were added NaH (239.7 mg, 5.99 mmol, 1.2 equiv., 60%) and 1-(bromomethyl)-2-methylbenzene (924.2 mg, 4.99 mmol, 1 equiv.) under nitrogen atmosphere. The reaction mixture was stirred at room temperature for 4 hours. The resulting mixture was extracted with ethyl acetate (3×20 mL). The combined organic layers were washed with water (3×100 mL), dried over anhydrous sodium sulfate. After filtration, the filtrate was concentrated under reduced pressure. The resulting solution was applied onto a reversed phase C18 column, eluted with 40%~80% (25 min) acetonitrile in water to afford tert-butyl 4-[(2-methylphenyl)methyl]-3-oxopiperazine-1-carboxylate (1320 mg, 85.97%) as a yellow oil.

1-[(2-methylphenyl)methyl]piperazin-2-one

To a solution of tert-butyl 4-[(2-methylphenyl)methyl]-3-oxopiperazine-1-carboxylate (1320 mg, 4.34 mmol, 1 equiv.) in DCM (20 mL, 314.60 mmol, 72.545 equiv.) was added TFA (5 mL, 67.32 mmol, 15.522 equiv.). The reaction mixture was stirred at room temperature for 16 hours. Upon completion, The resulting mixture was concentrated under reduced pressure to afford 1-[(2-methylphenyl)methyl]piperazin-2-one (1700 mg, 95.95%) as a yellow solid.

4-bromo-5-[4[(2-methylphenyl)methyl]-3-oxopiperazin-1-yl]-2,3-dihydropyridazin-3-one To a solution of 1-[(2-methylphenyl)methyl]piperazin-2-one (160.9 mg, 0.79 mmol, 2 equiv.) and K2CO3 (163.3 mg, 1.18 mmol, 3.00 equiv.) in DMA (3 mL, 32.27 mmol, 81.916 equiv.) was added 4,5-dibromo-2,3-dihydropyridazin-3-one (100 mg, 0.39 mmol, 1 equiv.) at ambient temperature. Then with stirring for 16 h at 70 degrees C. Trace desired product was detected by LCMS. The crude product was purified by Prep-HPLC with the following conditions (Column: XBridge Prep C18 OBD Column 19×150 mm 5 um; Mobile Phase A: Water (10 mmol/L NH4HCO3), Mobile Phase B: MeCN; Flow rate: 20 mL/min; Gradient: 20% B to 40% B in 9 min; 254/220 nm; Rt: 8.30 min) to afford 4-bromo-5-[4-[(2-methylphenyl)methyl]-3-oxopiperazin-1-yl]-2,3-dihydropyridazin-3-one (5.3 mg, 3.57%) as a white solid.

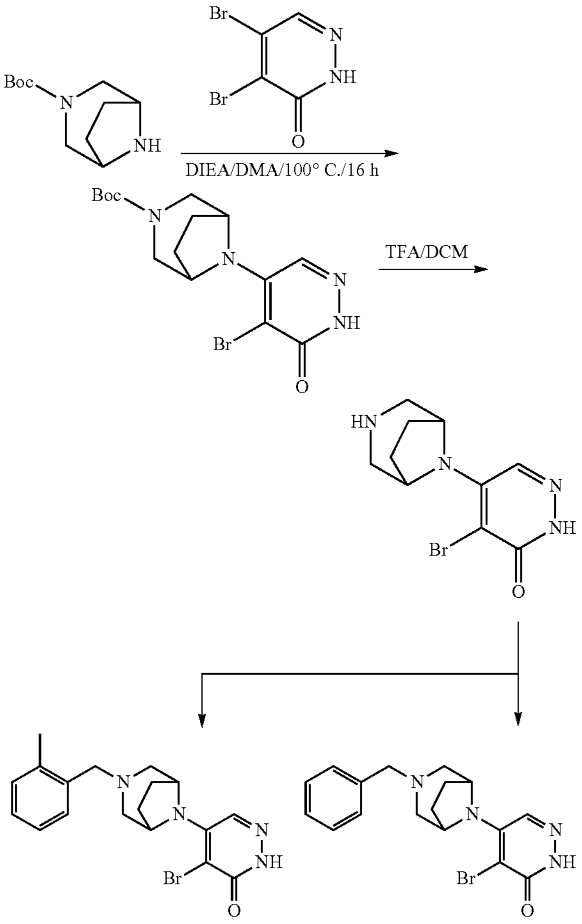

B C

Preparation of Compound B & Compound C

Tert-Butyl 8-(51-bromo-6-oxo-1,6-dihydropyridazin-4-yl)-3,8-diazabicyclo[3.2.1]octane-3-carboxylate A solution of tert-butyl 3,8-diazabicyclo[3.2.1]octane-3-carboxylate (600 mg, 2.828 mmol, 1 equiv.), 4,5-dibromo-2,3-dihydropyridazin-3-one (712 mg, 2.828 mmol, 1 equiv.) and DIEA (730.75 mg, 5.656 mmol, 2 equiv.) in DMA (3 mL) was stirred at 100 degrees C. overnight. The reaction mixture was purified by reverse phase flash with the following conditions: MeCN/H2O (0.05 mmol/L, NH4CO3) (5% to 60%, 30 min)) to afford tert-butyl 8-(5-bromo-6-oxo-1,6-dihydropyridazin-4-yl)-3,8-diazabicyclo[3.2.1]octane-3-carboxylate (500 mg, 45.92%) as a white solid.

4-bromo-5-[3,8-diazabicyclo[3.2.1]octan-8-yl]-2,3-dihydropyridazin-3-one

A solution of tert-butyl 8-(5-bromo-6-oxo-1,6-dihydropyridazin-4-yl)-3,8-diazabicyclo[3.2.1]octane-3-carboxylate (500 mg, 1.30 mmol, 1 equiv.) and 2,2,2-trifluoroacetaldehyde (3 mL) in DCM (10 mL) was stirred at rt overnight. The resulted mixture was purified by Prep-HPLC with the following conditions (Column: XBridge Prep C18 OBD Column 19*150 mm 5 um; Mobile Phase A: Water (10 mmol/L NH4HCO3), Mobile Phase B: MeCN; Flow rate: 20 mL/min; Gradient: 5% B to 26% B in 6.6 min; 254 nm; Rt: 5.58 min) to afford Products 4-bromo-5-[3,8-diazabicyclo[3.2.1]octan-8-yl]-2,3-dihydropyridazin-3-one (220 mg, 59.45%) as a light yellow solid.

Compound B 4-bromo-5-[4[(2-methylphenyl)methyl]piperazin-1-yl]-2,3-dihydropyridazin-3-one To a stirred solution of 4-bromo-5-[3,8-diazabicyclo[3.2.1]octan-8-yl]-2,3-dihydropyridazin-3-one (92 mg, 0.32 mmol, 1 equiv.) and Pyridine (51.0 mg, 0.65 mmol, 2 equiv.) in DMF (4 mL) was added 1-(bromomethyl)-2-methylbenzene (71.7 mg, 0.39 mmol, 1.201 equiv.) dropwise at rt. The reaction liquid was purified by Prep-HPLC with the following conditions (Column: XBridge Prep C18 OBD Column, 5 um, 19*150 mm; Mobile Phase A: Water (10 mmol/L NH4HCO3), Mobile Phase B: MeCN; Flow rate: 20 mL/min; Gradient: 50% B to 68% B in 7 min; 220 nm; Rt: 5.6 min) to afford 4-bromo-5-[4-[(2-methylphenyl)methyl]piperazin-1-yl]-2,3-dihydropyridazin-3-one (18.9 mg, 16.13%) as a white solid.

Compound C

5-[3-benzyl-3,8-diazabicyclo[3.2.1]octan-8-yl]-4-bromo-2,3-dihydropyridazin-3-one To a stirred solution of 4-bromo-5-[3,8-diazabicyclo[3.2.1]octan-8-yl]-2,3-dihydropyridazin-3-one (92 mg, 0.32 mmol, 1 equiv.) and pyridine (51.0 mg, 0.65 mmol, 2 equiv.) in DMF (4 mL) was added (bromomethyl)benzene (66.2 mg, 0.39 mmol, 1.2 equiv.) in portions at rt overnight. The reaction liquid was purified by Prep-HPLC with the following conditions (Column: XBridge Shield RP18 OBD Column, 5 um, 19*150 mm; Mobile Phase A: Water (10 mmol/L NH4HCO3), Mobile Phase B: MeCN; Flow rate: 20 mL/min; Gradient: 10% B to 90% B in 8 min; 254 nm; Rt: 7.53 min) to afford 5-[3-benzyl-3,8-diazabicyclo[3.2.1]octan-8-yl]-4-bromo-2,3-dihydropyridazin-3-one as a white solid.

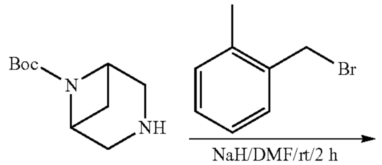

1

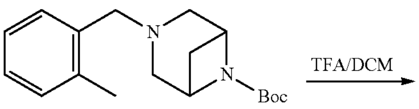

2

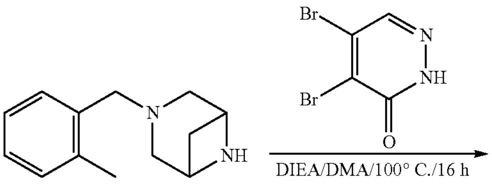

3

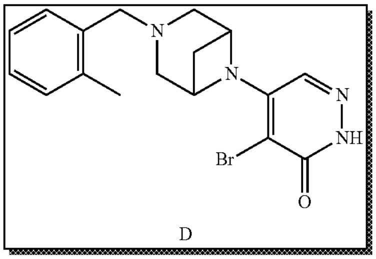

D

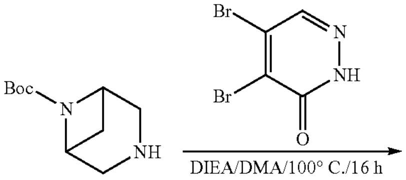

1

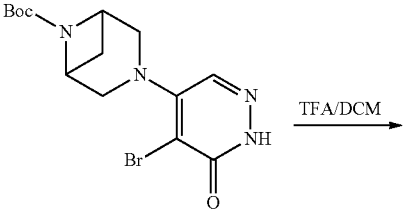

4

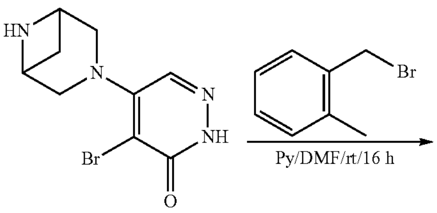

5

-continued

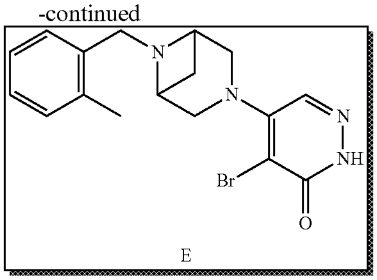

E

Preparation of D & E

Tert-Butyl 3-[(2-methylphenyl)methyl]-3,6-diazabicyclo[3.1.1]heptane-6-carboxylate To a solution of tert-butyl 3,6-diazabicyclo[3.1.1]heptane-6-carboxylate (300 mg, 1.51 mmol, 1 equiv.) was added NaH (90.8 mg, 2.27 mmol, 1.5 equiv., 60%) at room temperature. The reaction mixture was stirred for 1 h at room temperature. To the above mixture was added 1-(bromomethyl)-2-methylbenzene (420.0 mg, 2.27 mmol, 1.5 equiv.) dropwise at 0 degrees C. The resulted mixture was stirred for 16 h at room temperature. The reaction mixture was quenched by saturated aqueous NH4Cl. The resulted mixture was extracted with ethyl acetate (3*200 mL). The combined organic layers were washed with brine (200 mL), dried over anhydrous sodium sulfate and filtered. The filtrate was concentrated under reduced pressure. The residue was purified by Prep-TLC (petroleum ether/EA 30:1) to give tert-butyl 3-[(2-methylphenyl)methyl]-3,6-diazabicyclo[3.1.1]heptane-6-carboxylate (390 mg, 85.23%) as a light yellow solid.

3-[(2-methylphenyl)methyl]-3,6-diazabicyclo[3.1.1]heptane

To a solution of tert-butyl 3-[(2-methylphenyl)methyl]-3,6-diazabicyclo[3.1.1]heptane-6-carboxylate (390 mg, 1 equiv.) in DCM (10 mL) was added TFA (2 mL) at ambient temperature. The resulted mixture was stirred for 2 h at ambient temperature. The resulted mixture was concentrated under reduced pressure. The residue was basified to pH 8~9 with saturated NaHCO3 aqueous. The resulting mixture was diluted with water (50 mL) and extracted with ethyl acetate (3*50 mL). The combined organic layers were washed with brine (50 mL), dried over anhydrous sodium sulfate and filtered. The filtrate was concentrated under reduced pressure to afford 3-[(2-methylphenyl)methyl]-3,6-diazabicyclo[3.1.1]heptane (250 mg, 95.83%) as a yellow oil.

Compound D 4-bromo-5-[3-[(2-methylphenyl)methyl]-3,6-diazabicyclo[3.1.1]heptan-6-yl]-2,3-dihydropyridazin-3-one To a solution of 4,5-dibromo-2,3-dihydropyridazin-3-one (90.4 mg, 0.36 mmol, 1.2 equiv.) in DMA (2 mL, 21.51 mmol) were added 3-[(2-methylphenyl)methyl]-3,6-diazabicyclo[3.1.1]heptane (60 mg, 0.30 mmol, 1 equiv.) and DIEA (76.7 mg, 0.59 mmol, 2 equiv.) at room temperature. The resulted mixture was stirred for 16 h at 100 degrees C. The reaction mixture was purified by Prep-HPLC with the following conditions (Column: XBridge Prep C18 OBD Column 19×150 mm 5 um; Mobile Phase A: Water (10 mmol/L NH4HCO3), Mobile Phase B: MeCN; Flow rate: 20 mL/min; Gradient: 35% B to 65% B in 9 min; 254 nm; Rt: 7.4 min) to afford 4-bromo-5-[3-[(2-methylphenyl)methyl]-3,6-diazabicyclo[3.1.1]heptan-6-yl]-2,3-dihydropyridazin-3-one (5.1 mg, 4.58%) as a light yellow solid.

Tert-Butyl 3-(5-bromo-6-oxo-1,6-dihydropyridazin-4-yl)-3,6-diazabicyclo[3.1.1]heptane-6-carboxylate To a solution of 4,5-dibromo-2,3-dihydropyridazin-3-one (461.0 mg, 1.82 mmol, 1.2 equiv.) in DMA (10 mL, 107.55 mmol) were added tert-butyl 3,6-diazabicyclo[3.1.1]heptane-6-carboxylate (300 mg, 1.51 mmol, 1 equiv.) and DIEA (391.1 mg, 3.03 mmol, 2 equiv.) at ambient temperature. The resulted mixture was stirred for 16 h at 100 degrees C. The reaction mixture was diluted with water (200 mL) and extracted with ethyl acetate (3*200 mL). The combined organic layers were washed with brine (200 mL), dried over anhydrous sodium sulfate and filtered. The filtrate was concentrated under reduced pressure. The residue was purified by reverse phase flash with the following conditions (Column: spherical C18, 20-40 um, 330 g; Mobile Phase A: Water (5 mmol/L NH4HCO3), Mobile Phase B: MeCN; Flow rate: 80 mL/min; Gradient: 10% B to 60% B in 55 min; 254 nm) to afford tert-butyl 3-(5-bromo-6-oxo-1,6-dihydropyridazin-4-yl)-3,6-diazabicyclo[3.1.1]heptane-6-carboxylate (230 mg, 40.95%) as a light yellow solid.

4-bromo-5-[3,6-diazabicyclo[3.1.1]heptan-3-yl]-2,3-dihydropyridazin-3-one

To a solution of tert-butyl 3-(5-bromo-6-oxo-1,6-dihydropyridazin-4-yl)-3,6-diazabicyclo[3.1.1]heptane-6-carboxylate (230 mg, 0.62 mmol, 1 equiv.) in DCM (10 mL, 157.30 mmol) was added TFA (2 mL, 26.93 mmol) at ambient temperature. The resulted mixture was stirred for 2 h at ambient temperature. The resulted mixture was concentrated under reduced pressure. The residue was basified to pH 8~9 with saturated NaHCO3 (aq.). The resulted mixture was purified by Flash column with the following conditions (Column: spherical C18, 20-40 um, 330 g; Mobile Phase A: Water (5 mmol/L NH4HCO3), Mobile Phase B: MeCN; Flow rate: 80 mL/min; Gradient: 10% B to 60% B in 55 min; 254 nm) to afford 4-bromo-5-[3,6-diazabicyclo[3.1.1]heptan-3-yl]-2,3-dihydropyridazin-3-one (110 mg, 65.49%) as a white solid.

Compound E: 4-bromo-5-[6-[(2-methylphenyl)methyl]-3,6-diazabicyclo[3.1.1]heptan-3-yl]-2,3-dihydropyridazin-3-one To a solution of 4-bromo-5-[3,6-diazabicyclo[3.1.1]heptan-3-yl]-2,3-dihydropyridazin-3-one (70 mg, 0.26 mmol, 1 equiv.) and Pyridine (40.8 mg, 0.52 mmol, 2 equiv.) in DMF (2 mL, 25.84 mmol) was added 1-(bromomethyl)-2-methylbenzene (62.1 mg, 0.34 mmol, 1.3 equiv.) at room temperature. The resulted mixture was stirred for 16 h at room temperature. The reaction mixture was purified by Prep-HPLC with the following conditions (Column: XBridge Prep C18 OBD Column 19×150 mm 5 um; Mobile Phase A: Water (10 mmol/L NH4HCO3), Mobile Phase B: MeCN; Flow rate: 20 mL/min; Gradient: 28% B to 50% B in 7 min; 254 nm; Rt: 6.53 min) to afford 4-bromo-5-[6-[(2-methylphenyl)methyl]-3,6-diazabicyclo[3.1.1]heptan-3-yl]-2,3-dihydropyridazin-3-one (10.4 mg, 10.73%) as a white solid.

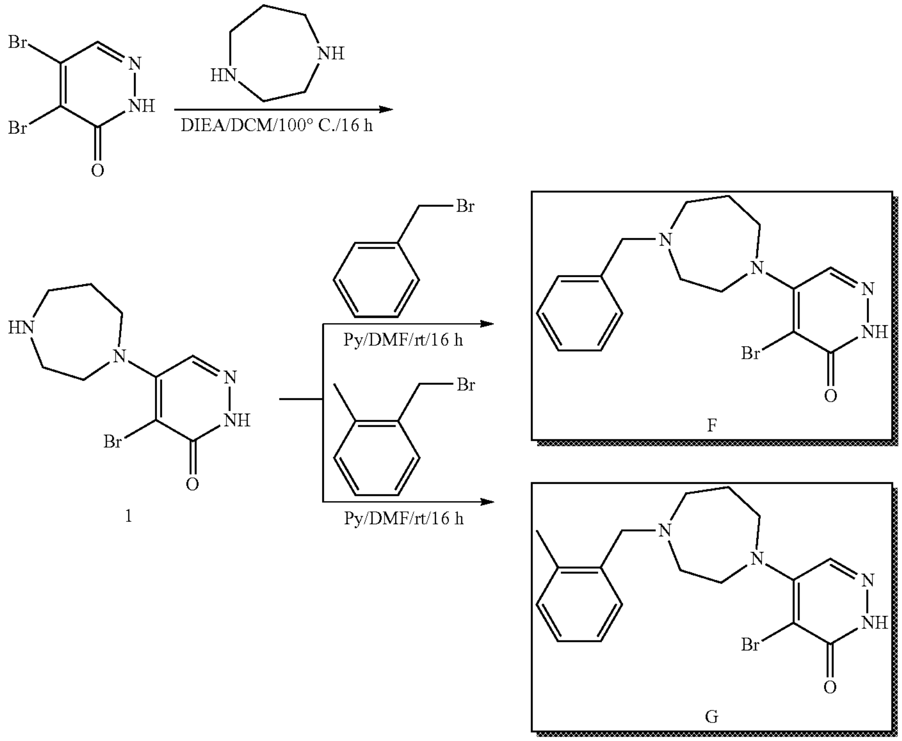

1

F

G

Preparation of F & G 4-bromo-5-(1,4-diazepan-1-yl)-2,3-dihydro-pyridazin-3-one

To a solution of 4,5-dibromo-2,3-dihydropyridazin-3-one (2.52 g, 9.93 mmol, 1 equiv.) and DIEA (3.8 g, 29.78 mmol, 3 equiv.) in DMA (30 mL) was added 1,4-diazepane (2.0 g, 19.85 mmol, 2 equiv.) at ambient temperature under air atmosphere. Then with stirring at 90 degrees C. for 16 h. Trace desired product was detected by LCMS. The solution was purified by reverse phase flash with the following conditions ((Column: c18 OBD Column, 5 um, 19*330 mm; Mobile Phase A: Water (5 mmol/L $NaHCO_3$), Mobile Phase B: MeCN; Flow rate: 80 mL/min; Gradient: 25% B to 65% B in 8 min; 254 nm; Rt: 7.3 min) to afford 4-bromo-5-(1,4-diazepan-1-yl)-2,3-dihydropyridazin-3-one (400 mg, 14.75°/o) as an off-white solid.

Compound F 5-(4-benzyl-1,4-diazepan-1-yl)-4-bromo-2,3-dihydropyridazin-3-one

To a solution of 4-bromo-5-(1,4-diazepan-1-yl)-2,3-dihydropyridazin-3-one (60 mg, 0.22 mmol, 1 equiv.) were added pyridine (34.8 mg, 0.44 mmol, 2 equiv.) and (bromomethyl)benzene (45.1 mg, 0.26 mmol, 1.200 equiv.) in DMF (5 mL) at 25 degrees C. The resulting mixture was stirred for 16 h at at ambient temperature. The desired product could be detected by LCMS. The reaction mixture was concentrated under reduced pressure. The crude product was purified by Prep-HPLC with the following conditions (Column: XBridge Prep C18 OBD Column 19×150 mm 5 um; Mobile Phase A: Water (10 mmol/L NH4HCO3), Mobile Phase B: MeCN; Flow rate: 20 mL/min; Gradient: 30% B to 52.5% B in 7 min; 254 nm; Rt: 6.33 min) to afford 5-(4-benzyl-1,4-diazepan-1-yl)-4-bromo-2,3-dihydro-pyridazin-3-one (27.5 mg, 34.46%) as a white solid.

Compound G 4-bromo-5-[4 [(2-methylphenyl)methyl]-1,4-diazepan-1-yl]-2,3-dihydropyridazin-3-one To a solution of 4-bromo-S-(1,4-diazepan-1-yl)-2,3-dihydropyridazin-3-one (60 mg, 0.22 mmol, 1 equiv.) were added 1-(bromomethyl)-2-methylbenzene (48.8 mg, 0.26 mmol, 1.200 equiv.) and pyridine (34.8 mg, 0.44 mmol, 2.003 equiv.) in DMF (4 mL) at 25 degrees C. The resulting mixture was stirred for 16 h at at ambient temperature. The desired product could be detected by LCMS. The reaction mixture was concentrated under reduced pressure. The crude product was purified by Prep-HPLC with the following conditions (Column: XBridge Prep C18 OBD Column 19×150 mm 5 um; Mobile Phase A: Water (10 mmol/L NH4HCO3), Mobile Phase B: MeCN; Flow rate: 20 mL/min; Gradient: 35% B to 61.3% B in 8 min; 254 nm; Rt: 7.45 min) to afford 4-bromo-5-[4-[(2-methylphenyl)methyl]-1,4-diazepan-1-yl]-2,3-dihydropyridazin-3-one (23.1 mg, 27.87%) as an off-white solid.

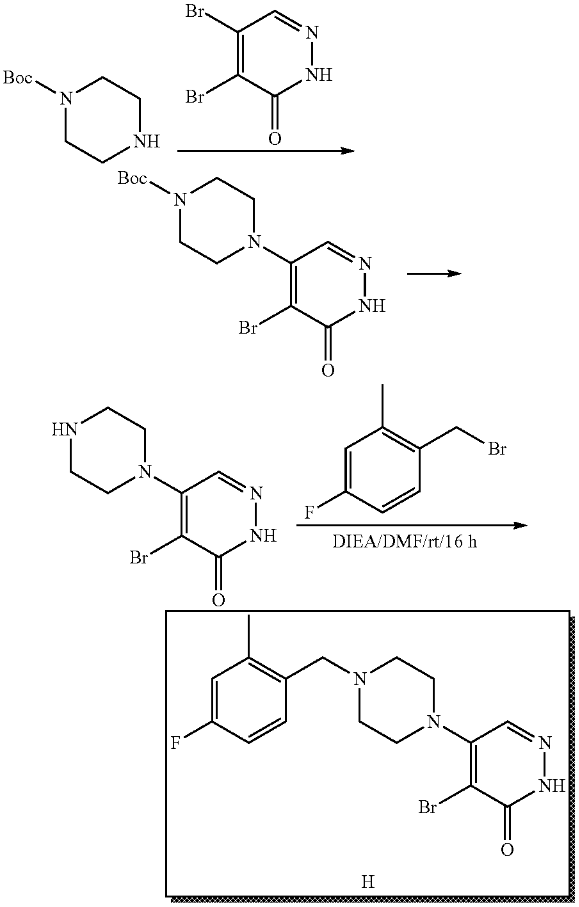

H

Preparation of Compound H

Tert-Butyl 4-(5-bromo-6-oxo-1,6-dihydropyridazin-4-yl) piperazine-1-carboxylate

To a solution of 4,5-dibromo-2,3-dihydropyridazin-3-one (2 g, 7.88 mmol, 1 equiv.) in DMA (40.0 mL, 459.14 mmol, 54.611 equiv.) were added tert-butyl piperazine-1-carboxylate (1.8 g, 9.45 mmol, 1.2 equiv.) and DIEA (2.0 g, 15.76 mmol, 2 equiv.) at room temperature. The resulted mixture was stirred for 16 h at 100 degrees C. The reaction mixture was diluted by water (200 mL) and extracted with ethyl acetate (3*200 mL). The combined organic layers were washed with brine (200 mL), dried over anhydrous sodium sulfate and filtered. The filtrate was concentrated under reduced pressure. The residue was purified by silica gel column chromatography, eluted with petroleum ether/EA (200:1 to 50:1) to afford tert-butyl 4-(5-bromo-6-oxo-1,6-dihydropyridazin-4-yl)piperazine-1-carboxylate (1.92 g, 67.85%) as a yellow solid.

4-bromo-5-(piperazin-1-yl)-2,3-dihydropyridazin-3-one

To a solution of tert-butyl 4-(5-bromo-6-oxo-1,6-dihydropyridazin-4-yl)piperazine-1-carboxylate (1.92 g, 1 equiv.) in DCM (40 mL) was added TFA (8 mL) at room temperature. The resulted mixture was stirred for 2 h at room temperature. The reaction mixture was concentrated under reduced pressure. The residue was basified to PH 8~9 with saturated NaHCO3 (aq.). The mixture was purified by reverse phase flash with the following conditions (Column: spherical C18, 20-40 um, 330 g; Mobile Phase A: Water (5 mmol/L NH4HCO3), Mobile Phase B: MeCN; Flow rate: 80 mL/min; Gradient: 10% B to 60% B in 55 min; 254 nm) to afford 4-bromo-5-(piperazin-1-yl)-2,3-dihydropyridazin-3-one (790 mg, 57.04%) as a yellow solid.

Compound H 4-bromo-5-[4[(4-fluoro-2-methylphenyl)methyl] piperazin-1-yl]-2,3-dihydropyridazin-3-one To a stirred solution/mixture of 4-bromo-5-(piperazin-1-yl)-2,3-dihydropyridazin-3-one (80 mg, 0.31 mmol, 1 equiv.) and Pyridine (48.8 mg, 0.62 mmol, 2 equiv.) in Solvents DMF (4 mL) was added 1-(bromomethyl)-4-fluoro-2-methylbenzene (69.0 mg, 0.34 mmol, 1.1 equiv.) in portions at rt overnight. The reaction liquid was purified by Prep-HPLC with the following conditions (Column: XBridge Prep C18 OBD Column, 5 um, 19*150 mm; Mobile Phase A: Water (10 mmol/L NH4HCO3), Mobile Phase B: MeCN; Flow rate: 20 mL/min; Gradient: 35% B to 65% B in 7 min; 254 nm; Rt: 6.03 min) to afford 4-bromo-5-[4-[(4-fluoro-2-methylphenyl)methyl]piperazin-1-yl]-2,3-dihydropyridazin-3-one as a white solid.

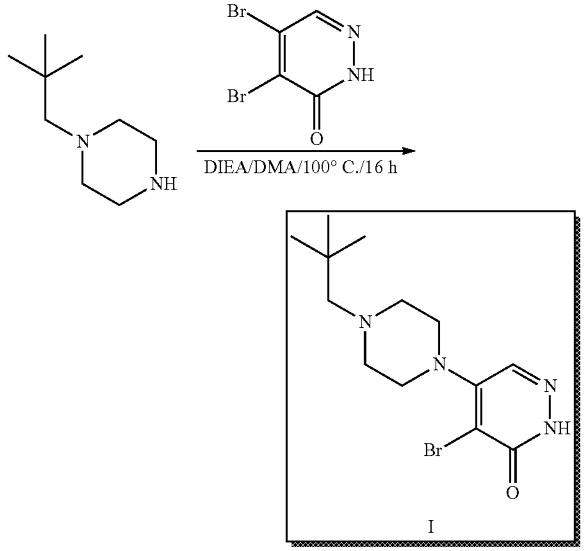

I

Preparation of Compound I 4-bromo-5-[4-(2,2-dimethylpropyl)piperazin-1-yl]-2,3-dihydropyridazin-3-one To a stirred solution of 1-(2,2-dimethylpropyl)piperazine (100 mg, 0.397 mmol, 1 equiv.) and DIEA (102.58 mg, 0.794 mmol, 2 equiv.) in DMF (2 mL) was added 4,5-dibromo-2,3-dihydropyridazin-3-one (93 mg, 0.595 mmol, 1.2 equiv.) in portions at 100 degrees C. for 12 hours. The reaction liquid was purified by Prep-HPLC with the following conditions (Column: XBridge Prep C18 OBD Column 19×150 mm 5 um; Mobile Phase A: Water (10 mmol/L NH4HCO3), Mobile Phase B: MeCN; Flow rate: 20 mL/min; Gradient: 50% B to 70% B in 9 min; 254/220 nm; Rt: 6.27 min) to afford 4-bromo-5-[4-(2,2-dimethylpropyl) piperazin-1-yl]-2,3-dihydropyridazin-3-one (19.4 mg, 9.21%) as a white solid.

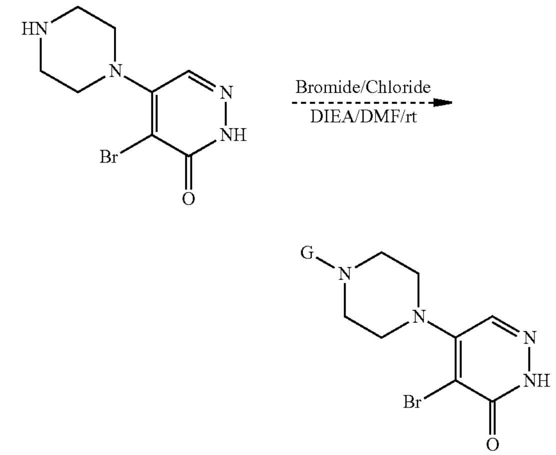

Targets

| Target ID | Structures |
|---|---|
| J | 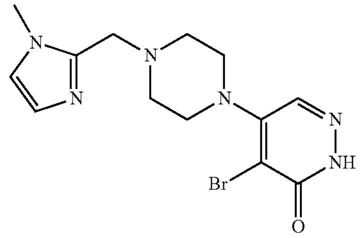 [SMILES: Cn1ccnc1CN1CCN(c2cn[nH]c(=O)c2Br)CC1] |
| K | 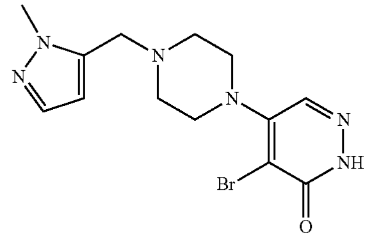 [SMILES: Cn1nccc1CN1CCN(c2cn[nH]c(=O)c2Br)CC1] |
| L | 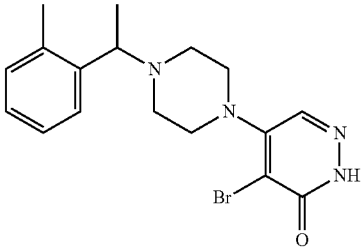 [SMILES: Cc1ccccc1C(C)N1CCN(c2cn[nH]c(=O)c2Br)CC1] |

Preparation of Compounds J, K, and L

Compound J: 4-bromo-5-[4-[(1-methyl-1H-imidazol-2-yl)methyl]piperazin-1-yl]-2,3-dihydropyridazin-3-one To a stirred solution of 4-bromo-5-(piperazin-1-yl)-2,3-dihydropyridazin-3-one (80 mg, 0.31 mmol, 1 equiv.) and DIEA (119.7 mg, 0.93 mmol, 3 equiv.) in DMF (4 mL) was added 2-(chloromethyl)-1-methyl-1H-imidazole (60.5 mg, 0.46 mmol, 1.5 equiv.) in portions at rt overnight. The reaction liquid was purified by Prep-HPLC with the following conditions (Column: XBridge Prep C18 OBD Column, 5 um, 19*150 mm; Mobile Phase A: Water (10 mmol/L NH4HCO3), Mobile Phase B: MeCN; Flow rate: 20 mL/min; Gradient: 5% B to 28% B in 7 min; 254 nm; Rt: 6.32 min) to afford 4-bromo-5-[4-[(1-methyl-1H-imidazol-2-yl)methyl]piperazin-1-yl]-2,3-dihydropyridazin-3-one (33.3 mg, 30.53%) as a white solid.

Compound K: 4-bromo-5-[4-[(1-methyl-1H-pyrazol-5-yl)methyl]piperazin-1-yl]-2,3-dihydropyridazin-3-one To a stirred solution of 4-bromo-5-(piperazin-1-yl)-2,3-dihydropyridazin-3-one (80 mg, 0.31 mmol, 1 equiv.) and DIEA (119.7 mg, 0.93 mmol, 3 equiv.) in Solvents DMF (4 mL) was added 5-(chloromethyl)-1-methyl-1H-pyrazole (60.5 mg, 0.46 mmol, 1.5 equiv.) in portions at rt overnight. The reaction liquid was purified by Prep-HPLC with the following conditions (Column: XBridge Prep C18 OBD Column, 5 um, 19*150 mm; Mobile Phase A: Water (10 mmol/L NH4HCO3), Mobile Phase B: MeCN; Flow rate: 20 mL/min; Gradient: 5% B to 34% B in 7 min; 254 nm; Rt: 6.47 min) to afford 4-bromo-5-[4-[(1-methyl-1H-pyrazol-5-yl)methyl]piperazin-1-yl]-2,3-dihydropyridazin-3-one (39 mg, 35.76%) as a white solid.

Preparation of Compound L 1-(1-chloroethyl)-2-methylbenzene

A solution of 1-(2-methylphenyl)ethan-1-ol (500 mg, 3.67 mmol, 1 equiv.) and sulfonyl chloride (873.6 mg, 7.34 mmol, 2 equiv.) in DCM (5 mL) was stirred at rt for 3 hours. The resulting mixture was concentrated under reduced pressure. This resulted in 1-(1-chloroethyl)-2-methylbenzene (400 mg, 70.46%) as a light yellow oil.

Compound L: 4-bromo-5-[4-[1-(2-methylphenyl)ethyl]piperazin-1-yl]-2,3-dihydropyridazin-3-one To a stirred solution of 4-bromo-5-(piperazin-1-yl)-2,3-dihydropyridazin-3-one (80 mg, 0.31 mmol, 1 equiv.) and DIEA (119.7 mg, 0.93 mmol, 3 equiv.) in DMF (4 mL) was added 1-(1-chloroethyl)-2-methylbenzene (71.6 mg, 0.46 mmol, 1.500 equiv.) in portions at rt overnight. The reaction liquid was purified by Prep-HPLC with the following conditions (Column: XBridge Prep C18 OBD Column 19*150 mm 5 um; Mobile Phase A: Water (10 mmol/L NH4HCO3), Mobile Phase B: MeCN; Flow rate: 20 mL/min; Gradient: 35% B to 50% B in 11 min; 254/220 nm; Rt: 10.14 min) to afford 4-bromo-5-[4-[1-(2-methylphenyl)ethyl]piperazin-1-yl]-2,3-dihydropyridazin-3-one (7.2 mg, 6.18%) as a white solid.

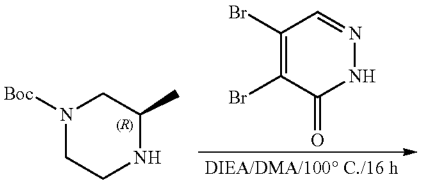

-continued

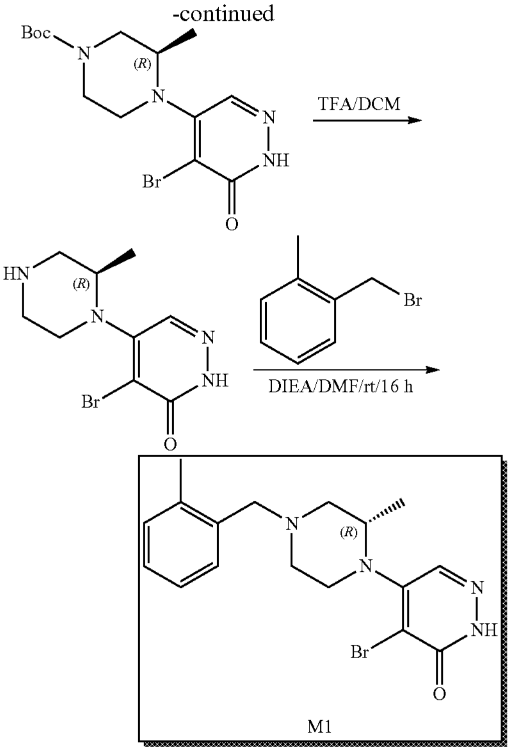

M1

Preparation of Compound M1

Tert-Butyl (3R)-4-(5-bromo-6-oxo-1,6-dihydropyridazin-4-yl)-3-methylpiperazine-1-carboxylate To a stirred solution of tert-butyl (3R)-3-methylpiperazine-1-carboxylate (500 mg, 2.50 mmol, 1 equiv.) and DIEA (645.3 mg, 4.99 mmol, 2 equiv.) in DMF (5 mL) was added 4,5-dibromo-2,3-dihydropyridazin-3-one (760.6 mg, 3.00 mmol, 1.2 equiv.) in portions at 100 degrees C. overnight. The residue product was purified by reverse phase flash with the following conditions: MeCN/H2O (35%~75°6.45 min) to afford tert-butyl (3R)-4-(5-bromo-6-oxo-1,6-dihydropyridazin-4-yl)-3-methylpiperazine-1-carboxylate (150 mg, 16.10%) as a yellow oil.

4-bromo-5-[(2R)-2-methylpiperazin-1-yl]-2,3-dihydropyridazin-3-one

To a stirred solution of tert-butyl (3R)-4-(5-bromo-6-oxo-1,6-dihydropyridazin-4-yl)-3-methylpiperazine-1-carboxylate (150 mg, 0.40 mmol, 1 equiv.) in DCM (3 mL) was added TFA (1 mL) in portions at rt overnight. The resulting mixture was concentrated under reduced pressure. This resulted in 4-bromo-5-[(2R)-2-methylpiperazin-1-yl]-2,3-dihydropyridazin-3-one (100 mg, 91.10%) as a yellow oil.

Compound M1: 4-bromo-5-[(2R)-2-methyl-4-[(2-methylphenyl)methyl]piperazin-1-yl]-2,3-dihydropyridazin-3-one To a stirred solution of 4-bromo-5-[(2R)-2-methylpiperazin-1-yl]-2,3-dihydropyridazin-3-one (150 mg, 0.55 mmol, 1 equiv.) and DIEA (142.0 mg, 1.10 mmol, 2 equiv.) in DMF (4 mL) was added 1-(bromomethyl)-2-methylbenzene (122.0 mg, 0.66 mmol, 1.200 equiv.) in portions at rt overnight. The reaction liquid was purified by Prep-HPLC with the following conditions (Column: XBridge Prep C18 OBD Column, 5 um, 19*150 mm; Mobile Phase A: Water (10 mmol/L NH4HCO3), Mobile Phase B: MeCN; Flow rate: 20 mL/min; Gradient: 45% B to 65% B in 9 min; 254 nm; Rt: 7.55 min) to afford 4-bromo-5-[(2R)-2-methyl-4-[(2-methylphenyl)methyl]piperazin-1-yl]-2,3-dihydro-pyridazin-3-one (13.6 mg, 6.56%) as a white solid.

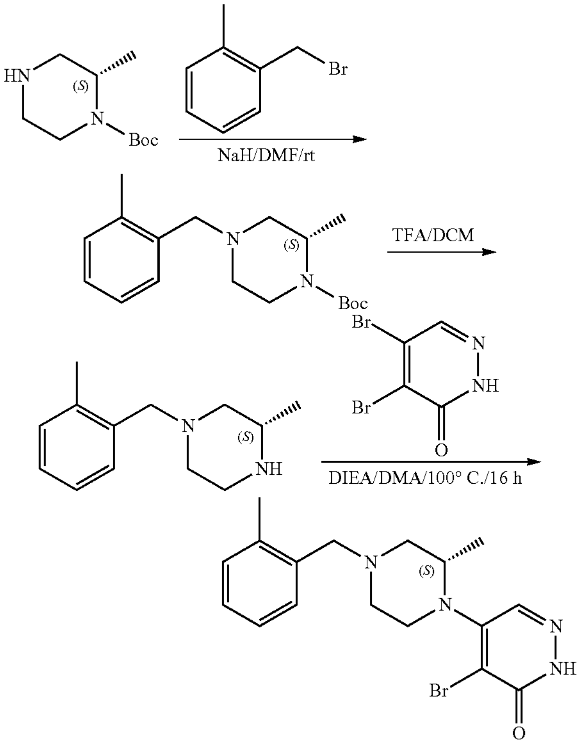

M2

Preparation of Compound M2

Tert-Butyl (3S)-4-(5-bromo-6-oxo-1,6-dihydro-pyridazin-4-yl)-3-methylpiperazine-1-carboxylate To a stirred solution of tert-butyl (2S)-2-methylpiperazine-1-carboxylate (500 mg, 2.50 mmol, 1 equiv.) and NaH (89.9 mg, 3.74 mmol, 1.5 equiv.) in DMF (5 mL) was added 1-(bromomethyl)-2-methylbenzene (693.0 mg, 3.74 mmol, 1.5 equiv.) dropwise at rt overnight. The reaction liquid was purified by reverse phase flash with the following conditions: MeCN/H2O(NH4CO3:5%) (MeCN: 45%~90%, 30 min) to afford tert-butyl (2S)-2-methyl-4-[(2-methylphenyl) methyl]piperazine-1-carboxylate as a light yellow solid.

(3S)-3-methyl-1-[(2-methylphenyl)methyl]piperazine

To a stirred solution of tert-butyl (2S)-2-methyl-4-[(2-methylphenyl)methyl]piperazine-1-carboxylate (770 mg, 2.53 mmol, 1 equiv.) in DCM (6 mL) was added TFA (2 mL) in portions at rt for 1.5 hours. The resulting mixture was concentrated under reduced pressure. This resulted in (3S)-3-methyl-1-[(2-methylphenyl)methyl]piperazine (500 mg, 96.75%) as a yellow oil.

Compound M2: 4-bromo-5-[(2S)-2-methyl-4-[(2-methylphenyl)methyl]piperazin-1-yl]-2,3-dihydro-pyridazin-3-one To a stirred solution of (3S)-3-methyl-1-[(2-methylphenyl)methyl]piperazine (500 mg, 2.45 mmol, 1 equiv.) and DIEA (632.6 mg, 4.89 mmol, 2 equiv.) in DMA (5 mL) was added 4,5-dibromo-2,3-dihydropyridazin-3-one (745.6 mg, 2.94 mmol, 1.2 equiv.) in portions at 100 degrees C. overnight.

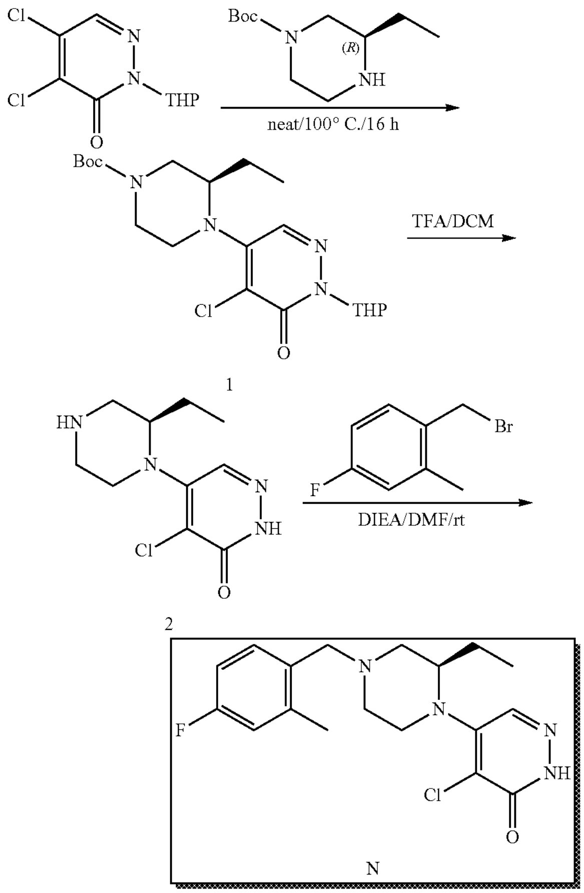

Tert-Butyl (3R)-4-[5-chloro-1-(oxan-2-yl)-6-oxo-1,6-dihydropyridazin-4-yl]-3-ethylpiperazine-1-carboxylate To a seal tube was added 4,5-dichloro-2-(oxan-2-yl)-2,3-dihydropyridazin-3-one (500 mg, 2.01 mmol, 1 equiv.) with tert-butyl (3R)-3-ethylpiperazine-1-carboxylate (645.3 mg, 3.01 mmol, 1.500 equiv.). The mixture was kept at 100 degrees C. for 16 h. after cooling to ambient temperature. The mixture was dissolved into DMF (4 mL) and purified by seal tube reversed phase chromatography (120 g column), eluting with 40%~60% MeCN in water (plus 10 mmol NH4HCO3). Desired fractions was collected at 60% and concentrated to give desired product tert-butyl (3R)-4-[5-chloro-1-(oxan-2-yl)-6-oxo-1,6-dihydropyridazin-4-yl]-3-ethylpiperazine-1-carboxylate (400 mg, 46.68%) as light yellow solid (400 mg). The resulting was used in the next step directly.

4-chloro-5-[(2R)-2-ethylpiperazin-1-yl]-2,3-dihydro-pyridazin-3-one

The residue/crude product was purified by reverse phase flash with the following conditions ( ) to afford Products as a Color State. To a solution of tert-butyl (3R)-4-[5-chloro-1-(oxan-2-yl)-6-oxo-1,6-dihydropyridazin-4-yl]-3-ethylpiperazine-1-carboxylate (400 mg, 0.94 mmol, 1 equiv.) in DCM (20 mL) were added TFA (3 mL, 40.39 mmol, 43.109 equiv.) in portions at room temperature. The mixture was stirred for 16 h and monitored by LCMS. The resulting mixture was concentrated under reduced pressure.

Compound N: 4-chloro-5-[(2R)-2-ethyl-4-[(4-fluoro-2-methylphenyl)methyl]piperazin-1-yl]-2,3-dihydropyridazin-3-one To a stirred solution of 4-bromo-5-[(2R)-2-ethylpiperazin-1-yl]-2,3-dihydropyridazin-3-one (30 mg, 0.12 mmol, 1 equiv.) and DIEA (48 mg, 0.37 mmol, 2 equiv.) in DMF was added 1-(bromomethyl)-2-methylbenzene (37.6 mg, 0.19 mmol, 1.5 equiv.). The reaction liquid was purified by Prep-HPLC with the following conditions (Column: XBridge Prep C18 OBD Column, 5 um, 19*150 mm; Mobile Phase to afford 4-chloro-5-[(2R)-2-ethyl-4-[(4-fluoro-2-methylphenyl)methyl]piperazin-1-yl]-2,3-dihydropyridazin-3-one as a white solid.

mmol, 2 equiv.) in portions at rt overnight. The crude product was purified by reverse phase flash with the following conditions: MeCN/H2O(NH4CO3: 5%) (MeCN: 50%-95%) to afford tert-butyl 6-(5-bromo-6-oxo-1,6-dihydropyridazin-4-yl)-2,6-diazaspiro[3.3]heptane-2-carboxylate (889 mg, 47.48%) as a dark yellow solid.

4-bromo-5-[2,6-diazaspiro[3.3]heptan-2-yl]-2,3-dihydropyridazin-3-one

A solution of tert-butyl 6-(5-bromo-6-oxo-1,6-dihydropyridazin-4-yl)-2,6-diazaspiro[3.3]heptane-2-carboxylate (899 mg, 2.42 mmol, 1 equiv.) and TFA (2 mL) in DCM (6 mL) was stirred at rt overnight. The resulting mixture was concentrated under reduced pressure. This resulted in 4-bromo-5-[2,6-diazaspiro[3.3]heptan-2-yl]-2,3-dihydropyridazin-3-one (600 mg, 91.39%) as a light yellow oil.

Compound O: 5-[6-benzyl-2,6-diazaspiro[3.3]heptan-2-yl]-4-bromo-2,3-dihydropyridazin-3-one To a stirred solution of 4-bromo-5-[2,6-diazaspiro[3.3]heptan-2-yl]-2,3-dihydropyridazin-3-one (200 mg, 0.74 mmol, 1 equiv.) and DIEA (190.7 mg, 1.48 mmol, 2 equiv.) in DMF (5 mL) was added (bromomethyl)benzene (151.4

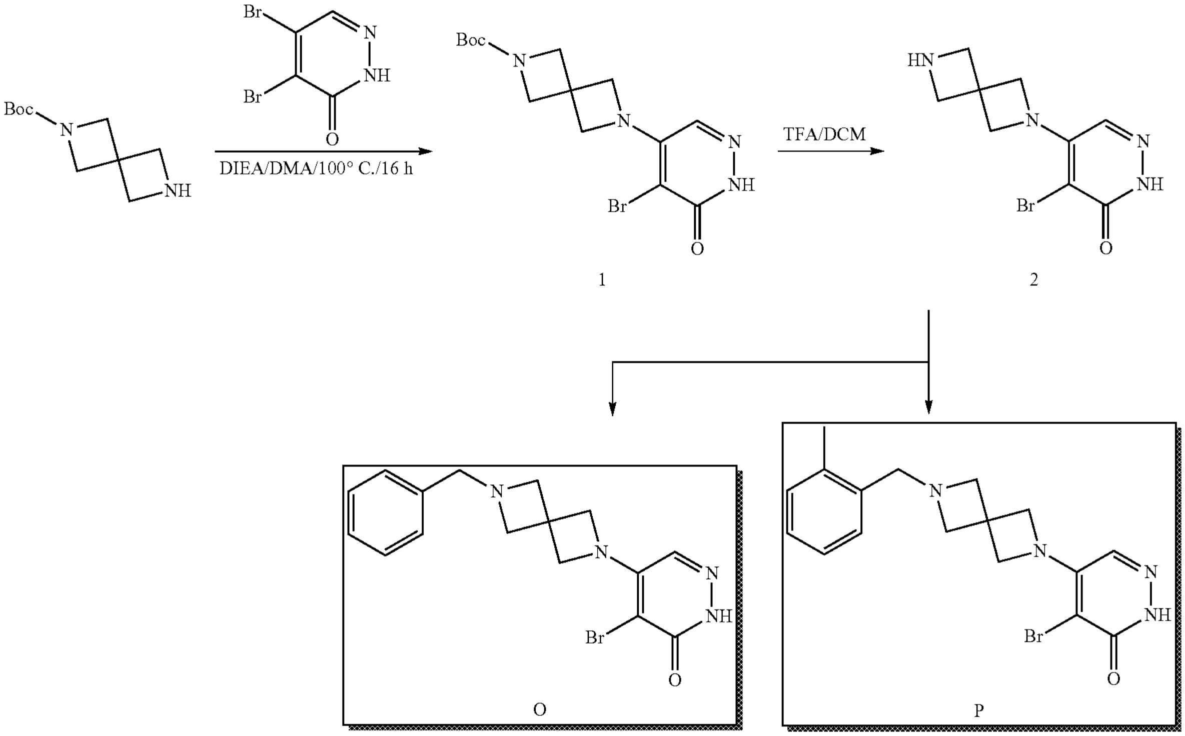

Preparation of: Tert-Butyl 6-(5-bromo-6-oxo-1,6-dihydropyridazin-4-yl)-2,6-diazaspiro[3.3]heptane-2-carboxylate To a stirred solution/mixture of tert-butyl 2,6-diazaspiro[3.3]heptane-2-carboxylate (1 g, 5.04 mmol, 1 equiv.) and 4,5-dibromo-2,3-dihydropyridazin-3-one (1.5 g, 6.05 mmol, 1.2 equiv.) in DMF (10 mL) was added DIEA (1.3 g, 10.09 mg, 0.89 mmol, 1.200 equiv.) in portions at rt overnight. The crude product was purified by Prep-HPLC with the following conditions (Column: XBridge Prep C18 OBD Column 19×150 mm 5 um; Mobile Phase A: Water (0.05% TFA), Mobile Phase B: MeCN; Flow rate: 20 mL/min; Gradient: 5% B to 35% B in 9 min; 254/220 nm; Rt: 6.74 min) to afford 5-[6-benzyl-2,6-diazaspiro[3.3]heptan-2-yl]-4-bromo-2,3-dihydropyridazin-3-one as a white solid.

Compound P: 4-bromo-5-[6-[(2-methylphenyl)methyl]-2,6-diazaspiro[3.3]heptan-2-yl]-2,3-dihydropyridazin-3-one To a stirred solution of 4-bromo-5-[2,6-diazaspiro[3.3]heptan-2-yl]-2,3-dihydropyridazin-3-one (200 mg, 0.74 mmol, 1 equiv.) and DIEA (190.7 mg, 1.48 mmol, 2 equiv.) in DMF (5 mL) was added 1-(bromomethyl)-2-methylbenzene (163.8 mg, 0.89 mmol, 1.2 equiv.) in portions at rt overnight. The crude product was purified by Prep-HPLC with the following conditions (Column: XBridge Prep C18 OBD Column 19×150 mm 5 um; Mobile Phase A: Water (0.05% TFA), Mobile Phase B: MeCN; Flow rate: 20 mL/min; Gradient: 5% B to 35% B in 9 min; 254/220 nm; Rt: 7.47 min) to afford 4-bromo-5-[6-[(2-methylphenyl)methyl]-2,6-diazaspiro[3.3]heptan-2-yl]-2,3-dihydropyridazin-3-one as a white solid.

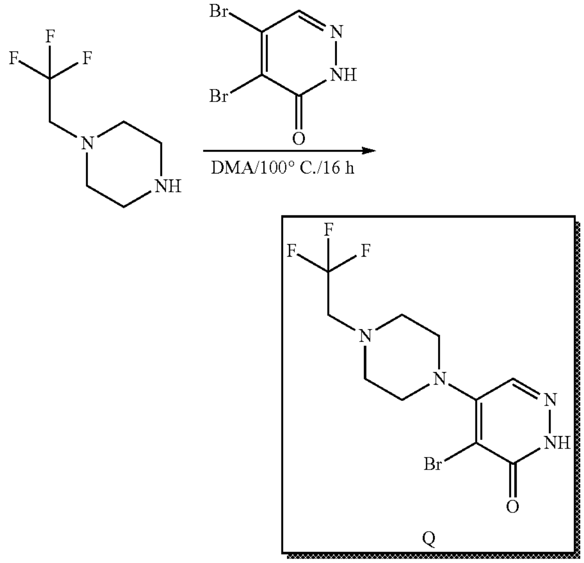

Q

Compound Q: 4-bromo-5-[4-(2,2,2-trifluoroethyl)piperazin-1-yl]-2,3-dihydropyridazin-3-one To a stirred solution of 4,5-dibromo-2,3-dihydropyridazin-3-one (60 mg, 0.238 mmol, 1 equiv.) and DIEA (61.5 mg, 0.476 mmol, 2 equiv.) in DMA (3 mL) was added 1-(2,2,2-trifluoroethyl)piperazine (48 mg, 0.286 mmol, 1.2 equiv.) in portions at 100 degrees C. for 1.5 hours. The reaction liquid was purified by Prep-HPLC with the following conditions (Column: XBridge Prep C18 OBD Column 19×150 mm 5 um; Mobile Phase A: Water (10 mmol/L NH4HCO3), Mobile Phase B: MeCN; Flow rate: 20 mL/min; Gradient: 20% B to 45% B in 7.5 min; 254/220 nm; Rt: 7.17 min) to afford 4-bromo-5-[4-(2,2,2-trifluoroethyl)piperazin-1-yl]-2,3-dihydropyridazin-3-one (12.3 mg, 15.26%) as a white solid.

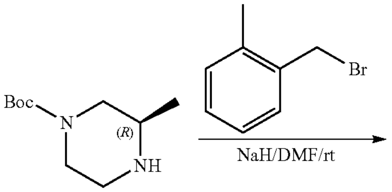

-continued

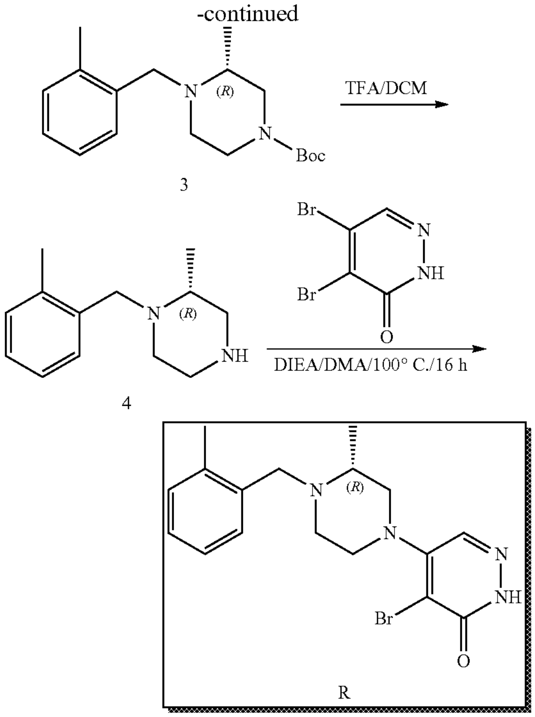

3

4

R

Preparation of Compound R

Tert-Butyl (3R)-3-methyl-4-[(2-methylphenyl)methyl]piperazine-1-carboxylate

To a stirred solution of tert-butyl (3R)-3-methylpiperazine-1-carboxylate (500 mg, 2.50 mmol, 1 equiv.) and NaH (89.9 mg, 3.74 mmol, 1.5 equiv.) in DMF (5 mL) was added 1-(bromomethyl)-2-methylbenzene (693.0 mg, 3.74 mmol, 1.5 equiv.) in portions at rt overnight. The crude product was purified by reverse phase flash with the following conditions: MeCN/H2O(NH4CO3: 5%) (MeCN: 45%~85%) to afford tert-butyl (3R)-3-methyl-4-[(2-methylphenyl)methyl]piperazine-1-carboxylate (400 mg, 52.63°%) as a light yellow solid.

(2R)-2-methyl-1-[(2-methylphenyl)methyl]piperazine

To a stirred solution of tert-butyl (3R)-3-methyl-4-[(2-methylphenyl)methyl]piperazine-1-carboxylate (600 mg, 1.97 mmol, 1 equiv.) in DCM (6 mL) was added TFA (2 mL) in portions at rt for 1.5 hours. The resulting mixture was concentrated under reduced pressure. This resulted in (2R)-2-methyl-1-[(2-methylphenyl)methyl]piperazine (400 mg) as a yellow oil.

Compound R: 4-bromo-5-[(3R)-3-methyl-4-[(2-methylphenyl)methyl]piperazin-1-yl]-2,3-dihydropyridazin-3-one To a stirred solution of (2R)-2-methyl-1-[(2-methylphenyl)methyl]piperazine (400 mg, 1.96 mmol, 1 equiv.) and DIEA (506.1 mg, 3.92 mmol, 2 equiv.) in DMA (5 mL) was added 4,5-dibromo-2,3-dihydropyridazin-3-one (596.5 mg, 2.35 mmol, 1.200 equiv.) in portions at 100 degrees C. overnight. The reaction liquid was purified by Prep-HPLC with the following conditions (Column: XBridge Prep C18 OBD Column 19×150 mm 5 um; Mobile Phase A: Water (10 mmol/L NH4HCO3), Mobile Phase B: MeCN; Flow rate: 20 mL/min; Gradient: 40% B to 60% B in 9 min; 254/220 nm; Rt: 8.45 min) to afford 4-bromo-5-[(3R)-3-methyl-4-[(2-methylphenyl)methyl]piperazin-1-yl]-2,3-dihydro-pyridazin-3-one (18.7 mg, 2.53%) as a white solid.

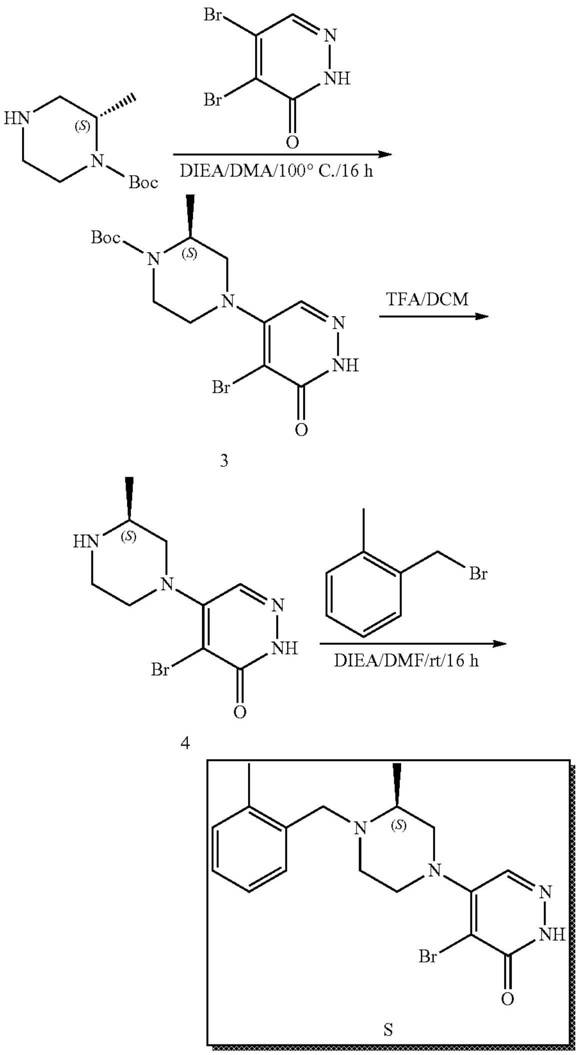

3

4

S

Preparation of Compound S

Tert-Butyl (2S)-4-(5-bromo-6-oxo-1,6-dihydro-pyridazin-4-yl)-2-methylpiperazine-1-carboxylate To a stirred solution of tert-butyl (2S)-2-methylpiperazine-1-carboxylate (1 g, 4.99 mmol, 1 equiv.) and DIEA (1.3 g, 9.99 mmol, 2 equiv.) in DMA (10 mL) was added 4,5-dibromo-2,3-dihydropyridazin-3-one (1.5 g, 5.91 mmol, 1.183 equiv.) in portions at 100 degrees C. overnight. The reaction liquid was purified by reverse phase flash with the following conditions: MeCN/H2O(NH4CO3: 5%) (MeCN: 50%-95%, 40 min) to afford tert-butyl (2S)-4-(5-bromo-6-oxo-1,6-dihydropyridazin-4-yl)-2-methylpiperazine-1-carboxylate (1.2 g, 64.39%) as a yellow solid.

4-bromo-5-[(3S)-3-methylpiperazin-1-yl]-2,3-dihydropyridazin-3-one

To a stirred solution of tert-butyl (2S)-4-(5-bromo-6-oxo-1,6-dihydropyridazin-4-yl)-2-methylpiperazine-1-carboxylate (1.2 g, 3.22 mmol, 1 equiv.) in DCM (9 mL) was added TFA (3 mL, 40.39 mmol) in portions at rt for 1.5 hours. The resulting mixture was concentrated under reduced pressure. This resulted in 4-bromo-5-[(3S)-3-methylpiperazin-1-yl]-2,3-dihydropyridazin-3-one (900 mg, 102.49%) as a yellow oil.

Compound S: 4-bromo-5-[(3S)-3-methyl-4-[(2-methylphenyl)methyl]piperazin-1-yl]-2,3-dihydro-pyridazin-3-one To a stirred solution of 4-bromo-5-[(3S)-3-methylpiperazin-1-yl]-2,3-dihydropyridazin-3-one (900 mg, 3.30 mmol, 1 equiv.) and DIEA (851.7 mg, 6.59 mmol, 2 equiv.) in DMF (8 mL) was added 1-(bromomethyl)-2-methylbenzene (731.8 mg, 3.95 mmol, 1.2 equiv.) in portions at rt overnight. The reaction liquid was purified by Prep-HPLC with the following conditions (Column: XBridge Prep C18 OBD Column 19×150 mm 5 um; Mobile Phase A: Water (10 mmol/L NH4HCO3), Mobile Phase B: MeCN; Flow rate: 20 mL/min; Gradient: 40% B to 65% B in 9 min; 254/220 nm; Rt: 7.97 min) to afford 4-bromo-5-[(3S)-3-methyl-4-[(2-methylphenyl)methyl]piperazin-1-yl]-2,3-dihydro-pyridazin-3-one (40.3 mg, 3.24%) as a light yellow solid.

Preparation of compounds T-AS shown in the tables below follows the methods and protocols as described for the synthesis of AM starting with the appropriate benzylic bromide or chloride and using either 4,5-dibromo-2,3-dihydropyridazin-3-one or 4,5-dichloro-2,3-dihydropyridazin-3-one as appropriate.

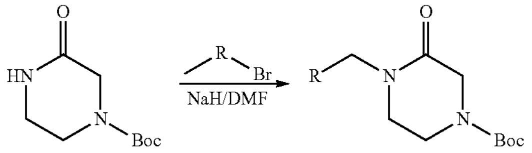

1

| Target ID | 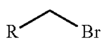 |
|---|---|
| T | 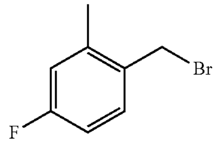 |
| U | 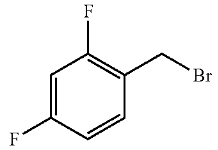 |
| V | 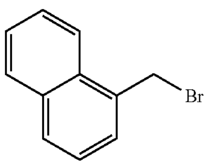 [SMILES: BrCc1cccc2ccccc12] |

-continued
| | |
|---|---|
| W | 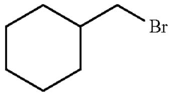 |
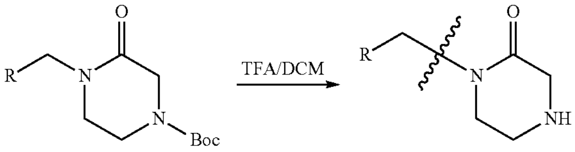
1 2
| Target ID | R |
|---|---|
| X | 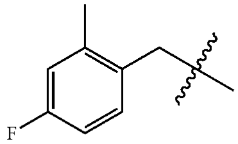 [SMILES: *Cc1ccc(F)cc1C] |
| Y | 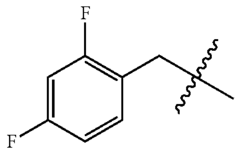 [SMILES: *Cc1ccc(F)cc1F] |
| Z | 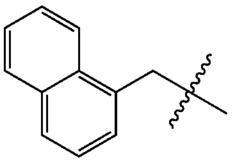 [SMILES: *Cc1cccc2ccccc12] |
| AA | 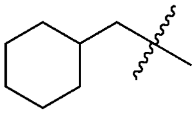 [SMILES: *CC1CCCCC1] |
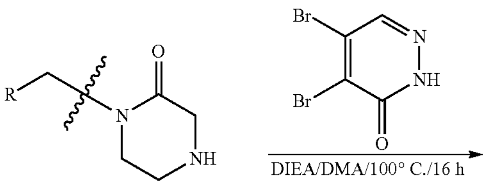
2
-continued
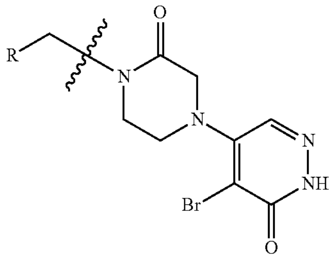
Targets
| Target ID | R |
|---|---|
| AB | 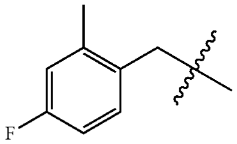 [SMILES: *Cc1ccc(F)cc1C] |
| AC | 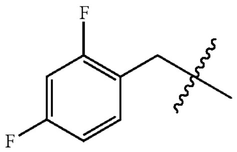 [SMILES: *Cc1ccc(F)cc1F] |
| AD | 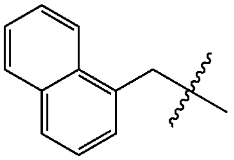 [SMILES: *Cc1cccc2ccccc12] |
| AE | 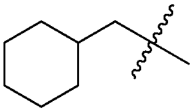 [SMILES: *CC1CCCCC1] |
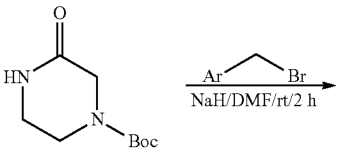
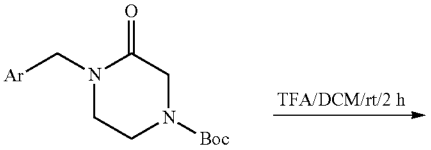
1

-continued

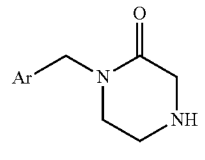

2

| Ar | Target ID |
|---|---|
| 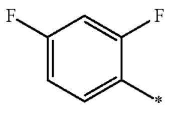 | AF |
| 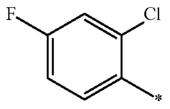 | AG |
| 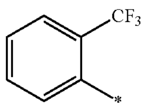 | AH |
| 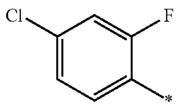 | AI |
| 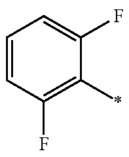 | AJ |
| 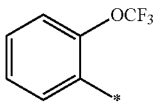 | AK |
| 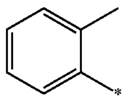 | AL |

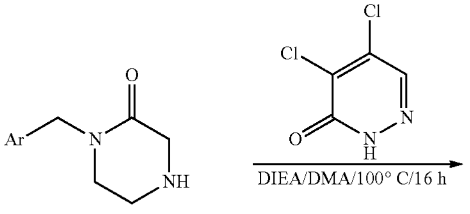

2

-continued

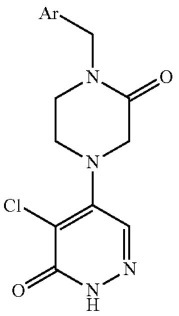

Targets

| Target ID | Ar |
|---|---|
| AM | 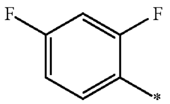 |
| AN | 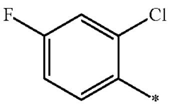 |
| AO | 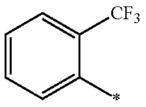 |
| AP | 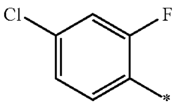 |
| AQ | 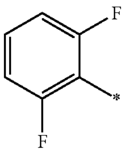 |
| AR | 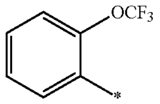 |
| AS | 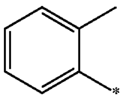 |

Tert-Butyl 4-[(2,4-difluorophenyl)methyl]-3-oxopiperazine-1-carboxylate

To a solution of tert-butyl 3-oxopiperazine-1-carboxylate (300 mg, 1.50 mmol, 1 equiv.) in DMF (5 mL) was added NaH (89.9 mg, 2.25 mmol, 1.5 equiv., 60%) at room temperature. The resulting mixture was stirred for 0.5 h at room temperature. To the above mixture was added 1-(bromomethyl)-2,4-difluorobenzene (465.2 mg, 2.25 mmol, 1.5 equiv.) dropwise at room temperation. The resulting mixture was stirred for additional 16 h at room temperature. The reaction was monitored by LCMS. The reaction was quenched with water (100 mL). The resulting mixture was extracted with EtOAc (3×100 mL). The combined organic layers were washed with brine (100 mL), dried over anhydrous MgSO4. After filtration, the filtrate was concentrated under reduced pressure. The residue was purified by Prep-TLC (petroleum ether/EA 3:1) to afford tert-butyl 4-[(2,4-difluorophenyl)methyl]-3-oxopiperazine-1-carboxylate (410 mg, 83.86%) as a white solid.

1-[(2,4-difluorophenyl)methyl]piperazin-2-one

To a solution of tert-butyl 4-[(2,4-difluorophenyl)methyl]-3-oxopiperazine-1-carboxylate (410 mg, 1.26 mmol, 1 equiv.) in DCM (10 mL) was added TFA (2 mL, 26.93 mmol, 21.432 equiv.) at room temperature. The resulting mixture was stirred for 3 h at room temperature. The reaction was monitored by LCMS. The resulting mixture was concentrated under reduced pressure. The residue was basified to pH 8~9 with saturated NaHCO3 (aq.). The resulting mixture was extracted with EtOAc (3×50 mL). The combined organic layers were washed with brine (100 mL), dried over anhydrous MgSO4. After filtration, the filtrate was concentrated under reduced pressure to afford 1-[(2,4-difluorophenyl)methyl]piperazin-2-one (220 mg, 77.41%) as a light yellow oil.

Compound AM: 4-chloro-5-[4[(2,4-difluorophenyl)methyl]-3-oxopiperazin-1-yl]-2,3-dihydropyridazin-3-one To a solution of 4,5-dichloro-2,3-dihydropyridazin-3-one (65.6 mg, 0.40 mmol, 1 equiv.) in DMA (2 mL) were added 1-[(2,4-difluorophenyl)methyl]piperazin-2-one (90 mg, 0.40 mmol, 1 equiv.) and DIEA (102.8 mg, 0.80 mmol, 2 equiv.) at room temperation. The resulting mixture was stirred for 16 h at 100 degrees C. The reaction was monitored by LCMS. The product was purified by reverse phase flash with the following conditions (Column: spherical C18, 20-40 um, 120 g; Mobile Phase A: Water (5 mmol/L NH4HCO3), Mobile Phase B: MeCN; Flow rate:45 mL; min; Gradient: 20% B to 40% B in 25 min; 220 nm) to afford 4-chloro-5-[4-[(2,4-difluorophenyl)methyl]-3-oxopiperazin-1-yl]-2,3-dihydropyridazin-3-one (28.6 mg, 20.27%) as a yellow solid.

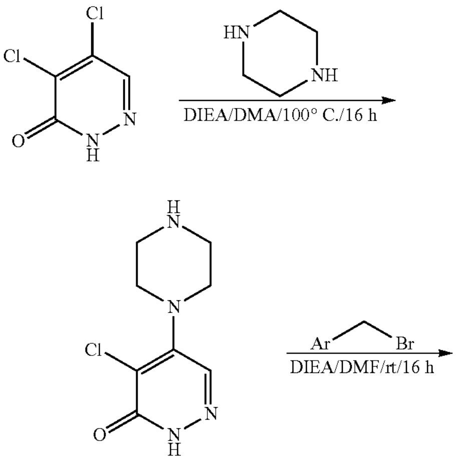

1

-continued

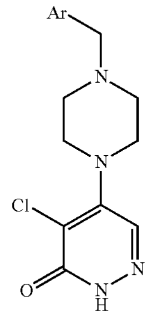

Targets

| Target ID | Ar |
|---|---|
| AT | 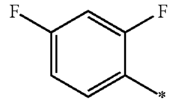 |
| AU | 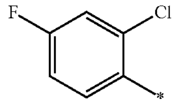 |
| AV | 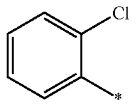 |
| AW | 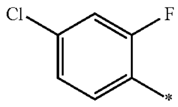 |
| AX | 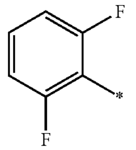 |
| AY | 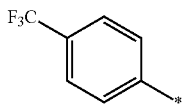 |

Preparation c f compounds AT-AY follows similar methods and protocols as described for the synthesis of AT starting with the appropriate benzylic bromide or chloride as appropriate.

4-chloro-5-(piperazin-1-yl)-2,3-dihydropyridazin-3-one

To a solution of 4,5-dichloro-2,3-dihydropyridazin-3-one (10 g, 60.61 mmol, 1 equiv.) in DMA (100 mL) were added piperazine (10.4 g, 121.23 mmol, 2 equiv.) and DIEA (15.7 g, 121.23 mmol, 2 equiv.) at room temperature. The resulting mixture was stirred for 16 h at 100 degrees C. The reaction was monitored by LCMS. The resulting mixture was filtered, the filter cake was washed with EtOH (100 mL). The filtrate was precipitated by the addition of Et2O (1000 mL). The crude mixture was washed with EtOH (100 mL) to afford 4-chloro-5-(piperazin-1-yl)-2,3-dihydropyridazin-3-one (10.31 g, 79.24%) as a yellow solid.

Compound AT: 4-chloro-5-[4[(2,4-difluorophenyl) methyl]piperazin-1-yl]-2,3-dihydropyridazin-3-one To a solution of 4-chloro-5-(piperazin-1-yl)-2,3-dihydropyridazin-3-one (100 mg, 0.47 mmol, 1 equiv.) and DIEA (120.4 mg, 0.93 mmol, 2 equiv.) in DMF (5 mL) was added 1-(bromomethyl)-2,4-difluorobenzene (144.7 mg, 0.70 mmol, 1.500 equiv.) at room temperature. The resulting mixture was stirred for 16 h at room temperature. The reaction was monitored by LCMS. The product was purified by reverse phase flash with the following conditions (Column: spherical C18, 20-40 um, 120 g; Mobile Phase A: Water (5 mmol/L NH4HCO3), Mobile Phase B: MeCN; Flow rate: 45 mL/min; Gradient: 10% B to 60% B in 55 min; 220 nm) to afford 4-chloro-5-[4-[(2,4-difluorophenyl) methyl]piperazin-1-yl]-2,3-dihydropyridazin-3-one (97.3 mg, 61.29%) as a white solid.

Synthesis of Compound AZ 4-methyl-5-[4 [(2-methylphenyl)methyl]-3-oxopiperazin-1-yl]-2,3-dihydropyridazin-3-one

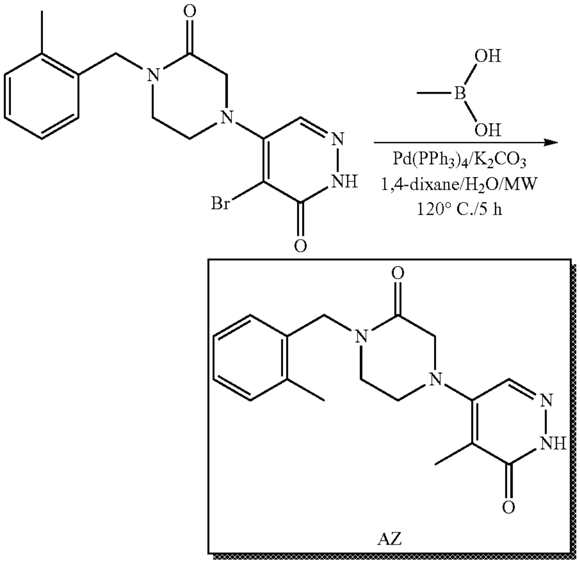

AZ

Synthesis of Compound BA

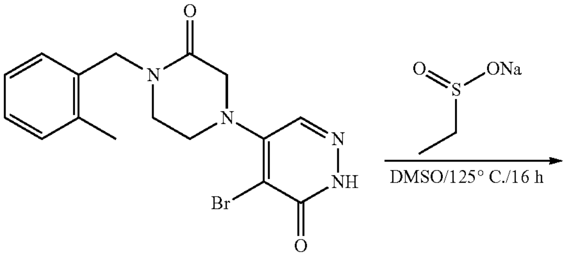

-continued

Synthesis of Compound BB

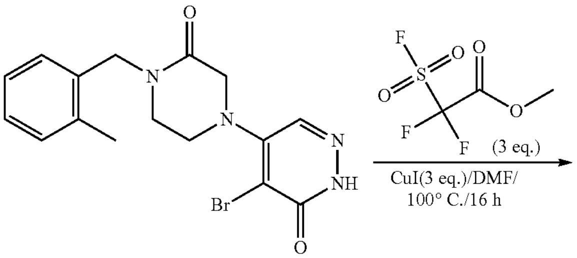

BB

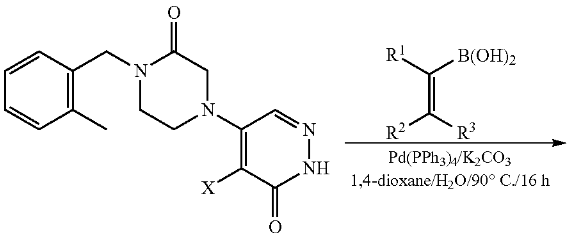

X = Br, Cl

-continued

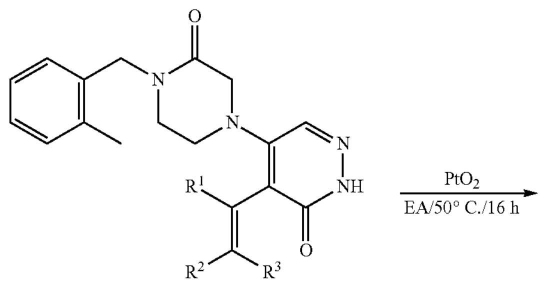

1

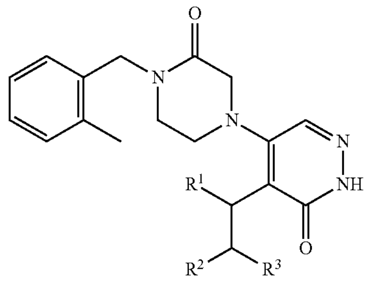

| Target ID | R group |
|---|---|
| BC | 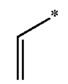 |
| BD | 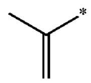 |
| BE | 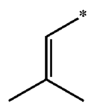 |
| BF | 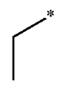 |
| BG | 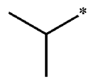 |
| BH | 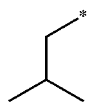 |

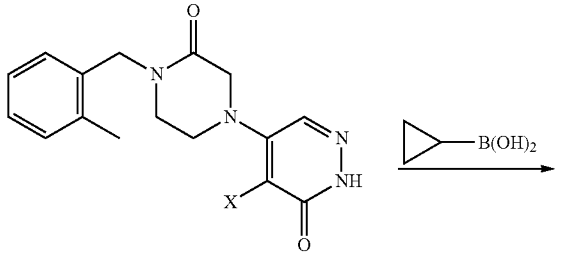

X = Br, Cl

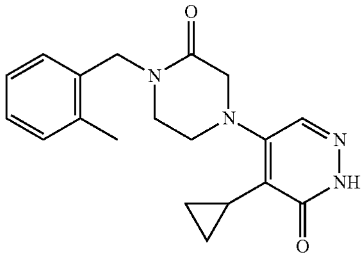

BI

| SM | Conditions |
|---|---|
| Chloride | $K_2CO_3$/Pd(OAc)/$PCy_3$ 1,4-dioxane/$H_2O$/MW/110° C./2 h |
| Bromide | $K_2CO_3$/Pd(OAc)/$PCy_3$ 1,4-dioxane/$H_2O$/MW/110° C./2 h |

Preparation of Compounds BC, and BE-BI follows the methods as described for preparation of BG below.

Compound BD: 5-[4-[(2-methylphenyl)methyl]-3-oxopiperazin-1-yl]-4-(prop-1-en-2-yl)-2,3-dihydro-pyridazin-3-one To a solution of 4-bromo-5-[4-[(2-methylphenyl)methyl]-3-oxopiperazin-1-yl]-2,3-dihydropyridazin-3-one (200 mg, 0.53 mmol, 1 equiv.) in 1,4-dioxane (5 mL) and water (1 mL) were added 4,4,5,5-tetramethyl-2-(prop-1-en-2-yl)-1,3,2-dioxaborolane (178.2 mg, 1.06 mmol, 2.000 equiv.), Pd(PPh3)4 (61.3 mg, 0.05 mmol, 0.1 equiv.) and K2CO3 (146.5 mg, 1.06 mmol, 2 equiv.) in a sealed table under nitrogen atmosphere at room temperature. The resulting mixture was stirred for 16 h at 90 degrees C. The desired product could be detected by LCMS. The reaction mixture was diluted with water (100 mL). extracted with EA (100 mL×2). The organic layers was washed with saturated brine (100 mL), dried over anhydrous Na2SO4, filtered and concentrated to give desired product. The residue was purified by Prep-TLC (DCM/MeOH 20:1) to afford crude product. The crude product was purified by Prep-HPLC with the following conditions ( ) to afford 5-[4-[(2-methylphenyl)methyl]-3-oxopiperazin-1-yl]-4-(prop-1-en-2-yl)-2,3-dihydropyridazin-3-one (10.1 mg, 5.63%) as a yellow solid.

Compound BG: 5-[4-[(2-methylphenyl)methyl]-3-oxopiperazin-1-yl]-4-(propan-2-yl)-2,3-dihydro-pyridazin-3-one To a solution of 5-[4-[(2-methylphenyl)methyl]-3-oxopiperazin-1-yl]-4-(prop-1-en-2-yl)-2,3-dihydro-pyridazin-3-one (40 mg, 0.12 mmol, 1 equiv.) in 15 mL EtOAc was added PtO2 (5.4 mg, 0.02 mmol, 0.201 equiv.)

under nitrogen atmosphere in a 100 mL round-bottom flask. The mixture was hydrogenated at 50 degrees C. for overnight under hydrogen atmosphere using a hydrogen balloon, filtered through a Celite pad and concentrated under reduced pressure. The crude product was purified by Prep-HPLC with the following conditions (Column: XBridge Prep OBD C18 Column 30×150 mm 5 um; Mobile Phase A: Water (10 mmol/L NH4HCO3), Mobile Phase B: MeCN; Flow rate: 60 mL/min; Gradient: 30% B to 50% B in 7 min; 254/220 nm; Rt: 5.03 min) to afford 5-[4-[(2-methylphenyl)methyl]-3-oxopiperazin-1-yl]-4-(propan-2-yl)-2,3-dihydropyridazin-3-one (14 mg, 34.79%) as a white solid.

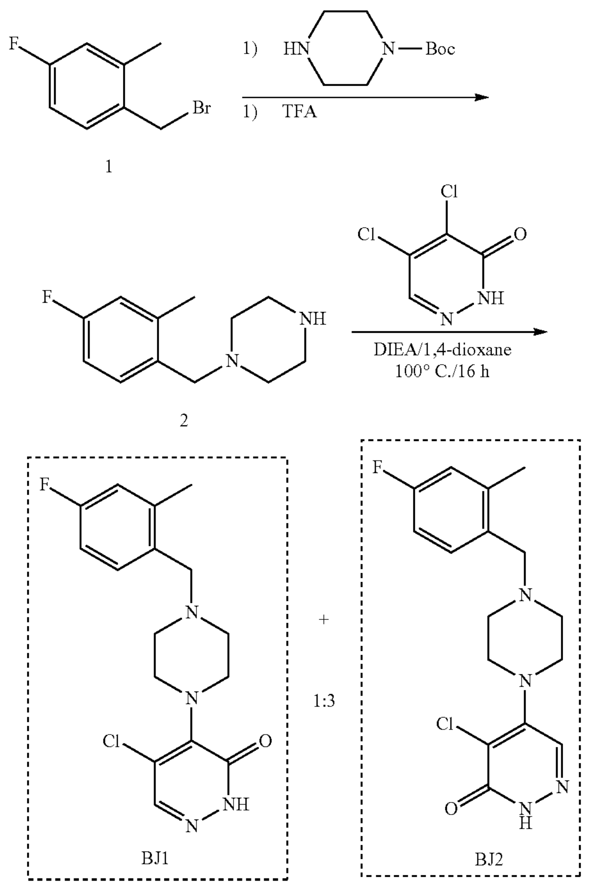

Compounds BJ1 and BJ2

Tert-Butyl 4-[(4-fluoro-2-methyl phenyl)methyl] piperazine-1-carboxylate

To a stirred solution of tert-butyl piperazine-1-carboxylate (9.2 g, 49.25 mol, 1 equiv.) and ethylbis(propan-2-yl) amine (12.7 g, 98.50 mol, 2 equiv.) in DCM was added 1-(bromomethyl)-4-fluoro-2-methylbenzene (10 g, 49.25 mmol, 1 equiv.) was stirred for 16 h at rt. The reaction was monitored by LCMS. The resulting mixture was extracted with DCM (3×100 mL). The combined organic layers were washed with brine (1×200 mL), dried over anhydrous Na2SO4. After filtration, the filtrate was concentrated under reduced pressure to afford tert-butyl 4-[(4-fluoro-2-methylphenyl)methyl]piperazine-1-carboxylate (14 g, 92.18%) as a white solid.

1-[(4-fluoro-2-methylphenyl)methyl]piperazine

To a stirred solution of tert-butyl 4-[(4-fluoro-2-methylphenyl)methyl]piperazine-1-carboxylate (14 g, 45.40 mmol, 1 equiv.) in DCM (300 mL) was added trifluoroacetic acid (30 mL) dropwise at rt. The resulting mixture was stirred for additional 1 h at rt. The reaction was monitored by LCMS. The resulting mixture was concentrated under reduced pressure. The mixture was basified to pH 8 with saturated NaHCO3 (aq.). The resulting mixture was extracted with DCM (3×300 mL). The combined organic layers were dried over anhydrous Na2SO4. After filtration, the filtrate was concentrated under reduced pressure to afford 1-[(4-fluoro-2-methylphenyl)methyl]piperazine (9.1 g, 96.24%) as colorless oil.

5-chloro-4-[4-[(4-fluoro-2-methylphenyl)methyl] piperazin-1-yl]-2,3-dihydropyridazin-3-one & 4-chloro-5-[4-[(4-fluoro-2-methylphenyl)methyl] piperazin-1-yl]-2,3-dihydropyridazin-3-one

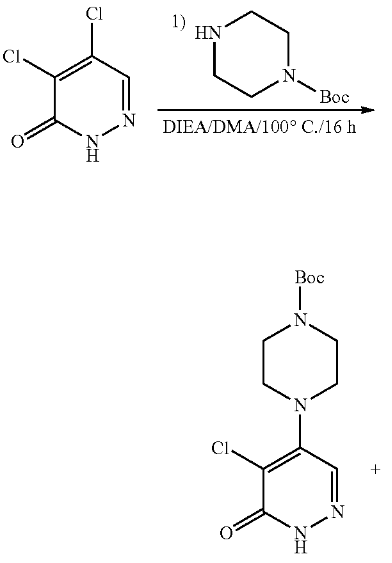

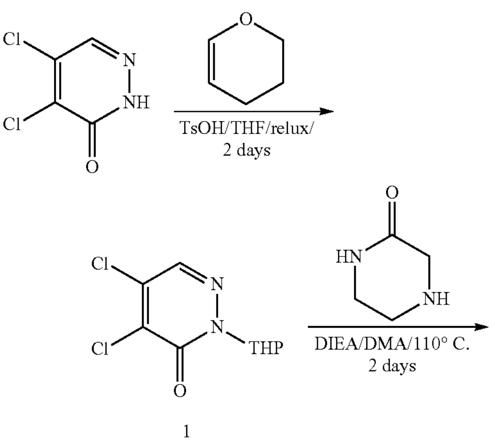

-continued

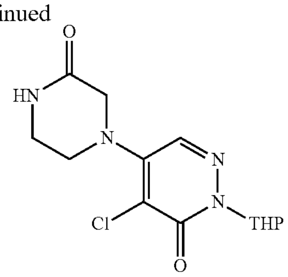

2

4,5-dichloro-2-(oxan-2-yl)-2,3-dihydropyridazin-3-one

To a stirred solution of 4,5-dichloro-2,3-dihydropyridazin-3-one (50 g, 303.07 mmol, 1 equiv.) and 3,4-dihydro-2H-pyran (203.9 g, 2424.58 mmol, 8 equiv.) in THF was added 4-methylbenzene-1-sulfonic acid (10.4 g, 60.61 mmol, 0.2 equiv.) in portions at room temperature under nitrogen atmosphere. The resulting mixture was stirred for 2 days at 70 degrees C. under nitrogen atmosphere. The reaction was monitored by LCMS. The mixture was allowed to cool down to room temperature. The resulting mixture was concentrated under reduced pressure. The residue was dissolved in water (500 mL). The resulting mixture was extracted with EtOAc (3×200 mL). The combined organic layers were washed with water (3×200 mL), dried over anhydrous Na2SO4. After filtration, the filtrate was concentrated under reduced pressure. The residue was purified by silica gel column chromatography, eluted with petroleum ether to afford 4,5-dichloro-2-(oxan-2-yl)-2,3-dihydropyridazin-3-one (57 g, 75.50%) as a light yellow solid.

4-chloro-2-(oxan-2-yl)-5-(3-oxopiperazin-1-yl)-2,3-dihydropyridazin-3-one

To a stirred solution of 4,5-dichloro-2-(oxan-2-yl)-2,3-dihydropyridazin-3-one (47 g, 188.68 mmol, 1 equiv.) and piperazin-2-one (28.3 g, 283.03 mmol, 1.5 equiv.) in DMA was added DIEA (48.8 g, 377.37 mmol, 2 equiv.) in portions at room temperature under nitrogen atmosphere. The resulting mixture was stirred for 2 days at 110 degrees C. under nitrogen atmosphere. The resulting mixture was concentrated under reduced pressure. The residue was dissolved in water (1 L). The resulting mixture was extracted with DCM (2×500 mL). The combined organic layers were washed with water (2×300 mL), dried over anhydrous Na2SO4. After filtration, the filtrate was concentrated under reduced pressure. The residue was purified by silica gel column chromatography, eluted with DCM/MeOH (200:1 to 40:1) to afford 4-chloro-2-(oxan-2-yl)-5-(3-oxopiperazin-1-yl)-2,3-dihydropyridazin-3-one (40 g, 67.78%) as an off-white solid.

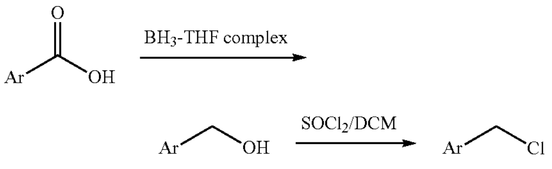

1 2

-continued

| Target ID | Ar |
|---|---|
| BK | 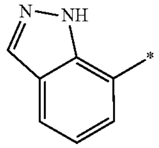 |
| BL | 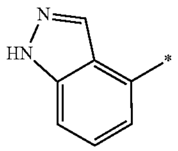 |
| BM | 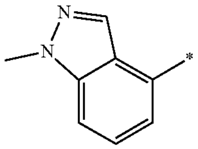 |
| BN | 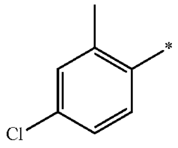 |
| BO | 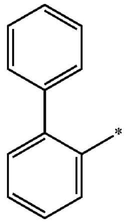 |
| BP | 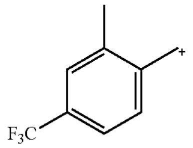 |
| BQ | 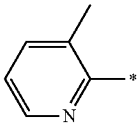 |
| BR | 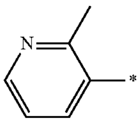 |
| BS | 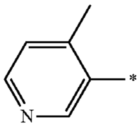 |
| BT | 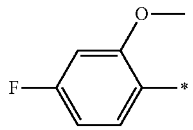 |

-continued
BU 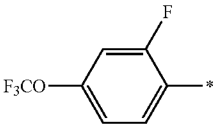
BV 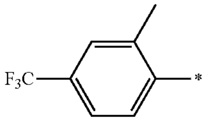
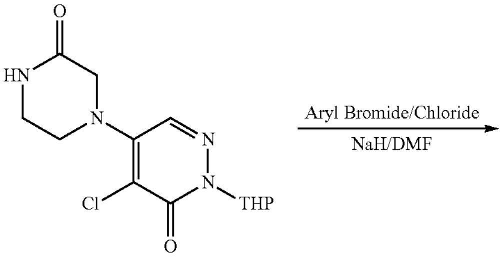
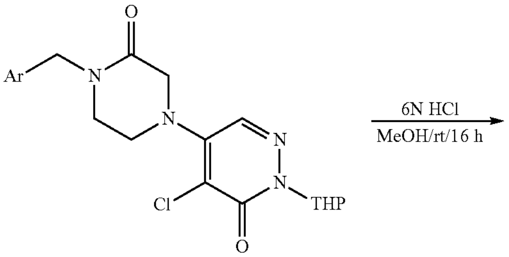
1
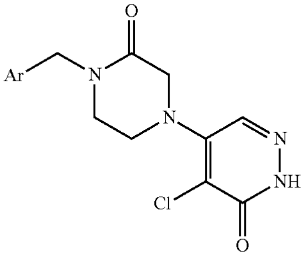
Targets
| Target ID | Ar |
|---|---|
| BW | 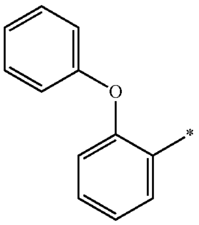 |
-continued
| | |
|---|---|
| BX | 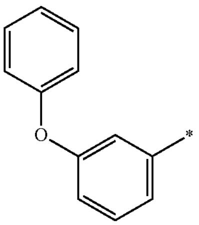 |
| BY | 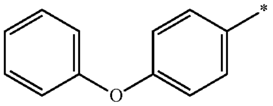 |
| BZ | 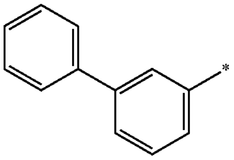 |
| CA | 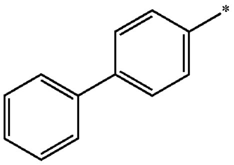 |
| CB | 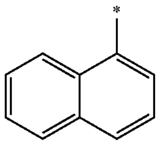 |
| CC | 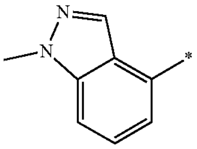 |
| CD | 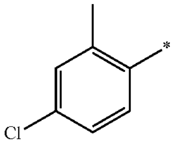 |
| CE | 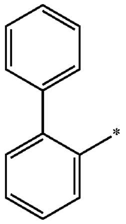 |

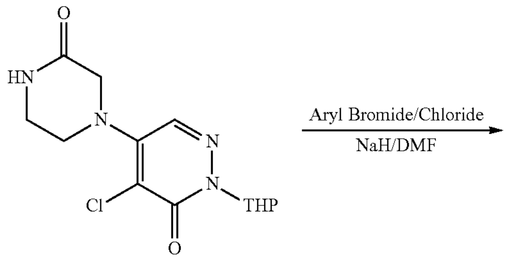

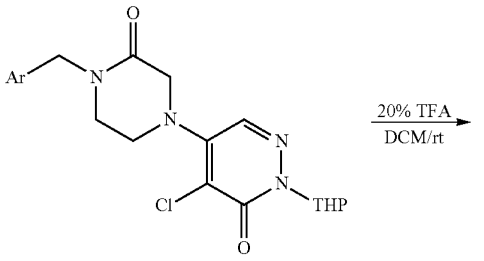

1

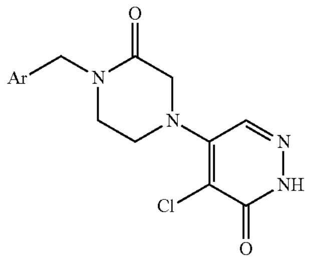

Targets

| Target ID | Ar |
|---|---|
| CF | 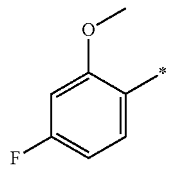 |
| CG | 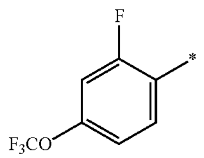 |
| CH | 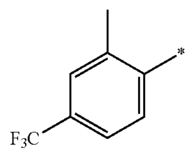 |
| CI | 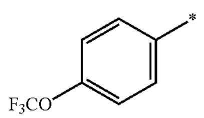 |

-continued

| | |
|---|---|
| CJ | 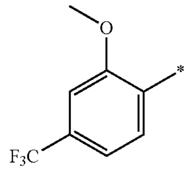 |

Compounds BX-CJ were prepared by the methods and procedures indicated in the schemes below.

General approach for synthesis follows protocols described as exemplified for the synthesis of compound CH below.

[2-methyl-4-(trifluoromethyl)phenyl]methanol

To a stirred solution of 2-methyl-4-(trifluoromethyl)benzoic acid (1000 mg, 4.90 mmol, 1 equiv.) in THE (40 mL) at rt under nitrogen atmosphere. The reaction was stirred for 2 h at 0 degrees C. Then borane (14.7 mL) was added. The reaction mixture was stirred for 16 h at 40 degrees C. The reaction was monitored by LCMS. The reaction was quenched with MeOH at rt. The resulting mixture was concentrated under reduced pressure. This resulted in [2-methyl-4-(trifluoromethyl)phenyl]methanol (900 mg, 96.62%) as a light yellow oil.

1-(chloromethyl)-2-methyl-4-(trifluoromethyl)benzene

To a stirred solution of [2-methyl-4-(trifluoromethyl)phenyl]methanol (250 mg, 1.31 mmol, 1 equiv.) in DCM (10 mL) was added sulfurooyl dichloride (312.8 mg, 2.63 mmol, 2.0 equiv.) in portions at 0 degrees C. The reaction mixture was stirred for 16 h at rt. The reaction was monitored by LCMS. The resulting mixture was extracted with EtOAc (3×300 mL). The combined organic layers were washed with water (3×100 mL), dried over anhydrous Na2SO4. After filtration, the filtrate was concentrated under reduced pressure. The residue was purified by Prep-TLC (petroleum ether/EtOAc 40/1 to 20/1) to afford 1-(chloromethyl)-2-methyl-4-(trifluoromethyl)benzene (123 mg, 44.85°/o) as a light yellow oil.

4-chloro-5-(4-[[2-methyl-4-(trifluoromethyl)phenyl]methyl]-3-oxopiperazin-1-yl)-2-(oxan-2-yl)-2,3-dihydropyridazin-3-one To a stirred mixture of 4-chloro-2-(oxan-2-yl)-5-(3-oxopiperazin-1-yl)-2,3-dihydropyridazin-3-one (100 mg, 0.32 mmol, 1 equiv.) and NaH (19.23 mg, 0.48 mmol, 1.504 equiv., 60%) in DMF (5 mL) under nitrogen atmosphere. The reaction was stirred for 0.5 h at rt. Then 1-(chloromethyl)-2-methyl-4-(trifluoromethyl)benzene (100.1 mg, 0.48 mmol, 1.5 equiv.) was added. The reaction mixture was stirred for 16 h at rt. The reaction was monitored by LCMS. The resulting mixture was extracted with EtOAc (3×300 mL). The combined organic layers were washed with water (3×50 mL), dried over anhydrous Na2SO4. After filtration, the filtrate was concentrated under reduced pressure. The residue was purified by Prep-TLC (petroleum ether/EtOAc 40/1 to 30/1) to afford 4-chloro-5-(4-[[2-methyl-4-(trifluoromethyl)phenyl]methyl]-3-oxopiperazin-1-yl)-2-(oxan-2-yl)-2,3-dihydropyridazin-3-one (80 mg, 51.60°%) as a light yellow oil.

Compound CH: 4-chloro-5-(4-[[2-methyl-4-(trifluoromethyl)phenyl]methyl]-3-oxopiperazin-1-yl)-2,3-dihydropyridazin-3-one To a stirred solution of 4-chloro-5-(4-[[2-methyl-4-(trifluoromethyl)phenyl]methyl]-3-oxopiperazin-1-yl)-2-(oxan-2-yl)-2,3-dihydropyridazin-3-one (80 mg, 0.16 mmol, 1 equiv.) and TFA (6 mL) in DCM (20 mL) under nitrogen atmosphere. The reaction mixture was stirred for 16 h at rt. The reaction was monitored by LCMS. The crude product was purified by Prep-HPLC with the following conditions (Column: XBridge Prep OBD C18 Column 30*150 mm 5 um; Mobile Phase A: Water (10 mmol/L NH4HCO3), Mobile Phase B: MeCN; Flow rate: 60 mL/min; Gradient: 21% B to 41% B in 7 min; 254 nm; Rt: 6.72 min) to afford 4-chloro-5-(4-[[2-methyl-4-(trifluoromethyl)phenyl] methyl]-3-oxopiperazin-1-yl)-2,3-dihydropyridazin-3-one (36.3 mg, 54.90%) as an off-white solid.

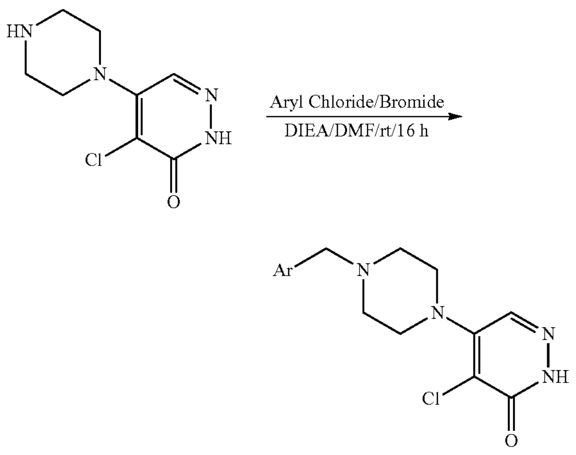

Targets

| Target ID | Aryl Substituent |
|---|---|
| CK | 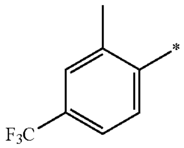 |
| CL | 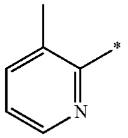 |
| CM | 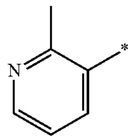 |
| CN | 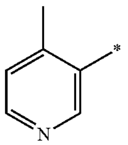 |
| CO | 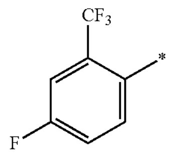 |

Compounds CK-CO were prepared by the methods and procedures indicated in the schemes below:

1-(chloromethyl)-2-methyl-4-(trifluoromethyl)benzene

To a stirred solution/mixture of [2-methyl-4-(trifluoromethyl)phenyl]methanol (901 mg, 4.74 mol, 1 equiv.) in DCM (20 mg, 0.24 mmol, 0.035 equiv.) was added sulfuroyl dichloride (1.7 g, 14.21 mol, 3 equiv.) dropwise at 0 degrees C. The resulting mixture was stirred for 2 h at room temperature. The reaction was monitored by LCMS. The resulting mixture was concentrated under reduced pressure to afford 1-(chloromethyl)-2-methyl-4-(trifluoromethyl) benzene (764 mg, 77.30%) as a dark yellow oil.

Compound CK: 4-chloro-5-(4-[[2-methyl-4-(trifluoromethyl)phenyl]methyl]piperazin-1-yl)-2,3-dihydropyridazin-3-one To a stirred solution of 4-chloro-5-(piperazin-1-yl)-2,3-dihydropyridazin-3-one (80 mg, 0.37 mmol, 1 equiv.) and DIEA (96.3 mg, 0.75 mmol, 2 equiv.) in DMF (5.0 mL, 58.87 mmol, 211.030 equiv.) was added 1-(chloromethyl)-2-methyl-4-(trifluoromethyl)benzene (116.6 mg, 0.56 mmol, 1.5 equiv.) dropwise at 0 degrees C. The resulting mixture was stirred for 16 h at room temperature. The reaction was monitored by LCMS. The residue product was purified by reverse phase flash with the following conditions (Column: XBridge Shield RP18 OBD Column, 5 um, 19*150 mm; Mobile Phase A: Water (10 mmol/L NH4HCO3), Mobile Phase B: MeCN; Flow rate: 45 mL/min; Gradient: 15% B to 54% B in 20 min; 220 nm) to afford 4-chloro-5-(4-[[2-methyl-4-(trifluoromethyl)phenyl]methyl]piperazin-1-yl)-2,3-dihydropyridazin-3-one (19.2 mg, 13.32%) as a white solid.

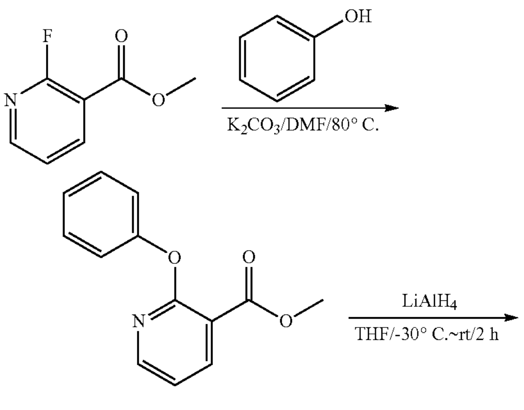

1

-continued

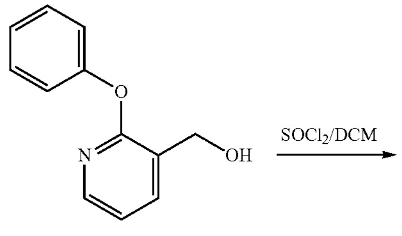

2

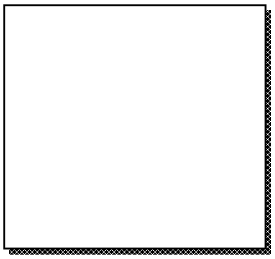

3

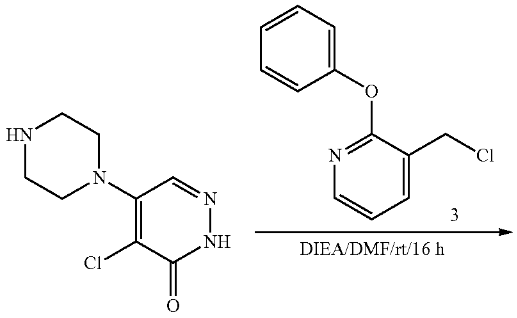

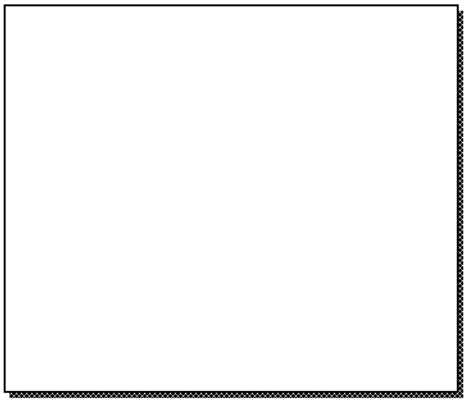

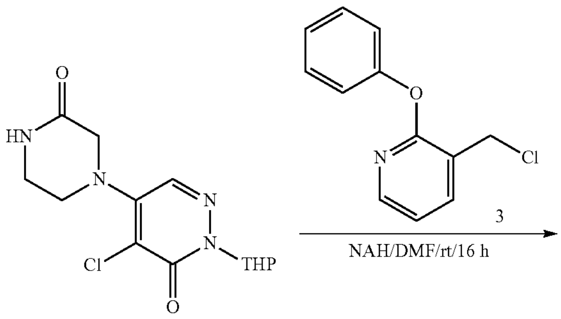

-continued

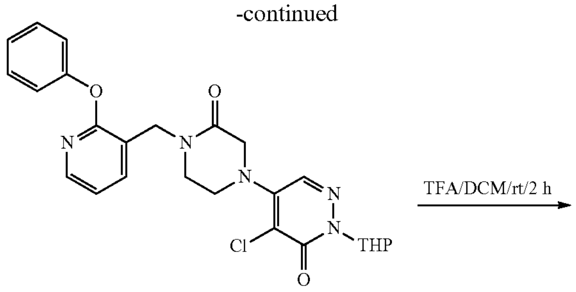

4

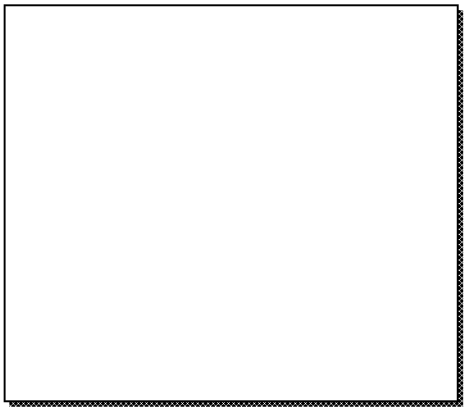

Methyl 2-phenoxypyridine-3-carboxylate

To a stirred mixture of methyl 2-fluoropyridine-3-carboxylate (2 g, 12.89 mmol, 1 equiv.) and phenol (1.8 g, 19.13 mmol, 1.483 equiv.) in DMF (30 mL) was added K2CO3 (5.3 g, 38.35 mmol, 2.974 equiv.) dropwise at room temperature under nitrogen atmosphere. The reaction mixture was stirred for 16 h at 80 degrees C. The reaction was monitored by LCMS. The residue was purified by silica gel column chromatography, eluted with petroleum ether/EtOAc (40/1 to 20/1) to afford methyl 2-phenoxypyridine-3-carboxylate (2.91 g, 98.46%) as a light yellow oil.

(2-phenoxypyridin-3-yl)methanol

To a stirred solution of methyl 2-phenoxypyridine-3-carboxylate (1.5 g, 6.54 mmol, 1 equiv.) was added LiAlH4 (0.5 g, 0.01 mmol, 2.0 equiv.) in portions at −30 degrees C. under nitrogen atmosphere. The reaction mixture was stirred for 16 h at rt. The reaction was monitored by LCMS. The residue was purified by silica gel column chromatography, eluted with petroleum ether/EtOAc (40/1 to 20/1) to afford (2-phenoxypyridin-3-yl)methanol (1.2 g, 91.14%) as a light yellow oil.

3-(chloromethyl)-2-phenoxypyridine

To a stirred solution of (2-phenoxypyridin-3-yl)methanol (1.2 g, 5.96 mmol, 1 equiv.) in DCM (25 mL) was added SOCl2 (1.4 g, 11.77 mmol, 1.973 equiv.) in portions at 0 degrees C. under nitrogen atmosphere. The reaction mixture was stirred for 16 h at rt. The reaction was monitored by LCMS. The residue was purified by Prep-TLC (petroleum ether/EtOAc 50/1 to 20/1) to afford 3-(chloromethyl)-2-phenoxypyridine (1.25 g, 95.42%) as a light yellow oil.

Compound CP: 4-chloro-5-[4[(2-phenoxypyridin-3-yl)methyl]piperazin-1-yl]-2,3-dihydropyridazin-3-one To a stirred solution/mixture of 4-chloro-5-(piperazin-1-yl)-2,3-dihydropyridazin-3-one (100 mg, 0.47 mmol, 1 equiv.) and 3-(chloromethyl)-2-phenoxypyridine (153.5 mg, 0.70 mmol, 1.500 equiv.) in DMF (5 mL) was added DIEA (240.8 mg, 1.86 mmol, 3.999 equiv.) dropwise at rt under nitrogen atmosphere. The reaction mixture was stirred for 16 h at rt. The reaction was monitored by LCMS. The crude product was purified by Prep-HPLC with the following conditions (Column: XBridge Shield RP18 OBD Column 30*150 mm, 5 um; Mobile Phase A: Water (10 mmol/L NH4HCO3), Mobile Phase B: MeCN; Flow rate: 60 mL/min; Gradient: 15% B to 37% B in 7 min; 254 nm; Rt: 6.47 min) to afford 4-chloro-5-[4-[(2-phenoxypyridin-3-yl)methyl]piperazin-1-yl]-2,3-dihydropyridazin-3-one (80.8 mg, 43.59°%) as a white solid.

4-chloro-2-(oxan-2-yl)-5-[3-oxo-4-[(2-phenoxypyridin-3-yl)methyl]piperazin-1-yl]-2,3-dihydropyridazin-3-one To a stirred mixture of 4-chloro-2-(oxan-2-yl)-5-(3-oxopiperazin-1-yl)-2,3-dihydropyridazin-3-one (200 mg, 0.64 mmol, 1 equiv.) and NaH (30.7 mg, 1.28 mmol, 2.001 equiv.) in DMF (5 mL) under nitrogen atmosphere. The reaction was stirred for 0.5 h at rt. Then 3-(chloromethyl)-2-phenoxypyridine (210.7 mg, 0.96 mmol, 1.500 equiv.) was added. The reaction mixture was stirred for 16 h at rt. The reaction was monitored by LCMS. The resulting mixture was extracted with EtOAc (3×300 mL). The combined organic layers were washed with water (3×50 mL), dried over anhydrous Na2SO4. After filtration, the filtrate was concentrated under reduced pressure. The residue was purified by Prep-TLC (petroleum ether/EtOAc 40/1 to 30/1) to afford 4-chloro-2-(oxan-2-yl)-5-[3-oxo-4-[(2-phenoxypyridin-3-yl)methyl]piperazin-1-yl]-2,3-dihydropyridazin-3-one (230 mg, 72.52%) as a light yellow oil.

Compound CQ: 4-chloro-5-[4-[(2-phenoxypyridin-3-yl)methyl]piperazin-1-yl]-2,3-dihydropyridazin-3-one To a stirred solution of 4-chloro-2-(oxan-2-yl)-5-[3-oxo-4-[(2-phenoxypyridin-3-yl)methyl]piperazin-1-yl]-2,3-dihydropyridazin-3-one (200 mg, 0.40 mmol, 1 equiv.) and TFA (2 mL, 26.93 mmol, 66.771 equiv.) in DCM (10 mL) under nitrogen atmosphere. The reaction mixture was stirred for 16 h at rt. The reaction was monitored by LCMS. The crude product was purified by Prep-HPLC with the following conditions (Column: XBridge Shield RP18 OBD Column, 5 um, 19*150 mm; Mobile Phase A: Water (10 mmol/L NH4HCO3), Mobile Phase B: MeCN; Flow rate: 20 mL/min; Gradient: 20% B to 50% B in 7 min; 254 nm; Rt: 5.53 min) to afford 4-chloro-5-[4-[(2-phenoxypyridin-3-yl)methyl]piperazin-1-yl]-2,3-dihydropyridazin-3-one (66.8 mg, 41.64%) as a white solid.

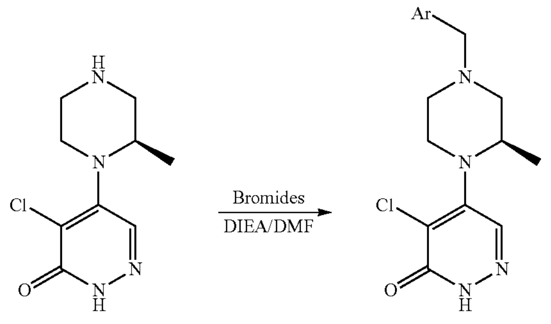

2 Targets

| Target ID | Ar |
|---|---|
| CR | 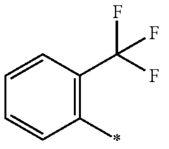 |
| CS | 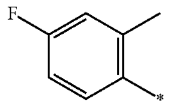 |
| CT | 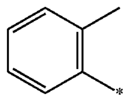 |
| CU | 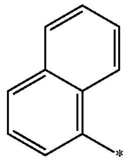 |

The compounds CR-CU were prepared by the methods and procedures indicated in the schemes as described for Compound CK above.

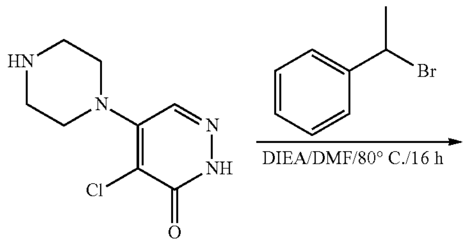

1

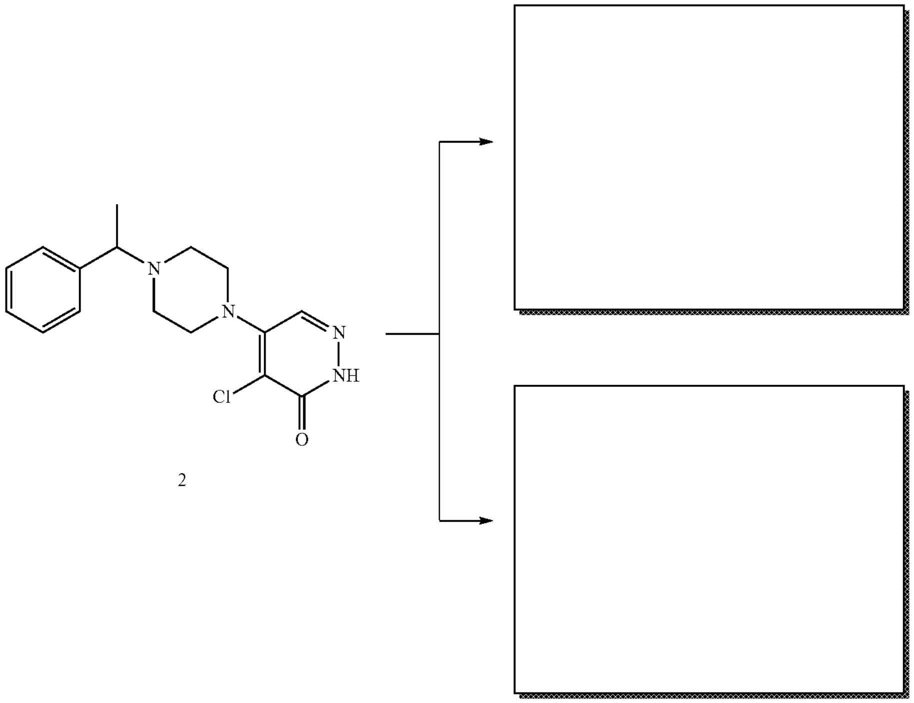

2

Compounds CV and CW 4-chloro-5-[4[(1S)-1-phenylethyl]piperazin-1-yl]-2,3-dihydropyridazin-3-one & 4-chloro-5-[4[(1R)-1-phenylethyl]piperazin-1-yl]-2,3-dihydropyridazin-3-one To a stirred mixture of 4-chloro-5-(piperazin-1-yl)-2,3-dihydropyridazin-3-one (200 mg, 930 mmol, 1 equiv.) and DIEA (361.3 mg, 2.80 mmol, 3 equiv.) in DMF (5 mL, 64.61 mmol, 69.342 equiv.) was added (1-bromoethyl)benzene (206.9 mg, 1.12 mol, 1.2 equiv.) at room temperature under nitrogen atmosphere. The resulting mixture was stirred for 16 h at room temperature. The reaction was monitored by LCMS. The residue was purified by reverse phase flash with the following conditions (Column: XBridge Shield RP18 OBD Column, 5 um, 19*150 mm; Mobile Phase A: Water (10 mmol/L NH4HCO3), Mobile Phase B: MeCN; Flow rate: 20 mL/min; Gradient: 20% B to 50% B in 20 min; 254 nm; Rt: 6.43 min) to afford crude product. The crude product (260 mg) was purified by Prep-HPLC with the following conditions (Column: CHIRALPAK IG, 20*250 mm, 5 um; Mobile Phase A: Hex-HPLC, Mobile Phase B: EtOH—HPLC; Flow rate: 20 mL/min; Gradient: 50 B to 50 B in 28 min; 254/220 nm; RT1:18.199; RT2:22.155) to afford 4-chloro-5-[4-[(1R)-1-phenylethyl]piperazin-1-yl]-2,3-dihydropyridazin-3-one (68 mg, 22.89%) and 4-chloro-5-[4-[(1S)-1-phenylethyl]piperazin-1-yl]-2,3-dihydropyridazin-3-one (58.5 mg, 19.69%) as a white solid.

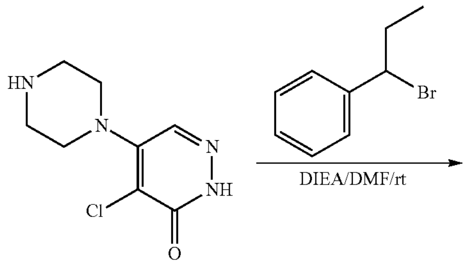
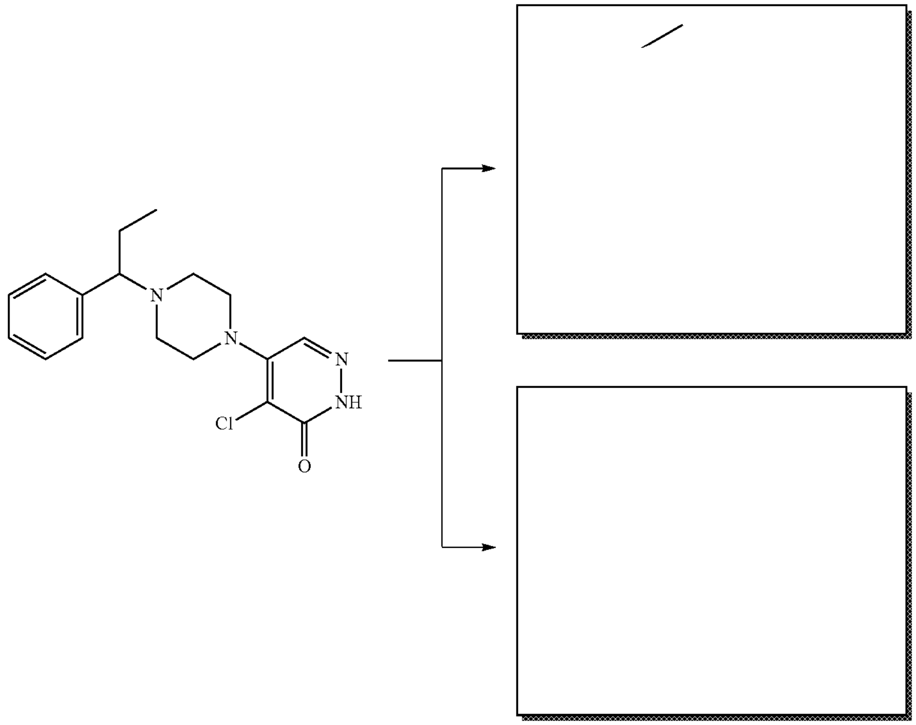
Compounds CX and CY were prepared following the schemes above and as described in the methods and schemes for Compounds CV and CW
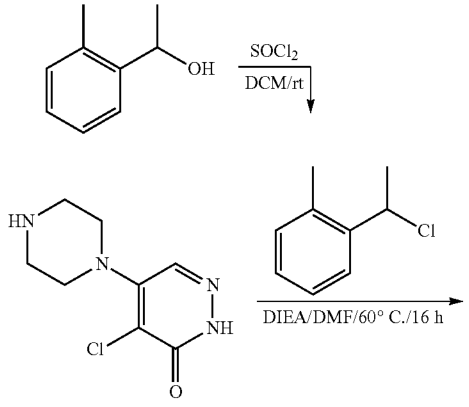
1

-continued
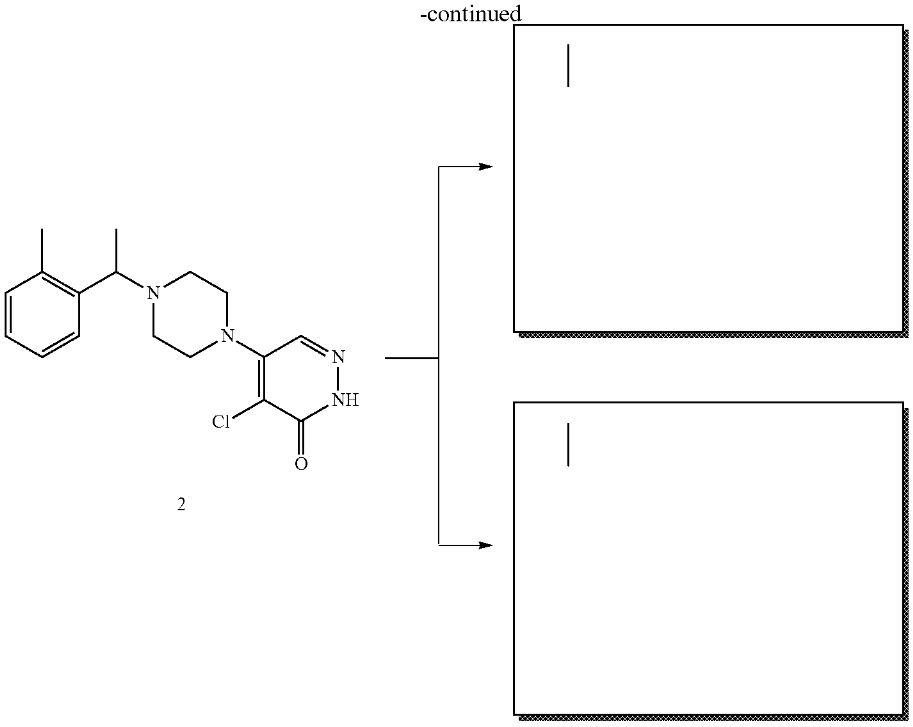
2
Compounds CZ and DA were prepared following the schemes above and as described in the methods and schemes for Compounds CV and CW.
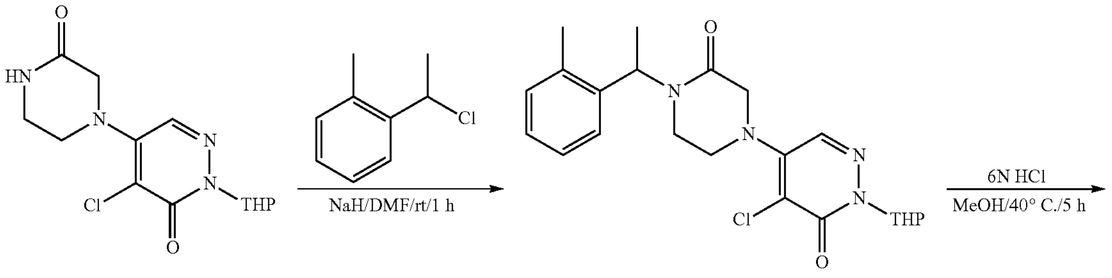
1

-continued

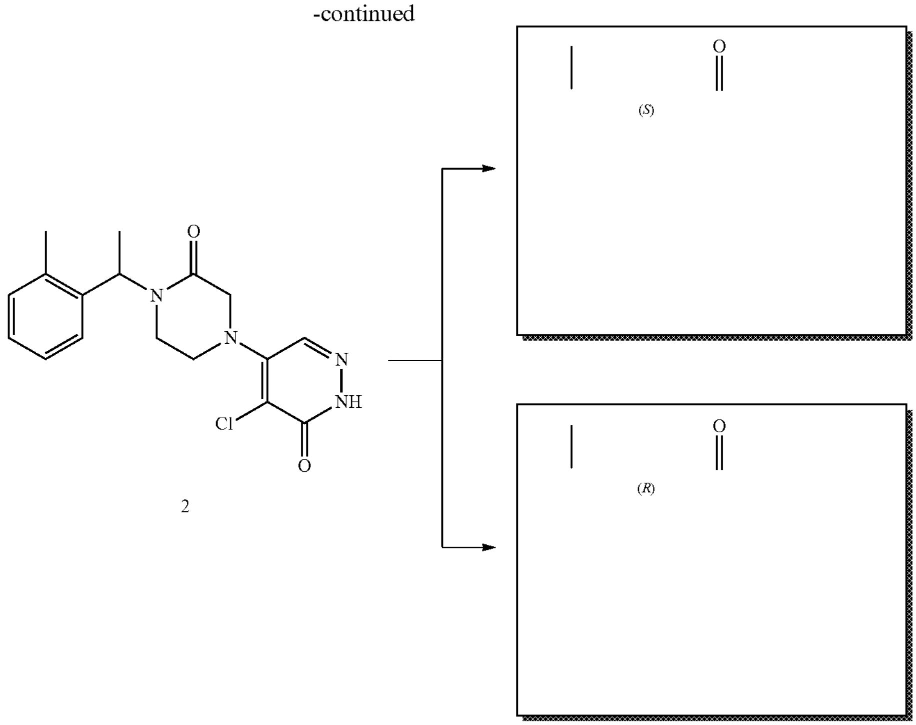

2

4-chloro-5-[4-[1-(2-methylphenyl)ethyl]-3-oxopiperazin-1-yl]-2-(oxan-2-yl)-2,3-dihydropyridazin-3-one To a stirred solution of 4-chloro-2-(oxan-2-yl)-5-(3-oxopiperazin-1-yl)-2,3-dihydropyridazin-3-one (400 mg, 1.28 mmol, 1 equiv.) in DMF (10 mL) was added NaH (102.3 mg, 2.56 mol, 2.000 equiv., 60%) at room temperature under nitrogen atmosphere. The resulting mixture was stirred for 30 min at room temperature. Then 1-(1-chloroethyl)-2-methylbenzene (237.3 mg, 1.53 mmol, 1.2 equiv.) was added and the resulting mixture was stirred for 16 h at room temperature. The reaction was monitored by LCMS. The residue was purified by reverse phase flash with the following conditions (Column: XBridge Prep C18 OBD Column 19×150 mm 5 um; Mobile Phase A: Water (10 mmol/L NH4HCO3), Mobile Phase B: MeCN; Flow rate: 20 mL; min; Gradient: 50% B to 70% B in 15 min; 254&220 nm; Rt: 4.8 min) to afford 4-chloro-5-[4-[1-(2-methylphenyl)ethyl]-3-oxopiperazin-1-yl]-2-(oxan-2-yl)-2,3-dihydropyridazin-3-one (60 mg, 10.89%) as a yellow oil.

Compounds DB and DC 4-chloro-5-[4 [(1R)-1-(2-methylphenyl)ethyl]-3-oxopiperazin-1-yl]-2,3-dihydropyridazin-3-one & 4-chloro-5-[4-[(1S)-1-(2-methylphenyl)ethyl]-3-oxopiperazin-1-yl]-2,3-dihydropyridazin-3-one To a stirred solution of 4-chloro-5-[4-[1-(2-methylphenyl)ethyl]-3-oxopiperazin-1-yl]-2-(oxan-2-yl)-2,3-dihydropyridazin-3-one (60 mg) in MeOH (4 mL) was added HCl (6M) (2 mL) at room temperature under nitrogen atmosphere. The resulting mixture was stirred for 4 h at 40 degrees C. The reaction was monitored by LCMS. The mixture was allowed to cool down to room temperature. The mixture was basified to pH 8 with saturated NaHCO3 (aq.). The resulting mixture was extracted with EtOAc (1×50 mL). The combined organic layers were washed with water (3×50 mL), dried over anhydrous Na2SO4. After filtration, the filtrate was concentrated under reduced pressure. The residue was purified by Prep-TLC (DCM/MeOH=20:1) to afford crude product. The crude product (30 mg) was purified by Prep-HPLC with the following conditions (Column: CHIRAL ART Cellulose-SB, 2*25 cm, 5 um; Mobile Phase A:Hex-HPLC, Mobile Phase B: EtOH—HPLC; Flow rate: 20 mL/min; Gradient: 50 B to 50 B in 16 min; 220/254 nm; RT1:10.11; RT2:12.033) to afford 4-chloro-5-[4-[(1R)-1-(2-methylphenyl)ethyl]-3-oxopiperazin-1-yl]-2,3-dihydropyridazin-3-one (5.2 mg) as an off-white solid and 4-chloro-5-[4-[(1S)-1-(2-methylphenyl)ethyl]-3-oxopiperazin-1-yl]-2,3-dihydropyridazin-3-one (6.1 mg) as an off-white solid.

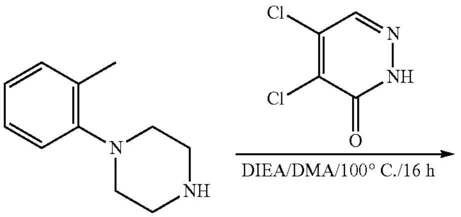

-continued

Synthesis of DD4-chloro-5-[4-(2-methylphenyl)piperazin-1-yl]-2,3-dihydropyridazin-3-one To a stirred mixture of 1-(2-methylphenyl)piperazine (80 mg, 0.45 mmol, 1 equiv.) and DIEA (176.0 mg, 1.36 mmol, 3 equiv.) in DMA (5 mL) was added 4,5-dichloro-2,3-dihydropyridazin-3-one (74.9 mg, 0.45 mmol, 1 equiv.) at room temperature under nitrogen atmosphere. The resulting mixture was stirred for 16 h at 100 degrees C. The reaction was monitored by LCMS. The mixture was allowed to cool down to room temperature. The crude product was purified by Prep-HPLC with the following conditions (Column: XBridge Shield RP18 OBD Column, 5 um, 19*150 mm; Mobile Phase A: Water (10 mmol/L NH4HCO3), Mobile Phase B: MeCN; Flow rate: 20 mL/min; Gradient: 30% B to 65% B in 7 min; 254 nm; Rt: 6.25 min) to afford 4-chloro-5-[4-(2-methylphenyl)piperazin-1-yl]-2,3-dihydropyridazin-3-one (23.1 mg, 16.70%) as a white solid.

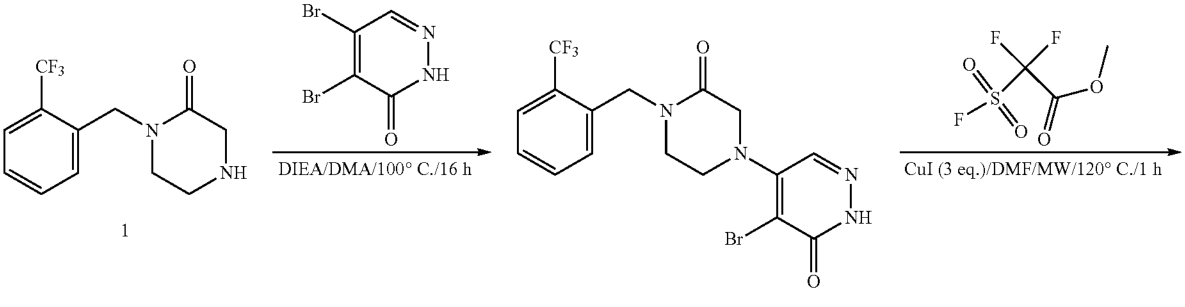

1

2

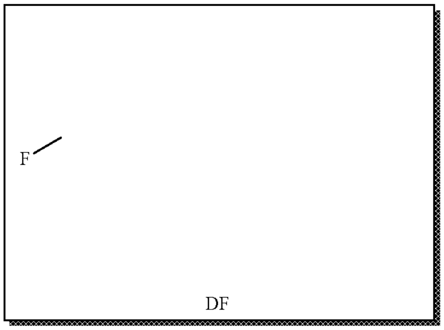

DF

4-bromo-5-(3-oxo-4-[[2-(trifluoromethyl)phenyl]methyl]piperazin-1-yl)-2,3-dihydropyridazin-3-one To a stirred solution of 1-[(2-tert-butylphenyl)methyl]piperazin-2-one (200 mg, 0.81 mmol, 1 equiv.) and 4,5-dibromo-2,3-dihydropyridazin-3-one (235.9 mg, 930 mmol, 1.2 equiv.) in DMA (5 mL, 53.78 mmol, 66.238 equiv.) was added DIEA (209.9 mg, 1.62 mmol, 2 equiv.) in portions at room temperature under nitrogen atmosphere. The resulting mixture was stirred for overnight at 100 degrees C. under nitrogen atmosphere. The reaction was monitored by LCMS. The residue/crude product was purified by reverse phase flash with the following conditions (Column: C18 80 g; Mobile Phase A: Water (10 mmol/L NH4HCO3), Mobile Phase B: MeCN; Flow rate: 40 mL/min; Gradient: 40% B to 60% B in 15 min; 254 nm; Rt: 6.12 min) to afford 4-bromo-5-(3-oxo-4-[[2-(trifluoromethyl)phenyl]methyl]piperazin-1-yl)-2,3-dihydropyridazin-3-one (150 mg, 44.92%) as a light yellow solid.

Compound DE

5-(3-oxo-4-[[2-(trifluoromethyl)phenyl]methyl]piperazin-1-yl)-4-(trifluoromethyl)-2,3-dihydropyridazin-3-one To a stirred solution of 4-bromo-5-(3-oxo-4-[[2-(trifluoromethyl)phenyl]methyl]piperazin-1-yl)-2,3-dihydropyridazin-3-one (150 mg, 0.35 mmol, 1 equiv.) and methyl 2,2-difluoro-2-(fluorosulfonyl)acetate (200.5 mg, 1.04 mmol, 3 equiv.) in DMF (3 mL) was added CuI (198.8 mg, 1.04 mmol, 3 equiv.) in portions at room temperature under nitrogen atmosphere. The final reaction mixture was irradiated with microwave radiation for 1 h at 130 degrees C. The reaction was monitored by LCMS. The crude product (25 mg) was purified by Prep-HPLC with the following conditions (Column: XBridge Prep C18 OBD Column, 5 um, 19*150 mm; Mobile Phase A: Water (10 mmol/L NH4HCO3), Mobile Phase B: MeCN; Flow rate: 20 mL/min; Gradient: 30% B to 52% B in 7 min; 254&220 nm; Rt: 6.5 min) to afford 5-(3-oxo-4-[[2-(trifluoromethyl)phenyl]methyl]piperazin-1-yl)-4-(trifluoromethyl)-2,3-dihydropyridazin-3-one (2.8 mg, 1.92%) as a white solid.

Compound DF was prepared following the schemes above and as described in the methods and schemes for Compound DE

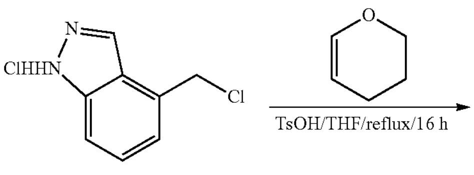

4

-continued

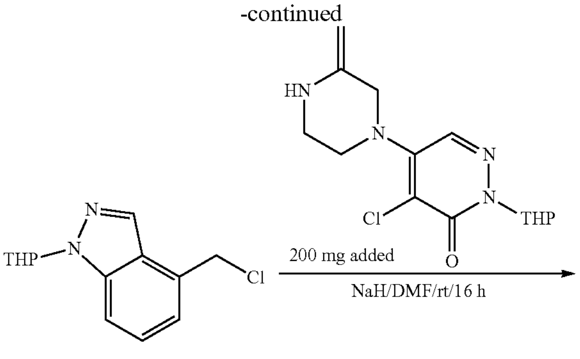

5

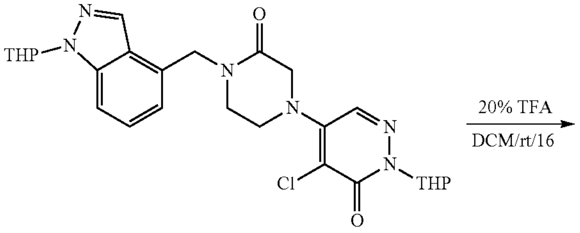

6

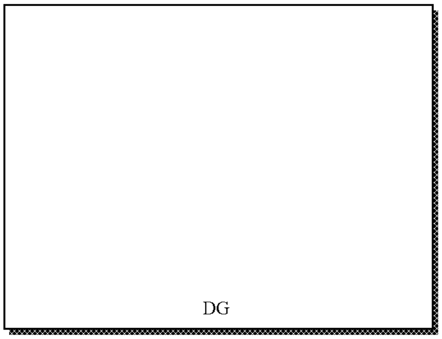

DG

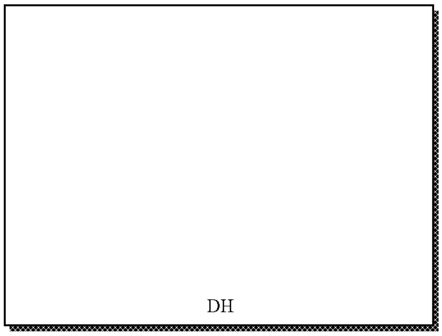

DH

Compound DH was prepared in by the scheme and methods described for Compound DG.

4-(chloromethyl)-1-(oxan-2-yl)-1H-indazole

To a stirred solution of 4-(chloromethyl)-1H-indazole (300 mg, 1.80 mmol, 1 equiv.) in THF (5 mL) was added TsOH (63 mg, 0.37 mmol, 0.203 equiv.)3, and 6-dihydro-2H-pyran (1215 mg, 14.44 mmol, 8.022 equiv.) in portions. The mixture was stirred at 70 degrees C. under nitrogen atmosphere The reaction was monitored by LCMS. The mixture was allowed to cool down to room temperature. The resulting solution was purified by Prep-TLC (petroleum ether/EtOAc 100:1 to 80:1) and concentrated under reduced pressure to afford 4-(chloromethyl)-1-(oxan-2-yl)-1H-indazole (460.2 mg, 101.94%) as a yellow solid.

4-chloro-2-(oxan-2-yl)-5-(4-[[1-(oxan-2-yl)-1H-indazol-4-yl]methyl]-3-oxopiperazin-1-yl)-2,3-dihydropyridazin-3-one To a stirred solution of 4-chloro-2-(oxan-2-yl)-5-(3-oxopiperazin-1-yl)-2,3-dihydropyridazin-3-one (200 mg, 1 equiv.) in DMF (10 mL) was added NaH (52 mg) in portions at room temperature were stirred for 30 min. To the above mixture was added 4-(chloromethyl)-1-(oxan-2-yl)-1H-indazole (193 mg, 1 equiv.) in portions. The resulting mixture was stirred for additional overnight at room temperature. The reaction was monitored by LCMS. The reaction was quenched with Water at room temperature. The resulting mixture was extracted with EtOAc (3×500 mL). The combined organic layers were washed with water (2×200 mL) and brine (2×200 mL), dried over anhydrous Na2SO4. The resulting solution was concentrated under reduced pressure. The residue was purified by Prep-TLC (petroleum ether/EtOAc 80:1) to afford 4-chloro-2-(oxan-2-yl)-5-(4-[[1-(oxan-2-yl)-1H-indazol-4-yl]methyl]-3-oxopiperazin-1-yl)-2,3-dihydropyridazin-3-one (254 mg) as a yellow oil. The crude product/resulting mixture was used in the next step directly without further purification Compound DG 4-chloro-5-[4-(1H-indazol-4-ylmethyl)-3-oxopiperazin-1-yl]-2,3-dihydropyridazin-3-one To a stirred solution of 4-chloro-2-(oxan-2-yl)-5-(4-[[1-(oxan-2-yl)-1H-indazol-4-yl]methyl]-3-oxopiperazin-1-yl)-2,3-dihydropyridazin-3-one (346 mg, 0.66 mmol, 1 equiv.) and TFA (6 mL) in DCM (20 mL) under nitrogen atmosphere. The reaction mixture was stirred for 16 h at rt. The reaction was monitored by LCMS. The crude product was purified by Prep-HPLC with the following conditions (Column: XBridge Prep OBD C18 Column 30*150 mm 5 um; Mobile Phase A: Water (10 mmol/L NH4HCO3), Mobile Phase B: MeCN; Flow rate: 20 mL/min; Gradient: 5% B to 20% B in 7 min; 254 nm; Rt: 6.38 min) to afford 4-chloro-5-[4-(1H-indazol-4-ylmethyl)-3-oxopiperazin-1-yl]-2,3-dihydropyridazin-3-one (51.1 mg, 21.69%) as a

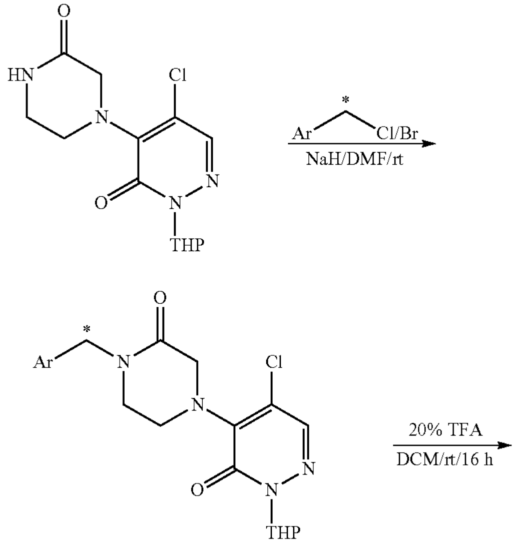

1

-continued

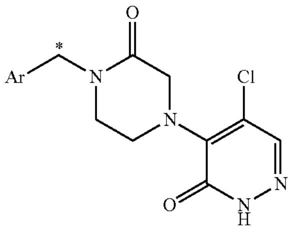

Targets

| Target ID | Ar |
|---|---|
| DI | 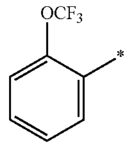 |
| DJ | 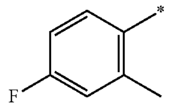 |
| DK | 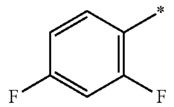 |
| DL | 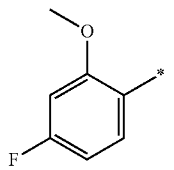 |

5-chloro-2-(oxan-2-yl)-4-(3-oxo-4-[[2-(trifluoromethoxy)phenyl]methyl]piperazin-1-yl)-2,3-dihydropyridazin-3-one To a stirred mixture of 5-chloro-2-(oxan-2-yl)-4-(3-oxopiperazin-1-yl)-2,3-dihydropyridazin-3-one (200 mg, 0.64 mmol, 1 equiv.) and NaH (51.2 mg, 1.28 mmol, 2.0 equiv., 60%) in DMF (5 mL) at room temperature under nitrogen atmosphere. The resulting mixture was stirred for 1 h at room temperature under nitrogen atmosphere. To the above mixture was added 1-(bromomethyl)-2-(trifluoromethoxy)benzene (195.7 mg, 0.77 mmol, 1.2 equiv.) portions at room temperature. The resulting mixture was stirred for additional 16 h at room temperature. The reaction was monitored by LCMS. To the above mixture was added 100 mL H2O. The resulting mixture was extracted with EtOAc (3×100 mL). The combined organic layers were washed with saturated NaCl (aq.)(3×200 mL), dried over anhydrous Na2SO4. After filtration, the filtrate was concentrated under reduced pressure. The crude product (100 mg) was used in the next step directly without further purification.

Compound DI 5-chloro-4-(3-oxo-4-[[2-(trifluoromethoxy)phenyl] methyl]piperazin-1-yl)-2,3-dihydropyridazin-3-one To a stirred solution of 5-chloro-2-(oxan-2-yl)-4-(3-oxo-4-[[2-(trifluoromethoxy)phenyl]methyl]piperazin-1-yl)-2,3-dihydropyridazin-3-one (100 mg, 0.21 mmol, 1 equiv.) and CF3COOH (5 mL, 67.32 mmol, 327.739 equiv.) in DCM (15 mL) at room temperature. The resulting mixture was stirred for 16 h at room temperature. The reaction was monitored by LCMS. The mixture was neutralized to pH 7 with saturated NH4HCO3 (aq.). The resulting mixture was extracted with EtOAc (3×100 mL). The combined organic layers were washed with saturated NaCl (aq.)(3×200 mL), dried over anhydrous Na2SO4. After filtration, the filtrate was concentrated under reduced pressure. The crude product (65 mg) was purified by Prep-HPLC with the following conditions (Column: XBridge Prep C18 OBD Column 19×150 mm 5 um; Mobile Phase A: Water (10 mmol/L NH4HCO3), Mobile Phase B: MeCN; Flow rate: 20 mL; min; Gradient: 25% B to 60% B in 7 min; 254&220 nm; Rt: 6.5 min) to afford 5-chloro-4-(3-oxo-4-[[2-(trifluoromethoxy)phenyl]methyl]piperazin-1-yl)-2,3-dihydropyridazin-3-one (21.3 mg, 25.75%) as a white solid.

Compounds DJ-DL were all prepared by the methods and schemes described for Compound DI above

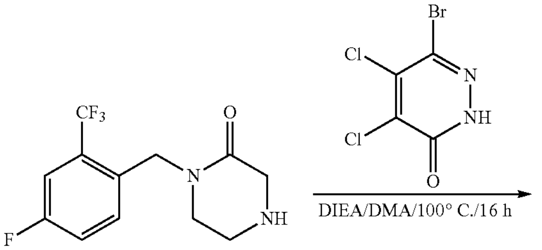

1

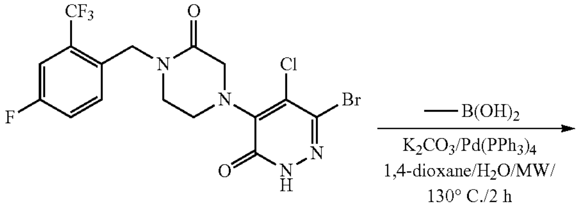

2

-continued

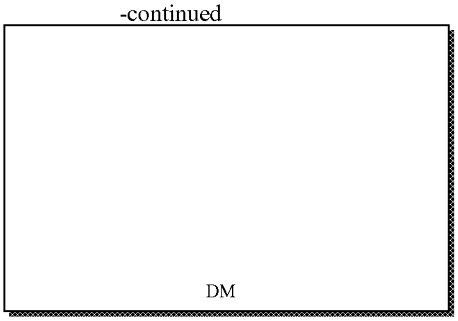

DM

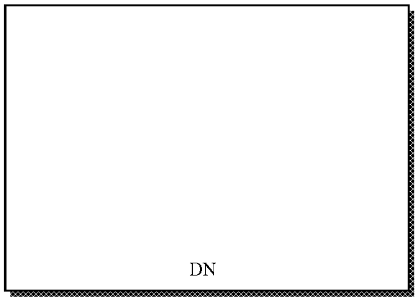

DN 6-bromo-5-chloro-4-(4 [[4-fluoro-2-(trifluoromethyl)phenyl]methyl]-3-oxopiperazin-1-yl)-2,3-dihydropyridazin-3-one To a stirred solution of 1-[[4-fluoro-2-(trifluoromethyl) phenyl]methyl]piperazin-2-one (200 mg, 720 mmol, 1 equiv.) and DIEA (187.2 mg, 1.45 mmol, 2 equiv.) in DMF (8 mL) was added 6-bromo-4,5-dichloro-2,3-dihydropyridazin-3-one (176.6 mg, 720 mmol, 1 equiv.) at 28 degrees C. The mixture as stirred at 80 degrees C. for 16 h. Desired product could be detected by LCMS. The crude product (20 mg) was purified by Prep-HPLC with the following conditions (Column: XBridge Shield RP18 OBD Column, 5 um, 19*150 mm; Mobile Phase A: Water (10 mmol/L NH4HCO3), Mobile Phase B: MeCN Flow rate: 20 mL/min; Gradient: 36% B to 68% B in 7 min; 254 nm; Rt: 6.5 min). The resulting mixture was concentrated under reduced pressure to afford 6-bromo-5-chloro-4-(4-[[4-fluoro-2-(trifluoromethyl)phenyl]methyl]-3-oxopiperazin-1-yl)-2,3-dihydropyridazin-3-one (8.1 mg, 2.31%) as a white solid.

Compound DM 5-chloro-4-(4-[[4-fluoro-2-(trifluoromethyl)phenyl] methyl]-3-oxopiperazin-1-yl)-6-methyl-2,3-dihydropyridazin-3-one To a solution of 6-bromo-5-chloro-4-(4-[[4-fluoro-2-(trifluoromethyl)phenyl]methyl]-3-oxopiperazin-1-yl)-2,3-dihydropyridazin-3-one (60 mg, 0.12 mmol, 1 equiv.) and methylboronic acid (14.9 mg, 0.25 mmol, 2.000 equiv.) in dioxane (4 mL) and H2O (1 mL) were added potassium potassium methaneperoxoate (34.5 mg, 0.25 mmol, 1.998 equiv.) and tetrakis(triphenylphosphane) palladium(14.3 mg, 0.01 mmol, 0.1 equiv.). After stirring for 2 h at 130 degrees C. with microwave under a nitrogen atmosphere, Desired product could be detected by LCMS. the resulting mixture was concentrated under reduced pressure. The residue was purified by Prep-HPLC (Column: XBridge Shield RP18 OBD Column, 5 um, 19*150 mm; Mobile Phase A: Water (10 mmol/L NH4HCO3), Mobile Phase B: MeCN; Flow rate: 20 mL/min; Gradient: 40% B to 65% B in 10 min; 254 nm, Rt: 6.42 9.35 min) to afford 5-chloro-4-(4-[[4-fluoro-2-(trifluoromethyl)phenyl]methyl]-3-oxopiperazin-1-yl)-6-methyl-2,3-dihydropyridazin-3-one (15 mg, 28.87%) as a white solid.

Compound DN was prepared by the methods and scheme described above for Compound DM.

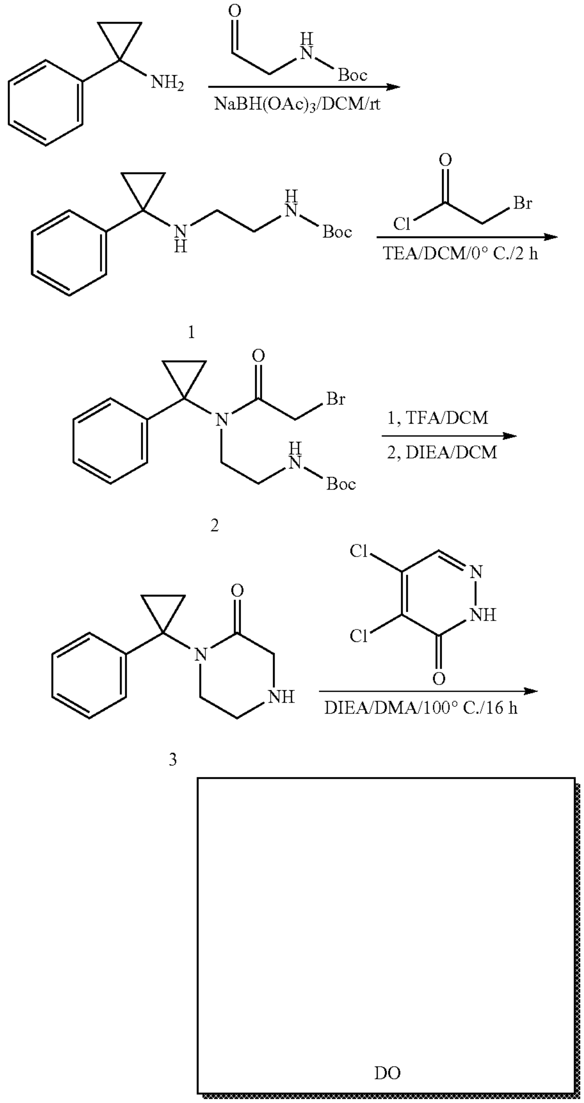

1

2

3

DO tert-butyl N-[2-[(1-phenylcyclopropyl)amino]ethyl]carbamate

To a stirred mixture of 1-phenylcyclopropan-1-amine (200 mg, 1.50 mmol, 1 equiv.) and NaBH(OAc)3 (636.5 mg, 3.00 mmol, 2 equiv.) in DCM (30 mL) was added tert-butyl N-(2-oxoethyl)carbamate (262.9 mg, 1.65 mmol, 1.1 equiv.) at room temperature under nitrogen atmosphere. The resulting mixture was stirred for 16 h at room temperature. The reaction was monitored by LCMS. The resulting mixture was filtered, the filter cake was washed with DCM (3×50 mL). The filtrate was concentrated under reduced pressure.

The residue was purified by Prep-TLC (petroleum ether/EtOAc=3:1) to afford tert-butyl N-[2-[(1-phenylcyclopropyl)amino]ethyl]carbamate (360 mg, 86.75%) as a yellow solid.

Tert-Butyl N-[2-[2-bromo-N-(1-phenylcyclopropyl)acetamido]ethyl]carbamate

To a stirred mixture of tert-butyl N-[2-[(1-phenylcyclopropyl)amino]ethyl]carbamate (360 mg, 1.30 mmol, 1 equiv.) and TEA (263.6 mg, 2.61 mmol, 2 equiv.) in DCM (20 mL) was added 2-bromoacetyl chloride (246.0 mg, 1.56 mmol, 1.2 equiv.) dropwise at 0 degrees C. under nitrogen atmosphere. The resulting mixture was stirred for 2 h at room temperature. The reaction was monitored by LCMS. The resulting mixture was concentrated under reduced pressure. The resulting mixture was extracted with DCM (3×50 mL). The combined organic layers were washed with brine (1×30 mL), dried over anhydrous MgSO4. After filtration, the filtrate was concentrated under reduced pressure. The residue was purified by Prep-TLC (petroleum ether/EtOAc=5:1) to afford tert-butyl N-[2-[2-bromo-N-(1-phenylcyclopropyl)acetamido]ethyl]carbamate (340 mg) as a yellow solid.

N-(2-aminoethyl)-2-bromo-N-(1-phenylcyclopropyl)acetamide

To a stirred solution of tert-butyl N-[2-[2-bromo-N-(1-phenylcyclopropyl)acetamido]ethyl]carbamate (340 mg) in DCM (5 mL) was added TFA (1 mL) at room temperature under nitrogen atmosphere. The resulting mixture was stirred for 16 h at room temperature. The reaction was monitored by LCMS. The resulting mixture was concentrated under reduced pressure. The mixture was basified to pH 8 with saturated NaHCO3 (aq.). The resulting mixture was extracted with DCM (3×100 mL). The combined organic layers were washed with brine (1×50 mL), dried over anhydrous MgSO4. After filtration, the filtrate was concentrated under reduced pressure. This resulted in N-(2-aminoethyl)-2-bromo-N-(1-phenylcyclopropyl)acetamide (180 mg) as a yellow solid.

1-(1-phenylcyclopropyl)piperazin-2-one

To a stirred solution of N-(2-aminoethyl)-2-bromo-N-(1-phenylcyclopropyl)acetamide (180 mg, 0.61 mmol, 1 equiv.) in DMF (5 mL) was added DIEA (234.8 mg, 1.82 mmol, 3 equiv.) at room temperature under nitrogen atmosphere. The resulting mixture was stirred for 16 h at room temperature. The reaction was monitored by LCMS. The crude product was purified by reverse phase flash with the following conditions (Column: XBridge Shield RP18 OBD Column, 5 um, 19*150 mm; Mobile Phase A: Water (10 mmol/L NH4HCO3), Mobile Phase B: MeCN; Flow rate: 20 mL/min; Gradient: 10% B to 30% B in 20 min; 254 nm; Rt: 6.17 min) to afford 1-(1-phenylcyclopropyl)piperazin-2-one (100 mg, 76.34%) as a white solid.

Compound DO 4-chloro-5-[3-oxo-4-(1-phenylcyclopropyl)piperazin-1-yl]-2,3-dihydropyridazin-3-one To a stirred mixture of 1-(1-phenylcyclopropyl)piperazin-2-one (50 mg, 0.23 mmol, 1 equiv.) and DIEA (89.6 mg, 0.69 mmol, 3 equiv.) in DMA (3 mL) was added 4,5-dichloro-2,3-dihydropyridazin-3-one (38.1 mg, 0.23 mmol, 1 equiv.) at room temperature under nitrogen atmosphere. The resulting mixture was stirred for 16 h at 100 degrees C. The reaction was monitored by LCMS. The mixture was allowed to cool down to room temperature. The crude product (80 mg) was purified by Prep-HPLC with the following conditions (Column: XBridge Shield RP18 OBD Column, 5 um, 19*150 mm; Mobile Phase A: Water (10 mmol/L NH4HCO3), Mobile Phase B: MeCN; Flow rate: 20 mL/min; Gradient: 20% B to 40% B in 7 min; 254 nm; Rt: 6.17 min) to afford 4-chloro-5-[3-oxo-4-(1-phenylcyclopropyl)piperazin-1-yl]-2,3-dihydropyridazin-3-one (32.4 mg, 40.65%) as a white solid.

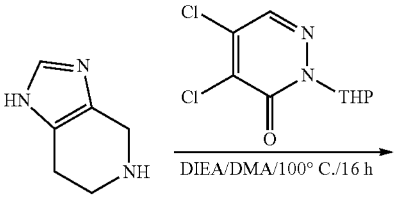

2HCl

-continued

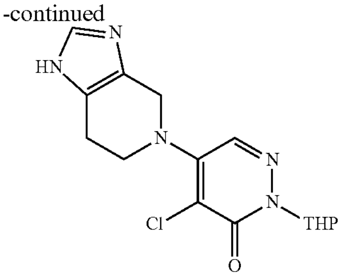

4-chloro-5-[1H,4H,5H,6H,7H-imidazo[4,5-c]pyridin-5-yl]-2-(oxan-2-yl)-2,3-dihydropyridazin-3-one To a stirred solution of 1H,4H,5H,6H,7H-imidazo[4,5-c]pyridine dihydrochloride (7 g, 35.70 mmol, 1 equiv.) and DIEA (13.8 g, 107.10 mmol, 3 equiv.) in DMA (150 mL) was added 4,5-dichloro-2-(oxan-2-yl)-2,3-dihydropyridazin-3-one (8.9 g, 35.70 mmol, 1 equiv.) at room temperature. The resulting mixture was stirred for 16 h at 100 degrees C. The product was purified by reverse phase flash with the following conditions (Column: spherical C18, 20-40 um, 330 g; Mobile Phase A: Water (5 mmol/L NH4HCO3), Mobile Phase B: MeCN; Flow rate: 80 mL/min; Gradient: 15% B to 30% B in 20 min; 220 nm) to afford 4-chloro-5-[1H,4H,5H,6H,7H-imidazo[4,5-c]pyridin-5-yl]-2-(oxan-2-yl)-2,3-dihydropyridazin-3-one (6.86 g, 57.23%) as a yellow solid.

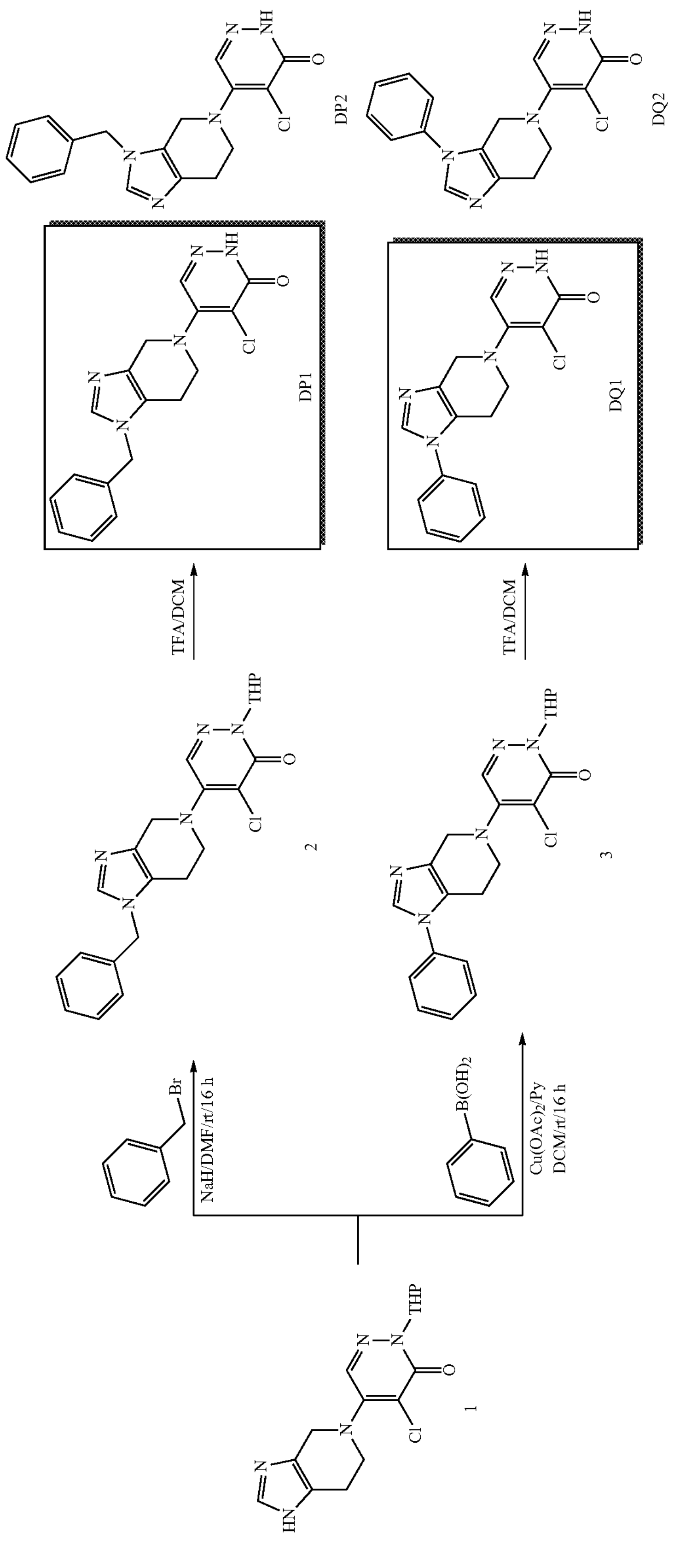
1
2
3
DP1
DQ1
DP2
DQ2

5-[1-benzyl-1H,4H,5H,6H,7H-imidazo[4,5-c]pyridin-5-yl]-4-chloro-2-(oxan-2-yl)-2,3-dihydropyridazin-3-one To a stirred solution of 4-chloro-5-[1H,4H,5H,6H,7H-imidazo[4,5-c]pyridin-5-yl]-2-(oxan-2-yl)-2,3-dihydropyridazin-3-one (150 mg, 0.45 mmol, 1 equiv.) in DMF (3 mL) was added NaH (26.8 mg, 0.67 mmol, 1.5 equiv., 600%) at room temperature. The resulting mixture was stirred for 0.5 h at room temperature. To the above mixture was added (bromomethyl)benzene (114.6 mg, 0.67 mmol, 1.5 equiv.) at 0 degrees C. The resulting mixture was stirred for additional 2 h at room temperature. The reaction was quenched with water (30 mL) at room temperature. The resulting mixture was extracted with EA (2×30 mL). The combined organic layers were washed with brine (30 mL), dried over anhydrous MgSO4. After filtration, the filtrate was concentrated under reduced pressure. The residue was purified by Prep-TLC (DCM/MeOH, 30:1) to afford 5-[1-benzyl-1H,4H,5H,6H,7H-imidazo[4,5-c]pyridin-5-yl]-4-chloro-2-(oxan-2-yl)-2,3-dihydropyridazin-3-one (100 mg, 52.56%) as a mixture of regioisomers as a yellow solid.

5-[1-benzyl-1H,4H,5H,6H,7H-imidazo[4,5-c]pyridin-5-yl]-4-chloro-2,3-dihydropyridazin-3-one & 5-[3-benzyl-3H,4H,5H,6H,7H-imidazo[4,5-c]pyridin-5-yl]-4-chloro-2,3-dihydropyridazin-3-one To a solution of 5-[1-benzyl-1H,4H,5H,6H,7H-imidazo[4,5-c]pyridin-5-yl]-4-chloro-2-(oxan-2-yl)-2,3-dihydropyridazin-3-one (100 mg, 230 mmol, 1 equiv.) in EtOH (10 mL) was added HCl (2.5 mL, 30440 mmol, 129.662 equiv., 37%) dropwise at room temperature. The resulting mixture was stirred for 16 h at 80 degrees C. The resulting mixture was concentrated under vacuum. The residue was basified to pH 8~9 with saturated NaHCO3 (aq.). The resulting mixture was extracted with EtOAc (2×50 mL). The combined organic layers were washed with brine (50 mL), dried over anhydrous MgSO4. After filtration, the filtrate was concentrated under reduced pressure. The residue was purified by Prep-TLC (DCM/MeOH 10:1) to afford crude product. The crude product was purified by Prep-HPLC with the following conditions ( ) to afford 5-[1-benzyl-1H,4H,5H,6H,7H-imidazo[4,5-c]pyridin-5-yl]-4-chloro-2,3-dihydropyridazin-3-one (21.2 mg, 26.42%) as a white solid and 5-[3-benzyl-3H,4H,5H,6H,7H-imidazo[4,5-c]pyridin-5-yl]-4-chloro-2,3-dihydropyridazin-3-one (12.8 mg, 15.95%) as a white solid.

Compounds DQ1 and DQ2

4-chloro-2-(oxan-2-yl)-5-[1-phenyl-1H,4H,5H,6H,7H-imidazo[4,5-c]pyridin-5-yl]-2,3-dihydropyridazin-3-one & 4-chloro-2-(oxan-2-yl)-5-[3-phenyl-3H,4H,5H,6H,7H-imidazo[4,5-c]pyridin-5-yl]-2,3-dihydropyridazin-3-one To a stirred solution of 4-chloro-5-[1H,4H,5H,6H,7H-imidazo[4,5-c]pyridin-5-yl]-2-(oxan-2-yl)-2,3-dihydropyridazin-3-one (200 mg, 0.60 mmol, 1 equiv.), phenylboronic acid (145.2 mg, 1.19 mmol, 2 equiv.) and Cu(OAc)2 (108.2 mg, 0.60 mmol, 1 equiv.) in DCM (5 mL) was added Pyridine (94.2 mg, 1.19 mmol, 2 equiv.) at room temperature. The resulting mixture was stirred for 36 h at room temperature under open air atmosphere. The resulting mixture was filtered. The filtrate was concentrated under reduced pressure. The residue was purified by Prep-TLC (DCM/MeOH 15:1) to afford 4-chloro-2-(oxan-2-yl)-5-[1-phenyl-1H,4H,5H,6H,7H-imidazo[4,5-c]pyridin-5-yl]-2,3-dihydropyridazin-3-one (150 mg, 61.14%) as a mixture of regioisomers and a yellow oil.

4-chloro-5-[1-phenyl-1H,4H,5H,6H,7H-imidazo[4,5-c]pyridin-5-yl]-2,3-dihydropyridazin-3-one & 4-chloro-5-[3-phenyl-3H,4H,5H,6H,7H-imidazo[4,5-c]pyridin-5-yl]-2,3-dihydropyridazin-3-one To a stirred solution of 4-chloro-2-(oxan-2-yl)-5-[1-phenyl-1H,4H,5H,6H,7H-imidazo[4,5-c]pyridin-5-yl]-2,3-dihydropyridazin-3-one (150 mg, 360 mmol, 1 equiv.) in EtOH (10 mL, 172.14 mmol, 472.666 equiv.) was added HCl (2.5 mL, 82.28 mmol, 225.932 equiv.) dropwise at room temperature. The resulting mixture was stirred for 16 h at 80 degrees C. The resulting mixture was concentrated under reduced pressure. The residue was basified to pH 8~9 with saturated NaHCO3 (aq.). The resulting mixture was extracted with EtOAc (2×50 mL). The combined organic layers were washed with brine (50 mL), dried over anhydrous MgSO4. After filtration, the filtrate was concentrated under reduced pressure. The crude product was purified by Prep-HPLC with the following conditions (Column: XBridge Shield RP18 OBD Column, 5 um, 19*150 mm; Mobile Phase A: Water (10 mmol/L NH4HCO3), Mobile Phase B: MeCN; Flow rate: 20 mL/min; Gradient: 18% B to 38% B in 7 min; 220 nm; Rt: 6.03, 6.93 min) to afford 4-chloro-5-[l-phenyl-1H,4H,5H,6H,7H-imidazo[4,5-c]pyridin-5-yl]-2,3-dihydropyridazin-3-one (4.4 mg, 3.69%) as a white solid and 4-chloro-5-[3-phenyl-3H,4H,5H,6H,7H-imidazo[4,5-c]pyridin-5-yl]-2,3-dihydropyridazin-3-one (17.4 mg, 14.58%) as a white solid.

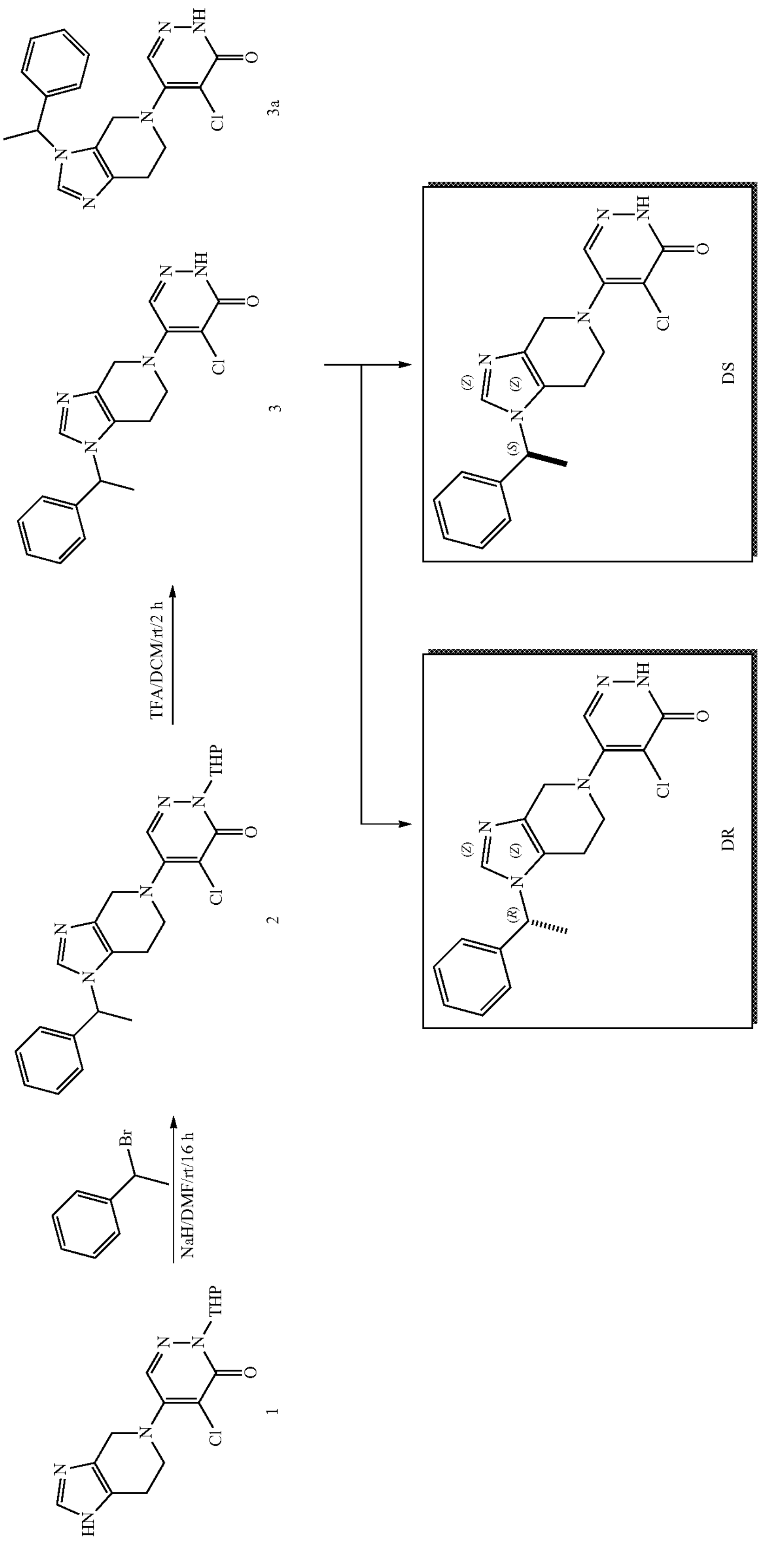
1
2
3
3a
DR
DS

Compounds DR and DS were prepared by the methods described for Compound DP1 and DP2.

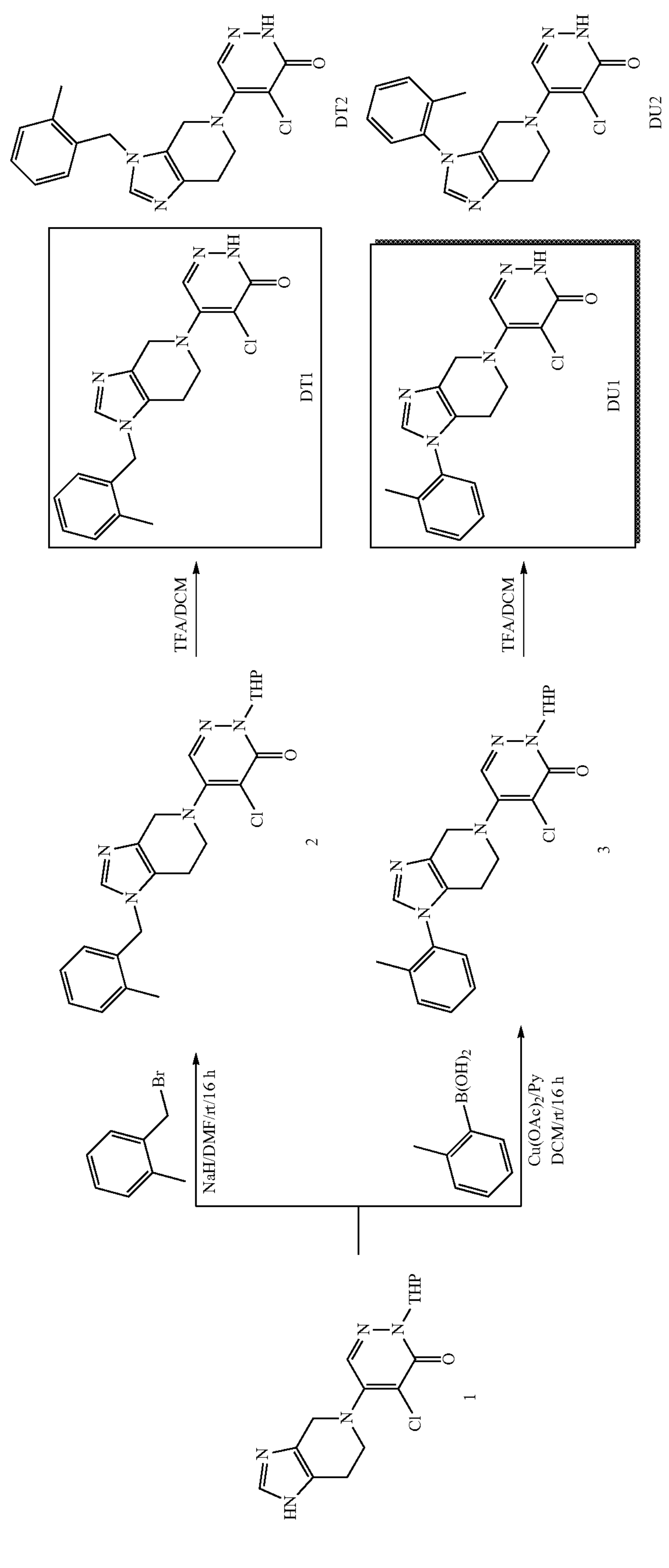
1 2 3 DT1 DT2 DU1 DU2

Compounds DT1 and DT2 were prepared by the methods and scheme described for Compounds DP1 and DP2 above. Compounds DU1 and DU2 were prepared by the methods and scheme described for compounds DQ1 and DQ2 above.

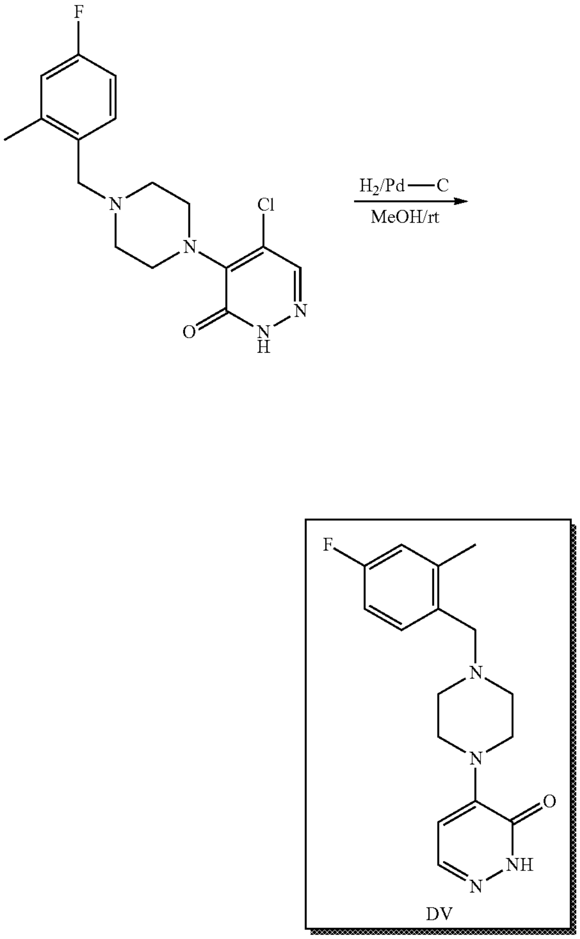

DV

Compound DV

4-[4-[(4-fluoro-2-methylphenyl)methyl]piperazin-1-yl]-2,3-dihydropyridazin-3-one To a stirred solution of 5-chloro-4-[4-[(4-fluoro-2-methylphenyl)methyl]piperazin-1-yl]-2,3-dihydropyridazin-3-one (80 mg) in MeOH (30 mL) was added MeOH (30 mL) at room temperature. The resulting mixture was stirred for 16 h at room temperature under hydrogen atmosphere. The reaction was monitored by LCMS. The resulting mixture was filtered, the filter cake was washed with MeOH (3×50 mL). The filtrate was concentrated under reduced pressure. The crude product (80 mg) was purified by Prep-HPLC with the following conditions (Column: XBridge Shield RP18 OBD Column, 5 um, 19*150 mm; Mobile Phase A: Water (10 mmol/L NH4HCO3), Mobile Phase B: MeCN; Flow rate: 20 mL/min; Gradient: 30% B to 65% B in 7 min; 254 nm; Rt: 5.8 min) to afford 4-[4-[(4-fluoro-2-methylphenyl)methyl]piperazin-1-yl]-2,3-dihydropyridazin-3-one (30.2 mg) as an off-white solid.

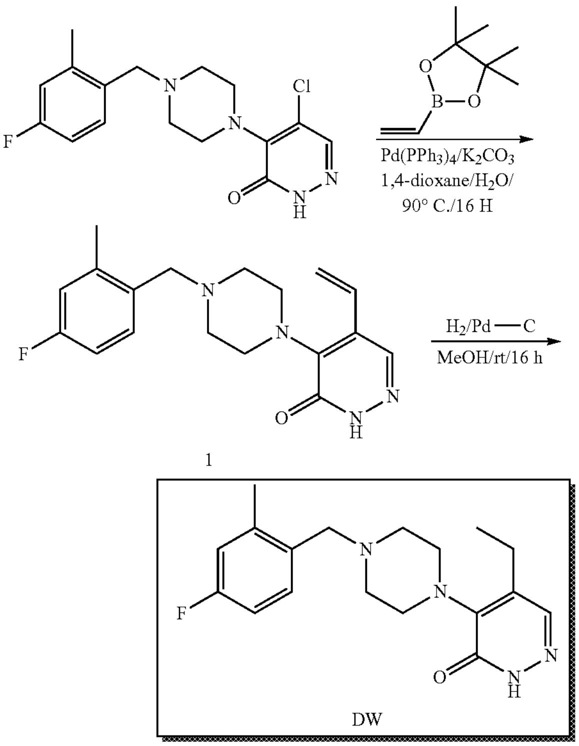

1

DW 5-ethenyl-4-[4-[(4-fluoro-2-methylphenyl)methyl]piperazin-1-yl]-2,3-dihydropyridazin-3-one To a mixture of 5-chloro-4-[4-[(4-fluoro-2-methylphenyl)methyl]piperazin-1-yl]-2,3-dihydropyridazin-3-one (200 mg, 0.59 mmol, 1 equiv.), 2-ethenyl-4,4,5,5-tetramethyl-1,3,2-dioxaborolane (182.9 mg, 1.19 mmol, 2 equiv.), Pd(PPh3)4 (68.6 mg, 0.06 mmol, 0.1 equiv.), K2CO3 (246.2 mg, 1.78 mmol, 3 equiv.) in 1,4-dioxane (10 mL) was added H2O (2 mL, 111.02 mmol, 186.948 equiv.) at rt under nitrogen atmosphere. The reaction was stirred for 16 h at 100 degrees C. The reaction was monitored by LCMS. The mixture was allowed to cool down to ambient temperature. The reaction mixture was diluted with water (100 mL). extracted with EA (100 mL×2). The organic layers was washed with saturated brine (100 ml), dried over anhydrous Na2SO4, filtered and concentrated to give desired product. The residue was purified by Prep-TLC (DCM/MeOH 30:1) to afford crude product. The crude product was purified by Prep-HPLC with the following conditions (Column: XBridge Shield RP18 OBD Column, 5 um, 19*150 mm; Mobile Phase A: Water (10 mmol/L NH4HCO3), Mobile Phase B: MeCN; Flow rate: 20 mL/min; Gradient: 35% B to 75% B in 7 min; 220 nm; Rt: 6.28 min) to afford 5-ethenyl-4-[4-[(4-fluoro-2-methylphenyl)methyl]piperazin-1-yl]-2,3-dihydropyridazin-3-one (31.1 mg, 15.95%) as a white solid.

Compound DW 5-ethyl-4-[4-[(4-fluoro-2-methylphenyl)methyl]piperazin-1-yl]-2,3-dihydropyridazin-3-one To a solution of 5-ethenyl-4-[4-[(4-fluoro-2-methylphenyl)methyl]piperazin-1-yl]-2,3-dihydropyridazin-3-one (100 mg, 0.30 mmol, 1 equiv.) in 15 mL EtOAc was added PtO2 (4.2 mg, 0.02 mmol) under nitrogen atmosphere in a 100 mL round-bottom flask. The mixture was hydrogenated at 50 degrees C. for overnight under hydrogen atmosphere using a hydrogen balloon, filtered through a Celite pad and concentrated under reduced pressure. The crude product was purified by Prep-HPLC with the following conditions (Column: XBridge Shield RP18 OBD Column 30*150 mm, 5 um; Mobile Phase A: Water (10 mmol/L NH4HCO3), Mobile Phase B: MeCN; Flow rate: 60 mL/min; Gradient: 33% B to 63% B in 7 min; 254 nm; Rt: 6.63 min) to afford 5-ethyl-4-[4-[(4-fluoro-2-methylphenyl)methyl]piperazin-1-yl]-2,3-dihydropyridazin-3-one (57.4 mg, 57.05%) as a white solid.

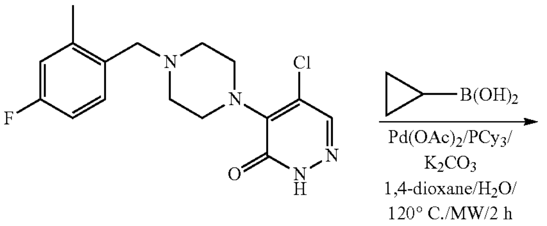

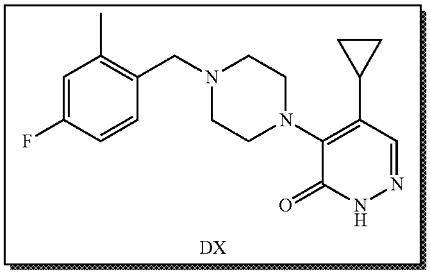

DX

Compound DX 5-cyclopropyl-4-[4-[(4-fluoro-2-methylphenyl) methyl]piperazin-1-yl]-2,3-dihydropyridazin-3-one To a solution of 5-chloro-4-[4-[(4-fluoro-2-methylphenvl) methyl]piperazin-1-yl]-2,3-dihydropyridazin-3-one (200 mg, 0.59 mmol, 1 equiv.) in 1,4-dioxane (5 mL) and water (1 mL) were added cyclopropylboronic acid (102.0 mg, 1.19 mmol, 2.000 equiv.), PCy3 (29.7 mg, 0.11 mmol, 0.4 equiv.), PCy3 (140.5 mg, 0.24 mmol, 0.4 equiv.), Pd(AcO)2 (26.7 mg, 0.12 mmol, 0.2 equiv.) and K2CO3 (164.1 mg, 1.19 mmol, 2 equiv.). The reaction was irradiated with microwave radiation at 130 degrees C. for 3 h. The desired product could be detected by LCMS. The reaction mixture was diluted with water (100 mL). extracted with EA (100 mL×2). The organic layers was washed with saturated brine (100 ml), dried over anhydrous Na2SO4, filtered and concentrated to give desired product. The residue was purified by Prep-TLC (DCM/MeOH 20:1) to afford crude product. The crude product was purified by Prep-HPLC with the following conditions (Column. XBridge Shield RP18 OBD Column 30*150 mm, 5 um; Mobile Phase A: Water (10 mmol/L NH4HCO3), Mobile Phase B: MeCN; Flow rate: 60 mL/min; Gradient: 33% B to 63% B in 7 min; 254 nm; Rt: 6.68 min) to afford 5-cyclopropyl-4-[4-[(4-fluoro-2-methylphenyl)methyl]piperazin-1-yl]-2,3-dihydropyridazin-3-one (21.6 mg, 10.62%) as an off-white solid.

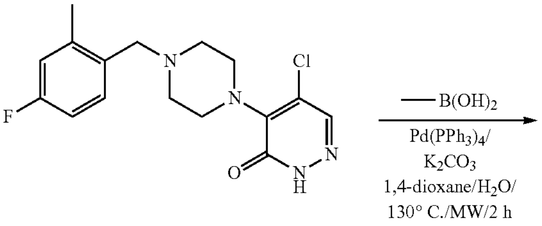

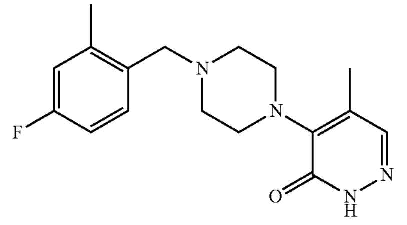

DY

Compound DY

4-[4-[(4-fluoro-2-methylphenyl)methyl]piperazin-1-yl]-5-methyl-2,3-dihydropyridazin-3-one To a solution of 5-chloro-4-[4-[(4-fluoro-2-methylphenyl) methyl]piperazin-1-yl]-2,3-dihydropyridazin-3-one (200 mg, 0.59 mmol, 1 equiv.) in 1,4-dioxane (10 mL) and water (2 mL) were added methylboronic acid (142.2 mg, 2.38 mmol, 4.000 equiv.), K2CO3 (164.1 mg, 1.19 mmol, 2 equiv.) and Pd(PPh3)4 (68.6 mg, 0.06 mmol, 0.1 equiv.). The reaction was irradiated with microwave radiation at 130 degrees C. for 2 h. The desired product could be detected by LCMS. The reaction mixture was diluted with water (00 mL). extracted with EA (100 mL×2). The organic layers was washed with saturated brine (100 ml), dried over anhydrous Na2SO4, filtered and concentrated to give desired product. The residue was purified by Prep-TLC (DCM/MeOH 20:1) to afford crude product. The crude product was purified by Prep-HPLC with the following conditions (Column; XBridge Shield RP18 OBD Column 30*150 mm, 5 um; Mobile Phase A: Water (10 mmol/L NH4HCO3), Mobile Phase B: MeCN; Flow rate: 60 mL/min; Gradient: 30% B to 60% B in 7 min. 254 nm; Rt: 6.13 min) to afford 4-[4-[(4-fluoro-2-methylphenvl)methyl]piperazin-1-yl]-5-methyl-2,3-dihydropyridazin-3-one (72 mg, 38.32%) as a light yellow solid

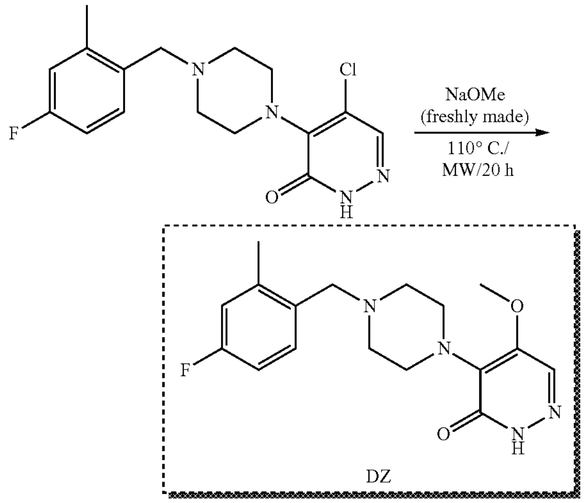

Compound DZ

4-[4-[(4-fluoro-2-methylphenyl)methyl]piperazin-1-yl]-5-methoxy-2,3-dihydropyridazin-3-one To a solution of 5-chloro-4-[4-[(4-fluoro-2-methylphenvl) methyl]piperazin-1-yl]-2,3-dihydropyridazin-3-one (200 mg, 0.59 mmol, 1 equiv.) in sodium methoxide solution (15 mL) was added 4-[4-[(4-fluoro-2-methylphenyl)methyl]piperazin-1-yl]-5-methoxy-2,3-dihydropyridazin-3-one (17.2 mg, 8.71%). The reaction was irradiated with microwave radiation at 100 degrees C. for 25 h. The reaction mixture was concentrated under reduced pressure. The crude product was purified by Prep-HPLC with the following conditions (Column: XBridge Shield RP18 OBD Column 30*150 mm, 5 um; Mobile Phase A: Water (10 mmol/L NH4HCO3), Mobile Phase B: MeCN; Flow rate: 60 mL/min; Gradient: 27% B to 65% B in 7 min; 254 nm; Rt: 6.37 min) to afford 4-[4-[(4-fluoro-2-methylphenyl)methyl]piperazin-1-yl]-5-methoxy-2,3-dihydropyridazin-3-one (17.2 mg, 8.71%) as a white solid.

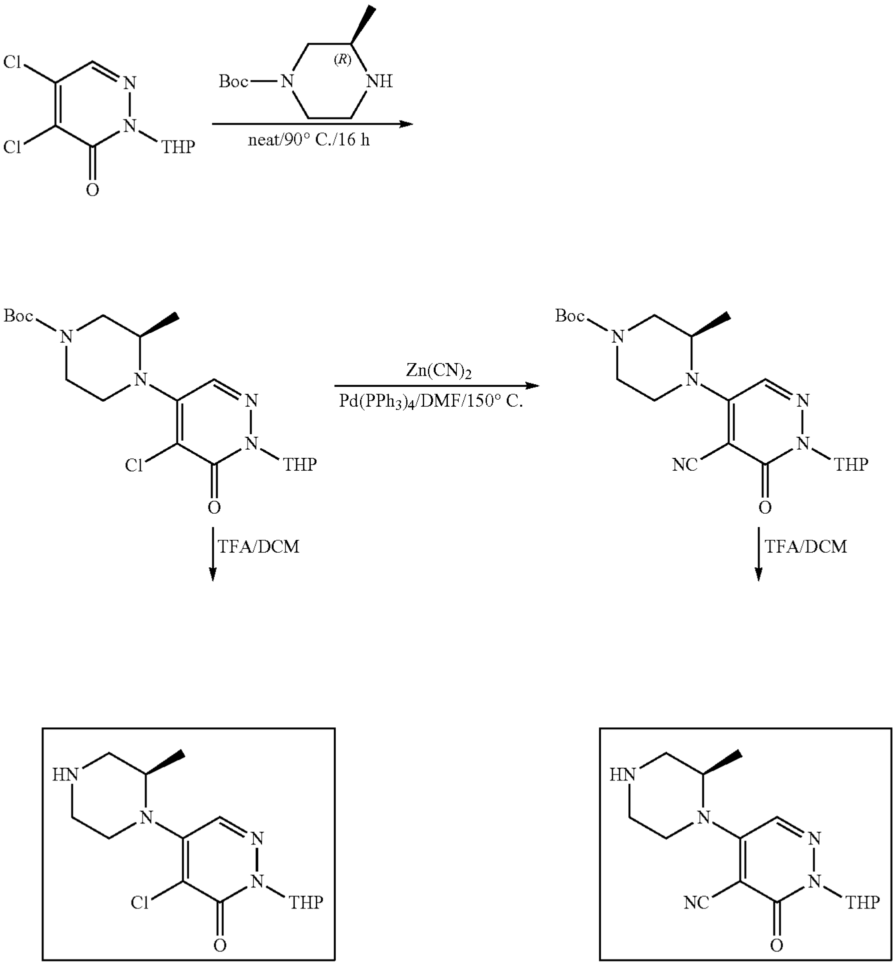

Int1
Tested: [a]$^{2C}$D = -40°
(c = 1 mg/mL, MeOH)

Int2
Tested: [a]$^{2C}$D = -150°
(c = 1 mg/mL, MeOH)

Preparation of Intermediates Int1 and Int2

(3R)-4-[5-chloro-1-(oxan-2-yl)-6-oxo-1,6-dihydro-pyridazin-4-yl]-3-methylpiperazine-1-carboxylate Into a 50 mL round-bottom flask were added 4,5-dichloro-2-(oxan-2-yl)-2,3-dihydropyridazin-3-one (2 g, 8.03 mmol, 1 equiv.) and tert-butyl (3R)-3-methylpiperazine-1-carboxylate (1.9 g, 9.49 mmol, 1.18 equiv.) at room temperature. The resulting mixture was stirred for 3 h at 60 degrees C. The reaction was monitored by LCMS. The residue product was purified by reverse phase flash with the following conditions (Column: Kinetex EVO C18 Column 30.150 mm 5 um; Mobile Phase A: Water (10 mmol/L NH4HCO3), Mobile Phase B: ACN; Flow rate: 60 mL/min; Gradient: 35% B to 70% B in 7 min; 220 nm; Rt: 6.80, 8.85 min) to afford tert-butyl (3R)-4-[5-chloro-1-(oxan-2-yl)-6-oxo-1,6-dihydropyridazin-4-yl]-3-methylpiperazine-1-carboxylate (1.5 g, 45.24%) as a yellow oil.

Int1: 4-chloro-5-[(2R)-2-methylpiperazin-1-yl]-2,3-dihydropyridazin-3-one

To a stirred solution of tert-butyl (3R)-4-[5-chloro-1-(oxan-2-yl)-6-oxo-1,6-dihydropyridazin-4-yl]-3-methylpiperazine-1-carboxylate (1500 mg, 3.63 mmol, 1 equiv.) in DCM (15 mL) was added TFA (5.0 mL, 69.35 mmol, 16.99 equiv.) at room temperature. The resulting mixture was stirred for 2 h at room temperature. The reaction was monitored by LCMS. The resulting mixture was concentrated under reduced pressure. The residue product was purified by reverse phase flash with the following conditions (Column: Kinetex EVO C18 Column, 5 um, 19*150 mm; Mobile Phase A: Water (0.05% TFA), Mobile Phase B: ACN; Flow rate: 20 mL/min; Gradient: 3% B to 20% B in 7 min; 220 nm; Rt: 5.38 min) to afford 4-chloro-5-[(2R)-2-methylpiperazin-1-yl]-2,3-dihydropyridazin-3-one (850 mg) as a yellow oil.

Tert-Butyl (3R)-4-[5-cyano-1-(oxan-2-yl)-6-oxo-1,6-dihydropyridazin-4-yl]-3-methylpiperazine-1-carboxylate To a stirred mixture of tert-butyl (3R)-4-[5-chloro-1-(oxan-2-yl)-6-oxo-1,6-dihydropyridazin-4-yl]-3-methylpiperazine-1-carboxylate (15 g, 36.33 mmol, 1 equiv.) and Zn(CN)2 (12.8 g, 108.98 mmol, 3 equiv.) in DMF (200 mL) were added Pd(PPh3)4 (2.1 g, 1.82 mmol, 0.05 equiv.) in portions at room temperature under nitrogen atmosphere. The resulting mixture was stirred for 16 h at 140 degrees C. under nitrogen atmosphere. The resulting mixture was concentrated under reduced pressure. The resulting mixture was extracted with DCM (5×300 mL). The combined organic layers were washed with Sat NaCl(aq) (2×50 mL), dried over anhydrous Na2SO4. After filtration, the filtrate was concentrated under reduced pressure. The residue was purified by silica gel column chromatography, eluted with PE:EA (80:1 to 3:1) to afford tert-butyl (3R)-4-[5-cyano-1-(oxan-2-yl)-6-oxo-1,6-dihydropyridazin-4-yl]-3-methylpiperazine-1-carboxylate (6 g, 40.94%) as a yellow solid.

5-((R)-2-methylpiperazin-1-yl)-3-oxo-2-(tetrahydro-2H-pyran-2-yl)-2,3-dihydropyridazine-4-carbonitrile tert-butyl (3R)-4-(5-cyano-6-oxo-1-(tetrahydro-2H-pyran-2-yl)-1,6-dihydropyridazin-4-yl)-3-methylpiperazine-1-carboxylate (2.00 g, 4.96 mmol) was dissolved into 1,4-dioxane (30 mL, contains HCl gas, 4M) and stirred for 3 h at ambient temperature. The reaction mixture was basified to pH=10 with saturated aqueous Na2CO3 and extracted with ethyl acetate (3×100 mL). The organic layers were collected, washed with brine (2×50 mL), dried over anhydrous Na2SO4 and filtered. The filtrate was concentrated under reduced pressure and the residue was purified by reverse phase flash chromatography with the following conditions: Column: WelFlash™ C18-I, 20-40 uM, 330 g; Mobile Phase A: Water (plus 10 mM NH4HCO3 and 0.05% NH3·H2O), Mobile Phase B: ACN; Flow rate: 65 mL/min; Gradient: 5%~10% B, 4 min; 10%~40%, 20 min; Detector: 254/220 nm). Desired fractions were collected and concentrated under reduced pressure to afford 5-((R)-2-methylpiperazin-1-yl)-3-oxo-2-(tetrahydro-2H-pyran-2-yl)-2,3-dihydropyridazine-4-carbonitrile as a light yellow solid. (900 mg, 60%)

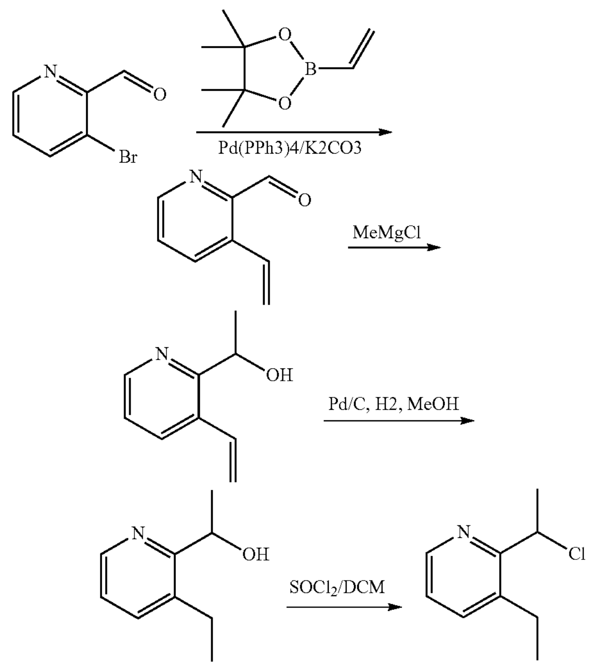

2-ethenylpyridine-3-carbaldehyde

To a stirred solution of 2-bromopyridine-3-carbaldehyde (3 g, 16.13 mmol, 1 equiv), 2-ethenyl-4,4,5,5-tetramethyl-1,3,2-dioxaborolane (3.7 g, 24.19 mmol, 1.5 equiv.) and Pd(PPh3)4 (1.9 g, 1.61 mmol, 0.1 equiv.) in dioxane (50 mL) was added K2CO3 (4.5 g, 32.26 mmol, 2 equiv.) in H2O (10 mL) at room temperature. The resulting mixture was stirred at 90 degrees C. for 16 h. The reaction mixture was filtered and the filtrate was concentrated to give the crude product which was purified by silica gel column chromatography, eluted with PE:EA (5:1 to 1:1) to afford 2-ethenylpyridine-3-carbaldehyde (1.3 g, 60.54%) as a brown oil.

1-(2-ethenylpyridin-3-yl)ethan-1-ol

To a stirred mixture of 2-ethenylpyridine-3-carbaldehyde (2.6 g, 19.53 mmol, 1 equiv.) in THF (50 mL) was added dropwise CH3MgBr (4.7 g, 39.05 mmol, 2.00 equiv.) at 0 degrees C. under nitrogen atmosphere. The resulting mixture was stirred for 2 hours at room temperature under nitrogen atmosphere. The reaction was quenched with sat. NH4Cl (aq). The resulting mixture was extracted with EtOAc (5×100 mL). The combined organic layers was washed with brine (2×50 mL), dried over anhydrous Na2SO4. After filtration, the filtrate was concentrated under reduced pressure to give the residue. The reside was purified by silica gel column chromatography, eluted with PE:EA (10:1 to 1:2) to afford 1-(2-ethenylpyridin-3-yl)ethan-1-ol (2.2 g, 75.52%) as a yellow oil.

1-(2-ethylpyridin-3-yl)ethan-1-ol

A mixture of 1-(2-ethenylpyridin-3-yl)ethan-1-ol (2.2 g, 14.75 mmol, 1 equiv.) and Pd/C (220 mg, 2.07 mmol, 0.14 equiv.) in CH3OH (50 mL) was stirred at room temperature for 3 hours under H2 atmosphere. The reaction mixture was filtered and the filtrate was concentrated under reduced pressure to give the residue. The residue was purified by silica gel column chromatography, eluted with PE:EtOAc (1:1 to 1:6) to afford 1-(2-ethylpyridin-3-yl)ethan-1-ol (2.2 g, 98.67%) as a light yellow oil.

Int2: 3-(1-chloroethyl)-2-ethylpyridine

A mixture of 1-(2-ethylpyridin-3-yl)ethan-1-ol (2.2 g, 14.55 mmol, 1 equiv.) and SOCl2 (5.2 g, 43.65 mmol, 3 equiv.) in DCM (50 mL) was stirred at room temperature for 2 hours. The resulting mixture was concentrated to give 3-(1-chloroethyl)-2-ethylpyridine (2 g, crude).

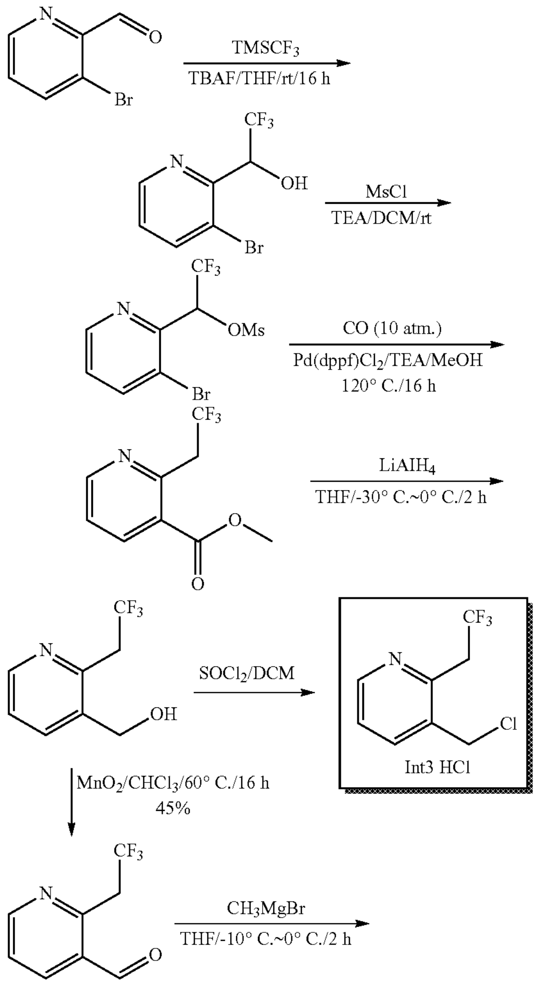

Int3 HCl

-continued

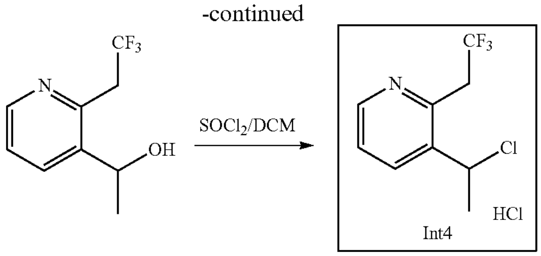

Int4

Preparation of Intermediates Int3 and Int4

1-(3-bromopyridin-2-yl)-2,2,2-trifluoroethan-1-ol

To a stirred mixture of 3-bromopyridine-2-carbaldehyde (10 g, 53.76 mmol, 1 equiv.) and trimethyl(trifluoromethyl) silane (15.3 g, 107.52 mmol, 2 equiv.) in THF (50 mL) was added TBAF (5.4 mL, 1.5 equiv.) dropwise at 0 degrees C. under nitrogen atmosphere. The resulting mixture was stirred for 10 h at room temperature. The reaction was monitored by LCMS. The resulting mixture was concentrated under reduced pressure. The residue was purified by silica gel column chromatography, eluted with PE/EtOAc (50:1 to 20:1) to afford 1-(3-bromopyridin-2-yl)-2,2,2-trifluoroethan-1-ol (10 g, 72.65%) as a yellow solid.

1-(3-bromopyridin-2-yl)-2,2,2-trifluoroethyl methanesulfonate

To a stirred mixture of 1-(3-bromopyridin-2-yl)-2,2,2-trifluoroethan-1-ol (10 g, 39.06 mmol, 1 equiv.) and DIEA (15.1 g, 117.18 mmol, 3 equiv.) in DCM (50 mL) was added methanesulfonyl chloride (5.4 g, 46.87 mmol, 1.2 equiv.) dropwise at 0 degrees C. under nitrogen atmosphere. The resulting mixture was stirred for 2 h at room temperature. The reaction was monitored by LCMS. The reaction was quenched with Water at room temperature. The resulting mixture was extracted with EtOAc (3×200 mL). The combined organic layers were washed with brine (1×100 mL), dried over anhydrous Na2SO4. After filtration, the filtrate was concentrated under reduced pressure. The residue was purified by silica gel column chromatography, eluted with PE/EtOAc (50:1 to 2:1) to afford 1-(3-bromopyridin-2-yl)-2,2,2-trifluoroethyl methanesulfonate (10.5 g, 80.46%) as a yellow oil.

Methyl 2-(2,2,2-trifluoroethyl)pyridine-3-carboxylate

To a solution of 1-(3-bromopyridin-2-yl)-2,2,2-trifluoroethyl methanesulfonate (10 g, 29.93 mmol, 1 equiv.) in 250 mL MeOH were added Pd(dppf)Cl2 (1.1 g, 1.50 mmol, 0.05 equiv), Pd(PPh3)4 (1.7 g, 1.50 mmol, 0.05 equiv.) and TEA (6.1 g, 59.86 mmol, 2 equiv.) in a pressure tank. The mixture was purged with nitrogen for 1 h and then was pressurized to 10 atm with carbon monoxide at 120 degrees C. for 16 h. The reaction mixture was cooled to room temperature and filtered to remove insoluble solids. The resulting mixture was concentrated under reduced pressure. The resulting mixture was diluted with water (200 mL). The resulting mixture was extracted with EtOAc (3×300 mL). The combined organic layers were washed with brine (1×100 mL), dried over anhydrous Na2SO4. After filtration, the filtrate was concentrated under reduced pressure. The residue was purified by silica gel column chromatography, eluted with PE/EtOAc (50:1 to 10:1) to afford methyl 2-(2,2,2-trifluoroethyl)pyridine-3-carboxylate (5 g, 76.22%) as a yellow oil.

[2-(2,2,2-trifluoroethyl)pyridin-3-yl]methanol

To a stirred solution of methyl 2-(2,2,2-trifluoroethyl) pyridine-3-carboxylate (5 g, 22.81 mmol, 1 equiv.) in THF (30 mL) was added LiAlH4 (1.0 g, 27.38 mmol, 1.2 equiv.) dropwise at 0 degrees C. The resulting mixture was stirred for 2 h at 0 degrees C. The reaction was monitored by TLC. The reaction was quenched with Water and 15% NaOH(aq.) at 0 degrees C. The resulting mixture was filtered, the filter cake was washed with EtOAc (5×20 mL). The filtrate was concentrated under reduced pressure. The residue was purified by silica gel column chromatography, eluted with PE/EtOAc (50:1 to 2:1) to afford [2-(2,2,2-trifluoroethyl) pyridin-3-yl]methanol (3.3 g, 75.67%) as a yellow solid.

Int3:
3-(chloromethyl)-2-(2,2,2-trifluoroethyl)pyridine

To a stirred solution of [2-(2,2,2-trifluoroethyl)pyridin-3-yl]methanol (500 mg, 2.62 mmol, 1 equiv.) in DCM (30 mL) was added SOCl2 (622.4 mg, 5.23 mmol, 2 equiv.) dropwise at room temperature. The resulting mixture was stirred for 16 h at room temperature. The reaction was monitored by LCMS. The resulting mixture was concentrated under reduced pressure. The residue was washed with 20 mL of hexane and stirred for 30 min. The resulting mixture was filtered, the filter cake was washed with hexane (3×3 mL). This resulted in 3-(chloromethyl)-2-(2,2,2-trifluoroethyl) pyridine (500 mg, 91.20%) as a white solid.

2-(2,2,2-trifluoroethyl)pyridine-3-carbaldehyde

To a stirred solution of [2-(2,2,2-trifluoroethyl)pyridin-3-yl]methanol (1 g, 5.23 mmol, 1 equiv.) in CHCl3 (50 mL) was added MnO2 (2.7 g, 31.39 mmol, 6 equiv.) at room temperature. The resulting mixture was stirred for 16 h at 50 degrees C. The reaction was monitored by LCMS. The mixture was allowed to cool down to room temperature. The resulting mixture was filtered, the filter cake was washed with EtOAc (3×20 mL). The filtrate was concentrated under reduced pressure. The residue was purified by silica gel column chromatography, eluted with PE/EtOAc (30:1 to 10:) to afford 2-(2,2,2-trifluoroethyl)pyridine-3-carbaldehyde (500 mg, 50.53%) as a yellow oil.

1-[2-(2,2,2-trifluoroethyl)pyridin-3-yl]ethan-1-ol

To a stirred solution of 2-(2,2,2-trifluoroethyl)pyridine-3-carbaldehyde (500 mg, 2.64 mmol, 1 equiv.) in THF (30 mL) was added bromo(methyl)magnesium (5.3 mL, 88.89 mmol, 33.63 equiv.) dropwise at −30 degrees C. under nitrogen atmosphere. The resulting mixture was stirred for 2 h at 0 degrees C. under nitrogen atmosphere. The reaction was monitored by LCMS. The reaction was quenched with sat. NH4Cl (aq.) at 0 degrees C. The resulting mixture was filtered, the filter cake was washed with EtOAc (3×10 mL). The filtrate was concentrated under reduced pressure. The residue was purified by silica gel column chromatography, eluted with PE/EtOAc (20:1 to 3:1) to afford 1-[2-(2,2,2-trifluoroethyl)pyridin-3-yl]ethan-1-ol (450 mg, 82.96%) as a yellow oil.

Int4:
3-(1-chloroethyl)-2-(2,2,2-trifluoroethyl)pyridine

To a stirred solution of 1-[2-(2,2,2-trifluoroethyl)pyridin-3-yl]ethan-1-ol (450 mg, 2.19 mmol, 1 equiv.) in DCM (20 mL) was added SOCl2 (521.8 mg, 4.39 mmol, 2 equiv.) dropwise at room temperature. The resulting mixture was stirred for 16 h at room temperature. The reaction was monitored by LCMS. The resulting mixture was concentrated under reduced pressure. Then hexane was added and resulting mixture was stirred for 1 h at room temperature. The resulting mixture was washed with 20 mL of hexane. The resulting mixture was filtered, the filter cake was washed with hexane (3×10 mL). The filtrate was concentrated under reduced pressure. This resulted in 3-(1-chloroethyl)-2-(2,2,2-trifluoroethyl)pyridine (500 mg, 101.95%) as a white solid.

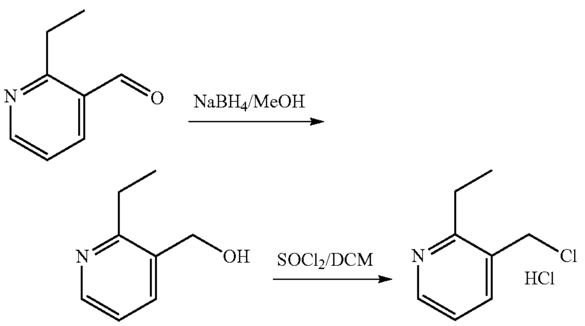

Int 5

Preparation of Intermediate 5 (Int5)

(2-ethylpyridin-3-yl)methanol

To a solution of 2-ethylpyridine-3-carbaldehyde (48 g, 355.12 mmol, 1 equiv.) in MeOH (500 mL) was added NaBH4 (20.2 g, 532.68 mmol, 1.5 equiv.) in portions at 0 degrees C. The reaction was stirred for 4 h at rt. The reaction was monitored by TLC (EA/PE=1/1). The resulting mixture was concentrated under reduced pressure. The residue was washed with 1 L of water. The resulting mixture was extracted with EtOAc (1×L). The combined organic layers were washed with brine (1×1 L), dried over anhydrous Na2SO4. After filtration, the filtrate was concentrated under reduced pressure. The residue was purified by silica gel column chromatography, eluted with PE/EtOAc (50:1 to 1:1) to afford (2-ethylpyridin-3-yl)methanol (40 g, 82.11%) as a light pink oil.

Int5: 3-(chloromethyl)-2-ethylpyridine Hydrogen Chloride

To a solution of (2-ethylpyridin-3-yl)methanol (370 mg, 2.70 mmol, 1 equiv.) in DCM (20 mL) was added SOCl2 (962.7 mg, 8.09 mmol, 3.0 equiv.) at 0 degrees C. The reaction was stirred for 16 h at rt. The reaction was monitored by LCMS. The resulting mixture was concentrated under reduced pressure. The residue (350 mg) was used in the next step directly without further purification.

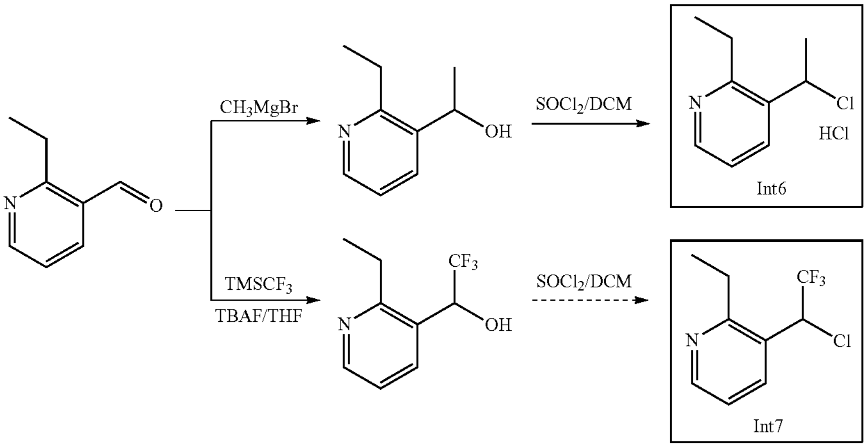

Intermediates 6 (Int6) and 7 (Int7) were Prepared by the Methods Described for Intermediate 3-(chloromethyl)-2-ethylpyridine hydrogen chloride

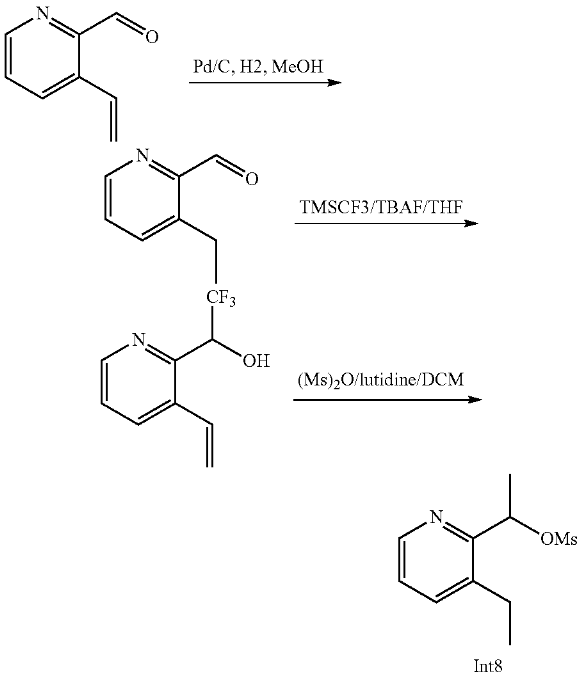

Preparation of Intermediate 8 (Int8)

2-ethylpyridine-3-carbaldehyde

To a stirred solution of 2-ethenylpyridine-3-carbaldehyde (3.4 g, 25.54 mmol, 1 equiv.) in MeOH (20 mL, 493.98 mmol) was added anhydrous Pd/C (340 mg, 319.49 mmol, 10%) at room temperature under nitrogen atmosphere. The resulting mixture was stirred for 1 h at room temperature under hydrogen atmosphere. The resulting mixture was filtered, the filter cake was washed with MeOH (6×300 mL). The filtrate was concentrated under reduced pressure. The residue was purified by silica gel column chromatography, eluted with PE/EtOAc (15% to 60%) to afford 2-ethylpyridine-3-carbaldehyde (1.4 g, 40.56%) as a red oil.

1-(2-ethylpyridin-3-yl)-2,2,2-trifluoroethan-1-ol

To a mixture of 2-ethylpyridine-3-carbaldehyde (2 g, 14.80 mmol, 1 equiv.) and TMSCF3 (4.2 g, 29.59 mmol, 2 equiv.) in THF (60 mL) was added TBAF (386.9 mg, 1.48 mmol, 0.1 equiv.) at 0 degrees C. for 0.5 h. The resulting mixture was stirred for additional 16 h at room temperature. The resulting mixture was added ethyl acetate (300 mL) and brine (100 mL), then the water layer was extracted with ethyl acetate (200 mL). The combined organic layer was dried over anhydrous Na2SO4 and filtered. The filtrate was concentrated to give the crude product which was purified by silica gel column chromatography, eluted with PE:EA (5:1 to 1:2) to afford 1-(2-ethylpyridin-3-yl)-2,2,2-trifluoroethan-1-ol (2.1 g, 69.17%) as an orange solid.

Int8: 1-(2-ethylpyridin-3-yl)-2,2,2-trifluoroethyl trifluoromethanesulfonate

To a stirred solution of 1-(2-ethylpyridin-3-yl)-2,2,2-trifluoroethan-1-ol (1.2 g, 5.85 mmol, 1 equiv.) in dry DCM (15 mL) at 0 degrees C. was added 2,6-lutidine (0.9 g, 8.77 mmol, 1.5 equiv.). The reaction was allowed to stir for 5 min. trifluoromethanesulfonic anhydride (2.5 g, 8.77 mmol, 1.5 equiv.) was added dropwise. The resulted mixture was stirred for 0.5 h at 0 degrees C. Then water (30 mL) and DCM (100 mL) were added. The organic layer was washed with H2O (2×50 mL) and brine (50 mL), dried over anhydrous Na2SO4, filtered. The filtrate was concentrated to give the crude product which was purified by silica gel column chromatography, eluted with PE:EA (20:1 to 4:1) to afford 1-(2-ethylpyridin-3-yl)-2,2,2-trifluoroethyl trifluoromethanesulfonate (1.2 g, 60.84%) as a red oil.

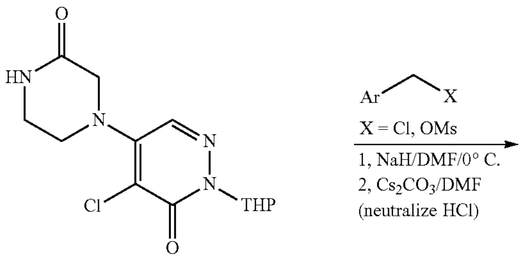

-continued

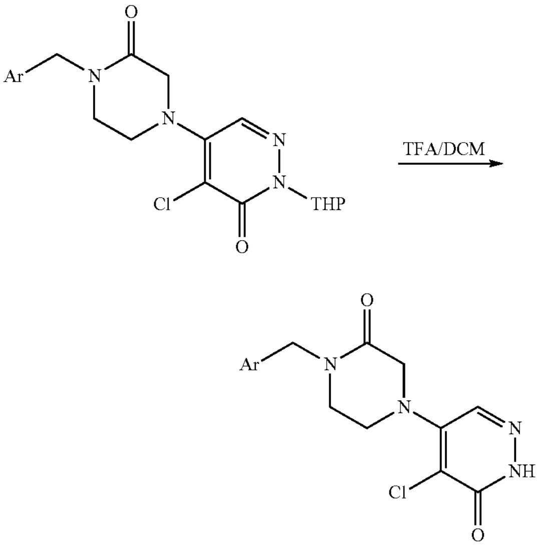

Final Targets

| 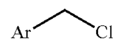 | Target ID |
|---|---|
| 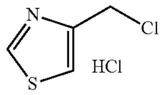 | EA |
| 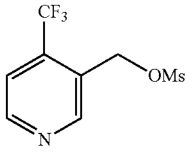 [SMILES: CS(=O)(=O)OCc1cnccc1C(F)(F)F] | EB |
| 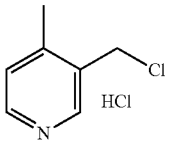 | EC |

Preparation of EA 4-chloro-2-(oxan-2-yl)-5-[3-oxo-4-[(1,3-thiazol-4-yl)methyl]piperazin-1-yl]-2,3-dihydropyridazin-3-one To a stirred solution of 4-chloro-2-(oxan-2-yl)-5-(3-oxopiperazin-1-yl)-2,3-dihydropyridazin-3-one (200 mg, 0.64 mmol, 1 equiv.) in DMF (6 mL, 77.53 mmol, 121.24 equiv.) was added NaH (30.7 mg, 0.77 mmol, 1.2 equiv, 60%) at 0 degrees C. under nitrogen atmosphere. The solution was stirred at 0 degrees C. for 30 min. To the above mixture were added 4-(chloromethyl)-1,3-thiazole hydrochloride (141.4 mg, 0.83 mmol, 1.3 equiv.) and Cs2CO3 (416.7 mg, 1.28 mmol, 2 equiv.) at rt. The mixture was stirred for additional 2 h at room temperature. To the mixture was added NH4Cl (aq). The crude product (200 mg) was purified by Prep-HPLC with the following conditions (Column: C18 Column 80 g; Mobile Phase A: Water (10 mmol/L NH4HCO3), Mobile Phase B: ACN; Flow rate: 50 mL/min; Gradient: 25% B to 50% B in 40 min; 254/220 nm) to afford 4-chloro-2-(oxan-2-yl)-5-[3-oxo-4-[(1,3-thiazol-4-yl)methyl]piperazin-1-yl]-2,3-dihydropyridazin-3-one (140 mg, 53.41%) as a purple solid.

4-chloro-5-[3-oxo-4-[(1,3-thiazol-4-yl)methyl]piperazin-1-yl]-2,3-dihydropyridazin-3-one To a stirred solution of 4-chloro-2-(oxan-2-yl)-5-[3-oxo-4-[(1,3-thiazol-4-yl)methyl]piperazin-1-yl]-2,3-dihydropyridazin-3-one (140 mg, 0.34 mmol, 1 equiv.) in DCM (10 mL) was added TFA (2 mL, 26.93 mmol, 78.83 equiv.) dropwise at room temperature. The mixture was concentrated under reduced pressure. The crude product (150 mg) was purified by Prep-HPLC with the following conditions (Column: XBridge Prep OBD C18 Column 30×150 mm 5 um; Mobile Phase A: Water (10 mmol/L NH4HCO3), Mobile Phase B: ACN; Flow rate: 60 mL/min; Gradient: 3% B to 30% B in 2.5 min; 220 nm; Rt: 6.2 min) to afford 4-chloro-5-[3-oxo-4-[(1,3-thiazol-4-yl)methyl]piperazin-1-yl]-2,3-dihydropyridazin-3-one (12 mg, 10.78%) as a white solid. Compounds EB and EC were prepared by the methods described for compound ED above.

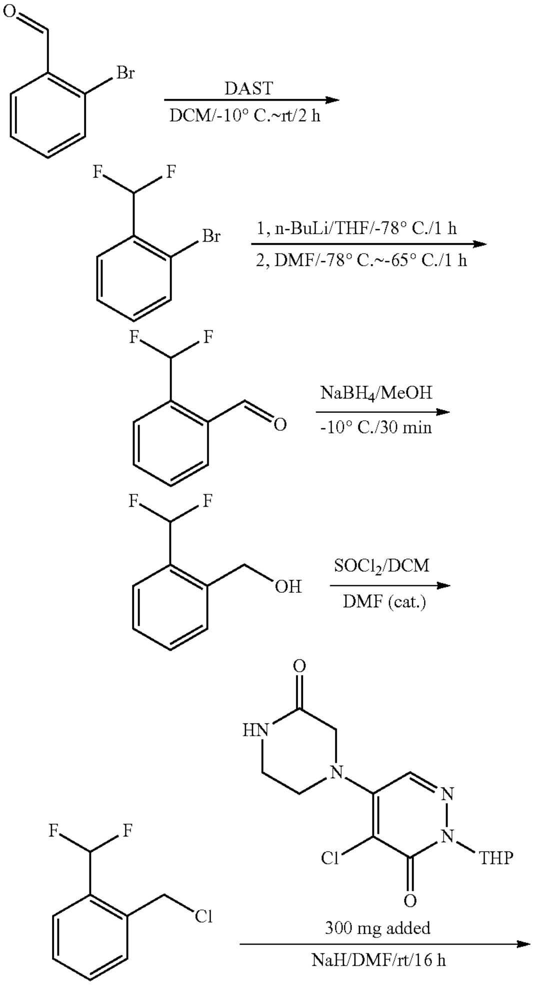

-continued

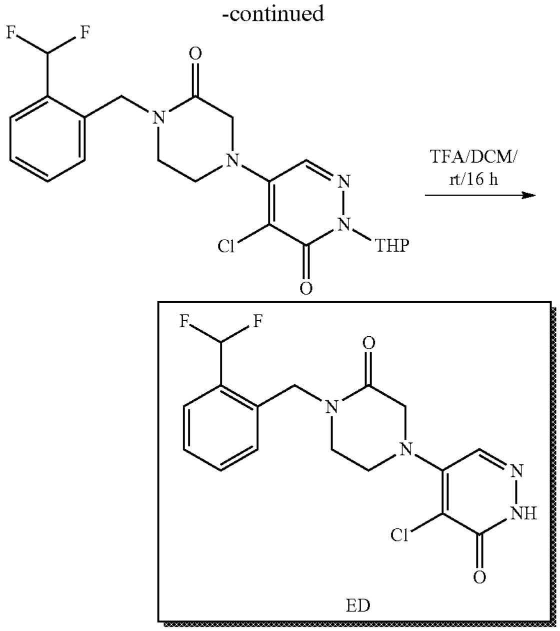

ED

Preparation of ED 1-bromo-2-(difluoromethyl)benzene

To a stirred solution of 2-bromobenzaldehyde (5 g, 27.02 mmol, 1 equiv.) in DCM (100 mL) was added diethyl (trifluoro-lambda4-sulfanyl)amine (8.7 g, 54.05 mmol, 2 equiv.) dropwise at 0 degrees C. under nitrogen atmosphere. The mixture was stirred at rt overnight New point could be detected by TLC. The reaction was quenched by the addition of saturated NaHCO3 (aq.) (50 mL) at 0 degrees C. The resulting mixture was concentrated under reduced pressure. To the mixture was added water (50 mL). The aqueous layer was extracted with EtOAc (3×50 mL). The organic layer was concentrated under reduced pressure. The residue was purified by silica gel column chromatography, eluted with PE/EtOAc (10:1) to afford 1-bromo-2-(difluoromethyl)benzene (3.5 g, 62.56%) as a colorless oil.

2-(difluoromethyl)benzaldehyde

To a stirred solution of 1-bromo-2-(difluoromethyl)benzene (3 g, 14.49 mmol, 1 equiv.) in THF (50 mL) was added n-BuLi (1.9 g, 28.98 mmol, 2 equiv.) dropwise at −78 degrees C. under nitrogen atmosphere. The mixture was stirred at −78 degrees C. for 1 h. To the mixture was added DMF (2.1 g, 28.98 mmol, 2 equiv.) at −78 degrees C. The mixture was stirred at −65 degrees C. for 1 h. Desired product could be detected by TLC. The reaction was quenched by the addition of sat. NH4Cl (aq.) (20 mL) at −65 degrees C. To the mixture was added EA (100 mL), The resulting mixture was washed with 3×60 mL of brine. The organic layer was concentrated. The residue was purified by silica gel column chromatography, eluted with PE/EtOAc (10:1) to afford 2-(difluoromethyl)benzaldehyde (2 g, 88.39%) as colorless oil.

[2-(difluoromethyl)phenyl]methanol

To a stirred solution of 2-(difluoromethyl)benzaldehyde (2 g, 12.81 mmol, 1 equiv.) in ethanol (35 mL) was added NaBH4 (1.0 g, 26.43 mmol, 2.06 equiv.) in portions at −45 degrees C. under nitrogen atmosphere. The mixture was stirred at −45 degrees C. for 30 min. New point could be detected by TLC. The resulting mixture was concentrated under reduced pressure. To the mixture was added water (40 mL), The aqueous layer was extracted with EtOAc (3×30 mL). The organic layer was concentrated. The residue was purified by silica gel column chromatography, eluted with PE/EtOAc (10:1 to 4:1) to afford [2-(difluoromethyl)phenyl] methanol (1.8 g, 88.85%) as colorless oil.

1-(chloromethyl)-2-(difluoromethyl)benzene

To a stirred solution of [2-(difluoromethyl)phenyl]methanol (500 mg, 3.16 mmol, 1 equiv.) in DCM (10 mL) was added SOCl2 (1880.7 mg, 15.81 mmol, 5.00 equiv.) and DMF (2.3 mg, 0.03 mmol, 0.01 equiv.) in portions at room temperature under nitrogen atmosphere. The mixture was stirred at rt for 2 h. Desired product could be detected by TLC. The resulting mixture was concentrated under reduced pressure to afford 1-(chloromethyl)-2-(difluoromethyl)benzene (480 mg, 85.97%) as colorless oil.

4-chloro-5-(4-[[2-(difluoromethyl)phenyl]methyl]-3-oxopiperazin-1-yl)-2-(oxan-2-yl)-2,3-dihydropyridazin-3-one To a stirred solution of 4-chloro-2-(oxan-2-yl)-5-(3-oxopiperazin-1-yl)-2,3-dihydropyridazin-3-one (315.2 mg, 1.01 mmol, 1.00 equiv.) in DMF (8 mL) was added NaH (60.5 mg, 1.51 mmol, 1.50 equiv, 60%) in portions at 0 degrees C. under nitrogen atmosphere. The mixture was stirred at rt for 1 h. To the mixture was added 1-(chloromethyl)-2-(difluoromethyl)benzene (178 mg, 1.01 mmol, 1 equiv.) at 0 degrees C. The mixture was stirred at rt for 1 h. The reaction was quenched with sat. NH4Cl (aq.) at 0 degrees C. To the mixture was added EA (20 mL), The resulting mixture was washed with 3×10 mL of brine. The organic layers were dried over anhydrous Na2SO4. After filtration, the filtrate was concentrated under reduced pressure. The crude product (300 mg) was purified by Prep-HPLC with the following conditions (Column: 300 g; Mobile Phase A: Water (10 mmol/L AcOH), Mobile Phase B: ACN; Flow rate: 80 mL/min; Gradient: 40% B to 60% B in 25 min; 220 nm; Rt: 50%) to afford 4-chloro-5-(4-[[2-(difluoromethyl)phenyl]methyl]-3-oxopiperazin-1-yl)-2-(oxan-2-yl)-2,3-dihydropyridazin-3-one (300 mg, 65.72%) as a white solid.

4-chloro-5-(4-[[2-(difluoromethyl)phenyl]methyl]-3-oxopiperazin-1-yl)-2,3-dihydropyridazin-3-one To a stirred solution of 4-chloro-5-(4-[[2-(difluoromethyl)phenyl]methyl]-3-oxopiperazin-1-yl)-2-(oxan-2-yl)-2,3-dihydropyridazin-3-one (150 mg, 0.33 mmol, 1 equiv.) in DCM (10 mL) was added AcCl (104.0 mg, 1.32 mmol, 4.00 equiv.) in portions at 0 degrees C. under nitrogen atmosphere. The mixture was stirred at rt for 16 h. Desired product could be detected by LCMS. The resulting mixture was concentrated under reduced pressure. The crude product (150 mg) was purified by Prep-HPLC with the following conditions (Column: XBridge Prep C18 OBD Column 19×150 mm 5 um; Mobile Phase A: Water (10 mmol/L NH4HCO3), Mobile Phase B: ACN; Flow rate: 20 mL/min; Gradient: 18% B to 48% B in 7 min; 254/220 nm; Rt: 6.22 min) to afford 4-chloro-5-(4-[[2-(difluoromethyl)phenyl]methyl]-3-oxopiperazin-1-yl)-2,3-dihydropyridazin-3-one (45 mg) as a white solid.

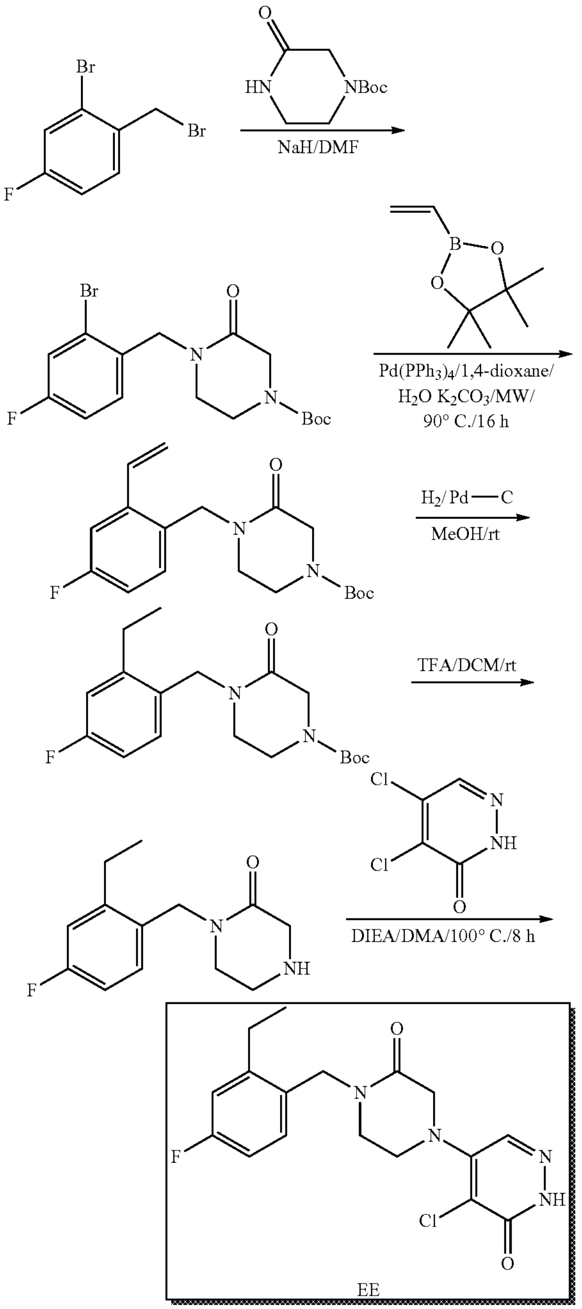

EE

Preparation of EE

4-[(2-bromo-4-fluorophenyl)methyl]-3-oxopiperazine-1-carboxylate

To a stirred solution of tert-butyl 3-oxopiperazine-1-carboxylate (2 g, 9.99 mmol, 1 equiv.) in DMF (20 mL) was added NaH (0.8 g, 20.00 mmol, 2.00 equiv, 60%) at rt under nitrogen atmosphere. The reaction was stirred for 1 h at rt. Then 2-bromo-1-(bromomethyl)-4-fluorobenzene (4.0 g, 14.93 mmol, 1.49 equiv.) was added. The reaction mixture was stirred for 16 h at rt. The reaction was monitored by LCMS. The reaction was quenched by the addition of Water (200 mL) at rt. The resulting mixture was extracted with EtOAc (3×500 mL). The combined organic layers were washed with brine (3×200 mL), dried over anhydrous Na2SO4. After filtration, the filtrate was concentrated under reduced pressure. The residue was purified by silica gel column chromatography, eluted with PE/EtOAc (20/1 to 10/1) to afford tert-butyl 4-[(2-bromo-4-fluorophenyl)methyl]-3-oxopiperazine-1-carboxylate (3 g, 77.56%) Products as a yellow semi-solid.

Tert-Butyl 4-[(2-ethenyl-4-fluorophenyl)methyl]-3-oxopiperazine-1-carboxylate

To a stirred mixture of tert-butyl 4-[(2-bromo-4-fluorophenyl)methyl]-3-oxopiperazine-1-carboxylate (500 mg, 1.29 mmol, 1 equiv.) and 2-ethenyl-4,4,5,5-tetramethyl-1,3,2-dioxaborolane (198.9 mg, 1.29 mmol, 1.0 equiv.) in 1,4-dioxane (10 mL) and H2O (2 mL) were added K2CO3 (535.3 mg, 3.87 mmol, 3.00 equiv.) and Pd(PPh3)4 (149.2 mg, 0.13 mmol, 0.10 equiv.) in portions at rt under nitrogen atmosphere. The final reaction mixture was irradiated with microwave radiation for 2 h at 90 degrees C. The reaction was monitored by LCMS. The mixture was allowed to cool down to rt. The residue was purified by silica gel column chromatography, eluted with PE/EtOAc (30/1 to 10/1) to afford tert-butyl 4-[(2-ethenyl-4-fluorophenyl)methyl]-3-oxopiperazine-1-carboxylate (550 mg, 127.39%) as a yellow oil.

Tert-Butyl 4-[(2-ethyl-4-fluorophenyl)methyl]-3-oxopiperazine-1-carboxylate

To a solution of tert-butyl 4-[(2-ethenyl-4-fluorophenyl)methyl]-3-oxopiperazine-1-carboxylate (550 mg, 1.64 mmol, 1 equiv.) in 30 mL MeOH was added Pd/C (10%, 0.175 g) under nitrogen atmosphere in a 100 mL round-bottom flask. The mixture was hydrogenated at room temperature for 4 h under hydrogen atmosphere using a hydrogen balloon, filtered through a celite pad and concentrated under reduced pressure. This resulted in tert-butyl 4-[(2-ethyl-4-fluorophenyl)methyl]-3-oxopiperazine-1-carboxylate (500 mg, 90.36%) as a yellow oil.

1-[(2-ethyl-4-fluorophenyl)methyl]piperazin-2-one

To a stirred solution of tert-butyl 4-[(2-ethyl-4-fluorophenyl)methyl]-3-oxopiperazine-1-carboxylate (500 mg, 1.49 mmol, 1 equiv.) in DCM (10 mL) was added TFA (2 mL, 26.93 mmol, 18.12 equiv.) dropwise at rt. The reaction mixture was stirred for 16 h at rt. The reaction was monitored by LCMS. The resulting mixture was concentrated under reduced pressure. The residue was basified to pH=8 with saturated NaHCO3 (aq.). The resulting mixture was extracted with CH2Cl2(3×100 mL). The combined organic layers were washed with brine (1×100 mL), dried over anhydrous Na2SO4. After filtration, the filtrate was concentrated under reduced pressure. This resulted in 1-[(2-ethyl-4-fluorophenyl)methyl]piperazin-2-one (300 mg, 85.42%) as a yellow oil.

4-chloro-5-[4-[(2-ethyl-4-fluorophenyl)methyl]-3-oxopiperazin-1-yl]-2,3-dihydropyridazin-3-one To a stirred mixture of 1-[(2-ethyl-4-fluorophenyl)methyl]piperazin-2-one (80 mg, 340 mmol, 1 equiv.) and 4,5-dichloro-2,3-dihydropyridazin-3-one (55.9 mg, 340 mmol, 1.00 equiv.) in DMA (5 mL) was added DIEA (236.3 mg, 1.83 mmol, 3.00 equiv.) dropwise at rt under nitrogen atmosphere. The reaction mixture was stirred for 16 h at 100 degrees C. The reaction was monitored by LCMS. The mixture was allowed to cool down to rt. The reaction mixture was purified by Prep-HPLC with the following conditions (Column: XBridge Shield RP18 OBD Column 30*150 mm, 5 um; Mobile Phase A: Water (10 mmol/L NH4HCO3), Mobile Phase B: ACN; Flow rate: 60 mL/min; Gradient: 20% B to 40% B in 10 min; 254 nm; Rt: 8.78 min) to afford 4-chloro-5-[4-[(2-ethyl-4-fluorophenyl)methyl]-3-oxopiperazin-1-yl]-2,3-dihydropyridazin-3-one (4.8 mg, 3.89%) as a light yellow solid.

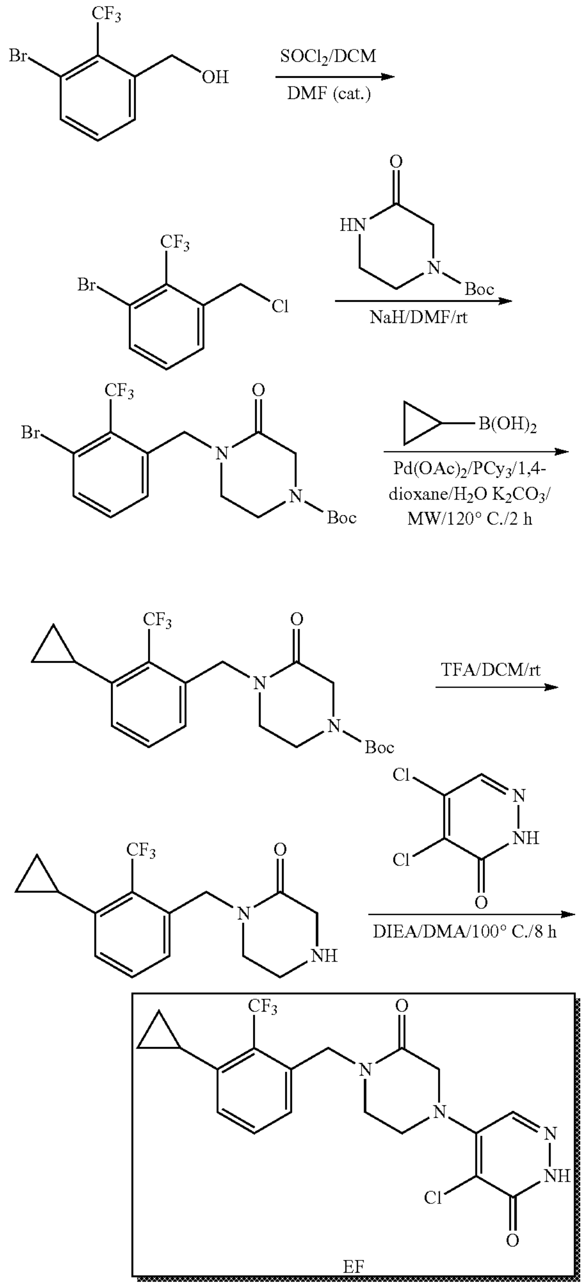

EF

Preparation of EF 1-bromo-3-(chloromethyl)-2-(trifluoromethyl)benzene

To a solution of [3-bromo-2-(trifluoromethyl)phenyl] methanol (1.6 g, 6.27 mmol, 1 equiv.) in DCM (60 mL, 943.80 mmol, 150.44 equiv.) were added DMF (59.6 mg, 0.82 mmol, 0.13 equiv.) and SO2Cl2 (8.5 g, 62.98 mmol, 10.04 equiv.) dropwise via syringe at 0 degrees C. under nitrogen atmosphere. The resulting mixture was stirred for 4 h at 0 degrees C. The desired product could be detected by LCMS. The mixture was concentrated to get crude product. The crude product was added water (200 mL) and extracted with EA (100 mL×2). The organic layers was concentrated to afford 1-bromo-3-(chloromethyl)-2-(trifluoromethyl)benzene (1.6 g, 93.26%) as a yellow liquid.

Tert-Butyl 4-[[3-bromo-2-(trifluoromethyl)phenyl] methyl]-3-oxopiperazine-1-carboxylate To a stirred solution of in DMF (10 mL) was added tert-butyl 3-oxopiperazine-1-carboxylate (439.3 mg, 2.19 mmol, 1.00 equiv.) at 0 degrees C. under nitrogen atmosphere. The resulting mixture was stirred for 1 h from 0 degrees C. to ambient temperature. The reaction was added 1-bromo-3-(chloromethyl)-2-(trifluoromethyl)benzene (600 mg, 2.19 mmol, 1 equiv.) at 0 degrees C. The resulting mixture was stirred for 16 h at ambient temperature. The desired product could be detected by LCMS. The reaction mixture was quenched by water (0.5 ml). The reaction mixture was purified by reverse phase flash with the following conditions (Column: c18 OBD Column, 5 um, 19*330 mm; Mobile Phase A: Water (5 mmol/L $NaHCO_3$), Mobile Phase B: ACN; Flow rate: 80 mL/min; Gradient: 35% B to 65% B in 30 min; 254 nm; Rt: 20 min) to afford tert-butyl 4-[[3-bromo-2-(trifluoromethyl)phenyl]methyl]-3-oxopiperazine-1-carboxylate (550 mg, 57.33%) as a light yellow solid.

Tert-Butyl 4-[[3-cyclopropyl-2-(trifluoromethyl) phenyl]methyl]-3-oxopiperazine-1-carboxylate To a solution of tert-butyl 4-[[3-bromo-2-(trifluoromethyl)phenyl]methyl]-3-oxopiperazine-1-carboxylate (150 mg, 0.34 mmol, 1 equiv.) in 1,4-dioxane (5 mL, 59.02 mmol, 172.05 equiv.) and water (1 mL, 55.51 mmol, 161.81 equiv.) were added cyclopropylboronic acid (58.9 mg, 0.69 mmol, 2 equiv), K2CO3 (94.8 mg, 0.69 mmol, 2 equiv), PCy3 (19.2 mg, 0.07 mmol, 0.2 equiv.) and Pd(AcO)2 (7.7 mg, 0.03 mmol, 0.10 equiv). The reaction was irradiated with microwave radiation at 110 degrees C. for 3 h. The desired product could be detected by LCMS. The reaction mixture was diluted with water (100 mL), extracted with EA (100 mL×2). The organic layer was washed with saturated brine (100 ml), dried over anhydrous Na2SO4, filtered and concentrated to give desired product. The residue was purified by Prep-TLC (CH2Cl2/MeOH 20:1) to afford tert-butyl 4-[[3-cyclopropyl-2-(trifluoromethyl)phenyl]methyl]-3-oxopiperazine-1-carboxylate (145 mg, 106.09%) as a yellow solid.

1-[[3-cyclopropyl-2-(trifluoromethyl)phenyl]methyl] piperazin-2-one

To a solution of TFA (2 mL, 26.93 mmol, 33.69 equiv.) in DCM (8 mL) was added tert-butyl 4-[[3-cyclopropyl-2-(trifluoromethyl)phenyl]methyl]-3-oxopiperazine-1-carboxylate (145 mg, 0.36 mmol, 1 equiv.) at 0 degrees C. then the mixture was stirred for 16 h from 0 degrees C. to ambient temperature. The desired product could be detected by LCMS. The resulting mixture was concentrated under reduced pressure. The mixture was acidified to pH 8 with NaHCO3 (aq.). The mixture was added DMF (25 mL) and was purified by reverse phase flash with the following conditions (Column: c18 OBD Column, 5 um, 19*330 mm; Mobile Phase A: Water (5 mmol/L NH4HCO3), Mobile Phase B: ACN; Flow rate: 80 mL/min; Gradient: 20% B to 55% B in 30 min; 254 nm; Rt: 15.0 min) to afford 1-[[3-cyclopropyl-2-(trifluoromethyl)phenyl]methyl]piperazin-2-one (100 mg, 92.11%) as a yellow liquid.

4-chloro-5-(4-[[3-cyclopropyl-2-(trifluoromethyl) phenyl]methyl]-3-oxopiperazin-1-yl)-2,3-dihydro-pyridazin-3-one To a solution of 1-[[3-cyclopropyl-2-(trifluoromethyl) phenyl]methyl]piperazin-2-one (100 mg, 0.34 mmol, 1 equiv.) in DMA (5 mL) were added 4,5-dichloro-2,3-dihydropyridazin-3-one (55.3 mg, 0.34 mmol, 1.00 equiv.) and DIEA (86.7 mg, 0.67 mmol, 2.00 equiv.) at ambient temperature. The resulting mixture was stirred for 16 h at 100 degrees C. The desired product could be detected by LCMS. The mixture was allowed to cool down to ambient temperature. The reaction mixture was purified by Prep-HPLC with the following conditions (Column: XSelect CSH Prep C18 OBD Column, 5 um, 19*150 mm; Mobile Phase A: Water (10 mmol/L NH4HCO3), Mobile Phase B: ACN; Flow rate: 20 mL/min; Gradient: 30% B to 75% B in 7 min; 254 nm; Rt: 8.9 min) to afford 4-chloro-5-(4-[[3-cyclopropyl-2-(trifluoromethyl)phenyl]methyl]-3-oxopiperazin-1-yl)-2,3-dihydropyridazin-3-one (12.3 mg, 8.60%) as a light yellow solid.

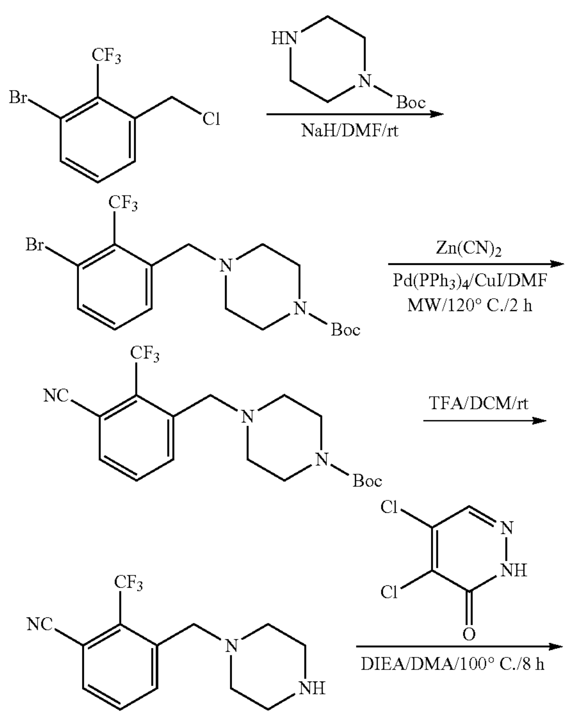

-continued

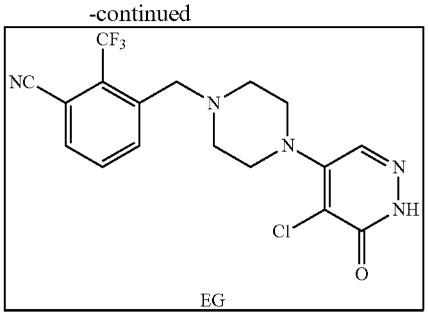

EG

Preparation of EG

Tert-Butyl 4-[[3-cyano-2-(trifluoromethyl)phenyl] methyl]piperazine-1-carboxylate To a stirred solution of tert-butyl 4-[[3-bromo-2-(trifluoromethyl)phenyl]methyl]piperazine-1-carboxylate (300 mg, 710 mmol, 1 equiv.) and Zn(CN)2 (83.2 mg, 0.71 mmol, 1.00 equiv.) in DMF (5 mL) was added Pd(PPh3)4 (81.9 mg, 0.07 mmol, 0.1 equiv). The final reaction mixture was irradiated with microwave radiation for 2 h at 150 degrees C. The resulting mixture was concentrated under vacuum. The residue was purified by silica gel column chromatography, eluted with hexane/EtOAc (1:1) to afford tert-butyl 4-[[3-cyano-2-(trifluoromethyl)phenyl]methyl]piperazine-1-carboxylate (200 mg, 76.39%) as a light yellow solid.

3-[(piperazin-1-yl)methyl]-2-(trifluoromethyl)benzonitrile

To a stirred solution of tert-butyl 4-[[3-cyano-2-(trifluoromethyl)phenyl]methyl]piperazine-1-carboxylate (200 mg, 0.54 mmol, 1 equiv.) in DCM (3 mL) was added TFA (1 mL). The resulting mixture was stirred for 2 h at room temperature. The resulting mixture was concentrated under reduced pressure. This resulted in 3-[(piperazin-1-yl) methyl]-2-(trifluoromethyl)benzonitrile (130 mg, crude) as a dark yellow oil.

3-[[4-(6-oxo-1,6-dihydropyridazin-4-yl)piperazin-1-yl]methyl]-2-(trifluoromethyl)benzonitrile To a stirred solution of 3-[(piperazin-1-yl)methyl]-2-(trifluoromethyl)benzonitrile (130 mg, 0.48 mmol, 1 equiv.) and 4,5-dichloro-2,3-dihydropyridazin-3-one (95.6 mg, 0.58 mmol, 1.20 equiv.) in DMA (5 mL) was added DIEA (249.6 mg, 1.93 mmol, 4 equiv). The resulting mixture was stirred for overnight at 100 degrees C. The solution was purified by Prep-HPLC with the following conditions (Column: XBridge Shield RP18 OBD Column 30×150 mm, 5 um; Mobile Phase A: Water (10 mmol/L NH4HCO3), Mobile Phase B: ACN; Flow rate: 60 mL/min; Gradient: 25% B to 55% B in 7 min; 254 nm; Rt: 6.82 min) to afford 3-[[4-(6-oxo-1,6-dihydropyridazin-4-yl)piperazin-1-yl]methyl]-2-(trifluoromethyl)benzonitrile (25.0 mg, 14.25%) as a yellow solid.

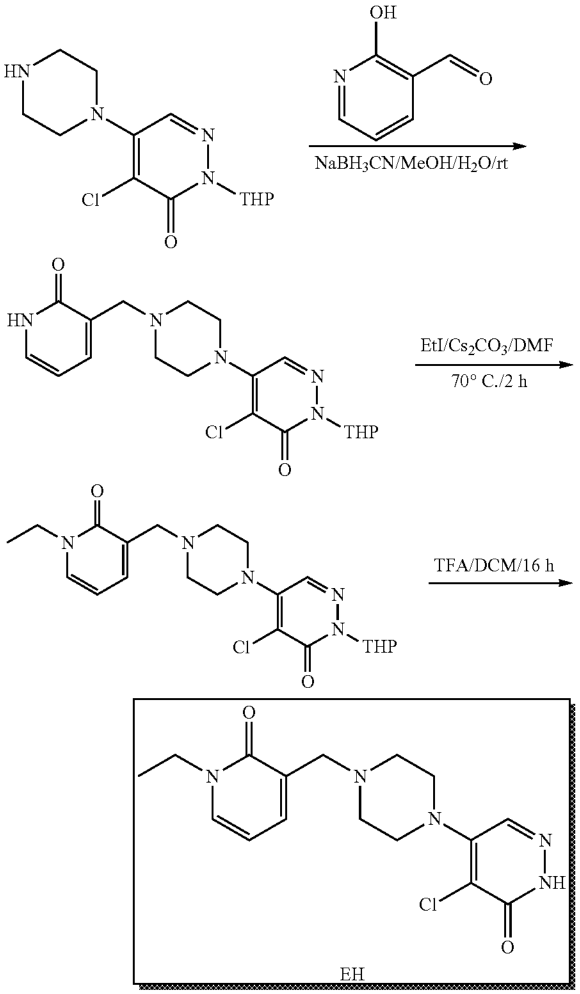

EH

Preparation of EH 4-chloro-2-(oxan-2-yl)-5-[4-[(2-oxo-1,2-dihydropyridin-3-yl)methyl]piperazin-1-yl]-2,3-dihydropyridazin-3-one To a stirred mixture of 4-chloro-2-(oxan-2-yl)-5-(piperazin-1-yl)-2,3-dihydropyridazin-3-one (900 mg, 3.01 mmol, 1 equiv.) and 2-hydroxypyridine-3-carbaldehyde (741.7 mg, 6.02 mmol, 2.0 equiv.) in MeOH (15 mL) and H2O (3 mL) was added NaBH3CN (378.6 mg, 6.02 mmol, 2.0 equiv.) at room temperature. The resulting mixture was stirred for 6 h at room temperature. The reaction was monitored by LCMS. The resulting mixture was concentrated under reduced pressure. The crude product was purified by reverse phase flash with the following conditions (Column: XBridge Prep C18 OBD Column 19×150 mm 5 um; Mobile Phase A: Water (10 mmol/L NH4HCO3), Mobile Phase B: ACN; Flow rate: 20 mL/min; Gradient: 5% B to 25% B in 7 min; 254 nm; Rt: 6.15 min) to afford 4-chloro-2-(oxan-2-yl)-5-[4-[(2-oxo-1,2-dihydropyridin-3-yl)methyl]piperazin-1-yl]-2,3-dihydropyridazin-3-one (500 mg, 40.89%) as a yellow solid.

4-chloro-5-[4-[(1-ethyl-2-oxo-1,2-dihydropyridin-3-yl)methyl]piperazin-1-yl]-2-(oxan-2-yl)-2,3-dihydropyridazin-3-one To a stirred mixture of 4-chloro-2-(oxan-2-yl)-5-[4-[(2-oxo-1,2-dihydropyridin-3-yl)methyl]piperazin-1-yl]-2,3-dihydropyridazin-3-one (250 mg, 0.62 mmol, 1 equiv.) and Cs2CO3 (602.1 mg, 1.85 mmol, 3.00 equiv.) in DMSO (10 mL) was added iodoethane (144.1 mg, 0.92 mmol, 1.50 equiv.) at room temperature. The resulting mixture was stirred for 2 h at 70 degrees C. The reaction was monitored by LCMS. The mixture was allowed to cool down to room temperature. The residue/crude product was purified by reverse phase flash with the following conditions (Column: XBridge Prep C18 OBD Column 19×150 mm 5 um; Mobile Phase A: Water (10 mmol/L NH4HCO3), Mobile Phase B: ACN; Flow rate: 20 mL/min; Gradient: 5% B to 25% B in 7 min; 254 nm; Rt: 6.15 min) to afford a mixture of 4-chloro-5-[4-[(1-ethyl-2-oxo-1,2-dihydropyridin-3-yl)methyl]piperazin-1-yl]-2-(oxan-2-yl)-2,3-dihydropyridazin-3-one and isomer (200 mg, 74.83%) as a white solid.

4-chloro-5-[4-[(1-ethyl-2-oxo-1,2-dihydropyridin-3-yl)methyl]piperazin-1-yl]-2,3-dihydropyridazin-3-one To a stirred solution of TFA (2 mL, 26.93 mmol, 58.42 equiv.) in DCM (9 mL) was added the mixture of 4-chloro-5-[4-[(1-ethyl-2-oxo-1,2-dihydropyridin-3-yl)methyl]piperazin-1-yl]-2-(oxan-2-yl)-2,3-dihydropyridazin-3-one and isomer (200 mg, 0.46 mmol, 1 equiv.) at room temperature. The resulting mixture was stirred for 2 h at room temperature. The reaction was monitored by LCMS. The resulting mixture was concentrated under vacuum. The crude product (200 mg) was purified by Prep-HPLC with the following conditions (Column: XBridge Prep C18 OBD Column 19×150 mm 5 um; Mobile Phase A: Water (10 mmol/L NH4HCO3), Mobile Phase B: ACN; Flow rate: 20 mL/min; Gradient: 5% B to 25% B in 7 min; 254 nm; Rt: 6.15 min) to afford 4-chloro-5-[4-[(1-ethyl-2-oxo-1,2-dihydropyridin-3-yl)methyl]piperazin-1-yl]-2,3-dihydropyridazin-3-one (21.3 mg, 13.21%) as a white solid and 4-chloro-5-[4-[(1-ethyl-2-oxo-1,2-dihydropyridin-3-yl)methyl]piperazin-1-yl]-2,3-dihydropyridazin-3-one (21.3 mg, 13.21%) as a white solid.

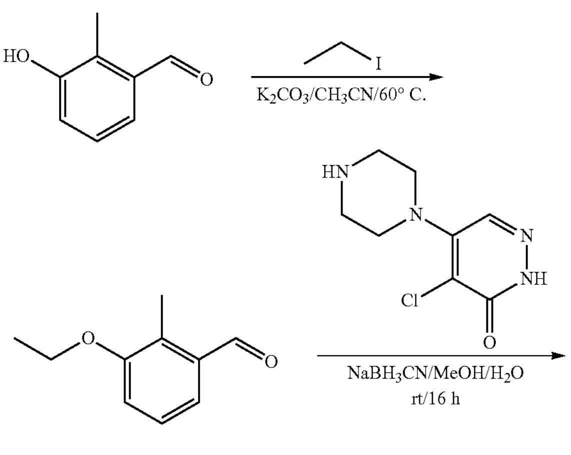

-continued

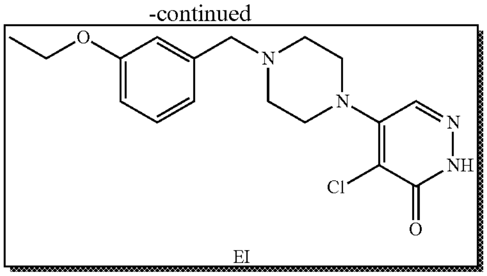

EI

Preparation of EI

3-ethoxy-2-methylbenzaldehyde

To a stirred mixture of 3-hydroxy-2-methylbenzaldehyde (500 mg, 3.67 mmol, 1 equiv.) and iodoethane (1145.5 mg, 7.34 mmol, 2.00 equiv.) in CH3CN (10 mL) was added K2CO3 (761.3 mg, 5.51 mmol, 1.50 equiv.) at room temperature. The resulting mixture was stirred for 5 h at 60 degrees C. The reaction was monitored by LCMS. The resulting mixture was concentrated under reduced pressure. The resulting mixture was extracted with EtOAc (3×250 mL). The combined organic layers were washed with brine (3×250 mL), dried over anhydrous Na2SO4. After filtration, the filtrate was concentrated under reduced pressure. The residue was purified by Prep-TLC (PE/EtOAc 5:1) to afford 3-ethoxy-2-methylbenzaldehyde (370 mg) as a light yellow oil.

4-chloro-5-[4-[(3-ethoxy-2-methylphenyl)methyl]piperazin-1-yl]-2,3-dihydropyridazin-3-one To a stirred mixture of 4-chloro-5-(piperazin-1-yl)-2,3-dihydropyridazin-3-one (100 mg, 0.47 mmol, 1 equiv.) and 3-ethoxy-2-methylbenzaldehyde (153.0 mg, 0.93 mmol, 2.00 equiv.) in MeOH (7 mL) and H2O (1 mL) was added NaBH3CN (58.6 mg, 0.93 mmol, 2.00 equiv.) in portions at 0 degrees C. The resulting mixture was stirred for 16 h at room temperature. The reaction was monitored by LCMS. The resulting mixture was concentrated under reduced pressure. The crude product (100 mg) was purified by Prep-HPLC with the following conditions (Column: XBridge Shield RP18 OBD Column, 5 um, 19*150 mm; Mobile Phase A: Water (0.05% TFA), Mobile Phase B: ACN; Flow rate: 20 mL/min; Gradient: 10% B to 35% B in 7 min; 254 nm; Rt: 6.43 min) to afford 4-chloro-5-[4-[(3-ethoxy-2-methylphenyl)methyl]piperazin-1-yl]-2,3-dihydropyridazin-3-one (35.4 mg) as a white solid.

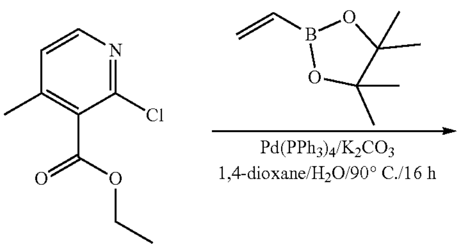

-continued

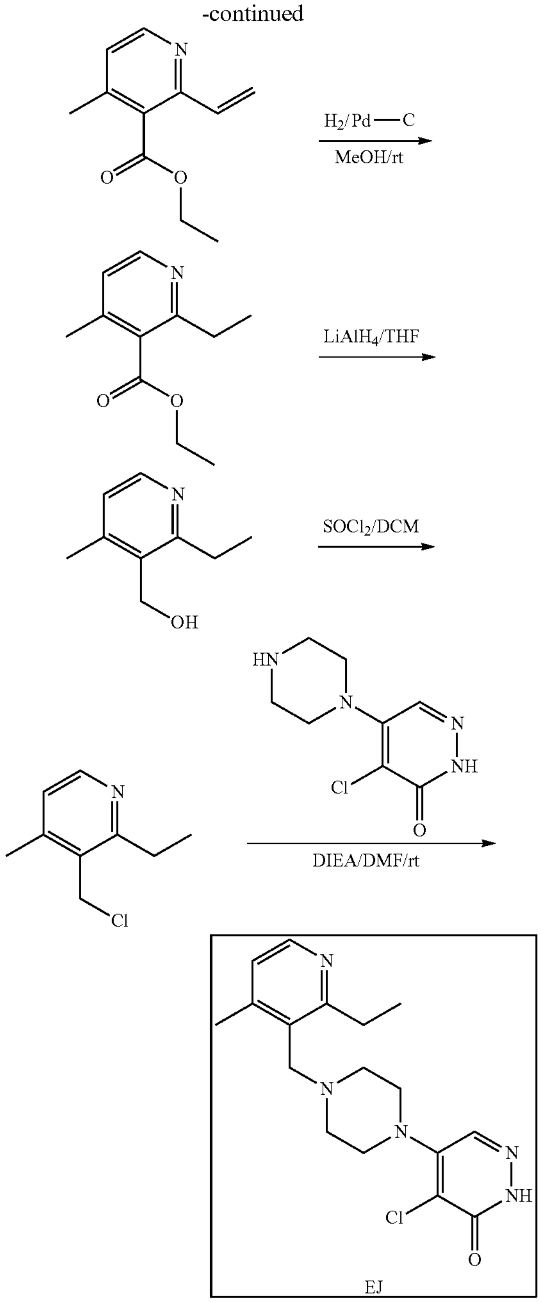

EJ

Preparation of EJ

Ethyl 2-ethenyl-4-methylpyridine-3-carboxylate

To a stirred mixture of ethyl 2-chloro-4-methylpyridine-3-carboxylate (500 mg, 2.50 mmol, 1 equiv.) and 2-ethenyl-4,4,5,5-tetramethyl-1,3,2-dioxaborolane (771.5 mg, 5.01 mmol, 2 equiv.) in 1,4-dioxane (30 mL) and H2O (6 mL) were added K2CO3 (1038.5 mg, 7.51 mmol, 3 equiv.) and Pd(PPh3)4 (289.4 mg, 0.25 mmol, 0.1 equiv.) at room temperature under nitrogen atmosphere. The resulting mixture was stirred for 16 h at 90 degrees C. under nitrogen atmosphere. The reaction was monitored by LCMS. The mixture was allowed to cool down to room temperature. The resulting mixture was concentrated under reduced pressure.

The residue was purified by Prep-TLC (PE/EtOAc=5:1) to afford ethyl 2-ethenyl-4-methylpyridine-3-carboxylate (520 mg, 98.70%) as a yellow liquid.

Ethyl 2-ethyl-4-methylpyridine-3-carboxylate

To a stirred solution of ethyl 2-ethenyl-4-methylpyridine-3-carboxylate (520 mg, 2.72 mmol, 1 equiv.) in MeOH (10 mL) was added Pd/C (28.9 mg, 0.27 mmol, 0.1 equiv.) at room temperature under hydrogen atmosphere. The resulting mixture was stirred for 2 h at room temperature under hydrogen atmosphere. The reaction was monitored by LCMS. The resulting mixture was filtered, the filter cake was washed with MeOH (3×5 mL). The filtrate was concentrated under reduced pressure. This resulted in ethyl 2-ethyl-4-methylpyridine-3-carboxylate (500 mg, crude) as a yellow liquid.

(2-ethyl-4-methylpyridin-3-yl)methanol

To a stirred solution of ethyl 2-ethyl-4-methylpyridine-3-carboxylate (520 mg, 2.69 mmol, 1 equiv.) in THF (20 mL) was added LiAlH4 (153.2 mg, 4.04 mmol, 1.5 equiv.) at 0 degrees C. The resulting mixture was stirred for 2 h at 0 degrees C. The reaction was monitored by LCMS. The reaction was quenched with Water and 15% NaOH at 0 degrees C. The resulting mixture was filtered, the filter cake was washed with EtOAc (3×10 mL). The filtrate was concentrated under reduced pressure. The residue was purified by Prep-TLC (PE/EtOAc=1:1) to afford (2-ethyl-4-methylpyridin-3-yl)methanol (220 mg, 54.07%) as a yellow solid.

4-chloro-5-[4-[(2-ethyl-4-methylpyridin-3-yl)methyl]piperazin-1-yl]-2,3-dihydropyridazin-3-one To a stirred solution of (2-ethyl-4-methylpyridin-3-yl)methanol (220 mg, 1.45 mmol, 1 equiv.) in DCM (10 mL) was added SOCl2 (346.2 mg, 2.91 mmol, 2 equiv.) at room temperature. The resulting mixture was stirred for 2 h at room temperature. The reaction was monitored by LCMS. The resulting mixture was concentrated under reduced pressure. The crude product was used in the next step directly without further purification.

To a stirred mixture of 4-chloro-5-(piperazin-1-yl)-2,3-dihydropyridazin-3-one (50 mg, 0.23 mmol, 1 equiv.) and DIEA (150.5 mg, 1.16 mmol, 5 equiv.) in DMF (3 ML) was added 3-(chloromethyl)-2-ethyl-4-methylpyridine (47.4 mg, 0.28 mmol, 1.2 equiv.) at room temperature. The resulting mixture was stirred for 16 h at room temperature. The reaction was monitored by LCMS. The crude product (50 mg) was purified by Prep-HPLC with the following conditions (Column: XBridge Prep C18 OBD Column 19×150 mm 5 um; Mobile Phase A: Water (10 mmol/L NH4HCO3), Mobile Phase B: ACN; Flow rate: 20 mL/min; Gradient: 22% B to 46% B in 7 min; 254/220 nm; Rt: 6.07 min) to afford 4-chloro-5-[4-[(2-ethyl-4-methylpyridin-3-yl)methyl]piperazin-1-yl]-2,3-dihydropyridazin-3-one (43.2 mg, 53.32%) as a white solid.

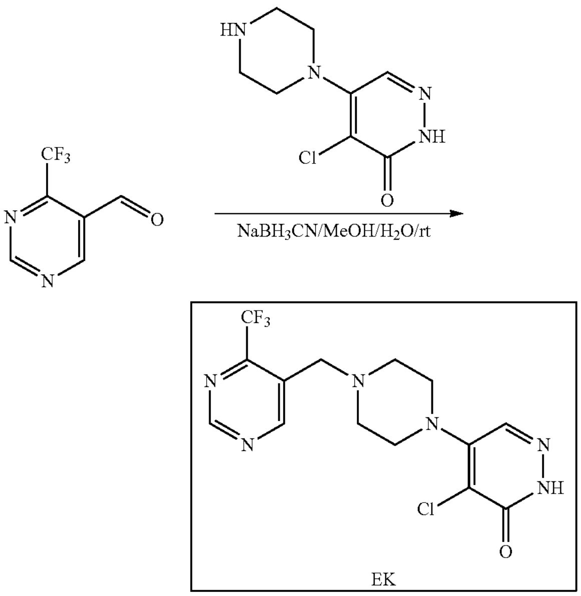

EK

Preparation of EK 4-chloro-5-(4-[[4-(trifluoromethyl)pyrimidin-5-yl]methyl]piperazin-1-yl)-2,3-dihydropyridazin-3-one To a stirred mixture of 4-(trifluoromethyl)pyrimidine-5-carbaldehyde (50 mg, 0.28 mmol, 1 equiv.) and 4-chloro-5-(piperazin-1-yl)-2,3-dihydropyridazin-3-one (121.9 mg, 0.57 mmol, 2.00 equiv.) in MeOH (5 mL) and H2O (1 mL) was added NaBH3CN (35.7 mg, 0.57 mmol, 2.00 equiv.) in portions at 0 degrees C. The resulting mixture was stirred for 72 h at room temperature. The reaction was monitored by LCMS. The resulting mixture was concentrated under reduced pressure. The crude product (50 mg) was purified by Prep-HPLC with the following conditions (Column: XBridge Shield RP18 OBD Column, 5 um, 19*150 mm; Mobile Phase A: Water (0.05% TFA), Mobile Phase B: ACN; Flow rate: 20 mL/min; Gradient: 3% B to 30% B in 7 min; 220 nm; Rt: 6.28 min) to afford 4-chloro-5-(4-[[4-(trifluoromethyl)pyrimidin-5-yl]methyl]piperazin-1-yl)-2,3-dihydropyridazin-3-one (14.8 mg, 13.91%) as a white solid.

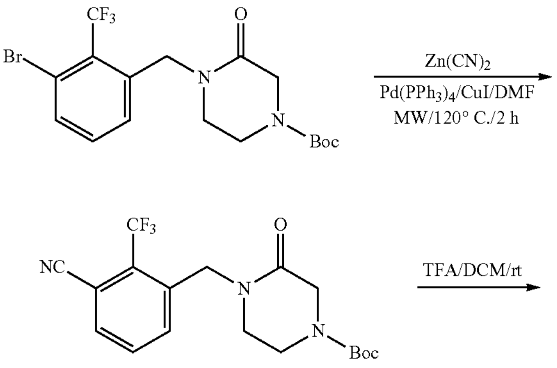

-continued

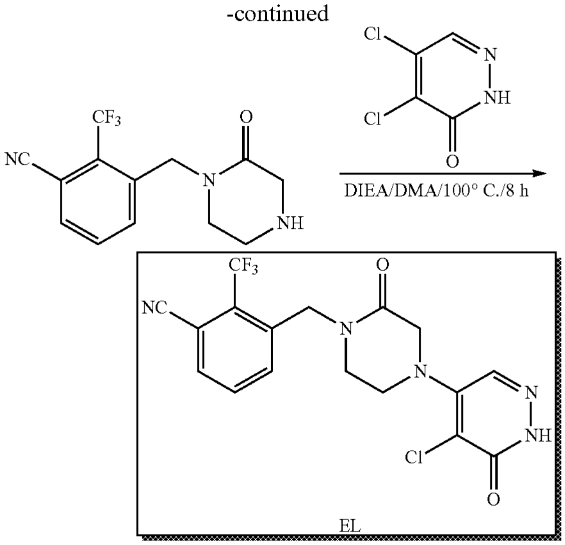

EL

Preparation of EL

Tert-Butyl 4-[[3-cyano-2-(trifluoromethyl)phenyl] methyl]-3-oxopiperazine-1-carboxylate To a solution of tert-butyl 4-[[3-bromo-2-(trifluoromethyl)phenyl]methyl]-3-oxopiperazine-1-carboxylate (280 mg, 0.64 mmol, 1 equiv.) in DMF (5 mL) were added zincdicarbonitrile (75.2 mg, 0.64 mmol, 1.00 equiv.) and Pd(PPh3)4 (74.0 mg, 0.06 mmol, 0.10 equiv.) at ambient temperature. The reaction was irradiated with microwave radiation at 120 degrees C. for 2 h. The desired product could be detected by LCMS. The mixture was allowed to cool down to ambient temperature. The resulting mixture was filtered. The filtrate was concentrated under reduced pressure. The crude product was purified by reverse phase flash with the following conditions (Column: c18 OBD Column, 5 um, 19*120 mm; Mobile Phase A: Water (5 mmol/L $NaHCO_3$), Mobile Phase B: ACN; Flow rate: 45 mL/min; Gradient: 20% B to 55% B in 40 min; 254 nm; Rt: 18 min) to afford tert-butyl 4-[[3-cyano-2-(trifluoromethyl) phenyl]methyl]-3-oxopiperazine-1-carboxylate (250 mg, 101.84%) as a yellow solid.

3-[(2-oxopiperazin-1-yl)methyl]-2-(trifluoromethyl) benzonitrile

To a solution of TFA (2 mL, 26.93 mmol, 33.69 equiv.) in DCM (8 mL) was added tert-butyl 4-[[3-cyano-2-(trifluoromethyl)phenyl]methyl]-3-oxopiperazine-1-carboxylate (250 mg, 0.65 mmol, 1 equiv.) at 0 degrees C. then the mixture was stirred for 16 h from 0 degrees C. to ambient temperature. The desired product could be detected by LCMS. The resulting mixture was concentrated under reduced pressure. The mixture was acidified to pH 8 with NaHCO3 (aq.). The mixture was added DMF (25 mL) and was purified by reverse phase flash with the following conditions (Column: c18 OBD Column, 5 um, 19*330 mm; Mobile Phase A: Water (5 mmol/L NH4HCO3), Mobile Phase B: ACN; Flow rate: 80 mL/min; Gradient: 25% B to 65% B in 40 min; 220 nm; Rt: 28.0 min) to afford 3-[(2-oxopiperazin-1-yl)methyl]-2-(trifluoromethyl)benzonitrile (170 mg, 92.03%) as a yellow liquid.

3-[[4-(5-chloro-6-oxo-1,6-dihydropyridazin-4-yl)-2-oxopiperazin-1-yl]methyl]-2-(trifluoromethyl)benzonitrile To a solution of 3-[(2-oxopiperazin-1-yl)methyl]-2-(trifluoromethyl)benzonitrile (170 mg, 0.60 mmol, 1 equiv.) in DMA (5 mL) were added 4,5-dichloro-2,3-dihydropyridazin-3-one (99.0 mg, 0.60 mmol, 1.00 equiv.) and DIEA (155.1 mg, 1.20 mmol, 2.00 equiv.) at ambient temperature. The resulting mixture was stirred for 16 h at 100 degrees C. The desired product could be detected by LCMS. The mixture was allowed to cool down to ambient temperature. The reaction mixture was purified by Prep-HPLC with the following conditions (Column: XSelect CSH Prep C18 OBD Column, 5 um, 19*150 mm; Mobile Phase A: Water (10 mmol/L NH4HCO3), Mobile Phase B: ACN; Flow rate: 20 mL/min; Gradient: 25% B to 75% B in 8 min; 220 nm; Rt: 6.9 min) to afford 3-[[4-(5-chloro-6-oxo-1,6-dihydropyridazin-4-yl)-2-oxopiperazin-1-yl]methyl]-2-(trifluoromethyl)benzonitrile (70 mg, 28.33%) as an off-white solid.

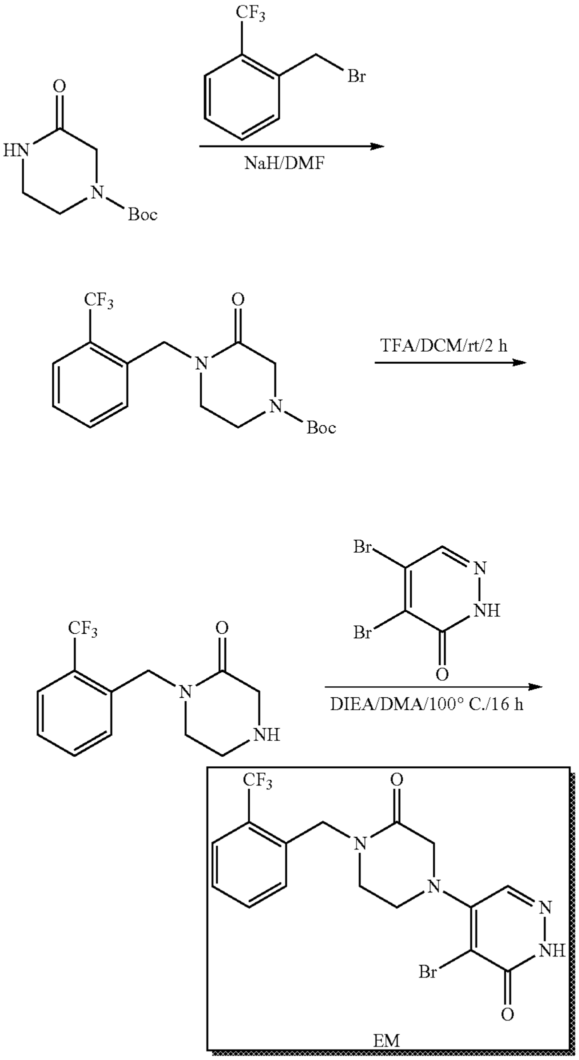

EM

EM was prepared by the methods described for Compound A above.

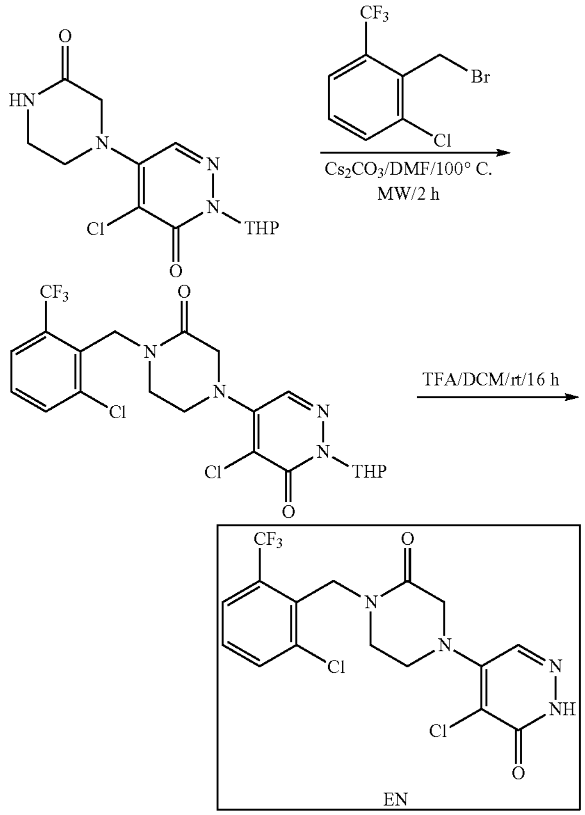

EN

Preparation of EN

4-chloro-5-(4-[[2-chloro-6-(trifluoromethyl)phenyl] methyl]-3-oxopiperazin-1-yl)-2-(oxan-2-yl)-2,3-dihydropyridazin-3-one To a stirred solution of 2-(bromomethyl)-1-chloro-3-(trifluoromethyl)benzene (100 mg, 0.37 mmol, 1 equiv.) and 4-chloro-2-(oxan-2-yl)-5-(3-oxopiperazin-1-yl)-2,3-dihydropyridazin-3-one (114.4 mg, 0.37 mmol, 1.00 equiv.) in DMF (3 mL) was added Cs2CO3 (357.4 mg, 1.10 mmol, 3 equiv). The resulting mixture was stirred for overnight at 100 degrees C. The residue was purified by silica gel column chromatography, eluted with hexane/EtOAc (10:1) to afford 4-chloro-5-(4-[[2-chloro-6-(trifluoromethyl)phenyl] methyl]-3-oxopiperazin-1-yl)-2-(oxan-2-yl)-2,3-dihydropyridazin-3-one (80 mg, 43.30%) as a light yellow solid.

4-chloro-5-(4-[[2-chloro-6-(trifluoromethyl)phenyl] methyl]-3-oxopiperazin-1-yl)-2,3-dihydropyridazin-3-one To a stirred solution of 4-chloro-5-(4-[[2-chloro-6-(trifluoromethyl)phenyl]methyl]-3-oxopiperazin-1-yl)-2-(oxan-2-yl)-2,3-dihydropyridazin-3-one (80 mg, 0.16 mmol, 1 equiv.) in DCM (3 mL) was added TFA (1 mL). The resulting mixture was stirred for 2 h at room temperature. The resulting mixture was concentrated under reduced pressure. The crude product was purified by Prep-HPLC with the following conditions (Column: XBridge Shield RP18 OBD Column, 5 um, 19×150 mm; Mobile Phase A: Water (10 mmol/L NH4HCO3), Mobile Phase B: ACN; Flow rate: 20 mL/min; Gradient: 25% B to 55% B in 7 min; 220 nm; Rt: 5.72 min) to afford 4-chloro-5-(4-[[2-chloro-6-(trifluoromethyl)phenyl]methyl]-3-oxopiperazin-1-yl)-2,3-dihydropyridazin-3-one (23.6 mg, 35.39%) as a white solid.

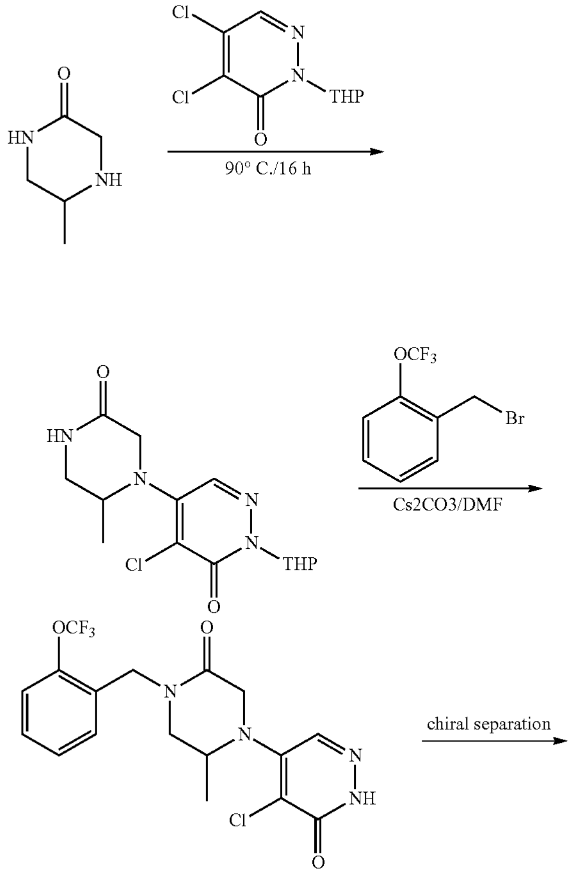

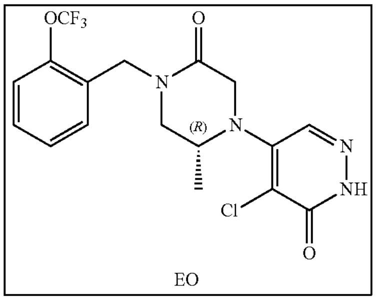

EO

+

Tested: $[a]^{25}D = +36°$ (c = 1 mg/mL, $CHCl_3$)

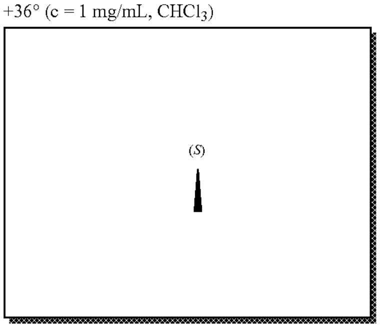

Tested: $[a]^{25}D = -40°$ (c = 1 mg/mL, $CHCl_3$)

Preparation of EO and EP

4-chloro-5-(2-methyl-5-oxopiperazin-1-yl)-2-(oxan-2-yl)-2,3-dihydropyridazin-3-one Into a 50 mL round-bottom flask were added 5-methylpiperazin-2-one (900 mg, 7.88 mmol, 1 equiv.) and 4,5-dichloro-2-(oxan-2-yl)-2,3-dihydropyridazin-3-one (2356.8 mg, 9.46 mmol, 1.20 equiv.) at room temperature. The resulting mixture was stirred for 16 h at 90 degrees C. The reaction was monitored by LCMS. The mixture was allowed to cool down to room temperature. The crude product was purified by reverse phase flash with the following conditions (Column: XBridge Prep OBD C18 Column 30×150 mm 5 um; Mobile Phase A: Water (10 mmol/L NH4HCO3), Mobile Phase B: ACN; Flow rate: 60 mL/min; Gradient: 10% B to 20% B in 15 min; 220 nm; Rt: 5.85 min) to afford 4-chloro-5-(2-methyl-5-oxopiperazin-1-yl)-2-(oxan-2-yl)-2,3-dihydropyridazin-3-one (970 mg, 37.65%) as a yellow oil.

4-chloro-5-[(2R)-2-methyl-5-oxo-4-[[2-(trifluoromethoxy)phenyl]methyl]piperazin-1-yl]-2,3-dihydropyridazin-3-one and 4-chloro-5-[(2S)-2-methyl-5-oxo-4-[[2-(trifluoromethoxy)phenyl]methyl]piperazin-1-yl]-2,3-dihydropyridazin-3-one To a stirred mixture of 4-chloro-5-(2-methyl-5-oxopiperazin-1-yl)-2-(oxan-2-yl)-2,3-dihydropyridazin-3-one (250 mg, 0.77 mmol, 1 equiv.) and Cs2CO3 (997.1 mg, 3.06 mmol, 4 equiv.) in DMF (10 mL) was added 1-(bromomethyl)-2-(trifluoromethoxy)benzene (292.7 mg, 1.15 mmol, 1.50 equiv.) at room temperature under nitrogen atmosphere. The final reaction mixture was irradiated with microwave radiation for 1 h at 120 degrees C. The reaction was monitored by LCMS. The mixture was allowed to cool down to room temperature. The mixture was purified by reverse phase flash with the following conditions (Column: XBridge Shield RP18 OBD Column, 5 um, 19*150 mm; Mobile Phase A: Water (5 mmol/L NH4HCO3), Mobile Phase B: ACN; Flow rate: 20 mL/min; Gradient: 255% B to 65% B in 10 min; 220 nm; Rt: 6.28 min) to afford racemic 4-chloro-5-(2-methyl-5-oxo-4-[[2-(trifluoromethoxy)phenyl]methyl]piperazin-1-yl)-2-(oxan-2-yl)-2,3-dihydropyridazin-3-one (120 mg, 31.31%) as a white solid.

The crude product (40 mg) was purified by Prep-Chiral-HPLC with the following conditions (Column: CHIRALPAK IF, 2*25 cm, 5 um; Mobile Phase A:MTBE (0.1% DEA)-HPLC, Mobile Phase B: EtOH—HPLC; Flow rate: 13 mL/min; Gradient: 15 B to 15 B in 25 min; 220/254 nm; RT1:15.458; RT2:21.25) to afford 4-chloro-5-[(2R)-2-methyl-5-oxo-4-[[2-(trifluoromethoxy)phenyl]methyl]piperazin-1-yl]-2,3-dihydropyridazin-3-one (8.9 mg, 22.25%) as a white solid and 4-chloro-5-[(2S)-2-methyl-5-oxo-4-[[2-(trifluoromethoxy)phenyl]methyl]piperazin-1-yl]-2,3-dihydropyridazin-3-one (13.9 mg, 34.75%) as a white solid.

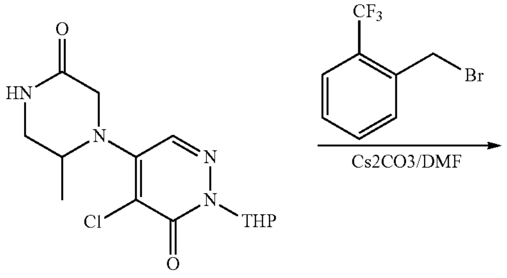

-continued

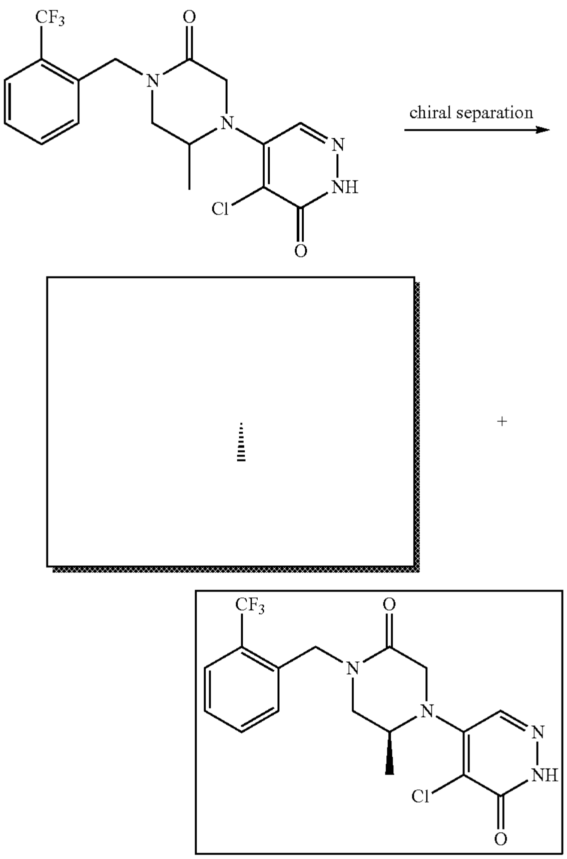

EQ prepared by the methods described for above for EO and EP.

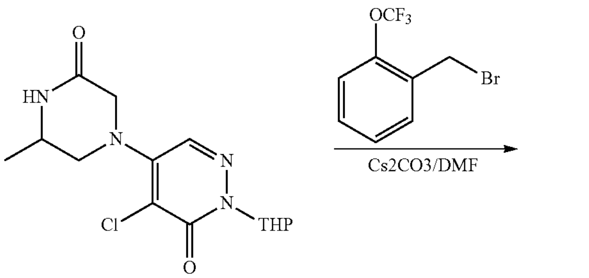

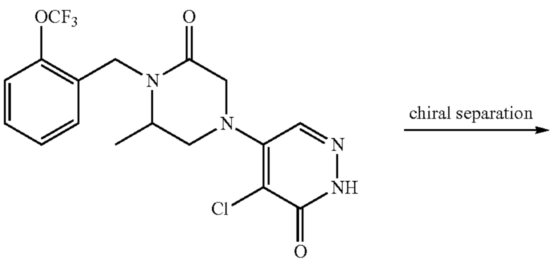

-continued

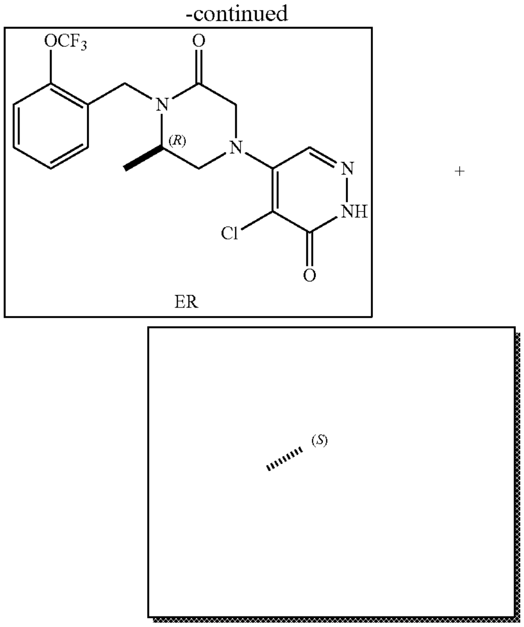

ER

ER and ES were prepared by the methods described for above for EQ and EP.

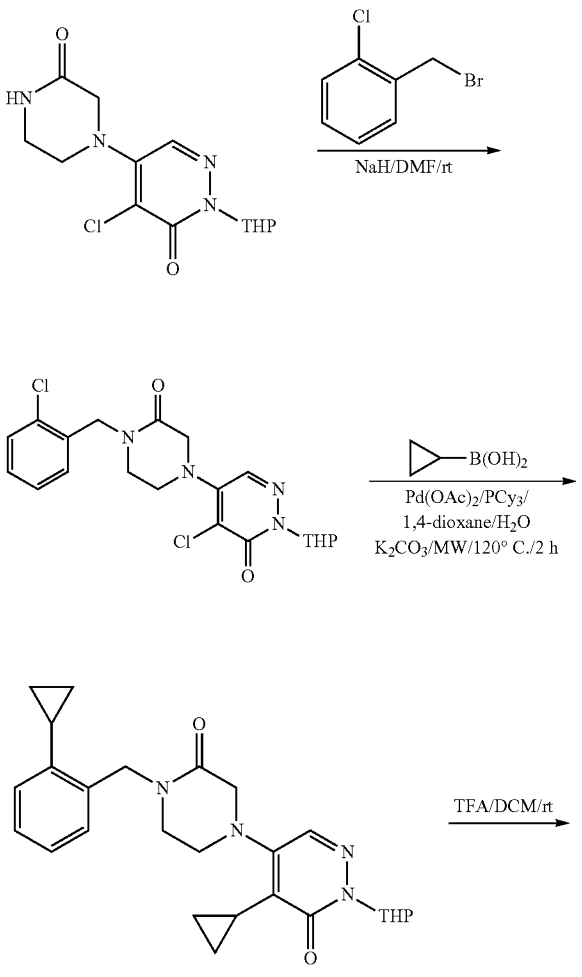

-continued

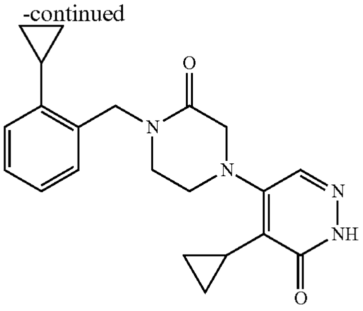

ET

Preparation of ET 4-chloro-5-[4-[(2-chlorophenyl)methyl]-3-oxopiperazin-1-yl]-2-(oxan-2-yl)-2,3-dihydropyridazin-3-one To a stirred solution of 4-chloro-2-(oxan-2-yl)-5-(3-oxopiperazin-1-yl)-2,3-dihydropyridazin-3-one (761.0 mg, 2.43 mmol, 1.00 equiv.) in DMF (15 mL) was added NaH (146.0 mg, 3.65 mmol, 1.5 equiv, 60%) in portions at 0 degrees C. under nitrogen atmosphere. The mixture was stirred at rt for 1 h. To the mixture was added 1-(bromomethyl)-2-chlorobenzene (500 mg, 2.43 mmol, 1 equiv.) at 0 degrees C. The mixture was stirred at rt for 1 h. Desired product could be detected by LCMS. The reaction was quenched by the addition of sat. NH4Cl (aq.) (10 mL) at 0 degrees C. The resulting mixture was washed with 3×30 mL of water. The organic layer was concentrated. The residue was purified by silica gel column chromatography, eluted with PE/EtOAc (1:1) to afford 4-chloro-5-[4-[(2-chlorophenyl)methyl]-3-oxopiperazin-1-yl]-2-(oxan-2-yl)-2,3-dihydropyridazin-3-one (400 mg, 37.59%) as a white solid.

4-cyclopropyl-5-[4-[(2-cyclopropylphenyl)methyl]-3-oxopiperazin-1-yl]-2-(oxan-2-yl)-2,3-dihydropyridazin-3-one To a solution of 4-chloro-5-[4-[(2-chlorophenyl)methyl]-3-oxopiperazin-1-yl]-2-(oxan-2-yl)-2,3-dihydropyridazin-3-one (200 mg, 0.46 mmol, 1 equiv.) and cyclopropylboronic acid (78.6 mg, 0.92 mmol, 2.00 equiv.) in 1,4-dioxane (5 mL) and H2O (1 mL) were added Pd(AcO)2 (10.3 mg, 0.05 mmol, 0.1 equiv), PCy3 (25.6 mg, 0.09 mmol, 0.2 equiv.) and K2CO3 (189.6 mg, 1.37 mmol, 3 equiv). The final reaction mixture was irradiated with microwave radiation for 3 h at 110 degrees C. under nitrogen atmosphere, the resulting mixture was concentrated under reduced pressure. The residue was purified by Prep-TLC (PE/EtOAc 10:1) to afford 4-cyclopropyl-5-[4-[(2-cyclopropylphenyl)methyl]-3-oxopiperazin-1-yl]-2-(oxan-2-yl)-2,3-dihydropyridazin-3-one (60 mg) as white solid.

4-cyclopropyl-5-[4-[(2-cyclopropylphenyl)methyl]-3-oxopiperazin-1-yl]-2,3-dihydropyridazin-3-one To a stirred solution of 4-cyclopropyl-5-[4-[(2-cyclopropylphenyl)methyl]-3-oxopiperazin-1-yl]-2-(oxan-2-yl)-2,3-dihydropyridazin-3-one (70 mg, 0.16 mmol, 1 equiv.) in DCM (10 mL) was added TFA (2 mL) in portions at 0 degrees C. under nitrogen atmosphere. The mixture was stirred at rt for 16 h. Desired product could be detected by LCMS. The resulting mixture was concentrated under reduced pressure. The crude product (60 mg) was purified by Prep-HPLC with the following conditions (Column: XBridge Prep C18 OBD Column 19×150 mm 5 um; Mobile Phase A: Water (10 mmol/L NH4HCO3), Mobile Phase B: ACN; Flow rate: 20 mL/min; Gradient: 20% B to 45% B in 10 min; 254/220 nm; Rt: 8.78 min) to afford 4-cyclopropyl-5-[4-[(2-cyclopropylphenyl)methyl]-3-oxopiperazin-1-yl]-2,3-dihydropyridazin-3-one (13 mg) as a white solid.

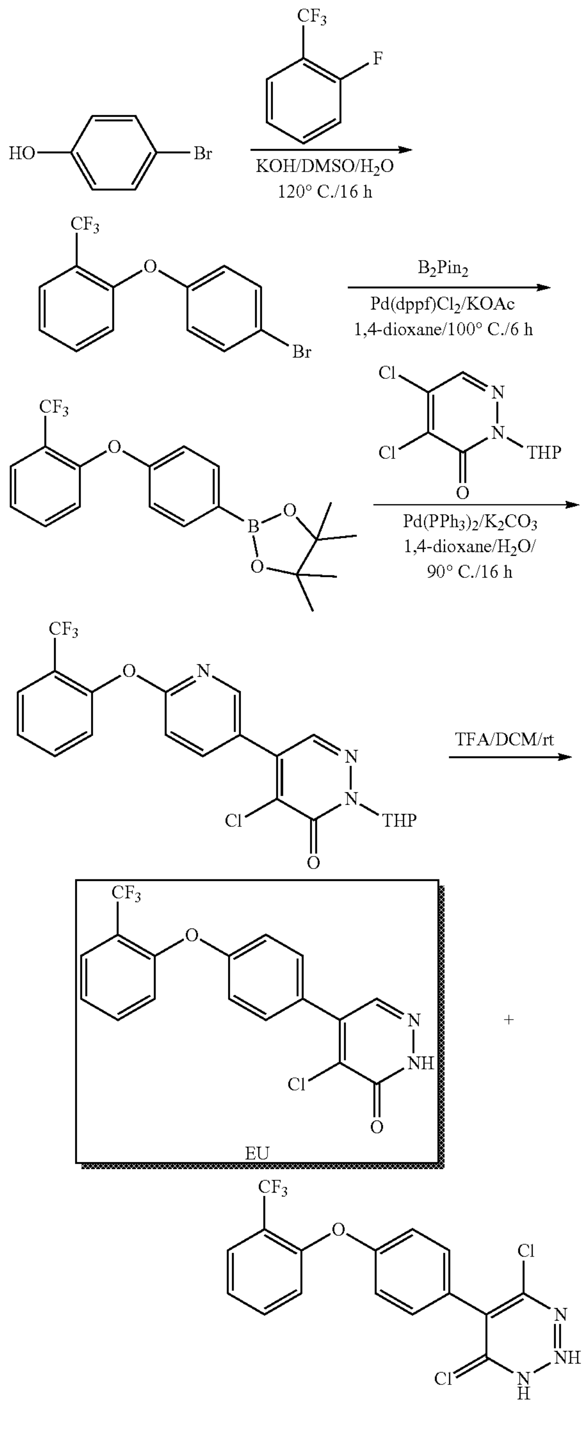

EU

EV

Preparation of EU and EV 1-(4-bromophenoxy)-2-(trifluoromethyl)benzene

To a stirred solution of 1-fluoro-2-(trifluoromethyl)benzene (5 g, 30.47 mmol, 1 equiv.) and 4-bromophenol (6.9 g, 39.88 mmol, 1.31 equiv.) in DMSO (17 mL) was added KOH (2.6 g, 45.70 mmol, 1.5 equiv). The resulting mixture was stirred for overnight at 120 degrees C. The resulting mixture was concentrated under vacuum. The residue was purified by silica gel column chromatography, eluted with PE/EtOAc (8:1) to afford 1-(4-bromophenoxy)-2-(trifluoromethyl)benzene (700 mg, 7.25%) as a light yellow oil.

4,4,5,5-tetramethyl-2-[4-[2-(trifluoromethyl)phenoxy]phenyl]-1,3,2-dioxaborolane To a stirred solution of 1-(4-bromophenoxy)-2-(trifluoromethyl)benzene (700 mg, 2.21 mmol, 1 equiv.) and 4,4,5,5-tetramethyl-2-(4,4,5,5-tetramethyl-1,3,2-dioxaborolan-2-yl)-1,3,2-dioxaborolane (840.8 mg, 3.31 mmol, 1.50 equiv.) in 1,4-dioxane (15 mL) were added KOAc (433.3 mg, 4.41 mmol, 2.0 equiv.) and Pd(dppf)$Cl_2$ (161.5 mg, 0.22 mmol, 0.1 equiv). The resulting mixture was stirred for 3 h at 90 degrees C. The resulting mixture was concentrated under reduced pressure. This resulted in 4,4,5,5-tetramethyl-2-[4-[2-(trifluoromethyl)phenoxy]phenyl]-1,3,2-dioxaborolane (600 mg, crude) as a dark yellow solid.

4-chloro-2-(oxan-2-yl)-5-[4-[2-(trifluoromethyl)phenoxy]phenyl]-2,3-dihydropyridazin-3-one and 5-chloro-2-(oxan-2-yl)-4-[4-[2-(trifluoromethyl)phenoxy]phenyl]-2,3-dihydropyridazin-3-one To a stirred solution of 4,4,5,5-tetramethyl-2-[4-[2-(trifluoromethyl)phenoxy]phenyl]-1,3,2-dioxaborolane (600 mg, 1.65 mmol, 1 equiv.) and 4,5-dichloro-2-(oxan-2-yl)-2,3-dihydropyridazin-3-one (451.4 mg, 1.81 mmol, 1.10 equiv.) in 1,4-dioxane (15 mL) were added Pd(PPh3)4 (95.2 mg, 0.08 mmol, 0.05 equiv.) and K2CO3 (455.4 mg, 3.30 mmol, 2.0 equiv). The resulting mixture was stirred for overnight at 90 degrees C. The resulting mixture was concentrated under reduced pressure. The residue was purified by silica gel column chromatography, eluted with hexane/EtOAc (5:1) to afford a mixture of 4-chloro-2-(oxan-2-yl)-5-[4-[2-(trifluoromethyl)phenoxy]phenyl]-2,3-dihydropyridazin-3-one and 5-chloro-2-(oxan-2-yl)-4-[4-[2-(trifluoromethyl)phenoxy]phenyl]-2,3-dihydropyridazin-3-one as a white solid (300 mg, 40.39%) as a light yellow solid.

4-chloro-5-[4-[2-(trifluoromethyl)phenoxy]phenyl]-2,3-dihydropyridazin-3-one and 5-chloro-4-[4-[2-(trifluoromethyl)phenoxy]phenyl]-2,3-dihydropyridazin-3-one To a stirred solution of a mixture of 4-chloro-2-(oxan-2-yl)-5-[4-[2-(trifluoromethyl)phenoxy]phenyl]-2,3-dihydropyridazin-3-one and 5-chloro-2-(oxan-2-yl)-4-[4-[2-(trifluoromethyl)phenoxy]phenyl]-2,3-dihydropyridazin-3-one (300 mg, 0.67 mmol, 1 equiv.) in DCM (3 mL) was added TFA (1 mL). The resulting mixture was stirred for 2 h at room temperature. The solution was purified by Prep-HPLC with the following conditions (Column: XBridge Shield RP18 OBD Column, 5 um, 19×150 mm; Mobile Phase A: Water (10 mmol/L NH4HCO3), Mobile Phase B: ACN; Flow rate: 20 mL/min; Gradient: 35% B to 65% B in 8 min; 220 nm; Rt: 7.35 min) to afford 4-chloro-5-[4-[2-(trifluoromethyl)phenoxy]phenyl]-2,3-dihydropyridazin-3-one (16.8 mg, 13.77%) as a white solid and 5-chloro-4-[4-[2-(trifluoromethyl)phenoxy]phenyl]-2,3-dihydropyridazin-3-one (52.1 mg, 21.35%) as a white solid.

EU'

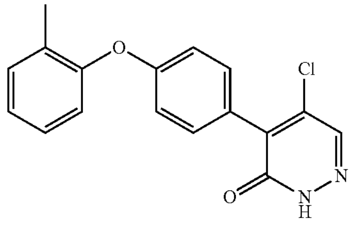

EV'

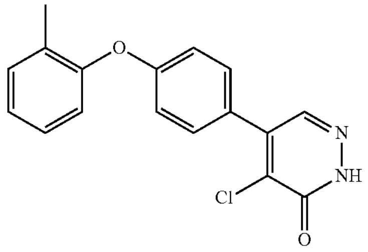

EU' and EV' were prepared by the methods described for EU and EV above.

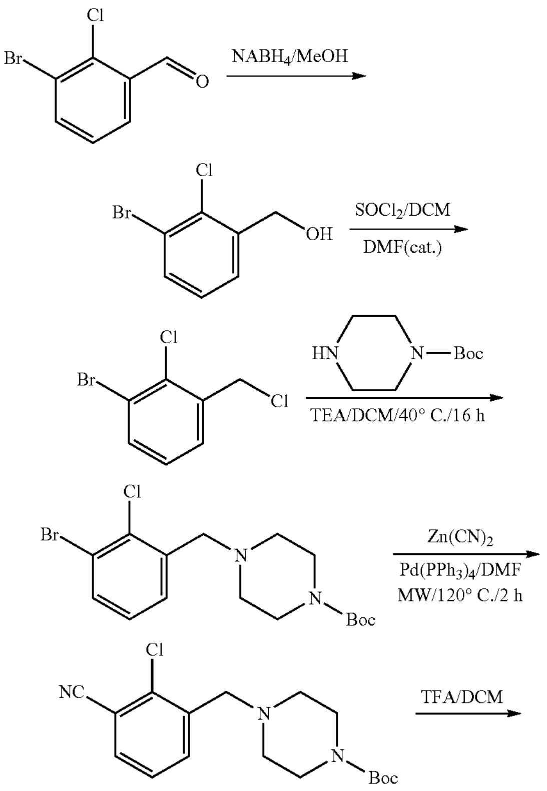

-continued

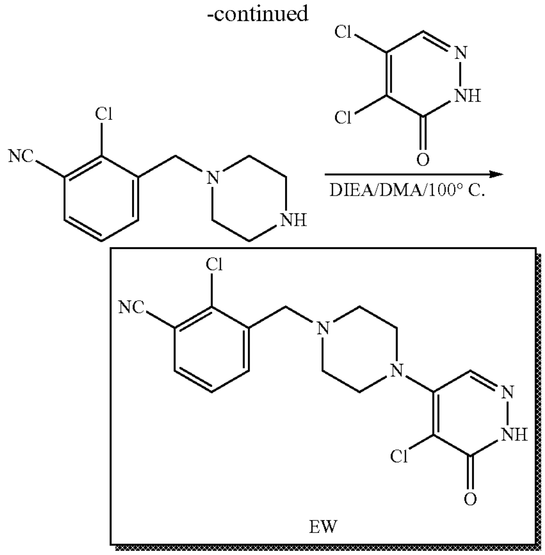

EW

Preparation of EW (3-bromo-2-chlorophenyl)methanol

To a solution of 3-bromo-2-chlorobenzaldehyde (5 g, 22.78 mmol, 1 equiv.) in MeOH (100 mL) were added NaBH4 (2.6 g, 68.72 mmol, 3.02 equiv.) at 0 degrees C. under nitrogen atmosphere. The resulting mixture was stirred for 4 h at 0 degrees C. The desired product could be detected by TLC. The mixture was concentrated and was diluted with water (400 mL) and extracted with EtOAc (3×400 mL). The combined organic layers were washed with water (1×300 mL), dried over anhydrous MgSO4. After filtration, the filtrate was concentrated under reduced pressure to afford (3-bromo-2-chlorophenyl)methanol (4.57 g, 90.57%) as a white solid.

1-bromo-2-chloro-3-(chloromethyl)benzene

To a solution of (3-bromo-2-chlorophenyl)methanol (4.57 g, 20.63 mmol, 1 equiv.) in DCM (200 mL) were added DMF (45.2 mg, 0.62 mmol, 0.03 equiv.) and SOCl2 (61.4 g, 516.10 mmol, 25.01 equiv.) dropwise at 0 degrees C. under nitrogen atmosphere. The resulting mixture was stirred for 2 days at ambient temperature. The desired product could be detected by LCMS. The mixture was concentrated to get crude product. The crude product was added water (400 mL) and extracted with EA (400 mL×2). The organic layers was washed with saturated brine (200 ml), dried over anhydrous Na2SO4, filtered and concentrated to give desired product. The residue was purified by silica gel column chromatography, eluted with EtOAc/PE (1:50 to 1:40) to afford 1-bromo-2-chloro-3-(chloromethyl)benzene (4.9 g, 98.98%) as a yellow liquid.

Tert-Butyl 4-[(3-bromo-2-chlorophenyl)methyl]piperazine-1-carboxylate

To a stirred mixture of 1-bromo-2-chloro-3-(chloromethyl)benzene (1.5 g, 6.25 mmol, 1 equiv.) and TEA (1.3 g, 12.85 mmol, 2.00 equiv.) in DCM (100 mL) was added tert-butyl piperazine-1-carboxylate (2.3 g, 12.35 mmol, 2.00 equiv.) at ambient temperature. The resulting mixture was stirred for 16 h at 40 degrees C. Upon completion, the mixture was cold to room temperature. The reaction mixture was poured into water (100 mL) and extracted with CH2Cl2 (2×100 mL). The combined organic layers were washed with brine (3×50 mL), dried over anhydrous Na2SO4. After filtration, the filtrate was concentrated under reduced pressure. The residue was purified by silica gel column chromatography, eluted with 10/~-30% ethyl acetate in petroleum ether to afford tert-butyl 4-[(3-bromo-2-chlorophenyl) methyl]piperazine-1-carboxylate as a yellow oil (1.95 g).

Tert-Butyl 4-[(2-chloro-3-cyanophenyl)methyl]piperazine-1-carboxylate

To a solution of tert-butyl 4-[(3-bromo-2-chlorophenyl) methyl]piperazine-1-carboxylate (1.93 g, 4.95 mmol, 1 equiv.) in DMF (20 mL) were added zincdicarbonitrile (581.5 mg, 4.95 mmol, 1.00 equiv.) and Pd(PPh3)4 (286.1 mg, 0.25 mmol, 0.05 equiv.) at ambient temperature. The reaction was irradiated with microwave radiation at 120 degrees C. for 2 h. The desired product could be detected by LCMS. The mixture was allowed to cool down to ambient temperature. The resulting mixture was filtered. The filtrate was concentrated under reduced pressure. The crude product was purified by reverse phase flash with the following conditions (Column: c18 OBD Column, 5 um, 19*330 mm; Mobile Phase A: Water (5 mmol/L $NaHCO_3$), Mobile Phase B: ACN; Flow rate: 45 mL/min; Gradient: 25% B to 75% B in 40 min; 254 nm; Rt: 24 min) to afford tert-butyl 4-[(2-chloro-3-cyanophenyl)methyl]piperazine-1-carboxylate (1.48 g, 88.99%) as a yellow solid.

2-chloro-3-[(piperazin-1-yl)methyl]benzonitrile

To a solution of TFA (2 mL) in DCM (8 mL) was added tert-butyl 4-[(2-chloro-3-cyanophenyl)methyl]piperazine-1-carboxylate (100 mg, 0.30 mmol, 1 equiv.) at ambient temperature. Then the mixture was stirred for 16 h at ambient temperature. The desired product could be detected by LCMS. The resulting mixture was concentrated under reduced pressure. The mixture was acidified to pH 8 with NaHCO3 (aq.). The reaction mixture was diluted with water (100 mL), extracted with EA (100 mL×2). The organic layers was washed with saturated brine (100 ml), dried over anhydrous Na2SO4, filtered and concentrated to give 2-chloro-3-[(piperazin-1-yl)methyl]benzonitrile (85 mg, 121.10%) as a yellow liquid.

2-chloro-3-[[4-(5-chloro-6-oxo-1,6-dihydropyridazin-4-yl)piperazin-1-yl]methyl]benzonitrile To a solution of 2-chloro-3-[(piperazin-1-yl)methyl]benzonitrile (85 mg, 0.36 mmol, 1 equiv.) in DMA (4 mL) was added DIEA (93.2 mg, 0.72 mmol, 2 equiv.) and DIEA (442.3 mg, 3.42 mmol, 4.00 equiv.) at ambient temperature under air atmosphere. The resulting mixture was stirred for 16 h at 100 degrees C. The desired product could be detected by LCMS. The reaction mixture was purified by reverse phase flash with the following conditions (Column: c18 OBD Column, 5 um, 19*120 mm; Mobile Phase A: Water (5 mmol/L NH4HCO3), Mobile Phase B: ACN; Flow rate: 45 mL/min; Gradient: 30% B to 70% B in 40 min; 254 nm; Rt: 30 min) to afford 2-chloro-3-[[4-(5-chloro-6-oxo-1,6-dihydropyridazin-4-yl)piperazin-1-yl]methyl]benzonitrile (17 mg, 12.94%) as a brown solid.

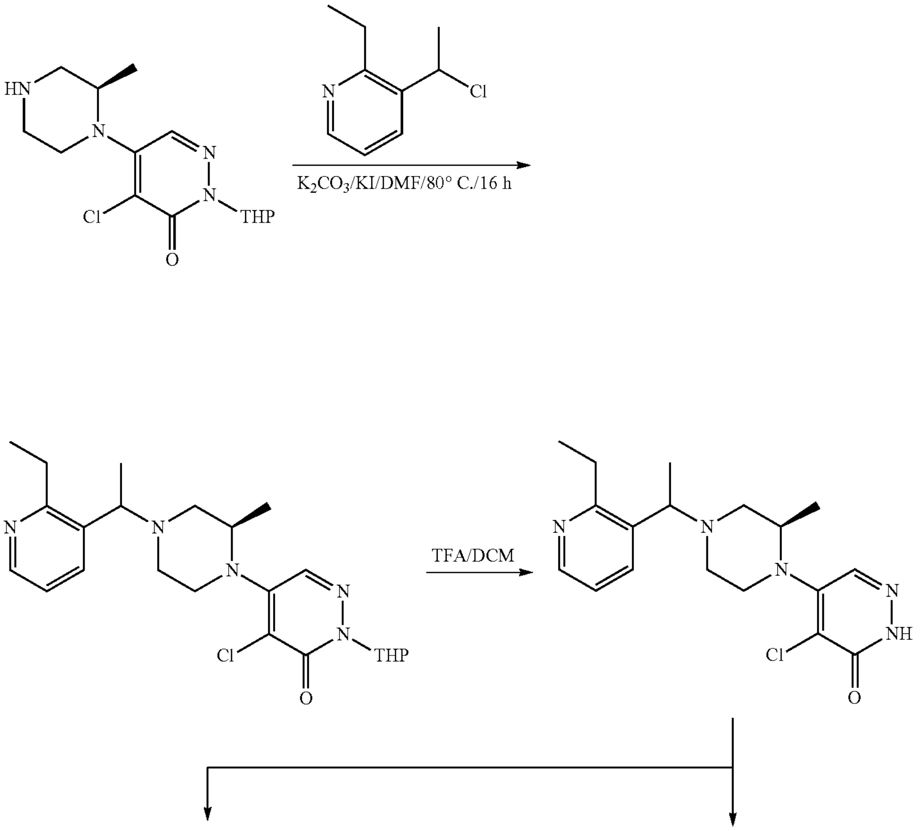

-continued

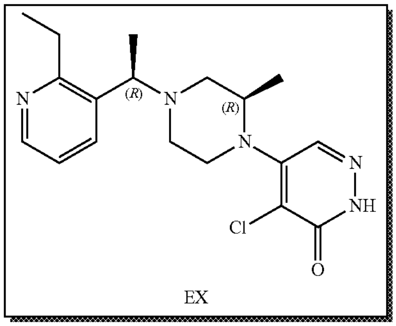

EX eluting faster on Chiral-HPLC
Tested: $(a)^{20}D = +31°(c = 1\ mg/mL,\ CHCl_3)$

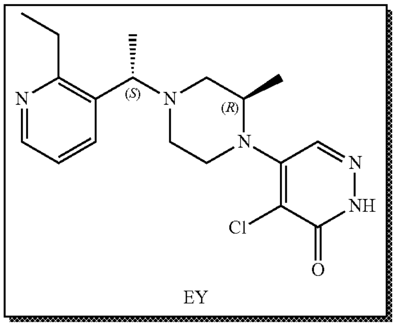

EY eluting slower on Chiral-HPLC
Tested: $(a)^{20}D = -84°(c = 1\ mg/mL,\ CHCl_3)$ Preparation of EX and EY 4-chloro-5-[(3S)-1-[1-(2-ethylpyridin-3-yl)ethyl]-3-methylpiperidin-4-yl]-2-(oxan-2-yl)-2,3-dihydropyridazin-3-one To a stirred mixture of 3-(1-chloroethyl)-2-ethylpyridine (54.4 mg, 320 mmol, 1 equiv.) and 4-chloro-5-[(3S)-3-methylpiperidin-4-yl]-2-(oxan-2-yl)-2,3-dihydropyridazin-3-one (100 mg, 320 mmol, 1 equiv.) in ACN (5 mL) were added K2CO3 (13.3 mg, 0.10 mmol, 1.5 equiv.) and KI (21.3 mg, 0.13 mmol, 2 equiv.) in portions at room temperature. The reaction was stirred overnight at 80 degrees C. The resulting mixture was concentrated under reduced pressure. The residue was purified by silica gel column chromatography, eluted with PE:EA (50% to 100%) to afford 4-chloro-5-[(3S)-1-[1-(2-ethylpyridin-3-yl)ethyl]-3-methylpiperidin-4-yl]-2-(oxan-2-yl)-2,3-dihydropyridazin-3-one (110 mg, 77.08%) as a yellow oil.

4-chloro-5-[(2R)-4-[(1R)-1-(2-ethylpyridin-3-yl)ethyl]-2-methylpiperazin-1-yl]-2,3-dihydropyridazin-3-one (10.9 mg, 8.40%) and 4-chloro-5-[(2R)-4-[(1S)-1-(2-ethylpyridin-3-yl)ethyl]-2-methylpiperazin-1-yl]-2,3-dihydropyridazin-3-one To a stirred solution of 4-chloro-5-[(2R)-4-[1-(2-ethylpyridin-3-yl)ethyl]-2-methylpiperazin-1-yl]-2-(oxan-2-yl)-2,3-dihydropyridazin-3-one (160 mg, 0.36 mmol, 1 equiv.) in DCM (30 mL) was added dropwise TFA (6 mL) at room temperature. Then the resulting mixture was stirred at room temperature for 2 hours. The reaction mixture was concentrated to give the crude product which was purified by prep chiral HPLC (Column: XBridge Prep C18 OBD Column 19×150 mm 5 um; Mobile Phase A: Water (10 mmol/L NH4HCO3), Mobile Phase B: ACN; Flow rate: 20 mL/min; Gradient: 15% B to 40% B in 7 min; 254 nm; Rt: 6.28 min) to afford 4-chloro-5-[(2R)-4-[(1R)-1-(2-ethylpyridin-3-yl)ethyl]-2-methylpiperazin-1-yl]-2,3-dihydropyridazin-3-one (10.9 mg, 8.40%) and 4-chloro-5-[(2R)-4-[(1S)-1-(2-ethylpyridin-3-yl)ethyl]-2-methylpiperazin-1-yl]-2,3-dihydropyridazin-3-one (14.3 mg, 11.02%) as white solid.

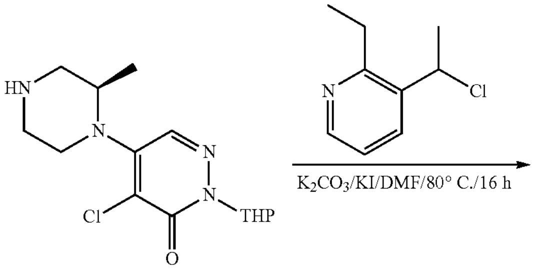

-continued

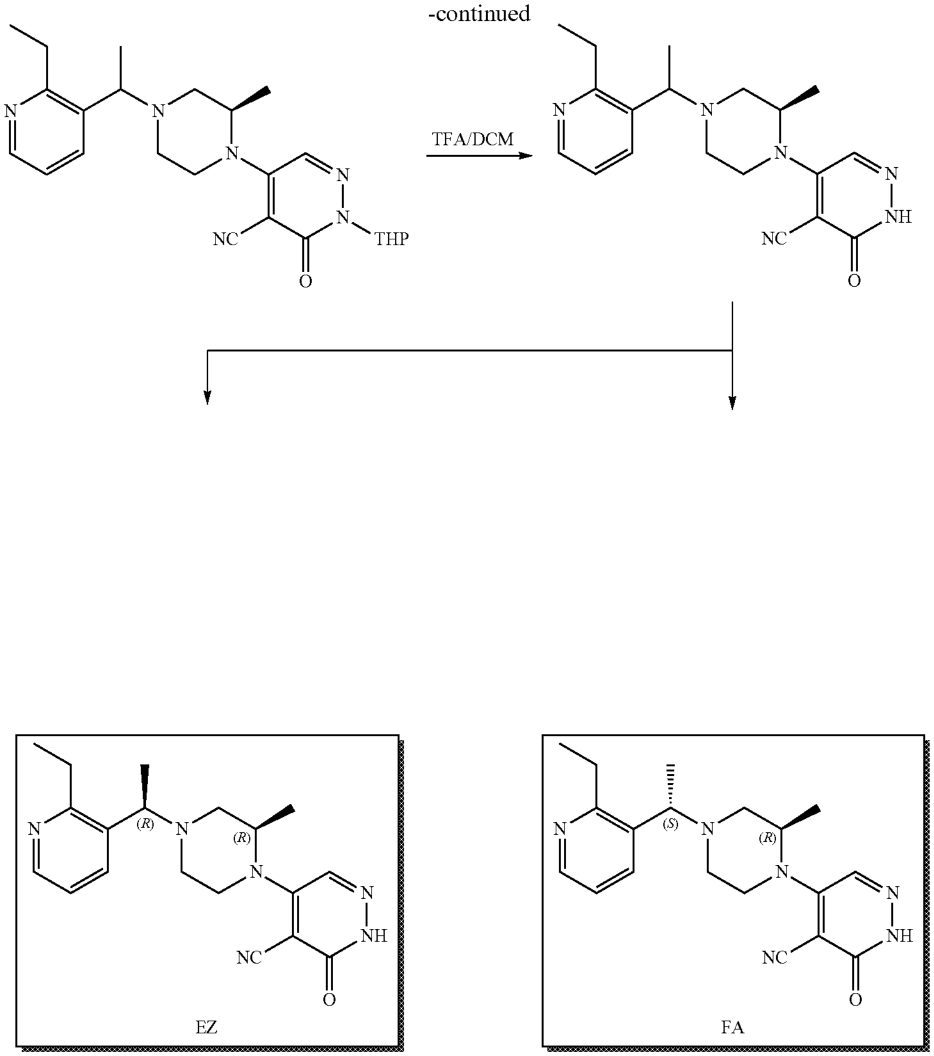

eluting faster on Chiral-HPLC
Tested: (a)$^{20}$D = -54°(c = 1 mg/mL, $CHCl_3$)

eluting slower on Chiral-HPLC
Tested: (a)$^{20}$D = -184°(c = 1 mg/mL, $CHCl_3$)

Preparation of EZ and FA

5-[(3S)-1-[1-(2-ethylpyridin-3-yl)ethyl]-3-methylpiperidin-4-yl]-2-(oxan-2-yl)-3-oxo-2,3-dihydropyridazine-4-carbonitrile To a stirred mixture of 3-(1-chloroethyl)-2-ethylpyridine (56.1 mg, 0.33 mmol, 1 equiv.) and 5-[(3S)-3-methylpiperidin-4-yl]-2-(oxan-2-yl)-3-oxo-2,3-dihydropyridazine-4-carbonitrile (100 mg, 0.33 mmol, 1 equiv.) in ACN (20 mL) were added K2CO3 (68.6 mg, 0.50 mmol, 1.5 equiv.) and KI (109.8 mg, 0.66 mmol, 2 equiv.) in portions at room temperature. The reaction was stirred overnight at 80 degrees C. The resulting mixture was concentrated under reduced pressure. The residue was purified by silica gel column chromatography, eluted with PE:EA (50% to 100%) to afford 5-[(3S)-1-[1-(2-ethylpyridin-3-yl)ethyl]-3-methylpiperidin-4-yl]-2-(oxan-2-yl)-3-oxo-2,3-dihydropyridazine-4-carbonitrile (120 mg, 83.31%) as a yellow oil.

4-chloro-5-[(2R)-4-[(1S)-1-(2-ethylpyridin-3-yl)ethyl]-2-methylpiperazin-1-yl]-2,3-dihydropyridazin-3-one and 5-[(2R)-4-[(1R)-1-(2-ethylpyridin-3-yl)ethyl]-2-methylpiperazin-1-yl]-3-oxo-2,3-dihydropyridazine-4-carbonitrile A mixture of 5-[(2R)-4-[1-(2-ethylpyridin-3-yl)-2,2,2-trifluoroethyl]-2-methylpiperazin-1-yl]-2-(oxan-2-yl)-3-oxo-2,3-dihydropyridazine-4-carbonitrile (120 mg, 0.24 mmol, 1 equiv.) and THF (3 mL, 37.03 mmol) in DCM (15 mL, 235.95 mmol) was stirred for 16 h at room temperature. The resulting mixture was concentrated under reduced pressure. The crude product was purified by reverse phase flash with the following conditions (Column: Spherical C18, 20-40 um, 120 g; Mobile Phase A: Water (0.05% TFA), Mobile Phase B: ACN; Flow rate: 45 mL/min; Gradient (B %): 5%~15%, 4 min; 15%~45%, 20 min; 45%~95%; 2 min; 95%, 5 min; Detector: 254 nm; Rt: 18 min.) to afford 4-chloro-5-[(2R)-4-[(1S)-1-(2-ethylpyridin-3-yl)ethyl]-2-methylpiperazin-1-yl]-2,3-dihydropyridazin-3-one (19 mg, 19.51%) as a white solid and 5-[(2R)-4-[(1R)-1-(2-ethylpyridin-3-yl)ethyl]-2-methylpiperazin-1-yl]-3-oxo-2,3-dihydropyridazine-4-carbonitrile (18.1 mg, 20.99%) as a white solid.

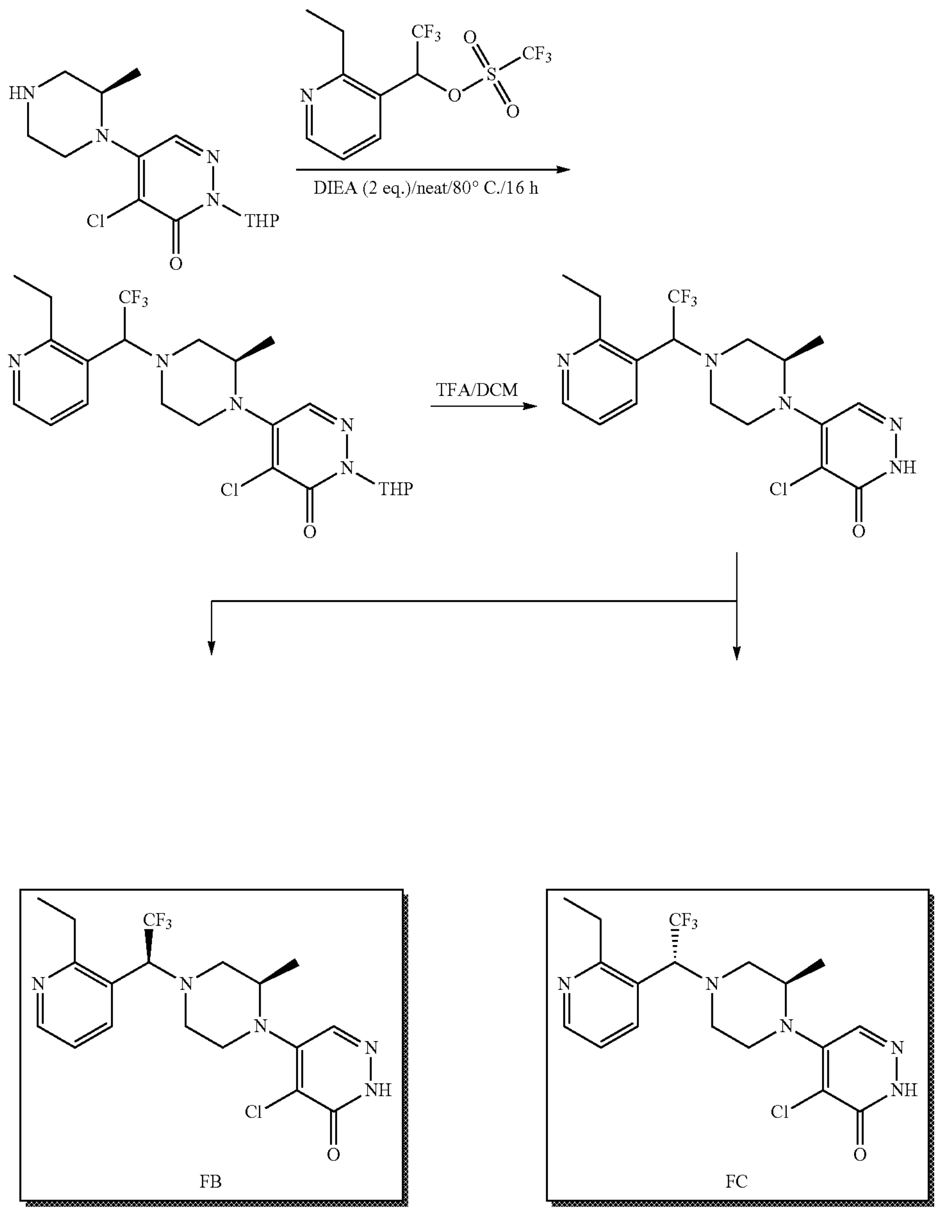

Preparation of FB and FC

A mixture of 1-(2-ethylpyridin-3-yl)-2,2,2-trifluoroethyl trifluoromethanesulfonate (150 mg, 0.44 mmol, 1 equiv.) and 4-chloro-5-[(2R)-2-methylpiperazin-1-yl]-2-(oxan-2-yl)-2,3-dihydropyridazin-3-one (167.0 mg, 0.53 mmol, 1.20 equiv.) in DIEA (115.0 mg, 0.89 mmol, 2 equiv.) was stirred for 16 h at 80 degrees C. Desired product could be detected by LCMS, the resulted mixture was worked up with next batch.

4-chloro-5-[(2R)-4-[(R)-1-(2-ethylpyridin-3-yl)-2,2,2-trifluoroethyl]-2-methylpiperazin-1-yl]-2,3-dihydropyridazin-3-one and 4-chloro-5-[(2R)-4-[(S)-1-(2-ethylpyridin-3-yl)-2,2,2-trifluoroethyl]-2-methylpiperazin-1-yl]-2,3-dihydropyridazin-3-one To a stirred solution of 4-chloro-5-[(2R)-4-[1-(2-ethylpyridin-3-yl)-2,2,2-trifluoroethyl]-2-methylpiperazin-1-yl]-2-(oxan-2-yl)-2,3-dihydropyridazin-3-one (150 mg) in DCM (30 mL) was added dropwise TFA (6 mL) at room temperature. Then the resulting mixture was stirred at room temperature for 2 hours. The reaction mixture was concentrated to give the crude product which was purified by prep chiral HPLC (Column: XBridge Prep C18 OBD Column 19×150 mm 5 um; Mobile Phase A: Water (10 mmol/L NH4HCO3), Mobile Phase B: ACN; Flow rate: 20 mL/min; Gradient: 15% B to 40% B in 7 min; 254 nm; Rt: 6.28 min) to afford 4-chloro-5-[(2R)-4-[(1S)-1-(2-ethylpyridin-3-yl)-2,2,2-trifluoroethyl]-2-methylpiperazin-1-yl]-2,3-dihydropyridazin-3-one (17.3 mg, 13.87%) as a white solid and 4-chloro-5-[(2R)-4-[(1R)-1-(2-ethylpyridin-3-yl)-2,2,2-trifluoroethyl]-2-methylpiperazin-1-yl]-2,3-dihydropyridazin-3-one (13.7 mg, 10.98%) as a white solid.

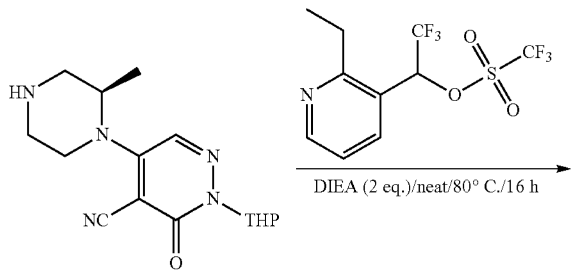
DIEA (2 eq.)/neat/80° C./16 h
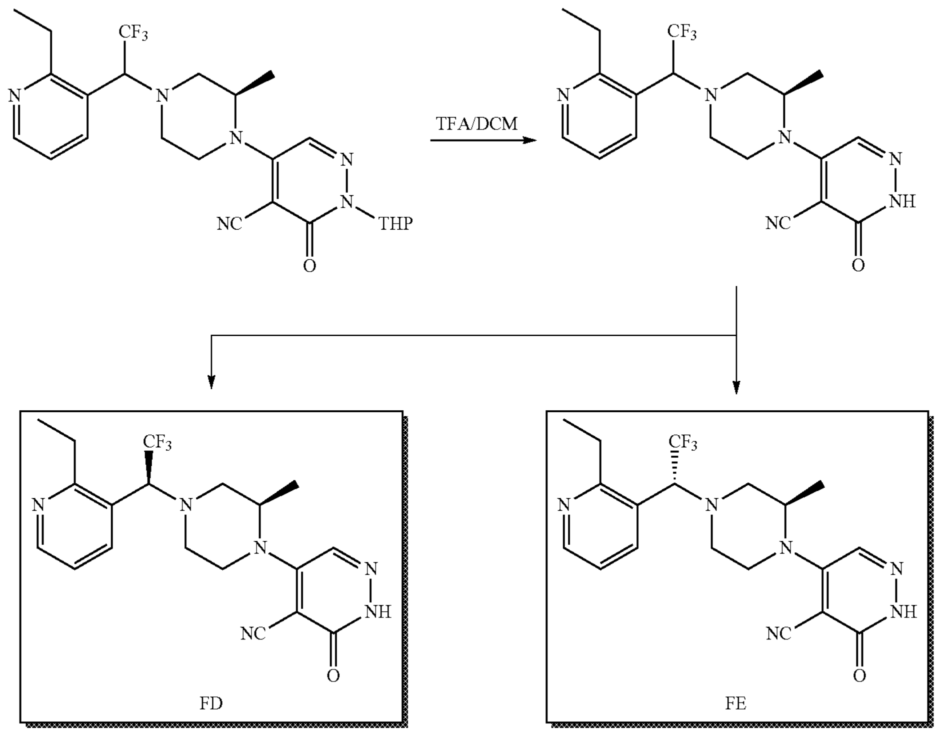
TFA/DCM
FD
FE

FD was prepared by the methods described above for FB.
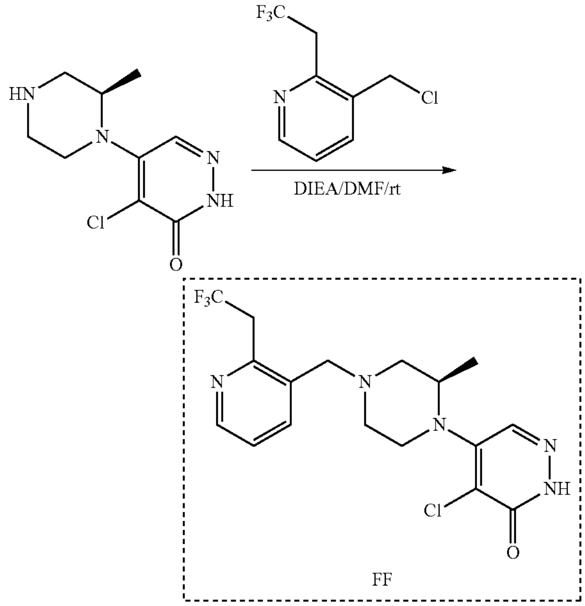
FF
FF was prepared by the methods described above for Compound H.
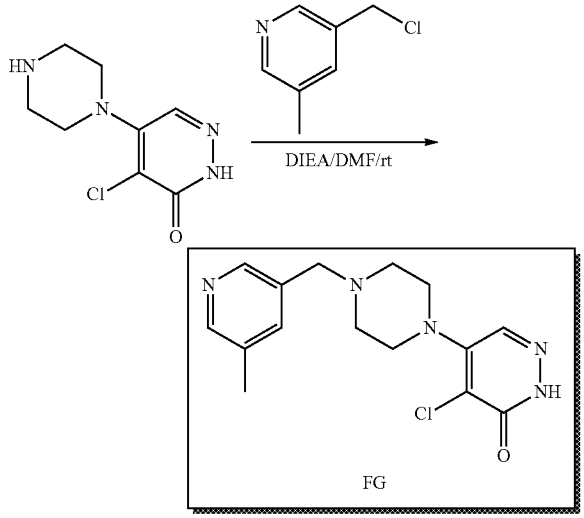
FG
FG was prepared by the methods described for above for Compound H.
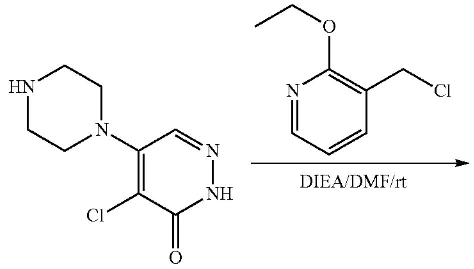
-continued
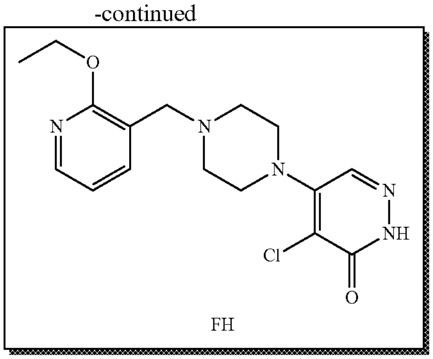
FH
FH was prepared by the methods described above for Compound H.
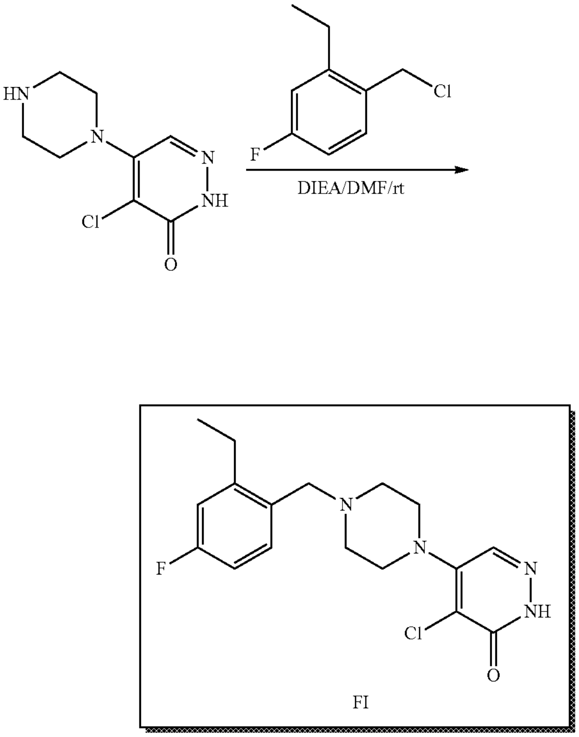
FI
FI was prepared by the methods described above for Compound H.
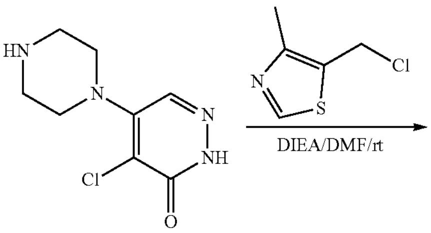

-continued

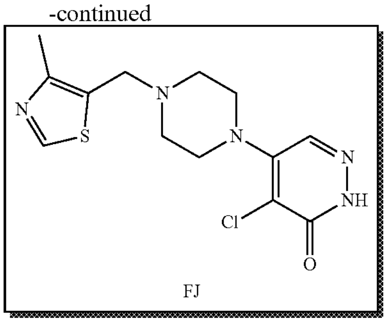

FJ

FJ was prepared by the methods described above for Compound H.

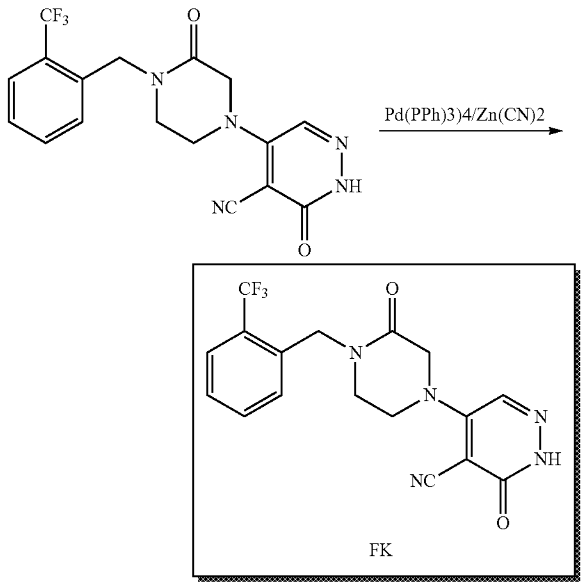

FK

Preparation of FK

3-oxo-5-(3-oxo-4-[[2-(trifluoromethyl)phenyl] methyl]piperazin-1-yl)-2,3-dihydropyridazine-4-carbonitrile To a stirred solution of 4-chloro-5-(3-oxo-4-[[2-(trifluoromethyl)phenyl]methyl]piperazin-1-yl)-2,3-dihydropyridazin-3-one (200 mg, 0.52 mmol, 1 equiv.) in DMF (10 mL) were added Pd(PPh3)4 (119.5 mg, 0.10 mmol, 0.2 equiv.) and Zn(CN)2 (60.7 mg, 0.52 mmol, 1 equiv.) at room temperature under N2 atmosphere. The resulting mixture was stirred for 16 h at 110 degrees C. under N2 atmosphere. The reaction was monitored by LCMS. The resulting mixture was filtered, the filter cake was washed with DMF (2×1 mL). The filtrate was concentrated under vacuum. The residue was purified by reverse phase flash with the following conditions (Column: Spherical C18 Column, 20-40 um, 120 g; Mobile Phase A: Water (0.1% NH4HCO3), Mobile Phase B: ACN; Flow rate: 60 mL/min; Gradient: 30% B to 50% B in 25 min, 254 nm) to afford 3-oxo-5-(3-oxo-4-[[2-(trifluoromethyl)phenyl]methyl]piperazin-1-yl)-2,3-dihydropyridazine-4-carbonitrile (70 mg, 35.87%) as a grey solid.

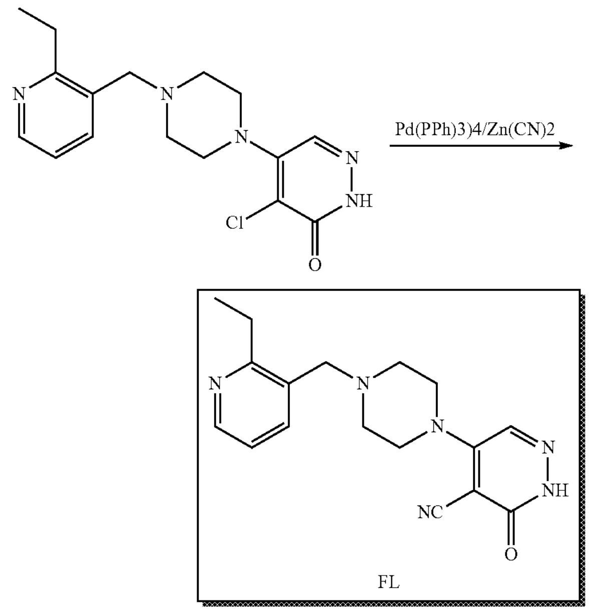

FL

FL was prepared by the methods described above for FK.

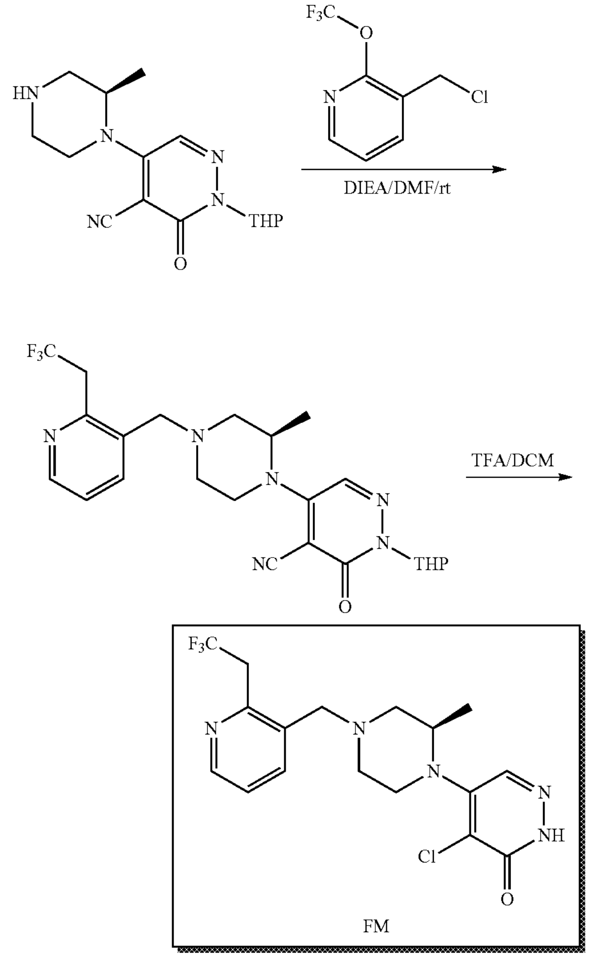

FM

Preparation of FM

5-[(2R)-2-methyl-4-[[2-(2,2,2-trifluoroethyl)pyridin-3-yl]methyl]piperazin-1-yl]-2-(oxan-2-yl)-3-oxo-2,3-dihydropyridazine-4-carbonitrile To a stirred mixture of 3-(chloromethyl)-2-(2,2,2-trifluoroethyl)pyridine (120 mg, 0.57 mmol, 1 equiv.) and DIEA (222.0 mg, 1.72 mmol, 3 equiv.) in DMF (5 mL) was added 5-[(2R)-2-methylpiperazin-1-yl]-2-(oxan-2-yl)-3-oxo-2,3-dihydropyridazine-4-carbonitrile (173.7 mg, 0.57 mmol, 1.00 equiv.) at room temperature. The resulting mixture was stirred for 16 h at room temperature. The reaction was monitored by LCMS. The crude product was purified by reverse phase flash with the following conditions (Column: XBridge Prep C18 OBD Column 19×150 mm 5 um; Mobile Phase A: Water (5 mmol/L NH4HCO3), Mobile Phase B: ACN; Flow rate: 20 mL/min; Gradient: 45% B to 55% B in 10 min; 220 nm; Rt: 6.12 min) to afford 5-[(2R)-2-methyl-4-[[2-(2,2,2-trifluoroethyl)pyridin-3-yl]methyl]piperazin-1-yl]-2-(oxan-2-yl)-3-oxo-2,3-dihydropyridazine-4-carbonitrile (120 mg, 43.99%) as a yellow solid.

5-[(2R)-2-methyl-4-[[2-(2,2,2-trifluoroethyl)pyridin-3-yl]methyl]piperazin-1-yl]-3-oxo-2,3-dihydropyridazine-4-carbonitrile To a stirred solution of 5-[(2R)-2-methyl-4-[[2-(2,2,2-trifluoroethyl)pyridin-3-yl]methyl]piperazin-1-yl]-2-(oxan-2-yl)-3-oxo-2,3-dihydropyridazine-4-carbonitrile (120 mg, 0.25 mmol, 1 equiv.) in DCM (10 mL) was added TFA (2 mL, 26.93 mmol, 106.92 equiv.) at room temperature. The resulting mixture was stirred for 16 h at room temperature. The reaction was monitored by LCMS. The resulting mixture was concentrated under reduced pressure. The residue was basified to pH 8 with saturated NaHCO3 (aq.). The resulting mixture was extracted with EtOAc (3×10 mL). The combined organic layers were washed with brine (1×10 mL), dried over anhydrous Na2SO4. After filtration, the filtrate was concentrated under reduced pressure. The crude product (60 mg) was purified by Prep-HPLC with the following conditions (Column: XBridge Prep C18 OBD Column 19×150 mm 5 um; Mobile Phase A: Water (10 mmol/L NH4HCO3), Mobile Phase B: ACN; Flow rate: 20 mL/min; Gradient: 25% B to 45% B in 7 min; 220 nm; Rt: 6.12 min) to afford 5-[(2R)-2-methyl-4-[[2-(2,2,2-trifluoroethyl)pyridin-3-yl]methyl]piperazin-1-yl]-3-oxo-2,3-dihydropyridazine-4-carbonitrile (55.2 mg, 55.86%) as a white solid.

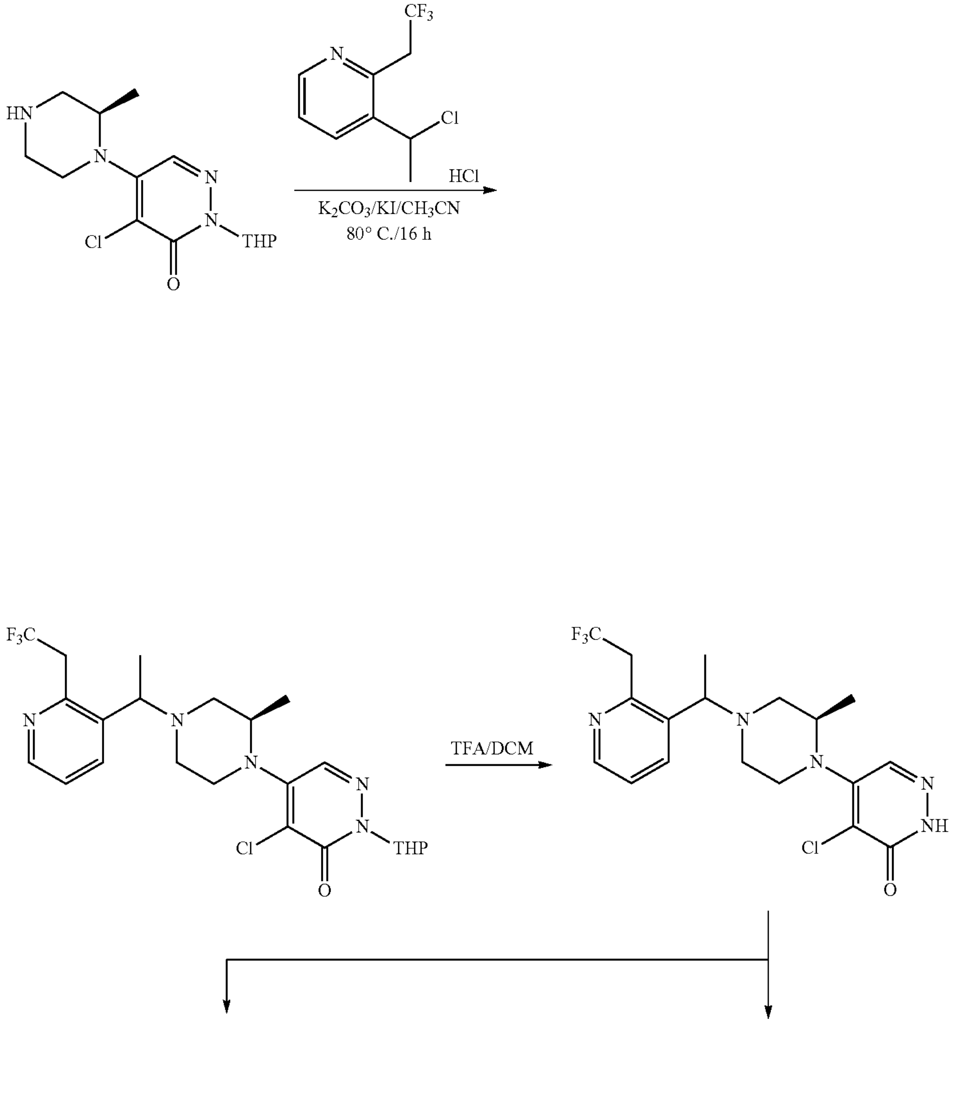

-continued
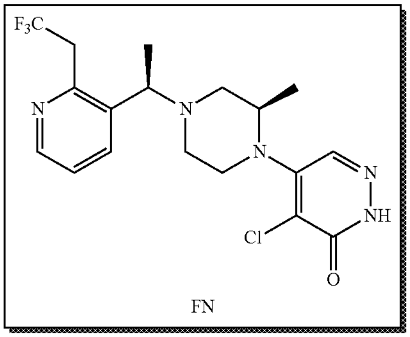
FN
FN and FO were prepared by the methods described above for EZ and FA.
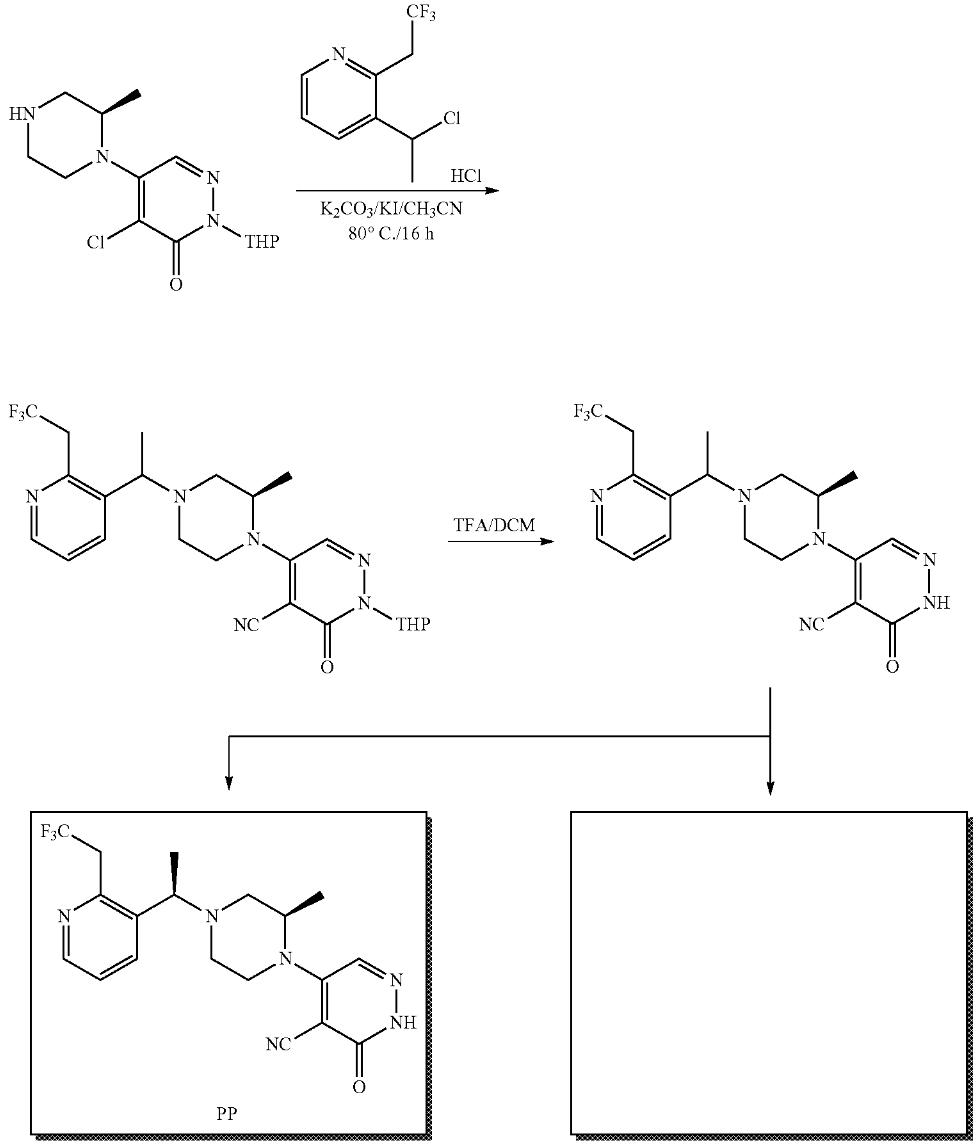
PP FQ was prepared by the methods described above for EZ and FA.

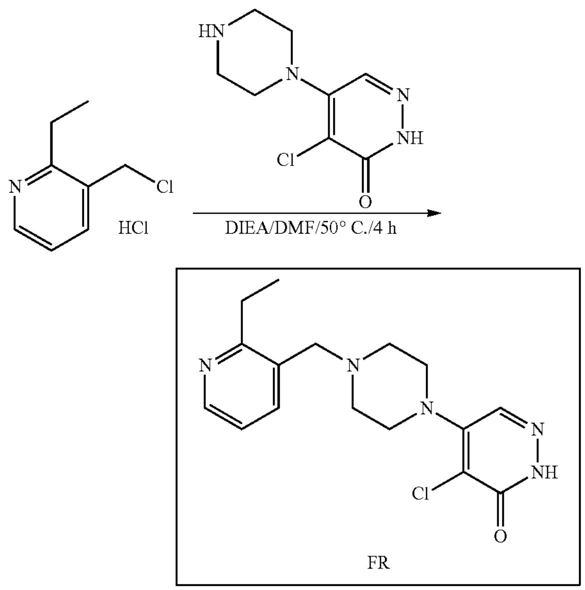

FR

Preparation of FR

4-chloro-5-[4-[(2-ethylpyridin-3-yl)methyl]piperazin-1-yl]-2,3-dihydropyridazin-3-one To a mixture of 4-chloro-5-(piperazin-1-yl)-2,3-dihydropyridazin-3-one (100 mg, 0.47 mmol, 1 equiv.) and DIEA (301.1 mg, 2.33 mmol, 5 equiv.) in DMF (5 mL) was added 3-(chloromethyl)-2-ethylpyridine (94.3 mg, 0.61 mmol, 1.30 equiv.) at rt. The reaction was stirred for 16 h at rt. The reaction was monitored by LCMS. The reaction mixture was purified by Prep-HPLC with the following conditions (Column: XBridge Shield RP18 OBD Column 30*150 mm, 5 um; Mobile Phase A: Water (10 mmol/L NH4HCO3), Mobile Phase B: ACN; Flow rate: 20 mL/min; Gradient: 10% B to 40% B in 7 min; 220 nm; Rt: 6.23 min) to afford 4-chloro-5-[4-[(2-ethylpyridin-3-yl)methyl]piperazin-1-yl]-2,3-dihydropyridazin-3-one (56.3 mg, 36.20%) as a white solid.

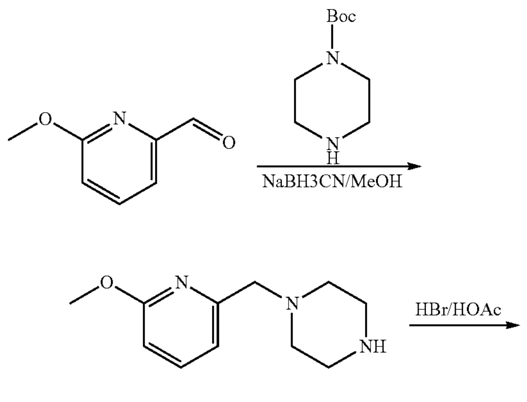

-continued

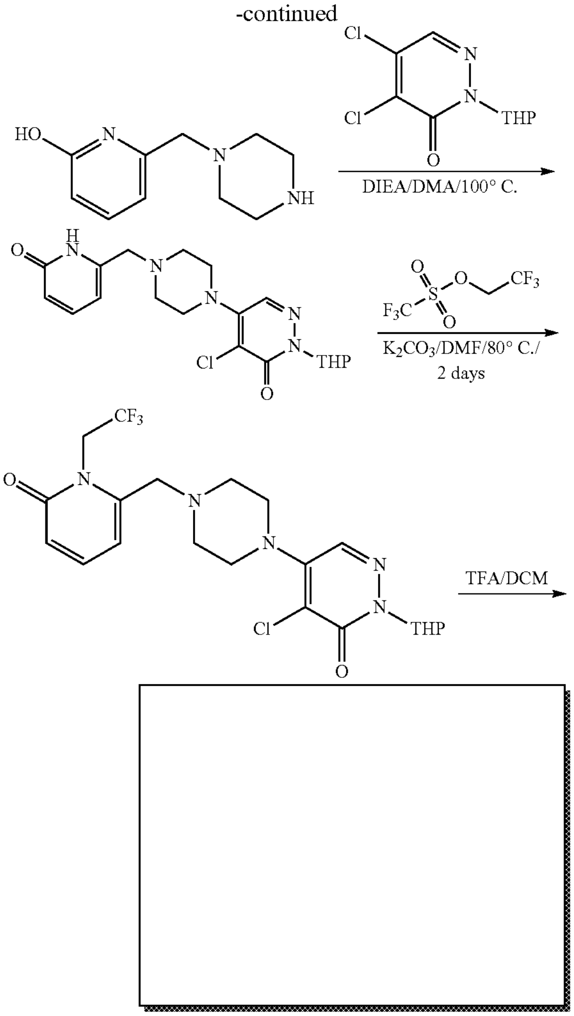

Preparation of FS

Tert-Butyl 1-[(6-methoxypyridin-2-yl)methyl]piperidine-4-carboxylate

To a stirred mixture of 6-methoxypyridine-2-carbaldehyde (5 g, 36.46 mmol, 1 equiv.) and tert-butyl piperazine-1-carboxylate (8.1 g, 43.49 mmol, 1.19 equiv.) in MeOH (25 mL) was added NaBH3CN (4.6 g, 73.20 mmol, 2.01 equiv.) in portions at 0 degrees C. The resulting mixture was stirred for 16 h at room temperature. The reaction was monitored by LCMS. The resulting mixture was concentrated under reduced pressure. The residue was purified by silica gel column chromatography, eluted with PE/EtOAc (40/1 to 1/1) to afford tert-butyl 1-[(6-methoxypyridin-2-yl)methyl]piperidine-4-carboxylate (8.5 g, 76.09%) as a light yellow oil.

6-[(piperazin-1-yl)methyl]-2,3-dihydropyridin-2-one

To a stirred solution of tert-butyl 4-[(6-methoxypyridin-2-yl)methyl]piperazine-1-carboxylate (8.5 g, 27.65 mmol, 1 equiv.) in AcOH (85 mL) was added HBr (42.5 mL, 525.28 mmol, 52.62 equiv.) dropwise at room temperature. The resulting mixture was stirred for 12 h at 90 degrees C. The reaction was monitored by LCMS. The resulting mixture was concentrated under reduced pressure. The mixture was basified to pH 8 with saturated NH4HCO3 (aq.). The filtrate was concentrated under reduced pressure. The crude product was re-crystallized from DCM/MeOH (5:1 200 mL) to afford 6-[(piperazin-1-yl)methyl]-2,3-dihydropyridin-2-one (9 g, 168422.25%) as a light brown solid.

4-chloro-2-(oxan-2-yl)-5-[4-[(6-oxo-1,6-dihydropyridin-2-yl)methyl]piperazin-1-yl]-2,3-dihydropyridazin-3-one To a stirred mixture of 6-[(piperazin-1-yl)methyl]pyridin-2-ol (2 g, 10.35 mmol, 1 equiv.) and 4,5-dichloro-2-(oxan-2-yl)-2,3-dihydropyridazin-3-one (2.6 g, 10.44 mmol, 1.01 equiv.) in DMA (7 mL) was added DIEA (2.7 g, 20.89 mmol, 2.02 equiv.) dropwise at room temperature. The resulting mixture was stirred for 16 h at 100 degrees C. The reaction was monitored by LCMS. The mixture was allowed to cool down to room temperature. The residue was purified by reverse flash chromatography with the following conditions: column, C18 silica gel; mobile phase, ACN in water, 30% to 50% gradient in 10 min; detector, UV 254 nm to afford 4-chloro-2-(oxan-2-yl)-5-[4-[(6-oxo-1,6-dihydropyridin-2-yl)methyl]piperazin-1-yl]-2,3-dihydropyridazin-3-one (1.32 g, 31.42%) as a Brown yellow solid.

4-chloro-2-(oxan-2-yl)-5-(4-[[6-oxo-1-(2,2,2-trifluoroethyl)-1,6-dihydropyridin-2-yl]methyl]piperazin-1-yl)-2,3-dihydropyridazin-3-one To a mixture of 4-chloro-2-(oxan-2-yl)-5-[4-[(6-oxo-1,6-dihydropyridin-2-yl)methyl]piperazin-1-yl]-2,3-dihydropyridazin-3-one (700 mg, 1.72 mmol, 1 equiv.) and 2,2,2-trifluoroethyl trifluoromethanesulfonate (800.6 mg, 3.45 mmol, 2.00 equiv.) in DMF (10 mL) was added K2CO3 (715.1 mg, 5.17 mmol, 3.00 equiv.) at room temperature. The resulting mixture was stirred for 72 h at 80 degrees C. The reaction was monitored by LCMS. The mixture was allowed to cool down to room temperature. The residue was purified by reverse flash chromatography with the following conditions: column, C18 silica gel; mobile phase, ACN in water, 30% to 70% gradient in 20 min; detector, UV 254 nm to afford 4-chloro-2-(oxan-2-yl)-5-(4-[[6-oxo-1-(2,2,2-trifluoroethyl)-1,6-dihydropyridin-2-yl]methyl]piperazin-1-yl)-2,3-dihydropyridazin-3-one (100 mg, 11.88%) as a yellow solid.

4-chloro-5-(4-[[6-oxo-1-(2,2,2-trifluoroethyl)-1,6-dihydropyridin-2-yl]methyl]piperazin-1-yl)-2,3-dihydropyridazin-3-one To a stirred solution of 4-chloro-2-(oxan-2-yl)-5-(4-[[6-oxo-1-(2,2,2-trifluoroethyl)-1,6-dihydropyridin-2-yl]methyl]piperazin-1-yl)-2,3-dihydropyridazin-3-one (100 mg, 0.20 mmol, 1 equiv.) in DCM (5 mL) was added TFA (2 mL) dropwise at room temperature. The resulting mixture was stirred for 2 h at room temperature. The reaction was monitored by LCMS. The mixture was basified to pH 8 with saturated NaHCO3 (aq.). The resulting mixture was concentrated under reduced pressure. The crude product (100 mg) was purified by Prep-HPLC with the following conditions (Column: XBridge Shield RP18 OBD Column, 5 um, 19*150 mm; Mobile Phase A: Water (0.05% TFA), Mobile Phase B: ACN; Flow rate: 20 mL/min; Gradient: 3% B to 30% B in 7 min; 220 nm; Rt: 6.28 min) to afford 4-chloro-5-(4-[[6-oxo-1-(2,2,2-trifluoroethyl)-1,6-dihydropyridin-2-yl]methyl]piperazin-1-yl)-2,3-dihydropyridazin-3-one (34.7 mg) as a white solid.

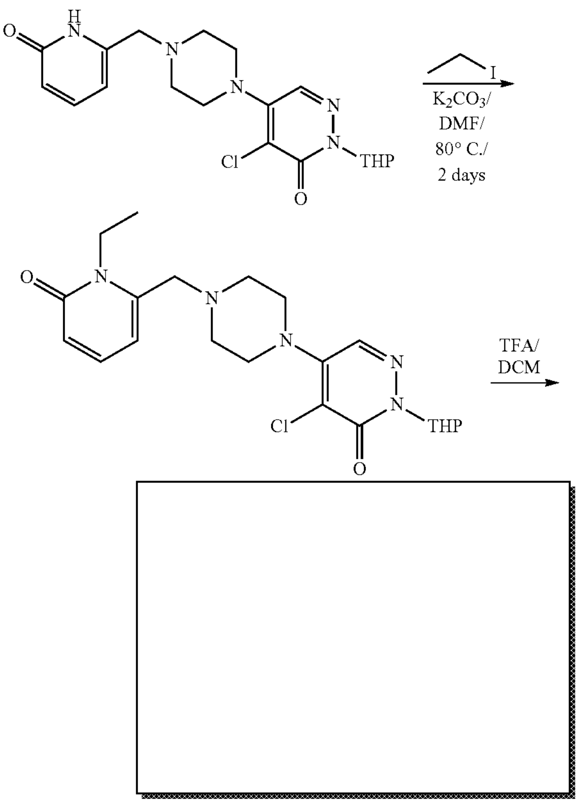

Preparation of FT 4-chloro-5-[4-[(1-ethyl-6-oxo-,6-dihydropyridin-2-yl)methyl]piperazin-1-yl]-2-(oxan-2-yl)-2,3-dihydropyridazin-3-one To a mixture of 4-chloro-2-(oxan-2-yl)-5-[4-[(6-oxo-1,6-dihydropyridin-2-yl)methyl]piperazin-1-yl]-2,3-dihydropyridazin-3-one (500 mg, 1.23 mmol, 1 equiv.) and iodoethane (384.3 mg, 2.46 mmol, 2.00 equiv.) in DMF (20 mL) was added K2CO3 (340.5 mg, 2.46 mmol, 2.00 equiv.) at room temperature. The resulting mixture was stirred for 16 h at 80 room temperature. The reaction was monitored by LCMS. The mixture was allowed to cool down to room temperature. The residue was purified by reverse flash chromatography with the following conditions: column, C18 silica gel; mobile phase, ACN in water, 40% to 75% gradient in 20 min; detector, UV 254 nm to afford 4-chloro-5-[4-[(1-ethyl-6-oxo-1,6-dihydropyridin-2-yl)methyl]piperazin-1-yl]-2-(oxan-2-yl)-2,3-dihydropyridazin-3-one (170 mg, 31.80%) as a yellow solid.

4-chloro-5-[4-[(1-ethyl-6-oxo-1,6-dihydropyridin-2-yl)methyl]piperazin-1-yl]-2,3-dihydropyridazin-3-one To a stirred solution of 4-chloro-5-[4-[(1-ethyl-6-oxo-1,6-dihydropyridin-2-yl)methyl]piperazin-1-yl]-2-(oxan-2-yl)-2,3-dihydropyridazin-3-one (170 mg, 0.39 mmol, 1 equiv.) in DCM (5 mL) was added TFA (2 mL) dropwise at room temperature. The resulting mixture was stirred for 2 h at room temperature. The reaction was monitored by LCMS. The mixture was basified to pH 8 with saturated NaHCO3 (aq.). The resulting mixture was concentrated under reduced pressure. The crude product (100 mg) was purified by Prep-HPLC with the following conditions (Column: XBridge Prep C18 OBD Column 19×150 mm 5 um; Mobile Phase A: Water (10 mmol/L NH4HCO3), Mobile Phase B: ACN; Flow rate: 20 mL/min; Gradient: 22% B to 43% B in 7 min; 254/220 nm; Rt: 6.62 min) to afford 4-chloro-5-[4-[(1-ethyl-6-oxo-1,6-dihydropyridin-2-yl)methyl]piperazin-1-yl]-2,3-dihydropyridazin-3-one (11.2 mg) as a Color solid.

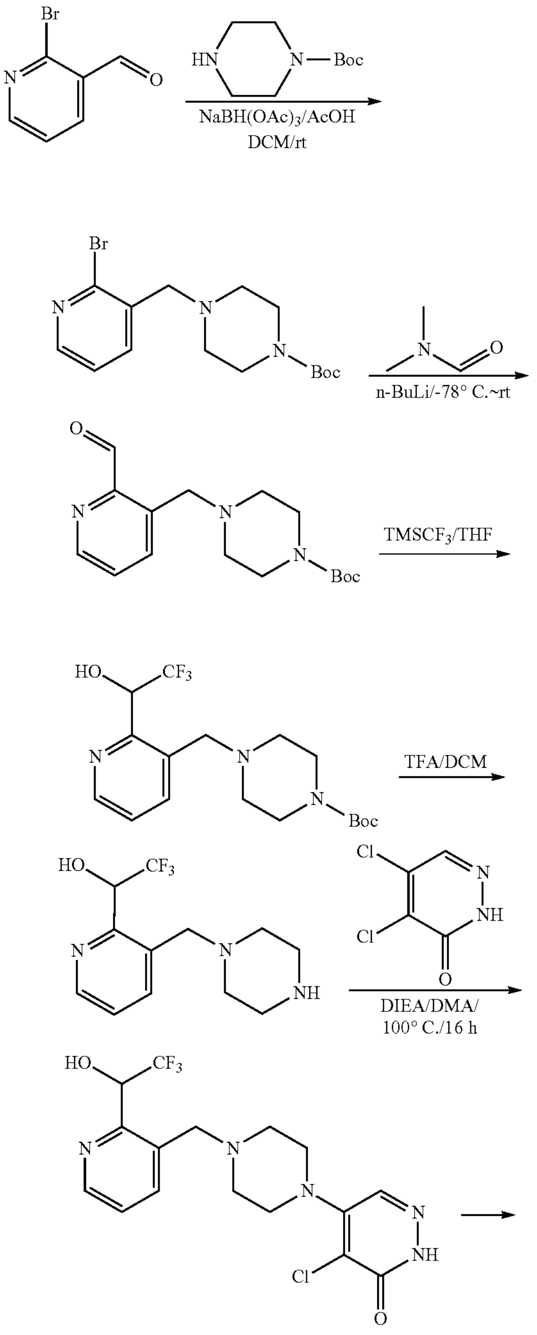

-continued

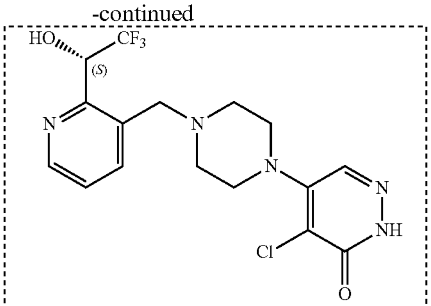

FU eluting faster on Chiral-HPLC

Tested: $[a]^{20}D$ = -15° (c = 1 mg/mL, $CHCl_3$)

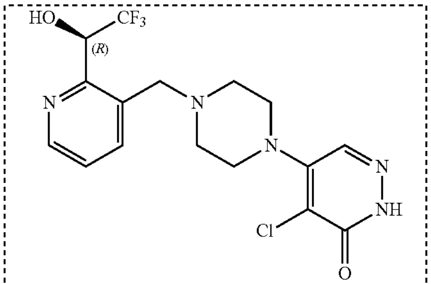

FV eluting slower on Chiral-HPLC

Tested: $[a]^{20}D$ = +30° (c = 1 mg/mL, $CHCl_3$)

Preparation of FU and FV

Tert-Butyl 4-[(2-bromopyridin-3-yl)methyl]piperazine-1-carboxylate

The mixture of 2-bromopyridine-3-carbaldehyde (8.05 g, 43.28 mmol, 1 equiv), tert-butyl piperazine-1-carboxylate (12.1 g, 64.96 mmol, 1.50 equiv.) and NaBH(OAc)3 (18.3 g, 86.34 mmol, 2.00 equiv.) in DCE (150 mL, 1894.72 mmol, 3524.34 equiv.) and HOAc(cat.) was stirred at 50 degrees C. for 16 hours. To the reaction mixture was added EtOAc (500 mL) and sat. Na2CO3 (aq, 150 mL), the organic layers were washed with sat. Na2CO3 (aq) (3×50 mL), dried over anhydrous Na2SO4. After filtration, the filtrate was concentrated under reduced pressure to give the residue. The residue was purified by silica gel column chromatography, eluted with PE:EtOAc (2:1 to 1:2) to afford Products tert-butyl 4-[(2-bromopyridin-3-yl)methyl]piperazine-1-carboxylate (14.8 g, 95.99%) as a white solid.

Tert-Butyl 4-[(2-formylpyridin-3-yl)methyl]piperazine-1-carboxylate

A solution of tert-butyl 4-[(2-bromopyridin-3-yl)methyl]piperazine-1-carboxylate (3.55 g, 9.96 mmol, 1 equiv.) in THF (50 mL) was added butyllithium (4.8 mL, 12.00 mmol, 1.20 equiv.) at −78 degrees C. The mixture was stirred for 1 h at −78 degrees C. Then, N,N-dimethylformamide (1.1 g, 14.95 mmol, 1.5 equiv.) was added into the reaction system at −78 degrees C. The mixture was stirred for 2 h at RT. The reaction was quenched by the addition of saturated NH4Cl. The mixture was extracted with EtOAc (3×200 mL). The combined organic layers were washed with NaCl (3×200 mL), dried over anhydrous sodium sulfate. After filtration, the filtrate was concentrated under reduced pressure and the residue was purified by silica gel column chromatography, eluted with EtOAc/PE (0% to 50%) to afford tert-butyl 4-[(2-formylpyridin-3-yl)methyl]piperazine-1-carboxylate (1.5 g, 49.29%) as a light yellow solid.

Tert-Butyl 4-[[2-(2,2,2-trifluoro-1-hydroxyethyl) pyridin-3-yl]methyl]piperazine-1-carboxylate A solution of tert-butyl 4-[(2-formylpyridin-3-yl)methyl] piperazine-1-carboxylate (0.5 g, 1.64 mmol, 1 equiv.) and K2CO3 (22.6 mg, 0.16 mmol, 0.1 equiv.) in DMF (20 mL) was stirred for 30 min at 0 degrees C. under N2 atmosphere. Then, trimethyl(trifluoromethyl)silane (279.4 mg, 1.96 mmol, 1.2 equiv.) was added into the reaction system at 0 degrees C. The mixture was stirred for 30 min at RT. Then, HCl (10 mL, 4 M) was added into the reaction system. After additional 4 hours at RT, the starting material was complete by LCMS. The reaction was quenched by saturated NaHCO3 (10 mL), and then, the mixture was extracted with EtOAc (3×200 mL). The combined organic layers were washed with brine (3×200 mL), dried over anhydrous sodium sulfate. After filtration, the filtrate was concentrated under reduced pressure and the residue was purified by silica gel column chromatography to afford tert-butyl 4-[[2-(2,2,2-trifluoro-1-hydroxyethyl)pyridin-3-yl]methyl]piperazine-1-carboxylate (150 mg, 24.40%) as a yellow oil.

(2,2,2-trifluoro-1-[3-[(piperazin-1-yl)methyl]pyridin-2-yl]ethan-1-ol)

A solution of tert-butyl 4-[[2-(2,2,2-trifluoro-1-hydroxyethyl)pyridin-3-yl]methyl]piperazine-1-carboxylate (150 mg, 0.40 mmol, 1 equiv.) in TFA (20 mL) and DCM (3 mL) was stirred for 2 h at RT. The mixture was concentrated under reduced pressure to afford the crude product (2,2,2-trifluoro-1-[3-[(piperazin-1-yl)methyl]pyridin-2-yl]ethan-1-ol) as a yellow oil.

4-chloro-5-[4-([2-[(1S)-2,2,2-trifluoro-1-hydroxyethyl]pyridin-3-yl]methyl)piperazin-1-yl]-2,3-dihydropyridazin-3-one and 4-chloro-5-[4-([2-[(1R)-2,2,2-trifluoro-1-hydroxyethyl]pyridin-3-yl]methyl)piperazin-1-yl]-2,3-dihydropyridazin-3-one To a solution of 2,2,2-trifluoro-1-[3-[(piperazin-1-yl)methyl]pyridin-2-yl]ethan-1-ol (100 mg, 0.36 mmol, 1 equiv.) in DMF (10 mL) were added 4,5-dichloro-2,3-dihydropyridazin-3-one (59.9 mg, 0.36 mmol, 1.00 equiv.) and DIEA (93.9 mg, 0.73 mmol, 2.00 equiv.) at ambient temperature. The resulting mixture was stirred for 16 h at at 100 degrees C. The desired product could be detected by LCMS. The mixture was allowed to cool down to ambient temperature. The reaction mixture was purified by reverse phase flash with the following conditions (Column: c18 OBD Column, 5 um, 19*330 mm; Mobile Phase A: Water (5 mmol/L ACOH), Mobile Phase B: ACN; Flow rate: 80 mL/min; Gradient: 20% B to 60% B in 40 min; 254 nm; Rt: 18.3 min) to afford Products (150 mg) as a yellow solid. The product was purified by Chiral-Prep-HPLC with the following conditions:Column: Chiralpak IA, 2*25 cm, 5 um; Mobile Phase A:MTBE (0.2% IPA)—HPLC, Mobile Phase B: EtOH—HPLC; Flow rate: 13 mL/min; Gradient: 30 B to 30 B in 20 min; 220/254 nm; RT1:9.12; RT2:15.237: 4-chloro-5-[4-([2-[(1S)-2,2,2-trifluoro-1-hydroxyethyl] pyridin-3-yl]methyl)piperazin-1-yl]-2,3-dihydropyridazin-3-one (33.2 mg, 22.63%) as a light yellow solid and 4-chloro-5-[4-([2-[(1R)-2,2,2-trifluoro-1-hydroxyethyl] pyridin-3-yl]methyl)piperazin-1-yl]-2,3-dihydropyridazin-3-one (33.1 mg, 22.57%) as a light yellow solid.

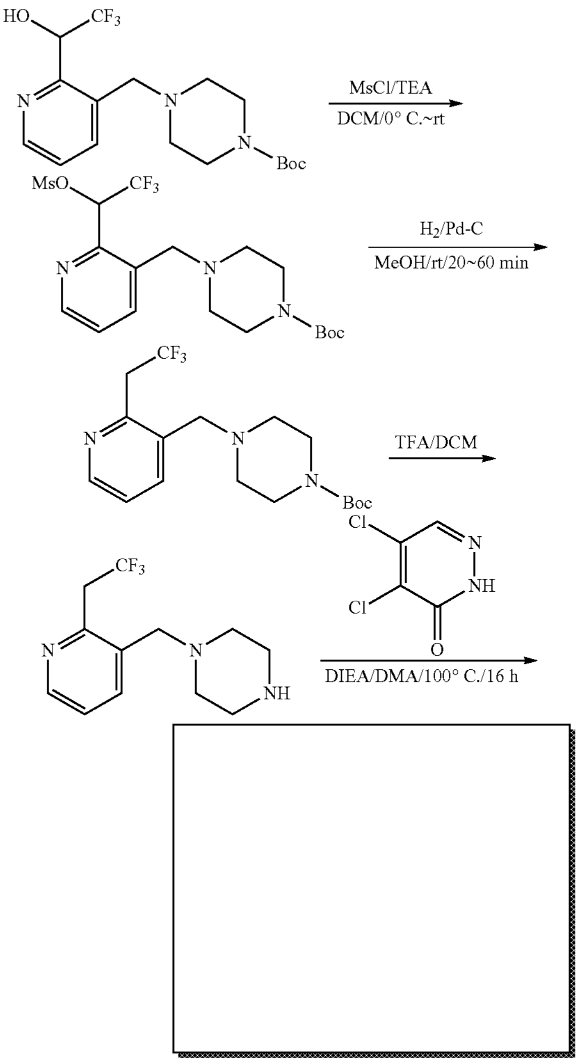

Preparation of FW

Tert-Butyl 4-([2-[2,2,2-trifluoro-1-(methanesulfonyloxy)ethyl]pyridin-3-yl]methyl)piperazine-1-carboxylate To a solution of tert-butyl 4-[[2-(2,2,2-trifluoro-1-hydroxyethyl)pyridin-3-yl]methyl]piperazine-1-carboxylate (650 mg, 1.73 mmol, 1 equiv.) in DCM (20 mL) at ambient temperature was added Et3N(350.4 mg, 3.46 mmol, 2.00 equiv). The resulting mixture was stirred for 10 min at 0 degrees C. Then the mixture was added MsCl (238.0 mg, 2.08 mmol, 1.2 equiv.) dropwise via syringe between 0 and 5 degrees C. with stirring for 4 h. The desired product could be detected by TLC. The reaction mixture was diluted with water (400 mL), extracted with DCM (500 mL×2). The organic layers was concentrated to afford tert-butyl 4-([2-[2,2,2-trifluoro-1-(methanesulfonyloxy)ethyl]pyridin-3-yl] methyl)piperazine-1-carboxylate (800 mg, 101.88%) as a yellow liquid.

Tert-Butyl 4-[[2-(2,2,2-trifluoroethyl)pyridin-3-yl]methyl]piperazine-1-carboxylate To a solution of tert-butyl 4-([2-[2,2,2-trifluoro-1-(methanesulfonyloxy)ethyl]pyridin-3-yl]methyl)piperazine-1-carboxylate (560 mg, 1.23 mmol, 1 equiv.) in 15 mL MeOH (25 mL) was added Pd/C (26.3 mg, 0.25 mmol, 0.20 equiv.) under nitrogen atmosphere in a 100 mL round-bottom flask. The mixture was hydrogenated at ambient temperature for 1 h under hydrogen atmosphere using a hydrogen balloon, filtered through a Celite pad and concentrated under reduced pressure. The crude product was purified by reverse phase flash with the following conditions (Column: c18 OBD Column, 5 um, 19*330 mm; Mobile Phase A: Water (5 mmol/L $NaHCO_3$), Mobile Phase B: ACN; Flow rate: 45 mL/min; Gradient: 15% B to 55% B in 40 min; 254 nm; Rt: 20.3 min) to afford tert-butyl 4-[[2-(2,2,2-trifluoroethyl)pyridin-3-yl]methyl]piperazine-1-carboxylate (277 mg, 62.41%) as a yellow liquid.

1-[[2-(2,2,2-trifluoroethyl)pyridin-3-yl]methyl]piperazine

To a solution of TFA (4 mL, 53.85 mmol, 71.68 equiv.) in DCM (16 mL) was added tert-butyl 4-[[2-(2,2,2-trifluoroethyl)pyridin-3-yl]methyl]piperazine-1-carboxylate (270 mg, 0.75 mmol, 1 equiv.) at ambient temperature. The resulting mixture was stirred for 3 h at ambient temperature. The desired product could be detected by LCMS. The resulting mixture was concentrated under reduced pressure. The mixture was acidified to pH 8 with NaHCO3 (aq.) and was added DMF (6 mL). The mixture was purified by reverse phase flash with the following conditions (Column: XBridge Shield RP18 OBD Column 30*150 mm, 5 um; Mobile Phase A: Water (5 mmol/L NH4HCO3), Mobile Phase B: ACN; Flow rate: 45 mL/min; Gradient: 20% B to 65% B in 30 min; 254,220 nm; Rt: 15.0 min) to afford 1-[[2-(2,2,2-trifluoroethyl)pyridin-3-yl]methyl]piperazine (110 mg, 56.47%) as a white solid.

4-chloro-5-(4-[[2-(2,2,2-trifluoroethyl)pyridin-3-yl]methyl]piperazin-1-yl)-2,3-dihydropyridazin-3-one To a solution of 1-[[2-(2,2,2-trifluoroethyl)pyridin-3-yl]methyl]piperazine (110 mg, 0.42 mmol, 1 equiv.) in DMA (4 mL) were added 4,5-dichloro-2,3-dihydropyridazin-3-one (70.0 mg, 0.42 mmol, 1.00 equiv.) and DIEA (109.7 mg, 0.85 mmol, 2.00 equiv.) at ambient temperature. The resulting mixture was stirred for 6 h at 100 degrees C. The desired product could be detected by LCMS. The mixture was allowed to cool down to ambient temperature. The mixture was purified by reverse phase flash with the following conditions (Column: c18 OBD Column, 5 um, 19*120 mm; Mobile Phase A: Water (5 mmol/L $NaHCO_3$), Mobile Phase B: ACN; Flow rate: 45 mL/min; Gradient: 25% B to 65% B in 40 min; 254 nm; Rt: 12.3 min, 20.0 min) to afford 4-chloro-5-(4-[[2-(2,2,2-trifluoroethyl)pyridin-3-yl]methyl]piperazin-1-yl)-2,3-dihydropyridazin-3-one (82.1 mg, 49.90%) as a white solid.

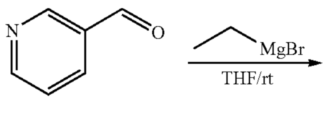

-continued

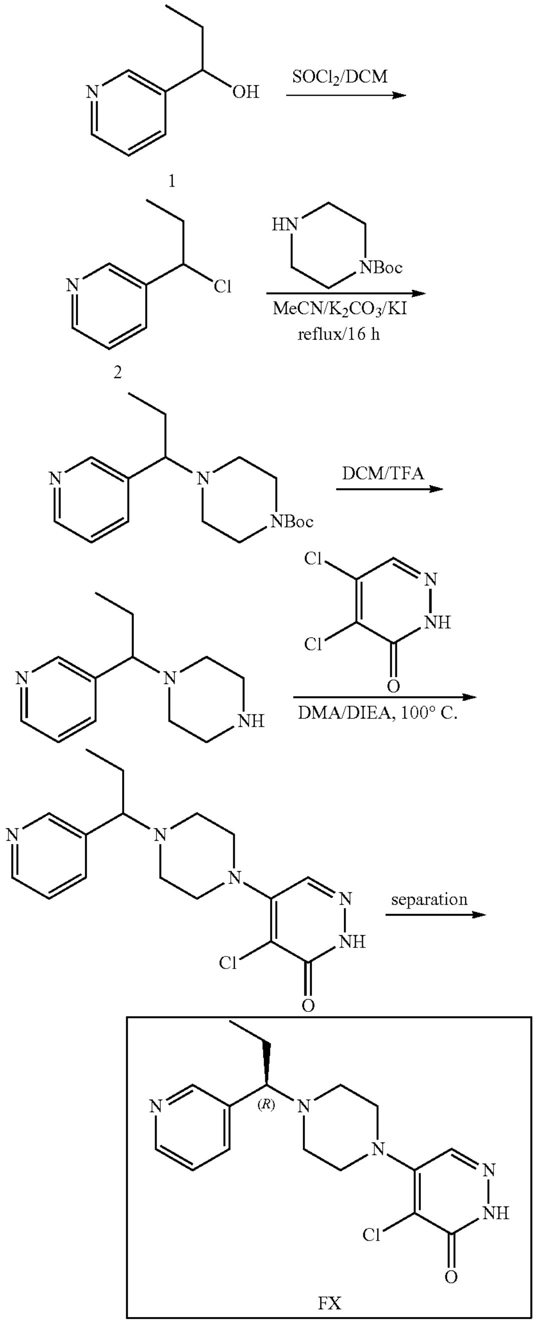

Tested: $[a]^{20}D = +53°$ (c = 1 mg/mL, $CHCl_3$)

Preparation of FX 1-(pyridin-3-yl)propan-1-ol

To a stirred mixture of pyridine-3-carbaldehyde (2 g, 18.67 mmol, 1 equiv.) in THF (20 mL) were added bromo(ethyl)magnesium (5.0 g, 37.34 mmol, 2 equiv.) dropwise at 0 degrees C. under nitrogen atmosphere. The reaction was quenched with sat. NH4Cl (aq.) at 0 degrees C. The mixture was extracted with EA (5×100 mL). The combined organic layers were washed with sat.NaCl (aq.) (2×20 mL), dried over anhydrous Na2SO4. After filtration, the filtrate was concentrated under reduced pressure. The residue was purified by silica gel column chromatography, eluted with DCM: MeOH (1:9) to afford 1-(pyridin-3-yl)propan-1-ol (1.93 g, 75.35%) as a yellow oil.

3-(1-chloropropyl)pyridine hydrochloride

To a stirred solution of 1-(pyridin-3-yl)propan-1-ol (1.3 g, 9.48 mol, 1 equiv.) in DCM (15 mL) was added SOCl2 (3.1 g, 26.24 mmol, 3.00 equiv.) dropwise at 0 degrees C. The resulting mixture was stirred for 2 h at room temperature. The reaction was monitored by LCMS. The resulting mixture was concentrated under reduced pressure to afford 3-(1-chloropropyl)pyridine hydrochloride (1.8 g, 98.89%) as a yellow oil.

Tert-Butyl 4-[1-(pyridin-3-yl)propyl]piperazine-1-carboxylate

To a stirred mixture of 3-(1-chloropropyl)pyridine (600 mg, 3.86 mmol, 1 equiv.) and tert-butyl piperazine-1-carboxylate (1077.1 mg, 5.78 mmol, 1.5 equiv.) in ACN (20 mL) were added K2CO3 (1065.6 mg, 7.71 mmol, 2 equiv.) and KI (960.0 mg, 5.78 mmol, 1.5 equiv.) in portions at room temperature. The resulting mixture was stirred for 16 h at 80 degrees C. The resulting mixture was concentrated under reduced pressure. The residue was purified by silica gel column chromatography, eluted with PE:EA (0 to 20%) to afford tert-butyl 4-[1-(pyridin-3-yl)propyl]piperazine-1-carboxylate (450 mg, 38.22%) as a yellow oil.

1-[1-(pyridin-3-yl)propyl]piperazine

To a stirred mixture of tert-butyl 4-[1-(pyridin-3-yl)propyl]piperazine-1-carboxylate (450 mg, 1.47 mmol, 1 equiv.) in DCM (20 mL, 0.24 mmol) were added TFA (4 mL) at room temperature. The resulting mixture was concentrated under reduced pressure. The crude product was purified by reverse phase flash with the following conditions (Column: Spherical C18, 20-40 um, 120 g; Mobile Phase A: Water (0.05% TFA), Mobile Phase B: ACN; Flow rate: 45 mL/min; Gradient (B %): 5%, 4 min; 5%~20%, 20 min; 20%~95%; 10 min; 95%, 5 min; Detector: 254 nm; Rt: 12 min.) to afford 1-[1-(pyridin-3-yl)propyl]piperazine (270 mg, 89.26%) as a colorless oil.

(R)-4-chloro-5-(4-(1-(pyridin-3-yl)propyl)piperazin-1-yl)pyridazin-3(2H)-one

To a stirred mixture of 1-(1-(pyridin-3-yl)propyl)piperazine (250 mg, 1.00 mmol, 1 equiv.) and 4,5-dichloro-2,3-dihydropyridazin-3-one (165.0 mg, 1.00 mol, 1 equiv.) in DMA (15 mL) was added DIEA (415.4 mg, 3.21 mmol, 3 equiv.) at room temperature. The resulting mixture was stirred for 3 h at 100 degrees C. Upon completion, the resulting mixture was cold to room temperature and concentrated under reduced pressure. The crude product was purified by reverse phase flash chromatography, with the following conditions (Column: Spherical C18, 20-40 um, 120 g; Mobile Phase A: Water (plus 10 mM NH4HCO3); Mobile Phase B: ACN; Flow rate: 45 mL/min; Gradient (B %): 5%~40%40 min; Detector: UV 254 nm; Rt: 23 min.) to afford racemic 4-chloro-5-[4-[1-(pyridin-3-yl)propyl]piperazin-1-yl]-2,3-dihydropyridazin-3-one as a light yellow solid (280 mg, 68%), which was separated by Chiral-HPLC to afford (R)-4-chloro-5-(4-(1-(pyridin-3-yl)propyl)piperazin-1-yl)pyridazin-3(2H)-one. Column: Chiralpak ID-2, 2*25 cm, 5 um; Mobile Phase A: MeOH (plus 8 mmol/L NH3·MeOH), Mobile Phase B: DCM; Flow rate: 15 mL/min; Gradient: 15 B to 15 B in 20 min; Detector: UV 220/254 nm; RT1: 8.952 min and RT2:13.337 min.

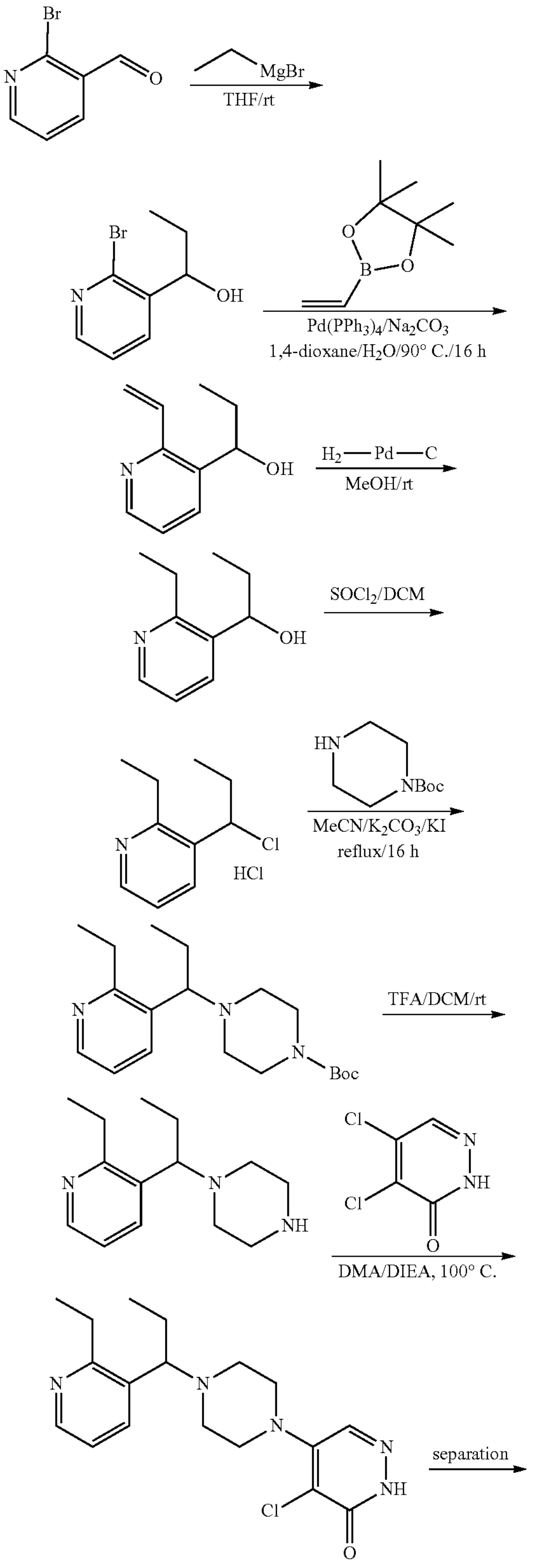

-continued

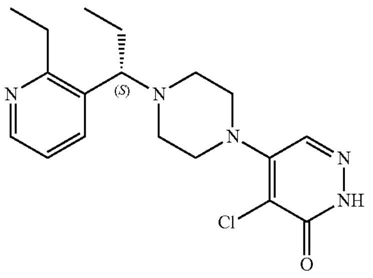

FZ

Preparation of FY and FZ 1-(2-bromopyridin-3-yl)propan-1-ol

To a stirred mixture of 2-bromopyridine-3-carbaldehyde (4 g, 21.50 mmol, 1 equiv.) in THF (65 mL) was added dropwise bromo(ethyl)magnesium (14.34 mL, 43.01 mmol, 2 equiv.) at 0 degrees C. under nitrogen atmosphere. The resulting mixture was stirred for 16 hours at room temperature under nitrogen atmosphere. The reaction was quenched with sat. NH4Cl (aq). The resulting mixture was extracted with EtOAc (5×200 mL). The combined organic layers was washed with brine (2×20 mL), dried over anhydrous Na2SO4. After filtration, the filtrate was concentrated under reduced pressure to give the residue. The reside was purified by Prep-HPLC with the following conditions (Column: silica-CS Column 120 g; Mobile Phase A:PE, Mobile Phase B: EA; Flow rate: 50 mL/min; Gradient: 0% B to 30% B in 40 min; 254/280 nm) to afford 1-(2-bromopyridin-3-yl) propan-1-ol (2.17 g, 46.70%) as a yellow oil.

1-(butan-2-yl)-2-ethenylbenzene

To a solution of 1-(2-bromopyridin-3-yl)propan-1-ol (2.17 g, 10.0 mmol) and 2-ethenyl-4,4,5,5-tetramethyl-1,3,2-dioxaborolan) in dioxane (50.0 mL, 567.51 mmol, 58.77 equiv.) and H2O (5.0 mL, 277.58 mmol, 27.64 equiv.) were added K2CO3 (2.8 g, 20.09 mmol, 2 equiv.) and Pd(PPh3)4 (1.2 g, 1.00 mmol, 0.1 equiv.) at room temperature under nitrogen atmosphere. The resulting mixture was stirred for 16 h at 100 degrees C. under nitrogen atmosphere. The reaction was monitored by LCMS. The mixture was allowed to cool down to room temperature. The resulting mixture was extracted with EtOAc (5×200 mL). The combined organic layers was washed with brine (2×20 mL), dried over anhydrous Na2SO4. After filtration, the filtrate was concentrated under reduced pressure to give the residue. The reside was purified by Prep-HPLC with the following conditions (Column: silica-CS Column 120 g; Mobile Phase A:PE, Mobile Phase B: EA; Flow rate: 50 mL/min; Gradient: 0% B to 30% B in 40 min; 254/280 nm) to afford 1-(butan-2-yl)-2-ethenylbenzene (1.5 g, 93.20%) as a yellow oil.

1-(2-ethylpyridin-3-yl)propan-1-ol

To a solution of 1-(butan-2-yl)-2-ethenylbenzene (1 g, 6.24 mmol, 1 equiv.) in MeOH (80 mL, 1975.91 mmol) was added Pd/C (0.1 g, 0.94 mmol, 0.15 equiv). The mixture was stirred at room temperature for 16 hours under H2 atmosphere. The reaction mixture was filtered and the filtrate was concentrated under reduced pressure to give the residue. The residue was purified by silica gel column chromatography, eluted with PE:EtOAc (1:1 to 1:2) to afford 1-(2-ethylpyridin-3-yl)propan-1-ol (590 mg, 57.22%) as a yellow oil.

Tert-Butyl 4-[1-(2-ethylpyridin-3-yl)propyl]piperazine-1-carboxylate

Into a DCM (10 mL) and SOCl2 (10 mL) were added 1-(2-ethylpyridin-3-yl)propan-1-ol (500 mg, 3.03 mmol, 1 equiv.) at room temperature. The resulting mixture was stirred for 2 h at room temperature. The resulting mixture was concentrated under reduced pressure. The crude product was used in the next step directly without further purification.

To a stirred mixture of 3-(1-chloropropyl)-2-ethylpyridine (500 mg, 2.72 mol, 1 equiv.) and tert-butyl piperazine-1-carboxylate (1014.0 mg, 5.44 mol, 2 equiv.) in ACN (5 mL) were added KI (677.8 mg, 4.08 mmol, 1.5 equiv.) and K2CO3 (752.4 mg, 5.44 mmol, 2 equiv.) in portions at room temperature. The resulting mixture was stirred for 16 h at 100 degrees C. The resulting mixture was concentrated under reduced pressure. The residue was purified by silica gel column chromatography, eluted with PE:EA (0 to 85%) to afford tert-butyl 4-[1-(2-ethylpyridin-3-yl)propyl]piperazine-1-carboxylate (448 mg, 49.35%) as a yellow oil.

1-[1-(2-ethylpyridin-3-yl)propyl]piperazine

To a stirred mixture of tert-butyl 4-[1-(2-ethylpyridin-3-yl)propyl]piperazine-1-carboxylate (440 mg, 1.32 mmol, 1 equiv.) in DCM (20 mL) was added TFA (5.0 ML) dropwise at room temperature. The resulting mixture was stirred for 2 h at room temperature. The resulting mixture was concentrated under reduced pressure. The residue/crude product was purified by reverse phase flash with the following conditions (Column: Spherical C18, 20-40 um, 120 g; Mobile Phase A: Water (10 mM NH4HCO3 and 0.05% NH3·H2O), Mobile Phase B: ACN; Flow rate: 45 mL/min; Gradient (B %): 5%, 4 min; 5%~25%, 20 min; 25%~95%; 2 min; 95%, 5 min; Detector: 254 nm; Rt: 12 min.) to afford 1-[1-(2-ethylpyridin-3-yl)propyl]piperazine (270 mg, 87.69%) as a yellow oil.

4-chloro-5-[4-[(1R)-1-(2-ethylpyridin-3-yl)propyl]piperazin-1-yl]-2,3-dihydropyridazin-3-one (25 mg, 16.12%) and 4-chloro-5-[4-[(1S)-1-(2-ethylpyridin-3-yl)propyl]piperazin-1-yl]-2,3-dihydropyridazin-3-one To a stirred mixture of 1-[1-(2-ethylpyridin-3-yl)propyl]piperazine (100 mg, 0.43 mmol, 1 equiv.) and 4,5-dichloro-2,3-dihydropyridazin-3-one (70.7 mg, 0.43 mmol, 1.00 equiv.) in DMA (10 mL) were added DIEA (415.4 mg, 3.21 mmol, 3 equiv.) dropwise at room temperature. The resulting mixture was stirred for 3 h at 100 degrees C. The resulting mixture was concentrated under reduced pressure. The crude product was purified by reverse phase flash with the following conditions (Column: Spherical C18, 20-40 um, 120 g; Mobile Phase A: Water (10 mM NH4HCO3 and 0.05%

NH3·H2O), Mobile Phase B: ACN; Flow rate: 45 mL/min; Gradient (B %): 5%~25%, 20 min; 22%~40%, 20 min; 40%~95%; 2 min; 95%, 5 min; Detector: 254 nm; Rt:18 min.) to afford 4-chloro-5-[4-[(1R)-1-(2-ethylpyridin-3-yl) propyl]piperazin-1-yl]-2,3-dihydropyridazin-3-one (25 mg, 16.12%) and 4-chloro-5-[4-[(1S)-1-(2-ethylpyridin-3-yl) propyl]piperazin-1-yl]-2,3-dihydropyridazin-3-one (30 mg, 19.35%) as a light yellow solid.

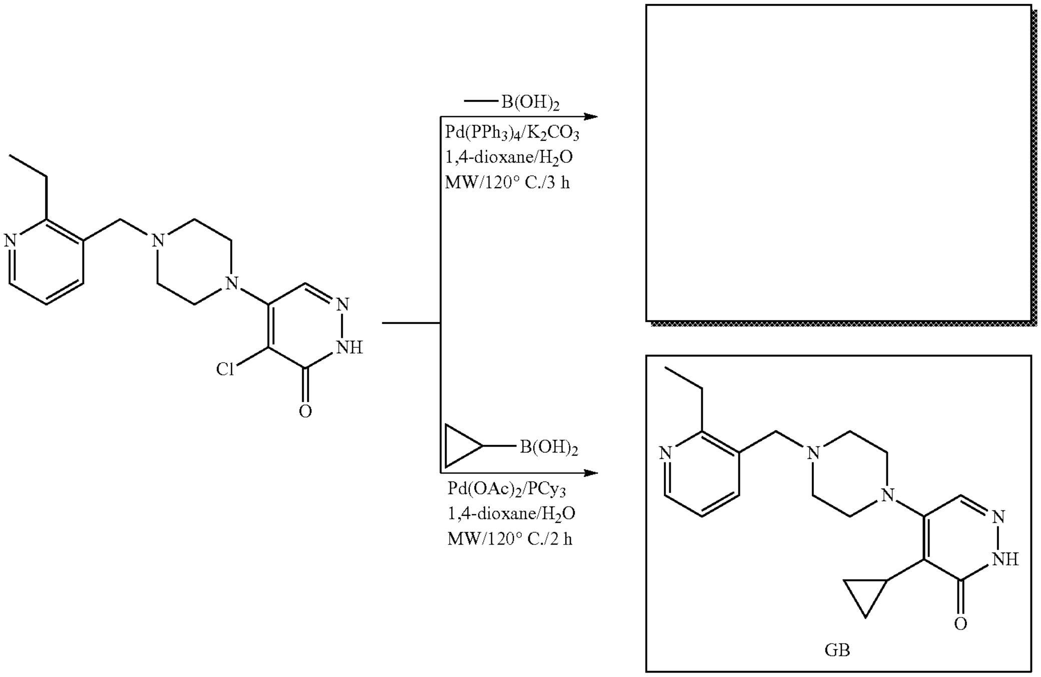

GB

GA and GB were prepared by the methods described above for Compound DX.

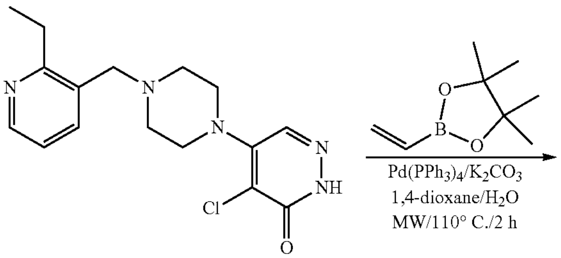

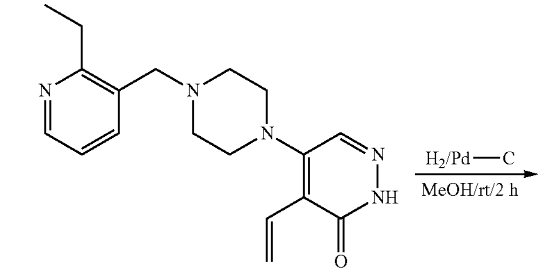

-continued

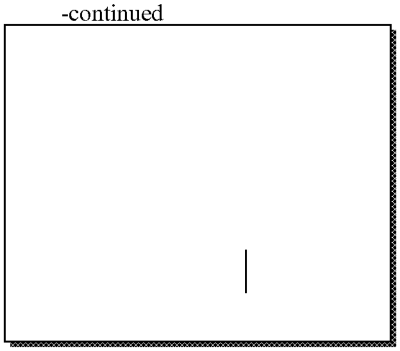

Preparation of GC 4-ethenyl-5-[4-[(2-ethylpyridin-3-yl)methyl]piperazin-1-yl]-2,3-dihydropyridazin-3-one To a stirred mixture of 4-chloro-5-[4-[(2-ethylpyridin-3-yl)methyl]piperazin-1-yl]-2,3-dihydropyridazin-3-one (300 mg, 0.9 mmol, 1 equiv.) and 2-ethenyl-4,4,5,5-tetramethyl-1,3,2-dioxaborolane (166.1 mg, 1.08 mmol, 1.0 equiv.) in 1,4-dioxane (10 mL) and H2O (2 mL) were added K2CO3 (248.7 mg, 1.88 mmol, 2.0 equiv.) and Pd(PPh3)4 (103.8 mg, 0.09 mmol, 0.10 equiv.) at ambient temperature under nitrogen atmosphere. The final reaction mixture was irradiated with microwave for 2 h at 90 degrees C. Upon completion, the mixture was allowed to cool down to room temperature. The residue was purified by reverse phase flash chromatography with the following conditions (Column: XBridge Shield RP18 OBD Column, 20-40 um, 19*150 mm; Mobile Phase A: Water (plus 10 mmol/L NH4HCO3); Mobile Phase B: ACN; Flow rate: 80 mL/min; Gradient: 30% B to 80% B in 20 min; Detector: UV 220/254 nm; Rt: 6.08 min) to afford 4-ethenyl-5-[4-[(2-ethylpyridin-3-yl)methyl]piperazin-1-yl]-2,3-dihydropyridazin-3-one as a yellow solid (150 mg).

4-ethyl-5-[4-[(2-ethylpyridin-3-yl)methyl]piperazin-1-yl]-2,3-dihydropyridazin-3-one To a solution of 4-ethenyl-5-[4-[(2-ethylpyridin-3-yl)methyl]piperazin-1-yl]-2,3-dihydropyridazin-3-one (120 mg, 0.369 mmol, 1 equiv.) in 30 mL MeOH was added Pd/C (0.020 g, 10%, w/w) under nitrogen atmosphere. The mixture was hydrogenated at room temperature for 2 h under hydrogen atmosphere using a hydrogen balloon. Upon completion, the mixture was filtered through a celite pad and concentrated under reduced pressure. The residue was purified by Prep-HPLC with the following conditions (Column: XBridge Prep OBD C18 Column 30×150 mm 5 um; Mobile Phase A: Water (plus 10 mmol/L NH4HCO3); Mobile Phase B: ACN; Flow rate: 60 mL/min; Gradient: 10% B to 33% B in 10 min; Detector: 220/254 nm; Rt: 9.75 min) to afford 4-ethyl-5-[4-[(2-ethylpyridin-3-yl)methyl]piperazin-1-yl]-2,3-dihydropyridazin-3-one as a white solid (20.0 mg).

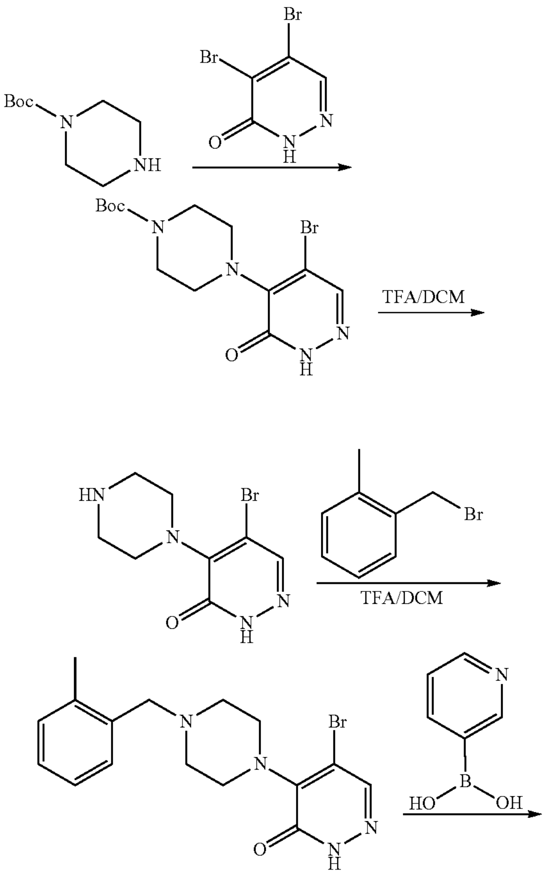

-continued

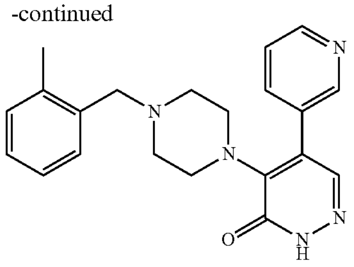

GD

Preparation of GD

Tert-Butyl 4-(5-bromo-3-oxo-2,3-dihydropyridazin-4-yl)piperazine-1-carboxylate To a stirred solution of tert-butyl 2-(piperazin-1-yl)acetate (20 g, 99.86 mmol) and 4,5-dibromo-2,3-dihydropyridazin-3-one (30.4 g, 119.83 mmol) in 1,4-dioxane (500 mL) was added DIEA (38.7 g, 299.58 mmol) at ambient temperature. The resulting mixture was refluxed for 2 days. Upon completion, the resulting mixture was concentrated under reduced pressure and the residue was purified by silica gel column chromatography, eluted with 0.5% to 2% methanol in dichloromethane to afford tert-butyl 2-[4-(5-bromo-3-oxo-2,3-dihydropyridazin-4-yl)piperazin-1-yl]acetate as a light yellow solid (2 g, 6%)

5-bromo-4-(piperazin-1-yl)-2,3-dihydropyridazin-3-one; Trifluoroacetic Acid To a solution of TFA (10 mL) in (40 mL) was added tert-butyl 4-(5-bromo-3-oxo-2,3-dihydropyridazin-4-yl)piperazine-1-carboxylate (2 g, 5.57 mmol, 1 equiv.) at ambient temperature. Then the mixture was stirred for 16 h at ambient temperature. The desired product could be detected by LCMS. The resulting mixture was concentrated under reduced pressure. The mixture was added DMF (3 mL) and was purified by reverse phase flash with the following conditions (Column: c18 OBD Column, 5 um, 19*330 mm; Mobile Phase A: Water (5 mmol/L NH4HCO3), Mobile Phase B: ACN; Flow rate: 80 mL/min; Gradient: 25% B to 65% B in 40 min; 220 nm; Rt: 19.0 min) to afford 5-bromo-4-(piperazin-1-yl)-2,3-dihydropyridazin-3-one; trifluoroacetic acid (3.6 g, 173.29%) as an off-white solid.

5-bromo-4-[4-[(2-methylphenyl)methyl]piperazin-1-yl]-2,3-dihydropyridazin-3-one To a solution of 5-bromo-4-(piperazin-1-yl)-2,3-dihydropyridazin-3-one; trifluoroacetic acid (3.6 g, 9.65 mmol, 1 equiv.) in DMA (40 mL) were added 1-(bromomethyl)-3-methylbenzene (1.78 g, 9.62 mmol, 1.00 equiv.) and DIEA (3.7 g, 28.63 mmol, 2.97 equiv.) at ambient temperature. The resulting mixture was stirred for 16 h at ambient temperature. The desired product could be detected by LCMS. The mixture was purified by reverse phase flash with the following conditions (Column: c18 OBD Column, 5 um, 19*330 mm; Mobile Phase A: Water (5 mmol/L $NaHCO_3$), Mobile Phase B: ACN; Flow rate: 80 mL/min; Gradient: 20% B to 55% B in 30 min; 220 nm; Rt: 12.3 min, 20.0 min) to afford 5-bromo-4-[4-[(2-methylphenyl)methyl]piperazin-1-yl]-2,3-dihydropyridazin-3-one (1.5 g, 42.80%) as a yellow solid.

GD 4-(4-(2-methylbenzyl)piperazin-1-yl)-5-(pyridin-3-yl)pyridazin-3(2H)-one

To a stirred solution of (pyridin-3-yl)boronic acid (40.6 mg, 0.33 mmol) and 5-bromo-4-[4-[(2-methylphenyl)methyl]piperazin-1-yl]-2,3-dihydropyridazin-3-one (80 mg, 0.22 mmol) in 1,4-dioxane (5 mL) and H2O (1 mL) were added tetrakis(triphenylphosphine)palladium (O) (12.7 mg, 0.01 mmol) and K2CO3 (60.9 mg, 0.44 mmol) at ambient temperature under nitrogen atmosphere. The reaction mixture was irradiated with microwave for 2 h at 100 degrees C. After cold to ambient temperature, the resulting mixture was concentrated under reduced pressure. The residue was purified by reverse phase flash chromatography with the following conditions: Column: WelFlash™ C18-I, 20-40 uM, 120 g; Mobile Phase A: Water (plus 5 mmol/L NH4HCO3), Mobile Phase B: ACN; Flow rate: 40 mL/min; Gradient: 65% B to 80% B in 7 min; Detector: 254/220 nm). Desired fractions were collected and concentrated under reduced pressure to afford 4-[4-[(2-methylphenyl)methyl]piperazin-1-yl]-5-(pyridin-3-yl)-2,3-dihydropyridazin-3-one as a white solid (37.7 mg, 48%)

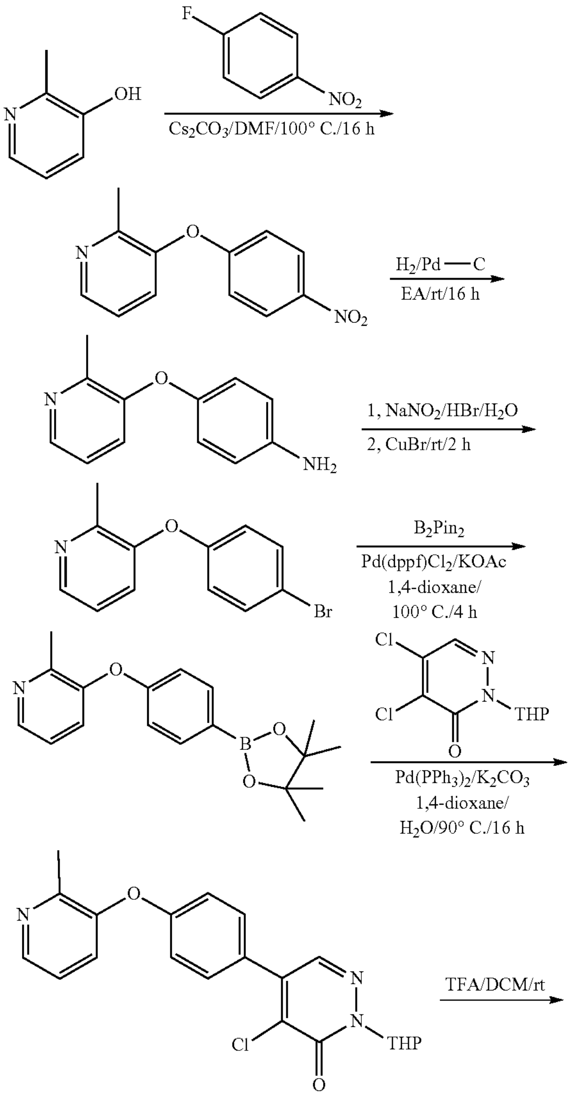

-continued

Preparation of GE 2-methyl-3-(4-nitrophenoxy)pyridine

To a stirred solution of 2-methylpyridin-3-ol (4 g, 36.65 mmol, 1 equiv.) and 1-fluoro-4-nitrobenzene (5.2 g, 36.65 mmol, 1 equiv.) in DMF (15 mL) was added Cs2CO3 (23.9 g, 73.31 mmol, 2 equiv). The resulting mixture was stirred for 10 h at 130 degrees C. under nitrogen atmosphere. The resulting mixture was concentrated under reduced pressure. The residue was purified by silica gel column chromatography, eluted with PE/EtOAc (10:1) to afford 2-methyl-3-(4-nitrophenoxy)pyridine (6 g, 71.10%) as a yellow solid.

4-[(2-methylpyridin-3-yl)oxy]aniline

To a solution of 2-methyl-3-(4-nitrophenoxy)pyridine (6 g, 26.06 mmol, 1 equiv.) in EtOAc (15 mL) was added Pd/C (10%, 0.5 g) under nitrogen atmosphere in a 1 L round-bottom flask. The mixture was hydrogenated at room temperature for overnight under hydrogen atmosphere using a hydrogen balloon, filtered through a Celite pad and concentrated under reduced pressure. The resulting mixture was filtered, the filter cake was washed with EtOAc (2×10 mL). The filtrate was concentrated under reduced pressure. The residue was purified by silica gel column chromatography, eluted with PE/EtOAc (5:1) to afford 4-[(2-methylpyridin-3-yl)oxy]aniline (4 g, 76.65%) as a yellow solid.

3-(4-bromophenoxy)-2-methylpyridine

To a stirred solution of 4-[(2-methylpyridin-3-yl)oxy]aniline (2 g, 9.99 mmol, 1 equiv.) and NaNO2 (1.4 g, 20.48 mmol, 2.05 equiv.) in HBr (25) and H2O (10 mL) was added CuBr (2.1 g, 14.98 mmol, 1.5 equiv). The resulting mixture was stirred for 14 h at 140 degrees C. The resulting mixture was extracted with EtOAc (3×20 mL). The combined organic layers were washed with brine (2×10 mL), dried over anhydrous Na2SO4. After filtration, the filtrate was concentrated under reduced pressure. The residue was purified by silica gel column chromatography, eluted with PE/EtOAc (8:1) to afford 3-(4-bromophenoxy)-2-methylpyridine (1.4 g, 53.07%) as a yellow solid.

2-methyl-3-[4-(4,4,5,5-tetramethyl-1,3,2-dioxaborolan-2-yl)phenoxy]pyridine

To a stirred solution of 3-(4-bromophenoxy)-2-methylpyridine (1.4 g, 5.30 mmol, 1 equiv.) and BPD (2.0 g, 7.95 mmol, 1.5 equiv.) in Solvents 1,4-dioxane (15 mL) were added KOAc (1.0 g, 10.60 mmol, 2 equiv.) and Pd(dppf)Cl2 (0.4 g, 0.53 mmol, 0.1 equiv). The resulting mixture was stirred for 2 h at 90 degrees C. under nitrogen atmosphere. The resulting mixture was concentrated under reduced pressure. The residue was purified by silica gel column chromatography, eluted with PE/EtOAc (5:1) to afford 2-methyl-3-[4-(4,4,5,5-tetramethyl-1,3,2-dioxaborolan-2-yl)phenoxy] pyridine (1.5 g, 90.94%) as a yellow oil.

4-chloro-5-[4-[(2-methylpyridin-3-yl)oxy]phenyl]-2-(oxan-2-yl)-2,3-dihydropyridazin-3-one To a solution of 4,5-dichloro-2-(oxan-2-yl)-2,3-dihydropyridazin-3-one (240.1 mg, 0.96 mmol, 1 equiv.) and 2-methyl-3-[4-(4,4,5,5-tetramethyl-1,3,2-dioxaborolan-2-yl)phenoxy]pyridine (300 mg, 0.96 mmol, 1 equiv.) in H2O (1 mL) and 1,4-dioxane (15 mL) were added K2CO3 (266.5 mg, 1.93 mmol, 2 equiv.) and Pd(PPh3)4 (55.7 mg, 0.05 mmol, 0.05 equiv). After stirring for 16 h at 90 degrees C. under a nitrogen atmosphere, the resulting mixture was concentrated under reduced pressure. The residue was purified by silica gel column chromatography, eluted with PE/EtOAc (5:1) to afford 4-chloro-5-[4-[(2-methylpyridin-3-yl)oxy]phenyl]-2-(oxan-2-yl)-2,3-dihydropyridazin-3-one (350 mg, 91.25%) as a light yellow solid.

4-chloro-5-[4-[(2-methylpyridin-3-yl)oxy]phenyl]-2,3-dihydropyridazin-3-one

To a stirred solution of 4-chloro-5-[4-[(2-methylpyridin-3-yl)oxy]phenyl]-2-(oxan-2-yl)-2,3-dihydropyridazin-3-one (200 mg, 0.50 mmol, 1 equiv.) in DCM (3 mL) was added TFA (1 mL). The resulting mixture was stirred for 2 h at room temperature. The resulting mixture was concentrated under reduced pressure. The crude product was purified by Prep-HPLC with the following conditions (Column: XBridge Prep C18 OBD Column 19×150 mm 5 um; Mobile Phase A: Water (10 mmol/L NH4HCO3), Mobile Phase B: ACN; Flow rate: 20 mL/min; Gradient: 15% B to 45% B in 7 min; 254 nm; Rt: 6.5 min) to afford 4-chloro-5-[4-[(2-methylpyridin-3-yl)oxy]phenyl]-2,3-dihydropyridazin-3-one (53.2 mg, 33.73%) as a white solid.

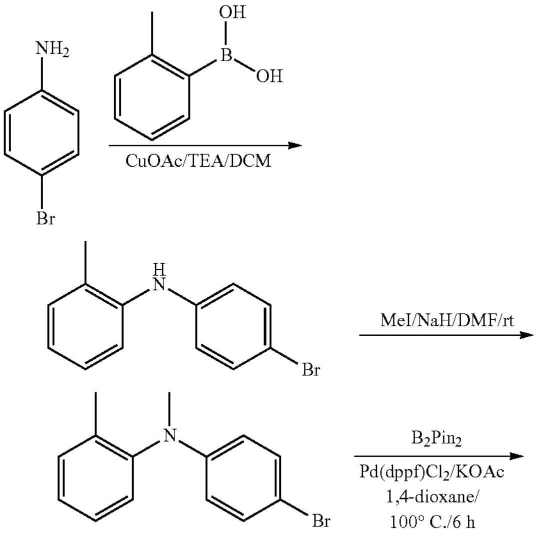

-continued

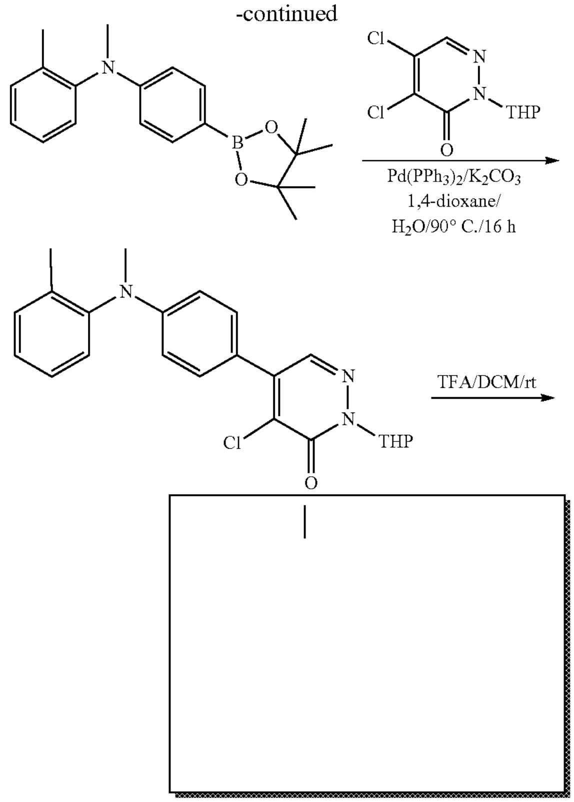

Preparation of GF 4-bromo-N-(2-methylphenyl)aniline

To a stirred mixture of 4-bromoaniline (4 g, 23.25 mmol, 1 equiv.) and (2-methylphenyl)boronic acid (4.7 g, 34.88 mmol, 1.5 equiv.) in DCM (100 mL) were added AcOCu (4.5 g, 37.20 mmol, 1.6 equiv.) and TEA (7.1 g, 69.76 mmol, 3.0 equiv.) at room temperature under nitrogen atmosphere. The resulting mixture was stirred for 3 h at room temperature under air atmosphere. The reaction was monitored by TLC. The resulting mixture was concentrated under reduced pressure. The residue was purified by silica gel column chromatography, eluted with PE/EtOAc (20:1 to 10:1) to afford 4-bromo-N-(2-methylphenyl)aniline (5.17 g, 84.81%) as a brown oil.

4-bromo-N-methyl-N-(2-methylphenyl)aniline

To a stirred solution of 4-bromo-N-(2-methylphenyl)aniline (1 g, 3.81 mmol, 1 equiv.) in DMF (10 mL) was added NaH (0.1 g, 4.96 mmol, 1.3 equiv.) at room temperature under nitrogen atmosphere. The resulting mixture was stirred for 30 min at room temperature under nitrogen atmosphere. Then MeI (0.8 g, 5.72 mmol, 1.5 equiv.) was added at 0 degrees C. under nitrogen atmosphere. The resulting mixture was stirred for 2 h at room temperature under nitrogen atmosphere. The reaction was monitored by TLC. The reaction was quenched with sat. NH4Cl (aq.) at room temperature. The resulting mixture was extracted with EtOAc (3×1 L). The combined organic layers were washed with brine (3×1 L), dried over anhydrous Na2SO4. After filtration, the filtrate was concentrated under reduced pressure. This resulted in 4-bromo-N-methyl-N-(2-methylphenyl)aniline (1.0 g, 94.92%) as a brown oil.

4-chloro-5-[4-[methyl(2-methylphenyl)amino]phenyl]-2-(oxan-2-yl)-2,3-dihydropyridazin-3-one To a stirred mixture of 4-bromo-N-methyl-N-(2-methylphenyl)aniline (1.1 g, 3.98 mmol, 1 equiv.) and 4,4,5,5-tetramethyl-2-(4,4,5,5-tetramethyl-1,3,2-dioxaborolan-2-yl)-1,3,2-dioxaborolane (1.5 g, 5.91 mmol, 1.48 equiv.) in 1,4-dioxane (20 ML) were added KOAc (1.2 g, 11.95 mmol, 3.0 equiv.) and Pd(dppf)Cl2 (0.3 g, 0.40 mmol, 0.1 equiv.) at room temperature under nitrogen atmosphere. The resulting mixture was stirred for 3 h at 90 degrees C. under nitrogen atmosphere. The reaction was monitored by TLC. The crude resulting mixture was used in the next step (E00293-162) directly without further purification.

To a stirred mixture of N-methyl-N-(2-methylphenyl)-4-(4,4,5,5-tetramethyl-1,3,2-dioxaborolan-2-yl)aniline (1.175 g, 3.64 mmol, 1 equiv.) and 4,5-dichloro-2-(oxan-2-yl)-2,3-dihydropyridazin-3-one (0.9 g, 3.61 mmol, 0.99 equiv.) in 1,4-dioxane (20 mL) and H2O (4 mL) were added K2CO3 (2.0 equiv.) and Pd(PPh3)4 (0.2 g, 0.18 mmol, 0.05 equiv.) at room temperature under nitrogen atmosphere. The resulting mixture was stirred for 16 h at 90 degrees C. under nitrogen atmosphere. The reaction was monitored by TLC. The resulting mixture was concentrated under reduced pressure. The residue was purified by silica gel column chromatography, eluted with PE/EtOAc (50:1 to 15:1) to afford 4-chloro-5-[4-[methyl(2-methylphenyl)amino]phenyl]-2-(oxan-2-yl)-2,3-dihydropyridazin-3-one (450 mg, 30.20%) as a yellow oil.

4-chloro-5-[4-[methyl(2-methylphenyl)amino]phenyl]-2,3-dihydropyridazin-3-one To a stirred solution of 5-chloro-4-[4-[methyl(2-methylphenyl)amino]phenyl]-2-(oxan-2-yl)-2,3-dihydropyridazin-3-one (240 mg, 0.59 mmol, 1 equiv.) in MeOH (10 mL) was added SOCl2 (696.6 mg, 5.85 mmol, 10 equiv.) at room temperature under nitrogen atmosphere. The resulting mixture was stirred for 2 h at room temperature. The reaction was monitored by LCMS. The resulting mixture was concentrated under reduced pressure. The crude product (100 mg) was purified by Prep-HPLC with the following conditions (Column: XBridge Shield RP18 OBD Column, 5 um, 19*150 mm; Mobile Phase A: Water (10 mmol/L NH4HCO3), Mobile Phase B: ACN; Flow rate: 20 mL/min; Gradient: 45% B to 70% B in 7 min; 254 nm; Rt: 6 min) to afford 5-chloro-4-[4-[methyl(2-methylphenyl)amino]phenyl]-2,3-dihydropyridazin-3-one (53.4 mg, 16.80%) as a yellow solid and 4-chloro-5-[4-[methyl(2-methylphenyl)amino]phenyl]-2,3-dihydropyridazin-3-one (43.8 mg, 13.78%) as a yellow solid

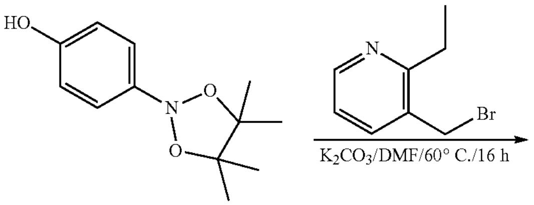

-continued

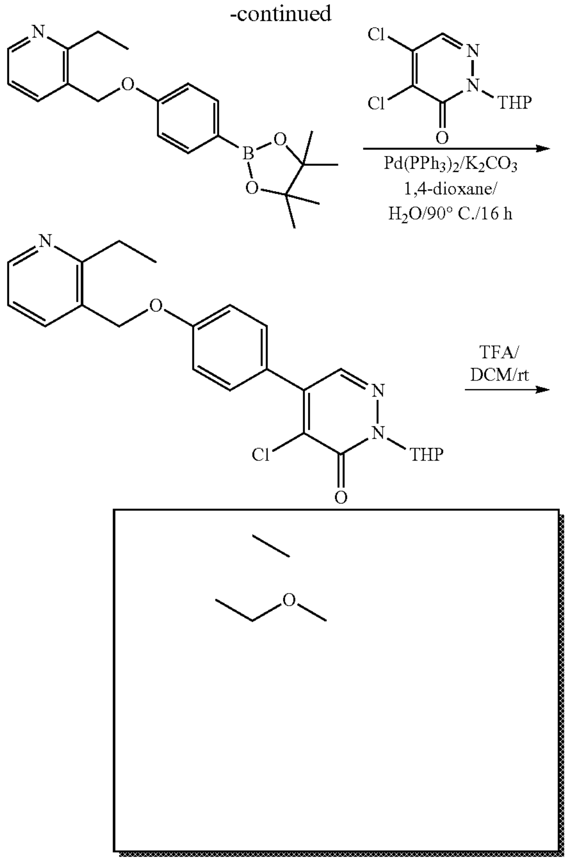

Preparation of GG

2-ethyl-3-[[4-(4,4,5,5-tetramethyl-1,3,2-dioxaborolan-2-yl)phenoxy]methyl]pyridine To a stirred solution of 4-(4,4,5,5-tetramethyl-1,3,2-dioxaborolan-2-yl)phenol (500 mg, 2.27 mmol, 1 equiv.) and 3-(bromomethyl)-2-ethylpyridine (545.5 mg, 2.73 mmol, 1.20 equiv.) in DMF (5 mL) was added K2CO3 (942.0 mg, 6.82 mmol, 3 equiv). The resulting mixture was stirred for 2 h at 60 degrees C. under air atmosphere. The resulting mixture was extracted with EtOEt (3×40 mL). The combined organic layers were washed with brine (2×10 mL), dried over anhydrous Na2SO4. After filtration, the filtrate was concentrated under reduced pressure. The residue was purified by silica gel column chromatography, eluted with PE/EtOAc (6:1) to afford 2-ethyl-3-[[4-(4,4,5,5-tetramethyl-1,3,2-dioxaborolan-2-yl)phenoxy]methyl]pyridine (460 mg, 59.68%) as a light yellow solid.

4-chloro-5-[4-[(2-ethylpyridin-3-yl)methoxy]phenyl]-2-(oxan-2-yl)-2,3-dihydropyridazin-3-one To a solution of 2-ethyl-3-[[4-(4,4,5,5-tetramethyl-1,3,2-dioxaborolan-2-yl)phenoxy]methyl]pyridine (460 mg, 1.36 mmol, 1 equiv.) and 4,5-dichloro-2-(oxan-2-yl)-2,3-dihydropyridazin-3-one (337.8 mg, 1.36 mmol, 1.00 equiv.) in H2O (2 ML) and 1,4-dioxane (30 mL) were added K2CO3 (374.8 mg, 2.71 mmol, 2 equiv.) and Pd(PPh3)4 (78.3 mg, 0.07 mmol, 0.05 equiv). After stirring for overnight at 90 degrees C. under a nitrogen atmosphere, the resulting mixture was concentrated under reduced pressure. The residue was purified by silica gel column chromatography, eluted with PE/EtOAc (5:1) to afford 4-chloro-5-[4-[(2-ethylpyridin-3-yl)methoxy]phenyl]-2-(oxan-2-yl)-2,3-dihydropyridazin-3-one (380 mg, 65.80%) as a light yellow solid.

4-chloro-5-[4-[(2-ethylpyridin-3-yl)methoxy]phenyl]-2,3-dihydropyridazin-3-one

To a stirred solution of 4-chloro-5-[4-[(2-ethylpyridin-3-yl)methoxy]phenyl]-2-(oxan-2-yl)-2,3-dihydropyridazin-3-one (150 mg, 0.35 mmol, 1 equiv.) in DCM (3 mL) was added TFA (0.4 mL). The resulting mixture was stirred for 2 h at room temperature. The resulting mixture was concentrated under reduced pressure. The crude product was purified by Prep-HPLC with the following conditions (Column: XBridge Shield RP18 OBD Column, 30×150 mm, 5 um; Mobile Phase A: Water (10 mmol/L NH4HCO3), Mobile Phase B: ACN; Flow rate: 60 mL/min; Gradient: 25% B to 45% B in 10 min, then from 45% B to 0% B, from 10 to 0 min; 254 nm; RT1:8.8) to afford 4-chloro-5-[4-[(2-ethylpyridin-3-yl)methoxy]phenyl]-2,3-dihydropyridazin-3-one (25.6 mg, 21.27%) as a white solid.

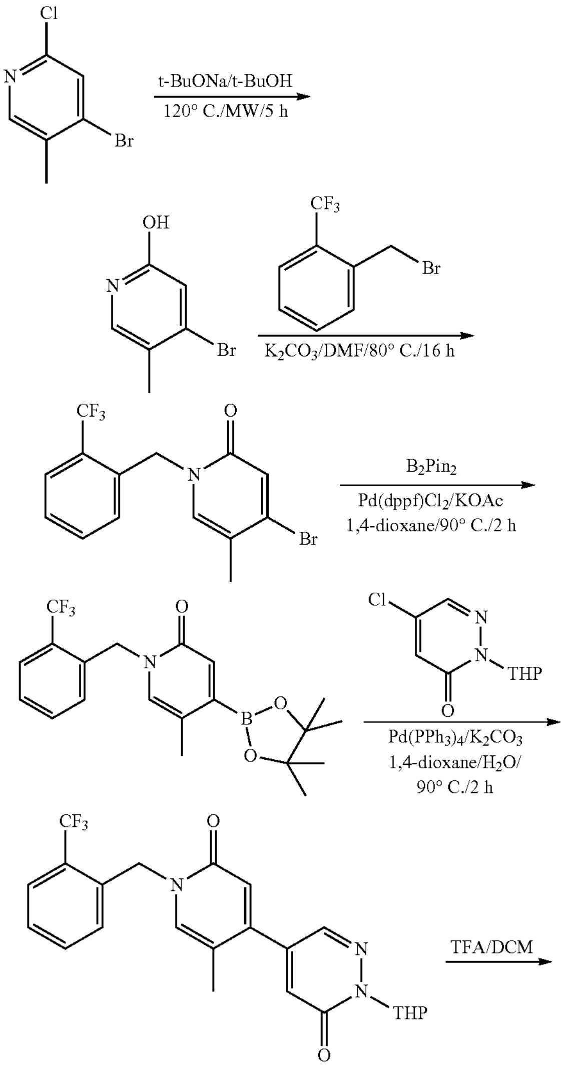

-continued

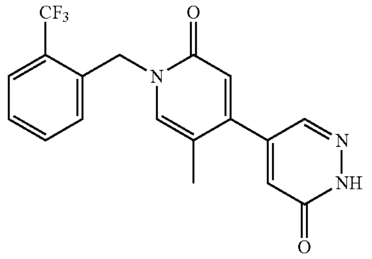

GH

Preparation of GH 4-bromo-5-methylpyridin-2-ol

To a stirred solution of 4-bromo-2-chloro-5-methylpyridine (2 g, 9.69 mmol, 1 equiv.) in t-BuOH (15 mL) was added t-BuONa (2.0 g, 20.34 mmol, 2.1 equiv.) at room temperature. The final reaction mixture was irradiated with microwave radiation for 5 h at 120 degrees C. The reaction was monitored by LCMS. The mixture was allowed to cool down to room temperature. The reaction solution was acidified to pH 6 with HCl (aq. IM). The resulting mixture was extracted with CH2Cl2(3×50 mL). The combined organic layers were washed with brine (1×100 mL), dried over anhydrous Na2SO4. After filtration, the filtrate was concentrated under reduced pressure. The residue was purified by reverse phase flash with the following conditions (Column: C18 Column 330 g; Mobile Phase A: Water (10 mmol/L AcOH), Mobile Phase B: ACN; Flow rate: 80 mL/min; Gradient: 10% B to 30% B in 40 min; 254/220 nm) to afford 4-bromo-5-methylpyridin-2-ol (1.2 g, 65.89%) as an off-white solid.

4-bromo-5-methyl-1-[[2-(trifluoromethyl)phenyl]methyl]-1,2-dihydropyridin-2-one

To a stirred solution of 4-bromo-5-methylpyridin-2-ol (1.2 g, 6.38 mmol, 1 equiv.) in DMF (20 mL) were added 1-(bromomethyl)-2-(trifluoromethyl)benzene (2.0 g, 8.30 mmol, 1.30 equiv.) and K2CO3 (1.5 g, 10.85 mmol, 1.7 equiv.) at room temperature. The resulting mixture was stirred for 16 h at 80 degrees C. The reaction was monitored by LCMS. The mixture was allowed to cool down to room temperature. The resulting mixture was concentrated under vacuum. The residue was purified by reverse phase flash with the following conditions (Column: C18 Column 330 g; Mobile Phase A: Water (10 mmol/L NH4HCO3), Mobile Phase B: ACN; Flow rate: 50 mL/min; Gradient: 5% B to 50% B in 40 min; 254/220 nm) to afford 4-bromo-5-methyl-1-[[2-(trifluoromethyl)phenyl]methyl]-1,2-dihydropyridin-2-one (1 g, 45.27%) as a light yellow solid.

5-(5-methyl-2-oxo-1-[[2-(trifluoromethyl)phenyl]methyl]-1,2-dihydropyridin-4-yl)-2-(oxan-2-yl)-2,3-dihydropyridazin-3-one To a stirred solution of 4-bromo-5-methyl-1-[[2-(trifluoromethyl)phenyl]methyl]-1,2-dihydropyridin-2-one (500 mg, 1.44 mmol, 1 equiv.) and AcOK (567.1 mg, 5.78 mmol, 4 equiv.) in 1,4-dioxane (10 mL) were added 4,4,5,5-tetramethyl-2-(4,4,5,5-tetramethyl-1,3,2-dioxaborolan-2-yl)-1,3,2-dioxaborolane (733.6 mg, 2.89 mmol, 2 equiv.)

and Pd(dppf)Cl2 (158.5 mg, 0.22 mmol, 0.15 equiv.) at room temperature under nitrogen atmosphere. The resulting mixture was stirred for 2 h at 90 degrees C. under nitrogen atmosphere. The reaction was monitored by LCMS. The mixture was allowed to cool down to room temperature. The resulting mixture was used in the next step directly without further purification.

To a solution of 5-methyl-4-(4,4,5,5-tetramethyl-1,3,2-dioxaborolan-2-yl)-1-[[2-(trifluoromethyl)phenyl]methyl]-1,2-dihydropyridin-2-one (568 mg, 1.44 mmol, 1 equiv.) and 5-chloro-2-(oxan-2-yl)-2,3-dihydropyridazin-3-one (248.1 mg, 1.16 mmol, 0.80 equiv.) in H2O (1 mL) and 1,4-dioxane (10 mL) were added K2CO3 (399.3 mg, 2.89 mmol, 2 equiv.) and Pd(PPh3)4 (250.4 mg, 0.22 mmol, 0.15 equiv). After stirring for 2 h at 90 degrees C. under a nitrogen atmosphere, the resulting mixture was concentrated under reduced pressure. The residue was purified by reverse phase flash with the following conditions (Column: C18 Column 80 g; Mobile Phase A: Water (10 mmol/L AcOH), Mobile Phase B: ACN; Flow rate: 60 mL/min; Gradient: 40% B to 60% B in 40 min; 254/220 nm) to afford 5-(5-methyl-2-oxo-1-[[2-(trifluoromethyl)phenyl]methyl]-1,2-dihydropyridin-4-yl)-2-(oxan-2-yl)-2,3-dihydropyridazin-3-one (400 mg, 62.16%) as a light yellow oil.

5-(5-methyl-2-oxo-1-[[2-(trifluoromethyl)phenyl]methyl]-1,2-dihydropyridin-4-yl)-2,3-dihydropyridazin-3-one To a stirred solution of 5-(5-methyl-2-oxo-1-[[2-(trifluoromethyl)phenyl]methyl]-1,2-dihydropyridin-4-yl)-2-(oxan-2-yl)-2,3-dihydropyridazin-3-one (400 mg, 0.90 mmol, 1 equiv.) in DCM (9 mL) was added TFA (1 mL) at room temperature. The resulting mixture was stirred for 3 h at room temperature. The reaction was monitored by LCMS. The resulting mixture was concentrated under vacuum. The residue was purified by reverse phase flash with the following conditions (Column: C18 Column 120 g; Mobile Phase A: Water (10 mmol/L NH4HCO3), Mobile Phase B: ACN; Flow rate: 60 mL/min; Gradient: 35% B to 50% B in 40 min; 254/220 nm) to afford 5-(5-methyl-2-oxo-1-[[2-(trifluoromethyl)phenyl]methyl]-1,2-dihydropyridin-4-yl)-2,3-dihydropyridazin-3-one (250 mg, 77.05%) as an off-white solid.

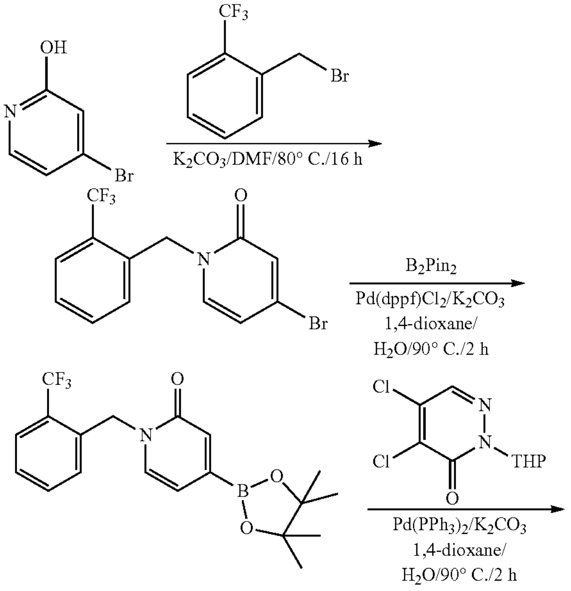

-continued

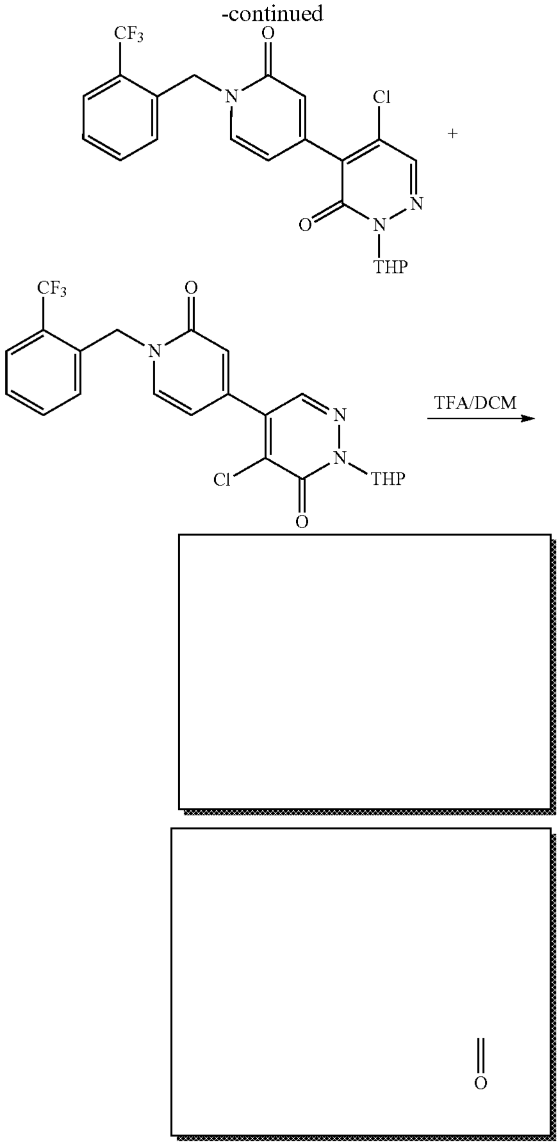

Preparation of GI

4-bromo-1-[[2-(trifluoromethyl)phenyl]methyl]-1,2-dihydropyridin-2-one

To a stirred solution of 4-bromopyridin-2-ol (5.0 g, 28.74 mmol) in DMF (50 mL) were added 1-(bromomethyl)-2-(trifluoromethyl)benzene (8.2 g, 34.48 mmol) and K2CO3 (7.9 g, 57.47 mmol) at ambient temperature. The resulting mixture was stirred for 16 h at 80 degrees C. Upon completion, the resulting mixture was cold to ambient temperature and concentrated under reduced pressure. The residue was purified by reverse phase flash chromatography with the following conditions: (Column: WelFlash™ C18-I, 20-40 uM, 330 g; Mobile Phase A: Water (plus 10 mmol/L NH4HCO3), Mobile Phase B: ACN; Flow rate: 50 mL/min; Gradient: 30% B to 60% B in 40 min; Detector: 254/220 nm). Desired fractions were collected and concentrated under reduced pressure to afford 4-bromo-1-[[2-(trifluoromethyl)phenyl]methyl]-1,2-dihydropyridin-2-one as a light yellow solid (6.0 g, 63%).

4-(4,4,5,5-tetramethyl-1,3,2-dioxaborolan-2-yl)-1-[[2-(trifluoromethyl)phenyl]methyl]-1,2-dihydropyridin-2-one To a stirred solution of 4-bromo-1-[[2-(trifluoromethyl)phenyl]methyl]-1,2-dihydropyridin-2-one (200 mg, 0.60 mmol, 1 equiv.) and KOAc (236.4 mg, 2.41 mmol, 4.00 equiv.) in 1,4-dioxane (3 mL) were added 4,4,5,5-tetramethyl-2-(4,4,5,5-tetramethyl-1,3,2-dioxaborolan-2-yl)-1,3,2-dioxaborolane (305.8 mg, 1.20 mmol, 2 equiv.) and Pd(dppf)Cl2·CH2Cl2 (73.8 mg, 0.09 mmol, 0.15 equiv.) at room temperature under nitrogen atmosphere. The resulting mixture was stirred for 2 h at 90 degrees C. under nitrogen atmosphere. The reaction was monitored by LCMS. The mixture was allowed to cool down to room temperature. The resulting mixture was used in the next step directly without further purification.

5-chloro-2-(oxan-2-yl)-4-(2-oxo-1-[[2-(trifluoromethyl)phenyl]methyl]-1,2-dihydropyridin-4-yl)-2,3-dihydropyridazin-3-one and isomer To a solution of 4-(4,4,5,5-tetramethyl-1,3,2-dioxaborolan-2-yl)-1-[[2-(trifluoromethyl)phenyl]methyl]-1,2-dihydropyridin-2-one (2.2 g, 5.80 mmol, 1 equiv.) and 4,5-dichloro-2-(oxan-2-yl)-2,3-dihydropyridazin-3-one (1.2 g, 4.64 mmol, 0.80 equiv.) in H2O (2 mL) and 1,4-dioxane (30 mL) were added K2CO3 (1.6 g, 11.60 mmol, 2 equiv.) and Pd(PPh3)4 (1.0 g, 0.87 mmol, 0.15 equiv). After stirring for 2 h at 90 degrees C. under a nitrogen atmosphere, the resulting mixture was concentrated under reduced pressure. The residue was purified by reverse phase flash with the following conditions (Column: C18 Column 80 g; Mobile Phase A: Water (10 mmol/L AcOH), Mobile Phase B: ACN; Flow rate: 60 mL/min; Gradient: 50% B to 70% B in 40 min; 254/220 nm) to afford 5-chloro-2-(oxan-2-yl)-4-(2-oxo-1-[[2-(trifluoromethyl)phenyl]methyl]-1,2-dihydropyridin-4-yl)-2,3-dihydropyridazin-3-one and isomer (550 mg, 20.35%) as a Brown yellow oil.

5-chloro-4-(2-oxo-1-[[2-(trifluoromethyl)phenyl]methyl]-1,2-dihydropyridin-4-yl)-2,3-dihydropyridazin-3-one To a stirred solution of 5-chloro-2-(oxan-2-yl)-4-(2-oxo-1-[[2-(trifluoromethyl)phenyl]methyl]-1,2-dihydropyridin-4-yl)-2,3-dihydropyridazin-3-one and isomer (550 mg, 1.18 mmol, 1 equiv.) in DCM (9 mL) were added TFA (1 mL, 26.93 mmol, 22.81 equiv.) at room temperature. The resulting mixture was stirred for additional 3 h at room temperature. The reaction was monitored by LCMS. The resulting mixture was concentrated under reduced pressure. The residue was purified by reverse phase flash with the following conditions (Column: XBridge Prep C18 OBD Column 19×150 mm 5 um; Mobile Phase A: Water (10 MMOL/L NH4HCO3), Mobile Phase B: ACN; Flow rate: 20 mL/min; Gradient: 17% B to 36% B in 10 min; 254/220 nm; Rt: 10.07 min) to afford 4-chloro-5-(2-oxo-1-[[2-(trifluoromethyl)phenyl]methyl]-1,2-dihydropyridin-4-yl)-2,3-dihydropyridazin-3-one (15 mg, 3.33%) as a off-white solid and 5-chloro-4-(2-oxo-1-[[2-(trifluoromethyl)phenyl]methyl]-1,2-dihydropyridin-4-yl)-2,3-dihydropyridazin-3-one (35 mg, 7.77%) as an off-white solid.

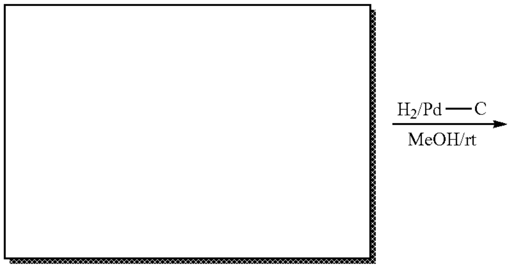

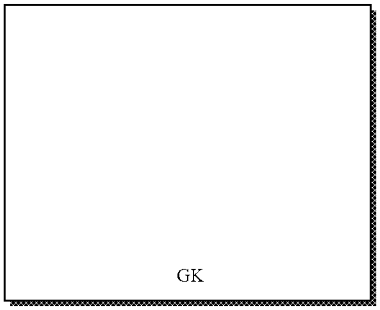
GK

Preparation of GK 4-(2-oxo-1-[[2-(trifluoromethyl)phenyl]methyl]-1,2-dihydropyridin-4-yl)-2,3-dihydropyridazin-3-one To a stirred solution of 5-chloro-4-(2-oxo-1-[[2-(trifluoromethyl)phenyl]methyl]-1,2-dihydropyridin-4-yl)-2,3-dihydropyridazin-3-one (150 mg, 0.39 mmol, 1 equiv.) in MeOH (3 mL) was added Pd/C (41.8 mg, 0.04 mmol, 0.1 equiv, 10%) at room temperature under H2 atmosphere. The resulting mixture was stirred for 2 h at room temperature under H2 atmosphere. The reaction was monitored by LCMS. The resulting mixture was concentrated under reduced pressure. The residue was purified by reverse phase flash with the following conditions (Column: XBridge Prep C18 OBD Column 19×150 mm 5 um; Mobile Phase A: Water (10 mmol/L NH4HCO3), Mobile Phase B: ACN; Flow rate: 20 mL/min; Gradient: 17% B to 36% B in 10 min; 254/220 nm; Rt: 10.07 min) to 4-(2-oxo-1-[[2-(trifluoromethyl)phenyl]methyl]-1,2-dihydropyridin-4-yl)-2,3-dihydropyridazin-3-one (20 mg, 14.66%) as a light yellow solid.

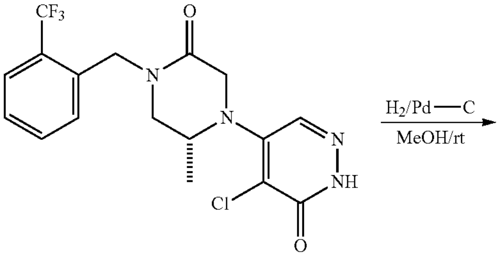

-continued

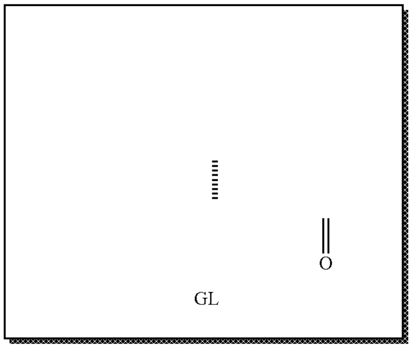

GL

GL was prepared by the methods described for GK above.

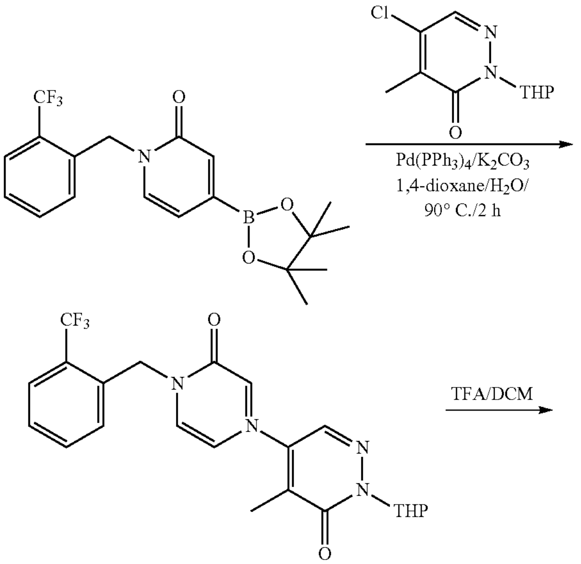

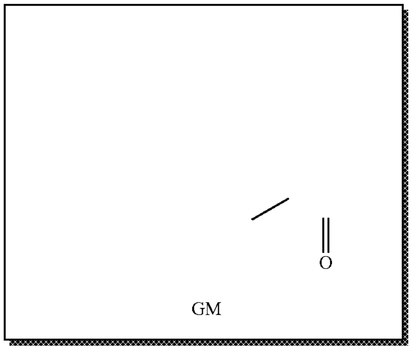

GM

Preparation of GM 4-methyl-2-(oxan-2-yl)-5-(2-oxo-1-[[2-(trifluoromethyl)phenyl]methyl]-1,2-dihydropyridin-4-yl)-2,3-dihydropyridazin-3-one To a solution of 4-(4,4,5,5-tetramethyl-1,3,2-dioxaborolan-2-yl)-1-[[2-(trifluoromethyl)phenyl]methyl]-1,2-dihydropyridin-2-one (227 mg, 0.60 mmol, 1 equiv.) and 5-chloro-4-methyl-2-(oxan-2-yl)-2,3-dihydropyridazin-3-one (109.5 mg, 0.48 mmol, 0.80 equiv.) in H2O (0.2 mL) and 1,4-dioxane (3 mL) were added K2CO3 (165.5 mg, 1.20 mmol, 2 equiv.) and Pd(PPh3)4 (103.8 mg, 0.09 mmol, 0.15 equiv). After stirring for 2 h at 90 degrees C. under a nitrogen atmosphere, the resulting mixture was concentrated under reduced pressure. The residue was purified by reverse phase flash with the following conditions (Column: C18 Column 80 g; Mobile Phase A: Water (10 mmol/L AcOH), Mobile Phase B: ACN; Flow rate: 60 mL/min; Gradient: 50% B to 70% B in 40 min; 254/220 nm) to afford 4-methyl-2-(oxan-2-yl)-5-(2-oxo-1-[[2-(trifluoromethyl)phenyl]methyl]-1,2-dihydropyridin-4-yl)-2,3-dihydropyridazin-3-one (210 mg, 78.75%) as a Brown yellow oil.

4-methyl-5-(2-oxo-1-[[2-(trifluoromethyl)phenyl]methyl]-1,2-dihydropyridin-4-yl)-2,3-dihydropyridazin-3-one To a stirred solution of 4-methyl-2-(oxan-2-yl)-5-(2-oxo-1-[[2-(trifluoromethyl)phenyl]methyl]-1,2-dihydropyridin-4-yl)-2,3-dihydropyridazin-3-one (210 mg, 0.47 mmol, 1 equiv.) in DCM (18 mL) were added TFA (2 mL, 26.93 mmol, 57.11 equiv.) dropwise at room temperature. The resulting mixture was stirred for 2 h at room temperature. The reaction was monitored by LCMS. The mixture was basified to pH 8 with saturated NaHCO3 (aq.). The resulting mixture was concentrated under reduced pressure. The residue was purified by reverse phase flash with the following conditions (Column: C18 Column 120 g; Mobile Phase A: Water (10 mmol/L NH4HCO3), Mobile Phase B: ACN; Flow rate: 60 mL/min; Gradient: 40% B to 70% B in 30 min; 254/220 nm) to afford 4-methyl-5-(2-oxo-1-[[2-(trifluoromethyl)phenyl]methyl]-1,2-dihydropyridin-4-yl)-2,3-dihydropyridazin-3-one (110 mg, 64.58%) as a light yellow solid.

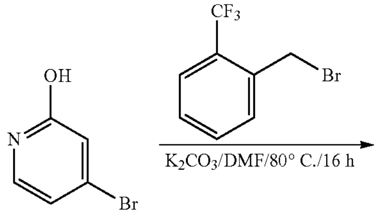

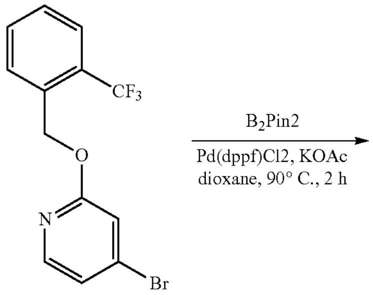

-continued

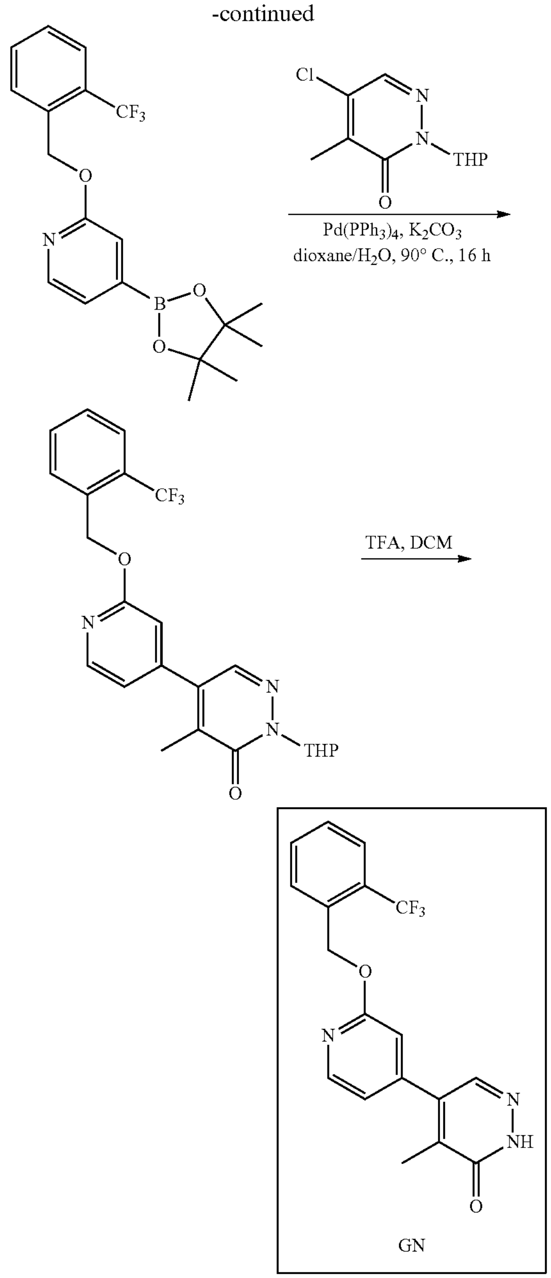

GN

Preparation of GN 4-bromo-2-[[2-(trifluoromethyl)phenyl]methoxy]pyridine

To a stirred solution of 4-bromopyridin-2-ol (5.0 g, 28.74 mmol) in DMF (50 mL) were added 1-(bromomethyl)-2-(trifluoromethyl)benzene (8.2 g, 34.48 mmol) and K2CO3 (7.9 g, 57.47 mmol) at ambient temperature. The resulting mixture was stirred for 16 h at 80 degrees C. Upon completion, the resulting mixture was cold to ambient temperature and concentrated under reduced pressure. The residue was purified by reverse phase flash chromatography with the following conditions: (Column: WelFlash™ C18-I, 20-40 uM, 330 g; Mobile Phase A: Water (plus 10 mmol/L NH4HCO3), Mobile Phase B: ACN; Flow rate: 50 mL/min; Gradient: 30% B to 60% B in 40 min; Detector: 254/220 nm). Desired fractions were collected and concentrated under reduced pressure to afford 4-bromo-2-[[2-(trifluoromethyl)phenyl]methoxy]pyridine as a light yellow oil (3.0 g, 32%)

4-methyl-2-(tetrahydro-2H-pyran-2-yl)-5-(2-(2-(trifluoromethyl)benzyloxy)pyridin-4-yl)pyridazin-3(2H)-one A solution of 4-bromo-2-[[2-(trifluoromethyl)phenyl]methoxy]pyridine (200 mg, 0.60 mmol) in 1,4-dioxane (10 mL) were added bis(pinacolato)diboron (305.8 mg, 1.20 mmol), bis(diphenylphosphino)ferrocene-palladium (II) dichloride dichloromethane complex (196.7 mg, 0.24 mmol) and KOAc (236.4 mg, 2.41 mmol). The resulting mixture was stirred for 2 h at 90 degrees C. under nitrogen atmosphere. Upon completion, the resulting mixture was cold to ambient temperature followed by the addition of tetrakis(triphenylphosphine)palladium (O) (139.2 mg, 0.12 mmol), K2CO3 (166.5 mg, 1.20 mmol) and H2O (2 mL). The resulting mixture was stirred for 16 h at 90 degrees C. under nitrogen atmosphere. Then the resulting mixture was concentrated under reduced pressure. The residue was purified by silica gel column chromatography, eluted with 20%~50% ethyl acetate in petroleum ether to afford 4-chloro-2-(oxan-2-yl)-5-(2-[[2-(trifluoromethyl)phenyl]methoxy]pyridin-4-yl)-2,3-dihydropyridazin-3-one as an off-white solid (180 mg, 65%)

4-methyl-5-(2-[[2-(trifluoromethyl)phenyl]methoxy]pyridin-4-yl)-2,3-dihydropyridazin-3-one A mixture of 4-methyl-2-(oxan-2-yl)-5-(2-[[2-(trifluoromethyl)phenyl]methoxy]pyridin-4-yl)-2,3-dihydropyridazin-3-one (120 mg, 0.27 mmol, 1 equiv.) in TFA (1 mL, 13.46 mmol, 49.98 equiv.) and DCM (10 mL) was stirred for 4 h at room temperature. The reaction was monitored by LCMS. The resulting mixture was concentrated under reduced pressure. The residue was purified by reverse phase flash with the following conditions (Column: Spherical C18 Column, 20-40 um, 120 g; Mobile Phase A: Water (0.1% NH4HCO3), Mobile Phase B: ACN; Flow rate: 60 mL/min; Gradient: 30% B to 50% B in 25 min, 254 nm) to afford 4-methyl-5-(2-[[2-(trifluoromethyl)phenyl]methoxy]pyridin-4-yl)-2,3-dihydropyridazin-3-one (55 mg, 56.50%) as an off-white solid.

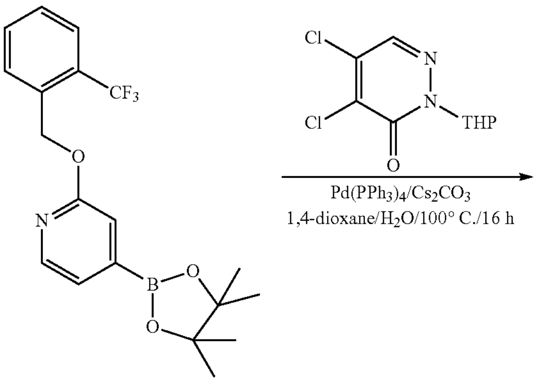

-continued

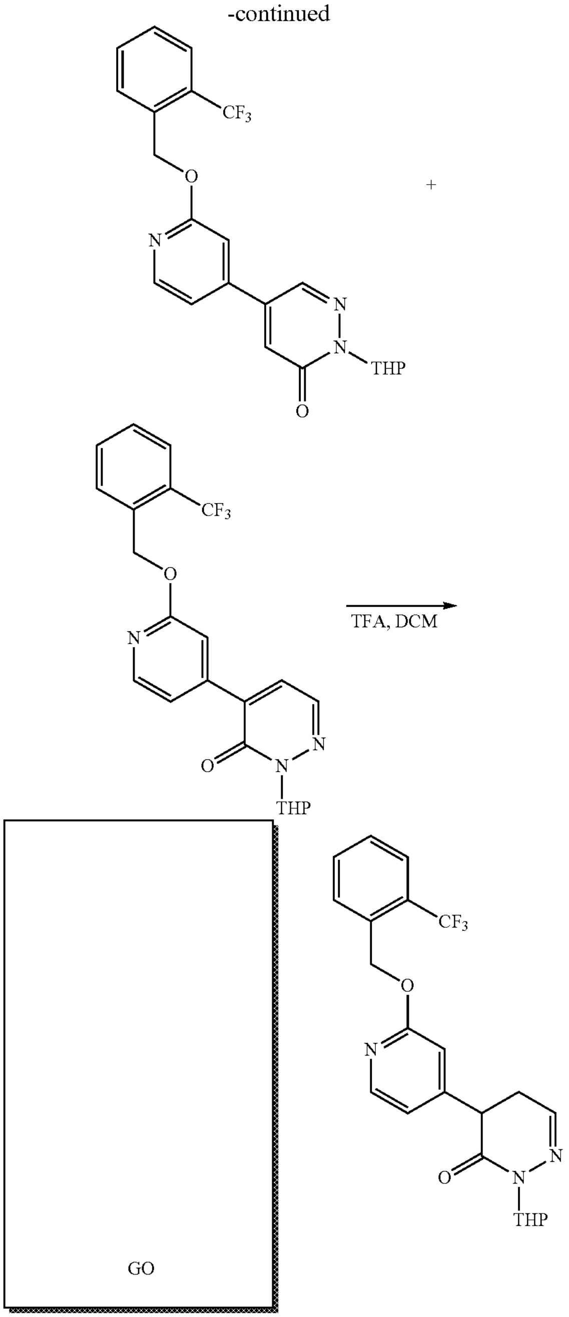

GO

GO was prepared by the methods described for GN above.

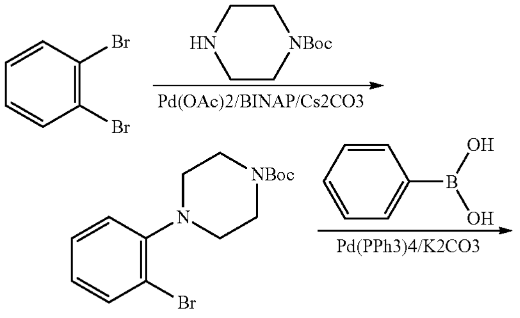

-continued

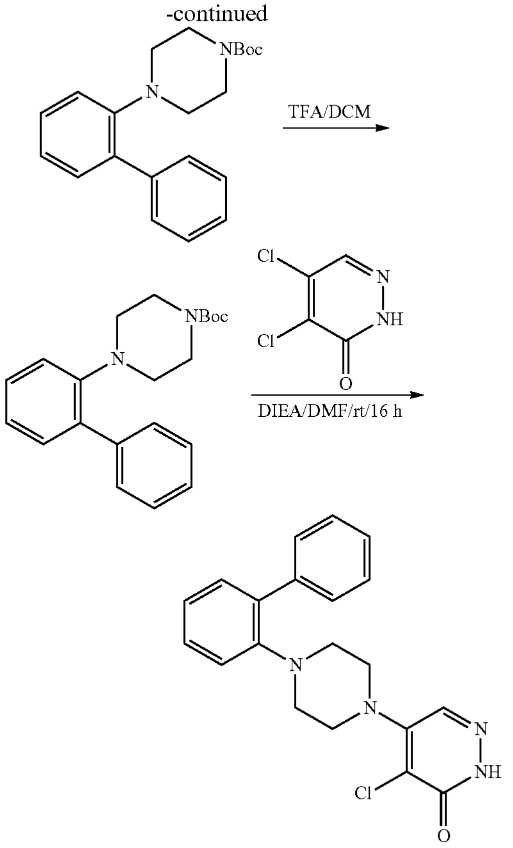

GP

Preparation of GP

Tert-Butyl 4-(2-bromophenyl)piperazine-1-carboxylate

To a stirred mixture of tert-butyl piperazine-1-carboxylate (1.6 g, 8.59 mmol, 1 equiv.) and Cs2CO3 (5.6 g, 17.19 mmol, 2.00 equiv.) in dioxane (4 mL) were added BINAP (1.1 g, 1.77 mmol, 0.21 equiv.) and Pd(AcO)2 (192.9 mg, 0.86 mmol, 0.10 equiv.) in portions at room temperature. To the above mixture was added 1,2-dibromobenzene (2.0 g, 8.48 mmol, 0.99 equiv.) in portions at room temperature under nitrogen atmosphere. The final reaction mixture was irradiated with microwave radiation for 3 h at 90 degrees C. The reaction was monitored by LCMS. The mixture was allowed to cool down to room temperature. The residue was purified by silica gel column chromatography, eluted with PE/EtOAc (30/1 to 10/1) to afford tert-butyl 4-(2-bromophenyl)piperazine-1-carboxylate (1.22 g, 41.62%) as a yellow oil.

Tert-Butyl 4-[[1,1-biphenyl]-2-yl]piperazine-1-carboxylate

To a solution of tert-butyl 4-(2-bromophenyl)piperazine-1-carboxylate (100 mg, 0.29 mmol, 1 equiv.) and Pd(PPh3)4 (33.9 mg, 0.03 mmol, 0.10 equiv.) in dioxane (2.5 mL) and H2O (0.5 mL) were added phenylboronic acid (53.6 mg, 0.44 mmol, 1.50 equiv.) and K2CO3 (121.5 mg, 0.88 mmol, 3.00 equiv.) in portions at room temperature under nitrogen atmosphere. The final reaction mixture was irradiated with microwave radiation for 2 h at 90 degrees C. The reaction was monitored by LCMS. The mixture was allowed to cool down to room temperature. The resulting mixture was concentrated under reduced pressure. The residue was purified by Prep-TLC (PE/EtOAc=100/1) to afford tert-butyl 4-[[1,1-biphenyl]-2-yl]piperazine-1-carboxylate (90 mg, 90.74%) as a light yellow oil.

1-[[1,1-biphenyl]-2-yl]piperazine

To a stirred solution of tert-butyl 4-[[1,1-biphenyl]-2-yl]piperazine-1-carboxylate (250 mg, 0.74 mmol, 1 equiv.) in DCM (2 mL) was added TFA (5 mL, 67.32 mmol, 91.13 equiv.) dropwise at room temperature. The resulting mixture was stirred for 2 h at room temperature. The reaction was monitored by LCMS. The resulting mixture was concentrated under reduced pressure. The residue was basified to pH 9 with saturated NaHCO3 (aq.). The resulting mixture was extracted with EtOAc (3×200 mL). The combined organic layers were washed with brine (3×200 mL), dried over anhydrous Na2SO4. After filtration, the filtrate was concentrated under reduced pressure to afford the 1-[[1,1-biphenyl]-2-yl]piperazine (180 mg, 102.25%) as yellow oil.

5-(4-[[1,1-biphenyl]-2-yl]piperazin-1-yl)-4-chloro-2,3-dihydropyridazin-3-one

To a stirred mixture of 1-[[1,1-biphenyl]-2-yl]piperazine (200 mg, 0.84 mmol, 1 equiv.) and DIEA (216.9 mg, 1.68 mmol, 2.00 equiv.) in DMA (5 mL) was added 4,5-dichloro-2,3-dihydropyridazin-3-one (138.4 mg, 0.84 mmol, 1.00 equiv.) in portions at room temperature. The resulting mixture was stirred for 16 h at 100 degrees C. The reaction was monitored by LCMS.

The mixture was allowed to cool down to room temperature. The residue was purified by Prep-HPLC with the following conditions (Column: XBridge Shield RP18 OBD Column 30*150 mm, 5 um; Mobile Phase A: Water (10 mmol/L NH4HCO3), Mobile Phase B: ACN; Flow rate: 60 mL/min; Gradient: 35% B to 70% B in 7 min; 254 nm; Rt: 6.58 8.4 min) to afford 5-(4-[[1,1-biphenyl]-2-yl]piperazin-1-yl)-4-chloro-2,3-dihydropyridazin-3-one (45.9 mg, 14.91%) as a yellow solid.

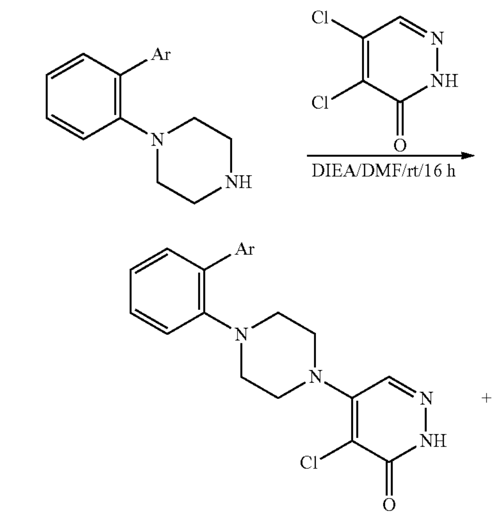

-continued

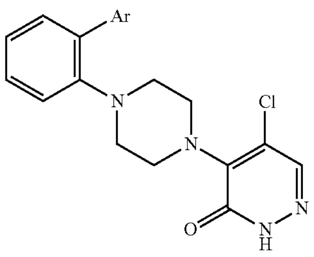

| Ar Group | Target ID |
|---|---|
| 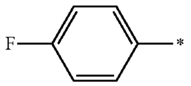 | GQ |
| 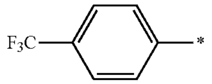 | GR |
| 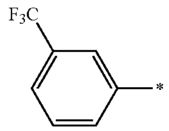 | GS |

GQ, GR and GS were prepared by the methods described for GP above.

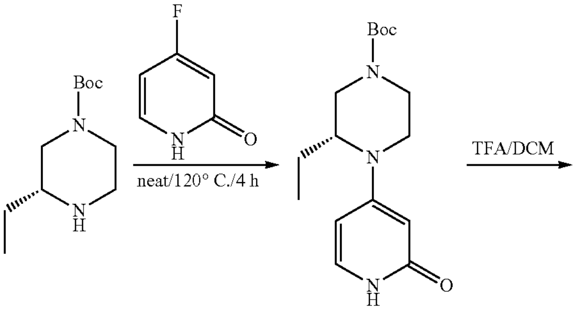

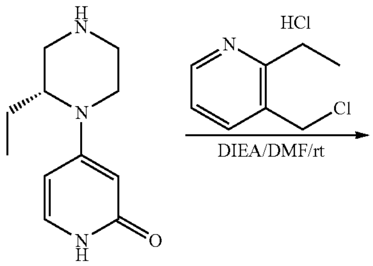

-continued

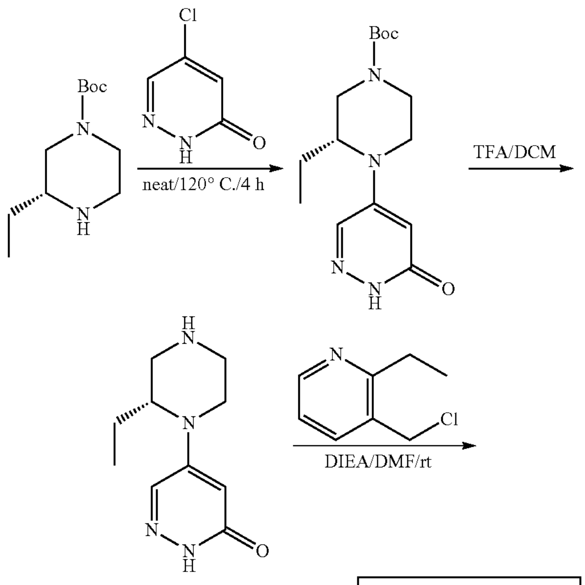

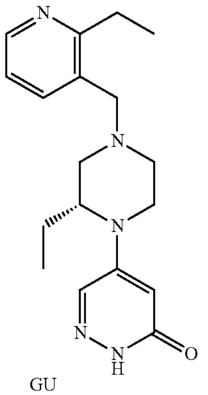

GU

Preparation of GT

Tert-Butyl (3R)-3-ethyl-4-(2-oxo-1,2-dihydropyridin-4-yl)piperazine-1-carboxylate Into a 25 mL round-bottom flask were added tert-butyl (3R)-3-ethylpiperazine-1-carboxylate (200 mg, 0.93 mmol, 1 equiv.) and 4-fluoro-1,2-dihydropyridin-2-one (126.6 mg, 1.12 mmol, 1.20 equiv.) at room temperature. The resulting mixture was stirred for 4 h at 120 degrees C. under nitrogen atmosphere. The reaction was monitored by LCMS. The mixture was allowed to cool down to room temperature. The residue was purified by reverse phase flash with the following conditions (Column: XBridge Prep C18 OBD Column 19×150 mm 5 um; Mobile Phase A: Water (5 mmol/L $CH_3COOH$), Mobile Phase B: ACN; Flow rate: 20 mL/min; Gradient: 30% B to 40% B in 10 min; 254/220 nm; Rt: 5.18 min) to afford tert-butyl (3R)-3-ethyl-4-(2-oxo-1,2-dihydropyridin-4-yl)piperazine-1-carboxylate (120 mg, 41.83%) as a yellow solid.

4-[(2R)-2-ethylpiperazin-1-yl]-1,2-dihydropyridin-2-one

To a stirred solution of tert-butyl (3R)-3-ethyl-4-(2-oxo-1,2-dihydropyridin-4-yl)piperazine-1-carboxylate (120 mg, 0.39 mmol, 1 equiv.) in DCM (12 mL) was added TFA (2 mL, 26.93 mmol, 68.97 equiv.) at room temperature under nitrogen atmosphere. The resulting mixture was stirred for 2 h at room temperature. The reaction was monitored by LCMS. The resulting mixture was concentrated under reduced pressure. The residue was basified to pH 8 with saturated $NaHCO_3$ (aq.). The resulting mixture was extracted with $CH_2Cl_2$(3×20 mL). The combined organic layers were washed with brine (1×20 mL), dried over anhydrous $Na_2SO_4$. After filtration, the filtrate was concentrated under reduced pressure. The residue was purified by reverse phase flash with the following conditions (Column: XBridge Prep C18 OBD Column 19×150 mm 5 um; Mobile Phase A: Water (5 mmol/L $NH_4HCO_3$), Mobile Phase B: ACN; Flow rate: 20 mL/min; Gradient: 0% B to 5% B in 12 min; 254/220 nm; Rt: 5.8 min) to afford 4-[(2R)-2-ethylpiperazin-1-yl]-1,2-dihydropyridin-2-one (90 mg, 111.23%) as a yellow solid.

4-[(2R)-2-ethyl-4-[(2-ethylpyridin-3-yl)methyl]piperazin-1-yl]-1,2-dihydropyridin-2-one To a stirred mixture of 4-[(2R)-2-ethylpiperazin-1-yl]-1,2-dihydropyridin-2-one (90 mg, 0.43 mmol, 1 equiv.) and DIEA (168.4 mg, 1.30 mmol, 3 equiv.) in DMF (5 mL) was added 3-(chloromethyl)-2-ethylpyridine (81.1 mg, 0.52 mmol, 1.20 equiv.) at room temperature under nitrogen atmosphere. The resulting mixture was stirred for 16 h at room temperature. The reaction was monitored by LCMS. The crude product (100 mg) was purified by Prep-HPLC with the following conditions (Column: XBridge Prep C18 OBD Column 19×150 mm 5 um; Mobile Phase A: Water (10 mmol/L $NH_4HCO_3$), Mobile Phase B: ACN; Flow rate: 20 mL/min; Gradient: 24% B to 48% B in 7 min; 254/220 nm; Rt: 5.15 min) to afford 4-[(2R)-2-ethyl-4-[(2-ethylpyridin-3-yl)methyl]piperazin-1-yl]-1,2-dihydropyridin-2-one (27.4 mg, 19.33%) as a white solid.

GU was prepared by the methods described for GT above.

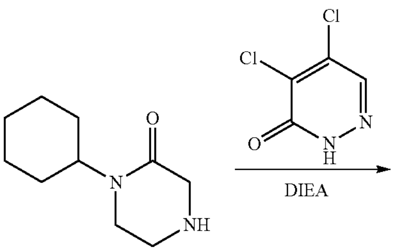

-continued

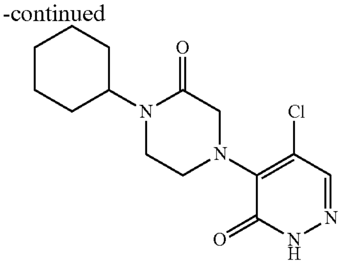

GV

Preparation of GV

5-chloro-4-(4-cyclohexyl-3-oxopiperazin-1-yl)-2,3-dihydropyridazin-3-one

To a solution of 1-cyclohexylpiperazin-2-one (150 mg, 0.82 mmol, 1 equiv.) in DMF (5 mL) was added DIEA (319.1 mg, 2.47 mmol, 3.00 equiv.) at ambient temperature under air atmosphere. The resulting mixture was stirred for 5 h at 100 degrees C. The desired product could be detected by LCMS. The reaction mixture was purified by reverse phase flash with the following conditions (Column: c18 OBD Column, 5 um, 19*330 mm; Mobile Phase A: Water (5 mmol/L NH4HCO3), Mobile Phase B: ACN; Flow rate: 45 mL/min; Gradient: 30% B to 60% B in 40 min; 254 nm; Rt: 15 min) to afford Products (80 mg) as a white solid. The product was purified by Chiral-Prep-HPLC with the following conditions: Column:CHIRALPAK IG-3, Column size: 0.46*5 cm; 3 um; Mobile phase:Hex (0.1% DEA): EtOH=80:20; Pressure:MPA; Flow:1.0 ml/min; Instrument: LC-08; Detector:254 nm; Temperature:25 degrees C. 4-chloro-5-(4-cyclohexyl-3-oxopiperazin-1-yl)-2,3-dihydropyridazin-3-one (26.5 mg, 10.36%) was obtained at 1.436 min as a white solid (26.5 mg) and 5-chloro-4-(4-cyclohexyl-3-oxopiperazin-1-yl)-2,3-dihydropyridazin-3-one (4 mg, 1.56%) was obtained at 1.725 min as an off-white solid (4 mg).

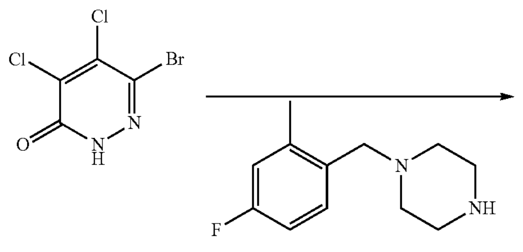

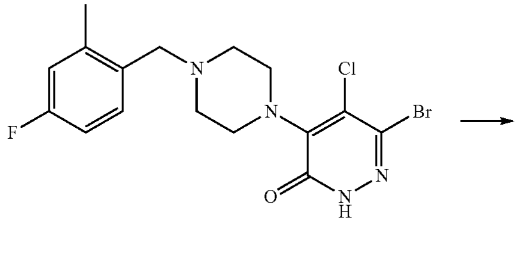

-continued

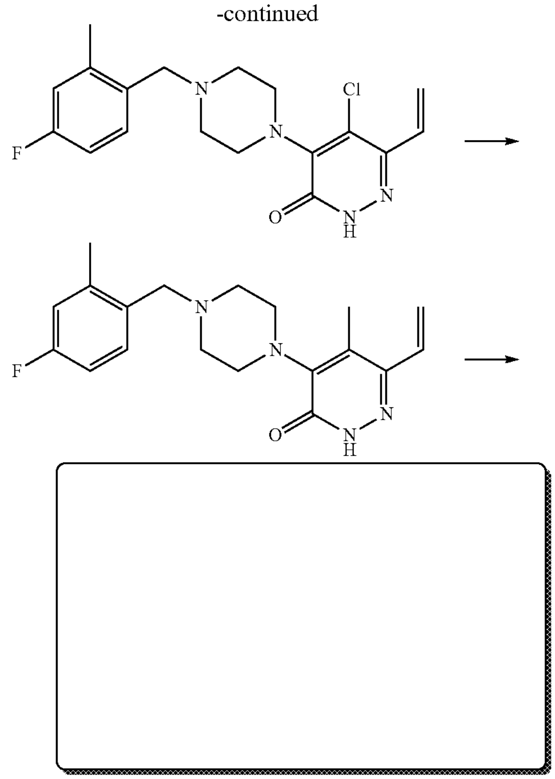

Preparation of JP

6-bromo-4-chloro-5-[4-[(4-fluoro-2-methylphenyl)methyl]piperazin-1-yl]-2,3-dihydropyridazin-3-one To a stirred mixture of 1-[(4-fluoro-2-methylphenyl)methyl]piperazine (3 g, 14.40 mmol, 1 equiv.) and 6-bromo-4,5-dichloro-2,3-dihydropyridazin-3-one (3.5 g, 14.40 mmol, 1 equiv.) in 1,4-dioxane (60 mL) was added ethylbis(propan-2-yl)amine (3.7 g, 28.81 mmol, 2 equiv.) at room temperature. The mixture was stirred 100 degrees Celsius for 16 h. Desired product could be detected by LCMS. The mixture was concentrated under reduced pressure. The crude product (3 g) was purified by Prep-HPLC with the following conditions (Column. XBridge Shield RP18 OBD Column, 5 um, 19*150 mm; Mobile Phase A: Water (10 mmol/L NH4HCO3), Mobile Phase B: ACN; Flow rate: 20 mL/min; Gradient: 50% B to 80% B in 7 min; 220 nm; Rt: 6.82 min) to afford 6-bromo-4-chloro-5-[4-[(4-fluoro-2-methylphenyl)methyl]piperazin-1-yl]-2,3-dihydropyridazin-3-one (2.5 g, 41.75%) as a white solid.

5-chloro-6-ethenyl-4-[4-[(4-fluoro-2-methylphenyl)methyl]piperazin-1-yl]-2,3-dihydropyridazin-3-one To a solution of 6-bromo-5-chloro-4-[4-[(4-fluoro-2-methylphenyl)methyl]piperazin-1-yl]-2,3-dihydropyridazin-3-one (200 mg) and 2-ethenyl-4,4,5,5-tetramethyl-1,3,2-dioxaborolane (74.1 mg, 480 mmol, 1 equiv.) in and 1,4-dioxane (8 mL) and H2O (2 mL) were added potassium potassium methaneperoxoate (134.0 mg, 960 mmol, 2 equiv.) and tetrakis(triphenylphosphane) palladium (55.6 mg, 50 mmol, 0.1 equiv). After stirring for 16 h at 90 degrees Celsius under a nitrogen atmosphere, the resulting mixture was concentrated under reduced pressure. The residue was purified by Prep-TLC(PE:EA=1:1) to afford 5-chloro-6-ethenyl-4-[4-[(4-fluoro-2-methylphenyl)methyl]piperazin-1-yl]-2,3-dihydropyridazin-3-one (150 mg) as a white solid.

6-ethenyl-4-[4-[(4-fluoro-2-methylphenyl)methyl]piperazin-1-yl]-5-methyl-2,3-dihydropyridazin-3-one To a solution of 5-chloro-6-ethenyl-4-[4-[(4-fluoro-2-methylphenyl)methyl]piperazin-1-yl]-2,3-dihydro-pyridazin-3-one (30 mg, 0.08 mmol, 1 equiv.) and methylboronic acid (4.9 mg, 0.08 mmol, 0.990 equiv.) in 1,4-dioxane (4 mL) and H2O (1 mg) were added K2CO3 (22.9 mg, 0.17 mmol, 2 equiv.) and Pd(PPh3)4 (9.6 mg, 0.01 mmol, 0.1 equiv). After stirring for 16 h at 100 degrees Celsius under nitrogen atmosphere, the resulting mixture was concentrated under reduced pressure. The residue was purified by Prep-TLC (PE:EA=1:1) to afford 6-ethenyl-4-[4-[(4-fluoro-2-methylphenyl)methyl]piperazin-1-yl]-5-methyl-2,3-dihydropyridazin-3-one (5 mg, 17.66%) as a white solid.

Compound JP: 6-ethyl-4-[4-[(4-fluoro-2-methylphenyl)methyl]piperazin-1-yl]-5-methyl-2,3-dihydro-pyridazin-3-one To a solution of 6-ethenyl-4-[4-[(4-fluoro-2-methylphenyl)methyl]piperazin-1-yl]-5-methyl-2,3-dihydropyridazin-3-one (40 mg, 0.12 mmol, 1 equiv.) in 40 mL EA was added PtO2 (27 mg, 0.01 mmol, 0.1 equiv.) under nitrogen atmosphere. The mixture was hydrogenated at room temperature overnight under hydrogen atmosphere using a hydrogen balloon, filtered through a Celite pad, the filtrate was concentrated under reduced pressure. the residue was purified by Prep-HPLC(Column: XBridge Shield RP18 OBD Column, 5 um, 19*150 mm; Mobile Phase A: Water (10 mmol/L NH4HCO3), Mobile Phase B: ACN; Flow rate: 20 mL/min; Gradient: 40% B to 65% B in 10 min; 254 nm; Rt: 6.42 9.35 min) to afford 6-ethyl-4-[4-[(4-fluoro-2-methylphenyl)methyl]piperazin-1-yl]-5-methyl-2,3-dihydropyridazin-3-one (6.7 mg, 16.65%) as white solid.

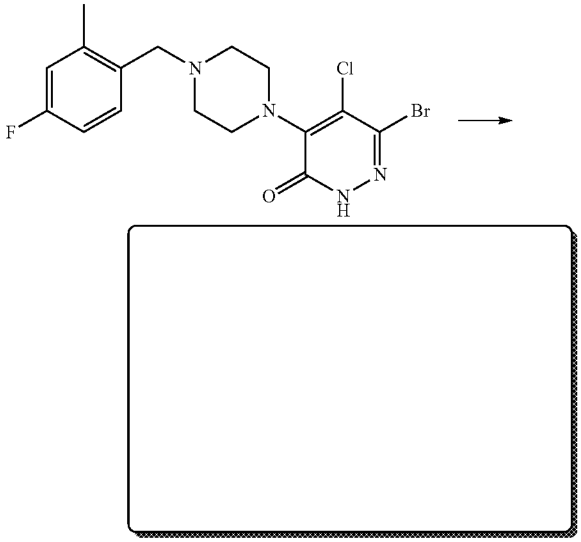

Preparation of JQ: 5-chloro-4-[4-[(4-fluoro-2-methylphenyl)methyl]piperazin-1-yl]-6-methyl-2,3-dihydropyridazin-3-one To a solution of 6-bromo-5-chloro-4-[4-[(4-fluoro-2-methylphenyl)methyl]piperazin-1-yl]-2,3-dihydro-pyridazin-3-one (300 mg, 0.72 mmol, 1 equiv.) and methylboronic acid (86.4 mg, 1.44 mmol, 2 equiv.) in 1,4-dioxane (5 mL) and H2O (1 mL) were added K2CO3 (299.2 mg, 2.17 mmol, 3 equiv.) and Pd(PPh3)4 (83.4 mg, 0.07 mmol, 0.1 equiv). After stirring for 16 h at 130 degrees Celsius under a nitrogen atmosphere, the mixture was concentrated under reduced pressure. Desired product could be detected by LCMS. The residue was purified by Prep-TLC (PE/EtOAc 1:1) to afford 5-chloro-4-[4-[(4-fluoro-2-methylphenyl)methyl]piperazin-1-yl]-6-methyl-2,3-dihydro-pyridazin-3-one (200 mg, 78.99%) as a white solid.

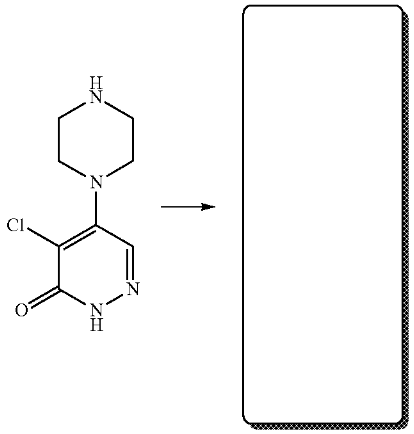

Preparation of JR 4-chloro-5-[4-(diphenylmethyl)piperazin-1-yl]-2,3-dihydropyridazin-3-one To a mixture of 4-chloro-5-(piperazin-1-yl)-2,3-dihydro-pyridazin-3-one (100 mg, 0.47 mmol, 1 equiv), [bromo(phenyl)methyl]benzene (149.7 mg, 0.61 mmol, 1.300 equiv.) and DIEA (180.6 mg, 1.40 mmol, 2.999 equiv.) in DMF (5 mL) was added TBAI (17.2 mg, 0.05 mmol, 0.100 equiv.) at room temperature. The reaction was stirred for 16 h at room temperature. The reaction was monitored by LCMS. The resulting mixture was purified by Prep-HPLC with the following conditions (Column: XBridge Shield RP18 OBD Column, 5 um, 19*150 mm; Mobile Phase A: Water (10 mmol/L TFA), Mobile Phase B: ACN; Flow rate: 20 mL/min; Gradient: 47% B to 68% B in 7 min; 254 nm; Rt: 6.1 min) to afford 4-chloro-5-[4-(diphenylmethyl)piperazin-1-yl]-2,3-dihydropyridazin-3-one (26.2 mg) as a white solid.

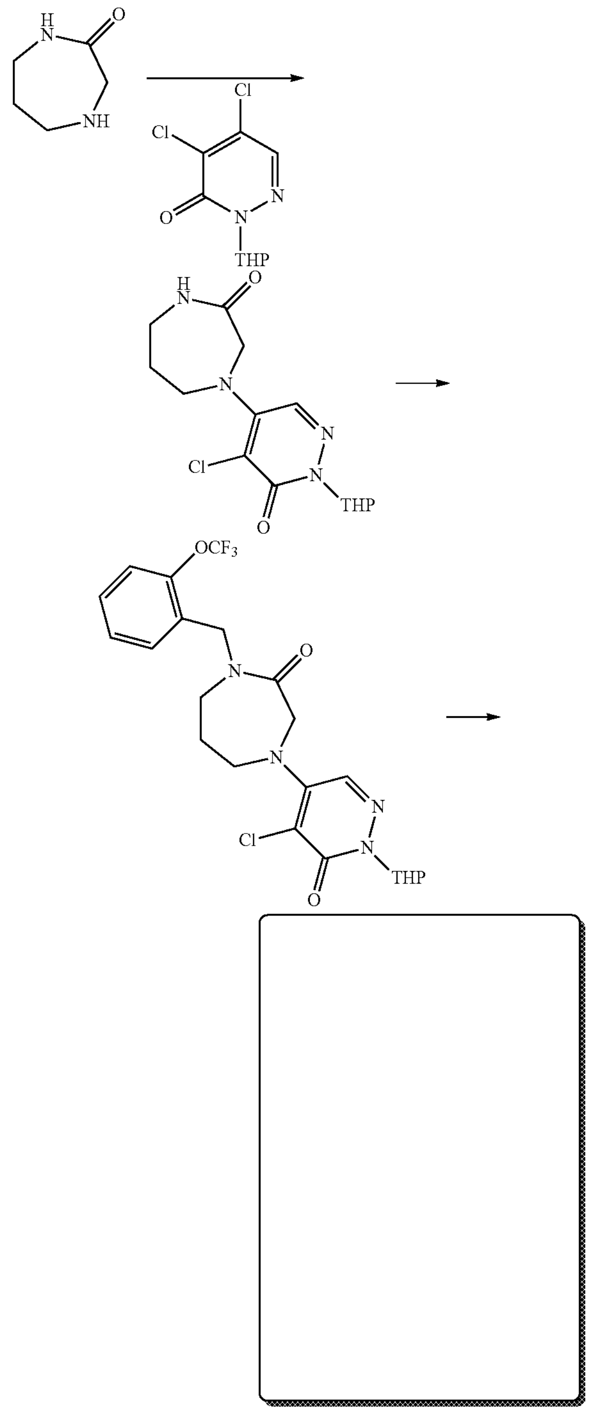

Preparation of JS

4-[5-chloro-1-(oxan-2-yl)-6-oxo-1,6-dihydro-pyridazin-4-yl]-1,4-diazepan-2-one

To a stirred solution of 1,4-diazepan-2-one (1 g, 8.76 mmol, 1 equiv.) and DIEA (2.3 g, 17.52 mmol, 2 equiv.) in DMA (15 mL) was added 4,5-dichloro-2-(oxan-2-yl)-2,3-dihydropyridazin-3-one (2.2 g, 8.76 mmol, 1 equiv). The resulting mixture was stirred for 16 h at 100 degrees Celsius. The solution was purified by reverse phase flash with the following conditions (Column: spnerical C18, 20-40 um, 330 g: Mobile Phase A: Water (5 mmol/L NH4HCO3), Mobile Phase B: ACN; Flow rate: 80 mL/min; Gradient: 20% B to 65% B in 40 min; 254 nm) to afford 4-[5-chloro-1-(oxan-2-yl)-6-oxo-1,6-dihydropyridazin-4-yl]-1,4-diazepan-2-one (1.5 g, 52.40%) as a light yellow solid.

4-[5-chloro-1-(oxan-2-yl)-6-oxo-1,6-dihydro-pyridazin-4-yl]-1-[[2-(trifluoromethoxy)phenyl]methyl]-1,4-diazepan-2-one To a stirred solution of 4-[5-chloro-1-(oxan-2-yl)-6-oxo-1,6-dihydropyridazin-4-yl]-1,4-diazepan-2-one (200 mg, 0.61 mmol, 1 equiv.) and NaH (29.4 mg, 1.22 mmol, 2 equiv.) in DMF was added 1-(bromomethyl)-2-(trifluoromethoxy)benzene (202.9 mg, 0.80 mmol, 1.3 equiv). The resulting mixture was stirred for overnight at room temperature. The solution was purified by reverse phase flash with the following conditions (Column: spnerical C18, 20-40 um, 120 g; Mobile Phase A: Water (5 mmol/L NH4HCO3), Mobile Phase B: ACN; Flow rate: 45 mL/min; Gradient: 20% B to 60% B in 40 min; 254 nm) to afford 4-[5-chloro-1-(oxan-2-yl)-6-oxo-1,6-dihydropyridazin-4-yl]-1-[[2-(trifluoromethoxy)phenyl]methyl]-1,4-diazepan-2-one (282 mg, 91.99%) as a yellow solid.

Compound JS: 4-(5-chloro-6-oxo-1,6-dihydro-pyridazin-4-yl)-1-[[2-(trifluoromethoxy)phenyl]methyl]-1,4-diazepan-2-one To a stirred solution of 4-[5-chloro-1-(oxan-2-yl)-6-oxo-1,6-dihydropyridazin-4-yl]-1-[[2-(trifluoromethoxy)phenyl]methyl]-1,4-diazepan-2-one (282 mg, 0.56 mmol, 1 equiv.) in DCM (5 mL) was added TFA (1.5 mL). The resulting mixture was stirred for 2 h at room temperature. The solution was purified by Prep-HPLC with the following conditions (Column: XBridge Prep C18 OBD Column, 5 um, 19×150 mm; Mobile Phase A: Water (10 mmol/L NH4HCO3), Mobile Phase B: ACN; Flow rate: 20 mL/min; Gradient: 20% B to 55% B in 7 min; 254/220 nm; Rt: 5.8 min) to afford 4-(5-chloro-6-oxo-1,6-dihydropyridazin-4-yl)-1-[[2-(trifluoromethoxy)phenyl]methyl]-1,4-diazepan-2-one (91 mg, 38.78%) as a off-white solid.

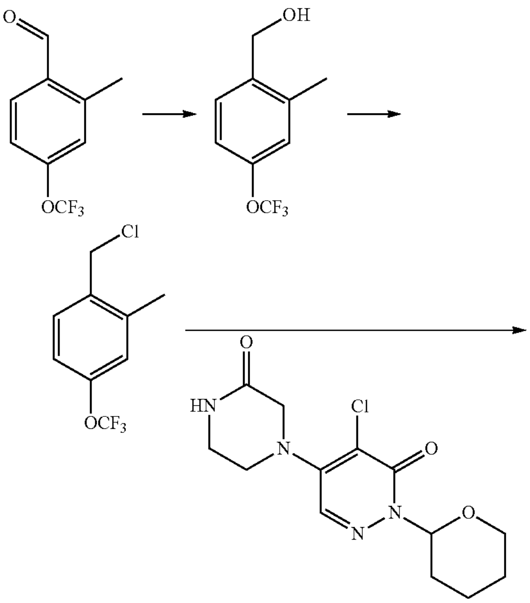

-continued

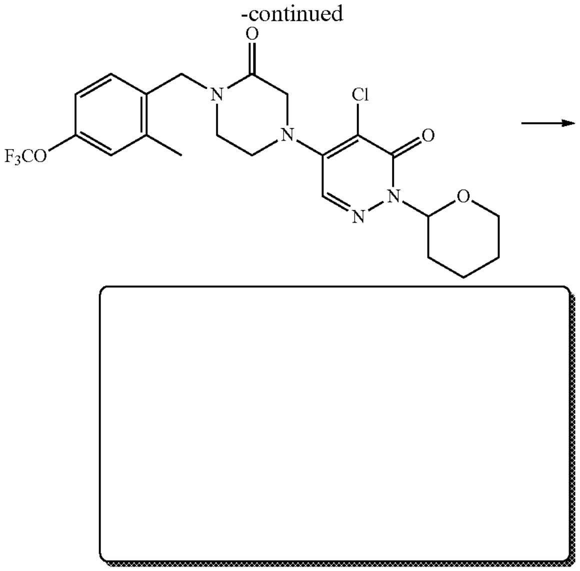

Preparation of JT

[2-methyl-4-(trifluoromethoxy)phenyl]methanol

To a stirred solution of 2-methyl-4-(trifluoromethoxy) benzaldehyde (1 g, 4.90 mmol, 1 equiv.) in MeOH (25 mL) was added NaBH4 (556.0 mg, 14.70 mmol, 3.000 equiv.) in portions at 0 degrees Celsius. The resulting mixture was stirred for 16 h at room temperature. The reaction was monitored by TLC (PE/EtOAc=10:1). The resulting mixture was concentrated under reduced pressure. The residue was purified by silica gel column chromatography, eluted with PE/EtOAc (50:1 to 1:1) to afford [2-methyl-4-(trifluoromethoxy)phenyl]methanol (950 mg, 94.07%) as a light yellow oil.

1-(chloromethyl)-2-methyl-4-(trifluoromethoxy) benzene

To a solution of [2-methyl-4-(trifluoromethoxy)phenyl] methanol (960 mg, 4.66 mmol, 1 equiv.) in DCM (20 mL) was added SOCl2 (1.7 g, 13.97 mmol, 3 equiv.) at 0 degrees Celsius. The reaction was stirred for 16 h at room temperature. The reaction was monitored by TLC (EA/PE=1/15). The resulting mixture was concentrated under reduced pressure. The residue was basified to pH 8 with saturated NaHCO3 (aq.). The resulting mixture was extracted with CH2Cl2 (3×50 mL). The combined organic layers were washed with brine (1×50 mL), dried over anhydrous Na2SO4. After filtration, the filtrate was concentrated under reduced pressure. The residue (850 mg) was used in the next step (E00386-047) directly without further purification.

4-chloro-5-(4-[[2-methyl-4-(trifluoromethoxy)phenyl]methyl]-3-oxopiperazin-1-yl)-2-(oxan-2-yl)-2,3-dihydropyridazin-3-one To a stirred mixture of 4-chloro-2-(oxan-2-yl)-5-(3-oxopiperazin-1-yl)-2,3-dihydropyridazin-3-one (200 mg, 0.64 mmol, 1 equiv.) and Cs2CO3 (625.1 mg, 1.92 mmol, 3.000 equiv.) in DMF (8 mL, 103.37 mmol, 161.652 equiv.) were added 1-(chloromethyl)-2-methyl-4-(trifluoromethoxy)benzene (215.4 mg, 0.96 mmol, 1.500 equiv.) and KI (10.6 mg, 0.06 mmol, 0.100 equiv.) in portions at room temperature. The final reaction mixture was irradiated with microwave radiation for 2 h at 100 degrees Celsius. The reaction was monitored by LCMS. The reaction was quenched by the addition of Water (25 mL) at room temperature. The resulting mixture was extracted with EtOAc (3×100 mL). The combined organic layers were washed with brine (3×100 mL), dried over anhydrous Na2SO4. After filtration, the filtrate was concentrated under reduced pressure. The residue was purified by Prep-TLC (PE/EtOAc=50:1) to afford 4-chloro-5-(4-[[2-methyl-4-(trifluoromethoxy)phenyl]methyl]-3-oxopiperazin-1-yl)-2-(oxan-2-yl)-2,3-dihydropyridazin-3-one (300 mg, 93.66%) as a yellow oil.

Compound JT: 4-chloro-5-(4-[[2-methyl-4-(trifluoromethoxy)phenyl]methyl]-3-oxopiperazin-1-yl)-2,3-dihydropyridazin-3-one To a stirred solution of 4-chloro-5-(4-[[2-methyl-4-(trifluoromethoxy)phenyl]methyl]-3-oxopiperazin-1-yl)-2-(oxan-2-yl)-2,3-dihydropyridazin-3-one (280 mg) in DCM (8 mL) was added TFA (2 mL) dropwise at room temperature. The reaction was stirred for 2 h at room temperature. The reaction was monitored by LCMS. The resulting mixture was concentrated under reduced pressure. The residue was basified to pH 8 with saturated NaHCO3 (aq.). The resulting mixture was extracted with EtOAc (3×100 mL). The combined organic layers were washed with brine (3×100 mL), dried over anhydrous Na2SO4. After filtration, the filtrate was concentrated under reduced pressure. The crude product (100 mg) was purified by Prep-HPLC with the following conditions (Column: XBridge Prep C18 OBD Column, 5 um, 19*150 mm; Mobile Phase A: Water (10 mmol/L NH4HCO3), Mobile Phase B: ACN; Flow rate: 20 mL/min; Gradient: 25% B to 60%/6 B in 7 min; 254 nm; Rt: 8.50 min) to afford 4-chloro-5-(4-[[2-methyl-4-(trifluoromethoxy)phenyl]methyl]-3-oxopiperazin-1-yl)-2,3-dihydropyridazin-3-one (71.1 mg) as a white solid.

JU

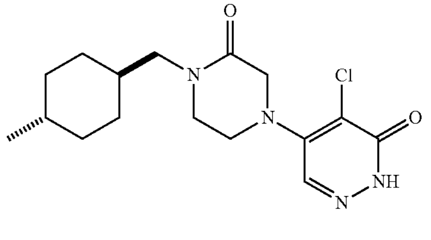

JU was prepared by the methods described for Compound JT above.

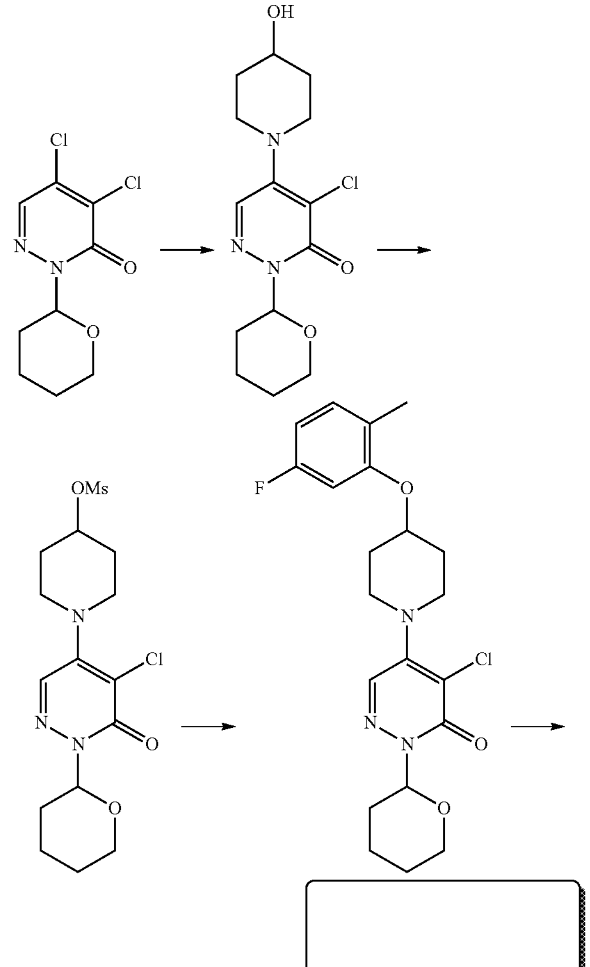

Preparation of Compound JV 4-chloro-5-(4-hydroxypiperidin-1-yl)-2-(oxan-2-yl)-2,3-dihydropyridazin-3-one To a stirred solution of 4,5-dichloro-2-(oxan-2-yl)-2,3-dihydropyridazin-3-one (28 g, 112.41 mmol, 1 equiv.) and piperidin-4-ol (17.1 g, 0.17 mmol, 1.5 equiv.) in DMA (200 mL) was added DIEA (29.1 g, 0.22 mmol, 2.0 equiv.) at room temperature. The resulting mixture was stirred for 48 h at 100 degrees Celsius. The mixture was allowed to cool down to room temperature. To the above mixture was added H2O (500 mL). The resulting mixture was extracted with CH2Cl2:MeOH (10:1)(5×200 mL). The combined organic layers were washed with saturated NaCl (aq.) (5×300 mL), dried over anhydrous Na2SO4. After filtration, the filtrate was concentrated under reduced pressure. The resulting mixture was concentrated under vacuum. The crude product (25 g) was purified by reverse phase flash with the following conditions (Column: C18 330 g; Mobile Phase A: Water (10 mmol/L NH4HCO3), Mobile Phase B: ACN; Flow rate: 40 mL/min; Gradient: 30% B to 80% B in 20 min; 254&220 nm; Rt: 6.5 min) to afford 4-chloro-5-(4-hydroxypiperidin-1-yl)-2-(oxan-2-yl)-2,3-dihydropyridazin-3-one (10 g, 28.35%) as a yellow solid.

1-[5-chloro-1-(oxan-2-yl)-6-oxo-1,6-dihydropyridazin-4-yl]piperidin-4-yl methanesulfonate To a stirred solution of 4-chloro-5-(4-hydroxypiperidin-1-yl)-2-(oxan-2-yl)-2,3-dihydropyridazin-3-one (5 g, 15.93 mmol, 1 equiv.) and triethylamine (3.2 g, 31.62 mmol, 1.985 equiv.) in DCM (70 mL) was added methanesulfonyl chloride (2.2 g, 19.12 mmol, 1.2 equiv.) dropwise over 10 min at 10 degrees Celsius. The resulting mixture was stirred for additional 5 h at room temperature. The reaction was monitored by LCMS. The reaction was quenched with Water (100 ml) at room temperature. The resulting mixture was extracted with EtOAc (5×200 mL). The combined organic layers were washed with saturated NaCl (aq.) (1×150 mL), dried over anhydrous Na2SO4. After filtration, the filtrate was concentrated under reduced pressure to afford 1-[5-chloro-1-(oxan-2-yl)-6-oxo-1,6-dihydropyridazin-4-yl]piperidin-4-yl methanesulfonate (6.5 g, crude) as a yellow solid.

4-chloro-5-[4-(5-fluoro-2-methylphenoxy)piperidin-1-yl]-2-(oxan-2-yl)-2,3-dihydropyridazin-3-one To a stirred solution of 1-[5-chloro-1-(oxan-2-yl)-6-oxo-1,6-dihydropyridazin-4-yl]piperidin-4-yl methanesulfonate (400 mg, 1.02 mmol, 1 equiv.) and 5-fluoro-2-methylphenol (193.1 mg, 1.53 mmol, 1.5 equiv.) in ACN (25 mL) was added Cs2CO3 (665.2 mg, 2.04 mmol, 2 equiv.) in portions at room temperature under nitrogen atmosphere. The resulting mixture was stirred for overnight at 75 degrees Celsius under nitrogen atmosphere. The reaction was monitored by LCMS. The resulting mixture was concentrated under reduced pressure. The resulting mixture was extracted with EtOAc (10× mL). The combined organic layers were washed with brine (3×10 mL), dried over anhydrous Na2SO4. After filtration, the filtrate was concentrated under reduced pressure. The residue was purified by Prep-TLC (PE/EtOAc 5:1) to afford 4-chloro-5-[4-(5-fluoro-2-methylphenoxy)piperidin-1-yl]-2-(oxan-2-yl)-2,3-dihydropyridazin-3-one (240 mg, 55.73%) as a white solid.

Compound JV: 4-chloro-5-[4-(5-fluoro-2-methylphenoxy)piperidin-1-yl]-2,3-dihydropyridazin-3-one A solution of 4-chloro-5-[4-(5-fluoro-2-methylphenoxy)piperidin-1-yl]-2-(oxan-2-yl)-2,3-dihydropyridazin-3-one (120 mg, 0.28 mmol, 1 equiv.) and CF3COOH (1 mL, 13.46 mmol, 47.333 equiv.) in DCM (9 mL, 141.57 mmol, 497.730 equiv.) was stirred for 3 h at 0 degrees Celsius. The reaction was monitored by LCMS. The crude product (120 mg) was purified by reverse phase flash with the following conditions (Column: XBridge Prep OBD C18 Column 30*150 mm 5 um; Mobile Phase A: Water (10 mmol/L NH4HCO3), Mobile Phase B: ACN; Flow rate: 60 mL/min; Gradient: 30% B to 60% B in 7 min; 220 nm; Rt: 6.65 min) to afford 4-chloro-5-[4-(5-fluoro-2-methylphenoxy)piperidin-1-yl]-2,3-dihydropyridazin-3-one (19.7 mg, 20.50%) as a white solid.

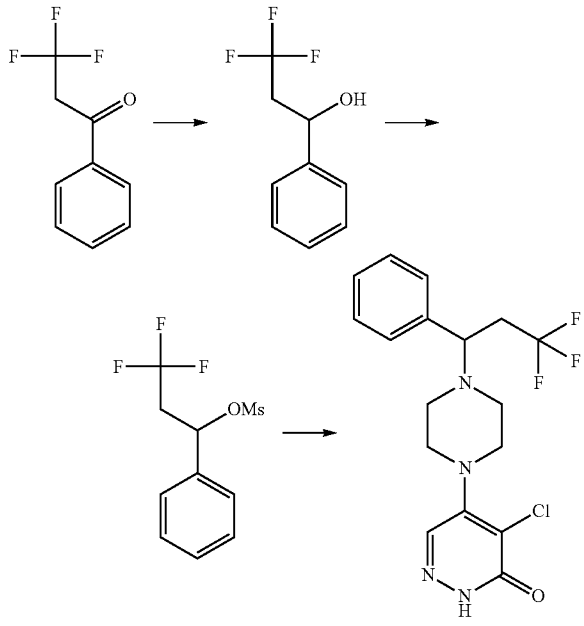

JW

Preparation of JW 3,3,3-trifluoro-1-phenylpropan-1-ol

To a solution of 3,3,3-trifluoro-1-phenylpropan-1-one (2.5 g, 13.29 mmol, 1 equiv.) in MeOH (50 mL) was added NaBH4 (1.5 g, 39.86 mmol, 3 equiv.) at 0 degrees Celsius. The reaction was stirred for 2 h at room temperature. The reaction was monitored by TLC (EA/PE=1/10). The resulting mixture was concentrated under reduced pressure. The residue was purified by silica gel column chromatography, eluted with PE/EtOAc (100/1 to 10/1) to afford 3,3,3-trifluoro-1-phenylpropan-1-ol (2 g, 98.94%) as a light yellow oil.

3,3,3-trifluoro-1-phenylpropyl methanesulfonate

To a mixture of 3,3,3-trifluoro-1-phenylpropan-1-ol (1 g, 5.26 mmol, 1 equiv.) and Et3N (1.6 g, 15.78 mmol, 3 equiv.) in DCM (50 mL) was added MsCl (722.9 mg, 6.31 mmol, 1.2 equiv.) at 0 degrees Celsius under nitrogen atmosphere. The reaction was stirred for 16 h at room temperature. The reaction was monitored by LCMS. The reaction was quenched by the addition of Water (50 mL) at room temperature. The resulting mixture was extracted with EtOAc (3×100 mL). The combined organic layers were washed with brine (1×100 mL), dried over anhydrous Na2SO4. After filtration, the filtrate was concentrated under reduced pressure. The residue was purified by Prep-TLC (PE/EtOAc 20/1) to afford 3,3,3-trifluoro-1-phenylpropyl methanesulfonate (600 mg, 42.53%) as a yellow oil.

Compound JW: 4-chloro-5-[4-[(1R)-3,3,3-trifluoro-1-phenylpropyl]piperazin-1-yl]-2,3-dihydropyridazin-3-one and 4-chloro-5-[4-[(1S)-3,3,3-trifluoro-1-phenylpropyl]piperazin-1-yl]-2,3-dihydropyridazin-3-one To a stirred mixture of 4-chloro-5-(piperazin-1-yl)-2,3-dihydropyridazin-3-one (600 mg, 2.80 mmol, 1 equiv.) and DIEA (1.1 g, 8.39 mmol, 3 equiv.) in DMF (20 mL) was added 3,3,3-trifluoro-1-phenylpropyl methanesulfonate (1.0 g, 3.63 mmol, 1.3 equiv.) in portions at room temperature under nitrogen atmosphere. The reaction was stirred for 16 h at room temperature. The reaction was monitored by LCMS. The reaction mixture was purified by reverse phase flash with the following conditions (Column: XBridge Shield RP18 OBD Column 30*150 mm, 5 um; Mobile Phase A: Water (10 mmol/L NH4HCO3), Mobile Phase B: ACN; Flow rate: 60 L/min; Gradient: 10% B to 40% B in 10 min; 254 nm; Rt: 9.72 min) to afford the product (50 mg). The product (50 mg) was purified by Chiral-Prep-HPLC with the following conditions: Column, Repaired IC, 0.46*5 cm; 3 um; mobile phase: Hex:EtOH (0.2% DEA)=50:50; Detector, UV-254 nm. 4-chloro-5-[4-[(1R)-3,3,3-trifluoro-1-phenylpropyl]piperazin-1-yl]-2,3-dihydropyridazin-3-one (7.3 mg, 0.68%) was obtained at 4.288 min as a white solid and 4-chloro-5-[4-[(1S)-3,3,3-trifluoro-1-phenylpropyl]piperazin-1-yl]-2,3-dihydropyridazin-3-one (7.4 mg, 0.68%) was obtained at 3.265 min as a white solid.

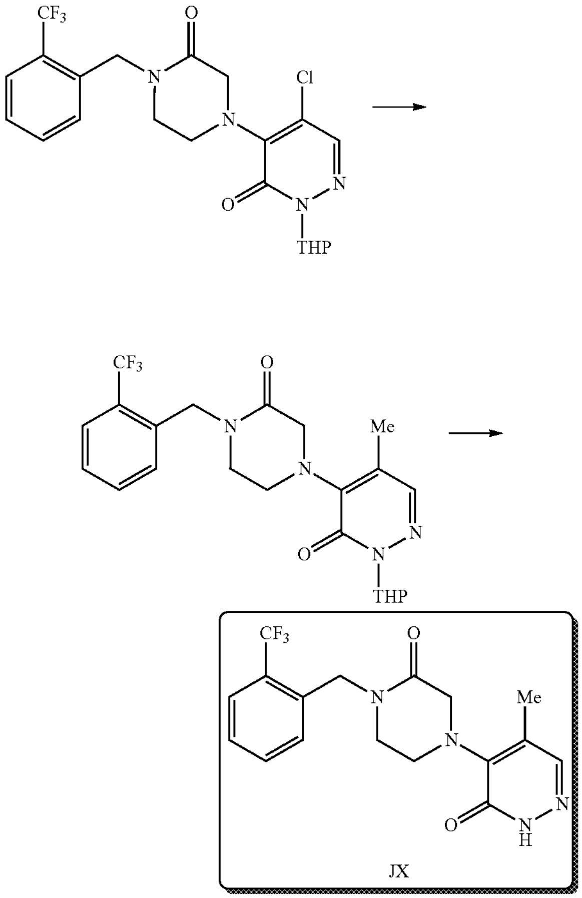

JX

Preparation of JX 5-methyl-2-(oxan-2-yl)-4-(3-oxo-4-[[2-(trifluoromethyl)phenyl]methyl]piperazin-1-yl)-2,3-dihydropyridazin-3-one To a solution of 5-chloro-2-(oxan-2-yl)-4-(3-oxo-4-[[2-(trifluoromethyl)phenyl]methyl]piperazin-1-yl)-2,3-dihydropyridazin-3-one (120 mg, 0.25 mmol, 1 equiv.) and methylboronic acid (45.8 mg, 760 mmol, 3 equiv.) in 1,4-dioxane (5 mL) and H2O (1 mL) were added K2CO3 (70.4 mg, 0.51 mmol, 2 equiv) and Pd(PPh3)4 (29.4 mg, 0.03 mmol, 0.1 equiv). The final reaction mixture was irradiated with microwave radiation for 3 h at 130 degrees Celsius under nitrogen atmosphere, the resulting mixture was concentrated under reduced pressure. The residue was purified by Prep-TLC (PE:EA=1:1) to afford 5-methyl-2-(oxan-2-yl)-4-(3-oxo-4-[[2-(trifluoromethyl)phenyl]methyl]piperazin-1-yl)-2,3-dihydropyridazin-3-one (100 mg, 87.11%) as a white solid.

Compound JX 5-methyl-4-(3-oxo-4-[[2-(trifluoromethyl)phenyl]methyl]piperazin-1-yl)-2,3-dihydropyridazin-3-one To a stirred solution of 5-methyl-2-(oxan-2-yl)-4-(3-oxo-4-[[2-(trifluoromethyl)phenyl]methyl]piperazin-1-yl)-2,3-dihydropyridazin-3-one (80 mg) in DCM (10 mL) was added TFA (2 mL) dropwise at room temperature under nitrogen atmosphere. The mixture was stirred at room temperature 2 h. Desired product could be detected by LCMS. The resulting mixture was concentrated under reduced pressure. The crude product (60 mg) was purified by Prep-HPLC with the following conditions (Column: XBridge Prep C18 OBD Column, 5 um, 19*150 mm; Mobile Phase A: Water (10 mmol/L NH4HCO3), Mobile Phase B: ACN; Flow rate: 20 mL/min; Gradient: 25% B to 60% B in 7 min; 254 nm; Rt: 5.58 min) to afford 5-methyl-4-(3-oxo-4-[[2-(trifluoromethyl)phenyl]methyl]piperazin-1-yl)-2,3-dihydropyridazin-3-one (8.6 mg, 13.22%) as a white solid.

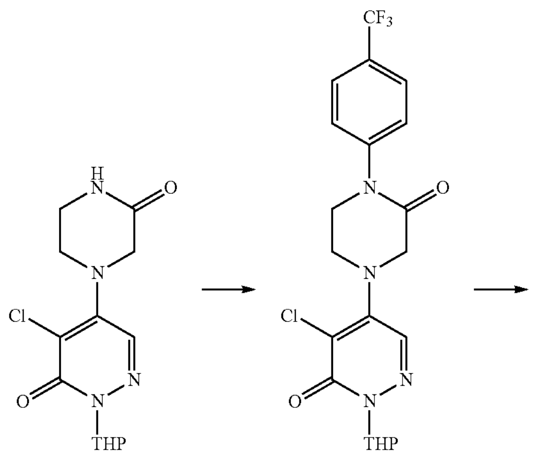

-continued

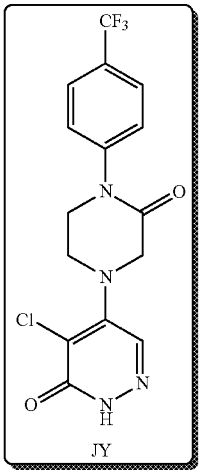

JY

Preparation of Compound JY 4-chloro-2-(oxan-2-yl)-5-[3-oxo-4-[4-(trifluoromethyl)phenyl]piperazin-1-yl]-2,3-dihydropyridazin-3-one To a stirred solution of 1-iodo-4-(trifluoromethyl)benzene (500 mg, 1.84 mmol, 1 equiv), K3PO4 (780.4 mg, 3.68 mmol, 2 equiv.) and 4-chloro-2-(oxan-2-yl)-5-(3-oxopiperazin-1-yl)-2,3-dihydropyridazin-3-one (632.4 mg, 2.02 mmol, 1.1 equiv.) in Toluene (8 mL) were added CuI (17.5 mg, 0.09 mmol, 0.05 equiv.) and N1,N2-dimethylethane-1,2-diamine (16.17 mg, Infinity mmol, Infinity equiv). The resulting mixture was stirred for overnight at 100 degrees Celsius. The resulting mixture was concentrated under vacuum. The residue was purified by silica gel column chromatography, eluted with PE/EtOAc (5:1) to afford 4-chloro-2-(oxan-2-yl)-5-[3-oxo-4-[4-(trifluoromethyl)phenyl]piperazin-1-yl]-2,3-dihydropyridazin-3-one (180 mg, 21.43%) as an off-white solid.

Compound JY: 4-chloro-5-[3-oxo-4-[4-(trifluoromethyl)phenyl]piperazin-1-yl]-2,3-dihydropyridazin-3-one To a stirred solution of 4-chloro-2-(oxan-2-yl)-5-[3-oxo-4-[4-(trifluoromethyl)phenyl]piperazin-1-yl]-2,3-dihydropyridazin-3-one (180 mg, 0.39 mmol, 1 equiv.) in CH2Cl2 was added TFA (1 mL). The resulting mixture was stirred for 1.5 h at room temperature. The crude product was purified by Prep-HPLC with the following conditions (Column: XBridge Shield RP18 OBD Column 30*150 mm, 5 um; Mobile Phase A: Water (10 mmol/L NH4HCO3), Mobile Phase B: ACN; Flow rate: 60 mL/min; Gradient: 10% B to 50% B in 7 min; 254 nm; Rt: 6.63 min) to afford 4-chloro-5-[3-oxo-4-[4-(trifluoromethyl)phenyl]piperazin-1-yl]-2,3-dihydropyridazin-3-one (74 mg, 50.39%) as a white solid.

JZ

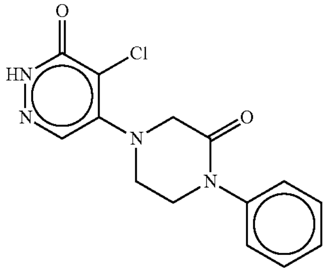

KA

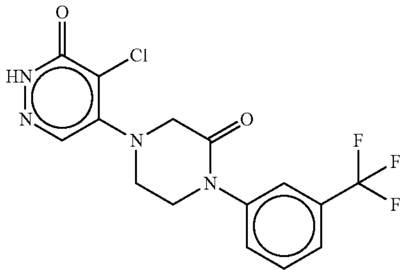

KB

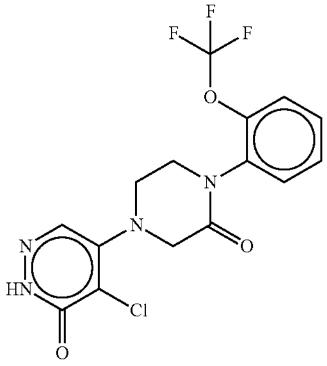

KC

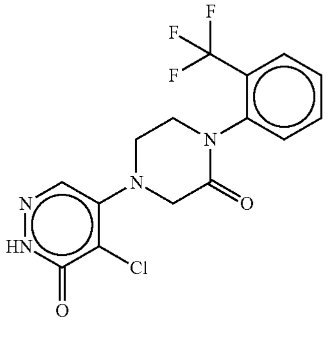

Compounds JZ, KA, KB, and KC were prepared by the methods described for compound JY above.

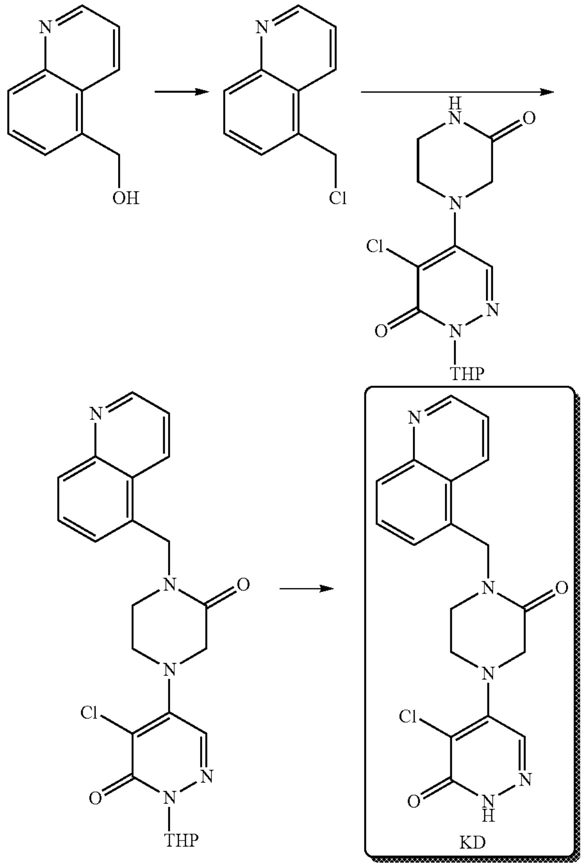

KD

Preparation of Compound KD 5-(chloromethyl)quinoline

To a stirred solution of quinolin-5-ylmethanol (400 mg, 2.51 mmol, 1 equiv.) in DCM (10 mL) was added SOCl2 (597.9 mg, 5.03 mmol, 2.000 equiv.) dropwise at 0 degrees Celsius. The reaction mixture was stirred for 16 h at room temperature. The reaction was monitored by LCMS. The resulting mixture was concentrated under reduced pressure. This resulted in 5-(chloromethyl)quinoline (400 mg, 89.62%) as a yellow solid.

4-chloro-2-(oxan-2-yl)-5-[3-oxo-4-(quinolin-5-ylmethyl)piperazin-1-yl]-2,3-dihydropyridazin-3-one To a stirred mixture of 4-chloro-2-(oxan-2-yl)-5-(3-oxopiperazin-1-yl)-2,3-dihydropyridazin-3-one (200 mg, 0.64 mmol, 1 equiv.) and 5-(chloromethyl)quinoline (170.4 mg, 0.96 mmol, 1.500 equiv.) in DMF (5 mL) was added Cs2CO3 (625.1 mg, 1.92 mmol, 3.000 equiv.) at room temperature under nitrogen atmosphere. The reaction mixture was stirred for 2 h at 100 degrees Celsius. The reaction was monitored by LCMS. The mixture was allowed to cool down to room temperature. The reaction was quenched by the addition of Water (50 mL) at room temperature. The resulting mixture was extracted with CH2Cl2(3×300 mL). The combined organic layers were washed with brine (3×50 mL), dried over anhydrous Na2SO4. After filtration, the filtrate was concentrated under reduced pressure. The residue was purified by Prep-TLC (CH2Cl2/MeOH 50/1 to 20/1) to afford 4-chloro-2-(oxan-2-yl)-5-[3-oxo-4-(quinolin-5-ylmethyl)piperazin-1-yl]-2,3-dihydropyridazin-3-one (160 mg, 55.12%) as a light yellow solid.

Compound KD: 4-chloro-5-[3-oxo-4-(quinolin-5-ylmethyl)piperazin-1-yl]-2,3-dihydropyridazin-3-one To a stirred solution of 4-chloro-2-(oxan-2-yl)-5-[3-oxo-4-(quinolin-5-ylmethyl)piperazin-1-yl]-2,3-dihydropyridazin-3-one (160 mg, 0.35 mmol, 1 equiv.) in DCM (10 mL) was added TFA (1 mL, 13.46 mmol, 38.195 equiv.) dropwise at room temperature. The reaction mixture was stirred for 16 h at room temperature. The reaction was monitored by LCMS. The resulting mixture was concentrated under reduced pressure. The residue was basified to pH=8 with saturated NaHCO3 (aq.). The resulting mixture was extracted with CH2Cl2(3×100 mL). The combined organic layers were washed with brine (1×80 mL), dried over anhydrous Na2SO4. After filtration, the filtrate was concentrated under reduced pressure. The residue was purified by Prep-HPLC with the following conditions (Column: XBridge Shield RP18 OBD Column 30*150 mm, 5 um; Mobile Phase A: Water (10 mmol/L NH4HCO3), Mobile Phase B: ACN; Flow rate: 60 mL/min; Gradient: 5% B to 27% B in 7 min; 254 nm; Rt: 6.78 min) to afford 4-chloro-5-[3-oxo-4-(quinolin-5-ylmethyl)piperazin-1-yl]-2,3-dihydropyridazin-3-one (34.5 mg, 26.47%) as a white solid.

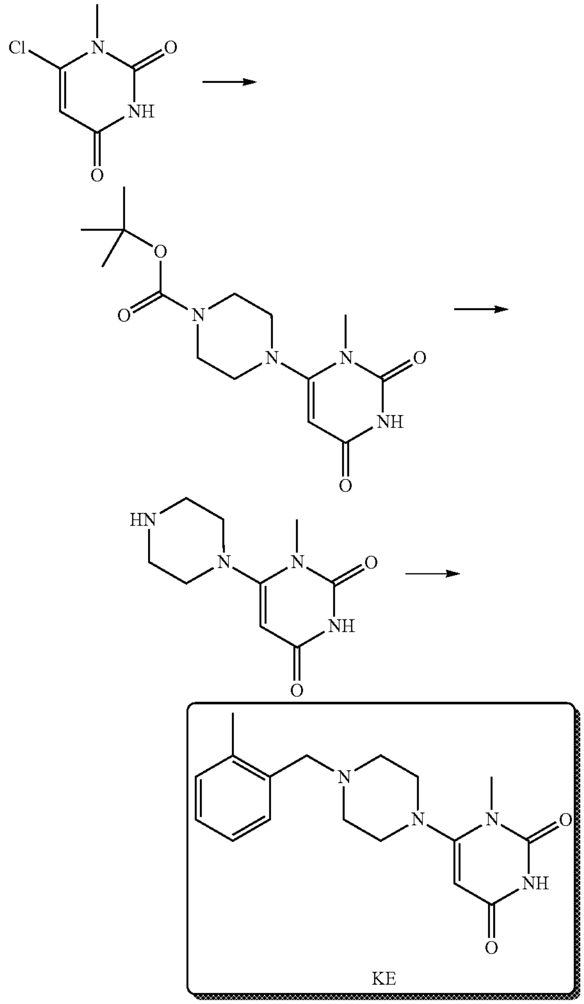

KE

Preparation of Compound KE

Tert-Butyl 4-(3-methyl-2,6-dioxo-1,2,3,6-tetrahydropyrimidin-4-yl)piperazine-1-carboxylate To a stirred solution of 6-chloro-1-methyl-1,2,3,4-tetrahydropyrimidine-2,4-dione (3 g, 18.68 mmol, 1 equiv.) and tert-butyl piperazine-1-carboxylate (4.2 g, 22.42 mmol, 1.2 equiv.) in EtOH (60 mL) was added NaHCO3 (3.1 g, 37.37 mmol, 2 equiv.) at room temperature. The mixture was stirred at 70 degrees Celsius for 5 h. The mixture was concentrated under reduced pressure. The residue was purified by silica gel column chromatography, eluted with CH2Cl2/MeOH (15:1 to 10:1) to afford tert-butyl 4-(3-methyl-2,6-dioxo-1,2,3,6-tetrahydropyrimidin-4-yl)piperazine-1-carboxylate (5.38 g, 92.78%) as a white solid.

1-methyl-6-(piperazin-1-yl)-1,2,3,4-tetrahydropyrimidine-2,4-dione TFA Salt

To a stirred solution of tert-butyl 4-(3-methyl-2,6-dioxo-1,2,3,6-tetrahydropyrimidin-4-yl)piperazine-1-carboxylate (5.38 g, 17.34 mol, 1 equiv.) in DCM (60 mL) was added 2,2,2-trifluoroacetaldehyde (10 mL) dropwise at room temperature. The mixture was stirred at room temperature for 5 h. The mixture was concentrated under reduced pressure. The precipitated solids were collected by filtration and washed with MeOH (3×3 mL). To afford 1-methyl-6-(piperazin-1-yl)-1,2,3,4-tetrahydropyrimidine-2,4-dione (5.28 g, crude) as a white solid.

Compound KE: 1-methyl-6-[4-[(2-methylphenyl)methyl]piperazin-1-yl]-1,2,3,4-tetrahydropyrimidine-2,4-dione To a stirred solution of 1-methyl-6-(piperazin-1-yl)-1,2,3,4-tetrahydropyrimidine-2,4-dione (100 mg, 0.48 mmol, 1 equiv.) in DMF (4 mL) was added DIEA (307.4 mg, 2.38 mmol, 5 equiv.) dropwise at room temperature. To above solution was added 1-(bromomethyl)-2-methylbenzene (88.0 mg, 0.48 mmol, 1 equiv.) at room temperature. The solution was stirred at room temperature for 16 h. The mixture was concentrated under reduced pressure. The crude product (40 mg) was purified by Prep-HPLC with the following conditions (Column: XBridge Shield RP18 OBD Column 30*150 mm, 5 um; Mobile Phase A: Water (10 mmol/L NH4HCO3), Mobile Phase B: ACN; Flow rate: 60 mL/min; Gradient: 20% B to 50% B in 7 min; 254 nm; Rt: 6.2 min) to afford 1-methyl-6-[4-[(2-methylphenyl)methyl]piperazin-1-yl]-1,2,3,4-tetrahydropyrimidine-2,4-dione (51.6 mg, 34.51%) as a white solid.

KF

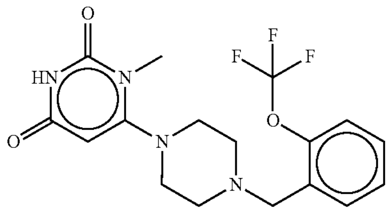

Compound KF was prepared by the methods described for Compound JY above.

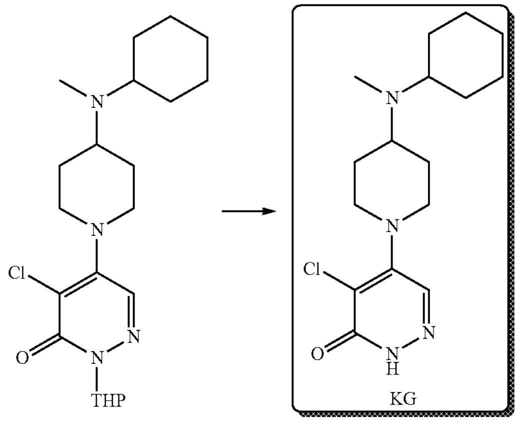

KG

Compound KG 4-chloro-5-[4-[cyclohexyl(methyl)amino]piperidin-1-yl]-2,3-dihydropyridazin-3-one To a stirred solution of 4-chloro-5-[4-[cyclohexyl(methyl)amino]piperidin-1-yl]-2-(oxan-2-yl)-2,3-dihydropyridazin-3-one (50 mg, 0.12 mmol, 1 equiv.) in DCM (6 mL) was added TFA (2 mL) dropwise/in portions at room temperature under nitrogen atmosphere. The resulting mixture was stirred for overnight at room temperature under nitrogen atmosphere. The reaction was monitored by LCMS. The resulting mixture was concentrated under reduced pressure. The crude product (20 mg) was purified by Prep-HPLC with the following conditions (Column: Kinetex EVO C18 Column 21.2*150.5 um; Mobile Phase A: Water (0.1% FA), Mobile Phase B: ACN; Flow rate: 20 mL/min; Gradient: 2% B to 25% B in 7 min; 254/220 nm; Rt: 6.5 min) to afford 4-chloro-5-[4-[cyclohexyl(methyl)amino]piperidin-1-yl]-2,3-dihydropyridazin-3-one (2.0 mg) as a white solid.

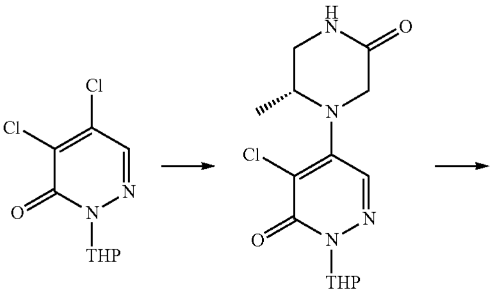

-continued

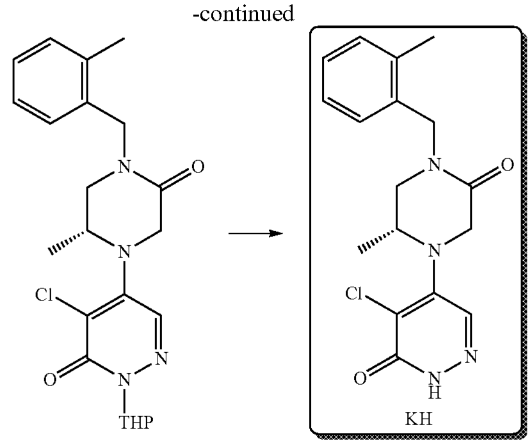

KH

Preparation of Compound KH 4-chloro-5-((R)-2-methyl-5-oxopiperazin-1-yl)-2-(tetrahydro-2H-pyran-2-yl)pyridazin-3(2H)-one To a stirred mixture of 4,5-dichloro-2-(tetrahydro-2H-pyran-2-yl)pyridazin-3(2H)-one (956.8 mg, 3.81 mmol, 1 equiv.) and (5R)-5-methylpiperazin-2-one (869.9 mg, 7.62 mmol, 2 equiv). The resulting mixture was stirred for overnight at 90 degrees Celsius. The crude product was purified by reverse phase flash with the following conditions (Column: spnerical C18, 20-40 um, 330 g; Mobile Phase A: Water (5 mmol/L NH4HCO3), Mobile Phase B: ACN; Flow rate: 80 mL/min; Gradient: 15% B to 60% B in 55 min; 254 nm) to afford 4-chloro-5-((R)-2-methyl-5-oxopiperazin-1-yl)-2-(tetrahydro-2H-pyran-2-yl)pyridazin-3(2H)-one (700 mg, 55.87%) as a yellow solid.

4-chloro-5-((R)-2-methyl-4-(2-methylbenzyl)-5-oxopiperazin-1-yl)-2-(tetrahydro-2H-pyran-2-yl)pyridazin-3(2H)-one To a stirred solution of 4-chloro-5-((R)-2-methyl-5-oxopiperazin-1-yl)-2-(tetrahydro-2H-pyran-2-yl)pyridazin-3(2H)-one (210 mg, 0.64 mmol, 1 equiv.) and NaH (46.0 mg, 1.92 mmol, 3 equiv.) in DMF (5 mL) was added 1-(bromomethyl)-2-methylbenzene (153.7 mg, 0.83 mmol, 1.300 equiv). The resulting mixture was stirred for 4 h at room temperature. The solution was purified by reverse phase flash with the following conditions (Column: spnerical C18, 20-40 um, 120 g; Mobile Phase A: Water (5 mmol/L NH4HCO3), Mobile Phase B: ACN; Flow rate: 45 mL/min; Gradient: 10% B to 60% B in 55 min; 254 nm) to afford 4-chloro-5-((R)-2-methyl-4-(2-methylbenzyl)-5-oxopiperazin-1-yl)-2-(tetrahydro-2H-pyran-2-yl)pyridazin-3(2H)-one (90 mg, 32.55%) as a white solid.

Compound KH: 4-chloro-5-[(2R)-2-methyl-4-[(2-methylphenyl)methyl]-5-oxopiperazin-1-yl]-2,3-dihydropyridazin-3-one To a stirred solution of 4-chloro-5-[2-methyl-4-[(2-methylphenyl)methyl]-5-oxopiperazin-1-yl]-2-(oxan-2-yl)-2,3-dihydropyridazin-3-one (105 mg, 0.24 mmol, 1 equiv.) in DCM was added TFA (1 mL, 13.46 mmol, 55.25 equiv). The solution was basified to pH 8 with saturated NaHCO3 (aq.). The resulting mixture was extracted with CH2Cl2(3×10 mL). The combined organic layers were washed with brine (3×10 mL), dried over anhydrous Na2SO4. After filtration, the filtrate was concentrated under reduced pressure. The crude product was purified by Prep-HPLC with the following conditions (Column: XBridge Shield RP18 OBD Column 30*150 mm, 5 um; Mobile Phase A: Water (10 mmol/L NH4HCO3), Mobile Phase B: ACN; Flow rate: 60 mL/min; Gradient: 10% B to 30% B in 7 min; 254 nm; Rt: 5.25 min) to afford 4-chloro-5-[(2S)-2-methyl-4-[(2-methylphenyl)methyl]-5-oxopiperazin-1-yl]-2,3-dihydropyridazin-3-one (4.7 mg, 5.56%) as a white solid and 4-chloro-5-[(2S)-2-methyl-4-[(2-methylphenyl)methyl]-5-oxopiperazin-1-yl]-2,3-dihydropyridazin-3-one as a dark yellow solid.

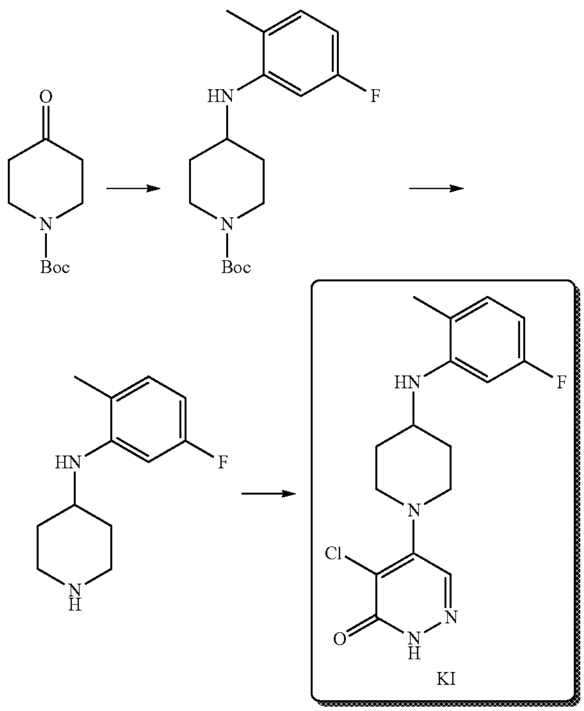

KI

Preparation of Compound KI

Tert-Butyl 4-[(5-fluoro-2-methylphenyl)amino]piperidine-1-carboxylate

To a stirred solution of 5-fluoro-2-methylaniline (2 g, 15.98 mmol, 1 equiv.) and tert-butyl 4-oxopiperidine-1-carboxylate (3.8 g, 19.07 mmol, 1.193 equiv.) in EtOH (50 mL) was added AcOH (0.25 mL) at 0 degrees Celsius. The resulting mixture was stirred for 1 h at 0 degrees Celsius. To the above mixture was added sodium triacetoxyborohydride (6 g) in portions over 0.5 min at 0 degrees Celsius. The resulting mixture was stirred for additional 1 h at 0 degrees Celsius. The reaction was monitored by LCMS. To the above mixture was added H2O (100 ml). The resulting mixture was extracted with CH2Cl2(3×200 mL). The combined organic layers were washed with saturated NaCl (aq.) (3×250 mL), dried over anhydrous Na2SO4. After filtration, the filtrate was concentrated under reduced pressure. The residue was purified by silica gel column chromatography, eluted with CHCl3/MeOH (50:0 to 50:1) to afford tert-butyl 4-[(5-fluoro-2-methylphenyl)amino]piperidine-1-carboxylate (2.2 g, 44.64%) as a yellow oil.

N-(5-fluoro-2-methylphenyl)piperidin-4-amine

A solution of tert-butyl 4-[(5-fluoro-2-methylphenyl)amino]piperidine-1-carboxylate (500 mg, 1.62 mmol, 1 equiv.) and DCM (7 mL) in DCM (7 mL) was stirred for 2 h at 0 degrees Celsius. The reaction was monitored by LCMS. The resulting mixture was concentrated under reduced pressure to afford N-(5-fluoro-2-methylphenyl)piperidin-4-amine (300 mg, crude) as a light yellow crude oil.

Compound KI: 4-chloro-5-[4-[(5-fluoro-2-methylphenyl)amino]piperidin-1-yl]-2,3-dihydropyridazin-3-one To a stirred solution/mixture of N-(5-fluoro-2-methylphenyl)piperidin-4-amine (200 mg, 0.96 mmol, 1 equiv.) and 4,5-dichloro-2,3-dihydropyridazin-3-one (190.1 mg, 1.15 mmol, 1.20 equiv.) in DMA (10 mL, 107.55 mmol, 112.00 equiv.) was added DIEA (372.3 mg, 2.88 mmol, 3.00 equiv.) in portions at room temperature under nitrogen atmosphere. The resulting mixture was stirred for overnight at 100 degrees Celsius under nitrogen atmosphere. The reaction was monitored by LCMS. The resulting mixture was extracted with EtOAc (50× mL). The combined organic layers were washed with brine (3×50 mL), dried over anhydrous Na2SO4. After filtration, the filtrate was concentrated under reduced pressure. The crude product (80 mg) was purified by Prep-HPLC with the following conditions (Column: XBridge Shield RP18 OBD Column 30*150 mm, 5 um; Mobile Phase A: Water (10 mmol/L NH4HCO3+0.1% NH3·H2O), Mobile Phase B: ACN; Flow rate: 60 mL/min; Gradient: 32% B to 50% B in 8 min; 254 nm; Rt: 7.5 min) to afford 4-chloro-5-[4-[(5-fluoro-2-methylphenyl)amino]piperidin-1-yl]-2,3-dihydropyridazin-3-one (20.9 mg) as a white solid.

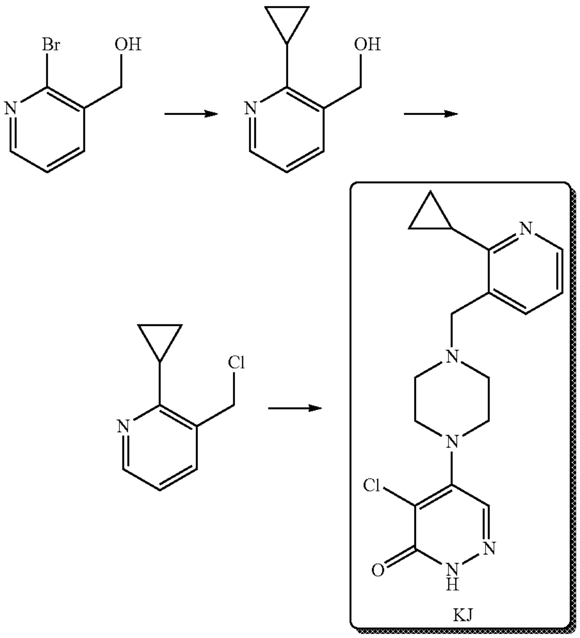

KJ

Preparation of KJ (2-cyclopropylpyridin-3-yl)methanol

To a solution of (2-bromopyridin-3-yl)methanol (500 mg, 2.66 mmol, 1 equiv.) and K2CO3 (1102.6 mg, 7.98 mmol, 3 equiv.) in 1,4-dioxane (10 mL) and H2O (2 mL) were added cyclopropylboronic acid (456.8 mg, 5.32 mmol, 2 equiv.) and Pd(PPh3)4 (307.3 mg, 0.27 mmol, 0.1 equiv). After stirring for 4 h at 110 degrees Celsius under a nitrogen atmosphere, the reaction was monitored by LCMS, the resulting mixture was concentrated under reduced pressure. The residue was purified by Prep-TLC (PE/EtOAc 5:1) to afford (2-cyclopropylpyridin-3-yl)methanol (270 mg, 68.06%) as a yellow oil.

3-(chloromethyl)-2-cyclopropylpyridine

To a solution of (2-cyclopropylpyridin-3-yl)methanol (270 mg, 1.81 mmol, 1 equiv.) in DCM (20 mL) was added SOCl2 (645.9 mg, 5.43 mmol, 3 equiv.) at 0 degrees Celsius. The reaction was stirred for 16 h at room temperature. The reaction was monitored by LCMS. The resulting mixture was concentrated under reduced pressure. The residue was used in the next step (E00350-110) directly without further purification.

Compound KJ: 4-chloro-5-[4-[(2-cyclopropylpyridin-3-yl)methyl]piperazin-1-yl]-2,3-dihydropyridazin-3-one To a mixture of 4-chloro-5-(piperazin-1-yl)-2,3-dihydropyridazin-3-one (100 mg, 0.47 mmol, 1 equiv.) and DIEA (301.1 mg, 2.33 mmol, 5 equiv.) in DMF (5 mL) was added 3-(chloromethyl)-2-cyclopropylpyridine (117.1 mg, 0.70 mmol, 1.5 equiv.) at room temperature. The reaction was stirred for 16 h at room temperature. The reaction was monitored by LCMS. The reaction mixture was purified by Prep-HPLC with the following conditions (Column: XBridge Shield RP18 OBD Column 30*150 mm, 5 um; Mobile Phase A: Water (10 mmol/L NH4HCO3), Mobile Phase B: ACN; Flow rate: 60 mL/min; Gradient: 10% B to 30% B in 15 min; 254 nm; Rt: 14.83 min) to afford 4-chloro-5-[4-[(2-cyclopropylpyridin-3-yl)methyl]piperazin-1-yl]-2,3-dihydropyridazin-3-one (28.4 mg, 17.63%) as a white solid.

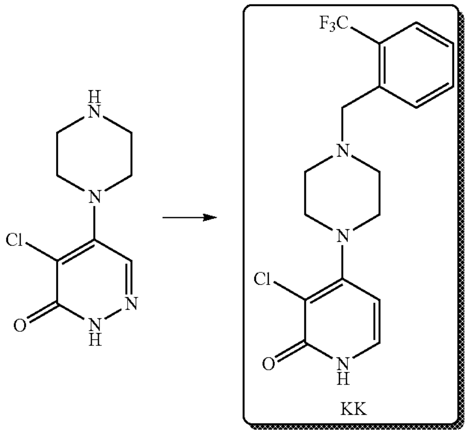

KK

Preparation of KK

3-chloro-4-(4-[[2-(trifluoromethyl)phenyl]methyl]piperazin-1-yl)-1,2-dihydropyridin-2-one To a stirred mixture of 3-chloro-4-(piperazin-1-yl)-1,2-dihydropyridin-2-one (50 mg, 0.23 mmol, 1 equiv.) and DIEA (90.7 mg, 0.70 mmol, 3 equiv.) in DMF (3 mL) was added 1-(bromomethyl)-2-(trifluoromethyl)benzene (55.9 mg, 0.23 mmol, 1 equiv.) at room temperature under nitrogen atmosphere. The resulting mixture was stirred for 16 h at room temperature. The reaction was monitored by LCMS. The crude product (30 mg) was purified by Prep-HPLC with the following conditions (Column: XBridge Prep OBD C18 Column 30×150 mm 5 um; Mobile Phase A: Water (10 mmol/L NH4HCO3), Mobile Phase B: ACN; Flow rate: 60 mL/min; Gradient: 40% B to 60% B in 7 min; 220 nm; Rt: 5.85 min) to afford 3-chloro-4-(4-[[2-(trifluoromethyl)phenyl]methyl]piperazin-1-yl)-1,2-dihydropyridin-2-one (9.9 mg, 11.38%) as a white solid.

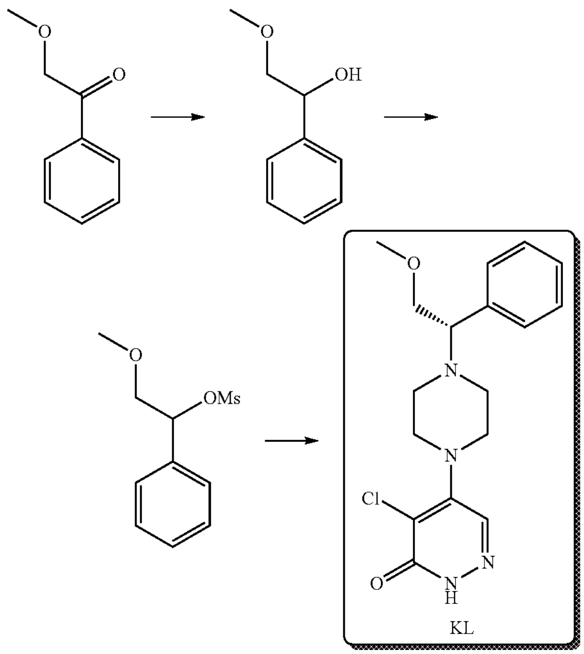

KL

Preparation of Compound KL

2-methoxy-1-phenylethan-1-ol

To a stirred solution of 2-methoxy-1-phenylethan-1-one (1 g, 6.66 mmol, 1 equiv.) in MeOH (20 mL) was added NaBH4 (0.755 g, 19.96 mmol, 2.997 equiv.) at 0 degrees Celsius. The resulting mixture was stirred for 2 h at room temperature. The reaction was monitored by LCMS. The resulting mixture was concentrated under reduced pressure. The residue was purified by silica gel column chromatography, eluted with PE/EtOAc (50:1 to 1:1) to afford 2-methoxy-1-phenylethan-1-ol (800 mg, 78.94%) as a light yellow oil.

2-methoxy-1-phenylethyl methanesulfonate

To a stirred solution of 2-methoxy-1-phenylethan-1-ol (500 mg, 3.29 mmol, 1 equiv.) in DCM (20 mL) was added TEA (1003 mg, 9.91 mmol, 3.017 equiv.) at room temperature. Then MsCl (526.9 mg, 4.60 mmol, 1.400 equiv.) was added at 0 degrees Celsius. The resulting mixture was stirred for 2 h at room temperature. The reaction was monitored by LCMS. The resulting mixture was concentrated under reduced pressure. The residue was purified by Prep-TLC (PE/EtOAc 10:1) to afford 2-methoxy-1-phenylethyl methanesulfonate (340 mg, 44.94%) as a light yellow oil.

Compound KL: 4-chloro-5-[4-[(1S)-2-methoxy-1-phenylethyl]piperazin-1-yl]-2,3-dihydropyridazin-3-one To a stirred mixture of 4-chloro-5-(piperazin-1-yl)-2,3-dihydropyridazin-3-one (463 mg, 1 equiv.) and DIEA (840 mg, 3 equiv.) in DMF (15 mL) was added 2-methoxy-1-phenylethyl methanesulfonate (500 mg, 1 equiv.) at room temperature under nitrogen atmosphere. The resulting mixture was stirred for 3 h at room temperature under nitrogen atmosphere. The reaction was monitored by TLC. The crude product (400 mg) was purified by Prep-HPLC with the following conditions (Column; CHIRALPAK IG, 20*250 mm, 5 um; Mobile Phase A:Hex?0.1% DEA?—HPLC, Mobile Phase B: EtOH—HPLC; Flow rate: 20 mL/min; Gradient: 50 B to 50 B in 20 min; 220/254 nm; RT1:15.045; RT2:17.252) to afford 4-chloro-5-[4-[(1R)-2-methoxy-1-phenylethyl]piperazin-1-yl]-2,3-dihydropyridazin-3-one (22 mg, 2.90%) as a light yellow solid and 4-chloro-5-[4-[(1S)-2-methoxy-1-phenylethyl]piperazin-1-yl]-2,3-dihydropyridazin-3-one (60 mg, 7.92%) as a light yellow solid.

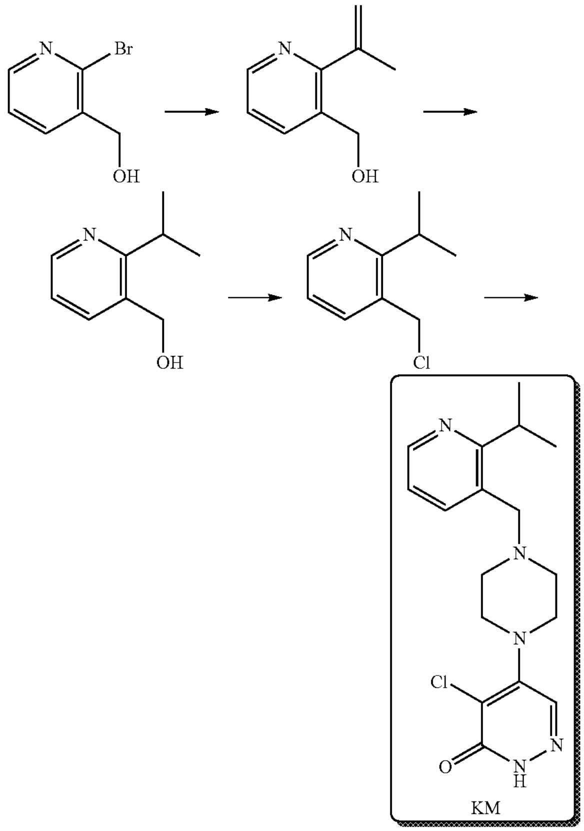

KM

Preparation of KM

[2-(prop-1-en-2-yl)pyridin-3-yl]methanol

To a stirred mixture of (2-bromopyridin-3-yl)methanol (500 mg, 2.66 mmol, 1 equiv), 4,4,5,5-tetramethyl-2-(prop-1-en-2-yl)-1,3,2-dioxaborolane (893.7 mg, 5.32 mmol, 2 equiv), Pd(PPh3)4 (307.3 mg, 0.27 mmol, 0.1 equiv.) and K2CO3 (1102.6 mg, 7.98 mmol, 3 equiv.) in 1,4-dioxane (5 mL) was added H2O (1 mL) at room temperature under nitrogen atmosphere. The final reaction mixture was irradiated with microwave radiation for 2 h at 90 degrees Celsius. The reaction was monitored by LCMS. The mixture was allowed to cool down to room temperature. The resulting mixture was concentrated under reduced pressure. The residue was purified by Prep-TLC (PE/EtOAc 1:1) to afford [2-(prop-1-en-2-yl)pyridin-3-yl]methanol (500 mg, 94.52%) as a yellow oil.

[2-(propan-2-yl)pyridin-3-yl]methanol

To a solution of [2-(prop-1-en-2-yl)pyridin-3-yl]methanol (500 mg, 2.51 mmol, 1 equiv.) in 50 mL MeOH was added Pd/C (10%, 26.7 mg) under nitrogen atmosphere in a 100 mL round-bottom flask. The mixture was hydrogenated at room temperature for 2 h under hydrogen atmosphere using a hydrogen balloon. The reaction was monitored by LCMS. The mixture was filtered through a Celite pad and concentrated under reduced pressure. The residue was purified by Prep-TLC (PE/EtOAc 5:1) to afford [2-(propan-2-yl)pyridin-3-yl]methanol (450 mg, 88.80%) as a colorless oil.

3-(chloromethyl)-2-(propan-2-yl)pyridine

To a solution of [2-(propan-2-yl)pyridin-3-yl]methanol (450 mg, 2.98 mmol, 1 equiv.) in DCM (20 mL) was added SOCl2 (1062.2 mg, 8.93 mmol, 3 equiv.) at 0 degrees Celsius. The reaction was stirred for 16 h at room temperature. The reaction was monitored by LCMS. The resulting mixture was concentrated under reduced pressure. The residue (400 mg) was used in the next step directly without further purification.

Compound KM: 4-chloro-5-(4-[[2-(propan-2-yl)pyridin-3-yl]methyl]piperazin-1-yl)-2,3-dihydropyridazin-3-one To a mixture of 4-chloro-5-(piperazin-1-yl)-2,3-dihydropyridazin-3-one (100 mg, 0.47 mmol, 1 equiv.) and DIEA (301.1 mg, 2.33 mmol, 5 equiv.) in DMF (5 mL) was added 3-(chloromethyl)-2-(propan-2-yl)pyridine (94.8 mg, 0.56 mmol, 1.2 equiv.) at room temperature. The reaction was stirred for 16 h at room temperature. The reaction was monitored by LCMS. The reaction mixture was purified by Prep-HPLC with the following conditions (Column: XBridge Shield RP18 OBD Column, 5 um, 19*150 mm; Mobile Phase A: Water (10 mmol/L NH4HCO3), Mobile Phase B: ACN; Flow rate: 20 mL/min; Gradient: 25% B to 40% B in 7 min; 220 nm; Rt: 6.68 min) to afford 4-chloro-5-(4-[[2-(propan-2-yl)pyridin-3-yl]methyl]piperazin-1-yl)-2,3-dihydropyridazin-3-one (42.6 mg, 26.29%) as a white solid.

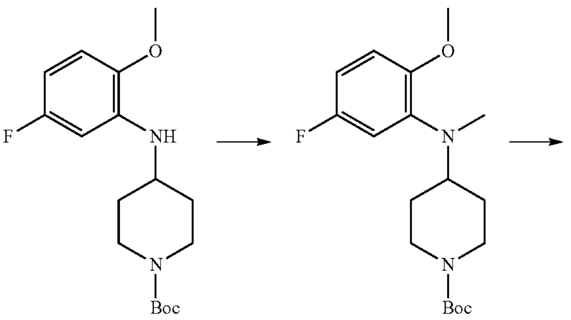

-continued

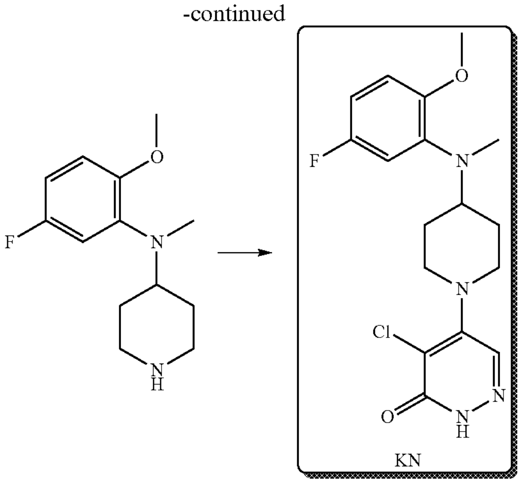

KN

Preparation of KN

Tert-Butyl 4-[(5-fluoro-2-methoxyphenyl)(methyl)amino]piperidine-1-carboxylate

To a stirred solution of tert-butyl 4-[(5-fluoro-2-methoxyphenyl)amino]piperidine-1-carboxylate (300 mg, 0.92 mmol, 1 equiv.) and NaH (44.4 mg, 1.85 mmol, 2.00 equiv.) in DMF (5 mL) was added MeI (157.5 mg, 1.11 mmol, 1.20 equiv.) in portions at room temperature under nitrogen atmosphere. The resulting mixture was stirred for 4 h at room temperature under nitrogen atmosphere. The reaction was monitored by LCMS. The reaction was quenched with Water/Ice at 0 degrees Celsius. The resulting mixture was extracted with EtOAc (30× mL). The combined organic layers were washed with brine (3×50 mL), dried over anhydrous Na2SO4. After filtration, the filtrate was concentrated under reduced pressure. The resulting mixture was used in the next step directly without further purification.

N-(5-fluoro-2-methoxyphenyl)-N-methylpiperidin-4-amine

To a stirred solution of tert-butyl 4-[(5-fluoro-2-methoxyphenyl)(methyl)amino]piperidine-1-carboxylate (200 mg, 0.59 mmol, 1 equiv.) in DCM (10 mL, 157.30 mmol, 266.17 equiv.) was added TFA (3 mL, 40.39 mmol, 68.34 equiv.) in portions at room temperature under nitrogen atmosphere. The resulting mixture was stirred for 4 h at room temperature under nitrogen atmosphere. The reaction was monitored by LCMS. The resulting mixture was concentrated under vacuum. The residue was purified by Prep-TLC (PE/EtOAc 5:1) to afford N-(5-fluoro-2-methoxyphenyl)-N-methylpiperidin-4-amine (60 mg, 42.60%) as a light yellow oil.

Compound KN: 4-chloro-5-[4-[(5-fluoro-2-methoxyphenyl)(methyl)amino]piperidin-1-yl]-2,3-dihydropyridazin-3-one To a stirred solution of N-(5-fluoro-2-methoxyphenyl)-N-methylpiperidin-4-amine (60 mg, 0.25 mmol, 1 equiv.) and 4,5-dichloro-2,3-dihydropyridazin-3-one (49.8 mg, 0.30 mmol, 1.20 equiv.) in DMA (5 mL) was added DIEA (65.1 mg, 0.50 mmol, 2.00 equiv.) in portions at room temperature under nitrogen atmosphere. The resulting mixture was stirred for overnight at 90 degrees Celsius under nitrogen atmosphere. The reaction was monitored by LCMS. The resulting mixture was concentrated under vacuum. The crude product (30 mg) was purified by Prep-HPLC with the following conditions (Column: Kinetex EVO C18 Column 21.2*150.5 um; Mobile Phase A: Water (10 mmol/L NH4HCO3), Mobile Phase B: ACN; Flow rate: 20 mL/min; Gradient: 30% B to 60% B in 7 min; 254&220 nm; Rt: 5.8 min) to afford 4-chloro-5-[4-[(5-fluoro-2-methoxyphenyl)(methyl)amino]piperidin-1-yl]-2,3-dihydropyridazin-3-one (12 mg, 12.99%) as a white solid.

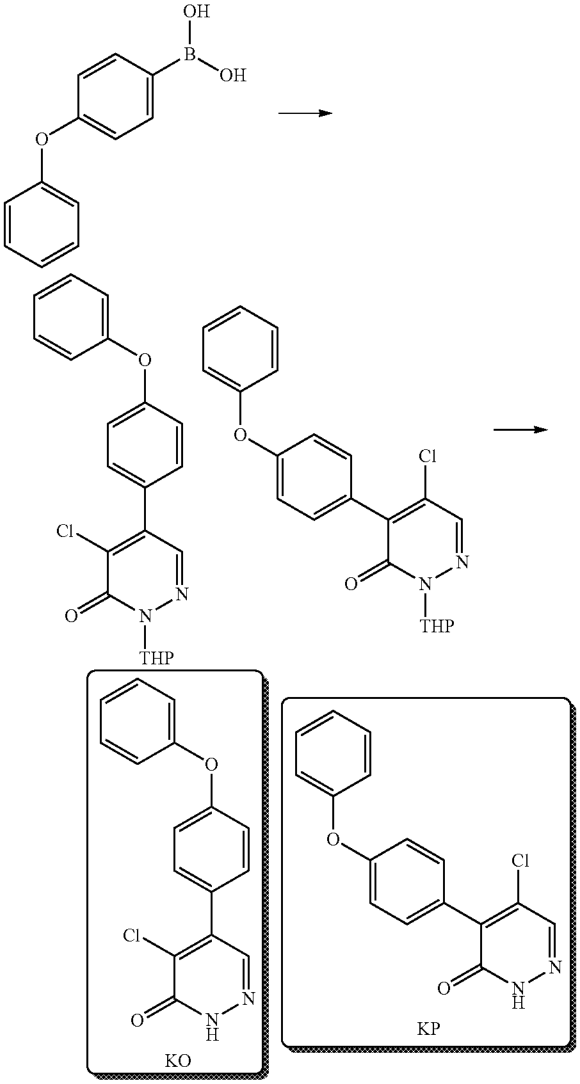

KO

KP

Preparation of KO and KP 4-chloro-2-(oxan-2-yl)-5-(4-phenoxyphenyl)-2,3-dihydropyridazin-3-one and 5-chloro-2-(oxan-2-yl)-4-(4-phenoxyphenyl)-2,3-dihydropyridazin-3-one To a stirred mixture of (4-phenoxyphenyl)boronic acid (347 mg, 0.8 equiv.) and 4,5-dichloro-2-(oxan-2-yl)-2,3-dihydropyridazin-3-one (500 mg, 1 equiv.) in H2O (1 mL) and 1,4-dioxane (10 mL) were added K2CO3 (560 mg, 2 equiv.) and Pd(PPh3)4 (116 mg, 0.05 equiv.) at room temperature under nitrogen atmosphere. The resulting mixture was stirred for 2 h at 90 degrees Celsius under nitrogen atmosphere. The reaction was monitored by LCMS. The mixture was allowed to cool down to room temperature. The resulting mixture was concentrated under reduced pressure. The residue was purified by silica gel column chromatography, eluted with PE/EtOAc (20:1 to 15:1) to afford 4-chloro-2-(oxan-2-yl)-5-(4-phenoxyphenyl)-2,3-dihydropyridazin-3-one (200 mg, 26.03%) as a white solid and 5-chloro-2-(oxan-2-yl)-4-(4-phenoxyphenyl)-2,3-dihydropyridazin-3-one (160 mg, 20.82%) as a white solid.

Compound KO and KP 5-chloro-4-(4-phenoxyphenyl)-2,3-dihydropyridazin-3-one and 4-chloro-5-(4-phenoxyphenyl)-2,3-dihydropyridazin-3-one To a stirred solution of TFA (2 mL) in DCM (18 mL) was added a mixture of 4-chloro-2-(oxan-2-yl)-5-(4-phenoxyphenyl)-2,3-dihydropyridazin-3-one and 5-chloro-2-(oxan-2-yl)-4-(4-phenoxyphenyl)-2,3-dihydropyridazin-3-one (340 mg) at room temperature. The resulting mixture was stirred for 1 h at room temperature. The reaction was monitored by LCMS. The resulting mixture was concentrated under reduced pressure. The crude product (150 mg) was purified by Prep-HPLC with the following conditions (Column: XBridge Shield RP18 OBD Column 30*150 mm, 5 um; Mobile Phase A: Water (10 mmol/L NH4HCO3), Mobile Phase B: ACN; Flow rate: 60 mL/min; Gradient: 25% B to 45% B in 10 min; 254 nm; Rt: 9.40 min) to afford 5-chloro-4-(4-phenoxyphenyl)-2,3-dihydropyridazin-3-one (59.4 mg) as a white solid and 4-chloro-5-(4-phenoxyphenyl)-2,3-dihydropyridazin-3-one (33 mg) as a light yellow solid.

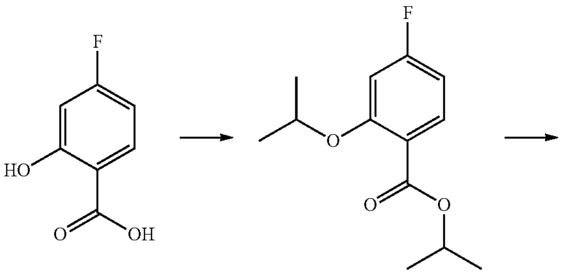

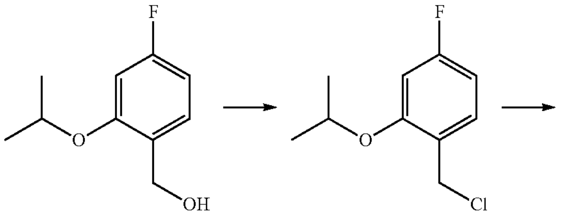

-continued

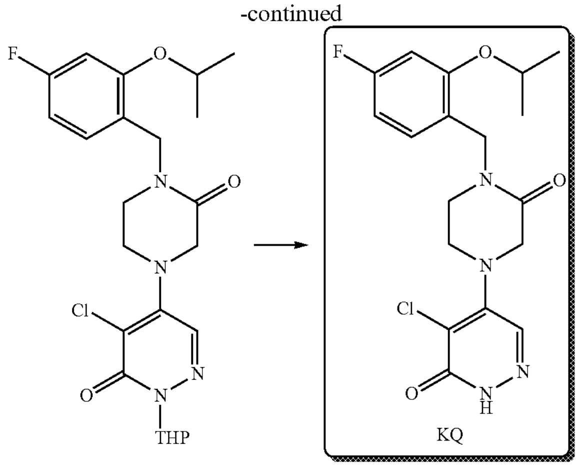

THP

KQ

Preparation of KQ propan-2-yl 4-fluoro-2-(propan-2-yloxy)benzoate

To a stirred mixture of 4-fluoro-2-hydroxybenzoic acid (2 g, 12.81 mmol, 1 equiv.) and K2CO3 (5.3 g, 38.35 mmol, 2.99 equiv.) in DMF (20 mL) was added 2-iodopropane (6.5 g, 38.24 mmol, 2.98 equiv.) at room temperature under nitrogen atmosphere. The resulting mixture was stirred for 3 h at 70 degrees Celsius under nitrogen atmosphere. The reaction was monitored by LCMS. The mixture was allowed to cool down to room temperature. The reaction was quenched by the addition of Water (100 mL) at room temperature. The resulting mixture was extracted with CH2Cl2(3×300 mL). The combined organic layers were washed with brine (3×50 mL), dried over anhydrous Na2SO4. After filtration, the filtrate was concentrated under reduced pressure. The residue was purified by silica gel column chromatography, eluted with PE/EtOAc (40/1 to 20/1) to afford propan-2-yl 4-fluoro-2-(propan-2-yloxy)benzoate (2.9 g, 94.21%) as a light yellow oil.

[4-fluoro-2-(propan-2-yloxy)phenyl]methanol

To a stirred solution of propan-2-yl 4-fluoro-2-(propan-2-yloxy)benzoate (1.5 g, 6.24 mmol, 1 equiv.) in THF (50 mL) was added LAH (473.9 mg, 12.49 mmol, 2.00 equiv.) in portions at −30 degrees Celsius under nitrogen atmosphere. The reaction mixture was stirred for 16 h at −10 degrees Celsius. The reaction was monitored by TLC (PE/EtOAc=5/1). The reaction was quenched by the addition of Water (1 mL) at −30 degrees Celsius. The precipitated solids were collected by filtration and washed with MeOH (3×40 mL). The resulting mixture was concentrated under vacuum. The residue was purified by silica gel column chromatography, eluted with PE/EtOAc (40/1 to 20/1) to afford [4-fluoro-2-(propan-2-yloxy)phenyl]methanol (1.2 g, 104.35%) as a light yellow oil.

1-(chloromethyl)-4-fluoro-2-(propan-2-yloxy)benzene

To a stirred solution of [4-fluoro-2-(propan-2-yloxy)phenyl]methanol (1.2 g, 6.51 mmol, 1 equiv.) in DCM (20 mL) was added SOCl2 (1.6 g, 13.45 mmol, 2.0 equiv.) dropwise at 0 degrees Celsius. The reaction mixture was stirred for 16 h at room temperature. The reaction was monitored by TLC (EA/PE=1/10). The resulting mixture was concentrated under vacuum. This resulted in 1-(chloromethyl)-4-fluoro-2-(propan-2-yloxy)benzene (1.1 g, 83.32%) as a light yellow oil.

4-chloro-5-(4-[[4-fluoro-2-(propan-2-yloxy)phenyl] methyl]-3-oxopiperazin-1-yl)-2-(oxan-2-yl)-2,3-dihydropyridazin-3-one To a stirred mixture of 4-chloro-2-(oxan-2-yl)-5-(3-oxopiperazin-1-yl)-2,3-dihydropyridazin-3-one (200 mg, 0.64 mmol, 1 equiv.) and 1-(chloromethyl)-4-fluoro-2-(propan-2-yloxy)benzene (259.2 mg, 1.28 mmol, 2.00 equiv.) in DMF (10 mL) was added Cs2CO3 (625.1 mg, 1.92 mmol, 3.00 equiv.) at room temperature under nitrogen atmosphere. The final reaction mixture was irradiated with microwave radiation for 2 h at 100 degrees Celsius. The reaction was monitored by LCMS. The mixture was allowed to cool down to room temperature. The reaction was quenched by the addition of Water (50 mL) at room temperature. The resulting mixture was extracted with CH2Cl2(3×300 mL). The combined organic layers were washed with brine (3×50 mL), dried over anhydrous Na2SO4. After filtration, the filtrate was concentrated under reduced pressure. The residue was purified by Prep-TLC (CH2Cl2/MeOH=40/1 to 20/1) to afford 4-chloro-5-(4-[[4-fluoro-2-(propan-2-yloxy) phenyl]methyl]-3-oxopiperazin-1-yl)-2-(oxan-2-yl)-2,3-dihydropyridazin-3-one (240 mg, 78.36%) as a yellow oil.

Compound KQ: 4-chloro-5-(4-[[4-fluoro-2-(propan-2-yloxy)phenyl]methyl]-3-oxopiperazin-1-yl)-2,3-dihydropyridazin-3-one To a stirred solution of 4-chloro-5-(4-[[4-fluoro-2-(propan-2-yloxy)phenyl]methyl]-3-oxopiperazin-1-yl)-2-(oxan-2-yl)-2,3-dihydropyridazin-3-one (210 mg, 440 mmol, 1 equiv.) in DCM (10 mL) was added TFA (2 mL, 26.93 mmol, 71.64 equiv.) dropwise at room temperature. The reaction mixture was stirred for 16 h at room temperature. The reaction was monitored by LCMS. The resulting mixture was concentrated under reduced pressure. The residue was basified to pH=8 with saturated NaHCO3 (aq.). The resulting mixture was extracted with CH2Cl2(3×100 mL). The combined organic layers were washed with brine (1×100 mL), dried over anhydrous Na2SO4. After filtration, the filtrate was concentrated under reduced pressure. The crude residue was purified by Prep-HPLC with the following conditions (Column: XBridge Shield RP18 OBD Column 30*150 mm, 5 um; Mobile Phase A: Water (10 mmol/L NH4HCO3), Mobile Phase B: ACN; Flow rate: 60 mL/min; Gradient: 20% B to 50% B in 7 min; 254 nm; Rt: 6.3 min) to afford 4-chloro-5-(4-[[4-fluoro-2-(propan-2-yloxy)phenyl]methyl]-3-oxopiperazin-1-yl)-2,3-dihydropyridazin-3-one (98.1 mg, 66.11%) as a white solid.

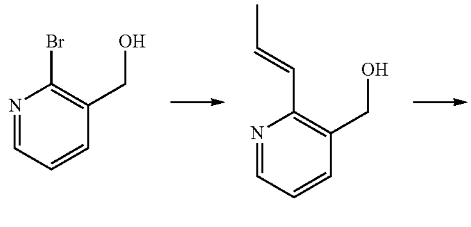

-continued

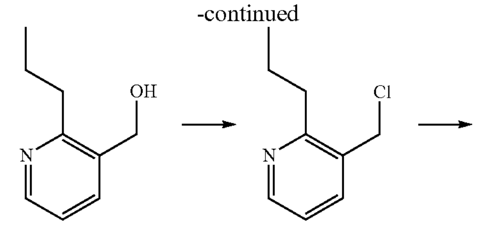

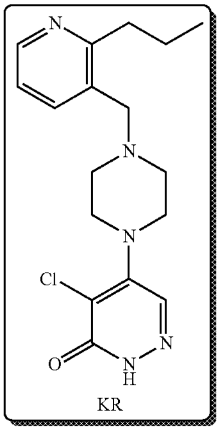

KR

Preparation of Compound KR

[2-[(1E)-prop-1-en-1-yl]pyridin-3-yl]methanol

To a solution of (2-bromopyridin-3-yl)methanol (500 mg, 2.66 mmol, 1 equiv.) and K2CO3 (1.1 g, 7.98 mmol, 3 equiv.) in 1,4-dioxane (10 mL) and H2O (2 mL) were added [difluoro(1E)-prop-1-en-1-yl-$1^[5]-boranylidene]fluoranium (579.1 mg, 5.32 mmol, 2 equiv.) and Pd(PPh3)4 (307.3 mg, 0.27 mmol, 0.1 equiv.) under a nitrogen atmosphere. The final reaction mixture was irradiated with microwave radiation for 2 h at 90 degrees Celsius. The reaction was monitored by LCMS. The mixture was allowed to cool down to room temperature. The resulting mixture was concentrated under reduced pressure. The residue was purified by Prep-TLC (PE/EtOAc 5:1) to afford [2-[(1E)-prop-1-en-1-yl]pyridin-3-yl]methanol (278 mg, 70.07%) as a yellow semi-solid.

(2-propylpyridin-3-yl)methanol

To a solution of [2-[(1E)-prop-1-en-1-yl]pyridin-3-yl] methanol (370 mg, 2.48 mmol, 1 equiv.) in 20 mL MeOH was added Pd/C (10%, 88.0 mg) under nitrogen atmosphere in a 100 mL round-bottom flask. The mixture was hydrogenated at room temperature for 2 h under hydrogen atmosphere using a hydrogen balloon, the reaction was monitored by LCMS. The reaction mixture was filtered through a Celite pad and concentrated under reduced pressure. The residue was purified by Prep-TLC (PE/EtOAc 5:1) to afford (2-propylpyridin-3-yl)methanol (290 mg, 77.33%) as a light yellow oil.

3-(chloromethyl)-2-propylpyridine

To a solution of (2-propylpyridin-3-yl)methanol (290 mg, 1.92 mmol, 1 equiv.) in DCM (20 mL) was added SOCl2 (684.5 mg, 5.75 mmol, 3 equiv.) at 0 degrees Celsius. The reaction was stirred for 2 h at room temperature. The reaction was monitored by LCMS. The resulting mixture was concentrated under reduced pressure. The residue was used in the next step directly without further purification.

Compound KR: 4-chloro-5-[4-[(2-propylpyridin-3-yl)methyl]piperazin-1-yl]-2,3-dihydropyridazin-3-one To a mixture of 4-chloro-5-(piperazin-1-yl)-2,3-dihydropyridazin-3-one (100 mg, 0.47 mmol, 1 equiv.) and 3-(chloromethyl)-2-propylpyridine (102.7 mg, 0.61 mmol, 1.3 equiv.) in DMF (5 mL) was added DIEA (180.6 mg, 1.40 mmol, 3 equiv.) at room temperature. The reaction was stirred for 16 h at room temperature. The reaction was monitored by LCMS. The reaction mixture was purified by Prep-HPLC with the following conditions (Column: XBridge Shield RP18 OBD Column 30*150 mm, 5 um; Mobile Phase A: Water (10 mmol/L NH4HCO3), Mobile Phase B: ACN; Flow rate: 60 mL/min; Gradient: 10% B to 30% B in 15 min; 254 nm; Rt: 14.83 min) to afford 4-chloro-5-[4-[(2-propylpyridin-3-yl)methyl]piperazin-1-yl]-2,3-dihydropyridazin-3-one (14.9 mg, 9.19%) as a white solid.

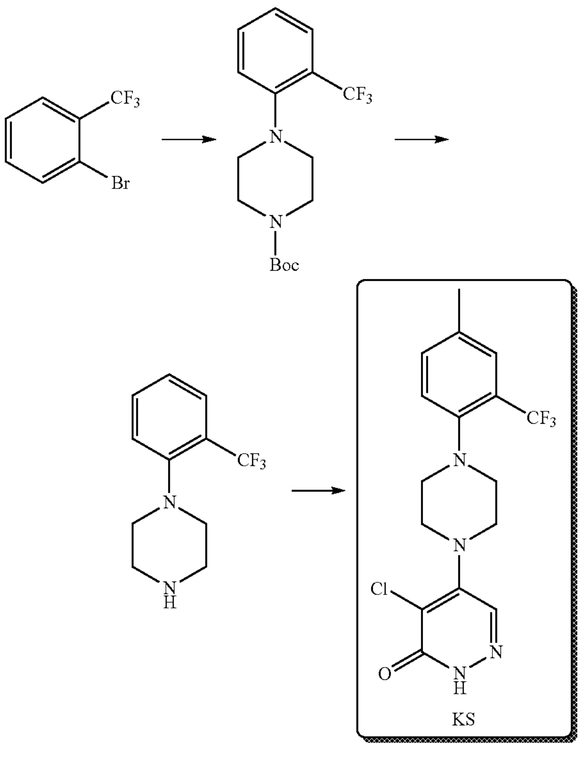

KS

Preparation of Compound KS

Tert-Butyl 4-[2-(trifluoromethyl)phenyl]piperazine-1-carboxylate

To a stirred solution of 1-bromo-2-(trifluoromethyl)benzene (1 g) and tert-butyl piperazine-1-carboxylate (993.3 mg, 5.33 mol, 1.20 equiv.) in Toluene (15 mL) were added BINAP (276.7 mg, 0.44 mmol, 0.1 equiv.) and t-BuONa (854.2 mg, 8.89 mmol, 2 equiv.) at room temperature under nitrogen atmosphere. To the solution was added Pd(AcO)2 (49.9 mg, 0.22 mmol, 0.05 equiv.) at room temperature. The solution was stirred at 110 degrees Celsius for 6 h. The mixture was concentrated under reduced pressure. The residue was purified by silica gel column chromatography, eluted with PE/EtOAc (10:1 to 1:1) to afford tert-butyl 4-[2-(trifluoromethyl)phenyl]piperazine-1-carboxylate (1.2 g, 81.73%) as a colorless oil.

1-[2-(trifluoromethyl)phenyl]piperazine

To a stirred solution of tert-butyl 4-[2-(trifluoromethyl)phenyl]piperazine-1-carboxylate (1.2 g, 3.63 mmol, 1 equiv.) and in DCM (18 mL, 283.14 mmol, 77.95 equiv.) was added TFA (3 mL, 40.39 mmol, 11.12 equiv.) at room temperature. The solution was stirred at room temperature for 3 h. The mixture was concentrated under reduced pressure. The crude product was used in the next step directly without further purification.

Compound KS: 4-chloro-5-[4-[2-(trifluoromethyl)phenyl]piperazin-1-yl]-2,3-dihydropyridazin-3-one To a stirred solution of 1-[2-(trifluoromethyl)phenyl]piperazine (252.6 mg, 1.10 mol, 1.81 equiv.) and 4,5-dichloro-2,3-dihydropyridazin-3-one (100 mg, 610 mmol, 1 equiv.) in DMA (4 mL, 43.02 mmol, 70.97 equiv.) was added DIEA (235.0 mg, 1.82 mmol, 3 equiv.) at room temperature. The solution was stirred at 100 degrees Celsius for 4 h. The mixture was concentrated under reduced pressure. The crude product (50 mg) was purified by Prep-HPLC with the following conditions (Column: XBridge Prep OBD C18 Column 30×150 mm 5 um; Mobile Phase A: Water (10 mmol/L NH4HCO3+0.1% NH3·H2O), Mobile Phase B: ACN; Flow rate: 60 mL/min; Gradient: 30% B to 68% B in 7 min; 254 nm; Rt: 6.05 min) to afford 4-chloro-5-[4-[2-(trifluoromethyl)phenyl]piperazin-1-yl]-2,3-dihydropyridazin-3-one (26.4 mg, 12.14%) as a off-white solid.

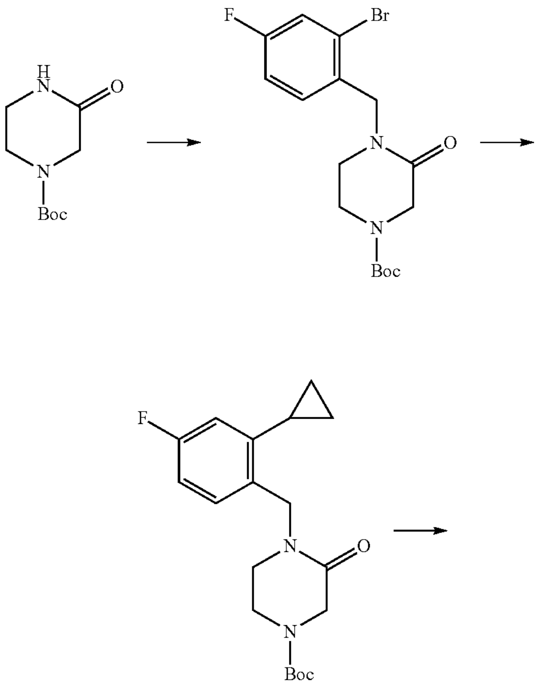

-continued

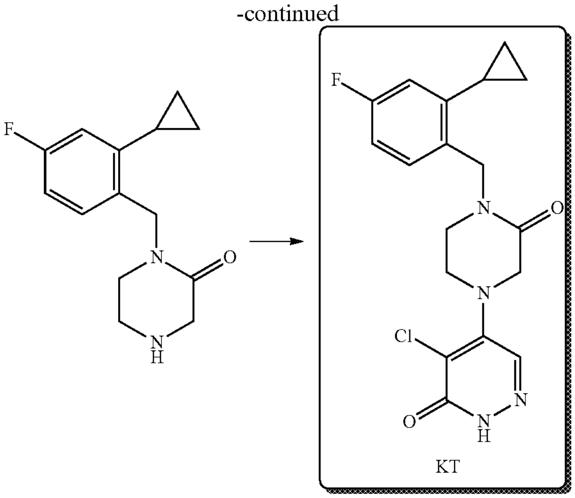

KT

Preparation of Compound KT

Tert-Butyl 4-[(2-bromo-4-fluorophenyl)methyl]-3-oxopiperazine-1-carboxylate

To a stirred solution of tert-butyl 3-oxopiperazine-1-carboxylate (2 g, 9.99 mmol, 1 equiv.) in DMF (20 mL) was added NaH (0.8 g, 20.00 mmol, 2.00 equiv, 60%) at room temperature under nitrogen atmosphere. The reaction was stirred for 1 h at room temperature. Then 2-bromo-1-(bromomethyl)-4-fluorobenzene (4.0 g, 14.93 mmol, 1.49 equiv.) was added. The reaction mixture was stirred for 16 h at room temperature. The reaction was monitored by LCMS. The reaction was quenched by the addition of Water (200 mL) at room temperature. The resulting mixture was extracted with EtOAc (3×500 mL). The combined organic layers were washed with brine (3×200 mL), dried over anhydrous Na2SO4. After filtration, the filtrate was concentrated under reduced pressure. The residue was purified by silica gel column chromatography, eluted with PE/EtOAc (20/1 to 10/1) to afford tert-butyl 4-[(2-bromo-4-fluorophenyl)methyl]-3-oxopiperazine-1-carboxylate (3 g, 77.56%) Products as a yellow semi-solid.

Tert-Butyl 4-[(2-cyclopropyl-4-fluorophenyl)methyl]-3-oxopiperazine-1-carboxylate To a stirred mixture of tert-butyl 4-[(2-bromo-4-fluorophenyl)methyl]-3-oxopiperazine-1-carboxylate (500 mg, 1.29 mmol, 1 equiv.) and cyclopropylboronic acid (221.8 mg, 2.58 mmol, 2.00 equiv.) in 1,4-dioxane (10 mL) and H2O (2 mL) were added Cs2CO3 (1262.1 mg, 3.87 mmol, 3.00 equiv), Pd(AcO)2 (29.0 mg, 0.13 mmol, 0.10 equiv.) and PCy3 (36.2 mg, 0.13 mmol, 0.10 equiv.) in portions at room temperature. The resulting mixture was stirred for 2 h at 120 degrees Celsius. The reaction was monitored by LCMS. The resulting mixture was concentrated under reduced pressure. The residue was purified by silica gel column chromatography, eluted with PE/EtOAc (30/1 to 5/1) to afford tert-butyl 4-[(2-cyclopropyl-4-fluorophenyl)methyl]-3-oxopiperazine-1-carboxylate (400 mg, 88.92%) as a yellow oil.

1-[(2-cyclopropyl-4-fluorophenyl)methyl]piperazin-2-one

To a stirred solution of tert-butyl 4-[(2-cyclopropyl-4-fluorophenyl)methyl]-3-oxopiperazine-1-carboxylate (300 mg, 0.86 mmol, 1 equiv.) in DCM (10 mL) was added TFA (2 mL, 26.93 mmol, 66.771 equiv.) dropwise at room temperature. The reaction mixture was stirred for 16 h at room temperature. The reaction was monitored by LCMS. The resulting mixture was concentrated under reduced pressure. The residue was basified to pH=8 with saturated NaHCO3 (aq.). The resulting mixture was extracted with CH2Cl2(3×100 mL). The combined organic layers were washed with brine (1×100 mL), dried over anhydrous Na2SO4. After filtration, the filtrate was concentrated under reduced pressure. This resulted in 1-[(2-cyclopropyl-4-fluorophenyl)methyl]piperazin-2-one (140 mg, 65.48%) as a yellow oil.

Compound KT: 4-chloro-5-[4-[(2-cyclopropyl-4-fluorophenyl)methyl]-3-oxopiperazin-1-yl]-2,3-dihydropyridazin-3-one To a stirred mixture of 1-[(2-cyclopropyl-4-fluorophenyl)methyl]piperazin-2-one (140 mg, 0.56 mmol, 1 equiv.) and 4,5-dichloro-2,3-dihydropyridazin-3-one (93.0 mg, 0.56 mmol, 1.00 equiv.) in DMA (5 mL) was added DIEA (218.6 mg, 1.69 mmol, 3.00 equiv.) dropwise at room temperature under nitrogen atmosphere. The reaction mixture was stirred for 8 h at 100 degrees Celsius. The reaction was monitored by LCMS. The reaction mixture was purified by Prep-HPLC with the following conditions (Column: XBridge Shield RP18 OBD Column 30*150 mm, 5 um; Mobile Phase A: Water (10 mmol/L NH4HCO3), Mobile Phase B: ACN; Flow rate: 60 mL/min; Gradient: 20% B to 40% B in 10 min; 254 nm; Rt: 9.07 min) to afford 4-chloro-5-[4-[(2-cyclopropyl-4-fluorophenyl)methyl]-3-oxopiperazin-1-yl]-2,3-dihydropyridazin-3-one (10.8 mg) as a light yellow solid.

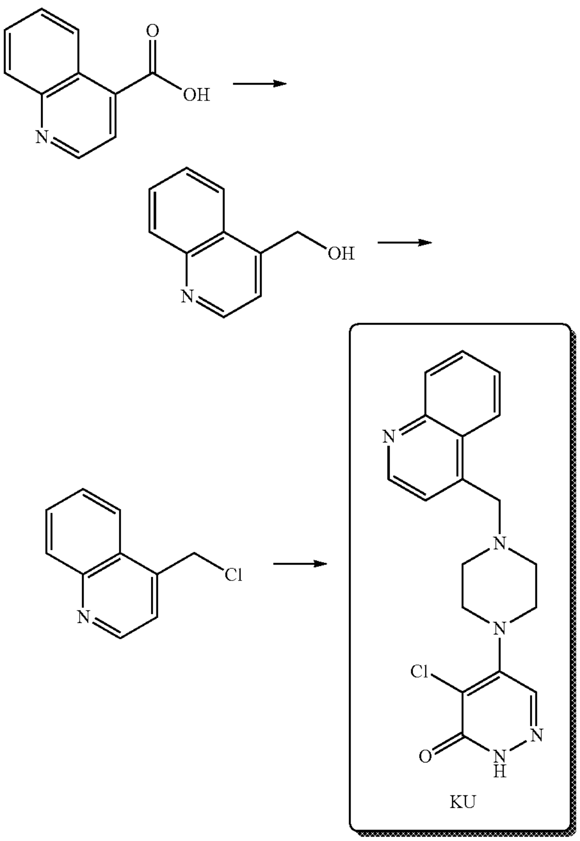

KU

Preparation of Compound KU quinolin-4-ylmethanol

To a stirred solution of quinoline-4-carboxylic acid (1 g, 5.77 mmol, 1 equiv.) in THF (15 mL) was added LiAlH4 (0.3 g, 8.66 mmol, 1.5 equiv). The resulting mixture was stirred for 3 h at 0 degrees Celsius. The resulting mixture was concentrated under reduced pressure. This resulted in quinolin-4-ylmethanol (500 mg, 54.39%) as a yellow solid.

1-(chloromethyl)naphthalene

To a stirred solution of (quinolin-4-yl)methanol (490 mg, 3.08 mmol, 1 equiv.) in DCM (5 mL) was added sulfurooyl dichloride (732.3 mg, 6.16 mmol, 2 equiv.) dropwise at 0 degrees Celsius. The solution was stirred at room temperature for 2 h. The mixture was concentrated under reduced pressure. The crude product was used in the next step directly without further purification.

Compound KU: 4-chloro-5-[4-[(quinolin-4-yl) methyl]piperazin-1-yl]-2,3-dihydropyridazin-3-one To a stirred solution of 4-(chloromethyl)quinoline (100 mg, 0.56 mmol, 1 equiv.) and 4-chloro-5-(piperazin-1-yl)-2,3-dihydropyridazin-3-one (120.8 mg, 0.56 mmol, 1.00 equiv.) in DMA (10 mL) was added DIEA (291.0 mg, 2.25 mmol, 4.00 equiv.) at room temperature. The solution was stirred at room temperature for 4 h. The mixture was concentrated under reduced pressure. The crude product (50 mg) was purified by Prep-HPLC with the following conditions (Column: Xselect CSH OBD Column 30*150 mm 5 um n; Mobile Phase A: Water (0.05% NH4HCO3), Mobile Phase B: ACN; Flow rate: 60 mL/min; Gradient: 3% B to 20% B in 7 min; 220 nm; Rt: 6 min) to afford 4-chloro-5-[4-[(quinolin-4-yl)methyl]piperazin-1-yl]-2,3-dihydropyridazin-3-one (29.1 mg, 14.53%) as a white solid.

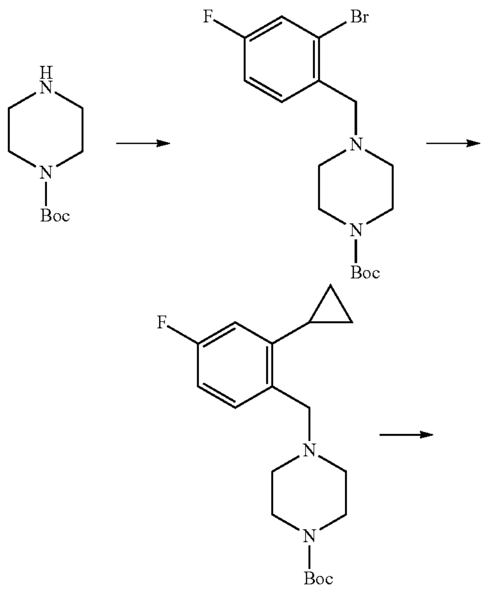

-continued

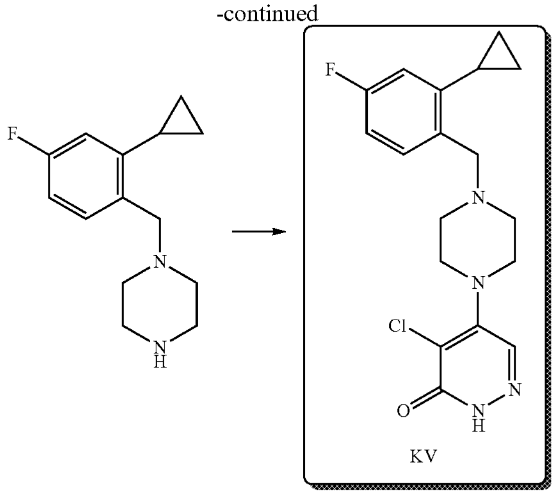

KV

Preparation of Compound KV

Tert-Butyl 4-[(2-bromo-4-fluorophenyl)methyl]piperazine-1-carboxylate

To a stirred mixture of tert-butyl piperazine-1-carboxylate (2 g, 10.74 mmol, 1 equiv.) and 2-bromo-1-(bromomethyl)-4-fluorobenzene (4.3 g, 16.05 mmol, 1.49 equiv.) in DCM (50 mL) was added DIEA (5.6 g, 43.33 mmol, 4.04 equiv.) in portions at room temperature under nitrogen atmosphere. The resulting mixture was stirred for 16 h at room temperature. The reaction was monitored by LCMS. The resulting mixture was concentrated under vacuum. The residue was purified by silica gel column chromatography, eluted with PE/EtOAc (20/1 to 8/1) to afford tert-butyl 4-[(2-bromo-4-fluorophenyl)methyl]piperazine-1-carboxylate (3.8 g, 94.81%) as a white solid.

Tert-Butyl 4-[(2-cyclopropyl-4-fluorophenyl) methyl]piperazine-1-carboxylate

To a stirred mixture of tert-butyl 4-[(2-bromo-4-fluorophenyl)methyl]piperazine-1-carboxylate (1 g, 2.68 mmol, 1 equiv.) and cyclopropylboronic acid (0.5 g, 5.82 mmol, 2.17 equiv.) in 1,4-dioxane (10 mL) and H2O (2 mL) were added K2CO3 (1.1 g, 7.96 mmol, 2.97 equiv.) and Pd(PPh3)4 (309.6 mg, 0.27 mmol, 0.10 equiv.) in portions at room temperature. The final reaction mixture was irradiated with microwave radiation for 4 h at 110 degrees Celsius. The reaction was monitored by LCMS. The resulting mixture was concentrated under reduced pressure. The residue was purified by silica gel column chromatography, eluted with PE/EtOAc (20/1 to 10/1) to tert-butyl 4-[(2-cyclopropyl-4-fluorophenyl)methyl]piperazine-1-carboxylate (300 mg, 33.48%) as a light yellow oil.

1-[(2-cyclopropyl-4-fluorophenyl)methyl]piperazine

To a stirred solution of tert-butyl 4-[(2-cyclopropyl-4-fluorophenyl)methyl]piperazine-1-carboxylate (400 mg, 1.20 mmol, 1 equiv.) in DCM (10 mL) was added TFA (2 mL, 26.93 mmol, 66.771 equiv.) dropwise at room temperature. The reaction mixture was stirred for 16 h at room temperature. The reaction was monitored by LCMS. The resulting mixture was concentrated under reduced pressure. The residue was basified to pH=8 with saturated NaHCO3

(aq.). The resulting mixture was extracted with CH2Cl2(3×100 mL). The combined organic layers were washed with brine (1×100 mL), dried over anhydrous Na2SO4. After filtration, the filtrate was concentrated under reduced pressure. This resulted in 1-[(2-cyclopropyl-4-fluorophenyl)methyl]piperazine (120 mg, 42.82%) as a yellow oil.

Compound KV: 4-chloro-5-[4-[(2-cyclopropyl-4-fluorophenyl)methyl]piperazin-1-yl]-2,3-dihydro-pyridazin-3-one To a stirred mixture of 1-[(2-cyclopropyl-4-fluorophenyl)methyl]piperazine (120 mg, 0.51 mmol, 1 equiv.) and 4,5-dichloro-2,3-dihydropyridazin-3-one (84.5 mg, 0.51 mmol, 1.00 equiv.) in DMA (5 mL) was added DIEA (198.6 mg, 1.54 mmol, 3.00 equiv.) dropwise at room temperature under nitrogen atmosphere. The reaction mixture was stirred for 8 h at 100 degrees Celsius. The reaction was monitored by LCMS. The reaction mixture was purified by Prep-HPLC with the following conditions (Column: XBridge Shield RP18 OBD Column 30*150 mm, 5 um; Mobile Phase A: Water (10 mmol/L NH4HCO3), Mobile Phase B: ACN; Flow rate: 60 mL/min; Gradient: 30% B to 63% B in 7 min; 254 nm; Rt: 6.6 min) to afford 4-chloro-5-[4-[(2-cyclopropyl-4-fluorophenyl)methyl]piperazin-1-yl]-2,3-dihydro-pyridazin-3-one (35.2 mg) as a yellow solid.

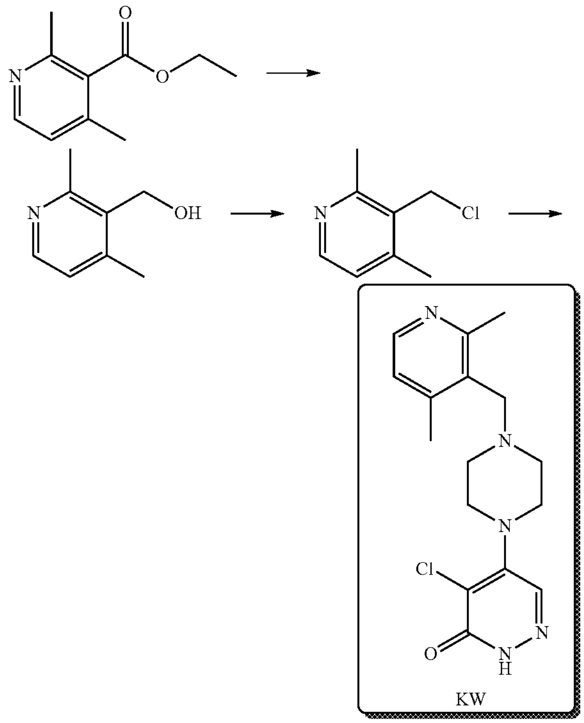

KW

Preparation of Compound KW (2,4-dimethylpyridin-3-yl)methanol

To a solution of ethyl 2,4-dimethylpyridine-3-carboxylate (1 g, 5.58 mmol, 1 equiv.) in THF (40 mL) was batch added LiAlH4 (317.7 mg, 8.37 mmol, 1.50 equiv.) at −30 degrees Celsius under nitrogen atmosphere. The resulting mixture was stirred for 3 h at −30 degrees Celsius~−10 degrees Celsius. The desired product could be detected by LCMS and TLC. The reaction mixture was quenched with water (0.5 mL) at −30 degrees Celsius and quenched with 15% NaOH(aq). The mixture was filtrated, the filtrate was concentrated under reduced pressure to crude product. The crude product was purified by Prep-TLC (PE/EA 1:1) to afford (2,4-dimethylpyridin-3-yl)methanol (670 mg, 87.53%) as a white solid.

3-(chloromethyl)-2,4-dimethylpyridine hydrochloride

To a solution of (2,4-dimethylpyridin-3-yl)methanol (670 mg, 4.88 mmol, 1 equiv.) in DCM (20 mL) were added SOCl2 (1743.2 mg, 14.65 mmol, 3.00 equiv.) dropwise via syringe at 0 degrees Celsius under nitrogen atmosphere. The resulting mixture was stirred for 16 h at ambient temperature. The desired product could be detected by LCMS. The mixture was concentrated to get crude product. The crude product was precipitated by the addition of Et2O. The precipitated solids were collected by filtration to get 3-(chloromethyl)-2,4-dimethylpyridine hydrochloride (840 mg, 89.54%) as a light yellow solid.

Compound KW: 4-chloro-5-[4-[(2,4-dimethylpyridin-3-yl)methyl]piperazin-1-yl]-2,3-dihydro-pyridazin-3-one To a solution of 2-chloro-3-[(piperazin-1-yl)methyl]benzonitrile (85 mg, 0.36 mmol, 1 equiv.) in DMF (4 mL) was added DIEA (93.2 mg, 0.72 mmol, 2 equiv.) and DIEA (442.3 mg, 3.42 mmol, 4.00 equiv.) at ambient temperature under air atmosphere. The resulting mixture was stirred for 16 h at ambient temperature. The desired product could be detected by LCMS. The reaction mixture was purified by reverse phase flash with the following conditions (Column: c18 OBD Column, 5 um, 19*120 mm; Mobile Phase A: Water (5 mmol/L NH4HCO3), Mobile Phase B: ACN; Flow rate: 45 L/min; Gradient: 30% B to 70% B in 40 min; 254 nm; Rt: 30 min) to afford 4-chloro-5-[4-[(2,4-dimethylpyridin-3-yl)methyl]piperazin-1-yl]-2,3-dihydropyridazin-3-one (81.7 mg, 65.67%) as a white solid.

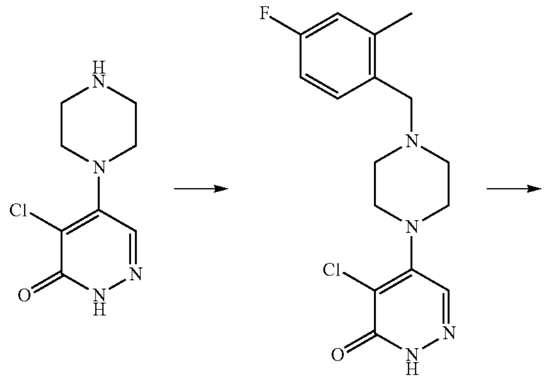

-continued

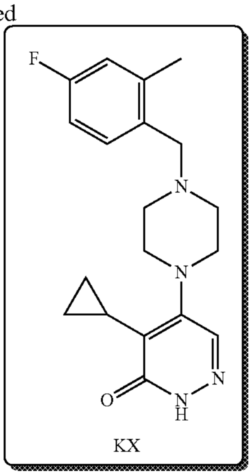

KX

Preparation of Compound KX 4-chloro-5-[4-[(4-fluoro-2-methylphenyl)methyl]piperazin-1-yl]-2,3-dihydropyridazin-3-one To a stirred solution of 4-chloro-5-(piperazin-1-yl)-2,3-dihydropyridazin-3-one; trifluoroacetic acid (656 mg, 2.00 mmol, 1 equiv.) in DCM (10 mL) was added DIEA (515.9 mg, 3.99 mmol, 2 equiv.) and 1-(bromomethyl)-4-fluoro-2-methylbenzene (405.3 mg, 2.00 mmol, 1.00 equiv.) in portions at 0 degrees Celsius under nitrogen atmosphere. The mixture was stirred at room temperature overnight. Desired product could be detected by LCMS. The resulting mixture was concentrated under reduced pressure. The residue was purified by silica gel column chromatography, eluted with PE/EtOAc (5:1 to 1:1) to afford 4-chloro-5-[4-[(4-fluoro-2-methylphenyl)methyl]piperazin-1-yl]-2,3-dihydropyridazin-3-one (400 mg, 59.51%) as a white solid.

Compound KX: 4-cyclopropyl-5-[4-[(4-fluoro-2-methylphenyl)methyl]piperazin-1-yl]-2,3-dihydropyridazin-3-one To a solution of 4-chloro-5-[4-[(4-fluoro-2-methylphenyl)methyl]piperazin-1-yl]-2,3-dihydropyridazin-3-one (120 mg, 0.36 mmol, 1 equiv.) and cyclopropylboronic acid (91.8 mg, 1.07 mol, 3.00 equiv.) in 1,4-dioxane (5 mL) and H2O (1 mL) were added Pd(AcO)2 (8.0 mg, 0.04 mmol, 0.10 equiv.), K2CO3 (98.5 mg, 0.71 mmol, 2.00 equiv.) and PCy3 (20.0 mg, 0.07 mmol, 0.20 equiv). The final reaction mixture was irradiated with microwave radiation for 3 h at 120 degrees Celsius under nitrogen atmosphere, the resulting mixture was concentrated under reduced pressure. The crude product (100 mg) was purified by Prep-HPLC with the following conditions (Column: XBridge Prep OBD C18 Column 30'150 mm 5 um; Mobile Phase A: Water (10 mmol/L NH4HCO3+0.1% NH3·H2O), Mobile Phase B: ACN; Flow rate: 60 mL/min; Gradient: 20% B to 45% B in 7 min; 254 nm; Rt: 6.73 min) to afford 4-cyclopropyl-5-[4-[(4-fluoro-2-methylphenyl)methyl]piperazin-1-yl]-2,3-dihydropyridazin-3-one (25.5 mg) as a white solid.

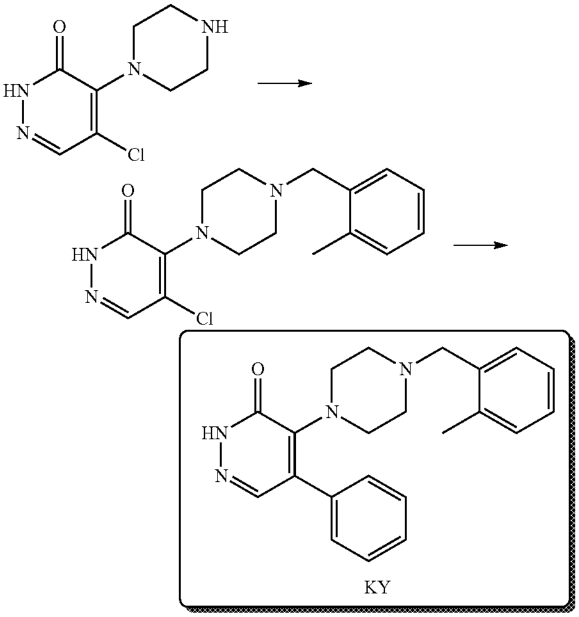

KY

Preparation of Compound KY 4-chloro-5-[4-(o-tolylmethyl)piperazin-1-yl]-1H-pyridazin-6-one A solution of 1-(bromomethyl)-2-methyl-benzene (120 mg, 0.648 mmol), DIPEA (0.6 ml, 3.49 mmol) and 4-chloro-5-piperazin-1-yl-1H-pyridazin-6-one (150 mg, 0.699 mmol) in DMF (2 ml) was stirred at room temperature overnight. The mixture was with EtOAc, washed with $NaHCO_3$, H2O, brine and concentrated to give a residue, which was purified by flash chromatography (0-100% EtOAc/DCM, 40 g), giving 4-chloro-5-[4-(o-tolylmethyl)piperazin-1-yl]-1H-pyridazin-6-one (125 mg, 0.373 mmol, 53% yield).

Compound KY: 5-[4-(o-tolylmethyl)piperazin-1-yl]-4-phenyl-1H-pyridazin-6-one

A mixture of 4-chloro-5-[4-(o-tolylmethyl)piperazin-1-yl]-1H-pyridazin-6-one (60 mg, 0.188 mmol), tetrakis(triphenylphosphine)palladium(O) (43.5 mg, 0.038 mmol), 2 N Na2CO3 (0.19 ml), and 4,4,5,5-tetramethyl-2-phenyl-1,3,2-dioxaborolane (46 mg, 0.223 mmol) in THF (1.5 ml) was stirred at 100° C. overnight. The mixture was diluted with EtOAc, washed with H2O, brine and concentrated to give a residue, which was purified by flash chromatography (0-100%/6 EtOAc/DCM, 40 g), giving 5-[4-(o-tolylmethyl)piperazin-1-yl]-4-phenyl-1H-pyridazin-6-one (45 mg, 0.119 mmol), 68% yield).

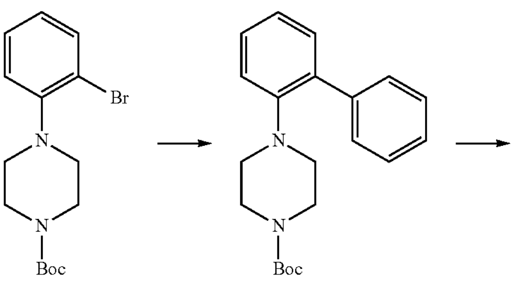

-continued

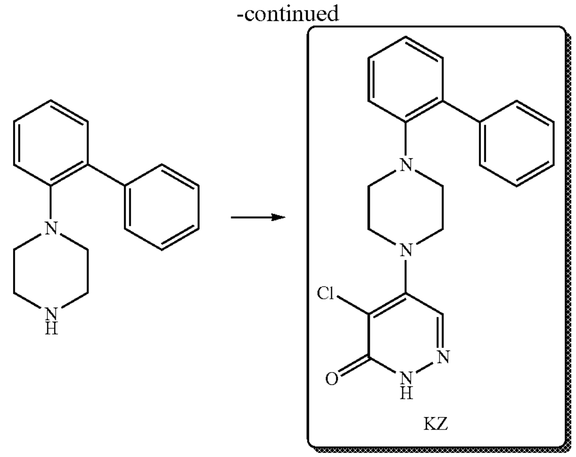

KZ

Preparation of Compound KZ

Tert-Butyl 4-[[1,1-biphenyl]-2-yl]piperazine-1-carboxylate

To a solution of tert-butyl 4-(2-bromophenyl)piperazine-1-carboxylate (100 mg, 0.29 mmol, 1 equiv.) and Pd(PPh3)4 (33.9 mg, 0.03 mmol, 0.10 equiv.) in dioxane (2.5 mL) and H2O (0.5 mL) were added phenylboronic acid (53.6 mg, 0.44 mmol, 1.50 equiv.) and K2CO3 (121.5 mg, 0.88 mmol, 3.00 equiv.) in portions at room temperature under nitrogen atmosphere. The final reaction mixture was irradiated with microwave radiation for 2 h at 90 degrees Celsius. The reaction was monitored by LCMS. The mixture was allowed to cool down to room temperature. The resulting mixture was concentrated under reduced pressure. The residue was purified by Prep-TLC (PE/EtOAc=100/1) to afford tert-butyl 4-[[1,1-biphenyl]-2-yl]piperazine-1-carboxylate (90 mg, 90.74%) as a light yellow oil.

1-[[1,1-biphenyl]-2-yl]piperazine

To a stirred solution of tert-butyl 4-[[1,1-biphenyl]-2-yl]piperazine-1-carboxylate (250 mg, 0.74 mmol, 1 equiv.) in DCM (2 mL) was added TFA (5 mL, 67.32 mmol, 91.13 equiv.) dropwise at room temperature. The resulting mixture was stirred for 2 h at room temperature. The reaction was monitored by LCMS. The resulting mixture was concentrated under reduced pressure. The residue was basified to pH 9 with saturated NaHCO3 (aq.). The resulting mixture was extracted with EtOAc (3×200 mL). The combined organic layers were washed with brine (3×200 mL), dried over anhydrous Na2SO4. After filtration, the filtrate was concentrated under reduced pressure to afford the 1-[[1,1-biphenyl]-2-yl]piperazine (180 mg, 102.25%) as yellow oil.

Compound KZ: 5-(4-[[1,1-biphenyl]-2-yl]piperazin-1-yl)-4-chloro-2,3-dihydropyridazin-3-one To a stirred mixture of 1-[[1,1-biphenyl]-2-yl]piperazine (200 mg, 0.84 mmol, 1 equiv.) and DIEA (216.9 mg, 1.68 mmol, 2.00 equiv.) in DMA (5 mL) was added 4,5-dichloro- 2,3-dihydropyridazin-3-one (138.4 mg, 0.84 mmol, 1.00 equiv.) in portions at room temperature. The resulting mixture was stirred for 16 h at 100 degrees Celsius. The reaction was monitored by LCMS. The mixture was allowed to cool down to room temperature. The residue was purified by Prep-HPLC with the following conditions (Column: XBridge Shield RP18 OBD Column 30*150 mm, 5 um; Mobile Phase A: Water (10 mmol/L NH4HCO3), Mobile Phase B: ACN; Flow rate: 60 mL/min; Gradient: 35% B to 70% B in 7 min; 254 nm; Rt: 6.58 8.4 min) to afford 5-(4-[[1,1-biphenyl]-2-yl]piperazin-1-yl)-4-chloro-2,3-dihydropyridazin-3-one (45.9 mg, 14.91%) as a yellow solid.

LA

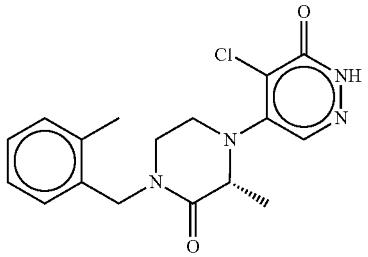

LB

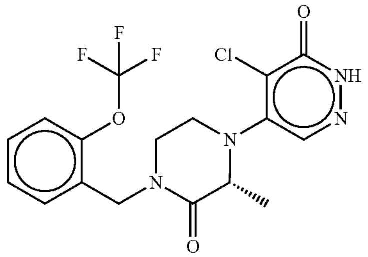

LC

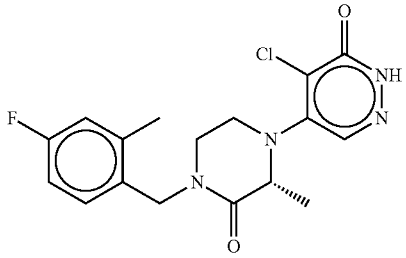

Compounds LA, LB, and LC were prepared by the methods described for Compound CF.

LD

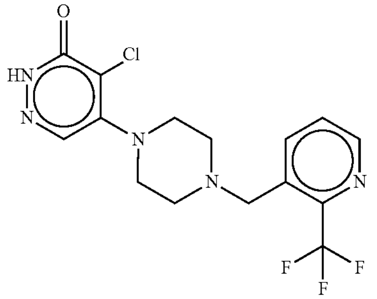

Compound LD was prepared by the methods described for Compound H.

LE
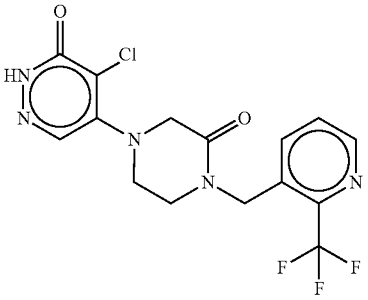
Compound LE was prepared by the methods described for Compound DH.
LF
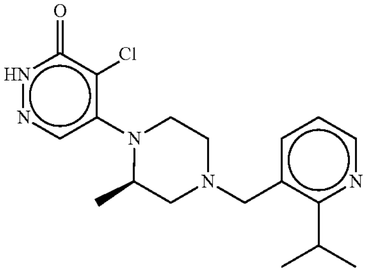
LG
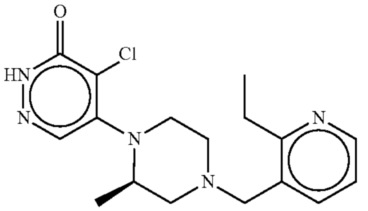
LH
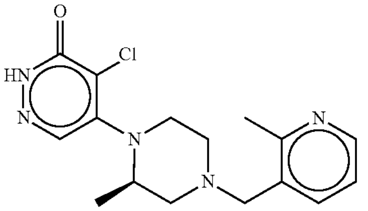
Compound LF, LG, and LH were prepared by the methods described for Compound M1 above.
LI
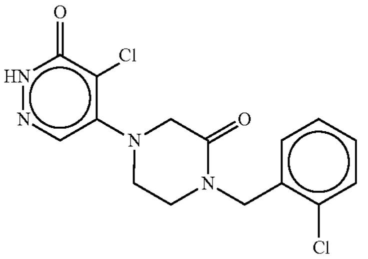
-continued
LJ
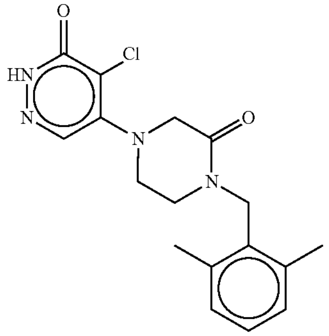
LK
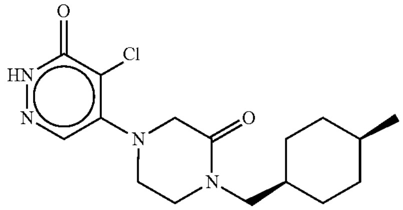
LL
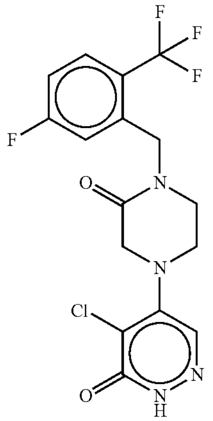
Compounds LI, LJ, LK, and LL were prepared by the methods described for Compound BW.
LM
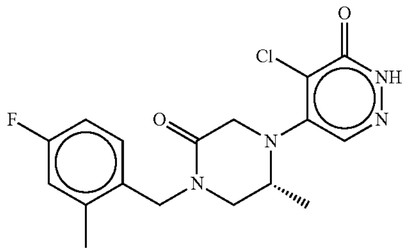
Compound LM was prepared by the methods described for Compound EO.
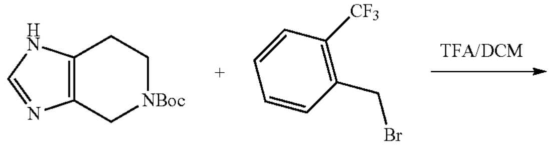

-continued

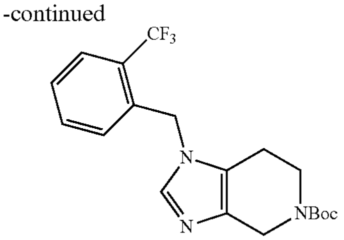

Preparation of Intermediate 1-[[2-(trifluoromethyl) phenyl]methyl]-1H,4H,5H,6H,7H-imidazo[4,5-c] pyridine

Tert-Butyl 1-[[2-(trifluoromethyl)phenyl]methyl]-1H,4H,5H,6H,7H-imidazo[4,5-c]pyridine-5-carboxylate To a stirred solution of tert-butyl 1H,4H,5H,6H,7H-imidazo[4,5-c]pyridine-5-carboxylate (1.9 g, 8.37 mmol, 1.00 equiv.) in DMF (25 mL) was added NaH (0.5 g, 12.55 mmol, 1.5 equiv., 60%) in portions at 0 degree Celsius under nitrogen atmosphere. The mixture was stirred at room temperature for 1 h. To the mixture was added 1-(bromomethyl)-2-(trifluoromethyl)benzene (2 g, 8.37 mmol, 1 equiv.) at 0 degree Celsius. The mixture was stirred at room temperature for 1 h. Desired product could be detected by LCMS. The reaction was quenched with sat. NH4Cl (aq.) at 0 degree Celsius. To the mixture was added EA (200 mL), The resulting mixture was washed with 3×100 mL of brine. The organic layers dried over anhydrous Na2SO4. After filtration, the filtrate was concentrated under reduced pressure. The crude product (3 g) was purified by Prep-HPLC with the following conditions (Column: 300 g; Mobile Phase A: Water (10 mmol/L AcOH), Mobile Phase B: ACN; Flow rate: 80 mL/min; Gradient: 40% B to 60% B in 25 min; 220 nm; Rt: 50%) to afford tert-butyl 1-[[2-(trifluoromethyl) phenyl]methyl]-1H,4H,5H,6H,7H-imidazo[4,5-c]pyridine-5-carboxylate (2.1 g, 65.81%) as yellow oil.

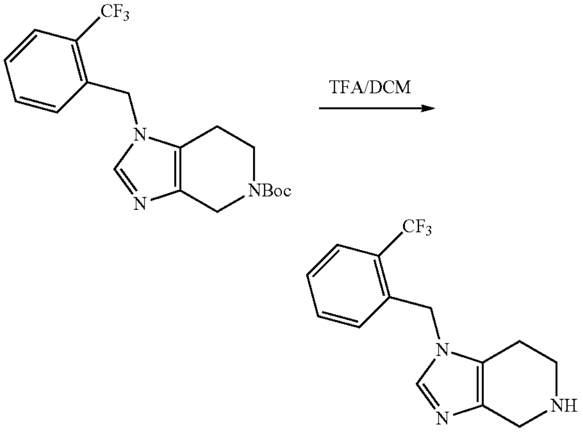

Preparation of Intermediate 1-[[2-(trifluoromethyl) phenyl]methyl]-1H,4H,5H,6H,7H-imidazo[4,5-c] pyridine

1-[[2-(trifluoromethyl)phenyl]methyl]-1H,4H,5H, 6H,7H-imidazo[4,5-c]pyridine To a stirred solution of tert-butyl 1-[[2-(trifluoromethyl) phenyl]methyl]-1H,4H,5H,6H,7H-imidazo[4,5-c]pyridine-5-carboxylate (760 mg, 1.99 mmol, 1 equiv.) in DCM (10 mL) was added TFA (2 mL, 26.93 mmol, 13.51 equiv.) dropwise at room temperature. The resulting mixture was stirred for 3 h at room temperature. The reaction was monitored by LCMS. The resulting mixture was concentrated under reduced pressure. The residue was basified to pH 8~9 with saturated NaHCO3 (aq.) The mixture was purified by reverse phase flash with the following conditions (Column: spnerical C18, 20-40 um, 330 g; Mobile Phase A: Water (5 mmol/L NH4HCO3), Mobile Phase B: ACN; Flow rate: 80 mL/min; Gradient: 20% B to 50% B in 35 min; 220 nm) to afford 1-[[2-(trifluoromethyl)phenyl]methyl]-1H,4H, 5H,6H,7H-imidazo[4,5-c]pyridine (500 mg, 89.21%) as a light yellow oil.

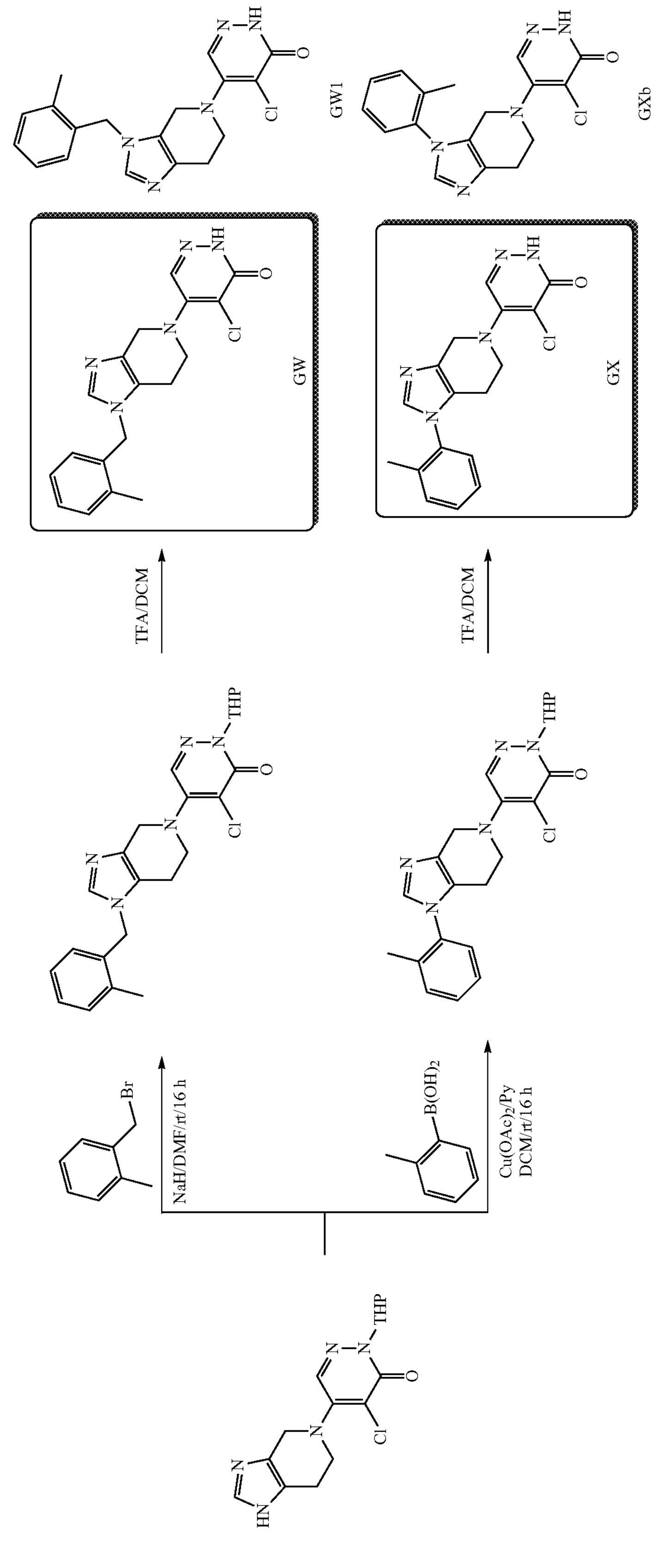
GW
GW1
GX
GXb

GW and GWb were prepared by the methods and scheme described for DP1 and DP2 above.
GX and GXb were prepared by the methods and scheme described for DQ1 and DQ2 above.
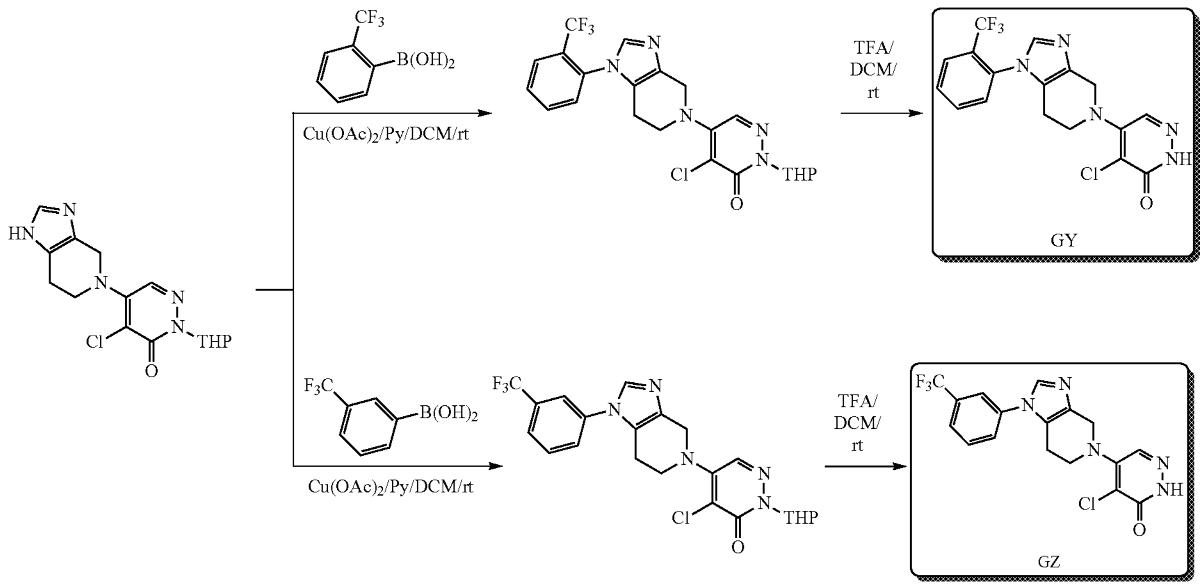
GY
GZ GY and GZ were prepared by the methods and scheme described for DQ1 above.

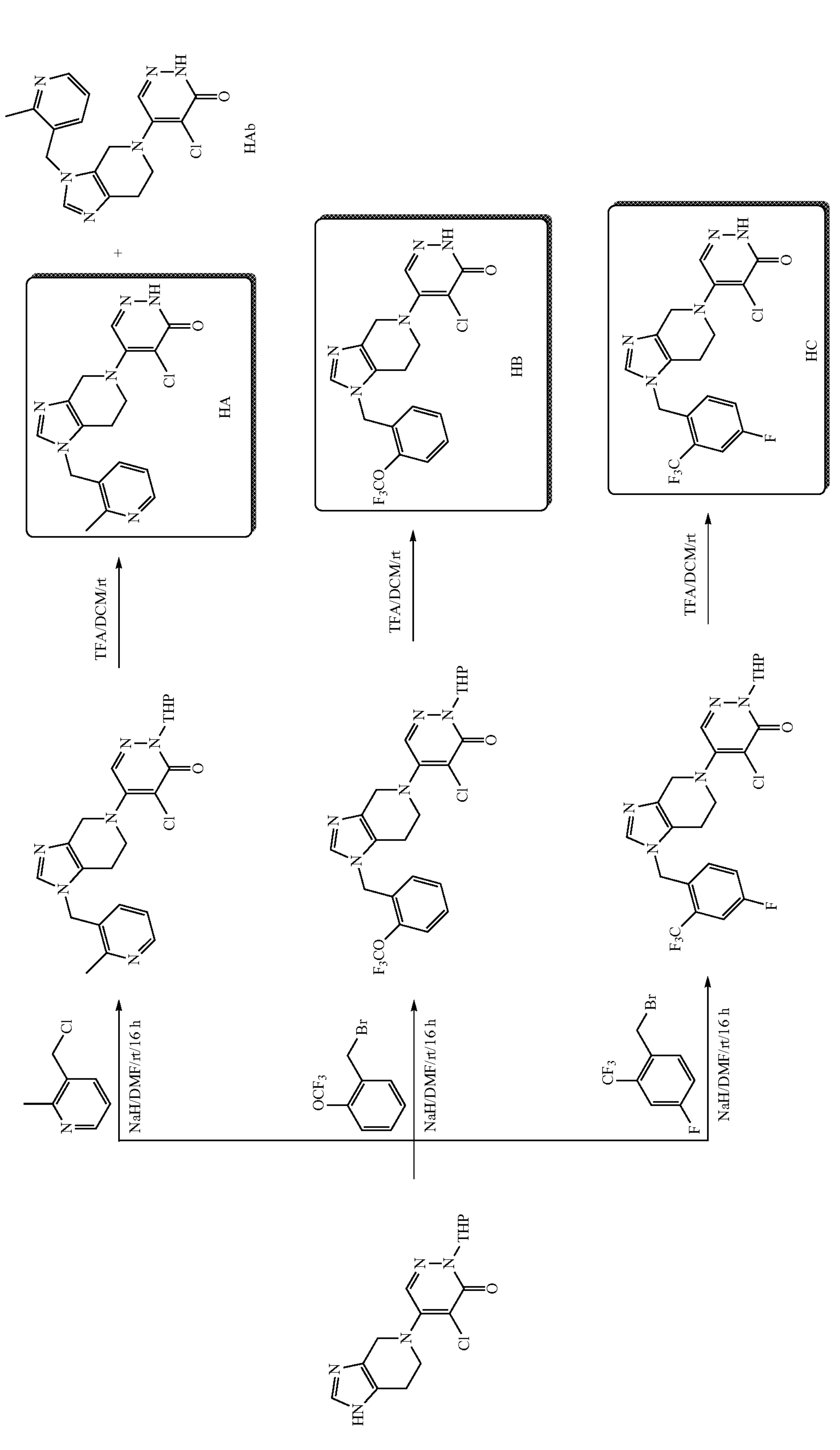
NaH/DMF/rt/16 h
NaH/DMF/rt/16 h
NaH/DMF/rt/16 h
TFA/DCM/rt
TFA/DCM/rt
TFA/DCM/rt
HA
HAb
HB
HC HA, HB, HC and HD were prepared by the methods and scheme described for DP2.
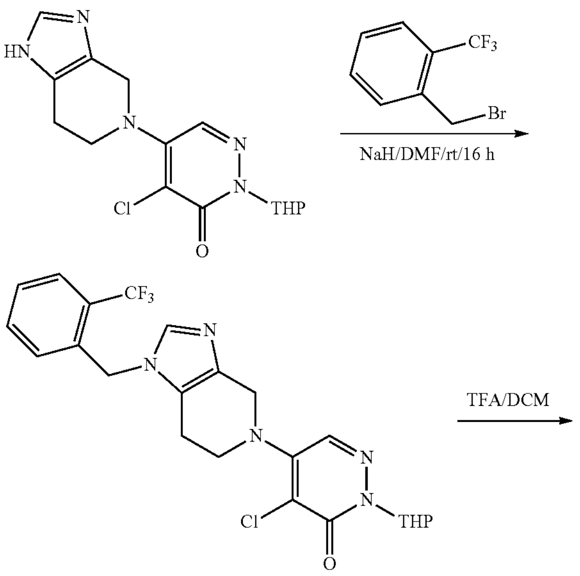
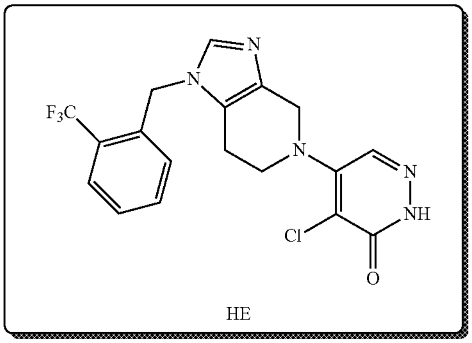
HE
HE was prepared by the methods and scheme described for DP2.
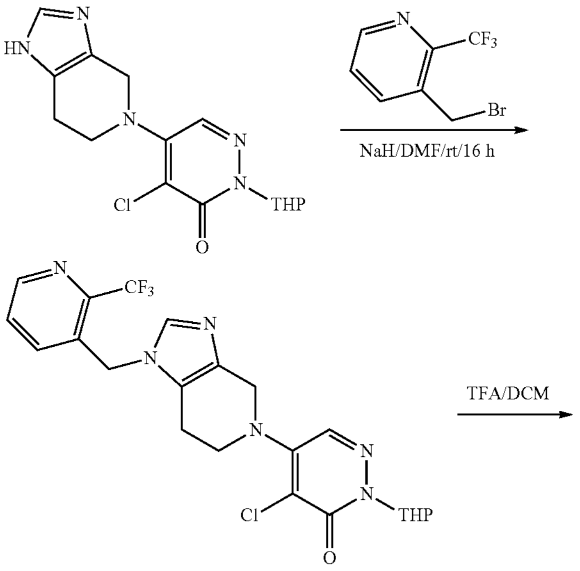
-continued
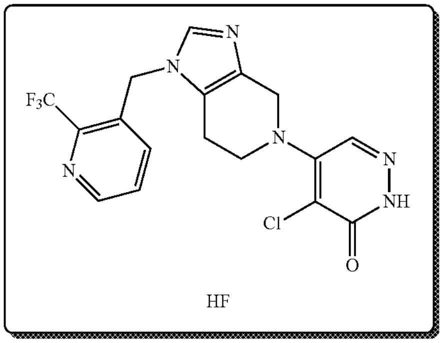
HF
HF was prepared by the methods and scheme described for DP2.
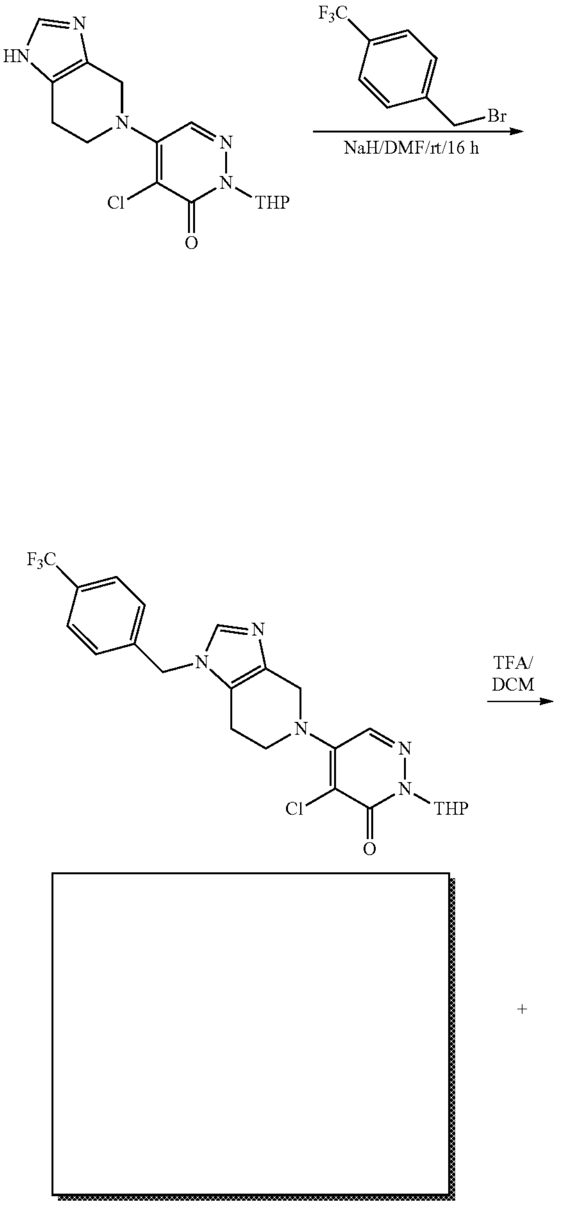

-continued
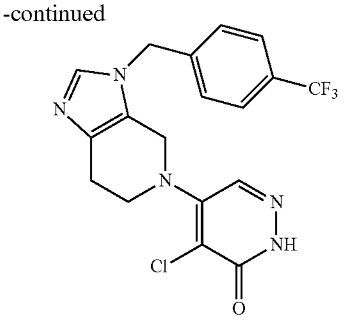
HGb
HG and HGb were prepared b the methods and scheme described for DP2.
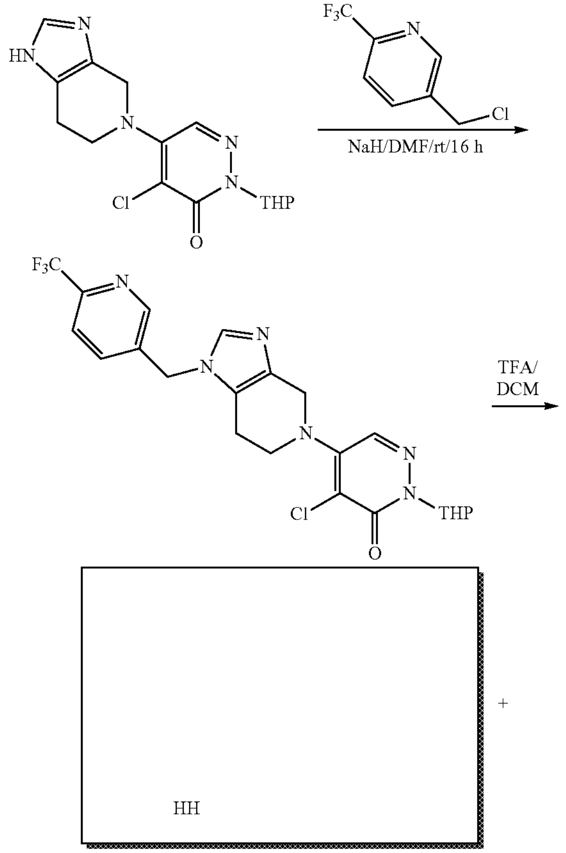
HH
+
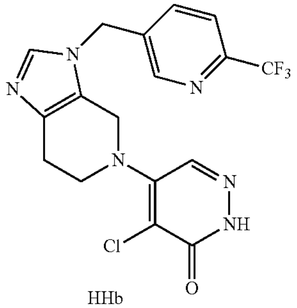
HHb
HH was prepared by the methods and scheme described for DP2.
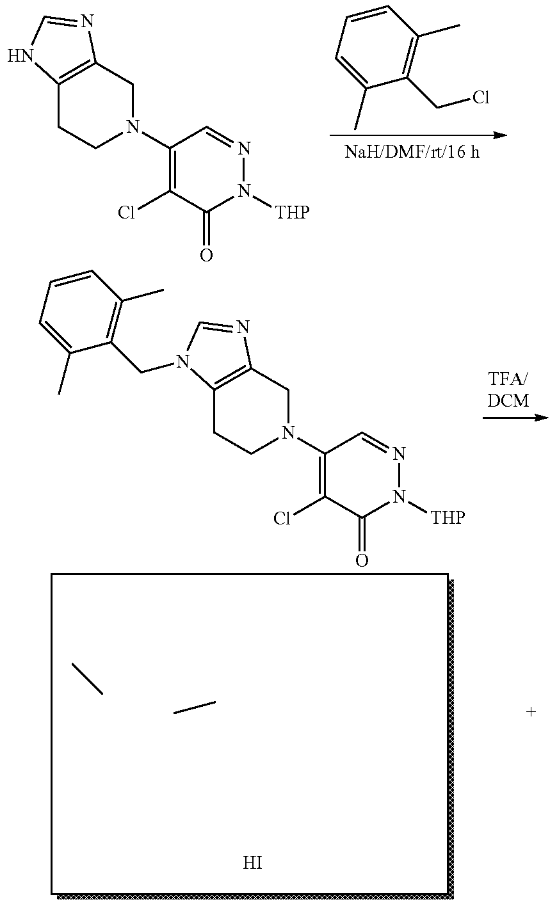
HI
+
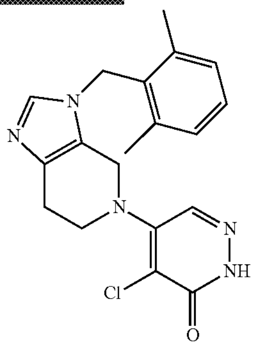
HIb
HI was prepared by the methods and scheme described for DP2
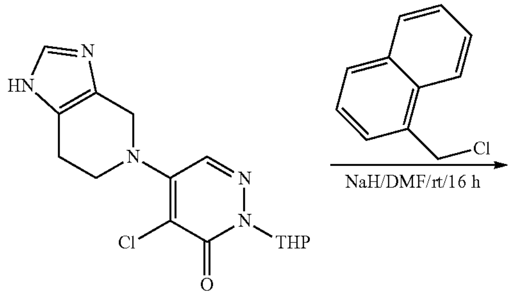

-continued
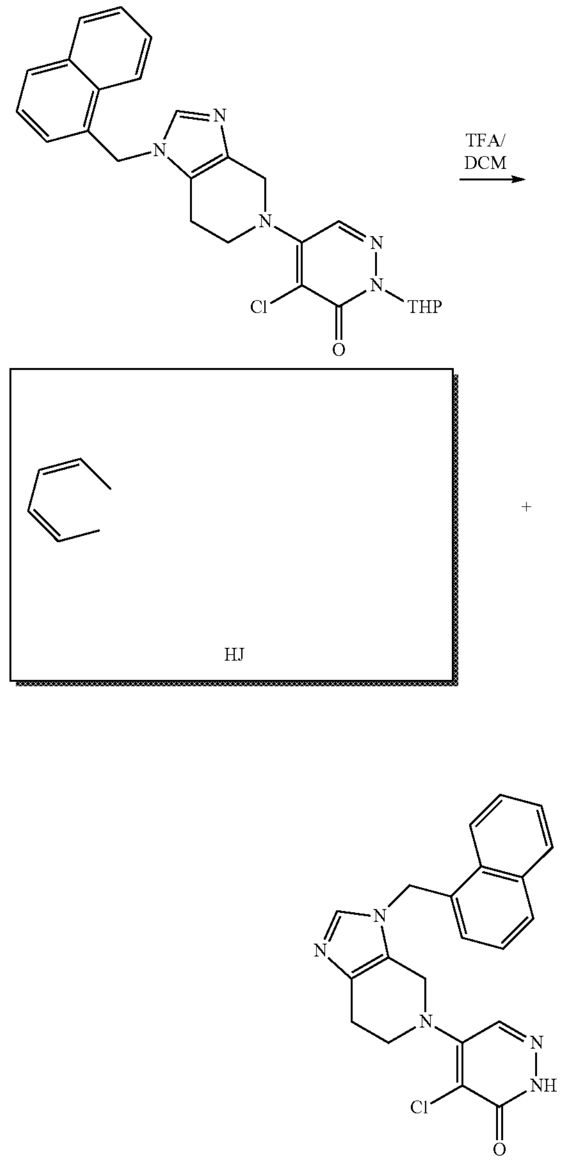
HJb
HJ was prepared by the methods and scheme described for DP2
-continued
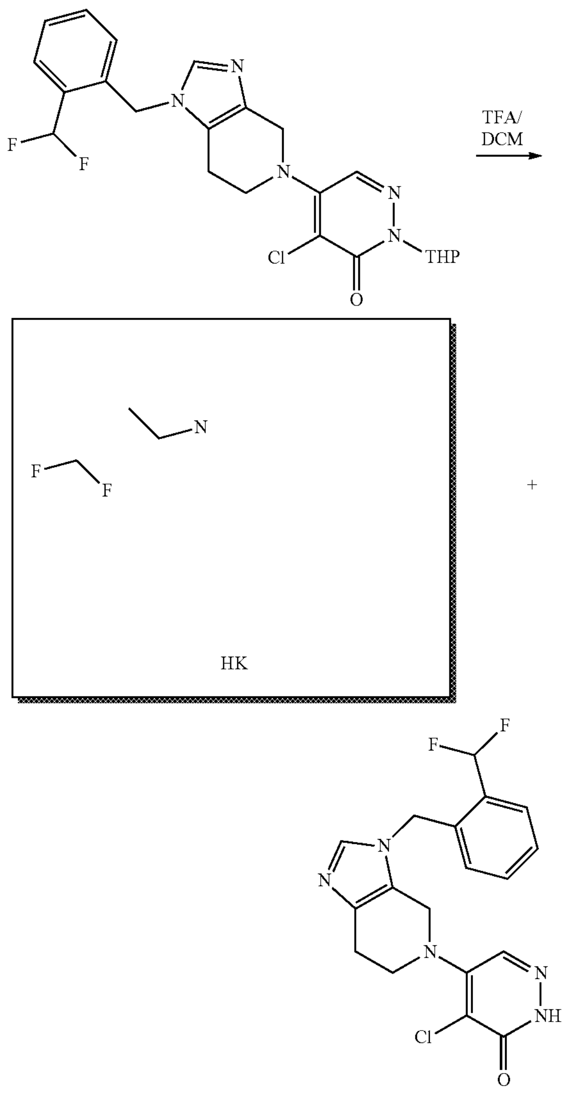
HKb
HK was prepared by the methods and scheme described for DP2
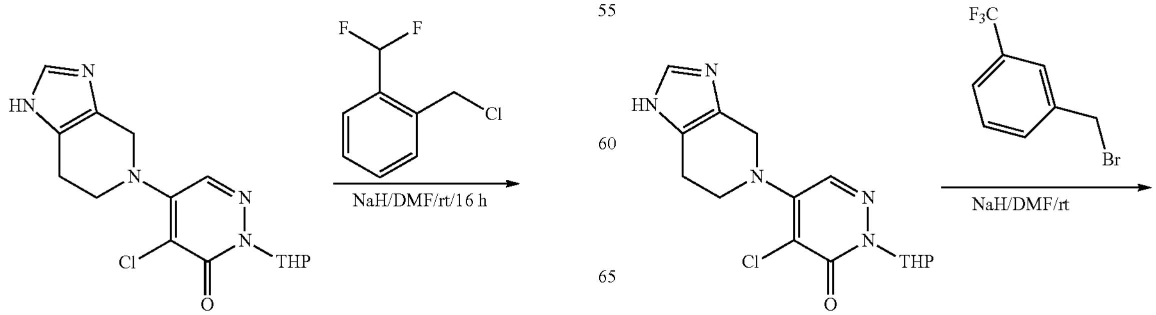

-continued
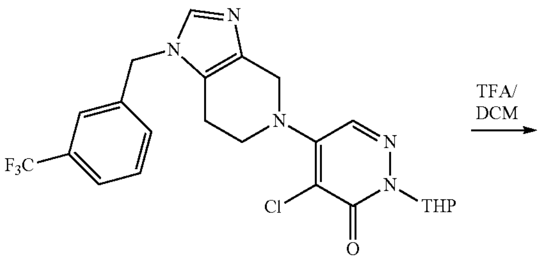
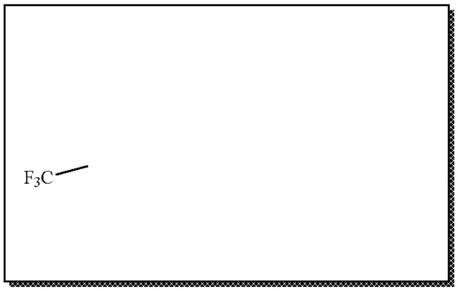
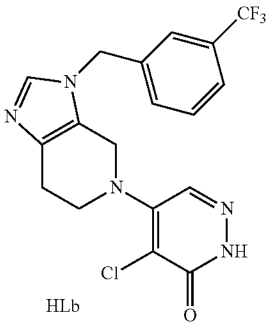
HLb
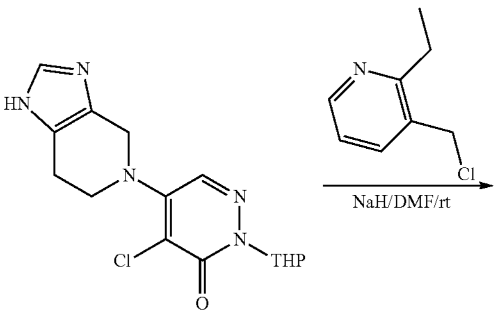
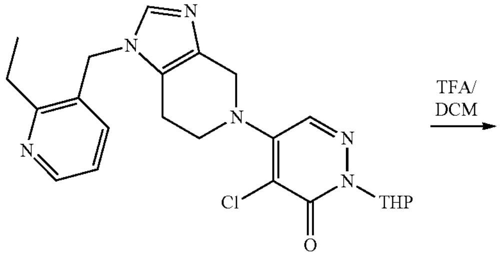
-continued
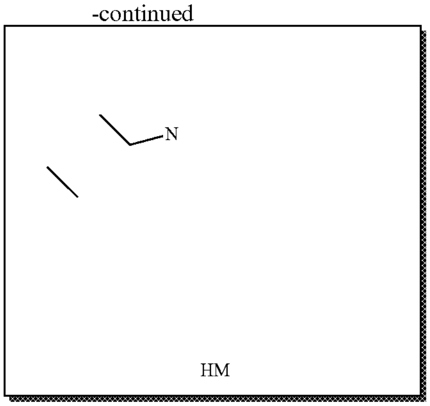
HM
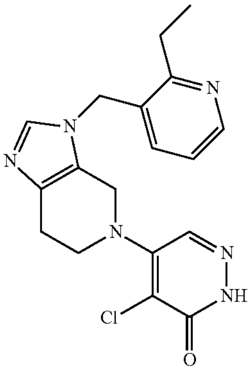
HMb
HL and HM were prepared by the methods and scheme described for DP2
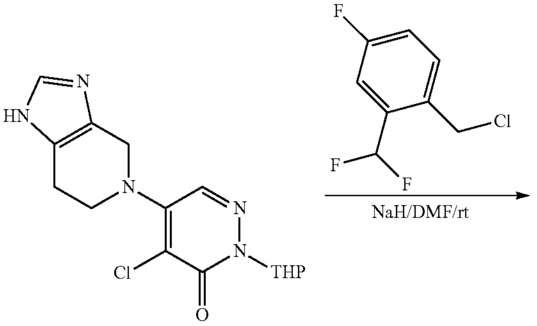
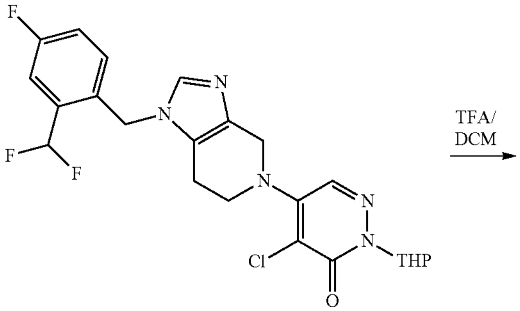

-continued
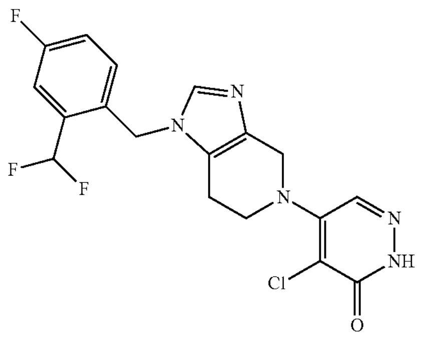
HN
HN was prepared by the methods and scheme described for DP2
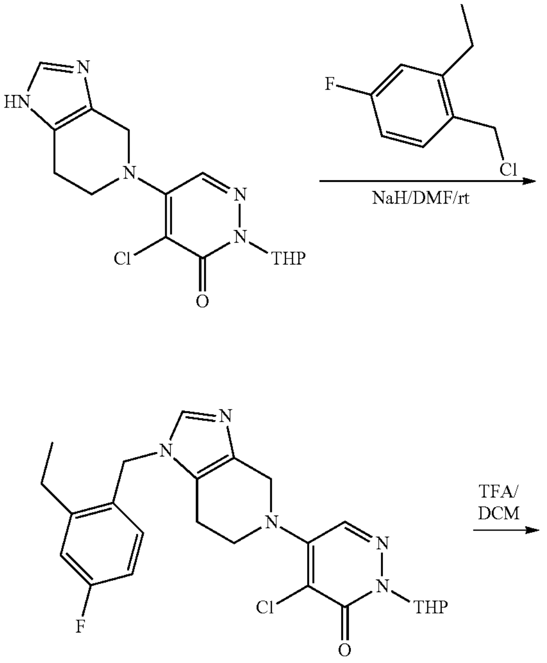
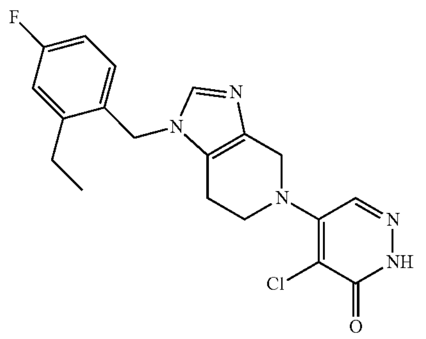
HO
-continued
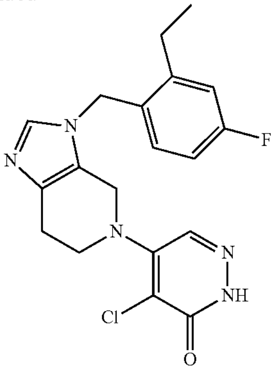
HOb
HO was prepared by the methods and scheme described for DP2
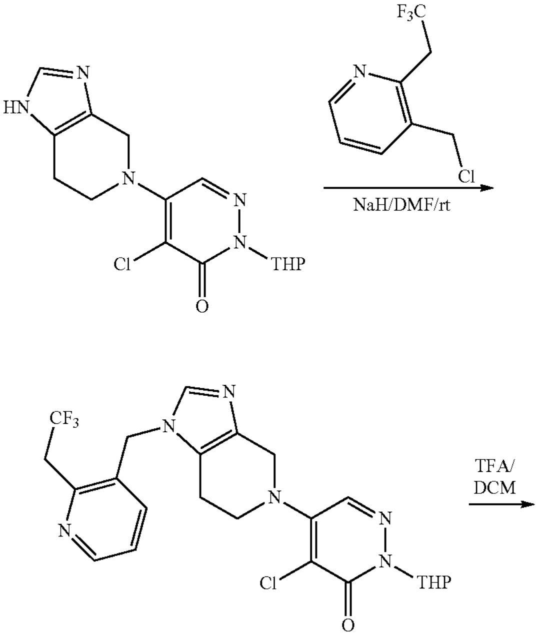
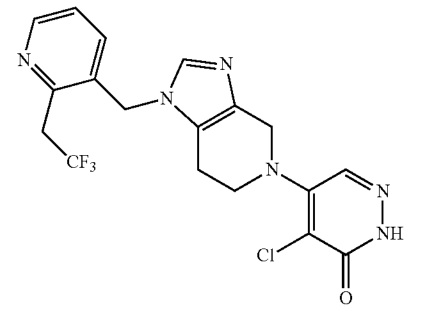
HP
HP was prepared by the methods and scheme described for DP2 by using 3-(chloromethyl)-2-(2,2,2-trifluoroethyl) pyridine

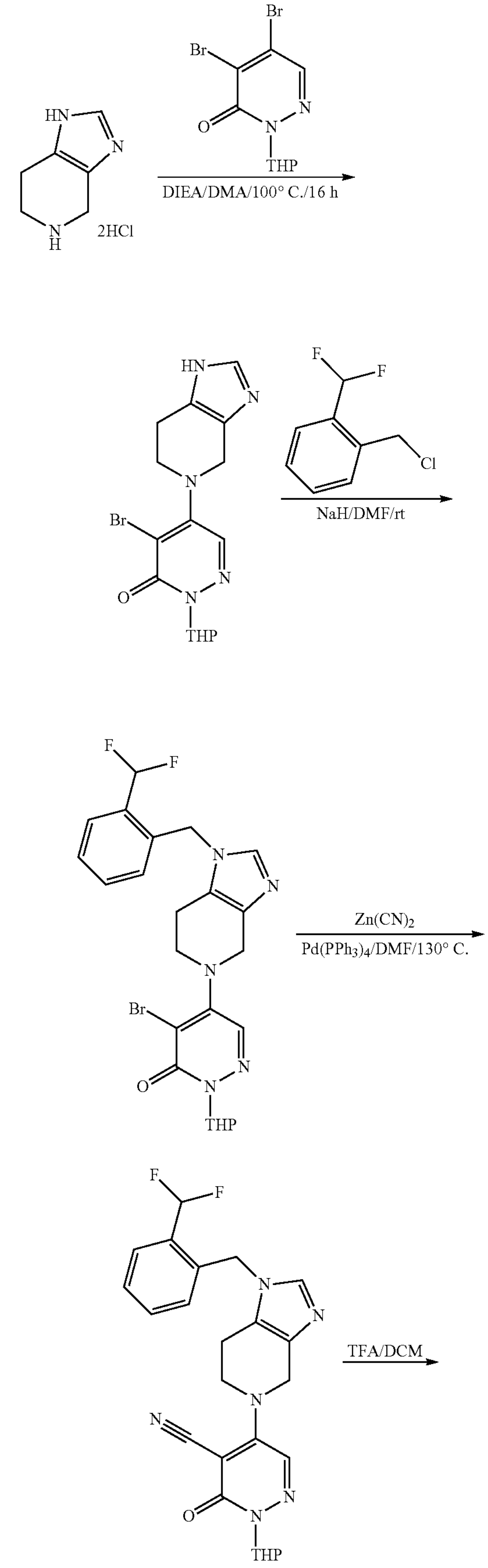

-continued

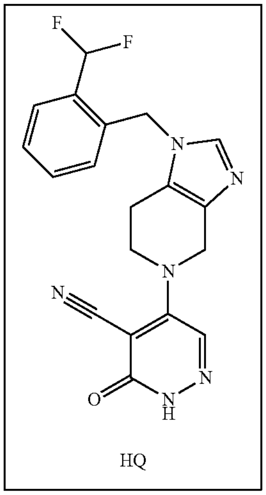

HQ

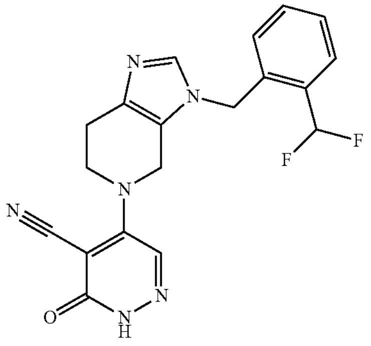

HQb

Preparation of HQ and HQb

4-bromo-5-[1H,4H,5H,6H,7H-imidazo[4,5-c]pyridin-5-yl]-2-(oxan-2-yl)-2,3-dihydropyridazin-3-one To a stirred solution of 4,5-dibromo-2-(oxan-2-yl)-2,3-dihydropyridazin-3-one (3 g, 8.88 mmol, 1 equiv.) and 1H,4H,5H,6H,7H-imidazo[4,5-c]pyridine (1.1 g, 8.88 mmol, 1.00 equiv.) in 1,4-dioxane (30 mL) was added DIEA (2.3 g, 17.75 mmol, 2 equiv.) dropwise at 0 degree Celsius under nitrogen atmosphere. The mixture was stirred at 100 degrees Celsius overnight Desired product could be detected by LCMS. The resulting mixture was concentrated under reduced pressure. The residue was purified by silica gel column chromatography, eluted with CH2Cl2/MeOH (10:1 to 5:1) to afford 4-bromo-5-[1H,4H,5H,6H,7H-imidazo[4,5-c]pyridin-5-yl]-2-(oxan-2-yl)-2,3-dihydropyridazin-3-one (3 g, 88.89%) as white solid.

4-bromo-5-(1-[[2-(difluoromethyl)phenyl]methyl]-1H,4H,5H,6H,7H-imidazo[4,5-c]pyridin-5-yl)-2-(oxan-2-yl)-2,3-dihydropyridazin-3-one and isomer To a solution of 4-bromo-5-[1H,4H,5H,6H,7H-imidazo[4,5-c]pyridin-5-yl]-2-(oxan-2-yl)-2,3-dihydropyridazin-3-one (200 mg, 0.53 mmol, 1 equiv.) in DMF (10 mL) was added sodium hydride (60% in oil, 31.6 mg) at 0 degree Celsius. The mixture was stirred for 15 min. 1-(chloromethyl)-2-(difluoromethyl)benzene (92.9 mg, 0.53 mmol, 1.00 equiv.) was added and the mixture was allowed to warm to room temperature and stirred for 1 h. The reaction mixture was quenched by water and extracted with DCM (3*25 mL). The organic layer was concentrated, the residue was purified by Prep-TLC (CH2Cl2/MeOH 6:1) to afford 4-bromo-5-(1-[[2-(difluoromethyl)phenyl]methyl]-1H,4H,5H,6H,7H-imidazo[4,5-c]pyridin-5-yl)-2-(oxan-2-yl)-2,3-dihydropyridazin-3-one (200 mg, 73.07%) as a white solid.

5-(1-[[2-(difluoromethyl)phenyl]methyl]-1H,4H,5H,6H,7H-imidazo[4,5-c]pyridin-5-yl)-2-(oxan-2-yl)-3-oxo-2,3-dihydropyridazine-4-carbonitrile and isomer Into a 5 mL vial were added 4-bromo-5-(1-[[2-(difluoromethyl)phenyl]methyl]-1H,4H,5H,6H,7H-imidazo[4,5-c]pyridin-5-yl)-2-(oxan-2-yl)-2,3-dihydropyridazin-3-one and isomer (300 mg, 0.58 mmol, 1 equiv.) and zincdicarbonitrile (300 mg, 1.00 equiv.), Pd(PPh3)4 (66.6 mg, 0.06 mmol, 0.10 equiv.) at room temperature. The final reaction mixture was irradiated with microwave radiation for 2 h at 145 degrees Celsius. Desired product could be detected by LCMS. The resulting mixture was concentrated under reduced pressure. The residue was purified by silica gel column chromatography, eluted with CH2Cl2/MeOH (8:1) to afford 5-(1-[[2-(difluoromethyl)phenyl]methyl]-1H,4H,5H,6H,7H-imidazo[4,5-c]pyridin-5-yl)-2-(oxan-2-yl)-3-oxo-2,3-dihydropyridazine-4-carbonitrile and isomer (230 mg, 85.52%) as a white solid.

5-(1-[[2-(difluoromethyl)phenyl]methyl]-1H,4H,5H,6H,7H-imidazo[4,5-c]pyridin-5-yl)-3-oxo-2,3-dihydropyridazine-4-carbonitrile and 5-(3-[[2-(difluoromethyl)phenyl]methyl]-3H,4H,5H,6H,7H-imidazo[4,5-c]pyridin-5-yl)-3-oxo-2,3-dihydropyridazine-4-carbonitrile To a stirred solution of 5-(1-[[2-(difluoromethyl)phenyl]methyl]-1H,4H,5H,6H,7H-imidazo[4,5-c]pyridin-5-yl)-2-(oxan-2-yl)-3-oxo-2,3-dihydropyridazine-4-carbonitrile (100 mg) and 5-(3-[[2-(difluoromethyl)phenyl]methyl]-3H,4H,5H,6H,7H-imidazo[4,5-c]pyridin-5-yl)-2-(oxan-2-yl)-3-oxo-2,3-dihydropyridazine-4-carbonitrile (60 mg) in DCM (10 mL) was added TFA (2 mL) dropwise at room temperature under nitrogen atmosphere. The mixture was stirred at room temperature overnight Desired product could be detected by LCMS. The resulting mixture was concentrated under vacuum. The crude product (120 mg) was purified by Prep-HPLC with the following conditions (Column: XBridge Shield RP18 OBD Column, 5 um, 19*150 mm; Mobile Phase A: Water (10 mmol/L NH4HCO3), Mobile Phase B: ACN; Flow rate: 20 mL/min; Gradient: 15% B to 50% B in 7 min; 220 nm; Rt: 5.92, 6.33 min) to afford 5-(1-[[2-(difluoromethyl)phenyl]methyl]-1H,4H,5H,6H,7H-imidazo[4,5-c]pyridin-5-yl)-3-oxo-2,3-dihydropyridazine-4-carbonitrile (43.5 mg) as white solid and 5-(3-[[2-(difluoromethyl)phenyl]methyl]-3H,4H,5H,6H,7H-imidazo[4,5-c]pyridin-5-yl)-3-oxo-2,3-dihydropyridazine-4-carbonitrile (18.2 mg) as white solid.

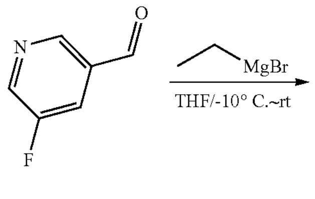

-continued

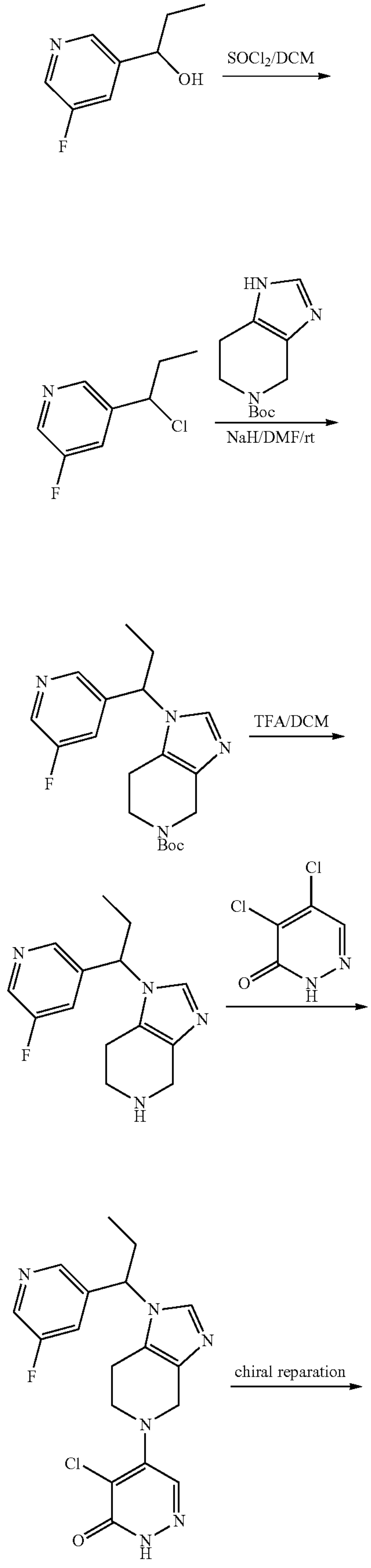

-continued

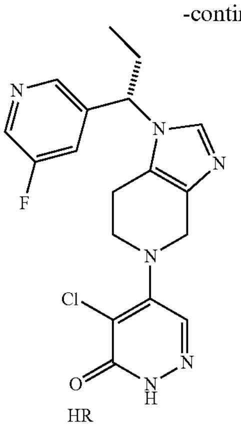

+

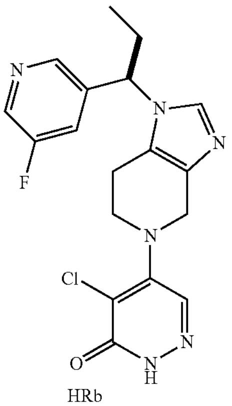

HR HRb

Preparation of HR and HRb 1-(5-fluoropyridin-3-yl)propan-1-ol

To a stirred solution of 5-fluoropyridine-3-carbaldehyde (1 g, 7.99 mmol, 1 equiv.) in oxolane (15 mL) was added bromo(ethyl)magnesium (2.1 g, 15.99 mmol, 2 equiv.) dropwise at 0 degree Celsius under nitrogen atmosphere. The resulting mixture was stirred for 16 h at room temperature under nitrogen atmosphere. The reaction was quenched with saturated NH4Cl (15 mL) at room temperature. The resulting mixture was extracted with EA (3×40 mL). The combined organic layers were dried over anhydrous Na2SO4. After filtration, the filtrate was concentrated under reduced pressure. The residue was purified by silica gel column chromatography, eluted with DCM:MeOH (10:1) to afford 1-(5-fluoropyridin-3-yl)propan-1-ol (410 mg, 33.05%) as a brown oil.

3-(1-chloropropyl)-5-fluoropyridine

To a stirred solution of 1-(5-fluoropyridin-3-yl)propan-1-ol (410 mg, 2.64 mol, 1 equiv.) in DCM (5 mL) was added sulfuroyl dichloride (943.0 mg, 7.93 mol, 3.00 equiv.) and N,N-dimethylformamide (0.2 mL) at 0 degree Celsius. The resulting mixture was stirred for 2 h at 25 degrees Celsius under nitrogen atmosphere. The solution was concentrated under reduced pressure. This resulted in 3-(1-chloropropyl)-5-fluoropyridine (440 mg, 95.91%) as a yellow solid.

1-[1-(5-fluoropyridin-3-yl)propyl]-1H,4H,5H,6H,7H-imidazo[4,5-c]pyridine-5-carboxylate To a stirred solution of tert-butyl 1H,4H,5H,6H,7H-imidazo[4,5-c]pyridine-5-carboxylate (400 mg, 1.79 mmol, 1 equiv.) in DMF (10 mL) was added NaH (107.5 mg, 2.69 mmol, 1.5 equiv., 60%) at room temperature. The resulting mixture was stirred for 0.5 h at room temperature. To the above mixture was added a solution of 3-(1-chloropropyl)-5-fluoropyridine hydrochloride (489.2 mg, 2.33 mmol, 1.3 equiv.) and Cs2CO3 dropwise at 0 degree Celsius. The resulting mixture was stirred for additional 8 h at room temperature. The reaction was monitored by LCMS. The reaction was quenched with Water (2 mL) at room temperature. The mixture was purified by reverse phase flash with the following conditions (Column: spnerical C18, 20-40 um, 330 g; Mobile Phase A: Water (5 mmol/L NH4HCO3), Mobile Phase B: ACN; Flow rate: 80 mL/min; Gradient: 40% B to 60% B in 25 min; 220 nm) to afford tert-butyl 1-[1-(5-fluoropyridin-3-yl)propyl]-1H,4H,5H,6H,7H-imidazo[4,5-c]pyridine-5-carboxylate (230 mg, 35.62%) as a light yellow oil.

3-fluoro-5-(1-[1H,4H,5H,6H,7H-imidazo[4,5-c]pyridin-1-yl]propyl)pyridine

To a stirred solution of tert-butyl 1-[1-(5-fluoropyridin-3-yl)propyl]-1H,4H,5H,6H,7H-imidazo[4,5-c]pyridine-5-carboxylate (230 mg, 1 equiv.) in DCM (10 mL) was added TFA (2 mL) dropwise at room temperature. The resulting mixture was stirred for 2 h at room temperature. The reaction was monitored by LCMS. The resulting mixture was concentrated under reduced pressure. The residue was basified to pH 8~9 with saturated NaHCO3 (aq.). The mixture was purified by reverse phase flash with the following conditions (Column: spnerical C18, 20-40 um, 330 g; Mobile Phase A: Water (5 mmol/L NH4HCO3), Mobile Phase B: ACN; Flow rate: 80 mL/min; Gradient: 15% B to 35% B in 25 min; 220 nm) to afford 3-fluoro-5-(1-[1H,4H,5H,6H,7H-imidazo[4,5-c]pyridin-1-yl]propyl)pyridine (80 mg, 48.16%) as a white solid.

4-chloro-5-[1-[(1R)-1-(5-fluoropyridin-3-yl)propyl]-1H,4H,5H,6H,7H-imidazo[4,5-c]pyridin-5-yl]-2,3-dihydropyridazin-3-one and 4-chloro-5-[1-[(1S)-1-(5-fluoropyridin-3-yl)propyl]-1H,4H,5H,6H,7H-imidazo[4,5-c]pyridin-5-yl]-2,3-dihydropyridazin-3-one To a solution of 3-fluoro-5-(1-[1H,4H,5H,6H,7H-imidazo[4,5-c]pyridin-1-yl]propyl)pyridine (80 mg, 0.31 mmol, 1 equiv.) and 4,5-dichloro-2,3-dihydropyridazin-3-one (50.7 mg, 0.31 mmol, 1 equiv.) in DMA (3 mL) was added DIEA (79.4 mg, 0.61 mmol, 2 equiv.) at room temperature. The resulting mixture was stirred for 5 h at 100 degrees Celsius. The reaction was monitored by LCMS. The mixture was purified by reverse phase flash to afford crude products which was purified by Prep-Chiral-HPLC with the following conditions (Column: CHIRALPAK IE, 2*25 cm, 5 um; Mobile Phase A:MTBE—HPLC, Mobile Phase B: EtOH—HPLC; Flow rate: 14 mL/min; Gradient: 40 B to 40 B in 30 min; 220/254 nm; RT1:18.5; RT2:24) to afford 4-chloro-5-[1-[(1R)-1-(5-fluoropyridin-3-yl)propyl]-1H,4H,5H,6H,7H-imidazo[4,5-c]pyridin-5-yl]-2,3-dihydropyridazin-3-one (12.1 mg, 24.20%) as a white solid and 4-chloro-5-[1-[(1S)-1-(5-fluoropyridin-3-yl)propyl]-1H,4H,5H,6H,7H-imidazo[4,5-c]pyridin-5-yl]-2,3-dihydropyridazin-3-one (12.5 mg, 25.00%) as a white solid.

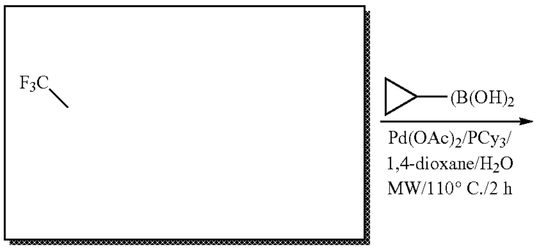

-continued

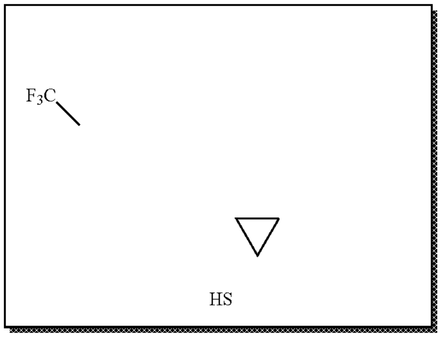

HS

Preparation of HS 4-cyclopropyl-5-(1-(2-(trifluoromethyl)benzyl)-1,4,6,7-tetrahydro-5H-imidazo[4,5-c]pyridin-5-yl)pyridazin-3(2H)-one To a stirred solution of 4-chloro-5-(1-[[2-(trifluoromethyl)phenyl]methyl]-1H,4H,5H,6H,7H-imidazo[4,5-c]pyridin-5-yl)-2,3-dihydropyridazin-3-one (90 mg, 0.22 mmol, 1 equiv.) in dioxane (5 mL, 59.02 mmol, 268.74 equiv.) and H2O (1 mL, 55.51 mmol, 252.74 equiv.) were added Pd(AcO)2 (6 mg, 0.03 mmol, 0.12 equiv.), tricyclohexylphosphane (6 mg, 0.02 mmol, 0.10 equiv.) and K2CO3 (90 mg, 0.65 mmol, 2.97 equiv.) in portions at room temperature. To the above mixture was added cyclopropylboronic acid (9 mg, 0.10 mmol, 1.43 equiv.) in portions at room temperature. The resulting mixture was stirred for 2 h at 110 degrees Celsius. The reaction was monitored by LCMS. The resulting mixture was concentrated under reduced pressure. The residue was purified by Prep-TLC (CH2Cl2/MeOH=50/1) to afford crude product. The crude product (100 mg) was purified by Prep-HPLC with the following conditions (Column: Kinetex EVO C18 Column 21.2*150.5 um; Mobile Phase A: Water (10 mmol/L NH4HCO3), Mobile Phase B: ACN; Flow rate: 20 mL/min; Gradient: 18% B to 36% B in 12 min; 254/220 nm; Rt: 12.6 min) to afford 4-cyclopropyl-5-(1-[[2-(trifluoromethyl)phenyl]methyl]-1H,4H,5H,6H,7H-imidazo[4,5-c]pyridin-5-yl)-2,3-dihydropyridazin-3-one (9.2 mg) as a white solid.

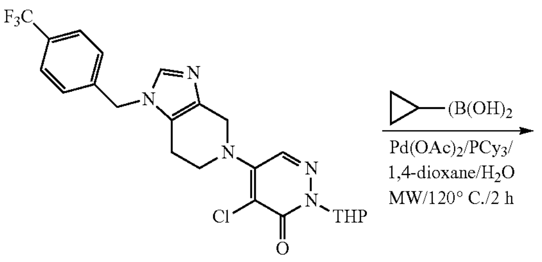

-continued

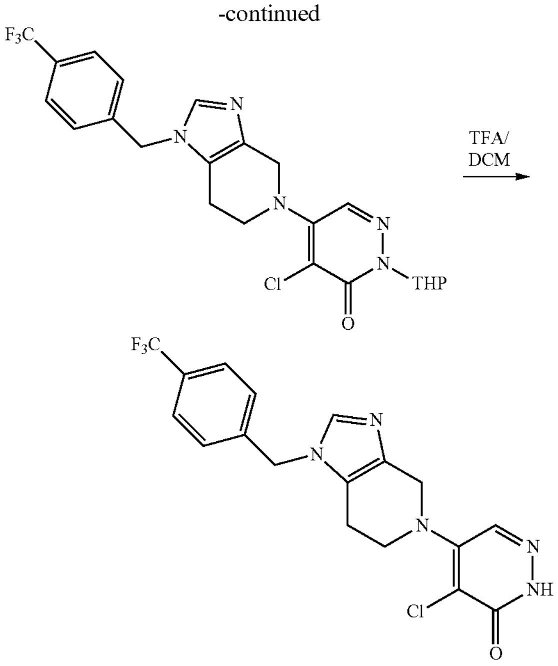

HT

Preparation of HT 4-chloro-2-(oxan-2-yl)-5-(1-[[4-(trifluoromethyl)phenyl]methyl]-1H,4H,5H,6H,7H-imidazo[4,5-c]pyridin-5-yl)-2,3-dihydropyridazin-3-one To a solution of 4-chloro-2-(oxan-2-yl)-5-(1-[[4-(trifluoromethyl)phenyl]methyl]-1H,4H,5H,6H,7H-imidazo[4,5-c]pyridin-5-yl)-2,3-dihydropyridazin-3-one (270 mg, 0.55 mmol, 1 equiv.) and cyclopropylboronic acid (140.9 mg, 1.64 mmol, 3 equiv.) in 1,4-dioxane (4 mL) and H2O (0.8 mL) were added K2CO3 (151.1 mg, 1.09 mmol, 2 equiv.), Pd(AcO)2 (24.5 mg, 0.11 mmol, 0.2 equiv.) and PCy3 (15.3 mg, 0.05 mmol, 0.1 equiv.). The final reaction mixture was irradiated with microwave radiation for 2 h at 110 degrees Celsius under a nitrogen atmosphere. The resulting mixture was concentrated under reduced pressure. The residue was purified by Prep-TLC, eluted with CH2Cl2/MeOH (15:1) to afford 4-cyclopropyl-2-(oxan-2-yl)-5-(1-[[4-(trifluoromethyl)phenyl]methyl]-1H,4H,5H,6H,7H-imidazo[4,5-c]pyridin-5-yl)-2,3-dihydropyridazin-3-one (120 mg, 43.94%) as a yellow solid.

4-cyclopropyl-5-(1-[[4-(trifluoromethyl)phenyl]methyl]-1H,4H,5H,6H,7H-imidazo[4,5-c]pyridin-5-yl)-2,3-dihydropyridazin-3-one To a stirred solution of 4-cyclopropyl-2-(oxan-2-yl)-5-(1-[[4-(trifluoromethyl)phenyl]methyl]-1H,4H,5H,6H,7H-imidazo[4,5-c]pyridin-5-yl)-2,3-dihydropyridazin-3-one (240 mg, 480 mmol, 1 equiv.) in DCM (10 mL) was added TFA (1 mL, 13.46 mmol, 28.02 equiv.) dropwise at room temperature. The resulting mixture was stirred for 2 h at room temperature. The reaction was monitored by LCMS. The resulting mixture was concentrated under reduced pressure. The residue was basified to pH 8~9 with saturated NaHCO3 (aq.). The mixture was purified by reverse phase flash with the following conditions (Column: spnerical C18, 20-40 um, 330 g; Mobile Phase A: Water (5 mmol/L NH4HCO3), Mobile Phase B: ACN; Flow rate: 80 mL/min; Gradient: 15% B to 60% B in 55 min; 220 nm) to afford crude products. The crude product (90 mg) was purified by Prep-HPLC with the following conditions (Column: Xselect CSH OBD Column 30*150 mm 5 um n; Mobile Phase A: Water (0.05% TFA), Mobile Phase B: ACN; Flow rate: 60 mL/min; Gradient: 3% B to 25% B in 17 min; 220 nm; 15.87 min) to afford crude product. The crude product was purified by Prep-HPLC with the following conditions (Column: XBridge Shield RP18 OBD Column, 5 um, 19*150 mm; Mobile Phase A: Water (10 mmol/L NH4HCO3), Mobile Phase B: ACN; Flow rate: 60 mL/min; Gradient: 15% B to 38% B in 20 min; 220 nm; 19.3 min) to afford 4-cyclopropyl-5-(1-[[4-(trifluoromethyl)phenyl]methyl]-1H,4H,5H,6H,7H-imidazo[4,5-c]pyridin-5-yl)-2,3-dihydropyridazin-3-one (5.9 mg, 2.96%) as a white solid.

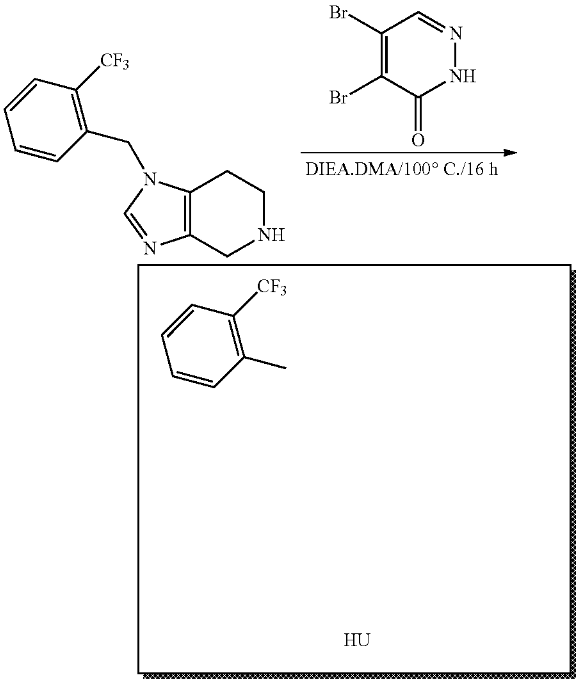

HU

Preparation of HU 4-bromo-5-(1-[[2-(trifluoromethyl)phenyl]methyl]-1H,4H,5H,6H,7H-imidazo[4,5-c]pyridin-5-yl)-2,3-dihydropyridazin-3-one To a stirred mixture of 1-[[2-(trifluoromethyl)phenyl]methyl]-1H,4H,5H,6H,7H-imidazo[4,5-c]pyridine (260 mg, 920 mmol, 2.35 equiv.) and 4,5-dibromo-2,3-dihydropyridazin-3-one (100 mg, 0.39 mmol, 1 equiv.) in DMA (3 mL) was added DIEA (203.6 mg, 1.58 mmol, 4 equiv.) dropwise at room temperature. The final reaction mixture was irradiated with microwave radiation for 2 h at 100 degrees Celsius. The reaction was monitored by LCMS. The mixture was allowed to cool down to room temperature. The residue was purified by reverse phase flash with the following conditions (Column: Spherical C18 Column, 20-40 um, 120 g; Mobile Phase A: Water (0.1% NH4HCO3), Mobile Phase B: ACN; Flow rate: 60 mL/min; Gradient: 30% B to 50% B in 25 min, 254 nm) to afford 4-bromo-5-(1-[[2-(trifluoromethyl)phenyl]methyl]-1H,4H,5H,6H,7H-imidazo[4,5-c]pyridin-5-yl)-2,3-dihydropyridazin-3-one (110 mg, 61.48%) as a white solid.

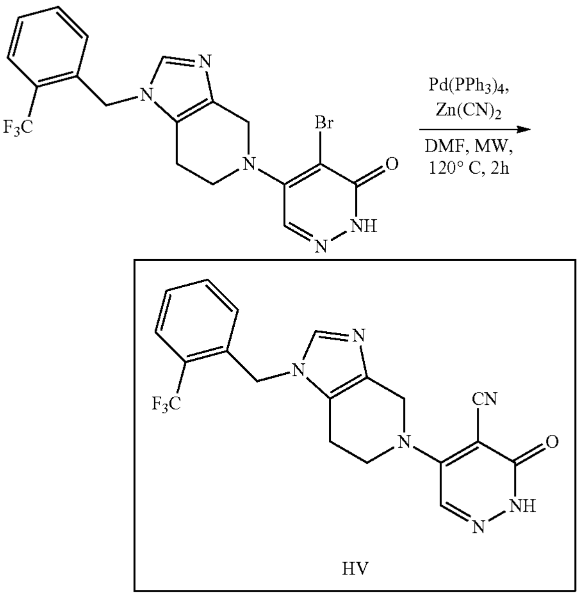

HV

Preparation of HV 3-oxo-5-(1-[[2-(trifluoromethyl)phenyl]methyl]-1H,4H,5H,6H,7H-imidazo[4,5-c]pyridin-5-yl)-2,3-dihydropyridazine-4-carbonitrile To a stirred solution of 4-bromo-5-(1-[[2-(trifluoromethyl)phenyl]methyl]-1H,4H,5H,6H,7H-imidazo[4,5-c]pyridin-5-yl)-2,3-dihydropyridazin-3-one (130 mg, 0.29 mmol, 1 equiv.) in DMF (10 mL) were added Pd(PPh3)4 (66.1 mg, 0.06 mmol, 0.2 equiv.) and Zn(CN)2 (67.2 mg, 0.57 mmol, 2 equiv.) at room temperature under N2 atmosphere. The resulting mixture was stirred for 16 h at 110 degrees Celsius under N2 atmosphere. The reaction was monitored by LCMS. The resulting mixture was filtered, the filter cake was washed with DMF (2×1 mL). The filtrate was concentrated under vacuum. The residue was purified by reverse phase flash with the following conditions (Column: Spherical C18 Column, 20-40 um, 120 g; Mobile Phase A: Water (0.1% NH4HCO3), Mobile Phase B: ACN; Flow rate: 60 mL/min; Gradient: 30% B to 50% B in 25 min, 254 nm) to afford 3-oxo-5-(1-[[2-(trifluoromethyl)phenyl]methyl]-1H,4H,5H,6H,7H-imidazo[4,5-c]pyridin-5-yl)-2,3-dihydropyridazine-4-carbonitrile (44 mg, 38.40%) as a grey solid.

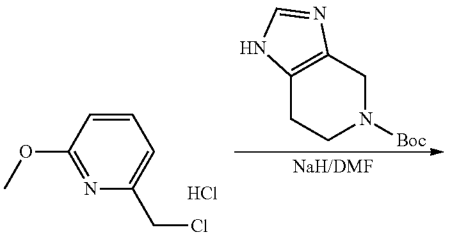

-continued

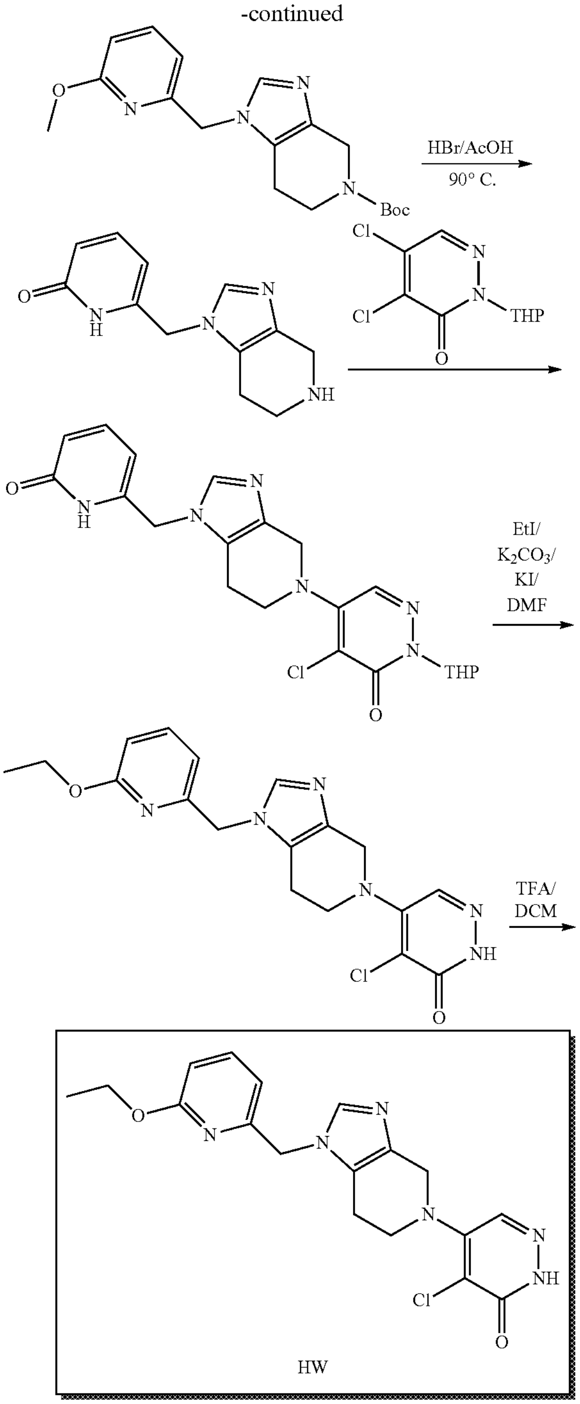

HW

Preparation of HW

Tert-Butyl 1-[(6-methoxypyridin-2-yl)methyl]-1H, 4H,5H,6H,7H-imidazo[4,5-c]pyridine-5-carboxylate A solution of tert-butyl 1H,4H,5H,6H,7H-imidazo[4,5-c] pyridine-5-carboxylate (1 g, 4.48 mmol, 1 equiv.) in DMF (10 mL) was stirred for 30 min at 0 degree Celsius. The reaction was added 2-(chloromethyl)-6-methoxypyridine (705.9 mg, 4.48 mmol, 1 equiv.) and Cs2CO3 (2.9 g, 8.90 mmol, 1.99 equiv.) at room temperature. The resulting mixture was stirred for 16 h at room temperature. The reaction was monitored by LCMS. The resulting mixture was extracted with EtOAc (3×250 mL). The combined organic layers were washed with brine (3×250 mL), dried over anhydrous Na2SO4. After filtration, the filtrate was concentrated under reduced pressure. The residue was purified by reverse flash chromatography with the following conditions: column, C18 silica gel; mobile phase, ACN in water, 35% to 75% gradient in 20 min; detector, UV 254 nm, to afford tert-butyl 1-[(6-methoxypyridin-2-yl)methyl]-1H, 4H,5H,6H,7H-imidazo[4,5-c]pyridine-5-carboxylate (550 mg, 35.66%) as yellow oil.

6-([1H,4H,5H,6H,7H-imidazo[4,5-c]pyridin-1-yl] methyl)-1,2-dihydropyridin-2-one

To a stirred solution of tert-butyl 1-[(6-methoxypyridin-2-yl)methyl]-1H,4H,5H,6H,7H-imidazo[4,5-c]pyridine-5-carboxylate (550 mg, 1.60 mmol, 1 equiv.) in AcOH (5 mL) was added HBr (2.5 mL, 85.59 mmol, 53.60 equiv.) dropwise at 90 degree Celsius. The resulting mixture was stirred for 16 h at 90 degrees Celsius. The reaction was monitored by LCMS. The resulting mixture was concentrated under reduced pressure. The residue was basified to pH 8 with saturated NaHCO3 (aq.). The residue was washed with MeOH/DCM (1/3) (3×200 mL). The resulting mixture was concentrated under reduced pressure. The residue was purified by reverse flash chromatography with the following conditions: column, C18 silica gel; mobile phase, ACN in water, 10% to 40% gradient in 20 min; detector, UV 254 nm, to afford 6-([1H,4H,5H,6H,7H-imidazo[4,5-c]pyridin-1-yl] methyl)-1,2-dihydropyridin-2-one (360 mg, 97.90%) as light yellow oil.

4-chloro-2-(oxan-2-yl)-5-[1-[(6-oxo-1,6-dihydro-pyridin-2-yl)methyl]-1H,4H,5H,6H,7H-imidazo[4,5-c]pyridin-5-yl]-2,3-dihydropyridazin-3-one To a stirred mixture of 6-([1H,4H,5H,6H,7H-imidazo[4, 5-c]pyridin-1-yl]methyl)-1,2-dihydropyridin-2-one (360 mg, 1.56 mmol, 1 equiv.) and 4,5-dichloro-2-(oxan-2-yl)-2, 3-dihydropyridazin-3-one (389.4 mg, 1.56 mmol, 1 equiv.) in DMA (10 mL) was added DIEA (404.1 mg, 3.13 mmol, 2.00 equiv.) at room temperature. The resulting mixture was stirred for 16 h at 100 degrees Celsius. The reaction was monitored by LCMS. The mixture was allowed to cool down to room temperature. The mixture was purified by reverse flash chromatography with the following conditions: column, C18 silica gel; mobile phase, ACN in water, 30% to 70% gradient in 25 min; detector, UV 254 nm, to afford 4-chloro-2-(oxan-2-yl)-5-[1-[(6-oxo-1,6-dihydropyridin-2-yl)methyl]-1H,4H,5H,6H,7H-imidazo[4,5-c]pyridin-5-yl]-2,3-dihydropyridazin-3-one (300 mg, 43.33%) as yellow solid.

4-chloro-5-[1-[(6-ethoxy-1,6-dihydropyridin-2-yl) methyl]-1H,4H,5H,6H,7H-imidazo[4,5-c]pyridin-5-yl]-2-(oxan-2-yl)-2,3-dihydropyridazin-3-one To a stirred mixture of 4-chloro-2-(oxan-2-yl)-5-[1-[(6-oxo-1,6-dihydropyridin-2-yl)methyl]-1H,4H,5H,6H,7H-imidazo[4,5-c]pyridin-5-yl]-2,3-dihydropyridazin-3-one (300 mg, 0.68 mmol, 1 equiv.) and iodoethane (211.3 mg, 1.35 mmol, 2 equiv.) in DMF (7 mL) was added K2CO3 (187.2 mg, 1.35 mmol, 2 equiv.) at room temperature. The resulting mixture was stirred for 72 h at 80 degrees Celsius. The reaction was monitored by LCMS. The mixture was allowed to cool down to room temperature. The residue was purified by reverse flash chromatography with the following conditions: column, C18 silica gel; mobile phase, in water, 30% to 70% gradient in 20 min; detector, UV 254 nm to afford 4-chloro-5-[1-[(6-ethoxy-1,6-dihydropyridin-2-yl)methyl]-1H,4H,5H,6H,7H-imidazo[4,5-c]pyridin-5-yl]-2-(oxan-2-yl)-2,3-dihydropyridazin-3-one (80 mg, 24.97%) as light yellow oil.

Afford 4-chloro-5-[1-[(6-ethoxypyridin-2-yl)methyl]-1H,4H,5H,6H,7H-imidazo[4,5-c]pyridin-5-yl]-2,3-dihydropyridazin-3-one To a stirred solution of 4-chloro-5-[1-[(6-ethoxy-1,6-dihydropyridin-2-yl)methyl]-1H,4H,5H,6H,7H-imidazo[4,5-c]pyridin-5-yl]-2-(oxan-2-yl)-2,3-dihydropyridazin-3-one (80 mg, 0.17 mmol, 1 equiv.) in DCM (5 mL) was added TFA (2.0 mL, 17.54 mmol, 159.19 equiv.) dropwise at room temperature. The resulting mixture was stirred for 2 h at room temperature. The reaction was monitored by LCMS. The resulting mixture was concentrated under reduced pressure. The residue was basified to pH 8 with saturated NaHCO3 (aq.). The crude product (50 mg) was purified by Prep-HPLC with the following conditions (Column: XBridge Shield RP18 OBD Column, 5 um, 19*150 mm; Mobile Phase A: Water (10 mmol/L NH4HCO3), Mobile Phase B: ACN; Flow rate: 20 mL/min; Gradient: 10% B to 40% B in 10 min; 220 nm; Rt: 8.97, 9.67 min) to afford 4-chloro-5-[1-[(6-ethoxypyridin-2-yl)methyl]-1H,4H,5H,6H,7H-imidazo[4,5-c]pyridin-5-yl]-2,3-dihydropyridazin-3-one (13.7 mg) as an off-white solid.

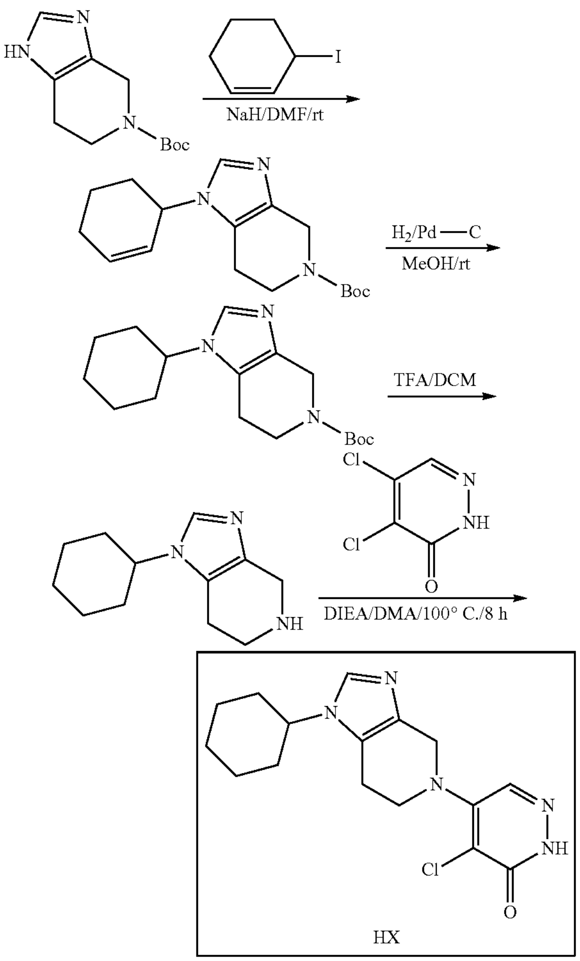

HX

-continued

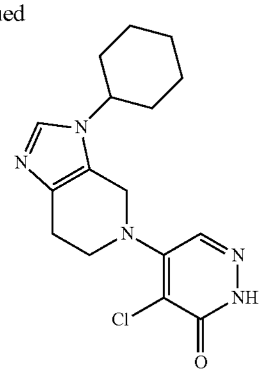

HXb

Preparation of HX

Tert-Butyl 1-(cyclohex-2-en-1-yl)-1H,4H,5H,6H,7H-imidazo[4,5-c]pyridine-5-carboxylate To a stirred solution of tert-butyl 1H,4H,5H,6H,7H-imidazo[4,5-c]pyridine-5-carboxylate (430 mg, 1.93 mol, 1 equiv.) in DMF (5 mL) were added DMF (5 mL) at room temperature. The resulting mixture was stirred for 1 h at room temperature. To the above mixture was added 3-bromocyclohex-1-ene (403.2 mg, 2.50 mol, 1.30 equiv.) dropwise at 0 degree Celsius. The resulting mixture was stirred for additional 2 h at room temperature. The reaction was monitored by LCMS. The reaction was quenched with MeOH (2 mL) at room temperature. The mixture was purified by reverse phase flash with the following conditions (Column: spnerical C18, 20-40 um, 330 g; Mobile Phase A: Water (5 mmol/L NH4HCO3), Mobile Phase B: ACN; Flow rate: 80 mL/min; Gradient: 50% B to 70% B in 25 min; 220 nm) to afford tert-butyl 1-(cyclohex-2-en-1-yl)-1H,4H,5H,6H,7H-imidazo[4,5-c]pyridine-5-carboxylate (210 mg, 35.94%) as a yellow oil.

Tert-Butyl 1-cyclohexyl-1H,4H,5H,6H,7H-imidazo[4,5-c]pyridine-5-carboxylate

To a solution of tert-butyl 1-(cyclohex-2-en-1-yl)-1H,4H,5H,6H,7H-imidazo[4,5-c]pyridine-5-carboxylate (270 mg, 0.89 mmol, 1 equiv.) in 10 mL MeOH was added Pd/C (10%, 150 mg) under nitrogen atmosphere in a 50 mL round-bottom flask. The mixture was hydrogenated at room temperature for 16 h under hydrogen atmosphere using a hydrogen balloon, filtered through a Celite pad and concentrated under reduced pressure. The residue was purified by reverse phase flash with the following conditions (Column: spnerical C18, 20-40 um, 330 g; Mobile Phase A: Water (5 mmol/L NH4HCO3), Mobile Phase B: ACN; Flow rate: 80 mL/min; Gradient: 45% B to 70% B in 30 min; 220 nm) to afford tert-butyl 1-cyclohexyl-1H,4H,5H,6H,7H-imidazo[4,5-c]pyridine-5-carboxylate (150 mg, 55.19%) as a colorless oil.

1-cyclohexyl-1H,4H,5H,6H,7H-imidazo[4,5-c]pyridine

To a stirred solution of tert-butyl 1-cyclohexyl-1H,4H,5H,6H,7H-imidazo[4,5-c]pyridine-5-carboxylate (150 mg, 0.49 mmol, 1 equiv.) in DCM (10 mL, 157.30 mmol, 320.29 equiv.) was added TFA (2 mL, 26.93 mmol, 54.83 equiv.)

dropwise at room temperature. The resulting mixture was stirred for 2 h at room temperature. The reaction was monitored by LCMS. The resulting mixture was concentrated under reduced pressure. The residue was basified to pH 8~9 with saturated NaHCO3 (aq.). The mixture was purified by reverse phase flash with the following conditions (Column: spnerical C18, 20-40 um, 330 g; Mobile Phase A: Water (5 mmol/L NH4HCO3), Mobile Phase B: ACN; Flow rate: 80 mL/min; Gradient: 20% B to 40% B in 25 min; 220 nm) to afford 1-cyclohexyl-1H,4H,5H,6H,7H-imidazo[4,5-c]pyridine (70 mg, 69.42%) as a colorless oil.

4-chloro-5-[1-cyclohexyl-1H,4H,5H,6H,7H-imidazo [4,5-c]pyridin-5-yl]-2,3-dihydropyridazin-3-one To a solution of 1-cyclohexyl-1H,4H,5H,6H,7H-imidazo [4,5-c]pyridine (70 mg, 0.34 mmol, 1 equiv.) and DIEA (88.1 mg, 0.68 mmol, 2 equiv.) in DMA (3 mL) was added 4,5-dichloro-2,3-dihydropyridazin-3-one (56.2 mg, 0.34 mmol, 1.00 equiv.) at room temperature. The resulting mixture was stirred for 5 h at 100 degrees Celsius. The reaction was monitored by LCMS. The mixture was purified by Prep-HPLC with the following conditions (Column: XBridge Prep C18 OBD Column 19×150 mm 5 um; Mobile Phase A: Water (10 mmol/L NH4HCO3), Mobile Phase B: ACN; Flow rate: 20 mL/min; Gradient: 20% B to 44% B in 7 min; 254 nm; Rt: 6.28 min) to afford 4-chloro-5-[1-cyclohexyl-1H,4H,5H,6H,7H-imidazo[4,5-c]pyridin-5-yl]-2,3-dihydropyridazin-3-one (36.4 mg, 31.98%) as a light yellow solid.

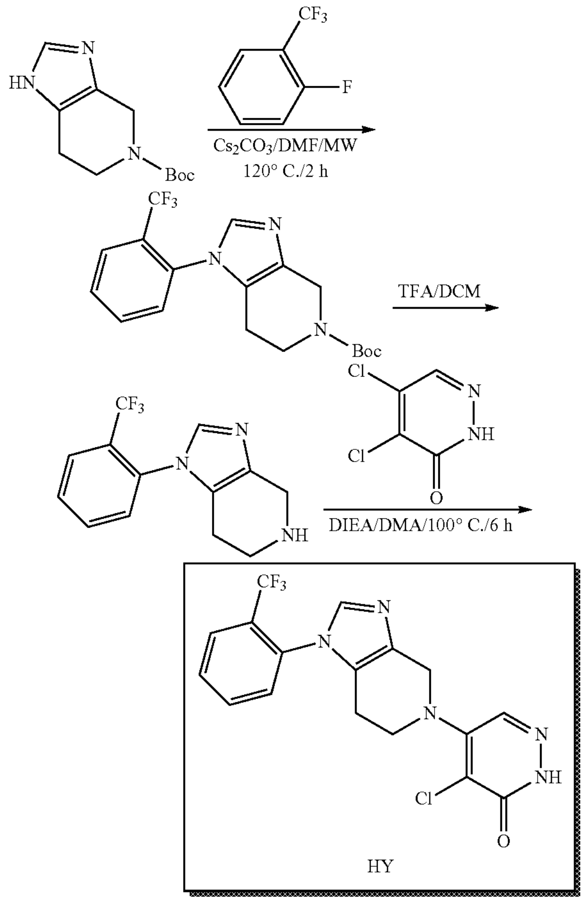

HY

-continued

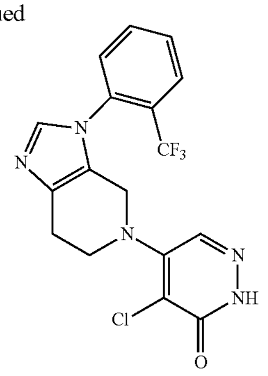

HYb

Preparation of HY

Tert-Butyl 1-[2-(trifluoromethyl)pyridin-3-yl]-1H, 4H,5H,6H,7H-imidazo[4,5-c]pyridine-5-carboxylate To a solution of tert-butyl 1H,4H,5H,6H,7H-imidazo[4,5-c]pyridine-5-carboxylate (380 mg, 1.70 mmol, 1 equiv.) and Cs2CO3 (1109.0 mg, 3.40 mmol, 2.00 equiv.) in DMF (5 mL) was added 3-fluoro-2-(trifluoromethyl)pyridine (281.0 mg, 1.70 mmol, 1 equiv.) at room temperature. The final reaction mixture was irradiated with microwave radiation for 2 h at 120 degrees Celsius. The reaction was monitored by LCMS. The mixture was purified by reverse phase flash with the following conditions (Column: spnerical C18, 20-40 um, 330 g; Mobile Phase A: Water (5 mmol/L NH4HCO3), Mobile Phase B: ACN; Flow rate: 80 mL/min; Gradient: 40% B to 60% B in 25 min; 220 nm) to afford tert-butyl 1-[2-(trifluoromethyl)pyridin-3-yl]-1H,4H,5H,6H,7H-imidazo[4,5-c]pyridine-5-carboxylate (370 mg, 59.02%) as a yellow oil.

3-[1H,4H,5H,6H,7H-imidazo[4,5-c]pyridin-1-yl]-2-(trifluoromethyl)pyridine

To a stirred solution of tert-butyl 1-[2-(trifluoromethyl)pyridin-3-yl]-1H,4H,5H,6H,7H-imidazo[4,5-c]pyridine-5-carboxylate (370 mg, 1.00 mmol, 1 equiv.) in DCM (10 mL) was added TFA (2 mL, 26.93 mmol, 26.81 equiv.) dropwise at room temperature. The resulting mixture was stirred for 2 h at room temperature. The reaction was monitored by LCMS. The resulting mixture was concentrated under reduced pressure. The residue was basified to pH 8~9 with saturated NaHCO3 (aq.). The mixture was purified by reverse phase flash with the following conditions (Column: spnerical C18, 20-40 um, 330 g; Mobile Phase A: Water (5 mmol/L NH4HCO3), Mobile Phase B: ACN; Flow rate: 80 mL/min; Gradient: 10% B to 40% B in 30 min; 220 nm) to afford 3-[1H,4H,5H,6H,7H-imidazo[4,5-c]pyridin-1-yl]-2-(trifluoromethyl)pyridine (230 mg, 85.36%) as a light yellow oil 4-chloro-5-[3-[2-(trifluoromethyl)pyridin-3-yl]-3H, 4H,5H,6H,7H-imidazo[4,5-c]pyridin-5-yl]-2,3-dihydropyridazin-3-one To a solution of 3-[1H,4H,5H,6H,7H-imidazo[4,5-c]pyridin-1-yl]-2-(trifluoromethyl)pyridine (230 mg, 0.86 mmol, 1 equiv.) and 4,5-dichloro-2,3-dihydropyridazin-3-one (141.5 mg, 0.86 mmol, 1 equiv.) in DMA (5 mL) was added DIEA (221.6 mg, 1.71 mmol, 2 equiv.) dropwise at room temperature. The resulting mixture was stirred for 6 h at 100 degrees Celsius. The reaction was monitored by LCMS. The mixture was purified by reverse phase flash with the following conditions (Column: spnerical C18, 20-40 um, 330 g; Mobile Phase A: Water (5 mmol/L NH4HCO3), Mobile Phase B: ACN; Flow rate: 80 mL/min; Gradient: 30% B to 50% B in 25 min; 220 nm) to afford crude products. The crude products was purified by Prep-HPLC with the following conditions (Column: XBridge Shield RP18 OBD Column, 5 um, 19*150 mm; Mobile Phase A: Water (10 mmol/L NH4HCO3), Mobile Phase B: ACN; Flow rate: 20 mL/min; Gradient: 5% B to 30% B in 10 min; 220 nm; Rt: 10.43, 11 min) to afford 4-chloro-5-[1-[2-(trifluoromethyl)pyridin-3-yl]-1H,4H,5H,6H,7H-imidazo[4,5-c]pyridin-5-yl]-2,3-dihydropyridazin-3-one (73.1 mg, 21.49%) as a white solid and 4-chloro-5-[3-[2-(trifluoromethyl)pyridin-3-yl]-3H,4H,5H,6H,7H-imidazo[4,5-c]pyridin-5-yl]-2,3-dihydropyridazin-3-one (42.8 mg, 12.58%) as a white solid.

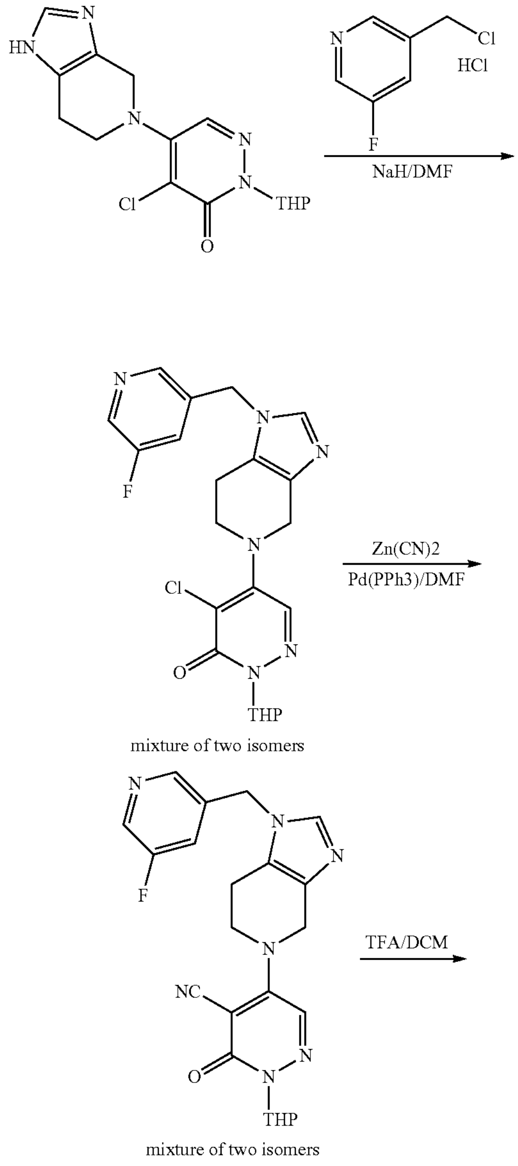

-continued

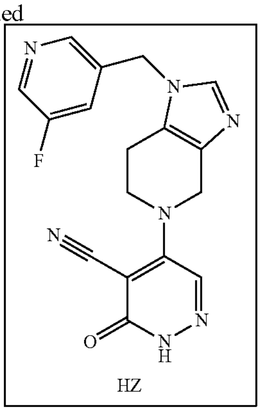

HZ

Preparation of HZ 4-chloro-5-[1H,4H,5H,6H,7H-imidazo[4,5-c]pyridin-5-yl]-2-(oxan-2-yl)-2,3-dihydropyridazin-3-one To a solution of 4-chloro-5-[1H,4H,5H,6H,7H-imidazo[4,5-c]pyridin-5-yl]-2-(oxan-2-yl)-2,3-dihydropyridazin-3-one (600 mg, 1.79 mmol, 1 equiv.) in DMF (10 mL) was added NaH (85.6 mg, 2.14 mmol, 1.2 equiv., 60% w/w dispersed into mineral oil) at 0 degree Celsius. The mixture was stirred for 15 min. To the above mixture was added the solution of 3-(chloromethyl)-5-fluoropyridine (338.1 mg, 2.32 mmol, 1.3 equiv.) pre-treated with Cs2CO3 (1164.4 mg, 3.57 mmol, 2.00 equiv.) in DMF (5 mL) for 5 min. The resulting mixture was stirred for overnight at room temperature. The reaction was quenched with water (0.5 mL). The resulting mixture was purified by reverse phase flash chromatography with the following conditions: (Column: spnerical C18, 20-40 um, 330 g; Mobile Phase A: Water (plus 5 mmol/L NH4HCO3), Mobile Phase B: ACN; Flow rate: 80 mL/min; Gradient: 10% B to 60% B in 55 min; Detector: 254 nm) to afford a mixture of the above two compounds (550 mg, 70%, ratio 1:1) as a light yellow solid: MS (ESI, m/z): 445.1 $[M+1]^+$ 5-[1-[(5-fluoropyridin-3-yl)methyl]-1H,4H,5H,6H,7H-imidazo[4,5-c]pyridin-5-yl]-2-(oxan-2-yl)-3-oxo-2,3-dihydropyridazine-4-carbonitrile To a stirred solution of the above mixture (250 mg, 0.56 mmol, 1 equiv.) and Zn(CN)2 (132.0 mg, 1.12 mmol, 2.00 equiv.) in DMF (4 mL) was added Pd(PPh3)4 (64.9 mg, 0.06 mmol, 0.1 equiv.). The final reaction mixture was irradiated with microwave for 2 h at 150 degrees Celsius. After cold to ambient temperature, the resulting mixture was filtered through celite. The filtrate was concentrated under reduced pressure. The residue was purified by silica gel column chromatography, eluted with PE/EtOAc (7:1) to afford a mixture of the above two cyanides (220 mg, 90%) as a light yellow solid: MS (ESI, m/z): 436.1 $[M+1]^+$.

5-[1-[(5-fluoropyridin-3-yl)methyl]-1H,4H,5H,6H,7H-imidazo[4,5-c]pyridin-5-yl]-3-oxo-2,3-dihydropyridazine-4-carbonitrile To a stirred solution of the above mixture (130 mg, 0.29 mmol) in DCM (3 mL) was added TFA (1 mL). The resulting mixture was stirred for 2 h at room temperature. The resulting mixture was concentrated under reduced pressure.

The crude product was purified by Prep-HPLC with the following conditions: (Column: XBridge Shield RP18 OBD Column 30*150 mm, 5 um; Mobile Phase A: Water (plus 10 mmol/L NH4HCO3); Mobile Phase B: ACN; Flow rate: 60 mL/min; Gradient: 2% B to 18% B in 15 min; Detector: 254 nm; Rt: 14.5 min) to afford 5-[1-[(5-fluoropyridin-3-yl)methyl]-1H,4H,5H,6H,7H-imidazo[4,5-c]pyridin-5-yl]-3-oxo-2,3-dihydropyridazine-4-carbonitrile (25.3 mg) as a white solid and isomer 5-(3-((5-fluoropyridin-3-yl)methyl)-3,4,6,7-tetrahydro-5H-imidazo[4,5-c]pyridin-5-yl)-3-oxo-2,3-dihydropyridazine-4-carbonitrile (19.8 mg) as a white solid.

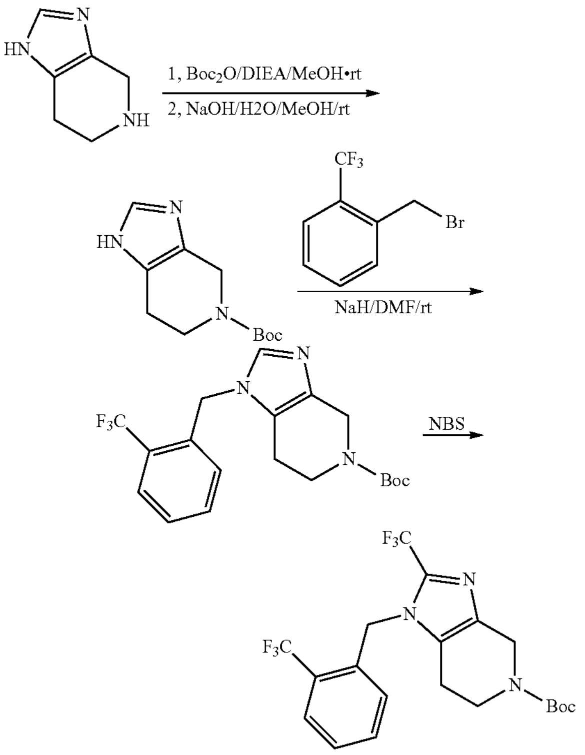

Int9

Preparation of intermediate 9 (Int9)

1,5-di-tert-butyl 1H,4H,5H,6H,7H-imidazo[4,5-c]pyridine-1,5-dicarboxylate

To a stirred solution of 1H,4H,5H,6H,7H-imidazo[4,5-c]pyridine dihydrochloride (22 g, 112.20 mmol, 1 equiv.) in MeOH (300 mL) was added di-tert-butyl decarbonate (61.2 g, 280.50 mmol, 2.5 equiv.) and ethylbis(propan-2-yl)amine (50.8 g, 392.70 mmol, 3.5 equiv.) dropwise at 0 degree Celsius under nitrogen atmosphere. The solution was stirred at room temperature overnight. Desired product could be detected by LCMS. The mixture was concentrated under reduced pressure. The residue was purified by silica gel column chromatography, eluted with PE/EtOAc (5:1 to 2:1) to afford 1,5-di-tert-butyl 1H,4H,5H,6H,7H-imidazo[4,5-c]pyridine-1,5-dicarboxylate (30 g, 82.68%) as white solid.

To a stirred solution of 1,5-di-tert-butyl 1H,4H,5H,6H,7H-imidazo[4,5-c]pyridine-1,5-dicarboxylate (7 g, 1 equiv.) in MeOH (80 mL) and H2O (17 mL) was added NaOH (1.7 g, 43.29 mmol, 2.00 equiv.) in portions at room temperature under nitrogen atmosphere. The mixture was stirred at room temperature for 2 h. Desired product could be detected by LCMS. The mixture was basified to pH 8 with citric acid. The resulting mixture was extracted with CH2C12(3×100 mL). The combined organic layers were washed with brine (1×100 mL), dried over anhydrous Na2SO4. After filtration, the filtrate was concentrated under reduced pressure to afford tert-butyl 1H,4H,5H,6H,7H-imidazo[4,5-c]pyridine-5-carboxylate (4.1 g, 84.84%) as an off-white semi-solid.

Tert-Butyl 1-[[2-(trifluoromethyl)phenyl]methyl]-1H,4H,5H,6H,7H-imidazo[4,5-c]pyridine-5-carboxylate To a stirred solution of tert-butyl 1H,4H,5H,6H,7H-imidazo[4,5-c]pyridine-5-carboxylate (93.4 mg, 0.42 mmol, 1 equiv.) in DMF (8 mL) was added NaH (25.1 mg, 0.63 mmol, 1.5 equiv., 60%) in portions at 0 degree Celsius under nitrogen atmosphere. The mixture was stirred at room temperature for 1 h. To the mixture was added 1-(bromomethyl)-2-(trifluoromethyl)benzene (100 mg, 0.42 mmol, 1 equiv.) at 0 degree Celsius. The mixture was stirred at room temperature for 1 h. Desired product could be detected by LCMS. It was a pilot reaction, no work up was performed.

Tert-Butyl 2-bromo-1-[[2-(trifluoromethyl)phenyl]methyl]-1H,4H,5H,6H,7H-imidazo[4,5-c]pyridine-5-carboxylate To a stirred solution of tert-butyl 1-[[2-(trifluoromethyl)phenyl]methyl]-1H,4H,5H,6H,7H-imidazo[4,5-c]pyridine-5-carboxylate (1 g, 2.62 mmol, 1 equiv.) in DMF (15 mL) was added NBS (0.5 g, 2.81 mmol, 1.07 equiv.) in portions at 0 degree Celsius under nitrogen atmosphere. The mixture was stirred at room temperature for 1 h. Desired product could be detected by LCMS. The resulting mixture was concentrated under reduced pressure. The residue was purified by silica gel column chromatography, eluted with PE/EtOAc (5:1 to 1:1) to afford tert-butyl 2-bromo-1-[[2-(trifluoromethyl)phenyl]methyl]-1H,4H,5H,6H,7H-imidazo[4,5-c]pyridine-5-carboxylate (800 mg, 66.29%) as colorless oil.

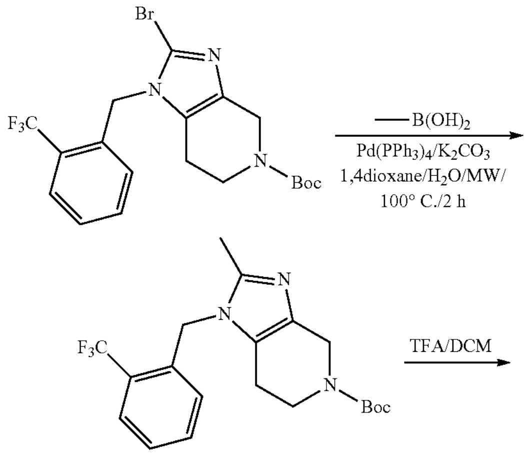

-continued

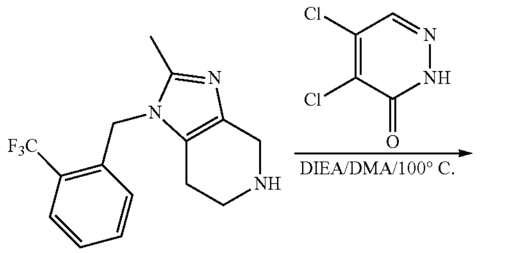

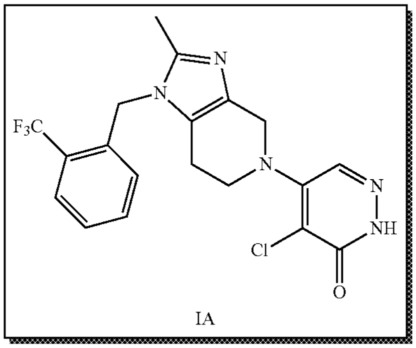

IA

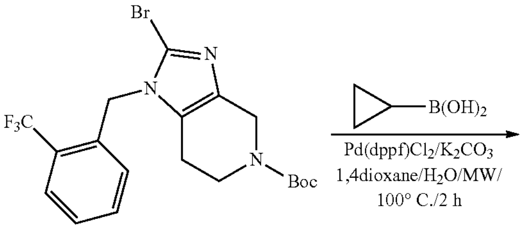

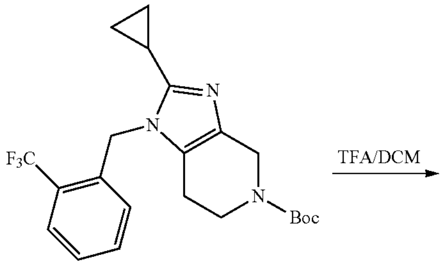

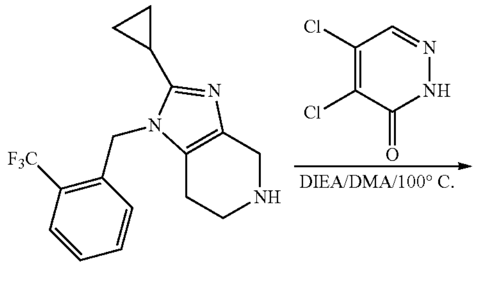

-continued

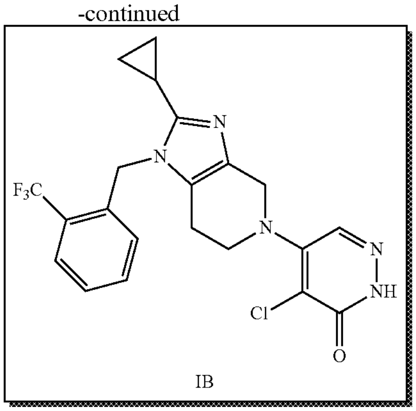

IB

Preparation of IA

Tert-Butyl 2-methyl-1-[[2-(trifluoromethyl)phenyl]methyl]-1H,4H,5H,6H,7H-imidazo[4,5-c]pyridine-5-carboxylate To a solution of tert-butyl 2-bromo-1-[[2-(trifluoromethyl)phenyl]methyl]-1H,4H,5H,6H,7H-imidazo[4,5-c]pyridine-5-carboxylate (400 mg, 0.87 mmol, 1 equiv.) and methylboronic acid (52.0 mg, 0.87 mmol, 1.00 equiv.) in 1,4-dioxane (5 mL) and H2O (1 mL) were added Pd(dppf) Cl2 (63.6 mg, 0.09 mmol, 0.1 equiv.) and K2CO3 (360.3 mg, 2.61 mmol, 3 equiv.). The final reaction mixture was irradiated with microwave radiation for 3 h at 110 degrees Celsius under nitrogen atmosphere, the resulting mixture was concentrated under reduced pressure. The crude product (100 mg) was purified by Prep-TLC with the following conditions (PE:EA=1:10) to afford tert-butyl 2-methyl-1-[[2-(trifluoromethyl)phenyl]methyl]-1H,4H,5H,6H,7H-imidazo[4,5-c]pyridine-5-carboxylate (200 mg, 58.20%) as white solid.

2-methyl-1-[[2-(trifluoromethyl)phenyl]methyl]-1H,4H,5H,6H,7H-imidazo[4,5-c]pyridine To a stirred solution of tert-butyl 2-methyl-1-[[2-(trifluoromethyl)phenyl]methyl]-1H,4H,5H,6H,7H-imidazo[4,5-c]pyridine-5-carboxylate (200 mg, 0.51 mmol, 1 equiv.) in DCM (10 mL) was added TFA (1 mL) in portions at 0 degree Celsius under nitrogen atmosphere. The mixture was stirred at room temperature for 3 h. Desired product could be detected by LCMS. The resulting mixture was concentrated under reduced pressure. The crude product (150 mg) was purified by Prep-HPLC with the following conditions (DCM:MeOH=10:1) to afford 2-methyl-1-[[2-(trifluoromethyl)phenyl]methyl]-1H,4H,5H,6H,7H-imidazo[4,5-c]pyridine (100 mg, 66.95%) as yellow oil.

4-chloro-5-(2-methyl-1-[[2-(trifluoromethyl)phenyl]methyl]-1H,4H,5H,6H,7H-imidazo[4,5-c]pyridin-5-yl)-2,3-dihydropyridazin-3-one To a stirred solution of 2-methyl-1-[[2-(trifluoromethyl)phenyl]methyl]-1H,4H,5H,6H,7H-imidazo[4,5-c]pyridine (60 mg, 0.20 mmol, 1 equiv.) and 4,5-dichloro-2,3-dihydropyridazin-3-one (50.3 mg, 0.30 mmol, 1.50 equiv.) in DMA (10 mL) was added DIEA (78.8 mg, 0.61 mmol, 3 equiv.) in portions at room temperature under nitrogen atmosphere. The mixture was stirred at 100 degrees Celsius for 2 h.

Desired product could be detected by LCMS. The resulting mixture was concentrated under reduced pressure. The crude product (60 mg) was purified by Prep-HPLC with the following conditions (Column: XBridge Prep C18 OBD Column 19×150 mm 5 um; Mobile Phase A: Water (10 mmol/L NH4HCO3), Mobile Phase B: ACN; Flow rate: 20 mL/min; Gradient: 18% B to 48% B in 7 min; 254/220 nm; Rt: 6.22 min) to afford 4-chloro-5-(2-methyl-1-[[2-(trifluoromethyl)phenyl]methyl]-1H,4H,5H,6H,7H-imidazo[4,5-c]pyridin-5-yl)-2,3-dihydropyridazin-3-one (13 mg, 15.10%) as a white solid and 5-chloro-4-(2-methyl-1-[[2-(trifluoromethyl)phenyl]methyl]-1H,4H,5H,6H,7H-imidazo[4,5-c]pyridin-5-yl)-2,3-dihydropyridazin-3-one (3.4 mg, 3.95%) as white solid.

IB was prepared by the methods and scheme described for IA.

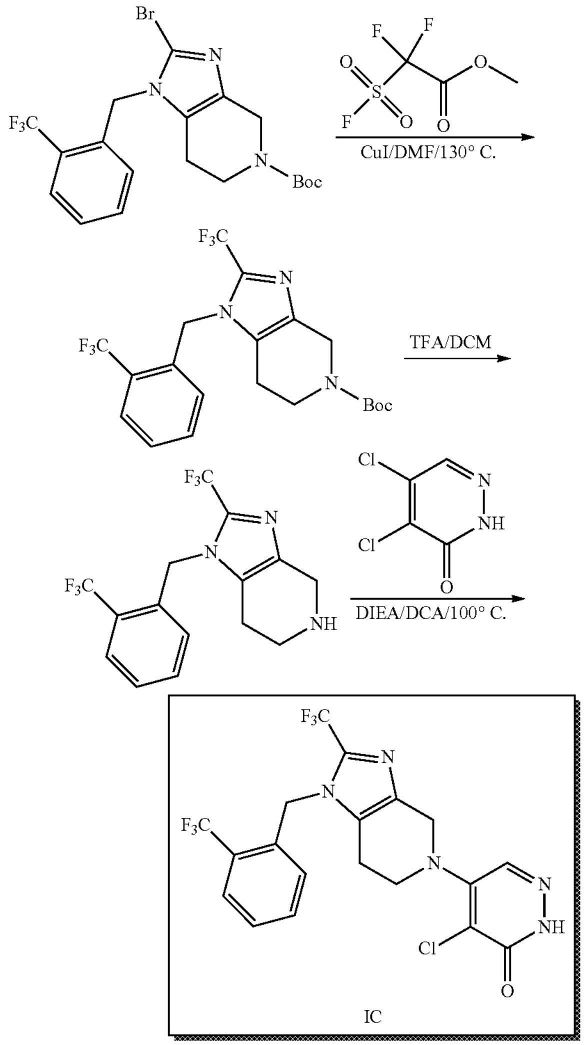

IC

Preparation of IC

Tert-Butyl 2-(trifluoromethyl)-1-[[2-(trifluoromethyl)phenyl]methyl]-1H,4H,5H,6H,7H-imidazo[4,5-c]pyridine-5-carboxylate To a solution of tert-butyl 2-bromo-1-[[2-(trifluoromethyl)phenyl]methyl]-1H,4H,5H,6H,7H-imidazo[4,5-c]pyridine-5-carboxylate (100 mg, 220 mmol, 1 equiv.) and methyl 2,2-difluoro-2-sulfoacetate (125.2 mg, 650 mmol, 3.00 equiv.) in DMF (4.0 mL, 51.69 mol, 237.91 equiv.) were added CuI (62.1 mg, 0.33 mmol, 3 equiv.). The final reaction mixture was irradiated with microwave radiation for 1 h at 110 degrees Celsius under nitrogen atmosphere, the resulting mixture was concentrated under reduced pressure. The residue was purified by Prep-TLC (PE:EA=3:1) to afford tert-butyl 2-(trifluoromethyl)-1-[[2-(trifluoromethyl)phenyl]methyl]-1H,4H,5H,6H,7H-imidazo[4,5-c]pyridine-5-carboxylate (60 mg, 61.46%) as a colorless oil.

2-(trifluoromethyl)-1-[[2-(trifluoromethyl)phenyl]methyl]-1H,4H,5H,6H,7H-imidazo[4,5-c]pyridine To a stirred solution of tert-butyl 2-(trifluoromethyl)-1-[[2-(trifluoromethyl)phenyl]methyl]-1H,4H,5H,6H,7H-imidazo[4,5-c]pyridine-5-carboxylate (160 mg, 1 equiv.) in DCM (10 mL) was added TFA (1 mL) in portions at 0 degree Celsius under nitrogen atmosphere. The mixture was stirred at room temperature for 3 h. Desired product could be detected by LCMS. The resulting mixture was concentrated under reduced pressure. The crude product (150 mg) was purified by Prep-HPLC with the following conditions (DCM:MeOH=10:1) to afford 2-(trifluoromethyl)-1-[[2-(trifluoromethyl)phenyl]methyl]-1H,4H,5H,6H,7H-imidazo[4,5-c]pyridine (90 mg, 72.37%) as colorless oil.

4-chloro-5-[2-(trifluoromethyl)-1-[[2-(trifluoromethyl)phenyl]methyl]-1H,4H,5H,6H,7H-imidazo[4,5-c]pyridin-5-yl]-2,3-dihydropyridazin-3-one To a stirred solution of 2-(trifluoromethyl)-1-[[2-(trifluoromethyl)phenyl]methyl]-1H,4H,5H,6H,7H-imidazo[4,5-c]pyridine (60 mg, 0.17 mmol, 1 equiv.) and 4,5-dichloro-2,3-dihydropyridazin-3-one (28.3 mg, 0.17 mmol, 1.00 equiv.) in DMA (8 mL) was added DIEA (51.8 mg, 0.40 mmol, 2.00 equiv.) at room temperature. The mixture was stirred at 100 degrees Celsius for 2 h. Desired product could be detected by LCMS. The resulting mixture was concentrated under reduced pressure. The crude product (60 mg) was purified by Prep-HPLC with the following conditions (Column: XBridge Prep C18 OBD Column 19×150 mm 5 um; Mobile Phase A: Water (10 mmol/L NH4HCO3), Mobile Phase B: ACN; Flow rate: 20 mL/min; Gradient: 18% B to 48% B in 7 min; 254/220 nm; Rt: 6.22 min) to afford 4-chloro-5-[2-(trifluoromethyl)-1-[[2-(trifluoromethyl)phenyl]methyl]-1H,4H,5H,6H,7H-imidazo[4,5-c]pyridin-5-yl]-2,3-dihydropyridazin-3-one (15.5 mg) (IC) as a white solid.

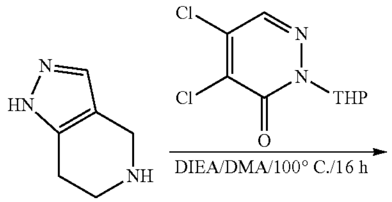

2HCl

-continued

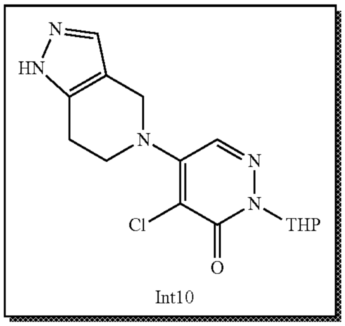

Int10

Preparation of Intermediate 10 (Int10): 4-chloro-2-(oxan-2-yl)-5-[1H,4H,5H,6H,7H-pyrazolo[4,3-c]pyridin-5-yl]-2,3-dihydropyridazin-3-one To a stirred solution of 1H,4H,5H,6H,7H-pyrazolo[4,3-c]pyridine dihydrochloride (7 g, 35.70 mmol, 1 equiv.) and 4,5-dichloro-2-(oxan-2-yl)-2,3-dihydropyridazin-3-one (10.7 g, 42.84 mmol, 1.2 equiv.) in DMA (100 mL) was added DIEA (13.8 g, 107.10 mmol, 3 equiv.) in portions at room temperature under nitrogen atmosphere. The resulting mixture was stirred for overnight at 100 degrees Celsius under nitrogen atmosphere. The reaction was monitored by LCMS. The resulting mixture was extracted with EtOAc (100× mL). The combined organic layers were washed with brine (3×100 mL), dried over anhydrous Na2SO4. After filtration, the filtrate was concentrated under reduced pressure. This resulted in 4-chloro-2-(oxan-2-yl)-5-[1H,4H,5H,6H,7H-pyrazolo[4,3-c]pyridin-5-yl]-2,3-dihydropyridazin-3-one (8.5 g, 70.91%) as a light yellow solid.

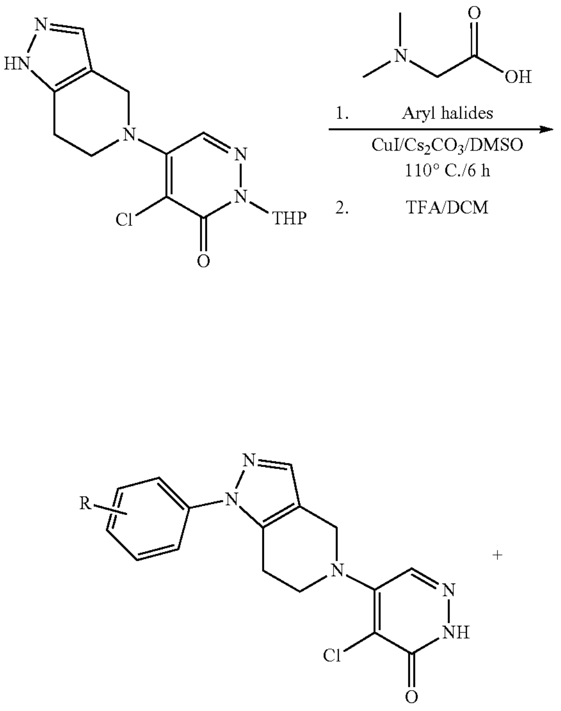

-continued

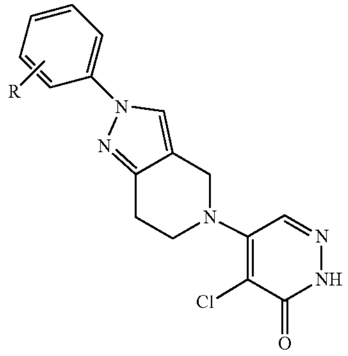

| Aryl halides | Target ID | Target ID |
|---|---|---|
| 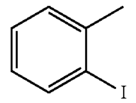 | ID | IDb |
| 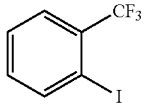 [SMILES: FC(F)(F)c1ccccc1I] | IE | IEb |

Preparation of ID and IDb 4-chloro-2-(tetrahydro-2H-pyran-2-yl)-5-(1-(o-tolyl)-1,4,6,7-tetrahydro-5H-pyrazolo[4,3-c]pyridin-5-yl)pyridazin-3(2H)-one and 4-chloro-2-(tetrahydro-2H-pyran-2-yl)-5-(2-(o-tolyl)-2,4,6,7-tetrahydro-5H-pyrazolo[4,3-c]pyridin-5-yl)pyridazin-3(2H)-one To a stirred solution of 4-chloro-2-(oxan-2-yl)-5-[1H,4H,5H,6H,7H-pyrazolo[4,3-c]pyridin-5-yl]-2,3-dihydropyridazin-3-one (300 mg, 0.89 mmol, 1 equiv.) Cs2CO3 (1164.4 mg, 3.57 mmol, 4 equiv.) and 1-iodo-4-methyl benzene (486.0 mg, 1.79 mmol, 2 equiv.) in DMSO (10 mL) was added CuI (102.1 mg, 0.54 mmol, 0.6 equiv.) and 2-(dimethylamino)acetic acid (55.3 mg, 0.54 mmol, 0.6 equiv.) in portions at room temperature under nitrogen atmosphere. The resulting mixture was stirred for 5 h at 100 degrees Celsius under nitrogen atmosphere. The reaction was monitored by LCMS. The residue was dissolved in brine (200 mL). The resulting mixture was extracted with EtOEt (2×100× mL). The combined organic layers were washed with brine (3×100 mL), dried over anhydrous Na2SO4. After filtration, the filtrate was concentrated under reduced pressure. The resulting mixture was used in the next step directly without further purification.

4-chloro-5-[1-(2-methylphenyl)-1H,4H,5H,6H,7H-pyrazolo[4,3-c]pyridin-5-yl]-2-(oxan-2-yl)-2,3-dihydropyridazin-3-one and 4-chloro-5-[2-(2-methylphenyl)-2H,4H,5H,6H,7H-pyrazolo[4,3-c]pyridin-5-yl]-2-(oxan-2-yl)-2,3-dihydropyridazin-3-one To a stirred solution of 4-chloro-5-[1-(2-methylphenyl)-1H,4H,5H,6H,7H-pyrazolo[4,3-c]pyridin-5-yl]-2-(oxan-2-yl)-2,3-dihydropyridazin-3-one (200 mg, 0.47 mmol, 1 equiv.) in DCM (10 mL) was added TFA (1 mL) dropwise at room temperature under nitrogen atmosphere. The resulting mixture was stirred for 4 h at room temperature under nitrogen atmosphere. The reaction was monitored by LCMS. The resulting mixture was concentrated under reduced pressure. The crude product (200 mg) was purified by Prep-HPLC with the following conditions (Column: XBridge Shield RP18 OBD Column 30*150 mm, 5 um; Mobile Phase A: Water (10 mmol/L NH4HCO3), Mobile Phase B: ACN; Flow rate: 60 mL/min; Gradient: 15% B to 45% B in 9 min; 254 nm; Rt: 7.52 8.12 min) to afford 4-chloro-5-[1-(2-methylphenyl)-1H,4H,5H,6H,7H-pyrazolo[4,3-c]pyridin-5-yl]-2-(oxan-2-yl)-2,3-dihydropyridazin-3-one (43.1 mg, 21.55%) as a white solid and 4-chloro-5-[2-(2-methylphenyl)-2H,4H,5H,6H,7H-pyrazolo[4,3-c]pyridin-5-yl]-2-(oxan-2-yl)-2,3-dihydropyridazin-3-one (77.6 mg, 38.80%) as a white solid.

IE and IEb were prepared by the methods and scheme described for ID and IDb.

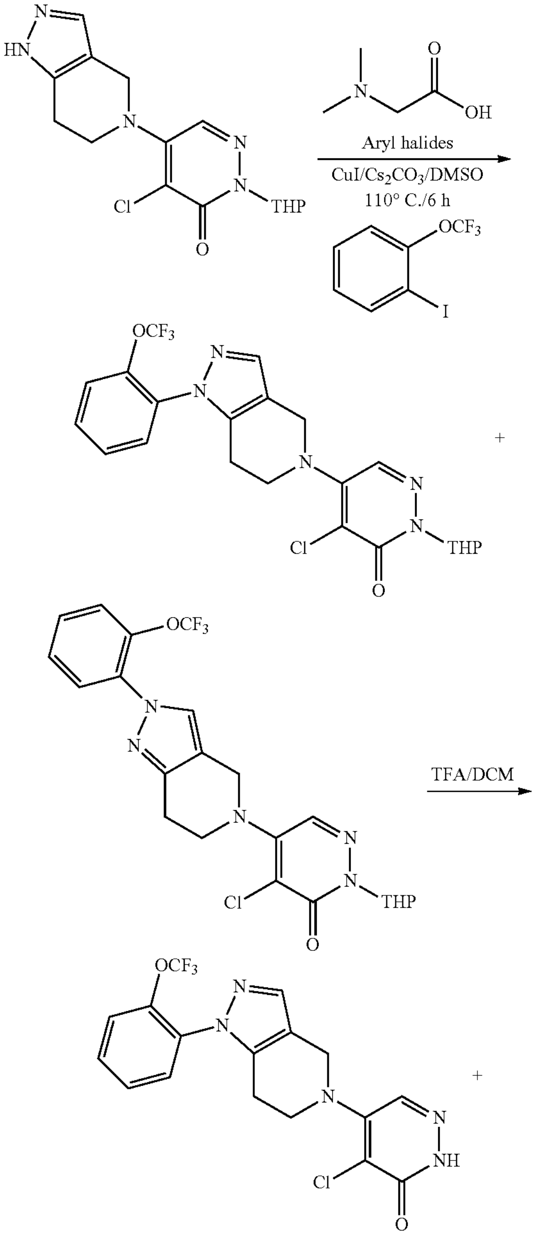

IF

-continued

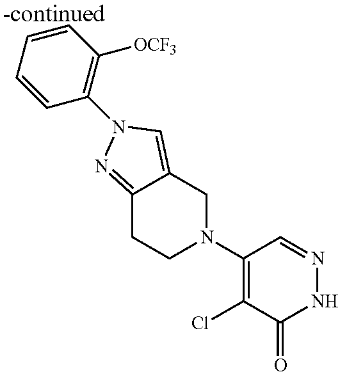

IFb

IF and IFb were prepared by the methods and scheme described for ID and db

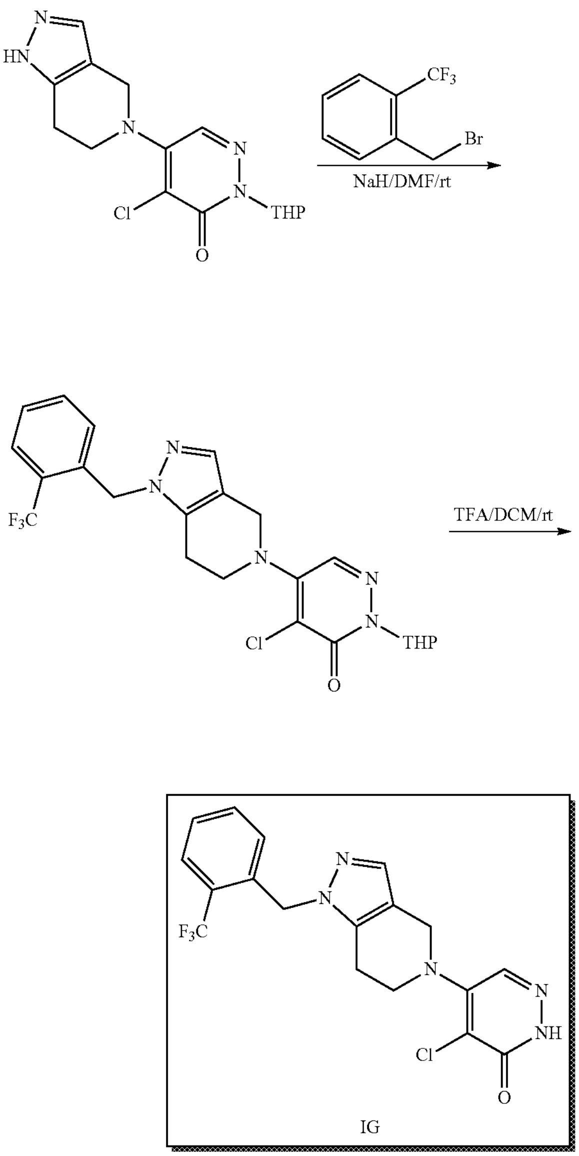

IG

Preparation of IG 4-chloro-2-(oxan-2-yl)-5-(1-[[2-(trifluoromethyl)phenyl]methyl]-1H,4H,5H,6H,7H-pyrazolo[4,3-c]pyridin-5-yl)-2,3-dihydropyridazin-3-one To a stirred solution of 4-chloro-2-(oxan-2-yl)-5-[1H,4H,5H,6H,7H-pyrazolo[4,3-c]pyridin-5-yl]-2,3-dihydropyridazin-3-one (200 mg, 0.60 mmol, 1 equiv.) and 1-(bromomethyl)-2-(trifluoromethyl)benzene (213.6 mg, 0.89 mmol, 1.5 equiv.) in DMF (10 ML) was added NaH (28.6 mg, 1.19 mmol, 2 equiv.) in portions at 0 degree Celsius under nitrogen atmosphere. The resulting mixture was stirred for 4 h at room temperature under nitrogen atmosphere. The reaction was monitored by LCMS. The reaction was quenched with Water/Ice at 0 degree Celsius. The resulting mixture was extracted with EtOAc (50× mL). The combined organic layers were washed with brine (3×50 mL), dried over anhydrous Na2SO4. After filtration, the filtrate was concentrated under reduced pressure. The residue was purified by Prep-TLC (PE/EtOAc 5:1) to afford 4-chloro-2-(oxan-2-yl)-5-(1-[[2-(trifluoromethyl)phenyl]methyl]-1H,4H,5H,6H,7H-pyrazolo[4,3-c]pyridin-5-yl)-2,3-dihydropyridazin-3-one (200 mg, 67.98%) as a light yellow oil.

4-chloro-5-(1-(2-(trifluoromethyl)benzyl)-1,4,6,7-tetrahydro-5H-pyrazolo[4,3-c]pyridin-5-yl)pyridazin-3(2H)-one To a stirred solution of 4-chloro-2-(oxan-2-yl)-5-(1-[[2-(trifluoromethyl)phenyl]methyl]-1H,4H,5H,6H,7H-pyrazolo[4,3-c]pyridin-5-yl)-2,3-dihydropyridazin-3-one (240 mg, 480 mmol, 1 equiv.) in DCM (10 mL) was added TFA (1 mL, 13.46 mmol, 28.02 equiv.) dropwise at room temperature. The resulting mixture was stirred for 2 h at room temperature. The reaction was monitored by LCMS. The resulting mixture was concentrated under reduced pressure. The residue was basified to pH 8~9 with saturated NaHCO3 (aq.). The mixture was purified by reverse phase flash with the following conditions (Column: spnerical C18, 20-40 um, 330 g; Mobile Phase A: Water (5 mmol/L NH4HCO3), Mobile Phase B: ACN; Flow rate: 80 mL/min; Gradient: 15% B to 60% B in 55 min; 220 nm) to afford crude products. The crude product (90 mg) was purified by Prep-HPLC with the following conditions (Column: Xselect CSH OBD Column 30*150 mm 5 um n; Mobile Phase A: Water (0.05% TFA), Mobile Phase B: ACN; Flow rate: 60 mL/min; Gradient: 3% B to 25% B in 17 min; 220 nm; 15.87 min) to afford crude product. The crude product was purified by Prep-HPLC with the following conditions (Column: XBridge Shield RP18 OBD Column, 5 um, 19*150 mm; Mobile Phase A: Water (10 mmol/L NH4HCO3), Mobile Phase B: ACN; Flow rate: 60 mL/min; Gradient: 15% B to 38% B in 20 min; 220 nm; 19.3 min) to afford 4-chloro-5-(1-(2-(trifluoromethyl)benzyl)-1,4,6,7-tetrahydro-5H-pyrazolo[4,3-c]pyridin-5-yl)pyridazin-3(2H)-one (5.9 mg, 2.96%) as a white solid.

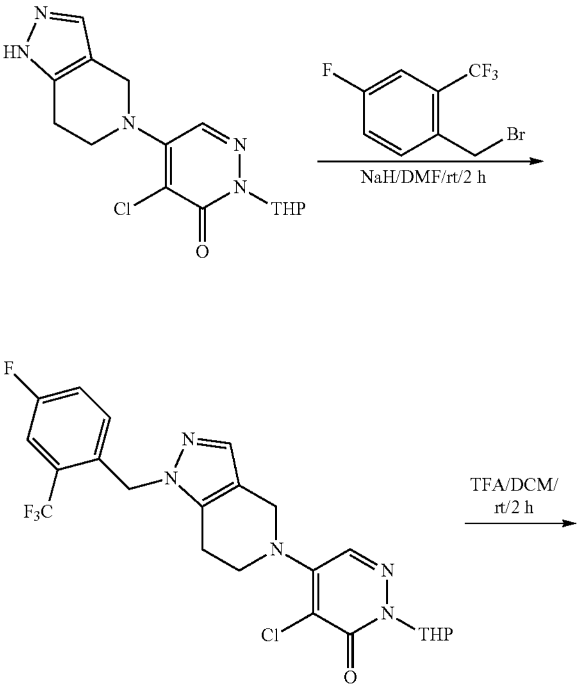

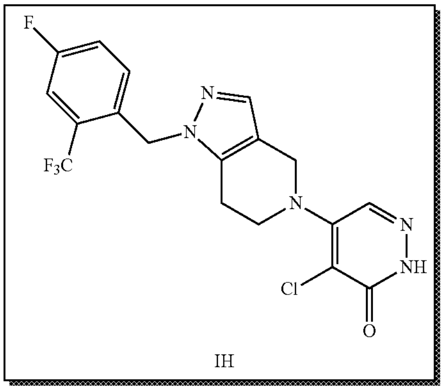

IH

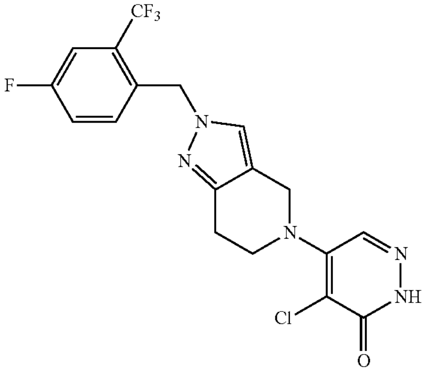

IHb

IH and IHb were prepared by the methods and scheme described for IG

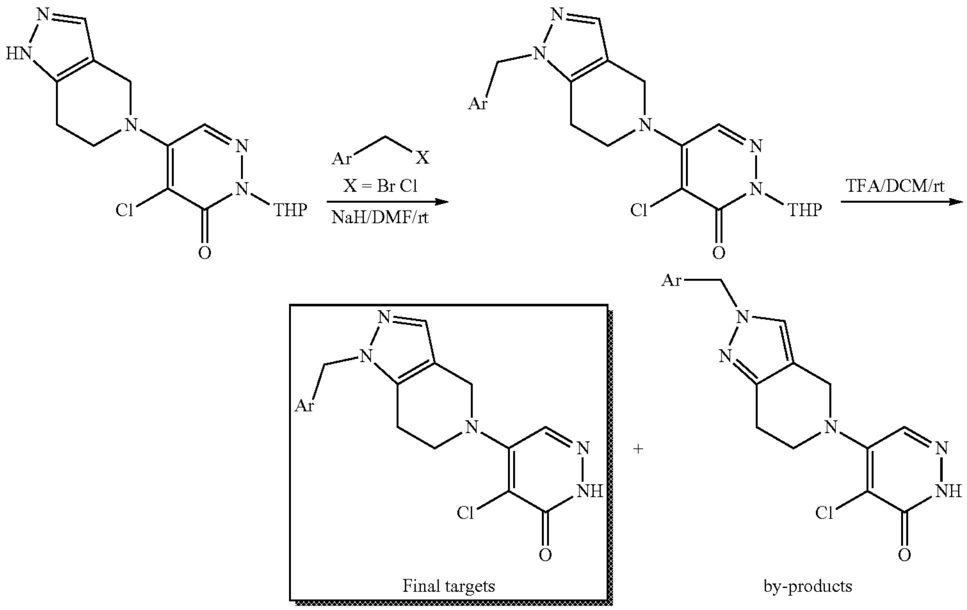
| Aryl halides | Target ID | Target ID(by-products) |
|---|---|---|
| 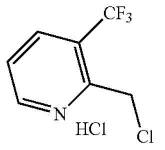 [SMILES: FC(F)(F)c1cccnc1CCl ; Cl] | II | IIb |
| 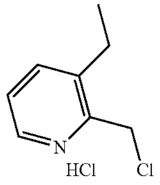 | IJ | IJb |
| 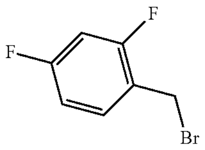 | IK | IKb |
| 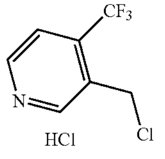 [SMILES: FC(F)(F)c1ccncc1CCl ; Cl] | IL | ILb |
| 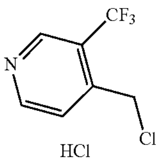 [SMILES: FC(F)(F)c1cnccc1CCl ; Cl] | IM | IMb |

II, IJ, IK, IL, and IM were prepared by the methods and scheme described for IG

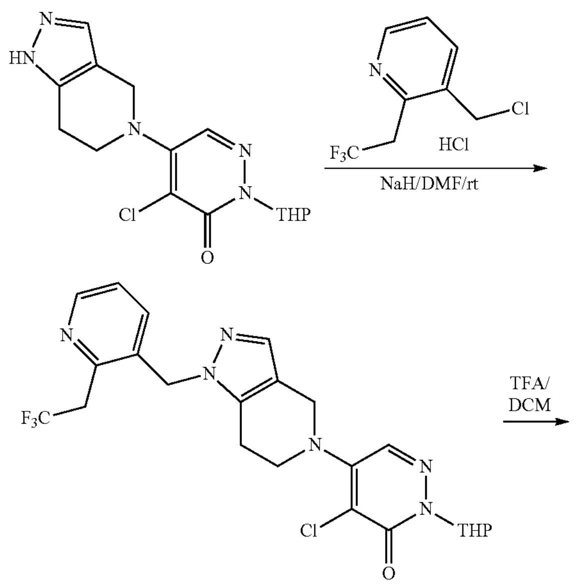

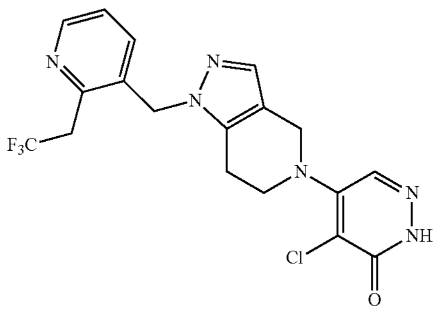

IN

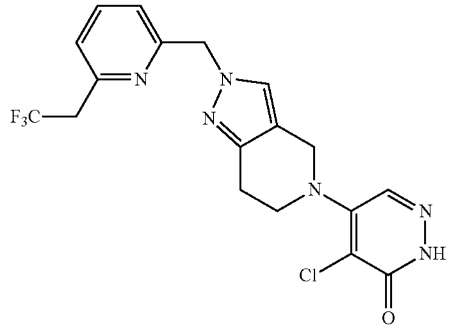

INb

IN was prepared by the methods and scheme described for IG

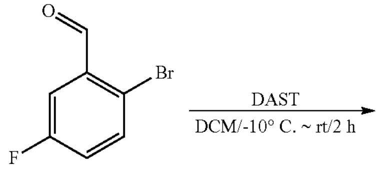

-continued

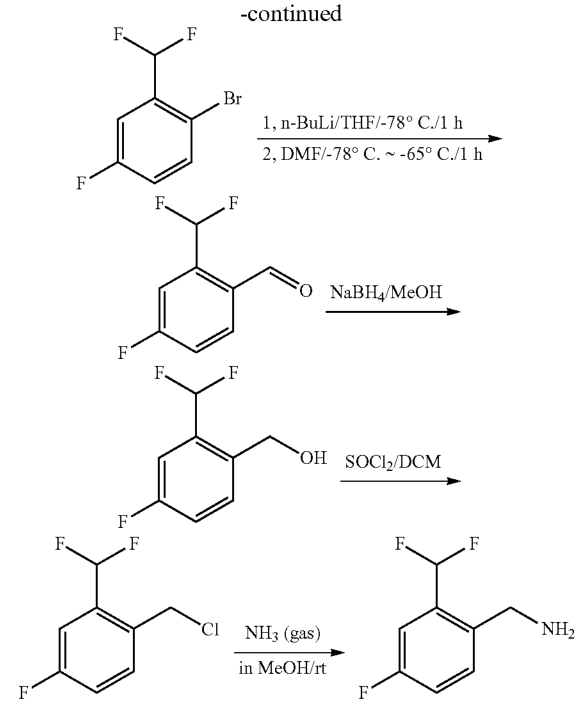

Int11

Preparation of Intermediate 11 (Int11): (2-(difluoromethyl)-4-fluorophenyl)methanamine 1-bromo-2-(difluoromethyl)-4-fluorobenzene To a stirred solution of 2-bromo-5-fluorobenzaldehyde (10 g, 49.26 mmol, 1 equiv.) in DCM (60 mL) was added DAST (15.9 g, 98.52 mmol, 2 equiv.). The resulting mixture was stirred for 2 h at −10 degree Celsius. The reaction was quenched with Water at −10 degrees Celsius. The resulting mixture was extracted with EtOAc (4×30 mL). The combined organic layers were washed with brine (2×40 mL), dried over anhydrous Na2SO4. After filtration, the filtrate was concentrated under reduced pressure. The residue was purified by silica gel column chromatography, eluted with PE/EtOAc (6:1) to afford 1-bromo-2-(difluoromethyl)-4-fluorobenzene (8 g, 72.18%) as a light yellow oil.

2-(difluoromethyl)-4-fluorobenzaldehyde

A solution of 2-bromo-5-fluorobenzaldehyde (5.7 g, 28.08 mmol, 1 equiv.) in THF (100 mL) was treated with n-BuLi (2.2 g, 33.69 mmol, 1.2 equiv.) for 2 h at −78 degrees Celsius under nitrogen atmosphere followed by the addition of DMF (3.078 g, 42.11 mmol, 1.50 equiv.). The resulting mixture was stirred for 2 h at −78 degrees Celsius under nitrogen atmosphere. The reaction was quenched with Water at −78 degrees Celsius. The resulting mixture was extracted with EtOAc (3×40 mL). The combined organic layers were washed with brine (2×40 mL), dried over anhydrous Na2SO4. After filtration, the filtrate was concentrated under reduced pressure. The residue was purified by silica gel column chromatography, eluted with PE/EtOAc (5:1) to afford 2-(difluoromethyl)-4-fluorobenzaldehyde (1.2 g, 24.55%) as a light yellow oil.

[2-(difluoromethyl)-4-fluorophenyl]methanol

To a stirred solution of 2-(difluoromethyl)-4-fluorobenzaldehyde (1.3 g, 7.47 mmol, 1 equiv.) in MeOH (10 mL) was added NaBH4 (0.8 g, 21.15 mmol, 2.83 equiv.). The resulting mixture was stirred for 4 h at room temperature. The resulting mixture was concentrated under reduced pressure. The residue was purified by silica gel column chromatography, eluted with PE/EtOAc (8:1) to afford [2-(difluoromethyl)-4-fluorophenyl]methanol (1.1 g, 83.65%) as a light yellow oil.

1-(chloromethyl)-2-(difluoromethyl)-4-fluorobenzene

To a stirred solution of [2-(difluoromethyl)-4-fluorophenyl]methanol (1.1 g, 6.25 mmol, 1 equiv.) in DCM (10 mL) was added SOCl2 (1.5 g, 0.01 mmol, 2 equiv.). The resulting mixture was stirred for 5 h at room temperature. The resulting mixture was concentrated under reduced pressure. The residue was purified by silica gel column chromatography, eluted with PE/EtOAc (10:1) to afford 1-(chloromethyl)-2-(difluoromethyl)-4-fluorobenzene (600 mg, 49.38%) as a light yellow solid.

1-[2-(difluoromethyl)-4-fluorophenyl]methanamine

To a stirred solution of 1-(chloromethyl)-2-(difluoromethyl)-4-fluorobenzene (1.1 g, 1 equiv.) in NH3/MeOH (100 mL). The resulting mixture was stirred for 2 h at 70 degree Celsius under NH3 atmosphere. The resulting mixture was concentrated under reduced pressure. The residue was purified by silica gel column chromatography, eluted with PE/EtOAc (1:1) to afford 1-[2-(difluoromethyl)-4-fluorophenyl]methanamine (0.9 g, 90.89%) as a light yellow solid.

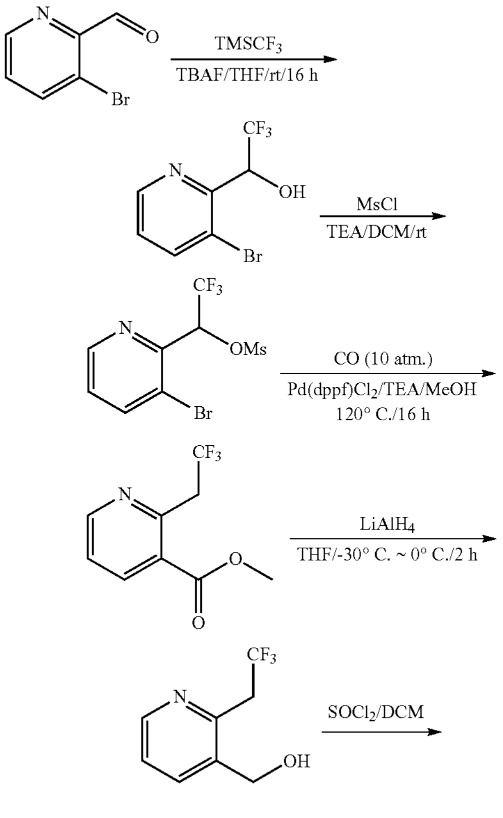

-continued

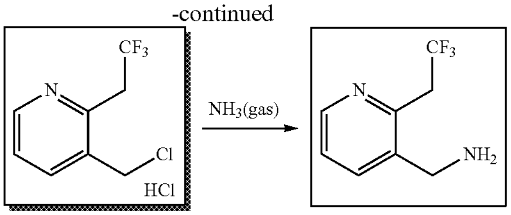

1-(3-bromopyridin-2-yl)-2,2,2-trifluoroethan-1-ol

To a stirred mixture of 3-bromopyridine-2-carbaldehyde (10 g, 53.76 mmol, 1 equiv.) and trimethyl(trifluoromethyl)silane (15.3 g, 107.52 mmol, 2 equiv.) in THF (50 mL) was added TBAF (5.4 mL, 1.5 equiv.) dropwise at 0 degree Celsius under nitrogen atmosphere. The resulting mixture was stirred for 10 h at room temperature. The reaction was monitored by LCMS. The resulting mixture was concentrated under reduced pressure. The residue was purified by silica gel column chromatography, eluted with PE/EtOAc (50:1 to 20:1) to afford 1-(3-bromopyridin-2-yl)-2,2,2-trifluoroethan-1-ol (10 g, 72.65%) as a yellow solid.

1-(3-bromopyridin-2-yl)-2,2,2-trifluoroethyl methanesulfonate

To a stirred mixture of 1-(3-bromopyridin-2-yl)-2,2,2-trifluoroethan-1-ol (10 g, 39.06 mmol, 1 equiv.) and DIEA (15.1 g, 117.18 mmol, 3 equiv.) in DCM (50 mL) was added methanesulfonyl chloride (5.4 g, 46.87 mmol, 1.2 equiv.) dropwise at 0 degree Celsius under nitrogen atmosphere. The resulting mixture was stirred for 2 h at room temperature. The reaction was monitored by LCMS. The reaction was quenched with Water at room temperature. The resulting mixture was extracted with EtOAc (3x200 mL). The combined organic layers were washed with brine (1x100 mL), dried over anhydrous Na2SO4. After filtration, the filtrate was concentrated under reduced pressure. The residue was purified by silica gel column chromatography, eluted with PE/EtOAc (50:1 to 2:1) to afford 1-(3-bromopyridin-2-yl)-2,2,2-trifluoroethyl methanesulfonate (10.5 g, 80.46%) as a yellow oil.

2-(2,2,2-trifluoroethyl)pyridine-3-carboxylate

To a solution of 1-(3-bromopyridin-2-yl)-2,2,2-trifluoroethyl methanesulfonate (10 g, 29.93 mmol, 1 equiv.) in 250 mL MeOH were added Pd(dppf)Cl2 (1.1 g, 1.50 mmol, 0.05 equiv.), Pd(PPh3)4 (1.7 g, 1.50 mmol, 0.05 equiv.) and TEA (6.1 g, 59.86 mmol, 2 equiv.) in a pressure tank. The mixture was purged with nitrogen for 1 h and then was pressurized to 10 atm with carbon monoxide at 120 degrees Celsius for 16 h. The reaction mixture was cooled to room temperature and filtered to remove insoluble solids. The resulting mixture was concentrated under reduced pressure. The resulting mixture was diluted with water (200 mL). The resulting mixture was extracted with EtOAc (3x300 mL). The combined organic layers were washed with brine (1x100 mL), dried over anhydrous Na2SO4. After filtration, the filtrate was concentrated under reduced pressure. The residue was purified by silica gel column chromatography, eluted with PE/EtOAc (50:1 to 10:1) to afford methyl 2-(2,2,2-trifluoroethyl)pyridine-3-carboxylate (5 g, 76.22%) as a yellow oil.

[2-(2,2,2-trifluoroethyl)pyridin-3-yl]methanol

To a stirred solution of methyl 2-(2,2,2-trifluoroethyl) pyridine-3-carboxylate (5 g, 22.81 mmol, 1 equiv.) in THF (30 mL) was added LiAlH4 (1.0 g, 27.38 mmol, 1.2 equiv.) dropwise at 0 degree Celsius. The resulting mixture was stirred for 2 h at 0 degree Celsius. The reaction was monitored by TLC. The reaction was quenched with Water and 15% NaOH (aq.) at 0 degree Celsius. The resulting mixture was filtered, the filter cake was washed with EtOAc (5×20 mL). The filtrate was concentrated under reduced pressure. The residue was purified by silica gel column chromatography, eluted with PE/EtOAc (50:1 to 2:1) to afford [2-(2,2,2-trifluoroethyl)pyridin-3-yl]methanol (3.3 g, 75.67%) as a yellow solid.

3-(chloromethyl)-2-(2,2,2-trifluoroethyl)pyridine

To a stirred solution of [2-(2,2,2-trifluoroethyl)pyridin-3-yl]methanol (500 mg, 2.62 mmol, 1 equiv.) in DCM (30 mL) was added SOCl2 (622.4 mg, 5.23 mmol, 2 equiv.) dropwise at room temperature. The resulting mixture was stirred for 16 h at room temperature. The reaction was monitored by LCMS. The resulting mixture was concentrated under reduced pressure. The residue was washed with 20 mL of hexane and stirred for 30 min. The resulting mixture was filtered, the filter cake was washed with hexane (3×3 mL). This resulted in 3-(chloromethyl)-2-(2,2,2-trifluoroethyl) pyridine (500 mg, 91.20%) as a white solid.

(2-(2,2,2-trifluoroethyl)pyridin-3-yl)methanamine

To a stirred solution of 3-(chloromethyl)-2-(2,2,2-trifluoroethyl)pyridine (1.1 g, 1 equiv.) in NH3/MeOH (100 mL). The resulting mixture was stirred for 2 h at 70 degree Celsius under NH3 atmosphere. The resulting mixture was concentrated under reduced pressure. The residue was purified by silica gel column chromatography, eluted with PE/EtOAc (1:1) to afford (2-(2,2,2-trifluoroethyl)pyridin-3-yl)methanamine (0.9 g, 90.89%) as a light yellow solid.

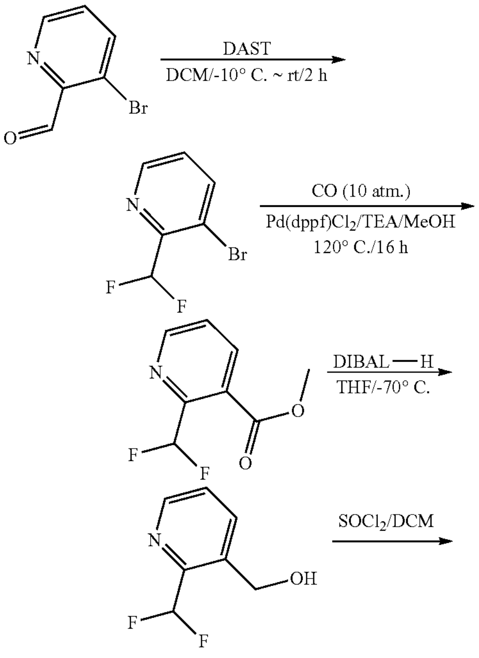

-continued

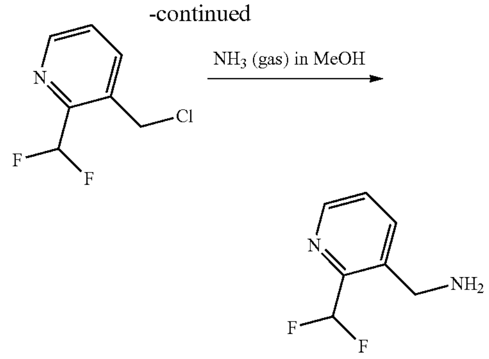

Int12

Preparation of Intermediate 12 (Int12) (2-(difluoromethyl)pyridin-3-yl)methanamine 3-bromo-2-(difluoromethyl)pyridine To a stirred solution of 3-bromopyridine-2-carbaldehyde (5 g, 26.88 mmol, 1 equiv.) in DCM (50 mL) was added DAST (8.7 g, 53.76 mmol, 2.0 equiv.) dropwise at −10 degrees Celsius under nitrogen atmosphere. The resulting mixture was stirred for 2 h at 0 degree Celsius under nitrogen atmosphere. The reaction was monitored by LCMS. The resulting mixture was concentrated under reduced pressure. The residue was purified by silica gel column chromatography, eluted with PE/EtOAc (5/1 to 1/1) to afford 3-bromo-2-(difluoromethyl)pyridine (3.6 g, 64.39%) as a yellow oil.

Methyl 2-(difluoromethyl)pyridine-3-carboxylate

To a solution of 3-bromo-2-(difluoromethyl)pyridine (2.6 g, 12.50 mmol, 1 equiv.) in MeOH (160 mL) was added Pd(PPh3)4 (1444.4 mg, 1.25 mmol, 0.10 equiv.) in a pressure tank. The mixture was purged with nitrogen for 10 min and then was pressurized to 10 atm with carbon monoxide at 120 degrees Celsius for 24 h. The reaction mixture was cooled to room temperature and filtered to remove insoluble solids. The reaction was monitored by LCMS. The resulting mixture was concentrated under reduced pressure. The residue was purified by silica gel column chromatography, eluted with PE/EtOAc (20/1 to 5/1) to afford methyl 2-(difluoromethyl)pyridine-3-carboxylate (1.1 g, 47.02%) as a yellow oil.

[2-(difluoromethyl)pyridin-3-yl]methanol

To a stirred solution of methyl 2-(difluoromethyl)pyridine-3-carboxylate (1.05 g, 5.61 mmol, 1 equiv.) in THF (30 mL) was added DIBAl-H (8 mL, 47.70 mmol, 8.50 equiv.) dropwise at −78 degree Celsius under nitrogen atmosphere. The resulting mixture was stirred for 16 h at −78 degrees Celsius under nitrogen atmosphere. The reaction was monitored by LCMS. The resulting mixture was extracted with EtOAc (3×500 mL). The combined organic layers were washed with brine (2×300 mL), dried over anhydrous Na2SO4. After filtration, the filtrate was concentrated under reduced pressure. This resulted in [2-(difluoromethyl)pyridin-3-yl]methanol (800 mg, 89.60%) as a yellow oil.

3-(chloromethyl)-2-(difluoromethyl)pyridine

To a stirred solution of [2-(difluoromethyl)pyridin-3-yl] methanol (300150 mg, 1886.12 mmol, 1 equiv.) in DCM (20 mL) was added SOCl2 (448.6 mg, 3.77 mmol, 2.00 equiv.) dropwise at 0 degree Celsius. The reaction mixture was stirred for 16 h at rt. The reaction was monitored by LCMS. The resulting mixture was concentrated under reduced pressure. This resulted in 3-(chloromethyl)-2-(difluoromethyl) pyridine (150 mg, 0.04%) as a yellow oil.

1-[2-(difluoromethyl)pyridin-3-yl]methanamine

To a stirred solution of 3-(chloromethyl)-2-(difluoromethyl)pyridine (150 mg, 0.84 mmol, 1 equiv.) in MeOH with NH3(g) at room temperature under nitrogen atmosphere. The resulting mixture was stirred for 4 h at 40 degrees Celsius under nitrogen atmosphere. The reaction was monitored by LCMS. The mixture was allowed to cool down to rt. The resulting mixture was concentrated under reduced pressure. The residue was purified by Prep-TLC (PE/EtOAc=2/1) to afford 1-[2-(difluoromethyl)pyridin-3-yl] methanamine (80 mg, 59.89%) as a yellow oil.

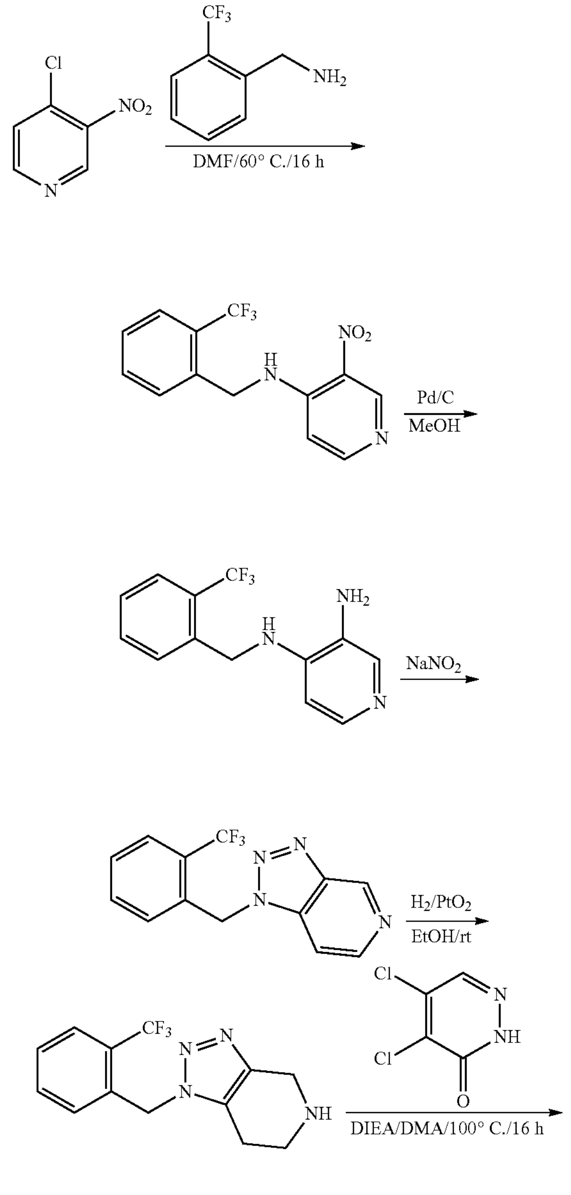

-continued

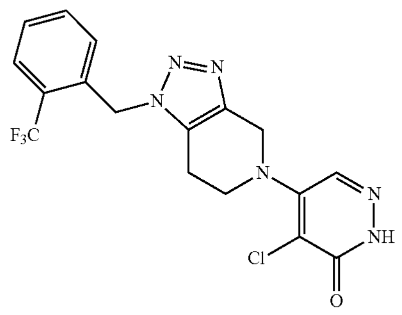

IO

Preparation of 10

3-nitro-N-[[2-(trifluoromethyl)phenyl]methyl]pyridin-4-amine

To a solution of 4-chloro-3-nitropyridine (4 g, 25.23 mmol, 1 equiv.) and 1-[2-(trifluoromethyl)phenyl]methanamine (4.4 g, 25.23 mmol, 1 equiv.) in dioxane (60 mL, 708.25 mmol, 28.07 equiv.) was added TEA (5.1 g, 50.46 mmol, 2 equiv.) at 25 degree Celsius. The solution was stirred at 90 degrees Celsius for 6 h. The resulting mixture was concentrated under reduced pressure. The residue was purified by silica gel column chromatography, eluted with EA/PE (10/1 to 1/1) to afford 3-nitro-N-[[2-(trifluoromethyl)phenyl]methyl]pyridin-4-amine (6 g, 80.01%) as a yellow solid.

N4-[[2-(trifluoromethyl)phenyl]methyl]pyridine-3,4-diamine

To a solution of 3-nitro-N-[[2-(trifluoromethyl)phenyl] methyl]pyridin-4-amine (3 g, 10.09 mmol, 1 equiv.) in MeOH (30 mL, 740.97 mmol, 73.41 equiv.) was added Pd/C (0.1 g, 1.01 mmol, 0.1 equiv.) at room temperature. The mixture was stirred at 25 degrees Celsius under hydrogen atmosphere. The resulting mixture was filtered, the filter cake was washed with EA (3×30 mL). The filtrate was concentrated under reduced pressure to afford N4-[[2-(trifluoromethyl)phenyl]methyl]pyridine-3,4-diamine (2.5 g, 92.68%) as a light yellow solid.

1-[[2-(trifluoromethyl)phenyl]methyl]-1H-[1,2,3] triazolo[4,5-c]pyridine

To a solution of N4-[[2-(trifluoromethyl)phenyl]methyl] pyridine-3,4-diamine (2 g, 7.48 mmol, 1 equiv.) in HCl (40 mL, 131.65 mmol, 17.59 equiv., 10%) were added NaNO2 (5.2 g, 74.83 mmol, 10 equiv.) in H2O (40 mL) dropwise at 0 degree Celsius. The mixture was stirred at 0 degree Celsius for 1 h. The resulting mixture was concentrated under reduced pressure. The residue was diluted with H2O (50 mL). The resulting mixture was extracted with EA (3×50 mL). The combined organic layers were washed with saturated NaCl (aq.) (2×50 mL), dried over anhydrous Na2SO4. After filtration, the filtrate was concentrated under reduced pressure to give 1-[[2-(trifluoromethyl)phenyl]methyl]-1H-[1,2,3]triazolo[4,5-c]pyridine (1.6 g, 76.84%) as a white solid.

1-[[2-(trifluoromethyl)phenyl]methyl]-1H,4H,5H,6H,7H-[1,2,3]triazolo[4,5-c]pyridine To a solution of 1-[[2-(trifluoromethyl)phenyl]methyl]-1H-[1,2,3]triazolo[4,5-c]pyridine (1 g, 3.59 mmol, 1 equiv.) in EtOH (30 mL, 516.41 mmol, 143.68 equiv.) was added PtO2 (81.6 mg, 0.36 mmol, 0.1 equiv.) at 25 degree Celsius. The mixture was stirred at 25 degrees Celsius under hydrogen atmosphere. The precipitated solids were collected by filtration and washed with MeOH (3×50 mL). To afford 1-[[2-(trifluoromethyl)phenyl]methyl]-1H,4H,5H,6H,7H-[1,2,3]triazolo[4,5-c]pyridine (800 mg, 78.86%) as brown oil.

4-chloro-5-(1-[[2-(trifluoromethyl)phenyl]methyl]-1H,4H,5H,6H,7H-[1,2,3]triazolo[4,5-c]pyridin-5-yl)-2,3-dihydropyridazin-3-one To a stirred mixture of 4,5-dichloro-2,3-dihydropyridazin-3-one (150 mg, 0.91 mmol, 1 equiv.) and DIEA (235.0 mg, 1.82 mmol, 2 equiv.) in DMA (10 mL) was added 1-[[2-(trifluoromethyl)phenyl]methyl]-1H,4H,5H,6H,7H-[1,2,3]triazolo[4,5-c]pyridine (282.3 mg, 1.00 mmol, 1.10 equiv.) at room temperature under nitrogen atmosphere. The resulting mixture was stirred for 2 h at 100 degrees Celsius. The reaction was monitored by LCMS. The mixture was allowed to cool down to room temperature. The crude product (150 mg) was purified by Prep-HPLC with the following conditions (Column: XBridge Shield RP18 OBD Column, 5 um, 19*150 mm; Mobile Phase A: Water (10 mmol/L NH4HCO3), Mobile Phase B: ACN; Flow rate: 20 mL/min; Gradient: 25% B to 50% B in 7 min; 220 nm; Rt: 6.25 min) to afford 4-chloro-5-(1-[[2-(trifluoromethyl)phenyl]methyl]-1H,4H,5H,6H,7H-[1,2,3]triazolo[4,5-c]pyridin-5-yl)-2,3-dihydropyridazin-3-one (74.6 mg, 19.97%) as a light yellow solid.

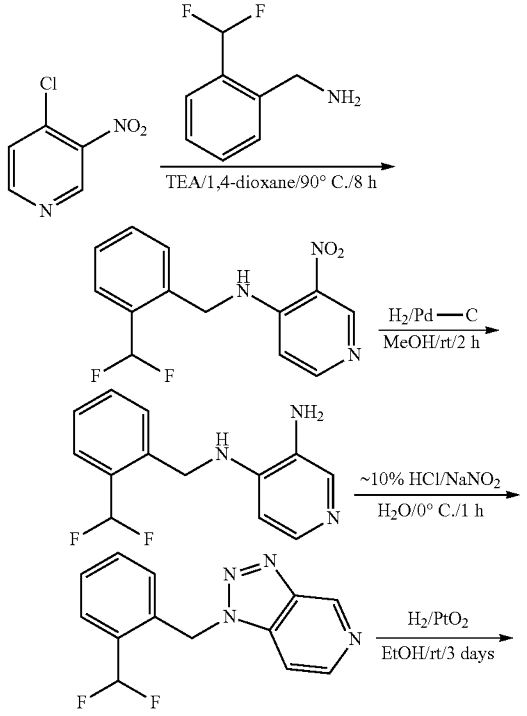

-continued

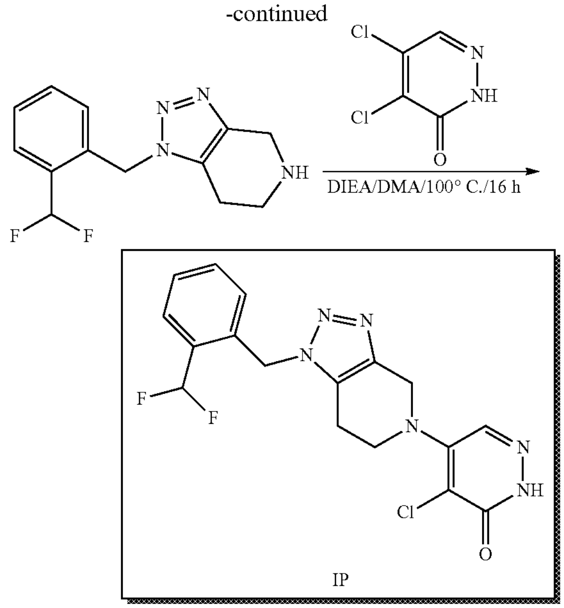

IP

IP was prepared by the methods and scheme described for IO by using (2-(difluoromethyl)phenyl)methanaieine

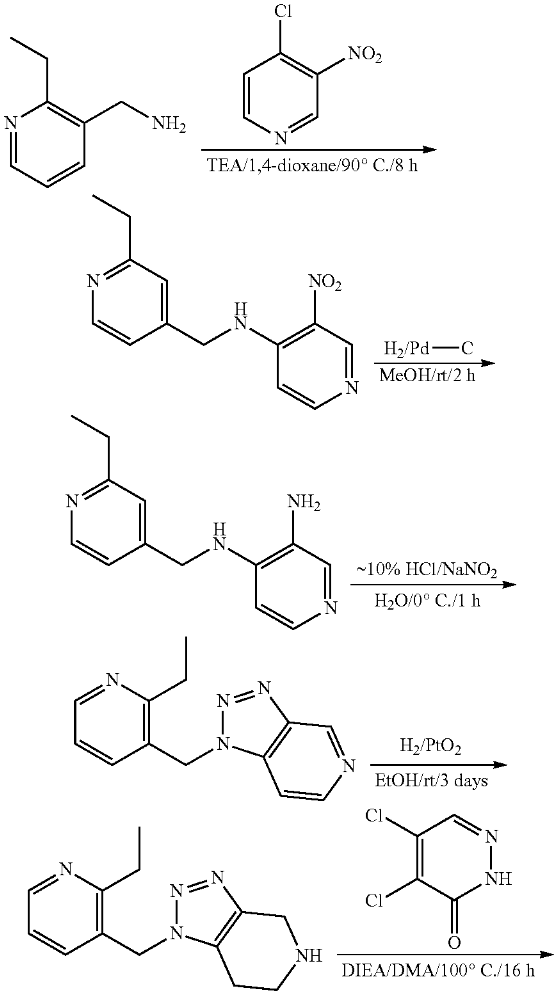

-continued
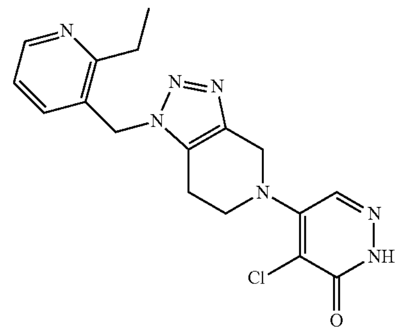
IQ
IQ was prepared by the methods and scheme described for IO by using (2-ethylpyridin-3-yl)methanamine.
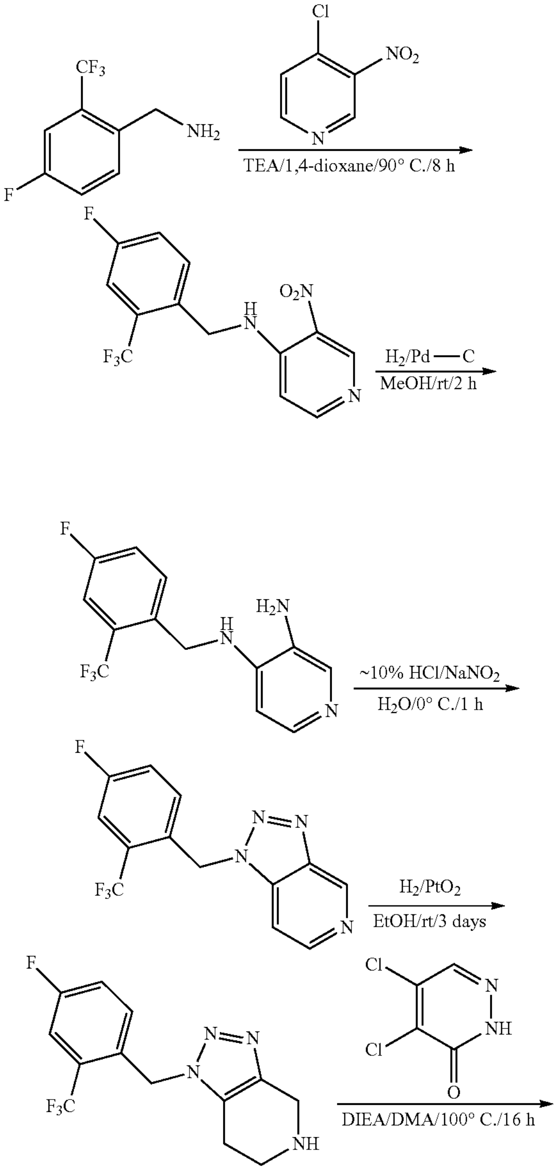
-continued
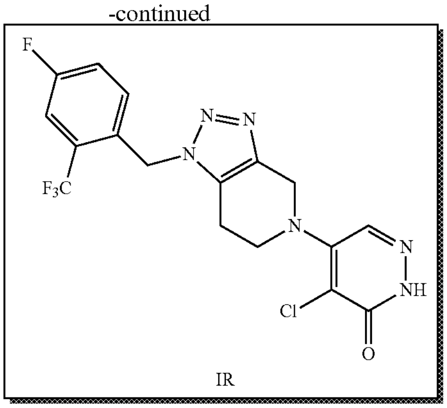
IR
IR was prepared by the methods and scheme described for IO by using (4-fluoro-2-(trifluoromethyl)phenyl)methanamine.
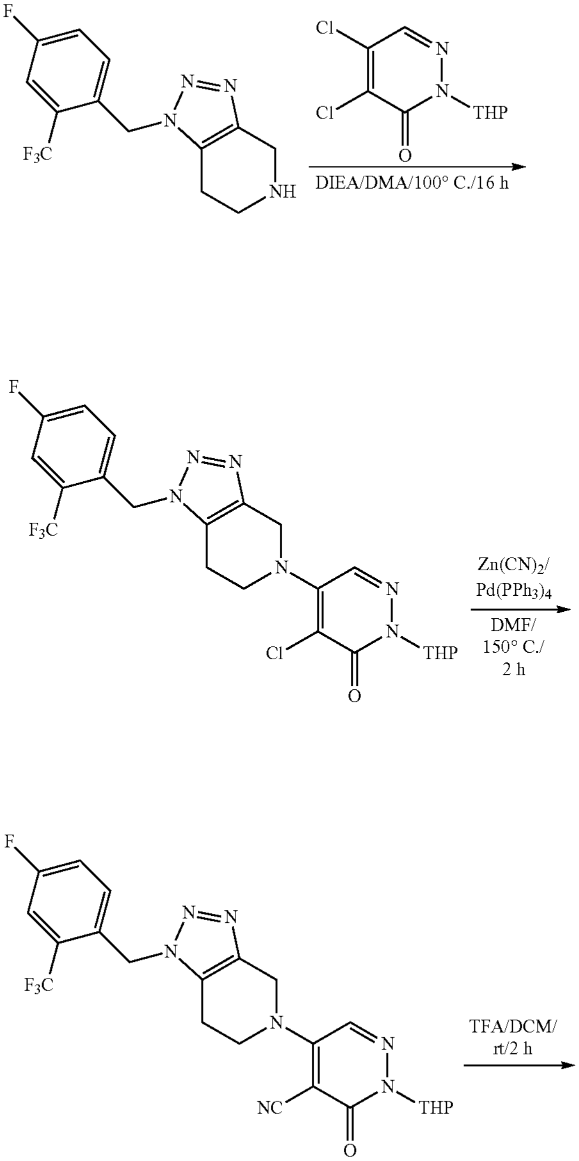

-continued

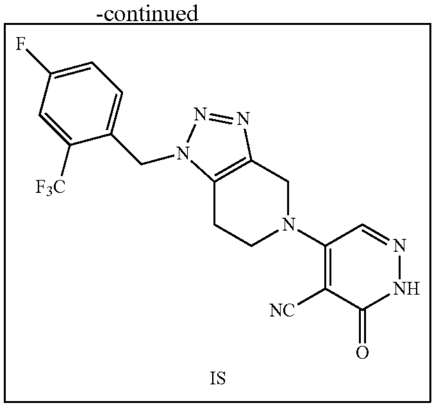

IS

Preparation of IS 4-chloro-5-(1-[[4-fluoro-2-(trifluoromethyl)phenyl] methyl]-1H,3aH,4H,5H,6H,7H,7aH-[1,2,3]triazolo [4,5-c]pyridin-5-yl)-2-(oxan-2-yl)-2,3,4,5-tetrahydropyridazin-3-one To a stirred solution of 1-[[4-fluoro-2-(trifluoromethyl) phenyl]methyl]-1H,3aH,4H,5H,6H,7H,7aH-[1,2,3]triazolo [4,5-c]pyridine (200 mg, 0.66 mmol, 1 equiv.) and DIEA (171.0 mg, 1.32 mmol, 2 equiv.) in DMA (5 mL) was added 4,5-dichloro-2-(oxan-2-yl)-2,3-dihydropyridazin-3-one (181.3 mg, 0.73 mmol, 1.1 equiv.). The resulting mixture was stirred for overnight at 100 degree Celsius. The residue was purified by reverse flash chromatography with the following conditions: column, C18 silica gel; mobile phase, MeOH in water, 20% to 55% gradient in 10 min; detector, UV 254 nm. This resulted in 4-chloro-5-(1-[[4-fluoro-2-(trifluoromethyl)phenyl]methyl]-1H,3aH,4H,5H,6H,7H,7aH-[1,2,3]triazolo[4,5-c]pyridin-5-yl)-2-(oxan-2-yl)-2,3,4,5-tetrahydropyridazin-3-one (100 mg, 29.24%) as a yellow solid.

5-(1-[[4-fluoro-2-(trifluoromethyl)phenyl]methyl]-1H,3aH,4H,5H,6H,7H,7aH-[1,2,3]triazolo[4,5-c] pyridin-5-yl)-2-(oxan-2-yl)-3-oxo-2,3-dihydropyridazine-4-carbonitrile To a stirred solution of 4-chloro-5-(1-[[4-fluoro-2-(trifluoromethyl)phenyl]methyl]-1H,3aH,4H,5H,6H,7H,7aH-[1,2,3]triazolo[4,5-c]pyridin-5-yl)-2-(oxan-2-yl)-2,3-dihydropyridazin-3-one (100 mg, 0.19 mmol, 1 equiv.) and Zn(CN)2 (45.6 mg, 0.39 mmol, 2.00 equiv.) in DMF (4 mL) was added Pd(PPh3)4 (22.4 mg, 0.02 mmol, 0.1 equiv.). The final reaction mixture was irradiated with microwave radiation for 2 h at 150 degree Celsius. The solution was purified by reverse phase flash with the following conditions (with the following conditions (Column: spnerical C18, 20-40 um, 330 g; Mobile Phase A: Water (5 mmol/L NH4HCO3), Mobile Phase B: ACN; Flow rate: 80 mL/min; Gradient: 10% B to 60% B in 55 min; 254 nm)) to afford 5-(1-[[4-fluoro-2-(trifluoromethyl)phenyl]methyl]-1H,3aH,4H,5H,6H,7H,7aH-[1,2,3]triazolo[4,5-c]pyridin-5-yl)-2-(oxan-2-yl)-3-oxo-2,3-dihydropyridazine-4-carbonitrile (90 mg, 91.68%) as an off-white solid.

5-(1-[[4-fluoro-2-(trifluoromethyl)phenyl]methyl]-1H,4H,5H,6H,7H-[1,2,3]triazolo[4,5-c]pyridin-5-yl)-3-oxo-2,3-dihydropyridazine-4-carbonitrile To a stirred solution of 5-(1-[[4-fluoro-2-(trifluoromethyl) phenyl]methyl]-1H,4H,5H,6H,7H-[1,2,3]triazolo[4,5-c] pyridin-5-yl)-2-(oxan-2-yl)-3-oxo-2,3-dihydropyridazine-4-carbonitrile (90 mg, 0.18 mmol, 1 equiv.) in Solvents DCM (3 mL) was added TFA (1 mL). The resulting mixture was stirred for 2 h at room temperature. The mixture/residue was basified to pH 8 with saturated NH4Cl (aq.). The resulting mixture was concentrated under reduced pressure. The crude product was purified by Prep-HPLC with the following conditions (Column: XBridge Shield RP18 OBD Column, 5 um, 19*150 mm; Mobile Phase A: Water (10 mmol/L NH4HCO3), Mobile Phase B: ACN; Flow rate: 20 mL/min; Gradient: 20% B to 50% B in 7 min; 220 nm; Rt: 6.9 min) to afford 5-(1-[[4-fluoro-2-(trifluoromethyl)phenyl]methyl]-1H,4H,5H,6H,7H-[1,2,3]triazolo[4,5-c]pyridin-5-yl)-3-oxo-2,3-dihydropyridazine-4-carbonitrile (5 mg, 6.67%) as a white solid.

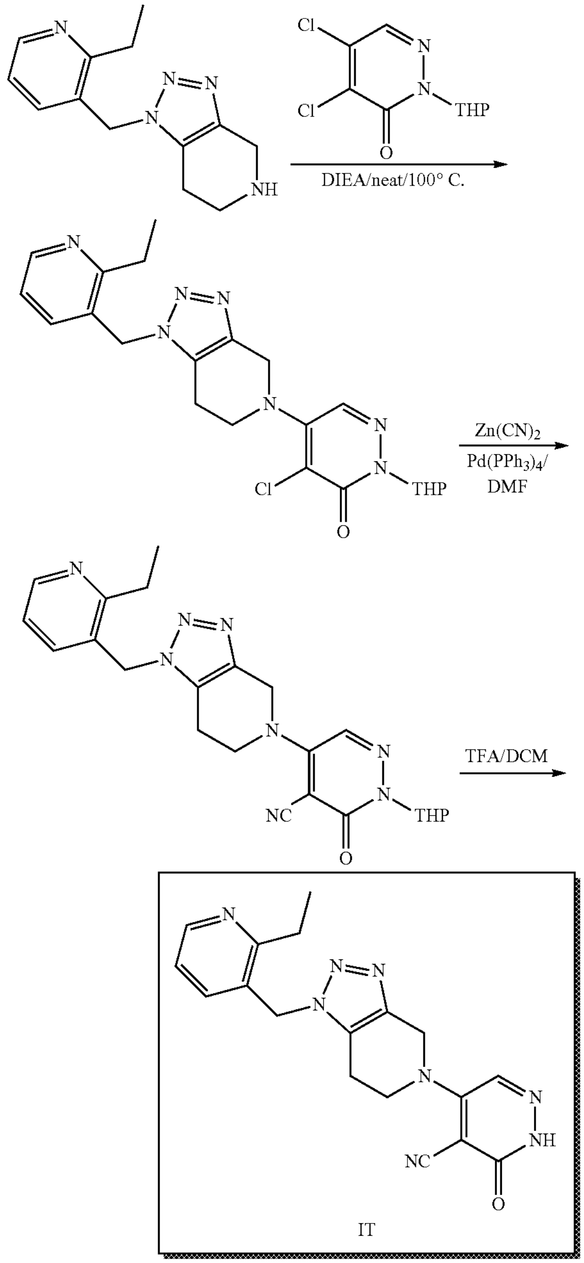

IT

IT was prepared by the methods and scheme described for IS by using 1-[[4-fluoro-2-(trifluoromethyl)phenyl]methyl]-1H,3aH,4H,5H,6H,7H,7aH-[1,2,3]triazolo[4,5-c]pyridine

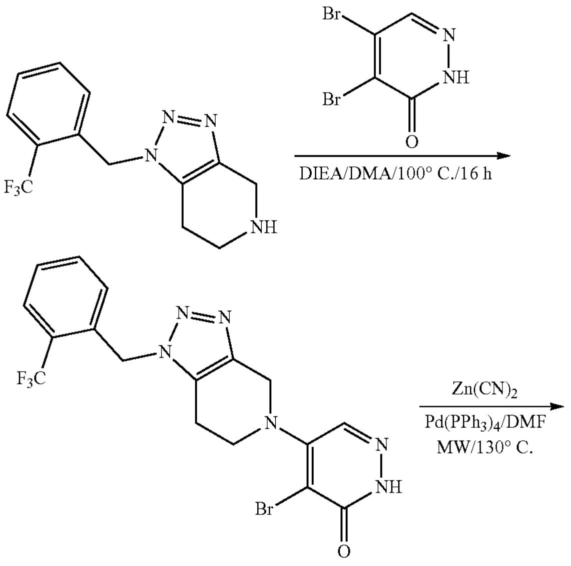

IU

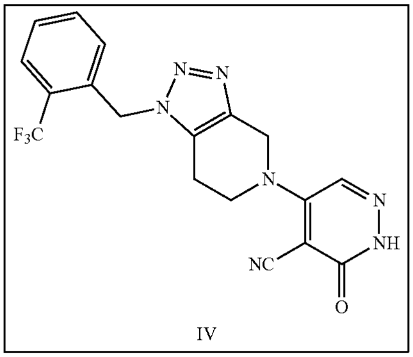

IV

Preparation of IU and IV

4-bromo-5-(1-[[2-(trifluoromethyl)phenyl]methyl]-1H,4H,5H,6H,7H-[1,2,3]triazolo[4,5-c]pyridin-5-yl)-2,3-dihydropyridazin-3-one To a solution of 1-[[2-(trifluoromethyl)phenyl]methyl]-1H,4H,5H,6H,7H-[1,2,3]triazolo[4,5-c]pyridine (500 mg, 1.77 mmol, 1 equiv.) and 4,5-dibromo-2,3-dihydropyridazin-3-one (449.7 mg, 1.77 mmol, 1 equiv.) in DMA (10 mL, 107.55 mmol, 60.72 equiv.) was added DIEA (457.9 mg, 3.54 mmol, 2 equiv.) at 25 degree Celsius. The solution was stirred at 100 degrees Celsius for 16 h. The resulting mixture was concentrated under reduced pressure. The residue was purified by Prep-TLC (DCM/MeOH 10/1) to afford 4-bromo-5-(1-[[2-(trifluoromethyl)phenyl]methyl]-1H,4H,5H,6H,7H-[1,2,3]triazolo[4,5-c]pyridin-5-yl)-2,3-dihydropyridazin-3-one (450 mg, 55.80%) as a white solid.

3-oxo-5-(1-[[2-(trifluoromethyl)phenyl]methyl]-1H,4H,5H,6H,7H-[1,2,3]triazolo[4,5-c]pyridin-5-yl)-2,3-dihydropyridazine-4-carbonitrile To a solution of 4-bromo-5-(1-[[2-(trifluoromethyl)phenyl]methyl]-1H,4H,5H,6H,7H-[1,2,3]triazolo[4,5-c]pyridin-5-yl)-2,3-dihydropyridazin-3-one (200 mg, 440 mmol, 1 equiv.) and Zn(CN)2 (154.8 mg, 1.32 mmol, 3.00 equiv.) in DMF (5 ML, 64.61 mmol, 147.06 equiv.) was added Pd(PPh3)4 (50.8 mg, 0.04 mmol, 0.1 equiv.) at 25 degree Celsius under nitrogen atmosphere. The mixture was stirred at 130 degrees Celsius for 3 h. The resulting mixture was concentrated under reduced pressure. The residue was purified by Prep-TLC (DCM/MeOH 10/1) to afford 3-oxo-5-(1-[[2-(trifluoromethyl)phenyl]methyl]-1H,4H,5H,6H,7H-[1,2,3]triazolo[4,5-c]pyridin-5-yl)-2,3-dihydropyridazine-4-carbonitrile (61.9 mg) as a white solid.

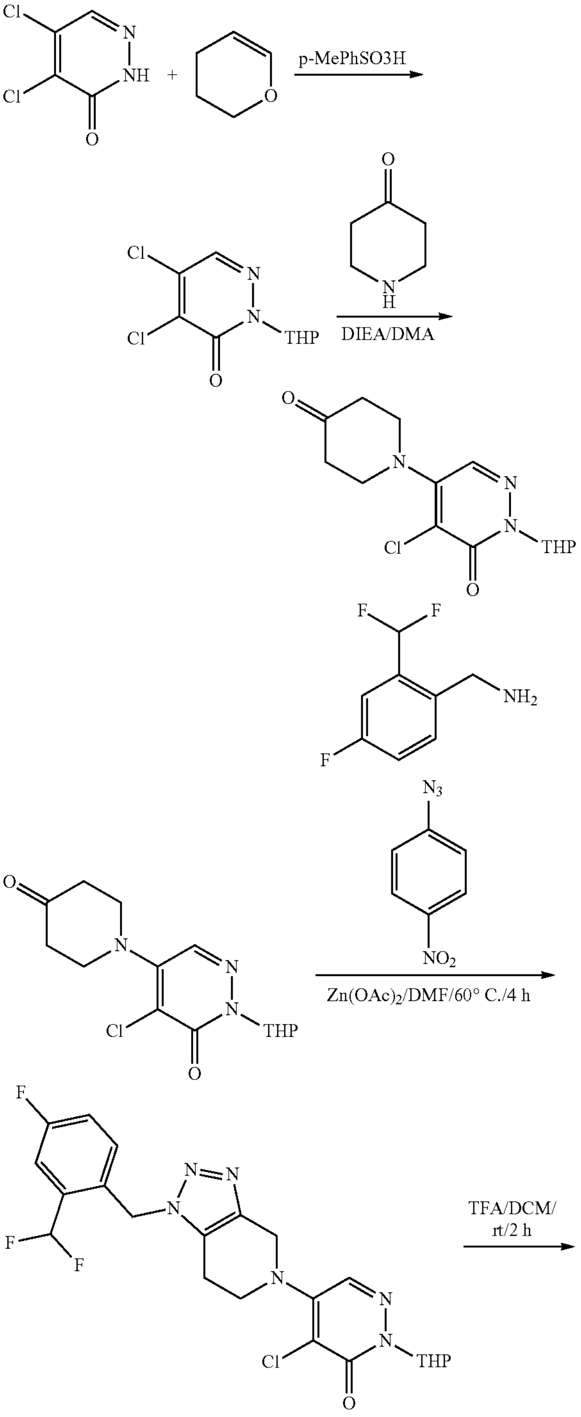

-continued

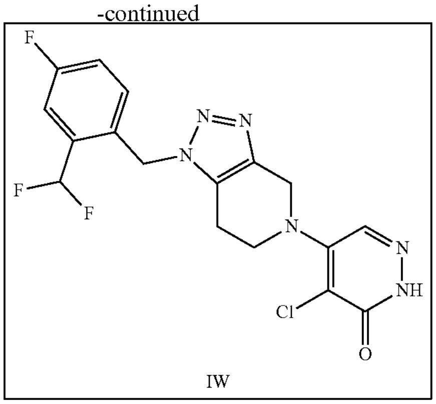

IW

Preparation of IW 4,5-dichloro-2-(oxan-2-yl)-2,3-dihydropyridazin-3-one

To a stirred solution of 4,5-dichloro-2,3-dihydropyridazin-3-one (20 g, 121.23 mmol, 1 equiv.) and 3,4-dihydro-2H-pyran (81.6 g, 969.83 mmol, 8 equiv.) in THF (800 mL) was added 4-methylbenzene-1-sulfonic acid (4.2 g, 24.25 mmol, 0.2 equiv.) dropwise at room temperature under nitrogen atmosphere. The resulting mixture was stirred at reflux for 2 days under nitrogen atmosphere. The reaction was monitored by TLC. The resulting mixture was concentrated under reduced pressure. The residue was purified by silica gel column chromatography, eluted with PE/EtOAc (40:1 to 20:1) to afford 4,5-dichloro-2-(oxan-2-yl)-2,3-dihydropyridazin-3-one (28 g, 92.72%) as a white solid.

4-chloro-2-(oxan-2-yl)-5-(4-oxopiperidin-1-yl)-2,3-dihydropyridazin-3-one

To a stirred solution of 4,5-dichloro-2-(oxan-2-yl)-2,3-dihydropyridazin-3-one (5 g, 20.07 mmol, 1 equiv.) and piperidin-4-one (4.1 g, 30.11 mmol, 1.5 equiv., 73%) in DMA (20 mL) was added DIEA (7.8 g, 60.35 mmol, 3.007 equiv.) at room temperature. The resulting mixture was stirred for 30 h at 100 degrees Celsius. The resulting mixture was concentrated under vacuum. The crude product (8 g) was purified by reverse phase flash with the following conditions (Column: C18 330 g; Mobile Phase A: Water (10 mmol/L NH4HCO3), MobilePhase B: ACN; Flow rate: 80 mL/min; Gradient: 30% B to 80% B in 30 min; 254&220 nm; Rt: 8 min) to afford 4-chloro-2-(oxan-2-yl)-5-(4-oxopiperidin-1-yl)-2,3-dihydropyridazin-3-one (1.96 g, 31.32%) as a yellow solid.

4-chloro-5-(1-[[2-(difluoromethyl)-4-fluorophenyl]methyl]-1H,3aH,4H,5H,6H,7H,7aH-[1,2,3]triazolo[4,5-c]pyridin-5-yl)-2-(oxan-2-yl)-2,3-dihydropyridazin-3-one To a stirred solution of 4-chloro-2-(oxan-2-yl)-5-(4-oxopiperidin-1-yl)-2,3-dihydropyridazin-3-one (300 mg, 0.96 mmol, 1 equiv.) and 1-[2-(difluoromethyl)-4-fluorophenyl]methanamine (337.1 mg, 1.92 mmol, 2.00 equiv.) in DMF (10 mL) were added 1-azido-4-nitrobenzene (221.1 mg, 1.35 mmol, 1.4 equiv.) and Zn(OAc)2 (176.6 mg, 0.96 mmol, 1 equiv.). The resulting mixture was stirred for 4 h at 60 degree Celsius. The residue was purified by reverse flash chromatography with the following conditions: column, C18 silica gel; mobile phase, MeOH in water, 20% to 65% gradient in 30 min; detector, UV 254 nm. This resulted in 4-chloro-5-(1-[[2-(difluoromethyl)-4-fluorophenyl]methyl]-1H,3aH,4H,5H,6H,7H,7aH-[1,2,3]triazolo[4,5-c]pyridin-5-yl)-2-(oxan-2-yl)-2,3-dihydropyridazin-3-one (230 mg, 48.10%) as a light yellow solid.

4-chloro-5-(1-[[2-(difluoromethyl)-4-fluorophenyl]methyl]-1H,3aH,4H,5H,6H,7H,7aH-[1,2,3]triazolo[4,5-c]pyridin-5-yl)-2,3-dihydropyridazin-3-one To a stirred solution of 4-chloro-5-(1-[[2-(difluoromethyl)-4-fluorophenyl]methyl]-1H,3aH,4H,5H,6H,7H,7aH-[1,2,3]triazolo[4,5-c]pyridin-5-yl)-2-(oxan-2-yl)-2,3-dihydropyridazin-3-one (60 mg, 0.12 mmol, 1 equiv.) in DCM (3 mL) was added TFA (1 mL). The resulting mixture was stirred for 2 h at room temperature. The mixture was basified to pH 8 with saturated NH4Cl (aq.). The resulting mixture was concentrated under reduced pressure. The crude product was purified by Prep-HPLC with the following conditions (Column: XBridge Shield RP18 OBD Column, 5 um, 19*150 mm; Mobile Phase A: Water (10 mmol/L NH4HCO3), Mobile Phase B: ACN; Flow rate: 20 mL/min; Gradient: 20% B to 42% B in 10 min; 220 nm; Rt: 8.98 min) to afford 4-chloro-5-(1-[[2-(difluoromethyl)-4-fluorophenyl]methyl]-1H,3aH,4H,5H,6H,7H,7aH-[1,2,3]triazolo[4,5-c]pyridin-5-yl)-2,3-dihydropyridazin-3-one (4.1 mg, 8.23%) as a white solid.

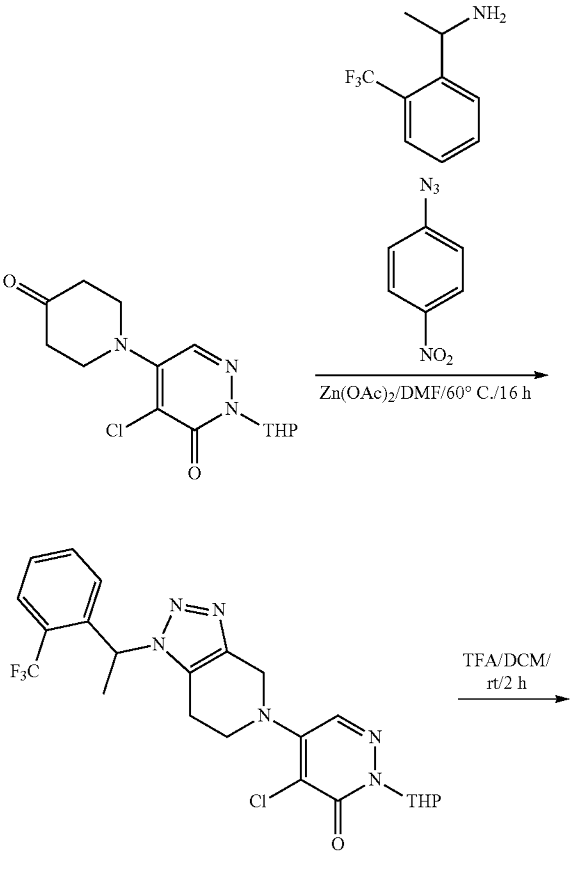

-continued

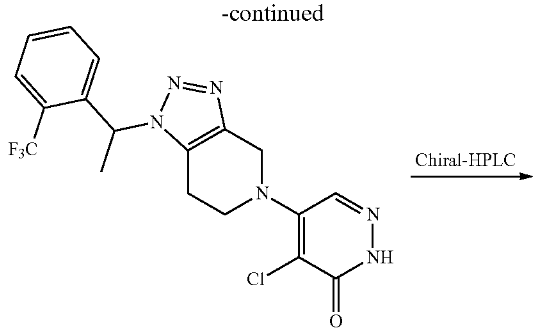

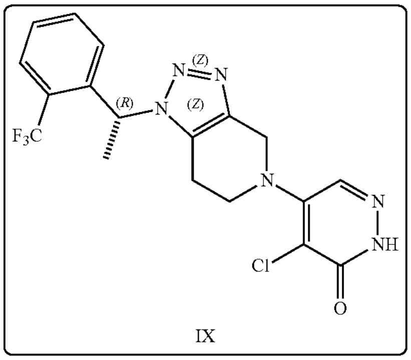

IX

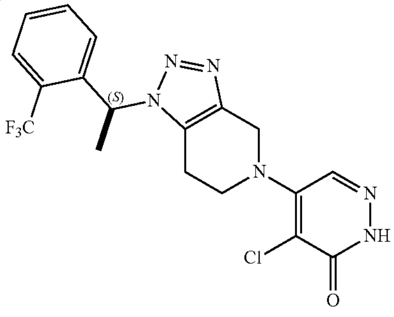

IXb

Preparation of IX and IXb

4-chloro-2-(oxan-2-yl)-5-(1-[1-[2-(trifluoromethyl)phenyl]ethyl]-1H,4H,5H,6H,7H-[1,2,3]triazolo[4,5-c]pyridin-5-yl)-2,3-dihydropyridazin-3-one To a stirred mixture of 4-chloro-2-(oxan-2-yl)-5-(4-oxopiperidin-1-yl)-2,3-dihydropyridazin-3-one (600 mg, 1.92 mmol, 1 equiv.) and 1-azido-4-nitrobenzene (442.2 mg, 2.69 mmol, 1.4 equiv.) in DMF (10 mL) were added 1-[2-(trifluoromethyl)phenyl]methanamine (674.2 mg, 3.85 mmol, 2.0 equiv.) and Zn(OAc)2 (353.1 mg, 1.92 mmol, 1.0 equiv.) at room temperature under nitrogen atmosphere. The resulting mixture was stirred for 3 h at 60 degrees Celsius under nitrogen atmosphere. The reaction was monitored by LCMS. The mixture was allowed to cool down to room temperature. The reaction was quenched with Water at room temperature. The resulting mixture was concentrated under reduced pressure. The resulting mixture was extracted with EtOAc (4×200 mL). The combined organic layers were washed with brine (3×300 mL), dried over anhydrous Na2SO4. After filtration, the filtrate was concentrated under reduced pressure. The residue was purified by silica gel column chromatography, eluted with PE/EtOAc (5:1 to 1:1) to afford 4-chloro-2-(oxan-2-yl)-5-(1-[1-[2-(trifluoromethyl)phenyl]ethyl]-1H,4H,5H,6H,7H-[1,2,3]triazolo[4,5-c]pyridin-5-yl)-2,3-dihydropyridazin-3-one (1 g, crude) as a brown solid.

4-chloro-5-[1-[(1R)-1-[2-(trifluoromethyl)phenyl]ethyl]-1H,4H,5H,6H,7H-[1,2,3]triazolo[4,5-c]pyridin-5-yl]-2,3-dihydropyridazin-3-one (37.9 mg) and 4-chloro-5-[1-[(1S)-1-[2-(trifluoromethyl)phenyl]ethyl]-1H,4H,5H,6H,7H-[1,2,3]triazolo[4,5-c]pyridin-5-yl]-2,3-dihydropyridazin-3-one To a stirred solution of 4-chloro-2-(oxan-2-yl)-5-(1-[1-[2-(trifluoromethyl)phenyl]ethyl]-1H,4H,5H,6H,7H-[1,2,3]triazolo[4,5-c]pyridin-5-yl)-2,3-dihydropyridazin-3-one (100 mg, 0.20 mmol, 1 equiv.) in DCM (10 mL, 157.30 mmol, 800.55 equiv.) was added TFA (3 mL, 40.39 mmol, 205.55 equiv.) at room temperature. The resulting mixture was stirred for 2 h at room temperature. The reaction was monitored by LCMS. The resulting mixture was concentrated under reduced pressure. The crude product (100 mg) was purified by Prep-HPLC with the following conditions (Column: XBridge Prep C18 OBD Column, 5 um, 19*150 mm; Mobile Phase A: Water (10 mmol/L NH4HCO3), Mobile Phase B: ACN; Flow rate: 20 mL/min; Gradient: 30% B to 46% B in 7 min; 220/254 nm; Rt: 6.27 min) to afford 4-chloro-5-[1-[(1R)-1-[2-(trifluoromethyl)phenyl]ethyl]-1H,4H,5H,6H,7H-[1,2,3]triazolo[4,5-c]pyridin-5-yl]-2,3-dihydropyridazin-3-one (37.9 mg) as a yellow solid and 4-chloro-5-[1-[(1S)-1-[2-(trifluoromethyl)phenyl]ethyl]-1H,4H,5H,6H,7H-[1,2,3]triazolo[4,5-c]pyridin-5-yl]-2,3-dihydropyridazin-3-one (39.7 mg) as a yellow solid.

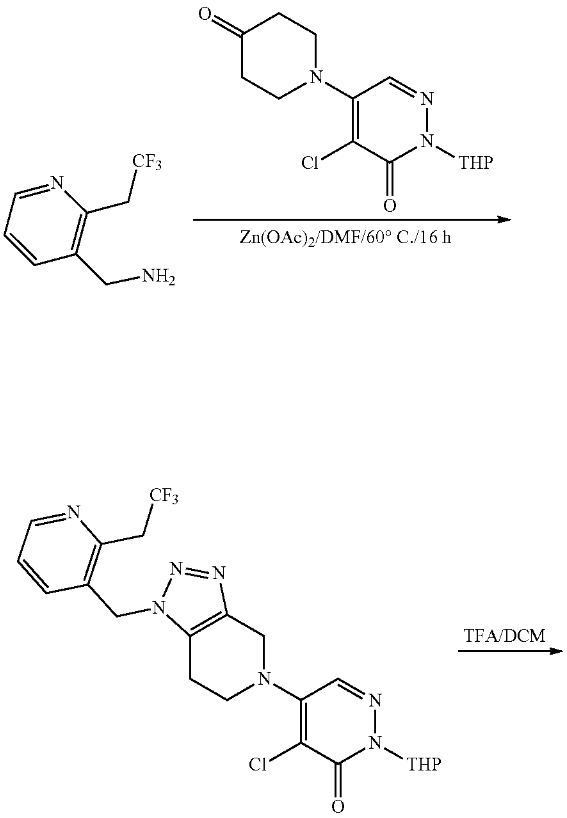

-continued
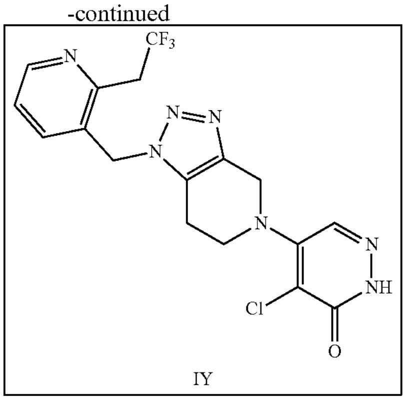
IY
IY was prepared by the methods and scheme described for IW by using (2-(2,2,2-trifluoroethyl)pyridin-3-yl)methanamine
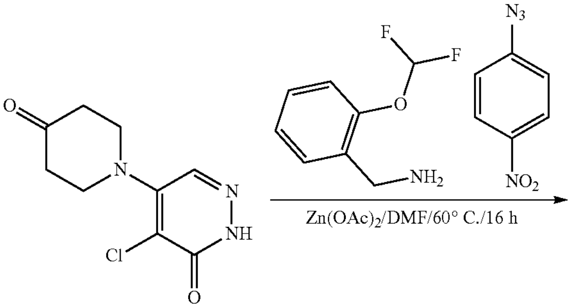
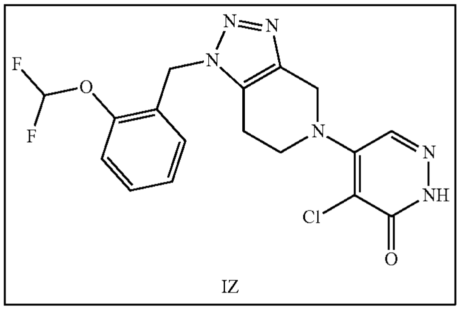
IZ
IZ was prepared by the methods and scheme described for IW by using (2-(difluoromethoxy)phenyl)methanamine
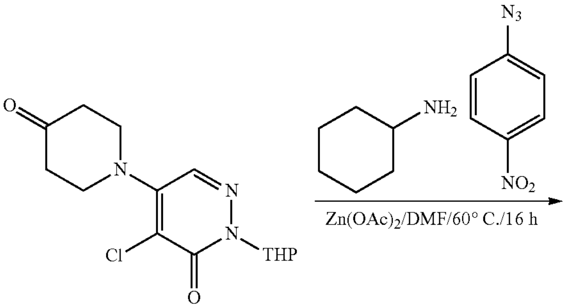
-continued
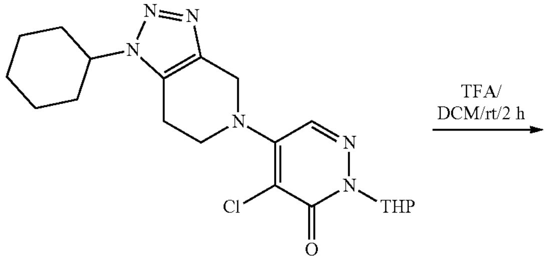
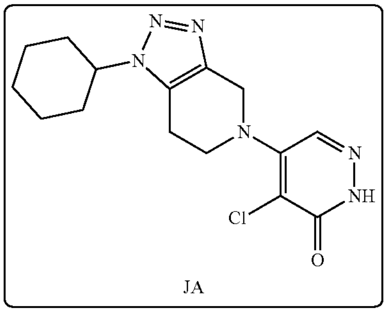
JA
JA was prepared by the methods and scheme described for IW by using cyclohexanamiine
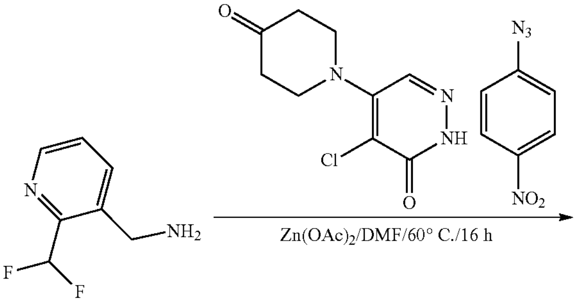
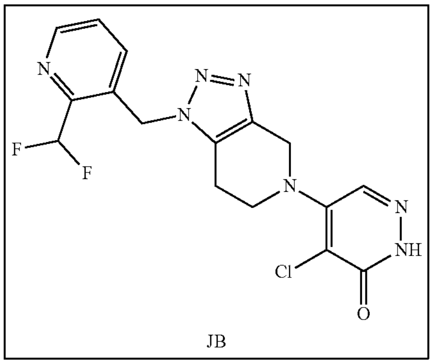
JB JB was prepared by the methods and scheme described for IW by using (2-(difluoromethyl)pyridin-3-yl)methanamine

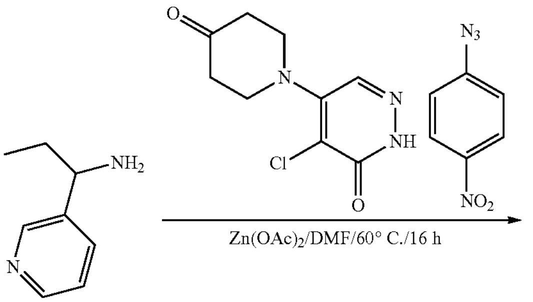

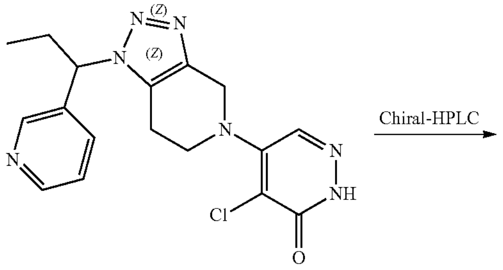

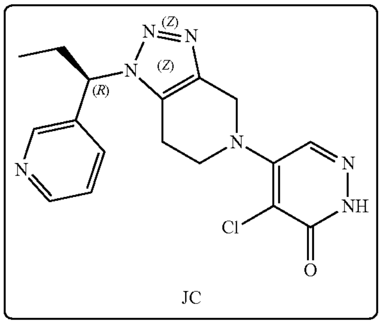

JC

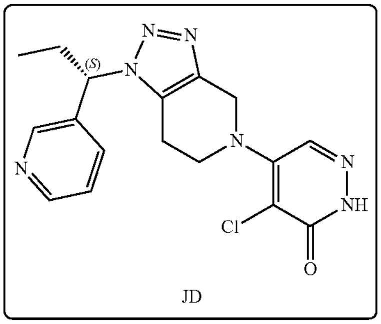

JD

Preparation of JC 4-chloro-5-[1-[(1R)-1-(pyridin-3-yl)propyl]-1H,4H, 5H,6H,7H-[1,2,3]triazolo[4,5-c]pyridin-5-yl]-2,3-dihydropyridazin-3-one To a stirred solution of 1-(pyridin-3-yl)propan-1-amine (355.8 mg, 2.61 mmol, 2.00 equiv.) and 4-chloro-5-(4-oxopiperidin-1-yl)-2,3,4,5-tetrahydropyridazin-3-one (300 mg, 1.31 mmol, 1 equiv.) in DMF (10 mL) were added 1-azido-4-nitrobenzene (300.1 mg, 1.83 mmol, 1.40 equiv.) and Zn(OAc)2 (239.7 mg, 1.31 mmol, 1 equiv.) at room temperature. The solution was stirred at 60 degrees Celsius for 16 h. The resulting mixture was concentrated under reduced pressure. The crude product (200 mg) was purified by Prep-HPLC with the following conditions (Column: XBridge Prep C18 OBD Column 19×150 mm 5 um; Mobile Phase A: Water (10 mmol/L NH4HCO3), Mobile Phase B: ACN; Flow rate: 60 mL/min; Gradient: 23% B to 55% B in 7 min; 254/220 nm; Rt: 6.4 min) to afford 4-chloro-5-[1-[1-(pyridin-3-yl)propyl]-1H,4H,5H,6H,7H-[1,2,3]triazolo[4,5-c]pyridin-5-yl]-2,3-dihydropyridazin-3-one (150 mg, 30.88%) as a colorless oil.

4-chloro-5-[1-[(1S)-1-(pyridin-3-yl)propyl]-1H,4H, 5H,6H,7H-[1,2,3]triazolo[4,5-c]pyridin-5-yl]-2,3-dihydropyridazin-3-one (JD) and 4-chloro-5-[1-[(1R)-1-(pyridin-3-yl)propyl]-1H,4H,5H,6H,7H-[1, 2,3]triazolo[4,5-c]pyridin-5-yl]-2,3-dihydropyridazin-3-one (JC)

The mixture product (150 mg) was purified by PREP CHIRAL HPLC with the following conditions (Column: CHIRALPAK IG, 20*250 mm, 5 um; Mobile Phase A:MTBE (10 mM NH3-MEOH)—HPLC, Mobile Phase B: EtOH—HPLC; Flow rate: 16 mL/min; Gradient: 50 B to 50 B in 19 min; 254/220 nm; RT1:11.653; RT2:15.005) to afford 4-chloro-5-[1-[(1S)-1-(pyridin-3-yl)propyl]-1H,4H, 5H,6H,7H-[1,2,3]triazolo[4,5-c]pyridin-5-yl]-2,3-dihydropyridazin-3-one (46.2 mg) (JD) as a white solid and afford 4-chloro-5-[1-[(1R)-1-(pyridin-3-yl)propyl]-1H,4H,5H,6H, 7H-[1,2,3]triazolo[4,5-c]pyridin-5-yl]-2,3-dihydropyridazin-3-one (40.4 mg) (JC) as an off-white solid.

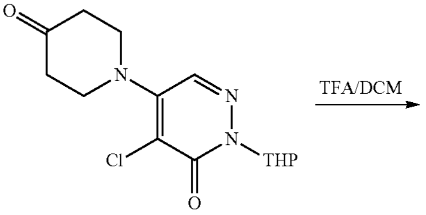

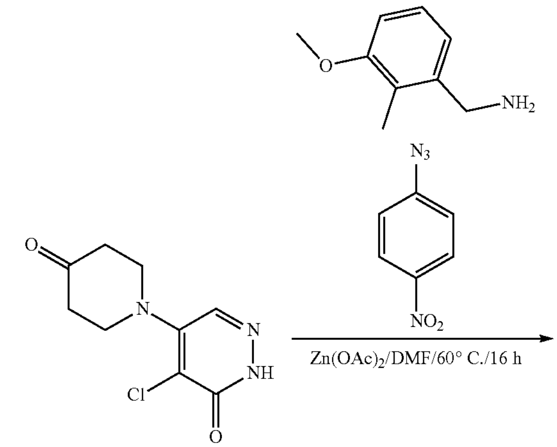

-continued

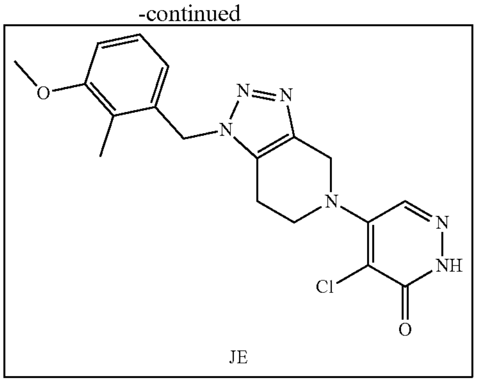

JE

Preparation of JE 4-chloro-5-(4-oxopiperidin-1-yl)pyridazin-3(2H)-one

To a stirred solution of 4-chloro-2-(oxan-2-yl)-5-(4-oxopiperidin-1-yl)-2,3-dihydropyridazin-3-one (4 g, 12.83 mmol, 1 equiv.) in DCM (10 mL, 0.12 mmol) was added 2,2,2-trifluoroacetaldehyde (3 mL, 0.03 mmol) at room temperature. The resulting mixture was stirred for 3 h at 25 degrees Celsius. The resulting mixture was concentrated under reduced pressure. The mixture was basified to pH 8 with NaHCO3 (aq.), extracted and concentrated to give product.

4-chloro-5-[1-[(3-methoxy-2-methylphenyl)methyl]-1H,4H,5H,6H,7H-[1,2,3]triazolo[4,5-c]pyridin-5-yl]-2,3-dihydropyridazin-3-one To a mixture of 4-chloro-5-(4-oxopiperidin-1-yl)-2,3-dihydropyridazin-3-one (100 mg, 0.44 mmol, 1 equiv.), 1-azido-4-nitrobenzene (100.9 mg, 0.61 mmol, 1.40 equiv.) and Zn(OAc)2 (80.6 mg, 0.44 mmol, 1.00 equiv.) in DMF (5 mL) was added 1-(3-methoxy-2-methylphenyl)methanamine (132.8 mg, 0.88 mmol, 2.00 equiv.) at rt. The resulting mixture was stirred for 16 h at 60 degrees Celsius under nitrogen atmosphere. The reaction was monitored by LCMS. The mixture was allowed to cool down to room temperature. The reaction mixture was purified by reverse flash chromatography with the following conditions: column, C18 silica gel; mobile phase, ACN in water, 30% to 50% gradient in 20 min; detector, UV 220 nm. The crude product (100 mg) was purified by Prep-HPLC with the following conditions ( ) to afford 4-chloro-5-[1-[(3-methoxy-2-methylphenyl)methyl]-1H,4H,5H,6H,7H-[1,2,3]triazolo[4,5-c]pyridin-5-yl]-2,3-dihydropyridazin-3-one (43.1 mg, 25.36%) as an off-white solid.

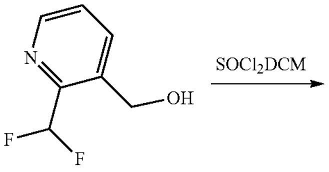

-continued

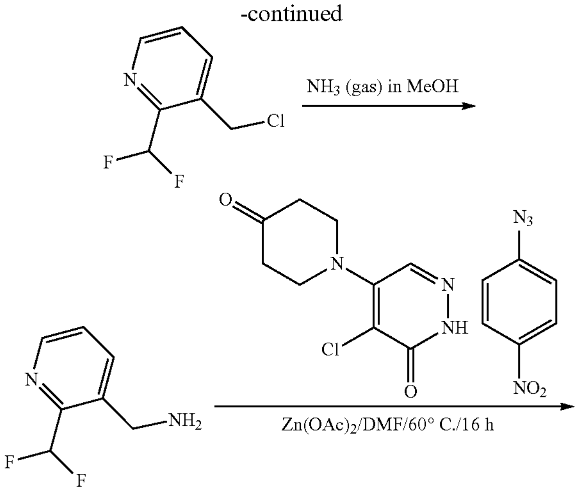

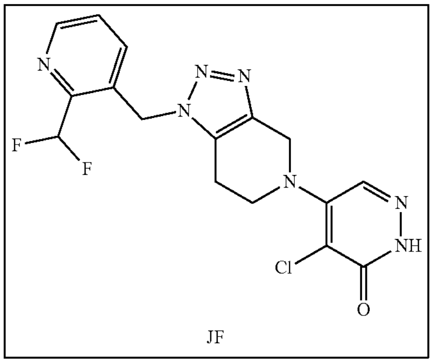

JF

Preparation of JF 3-(chloromethyl)-2-(difluoromethyl)pyridine

To a stirred solution of [2-(difluoromethyl)pyridin-3-yl]methanol (300150 mg, 1886.12 mmol, 1 equiv.) in DCM (20 mL) was added SOCl2 (448.6 mg, 3.77 mmol, 2.00 equiv.) dropwise at 0 degree Celsius. The reaction mixture was stirred for 16 h at rt. The reaction was monitored by LCMS. The resulting mixture was concentrated under reduced pressure. This resulted in 3-(chloromethyl)-2-(difluoromethyl)pyridine (150 mg, 0.04%) as a yellow oil.

1-[2-(difluoromethyl)pyridin-3-yl]methanamine

To a stirred solution of 3-(chloromethyl)-2-(difluoromethyl)pyridine (150 mg, 0.84 mmol, 1 equiv.) in MeOH with NH3(g) at room temperature under nitrogen atmosphere. The resulting mixture was stirred for 4 h at 40 degrees Celsius under nitrogen atmosphere. The reaction was monitored by LCMS. The mixture was allowed to cool down to rt. The resulting mixture was concentrated under reduced pressure. The residue was purified by Prep-TLC (PE/EtOAc=2/1) to afford 1-[2-(difluoromethyl)pyridin-3-yl]methanamine (80 mg, 59.89%) as a yellow oil.

4-chloro-5-(1-[[2-(difluoromethyl)pyridin-3-yl]methyl]-1H,4H,5H,6H,7H-[1,2,3]triazolo[4,5-c]pyridin-5-yl)-2,3-dihydropyridazin-3-one To a stirred mixture of 1-[2-(difluoromethyl)pyridin-3-yl]methanamine (59.7 mg, 0.38 mmol, 2.00 equiv.) and 4-chloro-5-(4-oxopiperidin-1-yl)-2,3-dihydropyridazin-3-one (43 mg, 0.19 mmol, 1 equiv.) in DMF (5 mL) were added 1-azido-4-nitrobenzene (43.4 mg, 0.26 mmol, 1.40 equiv.) and Zn(OAc)2 (34.7 mg, 0.19 mmol, 1.00 equiv.) in portions at room temperature under nitrogen atmosphere. The resulting mixture was stirred for 16 h at 60 degrees Celsius under nitrogen atmosphere. The reaction was monitored by LCMS. The mixture was allowed to cool down to rt. The residue was purified by Prep-HPLC with the following conditions (Column: XBridge Prep C18 OBD Column 19×150 mm 5 um; Mobile Phase A: Water (10 mmol/L NH4HCO3), Mobile Phase B: ACN; Flow rate: 60 mL/min; Gradient: 16% B to 38% B in 7 min; 254/220 nm; Rt: 6.33 min) to afford 4-chloro-5-(1-[[2-(difluoromethyl)pyridin-3-yl]methyl]-1H,4H,5H,6H,7H-[1,2,3]triazolo[4,5-c]pyridin-5-yl)-2,3-dihydropyridazin-3-one (7.1 mg) as a yellow solid.

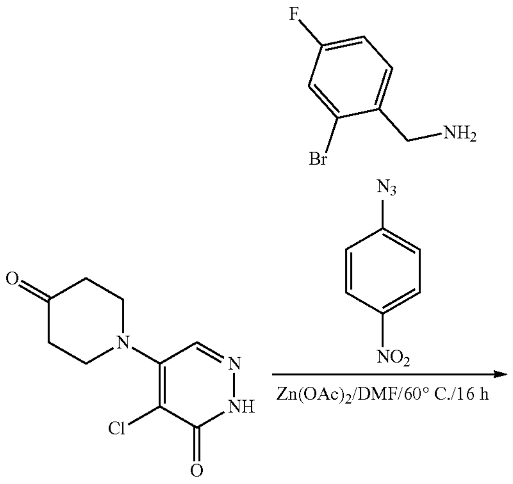

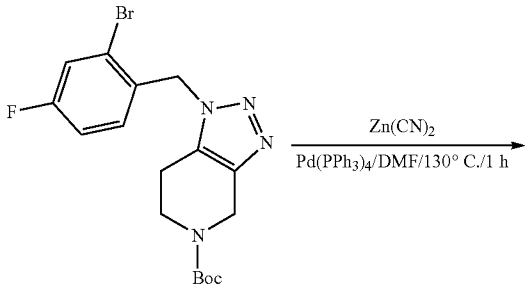

1

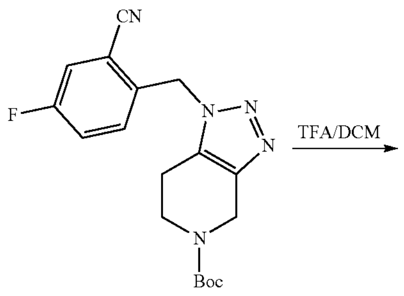

-continued

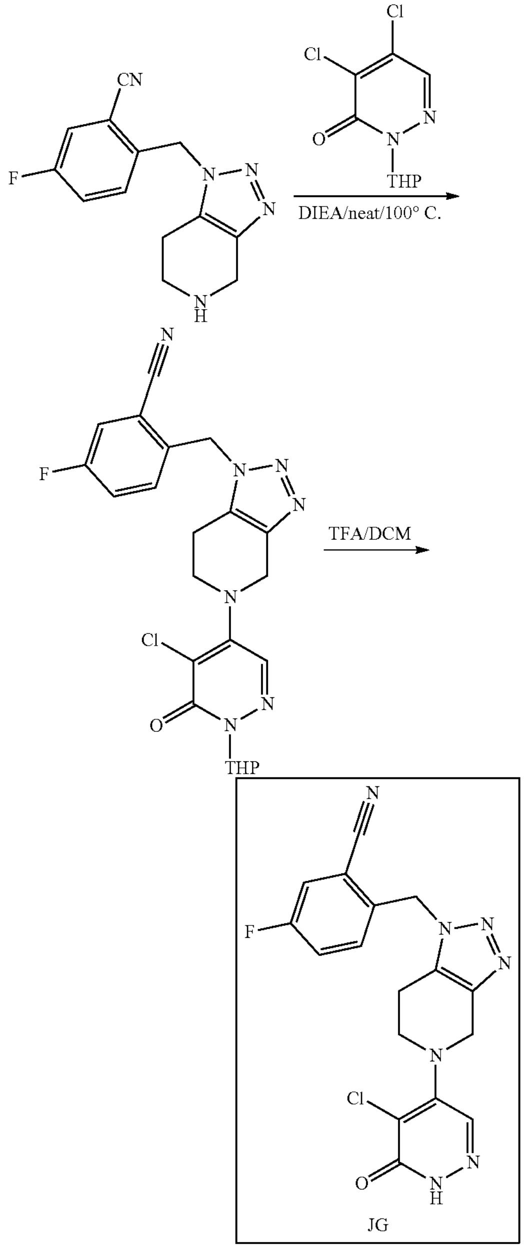

JG

Preparation of JG

Tert-Butyl 1-[(2-cyano-4-fluorophenyl)methyl]-1H,4H,5H,6H,7H-[1,2,3]triazolo[4,5-c]pyridine-5-carboxylate To a stirred mixture of tert-butyl 1-[(2-bromo-4-fluorophenyl)methyl]-1H,4H,5H,6H,7H-[1,2,3]triazolo[4,5-c]pyridine-5-carboxylate (200 mg, 0.49 mmol, 1 equiv.) and Zn(CN)2 (171.3 mg, 1.46 mmol, 3.0 equiv.) in DMF (10 mL) was added Pd(PPh3)4 (56.2 mg, 0.05 mmol, 0.1 equiv.) at room temperature under nitrogen atmosphere. The resulting mixture was stirred for 2 h at 130 degrees Celsius under nitrogen atmosphere. The reaction was monitored by LCMS. The mixture was allowed to cool down to room temperature. The crude product was purified by reverse phase flash with the following conditions (Column: XBridge Shield RP18 OBD Column, 5 um, 19*150 mm; Mobile Phase A: Water (10 mmol/L NH4HCO3), Mobile Phase B: ACN; Flow rate: 20 mL/min; Gradient: 20% B to 45% B in 10 min; 220 nm; Rt: 9.62 min) to afford tert-butyl 1-[(2-cyano-4-fluorophenyl)methyl]-1H,4H,5H,6H,7H-[1,2,3]triazolo[4,5-c]pyridine-5-carboxylate (160 mg, 92.06%) as a yellow solid.

5-fluoro-2-((4,5,6,7-tetrahydro-1H-[1,2,3]triazolo[4,5-c]pyridin-1-yl)methyl)benzonitrile To a stirred solution of tert-butyl 1-[(2-cyano-4-fluorophenyl)methyl]-1H,4H,5H,6H,7H-[1,2,3]triazolo[4,5-c]pyridine-5-carboxylate (170 mg, 0.48 mmol, 1 equiv.) in DCM (10 mL) was added TFA (3 mL, 40.39 mmol, 84.91 equiv.) at room temperature. The resulting mixture was stirred for 2 h at room temperature. The reaction was monitored by LCMS. The resulting mixture was concentrated under vacuum. The crude resulting mixture was used in the next step (E01109-008) directly without further purification.

2-((5-(5-chloro-6-oxo-1-(tetrahydro-2H-pyran-2-yl)-1,6-dihydropyridazin-4-yl)-4,5,6,7-tetrahydro-1H-[1,2,3]triazolo[4,5-c]pyridin-1-yl)methyl)-5-fluorobenzonitrile Into a 25 mL round-bottom flask were added 5-fluoro-2-([1H,4H,5H,6H,7H-[1,2,3]triazolo[4,5-c]pyridin-1-yl]methyl)benzonitrile (120 mg, 0.47 mmol, 1 equiv.) and 4,5-dichloro-2-(oxan-2-yl)-2,3-dihydropyridazin-3-one (139.4 mg, 0.56 mmol, 1.20 equiv.) at room temperature. Then DIEA (144.1 mg, 1.11 mmol, 2.39 equiv.) was added at room temperature. The resulting mixture was stirred for 16 h at 100 degree Celsius. The reaction was monitored by LCMS. The mixture was allowed to cool down to room temperature. The resulting mixture was used in the next step (E01109-009) directly without further purification.

2-[[5-(5-chloro-6-oxo-1,6-dihydropyridazin-4-yl)-1H,4H,5H,6H,7H-[1,2,3]triazolo[4,5-c]pyridin-1-yl]methyl]-5-fluorobenzonitrile To a stirred solution of 2-([5-[5-chloro-1-(oxan-2-yl)-6-oxo-1,6-dihydropyridazin-4-yl]-1H,4H,5H,6H,7H-[1,2,3]triazolo[4,5-c]pyridin-1-yl]methyl)-5-fluorobenzonitrile (100 mg, 0.21 mmol, 1 equiv.) in DCM (10 mL) was added TFA (3 mL, 0.03 mmol, 0.12 equiv.) at room temperature. The resulting mixture was stirred for 2 h at room temperature. The reaction was monitored by LCMS. The resulting mixture was concentrated under reduced pressure. The crude product (100 mg) was purified by Prep-HPLC with the following conditions (Column: XBridge Shield RP18 OBD Column 30*150 mm, 5 um; Mobile Phase A: Water (10 mmol/L NH4HCO3), Mobile Phase B: ACN; Flow rate: 60 mL/min; Gradient: 15% B to 35% B in 7 min; 220 nm; Rt: 6.35 min) to afford 2-[[5-(5-chloro-6-oxo-1,6-dihydropyridazin-4-yl)-1H,4H,5H,6H,7H-[1,2,3]triazolo[4,5-c]pyridin-1-yl]methyl]-5-fluorobenzonitrile (55.7 mg, 67.85%) as a white solid.

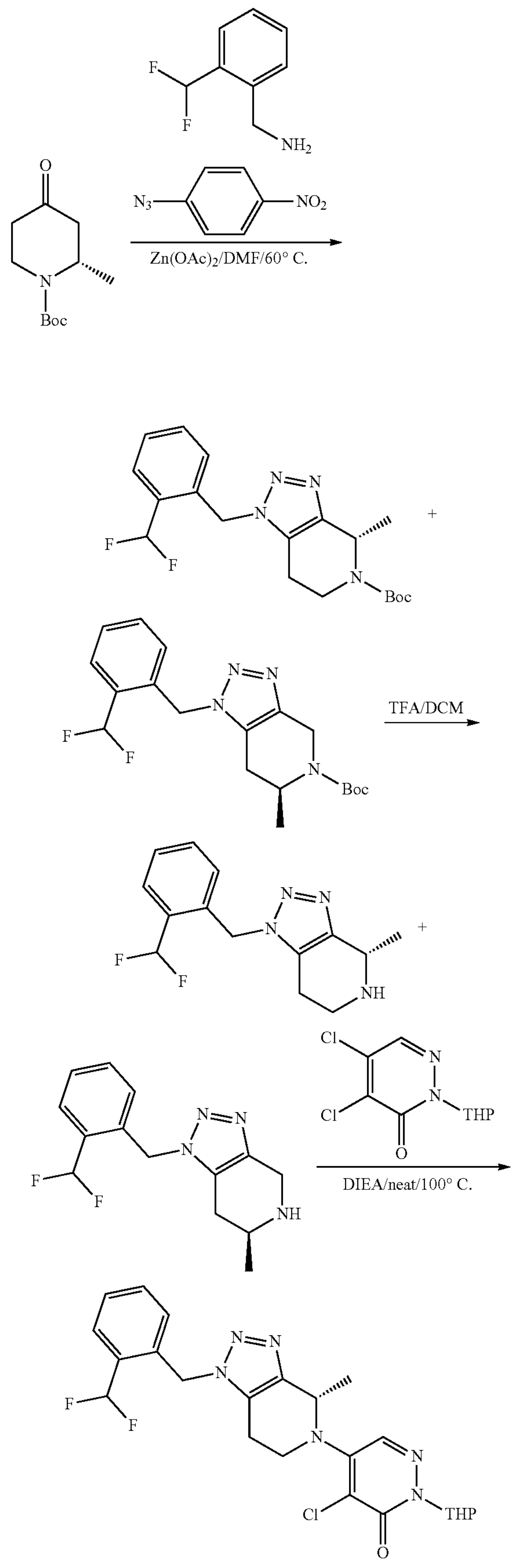

-continued

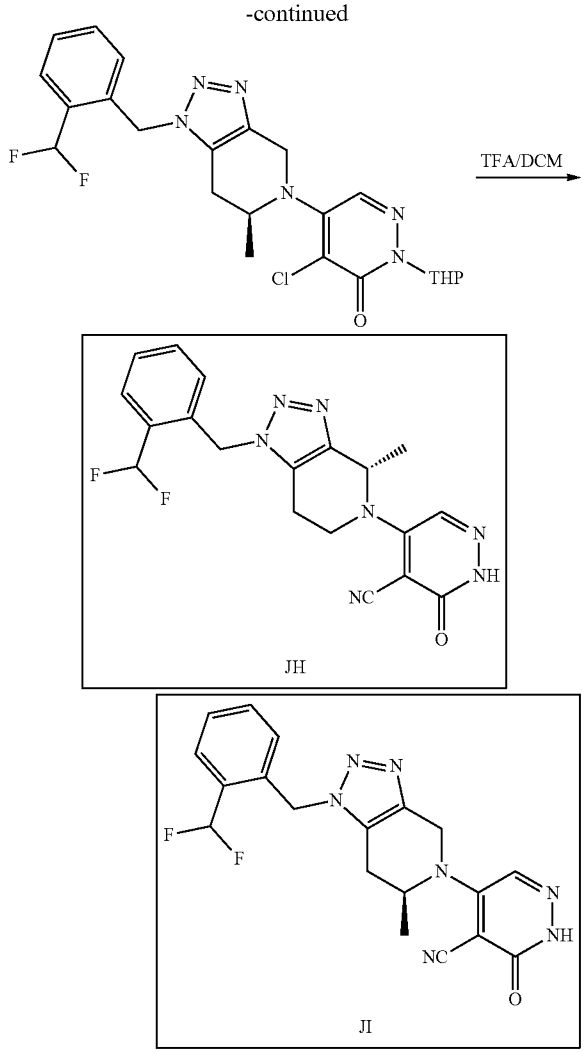

JH

JI

Preparation of JH and JI

Tert-Butyl (S)-1-[[2-(difluoromethyl)phenyl]methyl]-4-methyl-1H,4H,5H,6H,7H-[1,2,3]triazolo[4,5-c]pyridine-5-carboxylate and tert-butyl (S)-1-[[2-(difluoromethyl)phenyl]methyl]-6-methyl-1H,4H,5H,6H,7H-[1,2,3]triazolo[4,5-c]pyridine-5-carboxylate To a stirred mixture of tert-butyl (2S)-2-methyl-4-oxopiperidine-1-carboxylate (1 g, 4.69 mmol, 1 equiv.) and 1-azido-4-nitrobenzene (1.5 g, 9.38 mmol, 2.0 equiv.) in DMF (25 mL) were added 1-[2-(difluoromethyl)phenyl]methanamine (1.0 g, 6.56 mmol, 1.4 equiv.) and Zn(OAc)2 (0.9 g, 4.69 mmol, 1.0 equiv.) at room temperature. The resulting mixture was stirred for 24 h at 60 degrees Celsius. The reaction was monitored by LCMS. The crude product was purified by reverse phase flash with the following conditions (Column: XBridge Shield RP18 OBD Column 30*150 mm, 5 um; Mobile Phase A: Water (10 mmol/L NH4HCO3), Mobile Phase B: ACN; Flow rate: 60 mL/min; Gradient: 5% B to 35% B in 14 min; 254 nm; Rt: 13.5 min) to afford tert-butyl (S)-1-[[2-(difluoromethyl)phenyl]methyl]-4-methyl-1H,4H,5H,6H,7H-[1,2,3]triazolo[4,5-c]pyridine-5-carboxylate and afford tert-butyl (S)-1-[[2-(difluoromethyl)phenyl]methyl]-6-methyl-1H,4H,5H,6H,7H-[1,2,3]triazolo[4,5-c]pyridine-5-carboxylate (1.6 g, 90.17%) as a brown oil.

(S)-1-[[2-(difluoromethyl)phenyl]methyl]-4-methyl-1H,4H,5H,6H,7H-[1,2,3]triazolo[4,5-c]pyridine and (S)-3-[[2-(difluoromethyl)phenyl]methyl]-6-methyl-3H,4H,5H,6H,7H-[1,2,3]triazolo[4,5-c]pyridine To a stirred solution of (S)-1-[[2-(difluoromethyl)phenyl]methyl]-4-methyl-1H,4H,5H,6H,7H-[1,2,3]triazolo[4,5-c]pyridine (500 mg, 1.32 mmol, 1 equiv.) in DCM (10 mL, 157.30 mmol, 119.05 equiv.) was added TFA (3 mL, 40.39 mmol, 30.57 equiv.) at room temperature. The resulting mixture was stirred for 2 h at room temperature. The reaction was monitored by LCMS. The resulting mixture was concentrated under reduced pressure. The mixture was basified to pH 8 with saturated NaHCO3 (aq.). The crude product was purified by reverse phase flash with the following conditions (Column: XBridge Prep C18 OBD Column, 5 um, 19*150 mm; Mobile Phase A: Water (10 mmol/L NH4HCO3), Mobile Phase B: ACN; Flow rate: 20 mL/min; Gradient: 30% B to 46% B in 7 min; 220/254 nm; Rt: 6.27 min) to afford a mixture of (S)-1-[[2-(difluoromethyl)phenyl]methyl]-4-methyl-1H,4H,5H,6H,7H-[1,2,3]triazolo[4,5-c]pyridine (140 mg, 38.07%) as a brown oil and (S)-3-[[2-(difluoromethyl)phenyl]methyl]-6-methyl-3H,4H,5H,6H,7H-[1,2,3]triazolo[4,5-c]pyridine (100 mg, 27.19%) was obtained is a similar way as a brown oil.

4-chloro-5-[(4S)-1-[[2-(difluoromethyl)phenyl]methyl]-4-methyl-1H,4H,5H,6H,7H-[1,2,3]triazolo[4,5-c]pyridin-5-yl]-2-(oxan-2-yl)-2,3-dihydropyridazin-3-one and 4-chloro-5-[(6S)-1-[[2-(difluoromethyl)phenyl]methyl]-6-methyl-1H,4H,5H,6H,7H-[1,2,3]triazolo[4,5-c]pyridin-5-yl]-2-(oxan-2-yl)-2,3-dihydropyridazin-3-one Into a 50 mL round-bottom flask were added (4S)-1-[[2-(difluoromethyl)phenyl]methyl]-4-methyl-1H,4H,5H,6H,7H-[1,2,3]triazolo[4,5-c]pyridine (240 mg, 0.86 mmol, 1 equiv.) DIEA (260 mg, 2.01 mmol, 2.33 equiv.) and 4,5-dichloro-2-(oxan-2-yl)-2,3-dihydropyridazin-3-one (257.8 mg, 1.03 mmol, 1.2 equiv.) at room temperature. The resulting mixture was stirred for 16 h at 100 degrees Celsius. The reaction was monitored by LCMS. The mixture was allowed to cool down to room temperature. The residue was purified by Prep-TLC (PE/EtOAc 1:1) to afford 4-chloro-5-[(4S)-1-[[2-(difluoromethyl)phenyl]methyl]-4-methyl-1H,4H,5H,6H,7H-[1,2,3]triazolo[4,5-c]pyridin-5-yl]-2-(oxan-2-yl)-2,3-dihydropyridazin-3-one (160 mg, 37.79%) as a brown oil and 4-chloro-5-[(6S)-1-[[2-(difluoromethyl)phenyl]methyl]-6-methyl-1H,4H,5H,6H,7H-[1,2,3]triazolo[4,5-c]pyridin-5-yl]-2-(oxan-2-yl)-2,3-dihydropyridazin-3-one (100 mg, 23.62%) was obtained in a similar way as a brown oil.

4-chloro-5-[(4S)-1-[[2-(difluoromethyl)phenyl]methyl]-4-methyl-1H,4H,5H,6H,7H-[1,2,3]triazolo[4,5-c]pyridin-5-yl]-2,3-dihydropyridazin-3-one and 4-chloro-5-[(6S)-1-[[2-(difluoromethyl)phenyl]methyl]-6-methyl-1H,4H,5H,6H,7H-[1,2,3]triazolo[4,5-c]pyridin-5-yl]-2,3-dihydropyridazin-3-one To a stirred solution of 4-chloro-5-[(4S)-1-[[2-(difluoromethyl)phenyl]methyl]-4-methyl-1H,4H,5H,6H,7H-[1,2, 3]triazolo[4,5-c]pyridin-5-yl]-2-(oxan-2-yl)-2,3-dihydropyridazin-3-one (200 mg, 0.41 mmol, 1 equiv.) in DCM (10 mL) was added TFA (3 mL, 40.39 mmol, 198.29 equiv.) at room temperature. The resulting mixture was stirred for 2 h at room temperature. The reaction was monitored by LCMS. The resulting mixture was concentrated under reduced pressure. The crude product (150 mg) was purified by Prep-HPLC with the following conditions (Column: XBridge Prep C18 OBD Column 19×150 mm 5 um; Mobile Phase A: Water (10 mmol/L NH4HCO3), Mobile Phase B: ACN; Flow rate: 20 mL/min; Gradient: 26% B to 46% B in 7 min; 220/254 nm; Rt: 5.9 min) to afford 4-chloro-5-[(4S)-1-[[2-(difluoromethyl)phenyl]methyl]-4-methyl-1H,4H,5H,6H,7H-[1,2,3]triazolo[4,5-c]pyridin-5-yl]-2,3-dihydropyridazin-3-one (74 mg, 89.30%) as a white solid and 4-chloro-5-[(6S)-1-[[2-(difluoromethyl)phenyl]methyl]-6-methyl-1H,4H,5H,6H,7H-[1,2,3]triazolo[4,5-c]pyridin-5-yl]-2,3-dihydropyridazin-3-one (54.5 mg, 65.77%) was obtained as a white solid.

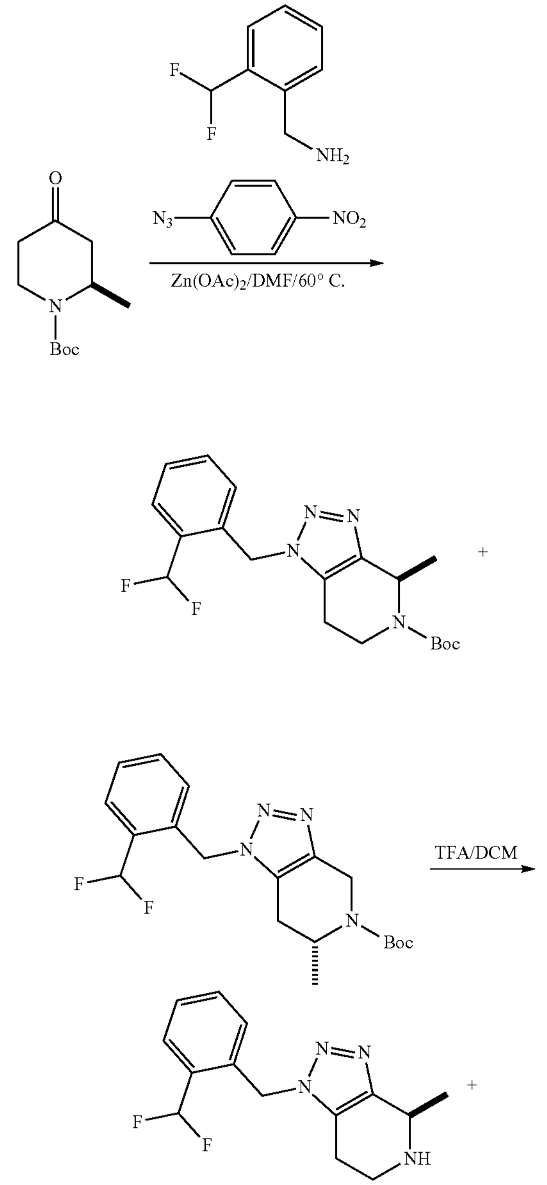

-continued

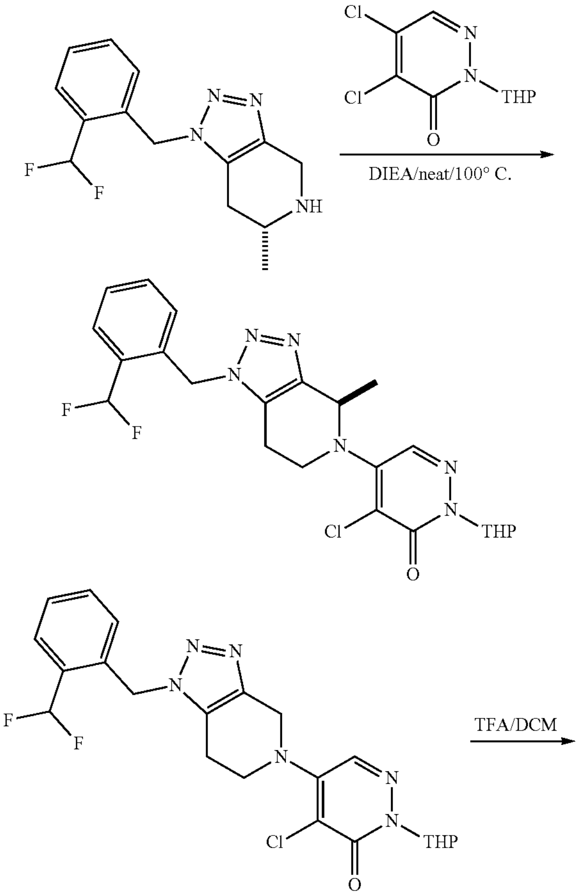

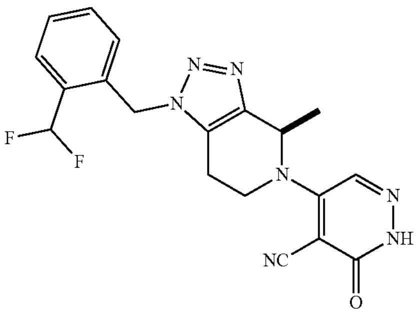

JJ

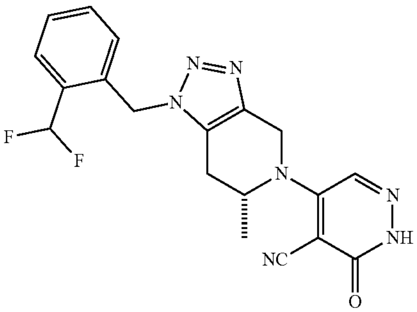

JK

JJ and JK were prepared by the methods and scheme described for JH and JI by using tert-butyl (R)-2-methyl-4-oxopiperdine-1-carboxylate

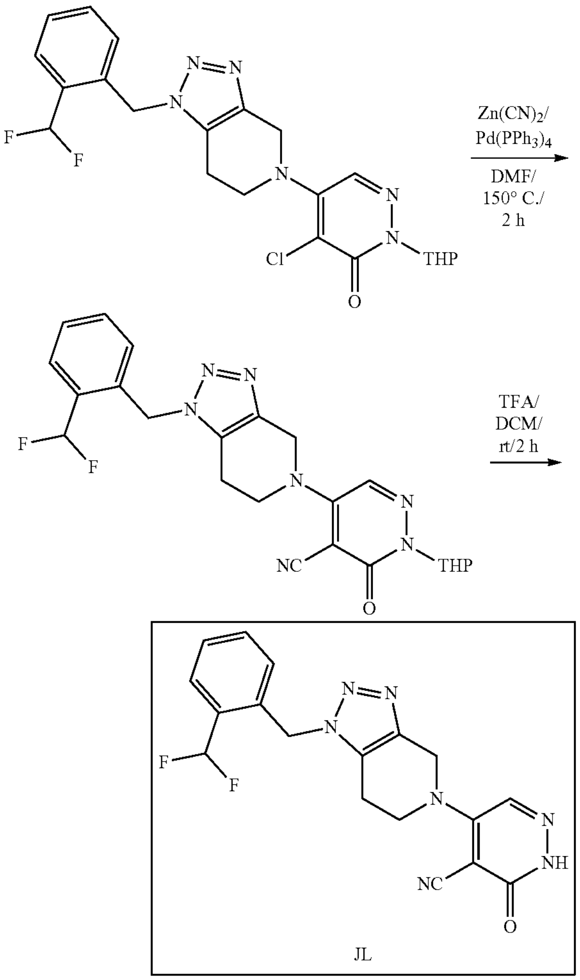

JL

Preparation of JL

Afford 5-(1-[[2-(difluoromethyl)phenyl]methyl]-1H,4H,5H,6H,7H-[1,2,3]triazolo[4,5-c]pyridin-5-yl)-2-(oxan-2-yl)-3-oxo-2,3-dihydropyridazine-4-carbonitrile To a stirred mixture of 4-chloro-5-(1-[[2-(difluoromethyl)phenyl]methyl]-1H,4H,5H,6H,7H-[1,2,3]triazolo[4,5-c]pyridin-5-yl)-2-(oxan-2-yl)-2,3-dihydropyridazin-3-one (600 mg, 1.26 mmol, 1 equiv.) and Zn(CN)2 (443.3 mg, 3.77 mmol, 3.00 equiv.) in DMF (10 mL) was added Pd(PPh3)4 (145.4 mg, 0.13 mmol, 0.1 equiv.) at room temperature under nitrogen atmosphere. The resulting mixture was stirred for 2 h at 150 degrees Celsius under nitrogen atmosphere. The reaction was monitored by LCMS. The mixture was allowed to cool down to room temperature. The crude product was purified by reverse phase flash with the following conditions (Column: XBridge Shield RP18 OBD Column, 5 um, 19*150 mm; Mobile Phase A: Water (10 mmol/L NH4HCO3), Mobile Phase B: ACN; Flow rate: 20 mL/min; Gradient: 20% B to 55% B in 7 min; 220 nm; Rt: 5.72 min) to afford 5-(1-[[2-(difluoromethyl)phenyl]methyl]-1H,4H,5H,6H,7H-[1,2,3]triazolo[4,5-c]pyridin-5-yl)-2-(oxan-2-yl)-3-oxo-2,3-dihydropyridazine-4-carbonitrile (100 mg, crude) as a white solid.

5-(1-[[2-(difluoromethyl)phenyl]methyl]-1H,4H,5H,6H,7H-[1,2,3]triazolo[4,5-c]pyridin-5-yl)-3-oxo-2,3-dihydropyridazine-4-carbonitrile To a stirred solution of TFA (2 mL, 26.93 mmol, 125.87 equiv.) in DCM (5 mL) was added 5-(1-[[2-(difluoromethyl)phenyl]methyl]-1H,4H,5H,6H,7H-[1,2,3]triazolo[4,5-c]pyridin-5-yl)-2-(oxan-2-yl)-3-oxo-2,3-dihydropyridazine-4-carbonitrile (100 mg, 0.21 mmol, 1 equiv.) at room temperature under nitrogen atmosphere. The resulting mixture was stirred for 2 h at room temperature. The reaction was monitored by LCMS. The resulting mixture was concentrated under reduced pressure. The mixture was basified to pH 8 with saturated NaHCO3 (aq.). The crude product (100 mg) was purified by Prep-HPLC with the following conditions (Column: XBridge Shield RP18 OBD Column 30*150 mm, 5 um; Mobile Phase A: Water (10 mmol/L NH4HCO3), Mobile Phase B: ACN; Flow rate: 60 mL/min; Gradient: 5% B to 35% B in 14 min; 254 nm; Rt: 13.5 min) to afford 5-(1-[[2-(difluoromethyl)phenyl]methyl]-1H,4H,5H,6H,7H-[1,2,3]triazolo[4,5-c]pyridin-5-yl)-3-oxo-2,3-dihydropyridazine-4-carbonitrile (22.1 mg, 26.95%) as a white solid.

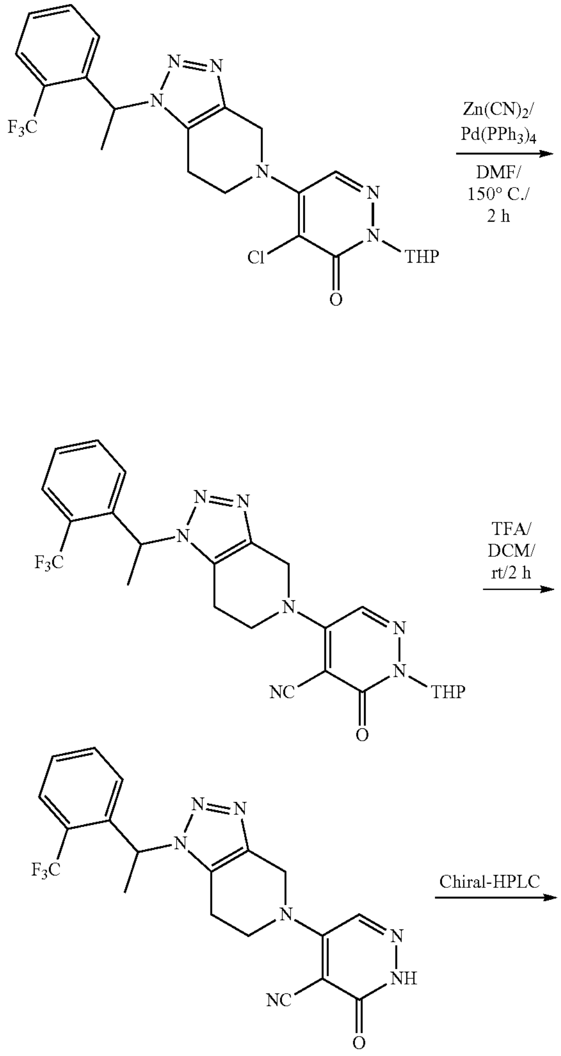

-continued

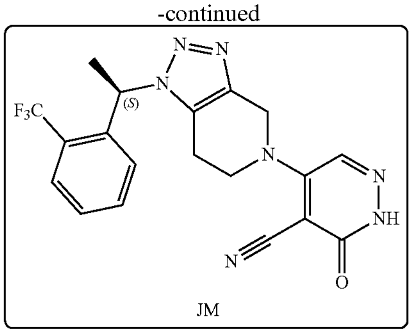

JM

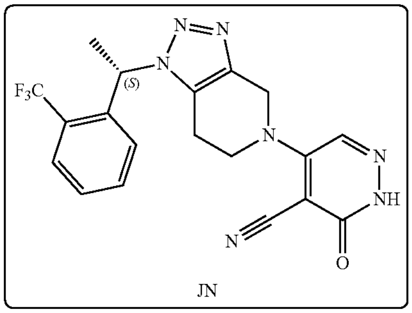

JN

Preparation of JM and JN 2-(oxan-2-yl)-3-oxo-5-(1-[1-[2-(trifluoromethyl) phenyl]ethyl]-1H,4H,5H,6H,7H-[1,2,3]triazolo[4,5-c]pyridin-5-yl)-2,3-dihydropyridazine-4-carbonitrile To a stirred mixture of 4-chloro-5-(1-[1-[2-(trifluoromethyl)phenyl]ethyl]-1H,4H,5H,6H,7H-[1,2,3]triazolo[4,5-c] pyridin-5-yl)-2,3-dihydropyridazin-3-one (300 mg, 0.71 mmol, 1 equiv.) and Zn(CN)2 (248.8 mg, 2.12 mmol, 3.0 equiv.) in DMF (10 mL) was added Pd(PPh3)4 (81.6 mg, 0.07 mmol, 0.1 equiv.) at room temperature under nitrogen atmosphere. The resulting mixture was stirred for 2 h at 150 degrees Celsius under nitrogen atmosphere. The reaction was monitored by LCMS. The mixture was allowed to cool down to room temperature. The crude product was purified by reverse phase flash with the following conditions (Column: XBridge Shield RP18 OBD Column, 5 um, 19*150 mm; Mobile Phase A: Water (10 mmol/L NH4HCO3), Mobile Phase B: ACN; Flow rate: 20 mL/min; Gradient: 20% B to 55% B in 7 min; 220 nm; Rt: 5.72 min) to afford 2-(oxan-2-yl)-3-oxo-5-(1-[1-[2-(trifluoromethyl)phenyl] ethyl]-1H,4H,5H,6H,7H-[1,2,3]triazolo[4,5-c]pyridin-5-yl)-2,3-dihydropyridazine-4-carbonitrile (180 mg, 51.03%) as a brown solid.

3-oxo-5-[1-[(1R)-1-[2-(trifluoromethyl)phenyl] ethyl]-1H,4H,5H,6H,7H-[1,2,3]triazolo[4,5-c]pyridin-5-yl]-2,3-dihydropyridazine-4-carbonitrile (21.6 mg, 25.97%) and 3-oxo-5-[1-[(1S)-1-[2-(trifluoromethyl)phenyl]ethyl]-1H,4H,5H,6H,7H-[1,2,3]triazolo [4,5-c]pyridin-5-yl]-2,3-dihydropyridazine-4-carbonitrile To a stirred solution of 2-(oxan-2-yl)-3-oxo-5-(1-[1-[2-(trifluoromethyl)phenyl]ethyl]-1H,4H,5H,6H,7H-[1,2,3]triazolo[4,5-c]pyridin-5-yl)-2,3-dihydropyridazine-4-carbonitrile (100 mg, 0.20 mmol, 1 equiv.) in DCM (10 mL) was added TFA (3 mL, 40.39 mmol, 201.74 equiv.) at room temperature. The resulting mixture was stirred for 2 h at room temperature. The reaction was monitored by LCMS. The crude product (100 mg) was purified by Prep-HPLC with the following conditions (Column: XBridge Shield RP18 OBD Column, 5 um, 19*150 mm; Mobile Phase A: Water (10 mmol/L NH4HCO3), Mobile Phase B: ACN; Flow rate: 20 mL/min; Gradient: 20% B to 45% B in 10 min; 220 nm; Rt: 9.62 min) to afford 3-oxo-5-[1-[(1R)-1-[2-(trifluoromethyl)phenyl]ethyl]-1H,4H,5H,6H,7H-[1,2,3]triazolo[4,5-c]pyridin-5-yl]-2,3-dihydropyridazine-4-carbonitrile (21.6 mg, 25.97%) as a white solid and 3-oxo-5-[1-[(1S)-1-[2-(trifluoromethyl)phenyl]ethyl]-1H,4H,5H,6H, 7H-[1,2,3]triazolo[4,5-c]pyridin-5-yl]-2,3-dihydropyridazine-4-carbonitrile (21.0 mg, 25.25%) as a white solid.

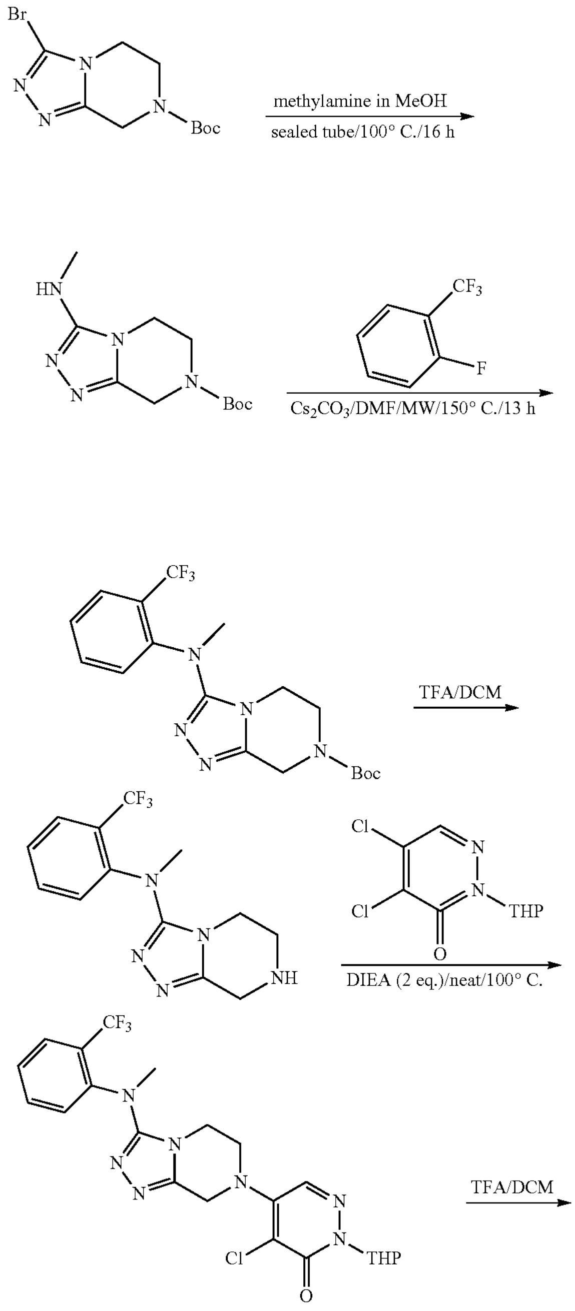

-continued

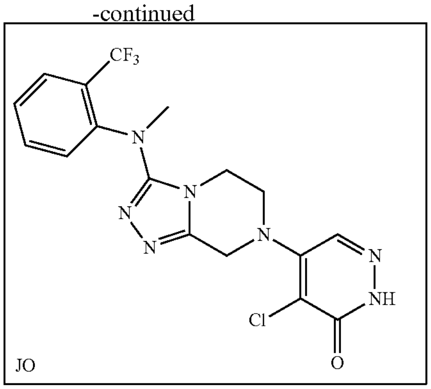

Preparation of JO

Tert-Butyl 3-(methylamino)-5H,6H,7H,8H-[1,2,4]triazolo[4,3-a]pyrazine-7-carboxylate A solution of tert-butyl 3-bromo-5H,6H,7H,8H-[1,2,4]triazolo[4,3-a]pyrazine-7-carboxylate (1 g, 3.30 mmol, 1 equiv.) in CH3NH2 (in EtOH) (7 mL) was stirred for 20 h at 100 degree Celsius. The reaction was monitored by LCMS. The mixture was allowed to cool down to room temperature. The resulting mixture was concentrated under reduced pressure. The residue was purified by reverse phase flash with the following conditions (Column: C18 Column 120 g; Mobile Phase A: Water (10 mmol/L AcOH), Mobile Phase B: ACN; Flow rate: 50 mL/min; Gradient: 20% B to 50% B in 40 min; 254/220 nm) to afford tert-butyl 3-(methylamino)-5H,6H,7H,8H-[1,2,4]triazolo[4,3-a]pyrazine-7-carboxylate (550 mg, 65.82%) as a off-white solid.

Tert-Butyl 3-[methyl[2-(trifluoromethyl)phenyl]amino]-5H,6H,7H,8H-[1,2,4]triazolo[4,3-a]pyrazine-7-carboxylate To a stirred solution of tert-butyl 3-(methylamino)-5H,6H,7H,8H-[1,2,4]triazolo[4,3-a]pyrazine-7-carboxylate (400 mg, 1.58 mmol, 1 equiv.) in DMF (5 mL) were added 1-fluoro-2-(trifluoromethyl)benzene (388.7 mg, 2.37 mmol, 1.50 equiv.) and Cs2CO3 (1029.0 mg, 3.16 mmol, 2 equiv.) at room temperature. The final reaction mixture was irradiated with microwave radiation for 13 h at 150 degrees Celsius. The mixture was allowed to cool down to room temperature. The reaction was monitored by LCMS. To the above mixture was added brine (100 mL). The resulting mixture was extracted with EtOAc (3×100 mL). The combined organic layers were washed with brine (1×100 mL), dried over anhydrous Na2SO4. After filtration, the filtrate was concentrated under reduced pressure. The residue was purified by reverse phase flash with the following conditions (Column: C18 Column 80 g; Mobile Phase A: Water (10 mmol/L AcOH), Mobile Phase B: ACN; Flow rate: 50 mL/min; Gradient: 30% B to 50% B in 40 min; 254/220 nm) to afford tert-butyl 3-[methyl[2-(trifluoromethyl)phenyl]amino]-5H,6H,7H,8H-[1,2,4]triazolo[4,3-a]pyrazine-7-carboxylate (45 mg, 7.17%) as a yellow solid.

N-methyl-N-[2-(trifluoromethyl)phenyl]-5H,6H,7H,8H-[1,2,4]triazolo[4,3-a]pyrazin-3-amine To a stirred solution of tert-butyl 3-[methyl[2-(trifluoromethyl)phenyl]amino]-5H,6H,7H,8H-[1,2,4]triazolo[4,3-a]pyrazine-7-carboxylate (45 mg, 0.11 mmol, 1 equiv.) in DCM (4.5 mL, 70.79 mmol, 625.12 equiv.) was added TFA (0.5 mL, 6.73 mmol, 59.45 equiv.) at room temperature. The reaction was monitored by LCMS. The resulting mixture was concentrated under reduced pressure. The residue was basified to pH 8 with saturated NaHCO3 (aq.). The resulting mixture was extracted with EtOAc (3×20 mL). The combined organic layers were washed with brine (1×10 mL), dried over anhydrous Na2SO4. After filtration, the filtrate was concentrated under reduced pressure. The residue was purified by reverse phase flash with the following conditions (Column: C18 Column 80 g; Mobile Phase A: Water (10 mmol/L NH4HCO3), Mobile Phase B: ACN; Flow rate: 50 mL/min; Gradient: 10% B to 30% B in 40 min; 254/220 nm) to afford N-methyl-N-[2-(trifluoromethyl)phenyl]-5H,6H,7H,8H-[1,2,4]triazolo[4,3-a]pyrazin-3-amine (30 mg, 89.12%) as a yellow oil.

4-chloro-5-(3-[methyl[2-(trifluoromethyl)phenyl]amino]-5H,6H,7H,8H-[1,2,4]triazolo[4,3-a]pyrazin-7-yl)-2-(oxan-2-yl)-2,3-dihydropyridazin-3-one Into a 25 mL sealed tube were added N-methyl-N-[2-(trifluoromethyl)phenyl]-5H,6H,7H,8H-[1,2,4]triazolo[4,3-a]pyrazin-3-amine (30 mg, 0.10 mmol, 1 equiv.), 4,5-dichloro-2-(oxan-2-yl)-2,3-dihydropyridazin-3-one (50.3 mg, 0.20 mmol, 2.00 equiv.) and DIEA (26.1 mg, 0.20 mmol, 2 equiv.) at room temperature. The resulting mixture was stirred for 2 h at 100 degrees Celsius. The reaction was monitored by LCMS. The mixture was allowed to cool down to room temperature. The mixture was purified by reverse phase flash with the following conditions (Column: C18 Column 80 g; Mobile Phase A: Water (10 mmol/L NH4HCO3), Mobile Phase B: ACN; Flow rate: 50 mL/min; Gradient: 10% B to 35% B in 40 min; 254/220 nm) to afford 4-chloro-5-(3-[methyl[2-(trifluoromethyl)phenyl]amino]-5H,6H,7H,8H-[1,2,4]triazolo[4,3-a]pyrazin-7-yl)-2-(oxan-2-yl)-2,3-dihydropyridazin-3-one (20 mg, 38.87%) as a yellow oil.

4-chloro-5-(3-[methyl[2-(trifluoromethyl)phenyl]amino]-5H,6H,7H,8H-[1,2,4]triazolo[4,3-a]pyrazin-7-yl)-2,3-dihydropyridazin-3-one To a stirred solution of 4-chloro-5-(3-[methyl[2-(trifluoromethyl)phenyl]amino]-5H,6H,7H,8H-[1,2,4]triazolo[4,3-a]pyrazin-7-yl)-2-(oxan-2-yl)-2,3-dihydropyridazin-3-one (35 mg, 0.07 mmol, 1 equiv.) in DCM (4.5 mL) was added TFA (0.5 mL, 6.73 mmol, 98.07 equiv.) at room temperature. The resulting mixture was stirred for 2 h at room temperature. The reaction was monitored by LCMS. The resulting mixture was concentrated under reduced pressure. The residue was purified by reverse phase flash with the following conditions (Column: C18 Column 40 g; Mobile Phase A: Water (10 mmol/L NH4HCO3), Mobile Phase B: ACN; Flow rate: 40 mL/min; Gradient: 40% B to 60% B in 40 min; 254/220 nm) to afford 4-chloro-5-(3-[methyl[2-(trifluoromethyl)phenyl]amino]-5H,6H,7H,8H-[1,2,4]triazolo[4,3-a]pyrazin-7-yl)-2,3-dihydropyridazin-3-one (20 mg, 68.43%) as an off-white solid.

Compounds LN and LO

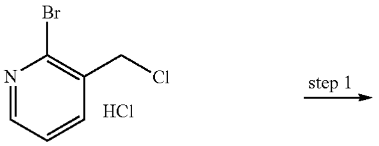

-continued

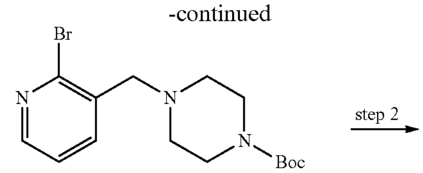

1

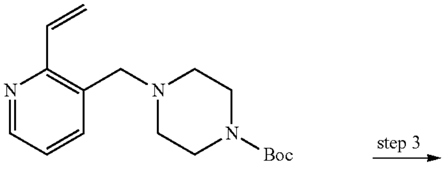

2

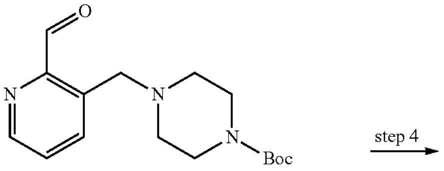

3

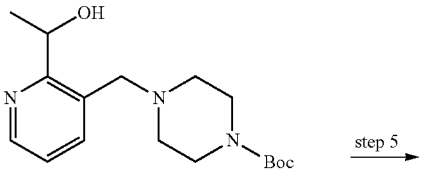

4

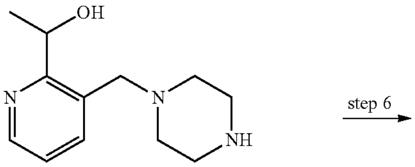

5

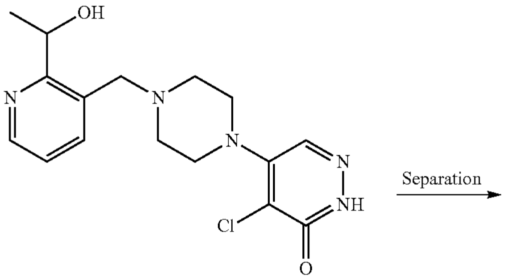

6

-continued

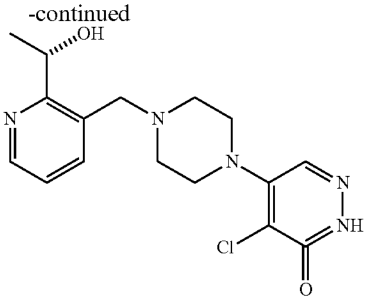

LN

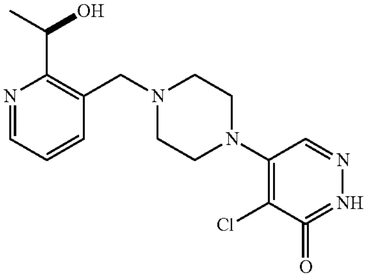

LO 2-bromo-3-(chloromethyl)pyridine

To a stirred mixture of (2-bromopyridin-3-yl)methanol (20 g, 106.37 mmol, 1 equiv.) and DIEA (27.5 g, 212.78 mmol, 2.00 equiv.) in DCM (100 mL) was added SOCl2 (38.0 g, 319.11 mmol, 3 equiv.) dropwise at 0 degrees C. The resulting mixture was stirred for 3 h at room temperature. The reaction was monitored by TLC (PE/EA=1/1). The resulting mixture was concentrated under reduced pressure. The resulting mixture was washed with 3×200 mL of EtOAc. The resulting solution was concentrated under reduced pressure to afford 2-bromo-3-(chloromethyl)pyridine (26 g, 118.39%) as a white solid.

Step 1

Tert-Butyl 4-[(2-bromopyridin-3-yl)methyl]piperazine-1-carboxylate

To a stirred mixture of 2-bromo-3-(chloromethyl)pyridine (5 g, 24.22 mmol, 1 equiv.) and tert-butyl piperazine-1-carboxylate (4.5 g, 24.22 mmol, 1 equiv.) in DCM (20 mL) was added DIEA (6.3 g, 48.75 mmol, 2.01 equiv.) dropwise at room temperature. The resulting mixture was stirred for 16 h at room temperature. The reaction was monitored by LCMS. The resulting mixture was concentrated under reduced pressure. The residue was purified by silica gel column chromatography, eluted with CH2Cl2/MeOH (50/1 to 30/1) to afford tert-butyl 4-[(2-bromopyridin-3-yl)methyl]piperazine-1-carboxylate (7 g, 81.14%) as a light yellow oil. Shimadzu LCMS2020, LC20ADXR, Column:Kinetex EVO, 3.0*50 mm, 2.6 um; Mobile phaseA:H2O 5 mM NH4HCO3, Mobile phaseB:Acetonitrile; Flow rate: 1.2 mL/min; Gradient:10% B to 95% B in 2.1 min, hold 0.5 min; Oven temp.:40 C Step 2

Tert-Butyl 4-[(2-ethenylpyridin-3-yl)methyl]piperazine-1-carboxylate

To a stirred mixture of tert-butyl 4-[(2-bromopyridin-3-yl)methyl]piperazine-1-carboxylate (4 g, 11.23 mmol, 1 equiv.) and 3-ethenyl-1,5-dimethyl-2,4-dioxa-3-borabicyclo [3.1.0]hexane (1.5 g, 11.23 mmol, 1 equiv.) in dioxane (40 mL) and H2O (8 mL) were added K2CO3 (4.7 g, 33.68 mmol, 3 equiv.) and Pd(PPh3)4 (648.7 mg, 0.56 mmol, 0.05 equiv.) at rt under nitrogen atmosphere. The resulting mixture was stirred for 16 h at 90 degrees C. under nitrogen atmosphere. The reaction was monitored by LCMS. The mixture was allowed to cool down to room temperature. The resulting mixture was concentrated under reduced pressure. The resulting mixture was extracted with EtOAc (3×300 mL). The combined organic layers were washed with brine (3×300 mL), dried over anhydrous Na2SO4. After filtration, the filtrate was concentrated under reduced pressure. The residue was purified by silica gel column chromatography, eluted with CH2Cl2/MeOH (80/1 to 20/1) to afford tert-butyl 4-[(2-ethenylpyridin-3-yl)methyl]piperazine-1-carboxylate (3.2 g, 93.94%) as a light yellow oil. Shimadzu LCMS2020, LC20ADXR, Column:Poroshell HPH-C18, 3.0*50 mm, 2.7 um; Mobile phaseA:H2O 5 mM NH4HCO3, Mobile phaseB:Acetonitrile; Flow rate: 1.2 mL/min; Gradient:10% B to 95% B in 2.1 min, hold 0.5 min; Oven temp.:40 C Step 3

Tert-Butyl 4-[(2-formylpyridin-3-yl)methyl]piperazine-1-carboxylate

To a solution of tert-butyl 4-[[2-(hydroxymethyl)pyridin-3-yl]methyl]piperazine-1-carboxylate (300 mg, 0.98 mmol, 1 equiv.) in CHCl3 (15 mL) was added MnO2 (509.1 mg, 5.86 mmol, 6.00 equiv.) at room temperature. The resulting mixture was stirred for 16 h at 60 degrees C. The reaction was monitored by LCMS. The mixture was allowed to cool down to room temperature. The resulting mixture was filtered, the filter cake was washed with DCM (3×100 mL). The filtrate was concentrated under reduced pressure. The residue was purified by silica gel column chromatography, eluted with CH2Cl2/MeOH (20:1) to afford tert-butyl 4-[(2-formylpyridin-3-yl)methyl]piperazine-1-carboxylate (230 mg, 77.17%) as a yellow oil.

Step 4

Tert-Butyl 4-[[2-(1-hydroxyethyl)pyridin-3-yl]methyl]piperazine-1-carboxylate

To a stirred solution of tert-butyl 4-[(2-formylpyridin-3-yl)methyl]piperazine-1-carboxylate (230 mg, 0.75 mmol, 1 equiv.) in THF (10 mL, 123.43 mmol, 163.88 equiv.) was added CH3MgBr (179.6 mg, 1.51 mmol, 2.00 equiv.) dropwise at −40 degrees C. under nitrogen atmosphere. The resulting mixture was stirred for 1 h at −10 degrees C. under nitrogen atmosphere. The reaction was monitored by LCMS. The reaction was quenched by the addition of sat. NH4Cl (aq.) (5 mL) at −40 degrees C. The resulting mixture was extracted with EtOAc (3×100 mL). The combined organic layers were washed with brine (1×200 mL), dried over anhydrous Na2SO4. After filtration, the filtrate was concentrated under reduced pressure to afford tert-butyl 4-[[2-(1-hydroxyethyl)pyridin-3-yl]methyl]piperazine-1-carboxylate (240 mg) as yellow oil. The crude product mixture was used in the next step directly without further purification.

Step 5

1-[3-[(piperazin-1-yl)methyl]pyridin-2-yl]ethan-1-ol

To a stirred solution of tert-butyl 4-[[2-(1-hydroxyethyl)pyridin-3-yl]methyl]piperazine-1-carboxylate (240 mg, 0.75 mmol, 1 equiv.) in DCM (5 mL) was added TFA (3 mL, 40.39 mmol, 54.09 equiv.) dropwise at room temperature. The resulting mixture was stirred for 2 h at room temperature. The reaction was monitored by LCMS. The mixture was basified to pH 8 with saturated NaHCO3 (aq.). The resulting mixture was concentrated under reduced pressure. The residue was purified by reverse flash chromatography with the following conditions: column, C18 silica gel; mobile phase, MeOH in water, 10% to 30% gradient in 15 min; detector, UV 254 nm, to afford 1-[3-[(piperazin-1-yl)methyl]pyridin-2-yl]ethan-1-ol (100 mg, 60.52%) as a yellow oil.

Step 6

Compounds LN and LO 4-chloro-5-[4-([2-[(1S)-1-hydroxyethyl]pyridin-3-yl]methyl)piperazin-1-yl]-2,3-dihydropyridazin-3-one & 4-chloro-5-[4-([2-[(1R)-1-hydroxyethyl]pyridin-3-yl]methyl)piperazin-1-yl]-2,3-dihydropyridazin-3-one To a stirred mixture of 1-[3-[(piperazin-1-yl)methyl]pyridin-2-yl]ethan-1-ol (100 mg, 0.45 mmol, 1 equiv.) and 4,5-dichloro-2,3-dihydropyridazin-3-one (74.5 mg, 0.45 mmol, 1 equiv.) in DMA (5 mL) was added DIEA (175.2 mg, 1.36 mmol, 3.00 equiv.) at room temperature. The resulting mixture was stirred for 16 h at 100 degrees C. The reaction was monitored by LCMS. The crude product (100 mg) was purified by Prep-HPLC with the following conditions (Column: XBridge Shield RP18 OBD Column 30*150 mm, 5 um; Mobile Phase A: Water (10 MMOL/L NH4HCO3), Mobile Phase B: ACN; Flow rate: 60 mL/min; Gradient: 14% B to 24% B in 7 min; 254; 220 nm; Rt: 6.13 min). The crude product (50 mg) was purified by Chiral-Prep-HPLC with the following conditions (Column: CHIRALPAK IG UL001, 20*250 mm, 5 um; Mobile Phase A:HEX:DCM=3:1—HPLC, Mobile Phase B: EtOH—HPLC; Flow rate: 20 mL/min; Gradient: 50 B to 50 B in 17 min; 220/254 nm; RT1:9.09; RT2:12.399). 4-chloro-5-[4-([2-[(1S)-1-hydroxyethyl]pyridin-3-yl]methyl)piperazin-1-yl]-2,3-dihydropyridazin-3-one (14 mg, 8.86%) was obtained at 9.09 min as a white solid. 4-chloro-5-[4-([2-[(1R)-1-hydroxyethyl]pyridin-3-yl]methyl)piperazin-1-yl]-2,3-dihydropyridazin-3-one (10 mg) was obtained at 12.399 min as a white solid.

Compound LP

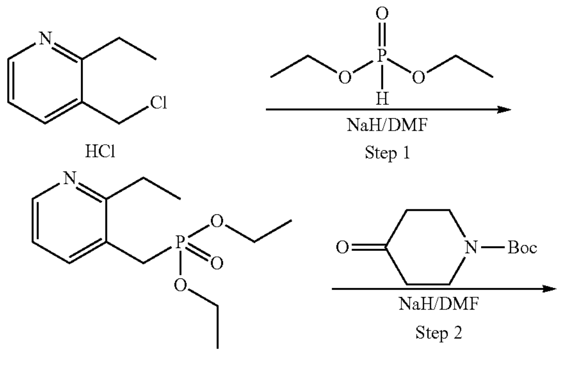

1

-continued

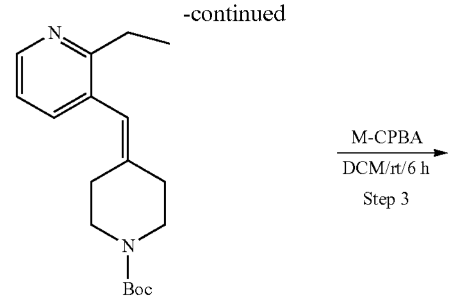

2

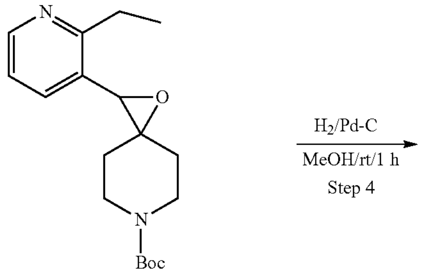

3

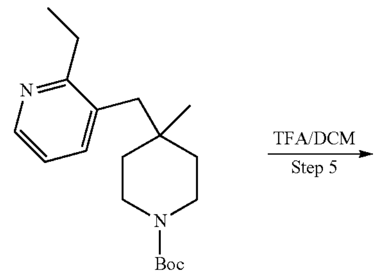

4

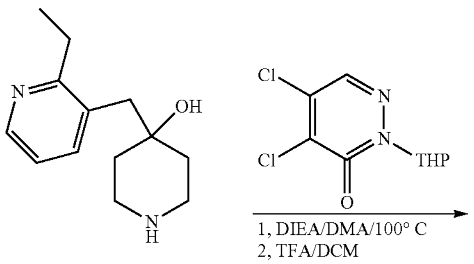

5

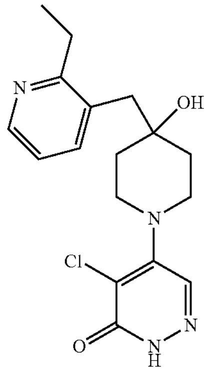

LP

Step 1

Diethyl [(2-ethylpyridin-3-yl)methyl]phosphonate

To a stirred solution of 3-(chloromethyl)-2-ethylpyridine (1 g, 6.43 mmol, 1 equiv.) in DMF (30 mL) was added NaH (0.5 g, 19.28 mmol, 3 equiv.) at room temperature. The resulting mixture was stirred for 30 min at 0 degrees C. Then diethyl phosphonate (1.8 g, 12.85 mmol, 2 equiv.) and Cs2CO3 (4.2 g, 12.89 mmol, 2.01 equiv.) in DMF was added at room temperature. The resulting mixture was stirred for 16 h at room temperature. The reaction was monitored by LCMS. The crude product was purified by reverse phase flash with the following conditions (Column: XBridge Prep C18 OBD Column 19×150 mm 5 um; Mobile Phase A: Water (5 MMOL/L NH4HCO3), Mobile Phase B: ACN; Flow rate: 60 mL/min; Gradient: 30% B to 40% B in 7 min; 254/220 nm; Rt: 6.30 min) to afford diethyl [(2-ethylpyridin-3-yl)methyl]phosphonate (1.3 g, 78.64%) as a yellow oil.

Step 2

Tert-Butyl 4-[(2-ethylpyridin-3-yl)methylidene]piperidine-1-carboxylate

To a stirred solution of diethyl [(2-ethylpyridin-3-yl) methyl]phosphonate (1.3 g, 5.05 mmol, 1 equiv.) in DMF (30 mL) was added NaH (0.6 g, 0.02 mmol, 2.97 equiv, 60%) at room temperature. The resulting mixture was stirred for 1 h at room temperature. Then tert-butyl 4-oxopiperidine-1-carboxylate (1.5 g, 0.01 mmol, 1.5 equiv.) was added and the resulting mixture was stirred for 16 h at room temperature. The reaction was monitored by LCMS. The mixture was purified by reverse phase flash with the following conditions (Column: XBridge Prep C18 OBD Column 19×150 mm 5 um; Mobile Phase A: Water (10 MMOL/L NH4HCO3), Mobile Phase B: ACN; Flow rate: 20 mL/min; Gradient: 50% B to 76% B in 7 min; 254/220 nm; Rt: 4.95 5.72 min) to afford crude product. The crude product (500 mg) was purified by Prep-HPLC with the following conditions (Column: XBridge Prep C18 OBD Column 19×150 mm 5 um; Mobile Phase A: Water (10 MMOL/L NH4HCO3), Mobile Phase B: ACN; Flow rate: 60 mL/min; Gradient: 20% B to 65% B in 7 min; 254/220 nm; Rt: 6.38 min) to afford tert-butyl 4-[(2-ethylpyridin-3-yl)methylidene]piperidine-1-carboxylate (180 mg, 11.78%) as a colorless oil and tert-butyl 4-[(2-ethylpyridin-3-yl) methyl]-1,2,3,6-tetrahydropyridine-1-carboxylate (250 mg, 16.36%) as a colorless oil.

Step 3

Tert-Butyl 2-(2-ethylpyridin-3-yl)-1-oxa-6-azaspiro [2.5]octane-6-carboxylate

To a stirred solution of tert-butyl 4-[(2-ethylpyridin-3-yl) methylidene]piperidine-1-carboxylate (180 mg, 0.60 mmol, 1 equiv.) in DCM (20 mL) was added m-CPBA (123.3 mg, 0.71 mmol, 1.2 equiv.) at 0 degrees C. The resulting mixture was stirred for 1 h at 0 degrees C. The reaction was monitored by LCMS. The reaction was quenched with Water at 0 degrees C. The resulting mixture was extracted with CH2Cl2 (3×20 mL). The combined organic layers were washed with brine (1×10 mL), dried over anhydrous Na2SO4. After filtration, the filtrate was concentrated under reduced pressure. The residue was purified by Prep-TLC (CH2Cl2/MeOH=15:1) to afford tert-butyl 2-(2-ethylpyridin-3-yl)-1-oxa-6-azaspiro[2.5]octane-6-carboxylate (180 mg, 94.98%) as a colorless oil.

Step 4

Tert-Butyl 4-[(2-ethylpyridin-3-yl)methyl]-4-hydroxypiperidine-1-carboxylate

To a stirred solution of tert-butyl 2-(2-ethylpyridin-3-yl)-1-oxa-6-azaspiro[2.5]octane-6-carboxylate (180 mg, 0.57 mmol, 1 equiv.) in MeOH (10 mL) was added Pd/C (6.0 mg, 0.06 mmol, 0.1 equiv.) at room temperature under hydrogen atmosphere. The resulting mixture was stirred for 1 h at room temperature under hydrogen atmosphere. The reaction was monitored by LCMS. The resulting mixture was filtered, the filter cake was washed with MeOH (3×10 mL). The filtrate was concentrated under reduced pressure. The crude product was used in the next step directly without further purification.

Step 5

4-[(2-ethylpyridin-3-yl)methyl]piperidin-4-ol

To a stirred solution of tert-butyl 4-[(2-ethylpyridin-3-yl)methyl]-4-hydroxypiperidine-1-carboxylate (50 mg, 0.16 mmol, 1 equiv.) in DCM (8 mL) was added TFA (2 mL, 26.93 mmol, 172.56 equiv.) at room temperature. The resulting mixture was stirred for 2 h at room temperature. The reaction was monitored by LCMS. The resulting mixture was concentrated under reduced pressure. The residue was basified to pH 8 with saturated NaHCO3 (aq.). The residue was purified by reverse phase flash with the following conditions (Column:C18,330 g; Mobile Phase A: Water/0.05% NH4HCO3, Mobile Phase B:ACN; Flow rate:45 mL/min; Gradient:100% B to 20% B in 10 min; Detector, 254 nm and 220 nm) to afford 4-[(2-ethylpyridin-3-yl)methyl]piperidin-4-ol (30 mg, 87.27%) as a yellow solid.

Step 6

4-chloro-5-[4-[(2-ethylpyridin-3-yl)methyl]-4-hydroxypiperidin-1-yl]-2-(oxan-2-yl)-2,3-dihydropyridazin-3-one To a stirred solution of 4-[(2-ethylpyridin-3-yl)methyl]piperidin-4-ol (25 mg, 0.11 mmol, 1 equiv.) in DIEA (0.5 mL) was added 4,5-dichloro-2-(oxan-2-yl)-2,3-dihydropyridazin-3-one (56.5 mg, 0.23 mmol, 2 equiv.) at room temperature. The resulting mixture was stirred for 3 h at 90 degrees C. The reaction was monitored by LCMS. The mixture was allowed to cool down to room temperature. The residue was purified by reverse phase flash with the following conditions (Column:C18,330 g; Mobile Phase A: Water/0.05% NH4HCO3, Mobile Phase B:ACN; Flow rate:45 mL/min; Gradient:35% B to 45% B in 10 min; Detector, 254 nm and 220 nm) to afford 4-chloro-5-[4-[(2-ethylpyridin-3-yl)methyl]-4-hydroxypiperidin-1-yl]-2-(oxan-2-yl)-2,3-dihydropyridazin-3-one (50 mg, 101.77%) as a yellow solid.

Step 7

Compound LP 4-chloro-5-[4-[(2-ethylpyridin-3-yl)methyl]-4-hydroxypiperidin-1-yl]-2,3-dihydropyridazin-3-one To a stirred solution of 4-chloro-5-[4-[(2-ethylpyridin-3-yl)methyl]-4-hydroxypiperidin-1-yl]-2-(oxan-2-yl)-2,3-dihydropyridazin-3-one (50 mg, 0.12 mmol, 1 equiv.) in DCM (12 mL) was added TFA (3 mL, 40.39 mmol, 349.73 equiv.) at room temperature. The resulting mixture was stirred for 2 h at room temperature. The reaction was monitored by LCMS. The resulting mixture was concentrated under reduced pressure. The residue was basified to pH 8 with saturated NaHCO3 (aq.). The resulting mixture was extracted with CH2Cl2 (3×5 mL). The combined organic layers were washed with brine (1×5 mL), dried over anhydrous Na2SO4. After filtration, the filtrate was concentrated under reduced pressure. The crude product (30 mg) was purified by Prep-HPLC with the following conditions (Column: XBridge Prep C18 OBD Column 19×150 mm 5 um; Mobile Phase A: Water (10 MMOL/L NH4HCO3), Mobile Phase B: ACN; Flow rate: 60 mL/min; Gradient: 15% B to 34% B in 7 min; 254/220 nm; Rt: 6.66 min) to afford 4-chloro-5-[4-[(2-ethylpyridin-3-yl)methyl]-4-hydroxypiperidin-1-yl]-2,3-dihydropyridazin-3-one (10 mg, 24.82%) as a white solid.

Compound LQ

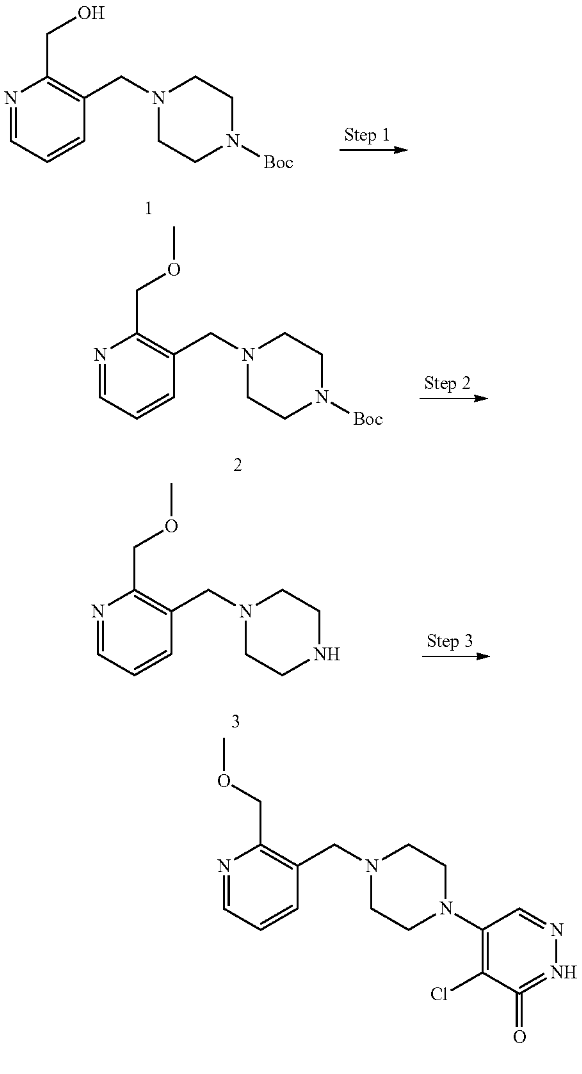

1
2
3

LQ

Step 1

Tert-Butyl 4-[[2-(methoxymethyl)pyridin-3-yl]methyl]piperazine-1-carboxylate

The mixture of tert-butyl 4-[[2-(hydroxymethyl)pyridin-3-yl]methyl]piperazine-1-carboxylate (160 mg, 0.521 mmol, 1 equiv.), MeI (148 mg, 1.043 mmol, 2.00 equiv.) and NaH (41.64 mg, 1.041 mmol, 2.00 equiv, 60%) in DMF (5 mL, 0.068 mmol, 0.13 equiv.) was stirred at room temperature for 2 hours. The mixture was added H2O (100 mL). The resulting mixture was extracted with ethyl acetate (100 mL×3), the organic layer was washed with brine (100 mL) and concentrated to give the residue. The residue was purified by reverse flash chromatography with the following conditions: column, C18 silica gel; mobile phase, ACN in water (5.0 mmol/L NH4HCO3), 40% to 60% gradient in 30 min; detector, UV 254 nm and 220 nm to afford tert-butyl 4-[[2-(methoxymethyl)pyridin-3-yl]methyl]piperazine-1-carboxylate (160 mg, 95.64%) as off-white solid.

Step 2

1-[[2-(methoxymethyl)pyridin-3-yl]methyl]piperazine

The mixture of tert-butyl 4-[[2-(methoxymethyl)pyridin-3-yl]methyl]piperazine-1-carboxylate (160 mg, 0.498 mmol, 1 equiv, 100%) in THF (1 mL, 12.343 mmol, 24.80 equiv.) and DCM (5 mL, 0.059 mmol, 0.12 equiv.) was stirred at room temperature for 2 hours. The resulting mixture was concentrated under reduced pressure. To the reaction mixture was added EtOAc (100 mL) and sat. NaHCO3 (aq, 30 mL), the organic layers were washed with sat. NaHCO3 (aq) (3×10 mL), dried over anhydrous Na2SO4. After filtration, the filtrate was concentrated under reduced pressure to give the residue. The residue was purified by reverse flash chromatography with the following conditions: column, C18 silica gel; mobile phase, ACN in water (5.0 mmol/L NH4HCO3), 40% to 60% gradient in 30 min; detector, UV 254 nm and 220 nm to afford 1-[[2-(methoxymethyl)pyridin-3-yl]methyl]piperazine (100 mg, 90.77%) as off-white solid.

Step 3

Compound LQ 4-chloro-5-(4-[[2-(methoxymethyl)pyridin-3-yl]methyl]piperazin-1-yl)-2,3-dihydropyridazin-3-one The mixture of 1-[[2-(methoxymethyl)pyridin-3-yl]methyl]piperazine (100 mg, 0.45 mmol, 1 equiv.), 4,5-dichloro-2,3-dihydropyridazin-3-one (74.5 mg, 0.45 mmol, 1 equiv.) and DIEA (116.8 mg, 0.90 mmol, 2.00 equiv.) in DMA (3 mL, 0.03 mmol, 0.08 equiv.) was stirred at 100 degrees C. for 2 hours. The mixture was cooled to room temperature and concentrated to give the residue. The residue was purified by reverse flash chromatography with the following conditions: Column: XBridge Prep C18 OBD Column 19×150 mm 5 um; Mobile Phase A: Water (10 MMOL/L NH4HCO3), Mobile Phase B: ACN; Flow rate: 60 mL/min; Gradient: 18% B to 38% B in 7 min; 254/220 nm; Rt: 6.17 min to afford 4-chloro-5-(4-[[2-(methoxymethyl)pyridin-3-yl]methyl]piperazin-1-yl)-2,3-dihydropyridazin-3-one (4.8 mg, 3.04%) as light yellow solid.

Compounds LR and LS

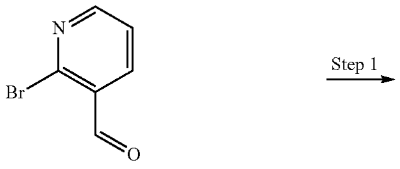

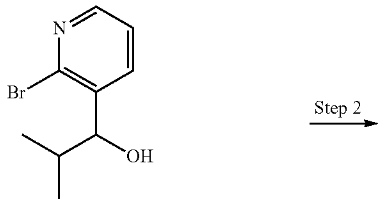

1

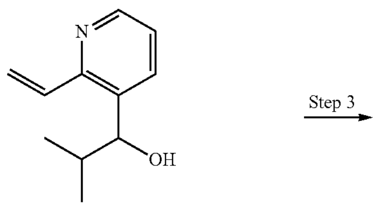

2

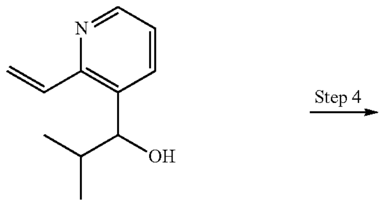

2

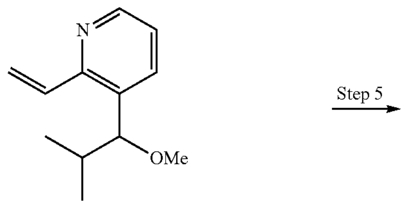

4

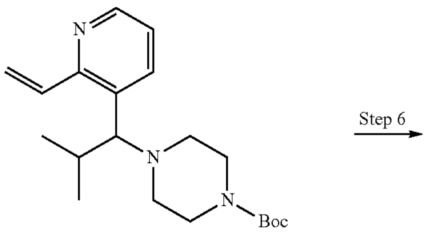

5

-continued

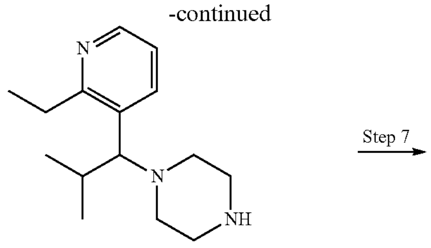

6

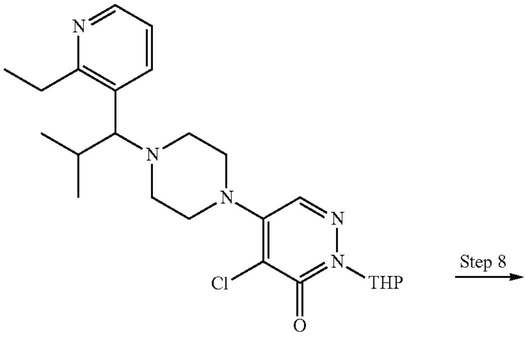

7

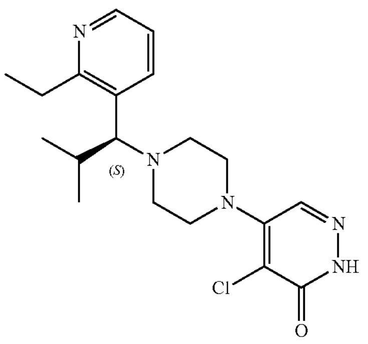

LR

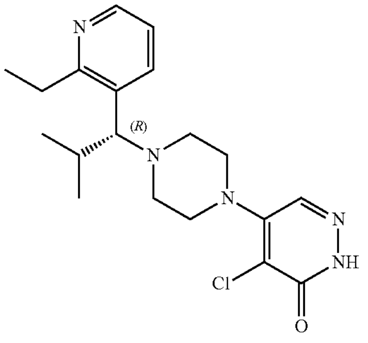

LS

Step 1

1-(2-bromopyridin-3-yl)-2-methylpropan-1-ol

To a stirred solution of 2-bromopyridine-3-carbaldehyde (10 g, 53.76 mmol, 1 equiv.) in THF (100 mL) was added bromo(propan-2-yl)magnesium (9.5 g, 64.50 mmol, 1.20 equiv.) dropwise at −40 degrees C. under nitrogen atmosphere. The resulting mixture was stirred for 2 h at −10 degrees C. under nitrogen atmosphere. The reaction was monitored by LCMS. The reaction was quenched by the addition of sat. NH4Cl (aq.) (100 mL) at −40 degrees C. The resulting mixture was extracted with EtOAc (3×500 mL). The combined organic layers were washed with brine (2×300 mL), dried over anhydrous Na2SO4. After filtration, the filtrate was concentrated under reduced pressure. The residue was purified by silica gel column chromatography, eluted with PE/EtOAc (20/1 to 5/1) to afford 1-(2-bromopyridin-3-yl)-2-methylpropan-1-ol (2.0 g, 16.17%) as a yellow oil.

Step 2

1-(2-ethenylpyridin-3-yl)-2-methylpropan-1-ol

To a stirred mixture of 1-(2-bromopyridin-3-yl)-2-methylpropan-1-ol (1.5 g, 6.52 mmol, 1 equiv.) and 2-ethenyl-4,4,5,5-tetramethyl-1,3,2-dioxaborolane (1.5 g, 9.78 mmol, 1.50 equiv.) in 1,4-dioxane (30 mL) and H2O (6 mL) were added K2CO3 (1.8 g, 13.02 mmol, 2.00 equiv.) and Pd(PPh3)4 (376.6 mg, 0.33 mmol, 0.05 equiv.) in portions at rt under nitrogen atmosphere. The resulting mixture was stirred for 16 h at 90 degrees C. under nitrogen atmosphere. The reaction was monitored by LCMS. The mixture was allowed to cool down to rt. The residue was purified by silica gel column chromatography, eluted with PE/EtOAc (20/1 to 5/1) to afford 1-(2-ethenylpyridin-3-yl)-2-methylpropan-1-ol (1.0 g, 86.55%) as a yellow oil.

Step 3

1-(2-ethylpyridin-3-yl)-2-methylpropan-1-ol

To a solution of 1-(2-ethenylpyridin-3-yl)-2-methylpropan-1-ol (1.0 g, 5.64 mmol, 1 equiv.) in 30 mL MeOH was added Pd/C (10%, 0.10 g) under nitrogen atmosphere in a 100 mL round-bottom flask. The mixture was hydrogenated at room temperature for 4 h under hydrogen atmosphere using a hydrogen balloon, filtered through a celite pad and concentrated under reduced pressure. This resulted in 1-(2-ethylpyridin-3-yl)-2-methylpropan-1-ol (0.9 g, 88.99%) as a yellow oil.

Step 4

1-(2-ethylpyridin-3-yl)-2-methylpropyl methanesulfonate

To a stirred mixture of 1-(2-ethylpyridin-3-yl)-2-methylpropan-1-ol (300 mg, 1.67 mmol, 1 equiv.) and TEA (338.7 mg, 3.35 mmol, 2.00 equiv.) in DCM (10 mL) was added MsCl (230.0 mg, 2.01 mmol, 1.2 equiv.) dropwise at 0 degrees C. under nitrogen atmosphere. The resulting mixture was stirred for 2 h at under nitrogen atmosphere. The reaction was monitored by LCMS. The residue was purified by Prep-TLC (CH2Cl2/MeOH 20/1) to afford 1-(2-ethylpyridin-3-yl)-2-methylpropyl methanesulfonate (350 mg, 81.27%) as a yellow oil.

Step 5

Tert-Butyl 4-[1-(2-ethylpyridin-3-yl)-2-methylpropyl]piperazine-1-carboxylate

Into a 50 mL round-bottom flask were added 1-(2-ethylpyridin-3-yl)-2-methylpropyl methanesulfonate (350 mg, 1.36 mmol, 1 equiv.) and tert-butyl piperazine-1-carboxylate (506.6 mg, 2.72 mmol, 2.00 equiv.) at rt. The resulting mixture was stirred for 16 h at 80 degrees C. The reaction was monitored by LCMS. The residue was purified by Prep-TLC (PE/EtOAc 3/1) to afford tert-butyl 4-[1-(2-ethylpyridin-3-yl)-2-methylpropyl]piperazine-1-carboxylate (300 mg, 63.48%) as a yellow oil.

Step 6

1-[1-(2-ethylpyridin-3-yl)-2-methylpropyl]piperazine

To a stirred solution of tert-butyl 4-[1-(2-ethylpyridin-3-yl)-2-methylpropyl]piperazine-1-carboxylate (300 mg, 0.86 mmol, 1 equiv.) in DCM (10 mL) was added TFA (1 mL, 13.46 mmol, 15.59 equiv.) dropwise at rt. The reaction mixture was stirred for 4 h at rt. The reaction was monitored by LCMS. The resulting mixture was concentrated under reduced pressure. The residue was basified to pH=8 with saturated NH4HCO3 (aq.). The resulting mixture was extracted with CH2Cl2(2×100 mL). The combined organic layers were washed with brine (1×100 mL), dried over anhydrous Na2SO4. The resulting mixture was concentrated under vacuum. The residue was purified by Prep-TLC (PE/EtOAc 2/1) to afford 1-[1-(2-ethylpyridin-3-yl)-2-methylpropyl]piperazine (200 mg, 93.65%) as a yellow oil.

Step 7

4-chloro-5-[4-[1-(2-ethylpyridin-3-yl)-2-methylpropyl]piperazin-1-yl]-2-(oxan-2-yl)-2,3-dihydropyridazin-3-one Into a 25 mL round-bottom flask were added 1-[1-(2-ethylpyridin-3-yl)-2-methylpropyl]piperazine (200 mg, 0.81 mmol, 1 equiv.), 4,5-dichloro-2-(oxan-2-yl)-2,3-dihydropyridazin-3-one (402.8 mg, 1.62 mmol, 2.00 equiv.) and DIEA (209.0 mg, 1.62 mmol, 2.00 equiv.) at rt under nitrogen atmosphere. The resulting mixture was stirred for 16 h at 90 degrees C. under nitrogen atmosphere. The residue was purified by Prep-TLC (PE/EtOAc=5/1) to afford 4-chloro-5-[4-[1-(2-ethylpyridin-3-yl)-2-methylpropyl]piperazin-1-yl]-2-(oxan-2-yl)-2,3-dihydropyridazin-3-one (280 mg, 75.29%) as a yellow oil.

Step 8

Compounds LR and LS 4-chloro-5-[4-[(1S)-1-(2-ethylpyridin-3-yl)-2-methylpropyl]piperazin-1-yl]-2,3-dihydropyridazin-3-one & 4-chloro-5-[4-[(1R)-1-(2-ethylpyridin-3-yl)-2-methylpropyl]piperazin-1-yl]-2,3-dihydropyridazin-3-one To a stirred solution of 4-chloro-5-[4-[1-(2-ethylpyridin-3-yl)-2-methylpropyl]piperazin-1-yl]-2-(oxan-2-yl)-2,3-dihydropyridazin-3-one (280 mg, 0.61 mmol, 1 equiv.) in DCM (20 mL) was added TFA (2 mL, 26.93 mmol, 44.24 equiv.) dropwise at rt. The reaction mixture was stirred for 4 h at rt. The reaction was monitored by LCMS. The resulting mixture was concentrated under reduced pressure. The residue was basified to pH=8 with saturated NH4HCO3 (aq.). The resulting mixture was extracted with CH2Cl2(3×100 mL). The combined organic layers were washed with brine (1×100 mL), dried over anhydrous Na2SO4. After filtration, the filtrate was concentrated under reduced pressure. The residue was purified by Chiral-Prep-HPLC with the following conditions (Column: XBridge Shield RP18 OBD Column, 5 um, 19*150 mm; Mobile Phase A: Water (10 MMOL/L NH4HCO3), Mobile Phase B: ACN; Flow rate: 20 mL/min; Gradient: 30% B to 60% B in 7 min; 220 nm; Rt: 6.6 min). 4-chloro-5-[4-[(1S)-1-(2-ethylpyridin-3-yl)-2-methylpropyl]piperazin-1-yl]-2,3-dihydropyridazin-3-one (36.3 mg) was obtained at 2.982 min as a white solid. 4-chloro-5-[4-[(1R)-1-(2-ethylpyridin-3-yl)-2-methylpropyl]piperazin-1-yl]-2-(oxan-2-yl)-2,3-dihydropyridazin-3-one (280 mg, 0.61 mmol, 1 equiv.) was obtained at 2.253 min as a white solid (E01224-062).

Compound LT

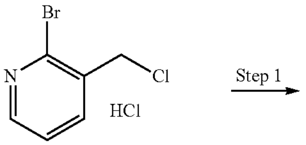

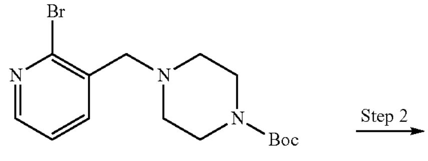

1

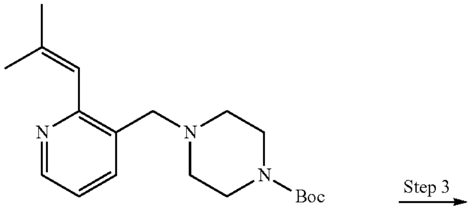

2

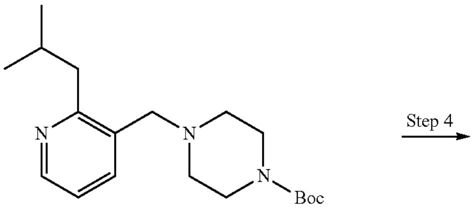

3

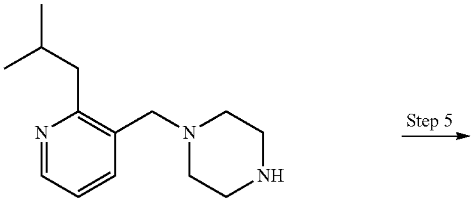

4

-continued

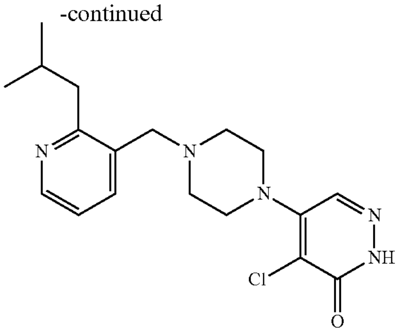

LT

Step 1

Tert-Butyl 4-[(2-bromopyridin-3-yl)methyl]piperazine-1-carboxylate

To a solution of 2-bromo-3-(chloromethyl)pyridine hydrochloride (10.8 g, 44.457 mmol, 1 equiv.) in DCM (400 mL) were added tert-butyl piperazine-1-carboxylate (8.28 g, 44.455 mmol, 1.00 equiv.) and TEA (13.50 g, 133.412 mmol, 3.00 equiv.) at ambient temperature. The resulting mixture was stirred for 16 h at 40 degrees C. The desired product could be detected by LCMS. The mixture was allowed to cool down to room temperature. The reaction mixture was concentrated under reduced pressure to crude product. The crude product was diluted with water (2000 mL) and extracted with DCM (3000 mL×2). The organic layers was washed with saturated brine (1000 mL), dried over anhydrous Na2SO4, filtered and concentrated to give desired product. The residue was purified by silica gel column chromatography, eluted with EtOAc/PE (1:20 to 1:10) to afford tert-butyl 4-[(2-bromopyridin-3-yl)methyl] piperazine-1-carboxylate (9.3 g, 58.72%) as a white solid.

Step 2

Tert-Butyl 4-[[2-(2-methylprop-1-en-1-yl)pyridin-3-yl]methyl]piperazine-1-carboxylate To a solution of tert-butyl 4-[(2-bromopyridin-3-yl) methyl]piperazine-1-carboxylate (400 mg, 1.123 mmol, 1 equiv.) and 4,4,5,5-tetramethyl-2-(2-methylprop-1-en-1-yl)-1,3-dioxolane (310.35 mg, 1.684 mmol, 1.5 equiv.) in 1,4-dioxane (5 mL) and H2O (1 mL) were added K2CO3 (310.34 mg, 2.246 mmol, 2 equiv.) and Pd(PPh3)4 (64.87 mg, 0.056 mmol, 0.05 equiv.). The final reaction mixture was irradiated with microwave radiation for 3 h at 100 degrees C. The resulting mixture was concentrated under reduced pressure. The residue was purified by silica gel column chromatography, eluted with PE/EtOAc (20:1 to 1:1) to afford tert-butyl 4-[[2-(2-methylprop-1-en-1-yl)pyridin-3-yl]methyl]piperazine-1-carboxylate (230 mg, 61.80%) as a light yellow oil.

Step 3

Tert-Butyl 4-[[2-(2-methylpropyl)pyridin-3-yl] methyl]piperazine-1-carboxylate

To a stirred solution of tert-butyl 4-[[2-(2-methylprop-1-en-1-yl)pyridin-3-yl]methyl]piperazine-1-carboxylate (230 mg, 0.694 mmol, 1 equiv.) in EA (10 mL) was added PtO2 (15.76 mg, 0.069 mmol, 0.1 equiv.) in portions at room temperature under nitrogen atmosphere. The resulting mixture was stirred for 2 h at room temperature under hydrogen atmosphere. The reaction was monitored by LCMS. The resulting mixture was filtered, the filter cake was washed with EtOAc (3×10 mL). The filtrate was concentrated under reduced pressure. The resulting mixture was used in the next step directly without further purification.

Step 4

1-[[2-(2-methylpropyl)pyridin-3-yl]methyl]piperazine

To a stirred solution of tert-butyl 4-[[2-(2-methylpropyl) pyridin-3-yl]methyl]piperazine-1-carboxylate (210 mg, 0.630 mmol, 1 equiv.) in DCM (10 mL) was added TFA (3 mL) in portions at room temperature under nitrogen atmosphere. The resulting mixture was stirred for 2 h at room temperature under nitrogen atmosphere. The reaction was monitored by LCMS. The mixture was basified to pH 8 with saturated NaHCO3 (aq.). The resulting mixture was extracted with EtOAc (10 mL). The combined organic layers were washed with brine (3×20 mL), dried over anhydrous Na2SO4. After filtration, the filtrate was concentrated under reduced pressure. The resulting mixture was used in the next step directly without further purification.

Step 5

Compound LT 4-chloro-5-(4-[[2-(2-methylpropyl)pyridin-3-yl] methyl]piperazin-1-yl)-2,3-dihydropyridazin-3-one To a stirred solution of 1-[[2-(2-methylpropyl)pyridin-3-yl]methyl]piperazine (120 mg, 0.514 mmol, 1 equiv.) and 4,5-dichloro-2,3-dihydropyridazin-3-one (127.25 mg, 0.771 mmol, 1.5 equiv.) in DMA (5 mL) was added DIEA (132.92 mg, 1.028 mmol, 2 equiv.) in portions at room temperature under nitrogen atmosphere. The resulting mixture was stirred for overnight at 100 degrees C. under nitrogen atmosphere. The reaction was monitored by LCMS. The mixture was allowed to cool down to room temperature. The crude product (100 mg) was purified by Prep-HPLC with the following conditions (Column: XBridge Shield RP18 OBD Column 19*250 mm, 10 um; Mobile Phase A: Water (10 MMOL/L NH4HCO3), Mobile Phase B: ACN; Flow rate: 60 mL/min; Gradient: 28% B to 38% B in 7 min; 254; 220 nm; Rt: 6.48, 9.18 min) to afford 4-chloro-5-(4-[[2-(2-methylpropyl)pyridin-3-yl]methyl]piperazin-1-yl)-2,3-dihydropyridazin-3-one (33.5 mg, 18.00%) as a white solid.

Compounds LU and LV

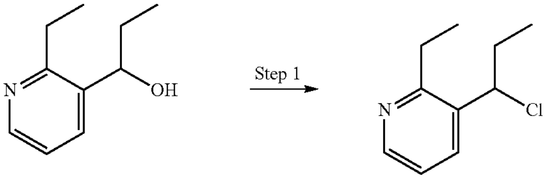

-continued

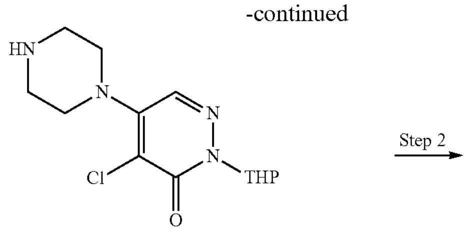

1

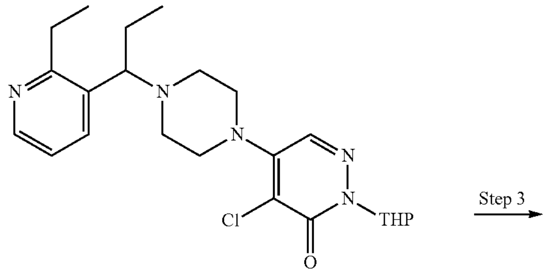

2

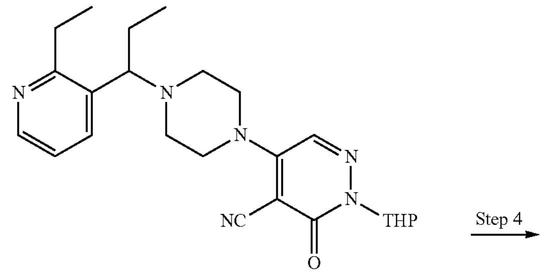

3

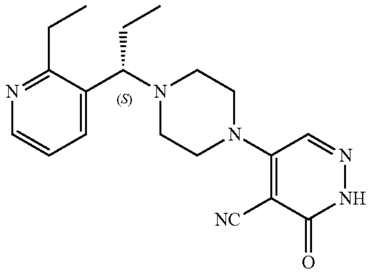

LU

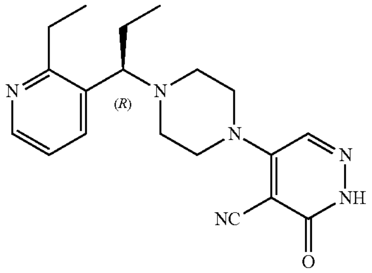

LV

Step 1

3-(1-chloropropyl)-2-ethylpyridine

To a stirred solution of 1-(2-ethylpyridin-3-yl)propan-1-ol (300 mg, 1.82 mmol, 1 equiv.) in DCM (20 mL) was added SOCl2 (432.0 mg, 3.63 mmol, 2.00 equiv.) dropwise at 0 degrees C. under nitrogen atmosphere. The resulting mixture was stirred for 16 h at under nitrogen atmosphere. The reaction was monitored by LCMS. The resulting mixture was concentrated under vacuum. This resulted in 3-(1-chloropropyl)-2-ethylpyridine (350 mg, 104.95%) as a yellow oil.

Step 2

4-chloro-5-[4-[1-(2-ethylpyridin-3-yl)propyl]piperazin-1-yl]-2-(oxan-2-yl)-2,3-dihydropyridazin-3-one To a stirred mixture of 4-chloro-2-(oxan-2-yl)-5-(piperazin-1-yl)-2,3-dihydropyridazin-3-one (150 mg, 0.50 mmol, 1 equiv.) and 3-(1-chloropropyl)-2-ethylpyridine (92.2 mg, 0.50 mmol, 1.00 equiv.) in ACN (10 mL) were added K2CO3 (138.8 mg, 1.00 mmol, 2.00 equiv.) and KI (166.7 mg, 1.00 mmol, 2.00 equiv.) in portions at rt under nitrogen atmosphere. The resulting mixture was stirred for 16 h at 70 degrees C. under nitrogen atmosphere. The reaction was monitored by LCMS. The resulting mixture was filtered, the filter cake was washed with ACN (2×30 mL). The filtrate was concentrated under reduced pressure. The residue was purified by Prep-TLC (CH2Cl2/MeOH 20/1) to afford 4-chloro-5-[4-[1-(2-ethylpyridin-3-yl)propyl]piperazin-1-yl]-2-(oxan-2-yl)-2,3-dihydropyridazin-3-one (110 mg, 49.13%) as a yellow oil.

Step 3

5-[4-[1-(2-ethylpyridin-3-yl)propyl]piperazin-1-yl]-2-(oxan-2-yl)-3-oxo-2,3-dihydropyridazine-4-carbonitrile To a stirred mixture of 4-chloro-5-[4-[1-(2-ethylpyridin-3-yl)propyl]piperazin-1-yl]-2-(oxan-2-yl)-2,3-dihydropyridazin-3-one (110 mg, 0.25 mmol, 1 equiv.) and Zn(CN)2 (86.9 mg, 0.74 mmol, 3.00 equiv.) in DMF (5 mL) was added Pd(PPh3)4 (28.5 mg, 0.02 mmol, 0.10 equiv.) in portions at rt under nitrogen atmosphere. The final reaction mixture was irradiated with microwave radiation for 3 h at 150 degrees C. The reaction was monitored by LCMS. The residue was purified by reverse flash chromatography with the following conditions (Column, C18 silica gel; mobile phase, ACN in water, 30% to 60% gradient in 15 min; detector, UV 220 nm) to afford 5-[4-[1-(2-ethylpyridin-3-yl)propyl]piperazin-1-yl]-2-(oxan-2-yl)-3-oxo-2,3-dihydropyridazine-4-carbonitrile (100 mg, 92.87%) as a yellow oil.

Step 4

LU and LV

5-[4-[(1S)-1-(2-ethylpyridin-3-yl)propyl]piperazin-1-yl]-3-oxo-2,3-dihydropyridazine-4-carbonitrile & 5-[4-[(1R)-1-(2-ethylpyridin-3-yl)propyl]piperazin-1-yl]-3-oxo-2,3-dihydropyridazine-4-carbonitrile To a stirred solution of 5-[4-[1-(2-ethylpyridin-3-yl)propyl]piperazin-1-yl]-2-(oxan-2-yl)-3-oxo-2,3-dihydropyridazine-4-carbonitrile (100 mg, 0.23 mmol, 1 equiv.) in DCM (10 mL) was added TFA (1 mL, 13.46 mmol, 58.77 equiv.) dropwise at rt. The reaction mixture was stirred for 4 h at rt. The reaction was monitored by LCMS. The resulting mixture was concentrated under reduced pressure. The residue was basified to pH=8 with saturated NH4HCO3 (aq.). The resulting mixture was extracted with CH2Cl2(3×100 mL). The combined organic layers were washed with brine (1×100 mL), dried over anhydrous Na2SO4. After filtration, the filtrate was concentrated under reduced pressure. The residue (50 mg) was purified by Chiral-Prep-HPLC with the following conditions (Column: Lux 5u Celluloes-3, AXIA Packed, 2.12*25 cm, 5 um; Mobile Phase A:Hex (8 mmol/L NH3·MeOH)—HPLC, Mobile Phase B: EtOH—HPLC; Flow rate: 20 mL/min; Gradient: 20 B to 20 B in 32 min; 220/254 nm; RT1:19.5; RT2:24). 5-[4-[(1S)-1-(2-ethylpyridin-3-yl)propyl]piperazin-1-yl]-3-oxo-2,3-dihydropyridazine-4-carbonitrile (4.5 mg) was obtained at 7.556 min as a white solid. 5-[4-[(1R)-1-(2-ethylpyridin-3-yl)propyl]piperazin-1-yl]-3-oxo-2,3-dihydropyridazine-4-carbonitrile (4.3 mg) was obtained at 6.287 min as a white solid.

LW and LX

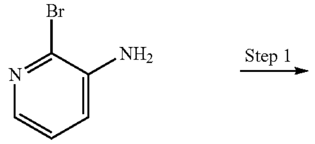

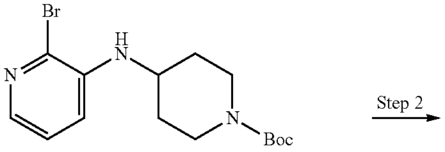

1

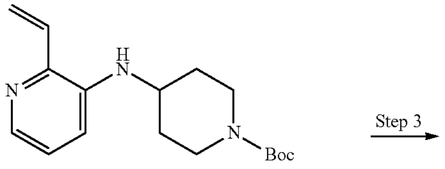

2

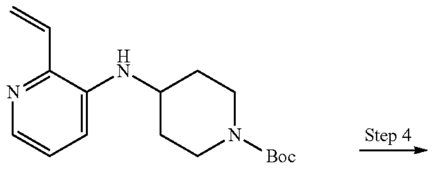

3

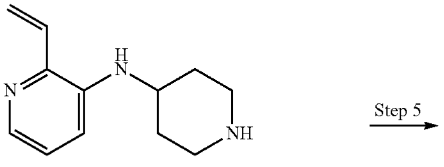

4

-continued

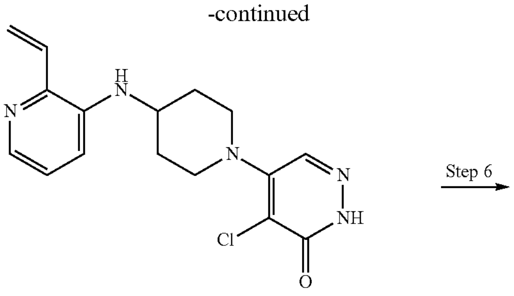

LX

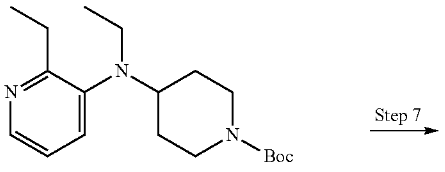

5

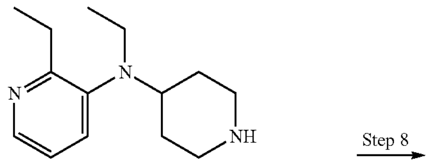

6

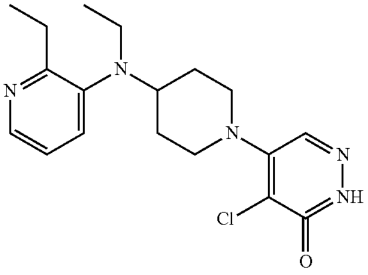

LW

Step 1

Tert-Butyl 4-[(2-bromopyridin-3-yl)amino]piperidine-1-carboxylate

To a stirred solution of 2-bromopyridin-3-amine (600 mg, 3.468 mmol, 1 equiv.) and tert-butyl 4-oxopiperidine-1-carboxylate (690.99 mg, 3.468 mmol, 1 equiv.) in DCM (20 mL) was added AcOH (208.26 mg, 3.468 mmol, 1 equiv.) dropwise/in portions at 0 degrees C. under nitrogen atmosphere. The mixture was stirred at rt for 2 h. NaBH(OAc)3 (1470.00 mg, 6.936 mmol, 2.00 equiv.) was added to the mixture at 0 degrees C. The mixture was stirred at rt overnight. Desired product could be detected by LCMS. The reaction was quenched by the addition of Water (40 mL) at 0 degrees C. The aqueous layer was extracted with CH2Cl2 (2×30 mL). The organic layer was concentrated under reduced pressure to afford tert-butyl 4-[(2-bromopyridin-3-yl)amino]piperidine-1-carboxylate (800 mg, 64.75%) as yellow solid.

Step 2

Tert-Butyl 4-[(2-ethenylpyridin-3-yl)amino]piperidine-1-carboxylate

To a solution of 2-ethenyl-4,4,5,5-tetramethyl-1,3,2-dioxaborolane (691.71 mg, 4.491 mmol, 2 equiv.) and tert-butyl 4-[(2-bromopyridin-3-yl)amino]piperidine-1-carboxylate (800 mg, 2.246 mmol, 1 equiv.) in 1,4-dioxane (10 mL) and H2O (2 mL) were added K2CO3 (931.03 mg, 6.737 mmol, 3 equiv.) and Pd(PPh3)4 (259.48 mg, 0.225 mmol, 0.1 equiv.). After stirring for overnight at 80 degrees C. under a nitrogen atmosphere, the resulting mixture was concentrated under reduced pressure. The residue was purified by silica gel column chromatography, eluted with PE/EtOAc (5:1 to 3:1) to afford tert-butyl 4-[(2-ethenylpyridin-3-yl)amino]piperidine-1-carboxylate (600 mg, 88.07%) as a yellow solid.

Step 3

Tert-Butyl 4-[(2-ethylpyridin-3-yl)amino]piperidine-1-carboxylate

To a solution of tert-butyl 4-[(2-ethenylpyridin-3-yl) amino]piperidine-1-carboxylate (600 mg, 1.978 mmol, 1 equiv.) in 30 mL MeOH was added Pd/C (10%, 21.05 mg) under nitrogen atmosphere in a 250 mL round-bottom flask. The mixture was hydrogenated at room temperature for 3 h under hydrogen atmosphere using a hydrogen balloon, filtered through a Celite pad and concentrated under reduced pressure to afford tert-butyl 4-[(2-ethylpyridin-3-yl)amino] piperidine-1-carboxylate (590 mg, 97.68%) as yellow solid.

Step 4

2-ethyl-N-(piperidin-4-yl)pyridin-3-amine

To a stirred solution of tert-butyl 4-[(2-ethylpyridin-3-yl) amino]piperidine-1-carboxylate (590 mg, 1 equiv.) in DCM (15 mL) was added TFA (3 mL) dropwise at 0 degrees C. under nitrogen atmosphere. The mixture was stirred at rt for 1 h. Desired product could be detected by LCMS. The resulting mixture was concentrated under reduced pressure to afford 2-ethyl-N-(piperidin-4-yl)pyridin-3-amine (390 mg, 98.34%) as white solid.

Step 5

Compound LX 4-chloro-5-[4-[(2-ethylpyridin-3-yl)amino]piperidin-1-yl]-2,3-dihydropyridazin-3-one To a stirred solution of 2-ethyl-N-(piperidin-4-yl)pyridin-3-amine (100 mg, 0.487 mmol, 1 equiv.) and 4,5-dichloro-2,3-dihydropyridazin-3-one (80.35 mg, 0.487 mmol, 1.00 equiv.) in DMA (8 mL) was added DIEA (125.90 mg, 0.974 mmol, 2 equiv.) dropwise at room temperature under nitrogen atmosphere. The mixture was stirred at 100 degrees C. overnight. Desired product could be detected by LCMS. The resulting mixture was concentrated under reduced pressure. The crude product (60 mg) was purified by Prep-HPLC with the following conditions (Column: XBridge Prep OBD C18 Column 30×150 mm 5 um; Mobile Phase A: Water (10 MMOL/L NH4HCO3), Mobile Phase B: ACN; Flow rate: 60 mL/min; Gradient: 18% B to 30% B in 6.5 min; 220 nm; Rt: 5.37 8.55 min) to afford 4-chloro-5-[4-[(2-ethylpyridin-3-yl)amino]piperidin-1-yl]-2,3-dihydropyridazin-3-one (20 mg) as a white solid and 5-chloro-4-[4-[(2-ethylpyridin-3-yl)amino]piperidin-1-yl]-2,3-dihydropyridazin-3-one (7 mg) as a white solid.

Step 6

Tert-Butyl 4-[ethyl(2-ethylpyridin-3-yl)amino]piperidine-1-carboxylate

To a stirred solution of tert-butyl 4-[(2-ethylpyridin-3-yl) amino]piperidine-1-carboxylate (150 mg, 0.491 mmol, 1 equiv.) and acetaldehyde (32.45 mg, 0.737 mmol, 1.5 equiv.) in DCM (10 mL) was added AcOH (29.49 mg, 0.491 mmol, 1 equiv.) dropwise at 0 degrees C. under nitrogen atmosphere. The mixture was stirred at rt for 2 h. NaBH3CN (92.59 mg, 1.473 mmol, 3 equiv.) was added to the mixture at 0 degrees C. The mixture was stirred at rt overnight. Desired product could be detected by LCMS. The reaction was quenched by the addition of Water (40 mL) at 0 degrees C. The aqueous layer was extracted with CH2Cl2 (2×30 mL). The organic layer was concentrated under reduced pressure to afford tert-butyl 4-[ethyl(2-ethylpyridin-3-yl) amino]piperidine-1-carboxylate (150 mg, 91.59%) as white solid.

Step 8

N,2-diethyl-N-(piperidin-4-yl)pyridin-3-amine

To a stirred solution of tert-butyl 4-[ethyl(2-ethylpyridin-3-yl)amino]piperidine-1-carboxylate (150 mg, 1 equiv.) in DCM (10 mL) was added TFA (2 mL) dropwise at 0 degrees C. under nitrogen atmosphere. The mixture was stirred at rt for 2 h. Desired product could be detected by LCMS. The resulting mixture was concentrated under reduced pressure to afford N,2-diethyl-N-(piperidin-4-yl)pyridin-3-amine (100 mg, 95.27%) as yellow solid.

Step 8

Compound LW 4-chloro-5-[4-[ethyl(2-ethylpyridin-3-yl)amino]piperidin-1-yl]-2,3-dihydropyridazin-3-one To a stirred solution of N,2-diethyl-N-(piperidin-4-yl) pyridin-3-amine (60 mg, 0.26 mmol, 1 equiv.) and 4,5-dichloro-2,3-dihydropyridazin-3-one (42.4 mg, 0.26 mmol, 1.00 equiv.) in DMA (5 mL, 53.78 mmol, 209.15 equiv.) was added DIEA (66.5 mg, 0.51 mmol, 2 equiv.) at room temperature under nitrogen atmosphere. The mixture was stirred at 100 degrees C. overnight. Desired product could be detected by LCMS. The mixture was concentrated under reduced pressure. The crude product (50 mg) was purified by Prep-HPLC with the following conditions (Column: XBridge Prep OBD C18 Column 30×150 mm 5 um; Mobile Phase A: Water (10 MMOL/L NH4HCO3), Mobile Phase B: ACN; Flow rate: 60 mL/min; Gradient: 25% B to 40% B in 8 min; 220 nm; Rt: 7.58 min) to afford 4-chloro-5-[4-[ethyl (2-ethylpyridin-3-yl)amino]piperidin-1-yl]-2,3-dihydropyridazin-3-one (24.3 mg) as a white solid.

LY and LZ

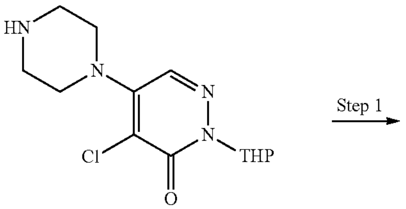

1

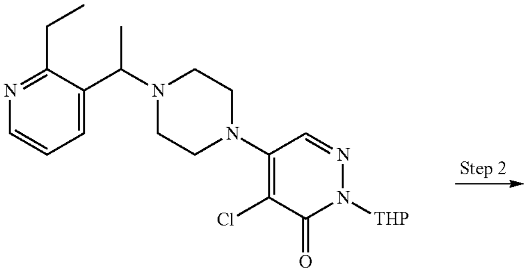

2

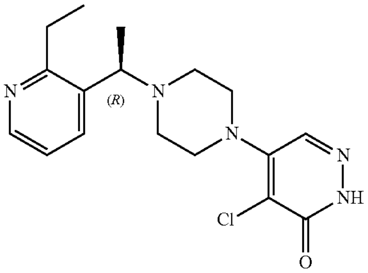

LZ

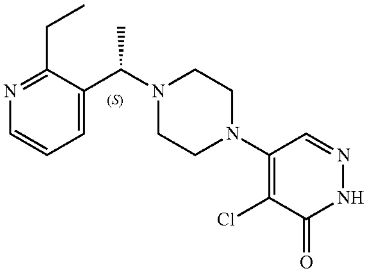

LY

Step 1

4-chloro-5-[4-[1-(2-ethylpyridin-3-yl)ethyl]piperazin-1-yl]-2-(oxan-2-yl)-2,3-dihydropyridazin-3-one To a stirred mixture of 4-chloro-2-(oxan-2-yl)-5-(piperazin-1-yl)-2,3-dihydropyridazin-3-one (100 mg, 0.33 mmol, 1 equiv.) and 3-(1-chloroethyl)-2-ethylpyridine (68.1 mg, 0.40 mmol, 1.20 equiv.) in ACN (10 mL) were added K2CO3 (92.5 mg, 0.67 mmol, 2.0 equiv.) and KI (111.1 mg, 0.67 mmol, 2.00 equiv.) in portions at rt under nitrogen atmosphere. The resulting mixture was stirred for 16 h at 70 degrees C. under nitrogen atmosphere. The reaction was monitored by LCMS. The resulting mixture was filtered, the filter cake was washed with ACN (2×30 mL). The filtrate was concentrated under reduced pressure. The residue was purified by Prep-TLC (CH2Cl2/MeOH 20/1) to afford 4-chloro-5-[4-[1-(2-ethylpyridin-3-yl)ethyl]piperazin-1-yl]-2-(oxan-2-yl)-2,3-dihydropyridazin-3-one (120 mg, 83.00%) as a yellow oil.

Step 2

LY and LZ 4-chloro-5-[4-[(1S)-1-(2-ethylpyridin-3-yl)ethyl]piperazin-1-yl]-2,3-dihydropyridazin-3-one & 4-chloro-5-[4-[(1R)-1-(2-ethylpyridin-3-yl)ethyl]piperazin-1-yl]-2,3-dihydropyridazin-3-one To a stirred solution of 4-chloro-5-[4-[1-(2-ethylpyridin-3-yl)ethyl]piperazin-1-yl]-2-(oxan-2-yl)-2,3-dihydropyridazin-3-one (120 mg, 0.28 mmol, 1 equiv.) in DCM (10 mL) was added TFA (1 mL, 13.46 mmol, 48.46 equiv.) dropwise at rt. The reaction mixture was stirred for 4 h at rt. The reaction was monitored by LCMS. The resulting mixture was concentrated under reduced pressure. The residue was basified to pH=8 with saturated NH4HCO3 (aq.). The resulting mixture was extracted with CH2Cl2(3×100 mL). The combined organic layers were washed with brine (1×50 mL), dried over anhydrous Na2SO4. After filtration, the filtrate was concentrated under reduced pressure. The residue (70 mg) was purified by Chiral-Prep-HPLC with the following conditions (Column: CHIRALPAK IE, 2*25 cm, 5 um; Mobile Phase:MTBE/EtOH=80/20; Flow rate: 20 mL/min; Gradient: 20 B to 20 B in 20 min; 220/254 nm; RT1:12.678; RT2:16.738). 4-chloro-5-[4-[(1S)-1-(2-ethylpyridin-3-yl)ethyl]piperazin-1-yl]-2,3-dihydropyridazin-3-one (9.5 mg, 9.83%) was obtained at 2.544 min as a light yellow solid. 4-chloro-5-[4-[(1R)-1-(2-ethylpyridin-3-yl)ethyl]piperazin-1-yl]-2,3-dihydropyridazin-3-one (14.2 mg) was obtained at 2.984 min as a light yellow solid.

Compound MA

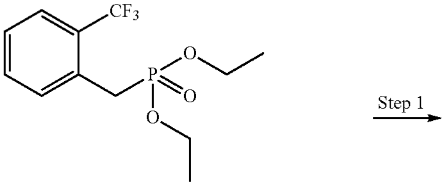

1

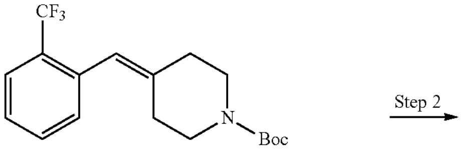

2

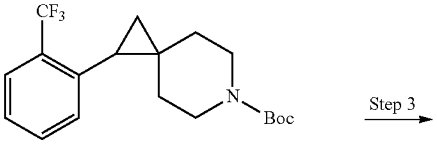

3

-continued

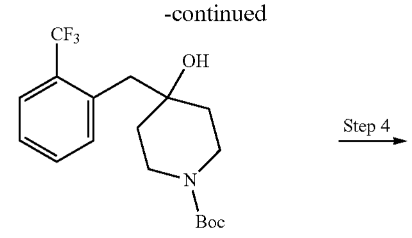

4

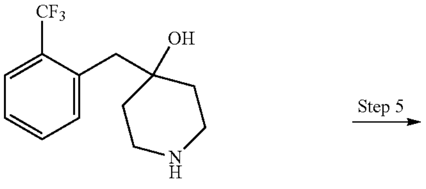

5

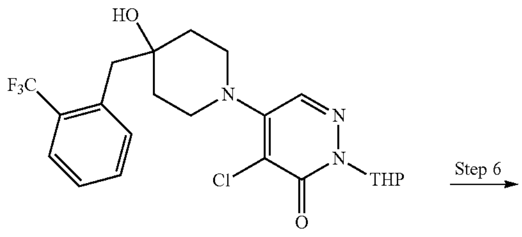

6

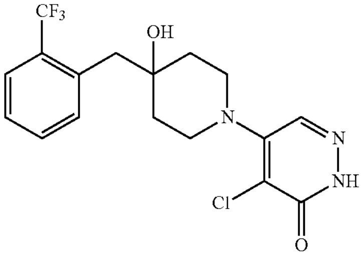

MA

Step 1

Tert-Butyl 4-[[2-(trifluoromethyl)phenyl]methylidene]piperidine-1-carboxylate

To a stirred mixture of diethyl [[2-(trifluoromethyl)phenyl]methyl]phosphonate (800 mg, 2.701 mmol, 1 equiv.) and tert-butyl 4-oxopiperidine-1-carboxylate (645.72 mg, 3.241 mmol, 1.2 equiv.) in THF (20 mL) was added NaH (162.02 mg, 4.051 mmol, 1.50 equiv, 60%) in portions at 0 degrees C. The resulting mixture was stirred for 16 h at room temperature. The reaction was monitored by LCMS. The reaction was quenched with Water at room temperature. The resulting mixture was concentrated under reduced pressure. The residue was purified by silica gel column chromatography, eluted with PE/EtOAc (100:1 to 40:1) to afford tert-butyl 4-[[2-(trifluoromethyl)phenyl]methylidene]piperidine-1-carboxylate (800 mg, 86.77%) as a yellow oil.

Step 2

Tert-Butyl 2-[2-(trifluoromethyl)phenyl]-1-oxa-6-azaspiro[2.5]octane-6-carboxylate To a stirred solution of tert-butyl 4-[[2-(trifluoromethyl)phenyl]methylidene]piperidine-1-carboxylate (800 mg, 2.343 mmol, 1 equiv.) in DCM (30 mL) was added m-CPBA (606.61 mg, 3.515 mmol, 1.50 equiv.) in portions at 0 degrees C. The resulting mixture was stirred for 16 h at room temperature. The reaction was monitored by LCMS. The residue was purified by reverse phase flash with the following conditions (Column:C18,330 g; Mobile Phase A: Water/0.05% TFA, Mobile Phase B:ACN; Flow rate:80 mL/min; Gradient: 70% B to 80% B in 10 min; Detector, 220 nm; Monitor, 254 nm) to afford tert-butyl 2-[2-(trifluoromethyl)phenyl]-1-oxa-6-azaspiro[2.5]octane-6-carboxylate (630 mg, 75.22%) as a yellow oil.

Step 3

Tert-Butyl 4-hydroxy-4-[[2-(trifluoromethyl)phenyl]methyl]piperidine-1-carboxylate To a stirred solution of tert-butyl 2-[2-(trifluoromethyl)phenyl]-1-oxa-6-azaspiro[2.5]octane-6-carboxylate (200 mg, 0.560 mmol, 1 equiv.) in MeOH (10 mL) was added Pd/C (5.96 mg, 0.056 mmol, 0.1 equiv.) at room temperature under hydrogen atmosphere. The resulting mixture was stirred for 4 h at room temperature under hydrogen atmosphere. The reaction was monitored by LCMS. The resulting mixture was filtered, the filter cake was washed with MeOH (3×5 mL). The filtrate was concentrated under reduced pressure. The residue was purified by reverse phase flash with the following conditions (Column: XBridge Prep C18 OBD Column 19×150 mm 5 um; Mobile Phase A: Water (10 MMOL/L NH4HCO3), Mobile Phase B: ACN; Flow rate: 60 mL/min; Gradient: 18% B to 38% B in 7 min; 254/220 nm; Rt: 6.25 min) to afford tert-butyl 4-hydroxy-4-[[2-(trifluoromethyl)phenyl]methyl]piperidine-1-carboxylate (160 mg, 79.55%) as a yellow oil.

Step 4

4-[[2-(trifluoromethyl)phenyl]methyl]piperidin-4-ol

To a stirred solution of tert-butyl 4-hydroxy-4-[[2-(trifluoromethyl)phenyl]methyl]piperidine-1-carboxylate (80 mg, 0.223 mmol, 1 equiv.) in DCM (4 mL) was added TFA (1 mL, 13.463 mmol, 60.48 equiv.) at room temperature. The resulting mixture was stirred for 2 h at room temperature. The reaction was monitored by LCMS. The resulting mixture was concentrated under reduced pressure. The mixture was basified to pH 8 with saturated NaHCO3 (aq.). The resulting mixture was concentrated under reduced pressure. This resulted in 4-[[2-(trifluoromethyl)phenyl]methyl]piperidin-4-ol (50 mg, 86.63%) as a yellow oil.

Step 5

4-chloro-5-(4-hydroxy-4-[[2-(trifluoromethyl)phenyl]methyl]piperidin-1-yl)-2-(oxan-2-yl)-2,3-dihydropyridazin-3-one To a stirred solution of 4-[[2-(trifluoromethyl)phenyl]methyl]piperidin-4-ol (50 mg, 0.193 mmol, 1 equiv.) in DIEA (0.5 mL) was added 4,5-dichloro-2-(oxan-2-yl)-2,3-dihydropyridazin-3-one (72.05 mg, 0.289 mmol, 1.5 equiv.) at room temperature. The resulting mixture was stirred for 2 h at 100 degrees C. The reaction was monitored by LCMS. The mixture was allowed to cool down to room temperature. The residue was purified by Prep-TLC (PE/EtOAc 1:1) to afford 4-chloro-5-(4-hydroxy-4-[[2-(trifluoromethyl)phenyl]methyl]piperidin-1-yl)-2-(oxan-2-yl)-2,3-dihydropyridazin-3-one (60 mg, 65.93%) as a yellow solid.

Step 6

MA 4-chloro-5-(4-hydroxy-4-[[2-(trifluoromethyl)phenyl]methyl]piperidin-1-yl)-2-(oxan-2-yl)-2,3-dihydropyridazin-3-one To a stirred solution of 4-[[2-(trifluoromethyl)phenyl]methyl]piperidin-4-ol (50 mg, 0.193 mmol, 1 equiv.) in DIEA (0.5 mL) was added 4,5-dichloro-2-(oxan-2-yl)-2,3-dihydropyridazin-3-one (72.05 mg, 0.289 mmol, 1.5 equiv.) at room temperature. The resulting mixture was stirred for 2 h at 100 degrees C. The reaction was monitored by LCMS. The mixture was allowed to cool down to room temperature. The residue was purified by Prep-TLC (PE/EtOAc 1:1) to afford 4-chloro-5-(4-hydroxy-4-[[2-(trifluoromethyl)phenyl]methyl]piperidin-1-yl)-2-(oxan-2-yl)-2,3-dihydropyridazin-3-one (60 mg, 65.93%) as a yellow solid.

MB and MC

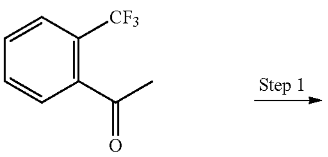

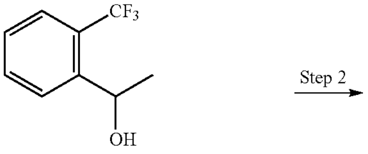

1

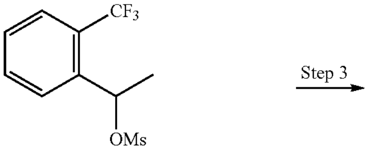

2

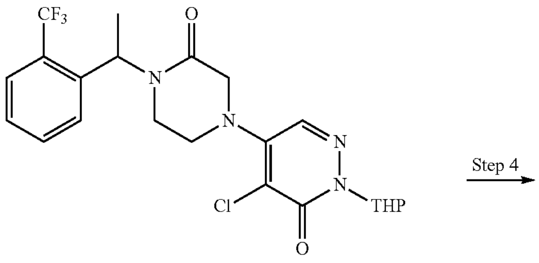

3

-continued

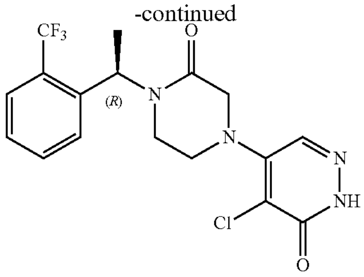

MC

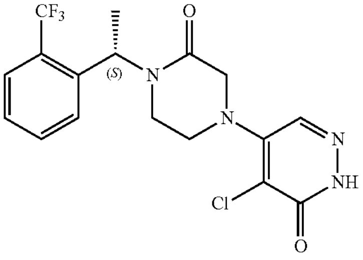

MB

Step 1

1-[2-(trifluoromethyl)phenyl]ethan-1-ol

To a stirred solution of 1-[2-(trifluoromethyl)phenyl]ethan-1-one (5 g, 26.575 mmol, 1 equiv.) in MeOH (15 mL) was added NaBH4 (2.01 g, 53.128 mmol, 2.00 equiv.) in portions at 0 degrees C. The resulting mixture was stirred for 3 h at room temperature. The reaction was monitored by TLC PE/EA (5:1). The resulting mixture was concentrated under vacuum. The residue was purified by silica gel column chromatography, eluted with PE/EtOAc (50:1 to 5:1) to afford 1-[2-(trifluoromethyl)phenyl]ethan-1-ol (4.6 g, 91.02%) as a light yellow oil.

Step 2

1-[2-(trifluoromethyl)phenyl]ethyl methanesulfonate

To a stirred mixture of 1-[2-(trifluoromethyl)phenyl]ethan-1-ol (1.3 g, 6.836 mmol, 1 equiv.) and Et3N (1.38 g, 13.638 mmol, 1.99 equiv.) in DCM (15 mL) was added MsCl (939.71 mg, 8.203 mmol, 1.2 equiv.) dropwise at 0 degrees C. The resulting mixture was stirred for 2 h at room temperature. The reaction was monitored by TLC PE/EA (5/1). The resulting mixture was concentrated under reduced pressure. The residue was purified by silica gel column chromatography, eluted with PE/EtOAc (20:1 to 5:1) to afford 1-[2-(trifluoromethyl)phenyl]ethyl methanesulfonate (1.3 g, 70.89%) as a colorless oil.

Step 3

4-chloro-2-(oxan-2-yl)-5-(3-oxo-4-[1-[2-(trifluoromethyl)phenyl]ethyl]piperazin-1-yl)-2,3-dihydropyridazin-3-one To a stirred mixture of 4-chloro-2-(oxan-2-yl)-5-(3-oxopiperazin-1-yl)-2,3-dihydropyridazin-3-one (500 mg, 1.599 mmol, 1 equiv.) and 1-[2-(trifluoromethyl)phenyl]

ethyl methanesulfonate (857.71 mg, 3.197 mmol, 2 equiv.) in CH3CN (7 mL) was added t-BuONa (230.46 mg, 2.398 mmol, 1.5 equiv.) at room temperature under nitrogen atmosphere. The final reaction mixture was irradiated with microwave radiation for 3 h at 110 degrees C. The reaction was monitored by LCMS. The resulting mixture was filtered, the filter cake was washed with CH3CN (3×200 mL). The filtrate was concentrated under reduced pressure. The residue was purified by reverse flash chromatography with the following conditions: column, C18 silica gel; mobile phase, ACN in water, 45% to 75% gradient in 20 min; detector, UV 254 nm to afford 4-chloro-2-(oxan-2-yl)-5-(3-oxo-4-[1-[2-(trifluoromethyl)phenyl]ethyl]piperazin-1-yl)-2,3-dihydropyridazin-3-one (200 mg, 25.80%) as yellow oil.

Step 4

MB and MC 4-chloro-5-[3-oxo-4-[(1R)-1-[2-(trifluoromethyl)phenyl]ethyl]piperazin-1-yl]-2,3-dihydropyridazin-3-one & 4-chloro-5-[3-oxo-4-[(1S)-1-[2-(trifluoromethyl)phenyl]ethyl]piperazin-1-yl]-2,3-dihydropyridazin-3-one To a mixture of 4-chloro-2-(oxan-2-yl)-5-(3-oxo-4-[1-[2-(trifluoromethyl)phenyl]ethyl]piperazin-1-yl)-2,3-dihydropyridazin-3-one (200 mg, 0.412 mmol, 1 equiv.) in DCM (6 mL) were added TFA (2.00 mL, 17.540 mmol, 65.28 equiv.) at room temperature. The resulting mixture was stirred for 2 h at RT. The reaction was monitored by LCMS. The crude product (100 mg) was purified by Prep-HPLC with the following conditions (Column: XBridge Prep OBD C18 Column 30×150 mm 5 um; Mobile Phase A: Water (10 MMOL/L NH4HCO3), Mobile Phase B: ACN; Flow rate: 60 mL/min; Gradient: 17% B to 32% B in 16 min; 220 nm; Rt: 14.23 min). The crude product (50 mg) was purified by Chiral-Prep-HPLC with the following conditions (Column: CHIRALPAK IG UL001, 20*250 mm, 5 um; Mobile Phase A:Hex—HPLC, Mobile Phase B: EtOH—HPLC; Flow rate: 20 mL/min; Gradient: 50 B to 50 B in 20 min; 220/254 nm; RT1:13.866; RT2:16.935). 4-chloro-5-[3-oxo-4-[(1R)-1-[2-(trifluoromethyl)phenyl]ethyl]piperazin-1-yl]-2,3-dihydropyridazin-3-one (29.9 mg) was obtained at 13.866 min as a white solid. 4-chloro-5-[3-oxo-4-[(1S)-1-[2-(trifluoromethyl)phenyl]ethyl]piperazin-1-yl]-2,3-dihydropyridazin-3-one (29.2 mg) was obtained at 16.935 min as a white solid.

MD and ME

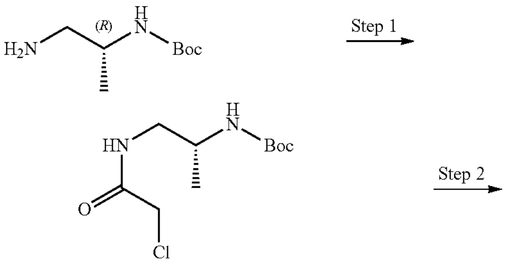

1

-continued

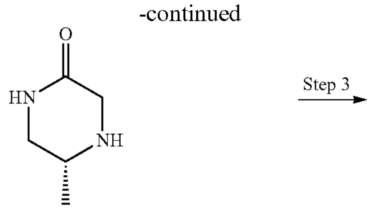

2

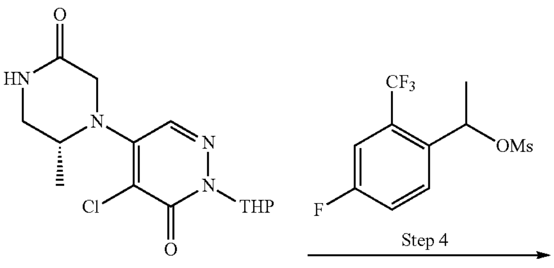

3

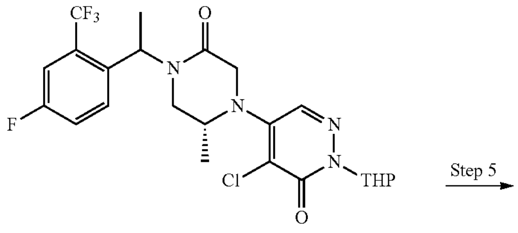

4

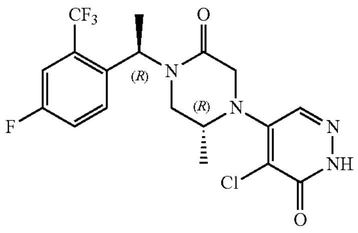

MD

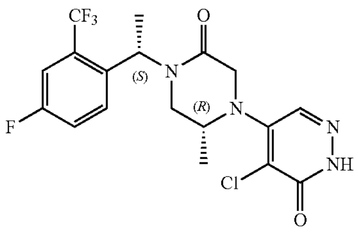

ME

Step 1

Tert-Butyl N-[(2R)-1-(2-chloroacetamido)propan-2-yl]carbamate

To a stirred solution of tert-butyl N-[(2R)-1-aminopropan-2-yl]carbamate (3 g, 17.217 mmol, 1 equiv.) in EA (50 mL) was added the solution of Na2CO3 (3649.65 mg, 34.434 mmol, 2 equiv.) in H2O (10 mL) at room temperature. Then the solution of 2-chloroacetyl chloride (3.89 g, 34.434 mmol, 2 equiv.) in EA (10 mL) was added dropwise at 0 degrees C. The resulting mixture was stirred for 2 h at room temperature. The reaction was monitored by LCMS. The reaction was quenched with Water at room temperature. The resulting mixture was extracted with EtOAc (3×100 mL). The combined organic layers were washed with brine (1×100 mL), dried over anhydrous Na2SO4. After filtration, the filtrate was concentrated under reduced pressure. This resulted in tert-butyl N-[(2R)-1-(2-chloroacetamido)propan-2-yl]carbamate (4.5 g, crude) as a white solid.

Step 2

(5R)-5-methylpiperazin-2-one

To a stirred solution of tert-butyl N-[(2R)-1-(2-chloroacetamido)propan-2-yl]carbamate (4.5 g, 17.948 mmol, 1 equiv.) in DCM (30 mL) was added the solution of TFA (10 mL, 134.630 mmol, 7.50 equiv.) in DCM (10 mL) dropwise at 0 degrees C. The resulting mixture was stirred for 2 h at room temperature. The reaction was monitored by LCMS. The resulting mixture was concentrated under reduced pressure. To the above mixture was added K2CO3 (4.96 g, 35.897 mmol, 2 equiv.) and KI (2.98 g, 17.948 mmol, 1 equiv.) at room temperature. The resulting mixture was stirred for additional 16 h at 80 degrees C. The reaction was monitored by LCMS. The resulting mixture was concentrated under reduced pressure. The residue was purified by silica gel column chromatography, eluted with CH2Cl2/MeOH (20:1 to 10:1) to afford (5R)-5-methylpiperazin-2-one (2.5 g, crude) as a yellow oil.

Step 3

4-chloro-5-[(2R)-2-methyl-5-oxopiperazin-1-yl]-2-(oxan-2-yl)-2,3-dihydropyridazin-3-one To a stirred solution of (5R)-5-methylpiperazin-2-one (2.5 g, 21.901 mmol, 1 equiv.) in DIEA (2 mL) was added 4,5-dichloro-2-(oxan-2-yl)-2,3-dihydropyridazin-3-one (5.46 g, 21.901 mmol, 1 equiv.) at room temperature. The resulting mixture was stirred for 16 h at 100 degrees C. The reaction was monitored by LCMS. The mixture was allowed to cool down to room temperature. The residue was purified by reverse phase flash with the following conditions (Column:C18,330 g; Mobile Phase A: Water/0.05% NH4HCO3, Mobile Phase B:ACN; Flow rate:80 mL/min; Gradient: 20% B to 30% B in 10 min; Detector, 220 nm; Monitor, 254 nm) to afford 4-chloro-5-[(2R)-2-methyl-5-oxopiperazin-1-yl]-2-(oxan-2-yl)-2,3-dihydropyridazin-3-one (600 mg, 8.38%) as a yellow solid.

Step 4

4-chloro-5-[(2R)-4-[1-[4-fluoro-2-(trifluoromethyl)phenyl]ethyl]-2-methyl-5-oxopiperazin-1-yl]-2-(oxan-2-yl)-2,3-dihydropyridazin-3-one To a stirred mixture of 4-chloro-5-[(2R)-2-methyl-5-oxopiperazin-1-yl]-2-(oxan-2-yl)-2,3-dihydropyridazin-3-one (500 mg, 1.530 mmol, 1 equiv.) and 1-[4-fluoro-2-(trifluoromethyl)phenyl]ethyl methanesulfonate (656.96 mg, 2.295 mmol, 1.5 equiv.) in ACN (20 mL) was added t-BuONa (220.57 mg, 2.295 mmol, 1.5 equiv.) at room temperature under nitrogen atmosphere. The final reaction mixture was irradiated with microwave radiation for 3 h at 110 degrees C. The reaction was monitored by LCMS. The mixture was allowed to cool down to room temperature. The resulting mixture was concentrated under reduced pressure. The residue was purified by reverse phase flash with the following conditions (Column:C18,330 g; Mobile Phase A: Water/0.05% NH4HCO3, Mobile Phase B:ACN; Flow rate: 80 mL/min; Gradient: 55% B to 75% B in 15 min; Detector, 220 nm; Monitor, 254 nm) to afford 4-chloro-5-[(2R)-4-[1-[4-fluoro-2-(trifluoromethyl)phenyl]ethyl]-2-methyl-5-oxopiperazin-1-yl]-2-(oxan-2-yl)-2,3-dihydropyridazin-3-one (120 mg, 15.17%) as a yellow solid.

Step 5

MD and ME 4-chloro-5-[(2R)-4-[(1S)-1-[4-fluoro-2-(trifluoromethyl)phenyl]ethyl]-2-methyl-5-oxopiperazin-1-yl]-2,3-dihydropyridazin-3-one & 4-chloro-5-[(2R)-4-[(1R)-1-[4-fluoro-2-(trifluoromethyl)phenyl]ethyl]-2-methyl-5-oxopiperazin-1-yl]-2,3-dihydropyridazin-3-one To a stirred solution of 4-chloro-5-[(2R)-4-[1-[4-fluoro-2-(trifluoromethyl)phenyl]ethyl]-2-methyl-5-oxopiperazin-1-yl]-2-(oxan-2-yl)-2,3-dihydropyridazin-3-one (120 mg, 0.232 mmol, 1 equiv.) in DCM (8 mL) was added TFA (2 mL, 26.926 mmol, 115.99 equiv.) at room temperature. The resulting mixture was stirred for 1 h at room temperature. The reaction was monitored by LCMS. The resulting mixture was concentrated under reduced pressure. The residue was basified to pH 8 with saturated NaHCO3 (aq.). The resulting mixture was concentrated under reduced pressure. The residue was purified by reverse phase flash with the following conditions (Column: XBridge Prep C18 OBD Column 19×150 mm 5 um; Mobile Phase A: Water (10 MMOL/L NH4HCO3), Mobile Phase B: ACN; Flow rate: 60 mL/min; Gradient: 22% B to 51% B in 7 min; 254/220 nm; Rt: 6.4 min) to afford 4-chloro-5-[(2R)-4-[(1S)-1-[4-fluoro-2-(trifluoromethyl)phenyl]ethyl]-2-methyl-5-oxopiperazin-1-yl]-2,3-dihydropyridazin-3-one (16.3 mg, 16.22%) as a white solid and 4-chloro-5-[(2R)-4-[(1R)-1-[4-fluoro-2-(trifluoromethyl)phenyl]ethyl]-2-methyl-5-oxopiperazin-1-yl]-2,3-dihydropyridazin-3-one (18.6 mg, 18.51%) as a white solid.

Compound MF

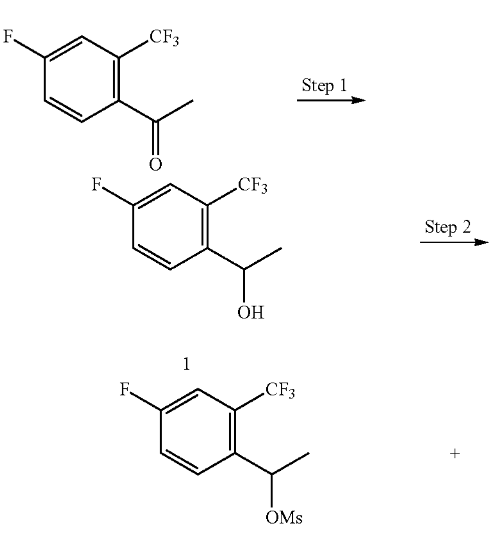

1

2

-continued

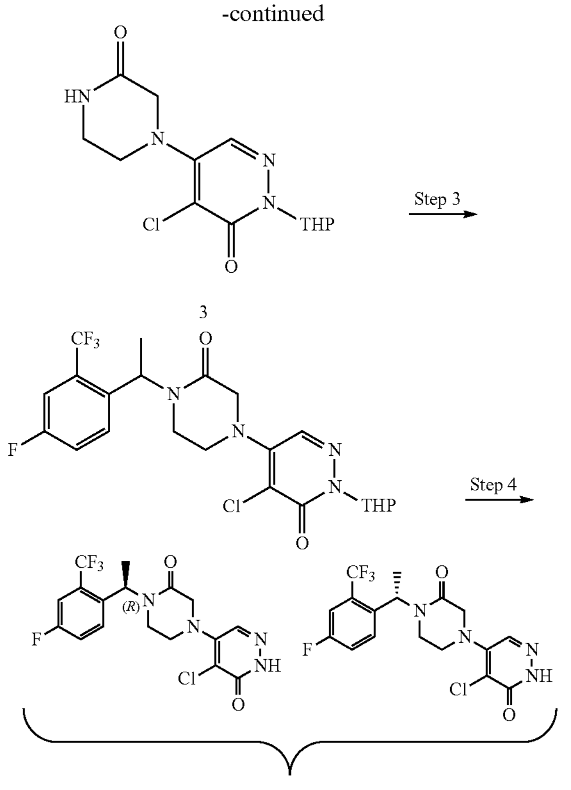

3

MF

Step 1

1-[4-fluoro-2-(trifluoromethyl)phenyl]ethan-1-ol

To a stirred solution of 4-fluoro-2-(trifluoromethyl)benzaldehyde (3 g, 15.616 mmol, 1 equiv.) in THF (50 mL) was added MeMgBr in Et2O (3 mol/L, 30 ml) dropwise at −30 degrees C. under nitrogen atmosphere. The resulting mixture was stirred for 2 h at room temperature under nitrogen atmosphere. The reaction was monitored by TLC. The reaction was quenched with sat. NH4Cl (aq.) at 0 degrees C. The resulting mixture was extracted with EtOAc (50 mL). The combined organic layers were washed with brine (3×50 mL), dried over anhydrous Na2SO4. After filtration, the filtrate was concentrated under reduced pressure. The resulting mixture was used in the next step directly without further purification.

Step 2

1-[4-fluoro-2-(trifluoromethyl)phenyl]ethyl methanesulfonate

To a stirred solution of 1-[4-fluoro-2-(trifluoromethyl)phenyl]ethan-1-ol (3 g, 14.412 mmol, 1 equiv.) and Et3N (2.92 g, 28.825 mmol, 2 equiv.) in DCM (60 mL) was added MsCl (2.48 g, 21.618 mmol, 1.5 equiv.) dropwise at 0 degrees C. under nitrogen atmosphere. The resulting mixture was stirred for 2 h at room temperature under nitrogen atmosphere. The reaction was monitored by TLC. The reaction was quenched by the addition of sat. NH4Cl (aq.) (50 mL) at 0 degrees C. The resulting mixture was extracted with EtOAc (50 mL). The combined organic layers were washed with brine (3×100 mL), dried over anhydrous Na2SO4. After filtration, the filtrate was concentrated under reduced pressure to afford 1-[4-fluoro-2-(trifluoromethyl)phenyl]ethyl methanesulfonate (1.6 g, 38.78%) as a light yellow oil.

Step 3

4-chloro-5-(4-[1-[4-fluoro-2-(trifluoromethyl)phenyl]ethyl]-3-oxopiperazin-1-yl)-2-(oxan-2-yl)-2,3-dihydropyridazin-3-one To a stirred solution of 4-chloro-2-(oxan-2-yl)-5-(3-oxopiperazin-1-yl)-2,3-dihydropyridazin-3-one (800 mg, 2.558 mmol, 1 equiv.) and 1-[4-fluoro-2-(trifluoromethyl)phenyl]ethyl methanesulfonate (878.63 mg, 3.070 mmol, 1.2 equiv.) in ACN (8 mL) was added sodium 2,2-dimethylpropan-1-olate (563.43 mg, 5.116 mmol, 2 equiv.) in portions at room temperature under nitrogen atmosphere. The final reaction mixture was irradiated with microwave radiation for 3 h at 110 degrees C. The reaction was monitored by LCMS. The mixture was allowed to cool down to room temperature. The resulting mixture was extracted with EtOAc (20 mL). The combined organic layers were washed with brine (3×10 mL), dried over anhydrous Na2SO4. After filtration, the filtrate was concentrated under reduced pressure. The resulting mixture was used in the next step directly without further purification.

Step 4

Compound MF 4-chloro-5-[4-[(1R)-1-[4-fluoro-2-(trifluoromethyl)phenyl]ethyl]-3-oxopiperazin-1-yl]-2,3-dihydropyridazin-3-one & 4-chloro-5-[4-[(1S)-1-[4-fluoro-2-(trifluoromethyl)phenyl]ethyl]-3-oxopiperazin-1-yl]-2,3-dihydropyridazin-3-one To a stirred solution of 4-chloro-5-(4-[1-[4-fluoro-2-(trifluoromethyl)phenyl]ethyl]-3-oxopiperazin-1-yl)-2-(oxan-2-yl)-2,3-dihydropyridazin-3-one (110 mg, 0.219 mmol, 1 equiv.) in DCM (10 mL) was added TFA (3 mL) in portions at room temperature under nitrogen atmosphere. The resulting mixture was stirred for 3 h at room temperature under nitrogen atmosphere. The reaction was monitored by LCMS. The resulting mixture was concentrated under vacuum. The residue was basified to pH 8 with saturated NaHCO3 (aq.). The resulting mixture was extracted with EtOAc (20 mL). The combined organic layers were washed with brine (3×20 mL), dried over anhydrous Na2SO4. After filtration, the filtrate was concentrated under reduced pressure. The crude product (50 mg) was purified by CHIRAL-HPLC with the following conditions (Column: XBridge Prep OBD C18 Column 30×150 mm 5 um; Mobile Phase A: Water (10 MMOL/L NH4HCO3), Mobile Phase B: ACN; Flow rate: 60 mL/min; Gradient: 20% B to 32% B in 16 min; 220 nm; Rt: 14.27 min) to afford 4-chloro-5-[4-[(1R)-1-[4-fluoro-2-(trifluoromethyl)phenyl]ethyl]-3-oxopiperazin-1-yl]-2,3-dihydropyridazin-3-one (6.0 mg, 6.55%) as a white solid and 4-chloro-5-[4-[(1S)-1-[4-fluoro-2-(trifluoromethyl)phenyl]ethyl]-3-oxopiperazin-1-yl]-2,3-dihydropyridazin-3-one (6.2 mg, 6.77%) as a white solid.

MG

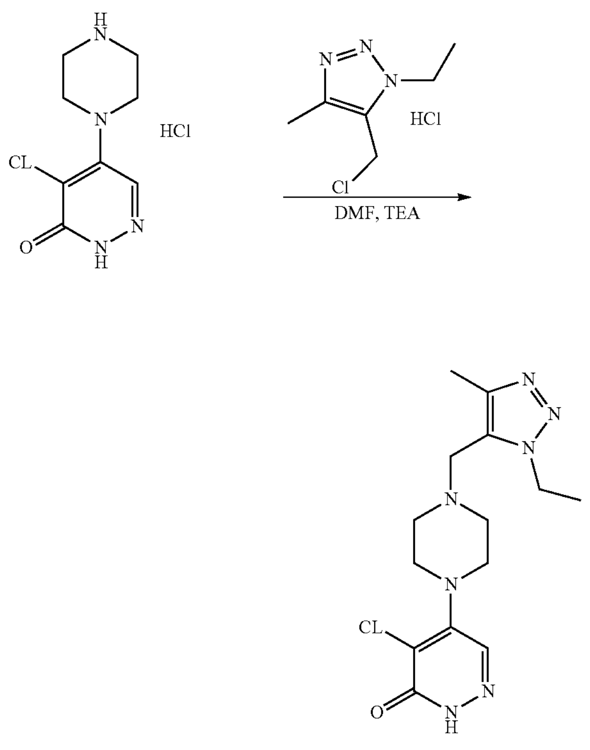

A mixture of 4-chloro-5-(piperazin-1-yl)-2H-pyridazin-3-one hydrochloride (100 mg, 0.398 mmol, 1 equiv.), 5-(chloromethyl)-1-ethyl-4-methyl-1,2,3-triazole hydrochloride (100 mg, 0.51 mmol, 1.281 equiv.) and Triethylamine (0.216 g, 0.3 mL, 2.135 mmol, 5.36 equiv.) in dimethyl-formamide (2 mL, 0.199 M, 20 Vols) was stirred at RT for 19 hr. Diluted with water then extracted with DCM. Dried organics over Na2SO4, filtered and concentrated in vacuo onto SiO2. Purified via flash chromatography (ISCO 4 g, 0-20% MeOH/DCM, then ISCO 4 g, 0-100% EtOAc/DCM followed by 0-20% MeOH/EtOAc, then ISCO 4 g, 0-100% Acetone/EtOAc). Obtained 4-chloro-5-(4-[(3-ethyl-5-methyl-1,2,3-triazol-4-yl)methyl]piperazin-1-yl)-2H-pyridazin-3-one (7.5 mg, 0.022 mmol, Yield 5.575%) as a white solid.

Calc'd $[M+H]^+$ for C14H21ClN7O=338.1, found 338.4.

1H NMR (CHLOROFORM-d) δ: 10.40-10.63 (m, 1H), 7.61 (s, 1H), 4.39 (q, J=7.3 Hz, 2H), 3.56 (s, 2H), 3.38-3.46 (m, 4H), 2.53-2.63 (m, 4H), 2.31 (s, 3H), 1.51-1.56 (m, 3H)

MH

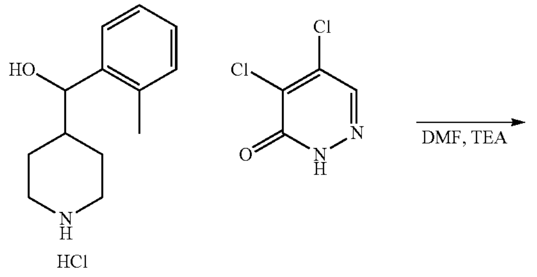

-continued

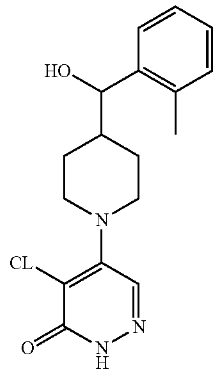

A mixture of (2-methylphenyl)(piperidin-4-yl)methanol hydrochloride (0.1 g, 0.414 mmol, 1 equiv.), 4,5-dichloro-2H-pyridazin-3-one (0.15 g, 0.909 mmol, 2.198 equiv.) and Triethylamine (0.216 g, 0.3 mL, 2.135 mmol, 5.161 equiv.) in dimethyl-formamide (2 mL, 0.207 M, 20 Vols) was stirred at 100° C. for 19 hr. Diluted with water and extracted with DCM. Dried organics over Na2SO4, filtered and concentrated in vacuo onto SiO2. Purified via flash chromatography (ISCO 4 g, 0-20% MeOH/DCM). Impure, so purified again (ISCO 4 g, 0-100% EtOAc/DCM followed by 0-20% EtOAc/MeOH). Obtained 4-chloro-5-(4-[hydroxy(2-methylphenyl)methyl]piperidin-1-yl)-2H-pyridazin-3-one (13.1 mg, 0.039 mmol, Yield 9.487%) as a yellow solid.

Calc'd $[M+H]^+$ for C17H21ClN3O2=334.1, found 334.3.

1H NMR (DMSO-d6) δ: 12.83 (s, 1H), 7.80 (s, 1H), 7.37 (d, J=7.6 Hz, 1H), 7.01-7.20 (m, 3H), 5.07 (br d, J=4.4 Hz, 1H), 4.47-4.64 (m, 1H), 3.67-3.86 (m, 2H), 2.80-2.93 (m, 2H), 2.28 (s, 3H), 1.58-1.89 (m, 2H), 1.25-1.52 (m, 3H)

MI

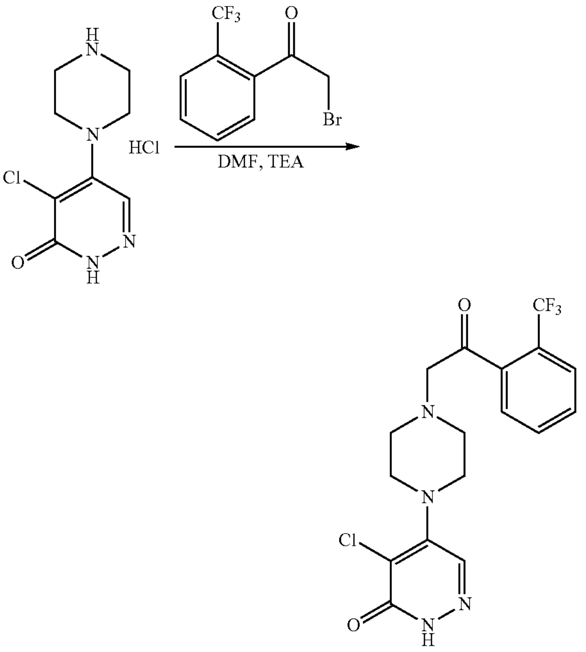

A mixture of 4-chloro-5-(piperazin-1-yl)-2H-pyridazin-3-one hydrochloride (168 mg, 0.669 mmol, 1.122 equiv.), 2-bromo-1-[2-(trifluoromethyl)phenyl]ethanone (159.2 mg, 0.1 mL, 0.596 mmol, 1 equiv.) and Triethylamine (0.216 g, 0.3 mL, 2.135 mmol, 3.581 equiv.) in dimethyl-formamide (2 mL, 0.298 M, 12.563 Vols) was stirred at RT for 16 hr. Diluted with water and extracted with DCM (3×). Dried organics over Na2SO4, filtered and concentrated in vacuo onto SiO2. Purified via flash chromatography (ISCO 4 g, 0-20% MeOH/DCM, then ISCO 4 g, 0-100% EtOAc/Heptane followed by 0-20% MeOH/EtOAc). Obtained 4-chloro-5-(4-(2-oxo-2-[2-(trifluoromethyl)phenyl]ethyl)piperazin-1-yl)-2H-pyridazin-3-one (5.4 mg, 0.013 mmol, Yield 2.26%) as a yellowish solid.

Calc'd $[M+H]^+$ for C17H17ClF3N4O2=401.1, found 401.4.

1H NMR (CHLOROFORM-d) δ: 10.25 (br s, 1H), 7.71-7.76 (m, 1H), 7.56-7.67 (m, 3H), 7.40-7.45 (m, 1H), 3.75 (s, 2H), 3.47-3.56 (m, 4H), 2.75-2.85 (m, 4H)

MJ

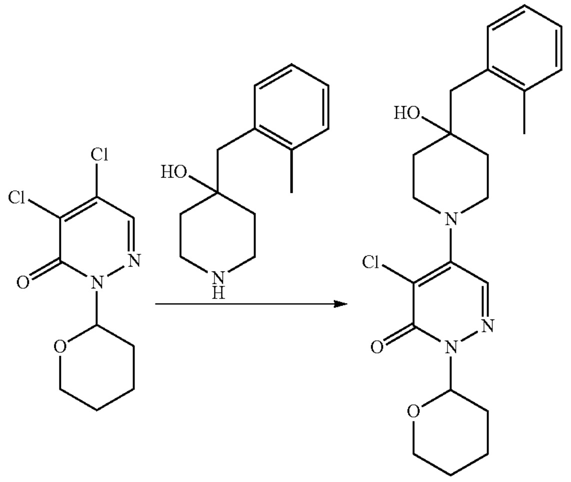

A mixture of 4-[(2-methylphenyl)methyl]piperidin-4-ol hydrochloride (250 mg, 1.034 mmol, 1 equiv.), 4,5-dichloro-2-(oxan-2-yl)pyridazin-3-one (0.35 g, 1.405 mmol, 1.359 equiv.) and Triethylamine (0.36 g, 0.5 mL, 3.558 mmol, 3.44 equiv.) Triethylamine (0.36 g, 0.5 mL, 3.558 mmol, 3.44 equiv.) in ethanol (5 mL, 0.207 M, 20 Vols) was stirred at 60° C. for 16 hr. Concentrated in vacuo onto SiO2 and purified via flash chromatography (ISCO 12 g, 0-100% EtOAc/Heptane). Obtained 4-chloro-5-(4-hydroxy-4-[(2-methylphenyl)methyl]piperidin-1-yl)-2-(oxan-2-yl) pyridazin-3-one (303 mg, 0.725 mmol, Yield 70.111%) as a yellowish solid.

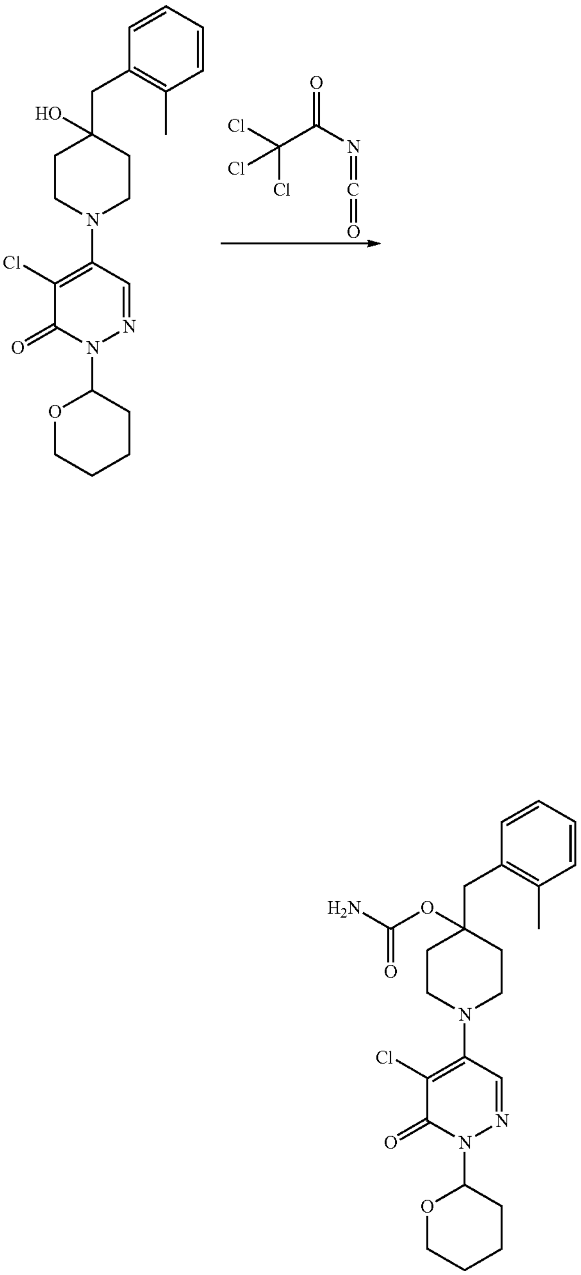

A 1-dram vial was charged with 4-chloro-5-(4-hydroxy-4-[(2-methylphenyl)methyl]piperidin-1-yl)-2-(oxan-2-yl) pyridazin-3-one (46 mg, 0.11 mmol, 1 equiv.) and DCM (0.5 ML, 0.22 M, 10.87 Vols). Cooled in an ice/water bath and added trichloroethanecarbonyl isocyanate (0.032 g, 20 μL, 0.168 mmol, 1.525 equiv.). Stirred at RT for 1.5 hr. Concentrated in vacuo, then charged with methanol (0.5 mL, 0.22 M, 10.87 Vols). Added Potassium carbonate (66 mg, 0.478 mmol, 4.339 equiv.) then stirred at RT for 17 hr. Concentrated in vacuo onto SiO2 and purified via flash chromatography (ISCO 12 g, 0-100% EtOAc/Heptane). Obtained 1-[5-chloro-1-(oxan-2-yl)-6-oxopyridazin-4-yl]-4-[(2-methylphenyl)methyl]piperidin-4-yl carbamate (28.1 mg, 0.061 mmol, Yield 55.385%) as a white solid.

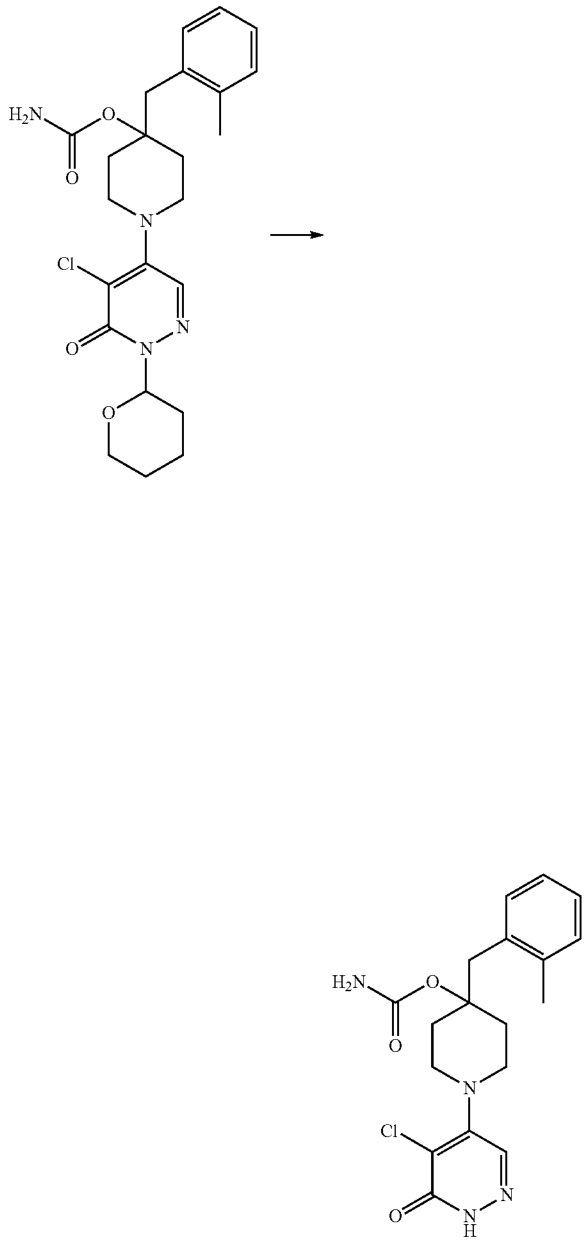

A mixture of 1-[5-chloro-1-(oxan-2-yl)-6-oxopyridazin-4-yl]-4-[(2-methylphenyl)methyl]piperidin-4-yl carbamate (28.1 mg, 0.061 mmol, 1 equiv.) in dichloromethane (0.5 mL, 0.122 M, 17.794 Vols) was charged with Trifluoroacetic acid (0.149 g, 0.1 mL, 1.307 mmol, 21.436 equiv.) and stirred at RT for 2 hr. Poured directly onto SiO2 and purified via flash chromatography (ISCO 12 g, 0-20% MeOH/DCM, then ISCO 4 g, 0-100% EtOAc/Heptane followed by 0-20% MeOH/EtOAc). Obtained 1-(5-chloro-6-oxo-1H-pyridazin-4-yl)-4-[(2-methylphenyl)methyl]piperidin-4-yl carbamate (8.9 mg, 0.024 mmol, Yield 38.743%) as a white solid.

Calc'd $[M+H]^+$ for C18H22ClN4O3=377.1, found 337.4.

1H NMR (CHLOROFORM-d) δ: 10.15 (br s, 1H), 7.60 (s, 1H), 7.09-7.21 (m, 4H), 4.65 (br s, 2H), 3.64 (br d, J=12.7 Hz, 2H), 3.36 (s, 2H), 3.17-3.28 (m, 2H), 2.45 (br d, J=12.3 Hz, 2H), 2.37 (s, 3H), 1.77 (td, J=13.2, 4.4 Hz, 2H)

MK

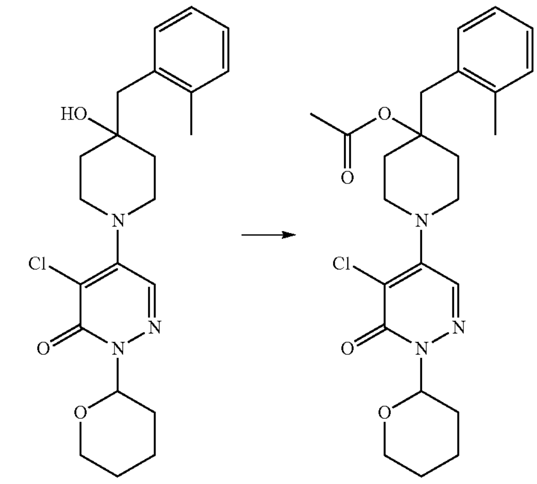 [SMILES: Cc1ccccc1CC1(O)CCN(c2cnn(C3CCCCO3)c(=O)c2Cl)CC1 ; CC(=O)OC1(Cc2ccccc2C)CCN(c2cnn(C3CCCCO3)c(=O)c2Cl)CC1]

A mixture of 4-chloro-5-(4-hydroxy-4-[(2-methylphenyl)methyl]piperidin-1-yl)-2-(oxan-2-yl)pyridazin-3-one (49.8 mg, 0.119 mmol, 1 equiv.) in Acetic anhydride (0.119 g, 0.11 mL, 1.164 mmol, 9.766 equiv.) and Triethylamine (0.122 g, 0.17 mL, 1.21 mmol, 10.151 equiv.) was charged with 4-(Dimethylamino)pyridine (1 mg, 0.008 mmol, 0.069 equiv.) and stirred at RT for 18 hr. Concentrated in vacuo onto SiO2 and purified via flash chromatography (ISCO 12 g, 0-20% EtOAc/Heptane) to provide 1-[5-chloro-1-(oxan-2-yl)-6-oxopyridazin-4-yl]-4-[(2-methylphenyl)methyl]piperidin-4-yl acetate as an orange oil.

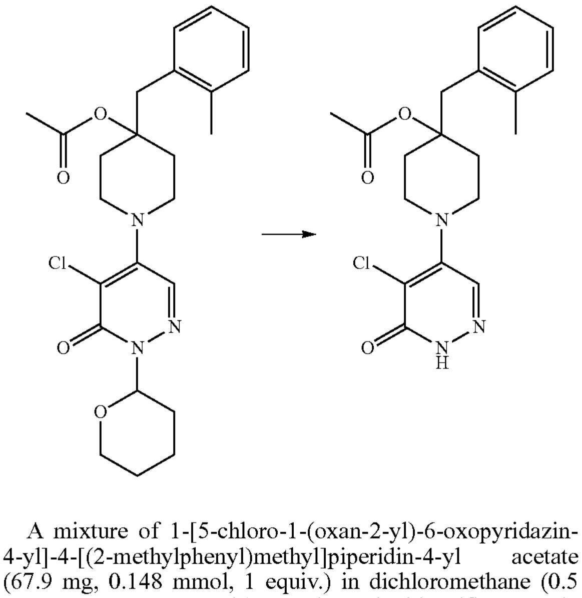

A mixture of 1-[5-chloro-1-(oxan-2-yl)-6-oxopyridazin-4-yl]-4-[(2-methylphenyl)methyl]piperidin-4-yl acetate (67.9 mg, 0.148 mmol, 1 equiv.) in dichloromethane (0.5 mL, 0.295 M, 7.364 Vols) was charged with Trifluoroacetic acid (0.149 g, 0.1 mL, 1.307 mmol, 8.852 equiv.) and stirred at RT for 2 hr. Loaded directly onto SiO2 and purified via flash chromatography (ISCO 12 g, 0-20% MeOH/EtOAc). Obtained 1-(5-chloro-6-oxo-1H-pyridazin-4-yl)-4-[(2-methylphenyl)methyl]piperidin-4-yl acetate (20.7 mg, 0.055 mmol, Yield 37.309%) as a white solid.

Calc'd $[M+H]^+$ for C19H23ClN3O3=376.1, found 376.4.

1H NMR (CHLOROFORM-d) δ: 10.36 (br s, 1H), 7.61 (s, 1H), 7.04-7.25 (m, 4H), 3.65 (br d, J=12.8 Hz, 2H), 3.35

(s, 2H), 3.13-3.26 (m, 2H), 3.09-3.11 (m, 1H), 2.46 (br d, J=12.5 Hz, 2H), 2.36 (s, 3H), 2.13 (s, 3H), 1.77 (td, J=13.1, 4.4 Hz, 2H)

ML

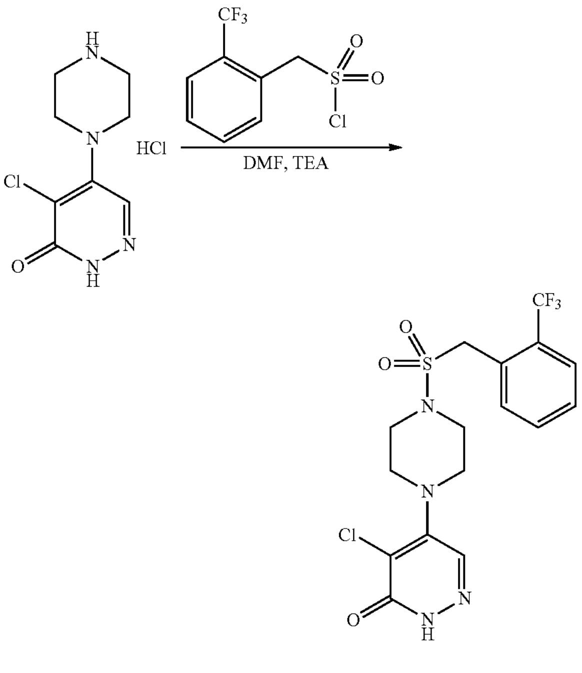

A mixture of 4-chloro-5-(piperazin-1-yl)-2H-pyridazin-3-one hydrochloride (0.12 g, 0.478 mmol, 1.236 equiv.), [2-(trifluoromethyl)phenyl]methanesulfonyl chloride (0.1 g, 0.387 mmol, 1 equiv.) and Triethylamine (0.144 g, 0.2 mL, 1.423 mmol, 3.681 equiv.) in dimethyl-formamide (2 mL, 0.193 M, 20 Vols) was stirred at RT for 16 hr. Diluted with water and filtered to collect solid. Purified via flash chromatography (ISCO 12 g, 0-100% EtOAc/Heptane followed by 0-20% MeOH/EtOAc). Obtained 4-chloro-5-(4-([2-(trifluoromethyl)phenyl]methanesulfonyl)piperazin-1-yl)-2H-pyridazin-3-one (42.8 mg, 0.098 mmol, Yield 25.341%) as a white solid.

Calc'd $[M+H]^+$ for C16H17ClF3N4O3S=437.1, found 437.2.

1H NMR (DMSO-d6) δ: 13.00 (s, 1H), 7.88 (s, 1H), 7.79 (d, J=7.9 Hz, 1H), 7.67-7.75 (m, 2H), 7.57-7.63 (m, 1H), 4.57 (s, 2H), 3.43-3.49 (m, 4H), 3.33-3.39 (m, 4H)

MM

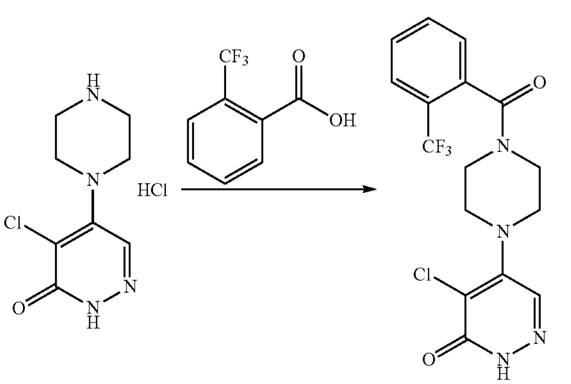

A mixture of 4-chloro-5-(piperazin-1-yl)-2H-pyridazin-3-one hydrochloride (0.15 g, 0.597 mmol, 1.136 equiv.), 2-trifluoromethylbenzoic acid (0.1 g, 0.526 mmol, 1 equiv.), HATU (0.25 g, 0.657 mmol, 1.25 equiv.) and Triethylamine (0.288 g, 0.4 mL, 2.846 mmol, 5.411 equiv.) in dimethyl-formamide (2 mL, 0.263 M, 20 Vols) was stirred at RT for 16 hr. Diluted with water and filtered to collect solid. Purified via flash chromatography (ISCO 12 g, 0-100% EtOAc/Heptane followed by 0-20% MeOH/EtOAc). Obtained 4-chloro-5-(4-[2-(trifluoromethyl)benzoyl]piperazin-1-yl)-2H-pyridazin-3-one (78.2 mg, 0.202 mmol, Yield 38.441%) as a white solid.

Calc'd $[M+H]^+$ for C16H15ClF3N4O2=387.1, found 387.3.

1H NMR (DMSO-d6) δ: 12.97 (s, 1H), 7.86 (s, 1H), 7.83 (d, J=7.9 Hz, 1H), 7.73-7.78 (m, 1H), 7.63-7.70 (m, 1H), 7.53 (d, J=7.5 Hz, 1H), 3.69-3.84 (m, 2H), 3.46-3.55 (m, 1H), 3.34-3.44 (m, 2H), 3.19-3.28 (m, 2H), 3.08-3.19 (m, 1H)

MN

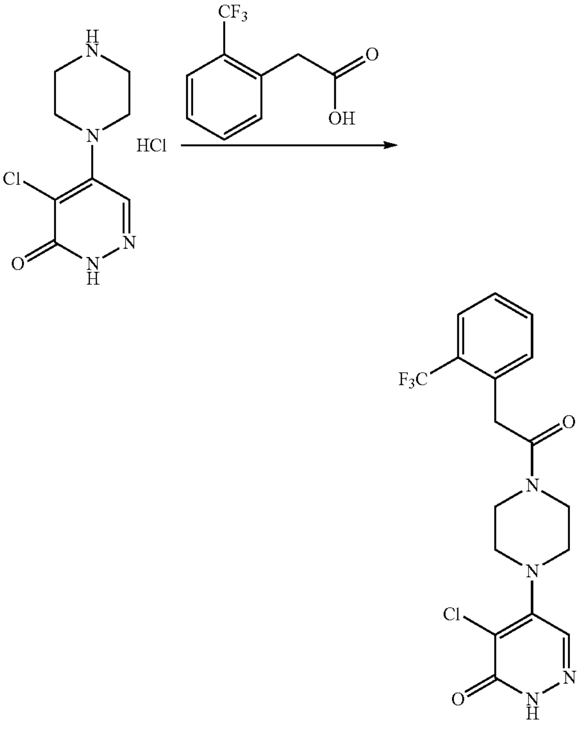

A mixture of 4-chloro-5-(piperazin-1-yl)-2H-pyridazin-3-one hydrochloride (0.15 g, 0.597 mmol, 1.219 equiv.), [2-(trifluoromethyl)phenyl]acetic acid (0.1 g, 0.49 mmol, 1 equiv.), HATU (0.25 g, 0.657 mmol, 1.342 equiv.) and Triethylamine (0.36 g, 0.5 mL, 3.558 mmol, 7.263 equiv.) in dimethyl-formamide (2 mL, 0.245 M, 20 Vols) was stirred at RT for 16 hr. Diluted with water and filtered to collect solid. Purified via flash chromatography (ISCO 12 g, 0-100% EtOAc/Heptane followed by 0-20% MeOH/EtOAc). The solid obtained was rinsed with copious amounts of water then dried under vacuum to provide 4-chloro-5-(4-(2-[2-(trifluoromethyl)phenyl]acetyl)piperazin-1-yl)-2H-pyridazin-3-one (82.9 mg, 0.207 mmol, Yield 42.226%) as a white solid.

Calc'd $[M+H]^+$ for C17H17ClF3N4O2=401.1, found 401.3.

1H NMR (DMSO-d6) δ: 12.97 (s, 1H), 7.88 (s, 1H), 7.68 (d, J=7.8 Hz, 1H), 7.56-7.64 (m, 1H), 7.41-7.52 (m, 1H), 7.38 (d, J=7.6 Hz, 1H), 3.91 (s, 2H), 3.52-3.74 (m, 4H), 3.34-3.50 (m, 4H)
MO

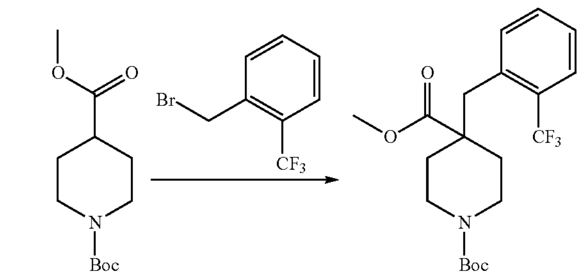

A solution of 1-tert-butyl 4-methyl piperidine-1,4-dicarboxylate (999.4 mg, 4.108 mmol, 1 equiv.) in THF (20 mL, 0.205 M, 20.012 Vols) was sparged with N2 then cooled in a dry ice/acetone bath. Slowly added LiHMDS (5 mL, 5 mmol, 1.217 equiv.) and then stirred at −78° C. for 2 hr. Added 1-(bromomethyl)-2-(trifluoromethyl)benzene (1.1 g, 0.7 mL, 4.601 mmol, 1.12 equiv.) then stirred over the weekend, allowing to warm to RT. Quenched with sat aq NH4Cl, then extracted with EtOAc (3×). Washed organics with brine, dried over Na2SO4, filtered and concentrated in vacuo. Purified via flash chromatography (ISCO 24 g, 0-40% EtOAc/Heptane). Obtained 345 mg of impure product as a white solid. Used as-is.

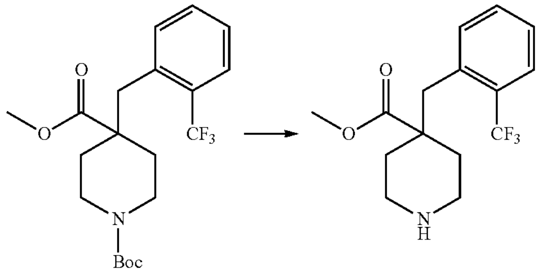 [SMILES: COC(=O)C1(Cc2ccccc2C(F)(F)F)CCN(C(=O)OC(C)(C)C)CC1 ; COC(=O)C1(Cc2ccccc2C(F)(F)F)CCNCC1]

A mixture of 1-tert-butyl 4-methyl 4-([2-(trifluoromethyl) phenyl]methyl)piperidine-1,4-dicarboxylate (345 mg, 0.859 mmol, 1 equiv.) in DCM (2 mL, 0.43 M, 5.797 Vols) was charged with TFA (0.5 mL, 1.719 M, 1.449 Vols) and stirred at RT For 4 hr. Concentrated in vacuo, and used as-is.

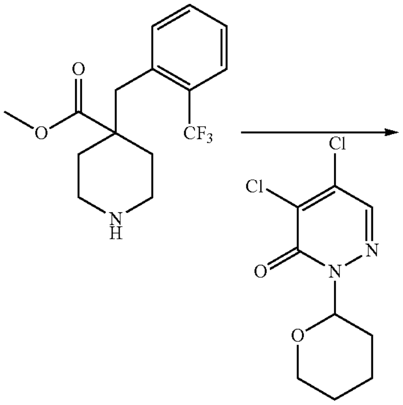

-continued

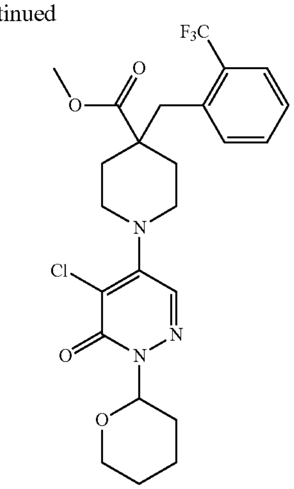

A mixture of methyl 4-([2-(trifluoromethyl)phenyl] methyl)piperidine-4-carboxylate (0.249 g, 0.826 mmol, 1 equiv.), 4,5-dichloro-2-(oxan-2-yl)pyridazin-3-one (0.3 g, 1.204 mmol, 1.457 equiv.) and Triethylamine (0.36 g, 0.5 mL, 3.558 mmol, 4.305 equiv.) in EtOH (2 mL, 0.413 M, 8.032 Vols) was heated to 60° C. overnight Concentrated in vacuo and purified via flash chromatography (ISCO 12 g, 0-100% EtOAc/Heptane). Obtained impure methyl 1-[5-chloro-1-(oxan-2-yl)-6-oxopyridazin-4-yl]-4-([2-(trifluoromethyl)phenyl]methyl)piperidine-4-carboxylate (0.401 g) as a tan solid. Used as-is.

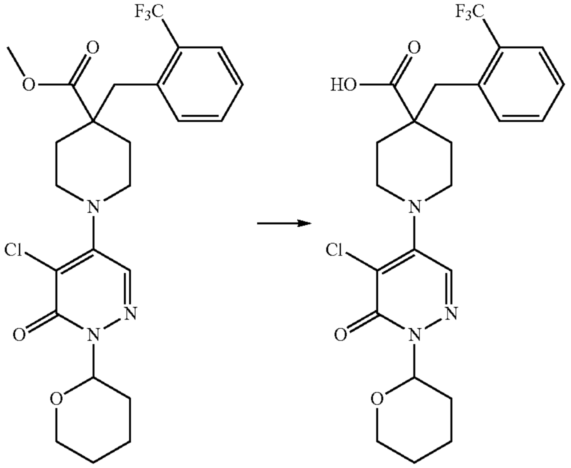 [SMILES: COC(=O)C1(Cc2ccccc2C(F)(F)F)CCN(c2cnn(C3CCCCO3)c(=O)c2Cl)CC1 ; O=C(O)C1(Cc2ccccc2C(F)(F)F)CCN(c2cnn(C3CCCCO3)c(=O)c2Cl)CC1]

A mixture of in MeOH (1 mL, 0.78 M, 2.494 Vols) and NH40H (1 mL, 0.78 M, 2.494 Vols) was stirred at RT for 115 hr. Heated to 60° C. for 24 hr, then added Lithium Hydroxide (0.06 g, 2.505 mmol, 3.211 equiv.) and water (1 mL, 0.78 M, 2.494 Vols), then stirred at 60° C. for 18 hr. Quenched with 1N HCl, then extracted with EtOAc (3×). Obtained crude 1-[5-chloro-1-(oxan-2-yl)-6-oxopyridazin-4-yl]-4-([2-(trifluoromethyl)phenyl]methyl)piperidine-4-carboxylic acid. Assumed 100% yield, used as-is.

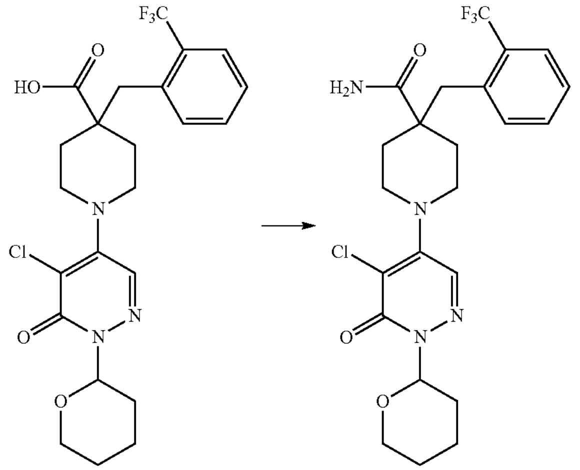 [SMILES: O=C(O)C1(Cc2ccccc2C(F)(F)F)CCN(c2cnn(C3CCCCO3)c(=O)c2Cl)CC1 ; NC(=O)C1(Cc2ccccc2C(F)(F)F)CCN(c2cnn(C3CCCCO3)c(=O)c2Cl)CC1]

A mixture of 1-[5-chloro-1-(oxan-2-yl)-6-oxopyridazin-4-yl]-4-([2-(trifluoromethyl)phenyl]methyl)piperidine-4-carboxylic acid (0.39 g, 0.78 mmol, 1 equiv.), carbonyldiimidazole (0.15 g, 0.925 mmol, 1.186 equiv.) and Ammonium hydroxide (0.88 g, 1 mL, 8.788 mmol, 11.267 equiv.) in DCM (2 mL, 0.39 M, 5.129 Vols) was stirred at 60° C. for 24 hr. Concentrated in vacuo onto SiO2 and purified via flash chromatography (ISCO 4 g, 0-20% MeOH/DCM). Obtained 1-[5-chloro-1-(oxan-2-yl)-6-oxopyridazin-4-yl]-4-([2-(trifluoromethyl)phenyl]methyl)piperidine-4-carboxamide (27 mg, 0.054 mmol, Yield 6.938%).

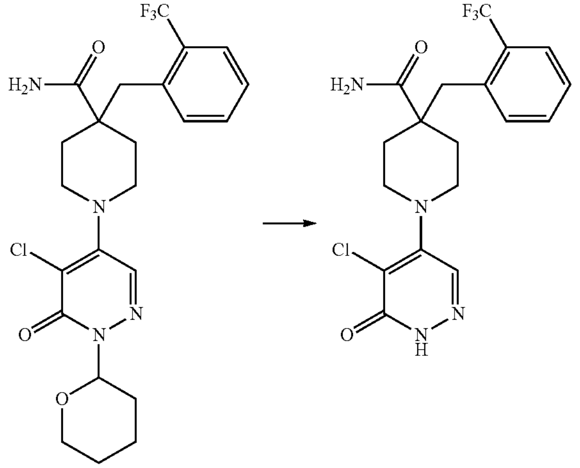 [SMILES: NC(=O)C1(Cc2ccccc2C(F)(F)F)CCN(c2cnn(C3CCCCO3)c(=O)c2Cl)CC1 ; NC(=O)C1(Cc2ccccc2C(F)(F)F)CCN(c2cn[nH]c(=O)c2Cl)CC1]

A mixture of 1-[5-chloro-1-(oxan-2-yl)-6-oxopyridazin-4-yl]-4-([2-(trifluoromethyl)phenyl]methyl)piperidine-4-carboxamide (27 mg, 0.054 mmol, 1 equiv.) and Trifluoroacetic acid (0.745 g, 0.5 mL, 6.534 mmol, 120.737 equiv.) Trifluoroacetic acid (0.745 g, 0.5 mL, 6.534 mmol, 120.737 equiv.) in DCM (1 mL, 0.054 M, 37.037 Vols) was stirred at RT for 1 hr. Concentrated in vacuo onto SiO2 and purified via flash chromatography (ISCO 4 g, 0-20% MeOH/DCM). Obtained 1-(5-chloro-6-oxo-1H-pyridazin-4-yl)-4-([2-(trifluoromethyl)phenyl]methyl)piperidine-4-carboxamide (10.8 mg, 0.026 mmol, Yield 48.112%).

Calc'd $[M+H]^+$ for C18H19ClF3N4O2=415.1, found 415.4.

MP

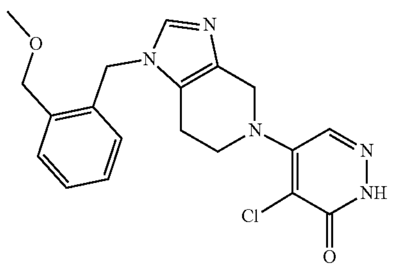 [SMILES: COCc1ccccc1Cn1cnc2c1CCN(c1cn[nH]c(=O)c1Cl)C2]

Step 1

4-chloro-5-(1-[[2-(methoxymethyl)phenyl]methyl]-1H,4H,5H,6H,7H-imidazo[4,5-c]pyridin-5-yl)-2-(oxan-2-yl)-2,3-dihydropyridazin-3-one To a stirred solution of 4-chloro-5-[1H,4H,5H,6H,7H-imidazo[4,5-c]pyridin-5-yl]-2-(oxan-2-yl)-2,3-dihydropyridazin-3-one (300 mg, 0.893 mmol, 1 equiv.) in DMF (10 mL) was added NaH (64.32 mg, 2.680 mmol, 3 equiv.) in portions at 0 degrees C. under nitrogen atmosphere. The resulting mixture was stirred for 1 h at 0 degrees C. under nitrogen atmosphere. To the above mixture was added 1-(chloromethyl)-2-(methoxymethyl)benzene (228.68 mg, 1.340 mmol, 1.5 equiv.) in portions over 5 min at 0 degrees C. The resulting mixture was stirred for additional 4 h at room temperature. The reaction was monitored by LCMS. The reaction was quenched by the addition of Water (5 mL) at 0 degrees C. The resulting mixture was extracted with EtOAc (30 mL). The combined organic layers were washed with brine (3×50 mL), dried over anhydrous Na2SO4. After filtration, the filtrate was concentrated under reduced pressure. The residue was purified by Prep-TLC (PE/EtOAc 5:1) to afford 4-chloro-5-(1-[[2-(methoxymethyl)-phenyl]methyl]-1H,4H,5H,6H,7H-imidazo[4,5-c]pyridin-5-yl)-2-(oxan-2-yl)-2,3-dihydropyridazin-3-one (320 mg) as a light yellow oil.

Step 2

MP 4-chloro-5-(1-[[2-(methoxymethyl)phenyl]methyl]-1H,4H,5H,6H,7H-imidazo[4,5-c]pyridin-5-yl)-2,3-dihydropyridazin-3-one To a stirred solution of 4-chloro-5-(1-[[2-(methoxymethyl)phenyl]methyl]-1H,4H,5H,6H,7H-imidazo[4,5-c]pyridin-5-yl)-2-(oxan-2-yl)-2,3-dihydropyridazin-3-one (150 mg, 0.319 mmol, 1 equiv.) in DCM (10 mL, 157.300 mmol, 492.84 equiv.) was added TFA (3 mL, 40.389 mmol, 126.54 equiv.) in portions at room temperature under nitrogen atmosphere. The resulting mixture was stirred for 2 h at room temperature under nitrogen atmosphere. The reaction was monitored by LCMS. The resulting mixture was concentrated under reduced pressure. The crude product (80 mg) was purified by Prep-HPLC with the following conditions (Column: XBridge Prep OBD C18 Column 30×150 mm 5 um; Mobile Phase A: Water (10 MMOL/L NH4HCO3), Mobile Phase B: ACN; Flow rate: 60 mL/min; Gradient: 10% B to 28% B in 16 min; 220 nm; Rt: 13.58 15.07 min) to afford 4-chloro-5-(1-[[2-(methoxymethyl) phenyl]methyl]-1H,4H,5H,6H,7H-imidazo[4,5-c]pyridin-5-yl)-2,3-dihydropyridazin-3-one (33.1 mg, 26.88%) as a white solid and 4-chloro-5-(3-[[2-(methoxymethyl)phenyl] methyl]-3H,4H,5H,6H,7H-imidazo[4,5-c]pyridin-5-yl)-2,3-dihydropyridazin-3-one (17.8 mg, 14.45%) as a white solid.

MQ

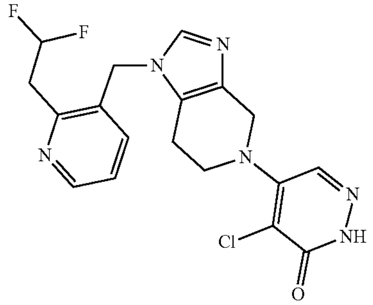 [SMILES: O=c1[nH]ncc(N2CCc3c(ncn3Cc3cccnc3CC(F)F)C2)c1Cl]

Step 1

4-chloro-5-(1-[[2-(2,2-difluoroethyl)pyridin-3-yl] methyl]-1H,4H,5H,6H,7H-imidazo[4,5-c]pyridin-5-yl)-2-(oxan-2-yl)-2,3-dihydropyridazin-3-one To a stirred mixture of 4-chloro-5-[1H,4H,5H,6H,7H-imidazo[4,5-c]pyridin-5-yl]-2-(oxan-2-yl)-2,3-dihydropyridazin-3-one (300 mg, 0.89 mmol, 1 equiv.) and 3-(chloromethyl)-2-(2,2-difluoroethyl)pyridine (85.6 mg, 0.45 mmol, 0.50 equiv.) in ACN (10 ML) was added K2CO3 (246.9 mg, 1.79 mmol, 2.00 equiv.) in portions at rt under nitrogen atmosphere. The resulting mixture was stirred for 48 h at 60 degrees C. under nitrogen atmosphere. The reaction was monitored by LCMS. The mixture was allowed to cool down to rt. The resulting mixture was concentrated under reduced pressure. The residue was purified by Prep-TLC (PE/EtOAc=2/1) to afford 4-chloro-5-(1-[[2-(2,2-difluoroethyl)pyridin-3-yl]methyl]-1H,4H,5H,6H,7H-imidazo [4,5-c]pyridin-5-yl)-2-(oxan-2-yl)-2,3-dihydropyridazin-3-one (120 mg, 27.36%) as a yellow oil.

Step 2

MQ 4-chloro-5-(1-[[2-(2,2-difluoroethyl)pyridin-3-yl] methyl]-1H,4H,5H,6H,7H-imidazo[4,5-c]pyridin-5-yl)-2,3-dihydropyridazin-3-one To a stirred solution of 4-chloro-5-(1-[[2-(2,2-difluoroethyl)pyridin-3-yl]methyl]-1H,4H,5H,6H,7H-imidazo[4,5-c]pyridin-5-yl)-2-(oxan-2-yl)-2,3-dihydropyridazin-3-one (120 mg, 0.24 mmol, 1 equiv.) in DCM (10 mL) was added TFA (1.0 mL, 8.77 mmol, 55.08 equiv.) dropwise at rt. The reaction mixture was stirred for 16 h at rt. The reaction was monitored by LCMS. The resulting mixture was concentrated under reduced pressure. The residue was basified to pH=8 with saturated NH4HCO3 (aq.). The resulting mixture was extracted with CH2Cl2(3×100 mL). The combined organic layers were washed with brine (1×100 mL), dried over anhydrous Na2SO4. After filtration, the filtrate was concentrated under reduced pressure. The residue was purified by Prep-HPLC with the following conditions (Column: XBridge Shield RP18 OBD Column, 5 um, 19*150 mm; Mobile Phase A: Water (10 MMOL/L NH4HCO3), Mobile Phase B: ACN; Flow rate: 60 mL/min; Gradient: 20% B to 40% B in 7 min; 220 nm; Rt: 8.48, 9.73 min) to afford 4-chloro-5-(1-[[2-(2,2-difluoroethyl)pyridin-3-yl]methyl]-1H,4H,5H,6H,7H-imidazo[4,5-c]pyridin-5-yl)-2,3-dihydropyridazin-3-one (4.7 mg, 4.73%) as a white solid.

QU

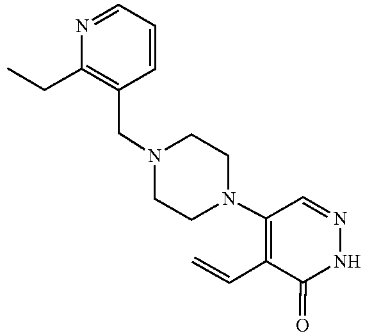 [SMILES: C=Cc1c(N2CCN(Cc3cccnc3CC)CC2)cn[nH]c1=O]

Step 1

4-ethenyl-5-[4-[(2-ethylpyridin-3-yl)methyl]piperazin-1-yl]-2,3-dihydropyridazin-3-one To a stirred solution of 4-chloro-5-[4-[(2-ethylpyridin-3-yl)methyl]piperazin-1-yl]-2,3-dihydropyridazin-3-one (300 mg, 0.899 mmol, 1 equiv.) and 2-ethenyl-4,4,5,5-tetramethyl-1,3,2-dioxaborolane (138.42 mg, 0.899 mmol, 1.00 equiv.) in dioxane (5 mL) and H2O (1 mL) were added K2CO3 (248.41 mg, 1.797 mmol, 2.00 equiv.) and Pd(PPh3)4 (51.92 mg, 0.045 mmol, 0.05 equiv.) in portions at room temperature under nitrogen atmosphere. The final reaction mixture was irradiated with microwave radiation for 1 h at 100 degrees C. The reaction was monitored by LCMS. The resulting mixture was concentrated under reduced pressure. The residue was purified by Prep-TLC/silica gel column chromatography, eluted with PE/EtOAc (5:1) to afford 4-ethenyl-5-[4-[(2-ethylpyridin-3-yl)methyl] piperazin-1-yl]-2,3-dihydropyridazin-3-one (150 mg, 51.29%) as a yellow solid.

Compound MR
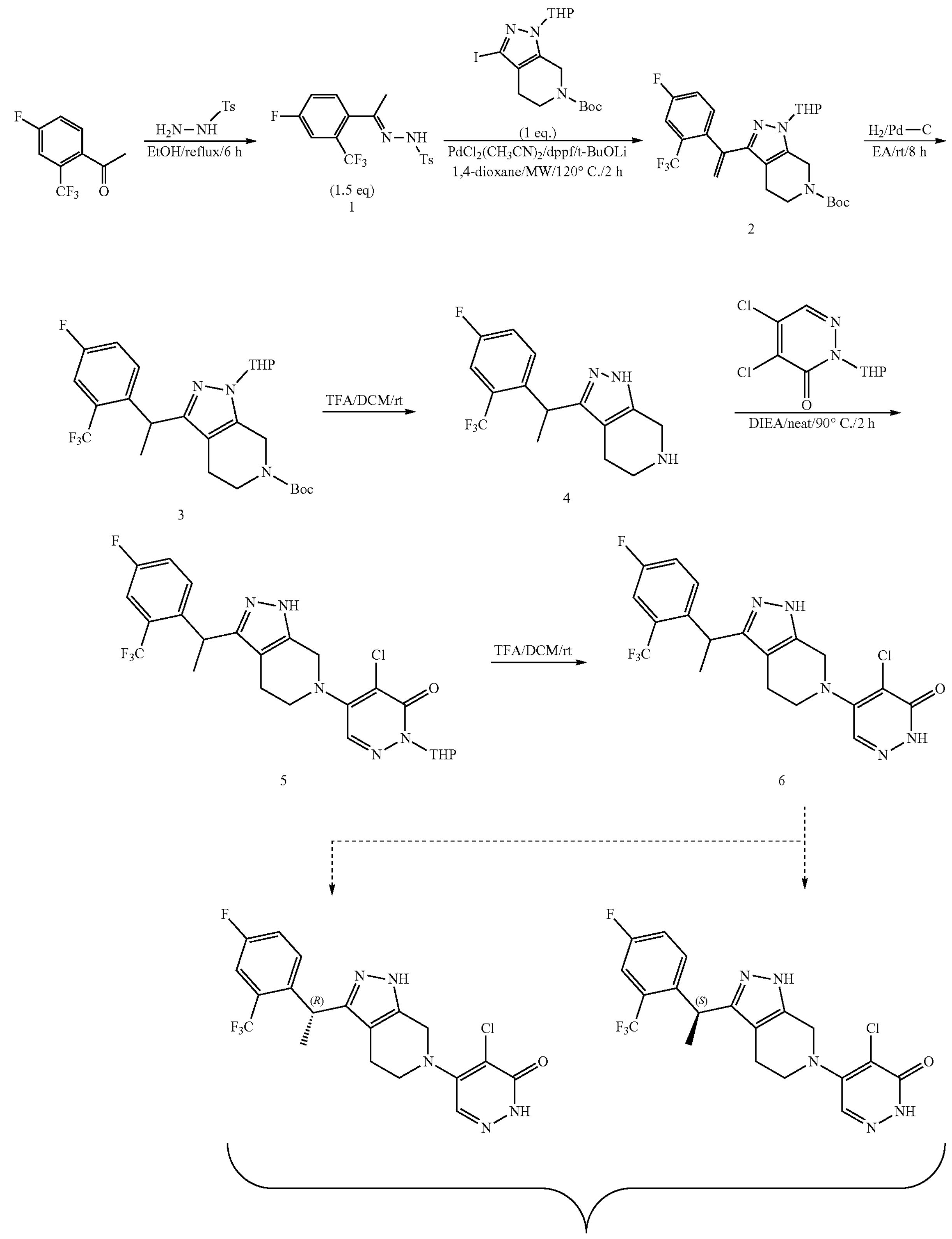
MR

Tert-Butyl 3-[1-[4-fluoro-2-(trifluoromethyl)phenyl]ethenyl]-1-(oxan-2-yl)-1H,4H,5H,6H,7H-pyrazolo[3,4-c]pyridine-6-carboxylate To a stirred mixture of tert-butyl 3-iodo-1-(oxan-2-yl)-1H,4H,5H,6H,7H-pyrazolo[3,4-c]pyridine-6-carboxylate (600 mg, 1.385 mmol, 1 equiv.) and N-[1-[4-fluoro-2-(trifluoromethyl)phenyl]ethylidene]-4-methylbenzene-1-sulfonohydrazide (1036.77 mg, 2.770 mmol, 2.00 equiv.) in 1,4-dioxane (30 mL) were added Dppf (152.98 mg, 0.277 mmol, 0.20 equiv.), Pd(CH3CN)2Cl2 (35.92 mg, 0.138 mmol, 0.10 equiv.) and t-BuOLi in THF (3.05 mL, 3.050 mmol, 2.20 equiv.) in portions at rt under nitrogen atmosphere. The final reaction mixture was irradiated with microwave radiation for 2 h at 120 degrees C. The reaction was monitored by LCMS. The mixture was allowed to cool down to rt. The precipitated solids were collected by filtration and washed with EtOAc (3×50 mL). The resulting mixture was concentrated under vacuum. The residue was purified by reverse phase flash chromatography with the following conditions: Column: Spherical C18, 20-40 um, 330 g; Mobile Phase A: Water (plus 5 mM NH4HCO3); Mobile Phase B: ACN; Flow rate: 80 mL/min; Gradient: 5%-5% B, 10 min, 70% B-95% B gradient in 20 min; Detector: 220 nm. The fractions containing the desired product were collected at 95% B and concentrated under reduced pressure to afford tert-butyl 3-[1-[4-fluoro-2-(trifluoromethyl)phenyl]ethenyl]-1-(oxan-2-yl)-1H,4H,5H,6H,7H-pyrazolo[3,4-c]pyridine-6-carboxylate (300 mg, 43.72%) as a yellow oil.

Tert-Butyl 3-[1-[4-fluoro-2-(trifluoromethyl)phenyl]ethyl]-1-(oxan-2-yl)-1H,4H,5H,6H,7H-pyrazolo[3,4-c]pyridine-6-carboxylate To a solution of tert-butyl 3-[1-[4-fluoro-2-(trifluoromethyl)phenyl]ethenyl]-1-(oxan-2-yl)-1H,4H,5H,6H,7H-pyrazolo[3,4-c]pyridine-6-carboxylate (300 mg) in 20 mL MeOH was added Pd/C (10%, 50 mg) under nitrogen atmosphere in a 100 mL round-bottom flask. The mixture was hydrogenated at room temperature for 4 h under hydrogen atmosphere using a hydrogen balloon, filtered through a celite pad and concentrated under reduced pressure. This resulted in tert-butyl 3-[1-[4-fluoro-2-(trifluoromethyl)phenyl]ethyl]-1-(oxan-2-yl)-1H,4H,5H,6H,7H-pyrazolo[3,4-c]pyridine-6-carboxylate (280 mg) as a yellow oil.

3-[1-[4-fluoro-2-(trifluoromethyl)phenyl]ethyl]-1H,4H,5H,6H,7H-pyrazolo[3,4-c]pyridine To a stirred solution of tert-butyl 3-[1-[4-fluoro-2-(trifluoromethyl)phenyl]ethyl]-1-(oxan-2-yl)-1H,4H,5H,6H,7H-pyrazolo[3,4-c]pyridine-6-carboxylate (280 mg) in DCM (20 mL) was added TFA (2 mL) dropwise at rt. The reaction mixture was stirred for 2 h at rt. The reaction was monitored by LCMS. The resulting mixture was concentrated under reduced pressure. The residue was basified to pH=8 with saturated NH4HCO3 (aq.). The resulting mixture was extracted with CH2Cl2(3×100 mL). The combined organic layers were washed with brine (50 mL), dried over anhydrous Na2SO4. After filtration, the filtrate was concentrated under reduced pressure. The residue was purified by reverse phase flash chromatography with the following conditions: Column: Spherical C18, 20-40 um, 120 g; Mobile Phase A: Water (plus 5 mM NH4HCO3); Mobile Phase B: ACN; Flow rate: 40 mL/min; Gradient: 5%-5% B, 10 min, 40% B-55% B gradient in 15 min; Detector: 220 nm. The fractions containing the desired product were collected at 51% B and concentrated under reduced pressure to afford 3-[1-[4-fluoro-2-(trifluoromethyl)phenyl]ethyl]-1H,4H,5H,6H,7H-pyrazolo[3,4-c]pyridine (120 mg) as a yellow oil.

4-chloro-5-(3-[1-[4-fluoro-2-(trifluoromethyl)phenyl]ethyl]-1H,4H,5H,6H,7H-pyrazolo[3,4-c]pyridin-6-yl)-2-(oxan-2-yl)-2,3-dihydropyridazin-3-one Into a 50 mL round-bottom flask were added 3-[1-[4-fluoro-2-(trifluoromethyl)phenyl]ethyl]-1H,4H,5H,6H,7H-pyrazolo[3,4-c]pyridine (120 mg, 0.383 mmol, 1 equiv.), 4,5-dichloro-2-(oxan-2-yl)-2,3-dihydropyridazin-3-one (114.49 mg, 0.460 mmol, 1.20 equiv.) and DIEA (148.51 mg, 1.149 mmol, 3.00 equiv.) at rt under nitrogen atmosphere. The resulting mixture was stirred for 2 h at 90 degrees C. under nitrogen atmosphere. The reaction was monitored by LCMS. The mixture was allowed to cool down to rt. The residue was purified by reverse phase flash chromatography with the following conditions: Column: Spherical C18, 20-40 um, 120 g; Mobile Phase A: Water (plus 5 mM NH4HCO3); Mobile Phase B: ACN; Flow rate: 45 mL/min; Gradient: 5%-5% B, 10 min, 40% B-60% B gradient in 15 min; Detector: 220 nm. The fractions containing the desired product were collected at 55% B and concentrated under reduced pressure to afford 4-chloro-5-(3-[1-[4-fluoro-2-(trifluoromethyl)phenyl]ethyl]-1H,4H,5H,6H,7H-pyrazolo[3,4-c]pyridin-6-yl)-2-(oxan-2-yl)-2,3-dihydropyridazin-3-one (140 mg, 69.50%) as a yellow oil. MR 4-chloro-5-[3-[(1S)-1-[4-fluoro-2-(trifluoromethyl)phenyl]ethyl]-1H,4H,5H,6H,7H-pyrazolo[3,4-c]pyridin-6-yl]-2,3-dihydropyridazin-3-one To a stirred solution of 4-chloro-5-(3-[1-[4-fluoro-2-(trifluoromethyl)phenyl]ethyl]-1H,4H,5H,6H,7H-pyrazolo[3,4-c]pyridin-6-yl)-2-(oxan-2-yl)-2,3-dihydropyridazin-3-one (100 mg) in DCM (20 mL) was added TFA (2 mL) dropwise at rt. The reaction mixture was stirred for 2 h at rt. The reaction was monitored by LCMS. The resulting mixture was concentrated under reduced pressure. The residue was basified to pH=8 with saturated NH4HCO3 (aq.). The resulting mixture was extracted with CH2Cl2(3×200 mL). The combined organic layers were washed with brine (1×80 mL), dried over anhydrous Na2SO4. After filtration, the filtrate was concentrated under reduced pressure. The residue was purified by Chiral-Prep-HPLC with the following conditions (Column: XBridge Prep Phenyl OBD Column 19×150 mm 5 um 13 nm; Mobile Phase A:, Mobile Phase B:; Flow rate: 60 mL/min; Gradient: 20% B to 37% B in 8 min; 220 nm; Rt: 7.97 min). 4-chloro-5-[3-[(1S)-1-[4-fluoro-2-(trifluoromethyl)phenyl]ethyl]-1H,4H,5H,6H,7H-pyrazolo[3,4-c]pyridin-6-yl]-2,3-dihydropyridazin-3-one (21.3 mg) was obtained at 1.433 min as a white solid. 4-chloro-5-[3-[(1R)-1-[4-fluoro-2-(trifluoromethyl)phenyl]ethyl]-1H,4H,5H,6H,7H-pyrazolo[3,4-c]pyridin-6-yl]-2,3-dihydropyridazin-3-one (22.3 mg) was obtained at 1.733 min as a white solid.

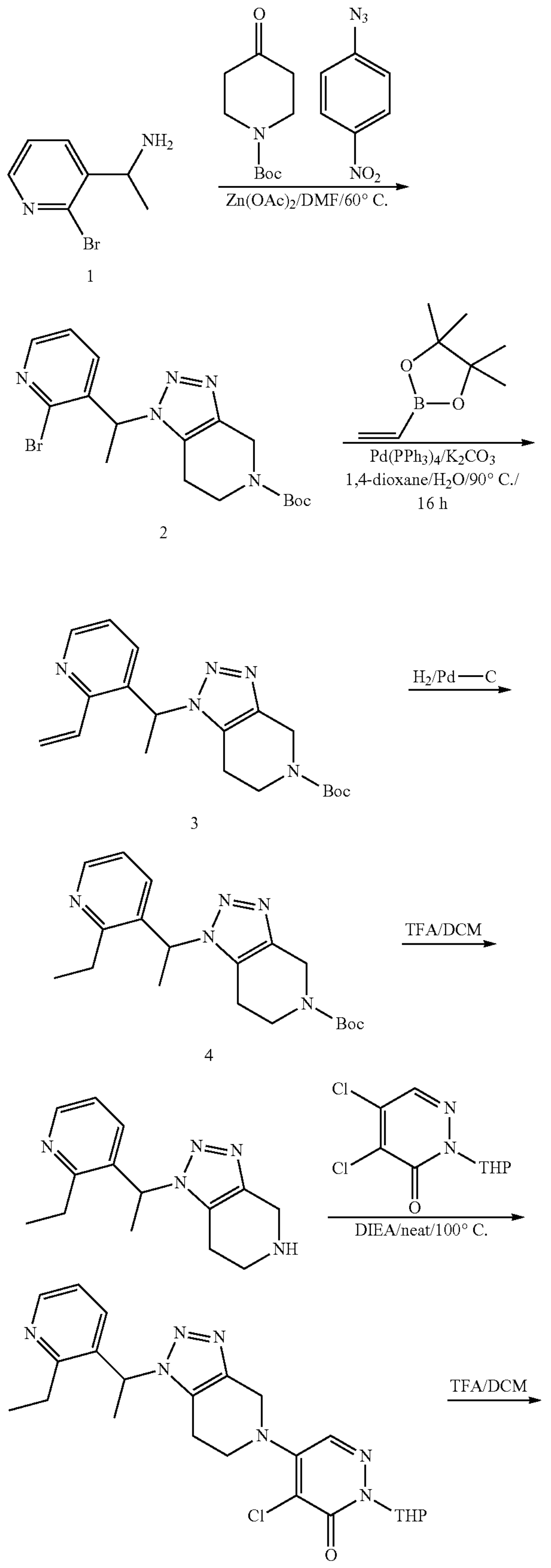

1

2

3

4

6

-continued

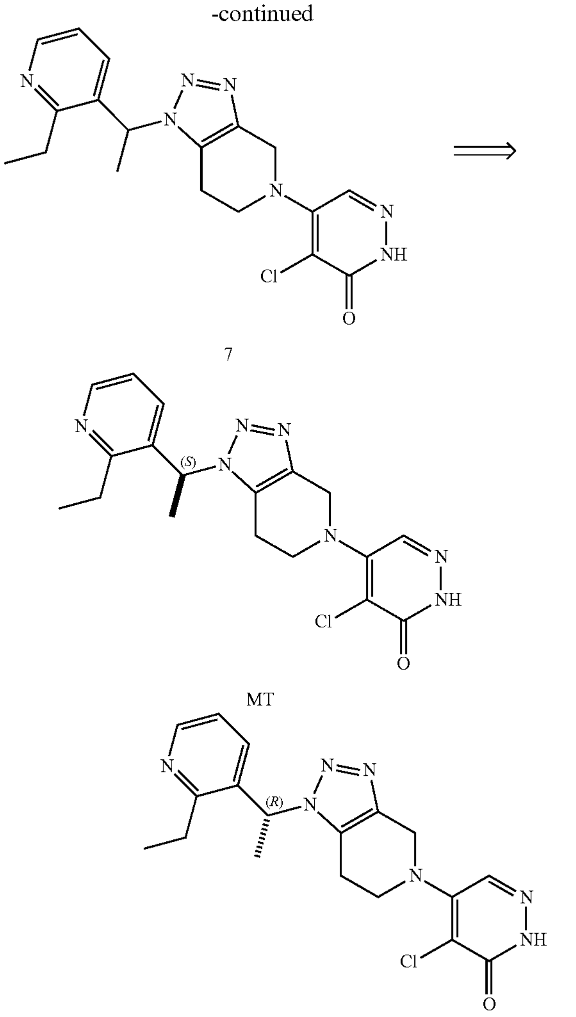

7

MT

MS

Preparation of MS and MT

Bert-Butyl 1-[1-(2-bromopyridin-3-yl)ethyl]-1H,4H, 5H,6H,7H-[1,2,3]triazolo[4,5-c]pyridine-5-carboxylate To a stirred mixture of 1-(2-bromopyridin-3-yl)ethan-1-amine (1009.1 mg, 5.02 mmol, 2.00 equiv.) and tert-butyl 4-oxopiperidine-1-carboxylate (500 mg, 2.51 mmol, 1 equiv.) in DMF (10 mL) were added 1-azido-4-nitrobenzene (576.6 mg, 3.51 mmol, 1.40 equiv.) and Zn(OAc)2 (460.5 mg, 2.51 mmol, 1.00 equiv.) in portions at rt under nitrogen atmosphere. The resulting mixture was stirred for 16 h at 60 degrees Celsius under nitrogen atmosphere. The reaction was monitored by LCMS. The mixture was allowed to cool down to rt. The residue was purified by reverse phase flash with the following conditions (Column: XBridge Shield RP18 OBD Column, 20-40 um, 19*150 mm; Mobile Phase A: Water (10 MMOL/L NH4HCO3), Mobile Phase B: ACN; Flow rate: 80 mL/min; Gradient: 40% B to 80% B in 30 min; 220 nm; Rt: 7.08 min) to afford tert-butyl 1-[1-(2-bromopyridin-3-yl)ethyl]-1H,4H,5H,6H,7H-[1,2,3]triazolo[4,5-c]pyridine-5-carboxylate (800 mg, 78.08%) as a yellow oil.

Tert-Butyl 1-[1-(2-ethenylpyridin-3-yl)ethyl]-1H,4H,5H,6H,7H-[1,2,3]triazolo[4,5-c]pyridine-5-carboxylate To a stirred mixture of tert-butyl 1-[1-(2-bromopyridin-3-yl)ethyl]-1H,4H,5H,6H,7H-[1,2,3]triazolo[4,5-c]pyridine-5-carboxylate (800 mg, 1.96 mmol, 1 equiv.) and 2-ethenyl-4,4,5,5-tetramethyl-1,3,2-dioxaborolane (301.8 mg, 1.96 mmol, 1.00 equiv.) in dioxane (30 mL) and H2O (6 mL) were added Pd(PPh3)4 (226.4 mg, 0.20 mmol, 0.10 equiv.) and K2CO3 (812.4 mg, 5.88 mmol, 3.00 equiv.) in portions at rt under nitrogen atmosphere. The resulting mixture was stirred for 16 h at 90 degrees celsius under nitrogen atmosphere. The reaction was monitored by LCMS. The mixture was allowed to cool down to rt. The resulting mixture was concentrated under reduced pressure. The residue was purified by silica gel column chromatography, eluted with PE/EtOAc (30/1 to 5/1) to afford tert-butyl 1-[1-(2-ethenylpyridin-3-yl)ethyl]-1H,4H,5H,6H,7H-[1,2,3]triazolo[4,5-c]pyridine-5-carboxylate (600 mg, 86.15%) as a yellow oil.

Tert-Butyl 1-[1-(2-ethylpyridin-3-yl)ethyl]-1H,4H,5H,6H,7H-[1,2,3]triazolo[4,5-c]pyridine-5-carboxylate To a solution of tert-butyl 1-[1-(2-ethenylpyridin-3-yl)ethyl]-1H,4H,5H,6H,7H-[1,2,3]triazolo[4,5-c]pyridine-5-carboxylate (300 mg, 0.84 mmol, 1 equiv.) in 20 mL MeOH was added Pd/C (10%, 0.02 g) under nitrogen atmosphere in a 50 mL round-bottom flask. The mixture was hydrogenated at room temperature for 2 h under hydrogen atmosphere using a hydrogen balloon, filtered through a celite pad and concentrated under reduced pressure. This resulted in tert-butyl 1-[1-(2-ethylpyridin-3-yl)ethyl]-1H,4H,5H,6H,7H-[1,2,3]triazolo[4,5-c]pyridine-5-carboxylate (260 mg, 86.18%) as a yellow oil.

2-Ethyl-3-(1-[1H,4H,5H,6H,7H-[1,2,3]triazolo[4,5-c]pyridin-1-yl]ethyl)pyridine

To a stirred solution of tert-butyl 1-[1-(2-ethylpyridin-3-yl)ethyl]-1H4H,5H,6H,7H-[1,2,3]triazolo[4,5-c]pyridine-5-carboxylate (260 mg, 0.73 mmol, 1 equiv.) in DCM (10 mL) was added TFA (1 mL, 13.46 mmol, 18.51 equiv.) dropwise at rt. The reaction mixture was stirred for 16 h at rt. The reaction was monitored by LCMS. The resulting mixture was concentrated under reduced pressure. The residue was basified to pH=8 with saturated NH4HCO3 (aq.). The resulting mixture was extracted with CH2Cl2(3×100 mL). The combined organic layers were washed with brine (1×100 mL), dried over anhydrous Na2SO4. After filtration, the filtrate was concentrated under reduced pressure. The residue was purified by Prep-TLC (PE/EtOAc 1/1) to afford 2-ethyl-3-(1-[1H,4H,5H,6H,7H-[1,2,3]triazolo[4,5-c]pyridin-1-yl]ethyl)pyridine (150 mg, 80.14%) as a yellow oil.

4-Chloro-5-[1-[1-(2-ethylpyridin-3-yl)ethyl]-1H,4H,5H,6H,7H-[1,2,3]triazolo[4,5-c]pyridin-5-yl]-2-(oxan-2-yl)-2,3-dihydropyridazin-3-one Into a 25 mL round-bottom flask were added 2-ethyl-3-(1-[1H,4H,5H,6H,7H-[1,2,3]triazolo[4,5-c]pyridin-1-yl]ethyl)pyridine (150 mg, 0.58 mmol, 1 equiv.), 4,5-dichloro-2-(oxan-2-yl)-2,3-dihydropyridazin-3-one (290.4 mg, 1.17 mmol, 2.00 equiv.) and DIEA (150.7 mg, 1.17 mmol, 2.00 equiv.) at rt under nitrogen atmosphere. The resulting mixture was stirred for 16 h at 90 degrees celsius under nitrogen atmosphere. The residue was purified by Prep-TLC (PE/EtOAc=1/1) to afford 4-chloro-5-[1-[1-(2-ethylpyridin-3-yl)ethyl]-1H,4H,5H,6H,7H-[1,2,3]triazolo[4,5-c]pyridin-5-yl]-2-(oxan-2-yl)-2,3-dihydropyridazin-3-one (145 mg, 52.93%) as a yellow oil.

4-chloro-5-[1-[(1R)-1-(2-ethylpyridin-3-yl)ethyl]-1H,4H,5H,6H,7H-[1,2,3]triazolo[4,5-c]pyridin-5-yl]-2,3-dihydropyridazin-3-one and 4-chloro-5-[1-[(1S)-1-(2-ethylpyridin-3-yl)ethyl]-1H,4H,5H,6H,7H-[1,2,3]triazolo[4,5-c]pyridin-5-yl]-2,3-dihydropyridazin-3-one To a stirred solution of 4-chloro-5-[1-[1-(2-ethylpyridin-3-yl)ethyl]-1H,4H,5H,6H,7H-[1,2,3]triazolo[4,5-c]pyridin-5-yl]-2-(oxan-2-yl)-2,3-dihydropyridazin-3-one (145 mg, 0.31 mmol, 1 equiv.) in DCM (10 mL) was added TFA (1 mL, 13.46 mmol, 43.64 equiv.) dropwise at rt. The reaction mixture was stirred for 4 h at rt. The reaction was monitored by LCMS. The resulting mixture was concentrated under reduced pressure. The residue was basified to pH=8 with saturated NH4HCO3 (aq.). The resulting mixture was extracted with CH2Cl2(3×100 mL). The combined organic layers were washed with brine (1×100 mL), dried over anhydrous Na2SO4. After filtration, the filtrate was concentrated under reduced pressure. The residue (75 mg) was purified by Chiral-Prep-HPLC with the following conditions (Column: CHIRALPAK IE, 2*25 cm, 5 um; Mobile Phase: (Hex/DCM=3/1)/EtOH=80/20; Flow rate: 20 mL/min; Gradient: 20 B to 20 B in 20 min; 220/254 nm; RT1:12.678; RT2:16.738). 4-chloro-5-[1-[(1R)-1-(2-ethylpyridin-3-yl)ethyl]-1H,4H,5H,6H,7H-[1,2,3]triazolo[4,5-c]pyridin-5-yl]-2,3-dihydropyridazin-3-one (16.8 mg, 14.11%) was obtained at 1.380 min as a white solid. 4-chloro-5-[1-[(1S)-1-(2-ethylpyridin-3-yl)ethyl]-1H,4H,5H,6H,7H-[1,2,3]triazolo[4,5-c]pyridin-5-yl]-2,3-dihydropyridazin-3-one (19.8 mg) was obtained at 1.832 min as a white solid (E01224-021).

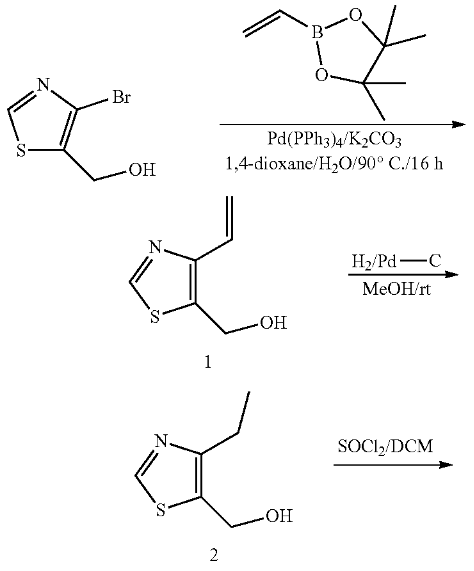

-continued

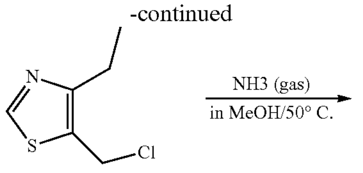

3

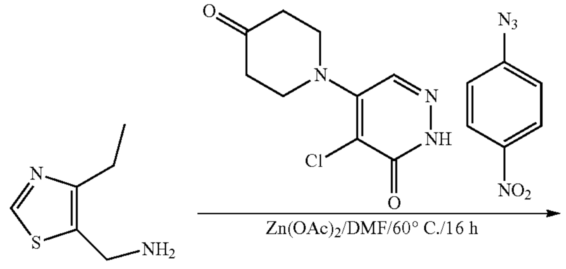

4

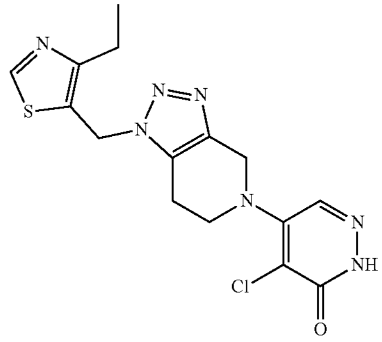

MU

Preparation of MU (4-Ethenyl-1,3-thiazol-5-yl)methanol

To a stirred mixture of (4-bromo-1,3-thiazol-5-yl)methanol (1 g, 5.15 mmol, 1 equiv.) and 2-ethenyl-4,4,5,5-tetramethyl-1,3,2-dioxaborolane (1.2 g, 7.73 mmol, 1.5 equiv.) in 1,4-dioxane (30 mL) were added K2CO3 (1.4 g, 10.31 mmol, 2 equiv.), H2O (6 mL) and Pd(PPh3)4 (297.7 mg, 0.26 mmol, 0.05 equiv.) at room temperature under nitrogen atmosphere. The resulting mixture was stirred for 16 h at 90 degrees celsius under nitrogen atmosphere. The reaction was monitored by LCMS. The resulting mixture was concentrated under reduced pressure. The residue was purified by silica gel column chromatography, eluted with PE/EtOAc (30:1 to 5:1) to afford (4-ethenyl-1,3-thiazol-5-yl)methanol (500 mg, 68.72%) as a yellow oil.

(4-Ethyl-1,3-thiazol-5-yl)methanol

To a stirred solution of (4-ethenyl-1,3-thiazol-5-yl)methanol (500 mg, 3.54 mmol, 1 equiv.) in MeOH (10 mL) was added Pd/C (37.7 mg, 0.35 mmol, 0.10 equiv.) at room temperature under hydrogen atmosphere. The resulting mixture was stirred for 1 h at room temperature under hydrogen atmosphere. The reaction was monitored by LCMS. The resulting mixture was filtered, the filter cake was washed with MeOH (3×10 mL). The filtrate was concentrated under reduced pressure. The crude product was used in the next step (E00848-085) directly without further purification.

5-(chloromethyl)-4-ethyl-1,3-thiazole

To a stirred solution of (4-ethyl-1,3-thiazol-5-yl)methanol (500 mg, 3.49 mmol, 1 equiv.) in DCM (20 mL) were added SOCl2 (830.8 mg, 6.98 mmol, 2.00 equiv.) and DMF (2.6 mg, 0.04 mmol, 0.01 equiv.) at 0 degrees C. The resulting mixture was stirred for 2 h at room temperature. The reaction was monitored by LCMS. The resulting mixture was concentrated under reduced pressure. The crude product was used in the next step (E00848-086) directly without further purification.

1-(4-Ethyl-1,3-thiazol-5-yl)methanamine

Into a 20 mL round-bottom flask were added 5-(chloromethyl)-4-ethyl-1,3-thiazole (550 mg, 3.40 mmol, 1 equiv.), NH3(g)(10 mL) and MeOH (10 mL) at room temperature. The resulting mixture was stirred for 2 h at 50 degrees celsius under nitrogen atmosphere. The reaction was monitored by LCMS. The resulting mixture was concentrated under reduced pressure. The residue was purified by reverse phase flash with the following conditions (Column: XBridge Prep C18 OBD Column 19×150 mm 5 um; Mobile Phase A: Water (10 MMOL/L NH4HCO3), Mobile Phase B: ACN; Flow rate: 20 mL/min; Gradient: 15% B to 25% B in 15 min; 254/220 nm; Rt: 4.95 5.72 min) to afford 1-(4-ethyl-1,3-thiazol-5-yl)methanamine (240 mg, 49.60%) as a yellow oil.

4-Chloro-5-[1-[(4-ethyl-1,3-thiazol-5-yl)methyl]-1H,4H,5H,6H,7H-[1,2,3]triazolo[4,5-c]pyridin-5-yl]-2,3-dihydropyridazin-3-one To a stirred mixture of 1-(4-ethyl-1,3-thiazol-5-yl)methanamine (100 mg, 0.70 mmol, 1 equiv.) and 4-chloro-5-(4-oxopiperidin-1-yl)-2,3-dihydropyridazin-3-one (160.1 mg, 0.70 mmol, 1 equiv.) in DMF (5 mL) were added 1-azido-4-nitrobenzene (161.6 mg, 0.98 mmol, 1.4 equiv.) and Zn(OAc)2 (129.0 mg, 0.70 mmol, 1 equiv.) at room temperature. The resulting mixture was stirred for 16 h at 60 degrees C. The reaction was monitored by LCMS. The mixture was purified by reverse phase flash with the following conditions (Column: XBridge Prep C18 OBD Column 19×150 mm 5 um; Mobile Phase A: Water (5 MMOL/L NH4HCO3), Mobile Phase B: ACN; Flow rate: 20 mL/min; Gradient: 35% B to 50% B in 12 min; 254/220 nm; Rt: 4.95 5.72 min) to afford crude product. The crude product (mg) was purified by Prep-HPLC with the following conditions (Column: XBridge Prep C18 OBD Column 19×150 mm 5 um; Mobile Phase A: Water (10 MMOL/L NH4HCO3), Mobile Phase B: ACN; Flow rate: 60 mL/min; Gradient: 17% B to 46% B in 7 min; 254/220 nm; Rt: 6.48 min) to afford 4-chloro-5-[1-[(4-ethyl-1,3-thiazol-5-yl)methyl]-1H,4H,5H,6H,7H-[1,2,3]triazolo[4,5-c]pyridin-5-yl]-2,3-dihydropyridazin-3-one (22.8 mg, 8.58%) as an off-white solid.

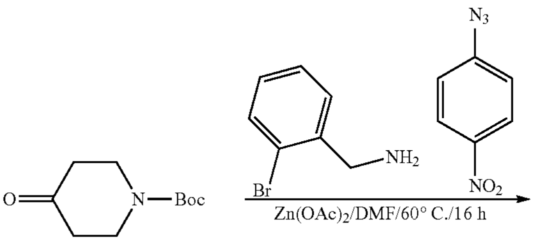

-continued

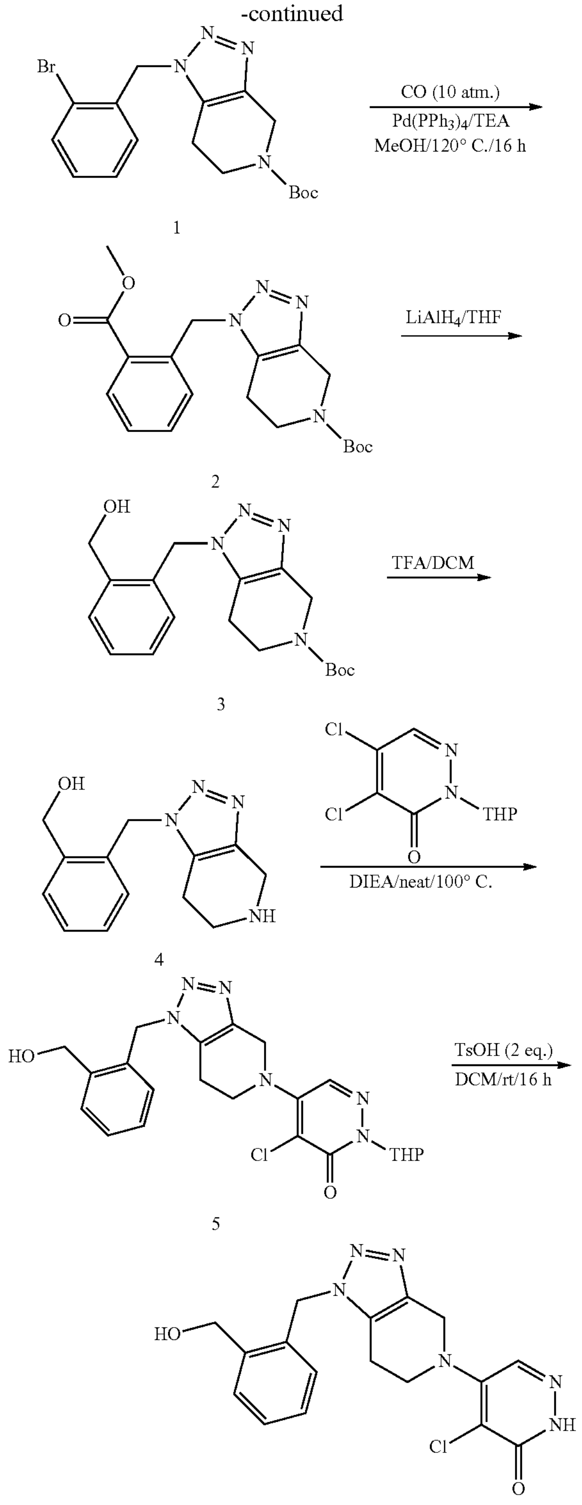

1

2

3

4

5

MV

Preparation of MV

Tert-Butyl 1-[(2-bromophenyl)methyl]-1H,4H,5H,6H,7H-[1,2,3]triazolo[4,5-c]pyridine-5-carboxylate To a stirred solution of tert-butyl 4-oxopiperidine-1-carboxylate (1 g, 5.019 mmol, 1 equiv.) and 1-azido-4-nitrobenzene (201.87 mg, 1.230 mmol, 1.4 equiv.) in DMF (20 ML) were added 1-(2-bromophenyl)methanamine (1.87 g, 10.038 mmol, 2 equiv.) and Zn(OAc)2 (0.92 g, 5.019 mmol, 1 equiv.) in portions at room temperature under nitrogen atmosphere. The resulting mixture was stirred for overnight at 60 degrees celsius under nitrogen atmosphere. The reaction was monitored by LCMS. The mixture was allowed to cool down to room temperature. The resulting mixture was extracted with EtOAc (50 mL). The combined organic layers were washed with brine (3×100 mL), dried over anhydrous Na2SO4. After filtration, the filtrate was concentrated under reduced pressure. The resulting mixture was used in the next step (E00692-106) directly without further purification.

Tert-Butyl 1-[[2-(methoxycarbonyl)phenyl]methyl]-1H,4H,5H,6H,7H-[1,2,3]triazolo[4,5-c]pyridine-5-carboxylate To a solution of tert-butyl 1-[(2-bromophenyl)methyl]-1H,4H,5H,6H,7H-[1,2,3]triazolo[4,5-c]pyridine-5-carboxylate (1.8 g, 4.577 mmol, 1 equiv.) in 15 mL MeOH were added Et3N (0.93 g, 9.154 mmol, 2 equiv.) and Pd(PPh3)4 (0.26 g, 0.229 mmol, 0.05 equiv.) in a pressure tank. The mixture was purged with nitrogen for 1 h and then was pressurized to 10 atm with carbon monoxide at 110 degrees celsius for overnight. The reaction mixture was cooled to room temperature and filtered to remove insoluble solids. The resulting mixture was filtered, the filter cake was washed with MeOH (3×20 mL). The filtrate was concentrated under reduced pressure. The resulting mixture was extracted with EtOAc (30 mL). The combined organic layers were washed with brine (3×50 mL), dried over anhydrous Na2SO4. After filtration, the filtrate was concentrated under reduced pressure. The resulting mixture was used in the next step (E00692-108) directly without further purification.

Tert-Butyl 1-[[2-(hydroxymethyl)phenyl]methyl]-1H,4H,5H,6H,7H-[1,2,3]triazolo[4,5-c]pyridine-5-carboxylate To a stirred solution of tert-butyl 1-[[2-(methoxycarbonyl)phenyl]methyl]-1H,4H,5H,6H,7H-[1,2,3]triazolo[4,5-c]pyridine-5-carboxylate (1.2 g, 3.222 mmol, 1 equiv.) in THF (20 mL) was added LiAlH4 (0.24 g, 6.444 mmol, 2 equiv.) in portions at −30 degrees celsius under nitrogen atmosphere. The resulting mixture was stirred for 2 h at room temperature under nitrogen atmosphere. The reaction was monitored by LCMS. The reaction was quenched by the addition of Water (0.24 mL) and sat. NaOH (aq.) (0.24 mL) at 0 degrees C. The resulting mixture was filtered, the filter cake was washed with EtOAc (3×50 mL). The filtrate was concentrated under reduced pressure. The resulting mixture was used in the next step (E00692-110) directly without further purification.

1-[(2-Ethylphenyl)methyl]-1H,4H,5H,6H,7H-[1,2,3]triazolo[4,5-c]pyridine

To a stirred solution of tert-butyl 1-[[2-(hydroxymethyl)phenyl]methyl]-1H,4H,5H,6H,7H-[1,2,3]triazolo[4,5-c]pyridine-5-carboxylate (600 mg, 1.742 mmol, 1 equiv.) in DCM (15 mL, 235.951 mmol, 135.44 equiv.) was added TFA (5 mL, 67.315 mmol, 38.64 equiv.) in portions at room temperature under nitrogen atmosphere. The resulting mixture was stirred for 3 h at room temperature under nitrogen atmosphere. The reaction was monitored by LCMS. The mixture/residue was basified to pH 8 with saturated NaHCO3 (aq.). The resulting mixture was extracted with EtOAc (20 mL). The combined organic layers were washed with brine (3×50 mL), dried over anhydrous Na2SO4. After filtration, the filtrate was concentrated under reduced pressure. The resulting mixture was used in the next step (E00692-111) directly without further purification.

4-Chloro-5-[1-[(2-ethylphenyl)methyl]-1H,4H,5H,6H,7H-[1,2,3]triazolo[4,5-c]pyridin-5-yl]-2-(oxan-2-yl)-2,3-dihydropyridazin-3-one To a stirred solution of 1-[(2-ethylphenyl)methyl]-1H,4H,5H,6H,7H-[1,2,3]triazolo[4,5-c]pyridine (140 mg, 0.578 mmol, 1 equiv.) and 4,5-dichloro-2-(oxan-2-yl)-2,3-dihydropyridazin-3-one (143.91 mg, 0.578 mmol, 1 equiv.) was added DIEA (1 mL) dropwise at room temperature under nitrogen atmosphere. The resulting mixture was stirred for overnight at 100 degrees celsius under nitrogen atmosphere for neat reaction. The reaction was monitored by LCMS. The mixture was allowed to cool down to room temperature. The resulting mixture was extracted with EtOAc (30 mL). The combined organic layers were washed with brine (3×50 mL), dried over anhydrous Na2SO4. After filtration, the filtrate was concentrated under reduced pressure. The residue was purified by Prep-TLC (CH2Cl2/MeOH 20:1) to afford 4-chloro-5-[1-[(2-ethylphenyl)methyl]-1H,4H,5H,6H,7H-[1,2,3]triazolo[4,5-c]pyridin-5-yl]-2-(oxan-2-yl)-2,3-dihydropyridazin-3-one (300 mg, 114.14%) as a white solid.

4-Chloro-5-(1-[[2-(hydroxymethyl)phenyl]methyl]-1H,4H,5H,6H,7H-[1,2,3]triazolo[4,5-c]pyridin-5-yl)-2,3-dihydropyridazin-3-one To a stirred solution of 4-chloro-5-(1-[[2-(hydroxymethyl)phenyl]methyl]-1H,4H,5H,6H,7H-[1,2,3]triazolo[4,5-c]pyridin-5-yl)-2-(oxan-2-yl)-2,3-dihydropyridazin-3-one (50 mg, 0.11 mmol, 1 equiv.) in DCM (3 mL) was added TFA (1 mL) in portions at room temperature under nitrogen atmosphere. The resulting mixture was stirred for 2 h at room temperature under nitrogen atmosphere. The reaction was monitored by LCMS. The resulting mixture was concentrated under vacuum. The crude product (30 mg) was purified by Prep-HPLC with the following conditions (Column: XBridge Prep OBD C18 Column 30×150 mm 5 um; Mobile Phase A: Water (10 MMOL/L NH4HCO3), Mobile Phase B: ACN; Flow rate: 60 mL/min; Gradient: 5% B to 28% B in 7 min; 220 nm; Rt: 6.62 min) to afford 4-chloro-5-(1-[[2-(hydroxymethyl)phenyl]methyl]-1H,4H,5H,6H,7H-[1,2,3]triazolo[4,5-c]pyridin-5-yl)-2,3-dihydropyridazin-3-one (9.1 mg, 22.31%) as a white solid.

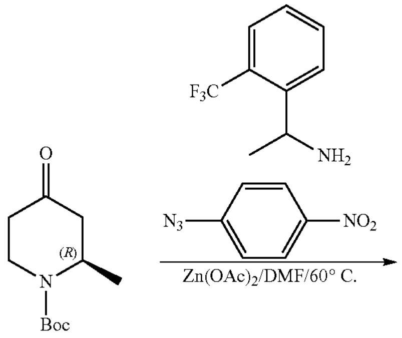

-continued

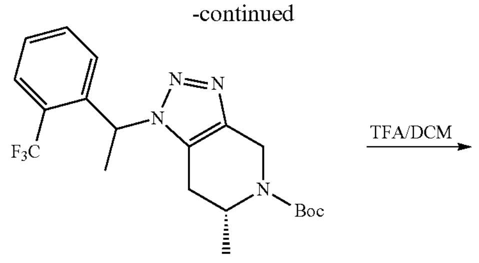

1

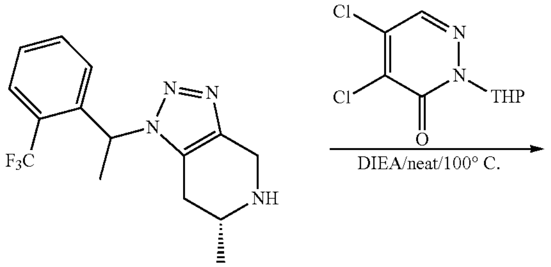

2

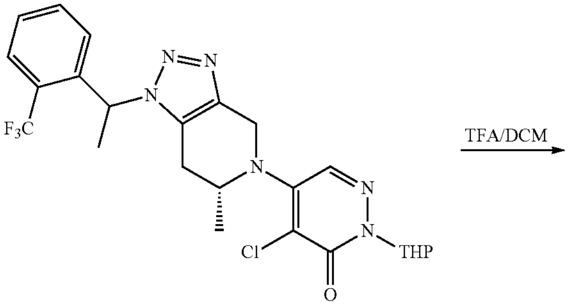

3

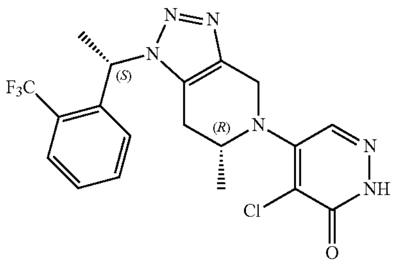

MW

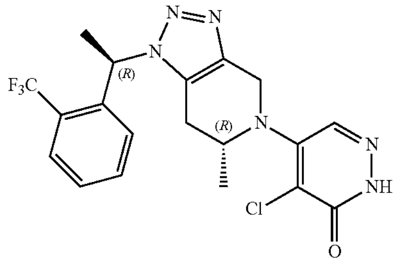

MX

Preparation of MW and MX

Tert-Butyl (4R)-4-methyl-1-[1-[2-(trifluoromethyl)phenyl]ethyl]-1H,4H,5H,6H,7H-[1,2,3]triazolo[4,5-c]pyridine-5-carboxylate To a stirred solution of tert-butyl (2R)-2-methyl-4-oxopiperidine-1-carboxylate (1 g, 4.69 mmol, 1 equiv.) and 1-[2-

(trifluoromethyl)phenyl]ethan-1-amine (0.9 g, 4.76 mmol, 1.01 equiv.) in DMF (20 mL) were added 1-azido-4-nitrobenzene (1.1 g, 6.56 mmol, 1.4 equiv.) and Zn(OAc)2 (0.9 g, 4.69 mmol, 1 equiv.). The resulting mixture was stirred for overnight at 60 degrees C. The residue was purified by reverse flash chromatography with the following conditions: column, C18 silica gel; mobile phase, MeCN in water, 20% to 60% gradient in 40 min; detector, UV 254 nm. This resulted in tert-butyl (4R)-4-methyl-1-[1-[2-(trifluoromethyl)phenyl]ethyl]-1H,4H,5H,6H,7H-[1,2,3]triazolo[4,5-c]pyridine-5-carboxylate (1.5 g, 77.94%) as a off-white solid.

(4R)-4-Methyl-1-[1-[2-(trifluoromethyl)phenyl]ethyl]-1H,4H,5H,6H,7H-[1,2,3]triazolo[4,5-c]pyridine To a stirred solution of tert-butyl (4R)-4-methyl-1-[1-[2-(trifluoromethyl)phenyl]ethyl]-1H,4H,5H,6H,7H-[1,2,3]triazolo[4,5-c]pyridine-5-carboxylate (1.5 g, 3.65 mmol, 1 equiv.) in DCM (9 mL) was added TFA (3 mL). The resulting mixture was stirred for 2 h at room temperature. The mixture was basified to pH 8 with saturated NH4HCO3 (aq.). The solution was concentrated under reduced pressure. The residue was purified by reverse flash chromatography with the following conditions: column, C18 silica gel; mobile phase, MeCN in water, 10% to 50% gradient in 30 min; detector, UV 254 nm. This resulted in (4R)-4-methyl-1-[1-[2-(trifluoromethyl)phenyl]ethyl]-1H,4H,5H,6H,7H-[1,2,3]triazolo[4,5-c]pyridine (1 g, 88.17%) as a yellow solid.

4-Chloro-5-[(6R)-6-methyl-1-[1-[2-(trifluoromethyl)phenyl]ethyl]-1H,4H,5H,6H,7H-[1,2,3]triazolo[4,5-c]pyridin-5-yl]-2-(oxan-2-yl)-2,3-dihydropyridazin-3-one To a stirred solution of (6R)-6-methyl-1-[1-[2-(trifluoromethyl)phenyl]ethyl]-1H,4H,5H,6H,7H-[1,2,3]triazolo[4,5-c]pyridine (200 mg, 0.64 mmol, 1 equiv.), 4,5-dichloro-2-(oxan-2-yl)-2,3-dihydropyridazin-3-one (192.6 mg, 0.77 mmol, 1.2 equiv.) and DIEA (249.9 mg, 1.93 mmol, 3 equiv.). The resulting mixture was stirred for overnight at 100 degrees C. The residue was purified by reverse flash chromatography with the following conditions: column, C18 silica gel; mobile phase, MeCN in water, 20% to 60% gradient in 40 min; detector, UV 254 nm. This resulted in 4-chloro-5-[(6R)-6-methyl-1-[1-[2-(trifluoromethyl)phenyl]ethyl]-1H,4H,5H,6H,7H-[1,2,3]triazolo[4,5-c]pyridin-5-yl]-2-(oxan-2-yl)-2,3-dihydropyridazin-3-one (250 mg, 74.17%) as a yellow solid.

4-chloro-5-[(6R)-6-methyl-1-[(1R)-1-[2-(trifluoromethyl)phenyl]ethyl]-1H,4H,5H,6H,7H-[1,2,3]triazolo[4,5-c]pyridin-5-yl]-2,3-dihydropyridazin-3-one and 4-chloro-5-[(6R)-6-methyl-1-[(1S)-1-[2-(trifluoromethyl)phenyl]ethyl]-1H,4H,5H,6H,7H-[1,2,3]triazolo[4,5-c]pyridin-5-yl]-2,3-dihydropyridazin-3-one To a stirred solution of 4-chloro-5-[(6R)-6-methyl-1-[1-[2-(trifluoromethyl)phenyl]ethyl]-1H,4H,5H,6H,7H-[1,2,3]triazolo[4,5-c]pyridin-5-yl]-2-(oxan-2-yl)-2,3-dihydropyridazin-3-one (240 mg, 0.46 mmol, 1 equiv.) in DCM (6 mL) was added TFA (2 mL). The resulting mixture was stirred for 2 h at room temperature. The resulting mixture was concentrated under reduced pressure. The crude product was purified by Prep-HPLC with the following conditions (Column: XBridge Prep OBD C18 Column 30×150 mm 5 um; Mobile Phase A: Water (10 MMOL/L NH4HCO3), Mobile Phase B: ACN; Flow rate: 60 mL/min; Gradient: 27% B to 50% B in 7 min; 220 nm; Rt: 6.38 min) to afford 4-chloro-5-[(6R)-6-methyl-1-[(1R)-1-[2-(trifluoromethyl)phenyl]ethyl]-1H,4H,5H,6H,7H-[1,2,3]triazolo[4,5-c]pyridin-5-yl]-2,3-dihydropyridazin-3-one (22.4 mg, 11.12%) as a yellow solid and 4-chloro-5-[(6R)-6-methyl-1-[(1S)-1-[2-(trifluoromethyl)phenyl]ethyl]-1H,4H,5H,6H,7H-[1,2,3]triazolo[4,5-c]pyridin-5-yl]-2,3-dihydropyridazin-3-one (58.5 mg, 29.05%) as a off-white solid.

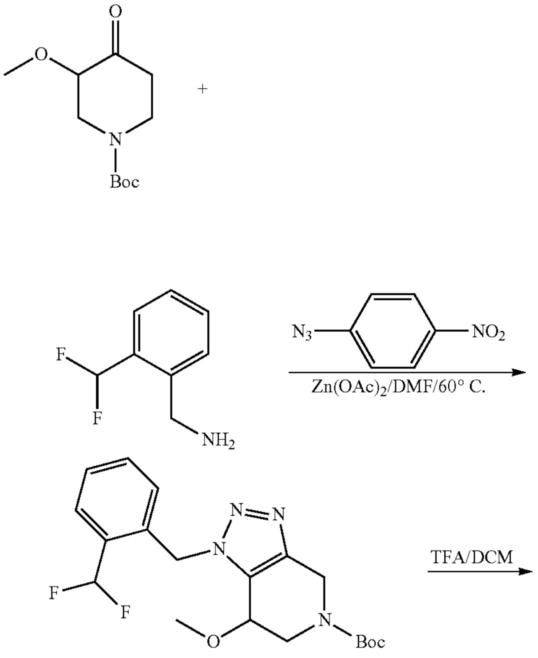

1

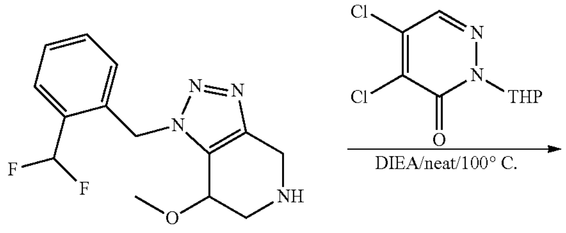

2

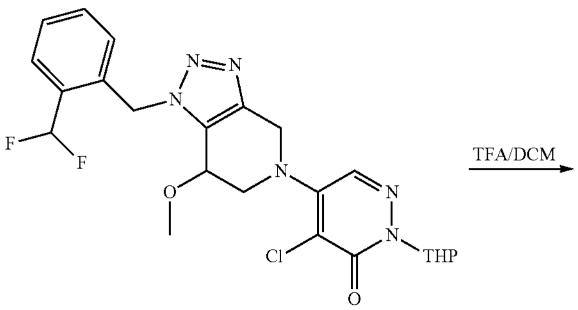

3

-continued

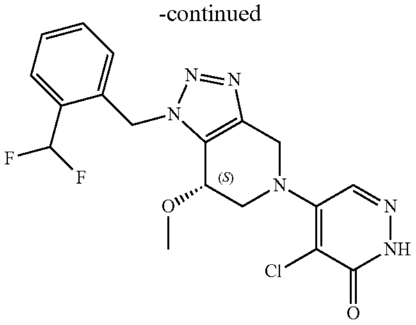

MZ

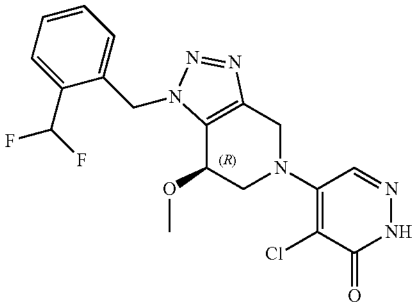

MY

Preparation of MY and MZ

Tert-Butyl 1-[[2-(difluoromethyl)phenyl]methyl]-7-methoxy-1H,4H,5H,6H,7H-[1,2,3]triazolo[4,5-c]pyridine-5-carboxylate To a solution of tert-butyl 3-methoxy-4-oxopiperidine-1-carboxylate (1000 mg, 4.36 mmol, 1 equiv.) and 1-[2-(difluoromethyl)phenyl]methanamine (1371.0 mg, 8.72 mmol, 2 equiv.) in DMF (20 mL, 258.44 mmol, 59.25 equiv.) were added 1-azido-4-nitrobenzene (1002.2 mg, 6.11 mmol, 1.4 equiv.) and Zn(OAc)2 (800.3 mg, 4.36 mmol, 1 equiv.) at 25 degrees C. The mixture was stirred at 70 degrees celsius for 16 h. The mixture was cooled to room temperature. The crude product was purified by Prep-HPLC with the following conditions (Column: XBridge Shield RP18 OBD Column 30*150 mm, 5 um; Mobile Phase A: Water (10 MMoL/L NH4HCO3), Mobile Phase B: ACN; Flow rate: 60 mL/min; Gradient: 60% B to 80% B in 7 min; 220 nm; Rt: 6.63 min) to afford tert-butyl 1-[[2-(difluoromethyl)phenyl]methyl]-7-methoxy-1H,4H,5H,6H,7H-[1,2,3]triazolo[4,5-c]pyridine-5-carboxylate (830 mg, 48.25%) as a yellow oil.

1-[[2-(Difluoromethyl)phenyl]methyl]-7-methoxy-1H,4H,5H,6H,7H-[1,2,3]triazolo[4,5-c]pyridine To a solution of tert-butyl 1-[[2-(difluoromethyl)phenyl]methyl]-7-methoxy-1H,4H,5H,6H,7H-[1,2,3]triazolo[4,5-c]pyridine-5-carboxylate (800 mg, 2.03 mmol, 1 equiv.) in DCM (10 mL, 157.30 mmol, 77.55 equiv.) was added TFA (2312.7 mg, 20.28 mmol, 10.00 equiv.) at 25 degrees C. The solution was stirred at 25 degrees celsius for 2 h. The resulting solution was concentrated under reduced pressure. The residue was purified by Prep-TLC (DCM/MeOH 10/1) to afford 1-[[2-(difluoromethyl)phenyl]methyl]-7-methoxy-1H,4H,5H,6H,7H-[1,2,3]triazolo[4,5-c]pyridine (500 mg, 83.76%) as a light yellow oil.

4-chloro-5-(1-[[2-(difluoromethyl)phenyl]methyl]-7-methoxy-1H,4H,5H,6H,7H-[1,2,3]triazolo[4,5-c]pyridin-5-yl)-2-(oxan-2-yl)-2,3-dihydropyridazin-3-one 1-[[2-(difluoromethyl)phenyl]methyl]-7-methoxy-1H,4H,5H,6H,7H-[1,2,3]triazolo[4,5-c]pyridine (300 mg, 1.02 mmol, 1 equiv.) and 4,5-dichloro-2-(oxan-2-yl)-2,3-dihydropyridazin-3-one (304.7 mg, 1.22 mmol, 1.20 equiv.) in DIEA (395.2 mg, 3.06 mmol, 3 equiv.) was stirred at 100 degrees celsius for 16 h. The resulting solution was purified by Prep-TLC (DCM/MeOH 15/1) to afford 4-chloro-5-(1-[[2-(difluoromethyl)phenyl]methyl]-7-methoxy-1H,4H,5H,6H,7H-[1,2,3]triazolo[4,5-c]pyridin-5-yl)-2-(oxan-2-yl)-2,3-dihydropyridazin-3-one (400 mg, 77.41%) as a light yellow solid.

4-chloro-5-[(7S)-1-[[2-(difluoromethyl)phenyl]methyl]-7-methoxy-1H,4H,5H,6H,7H-[1,2,3]triazolo[4,5-c]pyridin-5-yl]-2,3-dihydropyridazin-3-one and 4-chloro-5-[(7R)-1-[[2-(difluoromethyl)phenyl]methyl]-7-methoxy-1H,4H,5H,6H,7H-[1,2,3]triazolo[4,5-c]pyridin-5-yl]-2,3-dihydropyridazin-3-one To a solution of 4-chloro-5-(1-[[2-(difluoromethyl)phenyl]methyl]-7-methoxy-1H,4H,5H,6H,7H-[1,2,3]triazolo[4,5-c]pyridin-5-yl)-2-(oxan-2-yl)-2,3-dihydropyridazin-3-one (200 mg, 0.39 mmol, 1 equiv.) in DCM (10 mL, 157.30 mmol, 398.71 equiv.) was added TFA (449.8 mg, 3.94 mmol, 10.00 equiv.) at 25 degrees C. The solution was stirred at 25 degrees celsius for 2 h. The resulting solution was concentrated under reduced pressure. The residue was purified by Prep-TLC (DCM/MeOH 10/1) to afford 4-chloro-5-(1-(2-(difluoromethyl)benzyl)-7-methoxy-1,4,6,7-tetrahydro-5H-[1,2,3]triazolo[4,5-c]pyridin-5-yl)pyridazin-3(2H)-one (150 mg) as a light yellow solid. The residue (150 mg) was purified by Chiral-Prep-HPLC with the following conditions: Column: CHIRALPAK IE, 2*25 cm, 5 um; Mobile Phase A:MTBE (0.1% DEA)-HPLC, Mobile Phase B: IPA—HPLC; Flow rate: 18 mL/min; Gradient: 20 B to 20 B in 15 min; 220/254 nm. 4-chloro-5-[(7S)-1-[[2-(difluoromethyl)phenyl]methyl]-7-methoxy-1H,4H,5H,6H,7H-[1,2,3]triazolo[4,5-c]pyridin-5-yl]-2,3-dihydropyridazin-3-one (55.9 mg, 33.51%) was obtained at 9.688 min as a white solid. 4-chloro-5-[(7R)-1-[[2-(difluoromethyl)phenyl]methyl]-7-methoxy-1H,4H,5H,6H,7H-[1,2,3]triazolo[4,5-c]pyridin-5-yl]-2,3-dihydropyridazin-3-one (81.1 mg, 48.62%) was obtained at 11.813 min as a white solid.

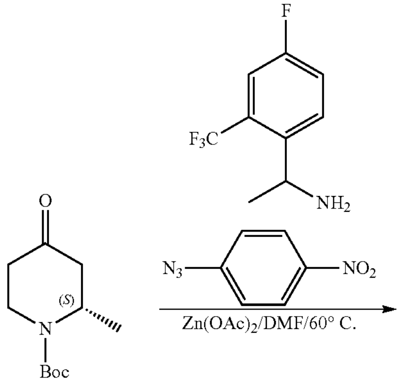

-continued

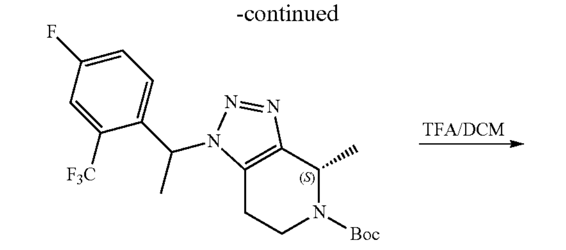

1

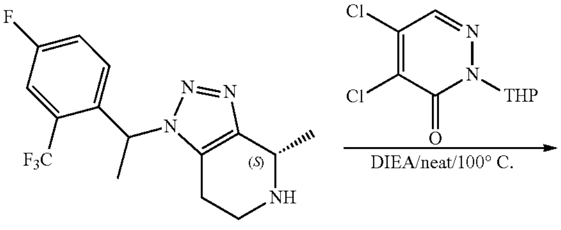

2

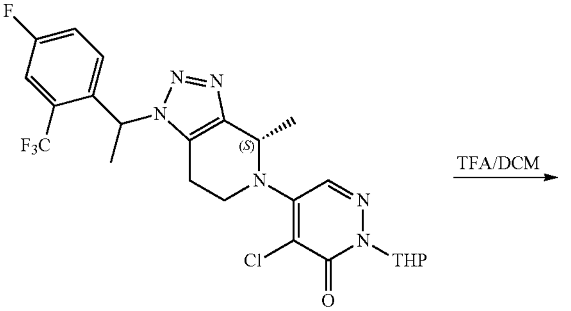

3

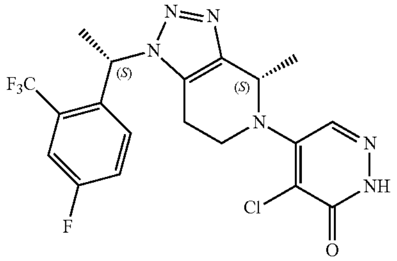

NA

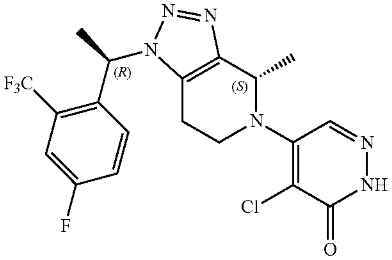

NB

Preparation of NA and NB

Tert-Butyl (4S)-1-[1-[4-fluoro-2-(trifluoromethyl) phenyl]ethyl]-4-methyl-1H,4H,5H,6H,7H-[1,2,3] triazolo[4,5-c]pyridine-5-carboxylate To a stirred solution of tert-butyl (2S)-2-methyl-4-oxopiperidine-1-carboxylate (1 g, 4.69 mmol, 1 equiv.) and 1-[4-fluoro-2-(trifluoromethyl)phenyl]ethan-1-amine (1.0 g, 4.83 mmol, 1.03 equiv.) in DMF (10 mL) were added 1-azido-4-nitrobenzene (1.1 g, 6.56 mmol, 1.4 equiv.) and Zn(OAc)2 (0.9 g, 4.69 mmol, 1 equiv.). The resulting mixture was stirred for overnight at 60 degrees C. The residue was purified by reverse flash chromatography with the following conditions: column, C18 silica gel; mobile phase, MeOH in water, 20% to 65% gradient in 35 min; detector, UV 254 nm. This resulted in tert-butyl (4S)-1-[1-[4-fluoro-2-(trifluoromethyl)phenyl]ethyl]-4-methyl-1H,4H,5H,6H,7H-[1,2,3]triazolo[4,5-c]pyridine-5-carboxylate (1.3 g, 64.72%) as a yellow solid.

(4S)-1-[1-[4-fluoro-2-(trifluoromethyl)phenyl]ethyl]-4-methyl-1H,4H,5H,6H,7H-[1,2,3]triazolo[4,5-c] pyridine To a stirred solution of tert-butyl (4S)-1-[1-[4-fluoro-2-(trifluoromethyl)phenyl]ethyl]-4-methyl-1H,4H,5H,6H,7H-[1,2,3]triazolo[4,5-c]pyridine-5-carboxylate (750 mg, 1.75 mmol, 1 equiv.) in DCM (6 mL) was added TFA (2 mL). The resulting mixture was stirred for 2 h at room temperature. The resulting mixture was concentrated under reduced pressure. The residue was basified to pH 8 with saturated NH4HCO3 (aq.). The residue was purified by reverse flash chromatography with the following conditions: column, C18 silica gel; mobile phase, MeOH in water, 10% to 50% gradient in 35 min; detector, UV 254 nm. This resulted in (4S)-1-[1-[4-fluoro-2-(trifluoromethyl)phenyl]ethyl]-4-methyl-1H,4H,5H,6H,7H-[1,2,3]triazolo[4,5-c]pyridine (500 mg, 87.00%) as a yellow solid.

4-Chloro-5-[(4S)-1-[1-[4-fluoro-2-(trifluoromethyl) phenyl]ethyl]-4-methyl-1H,4H,5H,6H,7H-[1,2,3] triazolo[4,5-c]pyridin-5-yl]-2-(oxan-2-yl)-2,3-dihydropyridazin-3-one To a stirred mixture of (4S)-1-[1-[4-fluoro-2-(trifluoromethyl)phenyl]ethyl]-4-methyl-1H,4H,5H,6H,7H-[1,2,3]triazolo[4,5-c]pyridine (300 mg, 0.91 mmol, 1 equiv.), 4,5-dichloro-2-(oxan-2-yl)-2,3-dihydropyridazin-3-one (273.1 mg, 1.10 mmol, 1.2 equiv.) and DIEA (236.2 mg, 1.83 mmol, 2 equiv.). The resulting mixture was stirred for overnight at 100 degrees C. The residue was purified by reverse flash chromatography with the following conditions: column, C18 silica gel; mobile phase, MeOH in water, 20% to 65% gradient in 30 min; detector, UV 254 nm. This resulted in 4-chloro-5-[(4S)-1-[1-[4-fluoro-2-(trifluoromethyl)phenyl]ethyl]-4-methyl-1H,4H,5H,6H,7H-[1,2,3]triazolo[4,5-c]pyridin-5-yl]-2-(oxan-2-yl)-2,3-dihydropyridazin-3-one (310 mg, 62.72%) as a light yellow solid.

4-chloro-5-[(4S)-1-[(1R)-1-[4-fluoro-2-(trifluoromethyl)phenyl]ethyl]-4-methyl-1H,4H,5H,6H,7H-[1,2,3]triazolo[4,5-c]pyridin-5-yl]-2,3-dihydropyridazin-3-one and 4-chloro-5-[(4S)-1-[(1S)-1-[4-fluoro-2-(trifluoromethyl)phenyl]ethyl]-4-methyl-1H,4H,5H,6H,7H-[1,2,3]triazolo[4,5-c]pyridin-5-yl]-2,3-dihydropyridazin-3-one To a stirred solution of 4-chloro-5-[(4S)-1-[1-[4-fluoro-2-(trifluoromethyl)phenyl]ethyl]-4-methyl-1H,4H,5H,6H,7H-[1,2,3]triazolo[4,5-c]pyridin-5-yl]-2-(oxan-2-yl)-2,3-dihydropyridazin-3-one (310 mg, 0.57 mmol, 1 equiv.) in DCM (3 mL) was added TFA (1 mL). The resulting mixture was stirred for 2 h at room temperature. The resulting mixture was concentrated under reduced pressure. The crude product was purified by Prep-HPLC with the following conditions (Column: XBridge Prep OBD C18 Column 30×150 mm 5 um; Mobile Phase A: Water (10 MMOL/L NH4HCO3), Mobile Phase B: ACN; Flow rate: 60 mL/min; Gradient: 22% B to 42% B in 10 min; 220 nm; Rt: 9.60 min) to afford 4-chloro-5-[(4S)-1-[(1R)-1-[4-fluoro-2-(trifluoromethyl)phenyl]ethyl]-4-methyl-1H,4H,5H,6H,7H-[1,2,3]triazolo[4,5-c]pyridin-5-yl]-2,3-dihydropyridazin-3-one (13.3 mg, 5.08%) and 4-chloro-5-[(4S)-1-[(1S)-1-[4-fluoro-2-(trifluoromethyl)phenyl]ethyl]-4-methyl-1H,4H,5H,6H,7H-[1,2,3]triazolo[4,5-c]pyridin-5-yl]-2,3-dihydropyridazin-3-one (46.6 mg, 17.80%) as a white solid.

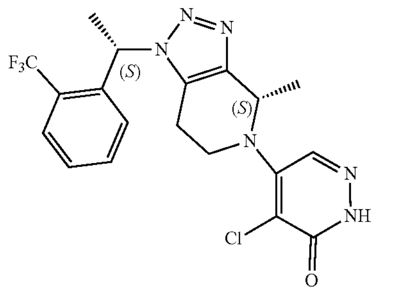

NC

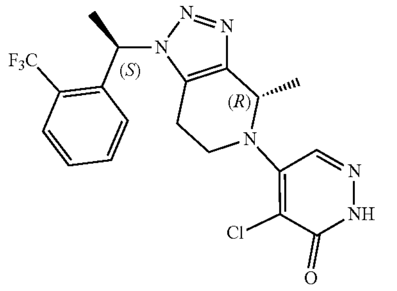

ND

NC and ND were prepared by the methods and scheme described for NA and NB by using 1-(2-(trifluoromethyl)phenyl)ethan-1-amine

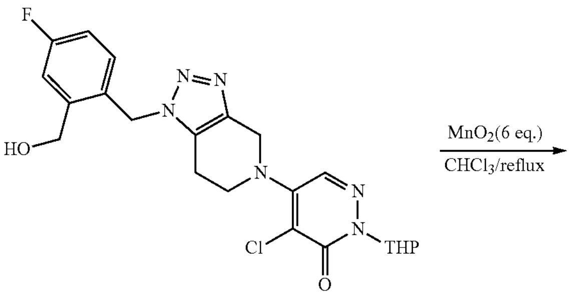

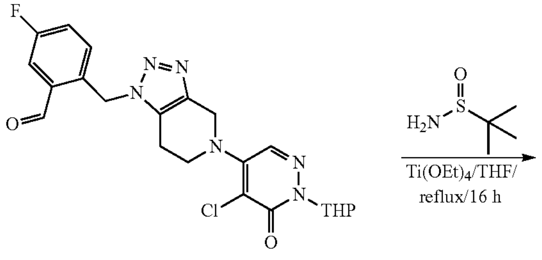

1

-continued

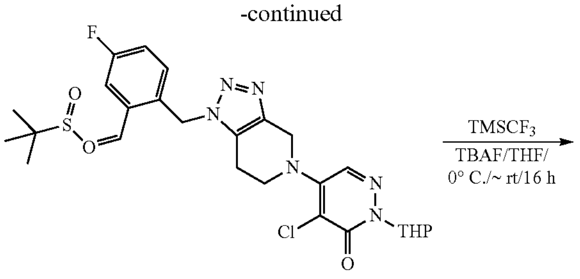

2

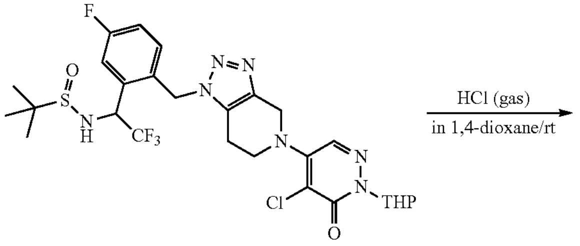

3

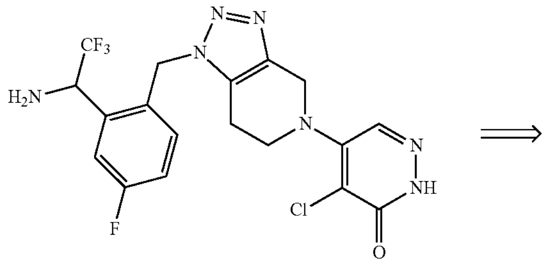

4

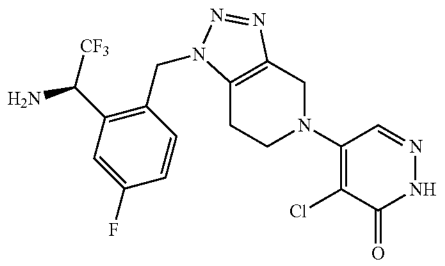

NE

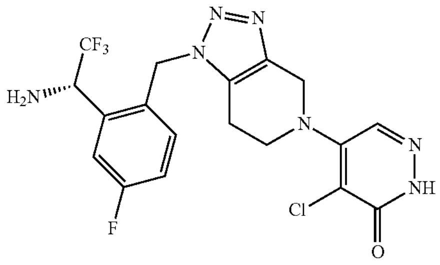

NF

Preparation of PNE and NF

2-([5-[5-Chloro-1-(oxan-2-yl)-6-oxo-1,6-dihydropyridazin-4-yl]-1H,4H,5H,6H,7H-[1,2,3]triazolo[4,5-c]pyridin-1-yl]methyl)-S-fluorobenzaldehyde To a solution of 4-chloro-5-(1-[[4-fluoro-2-(hydroxymethyl)phenyl]methyl]-1H,4H,5H,6H,7H-[1,2,3]triazolo[4,5-c]pyridin-5-yl)-2-(oxan-2-yl)-2,3-dihydropyridazin-3-one (300 mg, 0.63 mmol, 1 equiv.) in CHCl3 (10 mL) was added MnO2 (329.5 mg, 3.79 mmol, 6.00 equiv.) at room temperature. The resulting mixture was stirred for 16 h at 65 degrees C. The reaction was monitored by LCMS. The mixture was allowed to cool down to room temperature. The resulting mixture was filtered, the filter cake was washed with DCM (3×100 mL). The filtrate was concentrated under reduced pressure. The residue was purified by Prep-TLC (CH2Cl2/MeOH 20:1) to afford 2-([5-[5-chloro-1-(oxan-2-yl)-6-oxo-1,6-dihydropyridazin-4-yl]-1H,4H,5H,6H,7H-[1,2,3]triazolo[4,5-c]pyridin-1-yl]methyl)-5-fluorobenzaldehyde (230 mg) as a white solid.

N-[(1Z)-[2-([5-[5-chloro-1-(oxan-2-yl)-6-oxo-1,6-dihydropyridazin-4-yl]-1H,4H,5H,6H,7H-[1,2,3]triazolo[4,5-c]pyridin-1-yl]methyl)-5-fluorophenyl]methylidene]-2-methylpropane-2-sulfinamide To a solution of 2-([5-[5-chloro-1-(oxan-2-yl)-6-oxo-1,6-dihydropyridazin-4-yl]-1H,4H,5H,6H,7H-[1,2,3]triazolo[4,5-c]pyridin-1-yl]methyl)-5-fluorobenzaldehyde (230 mg, 0.49 mmol, 1 equiv.) and 2-methylpropane-2-sulfinamide (117.9 mg, 0.97 mmol, 2 equiv.) in THF (15 mL) was added Ti(OEt)4 (221.9 mg, 0.97 mmol, 2 equiv.) at room temperature. The resulting mixture was stirred for 16 h at 100 degrees C. The reaction was monitored by LCMS. The mixture was allowed to cool down to room temperature. The reaction was quenched by the addition of Water (10 mL) at room temperature. The resulting mixture was filtered, the filter cake was washed with EtOAc (3×50 mL). The filtrate was concentrated under reduced pressure. The resulting mixture was extracted with EtOAc (3×100 mL). The combined organic layers were washed with brine (3×50 mL), dried over anhydrous Na2SO4. After filtration, the filtrate was concentrated under reduced pressure. The residue was purified by Prep-TLC (CH2Cl2/MeOH 30:1) to afford N-[(1Z)-[2-([5-[5-chloro-1-(oxan-2-yl)-6-oxo-1,6-dihydropyridazin-4-yl]-1H,4H,5H,6H,7H-[1,2,3]triazolo[4,5-c]pyridin-1-yl]methyl)-5-fluorophenyl]methylidene]-2-methylpropane-2-sulfinamide (240 mg, 85.66%) as a yellow oil.

N-[1-[2-([5-[5-chloro-1-(oxan-2-yl)-6-oxo-1,6-dihydropyridazin-4-yl]-1H,4H,5H,6H,7H-[1,2,3]triazolo[4,5-c]pyridin-1-yl]methyl)-5-fluorophenyl]-2,2,2-trifluoroethyl]-2-methylpropane-2-sulfinamide To a stirred mixture of N-[(1Z)-[2-([5-[5-chloro-1-(oxan-2-yl)-6-oxo-1,6-dihydropyridazin-4-yl]-1H,4H,5H,6H,7H-[1,2,3]triazolo[4,5-c]pyridin-1-yl]methyl)-5-fluorophenyl]methylidene]-2-methylpropane-2-sulfinamide (240 mg, 0.42 mmol, 1 equiv.) and trimethyl(trifluoromethyl)silane(118.5 mg, 0.83 mmol, 2.00 equiv.) in THF (10 mL) was added TBAF (10.9 mg, 0.04 mmol, 0.10 equiv.) at 0 degrees C. The resulting mixture was stirred for 16 h at 0 degrees C. The reaction was monitored by LCMS. The resulting mixture was concentrated under reduced pressure. The resulting mixture was extracted with EtOAc (3×200 mL). The combined organic layers were washed with brine (3×100 mL), dried over anhydrous Na2SO4. After filtration, the filtrate was concentrated under reduced pressure. The residue was purified by Prep-TLC (CH2Cl2/MeOH 30:1) to afford N-[1-[2-([5-[5-chloro-1-(oxan-2-yl)-6-oxo-1,6-dihydropyridazin-4-yl]-1H,4H,5H,6H,7H-[1,2,3]triazolo[4,5-c]pyridin-1-yl]methyl)-5-fluorophenyl]-2,2,2-trifluoroethyl]-2-methylpropane-2-sulfinamide (160 mg, 59.44%) as a yellow oil.

5-[1-([2-[(1S)-1-amino-2,2,2-trifluoroethyl]-4-fluorophenyl]methyl)-1H,4H,5H,6H,7H-[1,2,3]triazolo[4,5-c]pyridin-5-yl]-4-chloro-2,3-dihydropyridazin-3-one and 4-chloro-5-[4-([2-[(1S)-1-hydroxyethyl]pyridin-3-yl]methyl)piperazin-1-yl]-2,3-dihydropyridazin-3-one To a solution of N-[1-[2-([5-[5-chloro-1-(oxan-2-yl)-6-oxo-1,6-dihydropyridazin-4-yl]-1H,4H,5H,6H,7H-[1,2,3]triazolo[4,5-c]pyridin-1-yl]methyl)-5-fluorophenyl]-2,2,2-trifluoroethyl]-2-methylpropane-2-sulfinamide (160 mg, 0.25 mmol, 1 equiv.) in dioxane was added HCl (1 mL, 32.91 mmol, 132.90 equiv.) in dioxane (4 mL) dropwise at room temperature. The resulting mixture was stirred for 3 h at room temperature. The reaction was monitored by LCMS. The resulting mixture was concentrated under reduced pressure. The mixture was basified to pH 8 with saturated NH3HCO3 (aq.). The resulting mixture was concentrated under reduced pressure. The resulting mixture was filtered, the filter cake was washed with DCM:MeOH (5:1) (3×200 mL). The filtrate was concentrated under reduced pressure. The residue was purified by reverse flash chromatography with the following conditions: column, C18 silica gel; mobile phase, MeOH in water, 25% to 55% gradient in 20 min; detector, UV 254 nm. The crude product (100 mg) was purified by Prep-HPLC with the following conditions (Column: XBridge Prep OBD C18 Column 30??150 mm 5 um; Mobile Phase A: Water (10 MMOL/L NH4HCO3), Mobile Phase B: ACN; Flow rate: 60 mL/min; Gradient: 15% B to 40% B in 7 min; 220 nm; Rt: 6.07 min). The crude product (50 mg) was purified by Chiral-Prep-HPLC with the following conditions (Column: CHIRALPAK IC, 2*25 cm, 5 um; Mobile Phase A:MTBE (0.1% DEA)-HPLC—????, Mobile Phase B: EtOH—HPLC; Flow rate: 17 mL/min; Gradient: 50 B to 50 B in 35 min; 220/254 nm; RT1:7.263; RT2:28.082). 5-[1-([2-[(1S)-1-amino-2,2,2-trifluoroethyl]-4-fluorophenyl]methyl)-1H,4H,5H,6H,7H-[1,2,3]triazolo[4,5-c]pyridin-5-yl]-4-chloro-2,3-dihydropyridazin-3-one (2.5 mg) was obtained at 28.082 min as a white solid. 4-chloro-5-[4-([2-[(1S)-1-hydroxyethyl]pyridin-3-yl]methyl)piperazin-1-yl]-2,3-dihydropyridazin-3-one (14 mg, 8.86%) was obtained at 9.09 min as a white solid. (E00386-175).

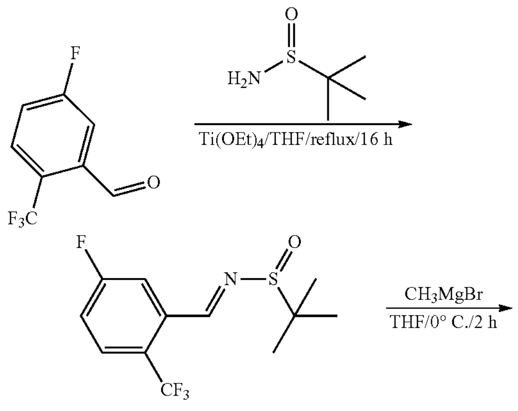

1

-continued

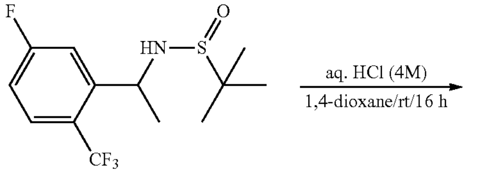

2

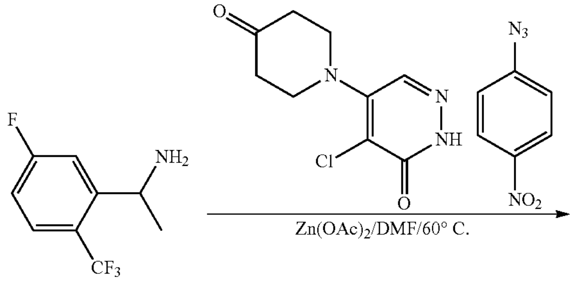

3

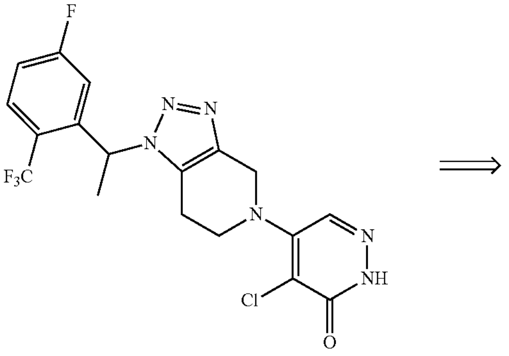

4

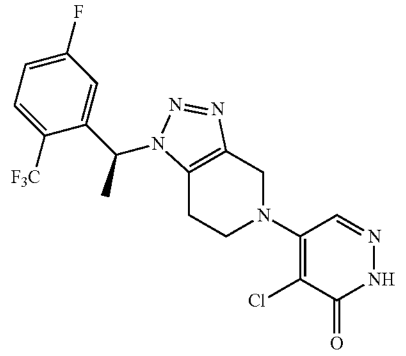

NH

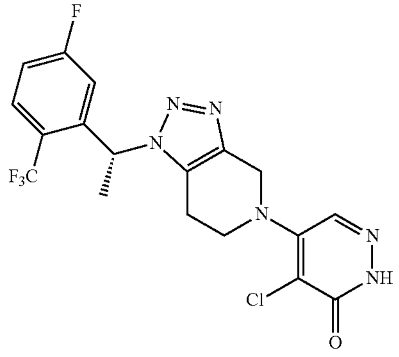

NG

Preparation of NG and NH

N-[[5-fluoro-2-(trifluoromethyl)phenyl]methylidene]-2-methylpropane-2-sulfinamide To a stirred solution of 5-fluoro-2-(trifluoromethyl)benzaldehyde (2 g, 10.41 mmol, 1 equiv.) and 2-methylpropane-2-sulfinamide (2.5 g, 20.82 mmol, 2 equiv.) in THF (30 mL) was added Ti(OEt)4 (4.7 g, 20.82 mmol, 2 equiv.) at room temperature. The solution was stirred at 65 degrees celsius for 16 h. To the solution was added water (3×200 mL). The mixture was extracted with EtOAc (3×200 mL). The combined organic layers were washed with brine (3×200 mL), dried over anhydrous MgSO4. After filtration, the filtrate was concentrated under reduced pressure. The residue was purified by Prep-TLC (PE/EtOAc 10:1) to afford N-[[5-fluoro-2-(trifluoromethyl)phenyl]methylidene]-2-methylpropane-2-sulfinamide (2.3 g, 74.82%) as a colorless oil.

N-[1-[5-fluoro-2-(trifluoromethyl)phenyl]ethyl]-2-methylpropane-2-sulfinamide

To a stirred solution of N-[(1E)-[5-fluoro-2-(trifluoromethyl)phenyl]methylidene]-2-methylpropane-2-sulfinamide (2.3 g, 7.79 mmol, 1 equiv.) in THF (20 mL) was added bromo(methyl)magnesium (2786.3 mg, 23.37 mmol, 3 equiv.) at −40 degrees celsius under nitrogen atmosphere. The solution was stirred at −40 degrees celsius for 2 h. To the solution was added water (3×200 mL). The resulting mixture was extracted with EtOEt (3×200 mL). The combined organic layers were washed with brine (3×200 mL), dried over anhydrous MgSO4. After filtration, the filtrate was concentrated under reduced pressure. The residue was purified by Prep-TLC (PE/EtOAc 1:1) to afford N-[1-[5-fluoro-2-(trifluoromethyl)phenyl]ethyl]-2-methylpropane-2-sulfinamide (1.9 g, 78.35%) as colorless oil.

4-Chloro-5-(4-oxopiperidin-1-yl)-2,3-dihydropyridazin-3-one

To a stirred solution of N-[1-[5-fluoro-2-(trifluoromethyl)phenyl]ethyl]-2-methylpropane-2-sulfinamide (1.9 g, 6.10 mmol, 1 equiv.) in dioxane (6 mL) was added HCl (2 mL, 65.82 mmol, 10.79 equiv.) at room temperature. The solution was stirred at rt for 4 h. Desired product could be detected by LCMS. To the mixture was added water (3×200 mL). The resulting mixture was extracted with CH2Cl2 (3×200 mL). The combined organic layers were washed with brine (3×300 mL), dried over anhydrous MgSO4. After filtration, the filtrate was concentrated under reduced pressure. The crude product was used in the next step directly without further purification.

4-Chloro-5-(1-[1-[5-fluoro-2-(trifluoromethyl)phenyl]ethyl]-1H,4H,5H,6H,7H-[1,2,3]triazolo[4,5-c]pyridin-5-yl)-2,3-dihydropyridazin-3-one To a stirred solution of 4-chloro-5-(4-oxopiperidin-1-yl)-2,3-dihydropyridazin-3-one (150 mg, 0.66 mmol, 1 equiv.) and 1-[5-fluoro-2-(trifluoromethyl)phenyl]ethan-1-amine (273.0 mg, 1.32 mmol, 2 equiv.) in DMF (10 mL) was added 1-azido-4-nitrobenzene (151.4 mg, 0.92 mmol, 1.4 equiv.) and Zn(OAc)2 (120.9 mg, 0.66 mmol, 1 equiv.) at room temperature. The mixture was concentrated under reduced pressure. The crude product (200 mg) was purified by Prep-HPLC with the following conditions (Column: XBridge Prep OBD C18 Column 30×150 mm 5 um; Mobile Phase A: Water (10 MMOL/L NH4HCO3), Mobile Phase B: ACN; Flow rate: 60 mL/min; Gradient: 27% B to 45% B in 7 min; 220 nm; Rt: 6.5 min) to afford 4-chloro-5-(1-[1-[5-fluoro-2-(trifluoromethyl)phenyl]ethyl]-1H,4H,5H,6H,7H-[1,2,3]triazolo[4,5-c]pyridin-5-yl)-2,3-dihydropyridazin-3-one (150 mg, 51.41%), which was purified by PREP CHIRAL HPLC with the following conditions (Column: CHIRALPAK IC, 2*25 cm, 5 um; Mobile Phase A:Hex: DCM=2:1—HPLC, Mobile Phase B: EtOH—HPLC; Flow rate: 18 mL/min; Gradient: 50 B to 50 B in 21 min; 220/254 nm; RT1:12.355; RT2:20.013) to afford 4-chloro-5-[1-[(1S)-1-[5-fluoro-2-(trifluoromethyl)phenyl]ethyl]-1H,4H,5H,6H,7H-[1,2,3]triazolo[4,5-c]pyridin-5-yl]-2,3-dihydropyridazin-3-one (20 mg) (NG) as an off-white solid and afford 4-chloro-5-[1-[(1R)-1-[5-fluoro-2-(trifluoromethyl)phenyl]ethyl]-1H,4H,5H,6H,7H-[1,2,3]triazolo[4,5-c]pyridin-5-yl]-2,3-dihydropyridazin-3-one (20 mg) (NH) as an off-white solid.

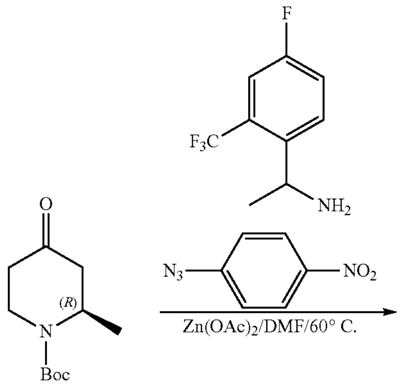

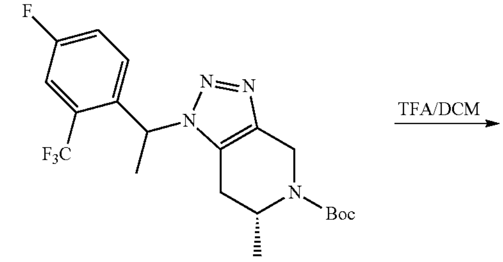

1

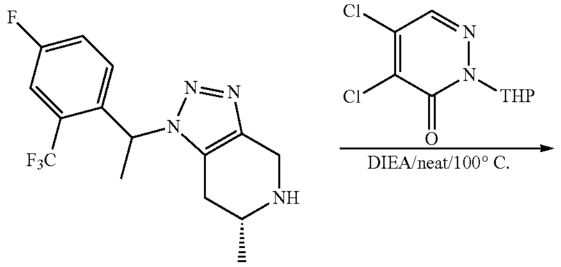

2

-continued

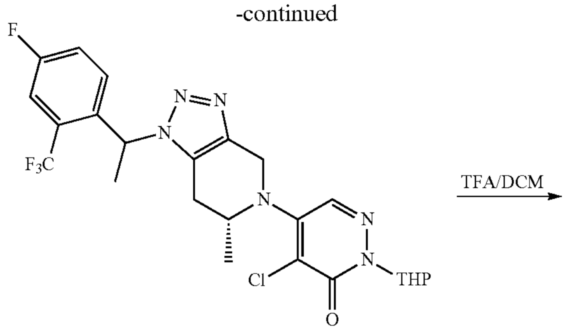

3

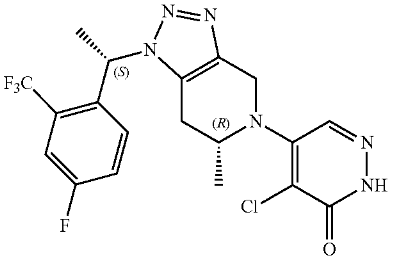

NJ

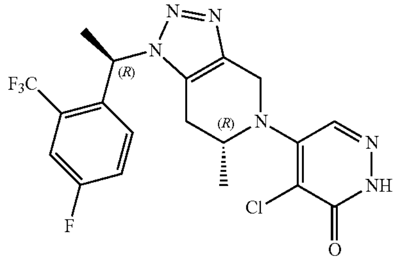

NI

Preparation of NI and NJ

Tert-Butyl (6R)-1-[1-[4-fluoro-2-(trifluoromethyl)phenyl]ethyl]-6-methyl-1H,4H,5H,6H,7H-[1,2,3]triazolo[4,5-c]pyridine-5-carboxylate To a stirred solution of tert-butyl (2R)-2-methyl-4-oxopiperidine-1-carboxylate (1.03 g, 4.83 mmol, 1 equiv.) and 1-[4-fluoro-2-(trifluoromethyl)phenyl]ethan-1-amine (1.0 g, 4.83 mmol, 1 equiv.) in DMF (50 mL) was added 1-azido-4-nitrobenzene (1.1 g, 6.76 mmol, 1.4 equiv.) and Zn(OAc)2 (0.9 g, 4.83 mmol, 1 equiv.) at rt. The solution was stirred at 80 degrees celsius for 16 h. The mixture was concentrated under reduced pressure. The residue was purified by reverse phase flash with the following conditions (Column: C18 Column 330 g; Mobile Phase A: Water (10 MMOL/L NH4HCO3), Mobile Phase B: ACN; Flow rate: 80 mL/min; Gradient: 15% B to 75% B in 40 min; 254/220 nm) The crude product was used in the next step directly without further purification.

(6R)-1-[1-[4-fluoro-2-(trifluoromethyl)phenyl]ethyl]-6-methyl-1H,4H,5H,6H,7H-[1,2,3]triazolo[4,5-c]pyridine To a stirred solution of tert-butyl (6R)-1-[1-[4-fluoro-2-(trifluoromethyl)phenyl]ethyl]-6-methyl-1H,4H,5H,6H,7H-[1,2,3]triazolo[4,5-c]pyridine-5-carboxylate (1.7 g, 3.97 mmol, 1 equiv.) in DCM (12 mL) was added TFA (2 mL, 26.93 mmol, 6.79 equiv.) at room temperature. The solution was stirred at rt for 2 h. The mixture was concentrated under reduced pressure. The crude product (800 mg) was purified by Prep-HPLC with the following conditions (Column: XBridge Prep OBD C18 Column 30×150 mm 5 um; Mobile Phase A: Water (10 MMOL/L NH4HCO3), Mobile Phase B: ACN; Flow rate: 60 mL/min; Gradient: 20% B to 40% B in 10 min; 220 nm; Rt: 9.23 10.28 min.) to afford (6R)-1-[1-[4-fluoro-2-(trifluoromethyl)phenyl]ethyl]-6-methyl-1H,4H,5H,6H,7H-[1,2,3]triazolo[4,5-c]pyridine (300 mg, 23.03%) as colorless oil.

4-Chloro-5-[(6R)-1-[1-[4-fluoro-2-(trifluoromethyl)phenyl]ethyl]-6-methyl-1H,4H,5H,6H,7H-[1,2,3]triazolo[4,5-c]pyridin-5-yl]-2-(oxan-2-yl)-2,3-dihydropyridazin-3-one To a stirred solution of (6R)-1-[1-[4-fluoro-2-(trifluoromethyl)phenyl]ethyl]-6-methyl-1H,4H,5H,6H,7H-[1,2,3]triazolo[4,5-c]pyridine (300 mg, 0.91 mmol, 1 equiv.) and 4,5-dichloro-2-(oxan-2-yl)-2,3-dihydropyridazin-3-one (227.6 mg, 0.91 mmol, 1 equiv.) was added DIEA (236.2 mg, 1.83 mmol, 2 equiv.) at room temperature. The solution was stirred at 100 degrees celsius for 4 h. The mixture was concentrated under reduced pressure. The residue was purified by Prep-TLC (PE/EtOAc 1:1) to afford 4-chloro-5-[(6R)-1-[1-[4-fluoro-2-(trifluoromethyl)phenyl]ethyl]-6-methyl-1H,4H,5H,6H,7H-[1,2,3]triazolo[4,5-c]pyridin-5-yl]-2-(oxan-2-yl)-2,3-dihydropyridazin-3-one (200 mg, 40.46%) as colorless oil.

4-chloro-5-[(6R)-1-[(1S)-1-[4-fluoro-2-(trifluoromethyl)phenyl]ethyl]-6-methyl-1H,4H,5H,6H,7H-[1,2,3]triazolo[4,5-c]pyridin-5-yl]-2,3-dihydropyridazin-3-one and 4-chloro-5-[(6R)-1-[(1R)-1-[4-fluoro-2-(trifluoromethyl)phenyl]ethyl]-6-methyl-1H,4H,5H,6H,7H-[1,2,3]triazolo[4,5-c]pyridin-5-yl]-2,3-dihydropyridazin-3-one The mixture product (60 mg) was purified by PREP CHIRAL HPLC with the following conditions (Column: CHIRALPAK IG, 20*250 mm, 5 um; Mobile Phase A:MTBE (10 mM NH3-MEOH)—HPLC, Mobile Phase B: EtOH—HPLC; Flow rate: 16 mL/min; Gradient: 50 B to 50 B in 19 min; 254/220 nm; RT1:11.653; RT2:15.005) to afford 4-chloro-5-[(6R)-1-[(1S)-1-[4-fluoro-2-(trifluoromethyl)phenyl]ethyl]-6-methyl-1H,4H,5H,6H,7H-[1,2,3]triazolo[4,5-c]pyridin-5-yl]-2,3-dihydropyridazin-3-one (33 mg) (NJ) as a white solid and afford 4-chloro-5-[(6R)-1-[(1R)-1-[4-fluoro-2-(trifluoromethyl)phenyl]ethyl]-6-methyl-1H,4H,5H,6H,7H-[1,2,3]triazolo[4,5-c]pyridin-5-yl]-2,3-dihydropyridazin-3-one (6 mg) (NI) as a white solid.

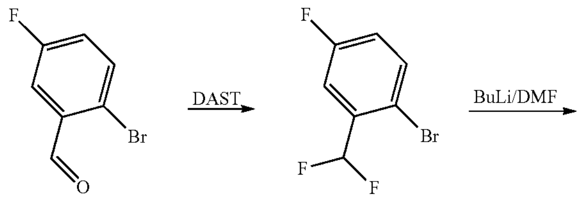

-continued

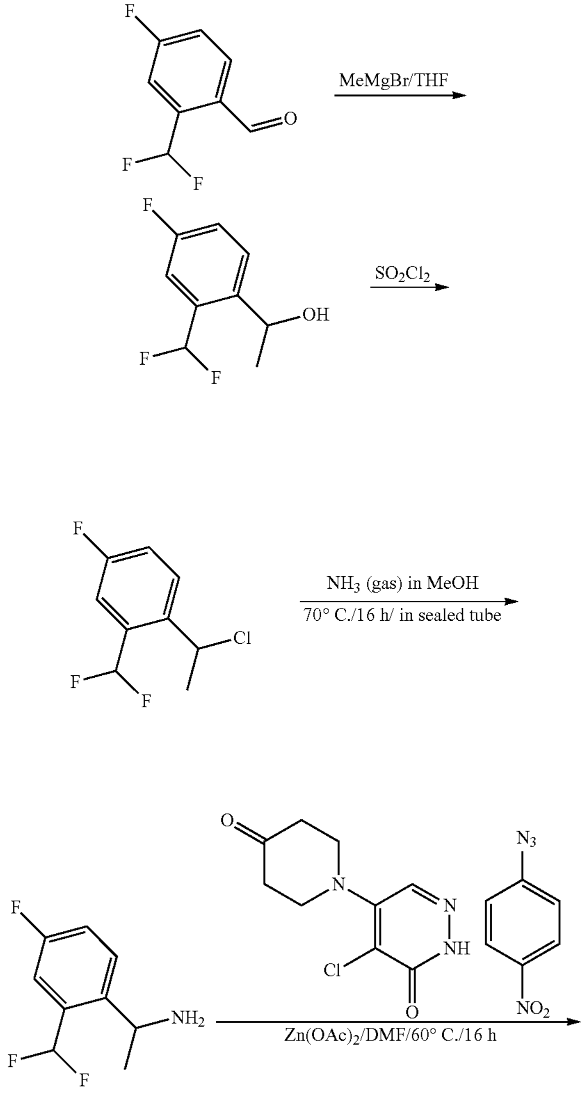

3

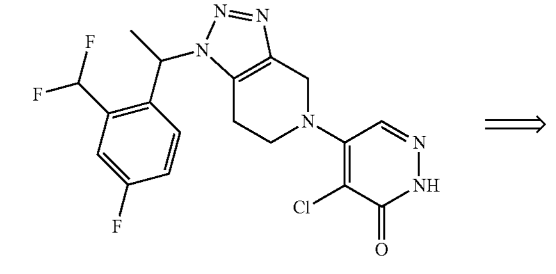

4

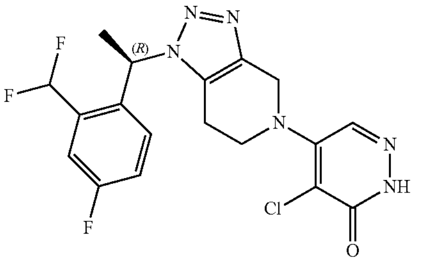

NK

-continued

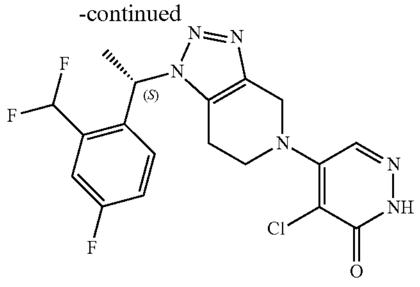

NL

Preparation of NK and NL

1-Bromo-2-(difluoromethyl)-4-fluorobenzene

To a stirred solution of 2-bromo-5-fluorobenzaldehyde (10 g, 49.26 mmol, 1 equiv.) in DCM (10 mL) was added DAST (15.9 g, 98.64 mmol, 2.00 equiv.). The resulting mixture was stirred for 2 h at −10 degrees C. The resulting mixture was concentrated under reduced pressure. The residue was purified by silica gel column chromatography, eluted with PE/EtOAc (5:1) to afford 1-bromo-2-(difluoromethyl)-4-fluorobenzene (8.2 g, 73.98%) as a light yellow oil.

2-(Difluoromethyl)-4-fluorobenzaldehyde

A solution of 1-bromo-2-(difluoromethyl)-4-fluorobenzene (8 g, 35.55 mmol, 1 equiv.) and n-BuLi (2.7 g, 42.15 mmol, 1.19 equiv.) in THF (150 mL) was stirred for 2 h at −78 degrees C. To the above mixture was added DMF (3.9 g, 53.33 mmol, 1.5 equiv.). The resulting mixture was stirred for 1 h at −78 degrees C. The reaction was quenched by the addition of Water (50 mL) at −70 degrees C. The solution was extracted with EtOAc (3×50 mL). The combined organic layers were washed with brine (2×30 mL), dried over anhydrous Na2SO4. After filtration, the filtrate was concentrated under reduced pressure. The residue was purified by silica gel column chromatography, eluted with PE/EtOAc (5:1) to afford 2-(difluoromethyl)-4-fluorobenzaldehyde (3 g, 48.46%) as a light yellow oil.

1-[2-(Difluoromethyl)-4-fluorophenyl]ethan-1-ol

To a stirred solution of 2-(difluoromethyl)-4-fluorobenzaldehyde (3 g, 17.23 mmol, 1 equiv.) in THF (30 mL, 416.06 mmol, 10 equiv.) was added CH3MgBr (25.84 mL, 25.84 mmol, 1.5 equiv.) dropwise at −30 degrees celsius under nitrogen atmosphere. The resulting mixture was stirred for 2 h at −10 degrees celsius under nitrogen atmosphere. The reaction was quenched with sat. NH4Cl (aq.) at 0 degrees C. The mixture was extracted with EtOAc (3×300 mL). The combined organic layers were washed with brine (3×300 mL), dried over anhydrous Na2SO4. After filtration, the filtrate was concentrated under reduced pressure. The residue was purified by silica gel column chromatography, eluted with PE/EtOAc (100:1 to 50:1) to afford 1-[2-(difluoromethyl)-4-fluorophenyl]ethan-1-ol (2.68 g, 81.80%) as red oil.

1-(1-Chloroethyl)-2-(difluoromethyl)-4-fluorobenzene

To a stirred solution/mixture of 1-[2-(difluoromethyl)-4-fluorophenyl]ethan-1-ol (2.68 g, 14.09 mmol, 1 equiv.) in DCM (30 mL, 140.93 mmol, 10 equiv.) was added SO2Cl2 (6.7 g, 49.64 mmol, 3.52 equiv.) dropwise in portions at 0 degrees celsius under air atmosphere. The resulting mixture was stirred for 2 h at 20 degrees C. The resulting oil was dried under vacuum. to afford 1-(1-chloroethyl)-2-(difluoromethyl)-4-fluorobenzene (2.36 g, 80.27%) as red oil.

1-[2-(difluoromethyl)-4-fluorophenyl]ethan-1-amine

To a stirred solution of 1-(1-chloroethyl)-2-(difluoromethyl)-4-fluorobenzene (300 mg, 1.44 mmol, 1 equiv.) in MeOH with NH3(g) at rt under nitrogen atmosphere. The resulting mixture was stirred for 20 h at 70 degrees celsius under nitrogen atmosphere. The reaction was monitored by LCMS. The mixture was allowed to cool down to rt. The resulting mixture was concentrated under reduced pressure. This resulted in 1-[2-(difluoromethyl)-4-fluorophenyl]ethan-1-amine (130 mg, 47.78%) as a yellow oil. The resulting mixture was used in the next step directly without further purification 4-chloro-5-[1-[(1S)-1-[2-(difluoromethyl)-4-fluorophenyl]ethyl]-1H,4H,5H,6H,7H-[1,2,3]triazolo[4,5-c]pyridin-5-yl]-2,3-dihydropyridazin-3-one and 4-chloro-5-[1-[(1R)-1-[2-(difluoromethyl)-4-fluorophenyl]ethyl]-1H,4H,5H,6H,7H-[1,2,3]triazolo[4,5-c]pyridin-5-yl]-2,3-dihydropyridazin-3-one To a stirred mixture of 1-[2-(difluoromethyl)-4-fluorophenyl]ethan-1-amine (130.0 mg, 0.69 mmol, 2.00 equiv.) and 4-chloro-5-(4-oxopiperidin-1-yl)-2,3-dihydropyridazin-3-one (78.2 mg, 0.34 mmol, 1 equiv.) in DMF (10 mL) were added 1-azido-4-nitrobenzene (78.9 mg, 0.48 mmol, 1.40 equiv.) and Zn(OAc)2 (63.0 mg, 0.34 mmol, 1.00 equiv.) in portions at rt under nitrogen atmosphere. The resulting mixture was stirred for 16 h at 60 degrees celsius under nitrogen atmosphere. The reaction was monitored by LCMS. The mixture was allowed to cool down to rt. The residue was purified by reverse phase flash with the following conditions (Column: XBridge Shield RP18 OBD Column, 20-40 um, 19*150 mm; Mobile Phase A: Water (10 MMOL/L NH4HCO3), Mobile Phase B: ACN; Flow rate: 80 mL/min; Gradient: 30% B to 70% B in 30 min; 220 nm; Rt: 7.08 min) to afford mixture product. The residue (100 mg) was purified by Chiral-Prep-HPLC with the following conditions: Column, CHIRALPAK IF-3, 0.46*5 cm; 3 um; Mobile phase: MtBE (0.1% DEA):EtOH=80:20; Detector:UV-254 nm. 4-chloro-5-[1-[(1S)-1-[2-(difluoromethyl)-4-fluorophenyl]ethyl]-1H,4H,5H,6H,7H-[1,2,3]triazolo[4,5-c]pyridin-5-yl]-2,3-dihydropyridazin-3-one (19.0 mg) was obtained at 3.835 min as a off-white solid. 4-chloro-5-[1-[(1R)-1-[2-(difluoromethyl)-4-fluorophenyl]ethyl]-1H,4H,5H,6H,7H-[1,2,3]triazolo[4,5-c]pyridin-5-yl]-2,3-dihydropyridazin-3-one (33.8 mg) was obtained at 3.185 min as a off-white solid.

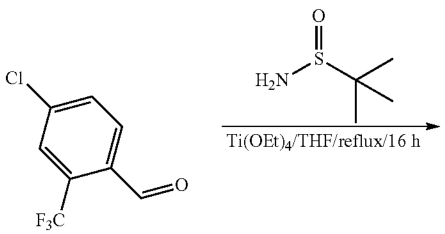

-continued

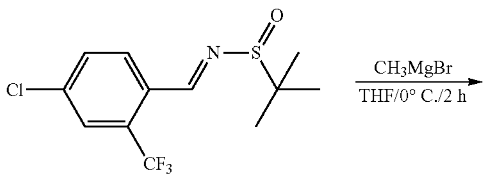

1

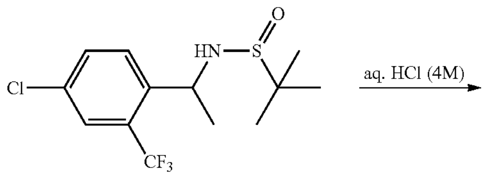

2

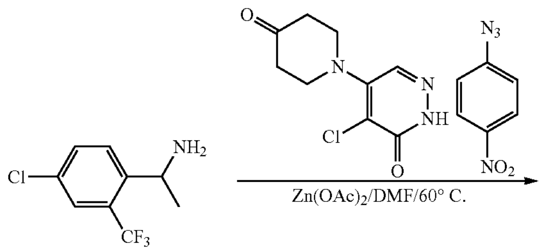

3

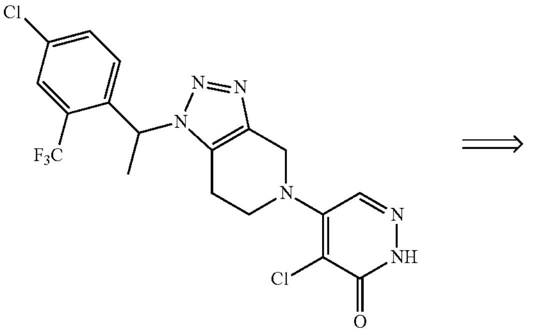

4

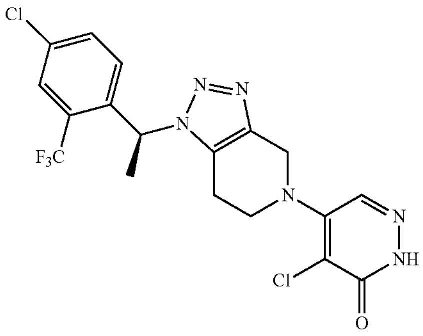

NM

-continued

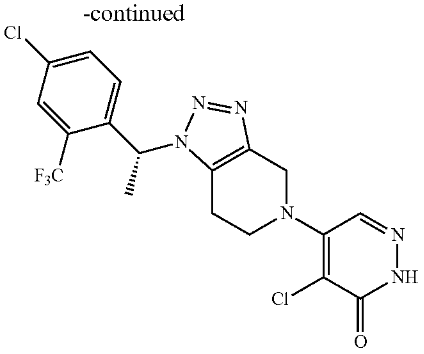

NN

Preparation of NM and NN

N-[(1E)-[4-chloro-2-(trifluoromethyl)phenyl]methylidene]-2-methylpropane-2-sulfinamide To a solution of 4-chloro-2-(trifluoromethyl)benzaldehyde (2 g, 9.590 mmol, 1 equiv.) and 2-methylpropane-2-sulfinamide (2.32 g, 19.142 mmol, 2.00 equiv.) in THF (20 mL) was added Ti(OEt)4 (4.37 g, 19.158 mmol, 2.00 equiv.) at room temperature. The resulting mixture was stirred for 16 h at 65 degrees C. The reaction was monitored by TLC [PE:EA (5:1)]. The mixture was allowed to cool down to room temperature. The reaction was quenched by the addition of Water (5 mL) at room temperature. The resulting mixture was filtered, the filter cake was washed with EtOAc (3x50 mL). The filtrate was concentrated under reduced pressure. The resulting mixture was extracted with EtOAc (3x100 mL). The combined organic layers were washed with brine (3x50 mL), dried over anhydrous Na2SO4. After filtration, the filtrate was concentrated under reduced pressure. The residue was purified by silica gel column chromatography, eluted with PE/EtOAc (50:1 to 30:1) to afford N-[(1E)-[4-chloro-2-(trifluoromethyl)phenyl]methylidene]-2-methylpropane-2-sulfinamide (2.5 g, 83.62%) as a yellow oil.

N-[1-[4-chloro-2-(trifluoromethyl)phenyl]ethyl]-2-methylpropane-2-sulfinamide

To a stirred solution of N-[(1E)-[4-chloro-2-(trifluoromethyl)phenyl]methylidene]-2-methylpropane-2-sulfinamide (1 g, 3.208 mmol, 1 equiv.) in THF (10 mL) was added CH3MgBr (573.75 mg, 4.812 mmol, 1.50 equiv.) dropwise at −40 degrees celsius under nitrogen atmosphere. The resulting mixture was stirred for 2 h at −10 degrees celsius under nitrogen atmosphere. The reaction was monitored by LCMS. The reaction was quenched by the addition of sat. NH4Cl (aq.) (10 mL) at −40 degrees C. The resulting mixture was extracted with EtOAc (3x200 mL). The combined organic layers were washed with brine (3x200 mL), dried over anhydrous Na2SO4. After filtration, the filtrate was concentrated under reduced pressure. The residue was purified by silica gel column chromatography, eluted with PE/EtOAc (50:1) to afford N-[1-[4-chloro-2-(trifluoromethyl)phenyl]ethyl]-2-methylpropane-2-sulfinamide (1 g, 95.11%) as a yellow oil.

1-[4-Chloro-2-(trifluoromethyl)phenyl]ethan-1-amine

To a stirred solution of N-[1-[4-chloro-2-(trifluoromethyl)phenyl]ethyl]-2-methylpropane-2-sulfinamide (1 g, 3.051 mmol, 1 equiv.) in DCM (4 mL) was added HCl (1.00 mL, 27.431 mmol, 10.79 equiv.) at room temperature. The resulting mixture was stirred for 2 h at room temperature. The reaction was monitored by LCMS. The resulting mixture was extracted with CH2Cl2 (2×100 mL). The combined organic layers were washed with brine (2×100 mL), dried over anhydrous Na2SO4. After filtration, the filtrate was concentrated under reduced pressure at 0 degrees celsius to afford 1-[4-chloro-2-(trifluoromethyl)phenyl]ethan-1-amine (800 mg, 117.27%) as yellow oil.

4-chloro-5-[1-[(1S)-1-[4-chloro-2-(trifluoromethyl)phenyl]ethyl]-1H,4H,5H,6H,7H-[1,2,3]triazolo[4,5-c]pyridin-5-yl]-2,3-dihydropyridazin-3-one and 4-chloro-5-[1-[(1R)-1-[4-chloro-2-(trifluoromethyl)phenyl]ethyl]-1H,4H,5H,6H,7H-[1,2,3]triazolo[4,5-c]pyridin-5-yl]-2,3-dihydropyridazin-3-one To a mixture of 1-[4-chloro-2-(trifluoromethyl)phenyl]ethan-1-amine (800 mg, 3.577 mmol, 1 equiv.) and 4-chloro-5-(4-oxopiperidin-1-yl)-2,3-dihydropyridazin-3-one (814.42 mg, 3.578 mmol, 1.00 equiv.) in DMF (10 mL) were added 1-azido-4-nitrobenzene (822.01 mg, 5.008 mmol, 1.40 equiv.) and Zn(OAc)2 (656.46 mg, 3.577 mmol, 1.00 equiv.) at room temperature. The resulting mixture was stirred for 16 h at 60 degrees C. The reaction was monitored by LCMS. The mixture was allowed to cool down to room temperature. The residue was purified by reverse flash chromatography with the following conditions: column, C18 silica gel; mobile phase, ACN in water, 50% to 70% nt in 10 min; detector, UV 254 nm. The crude product (100 mg) was purified by Prep-HPLC with the following conditions (Column: XBridge Prep OBD C18 Column 19*250 mm, 5 um; Mobile Phase A: Water (10 MMOL/L NH4HCO3), Mobile Phase B: ACN; Flow rate: 60 mL/min; Gradient: 25% B to 44% B in 15 min; 220 nm; Rt: 14.82 min). The crude product (50 mg) was purified by Chiral-Prep-HPLC with the following conditions (Column: CHIRAL ART Cellulose-SB, 2*25 cm, 5 um; Mobile Phase A:HexHPLC, Mobile Phase B: EtOH—HPLC; Flow rate: 20 mL/min; Gradient: 40 B to 40 B in 19 min; 220/254 nm; RT1:12.001; RT2:16.393). 4-chloro-5-[1-[(1S)-1-[4-chloro-2-(trifluoromethyl)phenyl]ethyl]-1H,4H,5H,6H,7H-[1,2,3]triazolo[4,5-c]pyridin-5-yl]-2,3-dihydropyridazin-3-one (16.2 mg, 0.99%) was obtained at 16.393 min as a white solid. 4-chloro-5-[1-[(1R)-1-[4-chloro-2-(trifluoromethyl)phenyl]ethyl]-1H,4H,5H,6H,7H-[1,2,3]triazolo[4,5-c]pyridin-5-yl]-2,3-dihydropyridazin-3-one (18.8 mg) was obtained at 12.001 min as a white solid.

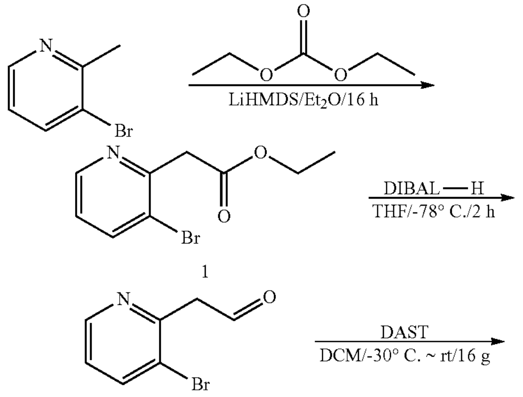

1

2

-continued

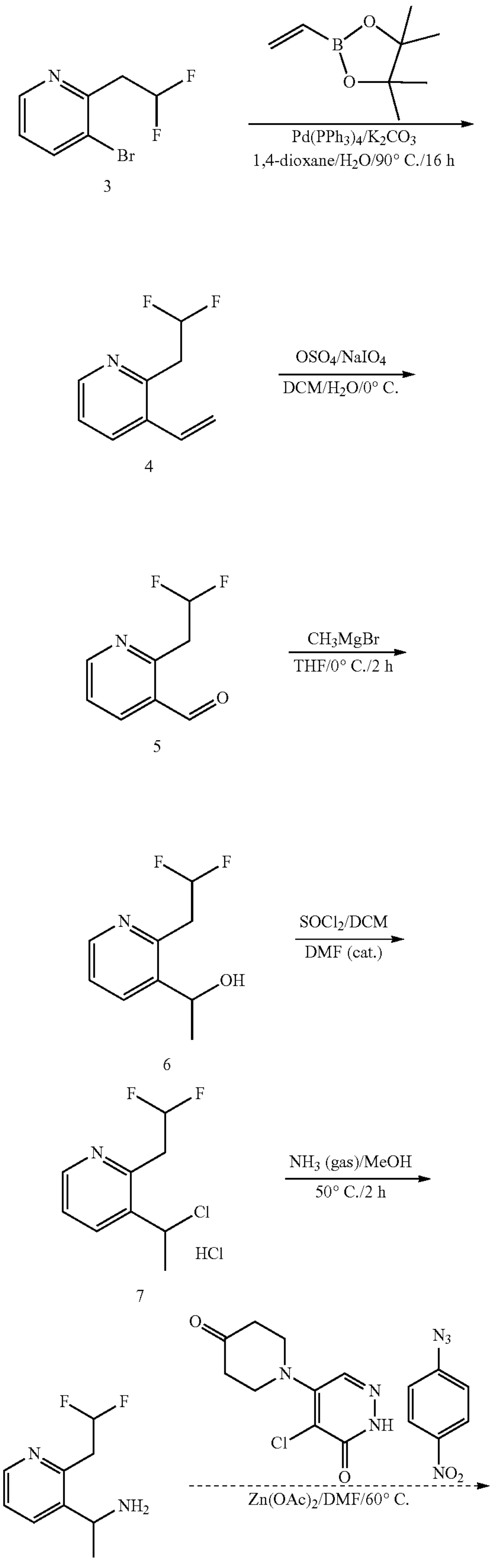

3

4

5

6

7

8

-continued

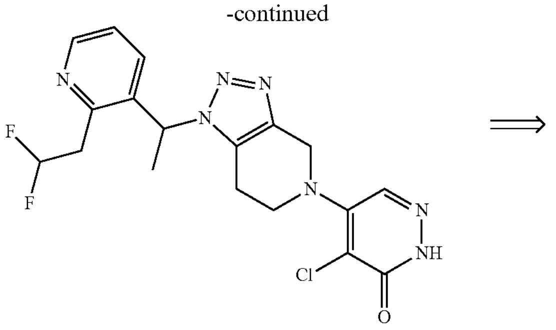

9

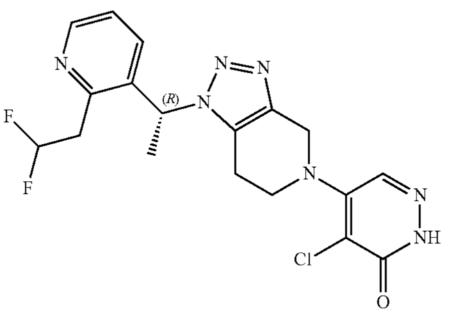

NO

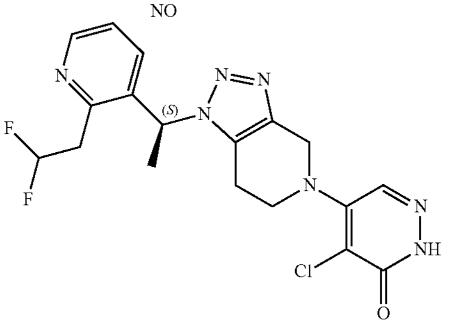

NP

Preparation of Compounds NO and NP

Ethyl 2-(3-bromopyridin-2-yl)acetate

To a stirred solution of LiHMDS (87.2 mL, 521.12 mmol, 1.5 equiv.) in THF (200 mL) was added 3-bromo-2-methylpyridine (10 g, 58.13 mmol, 1 equiv.) dropwise at 0 degrees celsius under nitrogen atmosphere. The mixture was stirred at rt for 2 h. diethyl carbonate (10.3 g, 87.20 mmol, 1.5 equiv.) was added to the mixture at 0 degrees C. Desired product could be detected by LCMS. The resulting mixture was concentrated under vacuum. To the mixture was added water (200 mL). The resulting mixture was extracted with EtOAc (2×200 mL). The combined organic layers were washed with brine (1×100 mL), dried over anhydrous Na2SO4. After filtration, the filtrate was concentrated under reduced pressure to afford ethyl 2-(3-bromopyridin-2-yl) acetate (13 g, 91.62%) as colorless oil.

2-(3-Bromopyridin-2-yl)acetaldehyde

To a stirred solution of ethyl 2-(3-bromopyridin-2-yl) acetate (10 g, 40.97 mmol, 1 equiv.) in Toluene (200 mL) was added DIBAl-H (10.3 mL, 61.42 mmol, 1.50 equiv.) dropwise at −78 degrees celsius under nitrogen atmosphere.

The mixture was stirred at −78 degrees for 10 min. Desired product could be detected by LCMS. The reaction was quenched by the addition of MeOH (4 mL) and water (20 mL) at −78 degrees C. The aqueous layer was extracted with EtOAc (3×50 mL). The combined organic layers were washed with brine (1×30 mL), dried over anhydrous Na2SO4. After filtration, the filtrate was concentrated under reduced pressure to afford 2-(3-bromopyridin-2-yl)acetaldehyde (7 g, 85.42%) as colorless oil.

3-Bromo-2-(2,2-difluoroethyl)pyridine

To a stirred solution of 2-(3-bromopyridin-2-yl)acetaldehyde (10 g, 49.991 mmol, 1 equiv.) in DCM (120 mL) was added DAST (16.12 g, 99.983 mmol, 2 equiv.) dropwise at 0 degrees celsius under nitrogen atmosphere. The mixture was stirred at rt overnight Desired product could be detected by LCMS. The resulting mixture was concentrated under reduced pressure. The residue was purified by silica gel column chromatography, eluted with PE/EtOAc (5:1 to 3:1) to afford 3-bromo-2-(2,2-difluoroethyl)pyridine (6 g, 54.06%) as a yellow oil.

2-(2,2-Difluoroethyl)-3-ethenylpyridine

To a solution of 3-bromo-2-(2,2-difluoroethyl)pyridine (100 mg, 0.45 mmol, 1 equiv.) and 2-ethenyl-4,4,5,5-tetramethyl-1,3,2-dioxaborolane (138.7 mg, 0.90 mmol, 2.00 equiv.) in 1,4-dioxane (5 mL) and H2O (1 mL) were added K2CO3 (186.7 mg, 1.35 mmol, 3 equiv.) and Pd(PPh3)4 (52.0 mg, 0.05 mmol, 0.1 equiv.). After stirring for 2 h at 100 degrees celsius under a nitrogen atmosphere, the resulting mixture was concentrated under reduced pressure. The residue was purified by silica gel column chromatography, eluted with PE/EtOAc (8:1 to 5:1) to afford 2-(2,2-difluoroethyl)-3-ethenylpyridine (60 mg, 78.75%) as colorless oil.

2-(2,2-Difluoroethyl)pyridine-3-carbaldehyde

To a stirred solution of 2-(2,2-difluoroethyl)-3-ethenylpyridine (1 g, 5.91 mmol, 1 equiv.) and K2OsO4.2H2O (0.2 g, 0.59 mmol, 0.1 equiv.) in THF (30 mL) was added NaIO4 (2.5 g, 11.82 mmol, 2.00 equiv.) in portions at 0 degrees celsius under nitrogen atmosphere. The mixture was stirred at 0 degrees celsius for 2 h. Desired product could be detected by LCMS. To the mixture was added water (40 mL). The resulting mixture was extracted with EtOAc (2×40 mL). The combined organic layers were washed with brine (1×30 mL), dried over anhydrous Na2SO4. After filtration, the filtrate was concentrated under reduced pressure to afford 2-(2,2-difluoroethyl)pyridine-3-carbaldehyde (1 g, 98.85%) as yellow oil.

1-[2-(2,2-Difluoroethyl)pyridin-3-yl]ethan-1-ol

To a stirred solution of 2-(2,2-difluoroethyl)pyridine-3-carbaldehyde (600 mg, 3.506 mmol, 1 equiv.) in THF (15 mL) was added MeMgBr (1254.12 mg, 10.517 mmol, 3 equiv.) dropwise at −30 degrees celsius under nitrogen atmosphere. The resulting mixture was stirred for 2 h at 0 degrees celsius under nitrogen atmosphere. The reaction was monitored by LCMS. The reaction was quenched with sat. NH4Cl (aq.) at 0 degrees C. The resulting mixture was filtered, the filter cake was washed with EtOAc (3×10 mL). The filtrate was concentrated under reduced pressure. The residue was purified by silica gel column chromatography, eluted with PE/EtOAc (20:1 to 3:1) to afford 1-[2-(2,2-difluoroethyl)pyridin-3-yl]ethan-1-ol (600 mg, 91.43%) as yellow oil.

3-(1-Chloroethyl)-2-(2,2-difluoroethyl)pyridine

To a stirred solution of 1-[2-(2,2-difluoroethyl)pyridin-3-yl]ethan-1-ol (500 mg, 2.67 mmol, 1 equiv.) in DCM (20 mL) were added SOCl2 (635.6 mg, 5.34 mmol, 2.00 equiv.) and DMF (0.1 mL, 1.29 mmol, 0.48 equiv.) dropwise at 0 degrees C. The resulting mixture was stirred for 2 h at room temperature. The reaction was monitored by LCMS. The resulting mixture was concentrated under reduced pressure. This resulted in 3-(1-chloroethyl)-2-(2,2-difluoroethyl)pyridine (540 mg, 98.32%) as dark yellow solid.

1-[2-(2,2-difluoroethyl)pyridin-3-yl]ethan-1-amine

Into a 20 mL pressure tank reactor were added 3-(1-chloroethyl)-2-(2,2-difluoroethyl)pyridine (50 mg, 0.243 mmol, 1 equiv.) in MeOH (10 mL) and NH3 (0.95 mg, 27.017 mmol, 100.00 equiv.) at room temperature. The mixture was stirred at 60 degrees celsius for 2 h. 21% Desired product could be detected by LCMS. The resulting mixture was concentrated under reduced pressure to afford 1-[2-(2,2-difluoroethyl)pyridin-3-yl]ethan-1-amine (20 mg, 35.34%) as yellow solid.

4-Chloro-5-[1-[(1R)-1-[2-(2,2-difluoroethyl)pyridin-3-yl]ethyl]-1H,4H,5H,6H,7H-[1,2,3]triazolo[4,5-c]pyridin-5-yl]-2,3-dihydropyridazin-3-one and 4-chloro-5-[1-[(1S)-1-[2-(2,2-difluoroethyl)pyridin-3-yl]ethyl]-1H,4H,5H,6H,7H-[1,2,3]triazolo[4,5-c]pyridin-5-yl]-2,3-dihydropyridazin-3-one To a stirred solution of 1-[2-(2,2-difluoroethyl)pyridin-3-yl]ethan-1-amine (200 mg, 1.074 mmol, 1 equiv.) and 1-azido-4-nitrobenzene (246.80 mg, 1.504 mmol, 1.40 equiv.) in DMF (8 mL) was added Zn(OAc)2 (197.09 mg, 1.074 mmol, 1 equiv.),4-chloro-5-(4-oxopiperidin-1-yl)-2,3-dihydropyridazin-3-one (244.51 mg, 1.074 mmol, 1.00 equiv.) at room temperature under nitrogen atmosphere. The mixture was stirred at 60 degrees celsius for 4 h. Desired product could be detected by LCMS. The resulting mixture was concentrated under reduced pressure. The residue was purified by Prep-TLC (CH2Cl2/MeOH 10:1) to afford 4-chloro-5-(1-[1-[2-(2,2-difluoroethyl)pyridin-3-yl]ethyl]-1H,4H,5H,6H,7H-[1,2,3]triazolo[4,5-c]pyridin-5-yl)-2,3-dihydropyridazin-3-one (140 mg, 30.90%) which was separated by CHIRAL-HPLC(Hex (0.1% DEA):EtOH=50:50) to afford 4-chloro-5-[1-[(1R)-1-[2-(2,2-difluoroethyl)pyridin-3-yl]ethyl]-1H,4H,5H,6H,7H-[1,2,3]triazolo[4,5-c]pyridin-5-yl]-2,3-dihydropyridazin-3-one (52 mg) as yellow solid and 4-chloro-5-[1-[(1S)-1-[2-(2,2-difluoroethyl)pyridin-3-yl]ethyl]-1H,4H,5H,6H,7H-[1,2,3]triazolo[4,5-c]pyridin-5-yl]-2,3-dihydropyridazin-3-one (48 mg) as yellow solid.

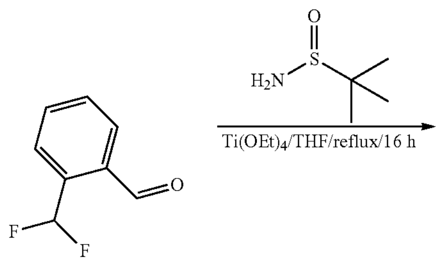

-continued

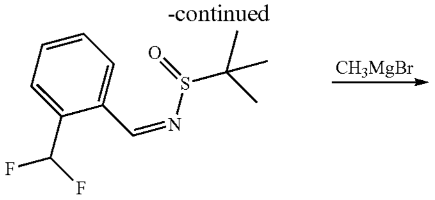

1

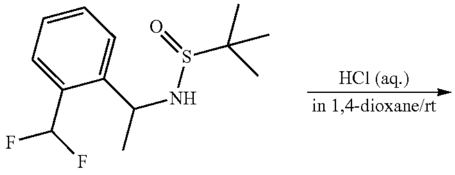

2

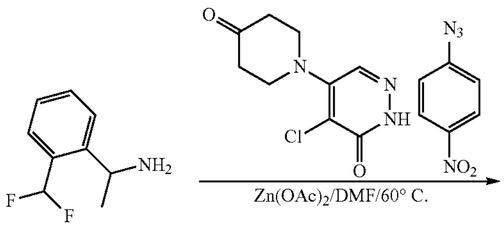

3

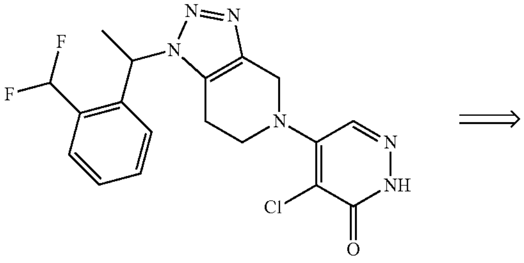

4

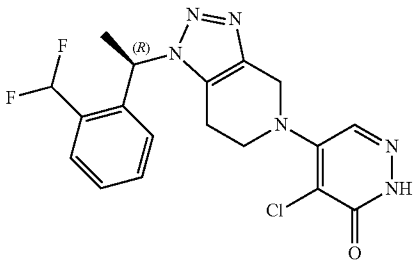

NQ

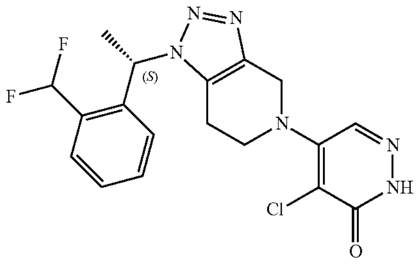

NR

Preparation of NQ and NR

N-[(1E)-[2-(difluoromethyl)phenyl]methylidene]-2-methylpropane-2-sulfinamide

To a stirred mixture of 2-(difluoromethyl)benzaldehyde (300 mg, 1.92 mmol, 1 equiv.) and 2-methylpropane-2-sulfinamide (256.2 mg, 2.11 mmol, 1.10 equiv.) in THF (20 mL) was added Ti(OEt)4 (876.6 mg, 3.84 mmol, 2.00 equiv.) in portions at rt under nitrogen atmosphere. The resulting mixture was stirred for 4 h at 70 degrees celsius under nitrogen atmosphere. The reaction was monitored by LCMS. The mixture was allowed to cool down to rt. The resulting mixture was extracted with EtOAc (3×100 mL). The combined organic layers were washed with brine (2×50 mL), dried over anhydrous Na2SO4. After filtration, the filtrate was concentrated under reduced pressure. This resulted in N-[(1E)-[2-(difluoromethyl)phenyl]methylidene]-2-methylpropane-2-sulfinamide (400 mg, 80.28%) as a yellow oil.

N-[1-[2-(difluoromethyl)phenyl]ethyl]-2-methylpropane-2-sulfinamide

To a stirred solution of N-[(1E)-[2-(difluoromethyl)phenyl]methylidene]-2-methylpropane-2-sulfinamide (380 mg, 1.47 mmol, 1 equiv.) in THF (20 mL) was added CH3MgBr (349.5 mg, 2.93 mmol, 2.00 equiv.) dropwise at −40 degrees celsius under nitrogen atmosphere. The resulting mixture was stirred for 2 h at −10 degrees celsius under nitrogen atmosphere. The reaction was monitored by LCMS. The reaction was quenched by the addition of sat. NH4Cl (aq.) (20 mL) at −40 degrees C. The resulting mixture was extracted with EtOAc (2×100 mL). The combined organic layers were washed with brine (2×50 mL), dried over anhydrous Na2SO4. After filtration, the filtrate was concentrated under reduced pressure. This resulted in N-[1-[2-(difluoromethyl)phenyl]ethyl]-2-methylpropane-2-sulfinamide (400 mg, 99.13%) as a yellow oil.

1-[2-(Difluoromethyl)phenyl]ethan-1-amine

To a stirred solution of N-[1-[2-(difluoromethyl)phenyl]ethyl]-2-methylpropane-2-sulfinamide (400 mg, 1.45 mmol, 1 equiv.) in dioxane (6 mL) was added HCl (4M)(2 mL, 65.82 mmol, 45.31 equiv.) dropwise at rt. The reaction mixture was stirred for 4 h at rt. The reaction was monitored by LCMS. The residue was basified to pH=8 with saturated NaHCO3 (aq.). The resulting mixture was extracted with CH2Cl2(3×100 mL). The combined organic layers were washed with brine (1×100 mL), dried over anhydrous Na2SO4. After filtration, the filtrate was concentrated under reduced pressure. This resulted 1-[2-(difluoromethyl)phenyl]ethan-1-amine (200 mg, 80.42%) as a yellow oil.

4-Chloro-5-(1-[1-[2-(difluoromethyl)phenyl]ethyl]-1H,4H,5H,6H,7H-[1,2,3]triazolo[4,5-c]pyridin-5-yl)-2-(oxan-2-yl)-2,3-dihydropyridazin-3-one To a stirred mixture of 1-[2-(difluoromethyl)phenyl]ethan-1-amine (197.7 mg, 1.15 mmol, 2.00 equiv.) and 4-chloro-2-(oxan-2-yl)-5-(4-oxopiperidin-1-yl)-2,3-dihydropyridazin-3-one (180 mg, 0.58 mmol, 1 equiv.) in DMF (10 mL) were added 1-azido-4-nitrobenzene (132.7 mg, 0.81 mmol, 1.40 equiv.) and Zn(OAc)2 (105.9 mg, 0.58 mmol, 1.00 equiv.) in portions at rt under nitrogen atmosphere. The resulting mixture was stirred for 16 h at 60 degrees celsius under nitrogen atmosphere. The reaction was monitored by LCMS. The mixture was allowed to cool down to rt. The residue was purified by reverse phase flash with the following conditions (Column: XBridge Shield RP18 OBD Column, 20-40 um, 19*150 mm; Mobile Phase A: Water (10 MMOL/L NH4HCO3), Mobile Phase B: ACN; Flow rate: 80 mL/min; Gradient: 30% B to 70% B in 30 min; 220 nm; Rt: 7.08 min) to afford 4-chloro-5-(1-[1-[2-(difluoromethyl)phenyl]ethyl]-1H,4H,5H,6H,7H-[1,2,3]triazolo[4,5-c]pyridin-5-yl)-2-(oxan-2-yl)-2,3-dihydropyridazin-3-one (150 mg, 52.92%) as a yellow oil.

4-chloro-5-[1-[(1R)-1-[2-(difluoromethyl)phenyl]ethyl]-1H,4H,5H,6H,7H-[1,2,3]triazolo[4,5-c]pyridin-5-yl]-2,3-dihydropyridazin-3-one and 4-chloro-5-[1-[(1S)-1-[2-(difluoromethyl)phenyl]ethyl]-1H,4H,5H,6H,7H-[1,2,3]triazolo[4,5-c]pyridin-5-yl]-2,3-dihydropyridazin-3-one To a stirred solution of 4-chloro-5-(1-[1-[2-(difluoromethyl)phenyl]ethyl]-1H,4H,5H,6H,7H-[1,2,3]triazolo[4,5-c]pyridin-5-yl)-2-(oxan-2-yl)-2,3-dihydropyridazin-3-one (150 mg, 0.31 mmol, 1 equiv.) in DCM (15 mL) was added TFA (2 mL, 26.93 mmol, 88.13 equiv.) dropwise at rt. The reaction mixture was stirred for 4 h at rt. The reaction was monitored by LCMS. The resulting mixture was concentrated under reduced pressure. The residue was basified to pH=8 with saturated NH4HCO3 (aq.). The resulting mixture was extracted with CH2Cl2(3×100 mL). The combined organic layers were washed with brine (1×50 mL), dried over anhydrous Na2SO4. After filtration, the filtrate was concentrated under reduced pressure. The residue was purified by Chiral-Prep-HPLC with the following conditions (Column: XBridge Prep OBD C18 Column 30×150 mm 5 um; Mobile Phase A: Water (10 MMOL/L NH4HCO3), Mobile Phase B: ACN; Flow rate: 60 mL/min; Gradient: 20% B to 45% B in 7 min; 220 nm; Rt: 6.18 min). 4-chloro-5-[1-[(1R)-1-[2-(difluoromethyl)phenyl]ethyl]-1H,4H,5H,6H,7H-[1,2,3]triazolo[4,5-c]pyridin-5-yl]-2,3-dihydropyridazin-3-one (19.6 mg) was obtained at 6.431 min as a off-white solid. 4-chloro-5-[1-[(1S)-1-[2-(difluoromethyl)phenyl]ethyl]-1H,4H,5H,6H,7H-[1,2,3]triazolo[4,5-c]pyridin-5-yl]-2,3-dihydropyridazin-3-one (18.7 mg) was obtained at 4.822 min as a off-white solid (E01224-053).

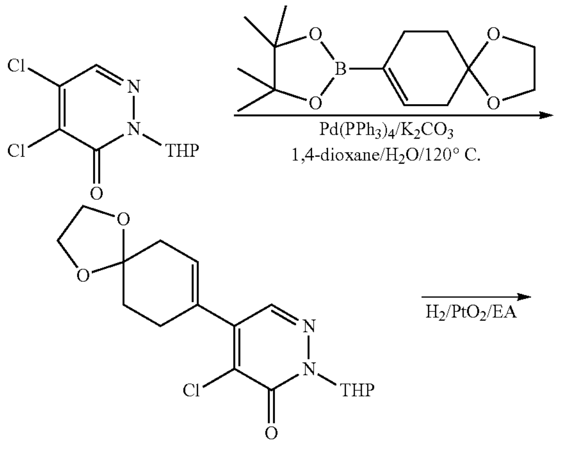

1

-continued

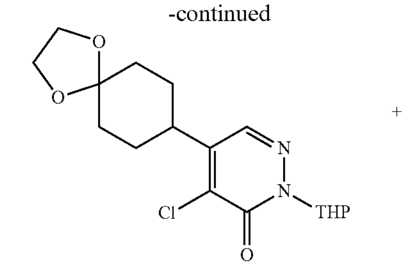

2

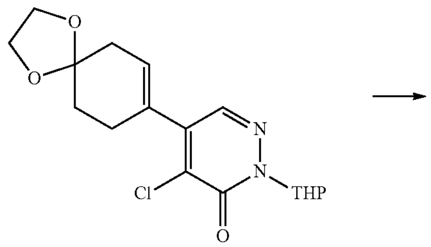

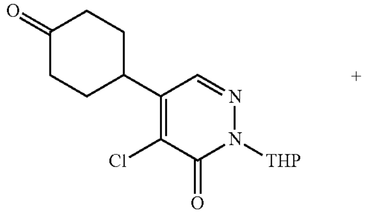

3

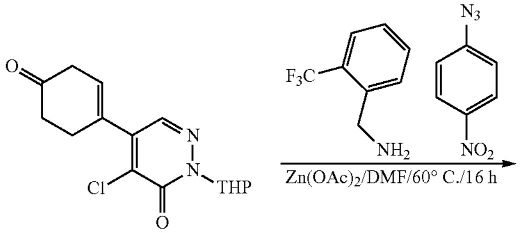

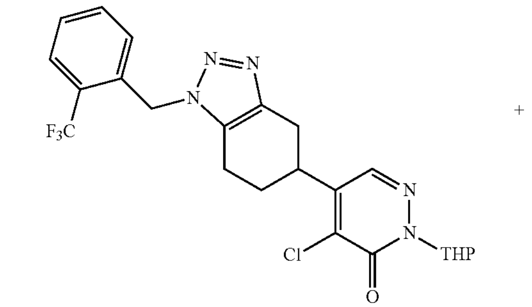

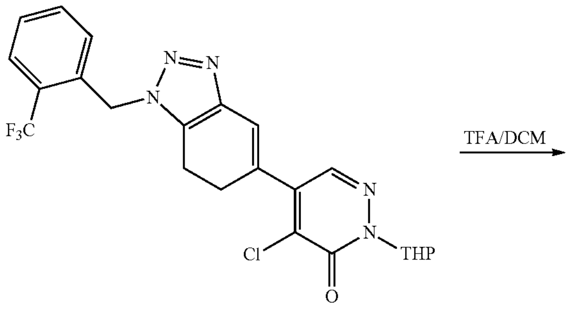

-continued

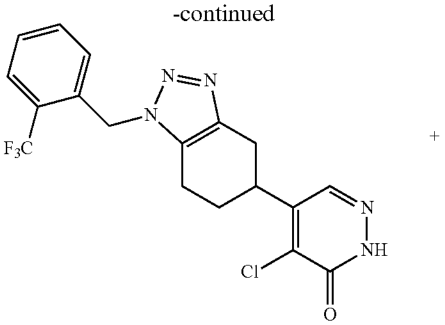

NS

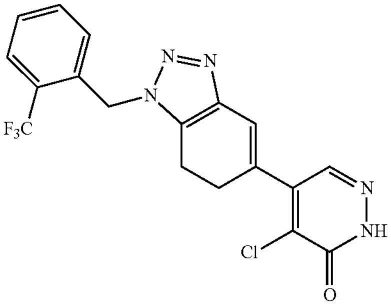

NT

Preparation of NS and NT

5-Chloro-4-[1,4-dioxaspiro[4.5]dec-7-en-8-yl]-2-(oxan-2-yl)-2,3-dihydropyridazin-3-one To a solution of 4,5-dichloro-2-(oxan-2-yl)-2,3-dihydropyridazin-3-one (100 mg, 0.40 mmol, 1 equiv.) and 2-[1,4-dioxaspiro[4.5]dec-7-en-8-yl]-4,4,5,5-tetramethyl-1,3,2-dioxaborolane (106.8 mg, 0.40 mmol, 1.00 equiv.) in 1,4-dioxane (5 mL) and H2O (1 mL) were added K2CO3 (111.0 mg, 0.80 mmol, 2 equiv.) and Pd(PPh3)4 (46.4 mg, 0.04 mmol, 0.10 equiv.). After stirring for overnight at 100 degrees celsius under a nitrogen atmosphere, the resulting mixture was concentrated under reduced pressure. The residue was purified by Prep-TLC, eluted with PE/EtOAc (1:1) to afford 4-chloro-5-[1,4-dioxaspiro[4.5]dec-7-en-8-yl]-2-(oxan-2-yl)-2,3-dihydropyridazin-3-one (20 mg, 14.12%) as a yellow solid and 5-chloro-4-[1,4-dioxaspiro[4.5]dec-7-an-8-yl]-2-(oxan-2-yl)-2,3-dihydropyridazin-3-one (20 mg, 14.12%) as a yellow solid.

4-Chloro-5-[1,4-dioxaspiro[4.5]decan-8-yl]-2-(oxan-2-yl)-2,3-dihydropyridazin-3-one To a stirred solution of 4-chloro-5-[1,4-dioxaspiro[4.5]dec-7-en-8-yl]-2-(oxan-2-yl)-2,3-dihydropyridazin-3-one (200 mg, 0.57 mmol, 1 equiv.) in EA (15 mL) was added PtO2 (12.9 mg, 0.06 mmol, 0.1 equiv.) at room temperature under hydrogen atmosphere. The resulting mixture was stirred for 1 h at room temperature under hydrogen atmosphere. The reaction was monitored by LCMS. The resulting mixture was filtered, the filter cake was washed with EtOAc (3×5 mL). The filtrate was concentrated under reduced pressure. This resulted in a mixture of 4-chloro-5-[1,4-dioxaspiro[4.5]decan-8-yl]-2-(oxan-2-yl)-2,3-dihydropyridazin-3-one (110 mg, crude) and starting material as yellow solid.

4-Chloro-2-(oxan-2-yl)-5-(4-oxocyclohexyl)-2,3-dihydropyridazin-3-one

To a stirred solution of the above mixture in THF (20 mL) was added HCl (1 mL, 32.91 mmol, 106.16 equiv.) dropwise at room temperature. The resulting mixture was stirred for 1 h at room temperature. The reaction was monitored by LCMS. The resulting mixture was extracted with EtOAc (3×30 mL). The combined organic layers were washed with brine (2×10 mL), dried over anhydrous Na2SO4. After filtration, the filtrate was concentrated under reduced pressure. This resulted in 4-chloro-2-(oxan-2-yl)-5-(4-oxocyclohexyl)-2,3-dihydropyridazin-3-one (30 mg, 0.10 mmol, 1 equiv.) and 4-chloro-2-(oxan-2-yl)-5-(4-oxocyclohex-1-en-1-yl)-2,3-dihydropyridazin-3-one as yellow solid 4-Chloro-2-(oxan-2-yl)-5-(1-[[2-(trifluoromethyl)phenyl]methyl]-4,5,6,7-tetrahydro-1H-1,2,3-benzotriazol-5-yl)-2,3-dihydropyridazin-3-one To a stirred mixture of 4-chloro-2-(oxan-2-yl)-5-(4-oxocyclohexyl)-2,3-dihydropyridazin-3-one (30 mg, 0.10 mmol, 1 equiv.) and 4-chloro-2-(oxan-2-yl)-5-(4-oxocyclohex-1-en-1-yl)-2,3-dihydropyridazin-3-one (30.1 mg, 0.10 mmol, 1.01 equiv.) in ACN (10 mL) were added 1-[2-(trifluoromethyl)phenyl]methanamine (16.9 mg, 0.10 mmol, 1.00 equiv.), 1-azido-4-nitrobenzene (22.2 mg, 0.14 mmol, 1.40 equiv.) and Zn(OAc)2 (17.7 mg, 0.10 mmol, 1 equiv.) at room temperature. The resulting mixture was stirred for 16 h at 60 degrees C. The reaction was monitored by LCMS. The mixture was allowed to cool down to room temperature. The resulting mixture was concentrated under reduced pressure. The residue was purified by reverse phase flash with the following conditions (Column:C18,330 g; Mobile Phase A: Water/0.05% NH4HCO3, Mobile Phase B:ACN; Flow rate:80 mL/min; Gradient: 40% B to 50% B in 10 min; Detector, 254 nm and 220 nm) to afford 4-chloro-2-(oxan-2-yl)-5-(1-[[2-(trifluoromethyl)phenyl]methyl]-4,5,6,7-tetrahydro-1H-1,2,3-benzotriazol-5-yl)-2,3-dihydropyridazin-3-one (18 mg, 37.75%) as a yellow solid and 4-chloro-2-(oxan-2-yl)-5-(1-[[2-(trifluoromethyl)phenyl]methyl]-6,7-dihydro-1H-1,2,3-benzotriazol-5-yl)-2,3-dihydropyridazin-3-one (10 mg, 21.06%) as a yellow solid.

4-Chloro-5-(1-[[2-(trifluoromethyl)phenyl]methyl]-4,5,6,7-tetrahydro-1H-1,2,3-benzotriazol-5-yl)-2,3-dihydropyridazin-3-one To a stirred solution of 4-chloro-2-(oxan-2-yl)-5-(1-[[2-(trifluoromethyl)phenyl]methyl]-4,5,6,7-tetrahydro-1H-1,2,3-benzotriazol-5-yl)-2,3-dihydropyridazin-3-one (18 mg, 0.04 mmol, 1 equiv.) in DCM (4 mL) was added TFA (1 mL, 13.46 mmol, 369.43 equiv.) at room temperature. The resulting mixture was stirred for 2 h at room temperature. The reaction was monitored by LCMS. The resulting mixture was concentrated under reduced pressure. The residue was basified to pH 8 with saturated NaHCO3 (aq.). The resulting mixture was concentrated under reduced pressure. The crude product (16 mg) was purified by Prep-HPLC with the following conditions (Column: XBridge Prep C18 OBD Column 19×150 mm 5 um; Mobile Phase A: Water (10 MMOL/L NH4HCO3), Mobile Phase B: ACN; Flow rate: 25 mL/min; Gradient: 25% B to 70% B in 7 min; 254/220 nm; Rt: 6.66 min) to afford 4-chloro-5-(1-[[2-(trifluoromethyl)phenyl]methyl]-4,5,6,7-tetrahydro-1H-1,2,3-benzotriazol-5-yl)-2,3-dihydropyridazin-3-one (9.4 mg, 62.94%) as an off-white solid.

4-Chloro-5-(1-[[2-(trifluoromethyl)phenyl]methyl]-6,7-dihydro-1H-1,2,3-benzotriazol-5-yl)-2,3-dihydropyridazin-3-one To a stirred solution of 4-chloro-2-(oxan-2-yl)-5-(1-[[2-(trifluoromethyl)phenyl]methyl]-6,7-dihydro-1H-1,2,3-benzotriazol-5-yl)-2,3-dihydropyridazin-3-one (10 mg) in DCM (4 mL) was added TFA (1 mL) at room temperature. The resulting mixture was stirred for 2 h at room temperature. The reaction was monitored by LCMS. The resulting mixture was concentrated under reduced pressure. The residue was basified to pH 8 with saturated NaHCO3 (aq.). The resulting mixture was concentrated under reduced pressure. The crude product (10 mg) was purified by Prep-HPLC with the following conditions (Column: XBridge Prep C18 OBD Column 19×150 mm 5 um; Mobile Phase A: Water (10 MMOL/L NH4HCO3), Mobile Phase B: ACN; Flow rate: 60 mL/min; Gradient: 26% B to 90% B in 7 min; 254/220 nm; Rt: 6.50 min) to afford 4-chloro-5-(1-[[2-(trifluoromethyl)phenyl]methyl]-6,7-dihydro-1H-1,2,3-benzotriazol-5-yl)-2,3-dihydropyridazin-3-one (5.5 mg) as a white solid.

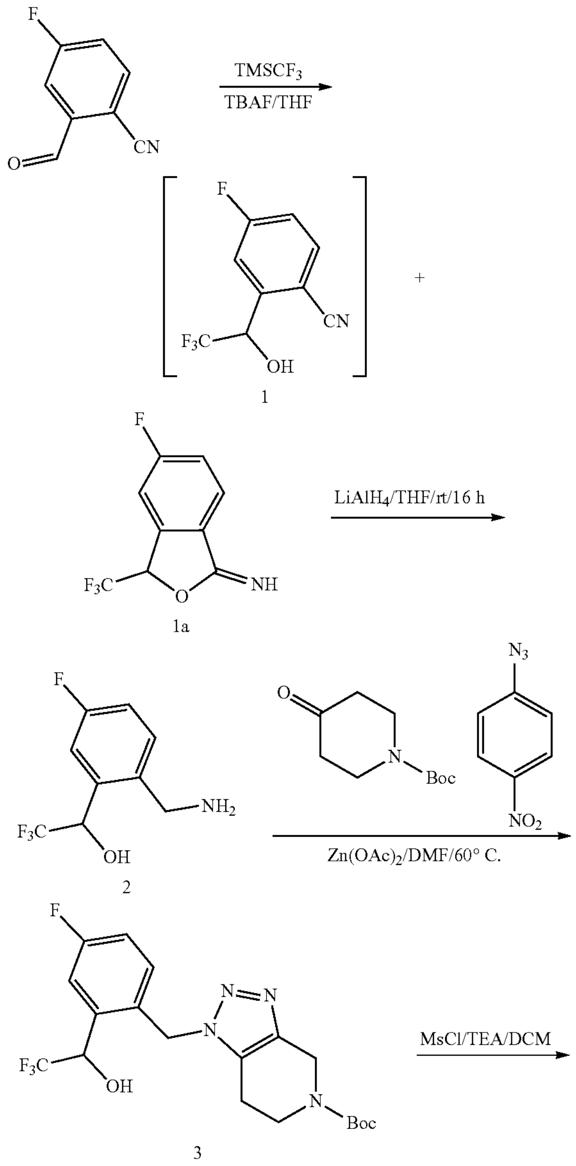

1 + 1a

2

3

-continued

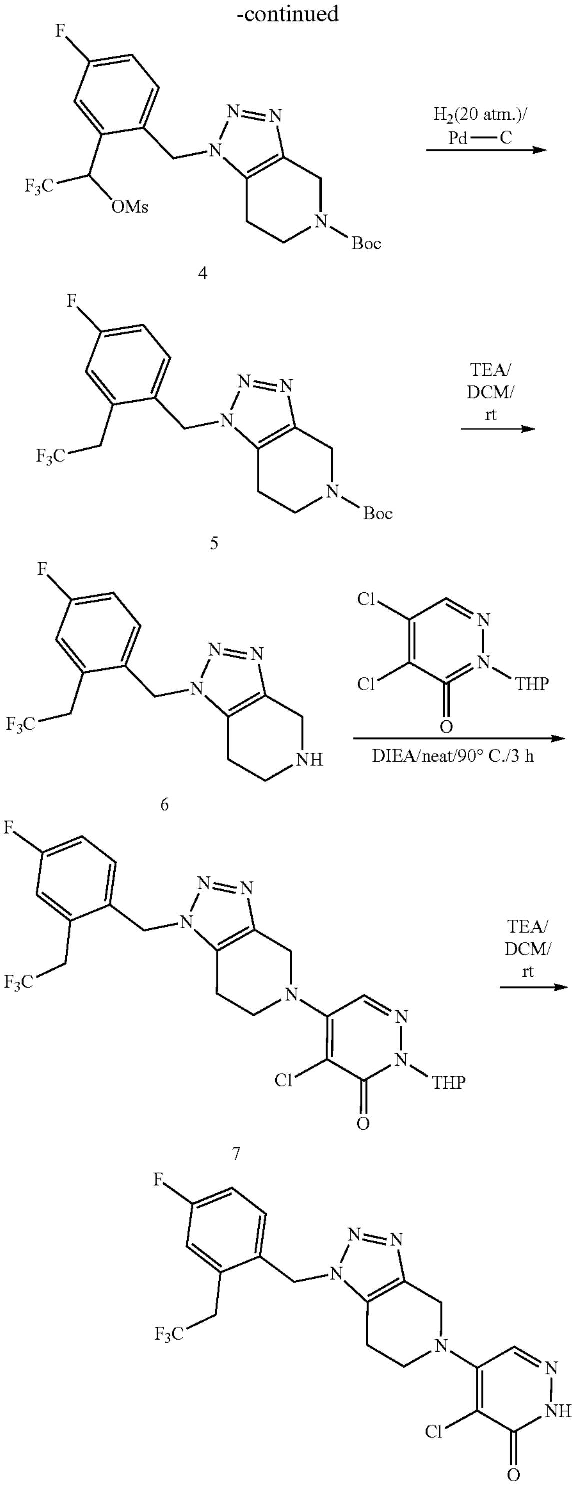

4

5

6

7

NU

Preparation of NU

4-Fluoro-2-[[(trimethylsilyl)oxy]methyl]benzonitrile

To a stirred mixture of 4-fluoro-2-formylbenzonitrile (2 g, 13.412 mmol, 1 equiv.) and TMSCF3 (3.81 g, 26.794 mmol, 2.00 equiv.) in THF (15 mL) was added TBAF (0.35 g, 1.341 mmol, 0.1 equiv.) dropwise at room temperature. The resulting mixture was stirred for 16 h at room temperature. The reaction was monitored by TLC PE/EA (5/1). The reaction was quenched by the addition of sat. NH4Cl (aq.) (5 mL) at room temperature. The resulting mixture was extracted with EtOAc (3×200 mL). The combined organic layers were washed with brine (3×200 mL), dried over anhydrous Na2SO4. After filtration, the filtrate was concentrated under reduced pressure. The residue was purified by silica gel column chromatography, eluted with PE/EtOAc (50:1) to DCM/MeOH (50/1) afford 4-fluoro-2-[[(trimethylsilyl)oxy]methyl]benzonitrile (1.4 g, 46.74%) as a light yellow oil.

5-Fluoro-3-(trifluoromethyl)-1,3-dihydro-2-benzofuran-1-imine

To a stirred solution of 4-fluoro-2-[2,2,2-trifluoro-1-[(trimethylsilyl)oxy]ethyl]benzonitrile (1.4 g, 4.806 mmol, 1 equiv.) in DCM (7 mL) was added TBAF (2.51 g, 9.600 mmol, 2.00 equiv.) at room temperature. The resulting mixture was stirred for 2 h at room temperature. The reaction was monitored by LCMS. The residue was purified by silica gel column chromatography, eluted with PE/EtOAc (50/1 to 30/1) to afford 5-fluoro-3-(trifluoromethyl)-1,3-dihydro-2-benzofuran-1-imine (800 mg, 75.97%) as a light yellow oil.

1-[2-(Aminomethyl)-5-fluorophenyl]-2,2,2-trifluoroethan-1-ol

To a stirred solution of 5-fluoro-3-(trifluoromethyl)-1,3-dihydro-2-benzofuran-1-imine (800 mg, 3.651 mmol, 1 equiv.) in THF (20 mL) was added LiAlH4 (277.11 mg, 7.301 mmol, 2.00 equiv.) dropwise at −30 degrees celsius under nitrogen atmosphere. The resulting mixture was stirred for 16 h at room temperature under nitrogen atmosphere. The reaction was monitored by LCMS. The mixture was allowed to cool down to −30 degrees C. The reaction was quenched with 10% NaOH·aq and water at −30 degrees C. The aqueous layer was extracted with DCM/MeOH (5/1) (3×200 mL). After filtration, the filtrate was concentrated under reduced pressure. The residue was purified by reverse flash chromatography with the following conditions: column, C18 silica gel; mobile phase, ACN in water, 10% to 50% gradient in 10 min; detector, UV 254 nm to afford 1-[2-(aminomethyl)-5-fluorophenyl]-2,2,2-trifluoroethan-1-ol (420 mg, 51.55%) as yellow oil.

1-[[4-Fluoro-2-(2,2,2-trifluoro-1-hydroxyethyl)phenyl]methyl]-1H,4H,5H,6H,7H-[1,2,3]triazolo[4,5-c]pyridine-5-carboxylate To a stirred mixture of 1-[2-(aminomethyl)-5-fluorophenyl]-2,2,2-trifluoroethan-1-ol (419.35 mg, 1.879 mmol, 1.2 equiv.) and tert-butyl 4-oxopiperidine-1-carboxylate (312 mg, 1.566 mmol, 1 equiv.) in DMF (15 mL) were added 1-azido-4-nitrobenzene (359.80 mg, 2.192 mmol, 1.40 equiv.) and Zn(OAc)2 (287.33 mg, 1.566 mmol, 1.00 equiv.) at room temperature. The resulting mixture was stirred for 16 h at 60 degrees C. The mixture was allowed to cool down to room temperature. The reaction was monitored by LCMS. The reaction was quenched by the addition of sat. NH4Cl (aq.) (5 mL) at room temperature. The resulting mixture was extracted with EtOAc (3×200 mL). The combined organic layers were washed with brine (3×200 mL), dried over anhydrous Na2SO4. After filtration, the filtrate was concentrated under reduced pressure. The residue was purified by reverse flash chromatography with the following conditions:

column, C18 silica gel; mobile phase, ACN in water, 40% to 70% gradient in 10 min; detector, UV 254 nm to afford tert-butyl 1-[[4-fluoro-2-(2,2,2-trifluoro-1-hydroxyethyl) phenyl]methyl]-1H,4H,5H,6H,7H-[1,2,3]triazolo[4,5-c] pyridine-5-carboxylate (300 mg, 44.51%) as light yellow.

Tert-Butyl 1-([4-fluoro-2-[2,2,2-trifluoro-1-(methanesulfonyloxy)ethyl]phenyl]methyl)-1H,4H,5H,6H,7H-[1,2,3]triazolo[4,5-c]pyridine-5-carboxylate To a stirred mixture of tert-butyl 1-[[4-fluoro-2-(2,2,2-trifluoro-1-hydroxyethyl)phenyl]methyl]-1H,4H,5H,6H,7H-[1,2,3]triazolo[4,5-c]pyridine-5-carboxylate (300 mg, 0.697 mmol, 1 equiv.) and Et3N (141.06 mg, 1.394 mmol, 2.00 equiv.) in DCM (10 mL) was added MsCl (95.81 mg, 0.836 mmol, 1.2 equiv.) dropwise at 0 degrees C. The resulting mixture was stirred for 2 h at room temperature. The reaction was monitored by TLC (CH2Cl2/MeOH 30:1). The residue was purified by Prep-TLC (CH2Cl2/MeOH 30:1) to afford tert-butyl 1-([4-fluoro-2-[2,2,2-trifluoro-1-(methanesulfonyloxy)ethyl]phenyl]methyl)-1H,4H,5H,6H,7H-[1,2,3]triazolo[4,5-c]pyridine-5-carboxylate (340 mg, 95.93%) as a yellow oil.

Tert-Butyl 1-[[4-fluoro-2-(2,2,2-trifluoroethyl)phenyl]methyl]-1H,4H,5H,6H,7H-[1,2,3]triazolo[4,5-c] pyridine-5-carboxylate To a solution of tert-butyl 1-([4-fluoro-2-[2,2,2-trifluoro-1-(methanesulfonyloxy)ethyl]phenyl]methyl)-1H,4H,5H,6H,7H-[1,2,3]triazolo[4,5-c]pyridine-5-carboxylate (260 mg, 0.511 mmol, 1 equiv.) in MeOH was added Pd/C (10%, 5.44 mg) under nitrogen atmosphere in a 30 mL pressure tank reactor. The mixture was hydrogenated at room temperature for 3 days under hydrogen atmosphere using a hydrogen balloon, filtered through a celite pad and concentrated under reduced pressure. The reaction was monitored by LCMS. The residue was purified by Prep-TLC (CH2Cl2/MeOH 5:1) to afford tert-butyl 1-[[4-fluoro-2-(2,2,2-trifluoroethyl)phenyl]methyl]-1H,4H,5H,6H,7H-[1,2,3]triazolo[4,5-c]pyridine-5-carboxylate (120 mg) as a yellow oil.

1-[[4-Fluoro-2-(2,2,2-trifluoroethyl)phenyl]methyl]-1H,4H,5H,6H,7H-[1,2,3]triazolo[4,5-c]pyridine To a stirred solution of tert-butyl 1-[[4-fluoro-2-(2,2,2-trifluoroethyl)phenyl]methyl]-1H,4H,5H,6H,7H-[1,2,3]triazolo[4,5-c]pyridine-5-carboxylate (60 mg, 0.145 mmol, 1 equiv.) in DCM (5 mL) was added TFA (2.00 mL, 17.540 mmol, 185.97 equiv.) dropwise at room temperature. The resulting mixture was stirred for 2 h at rt under nitrogen atmosphere. The reaction was monitored by LCMS. The resulting mixture was concentrated under reduced pressure. The residue was basified to pH 8 with saturated NaHCO3 (aq.). The resulting mixture was concentrated under reduced pressure. The residue was purified by Prep-TLC (CH2Cl2/MeOH 20:1) to afford 1-[[4-fluoro-2-(2,2,2-trifluoroethyl) phenyl]methyl]-1H,4H,5H,6H,7H-[1,2,3]triazolo[4,5-c] pyridine (40 mg, 87.90%) as a yellow oil.

4-Chloro-5-(1-[[4-fluoro-2-(2,2,2-trifluoroethyl) phenyl]methyl]-1H,4H,5H,6H,7H-[1,2,3]triazolo[4,5-c]pyridin-5-yl)-2-(oxan-2-yl)-2,3-dihydropyridazin-3-one Into a 50 mL round-bottom flask were added 1-[[4-fluoro-2-(2,2,2-trifluoroethyl)phenyl]methyl]-1H,4H,5H,6H,7H-[1,2,3]triazolo[4,5-c]pyridine (80 mg, 0.255 mmol, 1 equiv.) and 4,5-dichloro-2-(oxan-2-yl)-2,3-dihydropyridazin-3-one (63.40 mg, 0.255 mmol, 1 equiv.) at room temperature. To the above mixture was added DIEA (98.69 mg, 0.764 mmol, 3.00 equiv.) at room temperature. The resulting mixture was stirred for additional 2 h at 100 degrees C. The reaction was monitored by LCMS. The residue was purified by Prep-TLC (PE/EtOAc 1:1) to afford 4-chloro-5-(1-[[4-fluoro-2-(2,2,2-trifluoroethyl)phenyl]methyl]-1H,4H,5H,6H,7H-[1,2,3]triazolo[4,5-c]pyridin-5-yl)-2-(oxan-2-yl)-2,3-dihydropyridazin-3-one (50 mg, 37.28%) as a light yellow oil.

4-Chloro-5-(1-[[4-fluoro-2-(2,2,2-trifluoroethyl) phenyl]methyl]-1H,4H,5H,6H,7H-[1,2,3]triazolo[4,5-c]pyridin-5-yl)-2,3-dihydropyridazin-3-one To a stirred solution of 4-chloro-5-(1-[[4-fluoro-2-(2,2,2-trifluoroethyl)phenyl]methyl]-1H,4H,5H,6H,7H-[1,2,3]triazolo[4,5-c]pyridin-5-yl)-2-(oxan-2-yl)-2,3-dihydropyridazin-3-one (50 mg, 0.095 mmol, 1 equiv.) in DCM (5 mL) was added TFA (2.00 mL, 17.540 mmol, 283.76 equiv.) dropwise at room temperature. The resulting mixture was stirred for 1 h at room temperature. The reaction was monitored by LCMS. The resulting mixture was concentrated under reduced pressure. The residue was basified to pH 8 with saturated NaHCO3 (aq.). The resulting mixture was concentrated under vacuum. The crude product (30 mg) was purified by Prep-HPLC with the following conditions (Column: XBridge Prep Phenyl OBD Column 19×150 mm 5 um 13 nm; Mobile Phase A:, Mobile Phase B:; Flow rate: 60 mL/min; Gradient: 25% B to 40% B in 11 min; 220 nm; Rt: 9.55 min) to afford 4-chloro-5-(1-[[4-fluoro-2-(2,2,2-trifluoroethyl)phenyl]methyl]-1H,4H,5H,6H,7H-[1,2,3]triazolo[4,5-c]pyridin-5-yl)-2,3-dihydropyridazin-3-one (18.8 mg) as a white solid.

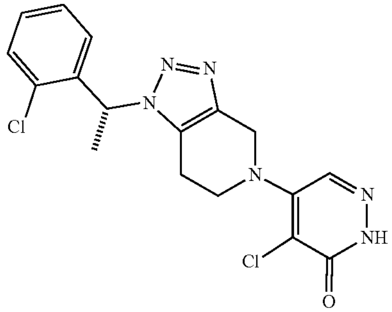

NV

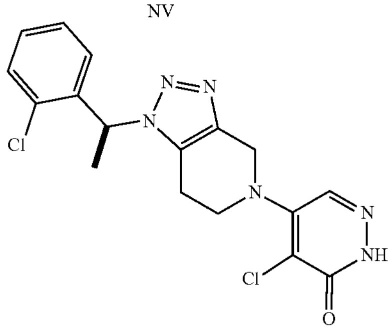

NW

NV and NW were prepared by the methods and scheme described for JC and JD by using 1-(2-chlorophenyl)ethan- 1-amine and by purified by Prep-Chiral-HPLC with the following conditions (Hex:EtOH=60:40).

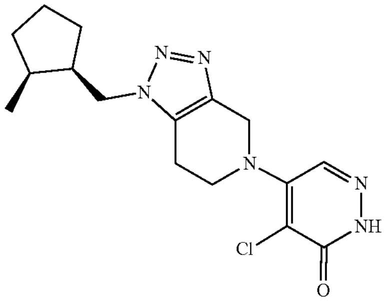

&

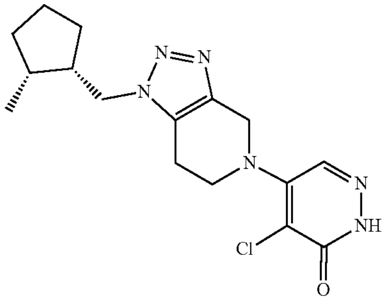

4-chloro-5-(1-[[(1S,2R)-2-methylcyclopentyl]methyl]-1H,4H,5H,6H,7H-[1,2,3]triazolo[4,5-c]pyridin-5-yl)-2,3-dihydropyridazin-3-one & 4-chloro-5-(1-[[(1R,2S)-2-methylcyclopentyl]methyl]-1H,4H,5H,6H,7H-[1,2,3]triazolo[4,5-c]pyridin-5-yl)-2,3-dihydropyridazin-3-one were prepared by the methods and schemes previously described followed by chiral separation. The crude product (100 mg) was purified by CHIRAL-HPLC with the following conditions (Column: CHIRALPAK IC, 2*25 cm, 5 um; Mobile Phase A:MTBE (10 mM NH3-MEOH)—HPLC—inport, Mobile Phase B: MeOH:EtOH=1:1—HPLC; Flow rate: 20 mL/min; Gradient: 20 B to 20 B in 40 min; 220/254 nm; RT1:24.737; RT2:31.483) to afford 4-chloro-5-(1-[[(1S,2R)-2-methylcyclopentyl]methyl]-1H,4H,5H,6H,7H-[1,2,3]triazolo[4,5-c]pyridin-5-yl)-2,3-dihydropyridazin-3-one (21.9 mg, 21.90%) as a white solid and 4-chloro-5-(1-[[(1R,2S)-2-methylcyclopentyl]methyl]-1H,4H,5H,6H,7H-[1,2,3]triazolo[4,5-c]pyridin-5-yl)-2,3-dihydropyridazin-3-one (15.7 mg, 15.70%) as a white solid.

Compound NY

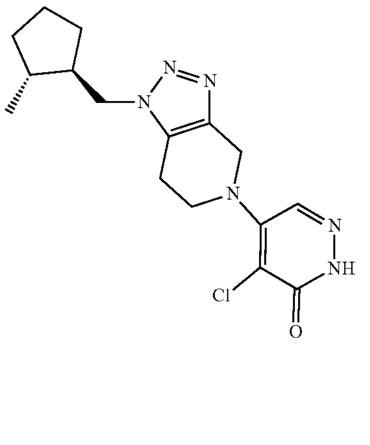

-continued

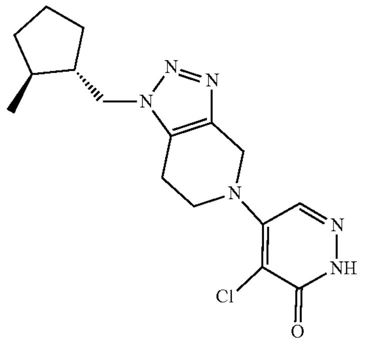

4-chloro-5-(1-[[(1R,2R)-2-methylcyclopentyl]methyl]-1H,4H,5H,6H,7H-[1,2,3]triazolo[4,5-c]pyridin-5-yl)-2,3-dihydropyridazin-3-one & 4-chloro-5-(1-[[(1S,2S)-2-methylcyclopentyl]methyl]-1H,4H,5H,6H,7H-[1,2,3]triazolo[4,5-c]pyridin-5-yl)-2,3-dihydropyridazin-3-one were prepared by the methods and schemes previously described followed by chiral separation. The crude product (100 mg) was purified by CHIRAL-HPLC with the following conditions (Column: CHIRALPAK IC, 2*25 cm, 5 um; Mobile Phase A:MTBE (10 mM NH3-MEOH)—HPLC—inport, Mobile Phase B: MeOH:EtOH=1:1—HPLC; Flow rate: 20 mL/min; Gradient: 20 B to 20 B in 40 min; 220/254 nm; RT1:24.737; RT2:31.483) to afford 4-chloro-5-(1-[[(1R,2R)-2-methylcyclopentyl]methyl]-1H,4H,5H,6H,7H-[1,2,3]triazolo[4,5-c]pyridin-5-yl)-2,3-dihydropyridazin-3-one (23.4 mg, 23.40%) as a white solid and 4-chloro-5-(1-[[(1S,2S)-2-methylcyclopentyl]methyl]-1H,4H,5H,6H,7H-[1,2,3]triazolo[4,5-c]pyridin-5-yl)-2,3-dihydropyridazin-3-one (30.6 mg, 30.60%) as a white solid.

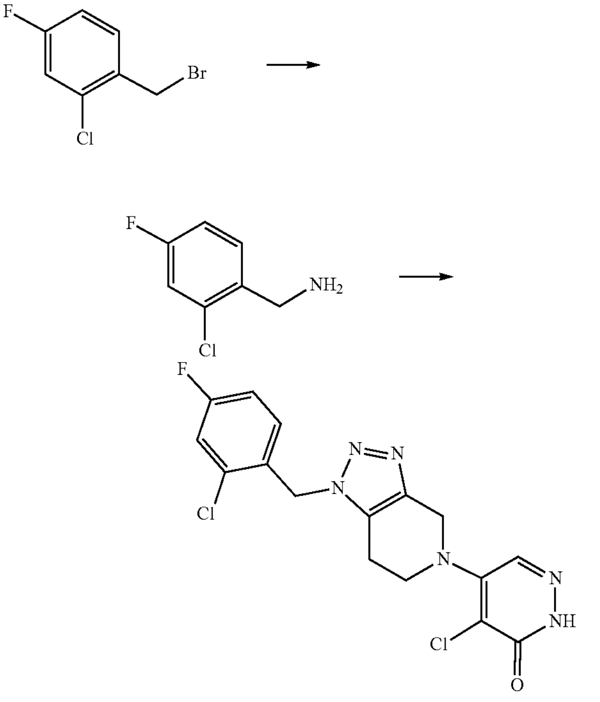

NZ

Preparation of NZ 1-(2-Chloro-4-fluorophenyl)methanamine

To a stirred solution of 1-(bromomethyl)-2-chloro-4-fluorobenzene (1 g, 1 equiv.) in DMF (5 mL) was added NH3(g) in MeOH (5 mL) at room temperature under nitrogen atmosphere. The resulting mixture was stirred for 2 h at 50 degrees celsius under nitrogen atmosphere. The mixture was allowed to cool down to room temperature. The reaction was monitored by LCMS. The resulting mixture was used in the next step (E00848-157) directly without further purification.

4-chloro-5-[1-[(2-chloro-4-fluorophenyl)methyl]-1H,4H,5H,6H,7H-[1,2,3]triazolo[4,5-c]pyridin-5-yl]-2,3-dihydropyridazin-3-one To a stirred mixture of 1-(2-chloro-4-fluorophenyl)methanamine (80 mg, 0.501 mmol, 1 equiv.) and 4-chloro-5-(4-oxopiperidin-1-yl)-2,3-dihydropyridazin-3-one (114.12 mg, 0.501 mmol, 1.00 equiv.) in DMF (5 mL) were added 1-azido-4-nitrobenzene (115.18 mg, 0.702 mmol, 1.4 equiv.) and Zn(OAc)2 (91.98 mg, 0.501 mmol, 1 equiv.) at room temperature. The resulting mixture was stirred for 16 h at 60 degrees C. The reaction was monitored by LCMS. The mixture was allowed to cool down to room temperature. The mixture was purified by reverse phase flash with the following conditions (Column:C18,330 g; Mobile Phase A: Water/0.05% NH4HCO3, Mobile Phase B:ACN; Flow rate: 80 mL/min; Gradient: 35% B to 50% B in 15 min; Detector, 220 nm and 254 nm) to afford crude product. The crude product (30 mg) was purified by Prep-HPLC with the following conditions (Column: XBridge Shield RP18 OBD Column, 5 um, 19*150 mm; Mobile Phase A: Water (10 MMOL/L NH4HCO3), Mobile Phase B: ACN; Flow rate: 25 mL/min; Gradient: 5% B to 16% B in 1 min; 254/220 nm; Rt: 7.47 min) to afford 4-chloro-5-[1-[(2-chloro-4-fluorophenyl)methyl]-1H,4H,5H,6H,7H-[1,2,3]triazolo[4,5-c]pyridin-5-yl]-2,3-dihydropyridazin-3-one (8.3 mg, 4.19%) as a white solid.

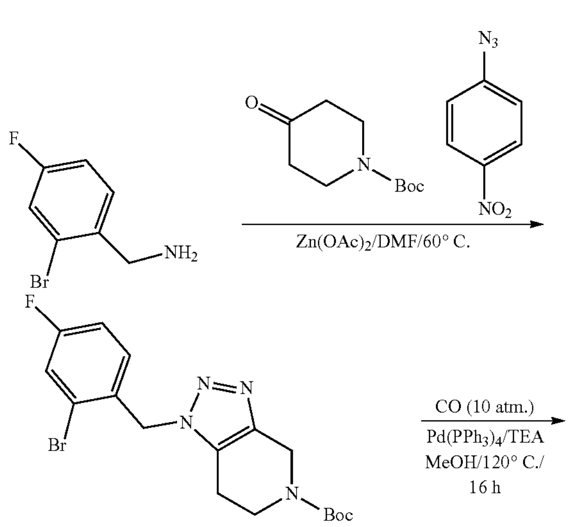

-continued

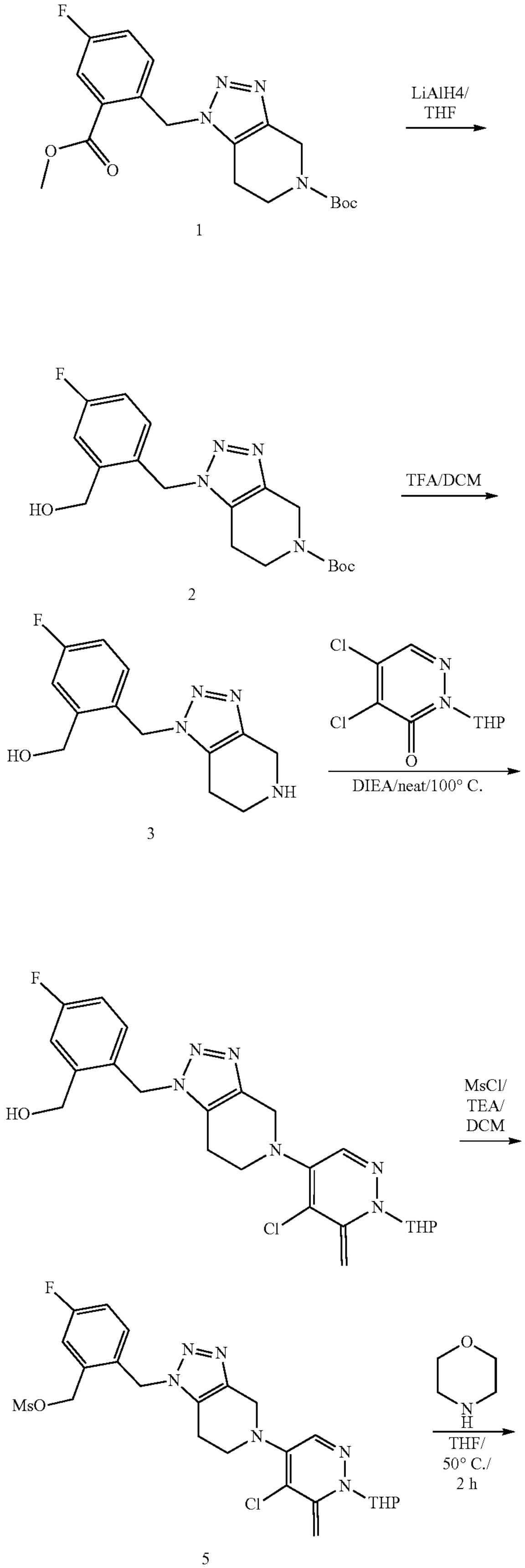

1

2

3

5

-continued

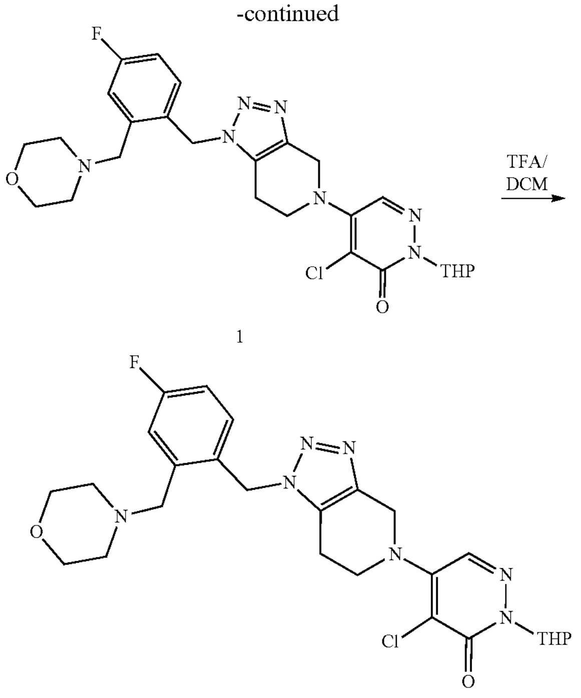

1

OA

Preparation of QOA

Tert-Butyl 1-[1-(2-bromo-4-fluorophenyl)methyl]-1H,4H,5H,6H,7H-[1,2,3]triazolo[4,5-c]pyridine-5-carboxylate To a stirred solution of tert-butyl 4-oxopiperidine-1-carboxylate (2.5 g, 12.55 mmol, 1 equiv.) and 1-(2-bromo-4-fluorophenyl)methan-1-amine (4.1 g, 0.02 mmol, 1.5 equiv.) in N,N-dimethylformamide (50 mL) were added (acetyloxy) zincio acetate (2.3 g, 0.01 mmol, 1 equiv.) and 1-azido-4-nitrobenzene (2.9 g, 0.02 mmol, 1.4 equiv.) at room temperature under nitrogen atmosphere. The resulting mixture was stirred for 16 h at 70 degrees celsius. LCMS was good. The residue was purified by reverse phase flash with the following conditions (Column: C18 330 g; Mobile Phase A: Water (10 MMOL/L NH4HCO3), Mobile Phase B: ACN; Flow rate: 70 mL/min; Gradient: 45% B to 65% B in 20 min; 254&220 nm; Rt: 3 min) to afford tert-butyl 1-[1-(2-bromo-4-fluorophenyl)methyl]-1H,4H,5H,6H,7H-[1,2,3]triazolo[4,5-c]pyridine-5-carboxylate (2.1 g) as a brown solid.

Tert-Butyl 1-[[4-fluoro-2-(methoxycarbonyl)phenyl]methyl]-1H,4H,5H,6H,7H-[1,2,3]triazolo[4,5-c]pyridine-5-carboxylate To a solution of tert-butyl 1-[(2-bromo-4-fluorophenyl)methyl]-1H,4H,5H,6H,7H-[1,2,3]triazolo[4,5-c]pyridine-5-carboxylate (2 g, 4.86 mmol, 1 equiv.) in 100 mL MeOH were added Pd(PPh3)4 (0.6 g, 0.52 mmol, 0.11 equiv.) and TEA (1.0 g, 9.88 mmol, 2.03 equiv.) in a pressure tank. The mixture was purged with nitrogen for 5 min and then was pressurized to 10 atm with carbon monoxide at 120 degrees celsius for overnight. The desired product could be detected by LCMS. The reaction mixture was cooled to room temperature and filtered to remove insoluble solids and was purified by silica gel column chromatography, eluted with EtOAc/PE (20:1 to 2:1) to afford tert-butyl 1-[[4-fluoro-2-(methoxycarbonyl)phenyl]methyl]-1H,4H,5H,6H,7H-[1,2,3]triazolo[4,5-c]pyridine-5-carboxylate (1.34 g, 70.58%) as a yellow liquid.

Tert-Butyl 1-[[4-fluoro-2-(hydroxymethyl)phenyl]methyl]-1H,4H,5H,6H,7H-[1,2,3]triazolo[4,5-c]pyridine-5-carboxylate To a solution of tert-butyl 1-[[4-fluoro-2-(methoxycarbonyl)phenyl]methyl]-1H,4H,5H,6H,7H-[1,2,3]triazolo[4,5-c]pyridine-5-carboxylate (1 g, 2.56 mmol, 1 equiv.) in THF (30 mL) was batch added LiAlH4 (145.8 mg, 3.84 mmol, 1.50 equiv.) at −30 degrees celsius under nitrogen atmosphere. The resulting mixture was stirred for 3 h at −30 degrees C.~−10 degrees C. The desired product could be detected by LCMS. The reaction mixture was quenched with water (0.5 mL) at −30 degrees celsius and quenched with 15% NaOH(aq). The mixture was filtrated, the filtrate was concentrated under reduced pressure to get tert-butyl 1-[[4-fluoro-2-(hydroxymethyl)phenyl]methyl]-1H,4H,5H,6H,7H-[1,2,3]triazolo[4,5-c]pyridine-5-carboxylate (1.3 g, 140.05%) as yellow liquid.

[5-Fluoro-2-([1H,4H,5H,6H,7H-[1,2,3]triazolo[4,5-c]pyridin-1-yl]methyl)phenyl]methanol To a solution of 2,2,2-trifluoroacetaldehyde (10 mL) in DCM (40 mL) was added tert-butyl 1-[[4-fluoro-2-(hydroxymethyl)phenyl]methyl]-1H,4H,5H,6H,7H-[1,2,3]triazolo[4,5-c]pyridine-5-carboxylate (1.5 g, 4.14 mmol, 1 equiv.) at ambient temperature. Then the mixture was stirred for 16 h at ambient temperature. The desired product could be detected by LCMS. The resulting mixture was concentrated under reduced pressure. The mixture was basified to pH 8 with NaHCO3 (aq.) The mixture was added DMF (6 mL) and was purified by reverse phase flash with the following conditions (Column: c18 OBD Column, 5 um, 19*330 mm; Mobile Phase A: Water (5 MMOL/L NH4HCO3), Mobile Phase B: ACN; Flow rate: 80 mL/min; Gradient: 20% B to 55% B in 40 min; 220 nm; Rt: 20.0 min) to afford [5-fluoro-2-([1H,4H,5H,6H,7H-[1,2,3]triazolo[4,5-c]pyridin-1-yl]methyl)phenyl]methanol (2.5 g, 230.28%) as an off-white solid.

[2-([5-[5-chloro-1-(oxan-2-yl)-6-oxo-1,6-dihydropyridazin-4-yl]-1H,4H,5H,6H,7H-[1,2,3]triazolo[4,5-c]pyridin-1-yl]methyl)-5-fluorophenyl]methyl methanesulfonate To a solution of 4-chloro-5-(1-[[4-fluoro-2-(hydroxymethyl)phenyl]methyl]-1H,4H,5H,6H,7H-[1,2,3]triazolo[4,5-c]pyridin-5-yl)-2-(oxan-2-yl)-2,3-dihydropyridazin-3-one (600 mg, 1.26 mmol, 1 equiv.) in DCM (15 mL) at ambient temperature was added Et3N (255.7 mg, 2.53 mmol, 2.00 equiv.). The resulting mixture was stirred for 10 min at 0 degrees C. Then the mixture was added MsCl (173.7 mg, 1.52 mmol, 1.20 equiv.) dropwise via syringe between 0 and 5 degrees celsius with stirring for 3 h. The desired product could be detected by LCMS. The reaction mixture was concentrated under reduced pressure to afford crude. The crude was diluted with water (400 mL) and extracted with EA (500 mL×2). The organic layers was washed with saturated brine (200 mL), dried over anhydrous Na2SO4, filtered and concentrated to afford as [2-([5-[5-chloro-1-(oxan-2-yl)-6-oxo-1,6-dihydropyridazin-4-yl]-1H,4H,5H, 6H,7H-[1,2,3]triazolo[4,5-c]pyridin-1-yl]methyl)-5-fluorophenyl]methyl methanesulfonate (800 mg, 114.51%) a yellow solid.

4-Chloro-5-[1-([4-fluoro-2-[(morpholin-4-yl)methyl]phenyl]methyl)-1H,4H,5H,6H,7H-[1,2,3]triazolo[4,5-c]pyridin-5-yl]-2-(oxan-2-yl)-2,3-dihydropyridazin-3-one To a solution of [2-([5-[5-chloro-1-(oxan-2-yl)-6-oxo-1,6-dihydropyridazin-4-yl]-1H,4H,5H,6H,7H-[1,2,3]triazolo[4,5-c]pyridin-1-yl]methyl)-5-fluorophenyl]methyl methanesulfonate (100 mg, 0.18 mmol, 1 equiv.) in THF (4 mL) was added morpholine (2 mL) in a sealed tabe under nitrogen atmosphere at ambient temperature. The resulting mixture was stirred for 2 h at 50 degrees C. The desired product could be detected by LCMS. The reaction mixture was diluted with water (100 mL) and extracted with EA (100 mL×2). The organic layer was washed with saturated brine (100 mL), dried over anhydrous Na2SO4, filtered and concentrated to give desired product. The residue was purified by Prep-TLC (CH2Cl2/MeOH 20:1) to afford 4-chloro-5-[1-([4-fluoro-2-[(morpholin-4-yl)methyl]phenyl]methyl)-1H,4H,5H,6H,7H-[1,2,3]triazolo[4,5-c]pyridin-5-yl]-2-(oxan-2-yl)-2,3-dihydropyridazin-3-one (50 mg, 50.83%) as a yellow liquid.

4-Chloro-5-[1-([4-fluoro-2-[(morpholin-4-yl)methyl]phenyl]methyl)-1H,4H,5H,6H,7H-[1,2,3]triazolo[4,5-c]pyridin-5-yl]-2,3-dihydropyridazin-3-one To a solution of TFA (2 mL) in DCM (8 mL) was added 4-chloro-5-[1-([4-fluoro-2-[(morpholin-4-yl)methyl]phenyl]methyl)-1H,4H,5H,6H,7H-[1,2,3]triazolo[4,5-c]pyridin-5-yl]-2-(oxan-2-yl)-2,3-dihydropyridazin-3-one (50 mg, 0.09 mmol, 1 equiv.) at ambient temperature. Then the mixture was stirred for 16 h at ambient temperature. The desired product could be detected by LCMS. The resulting mixture was concentrated under reduced pressure. The mixture was basified to pH 8 with NaHCO3 (aq.) and concentrated under reduced pressure to afford crude product. The crude product was purified by Prep-HPLC with the following conditions (Column: XBridge Shield RP18 OBD Column, 5 um, 19*150 mm; Mobile Phase A: Water (10 MMOL/L NH4HCO3), Mobile Phase B: ACN; Flow rate: 20 mL/min; Gradient: 20% B to 45% B in 7 min; 220 nm; Rt: 6.52 min) to afford 4-chloro-5-[1-([4-fluoro-2-[(morpholin-4-yl)methyl]phenyl]methyl)-1H,4H,5H,6H,7H-[1,2,3]triazolo[4,5-c]pyridin-5-yl]-2,3-dihydropyridazin-3-one (27.1 mg, 64.11%) as a white solid.

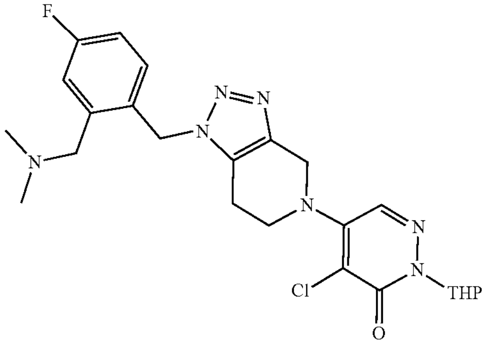

OB

OB was prepared by the methods and scheme described for OA by using dimethylamine

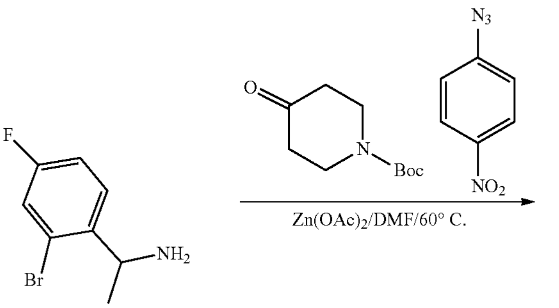

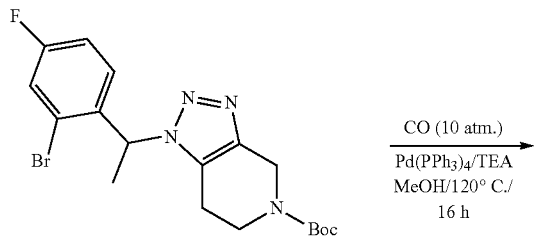

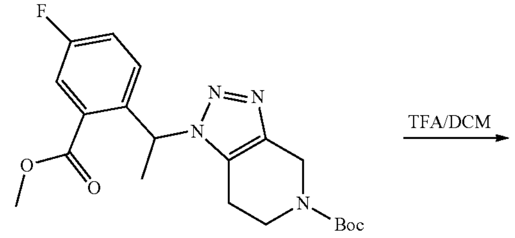

1

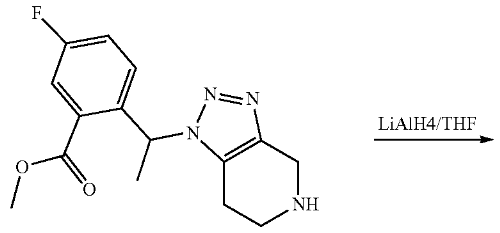

2

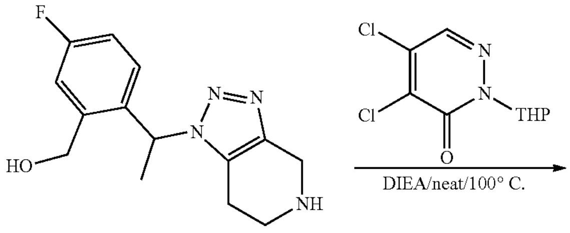

3

-continued

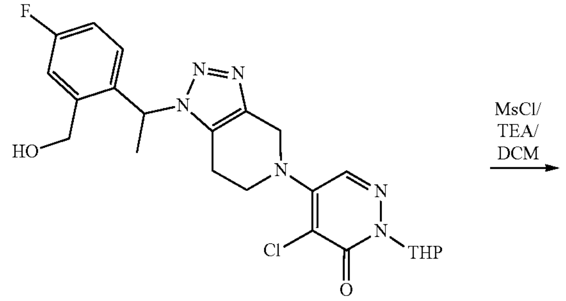

4

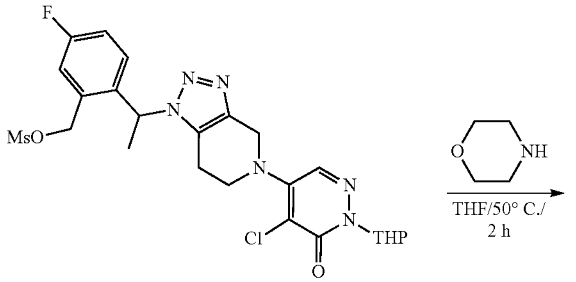

5

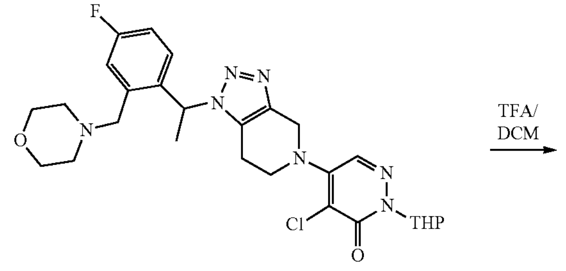

5

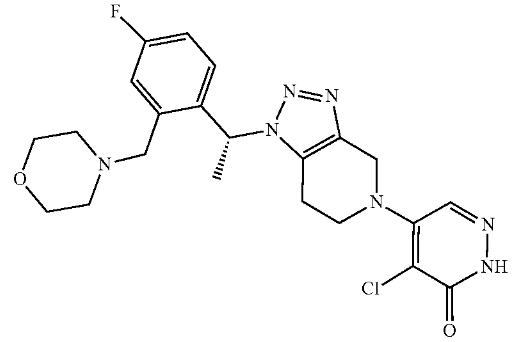

OC

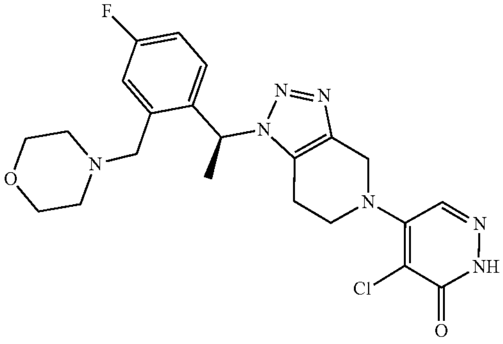

OD

Preparation of OC and OD

Tert-Butyl 1-[1-(2-bromo-4-fluorophenyl)ethyl]-1H,4H,5H,6H,7H-[1,2,3]triazolo[4,5-c]pyridine-5-carboxylate To a stirred solution of tert-butyl 4-oxopiperidine-1-carboxylate (2.5 g, 12.55 mmol, 1 equiv.) and 1-(2-bromo-4-fluorophenyl)ethan-1-amine (4.1 g, 0.02 mmol, 1.5 equiv.) in N,N-dimethylformamide (50 mL) were added (acetyloxy) zincio acetate (2.3 g, 0.01 mmol, 1 equiv.) and 1-azido-4-nitrobenzene (2.9 g, 0.02 mmol, 1.4 equiv.) at room temperature under nitrogen atmosphere. The resulting mixture was stirred for 16 h at 70 degrees celsius. LCMS was good. The residue was purified by reverse phase flash with the following conditions (Column: C18 330 g; Mobile Phase A: Water (10 MMOL/L NH4HCO3), Mobile Phase B: ACN; Flow rate: 70 mL/min; Gradient: 45% B to 65% B in 20 min; 254&220 nm; Rt: 3 min) to afford tert-butyl 1-[1-(2-bromo-4-fluorophenyl)ethyl]-1H,4H,5H,6H,7H-[1,2,3]triazolo[4,5-c]pyridine-5-carboxylate (2.1 g) as a brown solid.

Tert-Butyl 1-[1-[4-fluoro-2-(methoxycarbonyl)phenyl]ethyl]-1H,4H,5H,6H,7H-[1,2,3]triazolo[4,5-c]pyridine-5-carboxylate To a solution of tert-butyl 1-[1-(2-bromo-4-fluorophenyl)ethyl]-1H,4H,5H,6H,7H-[1,2,3]triazolo[4,5-c]pyridine-5-carboxylate (2 g, 4.703 mmol, 1 equiv.) in 100 mL MeOH were added Et3N (0.95 g, 9.405 mmol, 2 equiv.) and Pd(PPh3)4 (0.27 g, 0.235 mmol, 0.05 equiv.) in a pressure tank. The mixture was purged with nitrogen for 1 h and then was pressurized to 10 atm with carbon monoxide at 110 degrees celsius for overnight. The reaction mixture was cooled to room temperature and filtered to remove insoluble solids. The reaction was monitored by LCMS. The resulting mixture was filtered, the filter cake was washed with MeOH (3×20 mL). The filtrate was concentrated under reduced pressure. The resulting mixture was extracted with EtOAc (350 mL). The combined organic layers were washed with brine (3×100 mL), dried over anhydrous Na2SO4. After filtration, the filtrate was concentrated under reduced pressure. The resulting mixture was used in the next step (E00692-112) directly without further purification.

Methyl 5-fluoro-2-(1-[1H,4H,5H,6H,7H-[1,2,3]triazolo[4,5-c]pyridin-1-yl]ethyl)benzoate To a stirred solution of tert-butyl 1-[1-[4-fluoro-2-(methoxycarbonyl)phenyl]ethyl]-1H,4H,5H,6H,7H-[1,2,3]triazolo[4,5-c]pyridine-5-carboxylate (1.5 g, 3.709 mmol, 1 equiv.) in DCM (30 mL) was added TFA (10 mL) in portions at room temperature under nitrogen atmosphere. The resulting mixture was stirred for 2 h at room temperature under nitrogen atmosphere. The reaction was monitored by LCMS. The mixture was basified to pH 8 with saturated NaHCO3 (aq.). The resulting mixture was extracted with EtOAc (20 mL). The combined organic layers were washed with brine (3×50 mL), dried over anhydrous Na2SO4. After filtration, the filtrate was concentrated under reduced pressure. The resulting mixture was used in the next step (E00692-115) directly without further purification.

[5-Fluoro-2-(1-[1H,4H,5H,6H,7H-[1,2,3]triazolo[4,5-c]pyridin-1-yl]ethyl)phenyl]methanol To a stirred solution of methyl 5-fluoro-2-(1-[1H,4H,5H,6H,7H-[1,2,3]triazolo[4,5-c]pyridin-1-yl]ethyl)benzoate (1 g, 3.286 mmol, 1 equiv.) in THF (20 mL) was added LiAlH4 (249.43 mg, 6.572 mmol, 2 equiv.) in portions at −30 degrees celsius under nitrogen atmosphere. The resulting mixture was stirred for 2 h at 0 degrees celsius under nitrogen atmosphere. The reaction was monitored by LCMS. The reaction was quenched by the addition of sat. NaOH (aq. 15%) (0.25 mL) and Water (0.25 mL) at 0 degrees C. The resulting mixture was filtered, the filter cake was washed with EtOAc (3×10 mL). The filtrate was concentrated under reduced pressure. The resulting mixture was extracted with EtOAc (20 mL). The combined organic layers were washed with brine (3×50 mL), dried over anhydrous Na2SO4. After filtration, the filtrate was concentrated under reduced pressure. The resulting mixture was used in the next step (E00692-116) directly without further purification.

[2-(1-[5-[2-Chloro-4-(oxan-2-yl)-3-oxocyclohexa-1,5-dien-1-yl]-1H,4H,5H,6H,7H-[1,2,3]triazolo[4,5-c]pyridin-1-yl]ethyl)-5-fluorophenyl]methyl methanesulfonate To a stirred solution of [5-fluoro-2-(1-[1H,4H,5H,6H,7H-[1,2,3]triazolo[4,5-c]pyridin-1-yl]ethyl)phenyl]methanol (800 mg, 2.895 mmol, 1 equiv.) and 4,5-dichloro-2-(oxan-2-yl)-2,3-dihydropyridazin-3-one (721.18 mg, 2.895 mmol, 1 equiv.) was added DIEA (5 mL) in portions at room temperature under nitrogen atmosphere. The resulting mixture was stirred for overnight at 100 degrees celsius under nitrogen atmosphere as a neat reaction. The mixture was allowed to cool down to room temperature. The resulting mixture was extracted with EtOAc (50× mL). The combined organic layers were washed with brine (3×100 mL), dried over anhydrous Na2SO4. After filtration, the filtrate was concentrated under reduced pressure. The resulting mixture was used in the next step (E00692-120) directly without further purification.

2-Chloro-3-[1-(1-[4-fluoro-2-[(morpholin-4-yl)methyl]phenyl]ethyl)-1H,4H,5H,6H,7H-[1,2,3]triazolo[4,5-c]pyridin-5-yl]-6-(oxan-2-yl)cyclohexa-2,4-dien-1-one To a stirred solution of [2-(1-[5-[2-chloro-4-(oxan-2-yl)-3-oxocyclohexa-1,5-dien-1-yl]-1H,4H,5H,6H,7H-[1,2,3]triazolo[4,5-c]pyridin-1-yl]ethyl)-5-fluorophenyl]methyl methanesulfonate (150 mg, 0.265 mmol, 1 equiv.) in THF (3 mL) was added morpholine (231.27 mg, 2.655 mmol, 10 equiv.) in portions at room temperature under nitrogen atmosphere. The final reaction mixture was irradiated with microwave radiation for 2 h at 90 degrees C. The reaction was monitored by LCMS. The mixture was allowed to cool down to room temperature. The resulting mixture was concentrated under vacuum. The resulting mixture was extracted with EtOAc (10 mL). The combined organic layers were washed with brine (3×20 mL), dried over anhydrous Na2SO4. After filtration, the filtrate was concentrated under reduced pressure. The residue was purified by Prep-TLC (CH2Cl2/MeOH 20:1) to afford 2-chloro-3-[1-(1-[4-fluoro-2-[(morpholin-4-yl)methyl]phenyl]ethyl)-1H,4H,5H,6H,7H-[1,2,3]triazolo[4,5-c]pyridin-5-yl]-6-(oxan-2-yl)cyclohexa-2,4-dien-1-one (120 mg, 81.29%) as a light yellow oil.

4-Chloro-5-[1-[(1R)-1-[4-fluoro-2-[(morpholin-4-yl)methyl]phenyl]ethyl]-1H,4H,5H,6H,7H-[1,2,3]triazolo[4,5-c]pyridin-5-yl]-2,3-dihydropyridazin-3-one and 4-chloro-5-[1-[(1S)-1-[4-fluoro-2-[(morpholin-4-yl)methyl]phenyl]ethyl]-1H,4H,5H,6H,7H-[1,2,3]triazolo[4,5-c]pyridin-5-yl]-2,3-dihydropyridazin-3-one To a stirred solution of 4-chloro-5-[1-(1-[4-fluoro-2-[(morpholin-4-yl)methyl]phenyl]ethyl)-1H,4H,5H,6H,7H-[1,2,3]triazolo[4,5-c]pyridin-5-yl]-2-(oxan-2-yl)-2,3-dihydropyridazin-3-one (120 mg, 0.22 mmol, 1 equiv.) in DCM (10 mL) was added TFA (3 mL) in portions at room temperature under nitrogen atmosphere. The resulting mixture was stirred for 2 h at room temperature under nitrogen atmosphere. The reaction was monitored by LCMS. The resulting mixture was concentrated under vacuum. The crude product (60 mg) was purified by CHIRAL-HPLC with the following conditions (Column: CHIRALPAK IG UL001, 20*250 mm, 5 um; Mobile Phase A:MTBE—HPLC—inport, Mobile Phase B: IPA—HPLC; Flow rate: 20 mL/min; Gradient: 25 B to 25 B in 24 min; 220/254 nm; RT1:11.252; RT2:19.432) to afford 4-chloro-5-[1-[(1R)-1-[4-fluoro-2-[(morpholin-4-yl)methyl]phenyl]ethyl]-1H,4H,5H,6H,7H-[1,2,3]triazolo[4,5-c]pyridin-5-yl]-2,3-dihydropyridazin-3-one (5.7 mg, 5.59%) as a white solid and 4-chloro-5-[1-[(1S)-1-[4-fluoro-2-[(morpholin-4-yl)methyl]phenyl]ethyl]-1H,4H,5H,6H,7H-[1,2,3]triazolo[4,5-c]pyridin-5-yl]-2,3-dihydropyridazin-3-one (6.7 mg, 6.57%) as a white solid.

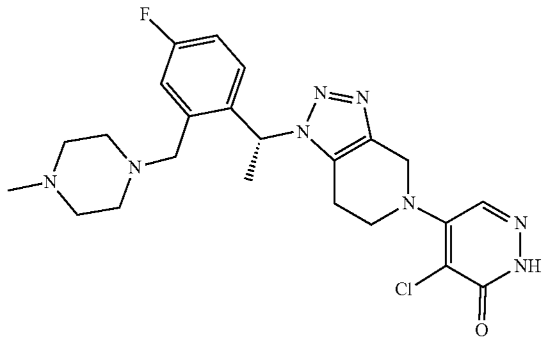

OE

OE was prepared by the methods and scheme described for OC and OD by using 1-(2-bromo-4-fluorophenyl)ethan-1-amine.

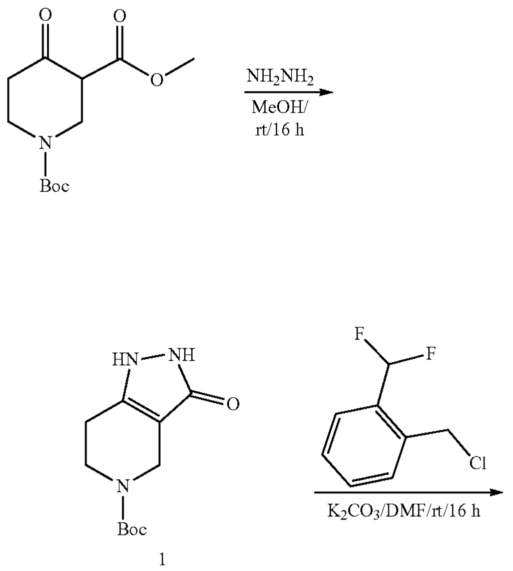

-continued

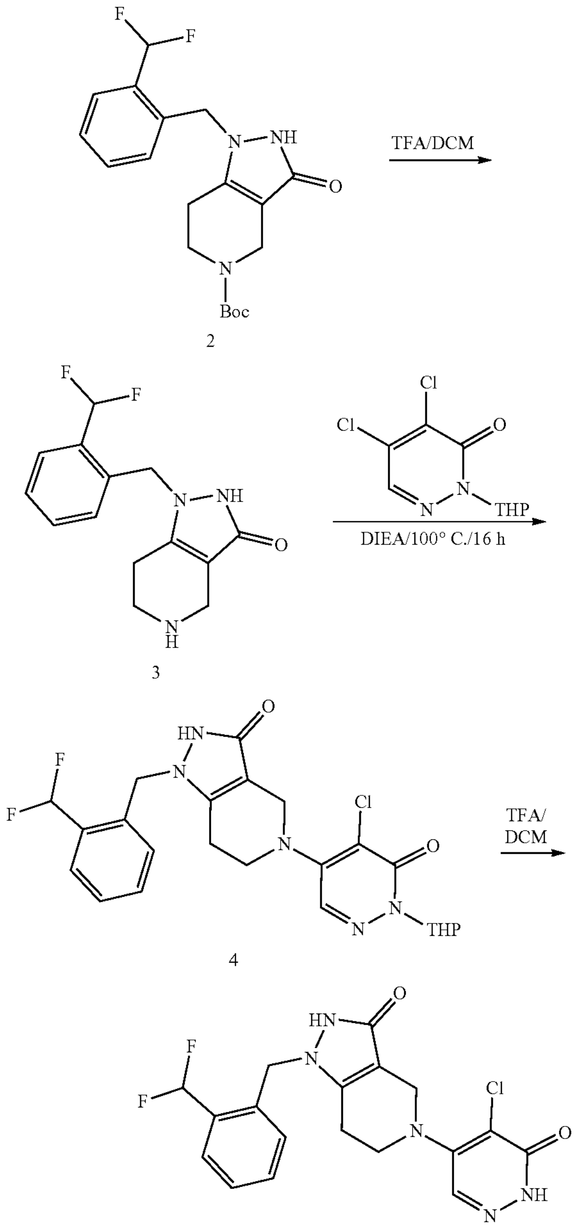

2

3

4

OF

Preparation of Compound OF

Tert-Butyl 3-oxo-1H,2H,3H,4H,5H,6H,7H-pyrazolo[4,3-c]pyridine-5-carboxylate

To a solution of 1-tert-butyl 3-methyl 4-oxopiperidine-1,3-dicarboxylate (2 g, 7.77 mmol, 1 equiv.) in EtOH (20 mL) was added NH2NH2·H2O (0.4 g, 8.55 mmol, 1.10 equiv.) dropwise at room temperature. The resulting mixture was stirred for 2.5 h at 85 degrees C. The reaction was monitored by LCMS. The resulting mixture was concentrated under reduced pressure to afford tert-butyl 3-oxo-1H,2H,3H,4H,5H,6H,7H-pyrazolo[4,3-c]pyridine-5-carboxylate (1.8 g, 96.77%) as a off-white solid.

Tert-Butyl 1-[[2-(difluoromethyl)phenyl]methyl]-3-oxo-1H,2H,3H,4H,5H,6H,7H-pyrazolo[4,3-c]pyridine-5-carboxylate To a stirred solution of tert-butyl 3-oxo-1H,2H,3H,4H,5H,6H,7H-pyrazolo[4,3-c]pyridine-5-carboxylate (1.5 g, 6.27 mmol, 1 equiv.) and K2CO3 (0.9 g, 6.27 mmol, 1 equiv.) in DMF (100 mL) was added 1-(chloromethyl)-2-(difluoromethyl)benzene (1.1 g, 6.27 mmol, 1.00 equiv.) dropwise at room temperature. The resulting mixture was stirred for 16 h at 40 degrees C. The reaction was monitored by LCMS. The mixture was purified by reverse phase flash with the following conditions (Column: spnerical C18, 20-40 um, 330 g; Mobile Phase A: Water (5 MMOL/L NH4HCO3), Mobile Phase B: ACN; Flow rate: 80 mL/mi; Gradient: 50%/B to 70% B in 25 mi; 220 nm) to afford tert-butyl 1-[[2-(difluoromethyl)phenyl]methyl]-3-oxo-1H,2H,3H,4H,5H,6H,7H-pyrazolo[4,3-c]pyridine-5-carboxylate (230 mg, 9.67%) as a yellow solid.

1-[[2-(Difluoromethyl)phenyl]methyl]-1H,2H,3H,4H,5H,6H,7H-pyrazolo[4,3-c]pyridin-3-one To a stirred solution of tert-butyl 1-[[2-(difluoromethyl)phenyl]methyl]-3-oxo-1H,2H,3H,4H,5H,6H,7H-pyrazolo[4,3-c]pyridine-5-carboxylate (100 mg, 0.26 mmol, 1 equiv.) in DCM (10 mL) was added TFA (2 mL, 26.93 mmol, 102.16 equiv.) dropwise at room temperature. The resulting mixture was stirred for 2 h at room temperature. The reaction was monitored by LCMS. The resulting mixture was concentrated under reduced pressure. The residue was basified to pH 8~9 with saturated NaHCO3 (aq.). The mixture was purified by reverse phase flash with the following conditions (Column: spnerical C18, 20-40 um, 120 g; Mobile Phase A: Water (5 MMOL/L NH4HCO3), Mobile Phase B: ACN; Flow rate: 45 mL/min; Gradient: 20% B to 40% B in 25 min; 220 nm) to afford 1-[[2-(difluoromethyl)phenyl]methyl]-1H,2H,3H,4H,5H,6H,7H-pyrazolo[4,3-c]pyridin-3-one (30 mg, 40.75%) as a white solid.

4-chloro-5-(1-[[2-(difluoromethyl)phenyl]methyl]-3-oxo-1H,2H,3H,4H,5H,6H,7H-pyrazolo[4,3-c]pyridin-5-yl)-2-(oxan-2-yl)-2,3-dihydropyridazin-3-one To a stirred solution of 1-[[2-(difluoromethyl)phenyl]methyl]-1H,2H,3H,4H,5H,6H,7H-pyrazolo[4,3-c]pyridin-3-one (30 mg, 0.11 mmol, 1 equiv.) and 4,5-dichloro-2-(oxan-2-yl)-2,3-dihydropyridazin-3-one (27.0 mg, 0.11 mmol, 1.01 equiv.) in DMA (2 mL) was added DIEA (27.8 mg, 0.21 mmol, 2 equiv.) at room temperature. The resulting mixture was stirred for 4 h at 100 degrees C. The reaction was monitored by LCMS. The resulting mixture was extracted with EtOAc (3x30 mL). The combined organic layers were washed with brine (30 mL), dried over anhydrous MgSO4. After filtration, the filtrate was concentrated under reduced pressure to afford 4-chloro-5-(1-[[2-(difluoromethyl)phenyl]methyl]-3-oxo-1H,2H,3H,4H,5H,6H,7H-pyrazolo[4,3-c]pyridin-5-yl)-2-(oxan-2-yl)-2,3-dihydropyridazin-3-one (45 mg, 85.16%) as a yellow oil.

4-Chloro-5-(1-[[2-(difluoromethyl)phenyl]methyl]-3-oxo-1H,2H,3H,4H,5H,6H,7H-pyrazolo[4,3-c]pyridin-5-yl)-2,3-dihydropyridazin-3-one To a stirred solution of 4-chloro-5-(1-[[2-(difluoromethyl)phenyl]methyl]-3-oxo-1H,2H,3H,4H,5H,6H,7H-pyrazolo[4,3-c]pyridin-5-yl)-2-(oxan-2-yl)-2,3-dihydropyridazin-3-one (45 mg, 1 equiv.) in DCM (5 mL) was added TFA (1 mL) dropwise at room temperature. The resulting mixture was stirred for 2 h at room temperature. The reaction was monitored by LCMS. The resulting mixture was concentrated under reduced pressure. The residue was basified to pH 8-9 with saturated NH4HCO3 (aq.). The resulting mixture was concentrated under reduced pressure. The mixture was purified by Prep-HPLC with the following conditions (Column: XBridge Shield RP18 OBD Column 30*150 mm, 5 um; Mobile Phase A: Water (10 MMOL/L NH4HCO3+ 0.1% NH3·H2O), Mobile Phase B: ACN; Flow rate: 60 mL/min; Gradient: 19% B to 29% B in 7 min; 254; 220 nm; Rt: 6.22 min) to afford 4-chloro-5-(1-[[2-(difluoromethyl) phenyl]methyl]-3-oxo-1H,2H,3H,4H,5H,6H,7H-pyrazolo [4,3-c]pyridin-5-yl)-2,3-dihydropyridazin-3-one (8.6 mg, 23.05%) as a white solid.

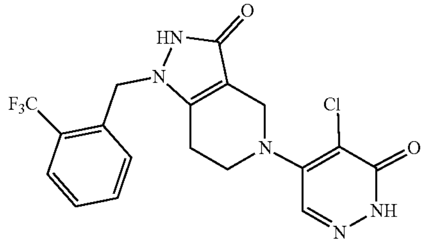

OG

Compound OG was prepared by the methods and scheme described for compound OF by using 1-(chloromethyl)-2-(trifluoromethyl)benzene

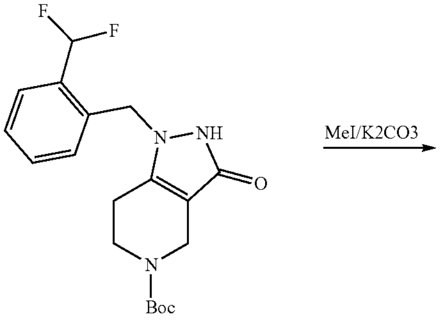

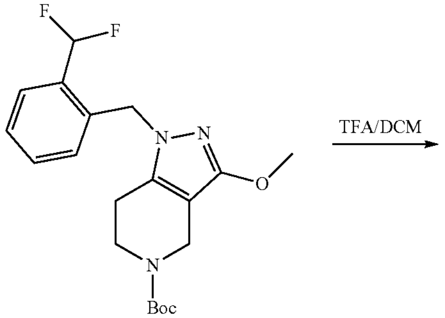

3a

-continued

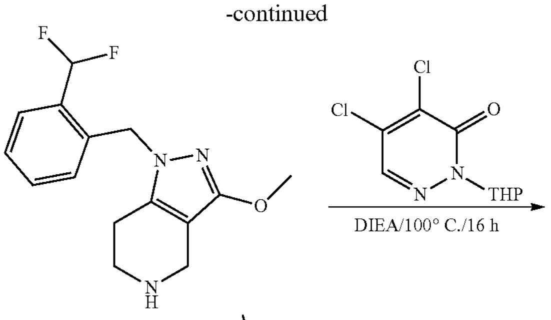

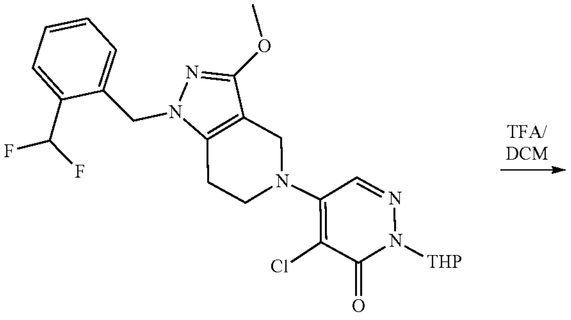

7

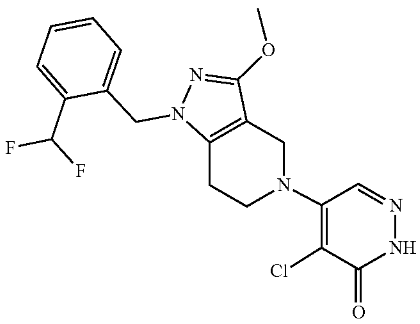

OH

Preparation of OH

Tert-Butyl 1-[[2-(difluoromethyl)phenyl]methyl]-3-methoxy-1H,4H,5H,6H,7H-pyrazolo[4,3-c]pyridine-5-carboxylate To a stirred solution of tert-butyl 1-[[2-(difluoromethyl) phenyl]methyl]-3-oxo-1H,2H,3H,4H,5H,6H,7H-pyrazolo [4,3-c]pyridine-5-carboxylate (130 mg, 0.34 mmol, 1 equiv.) and K2CO3 (56.8 mg, 0.41 mmol, 1.2 equiv.) in DMF (3 mL) was added MeI (97.3 mg, 0.69 mmol, 2 equiv.) dropwise at room temperature. The resulting mixture was stirred for 16 h at 50 degrees C. The reaction was monitored by LCMS. The resulting mixture was diluted with water (30 mL). The resulting mixture was extracted with EtOAc (2×30 mL). The combined organic layers were washed MeI/K2CO3 with brine (30 mL), dried over anhydrous MgSO4. After filtration, the filtrate was concentrated under reduced pressure. The residue was purified by Prep-TLC (CH2Cl2/MeOH 20:1) to afford tert-butyl 1-[[2-(difluoromethyl)phenyl]methyl]-3-methoxy-1H,4H,5H,6H,7H-pyrazolo[4,3-c] pyridine-5-carboxylate (85 mg, 63.05%) as a colorless oil.

1-[[2-(Difluoromethyl)phenyl]methyl]-3-methoxy-1H,4H,5H,6H,7H-pyrazolo[4,3-c]pyridine To a stirred solution of tert-butyl 1-[[2-(difluoromethyl) phenyl]methyl]-3-methoxy-1H,4H,5H,6H,7H-pyrazolo[4, 3-c]pyridine-5-carboxylate (85 mg, 0.22 mmol, 1 equiv.) in DCM (10 mL, 157.30 mmol, 728.09 equiv.) was added TFA (2 mL, 26.93 mmol, 124.63 equiv.) dropwise at room temperature. The resulting mixture was stirred for 2 h at room temperature. The reaction was monitored by LCMS. The resulting mixture was concentrated under reduced pressure. The residue was basified to pH 8~9 with saturated NaHCO3 (aq.). The mixture was purified by reverse phase flash with the following conditions (Column: spnerical C18, 20-40 um, 120 g; Mobile Phase A: Water (5 MMOL/L NH4HCO3), Mobile Phase B: ACN; Flow rate: 45 mL/min; Gradient: 25% B to 45% B in 25 min; 220 nm) to afford 1-[[2-(difluoromethyl)phenyl]methyl]-3-methoxy-1H,4H,5H,6H,7H-pyrazolo[4,3-c]pyridine (45 mg, 71.01%) as a colorless oil.

4-Chloro-5-(1-[[2-(difluoromethyl)phenyl]methyl]-3-methoxy-1H,4H,5H,6H,7H-pyrazolo[4,3-c]pyridin-5-yl)-2-(oxan-2-yl)-2,3-dihydropyridazin-3-one To a solution of 1-[[2-(difluoromethyl)phenyl]methyl]-3-methoxy-1H,4H,5H,6H,7H-pyrazolo[4,3-c]pyridine (45 mg, 0.15 mmol, 1 equiv.) and 4,5-dichloro-2-(oxan-2-yl)-2,3-dihydropyridazin-3-one (38.2 mg, 0.15 mmol, 1 equiv.) in DMA (2 mL) was added DIEA (39.7 mg, 0.31 mmol, 2 equiv.) dropwise at room temperature. The resulting mixture was stirred for 4 h at 100 degrees C. The reaction was monitored by LCMS. The resulting mixture was extracted with EtOAc (2×30 mL). The combined organic layers were washed with brine (30 mL), dried over anhydrous MgSO4. After filtration, the filtrate was concentrated under reduced pressure. The residue was purified by Prep-TLC (PE/EtOAc 2:1) to afford 4-chloro-5-(1-[[2-(difluoromethyl)phenyl]methyl]-3-methoxy-1H,4H,5H,6H,7H-pyrazolo[4,3-c]pyridin-5-yl)-2-(oxan-2-yl)-2,3-dihydropyridazin-3-one (50 mg, 64.42%) as a light yellow solid.

4-Chloro-5-(1-[[2-(difluoromethyl)phenyl]methyl]-3-methoxy-1H,4H,5H,6H,7H-pyrazolo[4,3-c]pyridin-5-yl)-2,3-dihydropyridazin-3-one To a stirred solution of 4-chloro-5-(1-[[2-(difluoromethyl)phenyl]methyl]-3-methoxy-1H,4H,5H,6H,7H-pyrazolo[4,3-c]pyridin-5-yl)-2-(oxan-2-yl)-2,3-dihydropyridazin-3-one (50 mg, 0.10 mmol, 1 equiv.) in DCM (5 mL) was added TFA (1 mL, 0.01 mmol, 0.09 equiv.) dropwise at room temperature. The resulting mixture was stirred for 2 h at room temperature. The reaction was monitored by LCMS. The resulting mixture was concentrated under reduced pressure. The residue was basified to pH 8~9 with saturated NH4HCO3 (aq.). The resulting mixture was concentrated under reduced pressure. The crude product was purified by Prep-HPLC with the following conditions (Column: Kinetex EVO C18 Column 21.2*150.5 um; Mobile Phase A: Water (10 MMOL/L NH4HCO3), Mobile Phase B: ACN; Flow rate: 20 mL/min; Gradient: 30% B to 55% B in 7 min; 254/220 nm; Rt: 6.42 min) to afford 4-chloro-5-(1-[[2-(difluoromethyl)phenyl]methyl]-3-methoxy-1H,4H,5H,6H,7H-pyrazolo[4,3-c]pyridin-5-yl)-2,3-dihydropyridazin-3-one (6.8 mg, 16.31%) as a white solid.

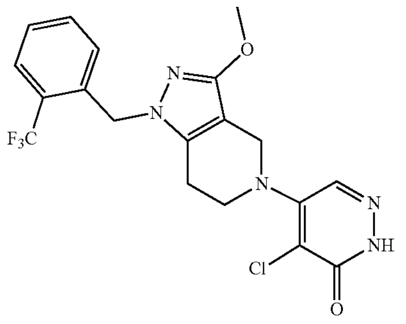

OI

Compound OI was prepared by the methods and scheme described for compound OH

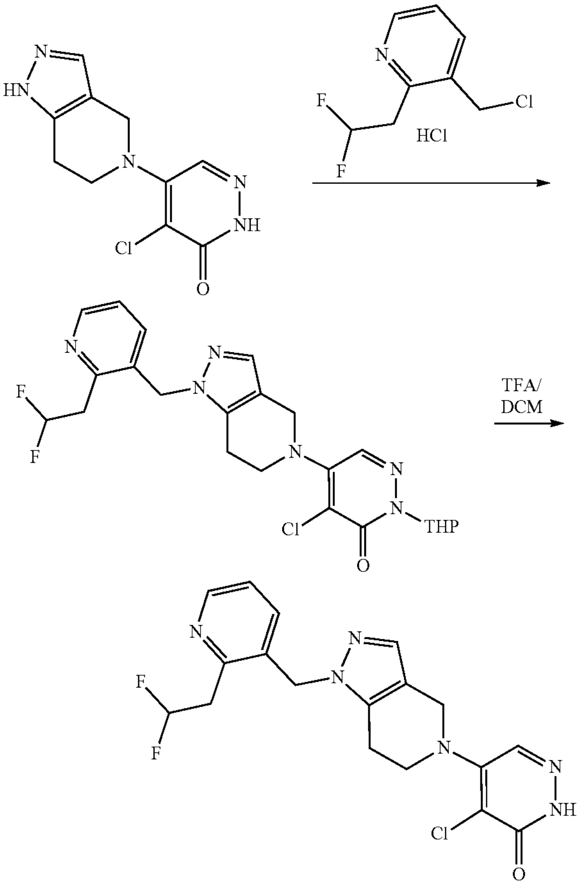

OJ

Preparation of OJ

4-Chloro-5-(1-[[2-(2,2-difluoroethyl)pyridin-3-yl]methyl]-1H,4H,5H,6H,7H-pyrazolo[4,3-c]pyridin-5-yl)-2-(oxan-2-yl)-2,3-dihydropyridazin-3-one To a stirred mixture of 2-(2,2-difluoroethyl)-3-(iodomethyl)pyridine (42.1 mg, 0.15 mmol, 0.50 equiv.) and 2-(2,2-difluoroethyl)-3-(iodomethyl)pyridine (42.1 mg, 0.15 mmol, 0.50 equiv.) in ACN (15 mL) was added K2CO3 (82.3 mg, 0.60 mmol, 2.00 equiv.) in portions at rt under nitrogen atmosphere. The resulting mixture was stirred for 48 h at 55 degrees celsius under nitrogen atmosphere. The reaction was monitored by LCMS. The mixture was allowed to cool down to room temperature. The resulting mixture was concentrated under reduced pressure. The residue was purified by Prep-TLC (PE/EtOAc 1/1) to afford 4-chloro-5-(1-[[2-(2,2-difluoroethyl)pyridin-3-yl]methyl]-1H,4H,5H,6H,7H-pyrazolo[4,3-c]pyridin-5-yl)-2-(oxan-2-yl)-2,3-dihydropyridazin-3-one (80 mg, 54.72%) as a yellow oil.

4-Chloro-5-(1-[[2-(2,2-difluoroethyl)pyridin-3-yl]methyl]-1H,4H,5H,6H,7H-pyrazolo[4,3-c]pyridin-5-yl)-2,3-dihydropyridazin-3-one To a stirred solution of 4-chloro-5-(1-[[2-(2,2-difluoroethyl)pyridin-3-yl]methyl]-1H,4H,5H,6H,7H-pyrazolo[4,3-c]pyridin-5-yl)-2-(oxan-2-yl)-2,3-dihydropyridazin-3-one (80 mg, 0.16 mmol, 1 equiv.) in DCM (10 mL) was added TFA (1 mL, 13.46 mmol, 82.62 equiv.) dropwise at rt. The reaction mixture was stirred for 16 h at rt. The reaction was monitored by LCMS. The resulting mixture was concentrated under reduced pressure. The residue was basified to pH=8 with saturated NH4HCO3 (aq.). The resulting mixture was extracted with CH2Cl2(3×100 mL). The combined organic layers were washed with brine (1×100 mL), dried over anhydrous Na2SO4. After filtration, the filtrate was concentrated under reduced pressure. The residue was purified by Prep-HPLC with the following conditions (Column: XBridge Prep OBD C18 Column 30×150 mm 5 um; Mobile Phase A: Water (10 MMOL/L NH4HCO3), Mobile Phase B: ACN; Flow rate: 60 mL/min; Gradient: 10% B to 30% B in 7 min; 220 nm; Rt: 6.22 min) to afford 4-chloro-5-(1-[[2-(2,2-difluoroethyl)pyridin-3-yl]methyl]-1H,4H,5H,6H,7H-pyrazolo[4,3-c]pyridin-5-yl)-2,3-dihydropyridazin-3-one (3.6 mg, 5.43%) as a white solid.

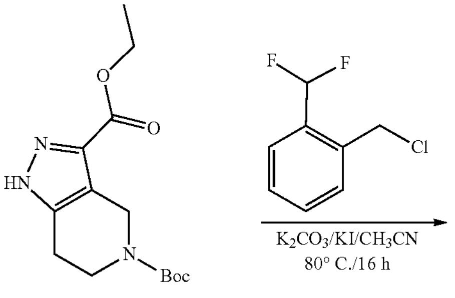

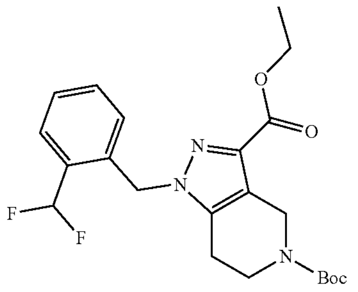

1

+

-continued

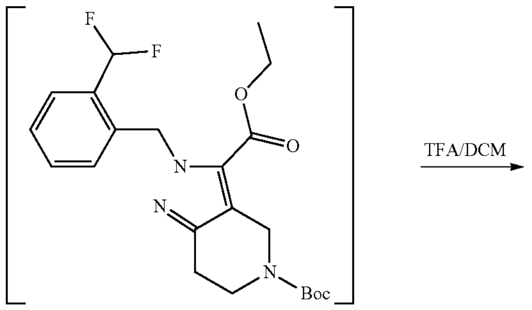

1a

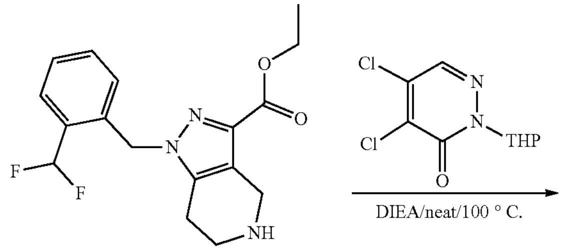

2

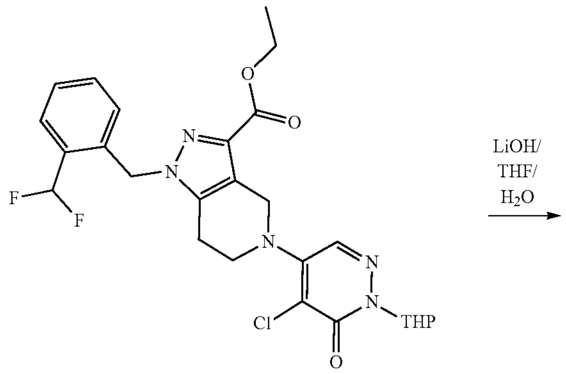

3

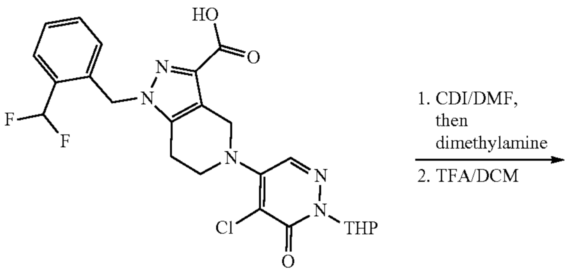

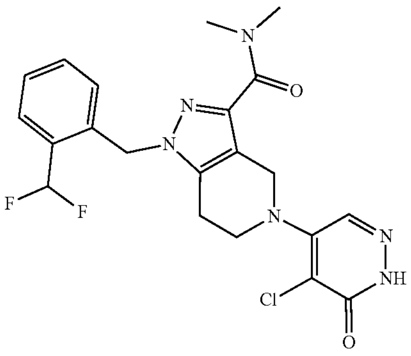

OK

Preparation of OK 5-tert-Butyl 3-ethyl 2-[[2-(difluoromethyl)phenyl]methyl]-2H,4H,5H,6H,7H-pyrazolo[4,3-c]pyridine-3,5-dicarboxylate To a stirred solution of 1-(chloromethyl)-2-(difluoromethyl)benzene (800 mg, 4.530 mmol, 1 equiv.) and 5-tert-butyl 3-ethyl 1H,4H,5H,6H,7H-pyrazolo[4,3-c]pyridine-3,5-dicarboxylate (1337.96 mg, 4.530 mmol, 1.00 equiv.) in MeCN (15 mL) was added KI (752.04 mg, 4.530 mmol, 1 equiv.) and K2CO3 (1252.22 mg, 9.061 mmol, 2 equiv.) at room temperature under nitrogen atmosphere. The mixture was stirred at 80 degrees celsius overnight Desired product could be detected by LCMS. The resulting mixture was concentrated under reduced pressure. The residue was purified by silica gel column chromatography, eluted with PE/EtOAc (5:1 to 3:1) to afford 5-tert-butyl 3-ethyl 1-[[2-(difluoromethyl)phenyl]methyl]-1H,4H,5H,6H,7H-pyrazolo[4,3-c]pyridine-3,5-dicarboxylate (500 mg, 25.34%) as a yellow solid and 5-tert-butyl 3-ethyl 2-[[2-(difluoromethyl)phenyl]methyl]-2H,4H,5H,6H,7H-pyrazolo[4,3-c]pyridine-3,5-dicarboxylate (200 mg, 10.14%) as a yellow solid.

Ethyl 1-[[2-(difluoromethyl)phenyl]methyl]-1H,4H,5H,6H,7H-pyrazolo[4,3-c]pyridine-3-carboxylate To a stirred solution of 5-tert-butyl 3-ethyl 1-[[2-(difluoromethyl)phenyl]methyl]-1H,4H,5H,6H,7H-pyrazolo[4,3-c]pyridine-3,5-dicarboxylate (500 mg, 1.148 mmol, 1 equiv.) in DCM (10 mL, 157.300 mmol, 137.00 equiv.) was added TFA (2 mL, 26.926 mmol, 23.45 equiv.) dropwise at room temperature under nitrogen atmosphere. The mixture was stirred at rt for 2 h. Desired product could be detected by LCMS. The resulting mixture was concentrated under reduced pressure to afford ethyl 1-[[2-(difluoromethyl)phenyl]methyl]-1H,4H,5H,6H,7H-pyrazolo[4,3-c]pyridine-3-carboxylate (380 mg, 98.69%) as yellow solid.

Ethyl 5-[5-chloro-1-(oxan-2-yl)-6-oxo-1,6-dihydropyridazin-4-yl]-1-[[2-(difluoromethyl)phenyl]methyl]-1H,4H,5H,6H,7H-pyrazolo[4,3-c]pyridine-3-carboxylate To a stirred solution of ethyl 1-[[2-(difluoromethyl)phenyl]methyl]-1H,4H,5H,6H,7H-pyrazolo[4,3-c]pyridine-3-carboxylate (380 mg, 1.133 mmol, 1 equiv.) in DIEA (292.90 mg, 2.266 mmol, 2 equiv.) was added 4,5-dichloro-2-(oxan-2-yl)-2,3-dihydropyridazin-3-one (282.25 mg, 1.133 mmol, 1.00 equiv.) in portions at room temperature under nitrogen atmosphere. The mixture was stirred at 100 degrees celsius overnight. Desired product could be detected by LCMS. The residue was purified by silica gel column chromatography, eluted with PE/EtOAc (5:1 to 3:1) to afford ethyl 5-[5-chloro-1-(oxan-2-yl)-6-oxo-1,6-dihydropyridazin-4-yl]-1-[[2-(difluoromethyl)phenyl]methyl]-1H,4H,5H,6H,7H-pyrazolo[4,3-c]pyridine-3-carboxylate (500 mg, 80.52%) as a yellow solid.

5-[5-chloro-1-(oxan-2-yl)-6-oxo-1,6-dihydropyridazin-4-yl]-1-[[2-(difluoromethyl)phenyl]methyl]-1H,4H,5H,6H,7H-pyrazolo[4,3-c]pyridine-3-carboxylic Acid To a stirred solution of ethyl 5-[5-chloro-1-(oxan-2-yl)-6-oxo-1,6-dihydropyridazin-4-yl]-1-[[2-(difluoromethyl)phenyl]methyl]-1H,4H,5H,6H,7H-pyrazolo[4,3-c]pyridine-3-carboxylate (460 mg, 0.839 mmol, 1 equiv.) in THF (5 mL) and H2O (5 mL) was added LiOH (100.51 mg, 4.197 mmol, 5 equiv.) in portions at room temperature under nitrogen atmosphere. The mixture was stirred at 50 degrees celsius overnight. Desired product could be detected by LCMS. The resulting mixture was concentrated under reduced pressure. The residue was purified by reverse phase flash with the following conditions (Column: XBridge Prep OBD C18 Column 30×150 mm 5 um; Mobile Phase A: Water (10 MMOL/L NH4HCO3), Mobile Phase B: ACN; Flow rate: 60 mL/min; Gradient: 27% B to 55% B in 8 min; 220 nm; Rt: 7.82 min) to afford 5-[5-chloro-1-(oxan-2-yl)-6-oxo-1,6-dihydropyridazin-4-yl]-1-[[2-(difluoromethyl)phenyl]methyl]-1H,4H,5H,6H,7H-pyrazolo[4,3-c]pyridine-3-carboxylic acid (430 mg, 98.52%) as a colorless oil.

5-[5-Chloro-1-(oxan-2-yl)-6-oxo-1,6-dihydropyridazin-4-yl]-1-[[2-(difluoromethyl)phenyl]methyl]-N,N-dimethyl-1H,4H,5H,6H,7H-pyrazolo[4,3-c]pyridine-3-carboxamide To a stirred solution of 5-[5-chloro-1-(oxan-2-yl)-6-oxo-1,6-dihydropyridazin-4-yl]-1-[[2-(difluoromethyl)phenyl]methyl]-1H,4H,5H,6H,7H-pyrazolo[4,3-c]pyridine-3-carboxylic acid (80 mg, 0.15 mmol, 1 equiv.) in DMF (5 mL) was added CDI (37.4 mg, 0.23 mmol, 1.5 equiv.) in portions at room temperature under nitrogen atmosphere. The mixture was stirred at 50 degrees celsius for 2 h. dimethylamine (13.9 mg, 0.31 mmol, 2.00 equiv.) was added to the mixture. The mixture was stirred at 50 degrees celsius overnight. Desired product could be detected by LCMS. The resulting mixture was concentrated under vacuum to afford 5-[5-chloro-1-(oxan-2-yl)-6-oxo-1,6-dihydropyridazin-4-yl]-1-[[2-(difluoromethyl)phenyl]methyl]-N,N-dimethyl-1H,4H,5H,6H,7H-pyrazolo[4,3-c]pyridine-3-carboxamide (60 mg, 71.29%) as yellow solid.

5-(5-Chloro-6-oxo-1,6-dihydropyridazin-4-yl)-1-[[2-(difluoromethyl)phenyl]methyl]-N,N-dimethyl-1H,4H,5H,6H,7H-pyrazolo[4,3-c]pyridine-3-carboxamide To a stirred solution of 5-[5-chloro-1-(oxan-2-yl)-6-oxo-1,6-dihydropyridazin-4-yl]-1-[[2-(difluoromethyl)phenyl]methyl]-N,N-dimethyl-1H,4H,5H,6H,7H-pyrazolo[4,3-c]pyridine-3-carboxamide (50 mg, 1 equiv.) in DCM (10 mL) was added TFA (2 mL) dropwise at room temperature under nitrogen atmosphere. The mixture was stirred at rt for 1 h. Desired product could be detected by LCMS. The resulting mixture was concentrated under reduced pressure. The crude product (30 mg) was purified by Prep-HPLC with the following conditions (Column: XBridge Prep OBD C18 Column 30×150 mm 5 um; Mobile Phase A: Water (10 MMOL/L NH4HCO3), Mobile Phase B: ACN; Flow rate: 60 mL/min; Gradient: 23% B to 45% B in 7 min; 220 nm; Rt: 6.47 min) to afford 5-(5-chloro-6-oxo-1,6-dihydropyridazin-4-yl)-1-[[2-(difluoromethyl)phenyl]methyl]-N,N-dimethyl-1H,4H,5H,6H,7H-pyrazolo[4,3-c]pyridine-3-carboxamide (25 mg) as a white solid.

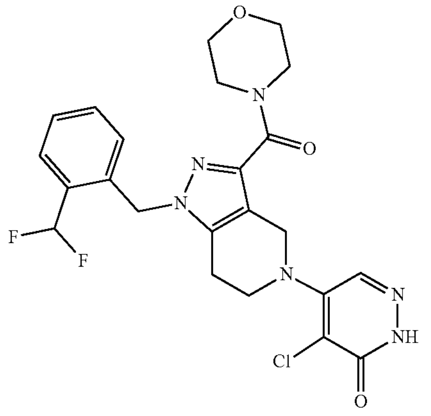

OL

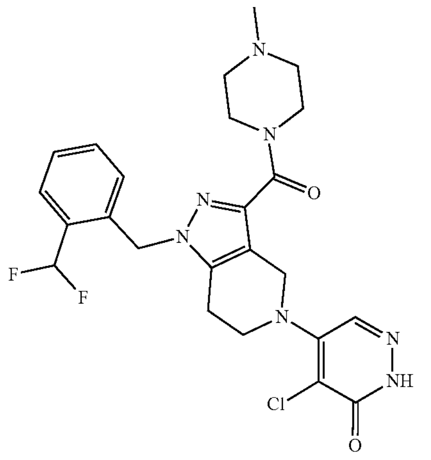

OM

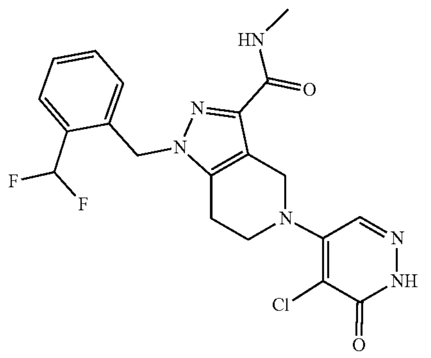

ON

Compound OL, OM, and ON were prepared by the methods and scheme described for OK by using corresponding amines.

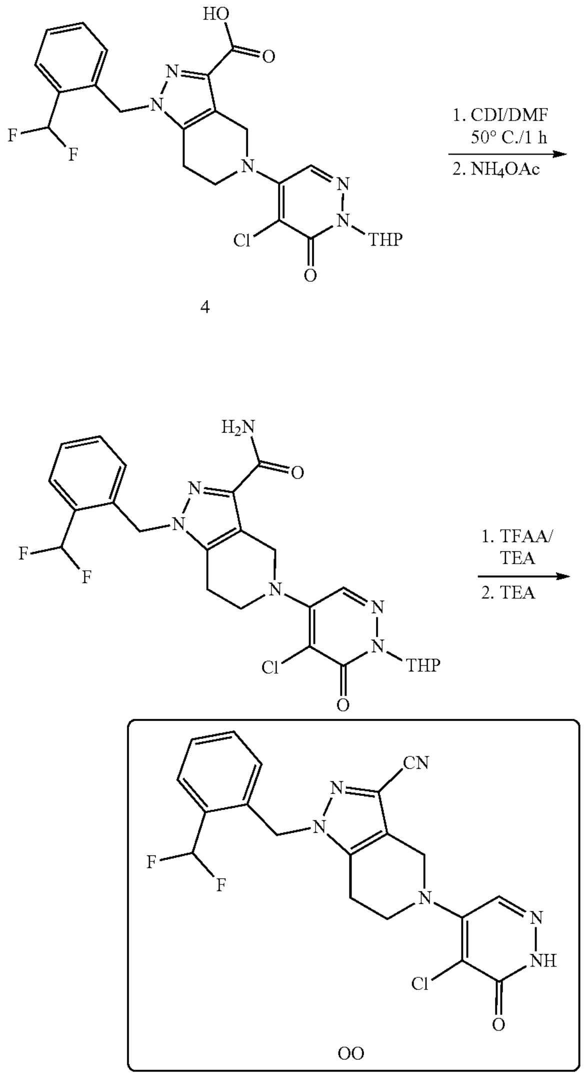

4

OO

Preparation of Compound 00

5-[5-chloro-1-(oxan-2-yl)-6-oxo-1,6-dihydro-pyridazin-4-yl]-1-[[2-(difluoromethyl)phenyl] methyl]-1H,4H,5H,6H,7H-pyrazolo[4,3-c]pyridine-3-carboxamide To a stirred solution of 5-[5-chloro-1-(oxan-2-yl)-6-oxo-1,6-dihydropyridazin-4-yl]-1-[[2-(difluoromethyl)phenyl] methyl]-1H,4H,5H,6H,7H-pyrazolo[4,3-c]pyridine-3-carboxylic acid (60 mg, 0.115 mmol, 1 equiv.) in DMF (5 mL) was added CDI (28.07 mg, 0.173 mmol, 1.5 equiv.) in portions at room temperature under nitrogen atmosphere. The mixture was stirred at 50 degrees celsius for 2 h. NH4OAc (17.79 mg, 0.231 mmol, 2 equiv.) was added to the mixture. The mixture was stirred at 50 degrees celsius overnight. Desired product could be detected by LCMS. The resulting mixture was concentrated under vacuum to afford 5-[5-chloro-1-(oxan-2-yl)-6-oxo-1,6-dihydropyridazin-4-yl]-1-[[2-(difluoromethyl)phenyl]methyl]-1H,4H,5H,6H,7H-pyrazolo[4,3-c]pyridine-3-carboxamide (56 mg, 93.51%) as yellow solid.

5-[5-chloro-1-(oxan-2-yl)-6-oxo-1,6-dihydro-pyridazin-4-yl]-1-[[2-(difluoromethyl)phenyl]methyl]-1H,4H,5H,6H,7H-pyrazolo[4,3-c]pyridine-3-carbonitrile To a stirred solution of 5-[5-chloro-1-(oxan-2-yl)-6-oxo-1,6-dihydropyridazin-4-yl]-1-[[2-(difluoromethyl)phenyl]methyl]-1H,4H,5H,6H,7H-pyrazolo[4,3-c]pyridine-3-carboxamide (200 mg, 0.385 mmol, 1 equiv.) and TEA (78.00 mg, 0.771 mmol, 2 equiv.) in THF (10 mL) was added TFAA (161.89 mg, 0.771 mmol, 2 equiv.) dropwise/in portions at 0 degrees celsius under nitrogen atmosphere. The mixture was stirred at 0 degrees celsius for 2 h. Desired product could be detected by LCMS. The resulting mixture was concentrated under reduced pressure. The residue was purified by silica gel column chromatography, eluted with PE/EtOAc (5:1 to 2:1) to afford 5-[5-chloro-1-(oxan-2-yl)-6-oxo-1,6-dihydropyridazin-4-yl]-1-[[2-(difluoromethyl)phenyl]methyl]-1H,4H,5H,6H,7H-pyrazolo[4,3-c]pyridine-3-carbonitrile (180 mg, 93.24%) as a white solid.

5-(5-chloro-6-oxo-1,6-dihydropyridazin-4-yl)-1-[[2-(difluoromethyl)phenyl]methyl]-1H,4H,5H,6H,7H-pyrazolo[4,3-c]pyridine-3-carbonitrile To a stirred solution of 5-[5-chloro-1-(oxan-2-yl)-6-oxo-1,6-dihydropyridazin-4-yl]-1-[[2-(difluoromethyl)phenyl]methyl]-1H,4H,5H,6H,7H-pyrazolo[4,3-c]pyridine-3-carbonitrile (60 mg, 1 equiv.) in DCM (10 mL) was added TFA (2 mL) dropwise at room temperature under nitrogen atmosphere. The mixture was stirred at rt for 2 h. Desired product could be detected by LCMS. The resulting mixture was concentrated under reduced pressure. The crude product (50 mg) was purified by Prep-HPLC with the following conditions (Column: XBridge Prep OBD C18 Column 30×150 mm 5 um; Mobile Phase A: Water (10 MMOL/L NH4HCO3), Mobile Phase B: ACN; Flow rate: 60 mL/min; Gradient: 27% B to 50% B in 7 min; 220 nm; Rt: 6.48 min) to afford 5-(5-chloro-6-oxo-1,6-dihydropyridazin-4-yl)-1-[[2-(difluoromethyl)phenyl]methyl]-1H,4H,5H,6H,7H-pyrazolo[4,3-c]pyridine-3-carbonitrile (30 mg) as a white solid.

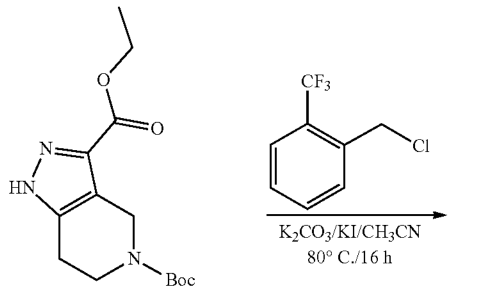

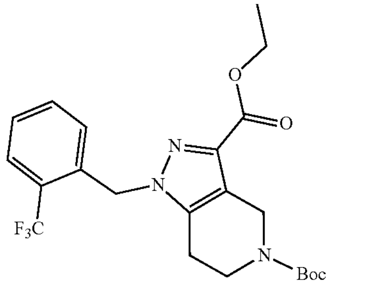

1

+

-continued

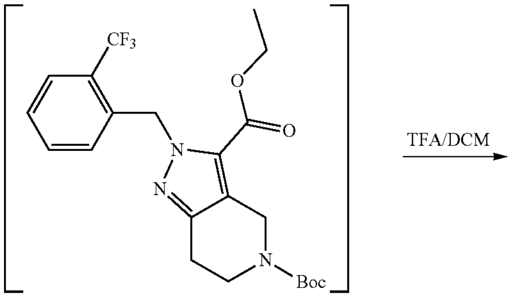

1a

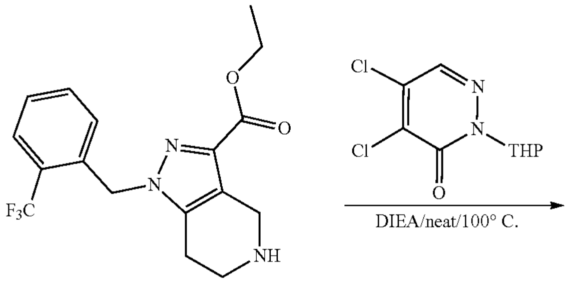

2

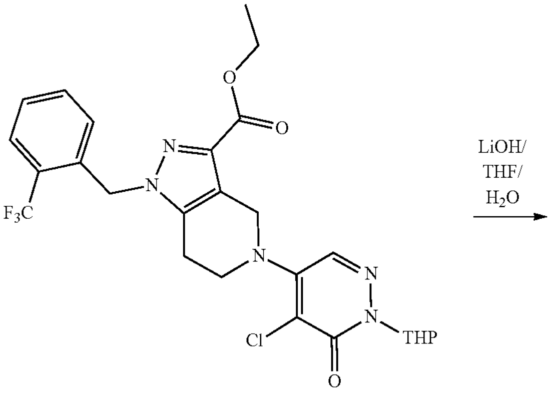

3

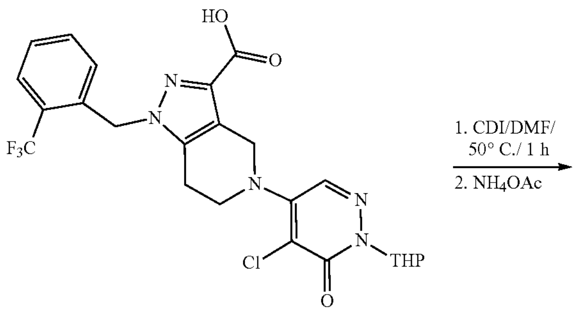

4

-continued

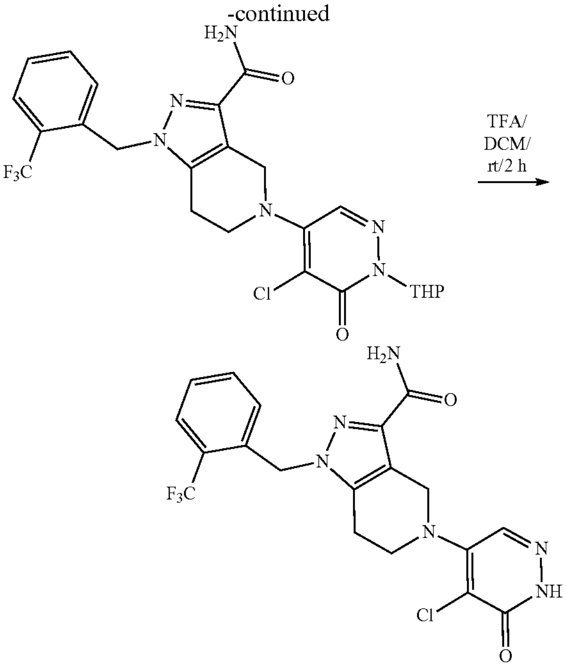

OP

Preparation of OP 2-tert-Butyl 7-ethyl 5-[[2-(trifluoromethyl)phenyl] methyl]-1H,2H,3H,4H,5H-cyclopenta[c]pyridine-2, 7-dicarboxylate To a stirred solution of 5-tert-butyl 3-ethyl 1H,4H,5H,6H, 7H-pyrazolo[4,3-c]pyridine-3,5-dicarboxylate (1.5 g, 5.079 mmol, 1 equiv.) and 1-(bromomethyl)-2-(trifluoromethyl) benzene (1.46 g, 6.095 mmol, 1.2 equiv.) in ACN (20 mL, 380.494 mmol) were added K2CO3 (1.40 g, 10.158 mmol, 2 equiv.) and KI (0.84 g, 5.079 mmol, 1 equiv.) in portions at room temperature under nitrogen atmosphere. The resulting mixture was stirred for 2 h at 80 degrees celsius under nitrogen atmosphere. The reaction was monitored by LCMS. The resulting mixture was concentrated under reduced pressure. The resulting mixture was extracted with EtOAc (50 mL). The combined organic layers were washed with brine (3×100 mL), dried over anhydrous Na2SO4. After filtration, the filtrate was concentrated under reduced pressure. The resulting mixture was used in the next step (E00692-127) directly without further purification.

Ethyl 1-[[2-(trifluoromethyl)phenyl]methyl]-1H,4H, 5H,6H,7H-pyrazolo[4,3-c]pyridine-3-carboxylate To a stirred solution of 2-tert-butyl 7-ethyl 5-[[2-(trifluoromethyl)phenyl]methyl]-1H,2H,3H,4H,5H-cyclopenta[c] pyridine-2,7-dicarboxylate (1 g, 2.215 mmol, 1 equiv.) in DCM (10 mL) was added TFA (3 mL) in portions at room temperature under nitrogen atmosphere. The resulting mixture was stirred for 2 h at room temperature under nitrogen atmosphere. The reaction was monitored by LCMS. The resulting mixture was concentrated under reduced pressure. The resulting mixture was used in the next step (E00692-129) directly without further purification.

Ethyl 5-[5-chloro-1-(oxan-2-yl)-6-oxo-1,6-dihydro-pyridazin-4-yl]-1-[[2-(trifluoromethyl)phenyl] methyl]-1H,4H,5H,6H,7H-pyrazolo[4,3-c]pyridine-3-carboxylate To a stirred solution of ethyl 1-[[2-(trifluoromethyl)phenyl]methyl]-1H,4H,5H,6H,7H-pyrazolo[4,3-c]pyridine-3-carboxylate (750 mg, 2.123 mmol, 1 equiv.) and 4,5-dichloro-2-(oxan-2-yl)-2,3-dihydropyridazin-3-one (528.71 mg, 2.123 mmol, 1 equiv.) was added DIEA (5 mL) in portions at room temperature under nitrogen atmosphere. The resulting mixture was stirred for overnight at 100 degrees celsius under nitrogen atmosphere as a neat reaction. The reaction was monitored by LCMS. The mixture was allowed to cool down to room temperature. The resulting mixture was extracted with EtOAc (30 mL). The combined organic layers were washed with brine (3×50 mL), dried over anhydrous Na2SO4. After filtration, the filtrate was concentrated under reduced pressure. The residue was purified by Prep-TLC (PE/EtOAc 1:1) to afford ethyl 5-[5-chloro-1-(oxan-2-yl)-6-oxo-1,6-dihydropyridazin-4-yl]-1-[[2-(trifluoromethyl)phenyl]methyl]-1H,4H,5H,6H,7H-pyrazolo[4,3-c]pyridine-3-carboxylate (1 g, 83.24%) as a light yellow oil.

5-[5-chloro-1-(oxan-2-yl)-6-oxo-1,6-dihydro-pyridazin-4-yl]-1-[[2-(trifluoromethyl)phenyl] methyl]-1H,4H,5H,6H,7H-pyrazolo[4,3-c]pyridine-3-carboxylic Acid To a stirred solution of ethyl 5-[5-chloro-1-(oxan-2-yl)-6-oxo-1,6-dihydropyridazin-4-yl]-1-[[2-(trifluoromethyl) phenyl]methyl]-1H,4H,5H,6H,7H-pyrazolo[4,3-c]pyridine-3-carboxylate (1 g, 1.767 mmol, 1 equiv.) in THF (5 mL) and H2O (5 mL) was added LiOH (0.21 g, 0.009 mmol, 5 equiv.) in portions at room temperature under nitrogen atmosphere. The resulting mixture was stirred for 3 h at 50 degrees celsius under nitrogen atmosphere. The reaction was monitored by LCMS. The mixture was acidified to pH 6 with HCl (aq.). The resulting mixture was extracted with EtOAc (30 mL). The combined organic layers were washed with brine (3×10 mL), dried over anhydrous Na2SO4. After filtration, the filtrate was concentrated under reduced pressure. The residue was purified by silica gel column chromatography, eluted with CH2Cl2/MeOH (50:1 to 5:1) to afford 5-[5-chloro-1-(oxan-2-yl)-6-oxo-1,6-dihydropyridazin-4-yl]-1-[[2-(trifluoromethyl)phenyl]methyl]-1H,4H,5H,6H,7H-pyrazolo[4,3-c]pyridine-3-carboxylic acid (700 mg, 73.65%) as a light yellow oil.

5-[5-Chloro-1-(oxan-2-yl)-6-oxo-1,6-dihydro-pyridazin-4-yl]-1-[[2-(trifluoromethyl)phenyl] methyl]-1H,4H,5H,6H,7H-pyrazolo[4,3-c]pyridine-3-carboxamide To a stirred solution of 5-[5-chloro-1-(oxan-2-yl)-6-oxo-1,6-dihydropyridazin-4-yl]-1-[[2-(trifluoromethyl)phenyl] methyl]-1H,4H,5H,6H,7H-pyrazolo[4,3-c]pyridine-3-carboxylic acid (700 mg, 1.301 mmol, 1 equiv.) in DMF (10 mL) was added CDI (316.51 mg, 1.952 mmol, 1.5 equiv.) in portions at room temperature under nitrogen atmosphere. The resulting mixture was stirred for 1 h at 50 degrees celsius under nitrogen atmosphere. To the above mixture was added NH4OAc (300.92 mg, 3.904 mmol, 3 equiv.) in portions over 5 min at 50 degrees C. The resulting mixture was stirred for additional 2 h at 50 degrees C. The reaction was monitored by LCMS. The mixture was allowed to cool down to room temperature. The resulting mixture was extracted with EtOAc (30 mL). The combined organic layers were washed with brine (3×50 mL), dried over anhydrous Na2SO4. After filtration, the filtrate was concentrated under reduced pressure. The residue was purified by silica gel column chromatography, eluted with PE/EtOAc (20:1 to 5:1) to afford 5-[5-chloro-1-(oxan-2-yl)-6-oxo-1,6-dihydropyridazin-4-yl]-1-[[2-(trifluoromethyl)phenyl]methyl]-1H,4H,5H,6H,7H-pyrazolo[4,3-c]pyridine-3-carboxamide (40 mg, 5.72%) as a light yellow oil.

5-(5-Chloro-6-oxo-1,6-dihydropyridazin-4-yl)-1-[[2-(trifluoromethyl)phenyl]methyl]-1H,4H,5H,6H,7H-pyrazolo[4,3-c]pyridine-3-carboxamide To a stirred solution of 5-[5-chloro-1-(oxan-2-yl)-6-oxo-1,6-dihydropyridazin-4-yl]-1-[[2-(trifluoromethyl)phenyl]methyl]-1H,4H,5H,6H,7H-pyrazolo[4,3-c]pyridine-3-carboxamide (40 mg, 0.074 mmol, 1 equiv.) in DCM (10 mL) was added TFA (3 mL, 40.389 mmol, 542.16 equiv.) at room temperature. The resulting mixture was stirred for 2 h at room temperature. The reaction was monitored by LCMS. The resulting mixture was concentrated under reduced pressure. The mixture was basified to pH 8 with saturated NaHCO3 (aq.). The crude product (30 mg) was purified by Prep-HPLC with the following conditions (Column: XBridge Shield RP18 OBD Column, 5 um, 19*150 mm; Mobile Phase A: Water (10 MMOL/L NH4HCO3), Mobile Phase B: ACN; Flow rate: 20 mL/min; Gradient: 24% B to 45% B in 7 min; 220/254 nm; Rt: 6.45 min) to afford 5-(5-chloro-6-oxo-1,6-dihydropyridazin-4-yl)-1-[[2-(trifluoromethyl)phenyl]methyl]-1H,4H,5H,6H,7H-pyrazolo[4,3-c]pyridine-3-carboxamide (12.5 mg, 37.06%) as a white solid.

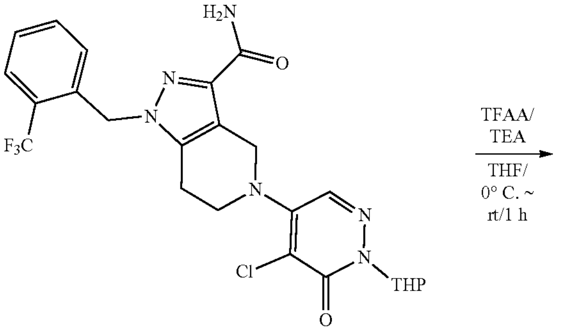

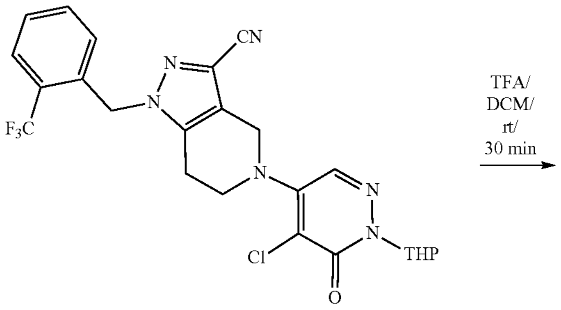

-continued

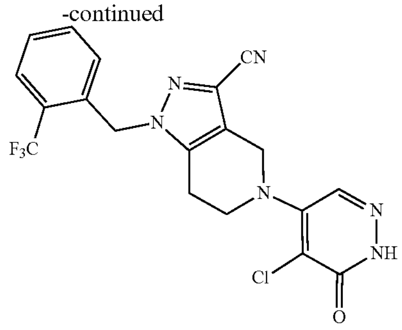

OQ

Preparation of OQ

5-[5-chloro-1-(oxan-2-yl)-6-oxo-1,6-dihydropyridazin-4-yl]-1-[[2-(trifluoromethyl)phenyl]methyl]-1H,4H,5H,6H,7H-pyrazolo[4,3-c]pyridine-3-carbonitrile To a stirred solution of 5-[5-chloro-1-(oxan-2-yl)-6-oxo-1,6-dihydropyridazin-4-yl]-1-[[2-(trifluoromethyl)phenyl]methyl]-1H,4H,5H,6H,7H-pyrazolo[4,3-c]pyridine-3-carboxamide (60 mg, 0.112 mmol, 1 equiv.) and TEA (22.61 mg, 0.223 mmol, 2 equiv.) in THF (5 mL, 61.715 mmol, 552.29 equiv.) was added TFAA (46.94 mg, 0.223 mmol, 2 equiv.) dropwise at 0 degrees celsius under nitrogen atmosphere. The mixture was stirred at rt for 2 h. Desired product could be detected by LCMS. The resulting mixture was concentrated under reduced pressure. The residue was purified by silica gel column chromatography, eluted with PE/EtOAc (5:1) to afford 5-[5-chloro-1-(oxan-2-yl)-6-oxo-1,6-dihydropyridazin-4-yl]-1-[[2-(trifluoromethyl)phenyl]methyl]-1H,4H,5H,6H,7H-pyrazolo[4,3-c]pyridine-3-carbonitrile (56 mg, 96.57%) as a yellow solid.

5-(5-chloro-6-oxo-1,6-dihydropyridazin-4-yl)-1-[[2-(trifluoromethyl)phenyl]methyl]-1H,4H,5H,6H,7H-pyrazolo[4,3-c]pyridine-3-carbonitrile To a stirred solution of 5-[5-chloro-1-(oxan-2-yl)-6-oxo-1,6-dihydropyridazin-4-yl]-1-[[2-(trifluoromethyl)phenyl]methyl]-1H,4H,5H,6H,7H-pyrazolo[4,3-c]pyridine-3-carbonitrile (55 mg, 1 equiv.) in DCM (10 mL) was added TFA (2 mL) dropwise/in portions at 0 degrees celsius under nitrogen atmosphere. The mixture was stirred at rt for 2 h. Desired product could be detected by LCMS. The resulting mixture was concentrated under reduced pressure. The crude product (50 mg) was purified by Prep-HPLC with the following conditions (Column: XBridge Prep OBD C18 Column 30×150 mm 5 um; Mobile Phase A: Water (10 MMOL/L NH4HCO3), Mobile Phase B: ACN; Flow rate: 60 mL/min; Gradient: 27% B to 55% B in 8 min; 220 nm; Rt: 7.82 min) to afford 5-(5-chloro-6-oxo-1,6-dihydropyridazin-4-yl)-1-[[2-(trifluoromethyl)phenyl]methyl]-1H,4H,5H,6H,7H-pyrazolo[4,3-c]pyridine-3-carbonitrile (20 mg) as a white solid.

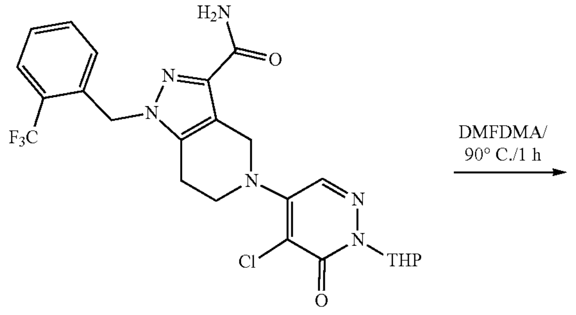

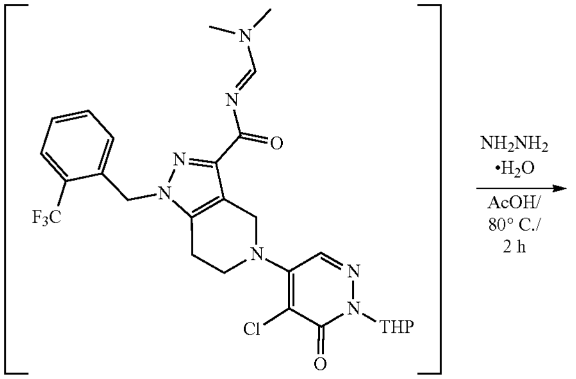

1

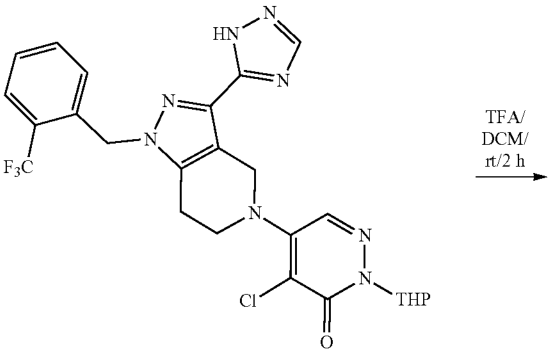

2

-continued

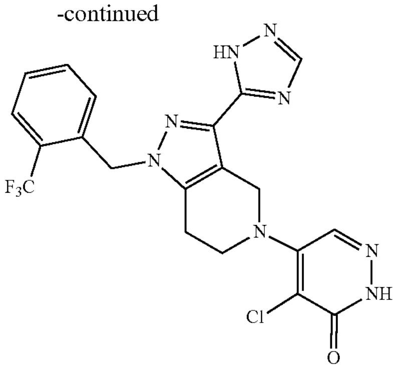

OR

Preparation of OR

4-Chloro-2-(oxan-2-yl)-5-[3-(1H-1,2,4-triazol-5-yl)-1-[[2-(trifluoromethyl)phenyl]methyl]-1H,4H,5H,6H,7H-pyrazolo[4,3-c]pyridin-5-yl]-2,3-dihydropyridazin-3-one A solution of 5-[5-chloro-1-(oxan-2-yl)-6-oxo-1,6-dihydropyridazin-4-yl]-1-[[2-(trifluoromethyl)phenyl]methyl]-1H,4H,5H,6H,7H-pyrazolo[4,3-c]pyridine-3-carboxamide (150 mg, 0.28 mmol, 1 equiv.) in DMF-DMA (5 mL, 37.34 mmol, 133.68 equiv.) was stirred for 1 h at 90 degrees celsius under nitrogen atmosphere. The resulting solution was concentrated under reduced pressure. The residue was in NH2NH2·H2O (174.8 mg, 2.79 mmol, 10 equiv, 80%) was added HAc (5 mL, 87.26 mmol, 312.35 equiv.) at 25 degrees C. The mixture was stirred at 80 degrees celsius for 2 h. The resulting mixture was concentrated under reduced pressure. The residue was purified by Prep-TLC (DCM/MeOH 15/1) to afford 4-chloro-2-(oxan-2-yl)-5-[3-(1H-1,2,4-triazol-5-yl)-1-[[2-(trifluoromethyl)phenyl]methyl]-1H,4H,5H,6H,7H-pyrazolo[4,3-c]pyridin-5-yl]-2,3-dihydropyridazin-3-one (100 mg, 63.81%) as a light yellow oil.

4-Chloro-5-[3-(1H-1,2,4-triazol-5-yl)-1-[[2-(trifluoromethyl)phenyl]methyl]-1H,4H,5H,6H,7H-pyrazolo[4,3-c]pyridin-5-yl]-2,3-dihydropyridazin-3-one To a solution of 4-chloro-2-(oxan-2-yl)-5-[3-(1H-1,2,4-triazol-5-yl)-1-[[2-(trifluoromethyl)phenyl]methyl]-1H,4H,5H,6H,7H-pyrazolo[4,3-c]pyridin-5-yl]-2,3-dihydropyridazin-3-one (100 mg, 0.18 mmol, 1 equiv.) in DCM (5 mL, 78.65 mmol, 441.20 equiv.) was added TFA (203.3 mg, 1.78 mmol, 10.00 equiv.) at 25 degrees C. The mixture was stirred at 25 degrees celsius for 2 h. The resulting solution was concentrated under reduced pressure. The residue was purified by Prep-TLC (DCM/MeOH 10/1) to afford 4-chloro-5-[3-(1H-1,2,4-triazol-5-yl)-1-[[2-(trifluoromethyl)phenyl]methyl]-1H,4H,5H,6H,7H-pyrazolo[4,3-c]pyridin-5-yl]-2,3-dihydropyridazin-3-one (20 mg, 23.53%) as a white solid.

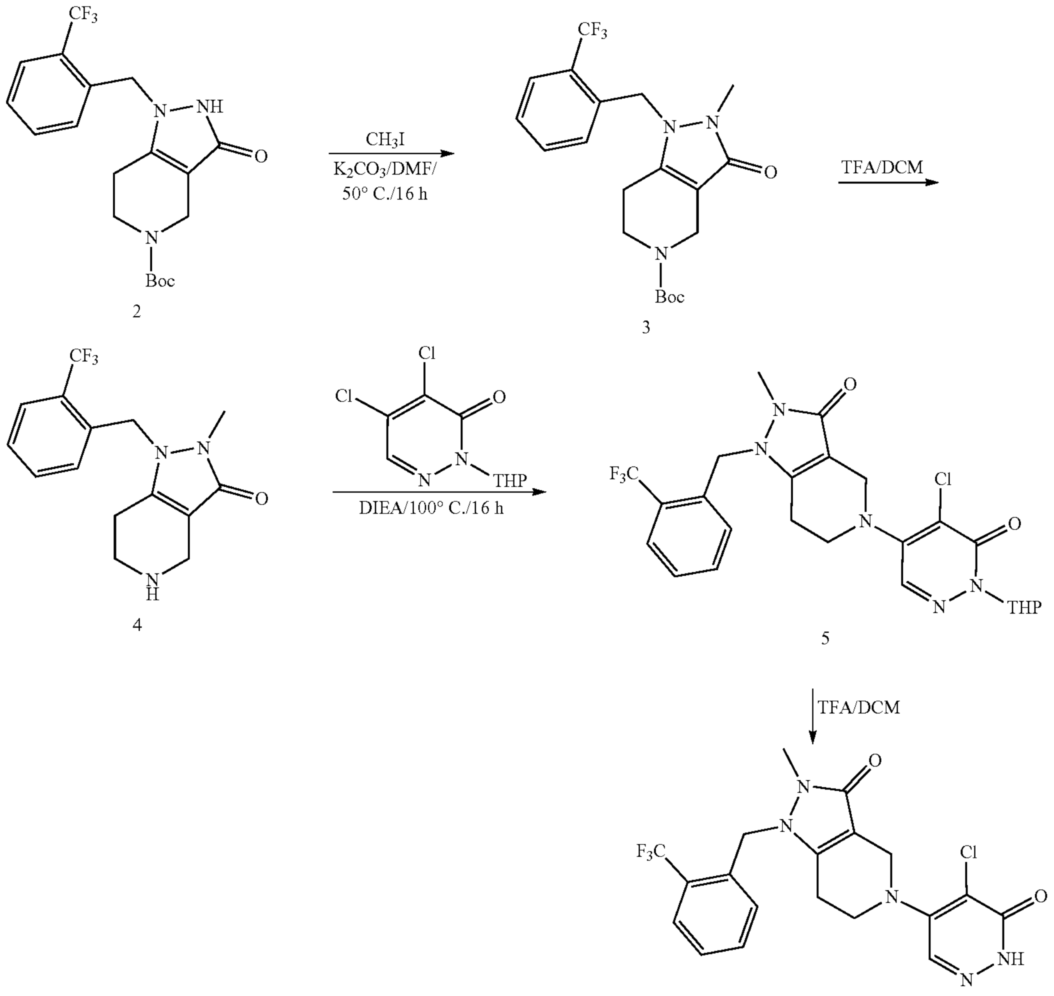

OS

Preparation of OS

Tert-Butyl 2-methyl-3-oxo-1-[[2-(trifluoromethyl) phenyl]methyl]-1H,2H,3H,4H,5H,6H,7H-pyrazolo [4,3-c]pyridine-5-carboxylate To a stirred solution of tert-butyl 3-oxo-1-[[2-(trifluoromethyl)phenyl]methyl]-1H,2H,3H,4H,5H,6H,7H-pyrazolo[4,3-c]pyridine-5-carboxylate (300 mg, 0.75 mmol, 1 equiv.) and K2CO3 (125.2 mg, 0.91 mmol, 1.2 equiv.) in DMF (10 mL) was added MeI (128.6 mg, 0.91 mmol, 1.20 equiv.) dropwise at room temperature. The resulting mixture was stirred for 16 h at 50 degrees C. The reaction was monitored by LCMS. The mixture was purified by reverse phase flash with the following conditions (Column: C18, 330 g; Mobile Phase A: Water/0.05% NH4HCO3, Mobile Phase B: ACN; Flow rate: 80 mL/min; Gradient: 40% B to 95% B in 30 min; Detector, 254 nm; Monitor, 220 nm) to afford tert-butyl 2-methyl-3-oxo-1-[[2-(trifluoromethyl)phenyl]methyl]-1H,2H,3H,4H,5H,6H,7H-pyrazolo[4,3-c]pyridine-5-carboxylate (80 mg, 25.76%) as a colorless solid.

2-Methyl-1-[[2-(trifluoromethyl)phenyl]methyl]-1H,2H,3H,4H,5H,6H,7H-pyrazolo[4,3-c]pyridin-3-one To a stirred solution of tert-butyl 2-methyl-3-oxo-1-[[2-(trifluoromethyl)phenyl]methyl]-1H,2H,3H,4H,5H,6H,7H-pyrazolo[4,3-c]pyridine-5-carboxylate (80 mg, 0.19 mmol, 1 equiv.) in DCM (10 mL, 157.30 mmol) was added TFA (2 mL, 26.93 mmol, 138.48 equiv.) dropwise at room temperature. The resulting mixture was stirred for 2 h at room temperature. The reaction was monitored by LCMS. The resulting mixture was concentrated under reduced pressure. The residue was basified to pH 8~9 with saturated Na2CO3 (aq.). The mixture was purified by reverse phase flash with the following conditions (Column: C18, 330 g; Mobile Phase A: Water/0.05% NH4HCO3, Mobile Phase B: ACN; Flow rate: 45 mL/min; Gradient: 20% B to 40% B in 25 min; Detector, 254 nm; Monitor, 220 nm) to afford 2-methyl-1-[[2-(trifluoromethyl)phenyl]methyl]-1H,2H,3H,4H,5H,6H,7H-pyrazolo[4,3-c]pyridin-3-one (60 mg, 99.12%) as a yellow solid.

4-Chloro-5-(2-methyl-3-oxo-1-[[2-(trifluoromethyl) phenyl]methyl]-1H,2H,3H,4H,5H,6H,7H-pyrazolo [4,3-c]pyridin-5-yl)-2-(oxan-2-yl)-2,3-dihydropyridazin-3-one To a stirred solution of 2-methyl-1-[[2-(trifluoromethyl) phenyl]methyl]-1H,2H,3H,4H,5H,6H,7H-pyrazolo[4,3-c] pyridin-3-one (60 mg, 0.19 mmol, 1 equiv.) and 4,5-dichloro-2-(oxan-2-yl)-2,3-dihydropyridazin-3-one (48.0 mg, 0.19 mmol, 1 equiv.) in DMA (2 mL) was added DIEA (49.8 mg, 0.39 mmol, 2 equiv.) dropwise at room temperature. The resulting mixture was stirred for 4 h at 100 degrees C. The reaction was monitored by LCMS. The mixture was purified by reverse phase flash with the following conditions (Column: C18, 330 g; Mobile Phase A: Water/0.05% NH4HCO3, Mobile Phase B: ACN; Flow rate: 80 mL/min; Gradient: 40% B to 60% B in 25 min; Detector, 220 nm; Monitor, 254 nm) to afford 4-chloro-5-(2-methyl-3-oxo-1-[[2-(trifluoromethyl)phenyl]methyl]-1H,2H,3H,4H,5H,6H,7H-pyrazolo[4,3-c]pyridin-5-yl)-2-(oxan-2-yl)-2,3-dihydropyridazin-3-one (55 mg, 65.36%) as a yellow solid.

4-Chloro-5-(2-methyl-3-oxo-1-[[2-(trifluoromethyl)phenyl]methyl]-1H,2H,3H,4H,5H,6H,7H-pyrazolo[4,3-c]pyridin-5-yl)-2,3-dihydropyridazin-3-one To a stirred solution of 4-chloro-5-(2-methyl-3-oxo-1-[[2-(trifluoromethyl)phenyl]methyl]-1H,2H,3H,4H,5H,6H,7H-pyrazolo[4,3-c]pyridin-5-yl)-2-(oxan-2-yl)-2,3-dihydropyridazin-3-one (55 mg, 0.10 mmol, 1 equiv.) in DCM (10 mL) was added TFA (2 mL, 26.93 mmol, 256.50 equiv.) dropwise at room temperature. The resulting mixture was stirred for 2 h at room temperature. The reaction was monitored by LCMS. The resulting mixture was concentrated under reduced pressure. The residue was basified to pH 8~9 with saturated NH4HCO3 (aq.). The resulting mixture was concentrated under reduced pressure. The crude product was purified by Prep-HPLC with the following conditions (Column: XBridge Prep C18 OBD Column 19×150 mm 5 um; Mobile Phase A: Water (10 MMOL/L NH4HCO3), Mobile Phase B: ACN; Flow rate: 20 mL/min; Gradient: 18% B to 40% B in 7 min; 254/220 nm; Rt: 6.27 min), Mobile Phase B: ACN; Flow rate: 60 mL/min; Gradient: 19% B to 29% B in 7 min; 254; 220 nm; Rt: 6.22 min) to afford 4-chloro-5-(2-methyl-3-oxo-1-[[2-(trifluoromethyl)phenyl]methyl]-1H,2H,3H,4H,5H,6H,7H-pyrazolo[4,3-c]pyridin-5-yl)-2,3-dihydropyridazin-3-one (26.6 mg, 57.61%) as a white solid.

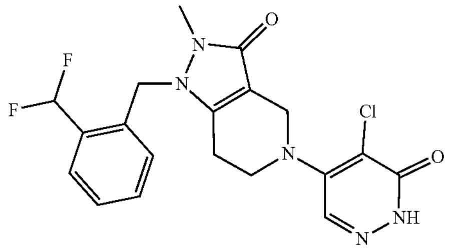

OT

Compound OT was prepared by the methods and scheme described for compound OS by using difluoro intermediate.

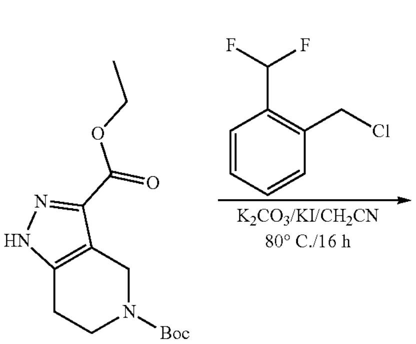

-continued

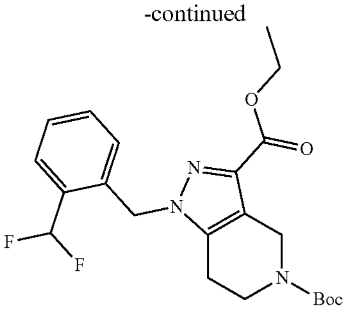

1

+

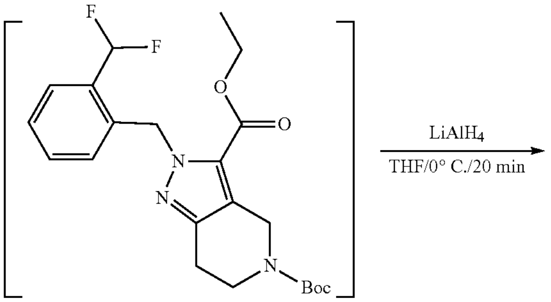

1a

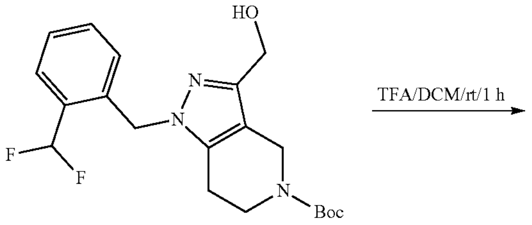

2

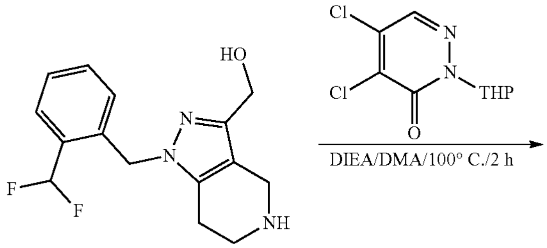

3

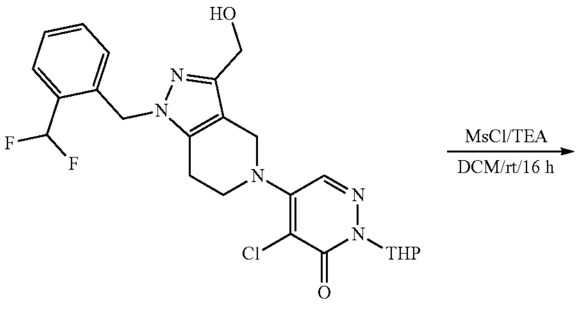

4

-continued

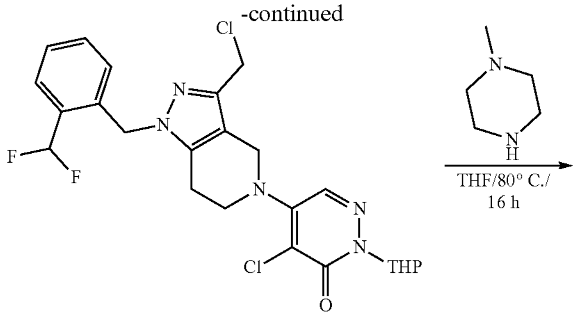

5

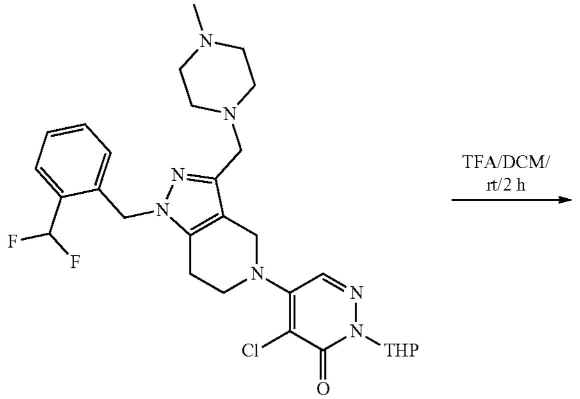

2

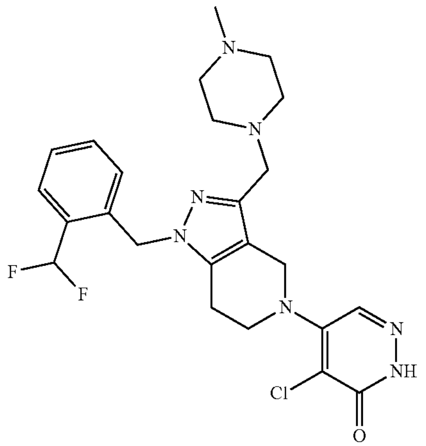

OU

Preparation of OU 5-tert-Butyl 3-ethyl 2-[[2-(difluoromethyl)phenyl]methyl]-2H,4H,5H,6H,7H-pyrazolo[4,3-c]pyridine-3,5-dicarboxylate To a stirred solution of 1-(chloromethyl)-2-(difluoromethyl)benzene (800 mg, 4.530 mmol, 1 equiv.) and 5-tert-butyl 3-ethyl 1H,4H,5H,6H,7H-pyrazolo[4,3-c]pyridine-3,5-dicarboxylate (1337.96 mg, 4.530 mmol, 1.00 equiv.) in MeCN (15 mL) was added KI (752.04 mg, 4.530 mmol, 1 equiv.) and K2CO3 (1252.22 mg, 9.061 mmol, 2 equiv.) at room temperature under nitrogen atmosphere. The mixture was stirred at 80 degrees celsius overnight. Desired product could be detected by LCMS. The resulting mixture was concentrated under reduced pressure. The residue was purified by silica gel column chromatography, eluted with PE/EtOAc (5:1 to 3:1) to afford 5-tert-butyl 3-ethyl 1-[[2-(difluoromethyl)phenyl]methyl]-1H,4H,5H,6H,7H-pyrazolo[4,3-c]pyridine-3,5-dicarboxylate (500 mg, 25.34%) as a yellow solid and 5-tert-butyl 3-ethyl 2-[[2-(difluoromethyl)phenyl]methyl]-2H,4H,5H,6H,7H-pyrazolo[4,3-c]pyridine-3,5-dicarboxylate (200 mg, 10.14%) as a yellow solid.

Tert-Butyl 1-[[2-(difluoromethyl)phenyl]methyl]-3-(hydroxymethyl)-1H,4H,5H,6H,7H-pyrazolo[4,3-c]pyridine-5-carboxylate To a stirred solution of 5-tert-butyl 3-ethyl 1-[[2-(difluoromethyl)phenyl]methyl]-1H,4H,5H,6H,7H-pyrazolo[4,3-c]pyridine-3,5-dicarboxylate (600 mg, 1.378 mmol, 1 equiv.) in THF (10 mL, 123.430 mmol, 89.58 equiv.) was added LiAlH4 (62.75 mg, 1.653 mmol, 1.2 equiv.) in portions at 0 degrees celsius under nitrogen atmosphere. The mixture was stirred at rt for 1 h. Desired product could be detected by LCMS. The reaction was quenched by the addition of Water (5 mL) at 0 degrees C. The mixture was concentrated and purified by silica gel column chromatography (PE:EA=2:1) to afford tert-butyl 1-[[2-(difluoromethyl)phenyl]methyl]-3-(hydroxymethyl)-1H,4H,5H,6H,7H-pyrazolo[4,3-c]pyridine-5-carboxylate (500 mg, 92.24%) as white solid.

(1-[[2-(Difluoromethyl)phenyl]methyl]-1H,4H,5H,6H,7H-pyrazolo[4,3-c]pyridin-3-yl)methanol To a stirred solution of tert-butyl 1-[[2-(difluoromethyl)phenyl]methyl]-3-(hydroxymethyl)-1H,4H,5H,6H,7H-pyrazolo[4,3-c]pyridine-5-carboxylate (500 mg, 1.271 mmol, 1 equiv.) in DCM (10 mL, 157.300 mmol, 123.78 equiv.) was added TFA (2 mL, 26.926 mmol, 21.19 equiv.) dropwise at 0 degrees celsius under nitrogen atmosphere. The mixture was stirred at rt for 2 h. Desired product could be detected by LCMS. The mixture was concentrated to afford (1-[[2-(difluoromethyl)phenyl]methyl]-1H,4H,5H,6H,7H-pyrazolo[4,3-c]pyridin-3-yl)methanol (370 mg, 99.26%) as yellow solid.

4-Chloro-5-(1-[[2-(difluoromethyl)phenyl]methyl]-3-(hydroxymethyl)-1H,4H,5H,6H,7H-pyrazolo[4,3-c]pyridin-5-yl)-2-(oxan-2-yl)-2,3-dihydropyridazin-3-one To a stirred solution of (1-[[2-(difluoromethyl)phenyl]methyl]-1H,4H,5H,6H,7H-pyrazolo[4,3-c]pyridin-3-yl)methanol (370 mg, 1.261 mmol, 1 equiv.) and 4,5-dichloro-2-(oxan-2-yl)-2,3-dihydropyridazin-3-one (471.31 mg, 1.892 mmol, 1.5 equiv.) in DMA (1 mL) was added DIEA (326.06 mg, 2.523 mmol, 2 equiv.) dropwise at room temperature under nitrogen atmosphere. The mixture was stirred at 100 degrees celsius overnight. Desired product could be detected by LCMS. The resulting mixture was concentrated under reduced pressure. The residue was purified by silica gel column chromatography, eluted with PE/EtOAc (6:1 to 3:1) to afford 4-chloro-5-(1-[[2-(difluoromethyl)phenyl]methyl]-3-(hydroxymethyl)-1H,4H,5H,6H,7H-pyrazolo[4,3-c]pyridin-5-yl)-2-(oxan-2-yl)-2,3-dihydropyridazin-3-one (420 mg, 65.81%) as a white solid.

4-Chloro-5-[3-(chloromethyl)-1-[[2-(difluoromethyl)phenyl]methyl]-1H,4H,5H,6H,7H-pyrazolo[4,3-c]pyridin-5-yl]-2-(oxan-2-yl)-2,3-dihydropyridazin-3-one To a stirred solution of 4-chloro-5-(1-[[2-(difluoromethyl)phenyl]methyl]-3-(hydroxymethyl)-1H,4H,5H,6H,7H-pyrazolo[4,3-c]pyridin-5-yl)-2-(oxan-2-yl)-2,3-dihydro-pyridazin-3-one (400 mg, 0.791 mmol, 1 equiv.) and TEA (160.00 mg, 1.581 mmol, 2 equiv.) in DCM (8 ML, 125.840 mmol, 159.17 equiv.) was added MsCl (108.68 mg, 0.949 mmol, 1.2 equiv.) dropwise at 0 degrees celsius under nitrogen atmosphere. The mixture was stirred at rt overnight. Desired product could be detected by LCMS. The resulting mixture was concentrated under reduced pressure. The residue was purified by silica gel column chromatography, eluted with PE/EtOAc (5:1) to afford 4-chloro-5-[3-(chloromethyl)-1-[[2-(difluoromethyl)phenyl]methyl]-1H,4H,5H,6H,7H-pyrazolo[4,3-c]pyridin-5-yl]-2-(oxan-2-yl)-2,3-dihydropyridazin-3-one (400 mg, 96.48%) as a yellow solid.

4-Chloro-5-(1-[[2-(difluoromethyl)phenyl]methyl]-3-[(4-methylpiperazin-1-yl)methyl]-1H,4H,5H,6H,7H-pyrazolo[4,3-c]pyridin-5-yl)-2-(oxan-2-yl)-2,3-dihydropyridazin-3-one To a stirred solution of 4-chloro-5-[3-(chloromethyl)-1-[[2-(difluoromethyl)phenyl]methyl]-1H,4H,5H,6H,7H-pyrazolo[4,3-c]pyridin-5-yl]-2-(oxan-2-yl)-2,3-dihydro-pyridazin-3-one (60 mg, 0.103 mmol, 1 equiv.) in MeCN (10 mL) was added 1-methylpiperazine (51.45 mg, 0.514 mmol, 5 equiv.) dropwise at room temperature under nitrogen atmosphere. The mixture was stirred at 80 degrees celsius overnight. Desired product could be detected by LCMS. The resulting mixture was concentrated under reduced pressure. The residue was purified by silica gel column chromatography, eluted with PE/EtOAc (5:1 to 1:1) to afford 4-chloro-5-(1-[[2-(difluoromethyl)phenyl]methyl]-3-[(4-methylpiperazin-1-yl)methyl]-1H,4H,5H,6H,7H-pyrazolo[4,3-c]pyridin-5-yl)-2-(oxan-2-yl)-2,3-dihydropyridazin-3-one (60 mg, 99.31%) as a white solid.

4-Chloro-5-(1-[[2-(difluoromethyl)phenyl]methyl]-3-[(4-methylpiperazin-1-yl)methyl]-1H,4H,5H,6H,7H-pyrazolo[4,3-c]pyridin-5-yl)-2,3-dihydro-pyridazin-3-one To a stirred solution of 4-chloro-5-(1-[[2-(difluoromethyl)phenyl]methyl]-3-[(4-methylpiperazin-1-yl)methyl]-1H,4H,5H,6H,7H-pyrazolo[4,3-c]pyridin-5-yl)-2-(oxan-2-yl)-2,3-dihydropyridazin-3-one (60 mg) in DCM (10 mL) were added TFA (2 mL) dropwise at 0 degrees celsius under nitrogen atmosphere. The mixture was stirred at rt for 2 h. Desired product could be detected by LCMS. The reaction was quenched by the addition of sat. NaHCO3 (aq.) (5 mL) at room temperature. The resulting mixture was concentrated under reduced pressure. The crude product (mg) was purified by Prep-HPLC with the following conditions (Column: XBridge Prep OBD C18 Column 30×150 mm 5 um; Mobile Phase A: Water (10 MMOL/L NH4HCO3), Mobile Phase B: ACN; Flow rate: 60 mL/min; Gradient: 20% B to 35% B in 8 min; 220 nm; Rt: 7.25 min) to afford 4-chloro-5-(1-[[2-(difluoromethyl)phenyl]methyl]-3-[(4-methylpiperazin-1-yl)methyl]-1H,4H,5H,6H,7H-pyrazolo[4,3-c]pyridin-5-yl)-2,3-dihydropyridazin-3-one (30 mg) as a white solid.

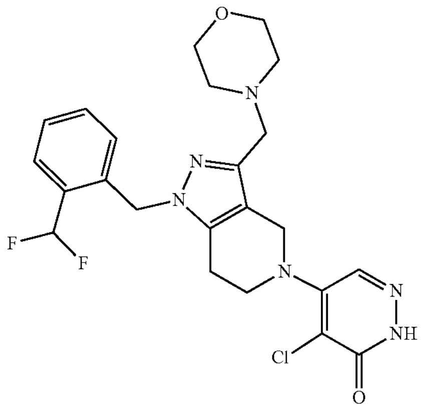

OV

Compound OV was prepared by the methods and scheme described for OU by using morpholine

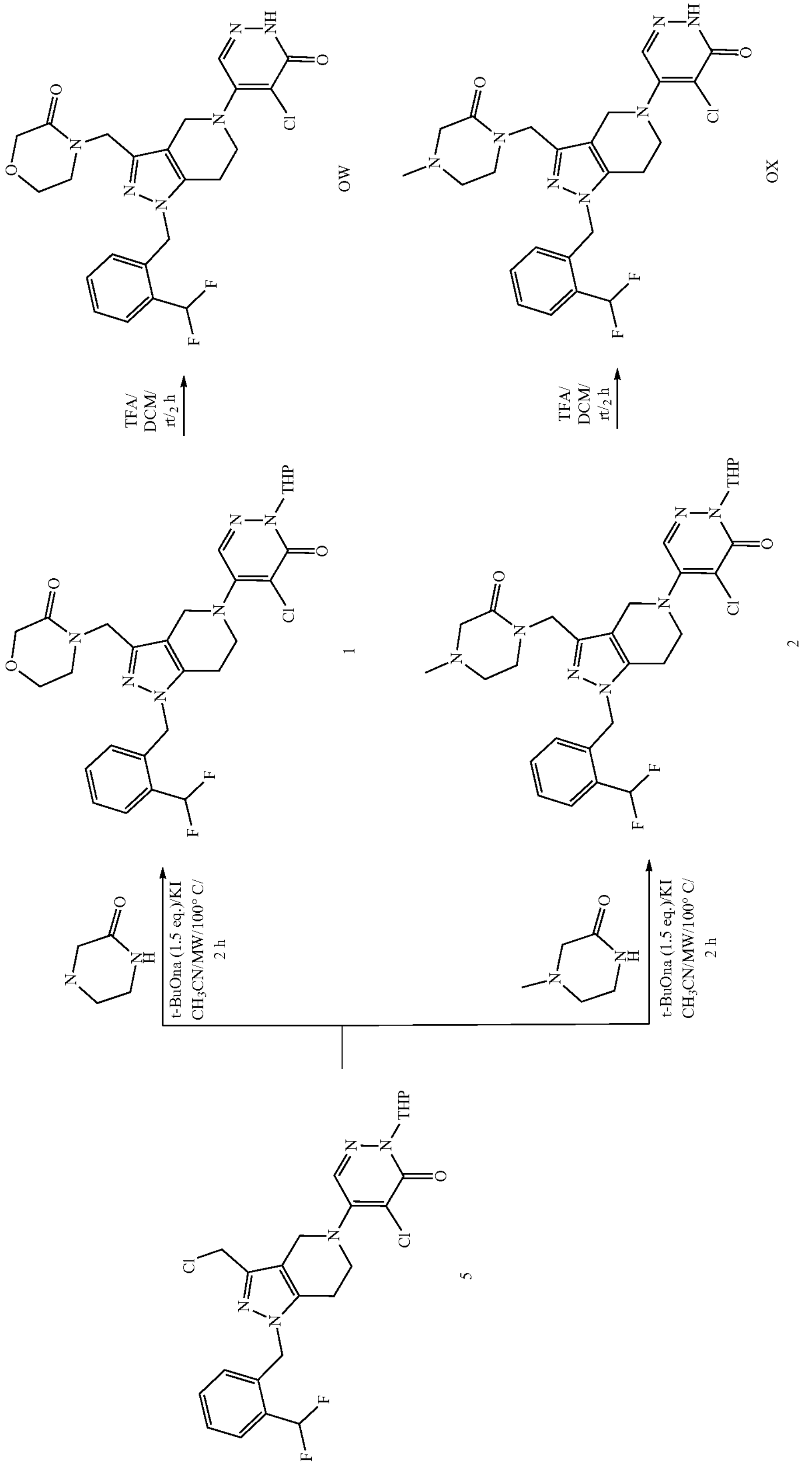
5
1
2
OW
OX

Preparation of OW and OX 4-([5-[5-Chloro-1-(oxan-2-yl)-6-oxo-1,6-dihydropyridazin-4-yl]-1-[[2-(difluoromethyl)phenyl]methyl]-1H,4H,5H,6H,7H-pyrazolo[4,3-c]pyridin-3-yl]methyl)morpholin-3-one To a stirred mixture of 4-chloro-5-[3-(chloromethyl)-1-[[2-(difluoromethyl)phenyl]methyl]-1H,4H,5H,6H,7H-pyrazolo[4,3-c]pyridin-5-yl]-2-(oxan-2-yl)-2,3-dihydropyridazin-3-one (130 mg, 0.248 mmol, 1 equiv.) and morpholin-3-one (75.19 mg, 0.744 mmol, 3.00 equiv.) in ACN (10 mL) were added KI (41.15 mg, 0.248 mmol, 1.00 equiv.) and t-BuONa (35.74 mg, 0.372 mmol, 1.50 equiv.) in portions at rt under nitrogen atmosphere. The final reaction mixture was irradiated with microwave radiation for 2 h at 100 degrees C. The reaction was monitored by LCMS. The mixture was allowed to cool down to rt. The resulting mixture was concentrated under reduced pressure. The resulting mixture was extracted with EtOAc (3×100 mL). The combined organic layers were washed with brine (2×50 mL), dried over anhydrous Na2SO4. After filtration, the filtrate was concentrated under reduced pressure. This resulted in 4-([5-[5-chloro-1-(oxan-2-yl)-6-oxo-1,6-dihydropyridazin-4-yl]-1-[[2-(difluoromethyl)phenyl]methyl]-1H,4H,5H,6H,7H-pyrazolo[4,3-c]pyridin-3-yl]methyl)morpholin-3-one (100 mg, 68.48%) as a yellow oil. The resulting mixture was used in the next step directly without further purification.

4-[[5-(5-Chloro-6-oxo-1,6-dihydropyridazin-4-yl)-1-[[2-(difluoromethyl)phenyl]methyl]-1H,4H,5H,6H,7H-pyrazolo[4,3-c]pyridin-3-yl]methyl]morpholin-3-one To a stirred solution of 4-([5-[5-chloro-1-(oxan-2-yl)-6-oxo-1,6-dihydropyridazin-4-yl]-1-[[2-(difluoromethyl)phenyl]methyl]-1H,4H,5H,6H,7H-pyrazolo[4,3-c]pyridin-3-yl]methyl)morpholin-3-one (100 mg, 0.170 mmol, 1 equiv.) in DCM (10 mL) was added TFA (1 mL, 13.463 mmol, 79.30 equiv.) dropwise at rt. The reaction mixture was stirred for 2 h at rt. The reaction was monitored by LCMS. The resulting mixture was concentrated under reduced pressure. The residue was basified to pH=8 with saturated NH4HCO3 (aq.). The resulting mixture was extracted with EtOAc (3×100 mL). The combined organic layers were washed with brine (1×100 mL), dried over anhydrous Na2SO4. After filtration, the filtrate was concentrated under reduced pressure. The residue was purified by Prep-HPLC with the following conditions (Column: XBridge Prep OBD C18 Column 30×150 mm 5 um; Mobile Phase A: Water (10 MMOL/L NH4HCO3), Mobile Phase B: ACN; Flow rate: 60 mL/min; Gradient: 20% B to 38% B in 7 min; 220 nm; Rt: 6.48 min) to afford 4-[[5-(5-chloro-6-oxo-1,6-dihydropyridazin-4-yl)-1-[[2-(difluoromethyl)phenyl]methyl]-1H,4H,5H,6H,7H-pyrazolo[4,3-c]pyridin-3-yl]methyl]morpholin-3-one (28.0 mg) as a white solid.

4-Chloro-5-(1-[[2-(difluoromethyl)phenyl]methyl]-3-[(4-methyl-2-oxopiperazin-1-yl)methyl]-1H,4H,5H,6H,7H-pyrazolo[4,3-c]pyridin-5-yl)-2-(oxan-2-yl)-2,3-dihydropyridazin-3-one To a stirred mixture of 4-chloro-5-[3-(chloromethyl)-1-[[2-(difluoromethyl)phenyl]methyl]-1H,4H,5H,6H,7H-pyrazolo[4,3-c]pyridin-5-yl]-2-(oxan-2-yl)-2,3-dihydropyridazin-3-one (150 mg, 0.286 mmol, 1 equiv.) and 4-methylpiperazin-2-one (97.95 mg, 0.858 mmol, 3.00 equiv.) in ACN (10 mL) were added KI (47.48 mg, 0.286 mmol, 1.00 equiv.) and t-BuONa (41.24 mg, 0.429 mmol, 1.50 equiv.) in portions at rt under nitrogen atmosphere. The final reaction mixture was irradiated with microwave radiation for 2 h at 100 degrees C. The reaction was monitored by LCMS. The mixture was allowed to cool down to rt. The resulting mixture was concentrated under reduced pressure. The resulting mixture was extracted with EtOAc (3×100 mL). The combined organic layers were washed with brine (2×50 mL), dried over anhydrous Na2SO4. After filtration, the filtrate was concentrated under reduced pressure. This resulted in 4-chloro-5-(1-[[2-(difluoromethyl)phenyl]methyl]-3-[(4-methyl-2-oxopiperazin-1-yl)methyl]-1H,4H,5H,6H,7H-pyrazolo[4,3-c]pyridin-5-yl)-2-(oxan-2-yl)-2,3-dihydropyridazin-3-one (110 mg, 63.87%) as a yellow oil. The resulting mixture was used in the next step directly without further purification.

4-Chloro-5-(1-[[2-(difluoromethyl)phenyl]methyl]-3-[(4-methyl-2-oxopiperazin-1-yl)methyl]-1H,4H,5H,6H,7H-pyrazolo[4,3-c]pyridin-5-yl)-2,3-dihydropyridazin-3-one To a stirred solution of 4-chloro-5-(1-[[2-(difluoromethyl)phenyl]methyl]-3-[(4-methyl-2-oxopiperazin-1-yl)methyl]-1H,4H,5H,6H,7H-pyrazolo[4,3-c]pyridin-5-yl)-2-(oxan-2-yl)-2,3-dihydropyridazin-3-one (110 mg, 0.183 mmol, 1 equiv.) in DCM (10 mL) was added TFA (1 mL, 13.463 mmol, 73.69 equiv.) dropwise at rt. The reaction mixture was stirred for 2 h at rt. The reaction was monitored by LCMS. The resulting mixture was concentrated under reduced pressure. The residue was basified to pH=8 with saturated NH4HCO3 (aq.). The resulting mixture was extracted with EtOAc (3×100 mL). The combined organic layers were washed with brine (1×100 mL), dried over anhydrous Na2SO4. After filtration, the filtrate was concentrated under reduced pressure. The residue was purified by Prep-HPLC with the following conditions (Column: XBridge Prep OBD C18 Column 30×150 mm 5 um; Mobile Phase A: Water (10 MMOL/L NH4HCO3), Mobile Phase B: ACN; Flow rate: 60 mL/min; Gradient: 13% B to 27% B in 16 min; 220 nm; Rt: 15.65 min) to afford 4-chloro-5-(1-[[2-(difluoromethyl)phenyl]methyl]-3-[(4-methyl-2-oxopiperazin-1-yl)methyl]-1H,4H,5H,6H,7H-pyrazolo[4,3-c]pyridin-5-yl)-2,3-dihydropyridazin-3-one (23.9 mg) as a white solid.

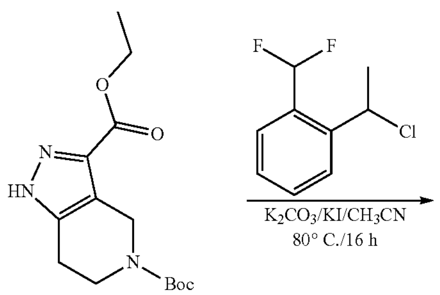

-continued
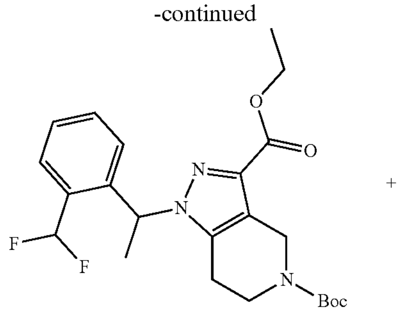
1
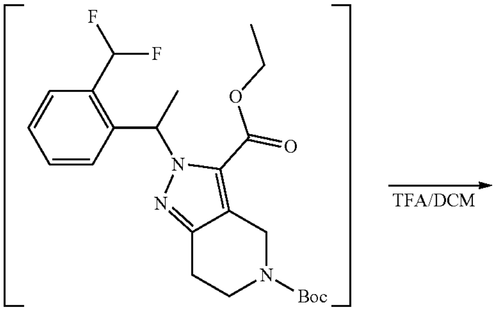
1a
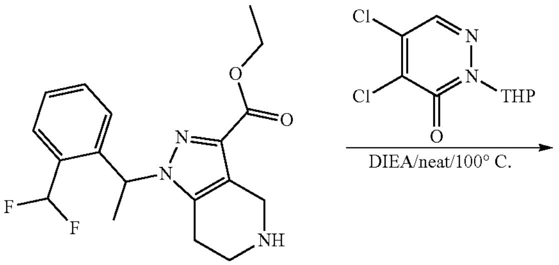
2
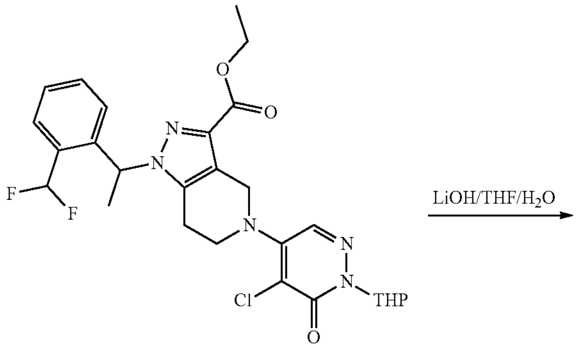
3
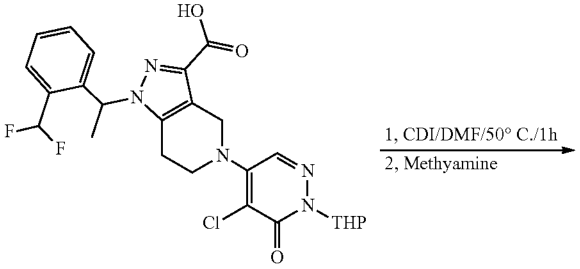
4
-continued
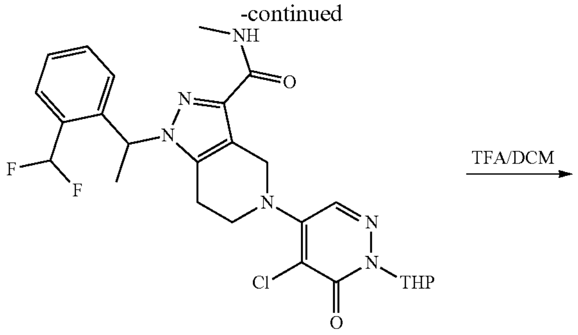
5
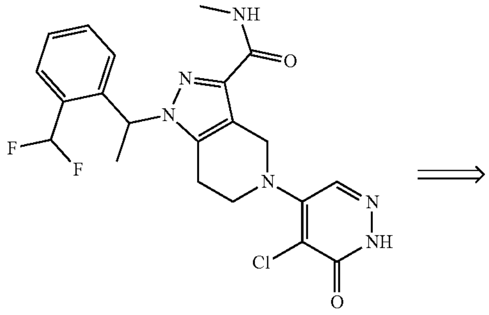
6
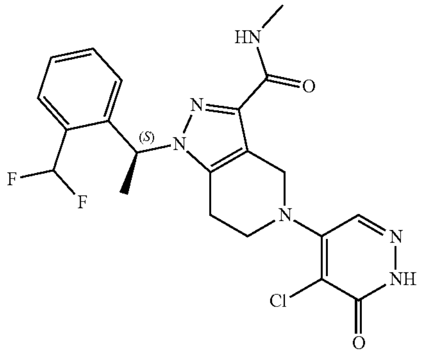
OY
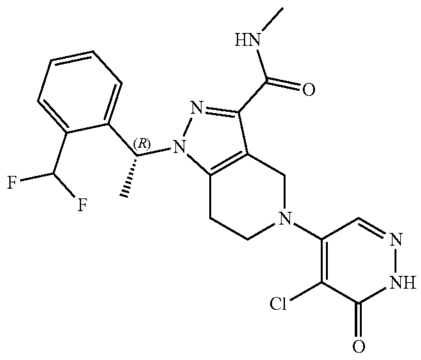
OZ
Preparation of OY and OZ
5-tert-Butyl 3-ethyl 1-[1-[2-(difluoromethyl)phenyl]ethyl]-1H,4H,5H,6H,7H-pyrazolo[4,3-c]pyridine-3,5-dicarboxylate
To a stirred solution of 5-tert-butyl 3-ethyl 1H,4H,5H,6H,7H-pyrazolo[4,3-c]pyridine-3,5-dicarboxylate (1 g, 3.39 mmol, 1 equiv.) and 1-(1-chloroethyl)-2-(difluoromethyl)

benzene (1.0 g, 5.08 mmol, 1.5 equiv.) in MeCN (40 mL) were added K2CO3 (0.9 g, 6.77 mmol, 2 equiv.) and KI (1.1 g, 6.77 mmol, 2 equiv.). The resulting mixture was stirred for overnight at 80 degrees C. The resulting mixture was concentrated under reduced pressure. The residue was purified by silica gel column chromatography, eluted with PE/EtOAc (7:1) to afford 5-tert-butyl 3-ethyl 1-[1-[2-(difluoromethyl)phenyl]ethyl]-1H,4H,5H,6H,7H-pyrazolo[4,3-c]pyridine-3,5-dicarboxylate (800 mg, 52.56%) as a light yellow solid.

Ethyl 1-[1-[2-(difluoromethyl)phenyl]ethyl]-1H,4H,5H,6H,7H-pyrazolo[4,3-c]pyridine-3-carboxylate To a stirred solution of 5-tert-butyl 3-ethyl 1-[1-[2-(difluoromethyl)phenyl]ethyl]-1H,4H,5H,6H,7H-pyrazolo[4,3-c]pyridine-3,5-dicarboxylate (800 mg, 1.78 mmol, 1 equiv.) in DCM (6 mL) was added TFA (2 mL). The resulting mixture was stirred for 2 h at room temperature. The resulting mixture was concentrated under reduced pressure. The residue was purified by reverse flash chromatography with the following conditions: column, C18 silica gel; mobile phase, MeCN in water, 20% to 50% gradient in 30 min; detector, UV 254 nm. This resulted in ethyl 1-[1-[2-(difluoromethyl)phenyl]ethyl]-1H,4H,5H,6H,7H-pyrazolo[4,3-c]pyridine-3-carboxylate (580 mg, 93.28%) as a light yellow solid.

5-[5-Chloro-1-(oxan-2-yl)-oxo-1,6-dihydropyridazin-4-yl]-1-[1-[2-(difluoromethyl)phenyl]ethyl]-1H,4H,5H,6H,7H-pyrazolo[4,3-c]pyridine-3-carboxylate To a stirred mixture of ethyl 1-[1-[2-(difluoromethyl)phenyl]ethyl]-1H,4H,5H,6H,7H-pyrazolo[4,3-c]pyridine-3-carboxylate (580 mg, 1.660 mmol, 1 equiv.),4,5-dichloro-2-(oxan-2-yl)-2,3-dihydropyridazin-3-one (413.51 mg, 1.660 mmol, 1 equiv.) and DIEA (429.11 mg, 3.320 mmol, 2 equiv.). The resulting mixture was stirred for overnight at 90 degrees C. The residue was purified by silica gel column chromatography, eluted with PE/EtOAc (7:1) to afford ethyl 5-[5-chloro-1-(oxan-2-yl)-6-oxo-1,6-dihydropyridazin-4-yl]-1-[1-[2-(difluoromethyl)phenyl]ethyl]-1H,4H,5H,6H,7H-pyrazolo[4,3-c]pyridine-3-carboxylate (850 mg, 91.11%) as a light yellow solid.

5-[5-Chloro-1-(oxan-2-yl)-oxo-1,6-dihydropyridazin-4-yl]-1-[1-[2-(difluoromethyl)phenyl]ethyl]-1H,4H,5H,6H,7H-pyrazolo[4,3-c]pyridine-3-carboxylic acid To a stirred solution of ethyl 5-[5-chloro-1-(oxan-2-yl)-6-oxo-1,6-dihydropyridazin-4-yl]-1-[1-[2-(difluoromethyl)phenyl]ethyl]-1H,4H,5H,6H,7H-pyrazolo[4,3-c]pyridine-3-carboxylate (850 mg, 1.512 mmol, 1 equiv.) in THF (10 mL) and H2O (10 mL) was added lithiumol (362.23 mg, 15.124 mmol, 10.00 equiv.). The resulting mixture was stirred for overnight at 40 degrees C. The resulting mixture was concentrated under reduced pressure. The residue was purified by reverse flash chromatography with the following conditions: column, C18 silica gel; mobile phase, MeCN in water, 25% to 55% gradient in 10 min; detector, UV 254 nm. This resulted in 5-[5-chloro-1-(oxan-2-yl)-6-oxo-1,6-dihydropyridazin-4-yl]-1-[1-[2-(difluoromethyl)phenyl]ethyl]-1H,4H,5H,6H,7H-pyrazolo[4,3-c]pyridine-3-carboxylic acid (700 mg, 86.68%) as a off-white solid.

5-[5-Chloro-1-(oxan-2-yl)6-oxo-1,6-dihydropyridazin-4-yl]-1-[1-[2-(difluoromethyl)phenyl]ethyl]-1H,4H,5H,6H,7H-pyrazolo[4,3-c]pyridine-3-carboxylate To a stirred solution of 5-[5-chloro-1-(oxan-2-yl)-6-oxo-1,6-dihydropyridazin-4-yl]-1-[1-[2-(difluoromethyl)phenyl]ethyl]-1H,4H,5H,6H,7H-pyrazolo[4,3-c]pyridine-3-carboxylic acid (250 mg, 0.468 mmol, 1 equiv.) in DMF (5 mL) was added CDI (113.88 mg, 0.702 mmol, 1.50 equiv.). The resulting mixture was stirred for 2 h at 40 degrees C. To the above mixture was added methanamine (63.21 mg, 0.936 mmol, 2 equiv.) in portions at 40 degrees C. The resulting mixture was stirred for additional overnight at 40 degrees C. The resulting mixture was extracted with EtOAc (2×50 mL). The combined organic layers were washed with brine (1×50 mL), dried over anhydrous Na2SO4. After filtration, the filtrate was concentrated under reduced pressure. The residue was purified by silica gel column chromatography, eluted with PE/EtOAc (6:1) to afford methylamino 5-[5-chloro-1-(oxan-2-yl)-6-oxo-1,6-dihydropyridazin-4-yl]-1-[1-[2-(difluoromethyl)phenyl]ethyl]-1H,4H,5H,6H,7H-pyrazolo[4,3-c]pyridine-3-carboxylate (210 mg, 79.67%) as a off-white solid.

5-(5-chloro-6-oxo-1,6-dihydropyridazin-4-yl)-1-[(1R)-1-[2-(difluoromethyl)phenyl]ethyl]-N-methyl-1H,4H,5H,6H,7H-pyrazolo[4,3-c]pyridine-3-carboxamide and 5-(5-chloro-6-oxo-1,6-dihydropyridazin-4-yl)-1-[(1S)-1-[2-(difluoromethyl)phenyl]ethyl]-N-methyl-1H,4H,5H,6H,7H-pyrazolo[4,3-c]pyridine-3-carboxamide To a stirred solution of 5-[5-chloro-1-(oxan-2-yl)-6-oxo-1,6-dihydropyridazin-4-yl]-1-[1-[2-(difluoromethyl)phenyl]ethyl]-N-methyl-1H,4H,5H,6H,7H-pyrazolo[4,3-c]pyridine-3-carboxamide (210 mg, 0.384 mmol, 1 equiv.) in DCM (3 mL) was added TFA (1 mL). The resulting mixture was stirred for 2 h at room temperature. The resulting mixture was concentrated under reduced pressure. The crude product was purified by Prep-HPLC with the following conditions (Column: XBridge Prep OBD C18 Column 30×150 mm 5 um; Mobile Phase A: Water (10 MMOL/L NH4HCO3), Mobile Phase B: ACN; Flow rate: 60 mL/min; Gradient: 22% B to 42% B in 10 min; 220 nm; Rt: 9.60 min) to afford 5-(5-chloro-6-oxo-1,6-dihydropyridazin-4-yl)-1-[(1R)-1-[2-(difluoromethyl)phenyl]ethyl]-N-methyl-1H,4H,5H,6H,7H-pyrazolo[4,3-c]pyridine-3-carboxamide (42.5 mg, 23.92%) and 5-(5-chloro-6-oxo-1,6-dihydropyridazin-4-yl)-1-[(1S)-1-[2-(difluoromethyl)phenyl]ethyl]-N-methyl-1H,4H,5H,6H,7H-pyrazolo[4,3-c]pyridine-3-carboxamide (38.8 mg, 21.83%) as a white solid.

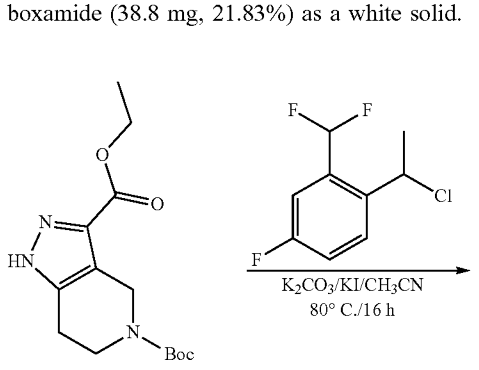

-continued
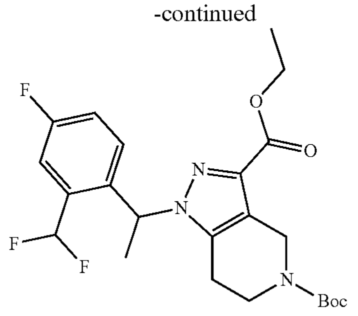
+
1
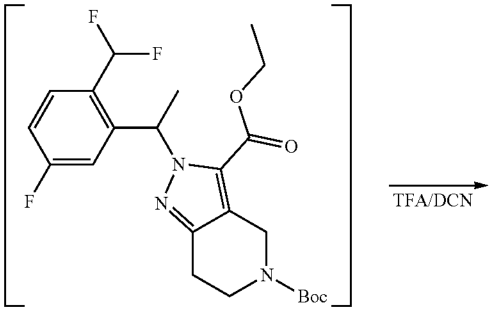
1a
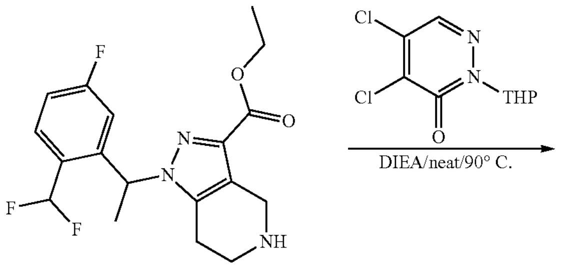
2
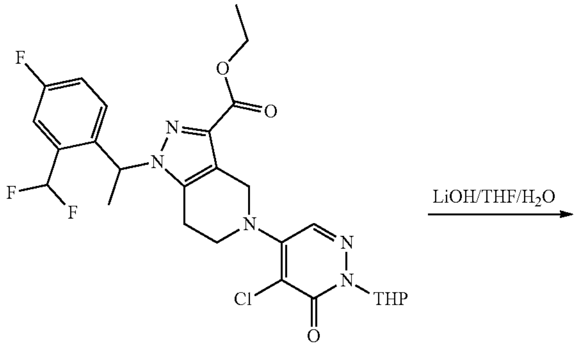
3
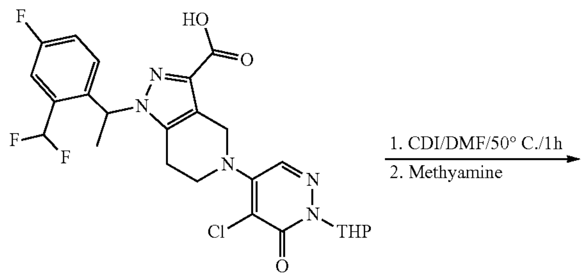
4
-continued
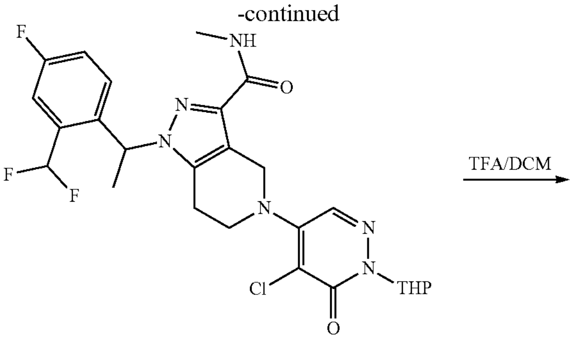
5
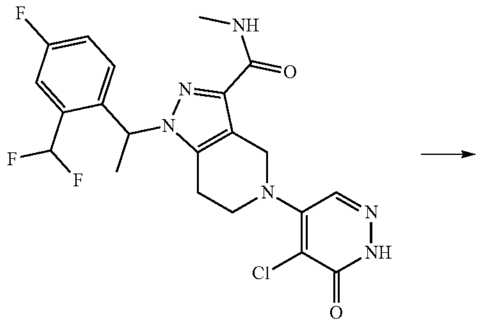
6
PA
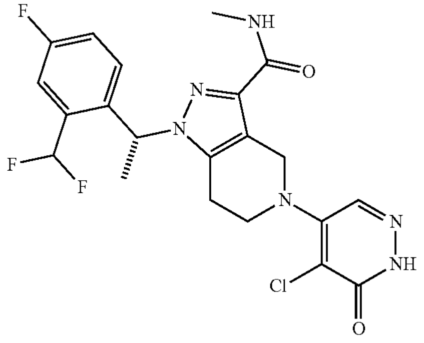
PB
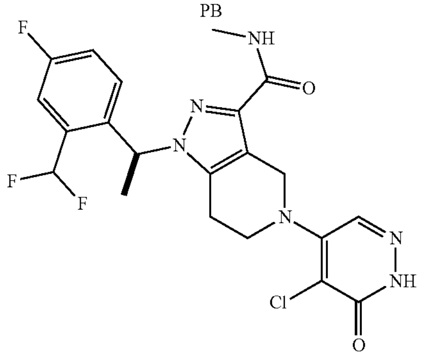
PC
Preparation of PA, PB, and PC
5-tert-Butyl 3-ethyl 1-[1-[2-(difluoromethyl)-4-fluorophenyl]ethyl]-1H,4H,5H,6H,7H-pyrazolo[4,3-c]pyridine-3,5-dicarboxylate
To a stirred solution of 5-tert-butyl 3-ethyl 1H,4H,5H,6H,7H-pyrazolo[4,3-c]pyridine-3,5-dicarboxylate (1 g, 3.39 mmol, 1 equiv.) and 1-(1-chloroethyl)-2-(difluoromethyl)-

4-fluorobenzene (1.1 g, 5.08 mmol, 1.5 equiv.) in ACN (20 mL) were added K2CO3 (0.9 g, 6.77 mmol, 2 equiv.) and KI (1.1 g, 6.77 mmol, 2 equiv.) at room temperature. The solution was stirred at 80 degrees celsius for 16 h. The mixture was concentrated under reduced pressure. The residue was purified by Prep-TLC (PE/EtOAc 5:1) to afford 5-tert-butyl 3-ethyl 1-[1-[2-(difluoromethyl)-4-fluorophenyl]ethyl]-1H,4H,5H,6H,7H-pyrazolo[4,3-c]pyridine-3,5-dicarboxylate (700 mg, 44.22%) as colorless oil.

Ethyl 1-[1-[2-(difluoromethyl)-5-fluorophenyl]ethyl]-1H,4H,5H,6H,7H-pyrazolo[4,3-c]pyridine-3-carboxylate To a stirred solution of 5-tert-butyl 3-ethyl 1-[1-[2-(difluoromethyl)-4-fluorophenyl]ethyl]-1H,4H,5H,6H,7H-pyrazolo[4,3-c]pyridine-3,5-dicarboxylate (700 mg, 1.50 mmol, 1 equiv.) in DCM (12 mL, 188.76 mmol, 126.06 equiv.) was added TFA (2 mL, 26.93 mmol, 17.98 equiv.) at room temperature. The solution was stirred at rt for 4 h. The mixture was concentrated under reduced pressure. The crude product (550 mg) was purified by Prep-HPLC with the following conditions (Column: C18 Column 330 g; Mobile Phase A: Water (10 MMOL/L NH4HCO3), Mobile Phase B: ACN; Flow rate:80 mL/min; Gradient: 40% B to 80% B in 40 min; 254/220 nm) to afford ethyl 1-[1-[2-(difluoromethyl)-5-fluorophenyl]ethyl]-1H,4H,5H,6H,7H-pyrazolo[4,3-c]pyridine-3-carboxylate (450 mg, 81.80%) as colorless oil.

Ethyl 5-[5-chloro-1-(oxan-2-yl)-6-oxo-1,6-dihydropyridazin-4-yl]-1-[1-[2-(difluoromethyl)-4-fluorophenyl]ethyl]-1H,4H,5H,6H,7H-pyrazolo[4,3-c]pyridine-3-carboxylate Into a 50 mL round-bottom flask were added ethyl 1-[1-[2-(difluoromethyl)-5-fluorophenyl]ethyl]-1H,4H,5H,6H,7H-pyrazolo[4,3-c]pyridine-3-carboxylate (450 mg, 1.22 mmol, 1 equiv.) and 4,5-dichloro-2-(oxan-2-yl)-2,3-dihydropyridazin-3-one (305.1 mg, 1.22 mmol, 1 equiv.) at room temperature. To the mixture was added DIEA (316.6 mg, 2.45 mmol, 2 equiv.) at rt. The mixture was stirred at 90 degrees celsius for 16 h. The mixture was concentrated under reduced pressure. The residue was purified by Prep-TLC (PE/EtOAc 1:1) to afford ethyl 5-[5-chloro-1-(oxan-2-yl)-6-oxo-1,6-dihydropyridazin-4-yl]-1-[1-[2-(difluoromethyl)-4-fluorophenyl]ethyl]-1H,4H,5H,6H,7H-pyrazolo[4,3-c]pyridine-3-carboxylate (650 mg, 91.49%) as colorless oil.

5-[5-Chloro-1-(oxan-2-yl)-6-oxo-1,6-dihydropyridazin-4-yl]-1-[1-[2-(difluoromethyl)-4-fluorophenyl]ethyl]-1H,4H,5H,6H,7H-pyrazolo[4,3-c]pyridine-3-carboxylic acid To a stirred solution of ethyl 5-[5-chloro-1-(oxan-2-yl)-6-oxo-1,6-dihydropyridazin-4-yl]-1-[1-[2-(difluoromethyl)-4-fluorophenyl]ethyl]-1H,4H,5H,6H,7H-pyrazolo[4,3-c]pyridine-3-carboxylate (670 mg, 1.16 mmol, 1 equiv.) in THF (8 mL) and H2O (8 mL) was added LiOH (276.6 mg, 11.55 mmol, 10 equiv.) at room temperature. The solution was stirred at 40 degrees celsius for 16 h. The mixture was concentrated under reduced pressure. The crude product (650 mg) was purified by Prep-HPLC with the following conditions (Column: C18 Column 330 g; Mobile Phase A: Water (10 MMOL/L NH4HCO3), Mobile Phase B: ACN; Flow rate: 50 mL/min; Gradient: 25% B to 55% B in 40 min; 254/220 nm) to afford 5-[5-chloro-1-(oxan-2-yl)-6-oxo-1,6-dihydropyridazin-4-yl]-1-[1-[2-(difluoromethyl)-4-fluorophenyl]ethyl]-1H,4H,5H,6H,7H-pyrazolo[4,3-c]pyridine-3-carboxylic acid (500 mg, 78.42%) as colorless oil.

5-[5-Chloro-1-(oxan-2-yl)-6-oxo-1,6-dihydropyridazin-4-yl]-1-[1-[2-(difluoromethyl)-4-fluorophenyl]ethyl]-1H,4H,5H,6H,7H-pyrazolo[4,3-c]pyridine-3-carboxamide To a stirred solution of 5-[5-chloro-1-(oxan-2-yl)-6-oxo-1,6-dihydropyridazin-4-yl]-1-[1-[2-(difluoromethyl)-4-fluorophenyl]ethyl]-1H,4H,5H,6H,7H-pyrazolo[4,3-c]pyridine-3-carboxylic acid (300 mg, 0.54 mmol, 1 equiv.) in DMF (10 mL) were added CDI (132.2 mg, 0.82 mmol, 1.5 equiv.) and NH4OAc (83.8 mg, 1.09 mmol, 2 equiv.) at room temperature. The solution was stirred at 45 degrees celsius for 4 h. The mixture was concentrated under reduced pressure. The crude product (300 mg) was purified by Prep-HPLC with the following conditions (Column: C18 Column 330 g; Mobile Phase A: Water (10 MMOL/L NH4HCO3), Mobile Phase B: ACN; Flow rate: 80 mL/min; Gradient: 25% B to 55% B in 40 min; 254/220 nm) to afford 5-[5-chloro-1-(oxan-2-yl)-6-oxo-1,6-dihydropyridazin-4-yl]-1-[1-[2-(difluoromethyl)-4-fluorophenyl]ethyl]-1H,4H,5H,6H,7H-pyrazolo[4,3-c]pyridine-3-carboxamide (200 mg, 66.79%) as colorless oil.

5-(5-Chloro-6-oxo-1,6-dihydropyridazin-4-yl)-1-[1-[2-(difluoromethyl)-4-fluorophenyl]ethyl]-1H,4H,5H,6H,7H-pyrazolo[4,3-c]pyridine-3-carboxamide To a stirred solution of 5-[5-chloro-1-(oxan-2-yl)-6-oxo-1,6-dihydropyridazin-4-yl]-1-[1-[2-(difluoromethyl)-4-fluorophenyl]ethyl]-1H,4H,5H,6H,7H-pyrazolo[4,3-c]pyridine-3-carboxamide (200 mg, 0.363 mmol, 1 equiv.) in DCM (10 mL, 157.300 mmol, 433.34 equiv.) was added TFA (2 mL, 26.926 mmol, 74.18 equiv.) at room temperature. The solution was stirred at rt for 4 h. The crude product (150 mg) was purified by Prep-HPLC with the following conditions (Column: XBridge Prep OBD C18 Column 30×150 mm 5 um; Mobile Phase A: Water (10 MMOL/L NH4HCO3), Mobile Phase B: ACN; Flow rate: 60 mL/min; Gradient: 25% B to 45% B in 8 min; 220 nm; Rt: 7.25 min) to afford 5-(5-chloro-6-oxo-1,6-dihydropyridazin-4-yl)-1-[1-[2-(difluoromethyl)-4-fluorophenyl]ethyl]-1H,4H,5H,6H,7H-pyrazolo[4,3-c]pyridine-3-carboxamide (110.4 mg, 65.15%) as a white solid.

5-(5-Chloro-6-oxo-1,6-dihydropyridazin-4-yl)-1-[(1R)-1-[2-(difluoromethyl)-4-fluorophenyl]ethyl]-1H,4H,5H,6H,7H-pyrazolo[4,3-c]pyridine-3-carboxamide and 5-(5-chloro-6-oxo-1,6-dihydropyridazin-4-yl)-1-[(1S)-1-[2-(difluoromethyl)-4-fluorophenyl]ethyl]-1H,4H,5H,6H,7H-pyrazolo[4,3-c]pyridine-3-carboxamide The above mixture product (100 mg) was purified by PREP CHIRAL HPLC with the following conditions (Column: CHIRALPAK IG, 20*250 mm, 5 um; Mobile Phase A:MTBE (10 mM NH3-MEOH)—HPLC, Mobile Phase B: EtOH—HPLC; Flow rate: 16 mL/min; Gradient: 50 B to 50 B in 19 min; 254/220 nm; RT1:11.653; RT2:15.005) to afford 5-(5-chloro-6-oxo-1,6-dihydropyridazin-4-yl)-1-[(1R)-1-[2-(difluoromethyl)-4-fluorophenyl]ethyl]-1H,4H,5H,6H,7H-pyrazolo[4,3-c]pyridine-3-carboxamide (23.5 mg) (Compound PB) as a white solid and afford 5-(5-chloro- 6-oxo-1,6-dihydropyridazin-4-yl)-1-[(1S)-1-[2-(difluoromethyl)-4-fluorophenyl]ethyl]-1H,4H,5H,6H,7H-pyrazolo[4,3-c]pyridine-3-carboxamide (18.2 mg) (Compound PC) as a white solid.
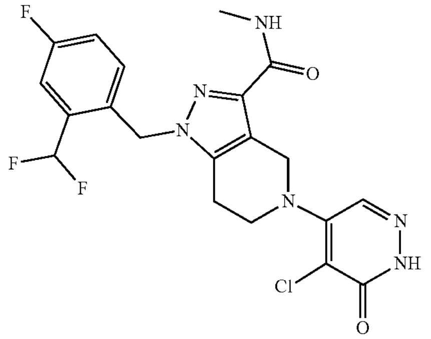
PD
Compound PD was prepared by the methods and scheme described for compound PA by using 1-(chloromethyl)-2-(difluoromethyl)-4-fluorobenzene
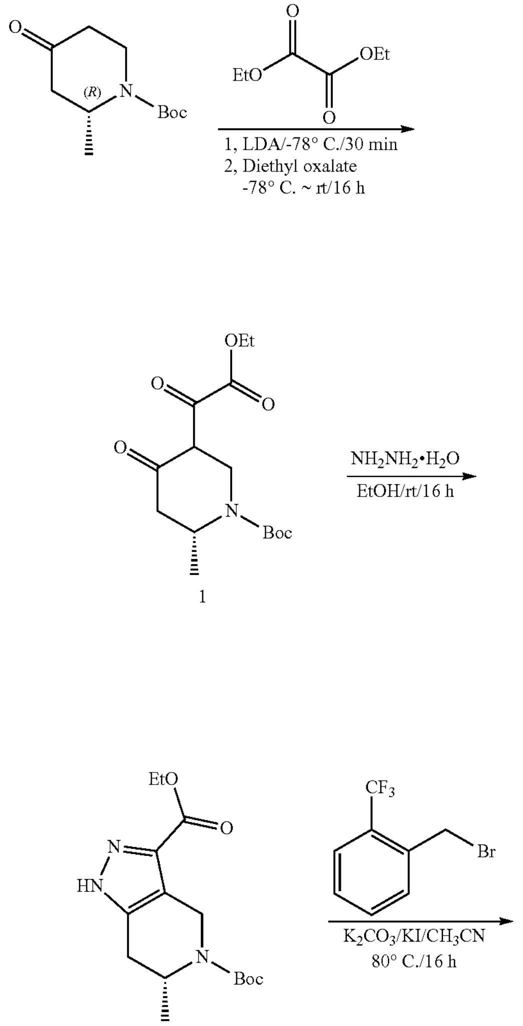
1
2
-continued
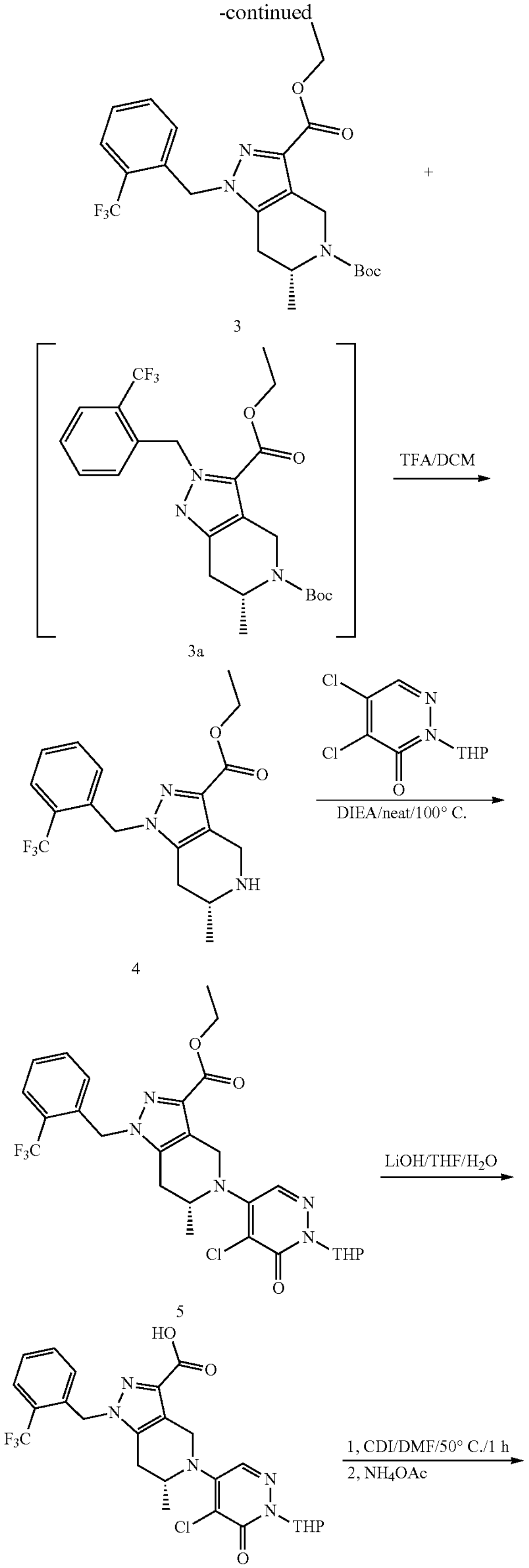
3
3a
4
5
6

-continued

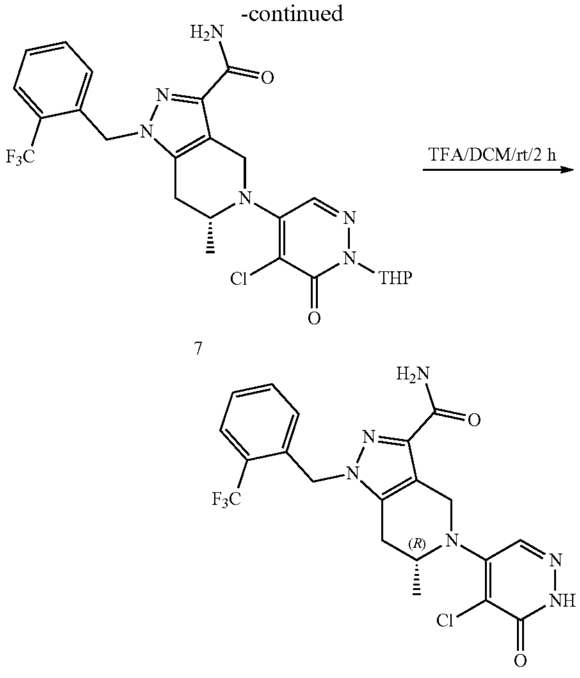

7

PE

Preparation of PE

Tert-Butyl (2R)-5-(2-ethoxy-2-oxoacetyl)-2-methyl-4-oxopiperidine-1-carboxylate

To a stirred solution of tert-butyl (2R)-2-methyl-4-oxopiperidine-1-carboxylate (2 g, 9.38 mmol, 1 equiv.) in THF (30 mL) was added LDA (4.9 mL, 45.96 mmol, 1.05 equiv.) dropwise at −65 degrees celsius under nitrogen atmosphere. The resulting mixture was stirred for 30 min at −65 degrees celsius under nitrogen atmosphere. To the above mixture was added diethyl oxalate (1.4 g, 9.85 mmol, 1.05 equiv.) dropwise at −65 degrees C. The resulting mixture was stirred for additional 16 h at room temperature. The reaction was monitored by LCMS. The reaction was quenched with sat. NH4Cl (aq.) at 0 degrees C. The resulting mixture was diluted with water (300 mL). The resulting mixture was extracted with EtOAc (2×300 ML). The combined organic layers were washed with brine (300 mL), dried over anhydrous MgSO4. After filtration, the filtrate was concentrated under reduced pressure to afford tert-butyl (2R)-5-(2-ethoxy-2-oxoacetyl)-2-methyl-4-oxopiperidine-1-carboxylate (2.66 g, 90.52%) as a yellow oil.

5-tert-Butyl 3-ethyl (6R)-6-methyl-1H,4H,5H,6H,7H-pyrazolo[4,3-c]pyridine-3,5-dicarboxylate To a stirred solution of tert-butyl (2R)-5-(2-ethoxy-2-oxoacetyl)-2-methyl-4-oxopiperidine-1-carboxylate (2.66 g, 8.49 mmol, 1 equiv.) in EtOH (30 mL) was added NH2NH2·H2O (637.4 mg, 10.19 mmol, 1.2 equiv, 80%) dropwise at 0 degrees C. The resulting mixture was stirred for 16 h at room temperature. The reaction was monitored by LCMS. The resulting mixture was concentrated under reduced pressure. The resulting mixture was diluted with water (300 mL). The resulting mixture was extracted with EtOAc (2×300 mL). The combined organic layers were washed with brine (300 mL), dried over anhydrous MgSO4. After filtration, the filtrate was concentrated under reduced pressure. The residue was purified by silica gel column chromatography, eluted with CH2Cl2/MeOH (100:1) to afford 5-tert-butyl 3-ethyl (6R)-6-methyl-1H,4H,5H,6H,7H-pyrazolo[4,3-c]pyridine-3,5-dicarboxylate (440 mg, 16.75%) as a yellow oil.

5-tert-Butyl 3-ethyl (6R)-6-methyl-1-[[2-(trifluoromethyl)phenyl]methyl]-1H,4H,5H,6H,7H-pyrazolo[4,3-c]pyridine-3,5-dicarboxylate To a solution of 5-tert-butyl 3-ethyl (6R)-6-methyl-1H,4H,5H,6H,7H-pyrazolo[4,3-c]pyridine-3,5-dicarboxylate (440 mg, 1.42 mmol, 1 equiv.), KI (472.2 mg, 2.84 mmol, 2 equiv.) and K2CO3 (393.1 mg, 2.84 mmol, 2 equiv.) in CH3CN (15 mL) was added 1-(bromomethyl)-2-(trifluoromethyl)benzene (510.0 mg, 2.13 mmol, 1.50 equiv.) dropwise at room temperature. The resulting mixture was stirred for 16 h at 80 degrees C. The reaction was monitored by LCMS. The mixture was purified by silica gel column chromatography, eluted with PE/EtOAc (50:1~10:1) to afford 5-tert-butyl 3-ethyl (6R)-6-methyl-1-[[2-(trifluoromethyl)phenyl]methyl]-1H,4H,5H,6H,7H-pyrazolo[4,3-c]pyridine-3,5-dicarboxylate (400 mg, 60.16%) as a light yellow oil.

Ethyl (6R)-6-methyl-1-[[2-(trifluoromethyl)phenyl]methyl]-1H,4H,5H,6H,7H-pyrazolo[4,3-c]pyridine-3-carboxylate To a stirred solution of 5-tert-butyl 3-ethyl (6R)-6-methyl-1-[[2-(trifluoromethyl)phenyl]methyl]-1H,4H,5H,6H,7H-pyrazolo[4,3-c]pyridine-3,5-dicarboxylate (400 mg, 0.86 mmol, 1 equiv.) in DCM (10 mL) was added TFA (2 ML, 26.93 mmol, 31.47 equiv.) dropwise at room temperature. The resulting mixture was stirred for 2 h at room temperature. The reaction was monitored by LCMS. The resulting mixture was concentrated under reduced pressure. The residue was basified to pH 8~9 with saturated NaHCO3 (aq.). The mixture was purified by reverse phase flash with the following conditions (Column: C18, 330 g; Mobile Phase A: Water/0.05% NH4HCO3, Mobile Phase B: ACN; Flow rate: 80 mL/min; Gradient: 55% B to 75% B in 25 min; Detector, 240 nm; Monitor, 254 nm) to afford ethyl (6R)-6-methyl-1-[[2-(trifluoromethyl)phenyl]methyl]-1H,4H,5H,6H,7H-pyrazolo[4,3-c]pyridine-3-carboxylate (260 mg, 82.71%) as a light yellow oil.

Ethyl (6R)-5-[5-chloro-1-(oxan-2-yl)-6-obo-1,6-dihydropyridazin-4-yl]-6-methyl-1-[[2-(trifluoromethyl)phenyl]methyl]-1H,4H,5H,6H,7H-pyrazolo[4,3-c]pyridine-3-carboxylate A mixture of ethyl (6R)-6-methyl-1-[[2-(trifluoromethyl)phenyl]methyl]-1H,4H,5H,6H,7H-pyrazolo[4,3-c]pyridine-3-carboxylate (160 mg, 0.436 mmol, 1 equiv.), 4,5-dichloro-2-(oxan-2-yl)-2,3-dihydropyridazin-3-one (216.97 mg, 0.871 mmol, 2 equiv.) and DIEA (168.87 mg, 1.307 mmol, 3 equiv.) was stirred for 16 h at 100 degrees C. The reaction was monitored by LCMS. The mixture was purified by reverse phase flash with the following conditions (Column: C18, 330 g; Mobile Phase A: Water/0.05% NH4HCO3, Mobile Phase B: ACN; Flow rate: 80 mL/min; Gradient: 50% B to 80% B in 25 min; Detector, 220 nm; Monitor, 254 nm) to afford ethyl (6R)-5-[5-chloro-1-(oxan-2-yl)-6-oxo-1,6-dihydropyridazin-4-yl]-6-methyl-1-[[2-(trifluoromethyl)

phenyl]methyl]-1H,4H,5H,6H,7H-pyrazolo[4,3-c]pyridine-3-carboxylate (250 mg, 60.90%) as a yellow solid.

(6R)-5-[5-chloro-1-(oxan-2-yl)-6-oxo-1,6-dihydropyridazin-4-yl]-6-methyl-1-[[2-(trifluoromethyl)phenyl]methyl]-1H,4H,5H,6H,7H-pyrazolo[4,3-c]pyridine-3-carboxylic Acid To a stirred solution of ethyl (6R)-5-[5-chloro-1-(oxan-2-yl)-6-oxo-1,6-dihydropyridazin-4-yl]-6-methyl-1-[[2-(trifluoromethyl)phenyl]methyl]-1H,4H,5H,6H,7H-pyrazolo[4,3-c]pyridine-3-carboxylate (250 mg, 0.431 mmol, 1 equiv.) in THF (5 mL) and H2O (1 mL) was added LiOH (30.97 mg, 1.293 mmol, 3 equiv.) at room temperature. The resulting mixture was stirred for 16 h at 50 degrees C. The reaction was monitored by LCMS. The mixture was acidified to pH 6-7 with 10% HCl (aq.). The resulting mixture was extracted with EtOAc (2×100 mL). The combined organic layers were washed with brine (100 mL), dried over anhydrous Na2SO4. After filtration, the filtrate was concentrated under reduced pressure to afford (6R)-5-[5-chloro-1-(oxan-2-yl)-6-oxo-1,6-dihydropyridazin-4-yl]-6-methyl-1-[[2-(trifluoromethyl)phenyl]methyl]-1H,4H,5H,6H,7H-pyrazolo[4,3-c]pyridine-3-carboxylic acid (200 mg, 84.07%) as a light yellow solid.

(6R)-5-[5-Chloro-1-(oxan-2-yl)-6-oxo-1,6-dihydropyridazin-4-yl]-6-methyl-1-[[2-(trifluoromethyl)phenyl]methyl]-1H,4H,5H,6H,7H-pyrazolo[4,3-c]pyridine-3-carboxamide To a stirred solution of (6R)-5-[5-chloro-1-(oxan-2-yl)-6-oxo-1,6-dihydropyridazin-4-yl]-6-methyl-1-[[2-(trifluoromethyl)phenyl]methyl]-1H,4H,5H,6H,7H-pyrazolo[4,3-c]pyridine-3-carboxylic acid (120 mg, 0.217 mmol, 1 equiv.) in DMF (2 mL) was added CDI (52.88 mg, 0.326 mmol, 1.50 equiv.) at room temperature. The resulting mixture was stirred for 1 h at 50 degrees C. To the above mixture was added NH4OAc (50.28 mg, 0.652 mmol, 3 equiv.) at 50 degrees C. The resulting mixture was stirred for additional 16 h at 50 degrees C. The reaction was monitored by LCMS. The mixture was purified by reverse phase flash with the following conditions (Column: C18, 120 g; Mobile Phase A: Water/0.05% NH4HCO3, Mobile Phase B: ACN; Flow rate: 45 mL/min; Gradient: 40% B to 70% B in 20 min; Detector, 220 nm; Monitor, 254 nm) to afford (6R)-5-[5-chloro-1-(oxan-2-yl)-6-oxo-1,6-dihydropyridazin-4-yl]-6-methyl-1-[[2-(trifluoromethyl)phenyl]methyl]-1H,4H,5H,6H,7H-pyrazolo[4,3-c]pyridine-3-carboxamide (100 mg, 83.48%) as a light yellow solid.

(6R)-5-(5-Chloro-6-oxo-1,6-dihydropyridazin-4-yl)-6-methyl-1-[[2-(trifluoromethyl)phenyl]methyl]-1H,4H,5H,6H,7H-pyrazolo[4,3-c]pyridine-3-carboxamide To a stirred solution of (6R)-5-[5-chloro-1-(oxan-2-yl)-6-oxo-1,6-dihydropyridazin-4-yl]-6-methyl-1-[[2-(trifluoromethyl)phenyl]methyl]-1H,4H,5H,6H,7H-pyrazolo[4,3-c]pyridine-3-carboxamide (100 mg, 0.181 mmol, 1 equiv.) in DCM (10 mL) was added TFA (2 mL) dropwise at room temperature. The resulting mixture was stirred for 2 h at room temperature. The reaction was monitored by LCMS. The resulting mixture was concentrated under reduced pressure. The residue was basified to pH 8~9 with saturated NH4HCO3 (aq.). The resulting mixture was concentrated under reduced pressure. The crude product was purified by Prep-HPLC with the following conditions (Column: XBridge Prep C18 OBD Column 19×150 mm 5 um; Mobile Phase A: Water (10 MMOL/L NH4HCO3), Mobile Phase B: ACN; Flow rate: 20 mL/min; Gradient: 25% B to 55% B in 7 min; 254/220 nm; Rt: 6.28 min) to afford (6R)-5-(5-chloro-6-oxo-1,6-dihydropyridazin-4-yl)-6-methyl-1-[[2-(trifluoromethyl)phenyl]methyl]-1H,4H,5H,6H,7H-pyrazolo[4,3-c]pyridine-3-carboxamide (18.8 mg, 22.19%) as a white solid.

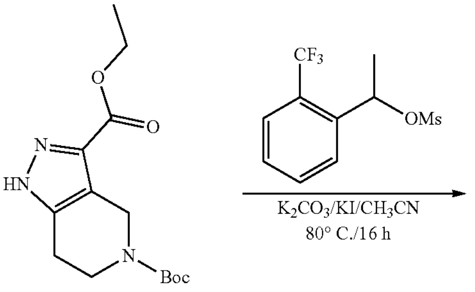

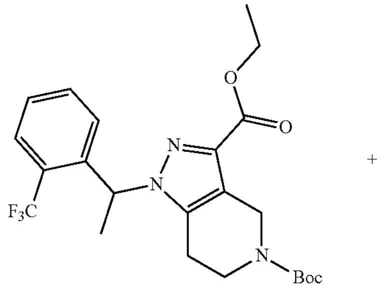

1

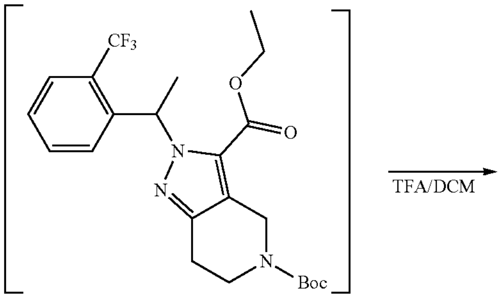

1a

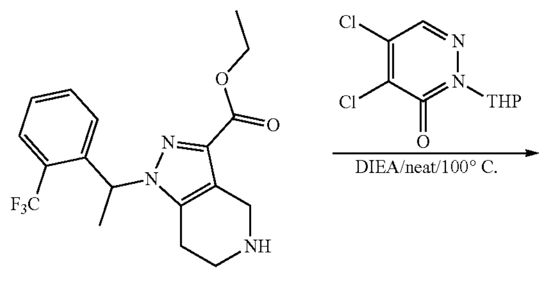

2

-continued

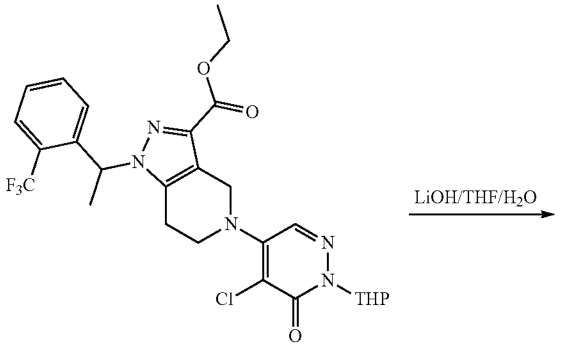

3

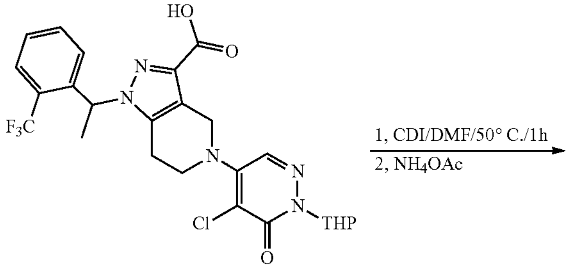

4

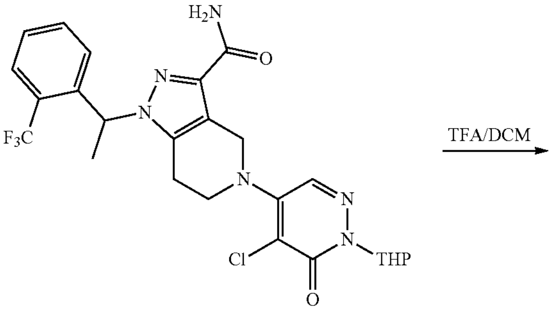

5

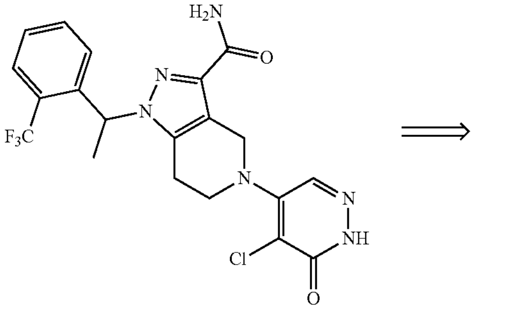

6

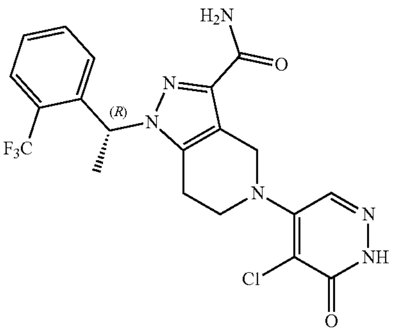

PF

-continued

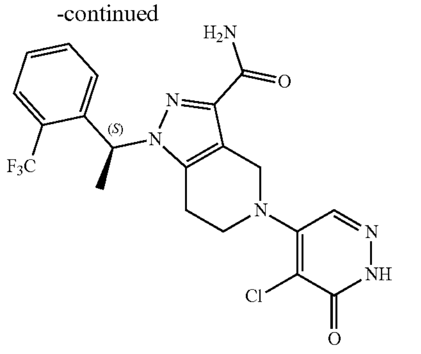

PG

Preparation of PF and PG

5-tert-Butyl 3-ethyl 1-[1-[2-(fluoromethyl)phenyl]ethyl]-1H,4H,5H,6H,7H-pyrazolo[4,3-c]pyridine-3,5-dicarboxylate To a stirred solution of 5-tert-butyl 3-ethyl 1H,4H,5H,6H,7H-pyrazolo[4,3-c]pyridine-3,5-dicarboxylate (500 mg, 1.693 mmol, 1 equiv.) and 1-[2-(trifluoromethyl)phenyl]ethyl methanesulfonate (681.21 mg, 2.539 mmol, 1.50 equiv.) in MeCN (20 mL) were added K2CO3 (467.96 mg, 3.386 mmol, 2 equiv.) and KI (562.08 mg, 3.386 mmol, 2 equiv.). The resulting mixture was stirred for overnight at 80 degrees C. The resulting mixture was extracted with EtOAc (2×60 mL). The combined organic layers were washed with brine (1×60 mL), dried over anhydrous Na2SO4. After filtration, the filtrate was concentrated under reduced pressure. The residue was purified by silica gel column chromatography, eluted with PE/EtOAc (6:1) to afford 5-tert-butyl 3-ethyl 1-[1-[2-(trifluoromethyl)phenyl]ethyl]-1H,4H,5H,6H,7H-pyrazolo[4,3-c]pyridine-3,5-dicarboxylate (420 mg, 53.07%) as a yellow oil.

Ethyl 1-[1-[2-(trifluoromethyl)phenyl]ethyl]-1H,4H,5H,6H,7H-pyrazolo[4,3-c]pyridine-3-carboxylate To a stirred solution of 5-tert-butyl 3-ethyl 1-[1-[2-(trifluoromethyl)phenyl]ethyl]-1H,4H,5H,6H,7H-pyrazolo[4,3-c]pyridine-3,5-dicarboxylate (420 mg, 0.898 mmol, 1 equiv.) in DCM (3 mL) was added TFA (1 mL). The resulting mixture was stirred for 2 h at room temperature. The resulting mixture was concentrated under reduced pressure. The residue was purified by reverse flash chromatography with the following conditions: column, C18 silica gel; mobile phase, MeCN in water, 30% to 70% gradient in 30 min; detector, UV 254 nm. This resulted in ethyl 1-[1-[2-(trifluoromethyl)phenyl]ethyl]-1H,4H,5H,6H,7H-pyrazolo[4,3-c]pyridine-3-carboxylate (270 mg, 81.80%) as a off-white solid.

Ethyl 5-[5-chloro-1-(oxan-2-yl)-6-oxo-1,6-dihydropyridazin-4-yl]-1-[1-[2-(trifluoromethyl)phenyl]ethyl]-1H,4H,5H,6H,7H-pyrazolo[4,3-c]pyridine-3-carboxylate To a stirred mixture of ethyl 1-[1-[2-(trifluoromethyl)phenyl]ethyl]-1H,4H,5H,6H,7H-pyrazolo[4,3-c]pyridine-3-carboxylate (260 mg, 0.708 mmol, 1 equiv.),4,5-dichloro-2-(oxan-2-yl)-2,3-dihydropyridazin-3-one (176.29 mg, 0.708 mmol, 1.00 equiv.) and DIEA (182.94 mg, 1.415 mmol, 2 equiv.). The resulting mixture was stirred for 4 h at 90 degrees C. The residue was purified by silica gel column chromatography, eluted with PE/EtOAc (1:1) to afford ethyl 5-[5-chloro-1-(oxan-2-yl)-6-oxo-1,6-dihydropyridazin-4-yl]-1-[1-[2-(trifluoromethyl)phenyl]ethyl]-1H,4H,5H,6H,7H-pyrazolo[4,3-c]pyridine-3-carboxylate (310 mg, 75.52%) as a light yellow solid.

5-[5-Chloro-1-(oxan-2-yl)-6-oxo-1,2,3,6-tetrahydropyridazin-4-yl]-1-[1-[2-(trifluoromethyl)phenyl]ethyl]-1H,4H,5H,6H,7H-pyrazolo[4,3-c]pyridine-3-carboxylic acid To a stirred solution of ethyl 5-[5-chloro-1-(oxan-2-yl)-6-oxo-1,2,3,6-tetrahydropyridazin-4-yl]-1-[1-[2-(trifluoromethyl)phenyl]ethyl]-1H,4H,5H,6H,7H-pyrazolo[4,3-c]pyridine-3-carboxylate (310 mg, 0.533 mmol, 1 equiv.) in H2O (6 mL) and THF (6 mL) was added LiOH (127.55 mg, 5.326 mmol, 10.00 equiv.). The resulting mixture was stirred for overnight at 40 degrees C. The resulting mixture was concentrated under reduced pressure. The crude product was purified by reverse phase flash with the following conditions (Column: spnerical C18, 20-40 um, 330 g; Mobile Phase A: Water (5 MMOL/L NH4HCO3), Mobile Phase B: ACN; Flow rate: 80 mL/min; Gradient: 10% B to 60% B in 30 min; 254 nm) to afford 5-[5-chloro-1-(oxan-2-yl)-6-oxo-1,2,3,6-tetrahydropyridazin-4-yl]-1-[1-[2-(trifluoromethyl)phenyl]ethyl]-1H,4H,5H,6H,7H-pyrazolo[4,3-c]pyridine-3-carboxylic acid (250 mg, 84.73%) as a light yellow solid.

5-[5-Chloro-1-(oxan-2-yl)-oxo-1,2,3,6-tetrahydropyridazin-4-yl]-1-[1-[2-(trifluoromethyl)phenyl]ethyl]-1H,4H,5H,6H,7H-pyrazolo[4,3-c]pyridine-3-carboxamide To a stirred solution of 5-[5-chloro-1-(oxan-2-yl)-6-oxo-1,2,3,6-tetrahydropyridazin-4-yl]-1-[1-[2-(trifluoromethyl)phenyl]ethyl]-1H,4H,5H,6H,7H-pyrazolo[4,3-c]pyridine-3-carboxylic acid (250 mg, 0.451 mmol, 1 equiv.) in DMF (4 mL) was added CDI (109.76 mg, 0.677 mmol, 1.50 equiv.). The resulting mixture was stirred for 2 h at 45 degrees C. To the above mixture was added NH4OAc (69.57 mg, 0.903 mmol, 2 equiv.) in portions at 45 degrees C. The resulting mixture was stirred for additional overnight at 45 degrees C. The residue was purified by reverse flash chromatography with the following conditions: column, C18 silica gel; mobile phase, MeCN in water, 40% to 75% gradient in 30 min; detector, UV 254 nm. This resulted in 5-[5-chloro-1-(oxan-2-yl)-6-oxo-1,2,3,6-tetrahydropyridazin-4-yl]-1-[1-[2-(trifluoromethyl)phenyl]ethyl]-1H,4H,5H,6H,7H-pyrazolo[4,3-c]pyridine-3-carboxamide (150 mg, 60.11%) as a off-white solid.

5-(5-Chloro-6-oxo-1,6-dihydropyridazin-4-yl)-1-[(1R)-1-[2-(trifluoromethyl)phenyl]ethyl]-1H,4H,5H,6H,7H-pyrazolo[4,3-c]pyridine-3-carboxamide and 5-(5-chloro-6-oxo-1,6-dihydropyridazin-4-yl)-1-[(1S)-1-[2-(trifluoromethyl)phenyl]ethyl]-1H,4H,5H,6H,7H-pyrazolo[4,3-c]pyridine-3-carboxamide To a stirred solution of 5-[5-chloro-1-(oxan-2-yl)-6-oxo-1,6-dihydropyridazin-4-yl]-1-[1-[2-(trifluoromethyl)phenyl]ethyl]-1H,4H,5H,6H,7H-pyrazolo[4,3-c]pyridine-3-carboxamide (150 mg) in DCM (2 mL) was added TFA (1 mL). The resulting mixture was stirred for 2 h at room temperature. The resulting mixture was concentrated under reduced pressure. The residue was basified to pH 8 with saturated NH4CO3 (aq.). The crude product was purified by Prep-HPLC with the following conditions (Column: XBridge Shield RP18 OBD Column 30*150 mm, 5 um; Mobile Phase A: Water (10 MMOL/L NH4HCO3), Mobile Phase B: ACN; Flow rate: 60 mL/min; Gradient: 28% B to 50% B in 7 min; 254 nm; Rt: 6.5 min) to afford 5-(5-chloro-6-oxo-1,6-dihydropyridazin-4-yl)-1-[(1R)-1-[2-(trifluoromethyl)phenyl]ethyl]-1H,4H,5H,6H,7H-pyrazolo[4,3-c]pyridine-3-carboxamide (13.6 mg) and 5-(5-chloro-6-oxo-1,6-dihydropyridazin-4-yl)-1-[(1S)-1-[2-(trifluoromethyl)phenyl]ethyl]-1H,4H,5H,6H,7H-pyrazolo[4,3-c]pyridine-3-carboxamide (12.3 mg) as a white solid.

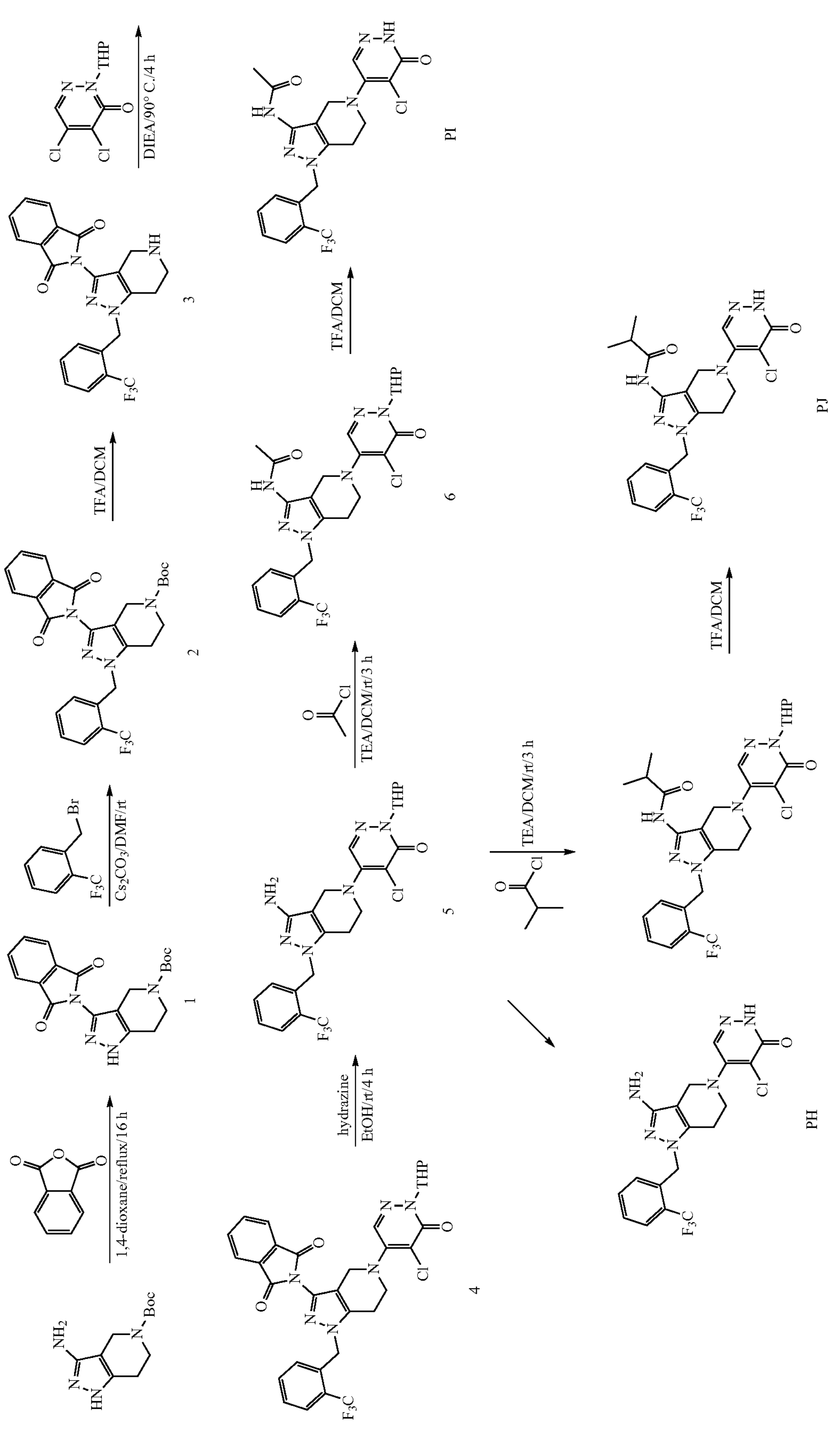
1,4-dioxane/reflux/16 h
1
Cs2CO3/DMF/rt
2
TFA/DCM
3
DIEA/90° C./4 h
4
hydrazine
EtOH/rt/4 h
5
TEA/DCM/rt/3 h
6
TFA/DCM
PI
TEA/DCM/rt/3 h
TFA/DCM
PJ
PH Preparation of PH, PI, and PJ Tert-Butyl 3-(1,3-dioxo-2,3-dihydro-1H-isoindol-2-yl)-1H,4H,5H,6H,7H-pyrazolo[4,3-c]pyridine-5-carboxylate A mixture of 1,3-dihydro-2-benzofuran-1,3-dione (3.73 g, 25.179 mmol, 2.00 equiv.) and tert-butyl 3-amino-1H,4H,5H,6H,7H-pyrazolo[4,3-c]pyridine-5-carboxylate (3 g, 12.590 mmol, 1 equiv.) in dioxane (200 mL) was stirred for 17 h at 120 degrees celsius under N2 atmosphere. The mixture was allowed to cool down to room temperature. Desired product could be detected by LCMS. The resulting mixture was concentrated under reduced pressure. The residue was purified by reverse phase flash with the following conditions (Column: Spherical C18 Column, 20-40 um, 120 g; Mobile Phase A: Water (0.1% FA), Mobile Phase B: ACN; Flow rate: 60 mL/min; Gradient: 20% B to 70% B in 45 min, 220 nm) to afford tert-butyl 3-(1,3-dioxo-2,3-dihydro-1H-isoindol-2-yl)-1H,4H,5H,6H,7H-pyrazolo[4,3-c]pyridine-5-carboxylate (0.6 g, 12.94%) as a light yellow solid.

Tert-Butyl 3-(1,3-dioxo-2,3-dihydro-1H-isoindol-2-yl)-1-[[2-(trifluoromethyl)phenyl]methyl]-1H,4H,5H,6H,7H-pyrazolo[4,3-c]pyridine-5-carboxylate To a stirred mixture of tert-butyl 3-(1,3-dioxo-2,3-dihydro-1H-isoindol-2-yl)-1H,4H,5H,6H,7H-pyrazolo[4,3-c]pyridine-5-carboxylate (550 mg, 1.493 mmol, 1 equiv.) and 1-(bromomethyl)-2-(trifluoromethyl)benzene (428 mg, 1.791 mmol, 1.20 equiv.) in DMF (8 ML) was added Cs2CO3 (1150 mg, 3.530 mmol, 2.36 equiv.) at room temperature under N2 atmosphere. The mixture was stirred for 16 h at room temperature. Desired product could be detected by LCMS. The resulting mixture was diluted with water (200 mL). The resulting mixture was extracted with EA (3×200 mL). The combined organic layers were washed with water (1×200 mL), dried over anhydrous Na2SO4. After filtration, the filtrate was concentrated under reduced pressure. The residue was purified by silica gel column chromatography, eluted with PE/EA (4/1) to afford tert-butyl 3-(1,3-dioxo-2,3-dihydro-1H-isoindol-2-yl)-1-[[2-(trifluoromethyl)phenyl]methyl]-1H,4H,5H,6H,7H-pyrazolo[4,3-c]pyridine-5-carboxylate (700 mg, 89.05%) as a yellow solid.

(2-(1-[[2-(trifluoromethyl)phenyl]methyl]-1H,4H,5H,6H,7H-pyrazolo[4,3-c]pyridin-3-yl)-2,3-dihydro-1H-isoindole-1,3-dione To a stirred solution of tert-butyl 3-(1,3-dioxo-2,3-dihydro-1H-isoindol-2-yl)-1-[[2-(trifluoromethyl)phenyl]methyl]-1H,4H,5H,6H,7H-pyrazolo[4,3-c]pyridine-5-carboxylate (740 mg, 1.405 mmol, 1 equiv.) in DCM (20 mL) was added TFA (10 mL) at 0 degrees C. The mixture was stirred for 2 h at room temperature. Desired product could be detected by LCMS. The resulting mixture was concentrated under reduced pressure. The crude product (2-(1-[[2-(trifluoromethyl)phenyl]methyl]-1H,4H,5H,6H,7H-pyrazolo[4,3-c]pyridin-3-yl)-2,3-dihydro-1H-isoindole-1,3-dione (580 mg, 96.78%)) was used in the next step directly without further purification.

2-[5-[5-Chloro-1-(oxan-2-yl)-6-oxo-1,6-dihydropyridazin-4-yl]-1-[[2-(trifluoromethyl)phenyl]methyl]-1H,4H,5H,6H,7H-pyrazolo[4,3-c]pyridin-3-yl]-2,3-dihydro-1H-isoindole-1,3-dione A mixture of 4,5-dichloro-2-(oxan-2-yl)-2,3-dihydropyridazin-3-one (666 mg, 2.674 mmol, 2.00 equiv.), 2-(1-[[2-(trifluoromethyl)phenyl]methyl]-1H,4H,5H,6H,7H-pyrazolo[4,3-c]pyridin-3-yl)-2,3-dihydro-1H-isoindole-1,3-dione (570 mg, 1.337 mmol, 1 equiv.) and DIEA (518 mg, 4.008 mmol, 3.00 equiv.) in DMA (8 mL) was stirred for 4 h at 90 degrees celsius under N2 atmosphere. The mixture was allowed to cool down to room temperature. Desired product could be detected by LCMS. The resulting mixture was purified by reverse phase flash with the following conditions (Column: Spherical C18 Column, 20-40 um, 120 g; Mobile Phase A: Water (0.1% FA), Mobile Phase B: ACN; Flow rate: 60 mL/min; Gradient: 20% B to 70% B in 40 min, 220 nm) to afford 2-[5-[5-chloro-1-(oxan-2-yl)-6-oxo-1,6-dihydropyridazin-4-yl]-1-[[2-(trifluoromethyl)phenyl]methyl]-1H,4H,5H,6H,7H-pyrazolo[4,3-c]pyridin-3-yl]-2,3-dihydro-1H-isoindole-1,3-dione (600 mg, 70.24%) as a off-white solid.

5-(3-Amino-1-[[2-(trifluoromethyl)phenyl]methyl]-1H,4H,5H,6H,7H-pyrazolo[4,3-c]pyridin-5-yl)-4-chloro-2-(oxan-2-yl)-2,3-dihydropyridazin-3-one A mixture of 2-[5-[5-chloro-1-(oxan-2-yl)-6-oxo-1,6-dihydropyridazin-4-yl]-1-[[2-(trifluoromethyl)phenyl]methyl]-1H,4H,5H,6H,7H-pyrazolo[4,3-c]pyridin-3-yl]-2,3-dihydro-1H-isoindole-1,3-dione (550 mg, 0.861 mmol, 1 equiv.) and NH2NH2·H2O (269.29 mg, 4.303 mmol, 5.00 equiv, 80%) in EtOH (15 mL) was stirred for 4 h at room temperature. Desired product could be detected by LCMS. The resulting mixture was concentrated under reduced pressure. The residue was purified by reverse phase flash with the following conditions (Column: Spherical C18 Column, 20-40 um, 120 g; Mobile Phase A: Water (0.1% FA), Mobile Phase B: ACN; Flow rate: 60 mL/min; Gradient: 20% B to 70% B in 30 min, 220 nm) to afford 5-(3-amino-1-[[2-(trifluoromethyl)phenyl]methyl]-1H,4H,5H,6H,7H-pyrazolo[4,3-c]pyridin-5-yl)-4-chloro-2-(oxan-2-yl)-2,3-dihydropyridazin-3-one (420 mg, 95.88%) as a light yellow solid.

5-(3-Amino-1-[[2-(trifluoromethyl)phenyl]methyl]-1H,4H,5H,6H,7H-pyrazolo[4,3-c]pyridin-5-yl)-4-chloro-2,3-dihydropyridazin-3-one To a stirred solution of 5-(3-amino-1-[[2-(trifluoromethyl)phenyl]methyl]-1H,4H,5H,6H,7H-pyrazolo[4,3-c]pyridin-5-yl)-4-chloro-2-(oxan-2-yl)-2,3-dihydropyridazin-3-one (120 mg, 0.236 mmol, 1 equiv.) in DCM (4.5 mL) was added TFA (0.40 mL, 3.508 mmol, 22.84 equiv.) dropwise at room temperature. The resulting mixture was stirred for 2 h at room temperature.

The reaction was monitored by LCMS. The resulting mixture was concentrated under reduced pressure. The residue was basified to pH 7 with saturated NaHCO3 (aq.). The aqueous layer was extracted with EtOAc (3×10 mL). The resulting mixture was concentrated under reduced pressure. The residue was purified by reverse phase flash with the following conditions (Column: C18 Column 120 g; Mobile Phase A: Water (10 MMOL/L NH4HCO3), Mobile Phase B: ACN; Flow rate: 50 mL/min; Gradient: 30% B to 50% B in 40 min; 254/220 nm) to afford 5-(3-amino-1-[[2-(trifluoromethyl)phenyl]methyl]-1H,4H,5H,6H,7H-pyrazolo[4,3-c]pyridin-5-yl)-4-chloro-2,3-dihydropyridazin-3-one (50 mg, 49.92%) as an off-white solid.

N-[5-[5-chloro-1-(oxan-2-yl)-6-oxo-1,6-dihydropyridazin-4-yl]-1-[[2-(trifluoromethyl)phenyl]methyl]-1H,4H,5H,6H,7H-pyrazolo[4,3-c]pyridin-3-yl]-2-methylpropanamide To a stirred solution of 5-(3-amino-1-[[2-(trifluoromethyl)phenyl]methyl]-1H,4H,5H,6H,7H-pyrazolo[4,3-c]

pyridin-5-yl)-4-chloro-2-(oxan-2-yl)-2,3-dihydropyridazin-3-one (80 mg, 0.157 mmol, 1 equiv.) in DCM (3 mL) were added 2-methylpropanoyl chloride (20.10 mg, 0.189 mmol, 1.2 equiv.) and TEA (47.72 mg, 0.472 mmol, 3 equiv.) at room temperature. The resulting mixture was stirred for 4 h at room temperature. The reaction was monitored by LCMS. The resulting mixture was concentrated under vacuum. The residue was purified by reverse phase flash with the following conditions (Column: C18 Column 120 g; Mobile Phase A: Water (10 MMOL/L NH4HCO3), Mobile Phase B: ACN; Flow rate: 50 mL/min; Gradient: 40% B to 60% B in 40 min; 254/220 nm) to afford N-[5-[5-chloro-1-(oxan-2-yl)-6-oxo-1,6-dihydropyridazin-4-yl]-1-[[2-(trifluoromethyl)phenyl]methyl]-1H,4H,5H,6H,7H-pyrazolo[4,3-c]pyridin-3-yl]-2-methylpropanamide (70 mg, 76.91%) as a colorless oil.

N-[5-(5-chloro-6-oxo-1,6-dihydropyridazin-4-yl)-1-[[2-(trifluoromethyl)phenyl]methyl]-1H,4H,5H,6H,7H-pyrazolo[4,3-c]pyridin-3-yl]-2-methylpropanamide To a stirred solution of N-[5-[5-chloro-1-(oxan-2-yl)-6-oxo-1,6-dihydropyridazin-4-yl]-1-[[2-(trifluoromethyl)phenyl]methyl]-1H,4H,5H,6H,7H-pyrazolo[4,3-c]pyridin-3-yl]-2-methylpropanamide (50 mg, 0.086 mmol, 1 equiv.) in DCM (4.5 mL) was added TFA (0.5 mL, 6.732 mmol, 77.95 equiv.) dropwise at room temperature. The resulting mixture was stirred for 2 h at room temperature. The reaction was monitored by LCMS. The resulting mixture was concentrated under vacuum. The residue/crude product was purified by reverse phase flash with the following conditions ( ) to afford N-[5-(5-chloro-6-oxo-1,6-dihydropyridazin-4-yl)-1-[[2-(trifluoromethyl)phenyl]methyl]-1H,4H,5H,6H,7H-pyrazolo[4,3-c]pyridin-3-yl]-2-methylpropanamide (20 mg, 46.80%) as an off-white solid.

N-[5-[5-chloro-1-(oxan-2-yl)-6-oxo-1,6-dihydropyridazin-4-yl]-1-[[2-(trifluoromethyl)phenyl]methyl]-1H,4H,5H,6H,7H-pyrazolo[4,3-c]pyridin-3-yl]acetamide To a stirred solution of 5-(3-amino-1-[[2-(trifluoromethyl)phenyl]methyl]-1H,4H,5H,6H,7H-pyrazolo[4,3-c]pyridin-5-yl)-4-chloro-2-(oxan-2-yl)-2,3-dihydropyridazin-3-one (90 mg, 0.177 mmol, 1 equiv.) in DCM (5 mL) was added acetyl chloride (16.66 mg, 0.212 mmol, 1.20 equiv.) dropwise at room temperature. The resulting mixture was stirred for 2 h at room temperature. The reaction was monitored by LCMS. The resulting mixture was concentrated under reduced pressure. The residue was purified by Prep-TLC (PE/EtOAc 1:50) to afford N-[5-[5-chloro-1-(oxan-2-yl)-6-oxo-1,6-dihydropyridazin-4-yl]-1-[[2-(trifluoromethyl)phenyl]methyl]-1H,4H,5H,6H,7H-pyrazolo[4,3-c]pyridin-3-yl]acetamide (70 mg, 71.84%) as a off-white solid.

N-[5-(5-chloro-6-oxo-1,6-dihydropyridazin-4-yl)-1-[[2-(trifluoromethyl)phenyl]methyl]-1H,4H,5H,6H,7H-pyrazolo[4,3-c]pyridin-3-yl]acetamide To a stirred solution of N-[5-[5-chloro-1-(oxan-2-yl)-6-oxo-1,6-dihydropyridazin-4-yl]-1-[[2-(trifluoromethyl)phenyl]methyl]-1H,4H,5H,6H,7H-pyrazolo[4,3-c]pyridin-3-yl]acetamide (50 mg, 0.091 mmol, 1 equiv.) in DCM (9 mL) was added TFA (1 mL) dropwise at room temperature. The resulting mixture was stirred for 1 h at room temperature. The reaction was monitored by LCMS. The resulting mixture was concentrated under reduced pressure. The residue was purified by reverse phase flash with the following conditions (Column: C18 Column 40 g; Mobile Phase A: Water (10 MMOL/L NH4HCO3), Mobile Phase B: ACN; Flow rate: 40 mL/min; Gradient: 20% B to 40% B in 40 min; 254/220 nm) to afford N-[5-(5-chloro-6-oxo-1,6-dihydropyridazin-4-yl)-1-[[2-(trifluoromethyl)phenyl]methyl]-1H,4H,5H,6H,7H-pyrazolo[4,3-c]pyridin-3-yl]acetamide (20 mg, 47.21%) as a off-white solid.

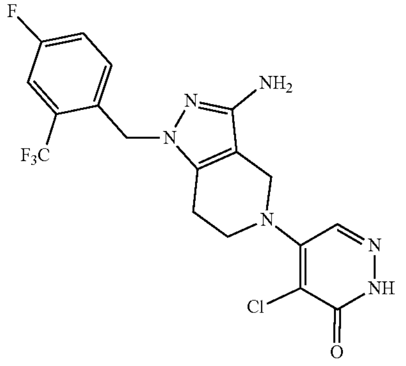

PK

PK was prepared by the methods and scheme described for PH by using 1-(bromomethyl)-2-(trifluoromethyl)-4-F-benzene

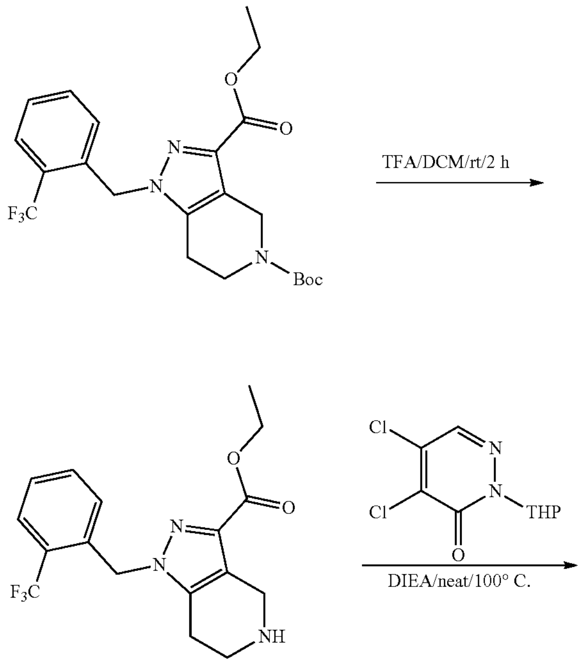

1

-continued
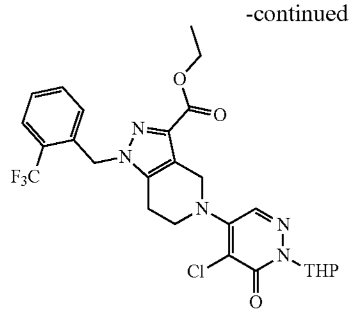
2
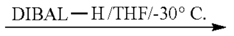
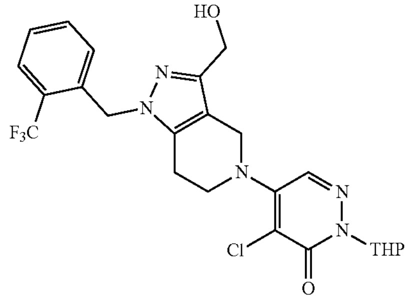
3
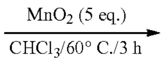
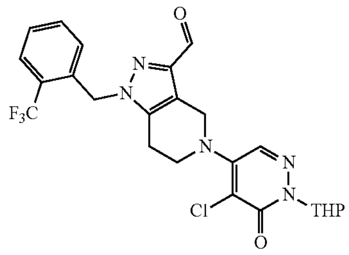
4
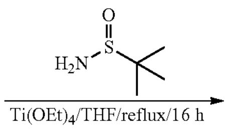
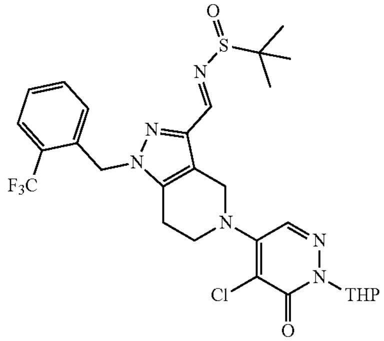
5
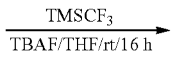
-continued
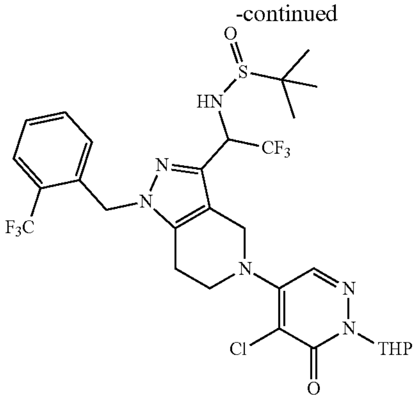
6
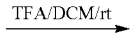
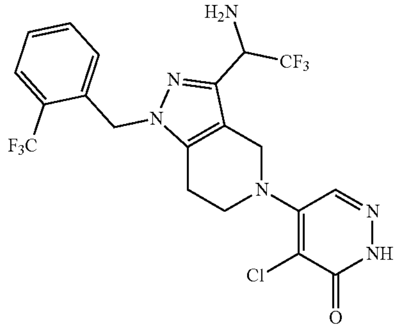
7
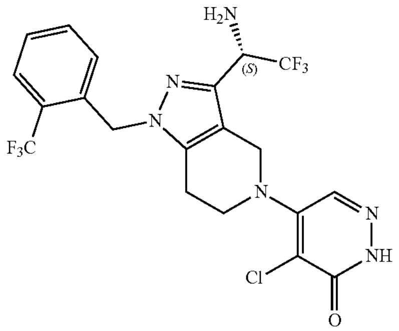
PL
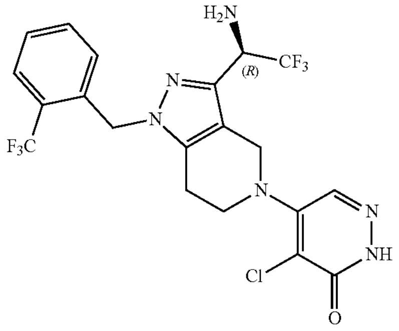
PM
Preparation of PL and PM
Ethyl 1-[[2-(trifluoromethyl)phenyl]methyl]-1H,4H,5H,6H,7H-pyrazolo[4,3-c]pyridine-3-carboxylate
To a stirred solution of 5-tert-butyl 3-ethyl 1-[[2-(trifluoromethyl)phenyl]methyl]-1H,4H,5H,6H,7H-pyrazolo[4,3-c]pyridine-3,5-dicarboxylate (400 mg, 0.882 mmol, 1 equiv.) in DCM (10 mL) was added TFA (2 mL, 26.926 mmol, 30.52 equiv.) at 0 degrees celsius under nitrogen atmosphere. The mixture was stirred at rt for 30 min. Desired product could be detected by LCMS. To the mixture was added water (40 mL). The resulting mixture was extracted with CH2Cl2 (3×40 mL). The combined organic layers were washed with brine (1×10 mL), dried over anhydrous Na2SO4. After filtration, the filtrate was concentrated under reduced pressure to afford ethyl 1-[[2-(trifluoromethyl)phenyl]methyl]-1H,4H,5H,6H,7H-pyrazolo[4,3-c]pyridine-3-carboxylate (300 mg, 96.25%) as yellow solid.

Ethyl 5-[5-chloro-1-(oxan-2-yl)-6-oxo-1,6-dihydropyridazin-4-yl]-1-[[2-(trifluoromethyl)phenyl]methyl]-1H,4H,5H,6H,7H-pyrazolo[4,3-c]pyridine-3-carboxylate A mixture of ethyl 1-[[2-(trifluoromethyl)phenyl]methyl]-1H,4H,5H,6H,7H-pyrazolo[4,3-c]pyridine-3-carboxylate (300 mg, 0.849 mmol, 1 equiv.) and 4,5-dichloro-2-(oxan-2-yl)-2,3-dihydropyridazin-3-one (253.78 mg, 1.019 mmol, 1.20 equiv.) was stirred at 100 degrees celsius for 12 h. Desired product could be detected by LCMS. The residue was purified by silica gel column chromatography, eluted with PE/EtOAc (5:1 to 3:1) to afford ethyl 5-[5-chloro-1-(oxan-2-yl)-6-oxo-1,6-dihydropyridazin-4-yl]-1-[[2-(trifluoromethyl)phenyl]methyl]-1H,4H,5H,6H,7H-pyrazolo[4,3-c]pyridine-3-carboxylate (350 mg, 72.84%) as yellow solid.

5-[5-chloro-1-(oxan-2-yl)-6-oxo-1,6-dihydropyridazin-4-yl]-1-[[2-(trifluoromethyl)phenyl]methyl]-1H,4H,5H,6H,7H-pyrazolo[4,3-c]pyridine-3-carbaldehyde To a stirred solution of ethyl 5-[5-chloro-1-(oxan-2-yl)-6-oxo-1,6-dihydropyridazin-4-yl]-1-[[2-(trifluoromethyl)phenyl]methyl]-1H,4H,5H,6H,7H-pyrazolo[4,3-c]pyridine-3-carboxylate (300 mg, 0.530 mmol, 1 equiv.) in THF (15 mL) was added DIBAl-H (0.09 mL, 0.537 mmol, 1.01 equiv.) dropwise at −70 degrees celsius under nitrogen atmosphere. The mixture was stirred at −70 degrees celsius for 30 min. Desired product could be detected by LCMS. The reaction was quenched with MeOH at −70 degrees C. The resulting mixture was concentrated under vacuum. The residue was purified by Prep-TLC (PE/EtOAc 1:1) to afford 5-[5-chloro-1-(oxan-2-yl)-6-oxo-1,6-dihydropyridazin-4-yl]-1-[[2-(trifluoromethyl)phenyl]methyl]-1H,4H,5H,6H,7H-pyrazolo[4,3-c]pyridine-3-carbaldehyde (150 mg, 54.22%) as a white solid.

N-[(1E)-[5-[5-chloro-1-(oxan-2-yl)-6-oxo-1,6-dihydropyridazin-4-yl]-1-[[2-(trifluoromethyl)phenyl]methyl]-1H,4H,5H,6H,7H-pyrazolo[4,3-c]pyridin-3-yl]methylidene]-2-methylpropane-2-sulfinamide To a stirred solution of 5-[5-chloro-1-(oxan-2-yl)-6-oxo-1,6-dihydropyridazin-4-yl]-1-[[2-(trifluoromethyl)phenyl]methyl]-1H,4H,5H,6H,7H-pyrazolo[4,3-c]pyridine-3-carbaldehyde (200 mg, 0.383 mmol, 1 equiv.) and 2-methylpropane-2-sulfinamide (46.44 mg, 0.383 mmol, 1.00 equiv.) in THF (8 mL) was added Ti(OEt)4 (8.74 mg, 0.038 mmol, 0.1 equiv.) dropwise at room temperature under nitrogen atmosphere. The mixture was stirred at 80 degrees celsius for 5 h. Desired product could be detected by LCMS. The resulting mixture was concentrated under vacuum. The residue was purified by Prep-TLC (PE/EtOAc 1:1) to afford N-[(1E)-[5-[5-chloro-1-(oxan-2-yl)-6-oxo-1,6-dihydropyridazin-4-yl]-1-[[2-(trifluoromethyl)phenyl]methyl]-1H,4H,5H,6H,7H-pyrazolo[4,3-c]pyridin-3-yl]methylidene]-2-methylpropane-2-sulfinamide (170 mg, 70.97%) as a white solid.

N-(1-[5-[5-chloro-1-(oxan-2-yl)-6-oxo-1,6-dihydropyridazin-4-yl]-1-[[2-(trifluoromethyl)phenyl]methyl]-1H,4H,5H,6H,7H-pyrazolo[4,3-c]pyridin-3-yl]-2,2,2-trifluoroethyl)-2-methylpropane-2-sulfinamide To a stirred solution of N-[(1E)-[5-[5-chloro-1-(oxan-2-yl)-6-oxo-1,6-dihydropyridazin-4-yl]-1-[[2-(trifluoromethyl)phenyl]methyl]-1H,4H,5H,6H,7H-pyrazolo[4,3-c]pyridin-3-yl]methylidene]-2-methylpropane-2-sulfinamide (170 mg, 0.272 mmol, 1 equiv.) in THF (15 mL, 185.145 mmol, 680.80 equiv.) was added TMSCF3 (77.34 mg, 0.544 mmol, 2 equiv.) and TBAF (71.11 mg, 0.272 mmol, 1.00 equiv.) at 0 degrees celsius under nitrogen atmosphere. The mixture was stirred at rt for 2 h. Desired product could be detected by LCMS. To the mixture was added water (20 mL). The aqueous layer was extracted with EtOAc (2×10 mL). The organic layer was concentrated under vacuum to afford N-(1-[5-[5-chloro-1-(oxan-2-yl)-6-oxo-1,6-dihydropyridazin-4-yl]-1-[[2-(trifluoromethyl)phenyl]methyl]-1H,4H,5H,6H,7H-pyrazolo[4,3-c]pyridin-3-yl]-2,2,2-trifluoroethyl)-2-methylpropane-2-sulfinamide (140 mg, 74.06%) as white solid.

5-[3-(1-amino-2,2,2-trifluoroethyl)-1-[[2-(trifluoromethyl)phenyl]methyl]-1H,4H,5H,6H,7H-pyrazolo[4,3-c]pyridin-5-yl]-4-chloro-2,3-dihydropyridazin-3-one To a stirred solution of N-(1-[5-[5-chloro-1-(oxan-2-yl)-6-oxo-1,6-dihydropyridazin-4-yl]-1-[[2-(trifluoromethyl)phenyl]methyl]-1H,4H,5H,6H,7H-pyrazolo[4,3-c]pyridin-3-yl]-2,2,2-trifluoroethyl)-2-methylpropane-2-sulfinamide (500 mg, 0.719 mmol, 1 equiv.) in DCM (10 mL, 157.300 mmol, 218.69 equiv.) was added TFA (2 mL, 26.926 mmol, 37.43 equiv.) dropwise at room temperature under nitrogen atmosphere. The mixture was stirred at rt for 1 h. Desired product could be detected by LCMS. The resulting mixture was concentrated under reduced pressure to afford 5-[3-(1-amino-2,2,2-trifluoroethyl)-1-[[2-(trifluoromethyl)phenyl]methyl]-1H,4H,5H,6H,7H-pyrazolo[4,3-c]pyridin-5-yl]-4-chloro-2,3-dihydropyridazin-3-one (350 mg, 96.00%) as white solid.

5-[3-[(1S)-1-amino-2,2,2-trifluoroethyl]-1-[[2-(trifluoromethyl)phenyl]methyl]-1H,4H,5H,6H,7H-pyrazolo[4,3-c]pyridin-5-yl]-4-chloro-2,3-dihydropyridazin-3-one and 5-[3-[(1R)-1-amino-2,2,2-trifluoroethyl]-1-[[2-(trifluoromethyl)phenyl]methyl]-1H,4H,5H,6H,7H-pyrazolo[4,3-c]pyridin-5-yl]-4-chloro-2,3-dihydropyridazin-3-one 5-[3-(1-amino-2,2,2-trifluoroethyl)-1-[[2-(trifluoromethyl)phenyl]methyl]-1H,4H,5H,6H,7H-pyrazolo[4,3-c]pyridin-5-yl]-4-chloro-2,3-dihydropyridazin-3-one (140 mg, 0.276 mmol, 1 equiv.) was separated by chiral-HPLC (Column: CHIRALPAK IG, 20*250 mm, 5 um; Mobile Phase A:Hex (0.2% DEA)—HPLC, Mobile Phase B: EtOH—HPLC; Flow rate: 20 mL/min; Gradient: 40 B to 40 B in 16 min; 220/254 nm; RT1:10.457; RT2:13.391) to afford 5-[3-[(1S)-1-amino-2,2,2-trifluoroethyl]-1-[[2-(trifluoromethyl)phenyl]methyl]-1H,4H,5H,6H,7H-pyrazolo[4,3-c]pyridin-5-yl]-4-chloro-2,3-dihydropyridazin-3-one (31 mg) and 5-[3-[(1R)-1-amino-2,2,2-trifluoroethyl]-1-[[2-(trifluoromethyl)phenyl]methyl]-1H,4H,5H,6H,7H-pyrazolo[4,3-c]pyridin-5-yl]-4-chloro-2,3-dihydropyridazin-3-one (40 mg) as white solid.

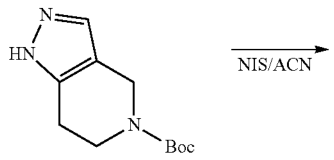

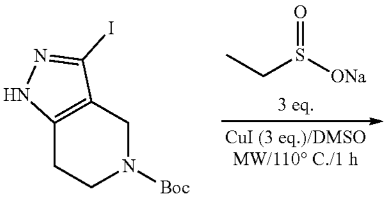

3

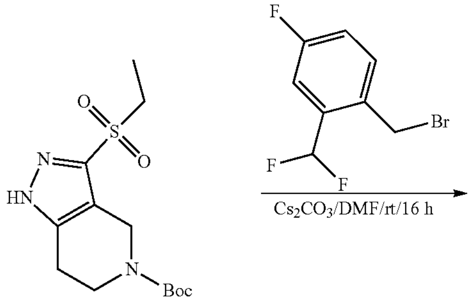

4

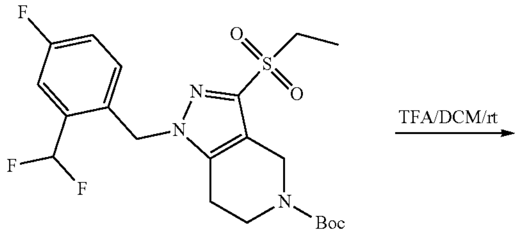

5

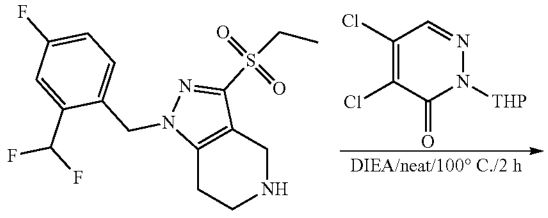

6

-continued

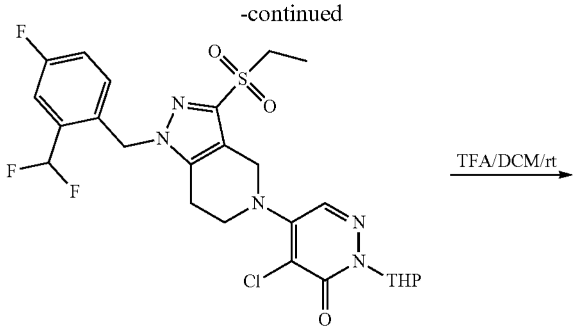

7

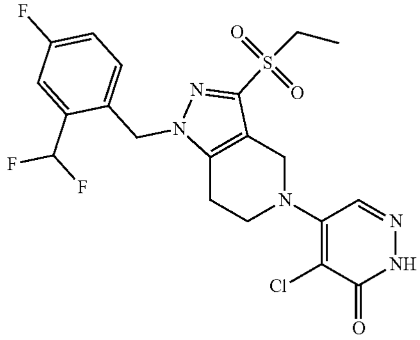

PN

Preparation of PN

Tert-Butyl 3-iodo-1H,4H,5H,6H,7H-pyrazolo[4,3-c]pyridine-5-carboxylate

To a stirred solution of tert-butyl 1H,4H,5H,6H,7H-pyrazolo[4,3-c]pyridine-5-carboxylate (1 g, 4.479 mmol, 1 equiv.) in MeCN (120 mL) was added NIS (1.11 g, 4.927 mmol, 1.1 equiv.) at room temperature. The resulting mixture was stirred for 4 h at 60 degrees C. The reaction was monitored by LCMS. The resulting mixture was concentrated under reduced pressure. The residue was purified by reverse phase flash with the following conditions (Column: C18, 330 g; Mobile Phase A: Water/0.05% TFA, Mobile Phase B: ACN; Flow rate: 80 mL/min; Gradient: 35% B to 55% B in 25 min; Detector, 220 nm; Monitor, 254 nm) to afford tert-butyl 3-iodo-1H,4H,5H,6H,7H-pyrazolo[4,3-c]pyridine-5-carboxylate (390 mg, 24.94%) as a dark yellow solid.

Tert-Butyl 3-(ethanesulfonyl)-1H,4H,5H,6H,7H-pyrazolo[4,3-c]pyridine-5-carboxylate Into a 10 mL Vessel were added tert-butyl 3-iodo-1H,4H,5H,6H,7H-pyrazolo[4,3-c]pyridine-5-carboxylate (230 mg, 0.659 mmol, 1 equiv.), iodocopper (376.35 mg, 1.976 mmol, 3.00 equiv.), (ethanesulfonyl) sodium (229.45 mg, 1.976 mmol, 3.00 equiv.) and DMSO (5 ML) at room temperature. The reaction mixture was irradiated with microwave radiation for 1 h at 110 degrees C. The mixture was allowed to cool down to room temperature. Desired product could be detected by LCMS. The mixture was purified by reverse phase flash with the following conditions (Column: Spherical C18 Column, 20-40 um, 120 g; Mobile Phase A: Water (0.1% FA), Mobile Phase B: ACN; Flow rate: 60 mL/min; Gradient: 40% B to 85% B in 30 min, 220 nm) to afford tert-butyl 3-(ethanesulfonyl)-1H,4H,5H,6H,7H-pyrazolo[4,3-c]pyridine-5-carboxylate (90 mg, 43.32%) as a yellow oil.

Tert-Butyl 1-[[2-(difluoromethyl)-4-fluorophenyl]methyl]-3-(ethanesulfonyl)-1H,4H,5H,6H,7H-pyrazolo[4,3-c]pyridine-5-carboxylate A mixture of tert-butyl 3-(ethanesulfonyl)-1H,4H,5H,6H,7H-pyrazolo[4,3-c]pyridine-5-carboxylate (190 mg, 0.602 mmol, 1 equiv.) and 1-(chloromethyl)-2-(difluoromethyl)-4-fluorobenzene (141 mg, 0.725 mmol, 1.20 equiv.) in DMF (5 mL) was added Cs2CO3 (294 mg, 0.902 mmol, 1.50 equiv.) and stirred for 12 h at room temperature under N2 atmosphere. Desired product could be detected by LCMS. The reaction was quenched with water (100 mL) at room temperature. The resulting mixture was extracted with EA (3×200 mL). The combined organic layers were washed with water (1×100 mL), dried over anhydrous Na2SO4. After filtration, the filtrate was concentrated under reduced pressure. The crude product was purified by reverse phase flash with the following conditions (Column: Spherical C18 Column, 20-40 um, 120 g; Mobile Phase A: Water (0.1% FA), Mobile Phase B: ACN; Flow rate: 60 mL/min; Gradient: 30% B to 80% B in 30 min, 220 nm) to afford tert-butyl 1-[[2-(difluoromethyl)-4-fluorophenyl]methyl]-3-(ethanesulfonyl)-1H,4H,5H,6H,7H-pyrazolo[4,3-c]pyridine-5-carboxylate (92 mg, 32.25%) as a yellow oil.

1-[[2-(Difluoromethyl)-4-fluorophenyl]methyl]-3-(ethanesulfonyl)-1H,4H,5H,6H,7H-pyrazolo[4,3-c]pyridine A mixture of tert-butyl 1-[[2-(difluoromethyl)-4-fluorophenyl]methyl]-3-(ethanesulfonyl)-1H,4H,5H,6H,7H-pyrazolo[4,3-c]pyridine-5-carboxylate (80 mg, 0.169 mmol, 1 equiv.) and TFA (2 mL) in DCM (8 mL) was stirred for 2 h at room temperature under N2 atmosphere. Desired product could be detected by LCMS. The resulting mixture was concentrated under reduced pressure to afford 1-[[2-(difluoromethyl)-4-fluorophenyl]methyl]-3-(ethanesulfonyl)-1H,4H,5H,6H,7H-pyrazolo[4,3-c]pyridine (60 mg, 95.11%). The crude product was used in the next step directly without further purification.

4-Chloro-5-(1-[[2-(difluoromethyl)-4-fluorophenyl]methyl]-3-(ethanesulfonyl)-1H,4H,5H,6H,7H-pyrazolo[4,3-c]pyridin-5-yl)-2-(oxan-2-yl)-2,3-dihydropyridazin-3-one To a stirred mixture of 1-[[2-(difluoromethyl)-4-fluorophenyl]methyl]-3-(ethanesulfonyl)-1H4H,5H,6H,7H-pyrazolo[4,3-c]pyridine (60 mg, 0.161 mmol, 1 equiv.) and 4,5-dichloro-2-(oxan-2-yl)-2,3-dihydropyridazin-3-one (44.03 mg, 0.177 mmol, 1.10 equiv.) in DMA (2 mL) was added DIEA (83.07 mg, 0.643 mmol, 4 equiv.) at room temperature under N2 atmosphere. The mixture was stirred for 5 h at 90 degrees C. The mixture was allowed to cool down to room temperature. Desired product could be detected by LCMS. The crude product was purified by reverse phase flash with the following conditions (Column: Spherical C18 Column, 20-40 um, 120 g; Mobile Phase A: Water (0.1% FA), Mobile Phase B: ACN; Flow rate: 60 mL/min; Gradient:30% B to 70% B in 30 min, 220 nm) to afford 4-chloro-5-(1-[[2-(difluoromethyl)-4-fluorophenyl]methyl]-3-(ethanesulfonyl)-1H,4H,5H,6H,7H-pyrazolo[4,3-c]pyridin-5-yl)-2-(oxan-2-yl)-2,3-dihydropyridazin-3-one (50 mg, 53.10%) as a yellow solid.

4-Chloro-5-(1-[[2-(difluoromethyl)-4-fluorophenyl]methyl]-3-(ethanesulfonyl)-1H,4H,5H,6H,7H-pyrazolo[4,3-c]pyridin-5-yl)-2,3-dihydropyridazin-3-one A mixture of 4-chloro-5-(1-[[2-(difluoromethyl)-4-fluorophenyl]methyl]-3-(ethanesulfonyl)-1H,4H,5H,6H,7H-pyrazolo[4,3-c]pyridin-5-yl)-2-(oxan-2-yl)-2,3-dihydropyridazin-3-one (75 mg, 0.128 mmol, 1 equiv.) and TFA (2 mL) in DCM (8 mL) was stirred for 2 h at room temperature under N2 atmosphere. Desired product could be detected by LCMS. The resulting mixture was concentrated under vacuum. The crude product was purified by reverse phase flash with the following conditions (Column: Spherical C18 Column, 20-40 um, 120 g; Mobile Phase A: Water (0.1% FA), Mobile Phase B: ACN; Flow rate: 60 mL/min; Gradient: 30% B to 60% B in 30 min, 220 nm) to afford 4-chloro-5-(1-[[2-(difluoromethyl)-4-fluorophenyl]methyl]-3-(ethanesulfonyl)-1H,4H,5H,6H,7H-pyrazolo[4,3-c]pyridin-5-yl)-2,3-dihydropyridazin-3-one (30 mg, 46.70%) as a white solid.

PO

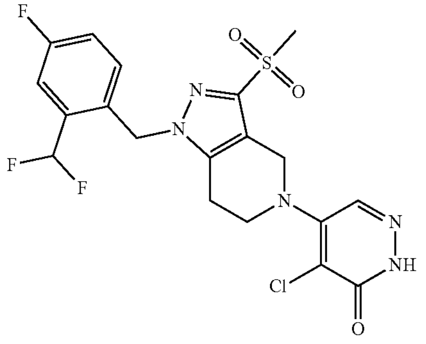

PP

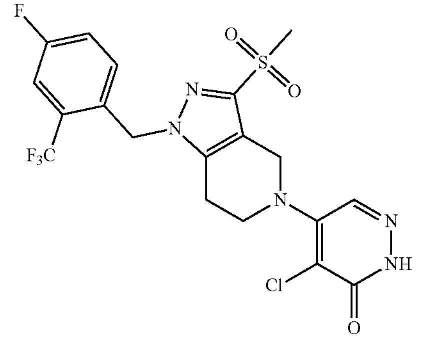

PO and PP were prepared by the methods and scheme described for PN by using corresponding (methanesulfonyl) sodium and bromides

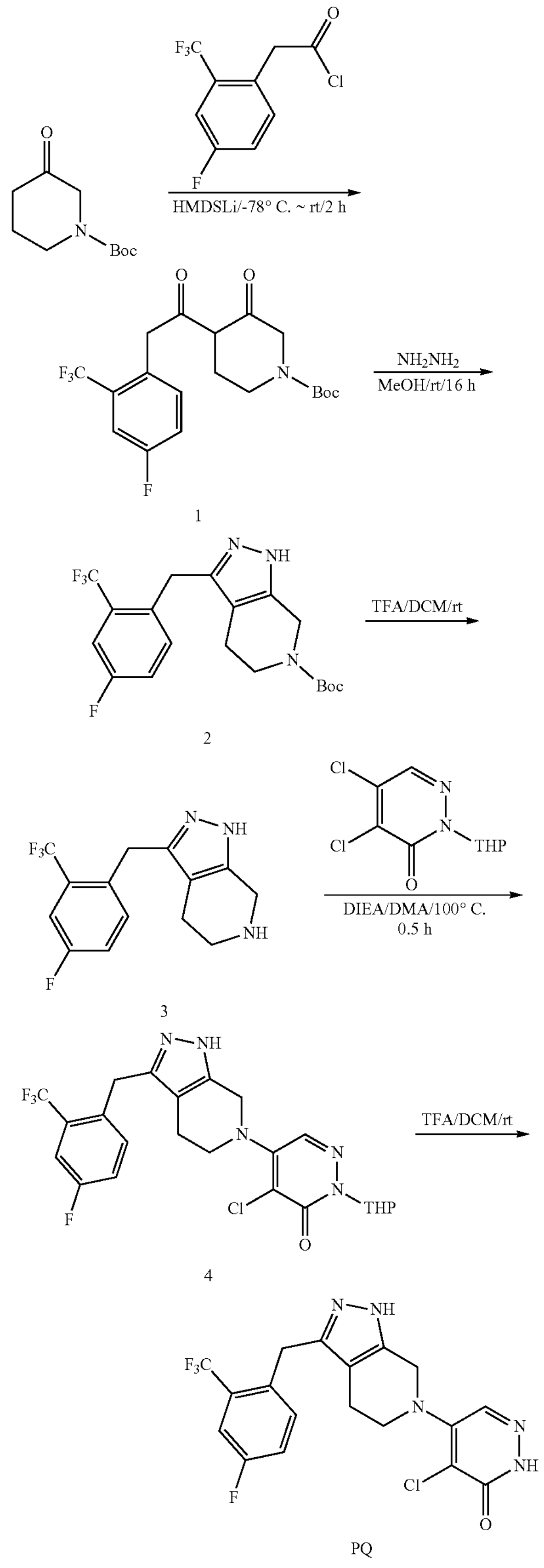

Preparation of PQ

Tert-Butyl 4-[2-[4-fluoro-2-(trifluoromethyl)phenyl]acetyl]-3-oxopiperidine-1-carboxylate To a stirred solution of tert-butyl 3-oxopiperidine-1-carboxylate (5 g, 25.094 mmol, 1 equiv.) in THF (100 mL) was added LiHMDS (25.09 mL, 25.094 mmol, 1 equiv.) dropwise over 10 min at −78 degrees celsius under nitrogen atmosphere. The mixture was allowed to warm up to −40 degrees C. To the above mixture was added 2-[4-fluoro-2-(trifluoromethyl)phenyl]acetyl chloride (6.04 g, 25.094 mmol, 1 equiv.) dropwise over 5 min at −40 degrees C. The resulting mixture was stirred for additional 2 h at room temperature. The reaction was monitored by LCMS. The reaction was quenched by the addition of AcOH (3 mL) at room temperature. The resulting mixture was concentrated under to afford tert-butyl 4-[2-[4-fluoro-2-(trifluoromethyl)phenyl]acetyl]-3-oxopiperidine-1-carboxylate (9.5 g, crude) as a brown oil.

Tert-Butyl 3-[[4-fluoro-2-(trifluoromethyl)phenyl]methyl]-1H,4H,5H,6H,7H-pyrazolo[3,4-c]pyridine-6-carboxylate To a stirred solution of tert-butyl 4-[2-[4-fluoro-2-(trifluoromethyl)phenyl]acetyl]-3-oxopiperidine-1-carboxylate (2 g, 4.958 mmol, 1 equiv.) in MeOH (50 mL) was added NH2NH2·H2O (2.48 g, 49.582 mmol, 10 equiv.) at room temperature. The resulting mixture was stirred for 16 h at room temperature. The reaction was monitored by LCMS. The resulting mixture was concentrated under vacuum. The residue was purified by reverse phase flash with the following conditions (Column: C18 Column 330 g; Mobile Phase A: Water (10 MMOL/L FA), Mobile Phase B: ACN; Flow rate: 80 mL/min; Gradient: 50% B to 70% B in 40 min; 254/220 nm) to afford tert-butyl 3-[[4-fluoro-2-(trifluoromethyl)phenyl]methyl]-1H,4H,5H,6H,7H-pyrazolo[3,4-c]pyridine-6-carboxylate (350 mg, 17.67%) as a light yellow solid.

3-[[4-Fluoro-2-(trifluoromethyl)phenyl]methyl]-1H,4H,5H,6H,7H-pyrazolo[3,4-c]pyridine To a stirred solution of tert-butyl 3-[[4-fluoro-2-(trifluoromethyl)phenyl]methyl]-1H,4H,5H,6H,7H-pyrazolo[3,4-c]pyridine-6-carboxylate (350 mg, 0.876 mmol, 1 equiv.) in DCM (4 mL) was added TFA (1 mL, 13.463 mmol, 15.36 equiv.) dropwise at room temperature. The resulting mixture was stirred for 2 h at room temperature. The reaction was monitored by LCMS. The resulting mixture was concentrated under reduced pressure. The residue was dissolved in MeOH (3 mL). The solution was basified to pH 8 with $NaHCO_3$. The resulting mixture was filtered, the filter cake was washed with CH2Cl2 (3×10 mL). The filtrate was concentrated under reduced pressure to afford 3-[[4-fluoro-2-(trifluoromethyl)phenyl]methyl]-1H,4H,5H,6H,7H-pyrazolo[3,4-c]pyridine (200 mg, crude) as a light yellow oil.

4-Chloro-5-(3-[[4-fluoro-2-(trifluoromethyl)phenyl]methyl]-1H,4H,5H,6H,7H-pyrazolo[3,4-c]pyridin-6-yl)-2-(oxan-2-yl)-2,3-dihydropyridazin-3-one To a stirred solution of 3-[[4-fluoro-2-(trifluoromethyl)phenyl]methyl]-1H,4H,5H,6H,7H-pyrazolo[3,4-c]pyridine (200 mg, 0.668 mmol, 1 equiv.) and 4,5-dichloro-2-(oxan-2-yl)-2,3-dihydropyridazin-3-one (332.93 mg, 1.337 mmol, 2.00 equiv.) in DMA (2 mL) was added DIEA (172.74 mg, 1.337 mmol, 2 equiv.) at room temperature. The resulting mixture was stirred for 0.5 h at 100 degrees C. The reaction was monitored by LCMS. The mixture was allowed to cool down to room temperature. The solution was purified by reverse phase flash with the following conditions (Column: C18 Column 120 g; Mobile Phase A: Water (10 MMOL/L AcOH), Mobile Phase B: ACN; Flow rate: 50 mL/min; Gradient: 30% B to 50% B in 40 min; 254/220 nm) to afford 4-chloro-5-(3-[[4-fluoro-2-(trifluoromethyl)phenyl]methyl]-1H,4H,5H,6H,7H-pyrazolo[3,4-c]pyridin-6-yl)-2-(oxan-2-yl)-2,3-dihydropyridazin-3-one (70 mg, 20.46%) as a light yellow oil.

4-Chloro-5-(3-[[4-fluoro-2-(trifluoromethyl)phenyl]methyl]-1H,4H,5H,6H,7H-pyrazolo[3,4-c]pyridin-6-yl)-2,3-dihydropyridazin-3-one To a stirred solution of 4-chloro-5-(3-[[4-fluoro-2-(trifluoromethyl)phenyl]methyl]-1H,4H,5H,6H,7H-pyrazolo[3,4-c]pyridin-6-yl)-2-(oxan-2-yl)-2,3-dihydropyridazin-3-one (70 mg, 0.137 mmol, 1 equiv.) in DCM (4.5 mL) was added TFA (0.5 mL, 6.732 mmol, 49.23 equiv.) dropwise at room temperature. The resulting mixture was stirred for 2 h at room temperature. The reaction was monitored by LCMS. The resulting mixture was concentrated under reduced pressure. The residue was purified by reverse phase flash with the following conditions (Column: C18 Column 120 g; Mobile Phase A: Water (10 MMOL/L NH4HCO3), Mobile Phase B: ACN; Flow rate: 50 mL/min; Gradient: 30% B to 50% B in 40 min; 254/220 nm) to afford 4-chloro-5-(3-[[4-fluoro-2-(trifluoromethyl)phenyl]methyl]-1H,4H,5H,6H,7H-pyrazolo[3,4-c]pyridin-6-yl)-2,3-dihydropyridazin-3-one (20 mg, 34.19%) as a off-white solid.

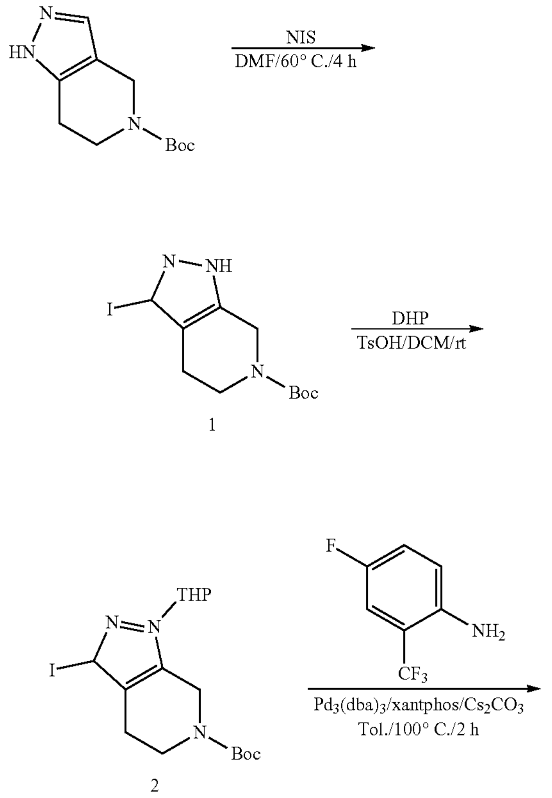

1

2

-continued

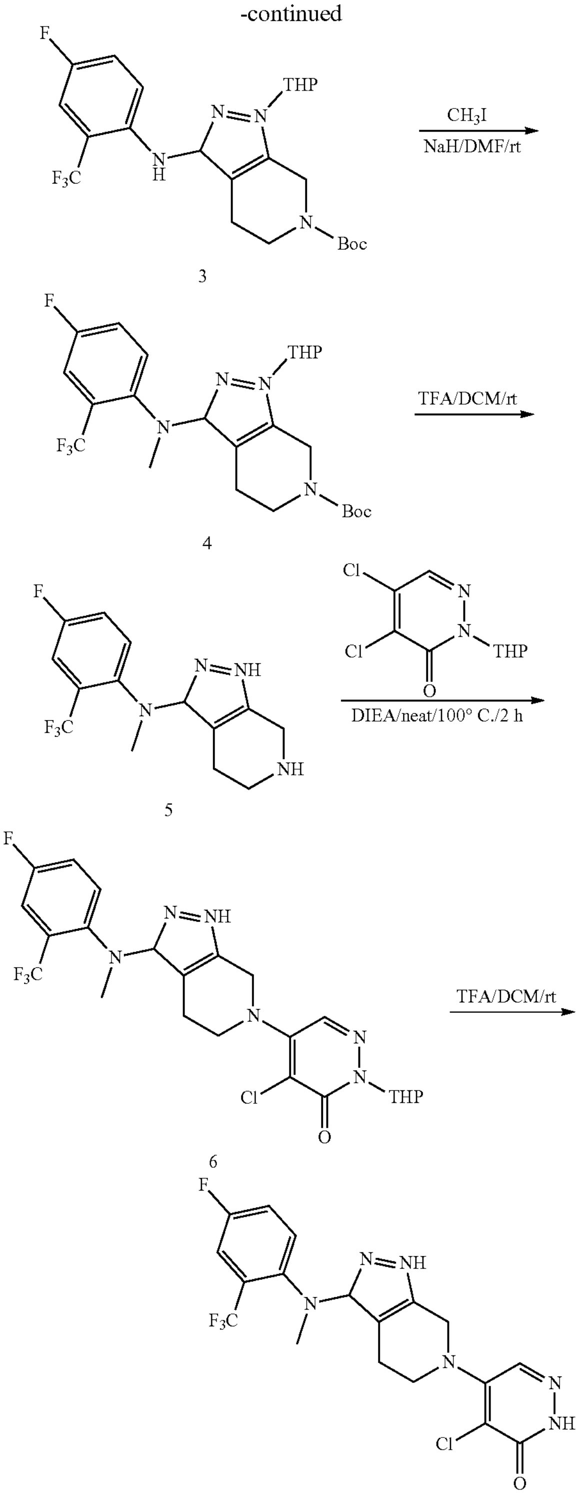

3

4

5

6

PR

Preparation of PR

Tert-Butyl 3-iodo-1H,4H,5H,6H,7H-pyrazolo[4,3-c]pyridine-5-carboxylate

To a stirred solution of tert-butyl 1H,4H,5H,6H,7H-pyrazolo[3,4-c]pyridine-6-carboxylate (1.0 g, 4.479 mmol, 1 equiv.) in DMF (20 mL) was added NIS (1209.18 mg, 5.375 mmol, 1.20 equiv.) in portions at rt under nitrogen atmosphere. The resulting mixture was stirred for 4 h at 60 degrees celsius under nitrogen atmosphere. The reaction was monitored by LCMS. The mixture was allowed to cool down to rt. The resulting mixture was extracted with EtOAc (3×200 mL). The combined organic layers were washed with brine (2×100 mL), dried over anhydrous Na2SO4. After filtration, the filtrate was concentrated under reduced pressure. The residue was purified by reverse phase flash chromatography with the following conditions: Column: Spherical C18, 20-40 um, 330 g; Mobile Phase A: Water (plus 5 mM NH4NO3); Mobile Phase B: ACN; Flow rate: 80 mL/min; Gradient: 5%-5% B, 10 min, 45% B-60% B gradient in 20 min; Detector: 220 nm. The fractions containing the desired product were collected at 55% B and concentrated under reduced pressure to afford tert-butyl 3-iodo-1H,4H,5H,6H,7H-pyrazolo[3,4-c]pyridine-6-carboxylate (1.1 g, 83.13%) as a yellow solid.

Tert-Butyl 3-iodo-1-(oxan-2-yl)-1H,4H,5H,6H,7H-pyrazolo[3,4-c]pyridine-6-carboxylate To a stirred mixture of tert-butyl 3-iodo-1H,4H,5H,6H,7H-pyrazolo[3,4-c]pyridine-6-carboxylate (1.1 g, 3.150 mmol, 1 equiv.) and 3,4-dihydro-2H-pyran (1.32 g, 15.692 mmol, 4.98 equiv.) in DCM (20 mL) was added TsOH (54.25 mg, 0.315 mmol, 0.10 equiv.) in portions at 0 degrees celsius under nitrogen atmosphere. The resulting mixture was stirred for 2 h at rt under nitrogen atmosphere. The reaction was monitored by LCMS. The resulting mixture was concentrated under reduced pressure. The resulting mixture was extracted with EtOAc (3×500 mL). The combined organic layers were washed with brine (2×300 mL), dried over anhydrous Na2SO4. After filtration, the filtrate was concentrated under reduced pressure. The residue was purified by reverse phase flash chromatography with the following conditions: Column: Spherical C18, 20-40 um, 330 g; Mobile Phase A: Water (plus 5 mM NH4NO3); Mobile Phase B: ACN; Flow rate: 80 mL/min; Gradient: 5%-5% B, 10 min, 55% B-70% B gradient in 20 min; Detector: 220 nm. The fractions containing the desired product were collected at 65% B and concentrated under reduced pressure to afford tert-butyl 3-iodo-1-(oxan-2-yl)-1H,4H,5H,6H,7H-pyrazolo[3,4-c]pyridine-6-carboxylate (1.3 g) as a yellow oil.

Tert-Butyl 3-[[4-fluoro-2-(trifluoromethyl)phenyl]amino]-1-(oxan-2-yl)-1H,4H,5H,6H,7H-pyrazolo[3,4-c]pyridine-6-carboxylate To a stirred mixture of tert-butyl 3-iodo-1-(oxan-2-yl)-1H,4H,5H,6H,7H-pyrazolo[3,4-c]pyridine-6-carboxylate (1.0 g, 2.308 mmol, 1 equiv.) and 4-fluoro-2-(trifluoromethyl)aniline (0.62 g, 3.461 mmol, 1.50 equiv.) in Toluene (40 mL) were added XantPhos (534.16 mg, 0.923 mmol, 0.4 equiv.), Pd2(dba)3 (211.34 mg, 0.231 mmol, 0.1 equiv.) and Cs2CO3 (1503.93 mg, 4.616 mmol, 2.00 equiv.) in portions at rt under nitrogen atmosphere. The resulting mixture was stirred for 2 h at 100 degrees celsius under nitrogen atmosphere. The reaction was monitored by LCMS. The mixture was allowed to cool down to rt. The resulting mixture was extracted with EtOAc (3×300 mL). The combined organic layers were washed with brine (2×200 mL), dried over anhydrous Na2SO4. After filtration, the filtrate was concentrated under reduced pressure. The residue was purified by reverse phase flash chromatography with the following conditions: Column: Spherical C18, 20-40 um, 330 g; Mobile Phase A: Water (plus 5 mM NH4NO3); Mobile Phase B: ACN; Flow rate: 80 mL/min; Gradient: 5%-5% B, 10 min, 45% B-90% B gradient in 30 min; Detector: 220 nm. The fractions containing the desired product were collected at 85% B and concentrated under reduced pressure to afford tert-butyl 3-[[4-fluoro-2-(trifluoromethyl)phenyl]amino]-1-(oxan-2-yl)-1H,4H,5H,6H,7H-pyrazolo[3,4-c]pyridine-6-carboxylate (150 mg, 13.41%) as a yellow oil.

Tert-Butyl 3-[[4-fluoro-2-(trifluoromethyl)phenyl](methyl)amino]-1-(oxan-2-yl)-1H,4H,5H,6H,7H-pyrazolo[3,4-c]pyridine-6-carboxylate To a stirred solution of tert-butyl 3-[[4-fluoro-2-(trifluoromethyl)phenyl]amino]-1-(oxan-2-yl)-1H,4H,5H,6H,7H-pyrazolo[3,4-c]pyridine-6-carboxylate (100 mg, 0.206 mmol, 1 equiv.) in DMF (10 mL) was added NaH (9.91 mg, 0.248 mmol, 1.20 equiv, 60%) at rt under nitrogen atmosphere. The reaction was stirred for 0.5 h at rt. Then CH3I (43.94 mg, 0.310 mmol, 1.5 equiv.) was added. The reaction mixture was stirred for 2 h at rt. The reaction was monitored by LCMS. The resulting mixture was extracted with EtOAc (3×200 mL). The combined organic layers were washed with brine (2×100 mL), dried over anhydrous Na2SO4. After filtration, the filtrate was concentrated under reduced pressure. The residue was purified by reverse phase flash chromatography with the following conditions: Column: Spherical C18, 20-40 um, 120 g; Mobile Phase A: Water (plus 5 mM NH4NO3); Mobile Phase B: ACN; Flow rate: 40 mL/min; Gradient: 5%-5% B, 10 min, 40% B-60% B gradient in 15 min; Detector: 220 nm. The fractions containing the desired product were collected at 50% B and concentrated under reduced pressure to afford tert-butyl 3-[[4-fluoro-2-(trifluoromethyl)phenyl](methyl)amino]-1-(oxan-2-yl)-1H,4H,5H,6H,7H-pyrazolo[3,4-c]pyridine-6-carboxylate (100 mg, 97.19%) as a yellow solid.

N-[4-fluoro-2-(trifluoromethyl)phenyl]-N-methyl-1H,4H,5H,6H,7H-pyrazolo[3,4-c]pyridin-3-amine To a stirred solution of tert-butyl 3-[[4-fluoro-2-(trifluoromethyl)phenyl](methyl)amino]-1-(oxan-2-yl)-1H,4H,5H,6H,7H-pyrazolo[3,4-c]pyridine-6-carboxylate (100 mg) in DCM (10 mL) was added TFA (1 mL) dropwise at rt. The reaction mixture was stirred for 2 h at rt. The reaction was monitored by LCMS. The resulting mixture was concentrated under reduced pressure. The residue was basified to pH=8 with saturated NH4HCO3 (aq.). The resulting mixture was extracted with CH2Cl2(2×50 mL). The combined organic layers were washed with brine (1×50 mL), dried over anhydrous Na2SO4. After filtration, the filtrate was concentrated under reduced pressure. The residue was purified by reverse phase flash chromatography with the following conditions: Column: Spherical C18, 20-40 um, 120 g; Mobile Phase A: Water (plus 5 mM NH4NO3); Mobile Phase B: ACN; Flow rate: 80 mL/min; Gradient: 5%-5% B, 10 min, 35% B-55% B gradient in 20 min; Detector: 220 nm. The fractions containing the desired product were collected at 45% B and concentrated under reduced pressure to afford N-[4-fluoro-2-(trifluoromethyl)phenyl]-N-methyl-1H,4H,5H,6H,7H-pyrazolo[3,4-c]pyridin-3-amine (50 mg) as a yellow oil.

4-Chloro-5-(3-[[4-fluoro-2-(trifluoromethyl)phenyl](methyl)amino]-1H,4H,5H,6H,7H-pyrazolo[3,4-c]pyridin-6-yl)-2-(oxan-2-yl)-2,3-dihydropyridazin-3-one Into a 25 mL round-bottom flask were added N-[4-fluoro-2-(trifluoromethyl)phenyl]-N-methyl-1H,4H,5H,6H,7H-pyrazolo[3,4-c]pyridin-3-amine (50 mg, 0.159 mmol, 1 equiv.), 4,5-dichloro-2-(oxan-2-yl)-2,3-dihydropyridazin-3-one (79.26 mg, 0.318 mmol, 2.00 equiv.) and DIEA (61.68 mg, 0.477 mmol, 3.00 equiv.) at rt under nitrogen atmosphere. The resulting mixture was stirred for 2 h at 90 degrees celsius under nitrogen atmosphere. The reaction was monitored by LCMS. The mixture was allowed to cool down to rt. The residue was purified by reverse phase flash chromatography with the following conditions: Column: Spherical C18, 20-40 um, 120 g; Mobile Phase A: Water (plus 5 mM NH4NO3); Mobile Phase B: ACN; Flow rate: 40 mL/min; Gradient: 5%-5% B, 10 min, 50% B-65% B gradient in 20 min; Detector: 220 nm. The fractions containing the desired product were collected at 55% B and concentrated under reduced pressure to afford 4-chloro-5-(3-[[4-fluoro-2-(trifluoromethyl)phenyl](methyl)amino]-1H,4H,5H,6H,7H-pyrazolo[3,4-c]pyridin-6-yl)-2-(oxan-2-yl)-2,3-dihydropyridazin-3-one (80 mg) as a yellow oil.

4-Chloro-5-(3-[[4-fluoro-2-(trifluoromethyl)phenyl](methyl)amino]-1H,4H,5H,6H,7H-pyrazolo[3,4-c]pyridin-6-yl)-2,3-dihydropyridazin-3-one To a stirred solution of 4-chloro-5-(3-[[4-fluoro-2-(trifluoromethyl)phenyl](methyl)amino]-1H,4H,5H,6H,7H-pyrazolo[3,4-c]pyridin-6-yl)-2-(oxan-2-yl)-2,3-dihydropyridazin-3-one (80 mg, 0.152 mmol, 1 equiv.) in DCM (10 mL) was added TFA (1 mL, 13.463 mmol, 88.67 equiv.) dropwise at rt. The reaction mixture was stirred for 2 h at rt. The reaction was monitored by LCMS. The resulting mixture was concentrated under reduced pressure. The residue was basified to pH=8 with saturated NH4HCO3 (aq.). The resulting mixture was extracted with EtOAc (2×100 mL). The combined organic layers were washed with brine (1×100 mL), dried over anhydrous Na2SO4. After filtration, the filtrate was concentrated under reduced pressure. The residue was purified by Prep-HPLC with the following conditions (Column: Sunfire Prep C18 OBD Column, 10 um, 19*250 mm; Mobile Phase A: Water (0.1% FA), Mobile Phase B: ACN; Flow rate: 25 mL/min; Gradient: 35% B to 55% B in 7 min; 254 nm; Rt: 6.5 min) to afford 4-chloro-5-(3-[[4-fluoro-2-(trifluoromethyl)phenyl](methyl)amino]-1H,4H,5H,6H,7H-pyrazolo[3,4-c]pyridin-6-yl)-2,3-dihydropyridazin-3-one (10.4 mg) as a white solid.

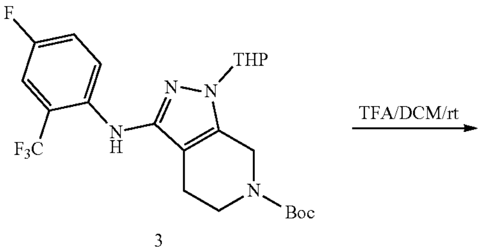

3

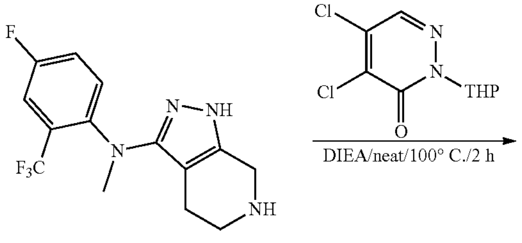

5

-continued

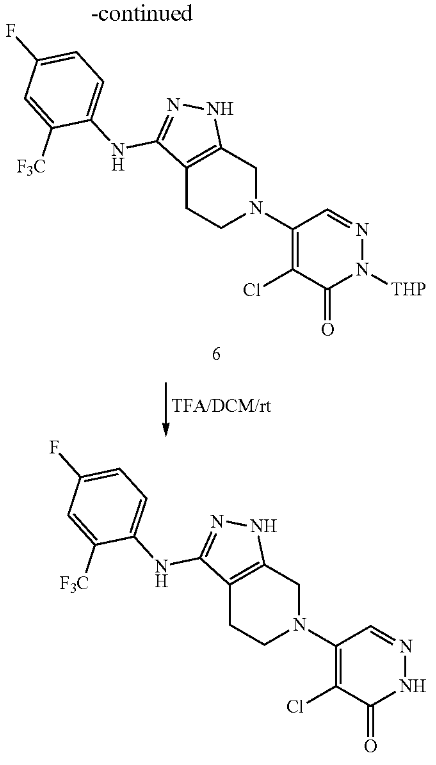

6

PS

Preparation of PS

N-[4-fluoro-2-(trifluoromethyl)phenyl]-1H,4H,5H,6H,7H-pyrazolo[3,4-c]pyridin-3-amine To a stirred solution of tert-butyl 3-[[4-fluoro-2-(trifluoromethyl)phenyl]amino]-1-(oxan-2-yl)-1H,4H,5H,6H,7H-pyrazolo[3,4-c]pyridine-6-carboxylate (50 mg, 0.103 mmol, 1 equiv.) in DCM (10 mL) was added TFA (1 mL, 13.463 mmol, 130.46 equiv.) dropwise at rt. The reaction mixture was stirred for 2 h at rt. The reaction was monitored by LCMS. The resulting mixture was concentrated under reduced pressure. The residue was basified to pH=8 with saturated NH4HCO3 (aq.). The resulting mixture was extracted with EtOAc (3×30 mL). The combined organic layers were washed with brine (1×20 mL), dried over anhydrous Na2SO4. After filtration, the filtrate was concentrated under reduced pressure. The residue was purified by Prep-HPLC with the following conditions (Column: XBridge Prep Phenyl OBD Column 19×150 mm 5 um 13 nm; Mobile Phase A:, Mobile Phase B:; Flow rate: 60 mL/min; Gradient: 13% B to 30% B in 7 min; 220 nm; Rt: 6.47 min) to afford N-[4-fluoro-2-(trifluoromethyl)phenyl]-1H,4H,5H,6H,7H-pyrazolo[3,4-c]pyridin-3-amine (25 mg, 80.68%) as a yellow oil.

4-Chloro-5-(3-[[4-fluoro-2-(trifluoromethyl)phenyl]amino]-1H,4H,5H,6H,7H-pyrazolo[3,4-c]pyridin-6-yl)-2-(oxan-2-yl)-2,3-dihydropyridazin-3-one Into a 25 mL round-bottom flask were added N-[4-fluoro-2-(trifluoromethyl)phenyl]-1H,4H,5H,6H,7H-pyrazolo[3,4-c]pyridin-3-amine (25 mg, 0.083 mmol, 1 equiv.), 4,5-dichloro-2-(oxan-2-yl)-2,3-dihydropyridazin-3-one (41.48 mg, 0.167 mmol, 2.00 equiv.) and DIEA (43.04 mg, 0.333 mmol, 4.00 equiv.) at rt under nitrogen atmosphere. The resulting mixture was stirred for 2 h at 90 degrees celsius under nitrogen atmosphere. The reaction was monitored by LCMS. The mixture was allowed to cool down to rt. The residue was purified by reverse phase flash chromatography with the following conditions: Column: Spherical C18, 20-40 um, 120 g; Mobile Phase A: Water (plus 5 mM NH4NO3); Mobile Phase B: ACN; Flow rate: 40 mL/min; Gradient: 5%-5% B, 10 min, 50% B-65% B gradient in 10 min; Detector: 220 nm. The fractions containing the desired product were collected at 58% B and concentrated under reduced pressure to afford 4-chloro-5-(3-[[4-fluoro-2-(trifluoromethyl)phenyl]amino]-1H,4H,5H,6H,7H-pyrazolo[3,4-c]pyridin-6-yl)-2-(oxan-2-yl)-2,3-dihydropyridazin-3-one (35 mg, 81.96%) as a yellow oil.

4-Chloro-5-(3-[[4-fluoro-2-(trifluoromethyl)phenyl]amino]-1H,4H,5H,6H,7H-pyrazolo[3,4-c]pyridin-6-yl)-2,3-dihydropyridazin-3-one To a stirred solution of 4-chloro-5-(3-[[4-fluoro-2-(trifluoromethyl)phenyl]amino]-1H,4H,5H,6H,7H-pyrazolo[3,4-c]pyridin-6-yl)-2-(oxan-2-yl)-2,3-dihydropyridazin-3-one (335 mg) in DCM (10 mL) was added TFA (1 mL) dropwise at rt. The reaction mixture was stirred for 2 h at rt. The reaction was monitored by LCMS. The resulting mixture was concentrated under reduced pressure. The residue was basified to pH=8 with saturated NH4HCO3 (aq.). The resulting mixture was extracted with EtOAc (2×30 mL). The combined organic layers were washed with brine (1×50 mL), dried over anhydrous Na2SO4. After filtration, the filtrate was concentrated under reduced pressure. The residue was purified by Prep-HPLC with the following conditions (Column: XBridge Prep Phenyl OBD Column 19×150 mm 5 um 13 nm; Mobile Phase A:, Mobile Phase B:; Flow rate: 60 mL/min; Gradient: 13% B to 30% B in 8 min; 220 nm; Rt: 7.67 min) to afford 4-chloro-5-(3-[[4-fluoro-2-(trifluoromethyl)phenyl]amino]-1H,4H,5H,6H,7H-pyrazolo[3,4-c]pyridin-6-yl)-2,3-dihydropyridazin-3-one (14.6 mg) as a white solid.

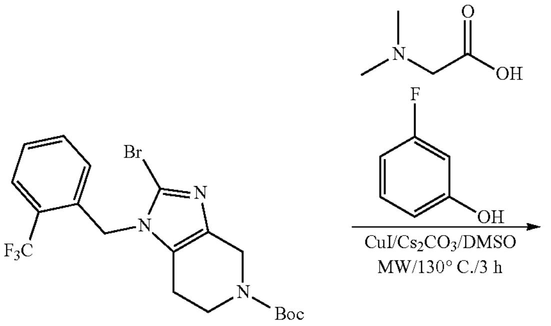

1

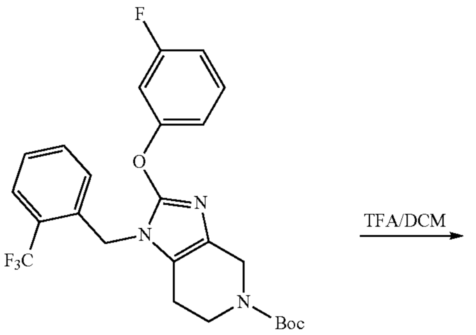

1

-continued

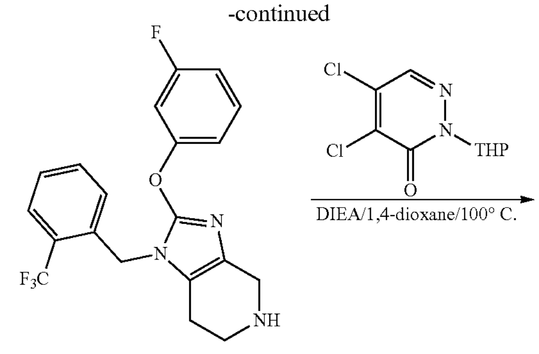

1

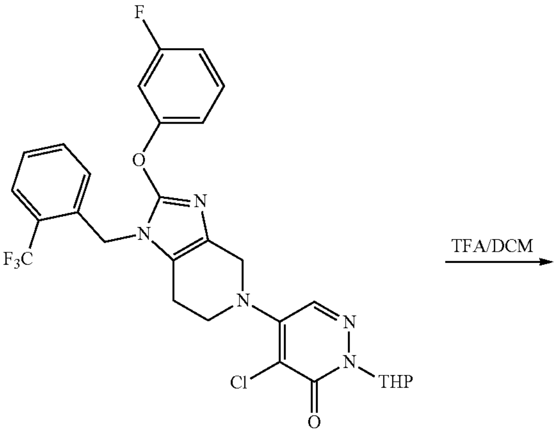

4

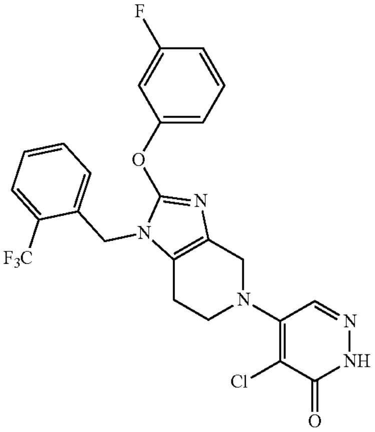

PT

Preparation of PT

Tert-Butyl 2-(3-fluorophenoxy)-1-[[2-(trifluoromethyl)phenyl]methyl]-1H,4H,5H,6H,7H-imidazo[4,5-c]pyridine-5-carboxylate To a stirred mixture of tert-butyl 2-bromo-1-[[2-(trifluoromethyl)phenyl]methyl]-1H,4H,5H,6H,7H-imidazo[4,5-c]pyridine-5-carboxylate (250 mg, 0.54 mmol, 1 equiv.) and 3-fluorophenol (121.8 mg, 1.09 mmol, 2.0 equiv.) in DMSO (5 mL) were added 2-(dimethylamino)acetic acid (33.6 mg, 0.33 mmol, 0.6 equiv.) and CuI (62.1 mg, 0.33 mmol, 0.6 equiv.) at room temperature under nitrogen atmosphere. Then Cs2CO3 (707.8 mg, 2.17 mmol, 4 equiv.) was added. The resulting mixture was stirred for 2 h at 130 degrees C. The reaction was monitored by LCMS. The mixture was allowed to cool down to room temperature. The reaction was quenched with Water at room temperature. The resulting mixture was extracted with EtOAc (3×200 mL). The combined organic layers were washed with brine (3×300 mL), dried over anhydrous Na2SO4. After filtration, the filtrate was concentrated under reduced pressure. The residue was purified by Prep-TLC (PE/EtOAc 5:1) to afford tert-butyl 2-(3-fluorophenoxy)-1-[[2-(trifluoromethyl)phenyl]methyl]-1H,4H,5H,6H,7H-imidazo[4,5-c]pyridine-5-carboxylate (100 mg, 37.46%) as a brown solid.

2-(3-Fluorophenoxy)-1-[[2-(trifluoromethyl)phenyl]methyl]-1H,4H,5H,6H,7H-imidazo[4,5-c]pyridine To a stirred solution of tert-butyl 2-(3-fluorophenoxy)-1-[[2-(trifluoromethyl)phenyl]methyl]-1H,4H,5H,6H,7H-imidazo[4,5-c]pyridine-5-carboxylate (350 mg, 0.71 mmol, 1 equiv.) in DCM (12 mL) was added TFA (2 mL, 26.93 mmol, 37.81 equiv.) at room temperature. The solution was stirred at rt for 2 h. The residue was purified by reverse phase flash to afford 2-(3-fluorophenoxy)-1-[[2-(trifluoromethyl)phenyl]methyl]-1H,4H,5H,6H,7H-imidazo[4,5-c]pyridine (220 mg, 78.94%) as colorless oil.

4-Chloro-5-[2-(3-fluorophenoxy)-1-[[2-(trifluoromethyl)phenyl]methyl]-1H,4H,5H,6H,7H-imidazo[4,5-c]pyridin-5-yl]-2-(oxan-2-yl)-2,3-dihydropyridazin-3-one To a stirred solution of 2-(3-fluorophenoxy)-1-[[2-(trifluoromethyl)phenyl]methyl]-1H,4H,5H,6H,7H-imidazo[4,5-c]pyridine (220 mg, 0.56 mmol, 1 equiv.) and 4,5-dichloro-2-(oxan-2-yl)-2,3-dihydropyridazin-3-one (140.0 mg, 0.56 mmol, 1 equiv.) was added DIEA (145.3 mg, 1.12 mmol, 2 equiv.) at room temperature. The solution was stirred at 100 degrees celsius for 16 h. The mixture was concentrated under reduced pressure. The residue was purified by Prep-TLC (PE/EtOAc 5:1) to afford 4-chloro-5-[2-(3-fluorophenoxy)-1-[[2-(trifluoromethyl)phenyl]methyl]-1H,4H,5H,6H,7H-imidazo[4,5-c]pyridin-5-yl]-2-(oxan-2-yl)-2,3-dihydropyridazin-3-one (100 mg, 29.45%) as a colorless oil.

4-Chloro-5-[2-(3-fluorophenoxy)-1-[[2-(trifluoromethyl)phenyl]methyl]-1H,4H,5H,6H,7H-imidazo[4,5-c]pyridin-5-yl]-2,3-dihydropyridazin-3-one To a stirred solution of 4-chloro-5-[2-(3-fluorophenoxy)-1-[[2-(trifluoromethyl)phenyl]methyl]-1H,4H,5H,6H,7H-imidazo[4,5-c]pyridin-5-yl]-2-(oxan-2-yl)-2,3-dihydropyridazin-3-one (100 mg, 0.17 mmol, 1 equiv.) in DCM (10 mL) was added TFA (2 mL, 26.93 mmol, 162.63 equiv.) at room temperature. The solution was stirred at rt for 4 h. The resulting mixture was concentrated under reduced pressure. The crude product (100 mg) was purified by Prep-HPLC with the following conditions (Column: XBridge Shield RP18 OBD Column, 5 um, 19*150 mm; Mobile Phase A: Water (10 MMOL/L NH4HCO3), Mobile Phase B: ACN; Flow rate: 20 mL/min; Gradient: 45% B to 60% B in 7 min; 220 nm; Rt: 6.18 min) to afford 4-chloro-5-[2-(3-fluorophenoxy)-1-[[2-(trifluoromethyl)phenyl]methyl]-1H,4H,5H,6H,7H-imidazo[4,5-c]pyridin-5-yl]-2,3-dihydropyridazin-3-one (74.4 mg, 86.44%) as a white solid.

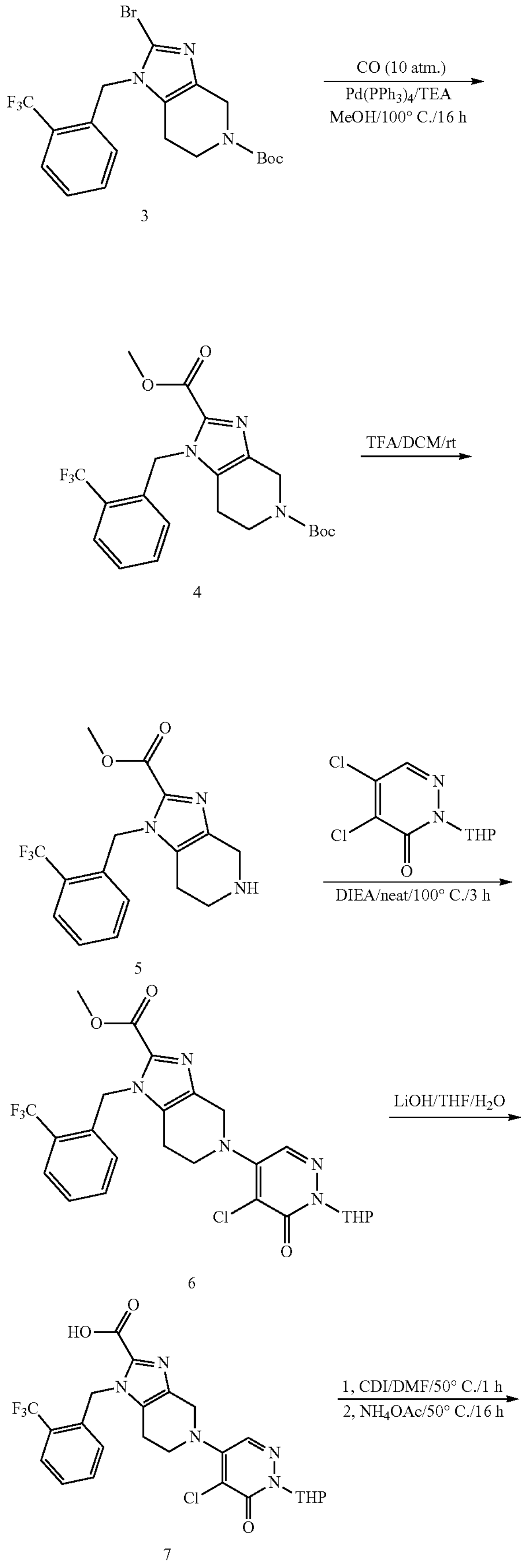

-continued

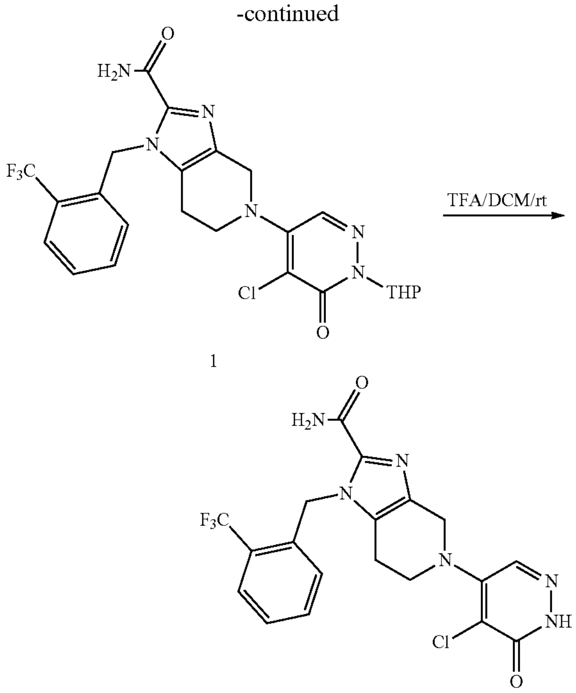

1

PU

Preparation of PU 5-tert-Butyl 2-methyl 1-[[2-(trifluoromethyl)phenyl] methyl]-1H,4H,5H,6H,7H-imidazo[4,5-c]pyridine-2, 5-dicarboxylate To a stirred mixture of tert-butyl 2-bromo-1-[[2-(trifluoromethyl)phenyl]methyl]-1H,4H,5H,6H,7H-imidazo[4,5-c] pyridine-5-carboxylate (1 g, 2.173 mmol, 1 equiv.) and TEA (0.44 g, 4.348 mmol, 2.00 equiv.) in MeOH (100 mL) was added Pd(PPh3)4 (0.25 g, 0.217 mmol, 0.1 equiv.) at room temperature under nitrogen atmosphere. The resulting mixture was stirred for 1 h at 100 degrees celsius under nitrogen atmosphere. The reaction was monitored by LCMS. The mixture was allowed to cool down to room temperature. The resulting mixture was concentrated under reduced pressure. The residue was purified by silica gel column chromatography, eluted with PE/EtOAc (10:1 to 1:1) to afford 5-tert-butyl 2-methyl 1-[[2-(trifluoromethyl)phenyl]methyl]-1H, 4H,5H,6H,7H-imidazo[4,5-c]pyridine-2,5-dicarboxylate (800 mg, 83.80%) as a brown solid.

Methyl 1-(2-(trifluoromethyl)benzyl)-4,5,6,7-tetrahydro-1H-imidazo[4,5-c]pyridine-2-carboxylate To a stirred solution of 5-tert-butyl 2-methyl 1-[[2-(trifluoromethyl)phenyl]methyl]-1H,4H,5H,6H,7H-imidazo[4, 5-c]pyridine-2,5-dicarboxylate (350 mg, 0.71 mmol, 1 equiv.) in DCM (12 mL) was added TFA (2 mL, 26.93 mmol, 37.81 equiv.) at room temperature. The solution was stirred at rt for 2 h. The residue was purified by reverse phase flash to afford methyl 1-(2-(trifluoromethyl)benzyl)-4,5,6,7-tetrahydro-1H-imidazo[4,5-c]pyridine-2-carboxylate (220 mg, 78.94%) as colorless oil.

Methyl 5-[5-chloro-1-(oxan-2-yl)-6-oxo-1,6-dihydropyridazin-4-yl]-1-[[2-(trifluoromethyl)phenyl] methyl]-1H,4H,5H,6H,7H-imidazo[4,5-c]pyridine-2-carboxylate To a stirred solution of methyl 1-[[2-(trifluoromethyl) phenyl]methyl]-1H,4H,5H,6H,7H-imidazo[4,5-c]pyridine-2-carboxylate (500 mg, 1.474 mmol, 1 equiv.) in DIEA (2 mL) was added 4,5-dichloro-2-(oxan-2-yl)-2,3-dihydropyridazin-3-one (734.09 mg, 2.947 mmol, 2.00 equiv.) at room temperature. The resulting mixture was stirred for 2 h at 90 degrees C. The reaction was monitored by LCMS. The mixture was allowed to cool down to room temperature. The residue was purified by silica gel column chromatography, eluted with PE/EtOAc (5:1 to 1:1) to afford methyl 5-[5-chloro-1-(oxan-2-yl)-6-oxo-1,6-dihydropyridazin-4-yl]-1-[[2-(trifluoromethyl)phenyl]methyl]-1H,4H,5H,6H,7H-imidazo[4,5-c]pyridine-2-carboxylate (600 mg, 73.77%) as a brown solid.

5-[5-chloro-1-(oxan-2-yl)-6-oxo-1,6-dihydropyridazin-4-yl]-1-[[2-(trifluoromethyl)phenyl] methyl]-1H,4H,5H,6H,7H-imidazo[4,5-c]pyridine-2-carboxylic Acid To a stirred solution of methyl 5-[5-chloro-1-(oxan-2-yl)-6-oxo-1,6-dihydropyridazin-4-yl]-1-[[2-(trifluoromethyl) phenyl]methyl]-1H,4H,5H,6H,7H-imidazo[4,5-c]pyridine-2-carboxylate (600 mg, 1.087 mmol, 1 equiv.) in THF (10 mL) and H2O (10 mL) was added LiOH (260.33 mg, 10.871 mmol, 10.00 equiv.) at room temperature. The resulting mixture was stirred for 16 h at 45 degrees C. The reaction was monitored by LCMS. The mixture was allowed to cool down to room temperature. The resulting mixture was concentrated under reduced pressure. The crude product was purified by reverse phase flash with the following conditions (Column: XBridge Prep OBD C18 Column 30×150 mm 5 um; Mobile Phase A: Water (10 MMOL/L NH4HCO3), Mobile Phase B: ACN; Flow rate: 60 mL/min; Gradient: 25% B to 45% B in 8 min; 220 nm; Rt: 7.48 min) to afford 5-[5-chloro-1-(oxan-2-yl)-6-oxo-1,6-dihydropyridazin-4-yl]-1-[[2-(trifluoromethyl)phenyl]methyl]-1H,4H,5H,6H, 7H-imidazo[4,5-c]pyridine-2-carboxylic acid (560 mg, 95.77%) as a brown solid.

5-[5-chloro-1-(oxan-2-yl)-6-oxo-1,6-dihydropyridazin-4-yl]-1-[[2-(trifluoromethyl)phenyl] methyl]-1H,4H,5H,6H,7H-imidazo[4,5-c]pyridine-2-carboxamide To a stirred mixture of 5-[5-chloro-1-(oxan-2-yl)-6-oxo-1,6-dihydropyridazin-4-yl]-1-[[2-(trifluoromethyl)phenyl] methyl]-1H,4H,5H,6H,7H-imidazo[4,5-c]pyridine-2-carboxylic acid (80 mg, 0.149 mmol, 1 equiv.) in DMF (10 mL) was added CDI (36.17 mg, 0.223 mmol, 1.5 equiv.) at room temperature under nitrogen atmosphere. The resulting mixture was stirred for 2 h at 45 degrees C. The reaction was monitored by LCMS. Then NH4OAc (22.93 mg, 0.297 mmol, 2.0 equiv.) was added at 45 degrees C. The resulting mixture was stirred for 16 h at 45 degrees C. The reaction was monitored by LCMS. The mixture was allowed to cool down to room temperature. The resulting mixture was concentrated under reduced pressure. The crude product was purified by reverse phase flash with the following conditions (Column: XBridge Prep OBD C18 Column 30×150 mm 5 um; Mobile Phase A: Water (10 MMOL/L NH4HCO3), Mobile Phase B: ACN; Flow rate: 60 mL/min; Gradient:

25% B to 48% B in 8 min; 220 nm; Rt: 7.78 min) to afford 5-[5-chloro-1-(oxan-2-yl)-6-oxo-1,6-dihydropyridazin-4-yl]-1-[[2-(trifluoromethyl)phenyl]methyl]-1H,4H,5H,6H,7H-imidazo[4,5-c]pyridine-2-carboxamide (30 mg, 37.57%) as a brown solid.

5-(5-chloro-6-oxo-1,6-dihydropyridazin-4-yl)-1-[[2-(trifluoromethyl)phenyl]methyl]-1H,4H,5H,6H,7H-imidazo[4,5-c]pyridine-2-carboxamide To a stirred solution of 5-[5-chloro-1-(oxan-2-yl)-6-oxo-1,6-dihydropyridazin-4-yl]-1-[[2-(trifluoromethyl)phenyl]methyl]-1H,4H,5H,6H,7H-imidazo[4,5-c]pyridine-2-carboxamide (30 mg, 0.056 mmol, 1 equiv.) in DCM (4 mL) was added TFA (1 mL) at room temperature. The resulting mixture was stirred for 1 h at room temperature. The reaction was monitored by LCMS. The resulting mixture was concentrated under reduced pressure. The mixture was basified to pH 7 with saturated NaHCO3 (aq.). The crude product (20 mg) was purified by Prep-HPLC with the following conditions (Column: XBridge Prep OBD C18 Column 30×150 mm 5 um; Mobile Phase A: Water (10 MMOL/L NH4HCO3), Mobile Phase B: ACN; Flow rate: 60 mL/min; Gradient: 25% B to 48% B in 8 min; 220 nm; Rt: 7.78 min) to afford 5-(5-chloro-6-oxo-1,6-dihydropyridazin-4-yl)-1-[[2-(trifluoromethyl)phenyl]methyl]-1H,4H,5H,6H,7H-imidazo[4,5-c]pyridine-2-carboxamide (10.7 mg, 42.29%) as a white solid.

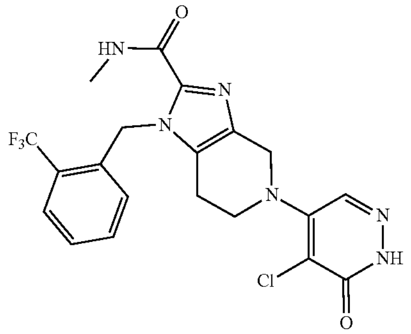

PV

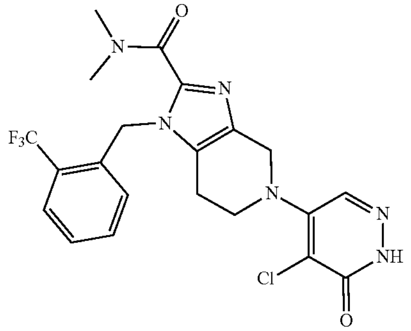

PW

PV and PW were prepared by the methods and scheme described for PU by using corresponding amines.

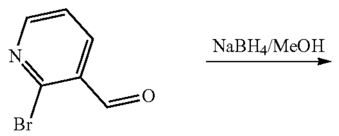

-continued

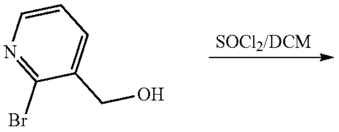

1

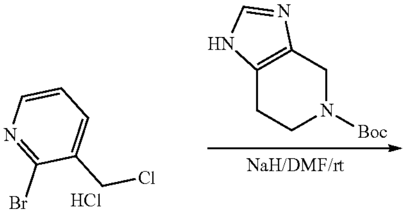

2

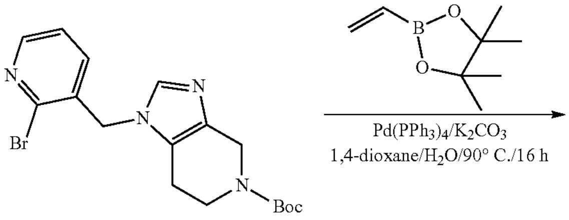

3

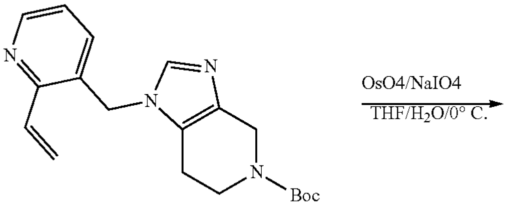

4

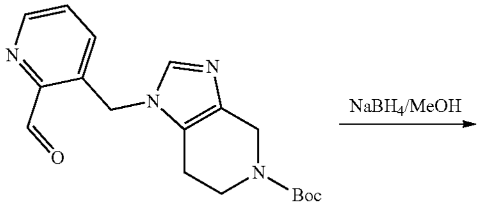

5

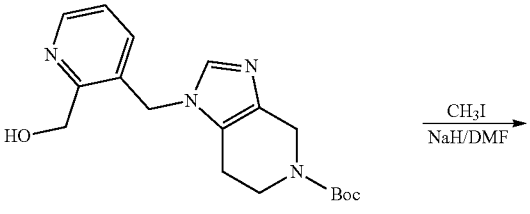

6

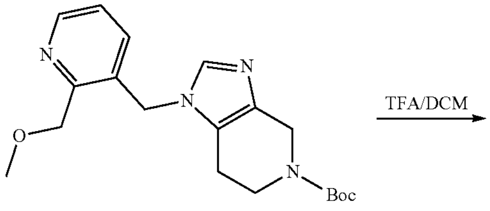

7

-continued

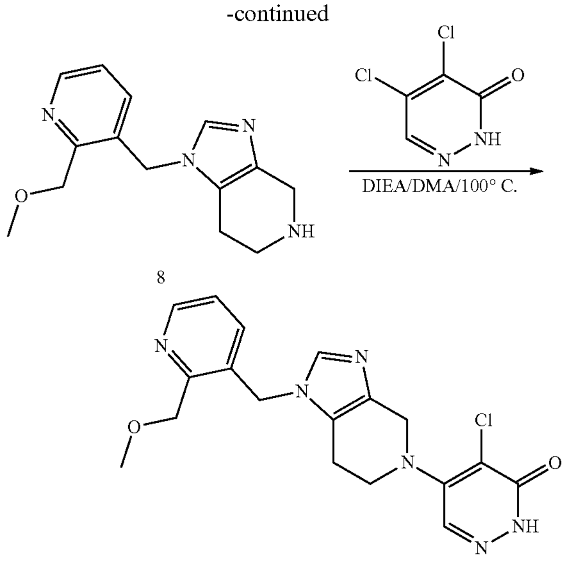

8

PX

Preparation of PX

(2-Bromopyridin-3-yl)methanol

To a stirred solution of 2-bromopyridine-3-carbaldehyde (10 g, 53.76 mmol, 1 equiv.) in MeOH was added NaBH4 (5.1 g, 134.40 mmol, 2.5 equiv.) in portions at 0 degrees celsius under nitrogen atmosphere. The reaction was monitored by TLC (DCM/MeOH=20/1). The resulting mixture was concentrated under vacuum. The residue was dissolved in EtOAc (200 mL). The resulting mixture was washed with 3×100 mL of water. The crude product was used in the next step (E01163-004) directly without further purification.

Tert-Butyl 1H,4H,5H,6H,7H-imidazo[4,5-c]pyridine-5-carboxylate

To a stirred solution of (2-bromopyridin-3-yl)methanol (9.0 g, 47.87 mmol, 1 equiv.) in DCM was added sulfurooyl dichloride (17.1 g, 143.60 mmol, 3 equiv.) dropwise at 0 degrees celsius under nitrogen atmosphere. The reaction was monitored by TLC (DCM/MeOH=20:1). The resulting mixture was concentrated under vacuum. The residue was purified by trituration with hexane (30 mL) to afford 2-bromo-3-(chloromethyl)pyridine (11 g) as an off-white solid.

Tert-Butyl 1-[(2-bromopyridin-3-yl)methyl]-1H,4H,5H,6H,7H-imidazo[4,5-c]pyridine-5-carboxylate To a stirred solution of tert-butyl 1H,4H,5H,6H,7H-imidazo[4,5-c]pyridine-5-carboxylate (3 g, 13.44 mmol, 1 equiv.) in DMF (60 mL) was added NaH (0.8 g, 20.15 mmol, 1.5 equiv, 60%) dropwise at 0 degrees celsius under nitrogen atmosphere. The resulting mixture was stirred for 30 min at 0 degrees C. Then the resulting mixture was stirred for 1.5 h at ambient temperature. The reaction was added 2-bromo-3-(chloromethyl)pyridine hydrochloride (4.2 g, 17.47 mmol, 1.3 equiv.) and Cs2CO3 (8.8 g, 26.87 mmol, 2 equiv.) at 0 degrees C. The resulting mixture was stirred for 16 h at ambient temperature. The desired product could be detected by LCMS. The reaction mixture was diluted with water (800 mL) and extracted with EA (600 mL×2). The organic layer was concentrated to afford crude product. The crude product was purified by reverse phase flash with the following conditions (Column: c18 OBD Column, 5 um, 19*330 mm; Mobile Phase A: Water (5 MMOL/L $NaHCO_3$), Mobile Phase B: ACN; Flow rate: 80 mL/min; Gradient: 25% B to 65% B in 40 min; 220 nm; Rt: 25.0 min) to afford tert-butyl 1-[(2-bromopyridin-3-yl)methyl]-1H,4H,5H,6H,7H-imidazo[4,5-c]pyridine-5-carboxylate (3.215 g, 60.84%) as a yellow solid.

Tert-Butyl 1-[(2-ethenylpyridin-3-yl)methyl]-1H,4H,5H,6H,7H-imidazo[4,5-c]pyridine-5-carboxylate To a solution of tert-butyl 1-[(2-bromopyridin-3-yl)methyl]-1H,4H,5H,6H,7H-imidazo[4,5-c]pyridine-5-carboxylate (3.2 g, 8.14 mmol, 1 equiv.) in 1,4-dioxane (50 mL) and water (10 mL) were added K2CO3 (2.2 g, 15.92 mmol, 1.96 equiv.) and Pd(PPh3)4 (0.9 g, 0.78 mmol, 0.10 equiv.) at room temperature under nitrogen atmosphere. The resulting mixture was stirred for 16 h at 90 degrees C. The desired product could be detected by LCMS and TLC. The mixture was allowed to cool down to room temperature. The reaction mixture was diluted with water (400 mL) and extracted with EA (500 mL×2). The organic layers was washed with saturated brine (200 mL), dried over anhydrous Na2SO4, filtered and concentrated to give desired product. The residue was purified by silica gel column chromatography, eluted with PE/EA (10:1 to 2:1) and DCM/MeoH (50:1 to 20:1) to afford tert-butyl 1-[(2-ethenylpyridin-3-yl)methyl]-1H,4H,5H,6H,7H-imidazo[4,5-c]pyridine-5-carboxylate (2.8 g, 101.09%) as a yellow liquid.

Tert-Butyl 1-[(2-formylpyridin-3-yl)methyl]-1H,4H,5H,6H,7H-imidazo[4,5-c]pyridine-5-carboxylate To a solution of tert-butyl 1-[(2-ethenylpyridin-3-yl)methyl]-1H,4H,5H,6H,7H-imidazo[4,5-c]pyridine-5-carboxylate (2.7 g, 7.93 mmol, 1 equiv.) in DCM (50 mL) and H2O (10 mL) was added K2OsO4.2H2O (0.3 g, 0.81 mmol, 0.10 equiv.) at ambient temperature. Then the resulting mixture was stirred for 5 min at 0 degrees C. The reaction was batch added NaIO4 (6.8 g, 31.79 mmol, 4.01 equiv.) at 0 degrees C. The resulting mixture was stirred for 7 h at 0 degrees C. The desired product could be detected by LCMS. The reaction mixture was diluted with Sodium Hyposulfite (aq) (400 mL) and extracted with EA (500 mL×2). The organic layer was washed with saturated brine (400 mL), dried over anhydrous Na2SO4, filtered and concentrated to give desired product. The residue was purified by silica gel column chromatography, eluted with PE/EA (40:1 to 2:1) to afford tert-butyl 1-[(2-formylpyridin-3-yl)methyl]-1H,4H,5H,6H,7H-imidazo[4,5-c]pyridine-5-carboxylate (800 mg, 29.46%) as a white solid.

Tert-Butyl 1-[[2-(hydroxymethyl)pyridin-3-yl]methyl]-1H,4H,5H,6H,7H-imidazo[4,5-c]pyridine-5-carboxylate To a stirred solution of tert-butyl 1-[(2-formylpyridin-3-yl)methyl]-1H,4H,5H,6H,7H-imidazo[4,5-c]pyridine-5-carboxylate (250 mg, 0.73 mmol, 1 equiv.) in MeOH (10 mL) was added NaBH4 (55.2 mg, 1.46 mmol, 2.00 equiv.) in portions at 0 degrees celsius under nitrogen atmosphere. The resulting mixture was stirred for 4 h at rt under nitrogen atmosphere. The reaction was monitored by LCMS. The resulting mixture was concentrated under reduced pressure.

The residue was purified by reverse phase flash with the following conditions (Column, C18 silica gel; mobile phase, ACN in water, 20% to 50% gradient in 10 min; detector, UV 254 nm) to afford tert-butyl 1-[[2-(hydroxymethyl)pyridin-3-yl]methyl]-1H,4H,5H,6H,7H-imidazo[4,5-c]pyridine-5-carboxylate (200 mg, 79.53%) as a yellow oil.

Tert-Butyl 1-[[2-(methoxymethyl)pyridin-3-yl] methyl]-1H,4H,5H,6H,7H-imidazo[4,5-c]pyridine-5-carboxylate To a stirred solution of tert-butyl 1-[[2-(hydroxymethyl) pyridin-3-yl]methyl]-1H,4H,5H,6H,7H-imidazo[4,5-c]pyridine-5-carboxylate (200 mg, 0.58 mmol, 1 equiv.) in DMF (8 mL) was added NaH (27.9 mg, 1.16 mmol, 2.00 equiv.) at 0 degrees celsius under nitrogen atmosphere. The reaction was stirred for 1 h at rt. Then CH3I (123.6 mg, 0.87 mmol, 1.50 equiv.) was added. The reaction mixture was stirred for 4 h at rt. The reaction was monitored by LCMS. The reaction was quenched by the addition of H2O (2 mL) at rt. The residue was purified by reverse phase flash with the following conditions (Column, C18 silica gel; mobile phase, ACN in water, 20% to 60% gradient in 25 min; detector, UV 220 nm) to afford tert-butyl 1-[[2-(methoxymethyl)pyridin-3-yl] methyl]-1H,4H,5H,6H,7H-imidazo[4,5-c]pyridine-5-carboxylate (200 mg, 96.09%) as a yellow oil.

3-([1H,4H,5H,6H,7H-imidazo[4,5-c]pyridin-1-yl] methyl)-2-(methoxymethyl)pyridine To a stirred solution of tert-butyl 1-[[2-(methoxymethyl) pyridin-3-yl]methyl]-1H,4H,5H,6H,7H-imidazo[4,5-c]pyridine-5-carboxylate (200 mg, 0.56 mmol, 1 equiv.) in DCM (10 mL) was added TFA (1 mL, 13.46 mmol, 24.13 equiv.) dropwise at rt. The reaction mixture was stirred for 2 h at rt. The reaction was monitored by LCMS. The resulting mixture was concentrated under reduced pressure. The residue was basified to pH=8 with saturated NH4HCO3 (aq.). The resulting mixture was extracted with CH2Cl2(3×100 mL). The combined organic layers were washed with brine (1×50 mL), dried over anhydrous Na2SO4. After filtration, the filtrate was concentrated under reduced pressure. The residue was purified by Prep-TLC (CH2Cl2/MeOH 15/1) to afford 3-([1H,4H,5H,6H,7H-imidazo[4,5-c]pyridin-1-yl] methyl)-2-(methoxymethyl)pyridine (120 mg, 83.25%) as a yellow oil.

4-Chloro-5-(1-[[2-(methoxymethyl)pyridin-3-yl] methyl]-1H,4H,5H,6H,7H-imidazo[4,5-c]pyridin-5-yl)-2-(oxan-2-yl)-2,3-dihydropyridazin-3-one Into a 25 mL round-bottom flask were added 3-([1H,4H,5H,6H,7H-imidazo[4,5-c]pyridin-1-yl]methyl)-2-(methoxymethyl)pyridine (120 mg, 0.46 mmol, 1 equiv.), 4,5-dichloro-2-(oxan-2-yl)-2,3-dihydropyridazin-3-one (231.4 mg, 0.93 mmol, 2.00 equiv.) and DIEA (120.1 mg, 0.93 mmol, 2.00 equiv.) at rt under nitrogen atmosphere. The resulting mixture was stirred for 16 h at 90 degrees celsius under nitrogen atmosphere. The residue was purified by Prep-TLC (PE/EtOAc=5/1) to afford 4-chloro-5-(1-[[2-(methoxymethyl)pyridin-3-yl]methyl]-1H,4H,5H,6H,7H-imidazo[4,5-c]pyridin-5-yl)-2-(oxan-2-yl)-2,3-dihydropyridazin-3-one (150 mg, 68.56%) as a yellow oil.

4-chloro-5-(1-[[2-(methoxymethyl)pyridin-3-yl] methyl]-1H,4H,5H,6H,7H-imidazo[4,5-c]pyridin-5-yl)-2,3-dihydropyridazin-3-one To a stirred solution of 4-chloro-5-(1-[[2-(methoxymethyl)pyridin-3-yl]methyl]-1H,4H,5H,6H,7H-imidazo[4,5-c]pyridin-5-yl)-2-(oxan-2-yl)-2,3-dihydropyridazin-3-one (150 mg, 0.32 mmol, 1 equiv.) in DCM (10 mL) was added TFA (1 mL, 13.46 mmol, 42.27 equiv.) dropwise at rt. The reaction mixture was stirred for 4 h at rt. The reaction was monitored by LCMS. The resulting mixture was concentrated under reduced pressure. The residue was basified to pH=8 with saturated NH4HCO3 (aq.). The resulting mixture was extracted with CH2Cl2(3×100 mL). The combined organic layers were washed with brine (1×100 mL), dried over anhydrous Na2SO4. After filtration, the filtrate was concentrated under reduced pressure. The residue was purified by Prep-HPLC with the following conditions (Column: XBridge Shield RP18 OBD Column 30*150 mm, 5 um; Mobile Phase A: Water (10 MMOL/L NH4HCO3), Mobile Phase B: ACN; Flow rate: 60 mL/min; Gradient: 10% B to 20% B in 7 min; 254; 220 nm; Rt: 6.4, 6.9 min) to afford 4-chloro-5-(1-[[2-(methoxymethyl)pyridin-3-yl]methyl]-1H,4H,5H,6H,7H-imidazo[4,5-c]pyridin-5-yl)-2,3-dihydropyridazin-3-one (9.8 mg) as a white solid.

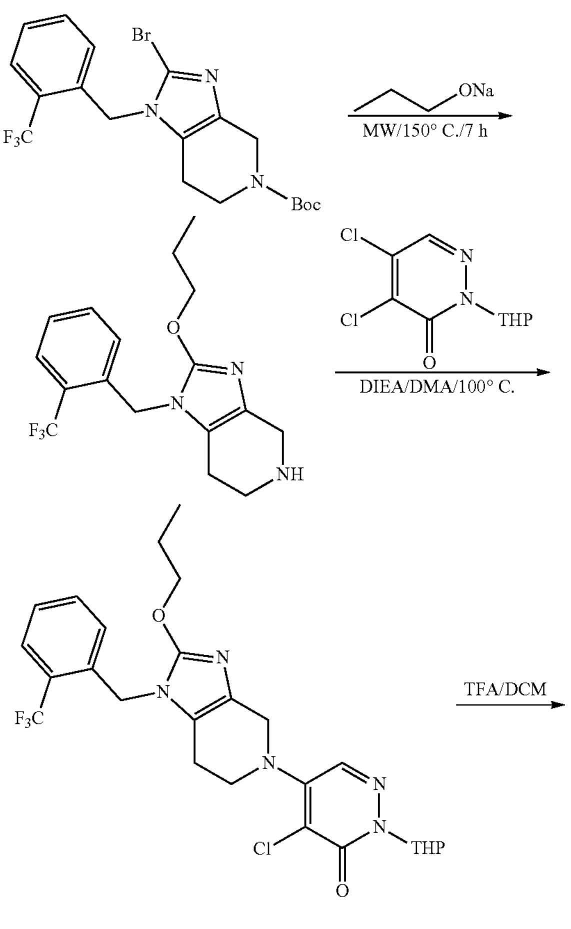

-continued

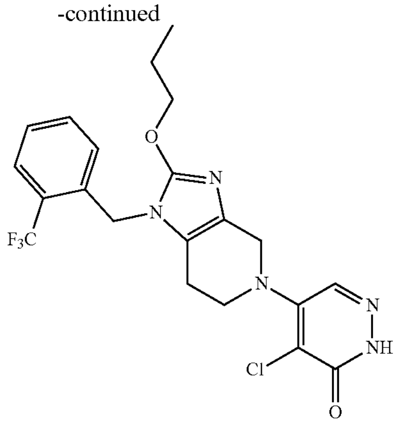

PY

Preparation of PY

Tert-Butyl 2-propoxy-1-[[2-(trifluoromethyl)phenyl]methyl]-1H,4H,5H,6H,7H-imidazo[4,5-c]pyridine-5-carboxylate To a stirred solution of Na (0.4 g, 17.40 mmol, 8.01 equiv.) in n-propanol (15 mL) was added tert-butyl 2-bromo-1-[[2-(trifluoromethyl)phenyl]methyl]-1H,4H,5H,6H,7H-imidazo[4,5-c]pyridine-5-carboxylate (1 g, 2.17 mmol, 1 equiv.) at room temperature under nitrogen atmosphere. The resulting mixture was stirred for 10 h at 130 degrees celsius under nitrogen atmosphere. The reaction was monitored by LCMS. The mixture was allowed to cool down to room temperature. The reaction was quenched by the addition of Water (300 mL) at room temperature. The resulting mixture was extracted with EtOAc (3×100 mL). The combined organic layers were washed with brine (3×100 mL), dried over anhydrous Na2SO4. After filtration, the filtrate was concentrated under reduced pressure. The crude product was purified by reverse phase flash with the following conditions (Column: XBridge Prep OBD C18 Column 30×150 mm 5 um; Mobile Phase A: Water (10 MMOL/L NH4HCO3), Mobile Phase B: ACN; Flow rate: 60 mL/min; Gradient: 40% B to 60% B in 7 min; 220 nm; Rt: 6.28 min) to afford tert-butyl 2-propoxy-1-[[2-(trifluoromethyl)phenyl]methyl]-1H,4H,5H,6H,7H-imidazo[4,5-c]pyridine-5-carboxylate (380 mg, 39.80%) as a brown solid.

4-Chloro-2-(oxan-2-yl)-5-(2-propoxy-1-[[2-(trifluoromethyl)phenyl]methyl]-1H,4H,5H,6H,7H-imidazo[4,5-c]pyridin-5-yl)-2,3-dihydropyridazin-3-one To a stirred solution of 2-propoxy-1-[[2-(trifluoromethyl)phenyl]methyl]-1H,4H,5H,6H,7H-imidazo[4,5-c]pyridine (380 mg, 1.12 mmol, 1 equiv.) in DIEA (3 mL, 2.0 equiv.) was added 4,5-dichloro-2-(oxan-2-yl)-2,3-dihydropyridazin-3-one (334.7 mg, 1.34 mmol, 1.2 equiv.) at room temperature under nitrogen atmosphere. The resulting mixture was stirred for 2 h at 100 degrees C. The reaction was monitored by LCMS. The mixture was allowed to cool down to room temperature. The residue was purified by Prep-TLC (PE/EtOAc 1:1) to afford 4-chloro-2-(oxan-2-yl)-5-(2-propoxy-1-[[2-(trifluoromethyl)phenyl]methyl]-1H,4H,5H,6H,7H-imidazo[4,5-c]pyridin-5-yl)-2,3-dihydropyridazin-3-one (400 mg, 64.71%) as a brown solid.

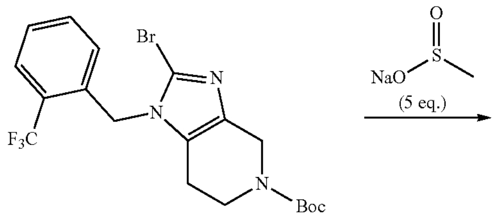

1

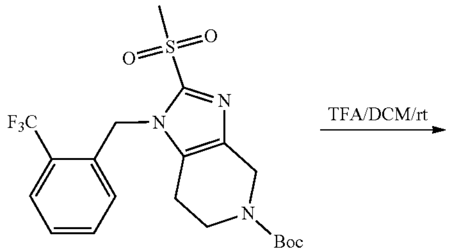

3

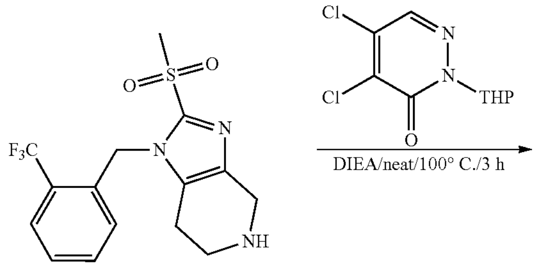

4

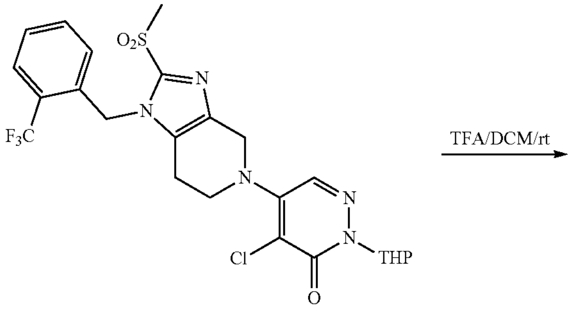

5

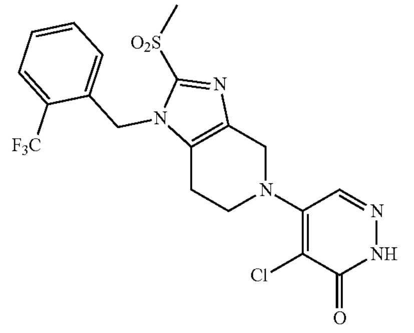

PZ

Preparation of PZ

Tert-Butyl 2-methanesulfonyl-1-[[2-(trifluoromethyl)phenyl]methyl]-1H,4H,5H,6H,7H-imidazo[4,5-c]pyridine-5-carboxylate To a stirred mixture of tert-butyl 2-bromo-1-[[2-(trifluoromethyl)phenyl]methyl]-1H,4H,5H,6H,7H-imidazo[4,5-c]pyridine-5-carboxylate (400 mg, 0.869 mmol, 1 equiv.) and sodium methanesulfinate (443.54 mg, 4.345 mmol, 5 equiv.) in DMSO (20 mL) was added CuI (16.55 mg, 0.087 mmol, 0.1 equiv.) at room temperature under nitrogen atmosphere. The final reaction mixture was irradiated with microwave radiation for 1 h at 130 degrees C. The reaction was monitored by LCMS. The mixture was allowed to cool down to room temperature. The crude product was purified by reverse phase flash with the following conditions (Column: C18,330 g; Mobile Phase A: Water/0.05% TFA, Mobile Phase B:ACN; Flow rate:80 mL/min; Gradient: 60% B to 75% B in 10 min; Detector, 220 nm and 254 nm) to afford tert-butyl 2-methanesulfonyl-1-[[2-(trifluoromethyl)phenyl]methyl]-1H,4H,5H,6H,7H-imidazo[4,5-c]pyridine-5-carboxylate (110 mg, 27.55%) as a yellow oil.

2-Methanesulfonyl-1-[[2-(trifluoromethyl)phenyl]methyl]-1H,4H,5H,6H,7H-imidazo[4,5-c]pyridine To a stirred solution of tert-butyl 2-methanesulfonyl-1-[[2-(trifluoromethyl)phenyl]methyl]-1H,4H,5H,6H,7H-imidazo[4,5-c]pyridine-5-carboxylate (110 mg, 0.239 mmol, 1 equiv.) in DCM (4 mL) was added TFA (1 mL, 13.463 mmol, 56.24 equiv.) at room temperature. The resulting mixture was stirred for 2 h at room temperature. The reaction was monitored by LCMS. The resulting mixture was concentrated under reduced pressure. The residue was basified to pH 8 with saturated NaHCO3 (aq.). The crude product was purified by reverse phase flash with the following conditions (Column:C18,120 g; Mobile Phase A: Water/0.05% NH4HCO3, Mobile Phase B:ACN; Flow rate:40 mL/min; Gradient: 30% B to 45% B in 10 min; Detector, 220 nm and 254 nm) to afford 2-methanesulfonyl-1-[[2-(trifluoromethyl)phenyl]methyl]-1H,4H,5H,6H,7H-imidazo[4,5-c]pyridine (60 mg, 69.74%) as a yellow oil.

4-Chloro-5-(2-methanesulfonyl-1-[[2-(trifluoromethyl)phenyl]methyl]-1H,4H,5H,6H,7H-imidazo[4,5-c]pyridin-5-yl)-2-(oxan-2-yl)-2,3-dihydropyridazin-3-one To a stirred solution of 2-methanesulfonyl-1-[[2-(trifluoromethyl)phenyl]methyl]-1H,4H,5H,6H,7H-imidazo[4,5-c]pyridine (60 mg, 0.167 mmol, 1 equiv.) in DIEA (0.5 mL) was added 4,5-dichloro-2-(oxan-2-yl)-2,3-dihydropyridazin-3-one (62.38 mg, 0.250 mmol, 1.5 equiv.) at room temperature. The resulting mixture was stirred for 2 h at 100 degrees C. The reaction was monitored by LCMS. The mixture was allowed to cool down to room temperature. The residue was purified by Prep-TLC (PE/EtOAc=1:1) to afford 4-chloro-5-(2-methanesulfonyl-1-[[2-(trifluoromethyl)phenyl]methyl]-1H,4H,5H,6H,7H-imidazo[4,5-c]pyridin-5-yl)-2-(oxan-2-yl)-2,3-dihydropyridazin-3-one (80 mg, 83.77%) as a yellow oil.

4-Chloro-5-(2-methanesulfonyl-1-[[2-(trifluoromethyl)phenyl]methyl]-1H,4H,5H,6H,7H-imidazo[4,5-c]pyridin-5-yl)-2,3-dihydropyridazin-3-one To a stirred solution of 4-chloro-5-(2-methanesulfonyl-1-[[2-(trifluoromethyl)phenyl]methyl]-1H,4H,5H,6H,7H-imidazo[4,5-c]pyridin-5-yl)-2-(oxan-2-yl)-2,3-dihydropyridazin-3-one (80 mg, 0.140 mmol, 1 equiv.) in DCM (4 mL) was added TFA (1 mL, 13.463 mmol, 96.26 equiv.) at room temperature. The resulting mixture was stirred for 2 h at room temperature. The reaction was monitored by LCMS. The resulting mixture was concentrated under reduced pressure. The residue was basified to pH 8 with saturated NaHCO3 (aq.). The crude product was purified by reverse phase flash with the following conditions (Column:C18,120 g; Mobile Phase A: Water/0.05% NH4HCO3, Mobile Phase B:ACN; Flow rate:45 mL/min; Gradient: 30% B to 50% B in 12 min; Detector, 220 nm and 254 nm) to afford 4-chloro-5-(2-methanesulfonyl-1-[[2-(trifluoromethyl)phenyl]methyl]-1H,4H,5H,6H,7H-imidazo[4,5-c]pyridin-5-yl)-2,3-dihydropyridazin-3-one (53.8 mg, 78.85%) as a white solid.

QA

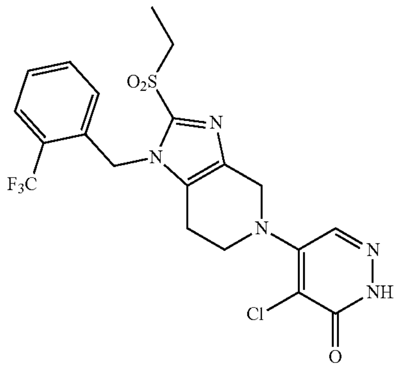

QA was prepared by the methods and scheme described for PZ by using sodium ethanesulfinate

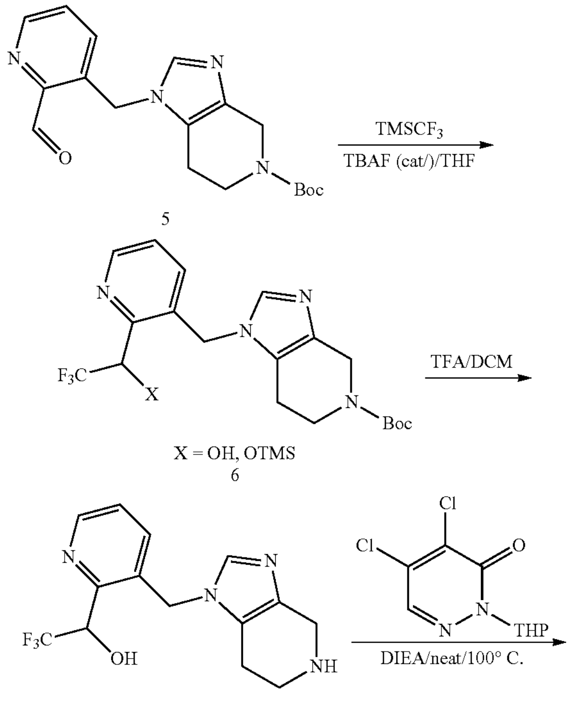

5

X = OH, OTMS
6

7

-continued

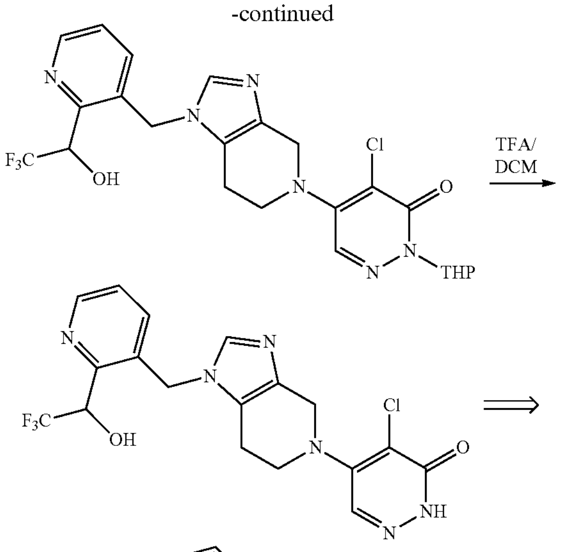

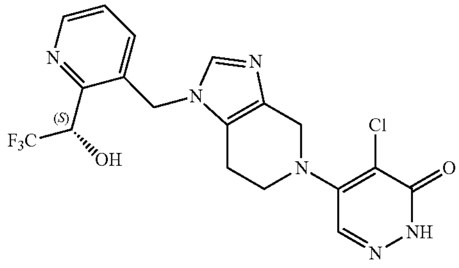

QB

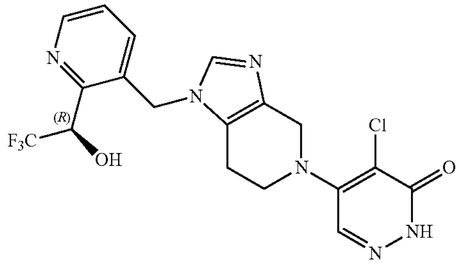

QC

Preparation of QB and QC

Tert-Butyl 1-[[2-(2,2,2-trifluoro-1-hydroxyethyl) pyridin-3-yl]methyl]-1H,4H,5H,6H,7H-imidazo[4,5-c]pyridine-5-carboxylate To a solution of tert-butyl 1-[(2-formylpyridin-3-yl) methyl]-1H,4H,5H,6H,7H-imidazo[4,5-c]pyridine-5-carboxylate (500 mg, 1.46 mmol, 1 equiv.) in THF (20 mL) was added TMSCF3 (415.3 mg, 2.92 mmol, 2 equiv.) at 0 degrees celsius under nitrogen atmosphere. The resulting mixture was stirred for 2 min at 0 degrees C. Then the mixture was added TBAF (38.2 mg, 0.15 mmol, 0.10 equiv.) at 0 degrees C. The resulting mixture was stirred for 4 h at 0 degrees C. The desired product could be detected by LCMS. The reaction mixture was diluted with water (500 mL) and extracted with EtOAc (2×500 mL). The combined organic layers were washed with brine (1×300 mL), dried over anhydrous MgSO4. After filtration, the filtrate was concentrated under reduced pressure. This resulted in tert-butyl 1-[[2-(2,2,2-trifluoro-1-hydroxyethyl)pyridin-3-yl]

methyl]-1H,4H,5H,6H,7H-imidazo[4,5-c]pyridine-5-carboxylate (500 mg, 83.02%) as an off-white solid.

2,2,2-Trifluoro-1-[3-([1H,4H,5H,6H,7H-imidazo[4,5-c]pyridin-1-yl]methyl)pyridin-2-yl]ethan-1-ol To a solution of TFA (4 mL) in DCM (16 mL) was added tert-butyl 1-[[2-(2,2,2-trifluoro-1-hydroxyethyl)pyridin-3-yl]methyl]-1H,4H,5H,6H,7H-imidazo[4,5-c]pyridine-5-carboxylate (500 mg, 1 equiv.) at ambient temperature. Then the mixture was stirred for 5 h at ambient temperature. The desired product could be detected by LCMS. The resulting mixture was concentrated under reduced pressure. The mixture was added DMF (5 mL) and was purified by reverse phase flash with the following conditions (Column: c18 OBD Column, 5 um, 19*330 mm; Mobile Phase A: Water (5 MMOL/L $NaHCO_3$), Mobile Phase B: ACN; Flow rate: 80 mL/min; Gradient: 25% B to 65% B in 40 min; 254 nm; Rt: 20.3 min) to afford 2,2,2-trifluoro-1-[3-([1H,4H,5H,6H,7H-imidazo[4,5-c]pyridin-1-yl]methyl)pyridin-2-yl]ethan-1-ol (197 mg, 52.03%) as a light yellow solid.

4-Chloro-2-(oxan-2-yl)-5-(1-[[2-(2,2,2-trifluoro-1-hydroxyethyl)pyridin-3-yl]methyl]-1H,4H,5H,6H,7H-imidazo[4,5-c]pyridin-5-yl)-2,3-dihydropyridazin-3-one To reactant of 2,2,2-trifluoro-1-[3-([1H,4H,5H,6H,7H-imidazo[4,5-c]pyridin-1-yl]methyl)pyridin-2-yl]ethan-1-ol (197 mg, 0.63 mmol, 1 equiv.) were added 4,5-dichloro-2-(oxan-2-yl)-2,3-dihydropyridazin-3-one (157.1 mg, 0.63 mmol, 1.00 equiv.) and DIEA (163.1 mg, 1.26 mmol, 2.00 equiv.) at ambient temperature. The resulting mixture was stirred for 2 h at 100 degrees C. The desired product could be detected by LCMS. The mixture was allowed to cool down to ambient temperature. The mixture was purified by reverse phase flash with the following conditions (Column: c18 OBD Column, 5 um, 19*120 mm; Mobile Phase A: Water (5 MMOL/L NH4HCO3), Mobile Phase B: ACN; Flow rate: 45 mL/min; Gradient: 20% B to 65% B in 40 min; 220 nm; Rt: 30.0 min) to afford 4-chloro-2-(oxan-2-yl)-5-(1-[[2-(2,2,2-trifluoro-1-hydroxyethyl)pyridin-3-yl] methyl]-1H,4H,5H,6H,7H-imidazo[4,5-c]pyridin-5-yl)-2,3-dihydropyridazin-3-one (127 mg, 38.35%) as an off-white solid

4-Chloro-5-[1-([2-[(1S)-2,2,2-trifluoro-1-hydroxyethyl]pyridin-3-yl]methyl)-1H,4H,5H,6H,7H-imidazo[4,5-c]pyridin-5-yl]-2,3-dihydropyridazin-3-one and 4-chloro-5-[1-([2-[(1R)-2,2,2-trifluoro-1-hydroxyethyl]pyridin-3-yl]methyl)-1H,4H,5H,6H,7H-imidazo[4,5-c]pyridin-5-yl]-2,3-dihydropyridazin-3-one To a solution of TFA (4 mL) in DCM (16 mL) was added 4-chloro-2-(oxan-2-yl)-5-(1-[[2-(2,2,2-trifluoro-1-hydroxyethyl)pyridin-3-yl]methyl]-1H,4H,5H,6H,7H-imidazo[4,5-c]pyridin-5-yl)-2,3-dihydropyridazin-3-one (127 mg, 0.242 mmol, 1 equiv.) at ambient temperature. Then the mixture was stirred for 16 h at ambient temperature. The desired product could be detected by LCMS. The resulting mixture was concentrated under reduced pressure. The mixture was basified to pH 8 with NaHCO3 (aq.) and concentrated under reduced pressure to afford crude product. The crude product was purified by reverse phase flash with the following conditions (Column: c18 OBD Column, 5 um, 19*330 mm; Mobile Phase A: Water (5 MMOL/L NH4HCO3), Mobile Phase B: ACN; Flow rate: 80 mL/min; Gradient: 30% B to 50% B in 40 min; 254 nm; Rt: 7.3 min) to afford crude Products (90 mg) as a white solid. The product was purified by Prep-Chiral-HPLC with the following conditions: Column:CHIRALPAK IG-3, Column size: 0.46*5 cm; 3 um; Mobile phase:Hex (0.1% DEA):EtOH=85:15; Pressure: MPA; Flow:1.0 ml/min; Instrument:LC-08; Detector:220 nm; Temperature:25 degrees C. 4-chloro-5-[1-([2-[(1S)-2,2,2-trifluoro-1-hydroxyethyl]pyridin-3-yl]methyl)-1H,4H,5H,6H,7H-imidazo[4,5-c]pyridin-5-yl]-2,3-dihydropyridazin-3-one (13.2 mg) was obtained at 1.436 min as a light solid and 4-chloro-5-[1-([2-[(1R)-2,2,2-trifluoro-1-hydroxyethyl]pyridin-3-yl]methyl)-1H,4H,5H,6H,7H-imidazo[4,5-c]pyridin-5-yl]-2,3-dihydropyridazin-3-one (15.5 mg) was obtained at 1.725 min as a light yellow solid.

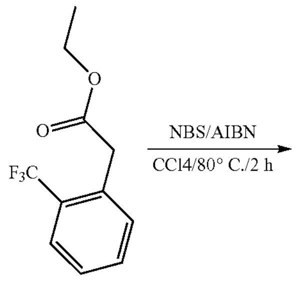

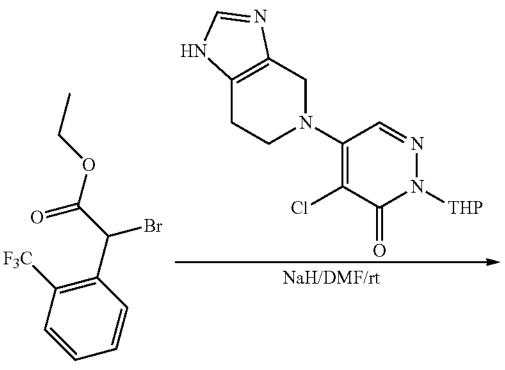

1

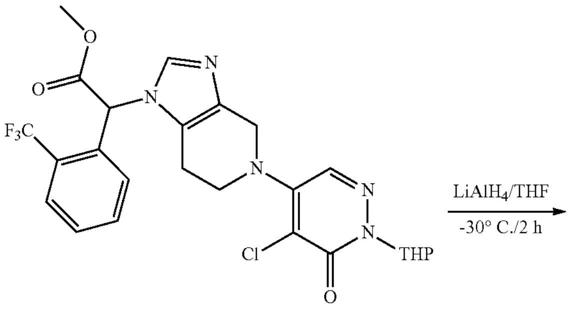

2

-continued

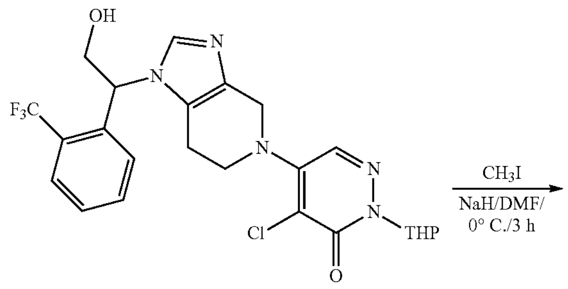

3

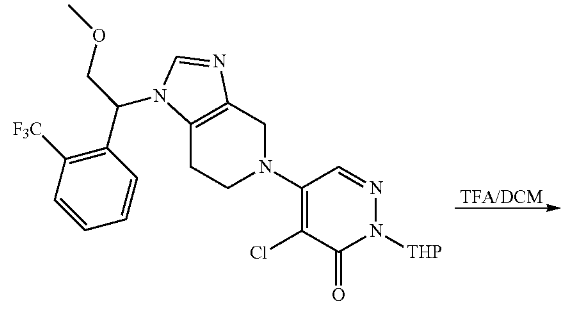

4

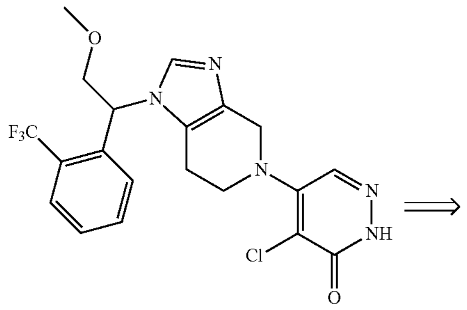

5

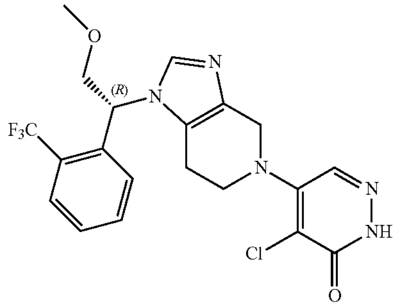

QD

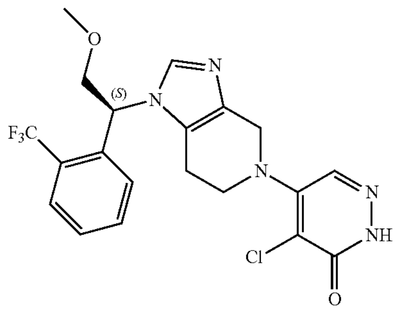

QE

Preparation of QD and QE

Ethyl 2-bromo-2-[2-(trifluoromethyl)phenyl]acetate

Into a 50 mL round-bottom flask were added ethyl 2-[2-(trifluoromethyl)phenyl]acetate (1.4 g, 6.03 mmol, 1 equiv.), CCl4 (10 mL), NBS (2.1 g, 12.06 mmol, 2.0 equiv.) and AIBN (0.3 g, 2.05 mmol, 0.34 equiv.) at 80 degrees C. The resulting mixture was stirred for 6 h at 80 degrees C. The reaction was monitored by LCMS. The mixture was allowed to cool down to room temperature. The resulting mixture was concentrated under reduced pressure. The residue was purified by Prep-TLC (PE/EtOAc=4:1) to afford ethyl 2-bromo-2-[2-(trifluoromethyl)phenyl]acetate (1.7 g, 90.63%) as a pink solid.

Ethyl 2-[5-[5-chloro-1-(oxan-2-yl)-6-oxo-1,6-dihydropyridazin-4-yl]-1H,4H,5H,6H,7H-imidazo[4,5-c]pyridin-1-yl]-2-[2-(trifluoromethyl)phenyl]acetate To a solution of 4-chloro-5-[1H,4H,5H,6H,7H-imidazo[4,5-c]pyridin-5-yl]-2-(oxan-2-yl)-2,3-dihydropyridazin-3-one (2.2 g, 6.55 mmol, 1.20 equiv.) in DMF was added sodium hydride (60% in oil, 460 mg) at 0 degrees C. The mixture was stirred for 15 min at 0 degrees C. ethyl 2-bromo-2-[2-(trifluoromethyl)phenyl]acetate (1.7 g, 5.46 mmol, 1 equiv.) was added and the mixture was allowed to warm to RT and stirred for 3 h. The reaction was monitored by LCMS. The reaction was quenched with sat. NH4Cl (aq.) at room temperature. The resulting mixture was extracted with EtOAc (3×20 mL). The combined organic layers were washed with brine (3×50 mL), dried over anhydrous Na2SO4. After filtration, the filtrate was concentrated under reduced pressure. The residue was purified by reverse phase flash with the following conditions (Column: C18, 330 g; Mobile Phase A: Water/0.05% NH4HCO3, Mobile Phase B: ACN; Flow rate: 80 mL/min; Gradient: 10% B to 30% B in 30 min; Detector, 254 nm; Monitor, 220 nm) to afford ethyl 2-[5-[5-chloro-1-(oxan-2-yl)-6-oxo-1,6-dihydropyridazin-4-yl]-1H,4H,5H,6H,7H-imidazo[4,5-c]pyridin-1-yl]-2-[2-(trifluoromethyl)phenyl]acetate (1.5 g, 48.50%) as a light pink solid.

4-Chloro-5-(1-[2-hydroxy-1-[2-(trifluoromethyl)phenyl]ethyl]-1H,4H,5H,6H,7H-imidazo[4,5-c]pyridin-5-yl)-2-(oxan-2-yl)-2,3-dihydropyridazin-3-one Into a 100 mL round-bottom flask were added ethyl 2-[5-[5-chloro-1-(oxan-2-yl)-6-oxo-1,6-dihydropyridazin-4-yl]-1H,4H,5H,6H,7H-imidazo[4,5-c]pyridin-1-yl]-2-[2-(trifluoromethyl)phenyl]acetate (1.1 g, 1.944 mmol, 1 equiv.), THF (20 mL) and LiAlH4 (92.21 mg, 2.429 mmol, 1.25 equiv.) at −30 degrees C. The resulting mixture was stirred for 3 h at −30 degrees C. The reaction was monitored by LCMS. The reaction was quenched with sat. NH4C1 (aq.) at room temperature. The resulting mixture was extracted with CH2C12 (3×20 mL). The combined organic layers were washed with brine (3×10 mL), dried over anhydrous Na2SO4. After filtration, the filtrate was concentrated under reduced pressure. The crude product was purified by reverse phase flash with the following conditions (Column: C18, 330 g; Mobile Phase A: Water/0.05% NH4HCO3, Mobile Phase B: ACN; Flow rate: 80 mL/min; Gradient: 10% B to 30% B in 30 min; Detector, 254 nm; Monitor, 220 nm) to afford 4-chloro-5-(1-[2-hydroxy-1-[2-(trifluoromethyl)phenyl]ethyl]-1H,4H,5H,6H,7H-imidazo[4,5-c]pyridin-5-yl)-2-(oxan-2-yl)-2,3-dihydropyridazin-3-one (540 mg, 53.03%) as a light yellow solid.

4-Chloro-5-(1-[2-methoxy-1-[2-(trifluoromethyl)phenyl]ethyl]-1H,4H,5H,6H,7H-imidazo[4,5-c]pyridin-5-yl)-2-(oxan-2-yl)-2,3-dihydropyridazin-3-one To a solution of 4-chloro-5-(1-[2-hydroxy-1-[2-(trifluoromethyl)phenyl]ethyl]-1H,4H,5H,6H,7H-imidazo[4,5-c]pyridin-5-yl)-2-(oxan-2-yl)-2,3-dihydropyridazin-3-one (450 mg, 0.859 mmol, 1 equiv.) in DMF (20 mL) was added NaH (41.22 mg, 1.031 mmol, 1.20 equiv, 60%) at 0 degrees C. The mixture was stirred for 15 min at 0 degrees C. MeI (366 mg, 3.00 equiv.) was added. The mixture was allowed to warm to RT and stirred for 3 h. The reaction mixture was quenched by water and extracted with DCM (3*25 mL). The combined organic layers were concentrated under reduced pressure. The residue was purified by reverse phase flash with the following conditions (Column: C18, 330 g; Mobile Phase A: Water/0.05% NH4HCO3, Mobile Phase B: ACN; Flow rate: 80 mL/min; Gradient: 10% B to 30% B in 30 min; Detector, 254 nm; Monitor, 220 nm) to afford 4-chloro-5-(1-[2-methoxy-1-[2-(trifluoromethyl)phenyl]ethyl]-1H,4H,5H,6H,7H-imidazo[4,5-c]pyridin-5-yl)-2-(oxan-2-yl)-2,3-dihydropyridazin-3-one (320 mg, 69.26%) and as a light yellow solid.

4-Chloro-5-[1-[(1S)-2-methoxy-1-[2-(trifluoromethyl)phenyl]ethyl]-1H,4H,5H,6H,7H-imidazo[4,5-c]pyridin-5-yl]-2,3-dihydropyridazin-3-one and 4-chloro-5-[1-[(1R)-2-methoxy-1-[2-(trifluoromethyl)phenyl]ethyl]-1H,4H,5H,6H,7H-imidazo[4,5-c]pyridin-5-yl]-2,3-dihydropyridazin-3-one Into a 25 mL round-bottom flask were added 4-chloro-5-(1-[2-methoxy-1-[2-(trifluoromethyl)phenyl]ethyl]-1H,4H,5H,6H,7H-imidazo[4,5-c]pyridin-5-yl)-2-(oxan-2-yl)-2,3-dihydropyridazin-3-one (320 mg), DCM (9 mL) and TFA (1 mL) at room temperature. The resulting mixture was stirred for 3 h at room temperature. The reaction was monitored by LCMS. The mixture was basified to pH 8 with saturated NaHCO3 (aq.). The resulting mixture was extracted with CH2Cl2 (3×10 mL). The combined organic layers were washed with brine (3×5 mL), dried over anhydrous Na2SO4. After filtration, the filtrate was concentrated under reduced pressure. The residue was purified by reverse phase flash with the following conditions (Column: C18, 330 g; Mobile Phase A: Water/0.05% NH4HCO3, Mobile Phase B: ACN; Flow rate: 80 mL/min; Gradient: 10% B to 30% B in 30 min; Detector, 254 nm; Monitor, 220 nm) to afford 4-chloro-5-[1-[(1S)-2-methoxy-1-[2-(trifluoromethyl)phenyl]ethyl]-1H,4H,5H,6H,7H-imidazo[4,5-c]pyridin-5-yl]-2,3-dihydropyridazin-3-one (40 mg) and 4-chloro-5-[1-[(1R)-2-methoxy-1-[2-(trifluoromethyl)phenyl]ethyl]-1H,4H,5H,6H,7H-imidazo[4,5-c]pyridin-5-yl]-2,3-dihydropyridazin-3-one (40 mg) as a off-white solid.

QF
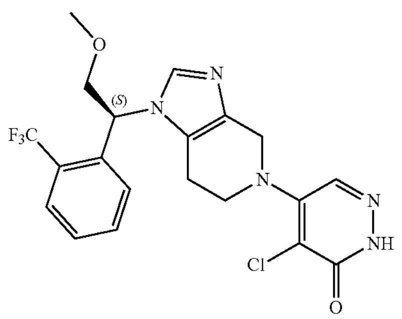
QG
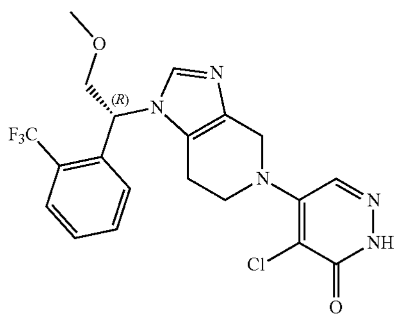
QF and QG were prepared by the methods and scheme described for QD and QE
QH
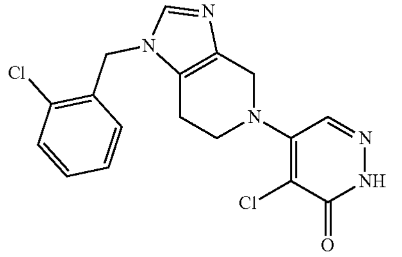
QI
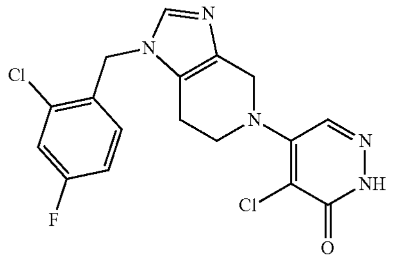
QH and QI were prepared by the methods and scheme described for HZ by using 1-(chloromethyl)-benzene and 2-chloro-1-(chloromethyl)-4-fluorobenzene respectively
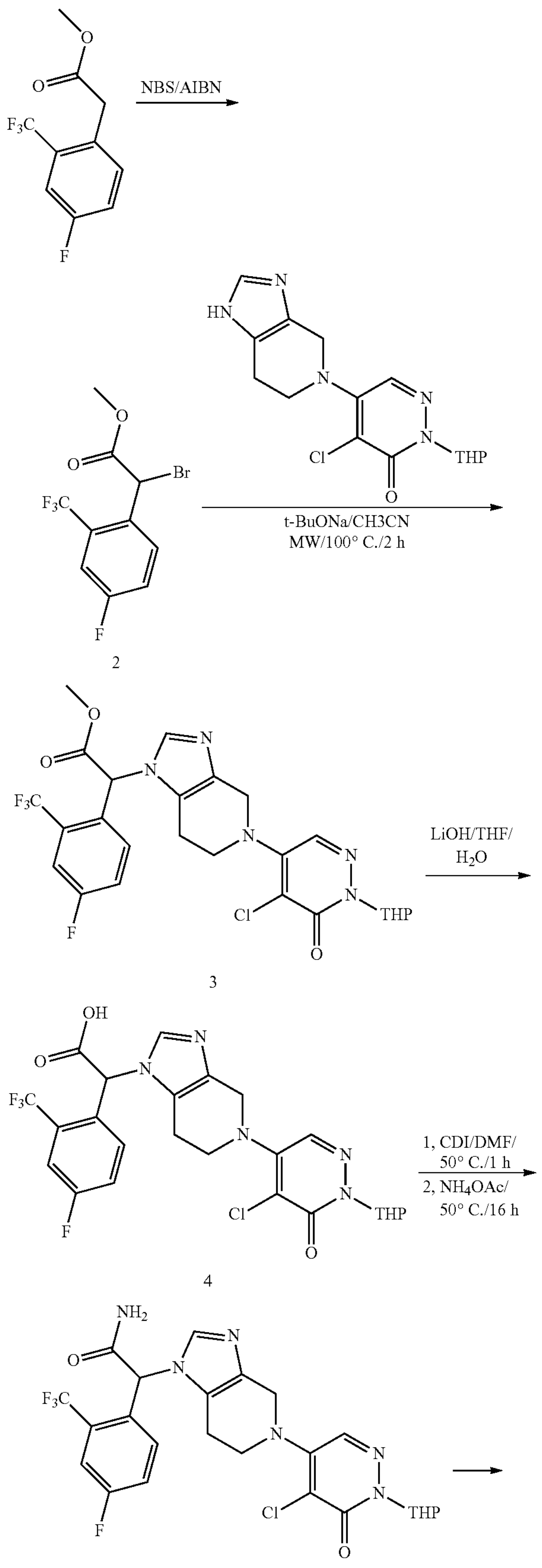
2
3
4
5

-continued

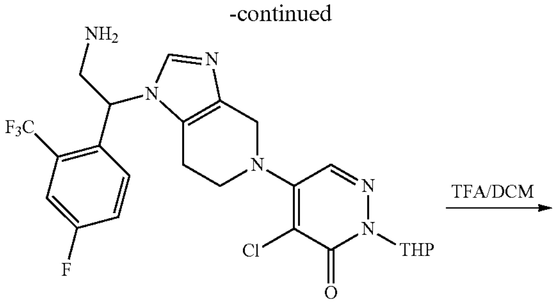

6

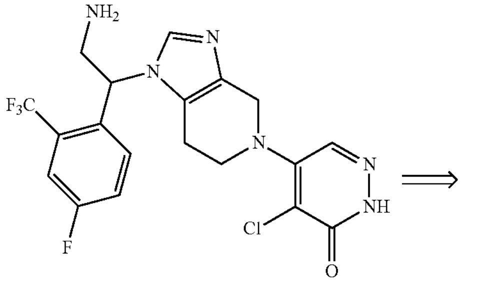

7

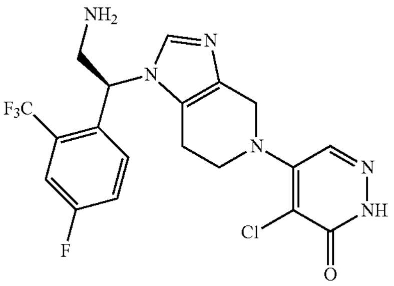

QJ

Preparation of QJ

Methyl 2-bromo-2-[4-fluoro-2-(trifluoromethyl) phenyl]acetate

To a stirred solution of methyl 2-[4-fluoro-2-(trifluoromethyl)phenyl]acetate (4.5 g, 19.054 mmol, 1 equiv.) in CCl4 (80 mL) were added NBS (3.73 g, 20.960 mmol, 1.1 equiv.) and AIBN (312.89 mg, 1.905 mmol, 0.1 equiv.) at room temperature. The resulting mixture was stirred for 16 h at 80 degrees C. The reaction was monitored by TLC (PE:EA=4:1). The mixture was allowed to cool down to room temperature. The resulting mixture was concentrated under reduced pressure. The residue was purified by silica gel column chromatography, eluted with PE (100%) to afford methyl 2-bromo-2-[4-fluoro-2-(trifluoromethyl)phenyl]acetate (3.7 g, 61.63%) as a light yellow oil.

Methyl 2-[5-[5-chloro-1-(oxan-2-yl)-6-oxo-1,6-dihydropyridazin-4-yl]-1H,4H,5H,6H,7H-imidazo[4,5-c]pyridin-1-yl]-2-[4-fluoro-2-(trifluoromethyl)phenyl]acetate To a stirred mixture of 4-chloro-5-[1H,4H,5H,6H,7H-imidazo[4,5-c]pyridin-5-yl]-2-(oxan-2-yl)-2,3-dihydropyridazin-3-one (1 g, 2.978 mmol, 1 equiv.) in ACN (15 mL) were added methyl 2-bromo-2-[4-fluoro-2-(trifluoromethyl) phenyl]acetate (1.41 g, 4.467 mmol, 1.5 equiv.) and Cs2CO3 (1.94 g, 5.956 mmol, 2 equiv.) at room temperature. The resulting mixture was stirred for 16 h at room temperature. The reaction was monitored by LCMS. The resulting mixture was concentrated under reduced pressure. The residue was purified by reverse phase flash with the following conditions (Column: C18 Column 80 g; Mobile Phase A: Water (10 MMOL/L NH4HCO3), Mobile Phase B: ACN; Flow rate: 50 mL/min; Gradient: 30% B to 50% B in 40 min; 254/220 nm) to afford methyl 2-[5-[5-chloro-1-(oxan-2-yl)-6-oxo-1,6-dihydropyridazin-4-yl]-1H,4H,5H,6H,7H-imidazo[4,5-c]pyridin-1-yl]-2-[4-fluoro-2-(trifluoromethyl) phenyl]acetate (420 mg, 24.75%) as a light yellow solid.

2-[5-[5-chloro-1-(oxan-2-yl)-6-oxo-1,6-dihydropyridazin-4-yl]-1H,4H,5H,6H,7H-imidazo[4,5-c]pyridin-1-yl]-2-[4-fluoro-2-(trifluoromethyl)phenyl]acetic acid To a stirred solution of methyl 2-[5-[5-chloro-1-(oxan-2-yl)-6-oxo-1,6-dihydropyridazin-4-yl]-1H,4H,5H,6H,7H-imidazo[4,5-c]pyridin-1-yl]-2-[4-fluoro-2-(trifluoromethyl) phenyl]acetate (600 mg, 1.053 mmol, 1 equiv.) in THF (10 mL) were added LiOH (252.11 mg, 10.527 mmol, 10 equiv.) and H2O (10 mL) at room temperature. The resulting mixture was stirred for 4 h at room temperature. The resulting mixture was concentrated under reduced pressure. The residue was purified by reverse phase flash with the following conditions (Column: C18 Column 330 g; Mobile Phase A: Water (10 MMOL/L AcOH), Mobile Phase B: ACN; Flow rate: 50 mL/min; Gradient: 40% B to 60% B in 40 min; 254/220 nm) to afford 2-[5-[5-chloro-1-(oxan-2-yl)-6-oxo-1,6-dihydropyridazin-4-yl]-1H,4H,5H,6H,7H-imidazo[4,5-c]pyridin-1-yl]-2-[4-fluoro-2-(trifluoromethyl) phenyl]acetic acid (500 mg, 85.44%) as an off-white solid.

2-[5-[5-chloro-1-(oxan-2-yl)-6-oxo-1,6-dihydropyridazin-4-yl]-1H,4H,5H,6H,7H-imidazo[4,5-c]pyridin-1-yl]-2-[4-fluoro-2-(trifluoromethyl)phenyl]acetamide To a stirred solution of 2-[5-[5-chloro-1-(oxan-2-yl)-6-oxo-1,6-dihydropyridazin-4-yl]-1H,4H,5H,6H,7H-imidazo[4,5-c]pyridin-1-yl]-2-[4-fluoro-2-(trifluoromethyl)phenyl] acetic acid (500 mg, 0.899 mmol, 1 equiv.) in DMF (10 mL) was added CDI (175.01 mg, 1.079 mmol, 1.2 equiv.) at room temperature. The resulting mixture was stirred for 1 h at 50 degrees C. To the above mixture was added AcONH4 (104.00 mg, 1.349 mmol, 1.5 equiv.) at room temperature. The resulting mixture was stirred for additional 1 h at 50 degrees C. To the above mixture was added TEA (273.04 mg, 2.698 mmol, 3 equiv.) at room temperature. The resulting mixture was stirred for additional 16 h at 50 degrees C. The reaction was monitored by LCMS. The solution was purified by reverse phase flash with the following conditions (Column: C18 Column 80 g; Mobile Phase A: Water (10 MMOL/L AcOH), Mobile Phase B: ACN; Flow rate: 50 mL/min; Gradient: 5% B to 20% B in 40 min; 254/220 nm) to afford 2-[5-[5-chloro-1-(oxan-2-yl)-6-oxo-1,6-dihydropyridazin-4-yl]-1H,4H,5H,6H,7H-imidazo[4,5-c]pyridin-1-yl]-2-[4-fluoro-2-(trifluoromethyl)phenyl]acetamide (200 mg, 40.07%) as a light yellow solid.

5-(1-[2-amino-1-[4-fluoro-2-(trifluoromethyl)phenyl]ethyl]-1H,4H,5H,6H,7H-imidazo[4,5-c]pyridin-5-yl)-4-chloro-2-(oxan-2-yl)-2,3-dihydropyridazin-3-one To a stirred solution of 2-[5-[5-chloro-1-(oxan-2-yl)-6-oxo-1,6-dihydropyridazin-4-yl]-1H,4H,5H,6H,7H-imidazo

[4,5-c]pyridin-1-yl]-2-[4-fluoro-2-(trifluoromethyl)phenyl] acetamide (170 mg, 0.306 mmol, 1 equiv.) and LiBH4 (13.35 mg, 0.613 mmol, 2 equiv.) in THF (5 mL) was added TMSCl (133.13 mg, 1.225 mmol, 4 equiv.) dropwise at 0 degrees C. The resulting mixture was stirred for 20 h at room temperature. The reaction was monitored by LCMS. The reaction was quenched with sat. KOH (aq.) at room temperature. The resulting mixture was extracted with DCN (3×10 mL). The combined organic layers were washed with brine (1×10 mL), dried over anhydrous Na2SO4. After filtration, the filtrate was concentrated under reduced pressure. The residue/crude product was purified by reverse phase flash with the following conditions (Column: C18 Column 40 g; Mobile Phase A: Water (10 MMOL/L NH4HCO3), Mobile Phase B: ACN; Flow rate: 50 mL/min; Gradient: 10% B to 30% B in 40 min; 254/220 nm) to afford 5-(1-[2-amino-1-[4-fluoro-2-(trifluoromethyl)phenyl] ethyl]-1H,4H,5H,6H,7H-imidazo[4,5-c]pyridin-5-yl)-4-chloro-2-(oxan-2-yl)-2,3-dihydropyridazin-3-one (100 mg, 60.34%) as a light yellow oil.

5-[1-[(1S)-2-amino-1-[4-fluoro-2-(trifluoromethyl) phenyl]ethyl]-1H,4H,5H,6H,7H-imidazo[4,5-c]pyridin-5-yl]-4-chloro-2,3-dihydropyridazin-3-one To a stirred solution of 5-(1-[2-amino-1-[4-fluoro-2-(trifluoromethyl)phenyl]ethyl]-1H,4H,5H,6H,7H-imidazo[4,5-c]pyridin-5-yl)-4-chloro-2-(oxan-2-yl)-2,3-dihydropyridazin-3-one (100 mg, 0.185 mmol, 1 equiv.) in DCM (4.5 mL) was added TFA (0.5 mL, 6.732 mmol, 36.41 equiv.) dropwise at room temperature. The resulting mixture was stirred for 2 h at room temperature. The reaction was monitored by LCMS. The residue was purified by reverse phase flash with the following conditions (Column: XBridge Shield RP18 OBD Column, 5 um, 19*150 mm; Mobile Phase A: Water (0.05% TFA), Mobile Phase B: ACN; Flow rate: 25 mL/min; Gradient: 5% B to 20% B in 7 min; 220 nm; Rt: 5.58, 6.3 min) to afford 5-[1-[(1S)-2-amino-1-[4-fluoro-2-(trifluoromethyl)phenyl]ethyl]-1H,4H,5H,6H,7H-imidazo[4,5-c]pyridin-5-yl]-4-chloro-2,3-dihydropyridazin-3-one (10 mg, 11.84%) as a light yellow solid as an off-white solid.

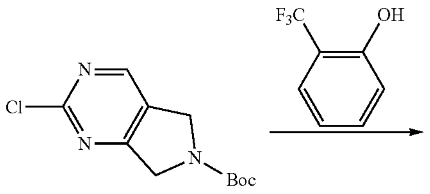

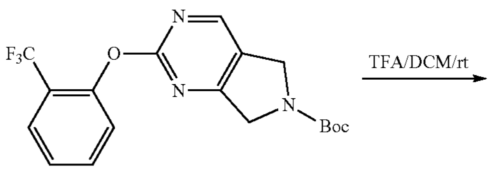

1

-continued

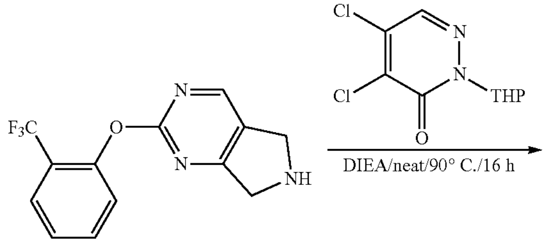

2

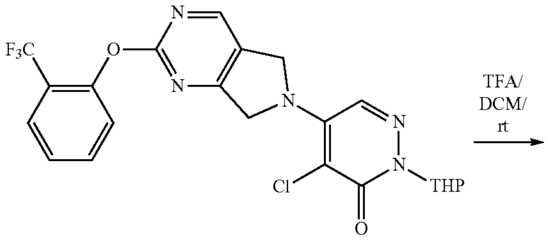

3

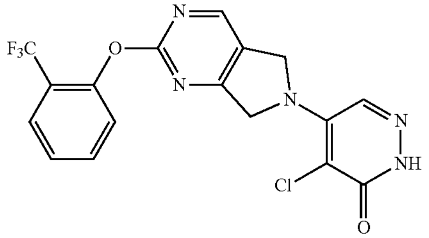

QK

Preparation of QK

Tert-Butyl 2-[2-(trifluoromethyl)phenoxy]-5H,6H,7H-pyrrolo[3,4-d]pyrimidine-6-carboxylate To a stirred mixture of tert-butyl 4-chloro-5H,6H,7H-pyrrolo[3,4-d]pyrimidine-6-carboxylate (100 mg, 0.39 mmol, 1 equiv.) and 2-(trifluoromethyl)phenol (95.1 mg, 0.59 mmol, 1.5 equiv.) in CH3CN (10 mL) was added DBU (119.1 mg, 0.78 mmol, 2.0 equiv.) dropwise at room temperature. The resulting mixture was stirred for 2 h at 70 degrees C. The reaction was monitored by LCMS. The mixture was allowed to cool down to room temperature. The resulting mixture was concentrated under reduced pressure. The residue was purified by Prep-TLC (PE/EtOAc 5:1) to afford tert-butyl 2-[2-(trifluoromethyl)phenoxy]-5H,6H,7H-pyrrolo[3,4-d]pyrimidine-6-carboxylate (150 mg, 25.14%) as a brown solid.

2-[2-(Trifluoromethyl)phenoxy]-5H,6H,7H-pyrrolo [3,4-d]pyrimidine

To a stirred solution of tert-butyl 2-[2-(trifluoromethyl) phenoxy]-5H,6H,7H-pyrrolo[3,4-d]pyrimidine-6-carboxylate (150 mg, 0.39 mmol, 1 equiv.) in DCM (4 mL) was added TFA (1 mL, 13.46 mmol, 34.23 equiv.) dropwise at room temperature. The resulting mixture was stirred for 1 h at room temperature. The reaction was monitored by LCMS. The resulting mixture was concentrated under reduced pressure. The mixture was basified to pH 8 with saturated NaHCO3 (aq.). The resulting mixture was concentrated under vacuum. The residue was purified by Prep-TLC (CH2Cl2/MeOH 10:1) to afford 2-[2-(trifluoromethyl)phenoxy]-5H,6H,7H-pyrrolo[3,4-d]pyrimidine (90 mg, 81.36%) as a brown solid.

4-Chloro-2-(oxan-2-yl)-5-[2-[2-(trifluoromethyl) phenoxy]-5H,6H,7H-pyrrolo[3,4-d]pyrimidin-6-yl]-2,3-dihydropyridazin-3-one To a stirred solution of 2-[2-(trifluoromethyl)phenoxy]-5H,6H,7H-pyrrolo[3,4-d]pyrimidine (80 mg, 0.28 mmol, 1 equiv.) in DIEA (0.5 mL) was added 4,5-dichloro-2-(oxan-2-yl)-2,3-dihydropyridazin-3-one (85.0 mg, 0.34 mmol, 1.2 equiv.) at room temperature. The resulting mixture was stirred for 2 h at 100 degrees C. The reaction was monitored by LCMS. The mixture was allowed to cool down to room temperature. The residue was purified by Prep-TLC (CH2Cl2/MeOH 10:1) to afford 4-chloro-2-(oxan-2-yl)-5-[2-[2-(trifluoromethyl)phenoxy]-5H,6H,7H-pyrrolo[3,4-d] pyrimidin-6-yl]-2,3-dihydropyridazin-3-one (170 mg, 121.01%) as a brown solid.

4-Chloro-5-[2-[2-(trifluoromethyl)phenoxy]-5H,6H, 7H-pyrrolo[3,4-d]pyrimidin-6-yl]-2,3-dihydro-pyridazin-3-one To a stirred solution of 4-chloro-2-(oxan-2-yl)-5-[2-[2-(trifluoromethyl)phenoxy]-5H,6H,7H-pyrrolo[3,4-d]pyrimidin-6-yl]-2,3-dihydropyridazin-3-one (170 mg, 0.34 mmol, 1 equiv.) in DCM (4 mL) was added TFA (1 mL, 13.46 mmol, 39.11 equiv.) at room temperature. The resulting mixture was stirred for 1 h at room temperature. The reaction was monitored by LCMS. The mixture was basified to pH 8 with saturated NaHCO3 (aq.). The resulting mixture was concentrated under reduced pressure. The crude product (50 mg) was purified by Prep-HPLC with the following conditions (Column: XBridge Prep OBD C18 Column 30×150 mm 5 um; Mobile Phase A: Water (10 MMOL/L NH4HCO3), Mobile Phase B: ACN; Flow rate: 60 mL/min; Gradient: 27% B to 50% B in 8 min; 220 nm; Rt: 7.47 min) to afford 4-chloro-5-[2-[2-(trifluoromethyl)phenoxy]-5H, 6H,7H-pyrrolo[3,4-d]pyrimidin-6-yl]-2,3-dihydro-pyridazin-3-one (36.7 mg, 26.02%) as a white solid.

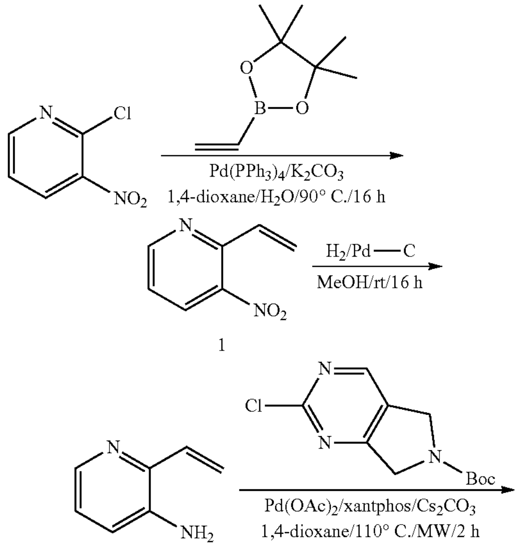

1

2

-continued

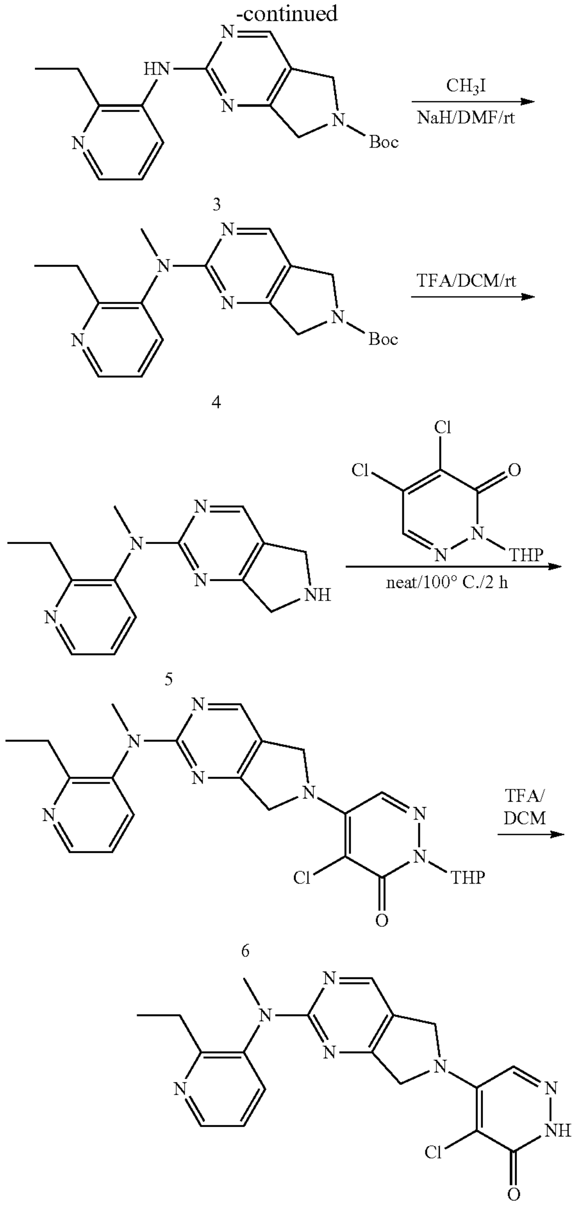

3

4

5

6

QL

Preparation of QL

2-Ethenyl-3-nitropyridine

To a stirred mixture of 2-chloro-3-nitropyridine (2 g, 12.615 mmol, 1 equiv.) and Na2CO3 (2.67 g, 25.230 mmol, 2.0 equiv.) in 1,4-dioxane (20 mL) and H2O (1 mL) were added Pd(PPh3)4 (0.73 g, 0.631 mmol, 0.05 equiv.) and 2-ethenyl-4,4,5,5-tetramethyl-1,3,2-dioxaborolane (1.94 g, 12.615 mmol, 1.00 equiv.) at 0 degrees celsius under nitrogen atmosphere. The resulting mixture was stirred for 3 h at room temperature under nitrogen atmosphere. The reaction was monitored by LCMS. The resulting mixture was concentrated under reduced pressure. The residue was purified by silica gel column chromatography, eluted with PE/EtOAc (10:1 to 5:1) to afford 2-ethenyl-3-nitropyridine (1.1 g, 58.08%) as a brown solid.

2-Ethylpyridin-3-amine

To a stirred solution of 2-ethenyl-3-nitropyridine (1.1 g, 7.327 mmol, 1 equiv.) in MeOH (10 mL) was added Pd/C (100 mg, 0.266 mmol, 0.04 equiv.) at room temperature under hydrogen atmosphere. The resulting mixture was stirred for 16 h at room temperature under hydrogen atmosphere. The reaction was monitored by LCMS. The resulting mixture was filtered, the filter cake was washed with MeOH (2×10 mL). The filtrate was concentrated under reduced pressure. The residue product was purified by reverse phase flash with the following conditions (Column: XBridge Prep OBD C18 Column 30×150 mm 5 um; Mobile Phase A: Water (10 MMOL/L NH4HCO3), Mobile Phase B: ACN; Flow rate: 60 mL/min; Gradient: 20% B to 40% B in 11 min; 220 nm; Rt: 11.77 min) to afford 2-ethylpyridin-3-amine (620 mg, 69.27%) as a white solid.

Tert-Butyl 2-[(2-ethylpyridin-3-yl)amino]-5H,6H,7H-pyrrolo[3,4-d]pyrimidine-6-carboxylate To a stirred mixture of tert-butyl 2-chloro-5H,6H,7H-pyrrolo[3,4-d]pyrimidine-6-carboxylate (200 mg, 0.782 mmol, 1 equiv.) and 2-ethyl-3-nitropyridine (238.02 mg, 1.564 mmol, 2.0 equiv.) in 1,4-dioxane (20 mL) were added Cs2CO3 (509.69 mg, 1.564 mmol, 2.0 equiv.) and Pd(AcO)2 (35.12 mg, 0.156 mmol, 0.2 equiv.) at room temperature under nitrogen atmosphere. Then XantPhos (181.03 mg, 0.313 mmol, 0.4 equiv.) was added at room temperature under nitrogen atmosphere. The final reaction mixture was irradiated with microwave radiation for 2 h at 110 degrees C. The reaction was monitored by LCMS. The mixture was allowed to cool down to room temperature. The resulting mixture was filtered, the filter cake was washed with CH2Cl2 (2×10 mL). The filtrate was concentrated under reduced pressure. The crude product was purified by reverse phase flash with the following conditions (Column: XBridge Prep OBD C18 Column 30×150 mm 5 um; Mobile Phase A: Water (10 MMOL/L NH4HCO3), Mobile Phase B: ACN; Flow rate: 60 mL/min; Gradient: 20% B to 40% B in 11 min; 220 nm; Rt: 11.77 min) to afford tert-butyl 2-[(2-ethylpyridin-3-yl)amino]-5H,6H,7H-pyrrolo[3,4-d]pyrimidine-6-carboxylate (250 mg, 93.62%) as a brown solid.

Tert-Butyl 2-[(2-ethylpyridin-3-yl)(methyl)amino]-5H,6H,7H-pyrrolo[3,4-d]pyrimidine-6-carboxylate To a stirred solution of tert-butyl 2-[(2-ethylpyridin-3-yl)amino]-5H,6H,7H-pyrrolo[3,4-d]pyrimidine-6-carboxylate (300 mg, 0.879 mmol, 1 equiv.) in DMF (10 mL) was added NaH (42.17 mg, 1.757 mmol, 2.0 equiv.) at 0 degrees celsius under nitrogen atmosphere. The resulting mixture was stirred for 1 h at degrees celsius under nitrogen atmosphere. Then CH3I (249.44 mg, 1.757 mmol, 2.00 equiv.) was added at 0 degrees celsius under nitrogen atmosphere. The resulting mixture was stirred for 1 h at room temperature under nitrogen atmosphere. The reaction was monitored by LCMS. The resulting mixture was diluted with water (2 mL). The crude product was purified by reverse phase flash with the following conditions (Column: XBridge Prep OBD C18 Column 30×150 mm 5 um; Mobile Phase A: Water (10 MMOL/L NH4HCO3), Mobile Phase B: ACN; Flow rate: 60 mL/min; Gradient: 20% B to 40% B in 11 min; 220 nm; Rt: 11.77 min) to afford tert-butyl 2-[(2-ethylpyridin-3-yl)(methyl)amino]-5H,6H,7H-pyrrolo[3,4-d]pyrimidin-6-carboxylate (250 mg, 80.04%) as a brown solid.

N-(2-ethylpyridin-3-yl)-N-methyl-6,7-dihydro-5H-pyrrolo[3,4-d]pyrimidin-2-amine

To a stirred solution of tert-butyl 2-[(2-ethylpyridin-3-yl)(methyl)amino]-5H,6H,7H-pyrrolo[3,4-d]pyrimidine-6-carboxylate (200 mg, 0.586 mmol, 1 equiv.) in DCM (4 mL) was added TFA (1 mL, 13.463 mmol, 22.98 equiv.) at room temperature. The resulting mixture was stirred for 1 h at room temperature. The reaction was monitored by LCMS. The resulting mixture was concentrated under reduced pressure. The mixture was basified to pH 8 with saturated NaHCO3 (aq.). The crude product was purified by reverse phase flash with the following conditions (Column: XBridge Prep OBD C18 Column 30×150 mm 5 um; Mobile Phase A: Water (10 MMOL/L NH4HCO3), Mobile Phase B: ACN; Flow rate: 60 mL/min; Gradient: 18% B to 35% B in 8 min; 220 nm; Rt: 7.12 min) to afford N-(2-ethylpyridin-3-yl)-N-methyl-6,7-dihydro-5H-pyrrolo[3,4-d]pyrimidin-2-amine (120 mg, 84.89%) as a brown solid.

4-Chloro-5-[2-[(2-ethylpyridin-3-ylmethyl)amino]-5H,6H,7H-pyrrolo[3,4-d]pyrimidin-6-yl]-2-(oxan-2-yl)-2,3-dihydropyridazin-3-one To a stirred solution of N-(2-ethylpyridin-3-yl)-N-methyl-6,7-dihydro-5H-pyrrolo[3,4-d]pyrimidin-2-amine (120 mg, 0.497 mmol, 1 equiv.) in DIEA (0.1 mL) was added 4,5-dichloro-2-(oxan-2-yl)-2,3-dihydropyridazin-3-one (99.10 mg, 0.398 mmol, 0.80 equiv.) at room temperature. The resulting mixture was stirred for 1 h at 90 degrees C. The reaction was monitored by LCMS. The mixture was allowed to cool down to room temperature. The resulting mixture was concentrated under reduced pressure. The residue was purified by Prep-TLC (CH2Cl2/MeOH 12:1) to afford 4-chloro-5-[2-[(2-ethylpyridin-3-yl)(methyl)amino]-5H,6H,7H-pyrrolo[3,4-d]pyrimidin-6-yl]-2-(oxan-2-yl)-2,3-dihydropyridazin-3-one (100 mg, 42.97%) as a brown solid.

4-Chloro-5-[2-[(2-ethylpyridin-3-ylmethyl)amino]-5H,6H,7H-pyrrolo[3,4-d]pyrimidin-6-yl]-2,3-dihydropyridazin-3-one To a stirred solution of 4-chloro-5-[2-[(2-ethylpyridin-3-yl)(methyl)amino]-5H,6H,7H-pyrrolo[3,4-d]pyrimidin-6-yl]-2-(oxan-2-yl)-2,3-dihydropyridazin-3-one (100 mg, 0.214 mmol, 1 equiv.) in DCM (4 mL) was added TFA (1 mL) at room temperature. The resulting mixture was stirred for 1 h at room temperature. The reaction was monitored by LCMS. The resulting mixture was concentrated under reduced pressure. The mixture was basified to pH 8 with saturated NaHCO3 (aq.). The crude product (80 mg) was purified by Prep-HPLC with the following conditions (Column: XBridge Prep OBD C18 Column 30×150 mm 5 um; Mobile Phase A: Water (10 MMOL/L NH4HCO3), Mobile Phase B: ACN; Flow rate: 60 mL/min; Gradient: 15% B to 35% B in 8 min; 220 nm; Rt: 6.65 min) to afford 4-chloro-5-[2-[(2-ethylpyridin-3-yl)(methyl)amino]-5H,6H,7H-pyrrolo[3,4-d]pyrimidin-6-yl]-2,3-dihydropyridazin-3-one (67.4 mg, 82.17%) as a white solid.

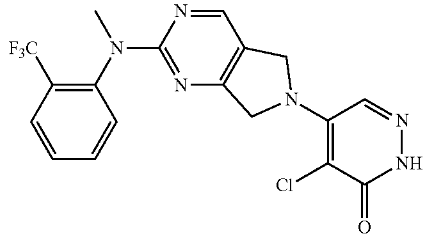

QM

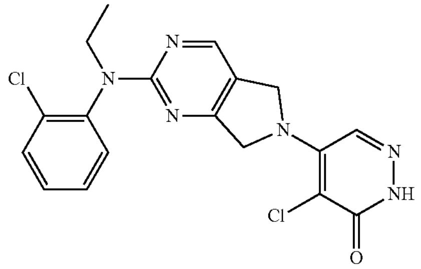

QN

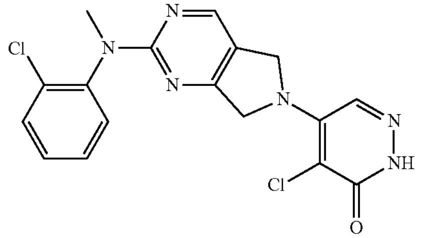

QO

QM, QN, and QO were prepared by the methods and scheme described for QL by using corresponding analines

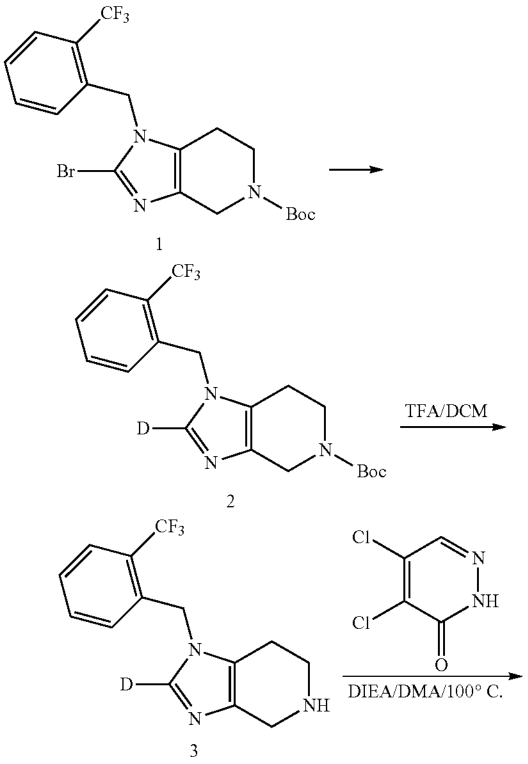

-continued

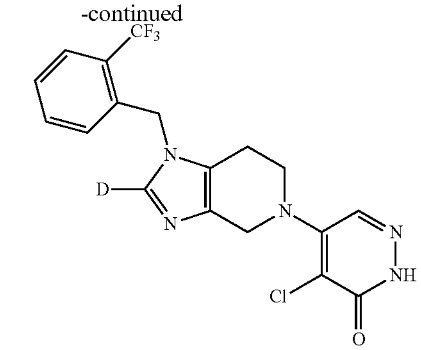

QP

Preparation of QP

Tert-Butyl 1-(2-(trifluoromethyl)benzyl)-1,4,6,7-tetrahydro-5H-imidazo[4,5-c]pyridine-5-carboxylate-2-d To a solution of tert-butyl 2-bromo-1-[[2-(trifluoromethyl)phenyl]methyl]-1H,4H,5H,6H,7H-imidazo[4,5-c]pyridine-5-carboxylate (300 mg, 0.65 mmol, 1 equiv.) in THF (30.0 mL, 416.05 mmol, 568.14 equiv.) was added LiAlD4 (54.7 mg, 1.30 mmol, 2 equiv.) at −30 degrees C. The mixture was stirred at −10 degrees celsius for 2 h. The mixture was quenched with D20 (1 mL). The resulting mixture was concentrated under reduced pressure. The residue was purified by Prep-TLC (PE/EA 1/1) to afford tert-butyl 1-(2-(trifluoromethyl)benzyl)-1,4,6,7-tetrahydro-5H-imidazo[4,5-c]pyridine-5-carboxylate-2-d (240 mg, 96.29%) as a light yellow oil.

1-(2-(trifluoromethyl)benzyl)-4,5,6,7-tetrahydro-1H-imidazo[4,5-c]pyridine-2-d

To a solution of tert-butyl 1-(2-(trifluoromethyl)benzyl)-1,4,6,7-tetrahydro-5H-imidazo[4,5-c]pyridine-5-carboxylate-2-d (250 mg, 0.65 mmol, 1 equiv.) in DCM (12.5 mL, 147.17 mmol, 300.76 equiv.) was added TFA (745.4 mg, 6.54 mmol, 10.00 equiv.) at 25 degrees C. The solution was stirred at 25 degrees celsius for 2 h. The resulting solution was concentrated under reduced pressure. The residue was purified by Prep-TLC (DCM/MeOH 10/1) to afford 1-(2-(trifluoromethyl)benzyl)-4,5,6,7-tetrahydro-1H-imidazo[4,5-c]pyridine-2-d (160 mg, 86.70%) as a light yellow oil.

4-Chloro-5-(1-(2-(trifluoromethyl)benzyl)-1,4,6,7-tetrahydro-5H-imidazo[4,5-c]pyridin-5-yl-2-d)pyridazin-3(2H)-one To a solution of 1-(2-(trifluoromethyl)benzyl)-4,5,6,7-tetrahydro-1H-imidazo[4,5-c]pyridine-2-d (80 mg, 0.28 mmol, 1 equiv.) and 4,5-dichloro-2,3-dihydropyridazin-3-one (46.8 mg, 0.28 mmol, 1.00 equiv.) in DMA (3 mL, 32.27 mmol, 113.85 equiv.) was added DIEA (73.3 mg, 0.57 mmol, 2 equiv.) at 25 degrees C. The mixture was stirred at 100 degrees celsius for 16 h. The crude product (200 mg) was purified by Prep-HPLC with the following conditions (Column: XBridge Shield RP18 OBD Column 30*150 mm, 5 um; Mobile Phase A: Water (10 MMoL/L NH4HCO3), Mobile Phase B: ACN; Flow rate: 60 mL/min; Gradient: 20% B to 40% B in 7 min; 220 nm; Rt: 6.63 min) to afford 4-chloro-5-(1-(2-(trifluoromethyl)benzyl)-1,4,6,7-tetrahydro-5H-imidazo[4,5-c]pyridin-5-yl-2-d)pyridazin-3(2H)-one (14.5 mg, 12.45%) as a white solid.

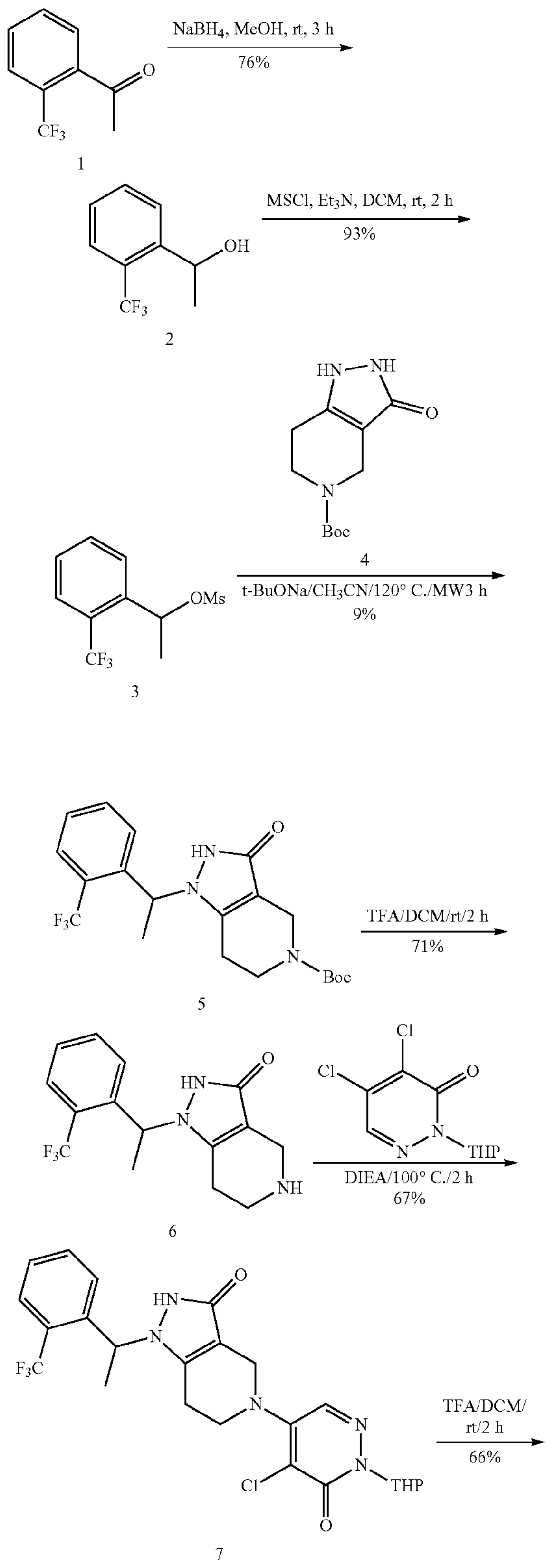

-continued

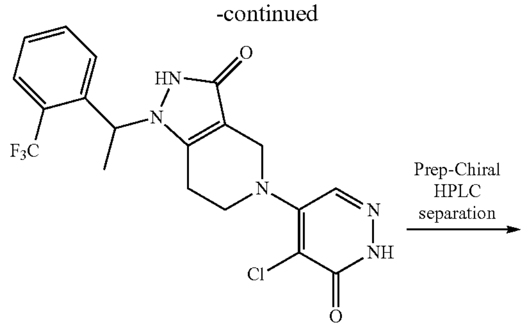

8

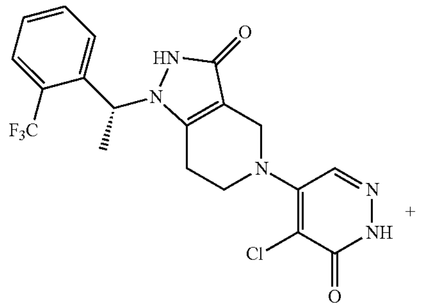

+

QQ

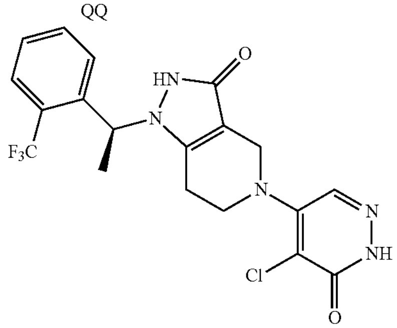

QR

Preparation of QQ and QR 1-(2-(trifluoromethyl)phenyl)ethan-1-ol

To a stirred solution of 1-[2-(trifluoromethyl)phenyl]ethan-1-one (3 g, 15.95 mmol) in MeOH (15 mL) was added NaBH4 (1.21 g, 31.89 mmol) in portions at 0° C. The resulting mixture was stirred for 3 h at room temperature. The resulting mixture was concentrated under vacuum. The residue was purified by silica gel column chromatography, eluted with 2% ethyl acetate in petroleum ether to afford 1-[2-(trifluoromethyl)phenyl]ethan-1-ol (2.3 g, 76%) as a light yellow oil.

1-(2-(trifluoromethyl)phenyl)ethyl methanesulfonate

To a solution of 1-[2-(trifluoromethyl)phenyl]ethan-1-ol (4.6 g, 24.2 mmol) in DCM (30 mL) were added Et3N (4.9 g, 48.4 mmol) and MsCl (3.3 g, 29.1 mmol) dropwise at 0° C. The resulting mixture was stirred for 2 h at room temperature. The resulting mixture was concentrated under reduced pressure. The residue was purified by silica gel column chromatography, eluted with 5%~20% ethyl acetate in petroleum ether to afford 1-[2-(trifluoromethyl)phenyl]ethyl methanesulfonate (6 g, 93%) as a light yellow oil.

Tert-Butyl 3-oxo-1-[1-[2-(trifluoromethyl)phenyl]ethyl]-1H,2H,3H,4H,5H,6H,7H-pyrazolo[4,3-c]pyridine-5-carboxylate To a stirred solution of tert-butyl 3-oxo-1H,2H,3H,4H,5H,6H,7H-pyrazolo[4,3-c]pyridine-5-carboxylate (3.0 g, 12.5 mmol) in acetonitrile (12 mL) were added 1-[2-(trifluoromethyl)phenyl]ethyl methanesulfonate (4.4 g, 16.3 mmol) and sodium tert-butoxide (2.4 g, 25.1 mmol) at room temperature under nitrogen atmosphere. The mixture was irradiated with microwave for 3 h at 120° C. After cooling to ambient temperature, the resulting mixture was filtered and the filter cake was washed with ethyl acetate (2×50 mL). The filtrate was concentrated under reduced pressure. The residue was purified by reverse phase flash chromatography with the following conditions: column: Spherical C18, 20-40 um, 330 g; Mobile Phase A: Water (plus 5 mM NH4CO3); Mobile Phase B: ACN; Flow rate: 85 mL/min; Gradient: 5%-5% B, 5 min, 30%-55% B in 25 min; Detector: 220 nm. The fractions containing the desired product were collected at 47% B and concentrated under reduced pressure to afford tert-butyl 3-oxo-1-[1-[2-(trifluoromethyl)phenyl]ethyl]-1H,2H,3H,4H,5H,6H,7H-pyrazolo[4,3-c]pyridine-5-carboxylate (450 mg, 9%) as an off-white solid.

1-[1-[2-(trifluoromethyl)phenyl]ethyl]-1H,2H,3H,4H,5H,6H,7H-pyrazolo[4,3-c]pyridin-3-one To a stirred solution of tert-butyl 3-oxo-1-[1-[2-(trifluoromethyl)phenyl]ethyl]-1H,2H,3H,4H,5H,6H,7H-pyrazolo[4,3-c]pyridine-5-carboxylate (450 mg, 1.09 mmol) in dichloromethane (80 mL) was added TFA (20 mL) at room temperature. The resulting mixture was stirred for 2 h at room temperature under nitrogen atmosphere. The resulting mixture was concentrated under reduced pressure. The residue was taken up between ethyl acetate (50 mL) and saturated aqueous sodium bicarbonate (50 mL). The organic layer was separated out and the aqueous layer was extracted with ethyl acetate (3×80 mL). The combined organic layers were washed with brine (120 mL) and dried over anhydrous sodium sulfate. After filtration, the filtrate was concentrated under reduced pressure. The residue was purified by reverse phase flash chromatography with the following conditions: column: Spherical C18, 20-40 um, 330 g; Mobile Phase A: water (plus 5 mM NH4CO3); Mobile Phase B: ACN; Flow rate: 85 mL/min; Gradient: 5%-5% B, 5 min, 33%-45% B in 20 min; Detector: 220 nm. The fractions containing the desired product were collected at 42% B and concentrated under reduced pressure to afford 1-[1-[2-(trifluoromethyl)phenyl]ethyl]-1H,2H,3H,4H,5H,6H,7H-pyrazolo[4,3-c]pyridin-3-one (240 mg, 71%) as a colorless oil.

4-chloro-2-(oxan-2-yl)-5-(3-oxo-1-[1-[2-(trifluoromethyl)phenyl]ethyl]-1H,2H,3H,4H,5H,6H,7H-pyrazolo[4,3-c]pyridin-5-yl)-2,3-dihydropyridazin-3-one To a sealed tube were added N,N-diisopropylethylamine (0.20 g, 1.54 mmol), 1-[1-[2-(trifluoromethyl)phenyl]ethyl]-1H,2H,3H,4H,5H,6H,7H-pyrazolo[4,3-c]pyridin-3-one (240 mg, 0.77 mmol) and 4,5-dichloro-2-(oxan-2-yl)-2,3-dihydropyridazin-3-one (192 mg, 0.77 mmol) at room temperature. The resulting mixture was stirred for 2 h at 100° C. under nitrogen atmosphere. After cooling to room temperature, the resulting mixture was diluted with water (100 mL) and extracted with ethyl acetate (3×100 mL). The combined organic layers were washed with brine (150 mL) and dried over anhydrous sodium sulfate. After filtration, the filtrate was concentrated under reduced pressure to afford 4-chloro-2-(oxan-2-yl)-5-(3-oxo-1-[1-[2-(trifluoromethyl)phenyl]ethyl]-1H,2H,3H,4H,5H,6H,7H-pyrazolo[4,3-c]pyridin-5-yl)-2,3-dihydropyridazin-3-one (270 mg, 67%) as an off-white solid which was used directly to next step without further purification: LC/MS (ESI, m/z): [(M+1)]+: 524.15.

4-chloro-5-(3-oxo-1-[1-[2-(trifluoromethyl)phenyl]ethyl]-1H,2H,3H,4H,5H,6H,7H-pyrazolo[4,3-c]pyridin-5-yl)-2,3-dihydropyridazin-3-one To a stirred solution of 4-chloro-2-(oxan-2-yl)-5-(3-oxo-1-[1-[2-(trifluoromethyl)phenyl]ethyl]-1H,2H,3H,4H,5H,6H,7H-pyrazolo[4,3-c]pyridin-5-yl)-2,3-dihydropyridazin-3-one (270 mg, 0.51 mmol) in dichloromethane (30 mL) was added TFA (5 mL) dropwise at room temperature under nitrogen atmosphere. The resulting mixture was stirred for 2 h at room temperature under nitrogen atmosphere. The resulting mixture was concentrated under reduced pressure. The residue was purified by Prep-HPLC with the following conditions: column: X Bridge Shield RP18 OBD column, 19×150 mm, 5 um; Mobile Phase A: water (plus, 10 mM FA); Mobile Phase B: ACN; Flow rate: 25 mL/min; Gradient: 30% to 50% B in 7 min; Detector: 220 nm; The fractions containing desired product were collected at 6.05 min and concentrated under reduced pressure to afford 4-chloro-5-(3-oxo-1-[1-[2-(trifluoromethyl)phenyl]ethyl]-1H,2H,3H,4H,5H,6H,7H-pyrazolo[4,3-c]pyridin-5-yl)-2,3-dihydropyridazin-3-one (150 mg, 66%) as an off-white solid.

4-chloro-5-[3-oxo-1-[(1R)-1-[2-(trifluoromethyl)phenyl]ethyl]-1H,2H,3H,4H,5H,6H,7H-pyrazolo[4,3-c]pyridin-5-yl]-2,3-dihydropyridazin-3-one and 4-chloro-5-[3-oxo-1-[(1S)-1-[2-(trifluoromethyl)phenyl]ethyl]-1H,2H,3H,4H,5H,6H,7H-pyrazolo[4,3-c]pyridin-5-yl]-2,3-dihydropyridazin-3-one The above racemic 4-chloro-5-(3-oxo-1-[1-[2-(trifluoromethyl)phenyl]ethyl]-1H,2H,3H,4H,5H,6H,7H-pyrazolo[4,3-c]pyridin-5-yl)-2,3-dihydropyridazin-3-one (150 mg, 0.34 mmol) was separated by Prep-Chiral-HPLC with the following condition: column: Chiralpak IA, 2×25 cm, 5 um; Mobile Phase A: Hexane (plus, 10 mM TFA); Mobile Phase B: EtOH; Flow rate: 20 mL/min; Gradient: 15% to 15% B in 20 min; Detector: 220/254 nm. The fractions containing desired product were collected and concentrated under reduced pressure to afford: the faster eluting isomer, retention time 15.05 min; 4-chloro-5-[3-oxo-1-[(1R)-1-[2-(trifluoromethyl)phenyl]ethyl]-1H,2H,3H,4H,5H,6H,7H-pyrazolo[4,3-c]pyridin-5-yl]-2,3-dihydropyridazin-3-one (29.6 mg, 20%) as an off-white solid.

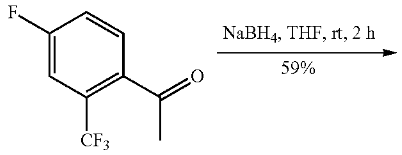

1

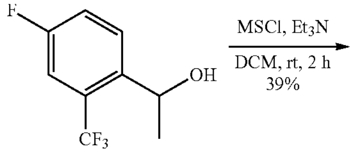

2

-continued

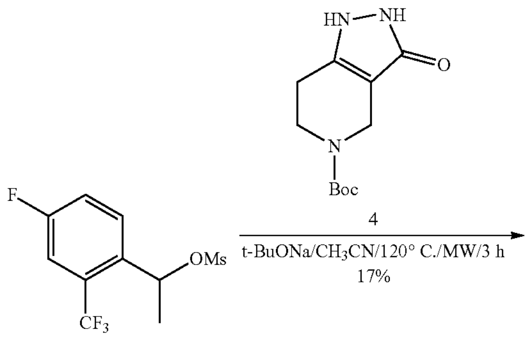

3

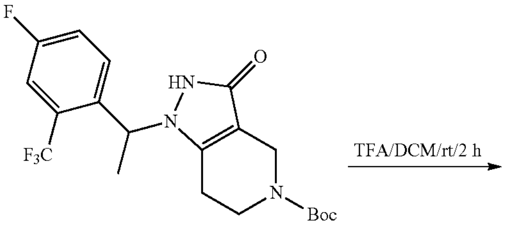

5

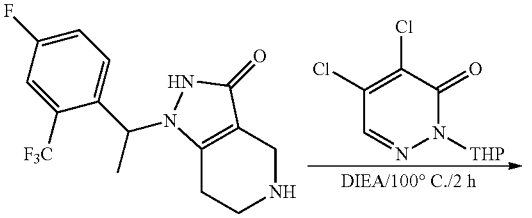

6

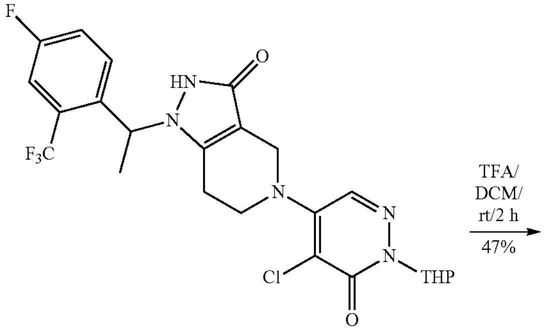

7

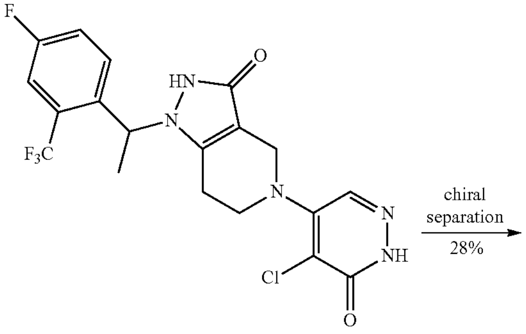

8

-continued

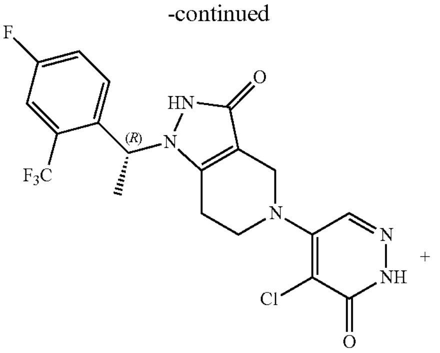

QS

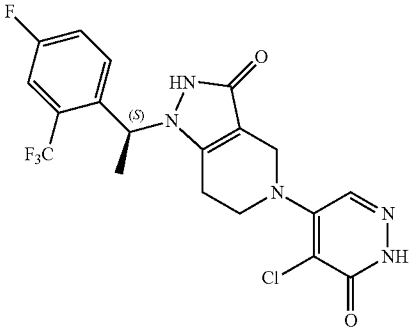

QT

Preparation of QS and QT

1-[4-fluoro-2-(trifluoromethyl)phenyl]ethan-1-ol

To a stirred solution of 1-[4-fluoro-2-(trifluoromethyl) phenyl]ethan-1-one (5.00 g, 24.3 mmol) in tetrahydrofuran (100 mL) was added sodium borohydride (1.84 g, 48.5 mmol) at 0° C. The resulting mixture was stirred at ambient temperature for 2 h. The resulting mixture was quenched with saturated aqueous solution of ammonium chloride (100 mL) and extracted with ethyl acetate (3×50 mL). The combined organic layers was washed with brine (3×50 mL), dried over anhydrous sodium sulfate and filtered. The filtrate was concentrated under reduced pressure to afford 1-[4-fluoro-2-(trifluoromethyl)phenyl]ethan-1-ol (3.00 g, 59%) as a light yellow solid: 1H NMR (400 MHz, DMSO-d6) δ 7.88 (dd, J=8.8 Hz, 5.7 Hz, 1H), 7.57 (m, 1H), 7.50 (d, J=9.0 Hz, 1H), 5.51 (d, J=4.0 Hz, 1H), 5.07-4.97 (mi, 1H), 1.31 (d, J=6.3 Hz, 3H).

1-[4-fluoro-2-(trifluoromethyl)phenyl]ethyl Methanesulfonate

To a stirred solution of 1-[4-fluoro-2-(trifluoromethyl) phenyl]ethan-1-ol (3.00 g, 14.4 mmol) and triethylamine (2.92 g, 28.8 mmol) in dichloromethane (60 mL) was added methylsulfonyl chloride (2.48 g, 21.6 mmol) dropwise at 0° C. The resulting mixture was stirred at ambient temperature for 2 h. The resulting mixture was quenched with saturated aqueous solution of ammonium chloride (50 mL) and extracted with ethyl acetate (3×50 mL). The combined organic layers was washed with brine (3×50 mL), dried over anhydrous sodium sulfate and filtered. The filtrate was concentrated under reduced pressure to afford 1-[4-fluoro-2-(trifluoromethyl)phenyl]ethyl methanesulfonate (1.60 g, 39%) as a light yellow oil.

Tert-Butyl 1-[1-[4-fluoro-2-(trifluoromethyl)phenyl]ethyl]-3-oxo-1H,2H,3H,4H,5H,6H,7H-pyrazolo[4,3-c]pyridine-5-carboxylate To a stirred solution of tert-butyl 3-oxo-1H,2H,3H,4H,5H,6H,7H-pyrazolo[4,3-c]pyridine-5-carboxylate (3.0 g, 12.5 mmol) and 1-[4-fluoro-2-(trifluoromethyl)phenyl]ethyl methanesulfonate (4.7 g, 16.3 mmol) in acetonitrile (12 mL) was added sodium tert-butoxide (2.4 g, 25.1 mmol) at ambient temperature under argon atmosphere. The resulting mixture was irradiated with microwave at 120° C. for 3 h. The resulting mixture was cooled to ambient temperature and filtered, the filter cake was washed with ethyl acetate (2×50 mL). The filtrate was concentrated under reduced pressure and purified by reverse phase flash chromatography with the following conditions: Column: C18, 20-40 um, 330 g; Mobile Phase A: Water (plus 5 mM $NH4CO3$); Mobile Phase B: ACN; Flow rate: 85 mL/min; Gradient: 33%-45% B in 20 min; Detector: UV 220 nm and 254 nm. The fractions containing desired product were collected at 42% B and concentrated under reduced pressure to afford tert-butyl 1-[1-[4-fluoro-2-(trifluoromethyl)phenyl]ethyl]-3-oxo-1H,2H,3H,4H,5H,6H,7H-pyrazolo[4,3-c]pyridine-5-carboxylate (0.9 g, 17%) as an off-white solid.

1-[1-[4-fluoro-2-(trifluoromethyl)phenyl]ethyl]-1H,2H,3H,4H,5H,6H,7H-pyrazolo[4,3-c]pyridin-3-one To a stirred solution of tert-butyl 1-[1-[4-fluoro-2-(trifluoromethyl)phenyl]ethyl]-3-oxo-1H,2H,3H,4H,5H,6H,7H-pyrazolo[4,3-c]pyridine-5-carboxylate (0.90 g, 2.10 mmol) in dichloromethane (80 mL) was added trifluoroacetic acid (20 mL) dropwise at ambient temperature. The resulting mixture was stirred at ambient temperature for 2 h. The resulting mixture was concentrated under reduced pressure, basified to pH 8 with saturated aqueous sodium bicarbonate (50 mL) and extracted with ethyl acetate (3×60 ML). The combined organic layers was washed with brine (100 mL), dried over anhydrous sodium sulfate and filtered. The filtrate was concentrated under reduced pressure to afford 1-[1-[4-fluoro-2-(trifluoromethyl)phenyl]ethyl]-1H,2H,3H,4H,5H,6H,7H-pyrazolo[4,3-c]pyridin-3-one (0.48 g, crude) as a colorless oil which was used in the next step without further purification: MS m/z (+ESI) [(M+1)]+=330.1.

4-chloro-5-(1-[1-[4-fluoro-2-(trifluoromethyl)phenyl]ethyl]-3-oxo-1H,2H,3H,4H,5H,6H,7H-pyrazolo[4,3-c]pyridin-5-yl)-2-(oxan-2-yl)-2,3-dihydropyridazin-3-one To a stirred solution of 1-[1-[4-fluoro-2-(trifluoromethyl)phenyl]ethyl]-1H,2H,3H,4H,5H,6H,7H-pyrazolo[4,3-c]pyridin-3-one (0.48 g, 1.46 mmol) in N,N-diisopropylethylamine (0.38 g, 2.92 mmol) was added 4,5-dichloro-2-(oxan-2-yl)-2,3-dihydropyridazin-3-one (0.36 g, 1.46 mmol) at ambient temperature. The resulting reaction was stirred at 100° C. for 2 h in a sealed tube. The resulting mixture was cooled down to ambient temperature and concentrated under reduced pressure. The resulting mixture was diluted with water (150 mL) and extracted with ethyl acetate (3×100 mL). The combined organic layers was washed with brine (100 mL), dried over anhydrous sodium sulfate and filtered. The filtrate was concentrated under reduced pressure to afford 4-chloro-5-(1-[1-[4-fluoro-2-(trifluoromethyl)phenyl]ethyl]-3-oxo-1H,2H,3H,4H,5H,6H,7H-pyrazolo[4,3-c]pyridin-5-yl)-2-(oxan-2-yl)-2,3-dihydropyridazin-3-one (0.500 g, crude) as an off-white solid which was used in the next step without further purification: MS m/z (+ESI) [(M+1)]+=542.1.

4-chloro-5-(1-[1-[4-fluoro-2-(trifluoromethyl)phenyl]ethyl]-3-oxo-1H,2H,3H,4H,5H,6H,7H-pyrazolo[4,3-c]pyridin-5-yl)-2,3-dihydropyridazin-3-one To a stirred solution of 4-chloro-5-(1-[1-[4-fluoro-2-(trifluoromethyl)phenyl]ethyl]-3-oxo-1H,2H,3H,4H,5H,6H,7H-pyrazolo[4,3-c]pyridin-5-yl)-2-(oxan-2-yl)-2,3-dihydropyridazin-3-one (0.50 g, 0.92 mmol) in dichloromethane (8 mL) was added trifluoroacetic acid (2 mL) at ambient temperature. The resulting mixture was stirred at ambient temperature for 2 h. The resulting mixture was concentrated under reduced pressure. The residue was purified directly by prep-HPLC with the following conditions: XBridge Shield RP18 OBD Column, 19×150 mm, 5 um; Mobile Phase A: Water (5 mM TFA); Mobile Phase B: ACN; Flow rate: 25 mL/min; Gradient: 25% to 55% B in 7 min; Detector: 220 nm; retention time: 6.83 min. The fractions containing desired product were collected and concentrated under reduced pressure to afford 4-chloro-5-(1-[1-[4-fluoro-2-(trifluoromethyl)phenyl]ethyl]-3-oxo-1H,2H,3H,4H,5H,6H,7H-pyrazolo[4,3-c]pyridin-5-yl)-2,3-dihydropyridazin-3-one (0.20 g, 47%) as an off-white solid.

(R)-5-(5-chloro-6-oxo-1,6-dihydropyridazin-4-yl)-1-(1-(4-fluoro-2-(trifluoromethyl)phenyl)ethyl)-1,2,4,5,6,7-hexahydro-3H-pyrazolo[4,3-c]pyridin-3-one and (S)-5-(5-chloro-6-oxo-1,6-dihydropyridazin-4-yl)-1-(1-(4-fluoro-2-(trifluoromethyl)phenyl)ethyl)-1,2,4,5,6,7-hexahydro-3H-pyrazolo[4,3-c]pyridin-3-one The racemic 4-chloro-5-(1-[1-[4-fluoro-2-(trifluoromethyl)phenyl]ethyl]-3-oxo-1H,2H,3H,4H,5H,6H,7H-pyrazolo[4,3-c]pyridin-5-yl)-2,3-dihydropyridazin-3-one (0.20 g, 0.44 mmol) was separated by prep-chiral-HPLC with the following conditions: Column: CHIRALPAK IE, 2×25 cm, 5 um; Mobile Phase A: Hex. (0.1% formic acid); Mobile Phase B: Ethanol; Flow rate: 18 mL/min; Gradient: 30% B in 22 min; Detector: 220/254 nm; The fractions containing the faster-eluting enantiomer were collected at 12.447 min and concentrated under reduced pressure to afford (R)-5-(5-chloro-6-oxo-1,6-dihydropyridazin-4-yl)-1-(1-(4-fluoro-2-(trifluoromethyl)phenyl)ethyl)-1,2,4,5,6,7-hexahydro-3H-pyrazolo[4,3-c]pyridin-3-one (54.8 mg, 27%) as an off-white solid. The fractions containing the slower-eluting enantiomer were collected at 15.288 min and concentrated under reduced pressure to afford (S)-5-(5-chloro-6-oxo-1,6-dihydropyridazin-4-yl)-1-(1-(4-fluoro-2-(trifluoromethyl)phenyl)ethyl)-1,2,4,5,6,7-hexahydro-3H-pyrazolo[4,3-c]pyridin-3-one (55.4 mg, 28%) as an off-white solid.

Example 2: TRPCx Assay Protocols

I. Plasmids

A. TRPC4

The following sequence represents the plasmid used to prepare TRPC4. The underlined portion of the sequence represents the portion encoding human TRPC4.

GACGGATCGGGAGATCTCCCGATCCCCTATGGTGCACTCTCAGTACAATCTGCTCTG
ATGCCGCATAGTTAAGCCAGTATCTGCTCCCTGCTTGTGTGTTGGAGGTCGCTGAGT
AGTGCGCGAGCAAAATTTAAGCTACAACAAGGCAAGGCTTGACCGACAATTGCATG
AAGAATCTGCTTAGGGTTAGGCGTTTTGCGCTGCTTCGCGATGTACGGGCCAGATAT
ACGCGTTGACATTGATTATTGACTAGTTATTAATAGTAATCAATTACGGGGTCATTA
GTTCATAGCCCATATATGGAGTTCCGCGTTACATAACTTACGGTAAATGGCCCGCCT
GGCTGACCGCCCAACGACCCCCGCCCATTGACGTCAATAATGACGTATGTTCCCATA
GTAACGCCAATAGGGACTTTCCATTGACGTCAATGGGTGGAGTATTTACGGTAAACT
GCCCACTTGGCAGTACATCAAGTGTATCATATGCCAAGTACGCCCCCTATTGACGTC
AATGACGGTAAATGGCCCGCCTGGCATTATGCCCAGTACATGACCTTATGGGACTTT
CCTACTTGGCAGTACATCTACGTATTAGTCATCGCTATTACCATGGTGATGCGGTTTT
GGCAGTACATCAATGGGCGTGGATAGCGGTTTGACTCACGGGGATTTCCAAGTCTCC
ACCCCATTGACGTCAATGGGAGTTTGTTTTGGCACCAAAATCAACGGGACTTTCCAA
AATGTCGTAACAACTCCGCCCCATTGACGCAAATGGGCGGTAGGCGTGTACGGTGG
GAGGTCTATATAAGCAGAGCTCTCCCTATCAGTGATAGAGATCTCCCTATCAGTGAT
AGAGATCGTCGACGAGCTCGTTTAGTGAACCGTCAGATCGCCTGGAGACGCCATCC
ACGCTGTTTTGACCTCCATAGAAGACACCGGGACCGATCCAGCCTCCGGACTCTAGC
GTTTAAACTTAAGCTTGGTACCGAGCTCGGATCCGCCACCATGGCCCAGTTCTACTA
TAAGAGAAACGTGAATGCCCCTTACCGCGACAGAATCCCCCTGAGAATCGTGAGGG
CAGAGTCCGAGCTGAGCCCATCCGAGAAGGCCTACCTGAACGCCGTGGAGAAGGGC
GACTATGCCAGCGTGAAGAAGTCCCTGGAGGAGGCCGAGATCTACTTTAAGATCAA
CATCAATTGCATCGATCCTCTGGGCAGAACCGCCCTGCTGATCGCCATCGAGAACGA
GAATCTGGAGCTGATCGAGCTGCTGCTGAGCTTCAACGTGTATGTGGGCGATGCCCT
GCTGCACGCCATCAGGAAGGAGGTGGTGGGAGCAGTGGAGCTGCTGCTGAATCACA
AGAAGCCAAGCGGAGAGAAGCAGGTGCCACCTATCCTGCTGGACAAGCAGTTCTCC
GAGTTTACCCCAGATATCACACCCATCATCCTGGCCGCCCACACCAACAATTACGAG
ATCATCAAGCTGCTGGTGCAGAAGGGCGTGTCCGTGCCTCGCCCACACGAGGTGCG
GTGCAACTGCGTGGAGTGCGTGAGCTCCTCTGACGTGGATTCTCTGAGGCACAGCCG
GAGCCGGCTGAACATCTATAAGGCCCTGGCCTCCCCATCTCTGATCGCCCTGAGCTC
CGAGGACCCCTTCCTGACCGCCTTTCAGCTGTCTTGGGAGCTGCAGGAGCTGAGCAA
GGTGGAGAACGAGTTTAAGAGCGAGTACGAGGAGCTGTCCAGACAGTGCAAGCAGT
TCGCCAAGGACCTGCTGGATCAGACACGCTCTAGCCGGGAGCTGGAGATCATCCTG
AACTATAGGGACGATAATTCTCTGATCGAGGAGCAGAGCGGAAACGACCTGGCACG
CCTGAAGCTGGCCATCAAGTACCGGCAGAAGGAGTTCGTGGCCCAGCCTAATTGTC
AGCAGCTGCTGGCCTCCCGCTGGTATGATGAGTTTCCAGGATGGCGGAGAAGGCAC
TGGGCAGTGAAGATGGTGACCTGCTTCATCATCGGCCTGCTGTTCCCCGTGTTCAGC
GTGTGCTACCTGATCGCCCCTAAGTCTCCACTGGGCCTGTTTATCCGGAAGCCTTTCA
TCAAGTTTATCTGCCACACCGCCAGCTATCTGACATTCCTGTTTCTGCTGCTGCTGGC
CTCCCAGCACATCGACAGATCTGATCTGAACAGGCAGGGCCCACCCCCTACCATCGT
GGAGTGGATGATCCTGCCATGGGTGCTGGGCTTCATCTGGGGCGAGATCAAGCAGA
TGTGGGACGGCGGCCTGCAGGACTACATCCACGATTGGTGGAACCTGATGGATTTTG

-continued

TGATGAATTCCCTGTACCTGGCCACAATCTCTCTGAAGATCGTGGCCTTCGTGAAGT

ATAGCGCCCTGAATCCCAGAGAGTCCTGGGACATGTGGCACCCTACCCTGGTGGCA

GAGGCCCTGTTCGCAATCGCCAACATCTTTTCCTCTCTGCGCCTGATCAGCCTGTTTA

CAGCCAATTCCCACCTGGGACCACTGCAGATCTCCCTGGGACGGATGCTGCTGGATA

TCCTGAAGTTCCTGTTTATCTACTGCCTGGTGCTGCTGGCCTTCGCCAACGGCCTGAA

TCAGCTGTACTTCTACTATGAGGAGACCAAGGGCCTGACATGCAAGGGCATCCGCTG

TGAGAAGCAGAACAATGCCTTCAGCACCCTGTTCGAGACACTGCAGTCTCTGTTCTG

GAGCATCTTTGGCCTGATCAACCTGTACGTGACCAATGTGAAGGCCCAGCACGAGTT

CACAGAGTTTGTGGGCGCCACCATGTTCGGCACATACAACGTGATCTCTCTGGTGGT

GCTGCTGAATATGCTGATCGCCATGATGAACAATAGCTATCAGCTGATCGCCGACCA

CGCCGATATCGAGTGGAAGTTCGCCCGGACCAAGCTGTGGATGTCCTACTTTGAGGA

GGGCGGCACCCTGCCCACACCTTTCAACGTGATCCCATCCCCCAAGTCTCTGTGGTA

TCTGATCAAGTGGATCTGGACACACCTGTGCAAGAAGAAGATGCGCCGGAAGCCTG

AGAGCTTTGGCACCATCGGCGTGCGCACACAGCACAGAAGGGCAGCAGACAACCTG

CGCCGGCACCACCAGTACCAGGAAGTGATGCGCAATCTGGTGAAGCGGTATGTGGC

CGCCATGATCAGGGACGCAAAGACCGAGGAGGGACTGACAGAGGAGAACTTCAAG

GAGCTGAAGCAGGATATCAGCTCCTTCAGATTTGAGGTGCTGGGCCTGCTGAGGGG

CAGCAAGCTGTCCACCATCCAGTCCGCCAACGCCTCTAAGGAGTCTAGCAATTCTGC

CGACAGCGATGAGAAGAGCGACTCCGAGGGCAACTCTAAGGATAAGAAGAAGAAC

TTCAGCCTGTTTGACCTGACCACACTGATCCACCCACGCAGCGCCGCAATCGCATCC

GAGCGGCACAACATCTCCAATGGCTCTGCCCTGGTGGTGCAGGAGCCACCAAGAGA

GAAGCAGAGGAAGGTGAACTTTGTGACAGATATCAAGAATTTCGGCCTGTTTCACA

GAAGGAGCAAGCAGAACGCCGCCGAGCAGAACGCCAATCAGATCTTCTCTGTGAGC

GAGGAGGTGGCAAGACAGCAGGCAGCAGGACCACTGGAGAGGAATATCCAGCTGG

AGAGCCGGGGACTGGCAAGCAGGGGCGACCTGTCCATCCCAGGACTGTCTGAGCAG

TGCGTGCTGGTGGACCACAGGGAGCGGAACACCGATACACTGGGACTGCAAGTGGG

CAAGCGGGTGTGCCCTTTCAAGAGCGAGAAGGTCGTGGTGGAGGACACCGTGCCCA

TCATCCCTAAGGAGAAGCACGCCAAGGAGGAGGATTCCTCTATCGACTACGATCTG

AATCTGCCAGACACCGTGACACACGAGGATTATGTGACCACAAGGCTGTGAGCGGC

CGCTCTAGAGGGCCCGTTTAAACCCGCTGATCAGCCTCGACTGTGCCTTCTAGTTGC

CAGCCATCTGTTGTTTGCCCCTCCCCCGTGCCTTCCTTGACCCTGGAAGGTGCCACTC

CCACTGTCCTTTCCTAATAAAATGAGGAAATTGCATCGCATTGTCTGAGTAGGTGTC

ATTCTATTCTGGGGGGTGGGGTGGGGCAGGACAGCAAGGGGGAGGATTGGGAAGAC

AATAGCAGGCATGCTGGGGATGCGGTGGGCTCTATGGCTTCTGAGGCGGAAAGAAC

CAGCTGGGGCTCTAGGGGGTATCCCCACGCGCCCTGTAGCGGCGCATTAAGCGCGG

CGGGTGTGGTGGTTACGCGCAGCGTGACCGCTACACTTGCCAGCGCCCTAGCGCCCG

CTCCTTTCGCTTTCTTCCCTTCCTTTCTCGCCACGTTCGCCGGCTTTCCCCGTCAAGCT

CTAAATCGGGGGCTCCCTTTAGGGTTCCGATTTAGTGCTTTACGGCACCTCGACCCC

AAAAAACTTGATTAGGGTGATGGTTCACGTAGTGGGCCATCGCCCTGATAGACGGTT

TTTCGCCCTTTGACGTTGGAGTCCACGTTCTTTAATAGTGGACTCTTGTTCCAAACTG

-continued

GAACAACACTCAACCCTATCTCGGTCTATTCTTTTGATTTATAAGGGATTTTGCCGAT

TTCGGCCTATTGGTTAAAAAATGAGCTGATTTAACAAAAATTTAACGCGAATTAATT

CTGTGGAATGTGTGTCAGTTAGGGTGTGGAAAGTCCCCAGGCTCCCCAGCAGGCAG

AAGTATGCAAAGCATGCATCTCAATTAGTCAGCAACCAGGTGTGGAAAGTCCCCAG

GCTCCCCAGCAGGCAGAAGTATGCAAAGCATGCATCTCAATTAGTCAGCAACCATA

GTCCCGCCCCTAACTCCGCCCATCCCGCCCCTAACTCCGCCCAGTTCCGCCCATTCTC

CGCCCCATGGCTGACTAATTTTTTTTATTTATGCAGAGGCCGAGGCCGCCTCTGCCTC

TGAGCTATTCCAGAAGTAGTGAGGAGGCTTTTTTGGAGGCCTAGGCTTTTGCAAAAA

GCTCCCGGGAGCTTGTATATCCATTTTCGGATCTGATCAGCACGTGATGAAAAAGCC

TGAACTCACCGCGACGTCTGTCGAGAAGTTTCTGATCGAAAAGTTCGACAGCGTCTC

CGACCTGATGCAGCTCTCGGAGGGCGAAGAATCTCGTGCTTTCAGCTTCGATGTAGG

AGGGCGTGGATATGTCCTGCGGGTAAATAGCTGCGCCGATGGTTTCTACAAAGATCG

TTATGTTTATCGGCACTTTGCATCGGCCGCGCTCCCGATTCCGGAAGTGCTTGACATT

GGGGAATTCAGCGAGAGCCTGACCTATTGCATCTCCCGCCGTGCACAGGGTGTCAC

GTTGCAAGACCTGCCTGAAACCGAACTGCCCGCTGTTCTGCAGCCGGTCGCGGAGG

CCATGGATGCGATCGCTGCGGCCGATCTTAGCCAGACGAGCGGGTTCGGCCCATTCG

GACCGCAAGGAATCGGTCAATACACTACATGGCGTGATTTCATATGCGCGATTGCTG

ATCCCCATGTGTATCACTGGCAAACTGTGATGGACGACACCGTCAGTGCGTCCGTCG

CGCAGGCTCTCGATGAGCTGATGCTTTGGGCCGAGGACTGCCCCGAAGTCCGGCAC

CTCGTGCACGCGGATTTCGGCTCCAACAATGTCCTGACGGACAATGGCCGCATAACA

GCGGTCATTGACTGGAGCGAGGCGATGTTCGGGGATTCCCAATACGAGGTCGCCAA

CATCTTCTTCTGGAGGCCGTGGTTGGCTTGTATGGAGCAGCAGACGCGCTACTTCGA

GCGGAGGCATCCGGAGCTTGCAGGATCGCCGCGGCTCCGGGCGTATATGCTCCGCA

TTGGTCTTGACCAACTCTATCAGAGCTTGGTTGACGGCAATTTCGATGATGCAGCTT

GGGCGCAGGGTCGATGCGACGCAATCGTCCGATCCGGAGCCGGGACTGTCGGGCGT

ACACAAATCGCCCGCAGAAGCGCGGCCGTCTGGACCGATGGCTGTGTAGAAGTACT

CGCCGATAGTGGAAACCGACGCCCCAGCACTCGTCCGAGGGCAAAGGAATAGCACG

TGCTACGAGATTTCGATTCCACCGCCGCCTTCTATGAAAGGTTGGGCTTCGGAATCG

TTTTCCGGGACGCCGGCTGGATGATCCTCCAGCGCGGGGATCTCATGCTGGAGTTCT

TCGCCCACCCCAACTTGTTTATTGCAGCTTATAATGGTTACAAATAAAGCAATAGCA

TCACAAATTTCACAAATAAAGCATTTTTTTCACTGCATTCTAGTTGTGGTTTGTCCAA

ACTCATCAATGTATCTTATCATGTCTGTATACCGTCGACCTCTAGCTAGAGCTTGGCG

TAATCATGGTCATAGCTGTTTCCTGTGTGAAATTGTTATCCGCTCACAATTCCACACA

ACATACGAGCCGGAAGCATAAAGTGTAAAGCCTGGGGTGCCTAATGAGTGAGCTAA

CTCACATTAATTGCGTTGCGCTCACTGCCCGCTTTCCAGTCGGGAAACCTGTCGTGC

CAGCTGCATTAATGAATCGGCCAACGCGCGGGGAGAGGCGGTTTGCGTATTGGGCG

CTCTTCCGCTTCCTCGCTCACTGACTCGCTGCGCTCGGTCGTTCGGCTGCGGCGAGCG

GTATCAGCTCACTCAAAGGCGGTAATACGGTTATCCACAGAATCAGGGGATAACGC

AGGAAAGAACATGTGAGCAAAAGGCCAGCAAAAGGCCAGGAACCGTAAAAAGGCC

GCGTTGCTGGCGTTTTTCCATAGGCTCCGCCCCCCTGACGAGCATCACAAAAATCGA

CGCTCAAGTCAGAGGTGGCGAAACCCGACAGGACTATAAAGATACCAGGCGTTTCC

-continued

CCCTGGAAGCTCCCTCGTGCGCTCTCCTGTTCCGACCCTGCCGCTTACCGGATACCTG

TCCGCCTTTCTCCCTTCGGGAAGCGTGGCGCTTTCTCATAGCTCACGCTGTAGGTATC

TCAGTTCGGTGTAGGTCGTTCGCTCCAAGCTGGGCTGTGTGCACGAACCCCCCGTTC

AGCCCGACCGCTGCGCCTTATCCGGTAACTATCGTCTTGAGTCCAACCCGGTAAGAC

ACGACTTATCGCCACTGGCAGCAGCCACTGGTAACAGGATTAGCAGAGCGAGGTAT

GTAGGCGGTGCTACAGAGTTCTTGAAGTGGTGGCCTAACTACGGCTACACTAGAAG

AACAGTATTTGGTATCTGCGCTCTGCTGAAGCCAGTTACCTTCGGAAAAAGAGTTGG

TAGCTCTTGATCCGGCAAACAAACCACCGCTGGTAGCGGTTGGTTTTTTTGTTTGCAA

GCAGCAGATTACGCGCAGAAAAAAAGGATCTCAAGAAGATCCTTTGATCTTTTCTAC

GGGGTCTGACGCTCAGTGGAACGAAAACTCACGTTAAGGGATTTTGGTCATGAGATT

ATCAAAAAGGATCTTCACCTAGATCCTTTTAAATTAAAAATGAAGTTTTAAATCAAT

CTAAAGTATATATGAGTAAACTTGGTCTGACAGTTACCAATGCTTAATCAGTGAGGC

ACCTATCTCAGCGATCTGTCTATTTCGTTCATCCATAGTTGCCTGACTCCCCGTCGTG

TAGATAACTACGATACGGGAGGGCTTACCATCTGGCCCCAGTGCTGCAATGATACCG

CGAGACCCACGCTCACCGGCTCCAGATTTATCAGCAATAAACCAGCCAGCCGGAAG

GGCCGAGCGCAGAAGTGGTCCTGCAACTTTATCCGCCTCCATCCAGTCTATTAATTG

TTGCCGGGAAGCTAGAGTAAGTAGTTCGCCAGTTAATAGTTTGCGCAACGTTGTTGC

CATTGCTACAGGCATCGTGGTGTCACGCTCGTCGTTTGGTATGGCTTCATTCAGCTCC

GGTTCCCAACGATCAAGGCGAGTTACATGATCCCCCATGTTGTGCAAAAAAGCGGTT

AGCTCCTTCGGTCCTCCGATCGTTGTCAGAAGTAAGTTGGCCGCAGTGTTATCACTC

ATGGTTATGGCAGCACTGCATAATTCTCTTACTGTCATGCCATCCGTAAGATGCTTTT

CTGTGACTGGTGAGTACTCAACCAAGTCATTCTGAGAATAGTGTATGCGGCGACCGA

GTTGCTCTTGCCCGGCGTCAATACGGGATAATACCGCGCCACATAGCAGAACTTTAA

AAGTGCTCATCATTGGAAAACGTTCTTCGGGGCGAAAACTCTCAAGGATCTTACCGC

TGTTGAGATCCAGTTCGATGTAACCCACTCGTGCACCCAACTGATCTTCAGCATCTTT

TACTTTCACCAGCGTTTCTGGGTGAGCAAAAACAGGAAGGCAAAATGCCGCAAAAA

AGGGAATAAGGGCGACACGGAAATGTTGAATACTCATACTCTTCCTTTTTCAATATT

ATTGAAGCATTTATCAGGGTTATTGTCTCATGAGCGGATACATATTTGAATGTATTTA

GAAAAATAAACAAATAGGGGTTCCGCGCACATTTCCCCGAAAAGTGCCACCTGACG

TC

B. TRPC5

The following sequence represents the plasmid used to prepare TRPC5. The underlined portion of the sequence represents the portion encoding human TRPC5.

GACGGATCGGGAGATCTCCCGATCCCCTATGGTGCACTCTCAGTACAATCTGCTCTG

ATGCCGCATAGTTAAGCCAGTATCTGCTCCCTGCTTGTGTGTTGGAGGTCGCTGAGT

AGTGCGCGAGCAAAATTTAAGCTACAACAAGGCAAGGCTTGACCGACAATTGCATG

AAGAATCTGCTTAGGGTTAGGCGTTTTGCGCTGCTTCGCGATGTACGGGCCAGATAT

ACGCGTTGACATTGATTATTGACTAGTTATTAATAGTAATCAATTACGGGGTCATTA

GTTCATAGCCCATATATGGAGTTCCGCGTTACATAACTTACGGTAAATGGCCCGCCT

-continued

GGCTGACCGCCCAACGACCCCCGCCCATTGACGTCAATAATGACGTATGTTCCCATA

GTAACGCCAATAGGGACTTTCCATTGACGTCAATGGGTGGAGTATTTACGGTAAACT

GCCCACTTGGCAGTACATCAAGTGTATCATATGCCAAGTACGCCCCCTATTGACGTC

AATGACGGTAAATGGCCCGCCTGGCATTATGCCCAGTACATGACCTTATGGGACTTT

CCTACTTGGCAGTACATCTACGTATTAGTCATCGCTATTACCATGGTGATGCGGTTTT

GGCAGTACATCAATGGGCGTGGATAGCGGTTTGACTCACGGGGATTTCCAAGTCTCC

ACCCCATTGACGTCAATGGGAGTTTGTTTTGGCACCAAAATCAACGGGACTTTCCAA

AATGTCGTAACAACTCCGCCCCATTGACGCAAATGGGCGGTAGGCGTGTACGGTGG

GAGGTCTATATAAGCAGAGCTCTCCCTATCAGTGATAGAGATCTCCCTATCAGTGAT

AGAGATCGTCGACGAGCTCGTTTAGTGAACCGTCAGATCGCCTGGAGACGCCATCC

ACGCTGTTTTGACCTCCATAGAAGACACCGGGACCGATCCAGCCTCCGGACTCTAGC

GTTTAAACTTAAGCCCAAGCTGGCTAGACCGCCATGGCCCAACTGTACTACAAAAA

GGTCAACTACTCACCGTACAGAGACCGCATCCCCCTGCAAATTGTGAGGGCTGAGA

CAGAGCTCTCTGCAGAGGAGAAGGCCTTCCTCAATGCTGTGGAGAAGGGGGACTAT

GCCACTGTGAAGCAGGCCCTTCAGGAGGCTGAGATCTACTATAATGTTAACATCAAC

TGCATGGACCCCTTGGGCCGGAGTGCCCTGCTCATTGCCATTGAGAACGAGAACCTG

GAGATCATGGAGCTACTGCTGAACCACAGCGTGTATGTGGGTGATGCATTGCTCTAT

GCCATACGCAAGGAAGTGGTGGGCGCTGTGGAGCTTCTGCTCAGCTACAGGCGGCC

CAGCGGAGAGAAGCAGGTCCCCACTCTGATGATGGACACGCAGTTCTCTGAATTCA

CACCGGACATCACTCCCATCATGCTGGCTGCCCACACCAACAACTACGAAATCATCA

AACTGCTTGTCCAAAAACGGGTCACTATCCCACGGCCCCACCAGATCCGCTGCAACT

GTGTGGAGTGTGTGTCTAGTTCAGAGGTAGACAGCCTGCGCCACTCTCGCTCCCGAC

TGAACATCTATAAGGCTCTGGCAAGCCCCTCACTCATTGCCTTATCAAGTGAGGACC

CCATCCTAACTGCCTTCCGTCTGGGCTGGGAGCTCAAGGAGCTCAGCAAGGTGGAG

AATGAGTTCAAGGCCGAGTATGAGGAGCTCTCTCAGCAGTGCAAGCTCTTTGCCAAA

GACCTGCTGGACCAAGCTCGGAGCTCCAGGGAACTGGAGATCATCCTCAACCATCG

AGATGACCACAGTGAAGAGCTTGACCCTCAGAAGTACCATGACCTGGCCAAGTTGA

AGGTGGCAATCAAATACCACCAGAAAGAGTTTGTTGCTCAGCCCAACTGCCAACAG

TTGCTTGCCACCCTGTGGTATGATGGCTTCCCTGGATGGCGGCGGAAACACTGGGTA

GTCAAGCTTCTAACCTGCATGACCATTGGGTTCCTGTTTCCCATGCTGTCTATAGCCT

ACCTGATCTCACCCAGGAGCAACCTTGGGCTGTTCATCAAGAAACCCTTTATCAAGT

TTATCTGCCACACAGCATCCTATTTGACCTTCCTCTTTATGCTTCTCCTGGCTTCTCAG

CACATTGTCAGGACAGACCTTCATGTACAGGGGCCTCCCCCAACTGTCGTGGAATGG

ATGATATTGCCTTGGGTTCTAGGTTTCATTTGGGGTGAGATTAAGGAAATGTGGGAT

GGTGGATTTACTGAATACATCCATGACTGGTGGAACCTGATGGATTTTGCAATGAAC

TCCCTCTACCTGGCAACTATTTCCCTGAAGATTGTGGCCTATGTCAAGTATAATGGTT

CTCGTCCAAGGGAGGAATGGGAAATGTGGCACCCGACTCTGATTGCGGAAGCACTC

TTCGCAATATCCAACATTTTAAGTTCGTTGCGTCTCATATCCCTGTTCACAGCCAACT

CCCACTTAGGACCTCTGCAGATCTCTTTGGGACGCATGCTGCTTGATATCCTCAAATT

CCTCTTTATCTACTGCCTGGTACTACTAGCTTTTGCCAATGGACTGAACCAGCTTTAC

TTCTATTATGAAACCAGAGCTATCGATGAGCCTAACAACTGCAAGGGGATCCGATGT

-continued

GAGAAACAGAACAATGCCTTCTCCACGCTCTTTGAGACTCTTCAGTCACTCTTCTGG

TCTGTATTTGGCCTTTTAAATCTATATGTCACCAATGTGAAAGCCAGACACGAATTC

ACCGAGTTTGTAGGAGCTACCATGTTTGGAACATACAATGTCATCTCCCTGGTAGTG

CTGCTGAACATGCTGATTGCTATGATGAACAACTCCTATCAGCTTATTGCCGATCAT

GCTGATATCGAGTGGAAGTTTGCAAGGACGAAGCTCTGGATGAGTTACTTTGATGAA

GGTGGCACCTTGCCACCTCCTTTCAACATCATCCCCAGCCCCAAGTCATTTCTATACC

TTGGTAACTGGTTCAACAACACCTTCTGCCCCAAAAGAGACCCTGACGGTAGACGG

AGAAGGCGCAACTTGAGAAGTTTCACAGAACGCAATGCTGACAGCCTGATACAAAA

TCAACATTATCAGGAAGTTATCAGGAATTTAGTCAAAAGATATGTGGCTGCTATGAT

AAGAAATTCCAAAACACATGAGGGACTTACAGAAGAAAATTTTAAGGAATTAAAGC

AAGACATCTCCAGCTTTCGGTATGAAGTGCTTGACCTCTTGGGAAATAGAAAACATC

CAAGGAGCTTTTCCACTAGCAGCACTGAACTGTCTCAGAGAGACGATAATAATGAT

GGCAGTGGTGGGGCTCGGGCCAAATCCAAGAGTGTCTCTTTTAATTTAGGCTGCAAG

AAAAAGACTTGCCATGGGCCACCTCTCATCAGAACCATGCCAAGGTCCAGTGGTGC

CCAAGGAAAGTCAAAAGCTGAGTCATCAAGCAAACGCTCCTTCATGGGTCCTTCTCT

CAAGAAACTGGGTCTCCTATTCTCCAAATTTAATGGTCATATGTCTGAACCCAGTTC

AGAGCCAATGTACACAATTTCTGATGGAATTGTTCAGCAGCACTGTATGTGGCAGGA

CATCAGATATTCTCAGATGGAGAAAGGGAAAGCAGAGGCCTGTTCTCAAAGTGAAA

TTAACCTCAGTGAGGTAGAATTAGGTGAAGTCCAGGGCGCTGCTCAGAGCAGTGAA

TGCCCTCTAGCCTGTTCCAGCTCTCTTCACTGTGCATCCAGCATCTGCTCCTCAAATT

CTAAACTTTTAGACTCCTCAGAGGATGTATTTGAAACTTGGGGAGAGGCTTGTGACT

TGCTCATGCACAAATGGGGTGATGGACAGGAAGAACAAGTTACAACTCGCCTCTAA

TGACTCGAGTCTAGAGGGCCCGTTTAAACCCGCTGATCAGCCTCGACTGTGCCTTCT

AGTTGCCAGCCATCTGTTGTTTGCCCCTCCCCCGTGCCTTCCTTGACCCTGGAAGGTG

CCACTCCCACTGTCCTTTCCTAATAAAATGAGGAAATTGCATCGCATTGTCTGAGTA

GGTGTCATTCTATTCTGGGGGGTGGGGTGGGGCAGGACAGCAAGGGGGAGGATTGG

GAAGACAATAGCAGGCATGCTGGGGATGCGGTGGGCTCTATGGCTTCTGAGGCGGA

AAGAACCAGCTGGGGCTCTAGGGGGTATCCCCACGCGCCCTGTAGCGGCGCATTAA

GCGCGGCGGGTGTGGTGGTTACGCGCAGCGTGACCGCTACACTTGCCAGCGCCCTA

GCGCCCGCTCCTTTCGCTTTCTTCCCTTCCTTTCTCGCCACGTTCGCCGGCTTTCCCCG

TCAAGCTCTAAATCGGGGGCTCCCTTTAGGGTTCCGATTTAGTGCTTTACGGCACCTC

GACCCCAAAAAACTTGATTAGGGTGATGGTTCACGTAGTGGGCCATCGCCCTGATAG

ACGGTTTTTCGCCCTTTGACGTTGGAGTCCACGTTCTTTAATAGTGGACTCTTGTTCC

AAACTGGAACAACACTCAACCCTATCTCGGTCTATTCTTTTGATTTATAAGGGATTTT

GCCGATTTCGGCCTATTGGTTAAAAAATGAGCTGATTTAACAAAAATTTAACGCGAA

TTAATTCTGTGGAATGTGTGTCAGTTAGGGTGTGGAAAGTCCCCAGGCTCCCCAGCA

GGCAGAAGTATGCAAAGCATGCATCTCAATTAGTCAGCAACCAGGTGTGGAAAGTC

CCCAGGCTCCCCAGCAGGCAGAAGTATGCAAAGCATGCATCTCAATTAGTCAGCAA

CCATAGTCCCGCCCCTAACTCCGCCCATCCCGCCCCTAACTCCGCCCAGTTCCGCCC

ATTCTCCGCCCCATGGCTGACTAATTTTTTTTATTTATGCAGAGGCCGAGGCCGCCTC

-continued

TGCCTCTGAGCTATTCCAGAAGTAGTGAGGAGGCTTTTTTGGAGGCCTAGGCTTTTG

CAAAAAGCTCCCGGGAGCTTGTATATCCATTTTCGGATCTGATCAGCACGTGATGAA

AAAGCCTGAACTCACCGCGACGTCTGTCGAGAAGTTTCTGATCGAAAAGTTCGACA

GCGTCTCCGACCTGATGCAGCTCTCGGAGGGCGAAGAATCTCGTGCTTTCAGCTTCG

ATGTAGGAGGGCGTGGATATGTCCTGCGGGTAAATAGCTGCGCCGATGGTTTCTACA

AAGATCGTTATGTTTATCGGCACTTTGCATCGGCCGCGCTCCCGATTCCGGAAGTGC

TTGACATTGGGGAATTCAGCGAGAGCCTGACCTATTGCATCTCCCGCCGTGCACAGG

GTGTCACGTTGCAAGACCTGCCTGAAACCGAACTGCCCGCTGTTCTGCAGCCGGTCG

CGGAGGCCATGGATGCGATCGCTGCGGCCGATCTTAGCCAGACGAGCGGGTTCGGC

CCATTCGGACCGCAAGGAATCGGTCAATACACTACATGGCGTGATTTCATATGCGCG

ATTGCTGATCCCCATGTGTATCACTGGCAAACTGTGATGGACGACACCGTCAGTGCG

TCCGTCGCGCAGGCTCTCGATGAGCTGATGCTTTGGGCCGAGGACTGCCCCGAAGTC

CGGCACCTCGTGCACGCGGATTTCGGCTCCAACAATGTCCTGACGGACAATGGCCGC

ATAACAGCGGTCATTGACTGGAGCGAGGCGATGTTCGGGGATTCCCAATACGAGGT

CGCCAACATCTTCTTCTGGAGGCCGTGGTTGGCTTGTATGGAGCAGCAGACGCGCTA

CTTCGAGCGGAGGCATCCGGAGCTTGCAGGATCGCCGCGGCTCCGGGCGTATATGC

TCCGCATTGGTCTTGACCAACTCTATCAGAGCTTGGTTGACGGCAATTTCGATGATG

CAGCTTGGGCGCAGGGTCGATGCGACGCAATCGTCCGATCCGGAGCCGGGACTGTC

GGGCGTACACAAATCGCCCGCAGAAGCGCGGCCGTCTGGACCGATGGCTGTGTAGA

AGTACTCGCCGATAGTGGAAACCGACGCCCCAGCACTCGTCCGAGGGCAAAGGAAT

AGCACGTGCTACGAGATTTCGATTCCACCGCCGCCTTCTATGAAAGGTTGGGCTTCG

GAATCGTTTTCCGGGACGCCGGCTGGATGATCCTCCAGCGCGGGGATCTCATGCTGG

AGTTCTTCGCCCACCCCAACTTGTTTATTGCAGCTTATAATGGTTACAAATAAAGCA

ATAGCATCACAAATTTCACAAATAAAGCATTTTTTTCACTGCATTCTAGTTGTGGTTT

GTCCAAACTCATCAATGTATCTTATCATGTCTGTATACCGTCGACCTCTAGCTAGAGC

TTGGCGTAATCATGGTCATAGCTGTTTCCTGTGTGAAATTGTTATCCGCTCACAATTC

CACACAACATACGAGCCGGAAGCATAAAGTGTAAAGCCTGGGGTGCCTAATGAGTG

AGCTAACTCACATTAATTGCGTTGCGCTCACTGCCCGCTTTCCAGTCGGGAAACCTG

TCGTGCCAGCTGCATTAATGAATCGGCCAACGCGCGGGGAGAGGCGGTTTGCGTATT

GGGCGCTCTTCCGCTTCCTCGCTCACTGACTCGCTGCGCTCGGTCGTTCGGCTGCGGC

GAGCGGTATCAGCTCACTCAAAGGCGGTAATACGGTTATCCACAGAATCAGGGGAT

AACGCAGGAAAGAACATGTGAGCAAAAGGCCAGCAAAAGGCCAGGAACCGTAAAA

AGGCCGCGTTGCTGGCGTTTTTCCATAGGCTCCGCCCCCCTGACGAGCATCACAAAA

ATCGACGCTCAAGTCAGAGGTGGCGAAACCCGACAGGACTATAAAGATACCAGGCG

TTTCCCCCTGGAAGCTCCCTCGTGCGCTCTCCTGTTCCGACCCTGCCGCTTACCGGAT

ACCTGTCCGCCTTTCTCCCTTCGGGAAGCGTGGCGCTTTCTCATAGCTCACGCTGTAG

GTATCTCAGTTCGGTGTAGGTCGTTCGCTCCAAGCTGGGCTGTGTGCACGAACCCCC

CGTTCAGCCCGACCGCTGCGCCTTATCCGGTAACTATCGTCTTGAGTCCAACCCGGT

AAGACACGACTTATCGCCACTGGCAGCAGCCACTGGTAACAGGATTAGCAGAGCGA

GGTATGTAGGCGGTGCTACAGAGTTCTTGAAGTGGTGGCCTAACTACGGCTACACTA

GAAGAACAGTATTTGGTATCTGCGCTCTGCTGAAGCCAGTTACCTTCGGAAAAAGAG

-continued

```
TTGGTAGCTCTTGATCCGGCAAACAAACCACCGCTGGTAGCGGTTGGTTTTTTGTTTG

CAAGCAGCAGATTACGCGCAGAAAAAAAGGATCTCAAGAAGATCCTTTGATCTTTT

CTACGGGGTCTGACGCTCAGTGGAACGAAAACTCACGTTAAGGGATTTTGGTCATGA

GATTATCAAAAAGGATCTTCACCTAGATCCTTTTAAATTAAAAATGAAGTTTTAAAT

CAATCTAAAGTATATATGAGTAAACTTGGTCTGACAGTTACCAATGCTTAATCAGTG

AGGCACCTATCTCAGCGATCTGTCTATTTCGTTCATCCATAGTTGCCTGACTCCCCGT

CGTGTAGATAACTACGATACGGGAGGGCTTACCATCTGGCCCCAGTGCTGCAATGAT

ACCGCGAGACCCACGCTCACCGGCTCCAGATTTATCAGCAATAAACCAGCCAGCCG

GAAGGGCCGAGCGCAGAAGTGGTCCTGCAACTTTATCCGCCTCCATCCAGTCTATTA

ATTGTTGCCGGGAAGCTAGAGTAAGTAGTTCGCCAGTTAATAGTTTGCGCAACGTTG

TTGCCATTGCTACAGGCATCGTGGTGTCACGCTCGTCGTTTGGTATGGCTTCATTCAG

CTCCGGTTCCCAACGATCAAGGCGAGTTACATGATCCCCCATGTTGTGCAAAAAAGC

GGTTAGCTCCTTCGGTCCTCCGATCGTTGTCAGAAGTAAGTTGGCCGCAGTGTTATC

ACTCATGGTTATGGCAGCACTGCATAATTCTCTTACTGTCATGCCATCCGTAAGATG

CTTTTCTGTGACTGGTGAGTACTCAACCAAGTCATTCTGAGAATAGTGTATGCGGCG

ACCGAGTTGCTCTTGCCCGGCGTCAATACGGGATAATACCGCGCCACATAGCAGAA

CTTTAAAAGTGCTCATCATTGGAAAACGTTCTTCGGGGCGAAAACTCTCAAGGATCT

TACCGCTGTTGAGATCCAGTTCGATGTAACCCACTCGTGCACCCAACTGATCTTCAG

CATCTTTTACTTTCACCAGCGTTTCTGGGTGAGCAAAAACAGGAAGGCAAAATGCCG

CAAAAAAGGGAATAAGGGCGACACGGAAATGTTGAATACTCATACTCTTCCTTTTTC

AATATTATTGAAGCATTTATCAGGGTTATTGTCTCATGAGCGGATACATATTTGAAT

GTATTTAGAAAAATAAACAAATAGGGGTTCCGCGCACATTTCCCCGAAAAGTGCCA

CCTGACGTC
```

II. Fluorescence-Based Assays

A. TRPC4

ICLN-1694 cells (HEK-TREx hTRPC4) expressing TRPC4 were generated as follows. Commercially available HekTrex-293 cells were seeded at $0.7\times10^6$ cells/well in a 1×6-well plate 24 hrs prior to transfection using 2 mL cell growth media containing no antibiotics (lx DMEM/high glucose (Hyclone #SH30022.02); 10% fetal bovine serum (Sigma) 2 mM sodium pyruvate, 10 mM HEPES). The human codon-optimized TRPC4 coding sequence was cloned into pcDNA5/TO(Invitrogen; Cat No. V103320) using hygromycin as the resistance gene and the plasmid (SEQ ID NO:1) propagated using T-Rex-293 cells (Invitrogen; Cat No. R71007) following manufacturer's directions. On day 2, 2 μg of plasmid DNA plus 6 μl of Xtreme-GENE HP reagent in Optimem (200 μl total volume) was prepared and incubated for 15 min at room temperature. This plasmid solution was then gently overlayed dropwise onto each well and the plate was gently swirled to mix complex with the media for approximately 30 seconds. Transfected cells were incubated at 37° C. in a 10% $CO_2$ incubator for 24 hrs. The transfected cells were harvested and transferred into 2×150 mm dishes containing cell growth media with no antibiotics at 37° C.

The next day selection was initiated to generate a stable pool by adding cell growth media containing 150 μg/mL Hygromycin and 5 μg/mL Blasticidin and cells were allowed to grow. Media with the selection agent was changed every 1-2 days as needed to remove dead cells. After 7 days, the hygromycin concentration was reduced to 75 μg/mL and cells growth was allowed to continue.

Single clones were selected as follows. The stable pool was diluted to 10 cells/mL and seeded (100 μl/well) into 24×96 well plates (~1 cell/well) and allowed to grow for 7 days in cell growth media. Fresh media (100 μl) was added and the cells allowed to grow for another 1-2 weeks and then stored frozen or used immediately.

TRPC4 Assay Procedure

HEK 293 cells expressing human TRPC4 cells were trypsinised, counted and seeded in black, clear-bottomed 96-well plates at a density of 50,000 cells per well and incubated overnight Next day, the cells were loaded with membrane potential dye. Dye solution was made up according to the manufacturer's instructions in HEPES buffered Hank's balanced salt solution (HBSS). Dye solution (10 μL) was added to the wells and incubated at 37° C. for 1 hour. The test compounds and standard inhibitors were added to the wells and incubated at room temperature for 10 minutes. The plates were then placed in the flexstation and fluorescence monitored every 1.52 seconds. After 20 seconds, 10 μL of the appropriate standard agonist was added and the fluorescence monitored for 2 minutes at ex/emm: 530 nm/565 nm.

TRPC4 FLIPR Assay: General Procedure Description
Materials

| Material | Vendor |
|---|---|
| TRPC4 Assay Buffer | Prepared as described below |
| 384-well, Black Poly-d-Lysine Coated Plates | Costar |
| Dimethyl Sulfoxide (DMSO) | Fisher |
| Englerin A (TRPC4 activator) | Cerilliant (cat # PHY82530) |
| 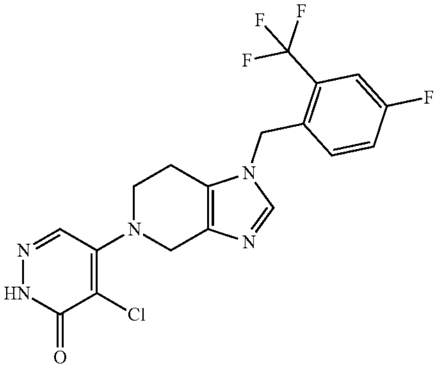 (Control Inhibitor) | Goldfinch |
| Fluo-4 (AM) | Invitrogen |
| Pluronic F-127 (20% DMSO) | Invitrogen |
| Equipment | Vendor |
| Echo-550 | Labcyte |
| FLIPR-II (384) | Molecular Devices |

Cell line: ICLN-001694
Base cell: HEK
Channel: TRPC4
Species: Human
Thaw ID: multiple
Passage: multiple FLIPR Assay Buffer (Earls Balanced Salt Solution (EBSS)) was prepared as follows:

| | Conc (mM) |
|---|---|
| NaCl | 142 |
| KCl | 5.4 |
| Glucose | 10 |
| $CaCl_2$ | 1.8 |
| $MgCl_2$ | 0.8 |
| HEPES | 10 |
| pH | 7.4 with NaOH |
| Osmolarity | ~290-300 mOsm |

Test Agent Preparation: Compounds were made up to, or supplied as, a 10 mM stock solution generally using DMSO as the vehicle. 10-point dose response curves were generated using the Echo-550 acoustic dispenser. Compound source plates were made by serially diluting compound stocks to create 10 mM, 1 mM, and 0.1 mM solutions in DMSO into Echo certified LDV plates. The Echo then serially spotted 100% DMSO stock solutions into source dose response plates to generate a 4-fold dilution scheme. 100% DMSO was added to the spotted dose response plates to bring the final volume to 5 µl. 300 nl of the dose response stock plate was then spotted into pre-incubation and stimulation assay plates. 50 µl of pre-incubation buffer and 100 µl of stimulation buffer was then added to the plates resulting in a final assay test concentration range of 30 µM to 0.0001 µM with a final DMSO concentration of 0.3%.

Experimental Methods: Cells expressing TRPC4 were plated onto 384 well, black pdl-coated microplates and maintained in TRPC4 growth media the day prior to use for experiments. TRPC4 expression was induced by the application of 1 µg/ml tetracycline at the time of plating. Media was removed from the plates and 10 µl of 4 µM of Fluo-4 AM (mixed with equal volume of Pluronic F-127) in EBSS was added to the cells. Cells were incubated at room temperature, protected from light, for 60-90 minutes. After the incubation period, the dye was removed and replaced with 10 µl of EBSS. Cell, pre-incubation and stimulation plates were loaded onto the FLIPR-II and the assay was initiated. The FLIPR measured a 10 second baseline and then added 10 µl of 2× compounds (or controls). Changes in fluorescence were monitored for an additional 5 minutes. After a 5 minute pre-incubation, 20 µl of 2× Englerin A (with 1× compound or controls) was added to the cell plate. The final Engerlin A stimulation concentration in the assay is 100 nM. After the Englerin A addition, changes in fluorescence were monitored for an additional 5 minutes.

Test Agent Effect: Test agent modulation of TRPC4 calcium response was determined as follows. After the Englerin A, fluorescence was monitored for a 5 minute period. The maximum relative fluorescence response (minus the control response of 1 µM of the control inhibitor) was captured and exported from the FLIPR Test agent effect was calculated as % inhibition using the following formula: % inhibition=((RFU TEST AGENT−Plate Average RFU REF INHIB)/(Plate Average RFU CONTROL−Plate Average RFU REF INHIB))×100

B. TRPC5

ICLN-1633 cells (HEK-TREx hTRPC5) expressing TRPC5 were generated as follows. Commercially available HekTrex-293 cells were seeded at $0.7\times10^6$ cells/well in a 1×6-well plate 24 hrs prior to transfection using 2 mL cell growth media containing no antibiotics (lx DMEM/high glucose (Hyclone #SH30022.02); 10% fetal bovine serum (Sigma) 2 mM sodium pyruvate, 10 mM HEPES). The human TRPC5 coding sequence (NM_012471 with a silent T478C mutation) was cloned into pcDNA5/TO(Invitrogen; Cat No. V103320) using hygromycin as the resistance gene and the plasmid (SEQ ID NO:2) propagated using T-Rex-293 cells (Invitrogen; Cat No. R71007) following manufacturer's directions. On day 2, 2 μg of plasmid DNA plus 6 μl of Xtreme-GENE HP reagent in Optimem (200 μl total volume) was prepared and incubated for 15 min at room temperature. This plasmid solution was then gently overlayed dropwise onto each well and the plate was gently swirled to mix complex with the media for approximately 30 seconds. Transfected cells were incubated at 37° C. in a 10% $CO_2$ incubator for 24 hrs. The transfected cells were harvested and transferred into 2×150 mm dishes containing cell growth media with no antibiotics at 37° C.

The next day selection was initiated to generate a stable pool by adding cell growth media containing 150 μg/mL Hygromycin and 5 μg/mL Blasticidin and cells were allowed to grow. Media with the selection agent was changed every 1-2 days as needed to remove dead cells. After 7 days, the hygromycin concentration was reduced to 75 μg/mL and cells growth was allowed to continue.

Single clones were selected as follows. The stable pool was diluted to 10 cells/mL and seeded (100 μl/well) into 24×96 well plates (~1 cell/well) and allowed to grow for 7 days in cell growth media. Fresh media (100 μl) was added and the cells allowed to grow for another 1-2 weeks and then stored frozen or used immediately.

Cell Line Generation: Stable Pool

Day 1

HekTrex-293 cells were seeded @ 0.7×106 cells per well on 1×6-well plate 24 hours prior to transfection using 2 mL volume of media containing no antibiotics.

Day 2

For each well, 2 μg of plasmid DNA+6 μL of Xtreme-GENE HP reagent in 200 μL of total volume was used. For example, 5 μL of DNA was combined with 189 μL of Optimem, and 6 μL of Streme-GENE HP reagent was added. The complex (Optimem+NDA+Xtreme-Gene HP) was incubated for 15 min at room temperature overlayed (dropwise) of the 200 μL of complex mixture onto each well of the 6 well plate containing the seeded HekTrex-293 cells, and the plate was gently swirled (using a figure eight pattern) to mix the complex with the media for approximately 30 seconds. Transfected cells were incubated at 37° C. in the 10% $CO_2$ incubator for 24 hours.

Day 3

Transfected cells were harvested and transferred into 2×150 mm dishes at 37° C. (no antibiotics in media).

Day 4

Selection was initiated to generate the stable pool: Media with selection agents was added: DMEM-HG+Hepes+Sodium pyruvate+150 ug/ml hygromycin+5 ug/ml blasticidin. Note: selection media was changed every 1-2 days as needed to remove dead cells. After 7 days, the hygromycin concentration was reduced to 75 ug/ml and cells were continued to be maintained in this media: DMEM-HG+Hepes+Sodium pyruvate+75 ug/ml hygromycin+5 ug/ml blasticidin.

Cell Line Generation: Dilution for Single Clones

Day 1

The stable pool was diluted to 10 cells/ml and seeded 100 uL/well into 24×96 well plates (=~1 cell/well).

Day 8

Plates were fed by adding 100 uL of fresh media to each well.

Day 15-20

Single clones were seeded to test on FLIPR (~1 clone/well, on average 30-60 clones per 96 well plate).

General Culture Notes

Black 96 well plates

10% $CO_2$

Weakly adherent

Inducible construct

PDL coated plates

Preparation of Media with Antibiotics (for Maintenance)

| | Vendor Information | Stock Conc. | Volume of Stock Used | Final Conc. |
|---|---|---|---|---|
| DMEM/high glucose | Hyclone #SH30022.02-1 L | 1x | 1000 ml | 1x |
| Fetal Bovine Serum | Sigma #F8067-500 mL | 100% | 116 ml | 10% |
| Sodium pyruvate | Hyclone #SH30239.01-100 mL | 100 mM | 23 ml | ~2 mM |
| Hepes | Hyclone #SH30237.01-100 mL | 1M | 12 ml | ~10 mM |
| Hygromycin B | Invitrogen 10687010-20 mL | 50 mg/ml | 1.7 ml | 75 ug/ml |
| Blasticidin S HCl | Gibco (Life Tech) #A11139-03 | 10 mg/ml | 0.58 ml | 5 ug/ml |
| | | Total volume: | ~1163 mL | |

Storage and Thawing Cells

Cells were stored in liquid nitrogen to preserve viability and performance. When ready to use the cells, each vial was thawed as follows:

The frozen vial (4E6 cells/vial frozen in FBS+10%/DMSO) was removed front the liquid nitrogen and placed immediately in a 370 water bath, and gentry shaken until the ice pellet nearly disappeared (2-3 minutes). The thrawed vial was then sprayed with 70%/ethanol, wiped dry, and placed in a biological safety cabinet. The content of each vial (~1 ml) was carefully transferred to a 50 ml centrifuge tube. This and all remaining steps were done in a sterile manner. The cryovial was rinsed with 1 ml of room temperature media without antibiotics to recover any residual cells from the vial. The 1 ml rinse was transferred to the 50 ml centrifuge tube containing the cell suspension (~1 drop/sec, to minimize the osmotic shock to the thawed cells). The tube was gently swirled while adding to completely mix the solution. An additional 8 ml of room temperature media was slowly added to the 50 ml centrifuge tube (~1-2 drop/sec), gently swirling the centrifuge tube while adding the media. The contents were gently mixed while avoiding vigorous shaking or vortexing. The celsl were then centrifuged for 5 min at 150-200 RCF, to change the media to eliminate DMSO from the freezing media. The media was aspirated and the pelleted cells were resuspended with 1 ml of media without antibiotics, avoiding fast pipetting to reduce formation of air bubbles. The 4E6 cells were placted in a T225 flask filled with ~45 ml of media without any antibiotics and incubated for approximately 16-24 hours at 37° in 10% $CO_2$ conditions. The media in the flask was then replaced with media and antibiotics, and the celsl were cultured until they appeared healthy and reached 80% confluency.

Harvesting Flasks

The media was aspirated from the flask (e.g., a T225 flask) using an aspirating pipette. The flask was rinsed with calcium- and magnesium-free phosphate buffered saline (PBS), and the PBS was aspirated and discareded. 3 ml of trypsin/EDTA was added, and the flask was rocked until the entire cell momolayer was bathed in enzyme solution. The cells were then incubated in trypsin/EDTA for 2-3 minutes at room temperature to detach the cells, and 17.0 ml of media was pipetted across the growth surface of the flask to dislodge cells. The cell suspension was then triturated to obtain a single cell suspension, and the cell suspension was transferred to a sterile tube containing 20 ml media. The cells were then counted to determine cell density (cells/ml).

Seeding Cells for SyncroPatch, FLIPR, QPatch, and Manual Patch

SyncroPatch: 48 hours prior to testing for electrophysiology assays, seeded @ 7E6 cells for T225, induced flask(s) with 1 ug/ml tetracycline 24 hours prior to testing.

QPatch: 48 hours prior to testing for electrophysiology assays, seeded 2E6 cells for T725, induced flask(s) with 1 ug/ml tetracycline 24 hours prior to testing.

FLIPR: 24 hours prior to testing, seeded cells @ 6.5E6 cells/plate ($65\times10^3$ cells/well) in the presence of 1 ug/ml tetracycline.

Manual Patch: 24-48 hours prior to testing: seeded 35 mm dish containing 4 round cover slips at $100\text{-}200\times10^3$ cells (induced with 1 ug/ml tetracycline 24 hour prior to testing).

TRPC5 Assay Procedure

HEK 293 cells expressing human TRPC5 cells were trypsinised, counted and seeded in black, clear-bottomed 96-well plates at a density of 50,000 cells per well and incubated overnight Next day, the cells were loaded with membrane potential dye. Dye solution was made up according to the manufacturer's instructions in HEPES buffered Hank's balanced salt solution (HBSS). Dye solution (10 μL) was added to the wells and incubated at 37° C. for 1 hour. The test compounds and standard inhibitors were added to the wells and incubated at room temperature for 10 minutes. The plates were then placed in the flexstation and fluorescence monitored every 1.52 seconds. After 20 seconds, 10 μL of the appropriate standard agonist was added and the fluorescence monitored for 2 minutes at ex/emm: 530 nm/565 nm.

TRPC5 Fluorescence Assay—FLIPR Format:

Test Materials and Key Reagents:

| Material | Vendor |
|---|---|
| TRPC5 Assay Buffer | Prepared as described below |
| 384-well, Black Poly-d-Lysine Coated Plates | Costar |
| Dimethyl sulfoxide (DMSO) | Fisher |
| Riluzole (TRPC5 activator) | Tocris |
| 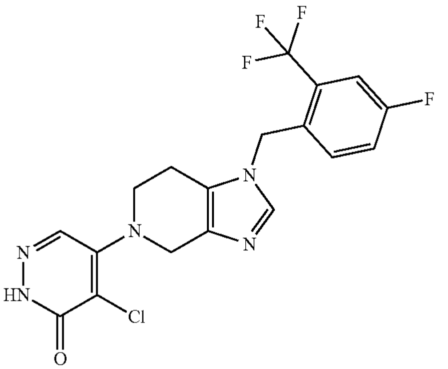 (Control TRPC5 Inhibitor) | Goldfinch Bio |
| Fluo-4 (AM) | Invitrogen |
| Pluronic F-127 (20% DMSO) | Invitrogen |
| Equipment | Vendor |
| Echo-550 | Labcyte |
| FLIPR-II (384) | Molecular Devices |

Cell line: ICLN-001633

Base Cell: HEK

Channel: TRPC5

Species: Human

Thaw ID: multiple

Passage: multiple

FLIPR Assay Buffer (Earls Balanced Salt Solution (EBSS)) was prepared as follows:

| | Conc (mM) |
|---|---|
| NaCl | 142 |
| KCl | 5.4 |
| Glucose | 10 |
| $CaCl_2$ | 1.8 |
| $MgCl_2$ | 0.8 |
| HEPES | 10 |
| pH | 7.4 with NaOH |
| Osmolarity | ~290-300 mOsm |

Test Agent Preparation: Compounds were made up to, or supplied as, a 10 mM stock solution generally using DMSO as the vehicle. 10-point dose response curves were generated using the Echo-550 acoustic dispenser. Compound source plates were made by serially diluting compound stocks to create 10 mM, 1 mM, and 0.1 mM solutions in DMSO into Echo certified LDV plates. The Echo then serially spotted 100% DMSO stock solutions into source dose response plates to generate a 4-fold dilution scheme. 100% DMSO was added to the spotted dose response plates to bring the final volume to 5 μl. 300 nl of the dose response stock plate was then spotted into pre-incubation and stimulation assay plates. 50 μl of pre-incubation buffer and 100 μl of stimulation buffer was then added to the plates resulting in a final assay test concentration range of 30 μM to 0.0001 μM with a final DMSO concentration of 0.3%.

Experimental Methods: Cells expressing TRPC5 (HEK-TREx hTRPC5) are plated onto 384 well, black PDL-coated microplates and maintained in TRPC5 growth media the day prior to use for experiments. TRPC5 expression is induced by the application of 1 μg/mL tetracycline at the time of plating. Media is removed from the plates and 10 μl of 4 μM of Fluo-4 AM (mixed with equal volume of Pluronic F-127) in EBSS is added to the cells. Cells are incubated at room temperature, protected from light, for 60-90 minutes. After the incubation period, the dye is removed and replaced with 10 μl of EBSS. Cell, pre-incubation and stimulation plates are loaded onto the FLIPR-II and the assay is initiated. The FLIPR measures a 10 second baseline and then adds 10 μl of 2× compounds (or controls). Changes in fluorescence are monitored for an additional 5 minutes. After the 5 minute pre-incubation, 20 μl of 2× Riluzole (with 1× compound or controls) is added to the cell plate. The final Riluzole stimulation concentration in the assay is 30 μM. After the Riluzole addition, changes in fluorescence are monitored for an additional 5 minutes.

Test Agent Effect: Test agent modulation of TRPC5 calcium response was determined as follows. After the Riluzole, fluorescence was monitored for a 5 minute period. The maximum relative fluorescene response (minus the control response of 1 μM of the control inhibitor) was captured and exported from the FLIPR Test agent effect was calculated as % inhibition using the following formula: % inhibition=((RFU Test Agent−Plate Average RFU REF INHIB)/(Plate Average RFU Control−Plate Average RFU REF INHIB))×100

C. TRPC6

HEK 293 cells expressing human TRPC6 cells were trypsinised, counted and seeded in black, clear-bottomed 96-well plates at a density of 50,000 cells per well and incubated overnight Next day, the cells were loaded with membrane potential dye (Molecular Devices, cat: R8127). Dye solution was made up according to the manufacturer's instructions in HEPES buffered Hank's balanced salt solution (HBSS). Dye solution was added to the wells and incubated at 37*C for 1 hour. The test compounds and standard inhibitors were added to the wells and incubated at room temperature for 10 minutes prior to addition of activator. The plates were then placed in the flexstation and fluorescence monitored every 1.52 seconds. After 20 seconds, the standard activator (Carbachol) was added and the fluorescence monitored for 2 minutes at ex/emm: 530 nm/565 nm.

III. Automated Patch Clamp assay (Qpatch)

A. TRPC5

HEK 293 cells expressing human TRPC5 were harvested, re-suspended in serum free medium, and added to the automated platform and used within 2-3 hours. Internal and external physiological solutions were freshly prepared prior to the assay. The external solution contained: 145 mM NaCl, 4 mM KCl, 2 mM CaCl2), 1 mM MgCl2, 10 mM HEPES, 10 mM glucose, pH 7.4 with NaOH and 300 mOsm/L. The internal solution contained 120 mM L-aspartic acid, 120 mM CsOH·H2O, 20 mM CsCl, 2 mM MgCl2, 8.8 mM CaCl2), 10 mM EGTA, 10 mM HEPES, 10 mM Glucose, 0.1 mM GTP and 2 mM Na2ATP; pH 7.2 with CsOH and 290 mOsm/L. The free internal Ca2+ concentration was buffered to 1 μM.

The automated electrophysiological platform QPatch 16 from Sophion (Denmark) was used to carry out the compounds profiling. The series resistance and quality of seals were continuously monitored during the experiments. Data was analyzed using Sophion QPatch assay software 5.6 (Odense). IC50 values were calculated using a least squares regression algorithm (Hill equation).

To monitor the ion currents, a voltage ramp from −100 mV to +100 mV, over 300 ms, was applied every 10 seconds, from a holding potential of −60 mV.

After recording for a minimum of 60 seconds control period, Rosiglitazone (30 uM), was applied to activate the channel.

TRPC5 (Syncropatch—Spatch Format)

The automated electrophysiological assay was carried out at room temperature. HEK-TRPC5 cells were cultured according to our standard operating procedures. Internal and external physiological solutions were freshly prepared prior to the assay. The free internal Ca2+ concentration was buffered to 1 μM according to the WCabuf software using 10 mMHEDTA. To monitor the ion currents, a voltage ramp from −100 mV to +80 mV, over 250 ms, was applied every 15 seconds, from a holding potential of −60 mV. To stabilize the inward and outward currents the voltage was kept steady at −100 mV and +80 mV for 20 ms. After recording for a minimum of 60 seconds control period, the activator (at 10, 15, 20 or 30 μM) was applied twice, before increasing concentrations of test compound (or vehicle) were applied to the cell. This was followed by a saturating concentration of the specific blocker ML 204 (100 μM). Graphs were plotted using the maximum outward current values obtained at +80 mV during the patch-clamp recordings. Data were normalized using the SyncroPatch384 equation Inorm=1−((Iconc−IFB)/(IRef−IFB)), where Iconc is the current amplitude at each concentration of agonist, IRef is the control current amplitude and IFB is the current in the presence of the saturating blocker ML204. Graphs were constrained between the maximum and minimum values. The series resistance (<15 MΩ) and quality of seals (>100 MΩ) were continuously monitored during the experiments. Data was analyzed using the Nanion Data Control384 software. EC/IC50 values were calculated using a least squares regression algorithm (Hill equation).

B. TRPC4

HEK 293 cells expressing human TRPC4 were harvested, re-suspended in serum free medium, added to the automated platform and used within 2-3 hours. Internal and external physiological solutions were freshly prepared prior the assay. The external solution contained: 145 mM NaCl, 4 mM KCl, 2 mM CaCl2), 1 mM MgCl2, 10 mM HEPES, 10 mM glucose, pH 7.4 with NaOH and 300 mOsm/L. The internal solution contained 120 mM L-aspartic acid, 120 mM CsOH·H2O, 20 mM CsCl, 2 mM MgCl2, 10 mM EGTA, 10 mM HEPES, 10 mM Glucose, and 2 mM Na2ATP; pH 7.2 with CsOH and 290 mOsm/L.

The TRPC4 channel agonist Englerin was used to activate and assess test compounds.

The automated electrophysiological platform Qpatch 16 from Sophion (Denmark) was used to carry out the compounds profiling. The series resistance and quality of seals were continuously monitored during the experiments. Data was analyzed using Sophion Qpatch assay software 5.6 (Odense) and Microsoft Office Excel 2007. IC50 values were calculated using a least squares regression algorithm (Hill equation).

C. TRPC6

HEK 293 cells expressing human TRPC6 were harvested, re-suspended in serum free medium, added to the automated platform and used within 2-3 hours. Internal and external physiological solutions were freshly prepared prior the assay. The external solution contained: 145 mM NaCl, 4 mM KCl, 2 mM CaCl2), 1 mM MgCl2, 10 mM HEPES, 10 mM glucose, pH 7.4 with NaOH and 300 mOsm/L. The internal solution contained 120 mM L-aspartic acid, 120 mM CsOH·H2O, 20 mM CsCl, 2 mM MgCl2, 10 mM EGTA, 10 mM HEPES, 10 mM Glucose, and 2 mM Na2ATP; pH 7.2 with CsOH and 290 mOsm/L.

The agonist OAG EC50 was used to activate TRPC6 and assess test compounds.

The automated electrophysiological platform Qpatch 16 from Sophion (Denmark) was used to carry out the compounds profiling. The series resistance and quality of seals were continuously monitored during the experiments. Data was analyzed using Sophion Qpatch assay software 5.6 (Odense) and Microsoft Office Excel 2007. IC50 values were calculated using a least squares regression algorithm (Hill equation).

Example 3: Exemplary Biological Assay Data

A: 0.00001 μM<$IC_{50}$<1 μM
B: 1 μM<$IC_{50}$<5 μM
C: 5 μM<$IC_{50}$<10 μM
D: 10 μM<$IC_{50}$<500 μM

TABLE 2

$IC_{50}$ values for representative compounds of the disclosure measured in an automated patch clamp assay utilizing HEK293 cells overexpressing TRPC5 (see above), with the readout as a current block utilizing whole cell automated patch following stimulation with rosiglitazone at either 80 or 100 mV.

| STRUCTURE | TRPC5_QP_XC50_100 | TRPC5_QP_XC50_80 |
|---|---|---|
| 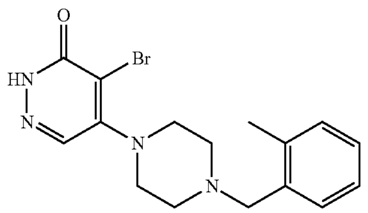 [SMILES: Cc1ccccc1CN1CCN(c2cn[nH]c(=O)c2Br)CC1] | B | B |
| 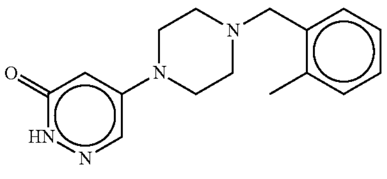 | D | D |
| 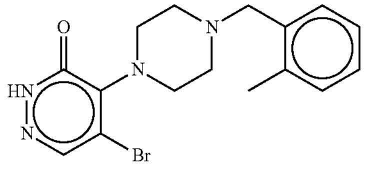 | B | B |

TABLE 2-continued
$IC_{50}$ values for representative compounds of the disclosure measured in an automated patch clamp assay utilizing HEK293 cells overexpressing TRPC5 (see above), with the readout as a current block utilizing whole cell automated patch following stimulation with rosiglitazone at either 80 or 100 mV.
| STRUCTURE | TRPC5_QP_XC50_100 | TRPC5_QP_XC50_80 |
|---|---|---|
| 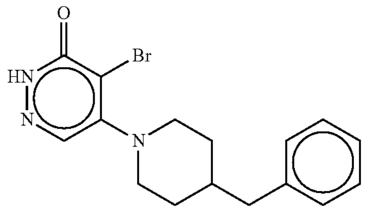 | D | D |
| 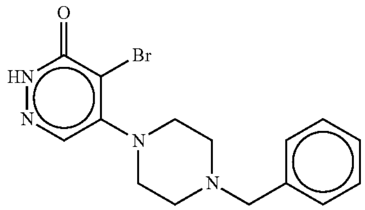 | C | C |
| 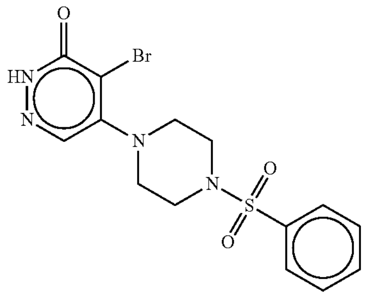 | D | D |
| 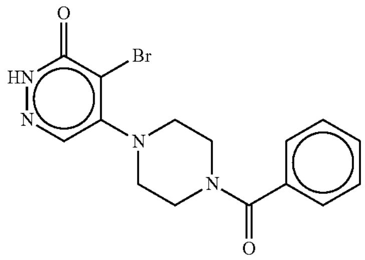 | D | D |
| 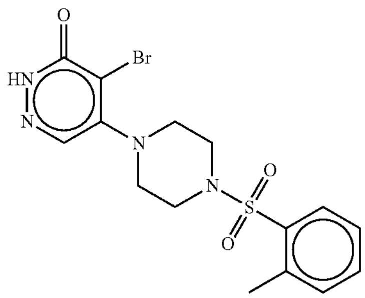 | D | D |

TABLE 2-continued
IC50 values for representative compounds of the disclosure measured in an automated patch clamp assay utilizing HEK293 cells overexpressing TRPC5 (see above), with the readout as a current block utilizing whole cell automated patch following stimulation with rosiglitazone at either 80 or 100 mV.
| STRUCTURE | TRPC5_QP_XC50_100 | TRPC5_QP_XC50_80 |
|---|---|---|
| 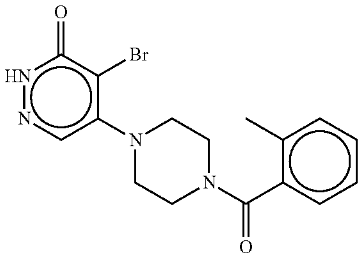 | C | C |
| 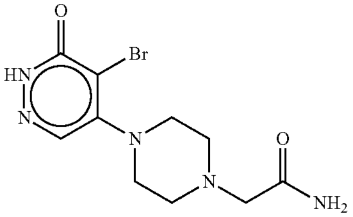 | D | D |
| 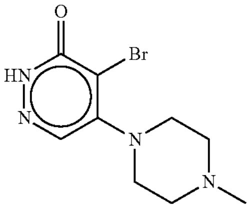 | D | D |
| 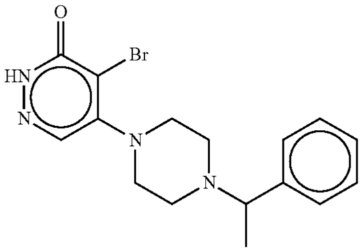 | C | B |
| 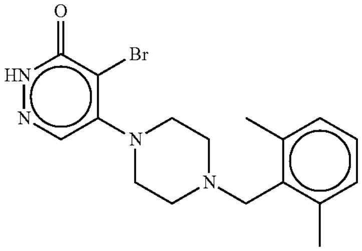 | B | B |

TABLE 2-continued
IC$_{50}$ values for representative compounds of the disclosure measured in an automated patch clamp assay utilizing HEK293 cells overexpressing TRPC5 (see above), with the readout as a current block utilizing whole cell automated patch following stimulation with rosiglitazone at either 80 or 100 mV.
| STRUCTURE | TRPC5_QP_XC50_100 | TRPC5_QP_XC50_80 |
|---|---|---|
| 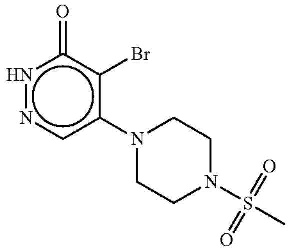 | D | D |
| 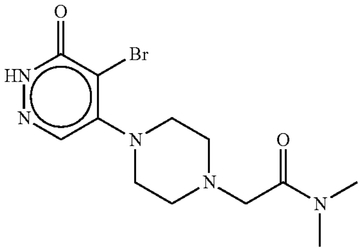 | D | D |
| 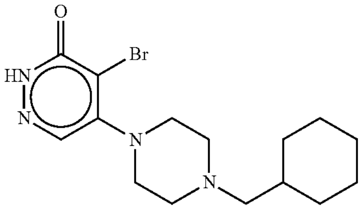 | B | B |
| 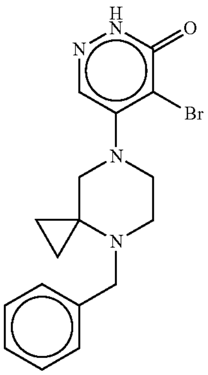 | D | D |
| 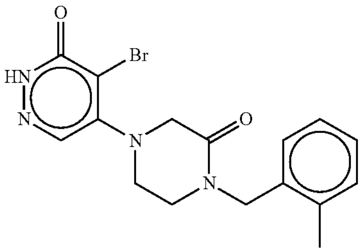 | A | A |

TABLE 2-continued

| $IC_{50}$ values for representative compounds of the disclosure measured in an automated patch clamp assay utilizing HEK293 cells overexpressing TRPC5 (see above), with the readout as a current block utilizing whole cell automated patch following stimulation with rosiglitazone at either 80 or 100 mV. | | |
|---|---|---|
| STRUCTURE | TRPC5_QP_XC50_100 | TRPC5_QP_XC50_80 |
| 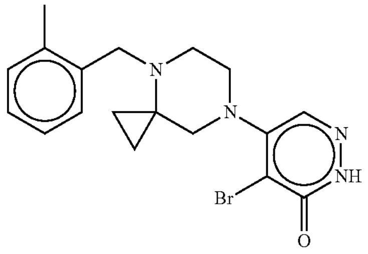 | D | D |
| 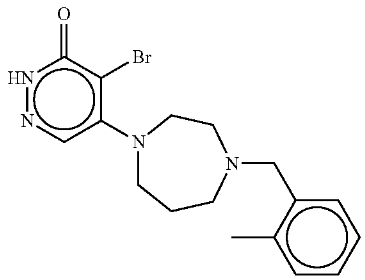 | C | C |
| 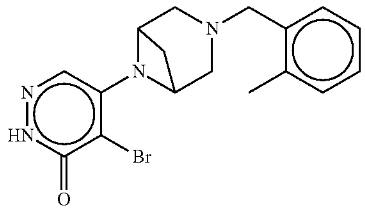 | D | D |
| 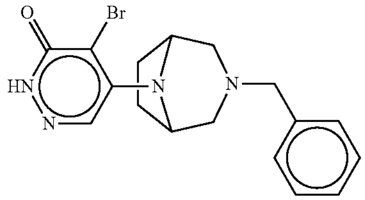 | D | D |

TABLE 3

| $IC_{50}$ values for representative compounds of the disclosure measured in an automated patch clamp assay utilizing HEK293 cells overexpressing TRPC5 (see above), with the readout as a current block utilizing whole cell automated patch following stimulation with rosiglitazone at either 80 or 100 mV. | | |
|---|---|---|
| Structure | TRPC5_QP_XC50_100 | TRPC5_QP_XC50_80 |
| 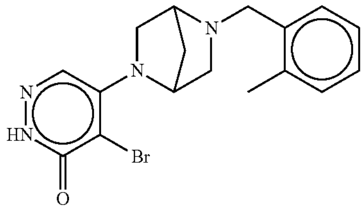 | D | D |

TABLE 3-continued
IC$_{50}$ values for representative compounds of the disclosure measured in an automated patch clamp assay utilizing HEK293 cells overexpressing TRPC5 (see above), with the readout as a current block utilizing whole cell automated patch following stimulation with rosiglitazone at either 80 or 100 mV.
| Structure | TRPC5_QP_XC50_100 | TRPC5_QP_XC50_80 |
|---|---|---|
| 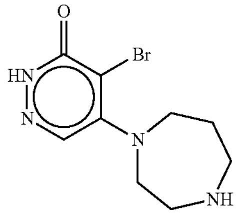 | D | D |
| 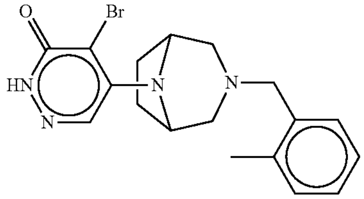 | D | D |
| 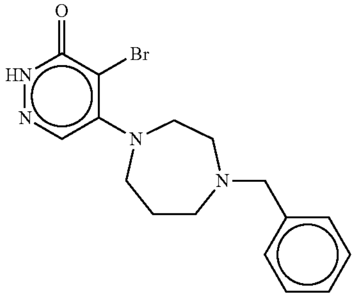 | D | D |
| 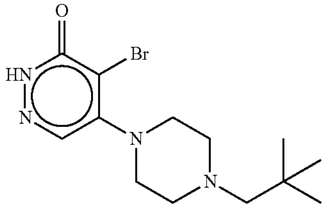 | D | D |
| 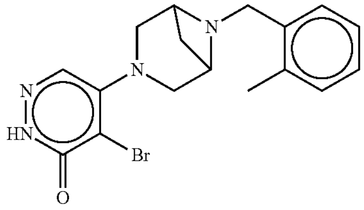 | D | D |
| 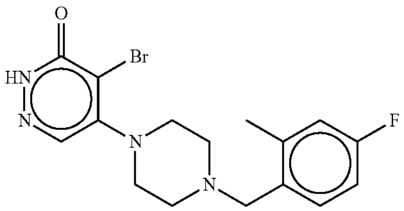 | B | B |

TABLE 3-continued
IC50 values for representative compounds of the disclosure measured in an automated patch clamp assay utilizing HEK293 cells overexpressing TRPC5 (see above), with the readout as a current block utilizing whole cell automated patch following stimulation with rosiglitazone at either 80 or 100 mV.
| Structure | TRPC5_QP_XC50_100 | TRPC5_QP_XC50_80 |
|---|---|---|
| 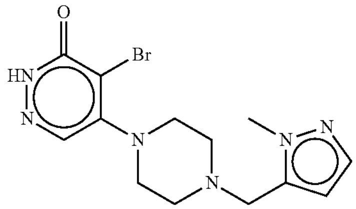 | C | C |
| 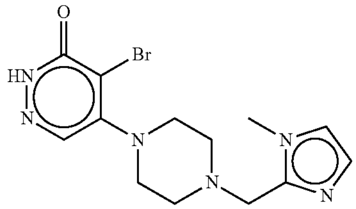 | D | D |
| 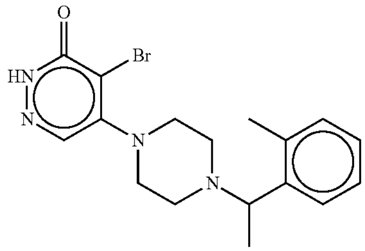 | B | B |
| 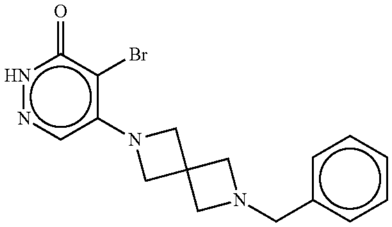 | D | D |
| 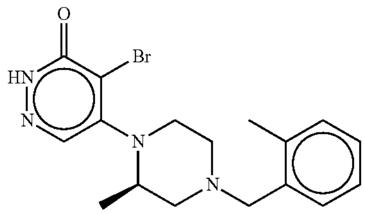 | B | B |
| 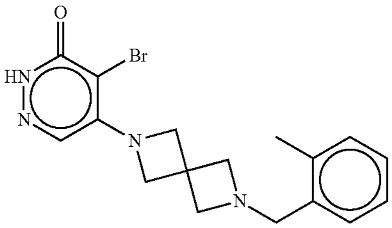 | D | D |

TABLE 3-continued
IC$_{50}$ values for representative compounds of the disclosure measured in an automated patch clamp assay utilizing HEK293 cells overexpressing TRPC5 (see above), with the readout as a current block utilizing whole cell automated patch following stimulation with rosiglitazone at either 80 or 100 mV.
| Structure | TRPC5_QP_XC50_100 | TRPC5_QP_XC50_80 |
|---|---|---|
| 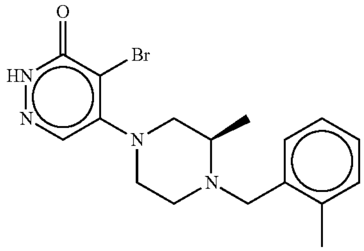 | D | D |
| 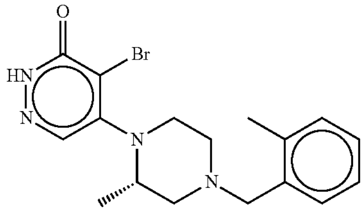 | D | D |
| 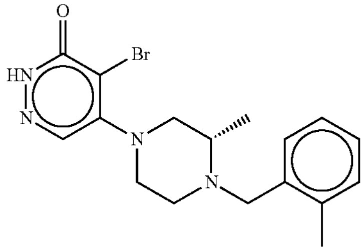 | D | D |
| 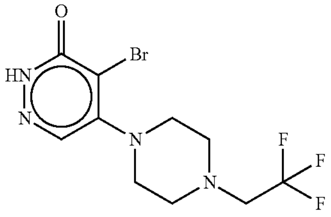 | D | D |
| 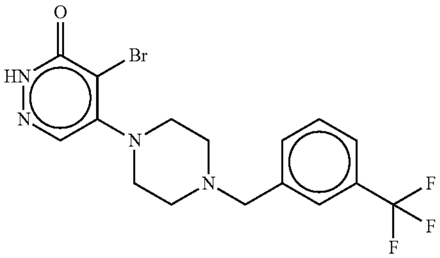 | B | B |
| 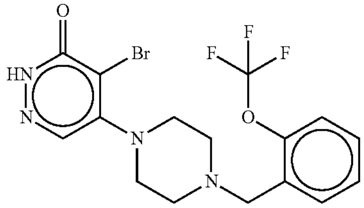 | B | B |

TABLE 3-continued
IC50 values for representative compounds of the disclosure measured in an automated patch clamp assay utilizing HEK293 cells overexpressing TRPC5 (see above), with the readout as a current block utilizing whole cell automated patch following stimulation with rosiglitazone at either 80 or 100 mV.
| Structure | TRPC5_QP_XC50_100 | TRPC5_QP_XC50_80 |
|---|---|---|
| 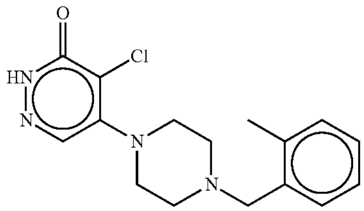 | B | B |
| 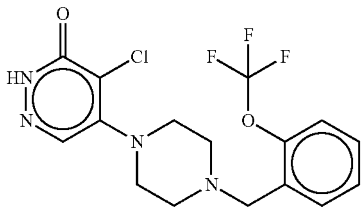 | B | B |
| 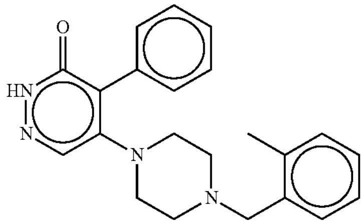 | C | C |
| 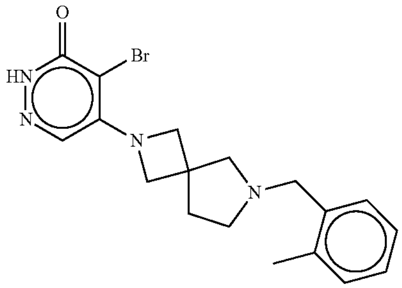 | D | D |
| 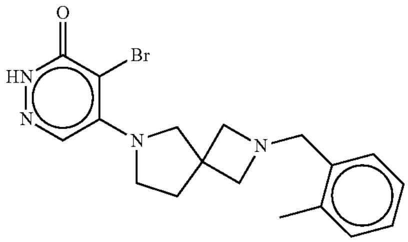 | D | D |

TABLE 3-continued
IC$_{50}$ values for representative compounds of the disclosure measured in an automated patch clamp assay utilizing HEK293 cells overexpressing TRPC5 (see above), with the readout as a current block utilizing whole cell automated patch following stimulation with rosiglitazone at either 80 or 100 mV.
| Structure | TRPC5_QP_XC50_100 | TRPC5_QP_XC50_80 |
| --- | --- | --- |
| 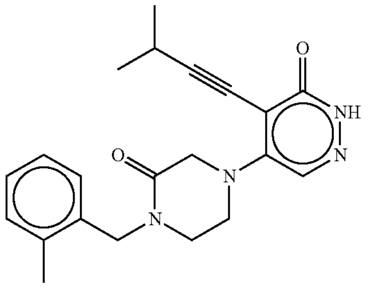 | D | D |
| 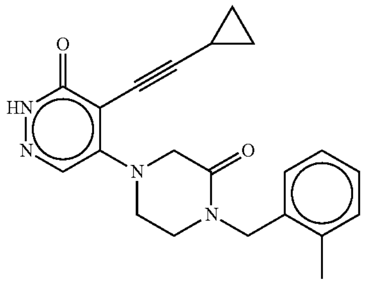 | D | D |
| 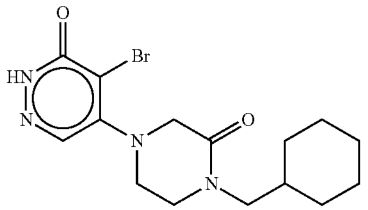 | B | B |
| 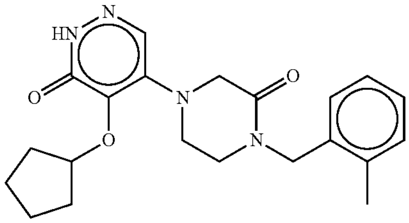 | C | C |
| 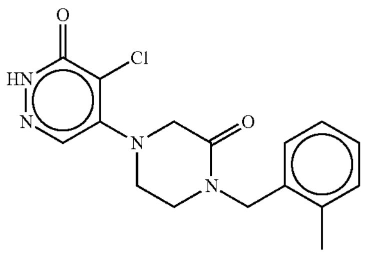 | A | A |

TABLE 3-continued
| IC$_{50}$ values for representative compounds of the disclosure measured in an automated patch clamp assay utilizing HEK293 cells overexpressing TRPC5 (see above), with the readout as a current block utilizing whole cell automated patch following stimulation with rosiglitazone at either 80 or 100 mV. | | |
|---|---|---|
| Structure | TRPC5_QP_XC50_100 | TRPC5_QP_XC50_80 |
| 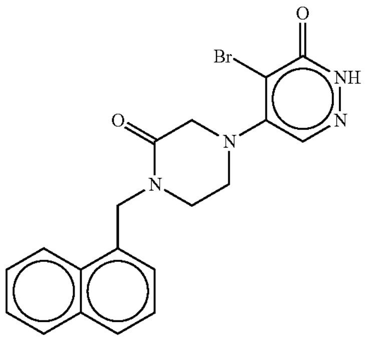 | A | A |
| 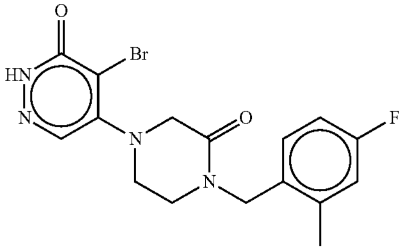 | B | A |
| 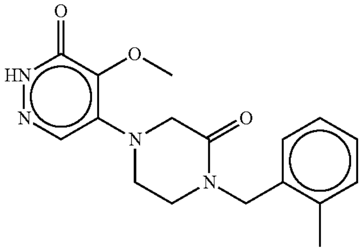 | D | D |
| 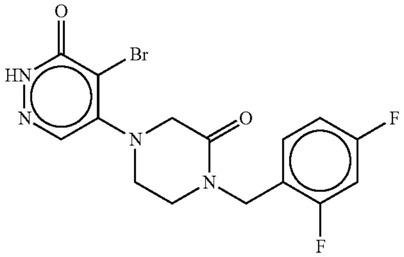 | B | B |
| 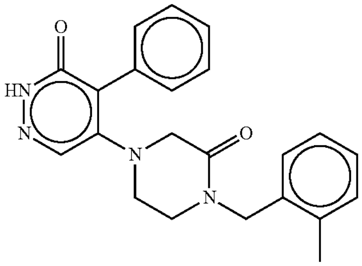 | D | D |

TABLE 3-continued
IC50 values for representative compounds of the disclosure measured in an automated patch clamp assay utilizing HEK293 cells overexpressing TRPC5 (see above), with the readout as a current block utilizing whole cell automated patch following stimulation with rosiglitazone at either 80 or 100 mV.
| Structure | TRPC5_QP_XC50_100 | TRPC5_QP_XC50_80 |
|---|---|---|
| 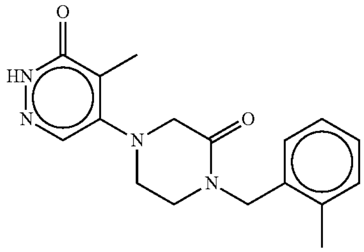 | C | C |
| 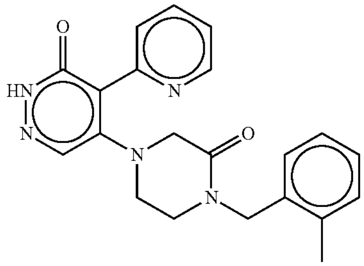 | D | D |
| 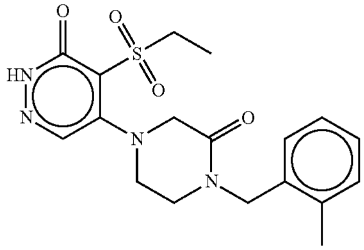 | D | D |
| 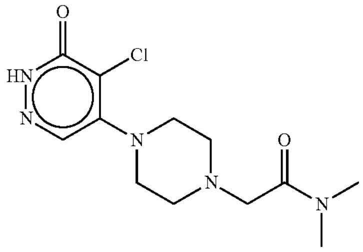 | D | D |
| 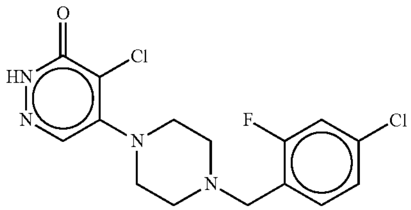 | D | C |

TABLE 3-continued
| IC$_{50}$ values for representative compounds of the disclosure measured in an automated patch clamp assay utilizing HEK293 cells overexpressing TRPC5 (see above), with the readout as a current block utilizing whole cell automated patch following stimulation with rosiglitazone at either 80 or 100 mV. | | |
|---|---|---|
| Structure | TRPC5_QP_XC50_100 | TRPC5_QP_XC50_80 |
| 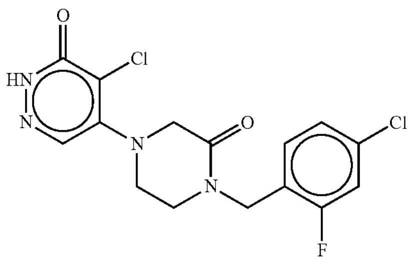 | C | C |
| 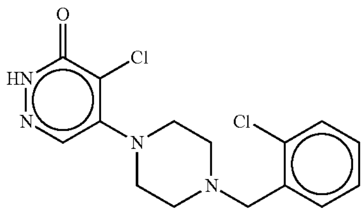 | B | B |
| 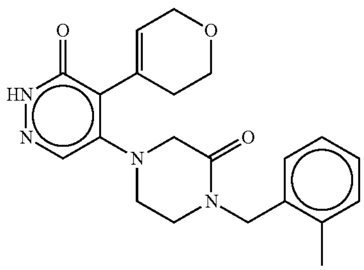 | D | D |
| 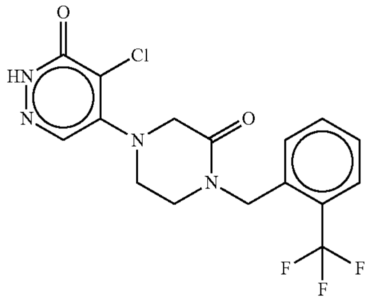 | A | A |
| 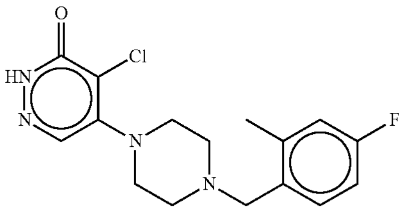 | B | B |

TABLE 3-continued
| Structure | TRPC5_QP_XC50_100 | TRPC5_QP_XC50_80 |
|---|---|---|
| $IC_{50}$ values for representative compounds of the disclosure measured in an automated patch clamp assay utilizing HEK293 cells overexpressing TRPC5 (see above), with the readout as a current block utilizing whole cell automated patch following stimulation with rosiglitazone at either 80 or 100 mV. | | |
| 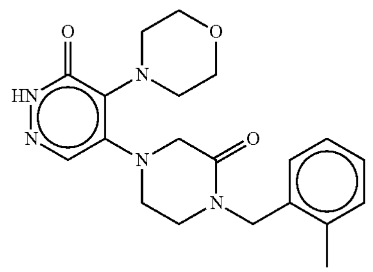 | D | D |
| 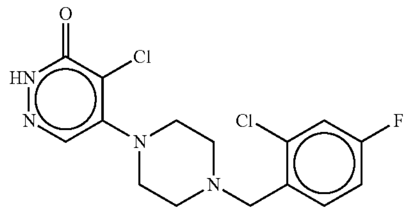 | C | B |
| 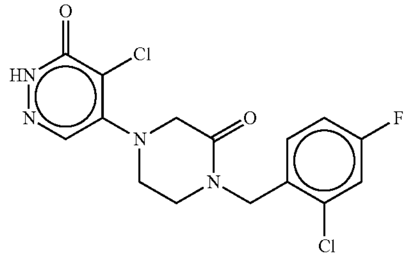 | B | B |
| 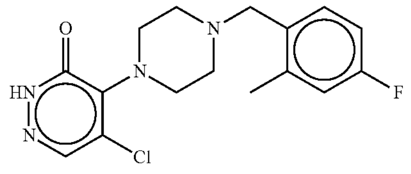 | B | B |
| 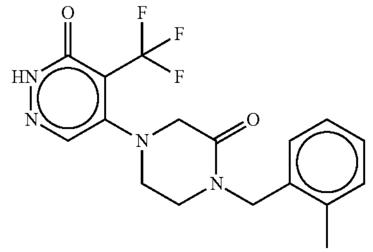 | C | B |
| 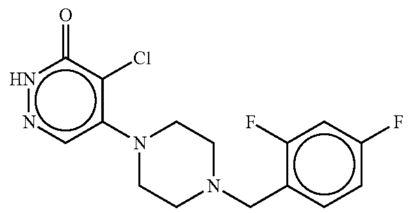 | C | C |

TABLE 3-continued
IC$_{50}$ values for representative compounds of the disclosure measured in an automated patch clamp assay utilizing HEK293 cells overexpressing TRPC5 (see above), with the readout as a current block utilizing whole cell automated patch following stimulation with rosiglitazone at either 80 or 100 mV.
| Structure | TRPC5_QP_XC50_100 | TRPC5_QP_XC50_80 |
|---|---|---|
| 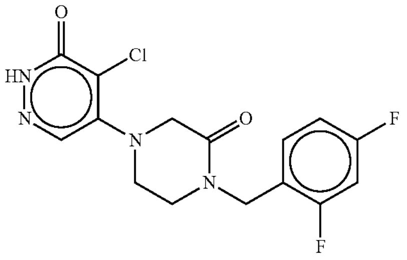 | B | B |
| 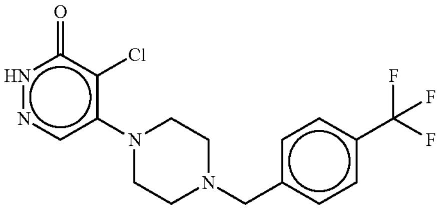 | D | D |
| 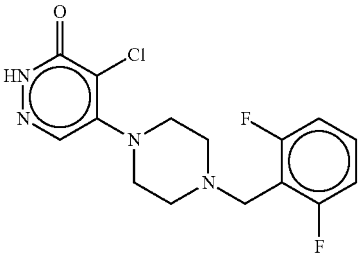 | B | B |
| 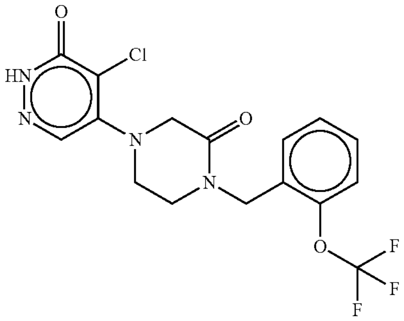 | A | A |
| 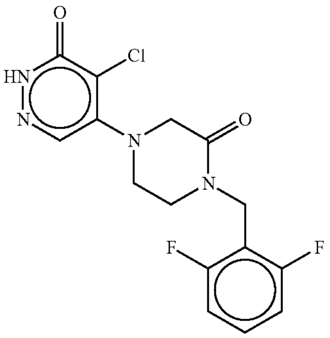 | B | B |

TABLE 3-continued
IC$_{50}$ values for representative compounds of the disclosure measured in an automated patch clamp assay utilizing HEK293 cells overexpressing TRPC5 (see above), with the readout as a current block utilizing whole cell automated patch following stimulation with rosiglitazone at either 80 or 100 mV.
| Structure | TRPC5_QP_XC50_100 | TRPC5_QP_XC50_80 |
|---|---|---|
| 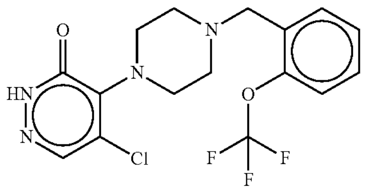 | C | C |
| 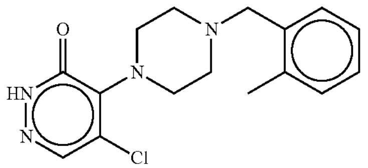 | C | C |
| 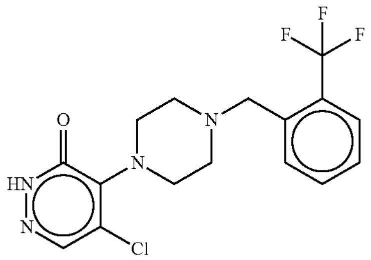 | C | C |
| 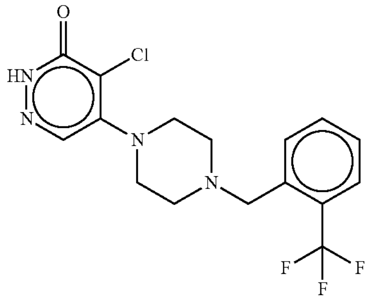 | B | B |
| 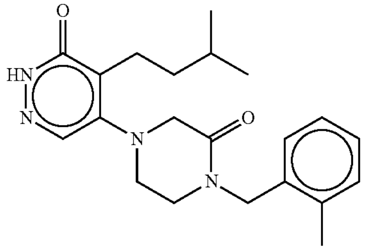 | D | D |

TABLE 4
IC50 values for representative compounds of the disclosure measured in an automated patch clamp assay utilizing HEK293 cells overexpressing TRPC5 (see above), with the readout as a current block utilizing whole cell automated patch following stimulation with rosiglitazone at either 80 or 100 mV.
| STRUCTURE | TRPC5_QP_XC50_100 | TRPC5_QP_XC50_80 |
|---|---|---|
| 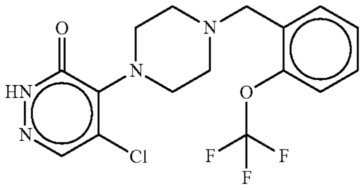 | C | C |
| 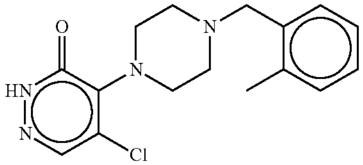 | C | C |
| 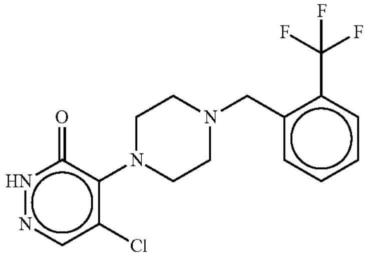 | C | C |
| 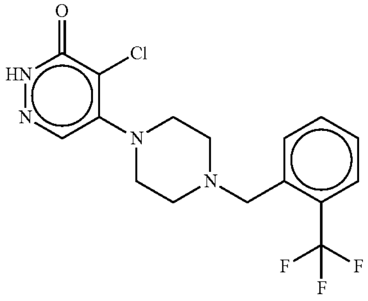 | B | B |
| 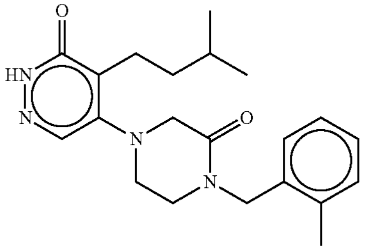 | D | D |

TABLE 4-continued
IC50 values for representative compounds of the disclosure measured in an automated patch clamp assay utilizing HEK293 cells overexpressing TRPC5 (see above), with the readout as a current block utilizing whole cell automated patch following stimulation with rosiglitazone at either 80 or 100 mV.
| STRUCTURE | TRPC5_QP_XC50_100 | TRPC5_QP_XC50_80 |
|---|---|---|
| 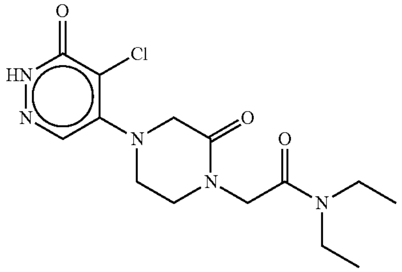 | D | D |
| 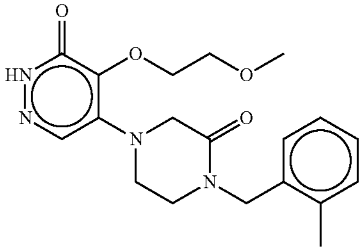 | D | D |
| 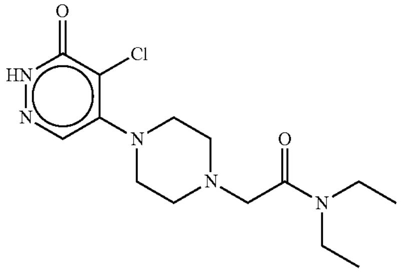 | D | D |
| 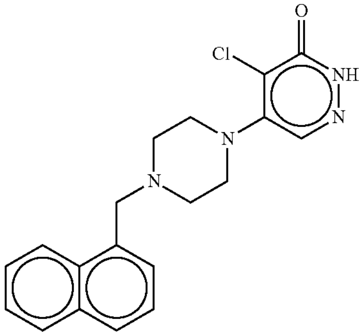 | B | B |
| 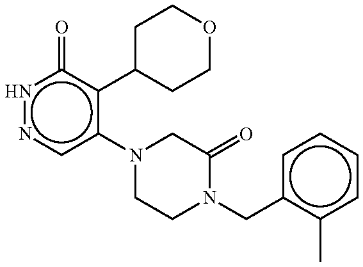 | D | D |

TABLE 4-continued
| IC50 values for representative compounds of the disclosure measured in an automated patch clamp assay utilizing HEK293 cells overexpressing TRPC5 (see above), with the readout as a current block utilizing whole cell automated patch following stimulation with rosiglitazone at either 80 or 100 mV. | | |
|---|---|---|
| STRUCTURE | TRPC5_QP_XC50_100 | TRPC5_QP_XC50_80 |
| 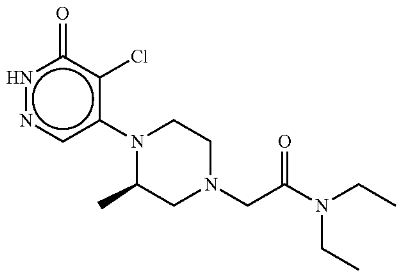 | D | D |
| 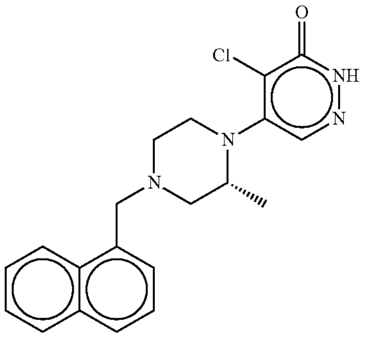 | C | C |
| 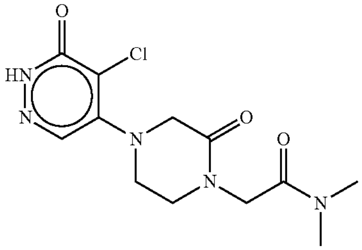 | D | D |
| 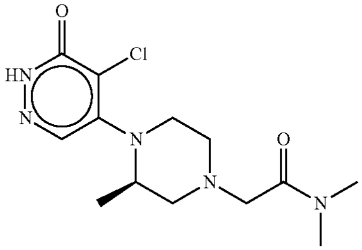 | D | D |
| 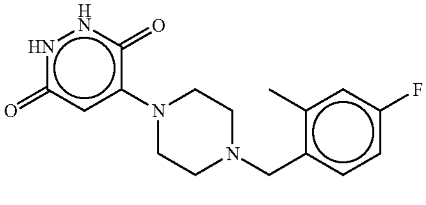 | D | D |

TABLE 4-continued
| IC$_{50}$ values for representative compounds of the disclosure measured in an automated patch clamp assay utilizing HEK293 cells overexpressing TRPC5 (see above), with the readout as a current block utilizing whole cell automated patch following stimulation with rosiglitazone at either 80 or 100 mV. | | |
|---|---|---|
| STRUCTURE | TRPC5_QP_XC50_100 | TRPC5_QP_XC50_80 |
| 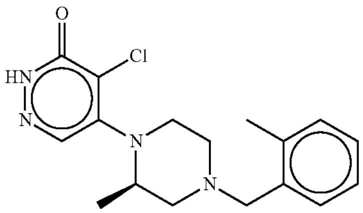 | B | B |
| 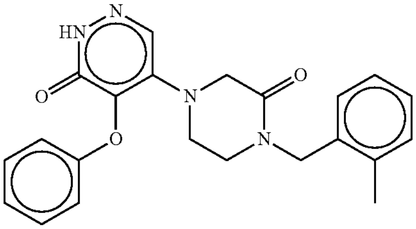 | D | D |
| 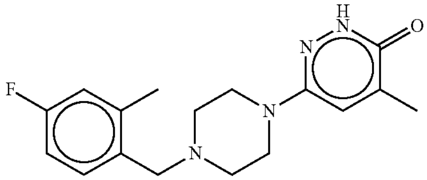 | C | C |
| 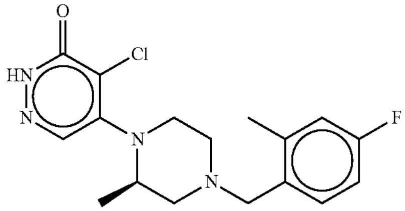 | B | B |
| 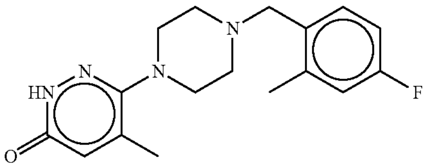 | D | D |
| 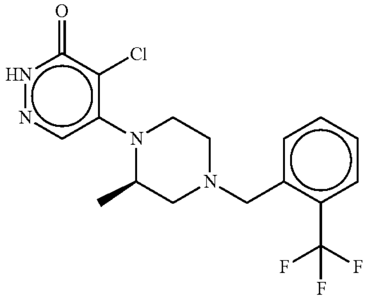 | B | B |

TABLE 4-continued
| IC50 values for representative compounds of the disclosure measured in an automated patch clamp assay utilizing HEK293 cells overexpressing TRPC5 (see above), with the readout as a current block utilizing whole cell automated patch following stimulation with rosiglitazone at either 80 or 100 mV. | | |
|---|---|---|
| STRUCTURE | TRPC5_QP_XC50_100 | TRPC5_QP_XC50_80 |
| 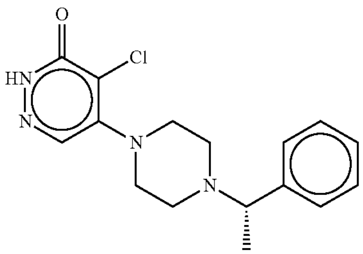 | B | C |
| 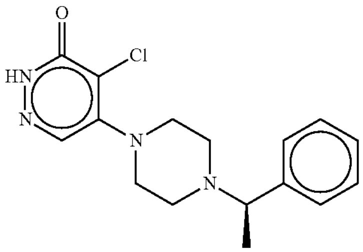 | B | B |
| 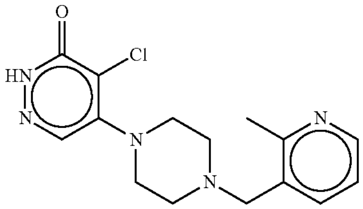 | A | A |
| 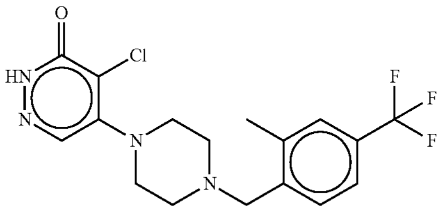 | D | D |
| 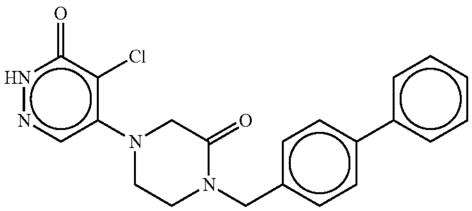 | D | D |
| 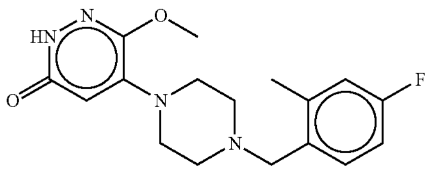 | D | D |

TABLE 4-continued
IC50 values for representative compounds of the disclosure measured in an automated patch clamp assay utilizing HEK293 cells overexpressing TRPC5 (see above), with the readout as a current block utilizing whole cell automated patch following stimulation with rosiglitazone at either 80 or 100 mV.
| STRUCTURE | TRPC5_QP_XC50_100 | TRPC5_QP_XC50_80 |
|---|---|---|
| 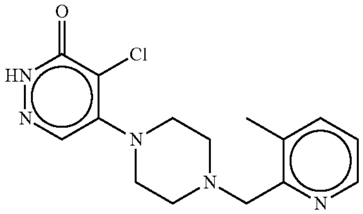 | C | C |
| 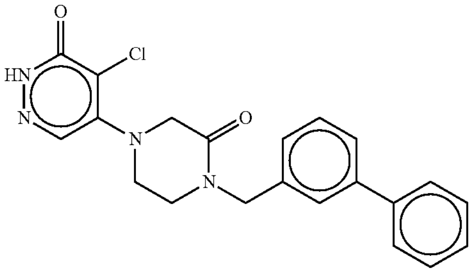 | D | D |
| 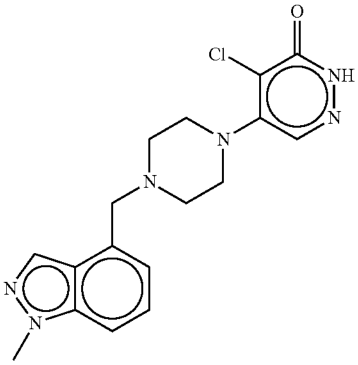 | D | D |
| 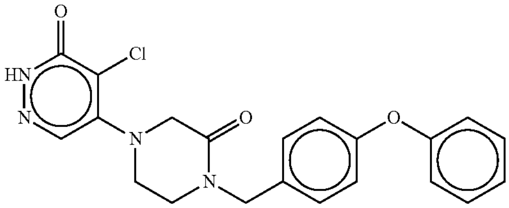 | D | D |
| 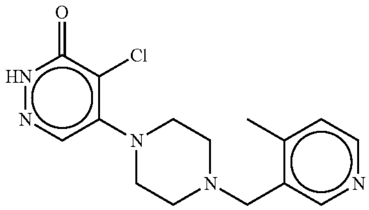 | C | C |

TABLE 4-continued
| IC$_{50}$ values for representative compounds of the disclosure measured in an automated patch clamp assay utilizing HEK293 cells overexpressing TRPC5 (see above), with the readout as a current block utilizing whole cell automated patch following stimulation with rosiglitazone at either 80 or 100 mV. | | |
|---|---|---|
| STRUCTURE | TRPC5_QP_XC50_100 | TRPC5_QP_XC50_80 |
| 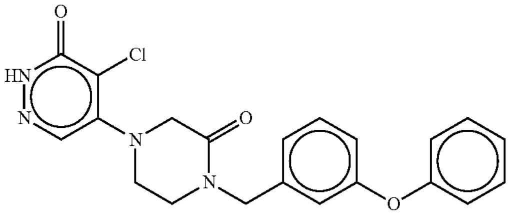 | B | B |
| 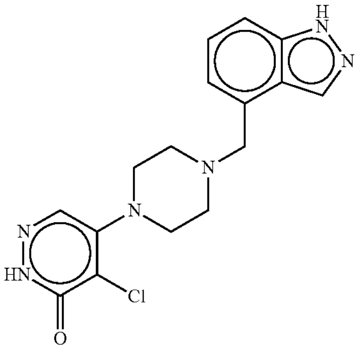 | D | D |
| 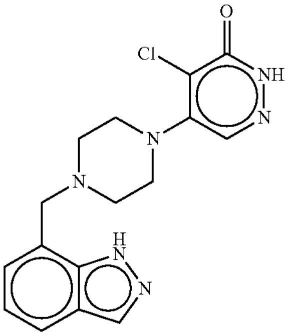 | D | D |
| 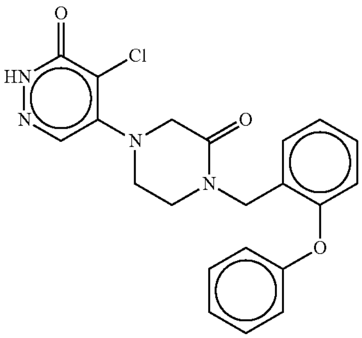 | C | C |

TABLE 4-continued
IC$_{50}$ values for representative compounds of the disclosure measured in an automated patch clamp assay utilizing HEK293 cells overexpressing TRPC5 (see above), with the readout as a current block utilizing whole cell automated patch following stimulation with rosiglitazone at either 80 or 100 mV.
| STRUCTURE | TRPC5_QP_XC50_100 | TRPC5_QP_XC50_80 |
|---|---|---|
| 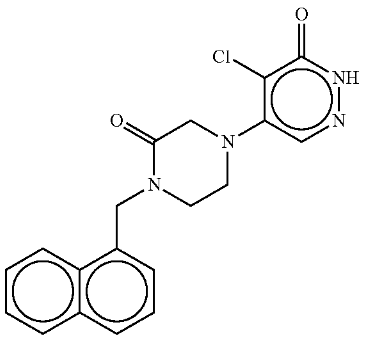 | A | A |
| 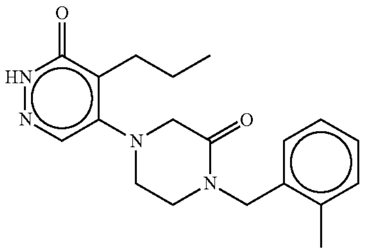 | D | D |
| 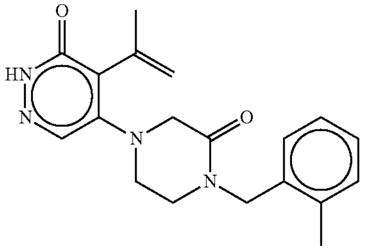 | D | D |
| 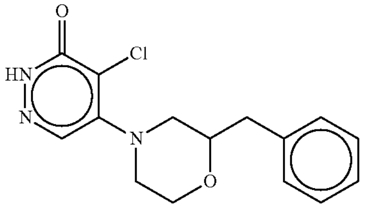 | D | D |
| 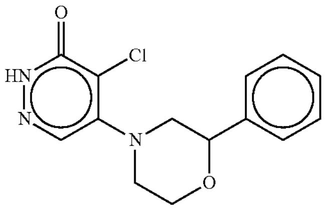 | D | D |

TABLE 4-continued
IC$_{50}$ values for representative compounds of the disclosure measured in an automated patch clamp assay utilizing HEK293 cells overexpressing TRPC5 (see above), with the readout as a current block utilizing whole cell automated patch following stimulation with rosiglitazone at either 80 or 100 mV.
| STRUCTURE | TRPC5_QP_XC50_100 | TRPC5_QP_XC50_80 |
|---|---|---|
| 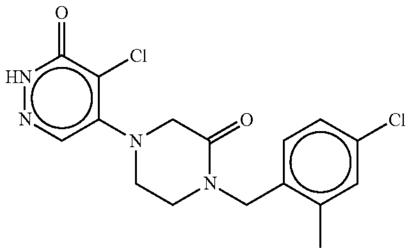 | B | B |
| 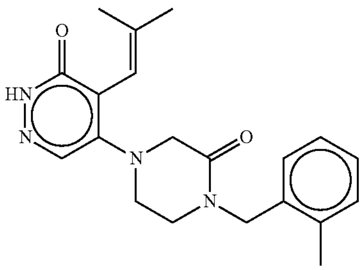 | D | D |
| 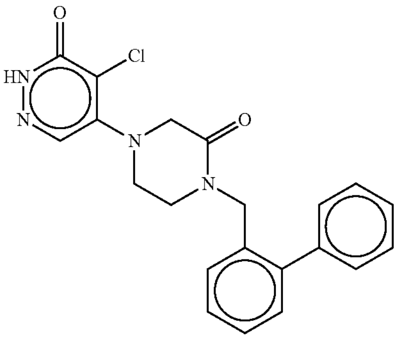 | B | B |
| 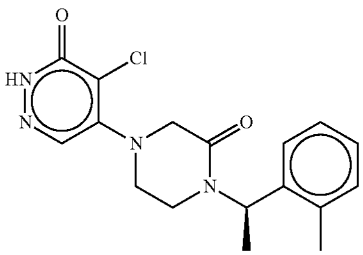 | A | A |
| 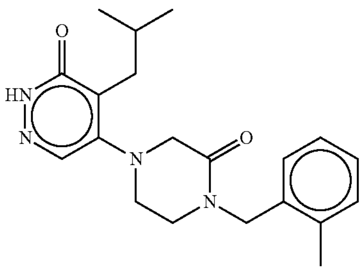 | D | D |

TABLE 4-continued
IC$_{50}$ values for representative compounds of the disclosure measured in an automated patch clamp assay utilizing HEK293 cells overexpressing TRPC5 (see above), with the readout as a current block utilizing whole cell automated patch following stimulation with rosiglitazone at either 80 or 100 mV.
| STRUCTURE | TRPC5_QP_XC50_100 | TRPC5_QP_XC50_80 |
|---|---|---|
| 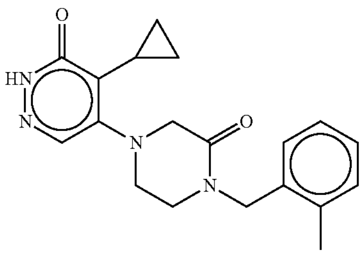 | B | B |
| 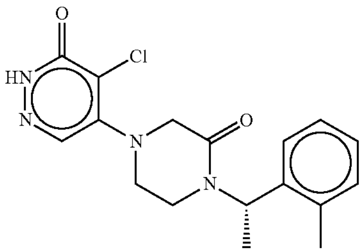 | A | A |
| 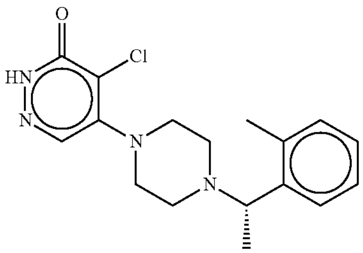 | B | B |
| 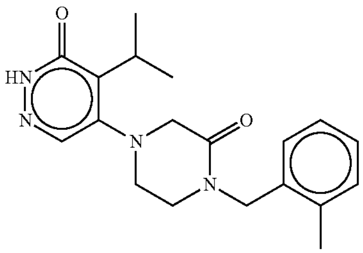 | B | B |
| 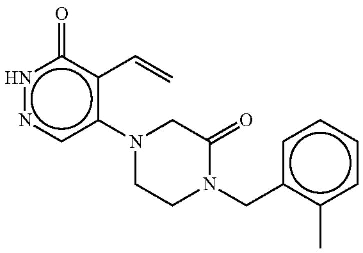 | B | B |

TABLE 4-continued
| IC$_{50}$ values for representative compounds of the disclosure measured in an automated patch clamp assay utilizing HEK293 cells overexpressing TRPC5 (see above), with the readout as a current block utilizing whole cell automated patch following stimulation with rosiglitazone at either 80 or 100 mV. | | |
|---|---|---|
| STRUCTURE | TRPC5_QP_XC50_100 | TRPC5_QP_XC50_80 |
| 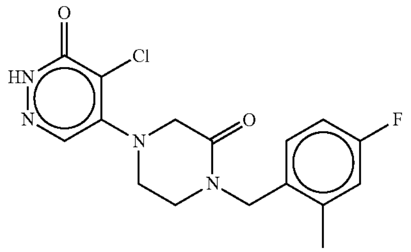 | B | B |
| 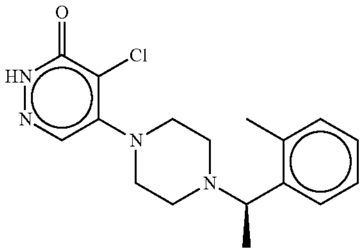 | B | B |
| 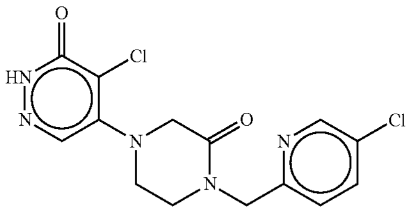 | D | D |
| 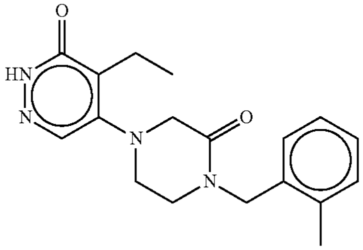 | C | C |
| 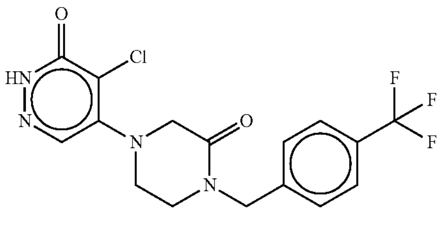 | A | A |

TABLE 4-continued
IC$_{50}$ values for representative compounds of the disclosure measured in an automated patch clamp assay utilizing HEK293 cells overexpressing TRPC5 (see above), with the readout as a current block utilizing whole cell automated patch following stimulation with rosiglitazone at either 80 or 100 mV.
| STRUCTURE | TRPC5_QP_XC50_100 | TRPC5_QP_XC50_80 |
|---|---|---|
| 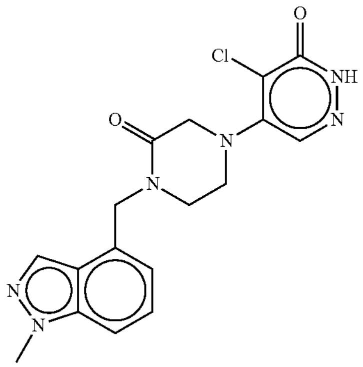 | B | B |
| 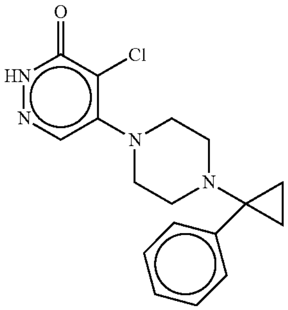 | C | C |
| 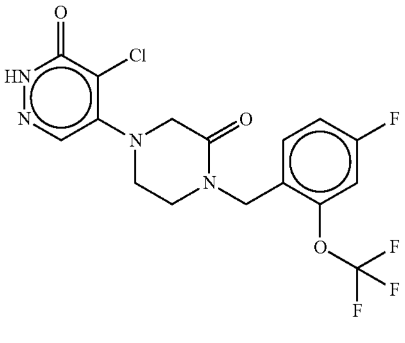 | B | B |
| 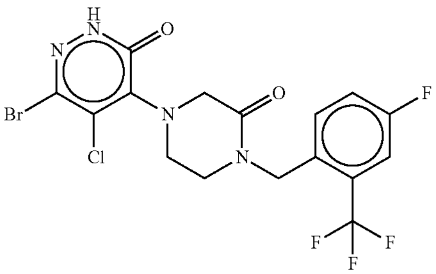 | D | D |

TABLE 4-continued
IC50 values for representative compounds of the disclosure measured in an automated patch clamp assay utilizing HEK293 cells overexpressing TRPC5 (see above), with the readout as a current block utilizing whole cell automated patch following stimulation with rosiglitazone at either 80 or 100 mV.
| STRUCTURE | TRPC5_QP_XC50_100 | TRPC5_QP_XC50_80 |
| --- | --- | --- |
| 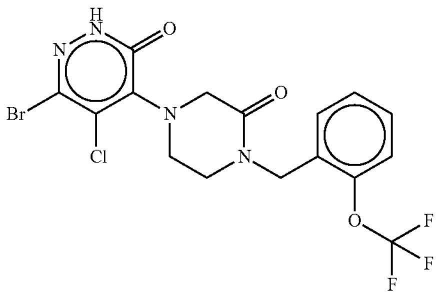 | D | D |
| 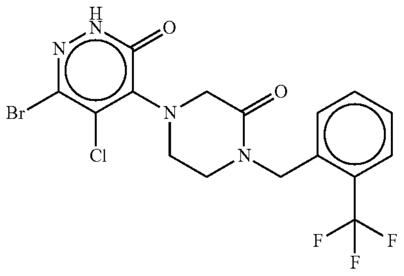 | C | B |
| 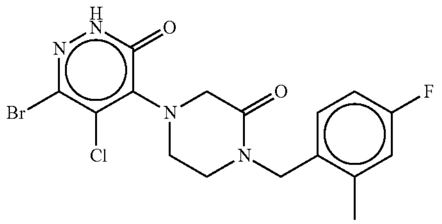 | D | D |
| 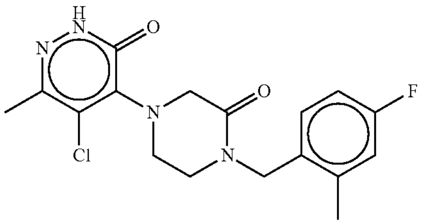 | D | D |

TABLE 5
$IC_{50}$ values for representative compounds of the disclosure measured in an automated patch clamp assay utilizing HEK293 cells overexpressing TRPC5 (see above), with the readout as a current block utilizing whole cell automated patch following stimulation with rosiglitazone at either 80 or 100 mV.
| STRUCTURE | TRPC5_QP_XC50_100 | TRPC5_QP_XC50_80 |
|---|---|---|
| 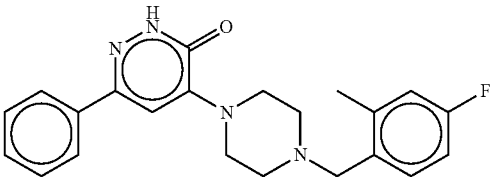 | | B |
| 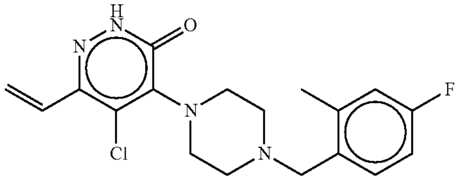 | D | D |
| 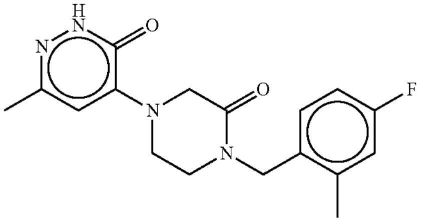 | D | D |
| 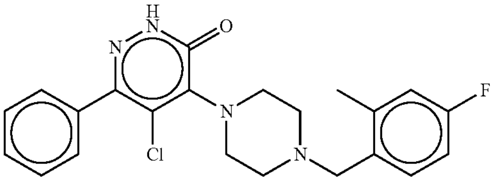 | D | D |
| 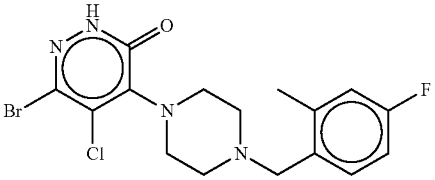 | D | D |
| 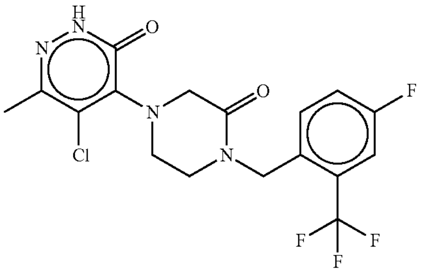 | D | D |

TABLE 5-continued
IC$_{50}$ values for representative compounds of the disclosure measured in an automated patch clamp assay utilizing HEK293 cells overexpressing TRPC5 (see above), with the readout as a current block utilizing whole cell automated patch following stimulation with rosiglitazone at either 80 or 100 mV.
| STRUCTURE | TRPC5_QP_XC50_100 | TRPC5_QP_XC50_80 |
|---|---|---|
| 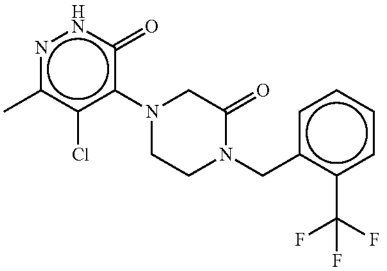 | C | C |
| 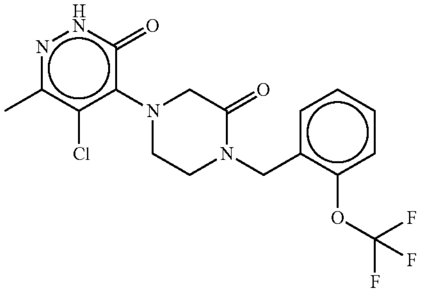 | C | C |
| 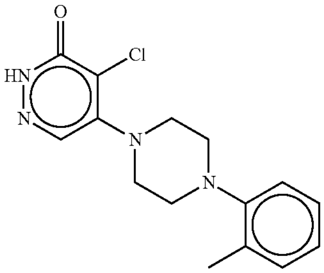 | B | B |
| 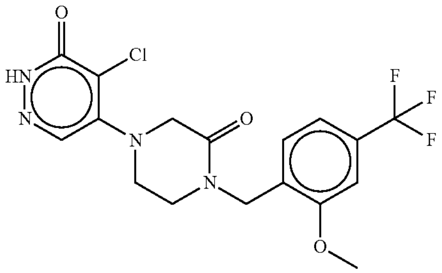 | C | B |
| 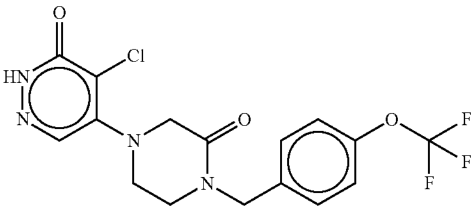 | B | B |

TABLE 5-continued
IC50 values for representative compounds of the disclosure measured in an automated patch clamp assay utilizing HEK293 cells overexpressing TRPC5 (see above), with the readout as a current block utilizing whole cell automated patch following stimulation with rosiglitazone at either 80 or 100 mV.
| STRUCTURE | TRPC5__QP__ XC50__100 | TRPC5__QP__ XC50__80 |
|---|---|---|
| 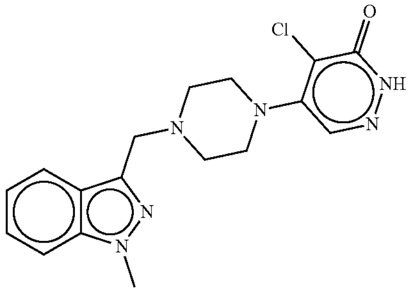 | D | C |
| 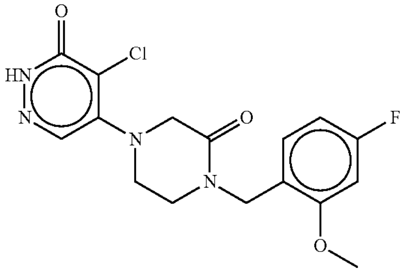 | B | B |
| 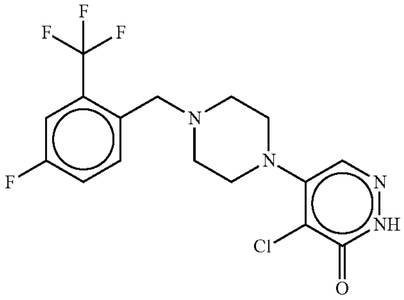 | B | B |
| 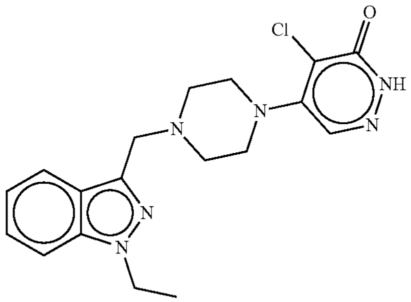 | D | D |
| 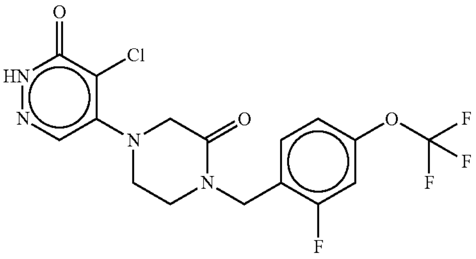 | C | C |

TABLE 5-continued
IC50 values for representative compounds of the disclosure measured in an automated patch clamp assay utilizing HEK293 cells overexpressing TRPC5 (see above), with the readout as a current block utilizing whole cell automated patch following stimulation with rosiglitazone at either 80 or 100 mV.
| STRUCTURE | TRPC5_QP_XC50_100 | TRPC5_QP_XC50_80 |
|---|---|---|
| 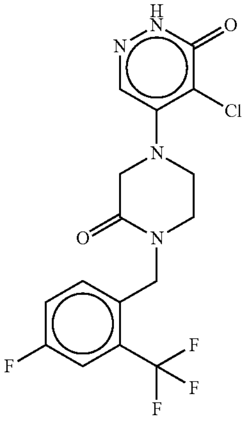 | A | A |
| 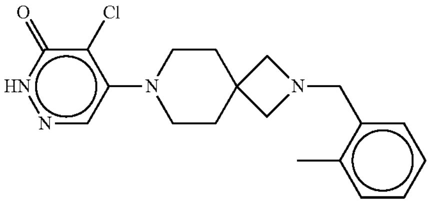 | B | B |
| 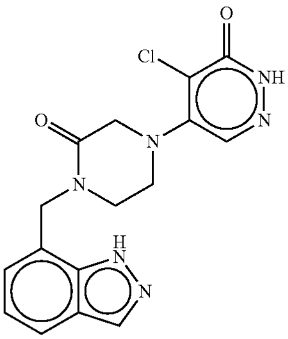 | D | D |
| 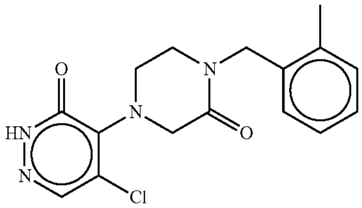 | D | D |

TABLE 5-continued
IC$_{50}$ values for representative compounds of the disclosure measured in an automated patch clamp assay utilizing HEK293 cells overexpressing TRPC5 (see above), with the readout as a current block utilizing whole cell automated patch following stimulation with rosiglitazone at either 80 or 100 mV.
| STRUCTURE | TRPC5_QP_ XC50_100 | TRPC5_QP_ XC50_80 |
|---|---|---|
| 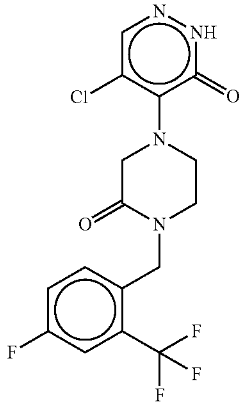 | D | D |
| 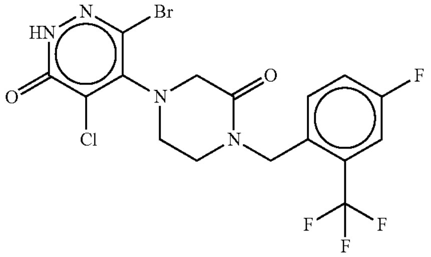 | D | D |
| 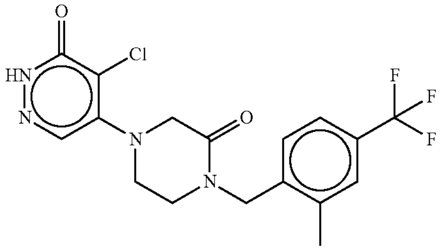 | D | B |
| 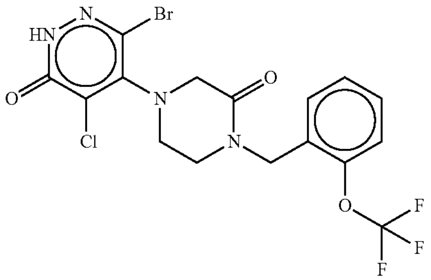 | D | D |
| 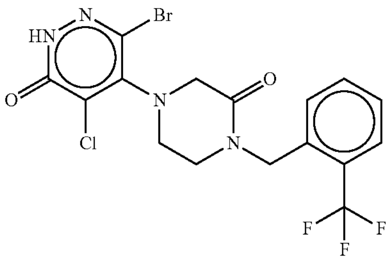 | C | B |

TABLE 5-continued
IC$_{50}$ values for representative compounds of the disclosure measured in an automated patch clamp assay utilizing HEK293 cells overexpressing TRPC5 (see above), with the readout as a current block utilizing whole cell automated patch following stimulation with rosiglitazone at either 80 or 100 mV.
| STRUCTURE | TRPC5_QP_XC50_100 | TRPC5_QP_XC50_80 |
|---|---|---|
| 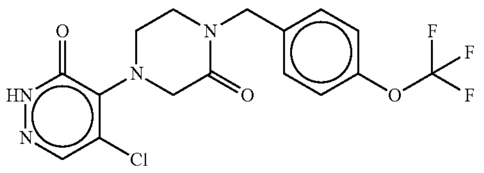 | D | D |
| 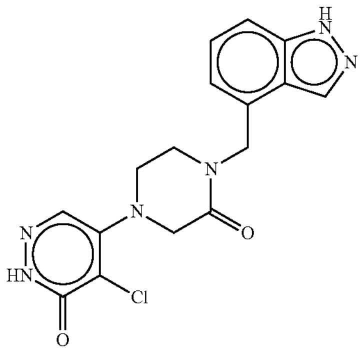 | D | D |
| 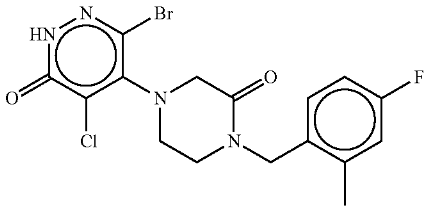 | D | D |
| 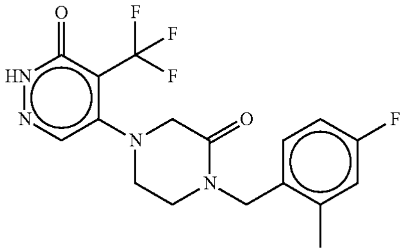 | C | C |
| 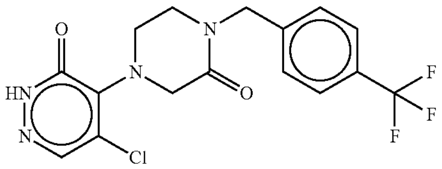 | D | D |
| 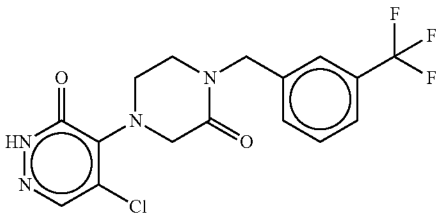 | D | D |

TABLE 5-continued
IC$_{50}$ values for representative compounds of the disclosure measured in an automated patch clamp assay utilizing HEK293 cells overexpressing TRPC5 (see above), with the readout as a current block utilizing whole cell automated patch following stimulation with rosiglitazone at either 80 or 100 mV.
| STRUCTURE | TRPC5_QP_ XC50_100 | TRPC5_QP_ XC50_80 |
|---|---|---|
| 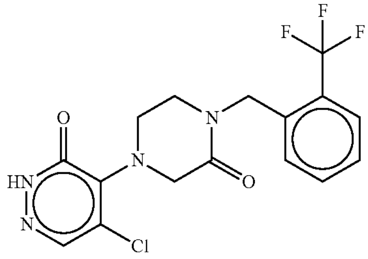 | C | C |
| 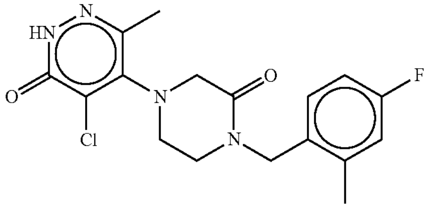 | D | D |
| 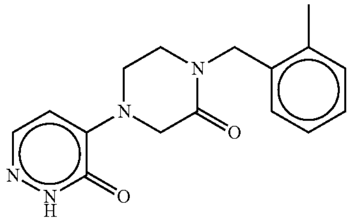 | D | D |
| 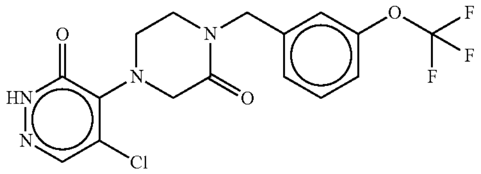 | D | D |
| 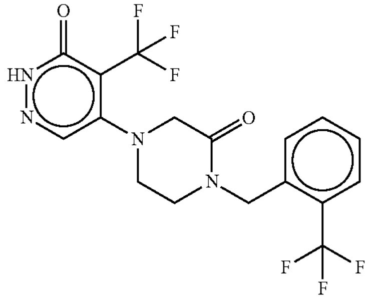 | B | B |
| 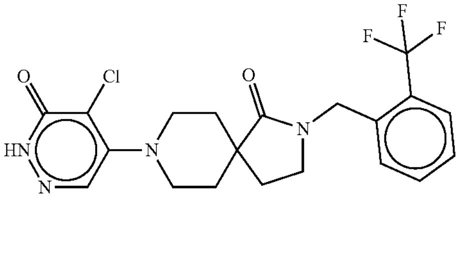 | D | D |

TABLE 5-continued
| IC50 values for representative compounds of the disclosure measured in an automated patch clamp assay utilizing HEK293 cells overexpressing TRPC5 (see above), with the readout as a current block utilizing whole cell automated patch following stimulation with rosiglitazone at either 80 or 100 mV. | | |
|---|---|---|
| STRUCTURE | TRPC5_QP_XC50_100 | TRPC5_QP_XC50_80 |
| 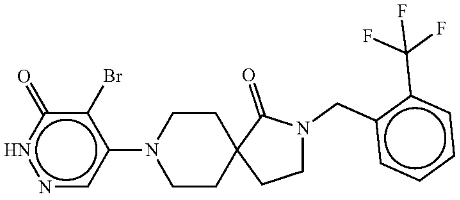 | D | D |
| 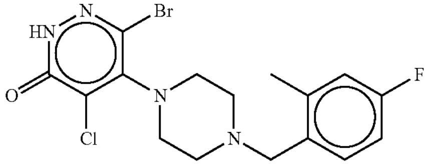 | D | D |
| 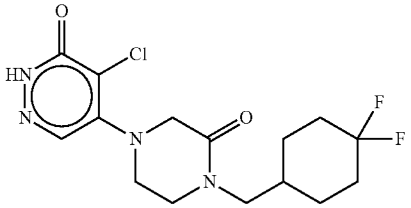 | C | C |
| 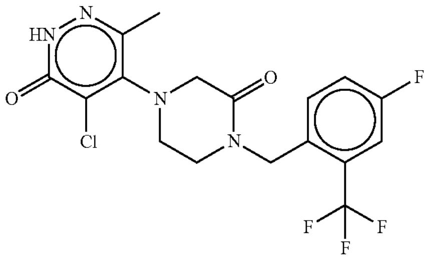 | C | C |
| 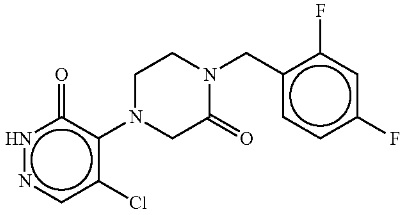 | D | D |
| 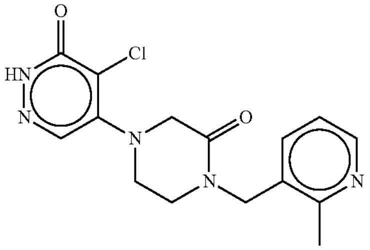 | D | D |

TABLE 5-continued
IC$_{50}$ values for representative compounds of the disclosure measured in an automated patch clamp assay utilizing HEK293 cells overexpressing TRPC5 (see above), with the readout as a current block utilizing whole cell automated patch following stimulation with rosiglitazone at either 80 or 100 mV.
| STRUCTURE | TRPC5_QP_XC50_100 | TRPC5_QP_XC50_80 |
|---|---|---|
| 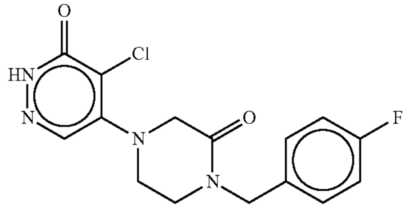 | C | C |
| 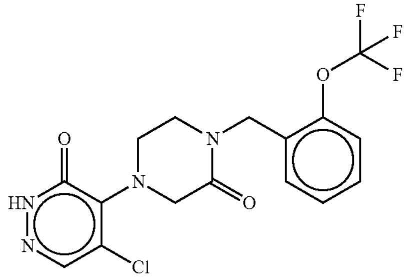 | D | D |
| 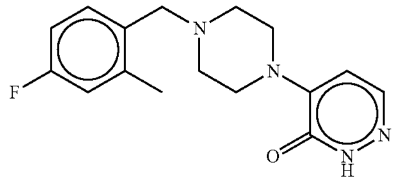 | D | D |
| 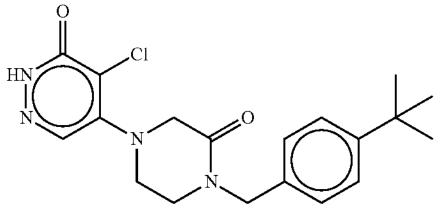 | D | D |
| 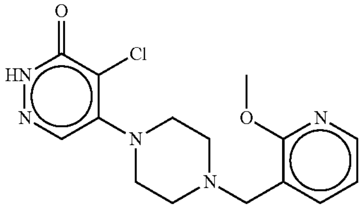 | B | B |
| 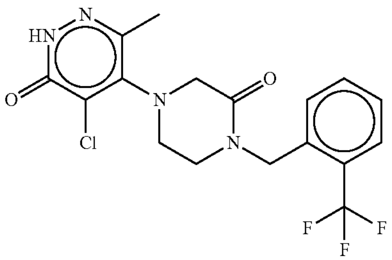 | C | C |

TABLE 5-continued
IC50 values for representative compounds of the disclosure measured in an automated patch clamp assay utilizing HEK293 cells overexpressing TRPC5 (see above), with the readout as a current block utilizing whole cell automated patch following stimulation with rosiglitazone at either 80 or 100 mV.
| STRUCTURE | TRPC5_QP_XC50_100 | TRPC5_QP_XC50_80 |
|---|---|---|
| 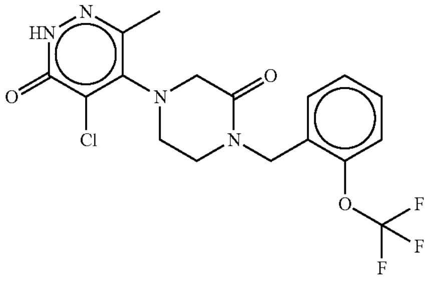 | C | C |
| 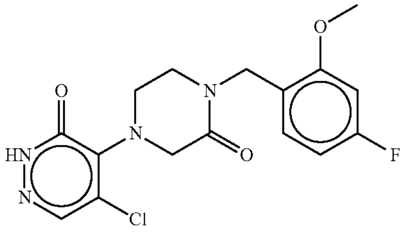 | D | D |
| 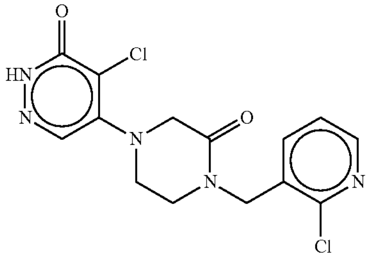 | D | D |
| 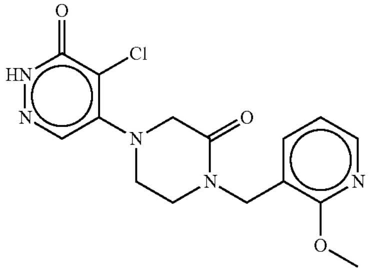 | C | C |
| 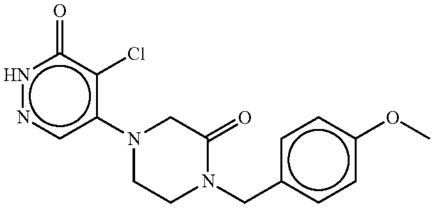 | C | C |

TABLE 5-continued
| $IC_{50}$ values for representative compounds of the disclosure measured in an automated patch clamp assay utilizing HEK293 cells overexpressing TRPC5 (see above), with the readout as a current block utilizing whole cell automated patch following stimulation with rosiglitazone at either 80 or 100 mV. | | |
|---|---|---|
| STRUCTURE | TRPC5__QP__ XC50__100 | TRPC5__QP__ XC50__80 |
| 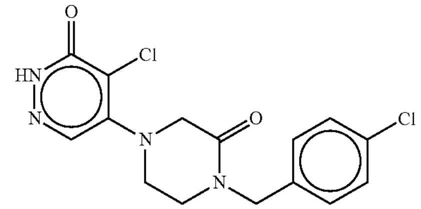 | C | B |
| 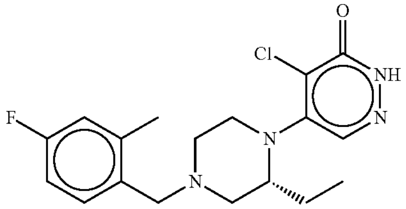 | D | D |
| 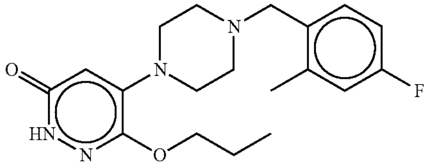 | D | D |
| 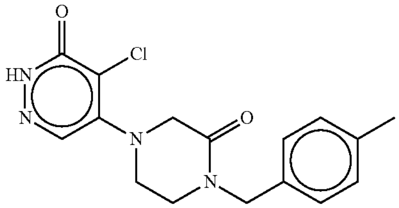 | C | C |
| 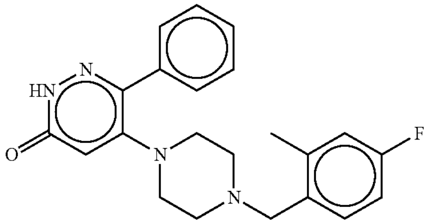 | B | B |
| 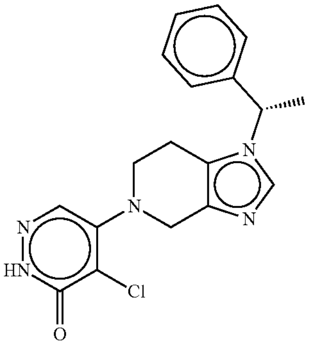 | B | B |

TABLE 5-continued
IC$_{50}$ values for representative compounds of the disclosure measured in an automated patch clamp assay utilizing HEK293 cells overexpressing TRPC5 (see above), with the readout as a current block utilizing whole cell automated patch following stimulation with rosiglitazone at either 80 or 100 mV.
| STRUCTURE | TRPC5_QP_ XC50_100 | TRPC5_QP_ XC50_80 |
|---|---|---|
| 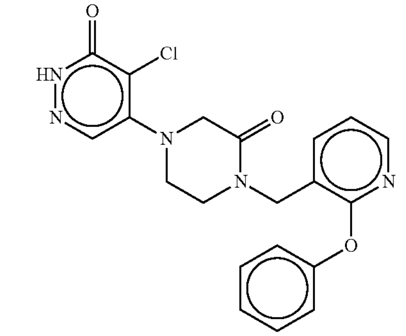 | C | C |
| 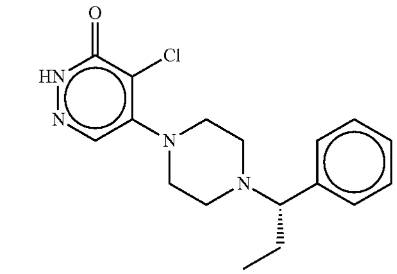 | B | B |
| 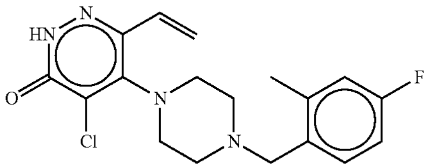 | D | D |
| 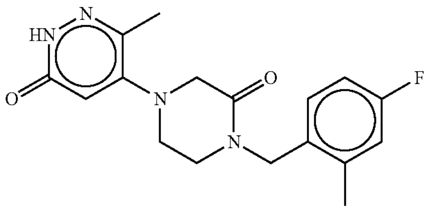 | D | D |
| 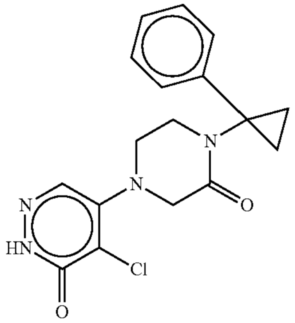 | B | B |

TABLE 5-continued
IC50 values for representative compounds of the disclosure measured in an automated patch clamp assay utilizing HEK293 cells overexpressing TRPC5 (see above), with the readout as a current block utilizing whole cell automated patch following stimulation with rosiglitazone at either 80 or 100 mV.
| STRUCTURE | TRPC5_QP_XC50_100 | TRPC5_QP_XC50_80 |
|---|---|---|
| 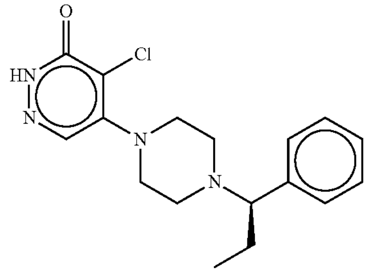 | B | B |
| 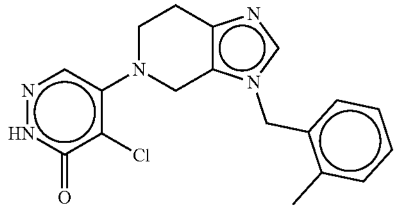 | D | D |
| 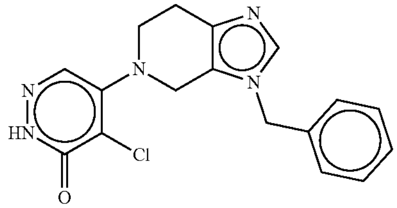 | D | D |
| 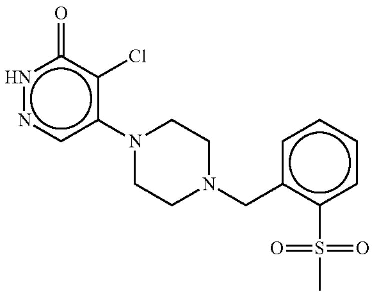 | C | C |
| 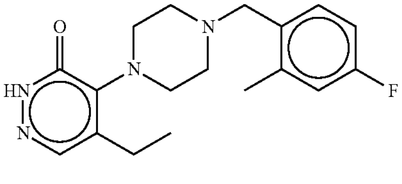 | B | B |

TABLE 5-continued
IC50 values for representative compounds of the disclosure measured in an automated patch clamp assay utilizing HEK293 cells overexpressing TRPC5 (see above), with the readout as a current block utilizing whole cell automated patch following stimulation with rosiglitazone at either 80 or 100 mV.
| STRUCTURE | TRPC5_QP_XC50_100 | TRPC5_QP_XC50_80 |
|---|---|---|
| 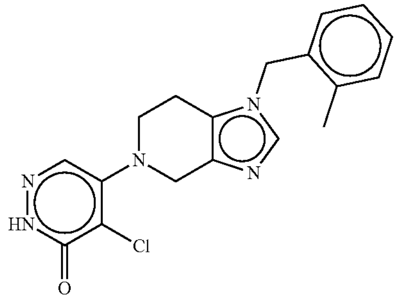 | A | A |
| 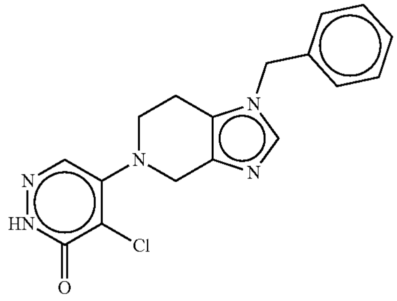 | B | B |
| 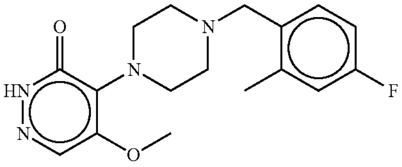 | B | B |
| 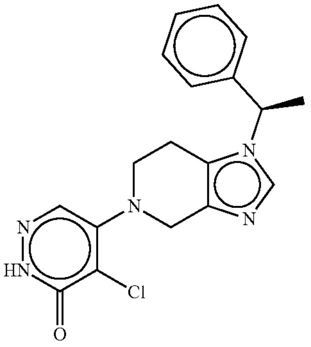 | B | B |
| 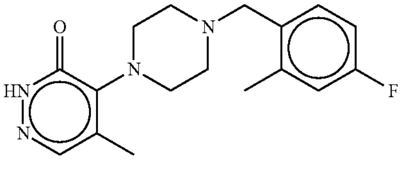 | B | B |

TABLE 5-continued

| IC50 values for representative compounds of the disclosure measured in an automated patch clamp assay utilizing HEK293 cells overexpressing TRPC5 (see above), with the readout as a current block utilizing whole cell automated patch following stimulation with rosiglitazone at either 80 or 100 mV. | | |
|---|---|---|
| STRUCTURE | TRPC5__QP___XC50__100 | TRPC5__QP__XC50__80 |
| 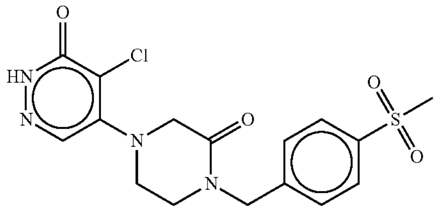 | D | D |
| 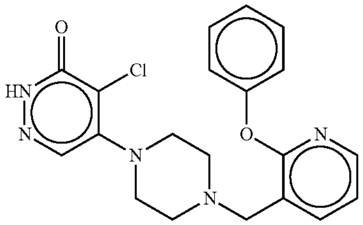 | C | C |
| 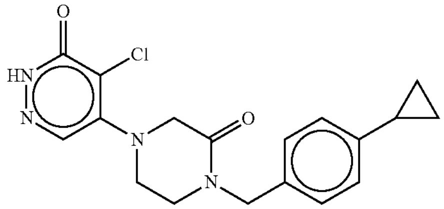 | D | D |

TABLE 6

IC$_{50}$ values for representative compounds of the disclosure measured in an automated patch clamp assay utilizing HEK293 cells overexpressing TRPC5 (see above).

| Structure | TRPC5-QPatch IC50 (uM) | TRPC5-FLEX IC50 (uM) | TRPC5-Spatch IC50 (uM) |
|---|---|---|---|
| 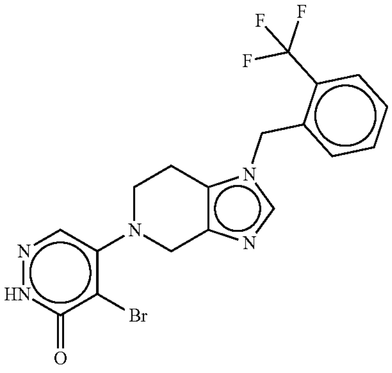 | B | A | |

TABLE 6-continued
| IC50 values for representative compounds of the disclosure measured in an automated patch clamp assay utilizing HEK293 cells overexpressing TRPC5 (see above). | | | |
|---|---|---|---|
| Structure | TRPC5-QPatch IC50 (uM) | TRPC5-FLEX IC50 (uM) | TRPC5-Spatch IC50 (uM) |
| 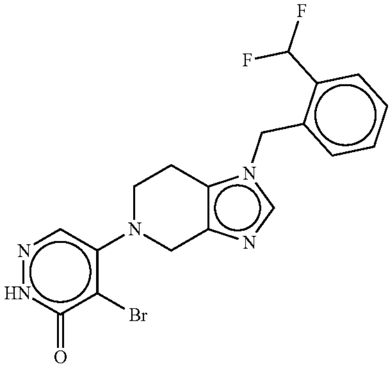 | C | | |
| 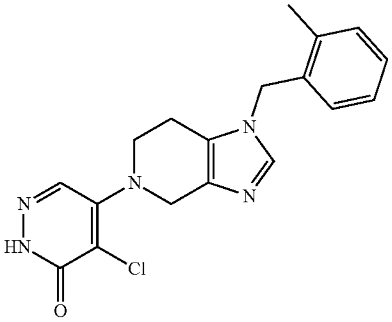 [SMILES: Cc1ccccc1Cn1cnc2c1CCN(c1cn[nH]c(=O)c1Cl)C2] | A | A | |
| 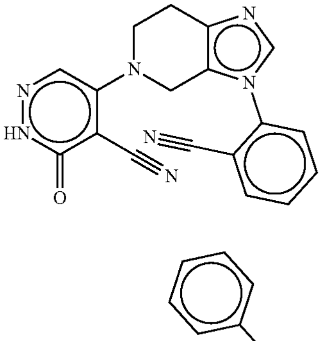 | B | A | |
| 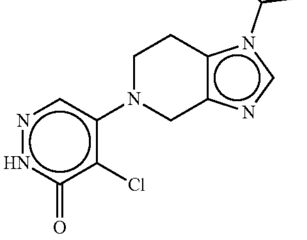 | B | A | |

TABLE 6-continued
IC50 values for representative compounds of the disclosure measured in an automated patch clamp assay utilizing HEK293 cells overexpressing TRPC5 (see above).
| Structure | TRPC5-QPatch IC50 (uM) | TRPC5-FLEX IC50 (uM) | TRPC5-Spatch IC50 (uM) |
|---|---|---|---|
| 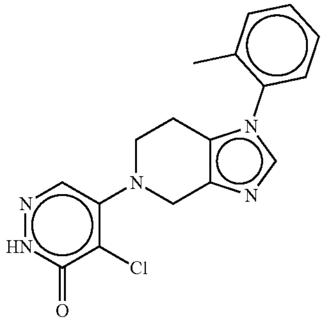 | B | D | |
| 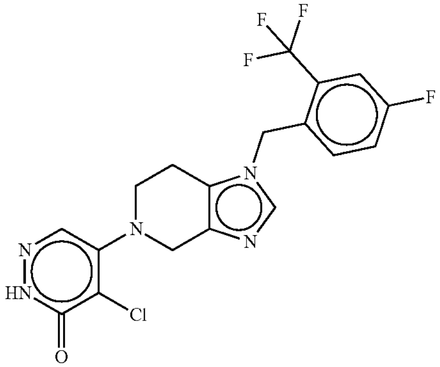 | A | A | |
| 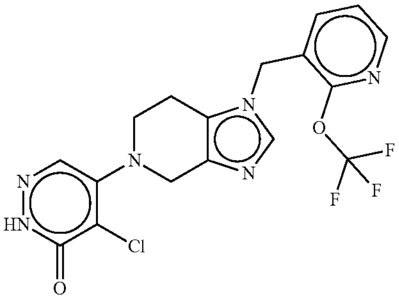 | A | A | |
| 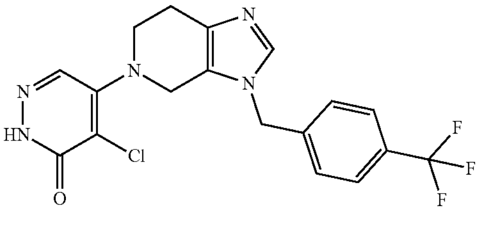 [SMILES: O=c1[nH]ncc(N2CCc3ncn(Cc4ccc(C(F)(F)F)cc4)c3C2)c1Cl] | D | B | |
| 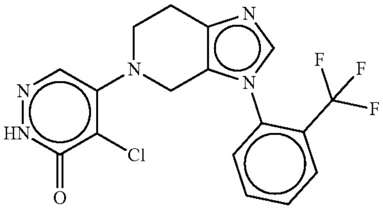 | C | D | |

TABLE 6-continued
IC$_{50}$ values for representative compounds of the disclosure measured in an automated patch clamp assay utilizing HEK293 cells overexpressing TRPC5 (see above).
| Structure | TRPC5-QPatch IC50 (uM) | TRPC5-FLEX IC50 (uM) | TRPC5-Spatch IC50 (uM) |
|---|---|---|---|
| 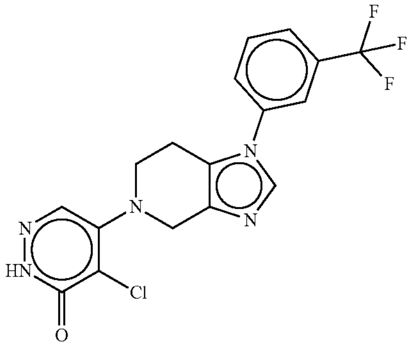 | B | A | |
| 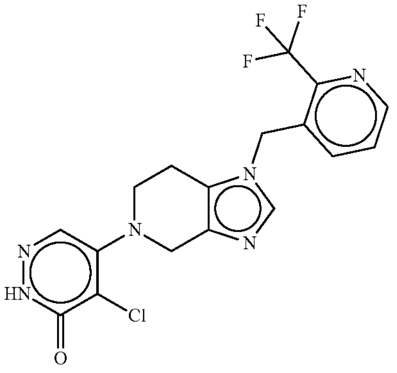 | B | B | |
| 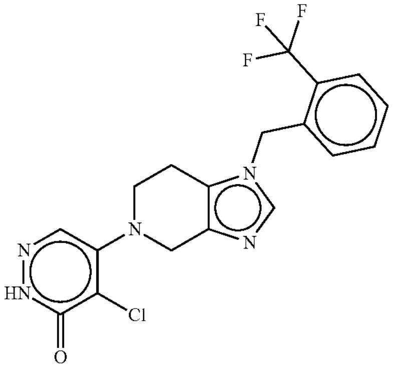 | A | A | |
| 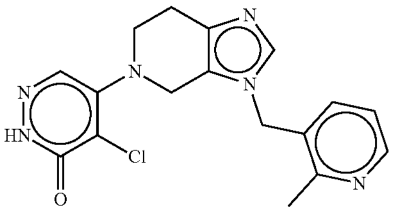 | | B | |

TABLE 6-continued
| IC50 values for representative compounds of the disclosure measured in an automated patch clamp assay utilizing HEK293 cells overexpressing TRPC5 (see above). | | | |
|---|---|---|---|
| Structure | TRPC5-QPatch IC50 (uM) | TRPC5-FLEX IC50 (uM) | TRPC5-Spatch IC50 (uM) |
| 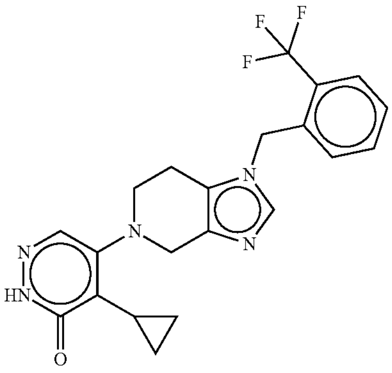 | C | C | |
| 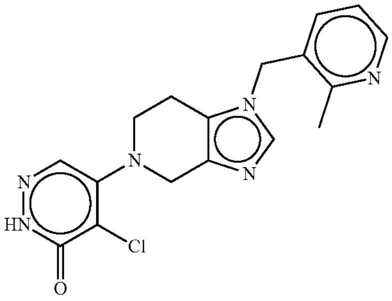 | B | B | |
| 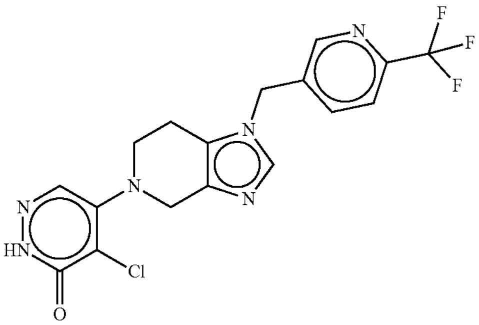 | D | D | |
| 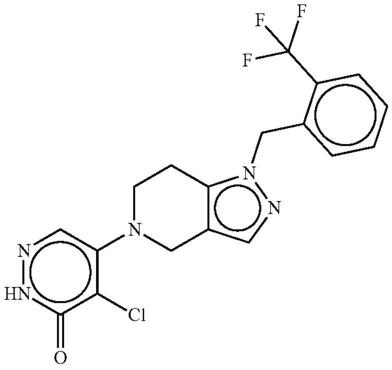 | A | A | |

TABLE 6-continued
IC50 values for representative compounds of the disclosure measured in an automated patch clamp assay utilizing HEK293 cells overexpressing TRPC5 (see above).
| Structure | TRPC5-QPatch IC50 (uM) | TRPC5-FLEX IC50 (uM) | TRPC5-Spatch IC50 (uM) |
|---|---|---|---|
| 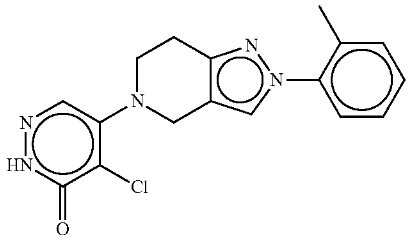 | D | B | |
| 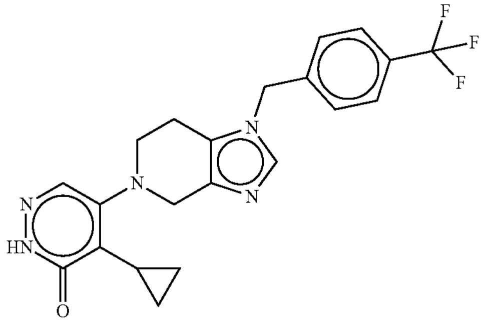 | D | D | |
| 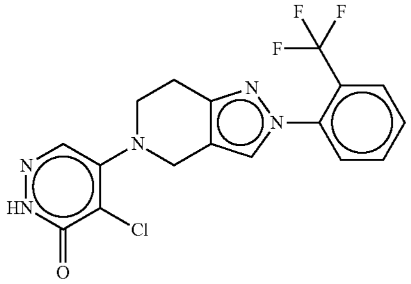 | D | A | |
| 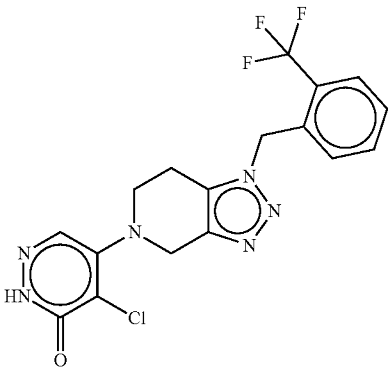 | A | A | |

TABLE 6-continued
IC50 values for representative compounds of the disclosure measured in an automated patch clamp assay utilizing HEK293 cells overexpressing TRPC5 (see above).
| Structure | TRPC5-QPatch IC50 (uM) | TRPC5-FLEX IC50 (uM) | TRPC5-Spatch IC50 (uM) |
|---|---|---|---|
| 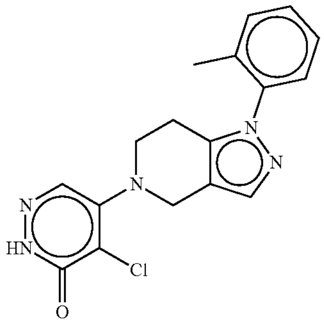 | A | A | |
| 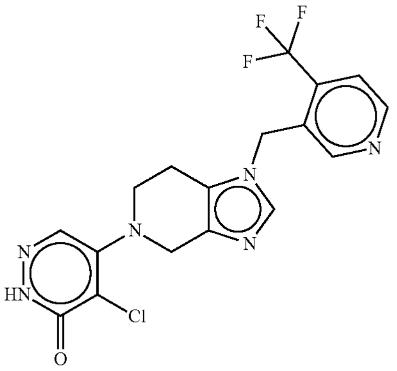 | B | A | |
| 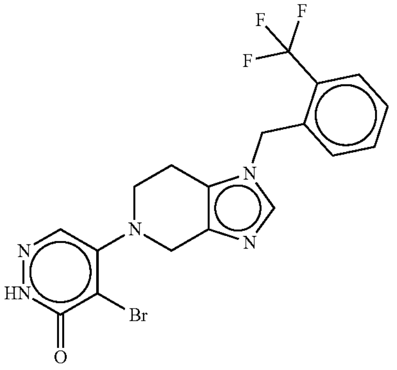 | A | A | |
| 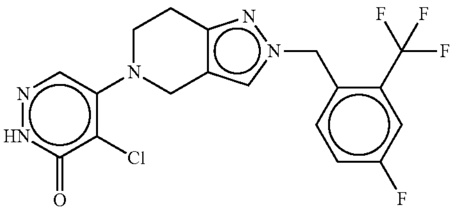 | | A | |

TABLE 6-continued
IC50 values for representative compounds of the disclosure measured in an automated patch clamp assay utilizing HEK293 cells overexpressing TRPC5 (see above).
| Structure | TRPC5-QPatch IC50 (uM) | TRPC5-FLEX IC50 (uM) | TRPC5-Spatch IC50 (uM) |
|---|---|---|---|
| 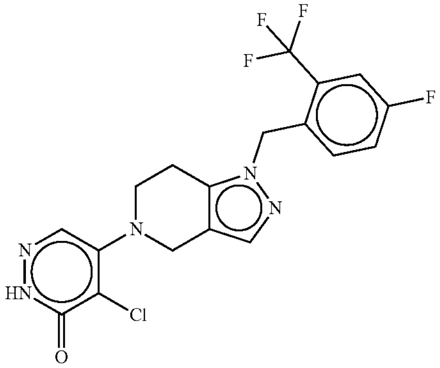 | A | A | |
| 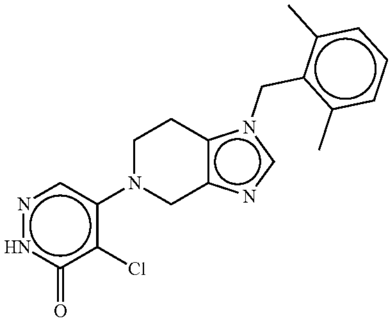 | | A | |
| 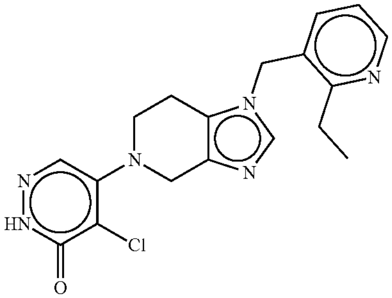 | A | A | |
| 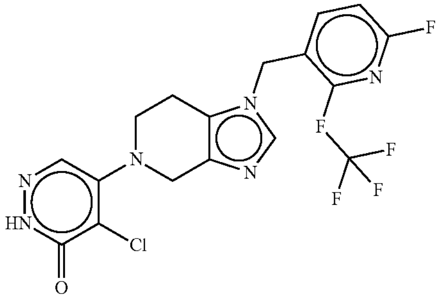 | A | B | |

TABLE 6-continued
IC50 values for representative compounds of the disclosure measured in an automated patch clamp assay utilizing HEK293 cells overexpressing TRPC5 (see above).
| Structure | TRPC5-QPatch IC50 (uM) | TRPC5-FLEX IC50 (uM) | TRPC5-Spatch IC50 (uM) |
|---|---|---|---|
| 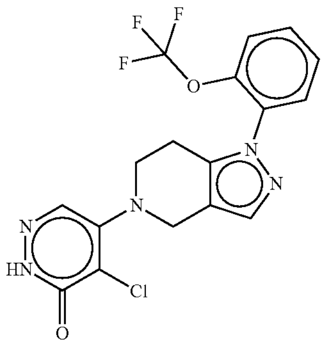 | B | A | |
| 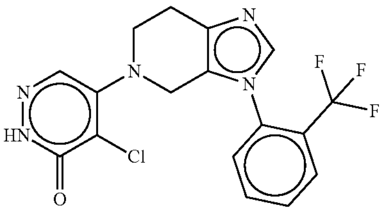 | | B | |
| 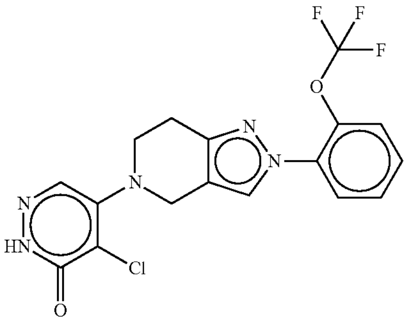 | | B | |
| 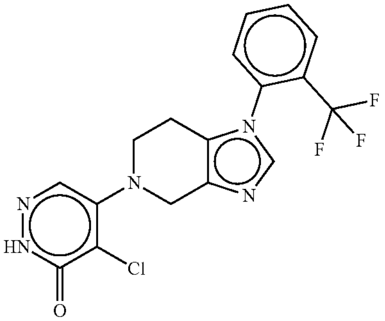 | A | A | |
| 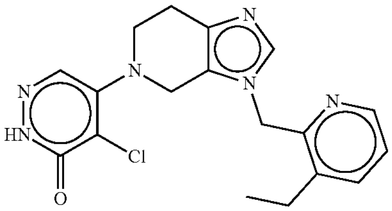 | | C | |

TABLE 6-continued
| IC$_{50}$ values for representative compounds of the disclosure measured in an automated patch clamp assay utilizing HEK293 cells overexpressing TRPC5 (see above). | | | |
|---|---|---|---|
| Structure | TRPC5-QPatch IC50 (uM) | TRPC5-FLEX IC50 (uM) | TRPC5-Spatch IC50 (uM) |
| 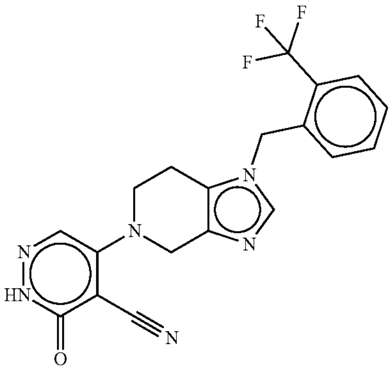 | A | A | |
| 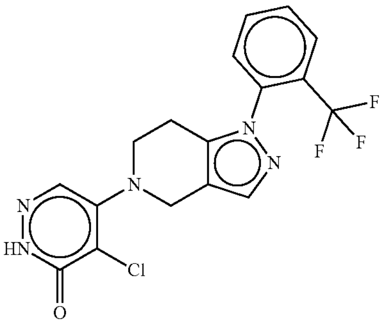 | | B | |
| 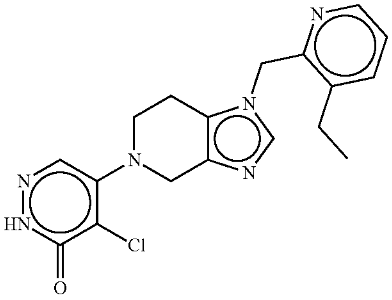 | B | A | |
| 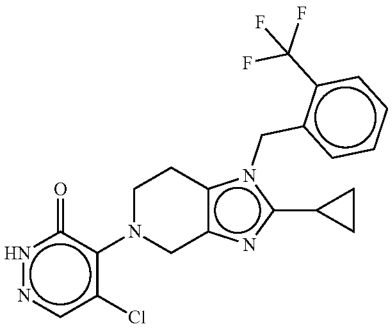 | | B | |

TABLE 6-continued
| IC$_{50}$ values for representative compounds of the disclosure measured in an automated patch clamp assay utilizing HEK293 cells overexpressing TRPC5 (see above). | | | |
|---|---|---|---|
| Structure | TRPC5-QPatch IC50 (uM) | TRPC5-FLEX IC50 (uM) | TRPC5-Spatch IC50 (uM) |
| 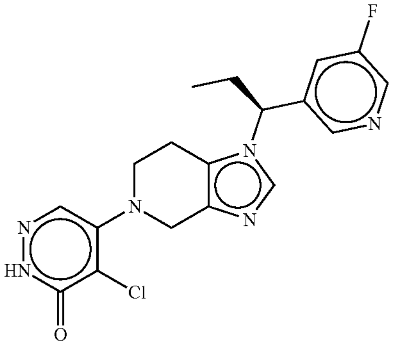 | C | A | |
| 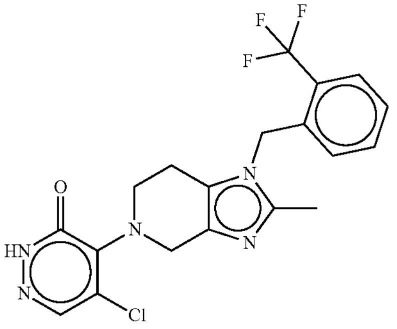 | | D | |
| 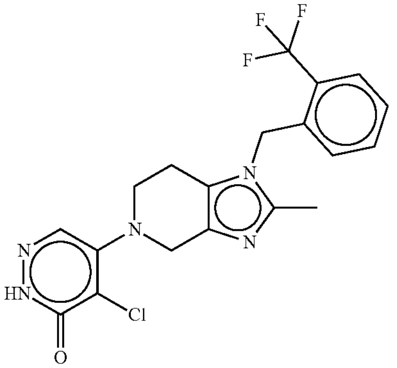 | A | A | |
| 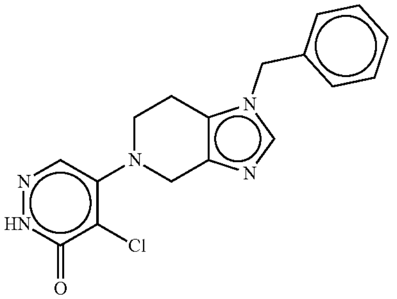 | B | A | |

TABLE 6-continued
IC50 values for representative compounds of the disclosure measured in an automated patch clamp assay utilizing HEK293 cells overexpressing TRPC5 (see above).
| Structure | TRPC5-QPatch IC50 (uM) | TRPC5-FLEX IC50 (uM) | TRPC5-Spatch IC50 (uM) |
| --- | --- | --- | --- |
| 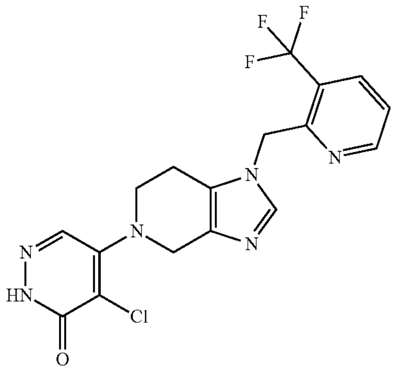 [SMILES: O=c1[nH]ncc(N2CCc3c(ncn3Cc3ncccc3C(F)(F)F)C2)c1Cl] | B | A | |
| 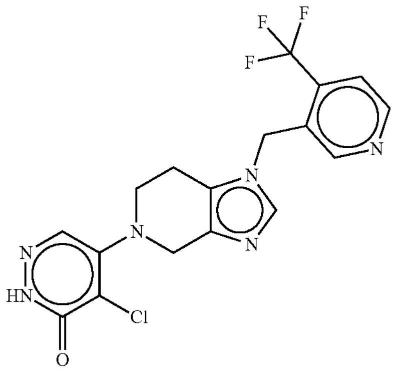 | B | B | |
| 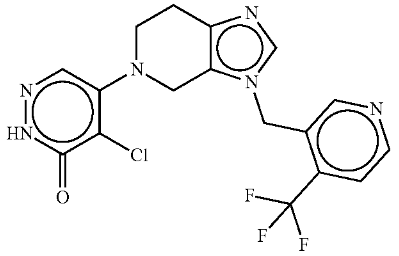 | | D | |
| 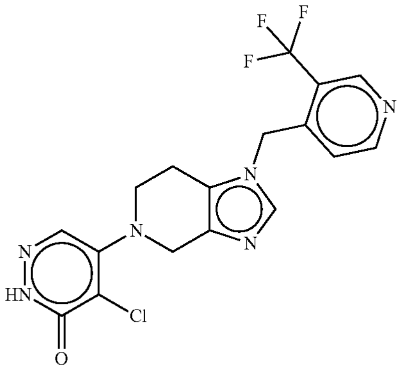 | B | A | |

TABLE 6-continued
IC$_{50}$ values for representative compounds of the disclosure measured in an automated patch clamp assay utilizing HEK293 cells overexpressing TRPC5 (see above).
| Structure | TRPC5-QPatch IC50 (uM) | TRPC5-FLEX IC50 (uM) | TRPC5-Spatch IC50 (uM) |
|---|---|---|---|
| 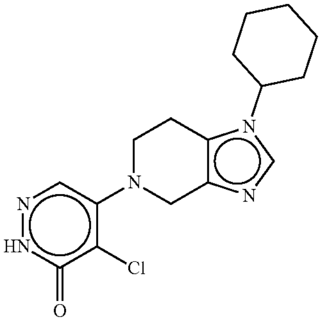 | C | D | |
| 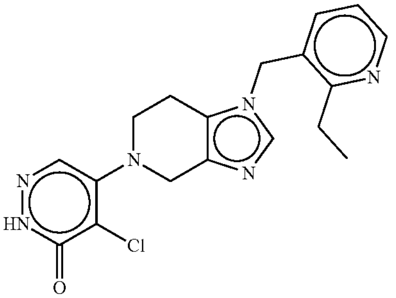 | A | | |
| 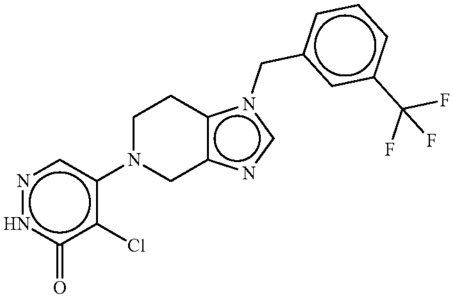 | B | | |
| 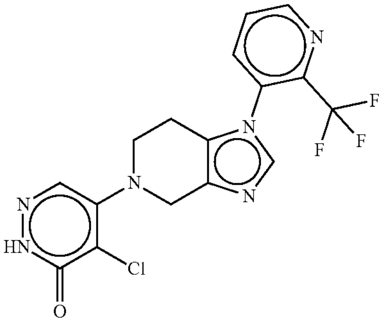 | B | | |

TABLE 6-continued
IC50 values for representative compounds of the disclosure measured in an automated patch clamp assay utilizing HEK293 cells overexpressing TRPC5 (see above).
| Structure | TRPC5-QPatch IC50 (uM) | TRPC5-FLEX IC50 (uM) | TRPC5-Spatch IC50 (uM) |
|---|---|---|---|
| 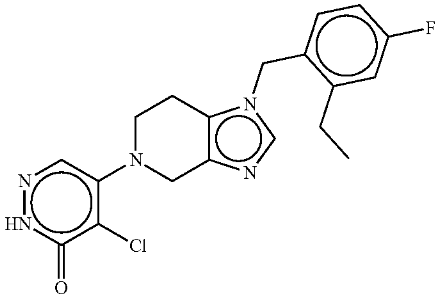 | A | | |
| 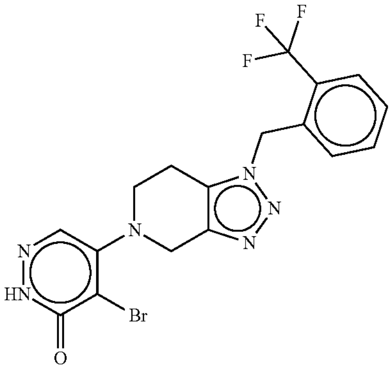 | B | A | |
| 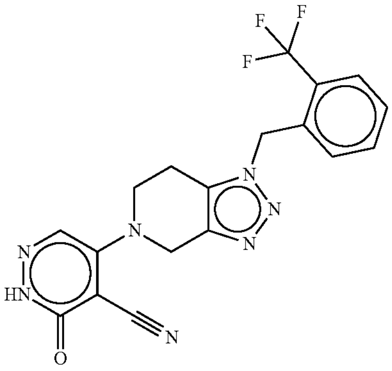 | B | | |
| 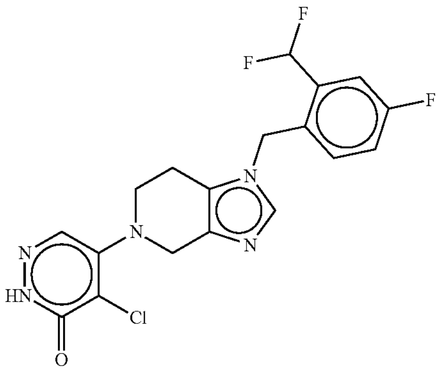 | A | A | |

TABLE 6-continued
IC$_{50}$ values for representative compounds of the disclosure measured in an automated patch clamp assay utilizing HEK293 cells overexpressing TRPC5 (see above).
| Structure | TRPC5-QPatch IC50 (uM) | TRPC5-FLEX IC50 (uM) | TRPC5-Spatch IC50 (uM) |
|---|---|---|---|
| 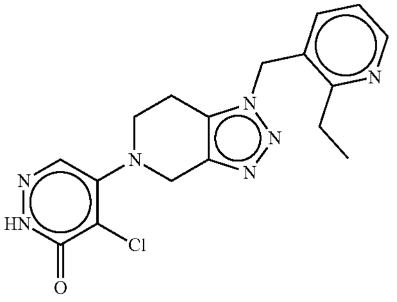 | B | A | |
| 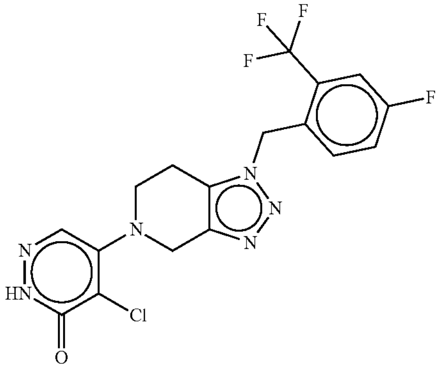 | A | A | |
| 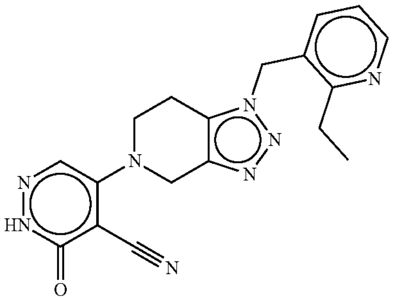 | C | D | |
| 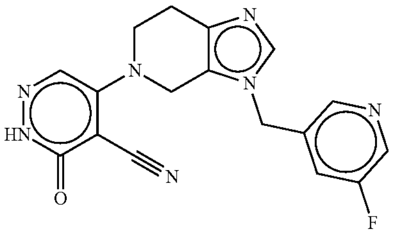 | | B | |

TABLE 6-continued
| IC$_{50}$ values for representative compounds of the disclosure measured in an automated patch clamp assay utilizing HEK293 cells overexpressing TRPC5 (see above). | | | |
|---|---|---|---|
| Structure | TRPC5-QPatch IC50 (uM) | TRPC5-FLEX IC50 (uM) | TRPC5-Spatch IC50 (uM) |
| 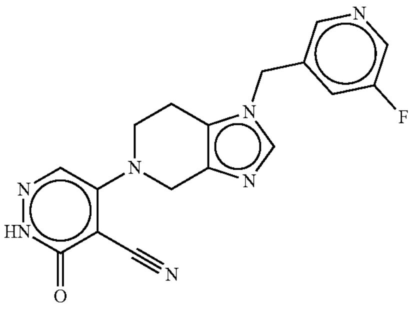 | | A | |
| 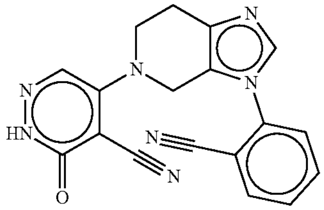 | | B | |
| 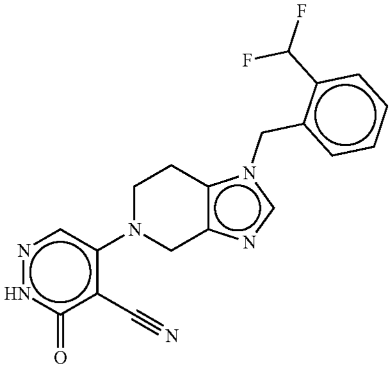 | B | A | |
| 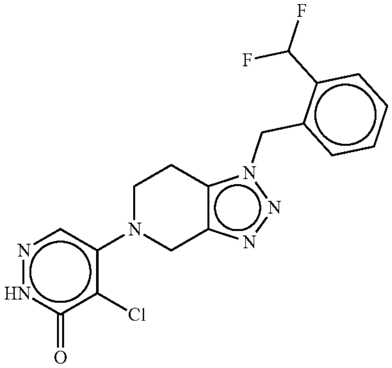 | A | A | |

TABLE 6-continued
IC$_{50}$ values for representative compounds of the disclosure measured in an automated patch clamp assay utilizing HEK293 cells overexpressing TRPC5 (see above).
| Structure | TRPC5-QPatch IC50 (uM) | TRPC5-FLEX IC50 (uM) | TRPC5-Spatch IC50 (uM) |
|---|---|---|---|
| 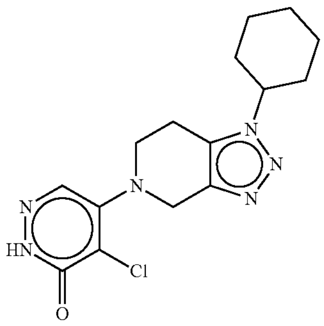 | C | D | |
| 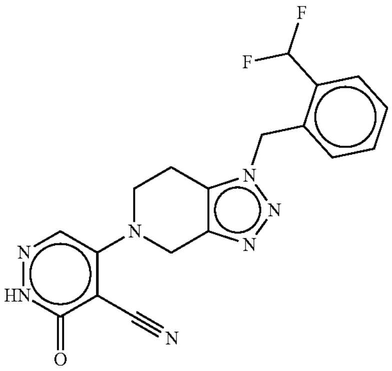 | B | D | |
| 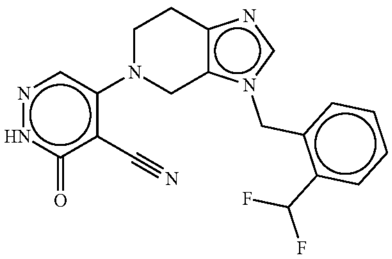 | | A | |
| 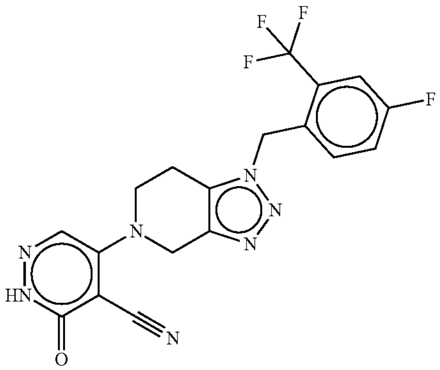 | B | D | |

TABLE 6-continued
IC50 values for representative compounds of the disclosure measured in an automated patch clamp assay utilizing HEK293 cells overexpressing TRPC5 (see above).
| Structure | TRPC5-QPatch IC50 (uM) | TRPC5-FLEX IC50 (uM) | TRPC5-Spatch IC50 (uM) |
|---|---|---|---|
| 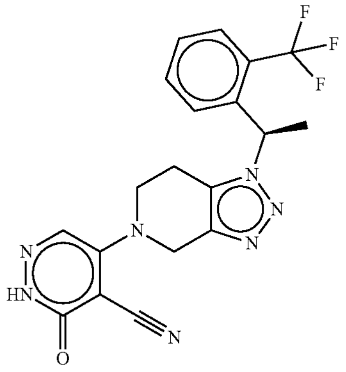 | | A | |
| 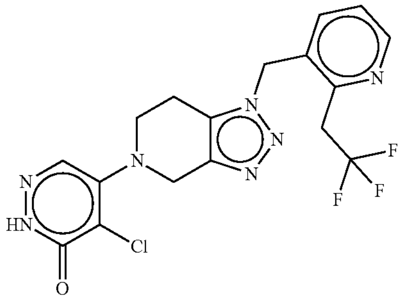 | | A | |
| 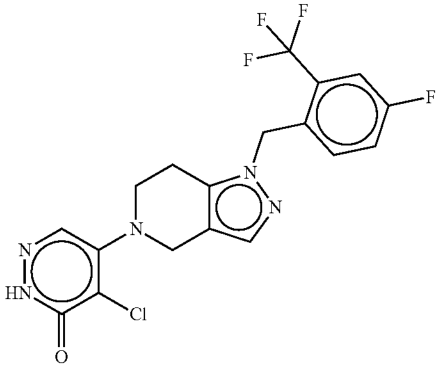 | | A | |
| 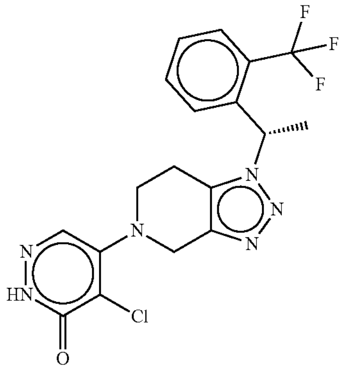 | | A | |

TABLE 6-continued
| IC$_{50}$ values for representative compounds of the disclosure measured in an automated patch clamp assay utilizing HEK293 cells overexpressing TRPC5 (see above). | | | |
|---|---|---|---|
| Structure | TRPC5-QPatch IC50 (uM) | TRPC5-FLEX IC50 (uM) | TRPC5-Spatch IC50 (uM) |
| 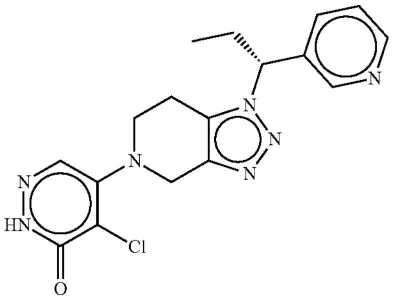 | | B | |
| 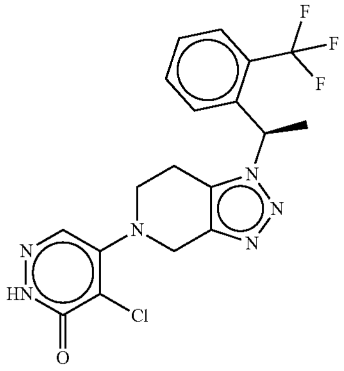 | | A | |
| 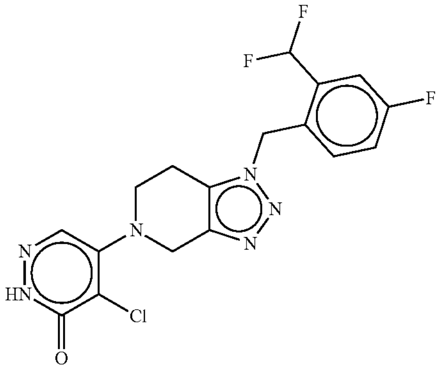 | | A | |
| 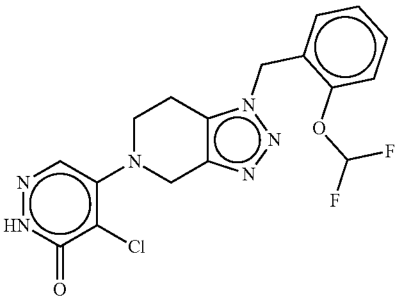 | | A | |

TABLE 6-continued
| IC50 values for representative compounds of the disclosure measured in an automated patch clamp assay utilizing HEK293 cells overexpressing TRPC5 (see above). | | | |
|---|---|---|---|
| Structure | TRPC5-QPatch IC50 (uM) | TRPC5-FLEX IC50 (uM) | TRPC5-Spatch IC50 (uM) |
| 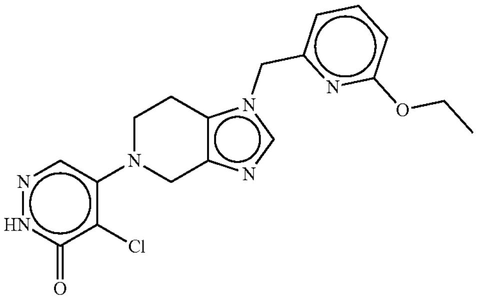 | | B | |
| 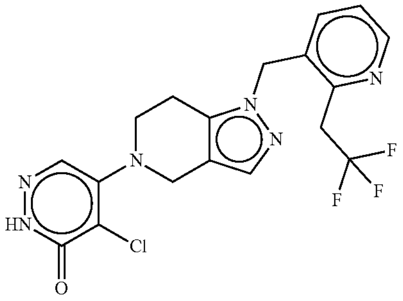 | | B | |
| 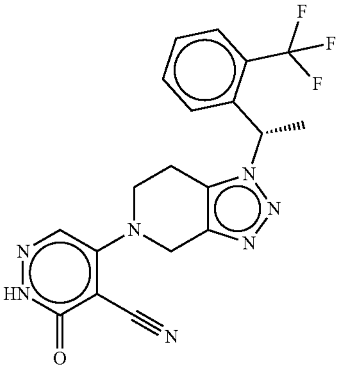 | | C | |
| 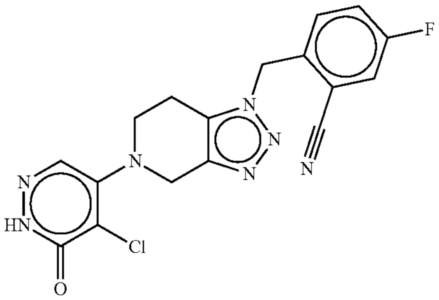 | | | C |

TABLE 6-continued
| IC$_{50}$ values for representative compounds of the disclosure measured in an automated patch clamp assay utilizing HEK293 cells overexpressing TRPC5 (see above). | | | |
|---|---|---|---|
| Structure | TRPC5-QPatch IC50 (uM) | TRPC5-FLEX IC50 (uM) | TRPC5-Spatch IC50 (uM) |
| 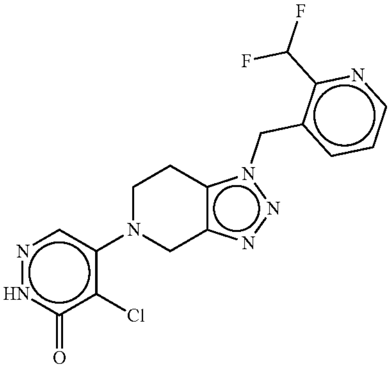 | | | C |
| 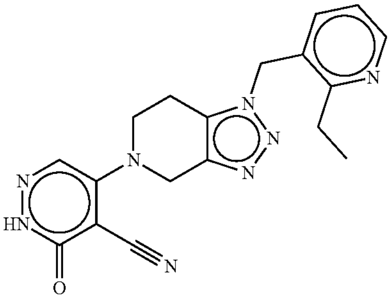 | | | B |
| 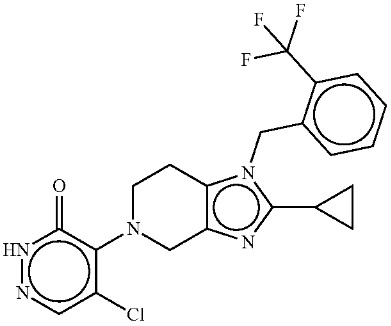 | | | D |
| 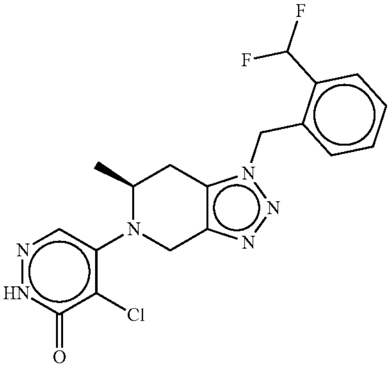 | | | D |

TABLE 6-continued
IC$_{50}$ values for representative compounds of the disclosure measured in an automated patch clamp assay utilizing HEK293 cells overexpressing TRPC5 (see above).
| Structure | TRPC5-QPatch IC50 (uM) | TRPC5-FLEX IC50 (uM) | TRPC5-Spatch IC50 (uM) |
|---|---|---|---|
| 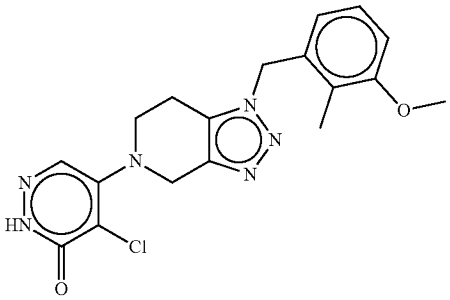 | | | B |
| 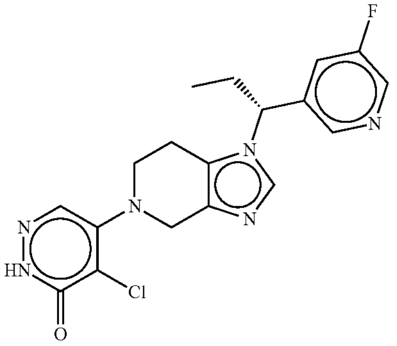 | | | B |
| 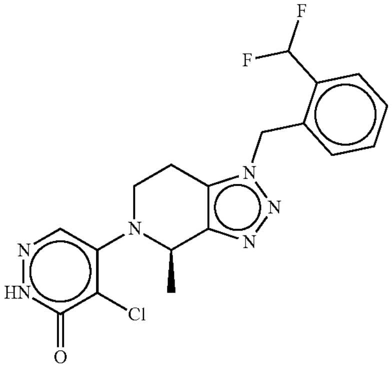 | | | D |
| 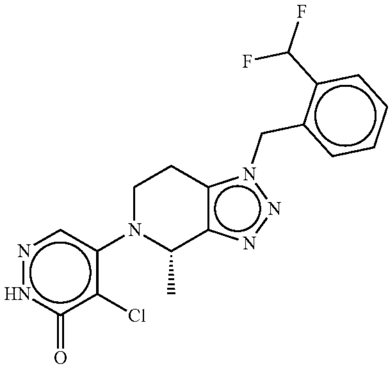 | | | A |

TABLE 6-continued

| IC$_{50}$ values for representative compounds of the disclosure measured in an automated patch clamp assay utilizing HEK293 cells overexpressing TRPC5 (see above). | | | |
|---|---|---|---|
| Structure | TRPC5-QPatch IC50 (uM) | TRPC5-FLEX IC50 (uM) | TRPC5-Spatch IC50 (uM) |
| 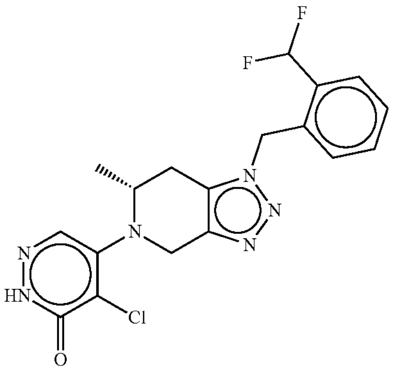 | | | A |

TABLE 7

| IC50 values for representative compounds of the disclosure measured in a Fluorescence assay - FLIPR format utilizing cells expressing TRPC5 (HEK-TREx hTRPC5) | |
|---|---|
| Structure | TRPC5-FLIPR IC50 (uM) |
| 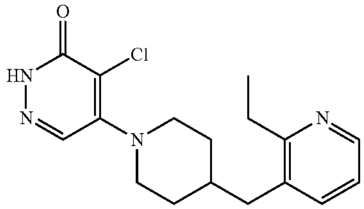 [SMILES: CCc1ncccc1CC1CCN(c2cn[nH]c(=O)c2Cl)CC1] | A |
| 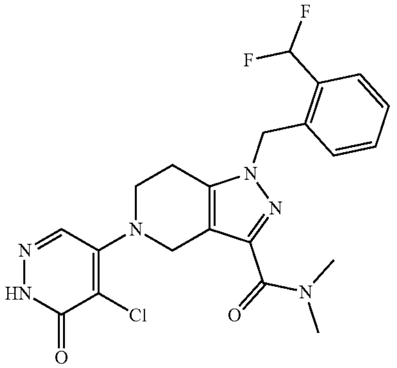 [SMILES: CN(C)C(=O)c1nn(Cc2ccccc2C(F)F)c2c1CN(c1cn[nH]c(=O)c1Cl)CC2] | A |

TABLE 7-continued

| IC50 values for representative compounds of the disclosure measured in a Fluorescence assay - FLIPR format utilizing cells expressing TRPC5 (HEK-TREx hTRPC5) | |
|---|---|
| Structure | TRPC5-FLIPR IC50 (uM) |
| 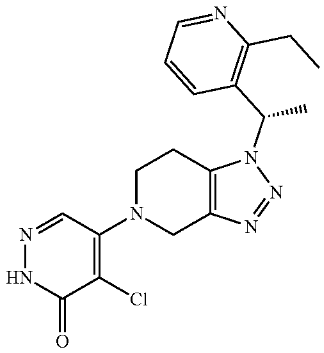 [SMILES: CCc1ncccc1[C@H](C)n1nnc2c1CCN(c1cn[nH]c(=O)c1Cl)C2] | A |
| 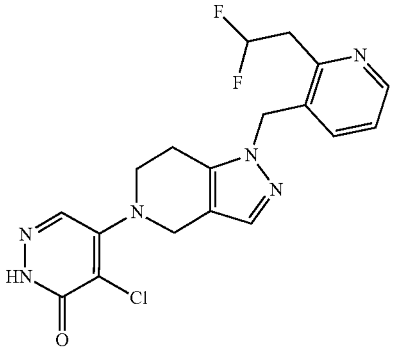 [SMILES: O=c1[nH]ncc(N2CCc3c(cnn3Cc3cccnc3CC(F)F)C2)c1Cl] | A |

TABLE 7-continued

| IC50 values for representative compounds of the disclosure measured in a Fluorescence assay - FLIPR format utilizing cells expressing TRPC5 (HEK-TREx hTRPC5) | |
|---|---|
| Structure | TRPC5-FLIPR IC50 (uM) |
| 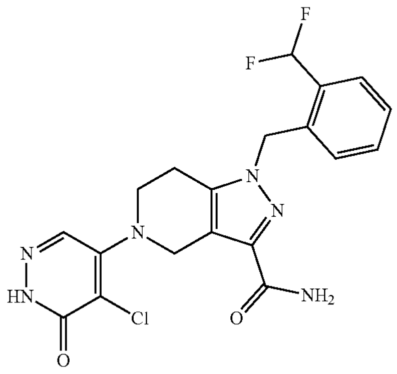 [SMILES: NC(=O)c1nn(Cc2ccccc2C(F)F)c2c1CN(c1cn[nH]c(=O)c1Cl)CC2] | A |
| 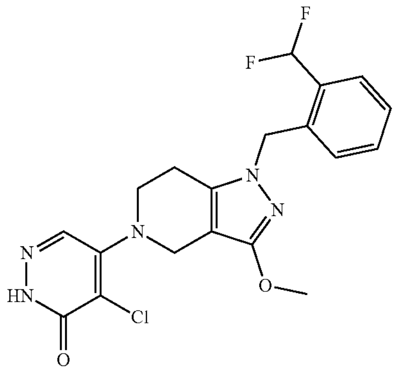 [SMILES: COc1nn(Cc2ccccc2C(F)F)c2c1CN(c1cn[nH]c(=O)c1Cl)CC2] | A |
| 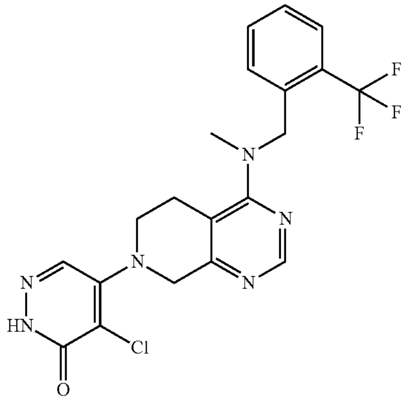 [SMILES: CN(Cc1ccccc1C(F)(F)F)c1ncnc2c1CCN(c1cn[nH]c(=O)c1Cl)C2] | C |

TABLE 7-continued

| IC50 values for representative compounds of the disclosure measured in a Fluorescence assay - FLIPR format utilizing cells expressing TRPC5 (HEK-TREx hTRPC5) | |
|---|---|
| Structure | TRPC5-FLIPR IC50 (uM) |
| 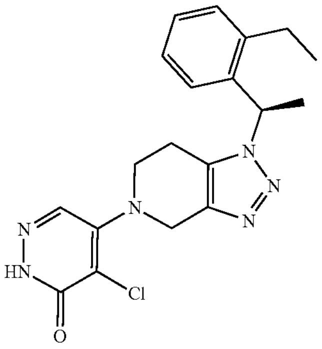 [SMILES: CCc1ccccc1[C@@H](C)n1nnc2c1CCN(c1cn[nH]c(=O)c1Cl)C2] | A |
| 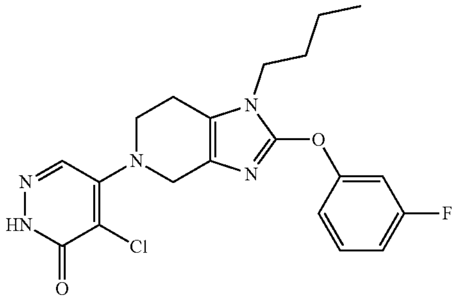 [SMILES: CCCCn1c(Oc2cccc(F)c2)nc2c1CCN(c1cn[nH]c(=O)c1Cl)C2] | B |
| 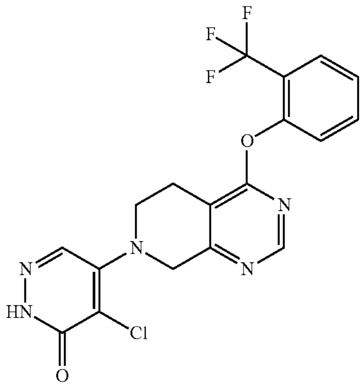 [SMILES: O=c1[nH]ncc(N2CCc3c(ncnc3Oc3ccccc3C(F)(F)F)C2)c1Cl] | A |
| 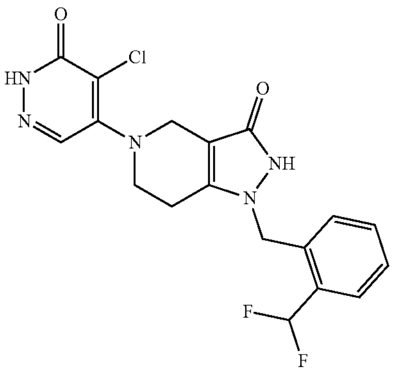 [SMILES: O=c1[nH]ncc(N2CCc3c(c(=O)[nH]n3Cc3ccccc3C(F)F)C2)c1Cl] | A |

TABLE 8

| IC$_{50}$ values for representative compounds of the disclosure measured in a Fluorescence assay - FLIPR format utilizing cells expressing TRPC4 (HEK-TREx hTRPC4) | |
|---|---|
| Structure | TRPC4 FLIPR IC$_{50}$ (uM) |
| 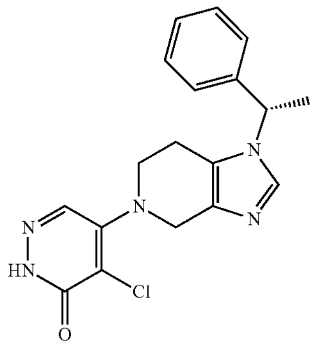 [SMILES: C[C@@H](c1ccccc1)n1cnc2c1CCN(c1cn[nH]c(=O)c1Cl)C2] | B |
| 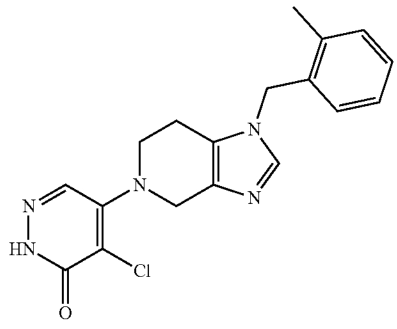 [SMILES: Cc1ccccc1Cn1cnc2c1CCN(c1cn[nH]c(=O)c1Cl)C2] | A |
| 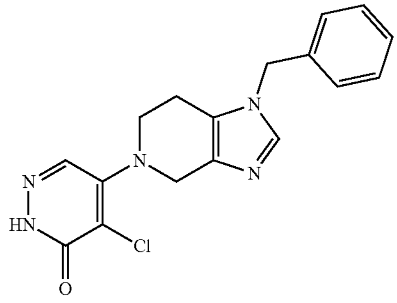 [SMILES: O=c1[nH]ncc(N2CCc3c(ncn3Cc3ccccc3)C2)c1Cl] | A |
| 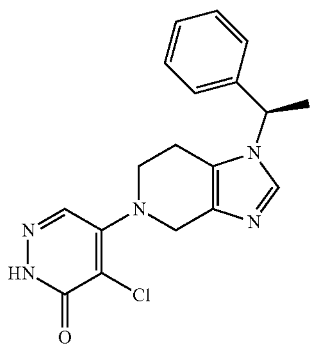 [SMILES: C[C@H](c1ccccc1)n1cnc2c1CCN(c1cn[nH]c(=O)c1Cl)C2] | A |

TABLE 8-continued

| IC$_{50}$ values for representative compounds of the disclosure measured in a Fluorescence assay - FLIPR format utilizing cells expressing TRPC4 (HEK-TREx hTRPC4) | |
|---|---|
| Structure | TRPC4 FLIPR IC$_{50}$ (uM) |
| 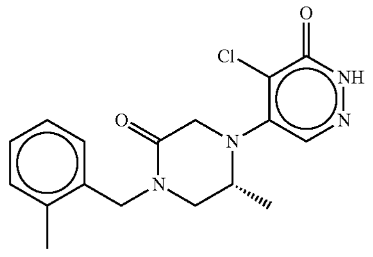 | C |
| 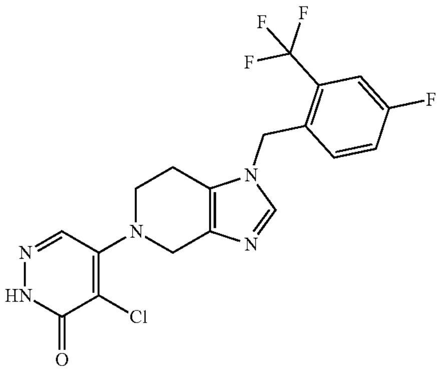 [SMILES: O=c1[nH]ncc(N2CCc3c(ncn3Cc3ccc(F)cc3C(F)(F)F)C2)c1Cl] | A |
| 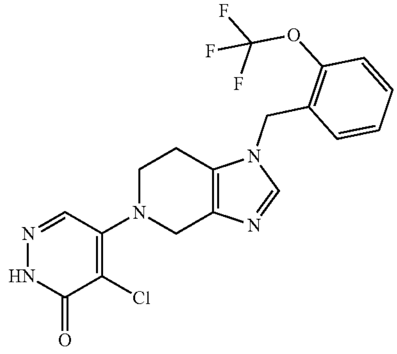 [SMILES: O=c1[nH]ncc(N2CCc3c(ncn3Cc3ccccc3OC(F)(F)F)C2)c1Cl] | A |
| 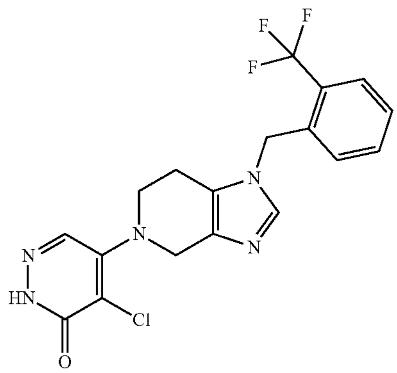 | A |

TABLE 8-continued

IC$_{50}$ values for representative compounds of the disclosure measured in a Fluorescence assay - FLIPR format utilizing cells expressing TRPC4 (HEK-TREx hTRPC4)

| Structure | TRPC4 FLIPR IC$_{50}$ (uM) |
|---|---|
| 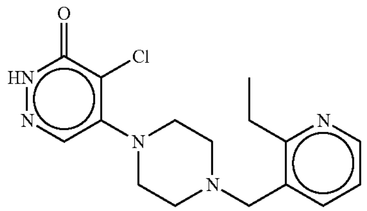 | A |
| 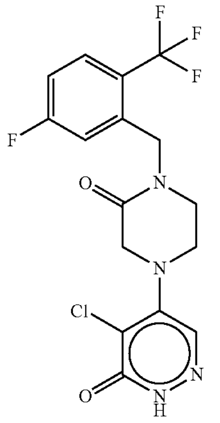 | A |
| 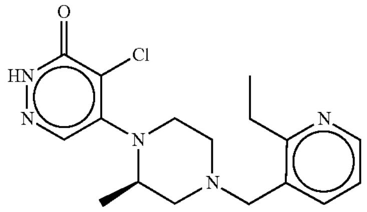 | C |
| 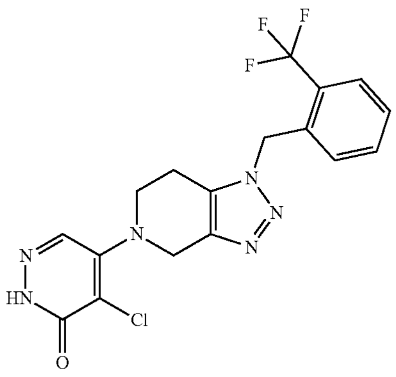 | A |

TABLE 8-continued

IC$_{50}$ values for representative compounds of the disclosure measured in a Fluorescence assay - FLIPR format utilizing cells expressing TRPC4 (HEK-TREx hTRPC4)

| Structure | TRPC4 FLIPR IC$_{50}$ (uM) |
|---|---|
| 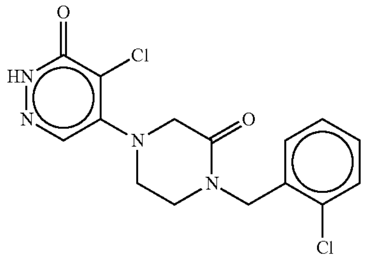 | A |
| 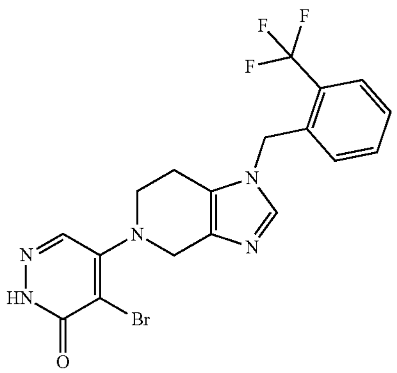 | A |
| 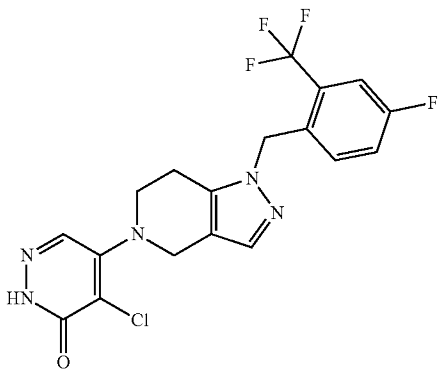 [SMILES: O=c1[nH]ncc(N2CCc3c(cnn3Cc3ccc(F)cc3C(F)(F)F)C2)c1Cl] | A |
| 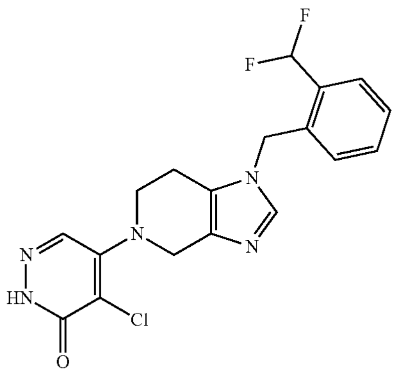 | A |

TABLE 8-continued

IC50 values for representative compounds of the disclosure measured in a Fluorescence assay - FLIPR format utilizing cells expressing TRPC4 (HEK-TREx hTRPC4)

| Structure | TRPC4 FLIPR $IC_{50}$ (uM) |
| --- | --- |
| 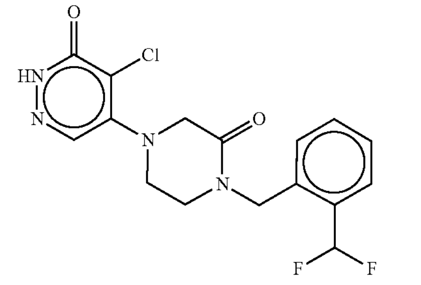 | A |
| 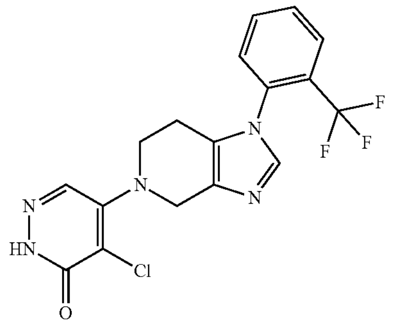 [SMILES: O=c1[nH]ncc(N2CCc3c(ncn3-c3ccccc3C(F)(F)F)C2)c1Cl] | B |
| 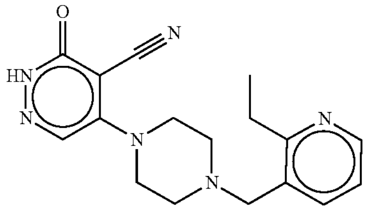 | C |
| 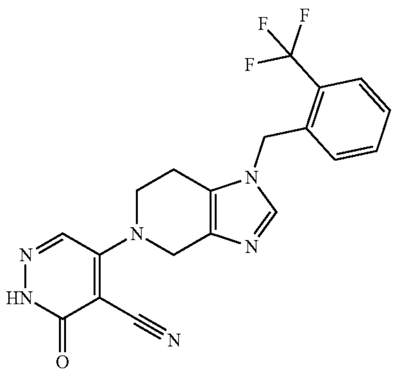 [SMILES: N#Cc1c(N2CCc3c(ncn3Cc3ccccc3C(F)(F)F)C2)cn[nH]c1=O] | B |

TABLE 8-continued

IC50 values for representative compounds of the disclosure measured in a Fluorescence assay - FLIPR format utilizing cells expressing TRPC4 (HEK-TREx hTRPC4)

| Structure | TRPC4 FLIPR $IC_{50}$ (uM) |
| --- | --- |
| 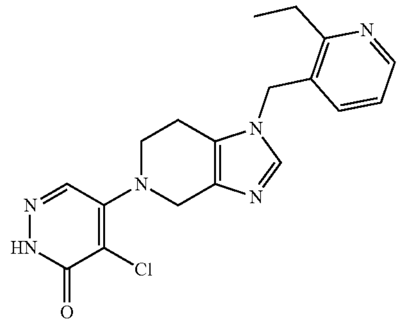 [SMILES: CCc1ncccc1Cn1cnc2c1CCN(c1cn[nH]c(=O)c1Cl)C2] | A |
| 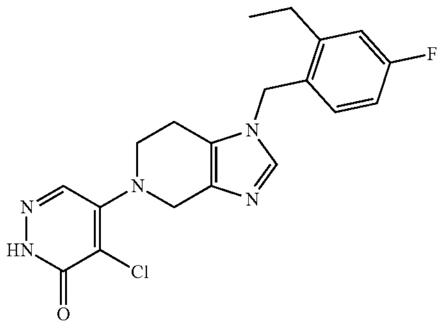 [SMILES: CCc1cc(F)ccc1Cn1cnc2c1CCN(c1cn[nH]c(=O)c1Cl)C2] | A |
| 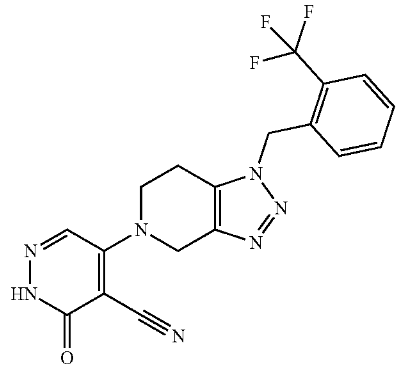 [SMILES: N#Cc1c(N2CCc3c(nnn3Cc3ccccc3C(F)(F)F)C2)cn[nH]c1=O] | B |
| 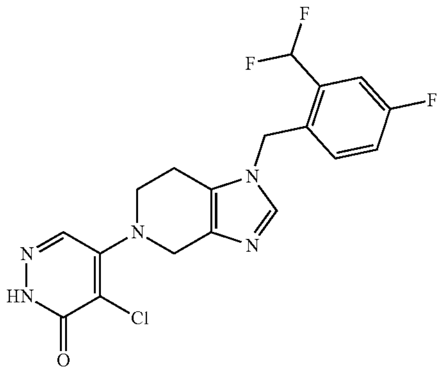 [SMILES: O=c1[nH]ncc(N2CCc3c(ncn3Cc3ccc(F)cc3C(F)F)C2)c1Cl] | A |

TABLE 8-continued

IC$_{50}$ values for representative compounds of the disclosure measured in a Fluorescence assay - FLIPR format utilizing cells expressing TRPC4 (HEK-TREx hTRPC4)

| Structure | TRPC4 FLIPR IC$_{50}$ (uM) |
|---|---|
| 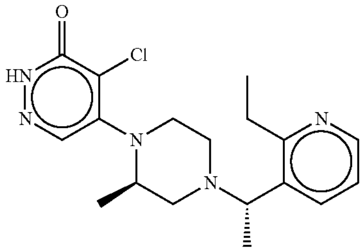 | A |
| 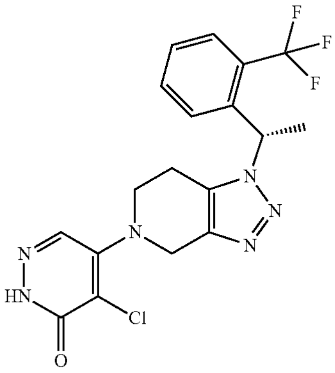 [SMILES: C[C@@H](c1ccccc1C(F)(F)F)n1nnc2c1CCN(c1cn[nH]c(=O)c1Cl)C2] | A |
| 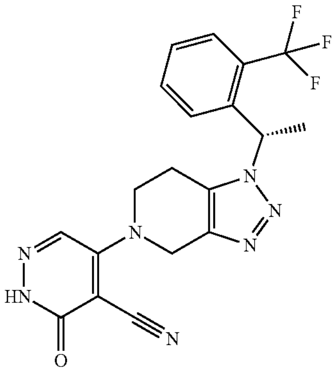 [SMILES: C[C@@H](c1ccccc1C(F)(F)F)n1nnc2c1CCN(c1cn[nH]c(=O)c1C#N)C2] | A |
| 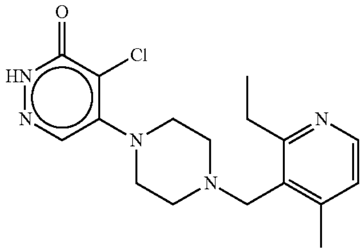 | B |

TABLE 8-continued

IC$_{50}$ values for representative compounds of the disclosure measured in a Fluorescence assay - FLIPR format utilizing cells expressing TRPC4 (HEK-TREx hTRPC4)

| Structure | TRPC4 FLIPR IC$_{50}$ (uM) |
|---|---|
| 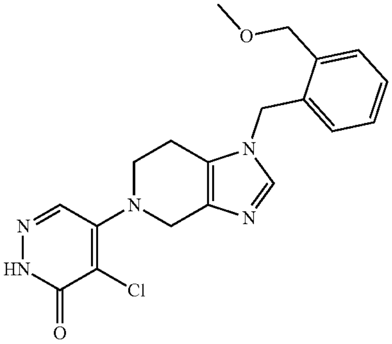 [SMILES: COCc1ccccc1Cn1cnc2c1CCN(c1cn[nH]c(=O)c1Cl)C2] | A |
| 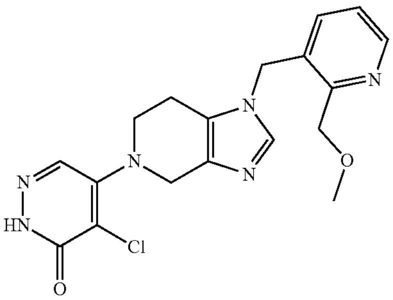 [SMILES: COCc1ncccc1Cn1cnc2c1CCN(c1cn[nH]c(=O)c1Cl)C2] | B |
| 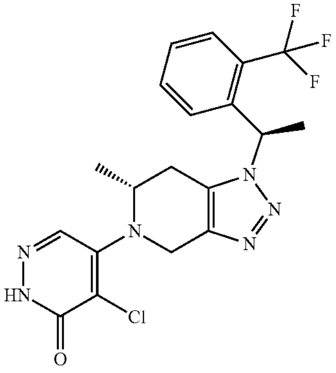 [SMILES: C[C@@H]1Cc2c(nnn2[C@H](C)c2ccccc2C(F)(F)F)CN1c1cn[nH]c(=O)c1Cl] | A |
| 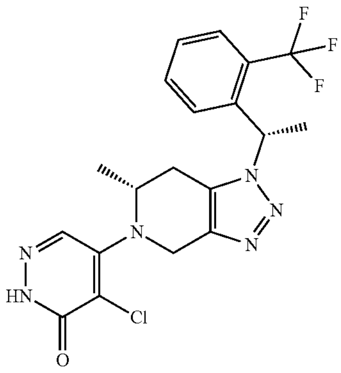 [SMILES: C[C@@H]1Cc2c(nnn2[C@@H](C)c2ccccc2C(F)(F)F)CN1c1cn[nH]c(=O)c1Cl] | A |

TABLE 8-continued $IC_{50}$ values for representative compounds of the disclosure measured in a Fluorescence assay - FLIPR format utilizing cells expressing TRPC4 (HEK-TREx hTRPC4)

| Structure | TRPC4 FLIPR $IC_{50}$ (uM) |
|---|---|
| 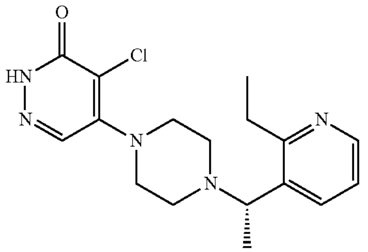 [SMILES: CCc1ncccc1[C@H](C)N1CCN(c2cn[nH]c(=O)c2Cl)CC1] | A |
| 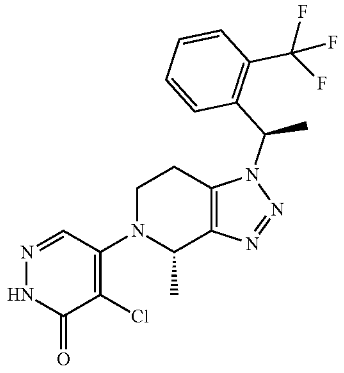 [SMILES: C[C@H](c1ccccc1C(F)(F)F)n1nnc2c1CCN(c1cn[nH]c(=O)c1Cl)[C@H]2C] | A |
| 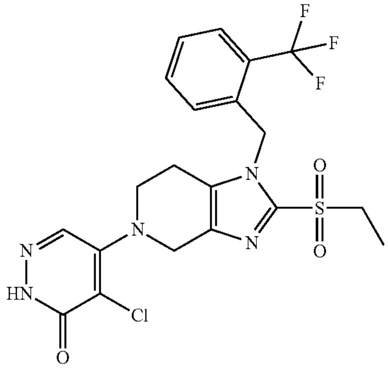 [SMILES: CCS(=O)(=O)c1nc2c(n1Cc1ccccc1C(F)(F)F)CCN(c1cn[nH]c(=O)c1Cl)C2] | A |
| 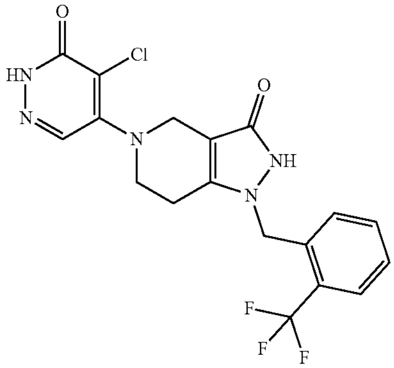 [SMILES: O=c1[nH]ncc(N2CCc3c(c(=O)[nH]n3Cc3ccccc3C(F)(F)F)C2)c1Cl] | A |

TABLE 8-continued $IC_{50}$ values for representative compounds of the disclosure measured in a Fluorescence assay - FLIPR format utilizing cells expressing TRPC4 (HEK-TREx hTRPC4)

| Structure | TRPC4 FLIPR $IC_{50}$ (uM) |
|---|---|
| 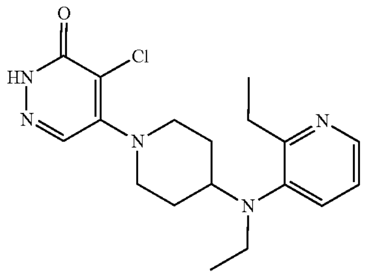 [SMILES: CCc1ncccc1N(CC)C1CCN(c2cn[nH]c(=O)c2Cl)CC1] | A |
| 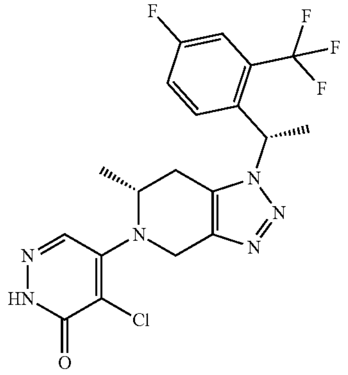 [SMILES: C[C@@H]1Cc2c(nnn2[C@@H](C)c2ccc(F)cc2C(F)(F)F)CN1c1cn[nH]c(=O)c1Cl] | A |
| 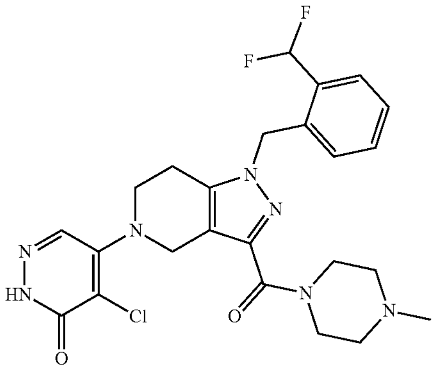 [SMILES: CN1CCN(C(=O)c2nn(Cc3ccccc3C(F)F)c3c2CN(c2cn[nH]c(=O)c2Cl)CC3)CC1] | A |
| 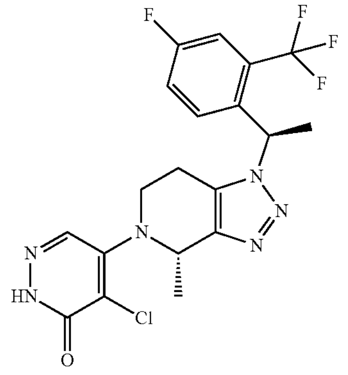 [SMILES: C[C@H](c1ccc(F)cc1C(F)(F)F)n1nnc2c1CCN(c1cn[nH]c(=O)c1Cl)[C@H]2C] | A |

TABLE 8-continued $IC_{50}$ values for representative compounds of the disclosure measured in a Fluorescence assay - FLIPR format utilizing cells expressing TRPC4 (HEK-TREx hTRPC4)

| Structure | TRPC4 FLIPR $IC_{50}$ (uM) |
|---|---|
| 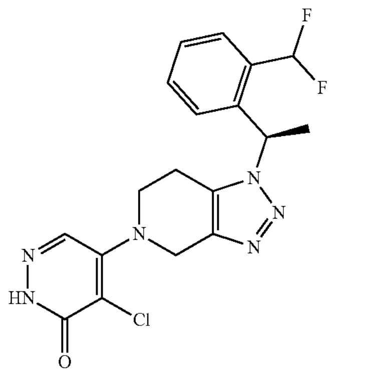 [SMILES: C[C@H](c1ccccc1C(F)F)n1nnc2c1CCN(c1cn[nH]c(=O)c1Cl)C2] | A |
| 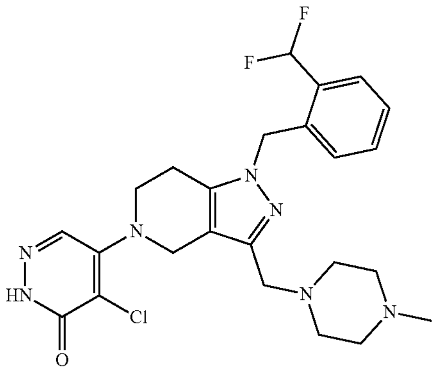 [SMILES: CN1CCN(Cc2nn(Cc3ccccc3C(F)F)c3c2CN(c2cn[nH]c(=O)c2Cl)CC3)CC1] | A |
| 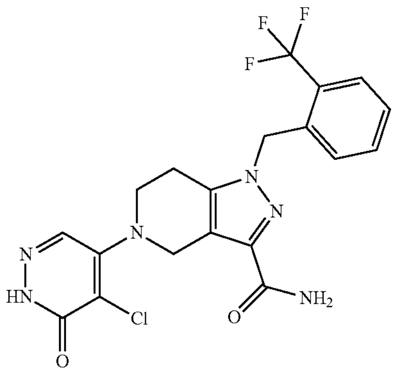 [SMILES: NC(=O)c1nn(Cc2ccccc2C(F)(F)F)c2c1CN(c1cn[nH]c(=O)c1Cl)CC2] | A |

TABLE 8-continued $IC_{50}$ values for representative compounds of the disclosure measured in a Fluorescence assay - FLIPR format utilizing cells expressing TRPC4 (HEK-TREx hTRPC4)

| Structure | TRPC4 FLIPR $IC_{50}$ (uM) |
|---|---|
| 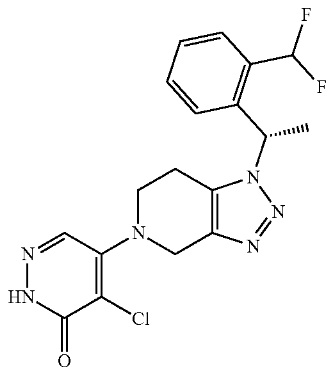 [SMILES: C[C@@H](c1ccccc1C(F)F)n1nnc2c1CCN(c1cn[nH]c(=O)c1Cl)C2] | A |
| 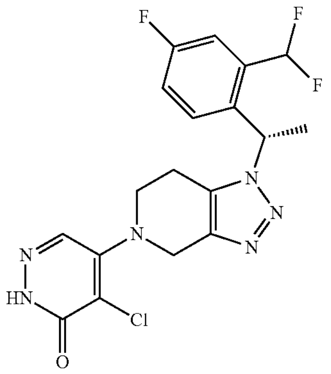 [SMILES: C[C@@H](c1ccc(F)cc1C(F)F)n1nnc2c1CCN(c1cn[nH]c(=O)c1Cl)C2] | A |
| 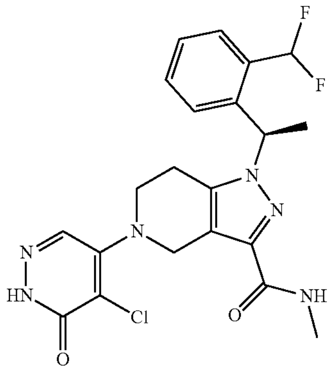 [SMILES: CNC(=O)c1nn([C@H](C)c2ccccc2C(F)F)c2c1CN(c1cn[nH]c(=O)c1Cl)CC2] | A |

TABLE 8-continued $IC_{50}$ values for representative compounds of the disclosure measured in a Fluorescence assay - FLIPR format utilizing cells expressing TRPC4 (HEK-TREx hTRPC4)

| Structure | TRPC4 FLIPR $IC_{50}$ (uM) |
| --- | --- |
| 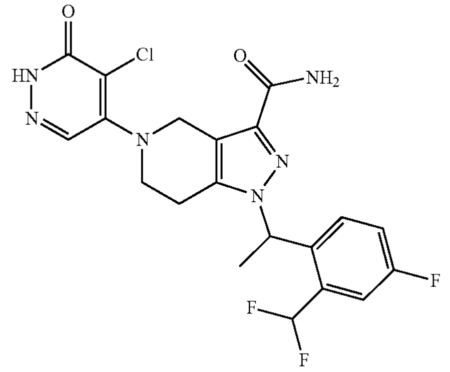 [SMILES: CC(c1ccc(F)cc1C(F)F)n1nc(C(N)=O)c2c1CCN(c1cn[nH]c(=O)c1Cl)C2] | A |
| 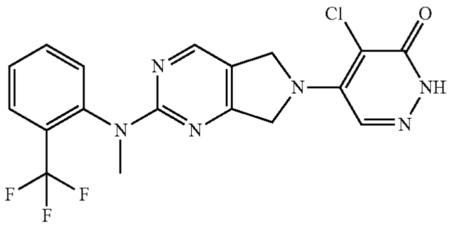 [SMILES: CN(c1ncc2c(n1)CN(c1cn[nH]c(=O)c1Cl)C2)c1ccccc1C(F)(F)F] | A |
| 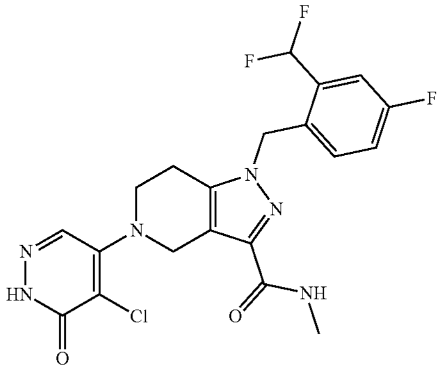 [SMILES: CNC(=O)c1nn(Cc2ccc(F)cc2C(F)F)c2c1CN(c1cn[nH]c(=O)c1Cl)CC2] | A |
| 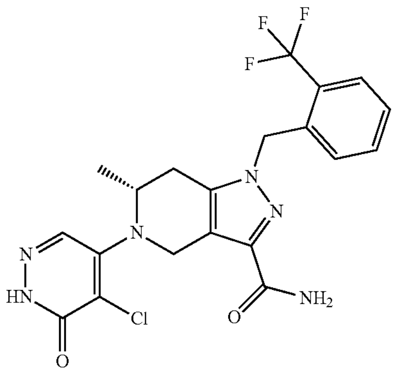 [SMILES: C[C@@H]1Cc2c(c(C(N)=O)nn2Cc2ccccc2C(F)(F)F)CN1c1cn[nH]c(=O)c1Cl] | A |

TABLE 8-continued $IC_{50}$ values for representative compounds of the disclosure measured in a Fluorescence assay - FLIPR format utilizing cells expressing TRPC4 (HEK-TREx hTRPC4)

| Structure | TRPC4 FLIPR $IC_{50}$ (uM) |
| --- | --- |
| 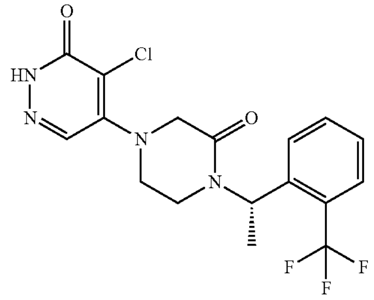 [SMILES: C[C@@H](c1ccccc1C(F)(F)F)N1CCN(c2cn[nH]c(=O)c2Cl)CC1=O] | A |
| 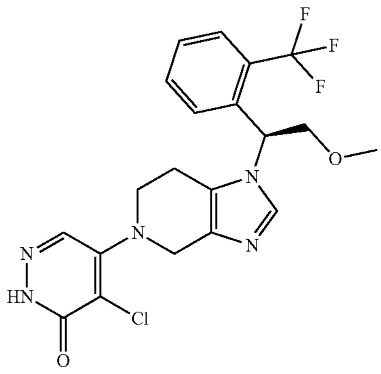 [SMILES: COC[C@H](c1ccccc1C(F)(F)F)n1cnc2c1CCN(c1cn[nH]c(=O)c1Cl)C2] | A |
| 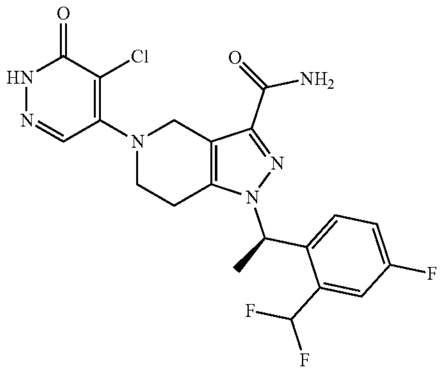 [SMILES: C[C@H](c1ccc(F)cc1C(F)F)n1nc(C(N)=O)c2c1CCN(c1cn[nH]c(=O)c1Cl)C2] | A |
| 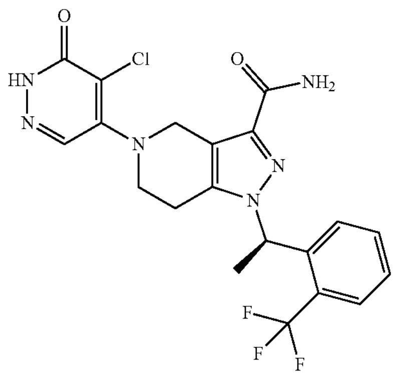 [SMILES: C[C@H](c1ccccc1C(F)(F)F)n1nc(C(N)=O)c2c1CCN(c1cn[nH]c(=O)c1Cl)C2] | A |

TABLE 8-continued

IC$_{50}$ values for representative compounds of the disclosure measured in a Fluorescence assay - FLIPR format utilizing cells expressing TRPC4 (HEK-TREx hTRPC4)

| Structure | TRPC4 FLIPR IC$_{50}$ (uM) |
|---|---|
| 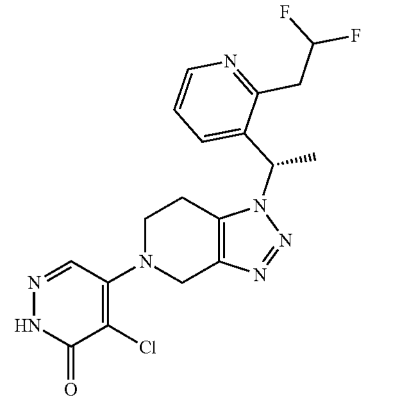 [SMILES: C[C@@H](c1cccnc1CC(F)F)n1nnc2c1CCN(c1cn[nH]c(=O)c1Cl)C2] | A |
| 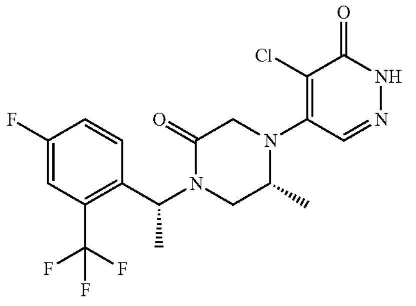 [SMILES: C[C@H](c1ccc(F)cc1C(F)(F)F)N1C[C@@H](C)N(c2cn[nH]c(=O)c2Cl)CC1=O] | A |
| 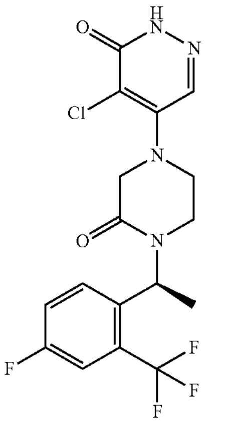 [SMILES: C[C@@H](c1ccc(F)cc1C(F)(F)F)N1CCN(c2cn[nH]c(=O)c2Cl)CC1=O] | A |
| 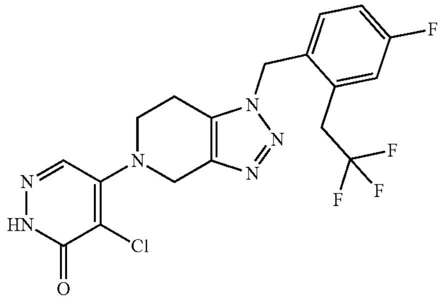 [SMILES: O=c1[nH]ncc(N2CCc3c(nnn3Cc3ccc(F)cc3CC(F)(F)F)C2)c1Cl] | A |

TABLE 8-continued

IC$_{50}$ values for representative compounds of the disclosure measured in a Fluorescence assay - FLIPR format utilizing cells expressing TRPC4 (HEK-TREx hTRPC4)

| Structure | TRPC4 FLIPR IC$_{50}$ (uM) |
|---|---|
| 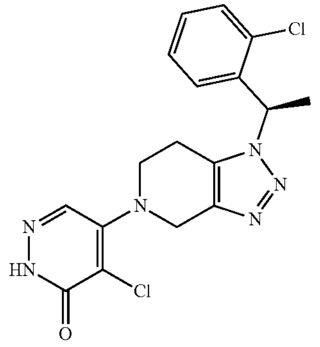 [SMILES: C[C@H](c1ccccc1Cl)n1nnc2c1CCN(c1cn[nH]c(=O)c1Cl)C2] | A |
| 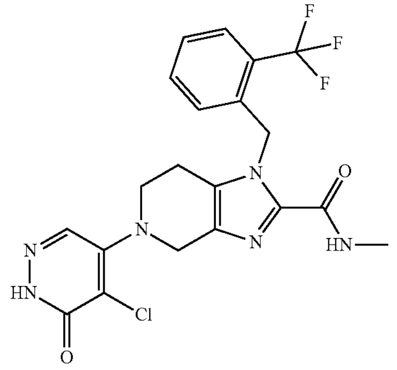 [SMILES: CNC(=O)c1nc2c(n1Cc1ccccc1C(F)(F)F)CCN(c1cn[nH]c(=O)c1Cl)C2] | A |
| 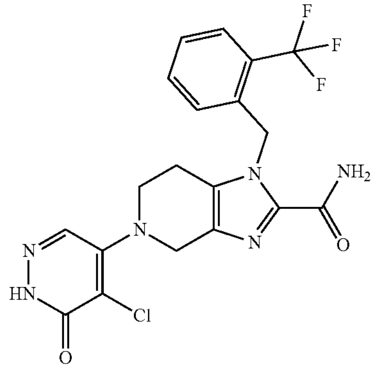 [SMILES: NC(=O)c1nc2c(n1Cc1ccccc1C(F)(F)F)CCN(c1cn[nH]c(=O)c1Cl)C2] | A |
| 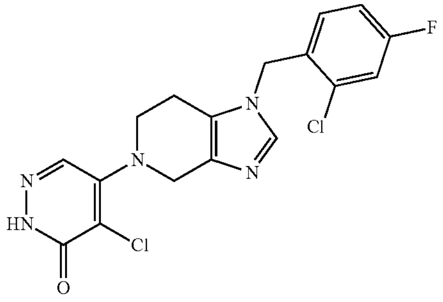 [SMILES: O=c1[nH]ncc(N2CCc3c(ncn3Cc3ccc(F)cc3Cl)C2)c1Cl] | A |

TABLE 8-continued

IC50 values for representative compounds of the disclosure measured in a Fluorescence assay - FLIPR format utilizing cells expressing TRPC4 (HEK-TREx hTRPC4)

| Structure | TRPC4 FLIPR $IC_{50}$ (uM) |
|---|---|
| 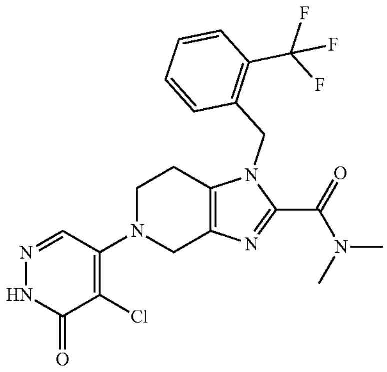 [SMILES: CN(C)C(=O)c1nc2c(n1Cc1ccccc1C(F)(F)F)CCN(c1cn[nH]c(=O)c1Cl)C2] | A |
| 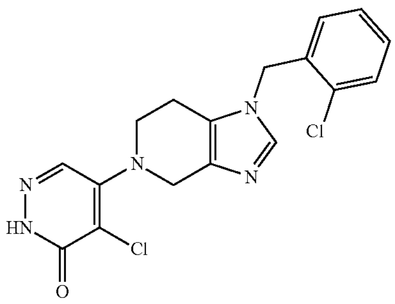 [SMILES: O=c1[nH]ncc(N2CCc3c(ncn3Cc3ccccc3Cl)C2)c1Cl] | A |
| 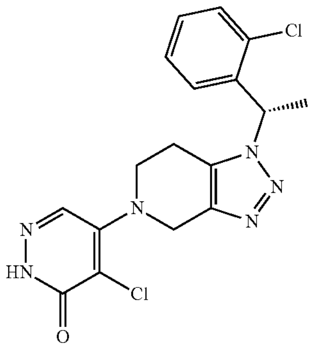 [SMILES: C[C@@H](c1ccccc1Cl)n1nnc2c1CCN(c1cn[nH]c(=O)c1Cl)C2] | A |
| 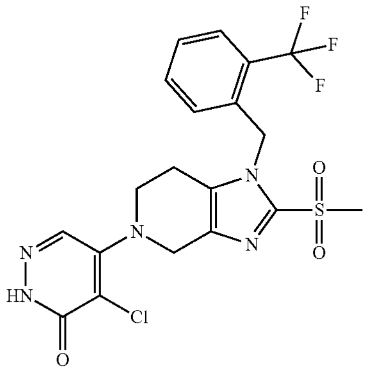 [SMILES: CS(=O)(=O)c1nc2c(n1Cc1ccccc1C(F)(F)F)CCN(c1cn[nH]c(=O)c1Cl)C2] | A |

TABLE 8-continued

IC50 values for representative compounds of the disclosure measured in a Fluorescence assay - FLIPR format utilizing cells expressing TRPC4 (HEK-TREx hTRPC4)

| Structure | TRPC4 FLIPR $IC_{50}$ (uM) |
|---|---|
| 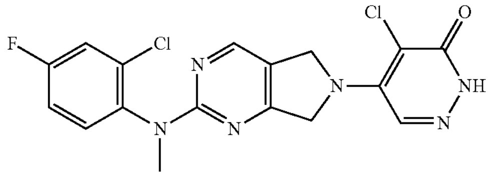 [SMILES: CN(c1ncc2c(n1)CN(c1cn[nH]c(=O)c1Cl)C2)c1ccc(F)cc1Cl] | A |
| 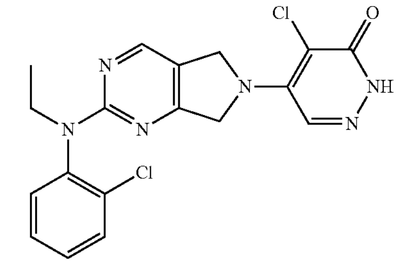 [SMILES: CCN(c1ncc2c(n1)CN(c1cn[nH]c(=O)c1Cl)C2)c1ccccc1Cl] | A |
| 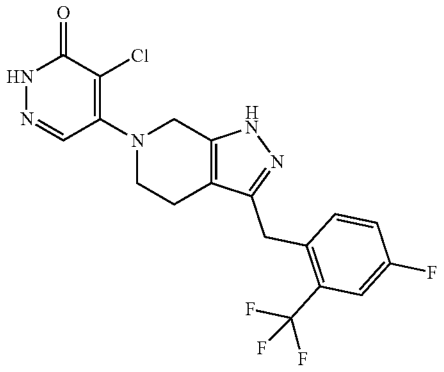 [SMILES: O=c1[nH]ncc(N2CCc3c(Cc4ccc(F)cc4C(F)(F)F)n[nH]c3C2)c1Cl] | A |
| 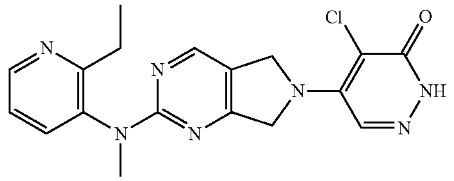 [SMILES: CCc1ncccc1N(C)c1ncc2c(n1)CN(c1cn[nH]c(=O)c1Cl)C2] | A |
| 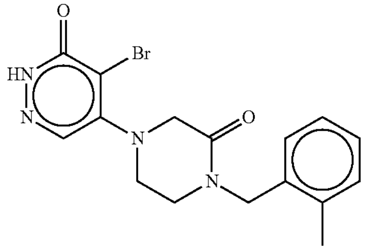 | A |

TABLE 8-continued

| $IC_{50}$ values for representative compounds of the disclosure measured in a Fluorescence assay - FLIPR format utilizing cells expressing TRPC4 (HEK-TREx hTRPC4) | |
|---|---|
| Structure | TRPC4 FLIPR $IC_{50}$ (uM) |
| 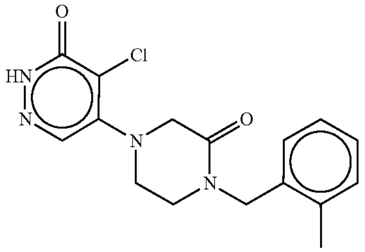 | A |
| 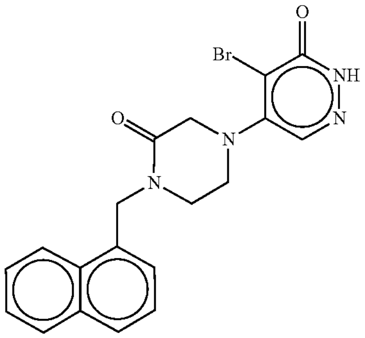 | A |
| 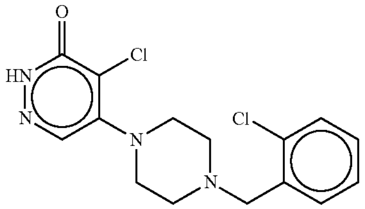 | B |
| 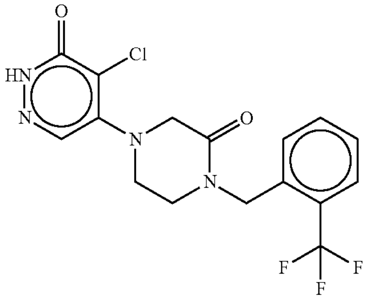 | A |
| 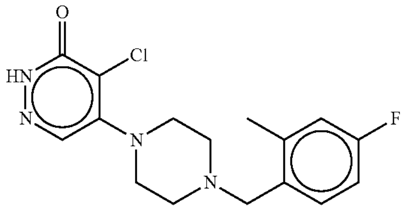 | C |

TABLE 8-continued

| $IC_{50}$ values for representative compounds of the disclosure measured in a Fluorescence assay - FLIPR format utilizing cells expressing TRPC4 (HEK-TREx hTRPC4) | |
|---|---|
| Structure | TRPC4 FLIPR $IC_{50}$ (uM) |
| 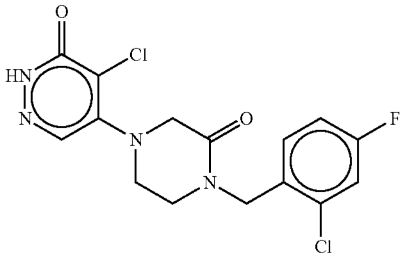 | A |
| 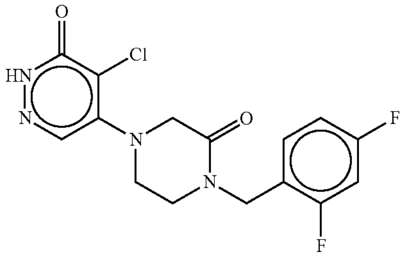 | B |
| 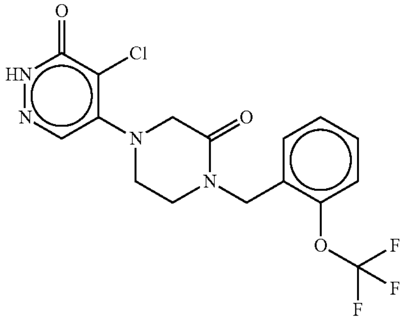 | A |
| 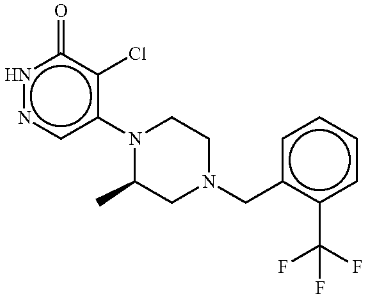 | C |
| 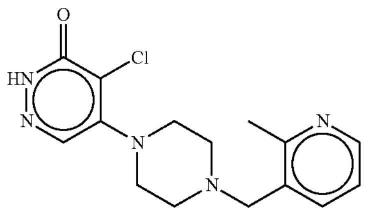 | B |

TABLE 8-continued

| $IC_{50}$ values for representative compounds of the disclosure measured in a Fluorescence assay - FLIPR format utilizing cells expressing TRPC4 (HEK-TREx hTRPC4) | |
|---|---|
| Structure | TRPC4 FLIPR $IC_{50}$ (uM) |
| 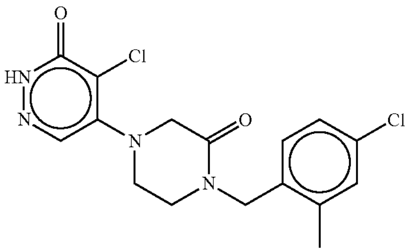 | B |
| 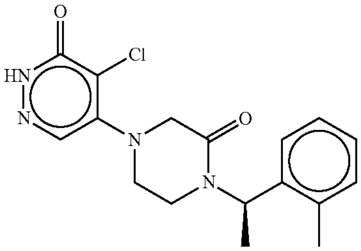 | A |
| 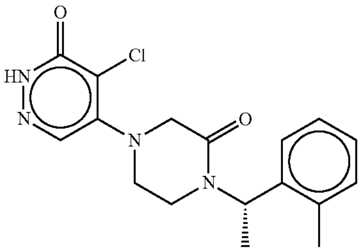 | D |
| 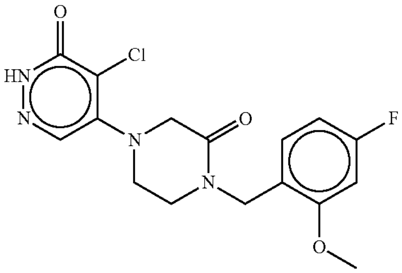 | B |
| 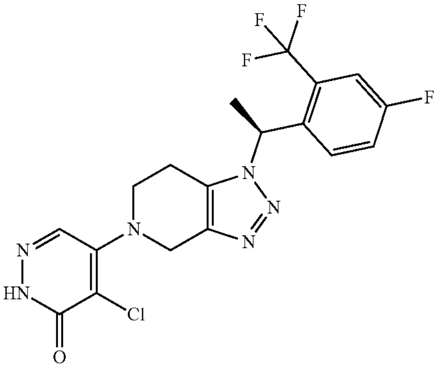 [SMILES: C[C@@H](c1ccc(F)cc1C(F)(F)F)n1nnc2c1CCN(c1cn[nH]c(=O)c1Cl)C2] | A |

TABLE 9

| $IC_{50}$ values for representative compounds of the disclosure measured in a Fluorescence assay - FLIPR format utilizing cells expressing TRPC5 (HEK-TREx hTRPC5) and TRPC4 (HEK-TREx hTRPC4). | | |
|---|---|---|
| | hTRPC5-IC50 (uM) | hTRPC4-FLIPR IC50 (uM) |
| 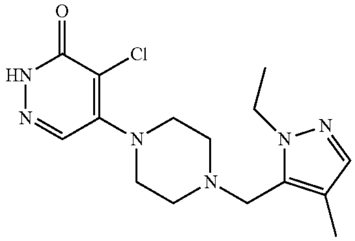 [SMILES: CCn1ncc(C)c1CN1CCN(c2cn[nH]c(=O)c2Cl)CC1] | B | |
| 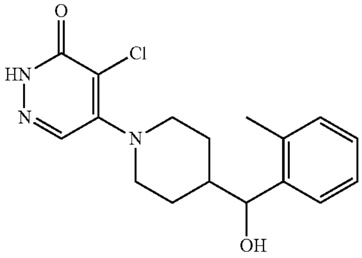 [SMILES: Cc1ccccc1C(O)C1CCN(c2cn[nH]c(=O)c2Cl)CC1] | B | |
| 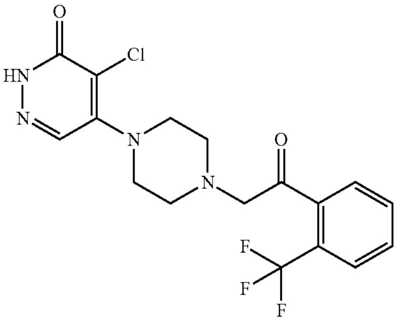 [SMILES: O=C(CN1CCN(c2cn[nH]c(=O)c2Cl)CC1)c1ccccc1C(F)(F)F] | B | |
| 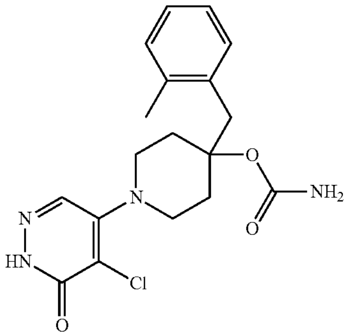 [SMILES: Cc1ccccc1CC1(OC(N)=O)CCN(c2cn[nH]c(=O)c2Cl)CC1] | B | |

TABLE 9-continued

IC$_{50}$ values for representative compounds of the disclosure measured in a Fluorescence assay - FLIPR format utilizing cells expressing TRPC5 (HEK-TREx hTRPC5) and TRPC4 (HEK-TREx hTRPC4).

| | hTRPC5-IC50 (uM) | hTRPC4-FLIPR IC50 (uM) |
|---|---|---|
| 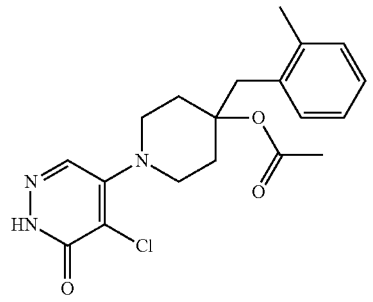 [SMILES: CC(=O)OC1(Cc2ccccc2C)CCN(c2cn[nH]c(=O)c2Cl)CC1] | B | |
| 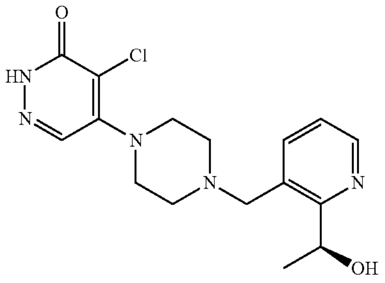 [SMILES: C[C@H](O)c1ncccc1CN1CCN(c2cn[nH]c(=O)c2Cl)CC1] | A | |
| 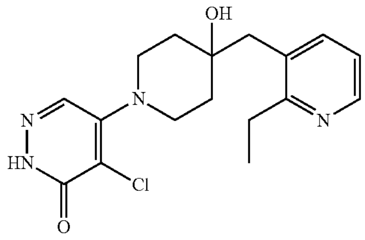 [SMILES: CCc1ncccc1CC1(O)CCN(c2cn[nH]c(=O)c2Cl)CC1] | B | |
| 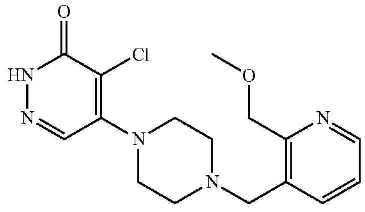 [SMILES: COCc1ncccc1CN1CCN(c2cn[nH]c(=O)c2Cl)CC1] | A | |
| 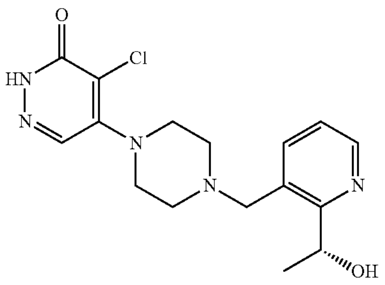 [SMILES: C[C@@H](O)c1ncccc1CN1CCN(c2cn[nH]c(=O)c2Cl)CC1] | B | |

TABLE 9-continued

IC$_{50}$ values for representative compounds of the disclosure measured in a Fluorescence assay - FLIPR format utilizing cells expressing TRPC5 (HEK-TREx hTRPC5) and TRPC4 (HEK-TREx hTRPC4).

| | hTRPC5-IC50 (uM) | hTRPC4-FLIPR IC50 (uM) |
|---|---|---|
| 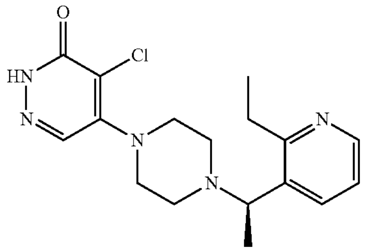 [SMILES: CCc1ncccc1[C@@H](C)N1CCN(c2cn[nH]c(=O)c2Cl)CC1] | A | |
| 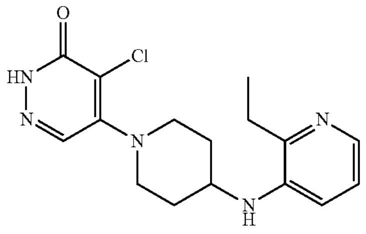 [SMILES: CCc1ncccc1NC1CCN(c2cn[nH]c(=O)c2Cl)CC1] | C | |
| 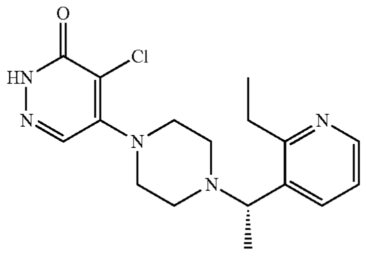 [SMILES: CCc1ncccc1[C@H](C)N1CCN(c2cn[nH]c(=O)c2Cl)CC1] | A | A |
| 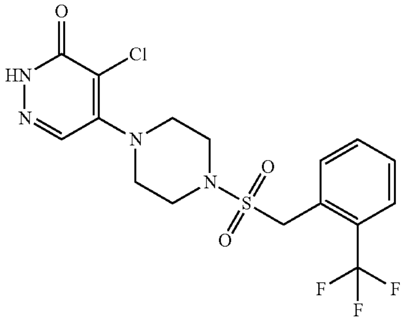 [SMILES: O=c1[nH]ncc(N2CCN(S(=O)(=O)Cc3ccccc3C(F)(F)F)CC2)c1Cl] | B | |
| 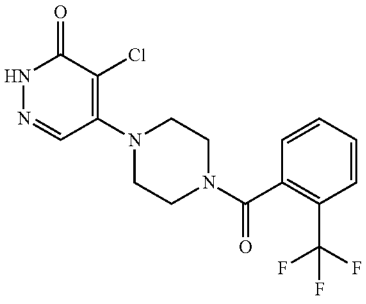 [SMILES: O=C(c1ccccc1C(F)(F)F)N1CCN(c2cn[nH]c(=O)c2Cl)CC1] | B | |

TABLE 9-continued
$IC_{50}$ values for representative compounds of the disclosure measured in a Fluorescence assay - FLIPR format utilizing cells expressing TRPC5 (HEK-TREx hTRPC5) and TRPC4 (HEK-TREx hTRPC4).
| | hTRPC5-IC50 (uM) | hTRPC4-FLIPR IC50 (uM) |
|---|---|---|
| 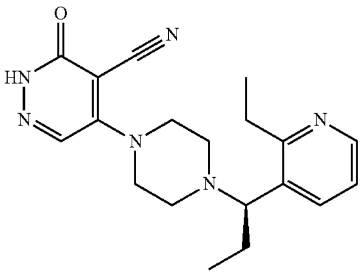 [SMILES: CCc1ncccc1[C@@H](CC)N1CCN(c2cn[nH]c(=O)c2C#N)CC1] | A | |
| 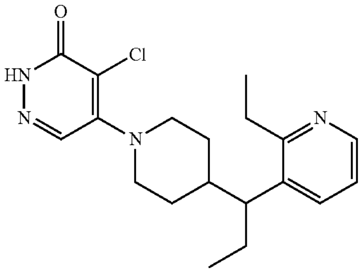 [SMILES: CCc1ncccc1C(CC)C1CCN(c2cn[nH]c(=O)c2Cl)CC1] | A | A |
| 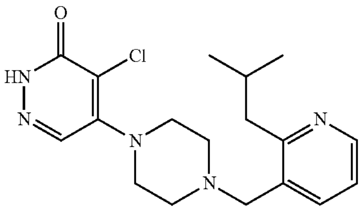 [SMILES: CC(C)Cc1ncccc1CN1CCN(c2cn[nH]c(=O)c2Cl)CC1] | A | |
| 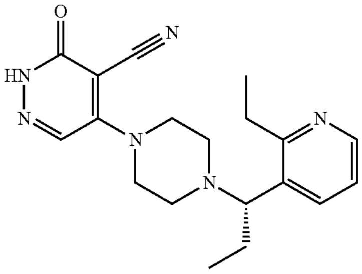 [SMILES: CCc1ncccc1[C@H](CC)N1CCN(c2cn[nH]c(=O)c2C#N)CC1] | B | |
| 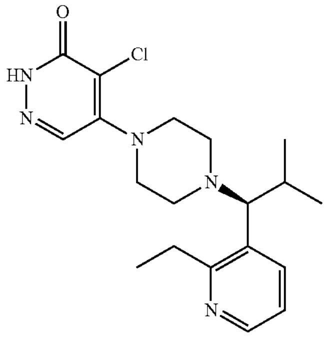 [SMILES: CCc1ncccc1[C@H](C(C)C)N1CCN(c2cn[nH]c(=O)c2Cl)CC1] | B | |
| 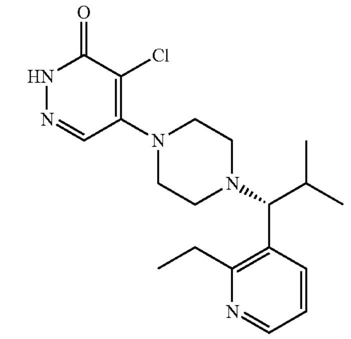 [SMILES: CCc1ncccc1[C@@H](C(C)C)N1CCN(c2cn[nH]c(=O)c2Cl)CC1] | A | |
| 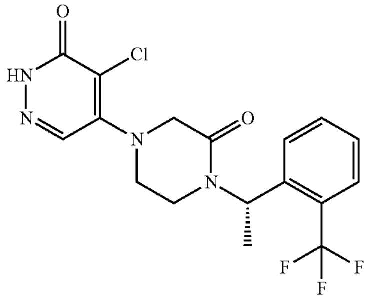 [SMILES: C[C@@H](c1ccccc1C(F)(F)F)N1CCN(c2cn[nH]c(=O)c2Cl)CC1=O] | A | A |
| 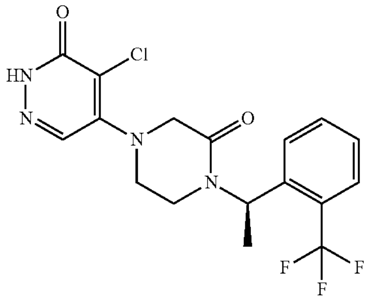 [SMILES: C[C@H](c1ccccc1C(F)(F)F)N1CCN(c2cn[nH]c(=O)c2Cl)CC1=O] | B | |
| 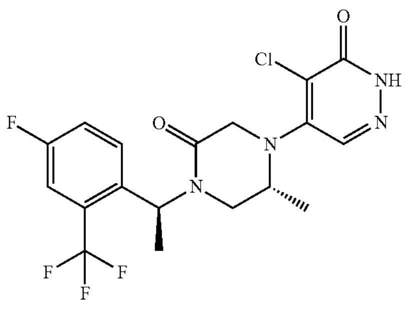 [SMILES: C[C@@H]1CN([C@@H](C)c2ccc(F)cc2C(F)(F)F)C(=O)CN1c1cn[nH]c(=O)c1Cl] | A | |

TABLE 9-continued

IC$_{50}$ values for representative compounds of the disclosure measured in a Fluorescence assay - FLIPR format utilizing cells expressing TRPC5 (HEK-TREx hTRPC5) and TRPC4 (HEK-TREx hTRPC4).

| | hTRPC5-IC50 (uM) | hTRPC4-FLIPR IC50 (uM) |
|---|---|---|
| 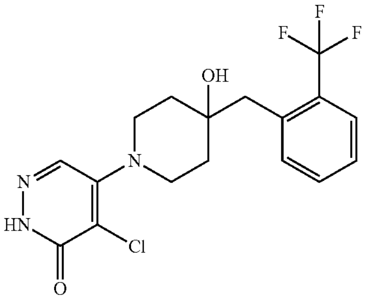 [SMILES: O=c1[nH]ncc(N2CCC(O)(Cc3ccccc3C(F)(F)F)CC2)c1Cl] | A | |
| 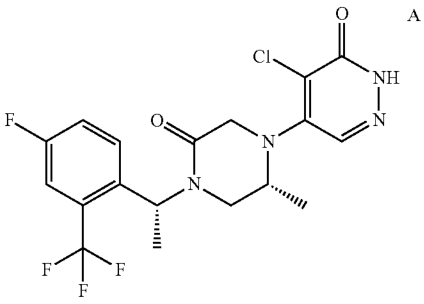 | A | A |
| 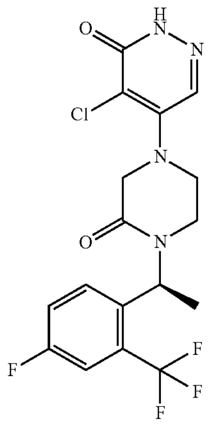 [SMILES: C[C@@H](c1ccc(F)cc1C(F)(F)F)N1CCN(c2cn[nH]c(=O)c2Cl)CC1=O] | A | A |
| 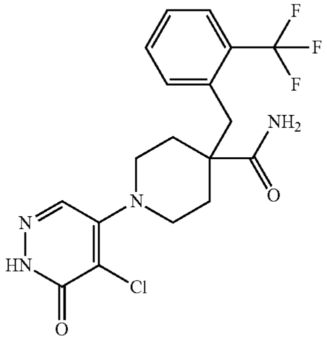 [SMILES: NC(=O)C1(Cc2ccccc2C(F)(F)F)CCN(c2cn[nH]c(=O)c2Cl)CC1] | B | |

TABLE 10

IC$_{50}$ values for representative compounds of the disclosure measured in a Fluorescence assay - FLIPR format utilizing cells expressing TRPC5 (HEK-TREx hTRPC5) and TRPC4 (HEK-TREx hTRPC4).

| | TRPC5-FLIPR IC50 (uM) | TRPC4-FLIPR IC50 (uM) |
|---|---|---|
| 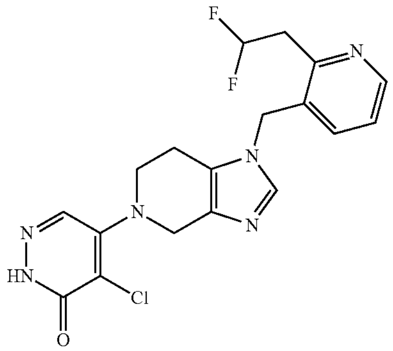 [SMILES: O=c1[nH]ncc(N2CCc3c(ncn3Cc3cccnc3CC(F)F)C2)c1Cl] | A | |
| 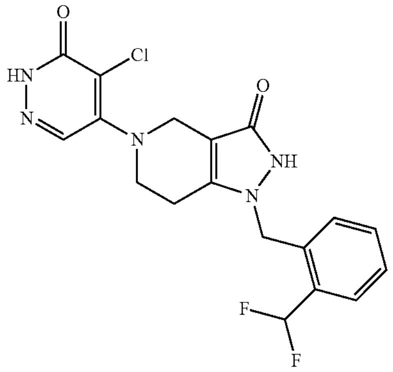 [SMILES: O=c1[nH]ncc(N2CCc3c(c(=O)[nH]n3Cc3ccccc3C(F)F)C2)c1Cl] | A | |
| 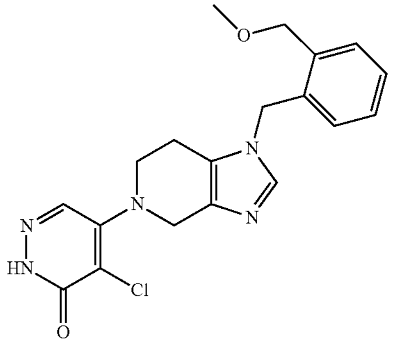 [SMILES: COCc1ccccc1Cn1cnc2c1CCN(c1cn[nH]c(=O)c1Cl)C2] | A | A |
| 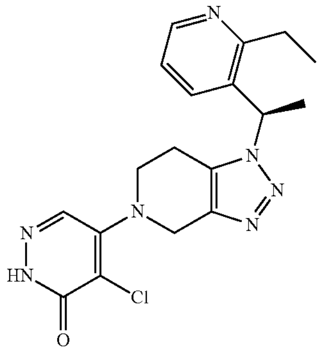 [SMILES: CCc1ncccc1[C@@H](C)n1nnc2c1CCN(c1cn[nH]c(=O)c1Cl)C2] | A | |

TABLE 10-continued

IC$_{50}$ values for representative compounds of the disclosure measured in a Fluorescence assay - FLIPR format utilizing cells expressing TRPC5 (HEK-TREx hTRPC5) and TRPC4 (HEK-TREx hTRPC4).

| | TRPC5-FLIPR IC50 (uM) | TRPC4-FLIPR IC50 (uM) |
|---|---|---|
| 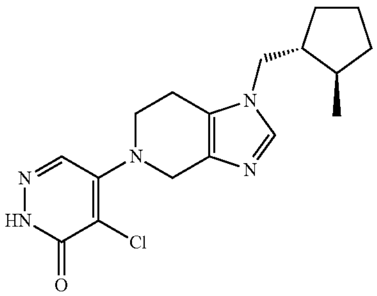 [SMILES: C[C@@H]1CCC[C@H]1Cn1cnc2c1CCN(c1cn[nH]c(=O)c1Cl)C2] | A | |
| 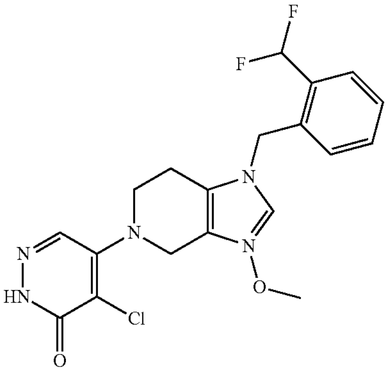 | A | |
| 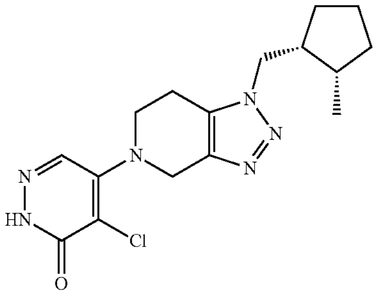 [SMILES: C[C@H]1CCC[C@H]1Cn1nnc2c1CCN(c1cn[nH]c(=O)c1Cl)C2] | A | |
| 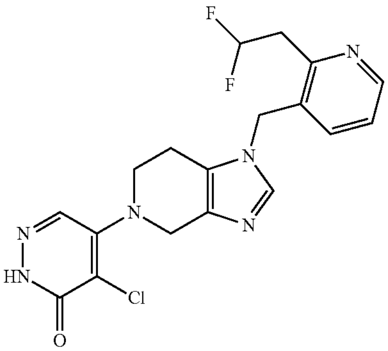 [SMILES: O=c1[nH]ncc(N2CCc3c(ncn3Cc3cccnc3CC(F)F)C2)c1Cl] | A | |

TABLE 10-continued

IC$_{50}$ values for representative compounds of the disclosure measured in a Fluorescence assay - FLIPR format utilizing cells expressing TRPC5 (HEK-TREx hTRPC5) and TRPC4 (HEK-TREx hTRPC4).

| | TRPC5-FLIPR IC50 (uM) | TRPC4-FLIPR IC50 (uM) |
|---|---|---|
| 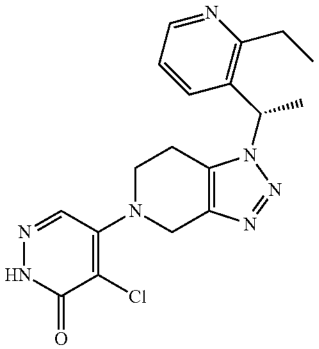 [SMILES: CCc1ncccc1[C@H](C)n1nnc2c1CCN(c1cn[nH]c(=O)c1Cl)C2] | A | |
| 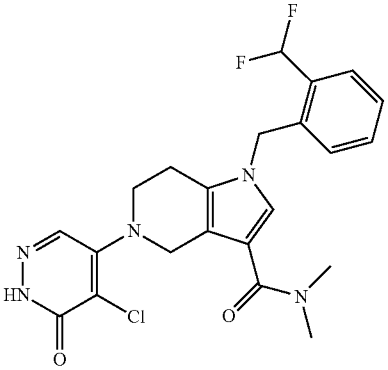 [SMILES: CN(C)C(=O)c1cn(Cc2ccccc2C(F)F)c2c1CN(c1cn[nH]c(=O)c1Cl)CC2] | A | |
| 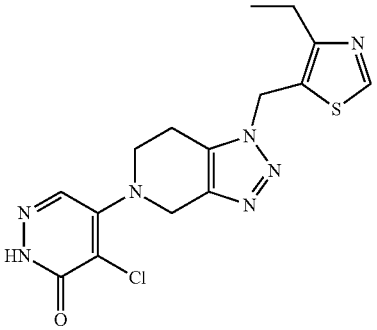 [SMILES: CCc1ncsc1Cn1nnc2c1CCN(c1cn[nH]c(=O)c1Cl)C2] | A | |
| 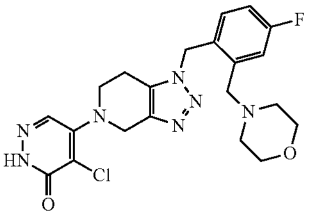 [SMILES: O=c1[nH]ncc(N2CCc3c(nnn3Cc3ccc(F)cc3CN3CCOCC3)C2)c1Cl] | B | |

TABLE 10-continued

IC$_{50}$ values for representative compounds of the disclosure measured in a Fluorescence assay - FLIPR format utilizing cells expressing TRPC5 (HEK-TREx hTRPC5) and TRPC4 (HEK-TREx hTRPC4).

| | TRPC5-FLIPR IC50 (uM) | TRPC4-FLIPR IC50 (uM) |
|---|---|---|
| 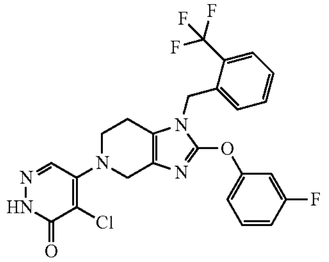 [SMILES: O=c1[nH]ncc(N2CCc3c(nc(Oc4cccc(F)c4)n3Cc3ccccc3C(F)(F)F)C2)c1Cl] | A | |
| 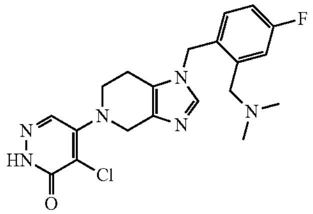 [SMILES: CN(C)Cc1cc(F)ccc1Cn1cnc2c1CCN(c1cn[nH]c(=O)c1Cl)C2] | B | |
| 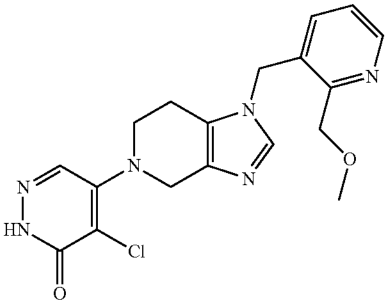 [SMILES: COCc1ncccc1Cn1cnc2c1CCN(c1cn[nH]c(=O)c1Cl)C2] | A | B |
| 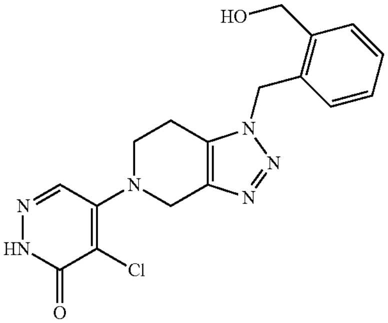 [SMILES: O=c1[nH]ncc(N2CCc3c(nnn3Cc3ccccc3CO)C2)c1Cl] | B | |

TABLE 10-continued

IC$_{50}$ values for representative compounds of the disclosure measured in a Fluorescence assay - FLIPR format utilizing cells expressing TRPC5 (HEK-TREx hTRPC5) and TRPC4 (HEK-TREx hTRPC4).

| | TRPC5-FLIPR IC50 (uM) | TRPC4-FLIPR IC50 (uM) |
|---|---|---|
| 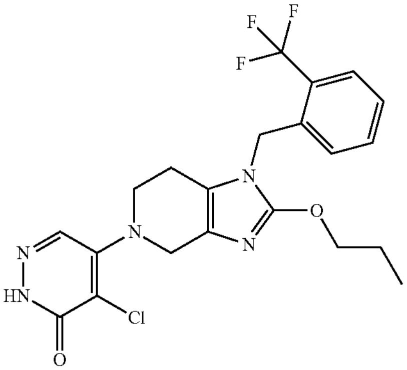 [SMILES: CCCOc1nc2c(n1Cc1ccccc1C(F)(F)F)CCN(c1cn[nH]c(=O)c1Cl)C2] | A | |
| 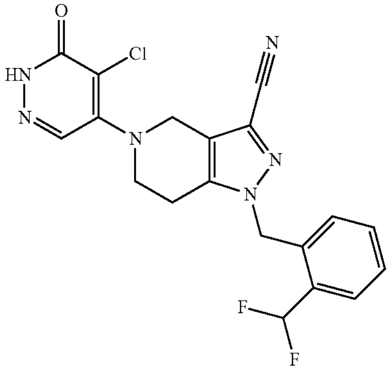 [SMILES: N#Cc1nn(Cc2ccccc2C(F)F)c2c1CN(c1cn[nH]c(=O)c1Cl)CC2] | A | |
| 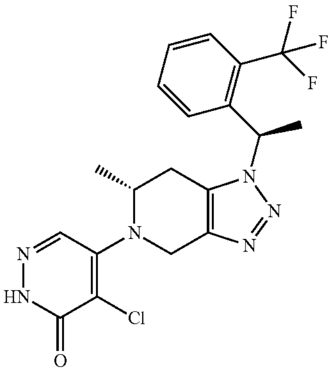 [SMILES: C[C@@H]1Cc2c(nnn2[C@H](C)c2ccccc2C(F)(F)F)CN1c1cn[nH]c(=O)c1Cl] | A | A |

TABLE 10-continued

IC$_{50}$ values for representative compounds of the disclosure measured in a Fluorescence assay - FLIPR format utilizing cells expressing TRPC5 (HEK-TREx hTRPC5) and TRPC4 (HEK-TREx hTRPC4).

| | TRPC5-FLIPR IC50 (uM) | TRPC4-FLIPR IC50 (uM) |
|---|---|---|
| 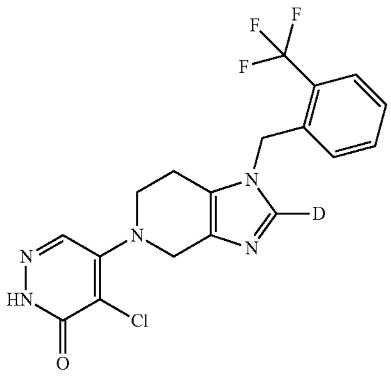 [SMILES: [2H]c1nc2c(n1Cc1ccccc1C(F)(F)F)CCN(c1cn[nH]c(=O)c1Cl)C2] | A | A |
| 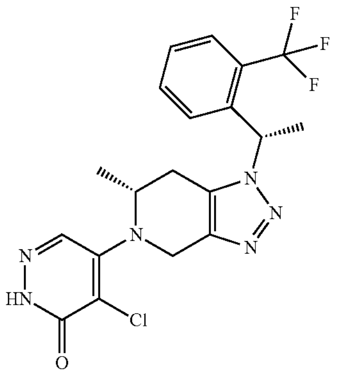 [SMILES: C[C@@H]1Cc2c(nnn2[C@@H](C)c2ccccc2C(F)(F)F)CN1c1cn[nH]c(=O)c1Cl] | A | A |
| 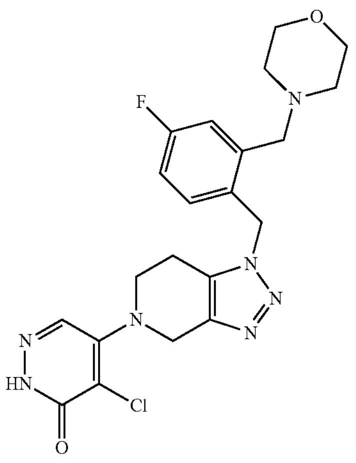 [SMILES: O=c1[nH]ncc(N2CCc3c(nnn3Cc3ccc(F)cc3CN3CCOCC3)C2)c1Cl] | B | |

TABLE 10-continued

IC$_{50}$ values for representative compounds of the disclosure measured in a Fluorescence assay - FLIPR format utilizing cells expressing TRPC5 (HEK-TREx hTRPC5) and TRPC4 (HEK-TREx hTRPC4).

| | TRPC5-FLIPR IC50 (uM) | TRPC4-FLIPR IC50 (uM) |
|---|---|---|
| 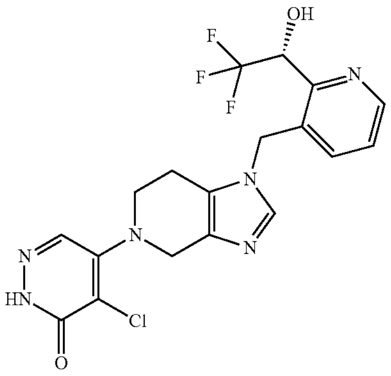 [SMILES: O=c1[nH]ncc(N2CCc3c(ncn3Cc3cccnc3[C@@H](O)C(F)(F)F)C2)c1Cl] | A | |
| 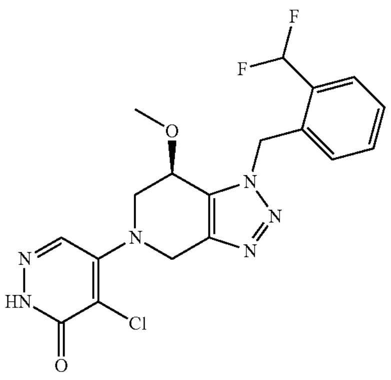 [SMILES: CO[C@@H]1CN(c2cn[nH]c(=O)c2Cl)Cc2nnn(Cc3ccccc3C(F)F)c21] | B | |
| 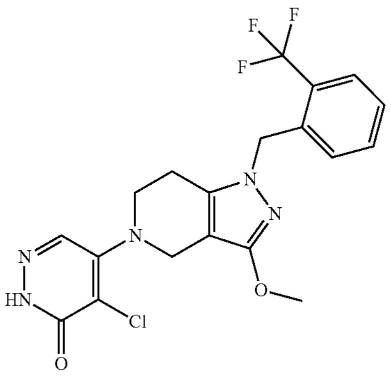 [SMILES: COc1nn(Cc2ccccc2C(F)(F)F)c2c1CN(c1cn[nH]c(=O)c1Cl)CC2] | A | |

TABLE 10-continued

IC$_{50}$ values for representative compounds of the disclosure measured in a Fluorescence assay - FLIPR format utilizing cells expressing TRPC5 (HEK-TREx hTRPC5) and TRPC4 (HEK-TREx hTRPC4).

| | TRPC5-FLIPR IC50 (uM) | TRPC4-FLIPR IC50 (uM) |
|---|---|---|
| 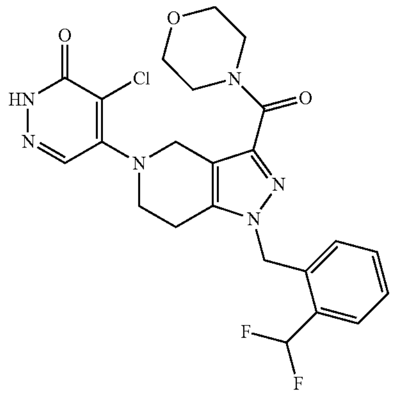 [SMILES: O=C(c1nn(Cc2ccccc2C(F)F)c2c1CN(c1cn[nH]c(=O)c1Cl)CC2)N1CCOCC1] | A | |
| 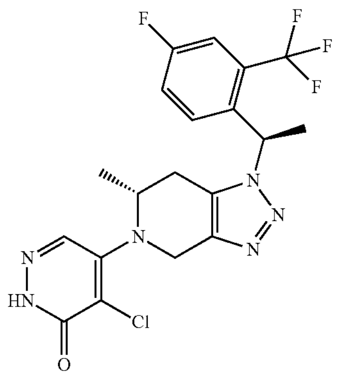 [SMILES: C[C@@H]1Cc2c(nnn2[C@H](C)c2ccc(F)cc2C(F)(F)F)CN1c1cn[nH]c(=O)c1Cl] | A | |
| 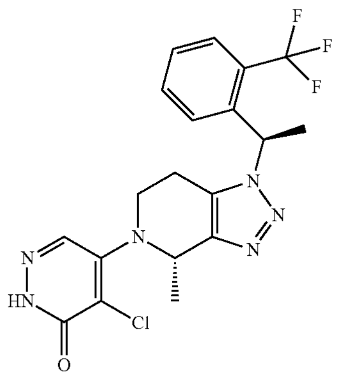 [SMILES: C[C@H](c1ccccc1C(F)(F)F)n1nnc2c1CCN(c1cn[nH]c(=O)c1Cl)[C@H]2C] | A | A |

TABLE 10-continued

IC$_{50}$ values for representative compounds of the disclosure measured in a Fluorescence assay - FLIPR format utilizing cells expressing TRPC5 (HEK-TREx hTRPC5) and TRPC4 (HEK-TREx hTRPC4).

| | TRPC5-FLIPR IC50 (uM) | TRPC4-FLIPR IC50 (uM) |
|---|---|---|
| 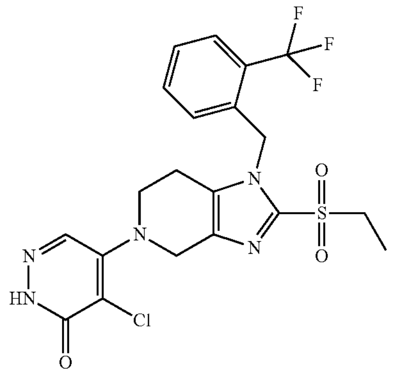 [SMILES: CCS(=O)(=O)c1nc2c(n1Cc1ccccc1C(F)(F)F)CCN(c1cn[nH]c(=O)c1Cl)C2] | A | A |
| 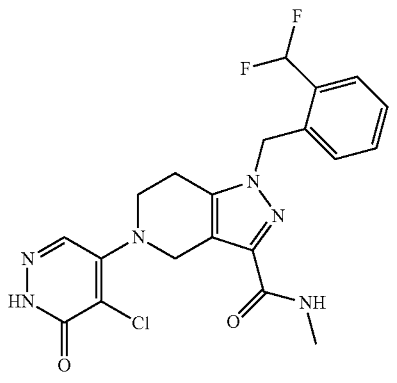 [SMILES: CNC(=O)c1nn(Cc2ccccc2C(F)F)c2c1CN(c1cn[nH]c(=O)c1Cl)CC2] | A | |
| 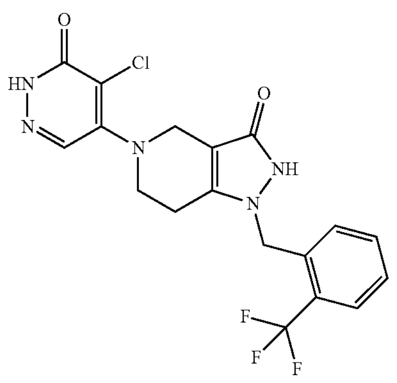 [SMILES: O=c1[nH]ncc(N2CCc3c(c(=O)[nH]n3Cc3ccccc3C(F)(F)F)C2)c1Cl] | A | A |

TABLE 10-continued

IC$_{50}$ values for representative compounds of the disclosure measured in a Fluorescence assay - FLIPR format utilizing cells expressing TRPC5 (HEK-TREx hTRPC5) and TRPC4 (HEK-TREx hTRPC4).

| | TRPC5-FLIPR IC50 (uM) | TRPC4-FLIPR IC50 (uM) |
|---|---|---|
| 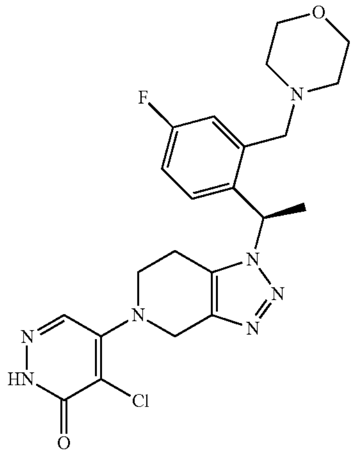 [SMILES: C[C@H](c1ccc(F)cc1CN1CCOCC1)n1nnc2c1CCN(c1cn[nH]c(=O)c1Cl)C2] | B | |
| 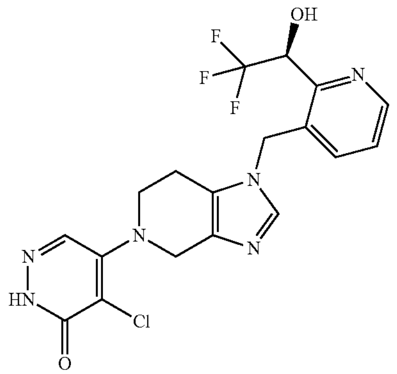 [SMILES: O=c1[nH]ncc(N2CCc3c(ncn3Cc3cccnc3[C@H](O)C(F)(F)F)C2)c1Cl] | A | |
| 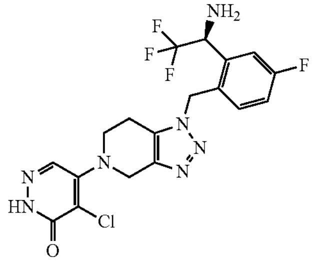 [SMILES: N[C@@H](c1cc(F)ccc1Cn1nnc2c1CCN(c1cn[nH]c(=O)c1Cl)C2)C(F)(F)F] | B | |
| 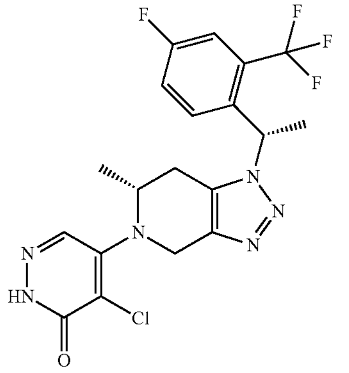 [SMILES: C[C@@H]1Cc2c(nnn2[C@@H](C)c2ccc(F)cc2C(F)(F)F)CN1c1cn[nH]c(=O)c1Cl] | A | A |

TABLE 10-continued

IC$_{50}$ values for representative compounds of the disclosure measured in a Fluorescence assay - FLIPR format utilizing cells expressing TRPC5 (HEK-TREx hTRPC5) and TRPC4 (HEK-TREx hTRPC4).

| | TRPC5-FLIPR IC50 (uM) | TRPC4-FLIPR IC50 (uM) |
|---|---|---|
| 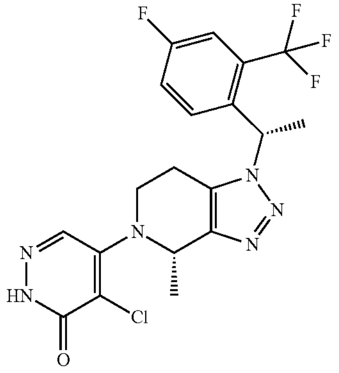 [SMILES: C[C@H]1c2nnn([C@@H](C)c3ccc(F)cc3C(F)(F)F)c2CCN1c1cn[nH]c(=O)c1Cl] | A | |
| 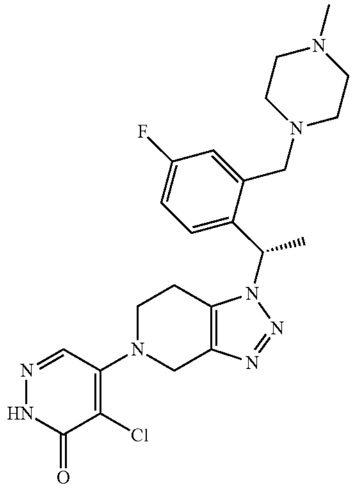 [SMILES: C[C@@H](c1ccc(F)cc1CN1CCN(C)CC1)n1nnc2c1CCN(c1cn[nH]c(=O)c1Cl)C2] | C | |
| 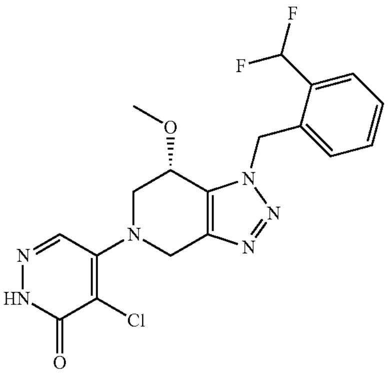 [SMILES: CO[C@H]1CN(c2cn[nH]c(=O)c2Cl)Cc2nnn(Cc3ccccc3C(F)F)c21] | B | |

TABLE 10-continued

IC$_{50}$ values for representative compounds of the disclosure measured in a Fluorescence assay - FLIPR format utilizing cells expressing TRPC5 (HEK-TREx hTRPC5) and TRPC4 (HEK-TREx hTRPC4).

| | TRPC5-FLIPR IC50 (uM) | TRPC4-FLIPR IC50 (uM) |
|---|---|---|
| 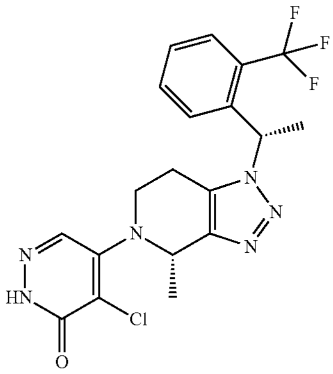 [SMILES: C[C@H]1c2nnn([C@@H](C)c3ccccc3C(F)(F)F)c2CCN1c1cn[nH]c(=O)c1Cl] | A | |
| 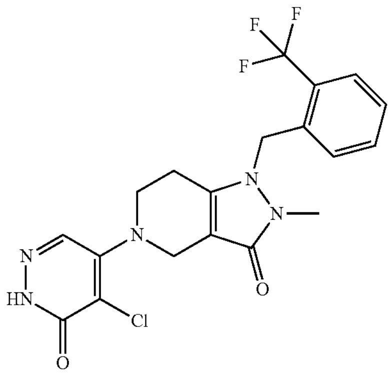 [SMILES: Cn1c(=O)c2c(n1Cc1ccccc1C(F)(F)F)CCN(c1cn[nH]c(=O)c1Cl)C2] | B | |
| 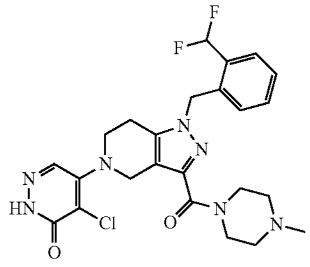 [SMILES: CN1CCN(C(=O)c2nn(Cc3ccccc3C(F)F)c3c2CN(c2cn[nH]c(=O)c2Cl)CC3)CC1] | A | A |
| 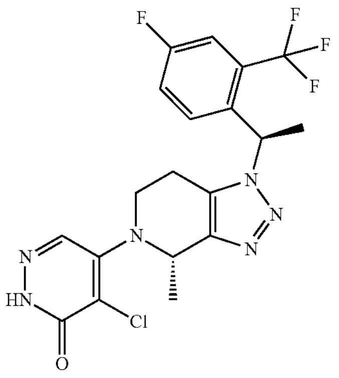 [SMILES: C[C@H](c1ccc(F)cc1C(F)(F)F)n1nnc2c1CCN(c1cn[nH]c(=O)c1Cl)[C@H]2C] | A | A |

TABLE 10-continued

IC$_{50}$ values for representative compounds of the disclosure measured in a Fluorescence assay - FLIPR format utilizing cells expressing TRPC5 (HEK-TREx hTRPC5) and TRPC4 (HEK-TREx hTRPC4).

| | TRPC5-FLIPR IC50 (uM) | TRPC4-FLIPR IC50 (uM) |
|---|---|---|
| 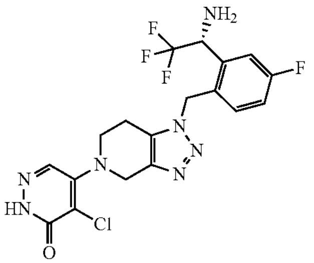 [SMILES: N[C@H](c1cc(F)ccc1Cn1nnc2c1CCN(c1cn[nH]c(=O)c1Cl)C2)C(F)(F)F] | A | |
| 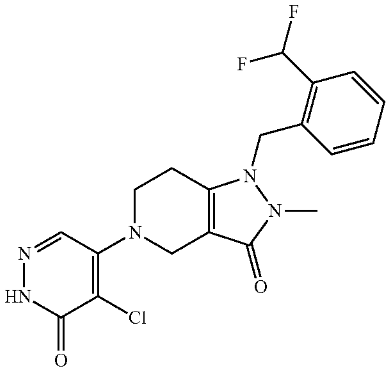 [SMILES: Cn1c(=O)c2c(n1Cc1ccccc1C(F)F)CCN(c1cn[nH]c(=O)c1Cl)C2] | A | |
| 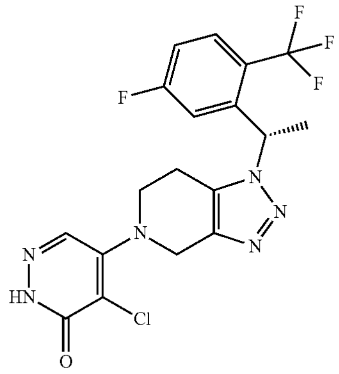 [SMILES: C[C@@H](c1cc(F)ccc1C(F)(F)F)n1nnc2c1CCN(c1cn[nH]c(=O)c1Cl)C2] | A | |
| 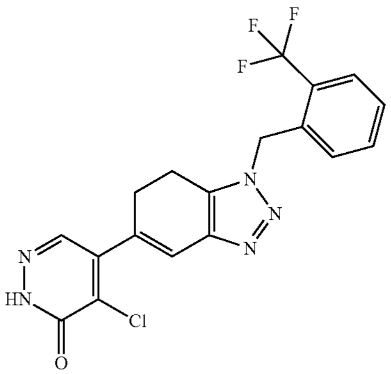 [SMILES: O=c1[nH]ncc(C2=Cc3nnn(Cc4ccccc4C(F)(F)F)c3CC2)c1Cl] | B | |

TABLE 10-continued

IC50 values for representative compounds of the disclosure measured in a Fluorescence assay - FLIPR format utilizing cells expressing TRPC5 (HEK-TREx hTRPC5) and TRPC4 (HEK-TREx hTRPC4).

| | TRPC5-FLIPR IC50 (uM) | TRPC4-FLIPR IC50 (uM) |
|---|---|---|
| 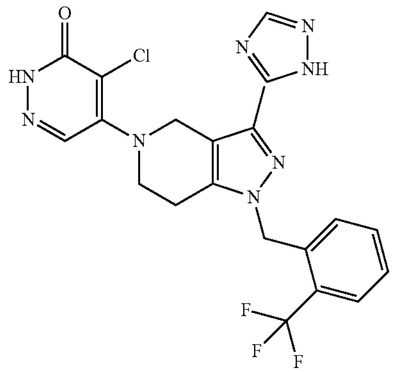 | B | |
| 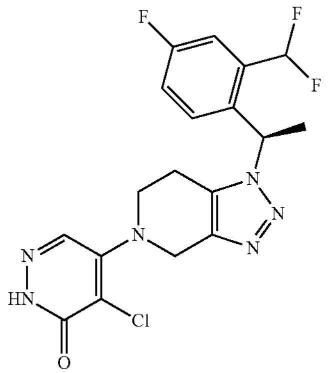 [SMILES: C[C@H](c1ccc(F)cc1C(F)F)n1nnc2c1CCN(c1cn[nH]c(=O)c1Cl)C2] | A | |
| 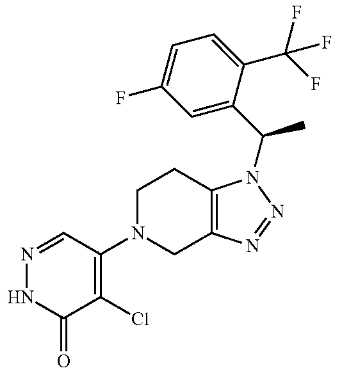 [SMILES: C[C@H](c1cc(F)ccc1C(F)(F)F)n1nnc2c1CCN(c1cn[nH]c(=O)c1Cl)C2] | A | |

TABLE 10-continued

IC50 values for representative compounds of the disclosure measured in a Fluorescence assay - FLIPR format utilizing cells expressing TRPC5 (HEK-TREx hTRPC5) and TRPC4 (HEK-TREx hTRPC4).

| | TRPC5-FLIPR IC50 (uM) | TRPC4-FLIPR IC50 (uM) |
|---|---|---|
| 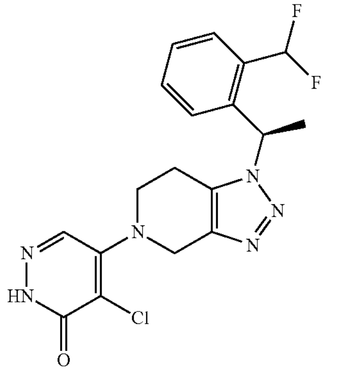 [SMILES: C[C@H](c1ccccc1C(F)F)n1nnc2c1CCN(c1cn[nH]c(=O)c1Cl)C2] | A | A |
| 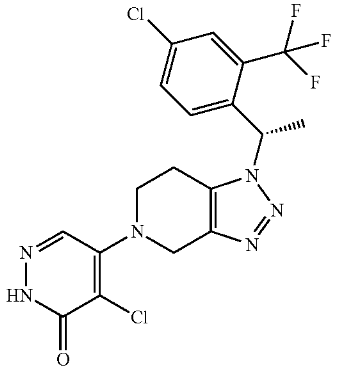 [SMILES: C[C@@H](c1ccc(Cl)cc1C(F)(F)F)n1nnc2c1CCN(c1cn[nH]c(=O)c1Cl)C2] | A | |
| 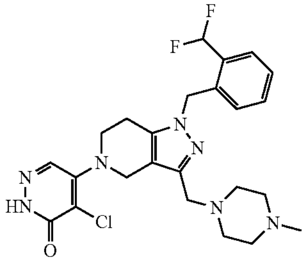 [SMILES: CN1CCN(Cc2nn(Cc3ccccc3C(F)F)c3c2CN(c2cn[nH]c(=O)c2Cl)CC3)CC1] | A | A |
| 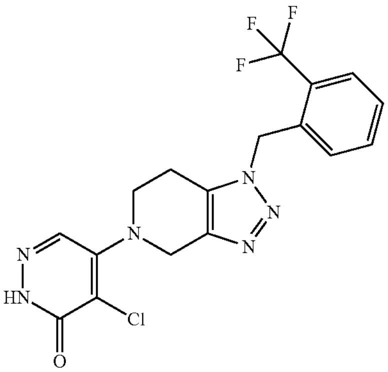 [SMILES: O=c1[nH]ncc(N2CCc3c(nnn3Cc3ccccc3C(F)(F)F)C2)c1Cl] | D | |

TABLE 10-continued

IC50 values for representative compounds of the disclosure measured in a Fluorescence assay - FLIPR format utilizing cells expressing TRPC5 (HEK-TREx hTRPC5) and TRPC4 (HEK-TREx hTRPC4).

| | TRPC5-FLIPR IC50 (uM) | TRPC4-FLIPR IC50 (uM) |
|---|---|---|
| 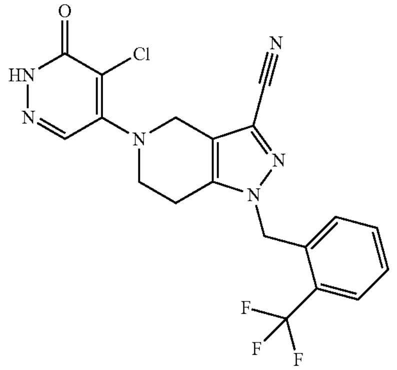 [SMILES: N#Cc1nn(Cc2ccccc2C(F)(F)F)c2c1CN(c1cn[nH]c(=O)c1Cl)CC2] | A | |
| 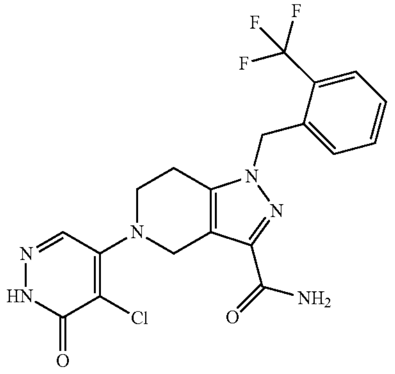 [SMILES: NC(=O)c1nn(Cc2ccccc2C(F)(F)F)c2c1CN(c1cn[nH]c(=O)c1Cl)CC2] | A | A |
| 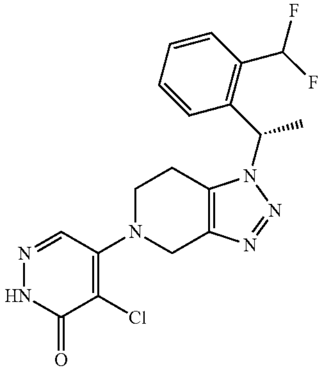 [SMILES: C[C@@H](c1ccccc1C(F)F)n1nnc2c1CCN(c1cn[nH]c(=O)c1Cl)C2] | A | A |

TABLE 10-continued

IC50 values for representative compounds of the disclosure measured in a Fluorescence assay - FLIPR format utilizing cells expressing TRPC5 (HEK-TREx hTRPC5) and TRPC4 (HEK-TREx hTRPC4).

| | TRPC5-FLIPR IC50 (uM) | TRPC4-FLIPR IC50 (uM) |
|---|---|---|
| 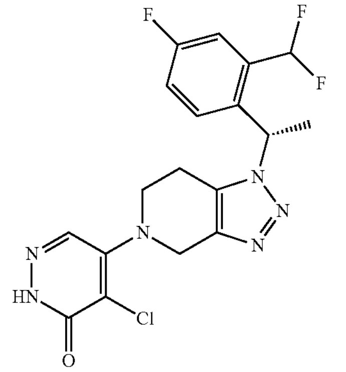 [SMILES: C[C@@H](c1ccc(F)cc1C(F)F)n1nnc2c1CCN(c1cn[nH]c(=O)c1Cl)C2] | A | A |
| 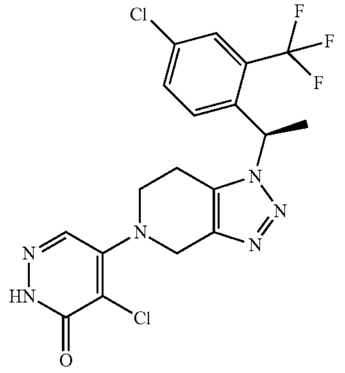 [SMILES: C[C@H](c1ccc(Cl)cc1C(F)(F)F)n1nnc2c1CCN(c1cn[nH]c(=O)c1Cl)C2] | A | |
| 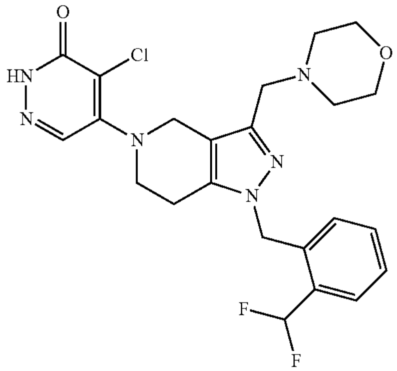 [SMILES: O=c1[nH]ncc(N2CCc3c(c(CN4CCOCC4)nn3Cc3ccccc3C(F)F)C2)c1Cl] | A | |

TABLE 10-continued

IC$_{50}$ values for representative compounds of the disclosure measured in a Fluorescence assay - FLIPR format utilizing cells expressing TRPC5 (HEK-TREx hTRPC5) and TRPC4 (HEK-TREx hTRPC4).

| | TRPC5-FLIPR IC50 (uM) | TRPC4-FLIPR IC50 (uM) |
|---|---|---|
| 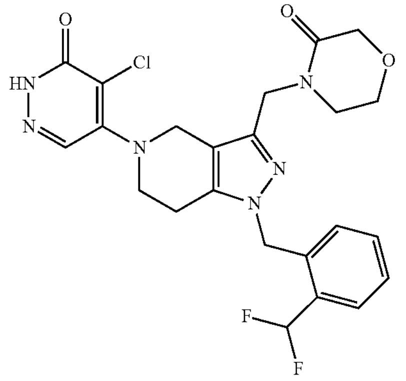 [SMILES: O=C1COCCN1Cc1nn(Cc2ccccc2C(F)F)c2c1CN(c1cn[nH]c(=O)c1Cl)CC2] | A | |
| 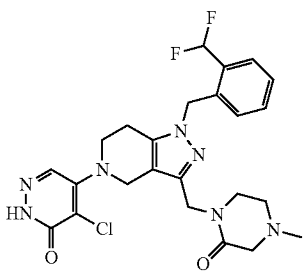 [SMILES: CN1CCN(Cc2nn(Cc3ccccc3C(F)F)c3c2CN(c2cn[nH]c(=O)c2Cl)CC3)C(=O)C1] | A | |
| 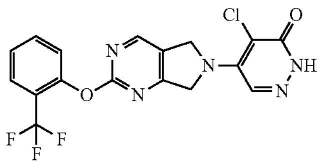 [SMILES: O=c1[nH]ncc(N2Cc3cnc(Oc4ccccc4C(F)(F)F)nc3C2)c1Cl] | A | |
| 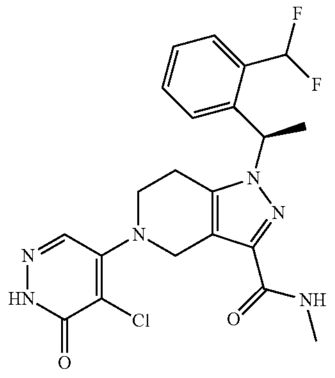 [SMILES: CNC(=O)c1nn([C@H](C)c2ccccc2C(F)F)c2c1CN(c1cn[nH]c(=O)c1Cl)CC2] | A | A |

TABLE 10-continued

IC$_{50}$ values for representative compounds of the disclosure measured in a Fluorescence assay - FLIPR format utilizing cells expressing TRPC5 (HEK-TREx hTRPC5) and TRPC4 (HEK-TREx hTRPC4).

| | TRPC5-FLIPR IC50 (uM) | TRPC4-FLIPR IC50 (uM) |
|---|---|---|
| 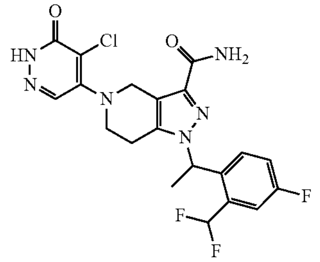 [SMILES: CC(c1ccc(F)cc1C(F)F)n1nc(C(N)=O)c2c1CCN(c1cn[nH]c(=O)c1Cl)C2] | A | A |
| 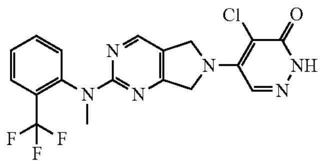 [SMILES: CN(c1ncc2c(n1)CN(c1cn[nH]c(=O)c1Cl)C2)c1ccccc1C(F)(F)F] | A | A |
| 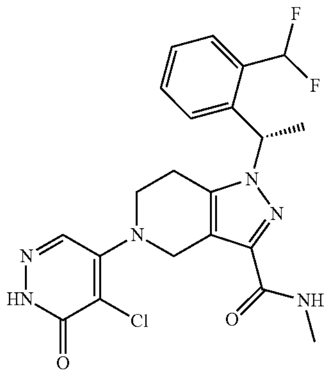 [SMILES: CNC(=O)c1nn([C@@H](C)c2ccccc2C(F)F)c2c1CN(c1cn[nH]c(=O)c1Cl)CC2] | A | |
| 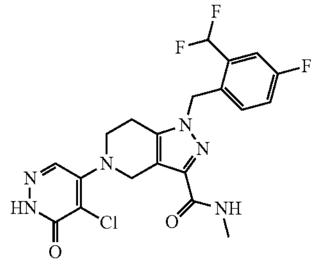 [SMILES: CNC(=O)c1nn(Cc2ccc(F)cc2C(F)F)c2c1CN(c1cn[nH]c(=O)c1Cl)CC2] | A | A |
| 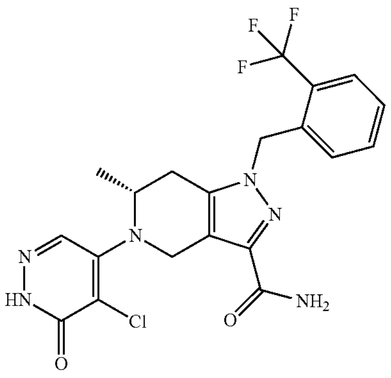 [SMILES: C[C@@H]1Cc2c(c(C(N)=O)nn2Cc2ccccc2C(F)(F)F)CN1c1cn[nH]c(=O)c1Cl] | A | A |

TABLE 10-continued
IC$_{50}$ values for representative compounds of the disclosure measured in a Fluorescence assay - FLIPR format utilizing cells expressing TRPC5 (HEK-TREx hTRPC5) and TRPC4 (HEK-TREx hTRPC4).
| | TRPC5-FLIPR IC50 (uM) | TRPC4-FLIPR IC50 (uM) |
|---|---|---|
| 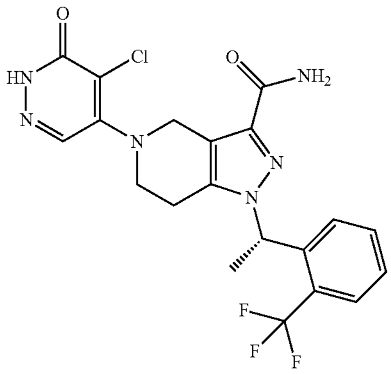 [SMILES: C[C@@H](c1ccccc1C(F)(F)F)n1nc(C(N)=O)c2c1CCN(c1cn[nH]c(=O)c1Cl)C2] | A | |
| 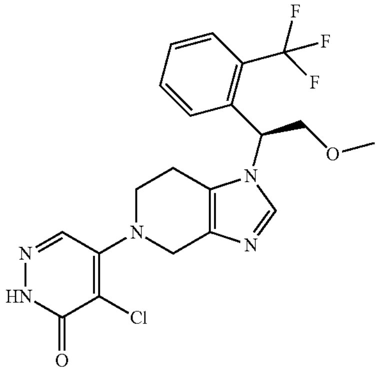 [SMILES: COC[C@H](c1ccccc1C(F)(F)F)n1cnc2c1CCN(c1cn[nH]c(=O)c1Cl)C2] | A | A |
| 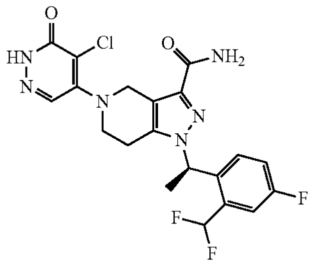 [SMILES: C[C@H](c1ccc(F)cc1C(F)F)n1nc(C(N)=O)c2c1CCN(c1cn[nH]c(=O)c1Cl)C2] | A | A |
| 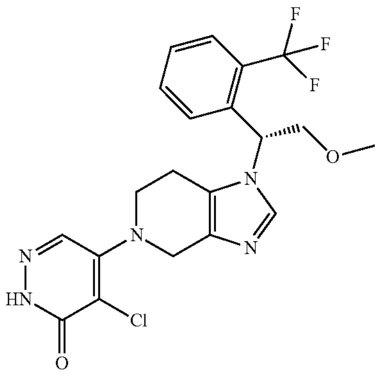 [SMILES: COC[C@@H](c1ccccc1C(F)(F)F)n1cnc2c1CCN(c1cn[nH]c(=O)c1Cl)C2] | A | |
| 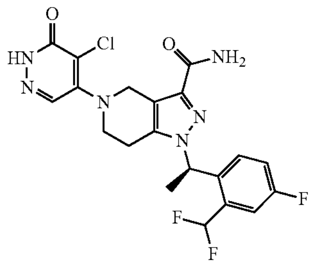 [SMILES: C[C@H](c1ccc(F)cc1C(F)F)n1nc(C(N)=O)c2c1CCN(c1cn[nH]c(=O)c1Cl)C2] | A | A |
| 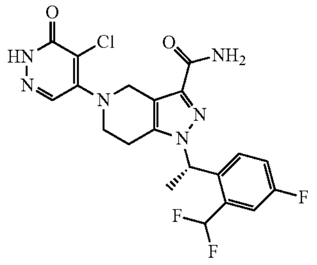 [SMILES: C[C@@H](c1ccc(F)cc1C(F)F)n1nc(C(N)=O)c2c1CCN(c1cn[nH]c(=O)c1Cl)C2] | A | |
| 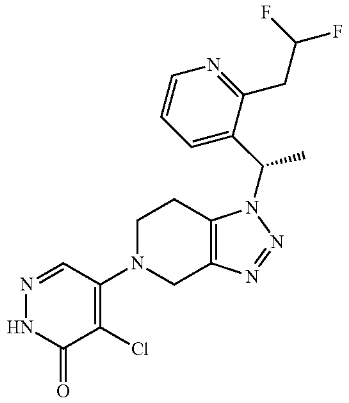 [SMILES: C[C@@H](c1cccnc1CC(F)F)n1nnc2c1CCN(c1cn[nH]c(=O)c1Cl)C2] | A | A |
| 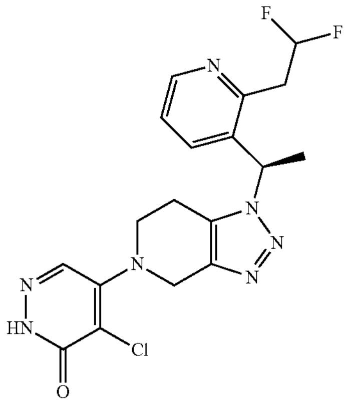 [SMILES: C[C@H](c1cccnc1CC(F)F)n1nnc2c1CCN(c1cn[nH]c(=O)c1Cl)C2] | A | |

TABLE 10-continued

IC50 values for representative compounds of the disclosure measured in a Fluorescence assay - FLIPR format utilizing cells expressing TRPC5 (HEK-TREx hTRPC5) and TRPC4 (HEK-TREx hTRPC4).

| | TRPC5-FLIPR IC50 (uM) | TRPC4-FLIPR IC50 (uM) |
|---|---|---|
| 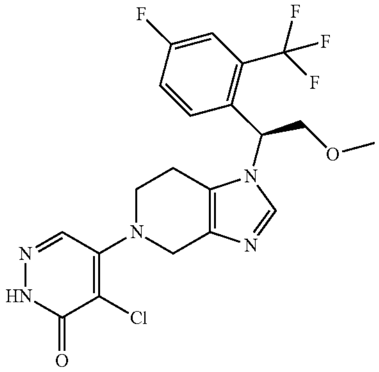 [SMILES: COC[C@H](c1ccc(F)cc1C(F)(F)F)n1cnc2c1CCN(c1cn[nH]c(=O)c1Cl)C2] | A | |
| 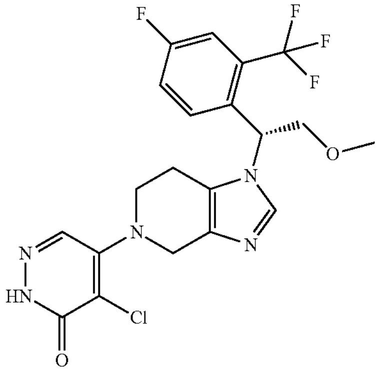 [SMILES: COC[C@@H](c1ccc(F)cc1C(F)(F)F)n1cnc2c1CCN(c1cn[nH]c(=O)c1Cl)C2] | B | |
| 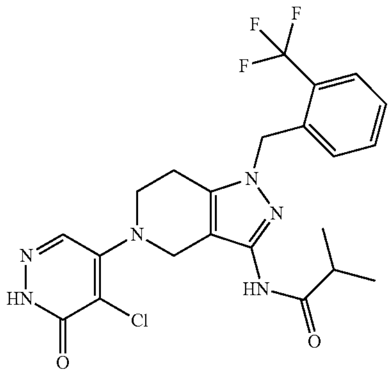 [SMILES: CC(C)C(=O)Nc1nn(Cc2ccccc2C(F)(F)F)c2c1CN(c1cn[nH]c(=O)c1Cl)CC2] | A | |

TABLE 10-continued

IC50 values for representative compounds of the disclosure measured in a Fluorescence assay - FLIPR format utilizing cells expressing TRPC5 (HEK-TREx hTRPC5) and TRPC4 (HEK-TREx hTRPC4).

| | TRPC5-FLIPR IC50 (uM) | TRPC4-FLIPR IC50 (uM) |
|---|---|---|
| 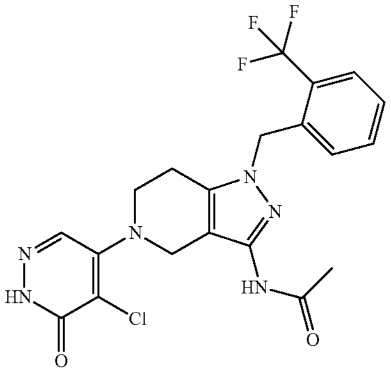 [SMILES: CC(=O)Nc1nn(Cc2ccccc2C(F)(F)F)c2c1CN(c1cn[nH]c(=O)c1Cl)CC2] | A | |
| 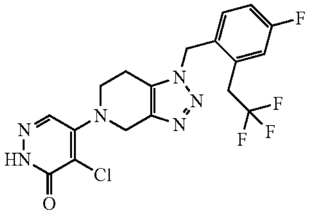 [SMILES: O=c1[nH]ncc(N2CCc3c(nnn3Cc3ccc(F)cc3CC(F)(F)F)C2)c1Cl] | A | A |
| 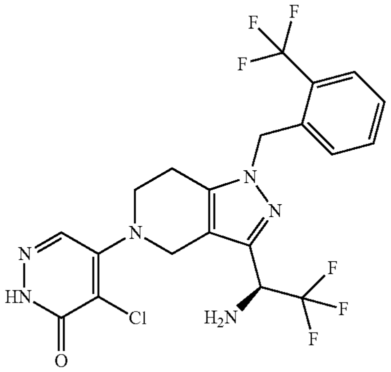 [SMILES: N[C@@H](c1nn(Cc2ccccc2C(F)(F)F)c2c1CN(c1cn[nH]c(=O)c1Cl)CC2)C(F)(F)F] | B | |
| 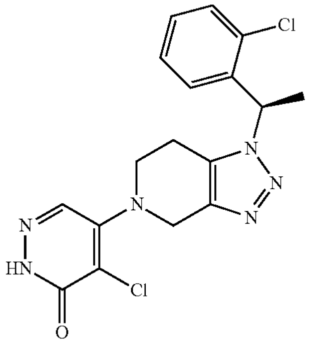 [SMILES: C[C@H](c1ccccc1Cl)n1nnc2c1CCN(c1cn[nH]c(=O)c1Cl)C2] | A | A |

TABLE 10-continued $IC_{50}$ values for representative compounds of the disclosure measured in a Fluorescence assay - FLIPR format utilizing cells expressing TRPC5 (HEK-TREx hTRPC5) and TRPC4 (HEK-TREx hTRPC4).

| | TRPC5-FLIPR IC50 (uM) | TRPC4-FLIPR IC50 (uM) |
|---|---|---|
| 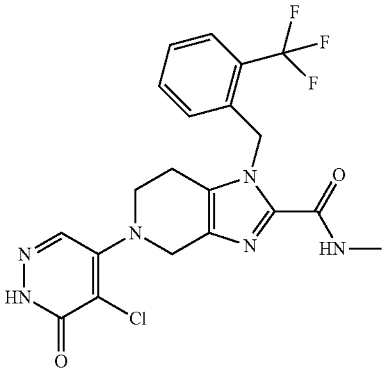 [SMILES: CNC(=O)c1nc2c(n1Cc1ccccc1C(F)(F)F)CCN(c1cn[nH]c(=O)c1Cl)C2] | A | A |
| 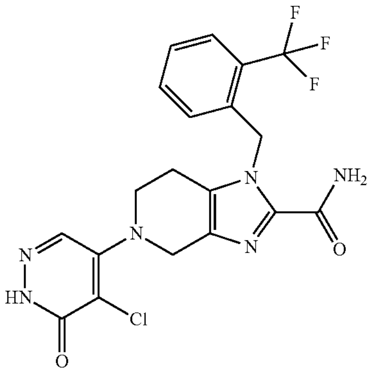 [SMILES: NC(=O)c1nc2c(n1Cc1ccccc1C(F)(F)F)CCN(c1cn[nH]c(=O)c1Cl)C2] | A | A |
| 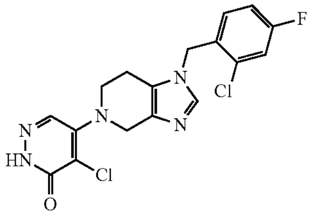 [SMILES: O=c1[nH]ncc(N2CCc3c(ncn3Cc3ccc(F)cc3Cl)C2)c1Cl] | A | A |
| 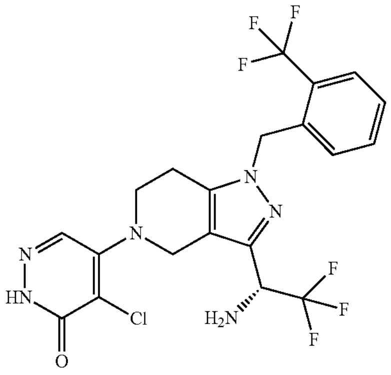 [SMILES: N[C@H](c1nn(Cc2ccccc2C(F)(F)F)c2c1CN(c1cn[nH]c(=O)c1Cl)CC2)C(F)(F)F] | B | |

TABLE 10-continued $IC_{50}$ values for representative compounds of the disclosure measured in a Fluorescence assay - FLIPR format utilizing cells expressing TRPC5 (HEK-TREx hTRPC5) and TRPC4 (HEK-TREx hTRPC4).

| | TRPC5-FLIPR IC50 (uM) | TRPC4-FLIPR IC50 (uM) |
|---|---|---|
| 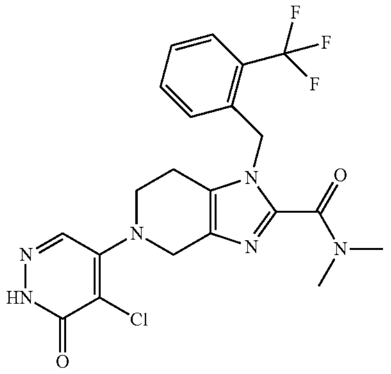 [SMILES: CN(C)C(=O)c1nc2c(n1Cc1ccccc1C(F)(F)F)CCN(c1cn[nH]c(=O)c1Cl)C2] | A | A |
| 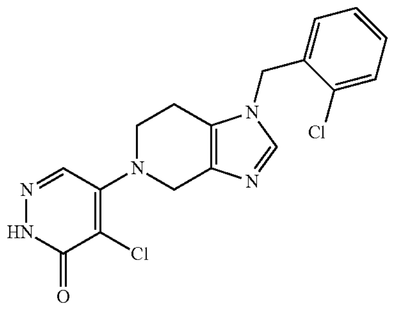 [SMILES: O=c1[nH]ncc(N2CCc3c(ncn3Cc3ccccc3Cl)C2)c1Cl] | A | A |
| 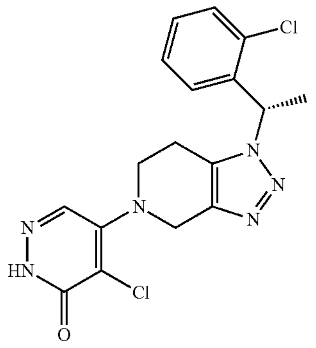 [SMILES: C[C@@H](c1ccccc1Cl)n1nnc2c1CCN(c1cn[nH]c(=O)c1Cl)C2] | A | A |
| 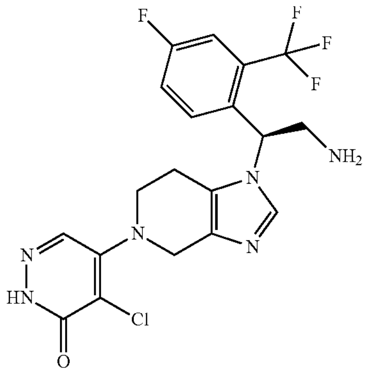 [SMILES: NC[C@H](c1ccc(F)cc1C(F)(F)F)n1cnc2c1CCN(c1cn[nH]c(=O)c1Cl)C2] | C | |

TABLE 10-continued

IC$_{50}$ values for representative compounds of the disclosure measured in a Fluorescence assay - FLIPR format utilizing cells expressing TRPC5 (HEK-TREx hTRPC5) and TRPC4 (HEK-TREx hTRPC4).

| | TRPC5-FLIPR IC50 (uM) | TRPC4-FLIPR IC50 (uM) |
|---|---|---|
| 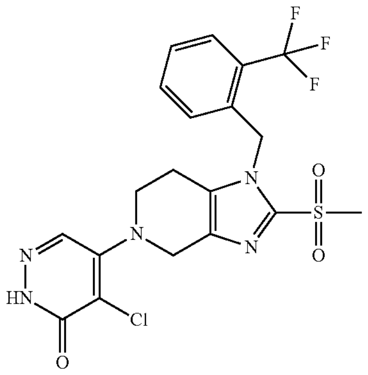 [SMILES: CS(=O)(=O)c1nc2c(n1Cc1ccccc1C(F)(F)F)CCN(c1cn[nH]c(=O)c1Cl)C2] | A | A |
| 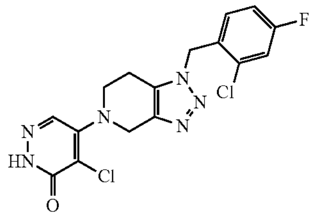 [SMILES: O=c1[nH]ncc(N2CCc3c(nnn3Cc3ccc(F)cc3Cl)C2)c1Cl] | A | |
| 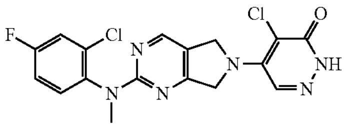 [SMILES: CN(c1ncc2c(n1)CN(c1cn[nH]c(=O)c1Cl)C2)c1ccc(F)cc1Cl] | A | A |
| 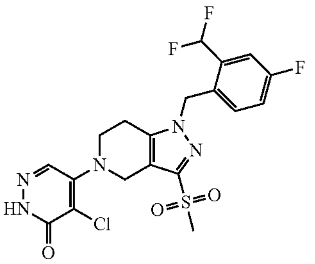 [SMILES: CS(=O)(=O)c1nn(Cc2ccc(F)cc2C(F)F)c2c1CN(c1cn[nH]c(=O)c1Cl)CC2] | A | |
| 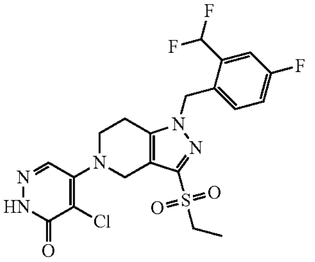 [SMILES: CCS(=O)(=O)c1nn(Cc2ccc(F)cc2C(F)F)c2c1CN(c1cn[nH]c(=O)c1Cl)CC2] | B | |

TABLE 10-continued

IC$_{50}$ values for representative compounds of the disclosure measured in a Fluorescence assay - FLIPR format utilizing cells expressing TRPC5 (HEK-TREx hTRPC5) and TRPC4 (HEK-TREx hTRPC4).

| | TRPC5-FLIPR IC50 (uM) | TRPC4-FLIPR IC50 (uM) |
|---|---|---|
| 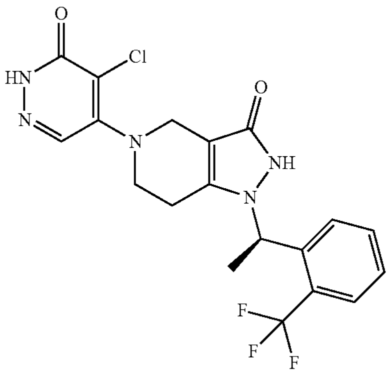 [SMILES: C[C@H](c1ccccc1C(F)(F)F)n1[nH]c(=O)c2c1CCN(c1cn[nH]c(=O)c1Cl)C2] | A | |
| 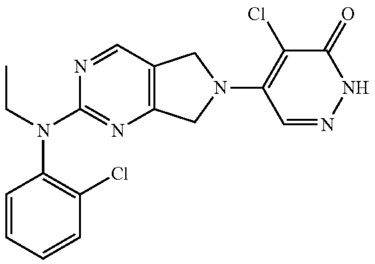 [SMILES: CCN(c1ncc2c(n1)CN(c1cn[nH]c(=O)c1Cl)C2)c1ccccc1Cl] | A | A |
| 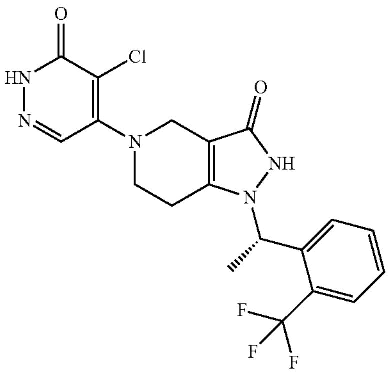 [SMILES: C[C@@H](c1ccccc1C(F)(F)F)n1[nH]c(=O)c2c1CCN(c1cn[nH]c(=O)c1Cl)C2] | A | |
| 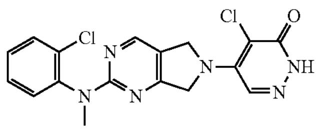 [SMILES: CN(c1ncc2c(n1)CN(c1cn[nH]c(=O)c1Cl)C2)c1ccccc1Cl] | A | |

TABLE 10-continued

IC50 values for representative compounds of the disclosure measured in a Fluorescence assay - FLIPR format utilizing cells expressing TRPC5 (HEK-TREx hTRPC5) and TRPC4 (HEK-TREx hTRPC4).

| | TRPC5-FLIPR IC50 (uM) | TRPC4-FLIPR IC50 (uM) |
|---|---|---|
| 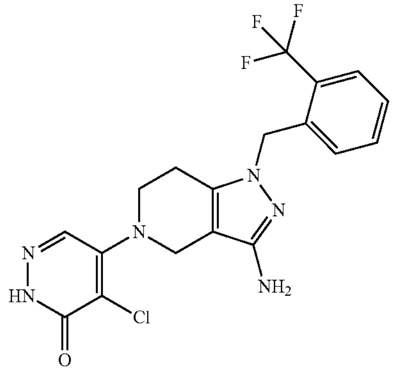 [SMILES: Nc1nn(Cc2ccccc2C(F)(F)F)c2c1CN(c1cn[nH]c(=O)c1Cl)CC2] | B | |
| 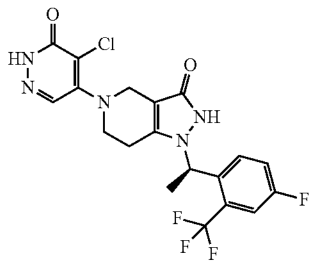 [SMILES: C[C@H](c1ccc(F)cc1C(F)(F)F)n1[nH]c(=O)c2c1CCN(c1cn[nH]c(=O)c1Cl)C2] | A | |
| 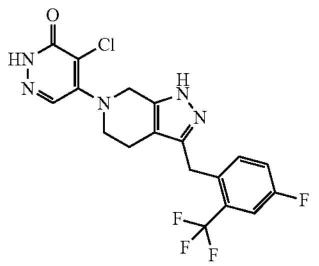 [SMILES: O=c1[nH]ncc(N2CCc3c(Cc4ccc(F)cc4C(F)(F)F)n[nH]c3C2)c1Cl] | A | A |
| 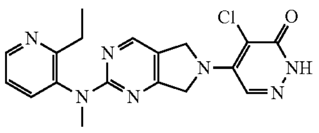 [SMILES: CCc1ncccc1N(C)c1ncc2c(n1)CN(c1cn[nH]c(=O)c1Cl)C2] | A | A |
| 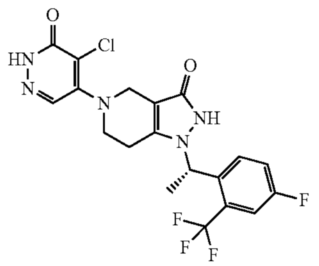 [SMILES: C[C@@H](c1ccc(F)cc1C(F)(F)F)n1[nH]c(=O)c2c1CCN(c1cn[nH]c(=O)c1Cl)C2] | A | |

TABLE 10-continued

IC50 values for representative compounds of the disclosure measured in a Fluorescence assay - FLIPR format utilizing cells expressing TRPC5 (HEK-TREx hTRPC5) and TRPC4 (HEK-TREx hTRPC4).

| | TRPC5-FLIPR IC50 (uM) | TRPC4-FLIPR IC50 (uM) |
|---|---|---|
| 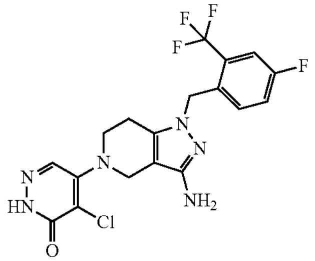 [SMILES: Nc1nn(Cc2ccc(F)cc2C(F)(F)F)c2c1CN(c1cn[nH]c(=O)c1Cl)CC2] | A | |
| 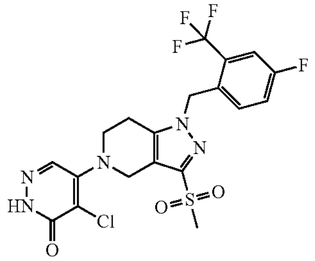 [SMILES: CS(=O)(=O)c1nn(Cc2ccc(F)cc2C(F)(F)F)c2c1CN(c1cn[nH]c(=O)c1Cl)CC2] | A | |
| 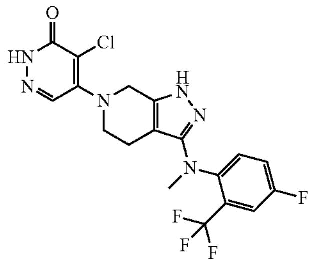 [SMILES: CN(c1ccc(F)cc1C(F)(F)F)c1n[nH]c2c1CCN(c1cn[nH]c(=O)c1Cl)C2] | A | |
| 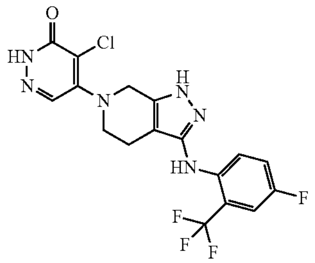 [SMILES: O=c1[nH]ncc(N2CCc3c(Nc4ccc(F)cc4C(F)(F)F)n[nH]c3C2)c1Cl] | A | |
| 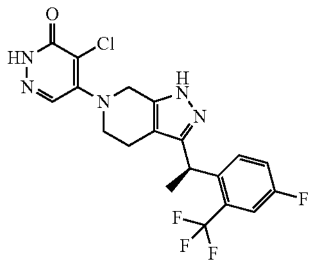 [SMILES: C[C@H](c1ccc(F)cc1C(F)(F)F)c1n[nH]c2c1CCN(c1cn[nH]c(=O)c1Cl)C2] | A | |

IV. Effects of Compound AO on Albuminuria in DOCA-Salt Hypertensive Rats

The aim of this study was to evaluate the effects of the TRCP5 inhibitor, AO, to attenuate the development and/or progression of albuminuria in deoxycorticosterone acetate (DOCA)-salt hypertensive rats.

The DOCA-salt hypertensive rat model is a well-established model of mineralocorticoid hypertension with renal dysfunction, characterized by increase levels of urinary protein and albumin excretion. [Schenk et al., "The pathogenesis of DOCA-salt hypertension," *J. Pharmacol. Toxicol. Methods* (May 1992) 27(3):161-170; Gomez-Sanchez et al., "Mineralocorticoids, salt and high blood pressure," *Steroids* (1996) 61:184-188.]

Six to seven weeks old Sprague Dawley rats were unilaterally nephrectomized; after one-week recovery, rats were implanted with a DOCA pellet (45 mg) and provided tap water containing 0.9% NaCl and 0.2% KCl (Day 1) for a 3 weeks treatment. On Day 1, DOCA-salt rats received one daily dose, subcutaneously (SC), of AO at 30 mg/kg for 3 weeks; control animals for DOCA treatment were administered vehicle or eplerenone, an aldosterone blocker; sham animals, implanted with a silicone-water pellet, were given tap water and received SC administration of the vehicle. Proteinuria, albuminuria and arterial blood pressure as well as body weight were recorded every week.

No adverse effects were observed in the animals administered AO. There was no significant difference in body weight and urinary creatinine excretion in rats treated with DOCA or DOCA-AO. Animals receiving DOCA and DOCA-AO had elevated mean arterial blood pressure (BP), diastolic and systolic BP, compared to sham animals, from week 1 to 3.

Water intake and urine volume produced per day were also elevated in animals receiving DOCA-salt treatment followed by vehicle or AO.

As shown in FIG. 2, AO attenuated urinary albumin excretion from week 1 to week 3 and the decrease reached significance at week 3, compared to DOCA-vehicle control rats (p value 0.0011). The albumin levels excreted in the urine were similar to the levels of the positive control animals that received eplerenone.

V. Effects of AO on Murine Podocytes with Protamine Sulfate Injury

Conditionally immortalized murine podocytes were differentiated for 14 days in gamma-interferon-free media [Synaptopodin Is a Coincidence Detector of Tyrosine versus Serine/Threonine Phosphorylation for the Modulation of Rho Protein Crosstalk in Podocytes. Buvall L, Wallentin H, Sieber J, Andreeva S, Choi H Y, Mundel P, Greka A. J Am Soc Nephrol. 2017 March; 28(3):837-851. doi: 10.1681/ASN.2016040414. Epub 2016 Sep. 14.]. Murine podocyte cells were pretreated with 0.1, 1, 10 uM of AO or DMSO for 20 minutes then insulted with 300 ug/mL of protamine sulfate (PS) for 1 hour; 3 technical replicate plates were treated for each condition. Murine cells were washed with 1×DPBS−/−, fixed in 4% PFA+4% sucrose for 10 minutes at room temperature, washed 3 times with 1×DPBS−/−, permeabilized with 0.3% triton, and probed for phalloidin, synaptopodin, and DAPI (Proteasomal degradation of Nck1 but not Nck2 regulates RhoA activation and actin dynamics. Buvall L, Rashmi P, Lopez-Rivera E, Andreeva S, Weins A, Wallentin H, Greka A, Mundel P. Nat Commun. (2013) 4:2863. doi: 10.1038/ncomms3863). Tiled images were acquired using a Zeiss LSM880 Airyscan super resolution confocal microscope using ZEN 2.3. Manual quantitation of cells with or without collapsed actin cytoskeleton were quantified. As shown in FIGS. 3A-3F, here we observe addition of AO protects~20% of murine cells from cytoskeletal collapse induced by protamine sulfate induced injury.

VI. Effects of Compound AO on Human iPSC Derived Kidney Organoids with Protamine Sulfate Injury Human iPSC derived kidney organoids differentiated for 22 days [Generation of kidney organoids from human pluripotent stem cells. Takasato M, Er P X, Chiu H S, Little M H. Nat Protoc. 2016 September; 11(9):1681-92. doi: 10.1038/nprot.2016.098. Epub 2016 Aug. 18.] were pretreated with 0.2, 2, 20 uM of AO or DMSO for 20 minutes then insulted with 300 ug/mL of protamine sulfate for 1 hour; 3 technical replicate organoids were treated for each condition. Organoids were washed twice with 1×DPBS−/−, fixed in 4% PFA for 25 minutes at room temperature, washed twice with 1×DPBS−/−, and transferred to 30% sucrose at 4° C. overnight, then snap frozen in Tissue-Tek O.C.T. compound. Organoids were cryosectioned at 5 uM thickness and stained for phalloidin. Tiled images were acquired using a Zeiss LSM880 Airyscan super resolution confocal microscope using ZEN 2.3. Mean intensity values were quantified using Fiji/ImagJ1.52d. As shown in FIGS. 4A-4F, here we observe human iPSC derived kidney organoids have decreased injury from protamine sulfate injury as indicated by a decrease in mean phalloidin intensity per organoid with AO treatment compared to protamine sulfate alone.

INCORPORATION BY REFERENCE

All of the U.S. patents and U.S. and PCT published patent applications cited herein are hereby incorporated by reference.

EQUIVALENTS

The foregoing written specification is sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A compound represented by Formula (I) or (III), or a tautomer or a pharmaceutically acceptable salt thereof;

(I)

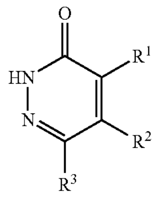

(III)

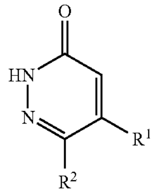

wherein $R^1$ and $R^3$ are independently selected from the group consisting of H, alkyl, alkenyl, alkynyl, aryl, heterocyclyl, heteroaryl, halogen, —OH, —CN, -cycloalkyl, —O-alkyl, —O-cycloalkyl, —O-aryl, -aryl-O-aryl, —$CF_3$, —C(H)$F_2$, alkylene-$CF_3$, alkylene-C(H)$F_2$, —$SO_2$-alkyl, and —O-alkylene-O-alkyl;

$R^2$ is a -heterocyclyl-L-$R^4$ selected from the group consisting of:

(A)

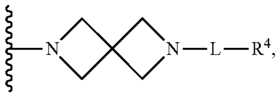

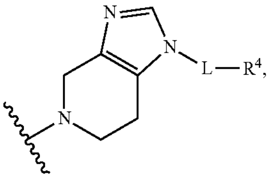

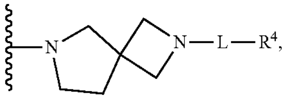

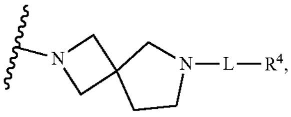

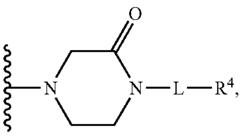

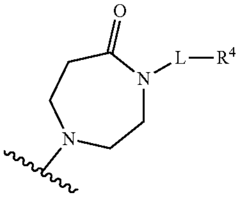

,

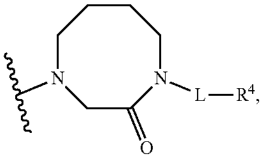

or

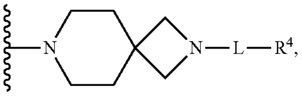

wherein L is methylene or —C($R^5$)($R^6$)-, and $R^4$ is aryl, alkylene-aryl, alkylene-heteroaryl, heteroaryl, or heterocyclyl;

(B)

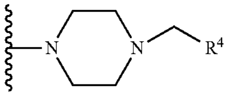

wherein $R^4$ is an oxazole ring, pyrazole ring, pyridine ring, pyrazine ring, pyridazine ring, or pyrimidine ring, wherein $R^4$ is substituted with at least one substituent independently selected from the group consisting of alkyl, cycloalkyl, halogen, —CN, —$CF_3$, and -C(H)$F_2$; and (C) a -heterocyclyl-L-$R^4$ wherein the heterocyclyl is selected from

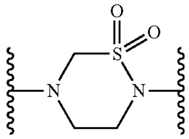,
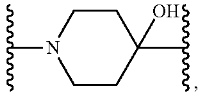,
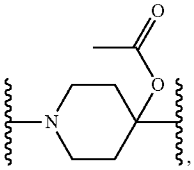,
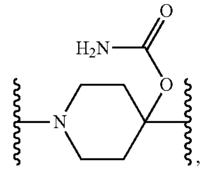,
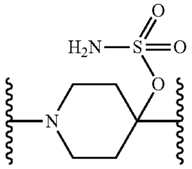
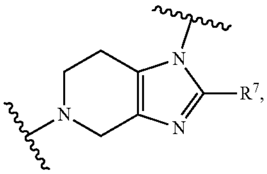 and
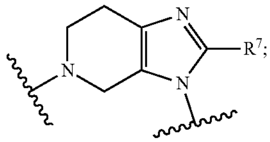

wherein $R^7$ is H, alkyl, —O-aryl, —O-alkyl, or cycloalkyl; L is methylene or —C($R^5$)($R^6$)-; and $R^4$ is aryl, alkylene-aryl, alkylene-heteroaryl, heteroaryl, or heterocyclyl;

$R^5$ is independently H or alkyl; and $R^6$ is selected from the group consisting of alkyl and -$CF_3$.

2. The compound of claim 1, wherein $R^2$ is

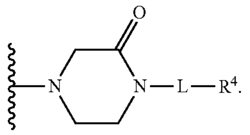

3. The compound of claim 1, wherein the heterocyclyl in $R^2$ is

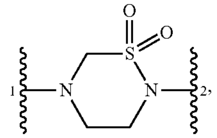 [SMILES: *N1CCN(*)S(=O)(=O)C1]

wherein "1" represents a point of attachment to the pyridazinone shown in Formula I or Formula III; "2" represents a point of attachment to -L-$R^4$.

4. The compound of claim 1, wherein the heterocyclyl in $R^2$ is selected from

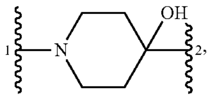
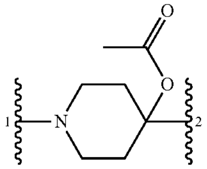
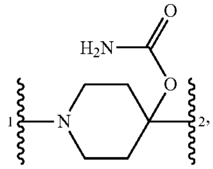 and
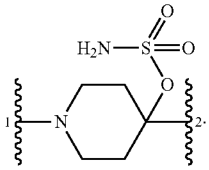

wherein "1" represents a point of attachment to the pyridazinone shown in Formula I or Formula III; and "2" represents a point of attachment to -L-$R^4$.

5. The compound of claim 1, wherein the heterocyclyl in $R^2$ is selected from

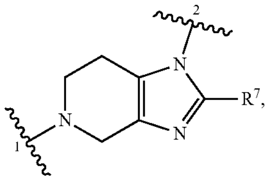 and
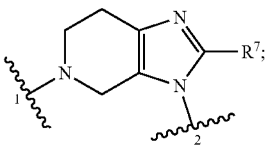

wherein $R^7$ is H, alkyl, —O-aryl, —O-alkyl, or cycloalkyl; "1" represents a point of attachment to the pyridazinone shown in Formula I or Formula III; and "2" represents a point of attachment to -L-$R^4$.

6. The compound of claim 1, wherein $R^4$ is phenyl optionally substituted with one or more moieties independently selected from alkyl, cycloalkyl, aryl, halogen, —CN, $CF_3$, C(H)$F_2$, —O$CF_3$, —O-aryl, —O-alkyl, —$SO_2$Me, OH, alkylene-$OR_5$, alkylene-$CF_3$, and alkylene-C(H)$F_2$; and wherein $R^5$ is hydrogen, methyl or ethyl.

7. The compound of claim 1, wherein L is methylene.
8. A composition, comprising a compound of claim 1 or a tautomer or a pharmaceutically acceptable salt thereof; and a pharmaceutically acceptable excipient.
9. A compound that is one of the following, or a pharmaceutically acceptable salt thereof:
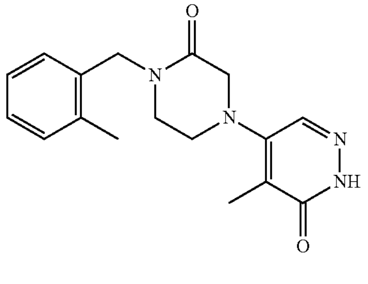
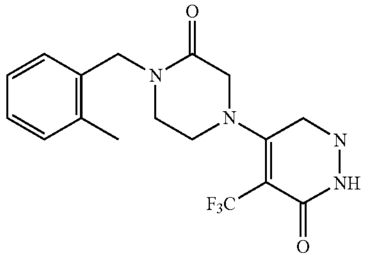
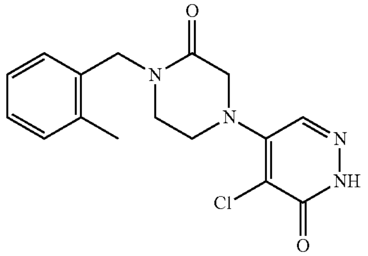
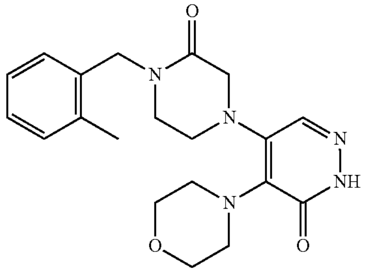
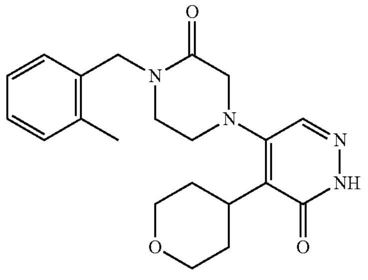
-continued
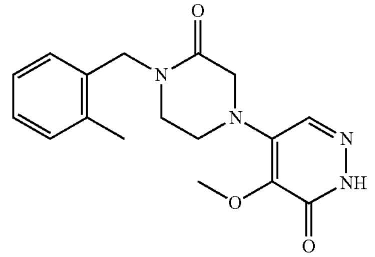
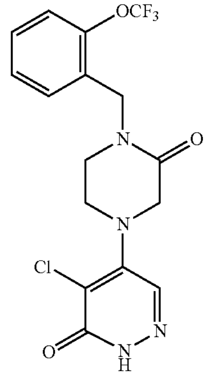
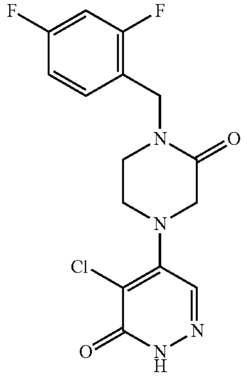
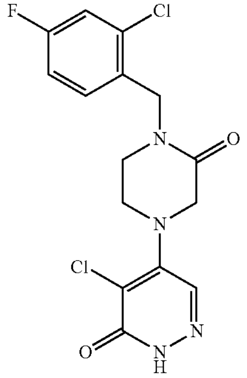
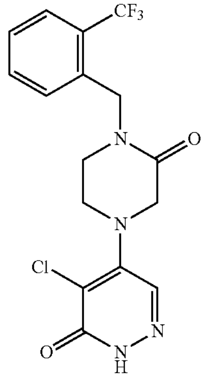
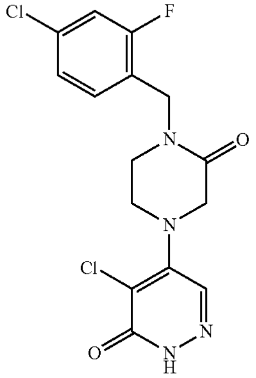
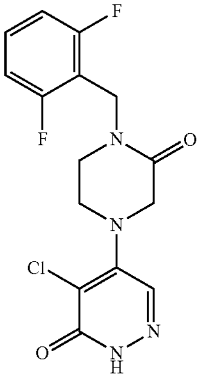
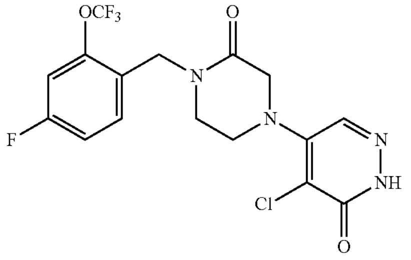

-continued
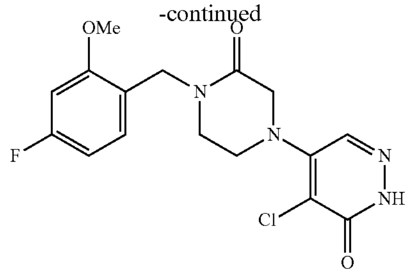
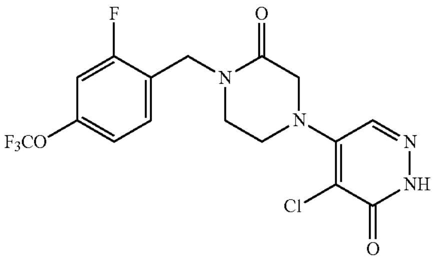
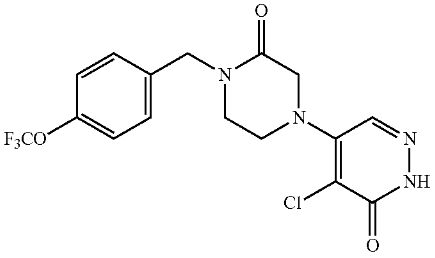
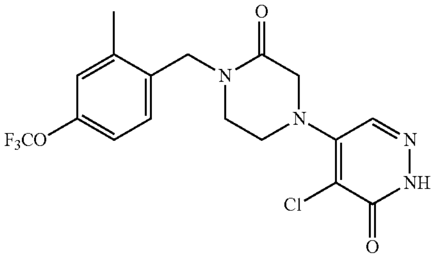
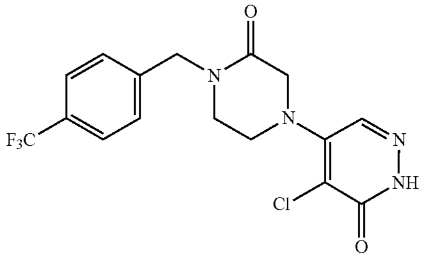
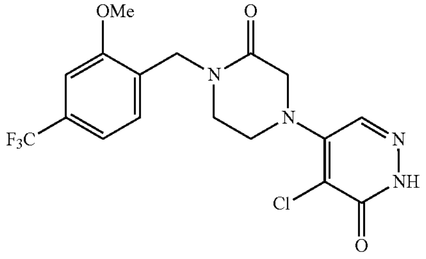
-continued
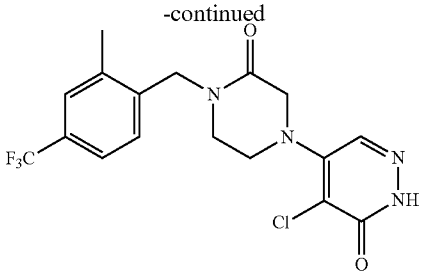
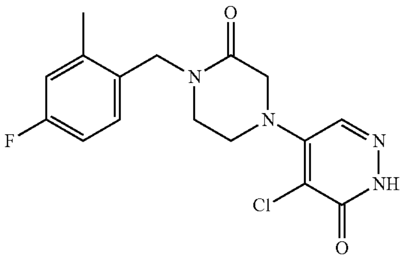
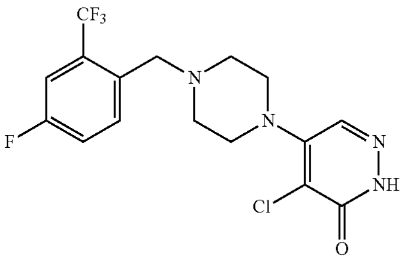
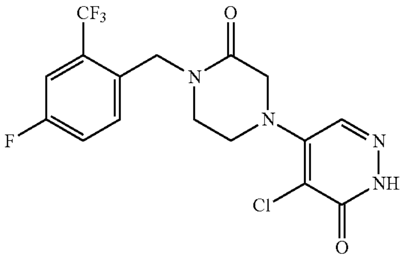
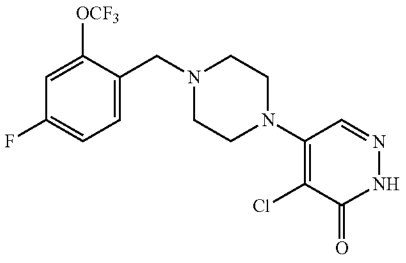
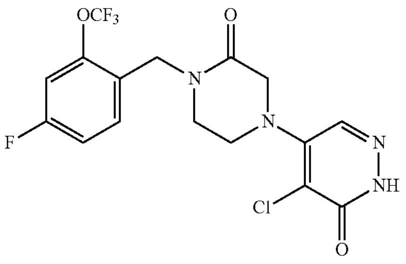

-continued
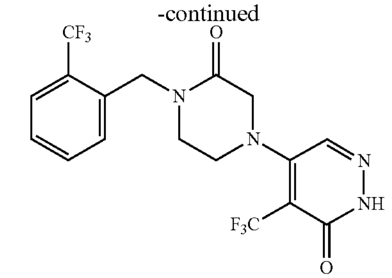
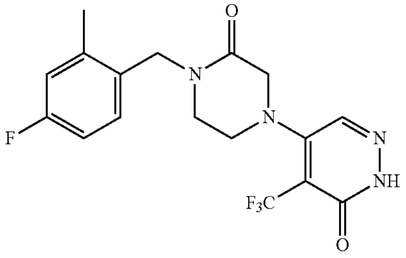
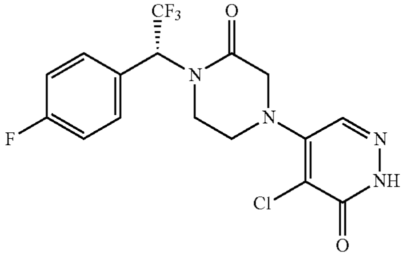
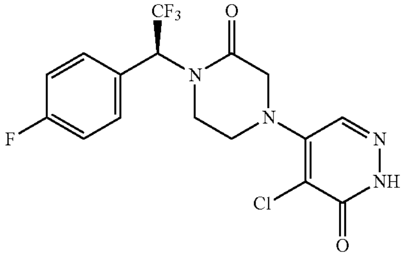
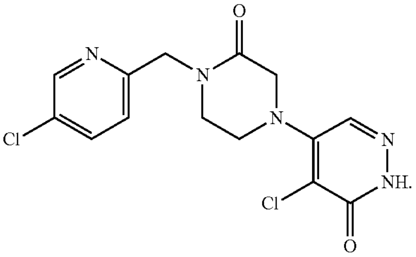
10. The compound of claim 1, wherein the compound is one of the following, or a pharmaceutically acceptable salt thereof:
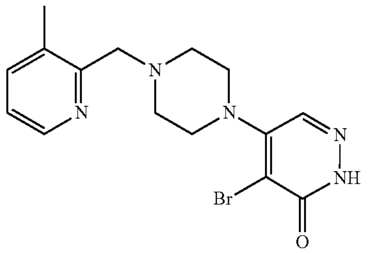
-continued
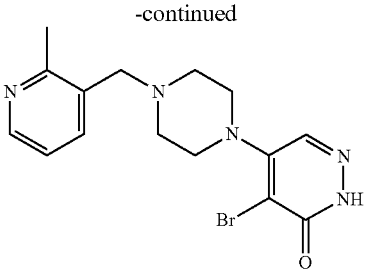
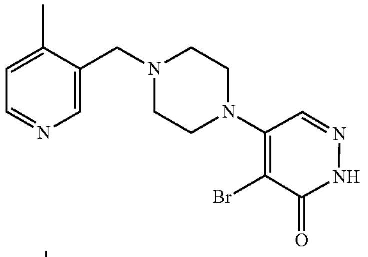
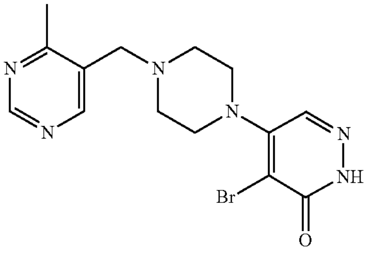
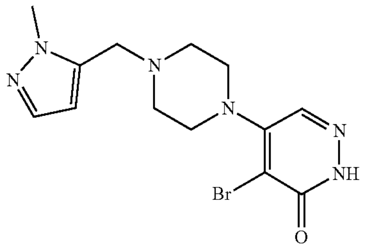
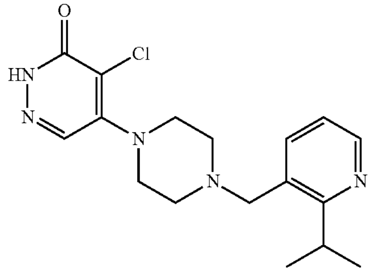
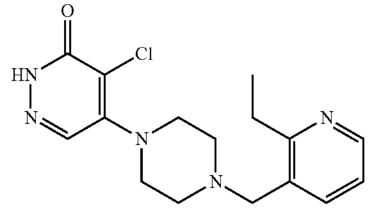
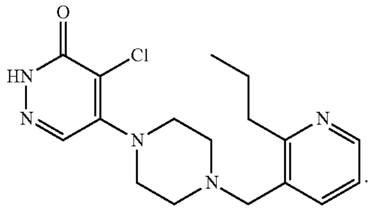
* * * * *

SEQUENCE LISTING

```
<160> NUMBER OF SEQ ID NOS: 2

<210> SEQ ID NO 1
<211> LENGTH: 8574
<212> TYPE: DNA
<213> ORGANISM: Artificial Sequence
<220> FEATURE:
<223> OTHER INFORMATION: Description of Artificial Sequence: Synthetic
```

polynucleotide

<400> SEQUENCE: 1

```
gacggatcgg gagatctccc gatcccctat ggtgcactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ccctatcagt gatagagatc    840
tccctatcag tgatagagat cgtcgacgag ctcgtttagt gaaccgtcag atcgcctgga    900
gacgccatcc acgctgtttt gacctccata gaagacaccg ggaccgatcc agcctccgga    960
ctctagcgtt taaacttaag cttggtaccg agctcggatc cgccaccatg gcccagttct   1020
actataagag aaacgtgaat gccccttacc gcgacagaat ccccctgaga atcgtgaggg   1080
cagagtccga gctgagccca tccgagaagg cctacctgaa cgccgtggag aagggcgact   1140
atgccagcgt gaagaagtcc ctggaggagg ccgagatcta ctttaagatc aacatcaatt   1200
gcatcgatcc tctgggcaga accgccctgc tgatcgccat cgagaacgag aatctggagc   1260
tgatcgagct gctgctgagc ttcaacgtgt atgtgggcga tgccctgctg cacgccatca   1320
ggaaggaggt ggtgggagca gtggagctgc tgctgaatca caagaagcca agcggagaga   1380
agcaggtgcc acctatcctg ctggacaagc agttctccga gtttacccca gatatcacac   1440
ccatcatcct ggccgcccac accaacaatt acgagatcat caagctgctg gtgcagaagg   1500
gcgtgtccgt gcctcgccca cacgaggtgc ggtgcaactg cgtggagtgc gtgagctcct   1560
ctgacgtgga ttctctgagg cacagccgga gccggctgaa catctataag gccctggcct   1620
ccccatctct gatcgccctg agctccgagg acccccttcct gaccgccttt cagctgtctt   1680
gggagctgca ggagctgagc aaggtggaga acgagtttaa gagcgagtac gaggagctgt   1740
ccagacagtg caagcagttc gccaaggacc tgctggatca gacacgctct agccgggagc   1800
tggagatcat cctgaactat agggacgata attctctgat cgaggagcag agcggaaacg   1860
acctggcacg cctgaagctg gccatcaagt accggcagaa ggagttcgtg gcccagccta   1920
attgtcagca gctgctggcc tcccgctggt atgatgagtt tccaggatgg cggagaaggc   1980
actgggcagt gaagatggtg acctgcttca tcatcggcct gctgttcccc gtgttcagcg   2040
tgtgctacct gatcgcccct aagtctccac tgggcctgtt tatccggaag cctttcatca   2100
agtttatctg ccacaccgcc agctatctga cattcctgtt tctgctgctg ctggcctccc   2160
agcacatcga cagatctgat ctgaacaggc agggcccacc ccctaccatc gtggagtgga   2220
tgatcctgcc atgggtgctg ggcttcatct ggggcgagat caagcagatg tgggacggcg   2280
```

gcctgcagga ctacatccac gattggtgga acctgatgga ttttgtgatg aattccctgt 2340
acctggccac aatctctctg aagatcgtgg ccttcgtgaa gtatagcgcc ctgaatccca 2400
gagagtcctg ggacatgtgg caccctaccc tggtggcaga ggccctgttc gcaatcgcca 2460
acatcttttc ctctctgcgc ctgatcagcc tgtttacagc caattcccac ctgggaccac 2520
tgcagatctc cctgggacgg atgctgctgg atatcctgaa gttcctgttt atctactgcc 2580
tggtgctgct ggccttcgcc aacggcctga atcagctgta cttctactat gaggagacca 2640
agggcctgac atgcaagggc atccgctgtg agaagcagaa caatgccttc agcaccctgt 2700
tcgagacact gcagtctctg ttctggagca tctttggcct gatcaacctg tacgtgacca 2760
atgtgaaggc ccagcacgag ttcacagagt ttgtgggcgc caccatgttc ggcacataca 2820
acgtgatctc tctggtggtg ctgctgaata tgctgatcgc catgatgaac aatagctatc 2880
agctgatcgc cgaccacgcc gatatcgagt ggaagttcgc ccggaccaag ctgtggatgt 2940
cctactttga ggagggcggc accctgccca cacctttcaa cgtgatccca tcccccaagt 3000
ctctgtggta tctgatcaag tggatctgga cacacctgtg caagaagaag atgcgccgga 3060
agcctgagag ctttggcacc atcggcgtgc gcacacagca cagaagggca gcagacaacc 3120
tgcgccggca ccaccagtac caggaagtga tgcgcaatct ggtgaagcgg tatgtggccg 3180
ccatgatcag ggacgcaaag accgaggagg gactgacaga ggagaacttc aaggagctga 3240
agcaggatat cagctccttc agatttgagg tgctgggcct gctgaggggc agcaagctgt 3300
ccaccatcca gtccgccaac gcctctaagg agtctagcaa ttctgccgac agcgatgaga 3360
agagcgactc cgagggcaac tctaaggata agaagaagaa cttcagcctg tttgacctga 3420
ccacactgat ccacccacgc agcgccgcaa tcgcatccga gcggcacaac atctccaatg 3480
gctctgccct ggtggtgcag gagccaccaa gagagaagca gaggaaggtg aactttgtga 3540
cagatatcaa gaatttcggc ctgtttcaca gaaggagcaa gcagaacgcc gccgagcaga 3600
acgccaatca gatcttctct gtgagcgagg aggtggcaag acagcaggca gcaggaccac 3660
tggagaggaa tatccagctg gagagccggg gactggcaag caggggcgac ctgtccatcc 3720
caggactgtc tgagcagtgc gtgctggtgg accacaggga gcggaacacc gatacactgg 3780
gactgcaagt gggcaagcgg gtgtgccctt tcaagagcga gaaggtcgtg gtggaggaca 3840
ccgtgcccat catccctaag gagaagcacg ccaaggagga ggattcctct atcgactacg 3900
atctgaatct gccagacacc gtgacacacg aggattatgt gaccacaagg ctgtgagcgg 3960
ccgctctaga gggcccgttt aaacccgctg atcagcctcg actgtgcctt ctagttgcca 4020
gccatctgtt gtttgcccct cccccgtgcc ttccttgacc ctggaaggtg ccactcccac 4080
tgtcctttcc taataaaatg aggaaattgc atcgcattgt ctgagtaggt gtcattctat 4140
tctggggggt ggggtggggc aggacagcaa gggggaggat tgggaagaca atagcaggca 4200
tgctggggat gcggtgggct ctatggcttc tgaggcggaa agaaccagct ggggctctag 4260
ggggtatccc cacgcgccct gtagcggcgc attaagcgcg gcgggtgtgg tggttacgcg 4320
cagcgtgacc gctacacttg ccagcgccct agcgcccgct cctttcgctt tcttcccttc 4380
ctttctcgcc acgttcgccg gctttccccg tcaagctcta aatcgggggc tccctttagg 4440
gttccgattt agtgctttac ggcacctcga ccccaaaaaa cttgattagg gtgatggttc 4500
acgtagtggg ccatcgccct gatagacggt ttttcgccct ttgacgttgg agtccacgtt 4560
ctttaatagt ggactcttgt tccaaactgg aacaacactc aaccctatct cggtctattc 4620
ttttgattta taagggattt tgccgatttc ggcctattgg ttaaaaaatg agctgattta 4680
acaaaaattt aacgcgaatt aattctgtgg aatgtgtgtc agttagggtg tggaaagtcc 4740
ccaggctccc cagcaggcag aagtatgcaa agcatgcatc tcaattagtc agcaaccagg 4800
tgtggaaagt ccccaggctc cccagcaggc agaagtatgc aaagcatgca tctcaattag 4860
tcagcaacca tagtcccgcc cctaactccg cccatcccgc ccctaactcc gcccagttcc 4920
gcccattctc cgccccatgg ctgactaatt ttttttattt atgcagaggc cgaggccgcc 4980
tctgcctctg agctattcca gaagtagtga ggaggctttt ttggaggcct aggcttttgc 5040
aaaaagctcc cgggagcttg tatatccatt ttcggatctg atcagcacgt gatgaaaaag 5100
cctgaactca ccgcgacgtc tgtcgagaag tttctgatcg aaaagttcga cagcgtctcc 5160
gacctgatgc agctctcgga gggcgaagaa tctcgtgctt tcagcttcga tgtaggaggg 5220
cgtggatatg tcctgcgggt aaatagctgc gccgatggtt tctacaaaga tcgttatgtt 5280
tatcggcact ttgcatcggc cgcgctcccg attccggaag tgcttgacat tggggaattc 5340
agcgagagcc tgacctattg catctcccgc cgtgcacagg gtgtcacgtt gcaagacctg 5400
cctgaaaccg aactgcccgc tgttctgcag ccggtcgcgg aggccatgga tgcgatcgct 5460
gcggccgatc ttagccagac gagcgggttc ggcccattcg gaccgcaagg aatcggtcaa 5520
tacactacat ggcgtgattt catatgcgcg attgctgatc cccatgtgta tcactggcaa 5580
actgtgatgg acgacaccgt cagtgcgtcc gtcgcgcagg ctctcgatga gctgatgctt 5640
tgggccgagg actgccccga agtccggcac ctcgtgcacg cggatttcgg ctccaacaat 5700
gtcctgacgg acaatggccg cataacagcg gtcattgact ggagcgaggc gatgttcggg 5760
gattcccaat acgaggtcgc caacatcttc ttctggaggc cgtggttggc ttgtatggag 5820
cagcagacgc gctacttcga gcggaggcat ccggagcttg caggatcgcc gcggctccgg 5880
gcgtatatgc tccgcattgg tcttgaccaa ctctatcaga gcttggttga cggcaatttc 5940
gatgatgcag cttgggcgca gggtcgatgc gacgcaatcg tccgatccgg agccgggact 6000
gtcgggcgta cacaaatcgc ccgcagaagc gcggccgtct ggaccgatgg ctgtgtagaa 6060
gtactcgccg atagtggaaa ccgacgcccc agcactcgtc cgagggcaaa ggaatagcac 6120
gtgctacgag atttcgattc caccgccgcc ttctatgaaa ggttgggctt cggaatcgtt 6180
ttccgggacg ccggctggat gatcctccag cgcggggatc tcatgctgga gttcttcgcc 6240
caccccaact tgtttattgc agcttataat ggttacaaat aaagcaatag catcacaaat 6300
ttcacaaata aagcattttt ttcactgcat tctagttgtg gtttgtccaa actcatcaat 6360
gtatcttatc atgtctgtat accgtcgacc tctagctaga gcttggcgta atcatggtca 6420
tagctgtttc ctgtgtgaaa ttgttatccg ctcacaattc cacacaacat acgagccgga 6480
agcataaagt gtaaagcctg gggtgcctaa tgagtgagct aactcacatt aattgcgttg 6540
cgctcactgc ccgctttcca gtcgggaaac ctgtcgtgcc agctgcatta atgaatcggc 6600
caacgcgcgg ggagaggcgg tttgcgtatt gggcgctctt ccgcttcctc gctcactgac 6660
tcgctgcgct cggtcgttcg gctgcggcga gcggtatcag ctcactcaaa ggcggtaata 6720
cggttatcca cagaatcagg ggataacgca ggaaagaaca tgtgagcaaa aggccagcaa 6780
aaggccagga accgtaaaaa ggccgcgttg ctggcgtttt tccataggct ccgcccccct 6840
gacgagcatc acaaaaatcg acgctcaagt cagaggtggc gaaacccgac aggactataa 6900
agataccagg cgtttccccc tggaagctcc ctcgtgcgct ctcctgttcc gaccctgccg 6960
cttaccggat acctgtccgc ctttctccct tcgggaagcg tggcgctttc tcatagctca 7020
cgctgtaggt atctcagttc ggtgtaggtc gttcgctcca agctgggctg tgtgcacgaa 7080
ccccccgttc agcccgaccg ctgcgcctta tccggtaact atcgtcttga gtccaacccg 7140
gtaagacacg acttatcgcc actggcagca gccactggta acaggattag cagagcgagg 7200
tatgtaggcg gtgctacaga gttcttgaag tggtggccta actacggcta cactagaaga 7260
acagtatttg gtatctgcgc tctgctgaag ccagttacct tcggaaaaag agttggtagc 7320
tcttgatccg gcaaacaaac caccgctggt agcggttggt ttttgtttg caagcagcag 7380 attacgcgca gaaaaaaagg atctcaagaa gatcctttga tcttttctac ggggtctgac 7440
gctcagtgga acgaaaactc acgttaaggg attttggtca tgagattatc aaaaaggatc 7500
ttcacctaga tccttttaaa ttaaaaatga agttttaaat caatctaaag tatatatgag 7560
taaacttggt ctgacagtta ccaatgctta atcagtgagg cacctatctc agcgatctgt 7620
ctatttcgtt catccatagt tgcctgactc cccgtcgtgt agataactac gatacgggag 7680
ggcttaccat ctggccccag tgctgcaatg ataccgcgag acccacgctc accggctcca 7740
gatttatcag caataaacca gccagccgga agggccgagc gcagaagtgg tcctgcaact 7800
ttatccgcct ccatccagtc tattaattgt tgccgggaag ctagagtaag tagttcgcca 7860
gttaatagtt tgcgcaacgt tgttgccatt gctacaggca tcgtggtgtc acgctcgtcg 7920
tttggtatgg cttcattcag ctccggttcc caacgatcaa ggcgagttac atgatccccc 7980
atgttgtgca aaaaagcggt tagctccttc ggtcctccga tcgttgtcag aagtaagttg 8040
gccgcagtgt tatcactcat ggttatggca gcactgcata attctcttac tgtcatgcca 8100
tccgtaagat gcttttctgt gactggtgag tactcaacca agtcattctg agaatagtgt 8160
atgcggcgac cgagttgctc ttgcccggcg tcaatacggg ataataccgc gccacatagc 8220
agaactttaa aagtgctcat cattggaaaa cgttcttcgg ggcgaaaact ctcaaggatc 8280
ttaccgctgt tgagatccag ttcgatgtaa cccactcgtg cacccaactg atcttcagca 8340
tcttttactt tcaccagcgt ttctgggtga gcaaaaacag gaaggcaaaa tgccgcaaaa 8400
aagggaataa gggcgacacg gaaatgttga atactcatac tcttcctttt tcaatattat 8460
tgaagcattt atcagggtta ttgtctcatg agcggataca tatttgaatg tatttagaaa 8520
aataaacaaa taggggttcc gcgcacattt ccccgaaaag tgccacctga cgtc 8574

<210> SEQ ID NO 2
<211> LENGTH: 8541
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 2
gacggatcgg gagatctccc gatcccctat ggtgcactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggag tatttacggt aaactgccca cttggcagta catcaagtgt 480

-continued

```
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ccctatcagt gatagagatc    840
tccctatcag tgatagagat cgtcgacgag ctcgtttagt gaaccgtcag atcgcctgga    900
gacgccatcc acgctgtttt gacctccata gaagacaccg ggaccgatcc agcctccgga    960
ctctagcgtt taaacttaag cccaagctgg ctagaccgcc atggcccaac tgtactacaa   1020
aaaggtcaac tactcaccgt acagagaccg catccccctg caaattgtga gggctgagac   1080
agagctctct gcagaggaga aggccttcct caatgctgtg gagaaggggg actatgccac   1140
tgtgaagcag gcccttcagg aggctgagat ctactataat gttaacatca actgcatgga   1200
ccccttgggc cggagtgccc tgctcattgc cattgagaac gagaacctgg agatcatgga   1260
gctactgctg aaccacagcg tgtatgtggg tgatgcattg ctctatgcca tacgcaagga   1320
agtggtgggc gctgtggagc ttctgctcag ctacaggcgg cccagcggag agaagcaggt   1380
ccccactctg atgatggaca cgcagttctc tgaattcaca ccggacatca ctcccatcat   1440
gctggctgcc cacaccaaca actacgaaat catcaaactg cttgtccaaa aacgggtcac   1500
tatcccacgg ccccaccaga tccgctgcaa ctgtgtggag tgtgtgtcta gttcagaggt   1560
agacagcctg cgccactctc gctcccgact gaacatctat aaggctctgg caagcccctc   1620
actcattgcc ttatcaagtg aggaccccat cctaactgcc ttccgtctgg gctgggagct   1680
caaggagctc agcaaggtgg agaatgagtt caaggccgag tatgaggagc tctctcagca   1740
gtgcaagctc tttgccaaag acctgctgga ccaagctcgg agctccaggg aactggagat   1800
catcctcaac catcgagatg accacagtga agagcttgac cctcagaagt accatgacct   1860
ggccaagttg aaggtggcaa tcaaatacca ccagaaagag tttgttgctc agcccaactg   1920
ccaacagttg cttgccaccc tgtggtatga tggcttccct ggatggcggc ggaaacactg   1980
ggtagtcaag cttctaacct gcatgaccat tgggttcctg tttcccatgc tgtctatagc   2040
ctacctgatc tcacccagga gcaaccttgg gctgttcatc aagaaaccct ttatcaagtt   2100
tatctgccac acagcatcct atttgacctt cctctttatg cttctcctgg cttctcagca   2160
cattgtcagg acagaccttc atgtacaggg gcctccccca actgtcgtgg aatggatgat   2220
attgccttgg gttctaggtt tcatttgggg tgagattaag gaaatgtggg atggtggatt   2280
tactgaatac atccatgact ggtggaacct gatggatttt gcaatgaact ccctctacct   2340
ggcaactatt tccctgaaga ttgtggccta tgtcaagtat aatggttctc gtccaaggga   2400
ggaatgggaa atgtggcacc cgactctgat tgcggaagca ctcttcgcaa tatccaacat   2460
tttaagttcg ttgcgtctca tatccctgtt cacagccaac tcccacttag gacctctgca   2520
gatctctttg ggacgcatgc tgcttgatat cctcaaattc ctctttatct actgcctggt   2580
actactagct tttgccaatg gactgaacca gctttacttc tattatgaaa ccagagctat   2640
cgatgagcct aacaactgca aggggatccg atgtgagaaa cagaacaatg ccttctccac   2700
gctctttgag actcttcagt cactcttctg gtctgtattt ggccttttaa atctatatgt   2760
caccaatgtg aaagccagac acgaattcac cgagtttgta ggagctacca tgtttggaac   2820
```

-continued atacaatgtc atctccctgg tagtgctgct gaacatgctg attgctatga tgaacaactc 2880
ctatcagctt attgccgatc atgctgatat cgagtggaag tttgcaagga cgaagctctg 2940
gatgagttac tttgatgaag gtggcacctt gccacctcct ttcaacatca tccccagccc 3000
caagtcattt ctataccttg gtaactggtt caacaacacc ttctgcccca aaagagaccc 3060
tgacggtaga cggagaaggc gcaacttgag aagtttcaca gaacgcaatg ctgacagcct 3120
gatacaaaat caacattatc aggaagttat caggaattta gtcaaaagat atgtggctgc 3180
tatgataaga aattccaaaa cacatgaggg acttacagaa gaaaatttta aggaattaaa 3240
gcaagacatc tccagctttc ggtatgaagt gcttgacctc ttgggaaata gaaaacatcc 3300
aaggagcttt tccactagca gcactgaact gtctcagaga gacgataata atgatggcag 3360
tggtggggct cgggccaaat ccaagagtgt ctcttttaat ttaggctgca agaaaaagac 3420
ttgccatggg ccacctctca tcagaaccat gccaaggtcc agtggtgccc aaggaaagtc 3480
aaaagctgag tcatcaagca aacgctcctt catgggtcct tctctcaaga aactgggtct 3540
cctattctcc aaatttaatg gtcatatgtc tgaacccagt tcagagccaa tgtacacaat 3600
ttctgatgga attgttcagc agcactgtat gtggcaggac atcagatatt ctcagatgga 3660
gaaagggaaa gcagaggcct gttctcaaag tgaaattaac ctcagtgagg tagaattagg 3720
tgaagtccag ggcgctgctc agagcagtga atgccctcta gcctgttcca gctctcttca 3780
ctgtgcatcc agcatctgct cctcaaattc taaactttta gactcctcag aggatgtatt 3840
tgaaacttgg ggagaggctt gtgacttgct catgcacaaa tggggtgatg gacaggaaga 3900
acaagttaca actcgcctct aatgactcga gtctagaggg cccgtttaaa cccgctgatc 3960
agcctcgact gtgccttcta gttgccagcc atctgttgtt tgcccctccc ccgtgccttc 4020
cttgaccctg gaaggtgcca ctcccactgt cctttcctaa taaaatgagg aaattgcatc 4080
gcattgtctg agtaggtgtc attctattct ggggggtggg gtggggcagg acagcaaggg 4140
ggaggattgg gaagacaata gcaggcatgc tggggatgcg gtgggctcta tggcttctga 4200
ggcggaaaga accagctggg gctctagggg gtatccccac gcgccctgta gcggcgcatt 4260
aagcgcggcg ggtgtggtgg ttacgcgcag cgtgaccgct acacttgcca gcgccctagc 4320
gcccgctcct ttcgctttct tcccttcctt tctcgccacg ttcgccggct ttccccgtca 4380
agctctaaat cgggggctcc ctttagggtt ccgatttagt gctttacggc acctcgaccc 4440
caaaaaactt gattagggtg atggttcacg tagtgggcca tcgccctgat agacggtttt 4500
tcgccctttg acgttggagt ccacgttctt taatagtgga ctcttgttcc aaactggaac 4560
aacactcaac cctatctcgg tctattcttt tgatttataa gggattttgc cgatttcggc 4620
ctattggtta aaaaatgagc tgatttaaca aaaatttaac gcgaattaat tctgtggaat 4680
gtgtgtcagt tagggtgtgg aaagtcccca ggctccccag caggcagaag tatgcaaagc 4740
atgcatctca attagtcagc aaccaggtgt ggaaagtccc caggctcccc agcaggcaga 4800
agtatgcaaa gcatgcatct caattagtca gcaaccatag tcccgcccct aactccgccc 4860
atcccgcccc taactccgcc cagttccgcc cattctccgc cccatggctg actaattttt 4920
tttatttatg cagaggccga ggccgcctct gcctctgagc tattccagaa gtagtgagga 4980
ggcttttttg gaggcctagg cttttgcaaa aagctcccgg gagcttgtat atccattttc 5040
ggatctgatc agcacgtgat gaaaaagcct gaactcaccg cgacgtctgt cgagaagttt 5100
ctgatcgaaa agttcgacag cgtctccgac ctgatgcagc tctcggaggg cgaagaatct 5160
cgtgctttca gcttcgatgt aggagggcgt ggatatgtcc tgcgggtaaa tagctgcgcc 5220

-continued gatggtttct acaaagatcg ttatgtttat cggcactttg catcggccgc gctcccgatt 5280
ccggaagtgc ttgacattgg ggaattcagc gagagcctga cctattgcat ctcccgccgt 5340
gcacagggtg tcacgttgca agacctgcct gaaaccgaac tgcccgctgt tctgcagccg 5400
gtcgcggagg ccatggatgc gatcgctgcg gccgatctta gccagacgag cgggttcggc 5460
ccattcggac cgcaaggaat cggtcaatac actacatggc gtgatttcat atgcgcgatt 5520
gctgatcccc atgtgtatca ctggcaaact gtgatggacg acaccgtcag tgcgtccgtc 5580
gcgcaggctc tcgatgagct gatgctttgg gccgaggact gccccgaagt ccggcacctc 5640
gtgcacgcgg atttcggctc caacaatgtc ctgacggaca atggccgcat aacagcggtc 5700
attgactgga gcgaggcgat gttcggggat tcccaatacg aggtcgccaa catcttcttc 5760
tggaggccgt ggttggcttg tatggagcag cagacgcgct acttcgagcg gaggcatccg 5820
gagcttgcag gatcgccgcg gctccgggcg tatatgctcc gcattggtct tgaccaactc 5880
tatcagagct tggttgacgg caatttcgat gatgcagctt gggcgcaggg tcgatgcgac 5940
gcaatcgtcc gatccggagc cgggactgtc gggcgtacac aaatcgcccg cagaagcgcg 6000
gccgtctgga ccgatggctg tgtagaagta ctcgccgata gtggaaaccg acgccccagc 6060
actcgtccga gggcaaagga atagcacgtg ctacgagatt tcgattccac cgccgccttc 6120
tatgaaaggt tgggcttcgg aatcgttttc cgggacgccg gctggatgat cctccagcgc 6180
ggggatctca tgctggagtt cttcgcccac cccaacttgt ttattgcagc ttataatggt 6240
tacaaataaa gcaatagcat cacaaatttc acaaataaag catttttttc actgcattct 6300
agttgtggtt tgtccaaact catcaatgta tcttatcatg tctgtatacc gtcgacctct 6360
agctagagct tggcgtaatc atggtcatag ctgtttcctg tgtgaaattg ttatccgctc 6420
acaattccac acaacatacg agccggaagc ataaagtgta aagcctgggg tgcctaatga 6480
gtgagctaac tcacattaat tgcgttgcgc tcactgcccg ctttccagtc gggaaacctg 6540
tcgtgccagc tgcattaatg aatcggccaa cgcgcgggga gaggcggttt gcgtattggg 6600
cgctcttccg cttcctcgct cactgactcg ctgcgctcgg tcgttcggct gcggcgagcg 6660
gtatcagctc actcaaaggc ggtaatacgg ttatccacag aatcagggga taacgcagga 6720
aagaacatgt gagcaaaagg ccagcaaaag gccaggaacc gtaaaaaggc cgcgttgctg 6780
gcgtttttcc ataggctccg cccccctgac gagcatcaca aaaatcgacg ctcaagtcag 6840
aggtggcgaa acccgacagg actataaaga taccaggcgt ttccccctgg aagctccctc 6900
gtgcgctctc ctgttccgac cctgccgctt accggatacc tgtccgcctt tctcccttcg 6960
ggaagcgtgg cgctttctca tagctcacgc tgtaggtatc tcagttcggt gtaggtcgtt 7020
cgctccaagc tgggctgtgt gcacgaaccc cccgttcagc ccgaccgctg cgccttatcc 7080
ggtaactatc gtcttgagtc caacccggta agacacgact tatcgccact ggcagcagcc 7140
actggtaaca ggattagcag agcgaggtat gtaggcggtg ctacagagtt cttgaagtgg 7200
tggcctaact acggctacac tagaagaaca gtatttggta tctgcgctct gctgaagcca 7260
gttaccttcg gaaaaagagt tggtagctct tgatccggca aacaaaccac cgctggtagc 7320
ggttggtttt ttgtttgcaa gcagcagatt acgcgcagaa aaaaaggatc tcaagaagat 7380
cctttgatct tttctacggg gtctgacgct cagtggaacg aaaactcacg ttaagggatt 7440
ttggtcatga gattatcaaa aaggatcttc acctagatcc ttttaaatta aaaatgaagt 7500
tttaaatcaa tctaaagtat atatgagtaa acttggtctg acagttacca atgcttaatc 7560

-continued

| | | | | | | |
|---|---|---|---|---|---|---|
| agtgaggcac | ctatctcagc | gatctgtcta | tttcgttcat | ccatagttgc | ctgactcccc | 7620 |
| gtcgtgtaga | taactacgat | acgggagggc | ttaccatctg | gccccagtgc | tgcaatgata | 7680 |
| ccgcgagacc | cacgctcacc | ggctccagat | ttatcagcaa | taaaccagcc | agccggaagg | 7740 |
| gccgagcgca | gaagtggtcc | tgcaacttta | tccgcctcca | tccagtctat | taattgttgc | 7800 |
| cgggaagcta | gagtaagtag | ttcgccagtt | aatagtttgc | gcaacgttgt | tgccattgct | 7860 |
| acaggcatcg | tggtgtcacg | ctcgtcgttt | ggtatggctt | cattcagctc | cggttcccaa | 7920 |
| cgatcaaggc | gagttacatg | atcccccatg | ttgtgcaaaa | aagcggttag | ctccttcggt | 7980 |
| cctccgatcg | ttgtcagaag | taagttggcc | gcagtgttat | cactcatggt | tatggcagca | 8040 |
| ctgcataatt | ctcttactgt | catgccatcc | gtaagatgct | tttctgtgac | tggtgagtac | 8100 |
| tcaaccaagt | cattctgaga | atagtgtatg | cggcgaccga | gttgctcttg | cccggcgtca | 8160 |
| atacgggata | ataccgcgcc | acatagcaga | actttaaaag | tgctcatcat | tggaaaacgt | 8220 |
| tcttcggggc | gaaaactctc | aaggatctta | ccgctgttga | gatccagttc | gatgtaaccc | 8280 |
| actcgtgcac | ccaactgatc | ttcagcatct | tttactttca | ccagcgtttc | tgggtgagca | 8340 |
| aaaacaggaa | ggcaaaatgc | cgcaaaaaag | ggaataaggg | cgacacggaa | atgttgaata | 8400 |
| ctcatactct | tcctttttca | atattattga | agcatttatc | agggttattg | tctcatgagc | 8460 |
| ggatacatat | ttgaatgtat | ttagaaaaat | aaacaaatag | gggttccgcg | cacatttccc | 8520 |
| cgaaaagtgc | cacctgacgt | c | | | | 8541 |